US011666658B2

(12) United States Patent
Nittoli et al.

(10) Patent No.: US 11,666,658 B2
(45) Date of Patent: Jun. 6, 2023

(54) RIFAMYCIN ANALOGS AND ANTIBODY-DRUG CONJUGATES THEREOF

(71) Applicant: Regeneron Pharmaceuticals, Inc., Tarrytown, NY (US)

(72) Inventors: Thomas Nittoli, Pearl River, NY (US); Seungyong Sean Choi, Bristol, PA (US); Mrinmoy Saha, Bristol, PA (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 157 days.

(21) Appl. No.: 16/722,958

(22) Filed: Dec. 20, 2019

(65) Prior Publication Data

US 2020/0368361 A1 Nov. 26, 2020

Related U.S. Application Data

(60) Provisional application No. 62/844,860, filed on May 8, 2019, provisional application No. 62/783,506, filed on Dec. 21, 2018.

(51) Int. Cl.
*A61K 47/68* (2017.01)
*C07D 498/18* (2006.01)

(52) U.S. Cl.
CPC ........ *A61K 47/6803* (2017.08); *C07D 498/18* (2013.01)

(58) Field of Classification Search
CPC .......................... A61K 47/6803; C07D 498/18
See application file for complete search history.

(56) References Cited

FOREIGN PATENT DOCUMENTS

| | | | |
|---|---|---|---|
| JP | S59231092 | A | 12/1984 |
| JP | S6345282 | A | 2/1988 |
| JP | H01175938 | A | 7/1989 |
| JP | H01207293 | A | 8/1989 |
| WO | 2017/152083 | A1 | 9/2017 |
| WO | 2017152083 | A1 | 9/2017 |
| WO | 2019/217591 | A1 | 11/2019 |
| WO | 20190217591 | A1 | 11/2019 |

OTHER PUBLICATIONS

Communication (International Search Report) issued by the International Searching Authority in International Application No. PCT/US19/67914 dated Jun. 25, 2020, 8 pages total.
Communication (Written Opinion) issued by the International Searching Authority in International Application No. PCT/US19/67914 dated Jun. 25, 2020, 15 pages total.
Kump, W. et al., "Zur Kenntnis von Rifamycinn-S. Reaktionen des Chinoiden Nucleus. Modifikationen von Antibiotica, 9.Mitteilung[1]" Helvetica Chimica Acta (1973) vol. 56, No. 7, pp. 2348-2377.
Bickel, H. et al., "New Derivatives of Rifamycin Antibiotics" Antimicrobial Agents and Chemotherapy, American Society for Microbiology (1966) vol. 6, pp. 352-358.
Bickel Hans et al.; "New derivatives of rifomycin antibiotics", Antimicrobial Agents and Chemotherapy, American Society for Microbiology, US, vol. 6, Jan. 1, 1966 (Jan. 1, 1966), pp. 352-358, XP009519333, ISSN: 0066-4804.
Kump Wilhelm et al.; "Zur Kenntnis von Rifamycin-S. Reaktionen des chinoiden Nucleus. Modifikationen von Antibiotica, 9. Mitteilung [1]", Helvetica Chimica Acta, Verlag Helvetica Chimica Acta vol. 56, No. 7 Nov. 7, 1973 (Nov. 7, 1973), pp. 2348-2377, XP009519300, ISSN: 0018-019X, DOI: 10.1002/HLCA.19730560720.
International Preliminary Report on Patentability dated Jun. 16, 2021, from corresponding International application No. PCT/US2019/067914.

*Primary Examiner* — Noble E Jarrell
(74) *Attorney, Agent, or Firm* — Troutman Pepper Hamilton Sanders LLP

(57) ABSTRACT

The disclosure relates to rifamycin analog compounds, intermediates and precursors thereof, and pharmaceutical compositions capable of inhibiting bacterial growth (e.g., *S. aureus* growth) and treating bacterial infections (e.g., *S. aureus* infections). The disclosure further relates to antibody-drug conjugates of rifamycin analog compounds and antibodies, for example, antibodies specific for infectious disease-related targets such as membrane glycoprotein receptor (MSR1), wall teichoic acids (WTA) or Protein A, and methods of use thereof to inhibit bacterial growth and treat bacterial infections.

32 Claims, 7 Drawing Sheets

Specification includes a Sequence Listing.

RIFAMYCIN ANALOGS AND ANTIBODY-DRUG CONJUGATES THEREOF

CROSS-REFERENCE TO RELATED APPLICATIONS

This application claims priority to U.S. Provisional Application Ser. No. 62/783,506, filed on Dec. 21, 2018, and 62/844,860, filed on May 8, 2019, the contents of which are incorporated herein by reference in their entirety.

FIELD OF DISCLOSURE

The present disclosure relates to rifamycin analog compounds and pharmaceutical compositions capable of inhibiting bacterial growth and treating bacterial infections, as well as antibody-drug conjugates of rifamycin analog compounds and antibodies, for example, antibodies specific for infectious disease-related targets, and methods of use thereof.

SEQUENCE LISTING

The instant application contains a Sequence Listing which has been submitted electronically in ASCII format and is hereby incorporated by reference in its entirety. Said ASCII copy, created on Dec. 19, 2019, is named 250298_000144_SL.TXT and is 392,570 bytes in size.

BACKGROUND OF THE DISCLOSURE

*Staphylococcus aureus* (*S. aureus*) is a Gram-positive, round-shaped bacterium that is a member of the Firmicutes, and it is a usual member of the microbiota of the body, frequently found in the upper respiratory tract and on the skin. It is often positive for catalase and nitrate reduction and is a facultative anaerobe that can grow without the need for oxygen. Although *S. aureus* usually acts as a commensal of the human microbiota, it can also become an opportunistic pathogen, being a common cause of skin infections including abscesses, respiratory infections such as sinusitis, and food poisoning. Pathogenic strains often promote infections by producing virulence factors such as potent protein toxins, and the expression of a cell-surface protein that binds and inactivates antibodies.

An estimated 20% to 30% of the human population are long-term carriers of *S. aureus*, which can be found as part of the normal skin flora, in the nostrils, and as a normal inhabitant of the lower reproductive tract of women. *S. aureus* can cause a range of illnesses, from minor skin infections, such as pimples, impetigo, boils, cellulitis, folliculitis, carbuncles, scalded skin syndrome, and abscesses, to life-threatening diseases such as pneumonia, meningitis, osteomyelitis, endocarditis, toxic shock syndrome, bacteremia, and sepsis. It is still one of the five most common causes of hospital-acquired infections and is often the cause of wound infections following surgery. Each year, around 500,000 patients in hospitals of the United States contract a staphylococcal infection, chiefly by *S. aureus*. Up to 50,000 deaths each year in the USA are linked with *S. aureus* infections. Schlecht L M et al, 2015, *Microbiology,* 161, 1, 168-181. Despite much research and development, no vaccine for *S. aureus* has been approved at present.

Initially, the treatment of choice for *S. aureus* infection was penicillin. Antibiotic resistance in *S. aureus* was uncommon when penicillin was first introduced in 1943. By 1950, 40% of hospital *S. aureus* isolates were penicillin-resistant;

by 1960, this had risen to 80%. Chambers HF, 2001, *Emerging Infectious Diseases,* 7, 2, 178-82. Today, *S. aureus* has become resistant to many commonly used antibiotics.

The emergence of antibiotic-resistant strains of *S. aureus* such as methicillin-resistant *S. aureus* (MRSA) is a worldwide problem in clinical medicine. MRSA strains are most often found associated with institutions such as hospitals, but are becoming increasingly prevalent in community-acquired infections. MRSA is one of a number of greatly feared strains of *S. aureus* which have become resistant to most β-lactam antibiotics. MRSA infections in both the hospital and community setting are commonly treated with non-β-lactam antibiotics, such as clindamycin (a lincosamine) and co-trimoxazole (also commonly known as trimethoprim/sulfamethoxazole). Resistance to these antibiotics has also led to the use of new, broad-spectrum anti-Gram-positive antibiotics, such as linezolid, because of its availability as an oral drug. First-line treatment for serious invasive infections due to MRSA is currently glycopeptide antibiotics (vancomycin and teicoplanin). A number of problems with these antibiotics occur, such as the need for intravenous administration (no oral preparation is available), toxicity, and the need to monitor drug levels regularly by blood tests. Also, glycopeptide antibiotics do not penetrate very well into infected tissues (this is a particular concern with infections of the brain and meninges and in endocarditis). Thus, there exists a strong unmet need for novel antibiotic treatments for *S. aureus* in general, and in addressing intracellular *S. aureus* infections in particular.

Rifamycins, a subclass of the ansamycin antibiotic family, are a group of antibiotics that are synthesized either naturally by the bacterium *Amycolatopsis rifamycinica* or artificially. Rifamycins are particularly effective against mycobacteria, and are therefore used to treat tuberculosis, leprosy, and *Mycobacterium avium* complex (MAC) infections. The rifamycin group includes the "classic" rifamycin drugs as well as the rifamycin analogs rifampicin (or rifampin), rifabutin, rifapentine, rifalazil and rifaximin. Rifamycin SV, sold under the trade name Aemcolo, is FDA-approved for treatment of travelers' diarrhea in some circumstances.

Rifamycin class antibiotics inhibit bacterial RNA polymerase (RNAP) and have potent activity against *S. aureus*. Monotherapy with this class of antibiotics, however, can lead to selection of a resistant population during treatment. Therefore, rifamycin antibiotics can be used in combination with first line antibiotics to improve outcomes, commonly in infections involving prostheses or foreign devices.

Macrophage scavenger receptor 1 (MSR1) is a single-pass, trimeric type II transmembrane glycoprotein pattern recognition receptor that mediates uptake of a series of negatively charged/polyanionic ligands, including modified low density lipoproteins (LDL) (Krieger, M. 1994. *Annu. Rev. Biochem.* 63:601-637; Platt, N. and S. Gordon. 2001. *J Clin Invest.* 108(5):649-654) and advanced glycation end products of bovine serum albumin (AGE-BSA) (Smedsrød et al. 1997. *Biochem J.* 322(Pt 2):567-573.) MSR1 receptors have been implicated in many macrophage-associated physiological and pathological processes including atherosclerosis, Alzheimer's disease, and host defense.

MSR1 expression was originally considered to be macrophage-specific. However, it has recently been demonstrated to be present on different classes of dendritic cells (Herber et al. 2010. *Nat. Med.* 16(8): 880-886). In addition, MSR1 appears to be expressed in endothelial cells and smooth muscle cells. It is internalized via coated pits at the cell surface and releases its ligand at acidic pH before being recycled back to the cell surface from the trans-Golgi apparatus (Doi et al. 1994. *Journal of Biological Chemistry*; Mori, T. 1994. *Lab Invest.*). It promotes conversion of monocyte-derived macrophages into foam cells, which is a critical step for atherosclerosis progression.

*S. aureus* is a facultative intracellular bacterium that can survive phagocytosis by macrophages and other cells types (Horn et al. 2018. Int. J. Med. Microbiol. 308(6): 607-624; Jubrail et al. 2016. Cell Microbiol. 18(1): 80-96; Mitchell et al. 2016. Microbiol. Spectr. 4(3)). Intravital imaging has demonstrated that macrophages can serve as a reservoir wherein *S. aureus* replicates and then seeds other organs during infection (Surewaard et al. 2016. J. Exp. Med. 213(7): 1141-51). Most antibiotics do not penetrate cells, including macrophages, very well, indicating that the intracellular *S. aureus* reservoir can evade treatment with standard of care antibiotics (Lehar et al. 2015. Nature. 527 (7578): 323-8). However, liposomal formulation of vancomycin increased penetration of the antibiotic into macrophages and reduced *S. aureus* organ burden more effectively than standard of care vancomycin (Surewaard et al. 2016. J. Exp. Med. 213(7): 1141-51). Together, these data indicate that delivering an antibiotic to macrophages may be an effective method to eliminate the intracellular *S. aureus* reservoir.

Teichoic acids are phosphate-rich molecules found on many glycan-binding proteins within the cell wall of most Gram-positive bacteria including *S. aureus*. Teichoic acids, as well as many other glycoproteins, form a thick layer of multiple peptidoglycan sheaths around the bacteria that not only stabilize the cell membrane but also provide many sites for other molecules to be attached to. Wall teichoic acids ("WTA") is one type of teichoic acids, which are covalently attached to peptidoglycan and extend through and beyond the cell wall. WTA can account for as much as 60% of the total cell wall mass in glycan-binding proteins. As a result, it presents a highly expressed cell surface antigen for Gram-positive bacteria including *S. aureus*.

*S. aureus* also expresses a number of surface determinant antigens, including the *S. aureus* Protein A (SpA) and polysaccharide poly-N-aceytlglucosamine (PNAG), iron-regulated surface determinant proteins IsdA, IsdB, IsdC, IsdE and IsdH, the clumping factor proteins ClfA and ClfB, capsular polysaccharide type (CP) 5 and CP8, the serine-aspartic acid repeat proteins SdrC, SdrD, and SdrE, fibronectin binding proteins A and B (FnBpA, FnBpB), Cna (collagen binding protein), and SasG (*S. aureus* surface protein G). These surface antigens play a role in colonization of host tissue, evasion of the host immune response, and bacterial fitness.

The development of ADCs comprising rifamycin analogs would thus allow for target-specific delivery of rifamycin analogs inside macrophage cells, or tethering of the rifamycin analogs onto the surface of the bacteria. Furthermore, such ADCs may provide improved activity against e.g., resistant bacterial targets, improved bioavailability, and improved therapeutic window. Therefore, there is a continuing need for effective treatments of antibiotic-resistant bacteria using antibody-drug conjugates of rifamycin analogs.

Thus, there exists a strong unmet need for developing effective analogs of rifamycin in order to combat the growing problem of antibiotic-resistant bacteria, including antibiotic-resistant *S. aureus* strains. MSR1 antibodies may provide a means for specific targeting of therapeutic molecules such as analogs of rifamycin to minimize unwanted side effects arising from systemic administration of such compounds as well as assist with these compounds' internalization into macrophage cells. Alternatively, conjugation to antibodies targeting a cell surface antigen (e.g., WTA, Protein A) may improve the therapeutic effects of the rifamycin analogs.

The foregoing discussion is presented solely to provide a better understanding of the nature of the problems confronting the art and should not be construed in any way as an admission as to prior art nor should the citation of any reference herein be construed as an admission that such reference constitutes "prior art" to the instant application.

SUMMARY OF THE DISCLOSURE

As discussed herein, there is a strong need to develop effective treatments for bacterial infections in general and *S. aureus* infections in particular. The present disclosure addresses these and other needs by providing new rifamycin analog compounds, intermediates and precursors thereof, antibody-drug conjugates, pharmaceutical compositions, and methods of treatment based on such compounds and pharmaceutical compositions.

Various non-limiting aspects and embodiments are described below.

In one aspect, the present disclosure provides a rifamycin analog compound, intermediate or precursor thereof having a structure of formula (A):

(A)

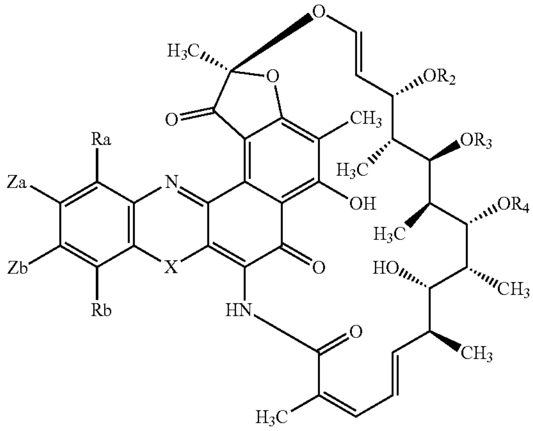

or a pharmaceutically acceptable salt thereof, wherein:

X is selected from —O— and —NR*—;

Za and Zb are independently selected from a hydrogen, —Cl, —Br, —$OR_1$ and —$R_N$; with the proviso that at least one of Za or Zb is not a hydrogen; wherein:

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3$+, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

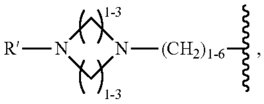,

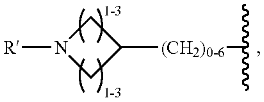,

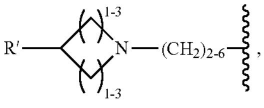, 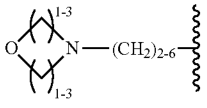,

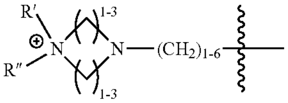,

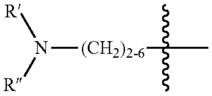,

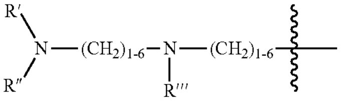,

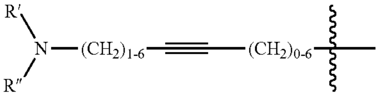 and

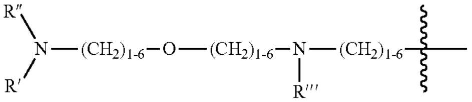;

wherein the symbol represents the point of attachment; and R', R" and R"' are selected from a hydrogen, a $C_1$-$C_6$ aliphatic hydrocarbon, and a protecting group selected from Fluorenylmethyloxycarbonyl (FMOC) and tert-Butyloxycarbonyl (BOC), or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S; $R_a$ is selected from hydrogen, —F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one aspect, the present disclosure provides a rifamycin analog compound having a structure of formula (I):

(I)

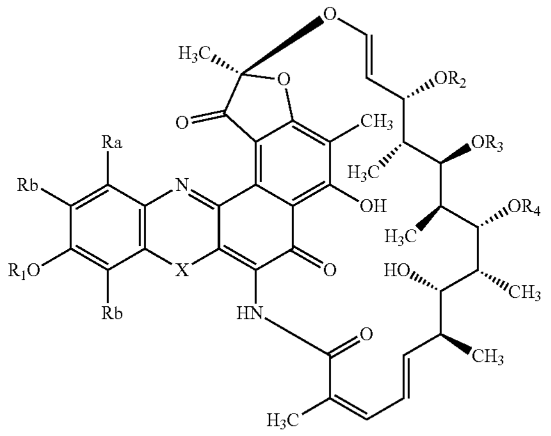

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

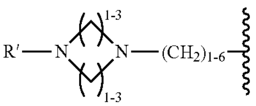,

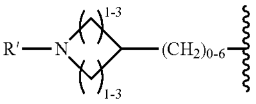,

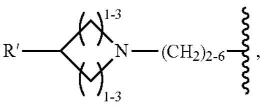, 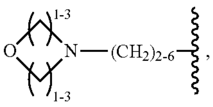,

-continued

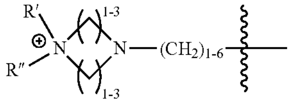,

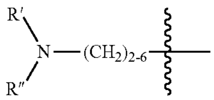,

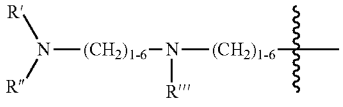,

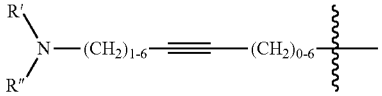 and

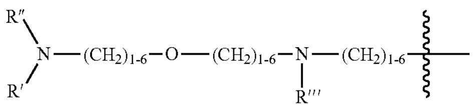;

wherein the symbol represents the point of attachment; and R', R" and R"' are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S; $R_a$ is selected from hydrogen, F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one aspect, the present disclosure provides a rifamycin analog compound having a structure of formula (I'):

(I')

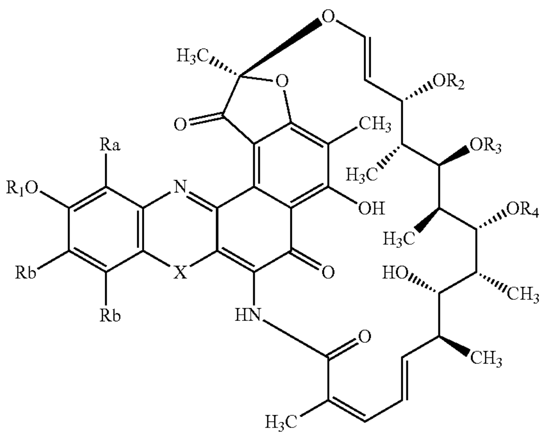

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—N$(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

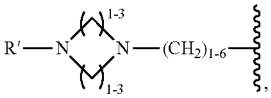,

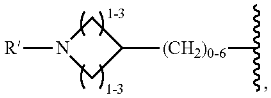,

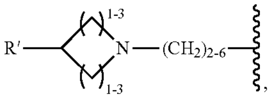, 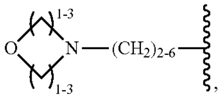,

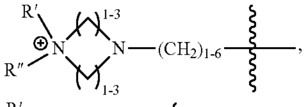,

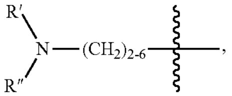,

-continued

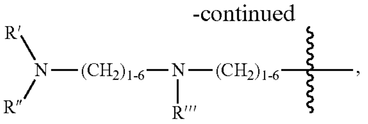

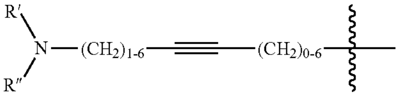

and

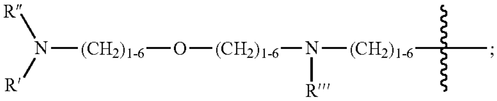

;

wherein the  symbol represents the point of attachment; and R', R'' and R''' are selected from a hydrogen, a $C_1$-$C_6$ aliphatic hydrocarbon, and a protecting group selected from $F_{MOC}$ and $B_{OC}$, or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In an embodiment of a compound of the formulas (A), (I), or (I'), X is —O—, $R_1$ is an aliphatic $C_1$-$C_3$ hydrocarbon, $R_2$ is a methyl group, $R_3$ is Ac (—(C═O)—$CH_3$), $R_4$ is a hydrogen, and $R_a$ is a hydrogen.

In an embodiment of a compound of the formulas (A), (I), or (I'), X is —O—, $R_1$ is a benzyl group, $R_2$ is a methyl group, $R_3$ is Ac (—(C═O)—$CH_3$), $R_4$ is a hydrogen; $R_a$ is a hydrogen and $R_b$ is hydrogen.

In an embodiment of a compound of the formulas (A), (I), or (I'), X is —O—, $R_1$ is an aliphatic $C_1$-$C_8$ hydrocarbon comprising 1-8 heteroatoms selected from O and N, $R_2$ is a methyl group, $R_3$ is Ac (—(C═O)—$CH_3$), $R_4$ is a hydrogen; $R_a$ is a hydrogen and $R_b$ is hydrogen.

In an embodiment of a compound of the formulas (A), (I), or (I'), X is —O—; $R_1$ is an aliphatic $C_1$-$C_8$ hydrocarbon substituted with one or more of —$NH_2$, —NHR*, —$N(R^*)_2$; R* is hydrogen or an aliphatic $C_1$-$C_3$ hydrocarbon; $R_2$ is a methyl group; $R_3$ is Ac (—(C═O)—$CH_3$); $R_4$ is a hydrogen; $R_a$ is a hydrogen and $R_b$ is hydrogen.

In an embodiment of a compound of the formulas (A), (I), or (I'), X is —$NCH_3$—, $R_1$ is —OH, $R_2$ is a methyl group, $R_3$ is Ac (—(C═O)—$CH_3$), $R_4$ is a hydrogen, $R_a$ is a hydrogen and $R_b$ is hydrogen.

In one embodiment, the rifamycin analog compounds of the disclosure have the structure of formula (II):

(II)

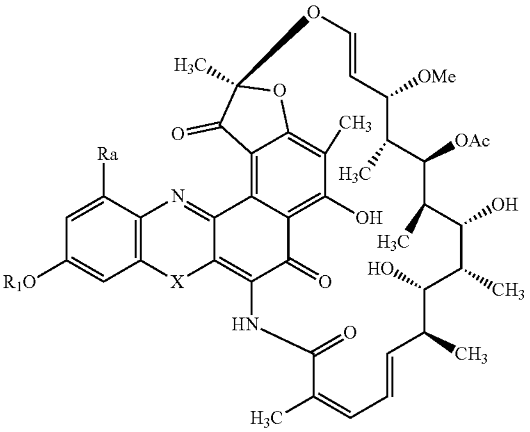

or a pharmaceutically acceptable salt thereof wherein:

X is selected from —O— and —NR*—;

$R_a$ is selected from hydrogen, —Cl, and —OR*;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with a proviso that $R_1$ is not an n-butyl group;

$R_N$ is selected from:

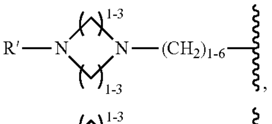

,

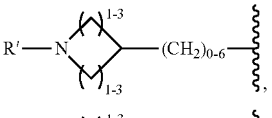

,

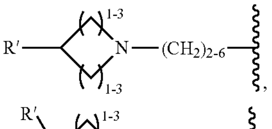

,

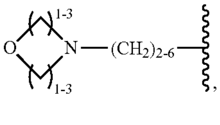

,

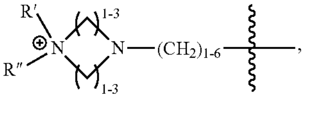

,

-continued

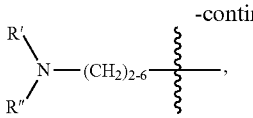,

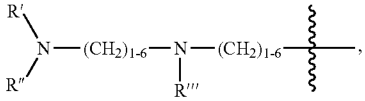,

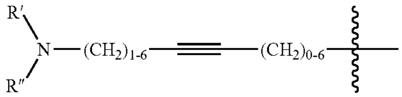 and

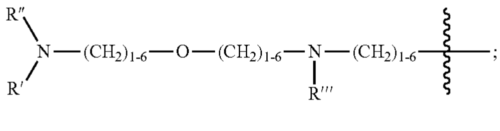;

wherein the symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (II'):

(II')

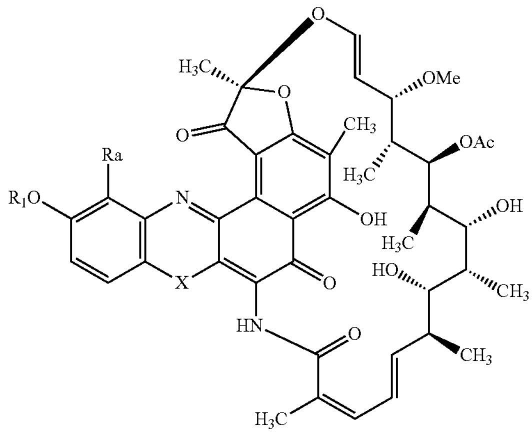

or a pharmaceutically acceptable salt thereof wherein:

X is selected from —O— and —NR*—;

$R_a$ is selected from hydrogen and —OR*;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, $—NO_2$, $—NO_3$, —O, $—N_3$, $—NH_2$, —NHR*, $—N(R^*)_2$, $—N(R^*)_3^+$, —N(R*)—OH, $—O—N(R^*)_2$, —N(R*)—O—R*, —CN, —NC, —(C═O)—R*, —CHO, $—CO_2H$, $—CO_2R^*$, —(C═O)—S—R*, —O—(C═O)—H, —O—(C═O)—R*, —S—(C═O)—R*, $—(C═O)—NH_2$, $—(C═O)—N(R^*)_2$, $—(C═O)—NHNH_2$, $—O—(C═O)—NHNH_2$, $—(C═S)—NH_2$, $—(C═S)—N(R^*)_2$, —N(R*)—CHO, —N(R*)—(C═O)—R*, —SCN, —NCS, —NSO, —SSR*, $—SO_2R^*$, $—SO_2—N(R^*)_2$, —S(═O)—OR*, —S(═O)—R*, $—Si(R^*)_3$, $—CF_3$, $—O—CF_3$ and combinations thereof, with a proviso that $R_1$ is not an n-butyl group; $R_N$ is selected from:

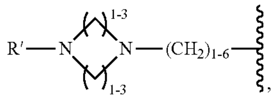,

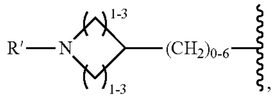,

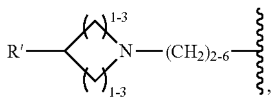, 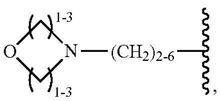,

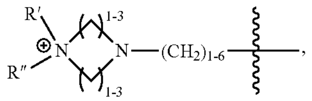,

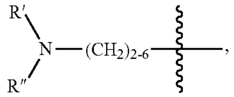,

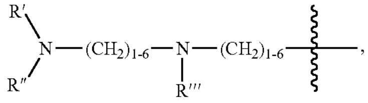,

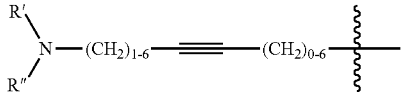 and

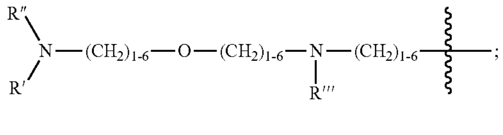;

wherein the symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (III):

(III)

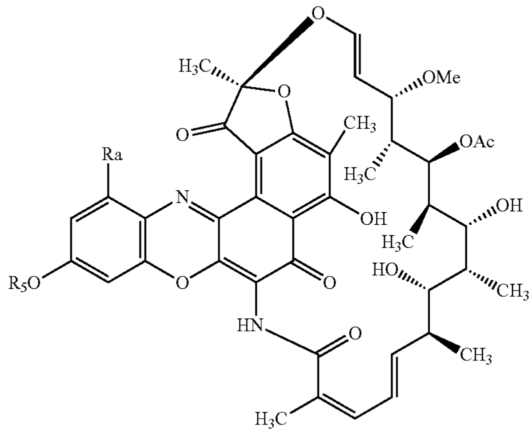

or a pharmaceutically acceptable salt thereof wherein:

$R_a$ is selected from hydrogen and —OR*;

$R_5$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_5$ is not an n-butyl group;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and $R_N$ is selected from:

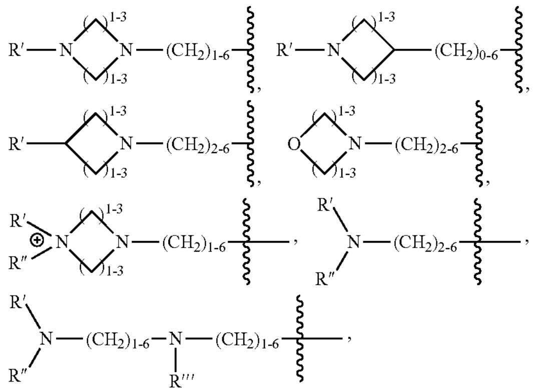

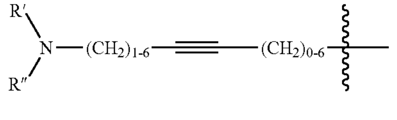

and

-continued

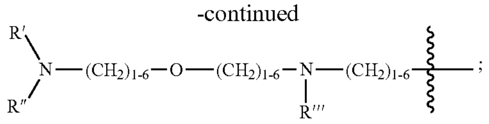

wherein the  symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In one embodiment, the rifamycin analog compounds of the disclosure have the structure of formula (III'):

(III')

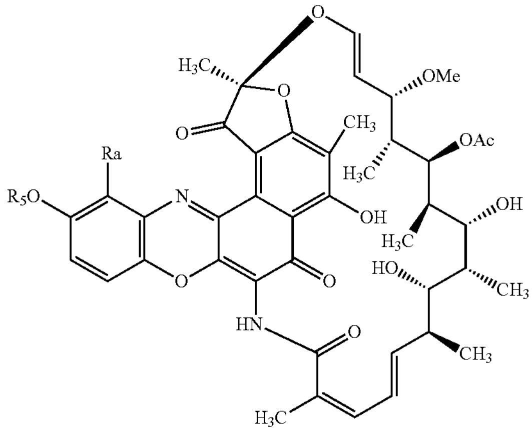

or a pharmaceutically acceptable salt thereof wherein:

$R_a$ is selected from hydrogen and —OR*;

$R_5$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_5$ is not an n-butyl group;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and $R_N$ is selected from:

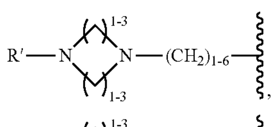

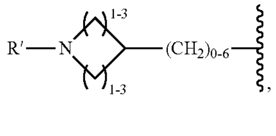

-continued

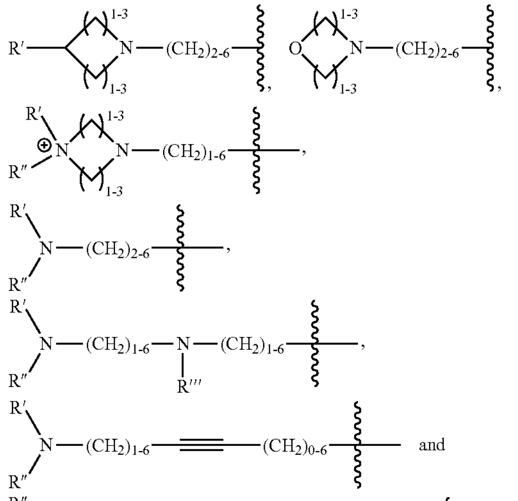

and

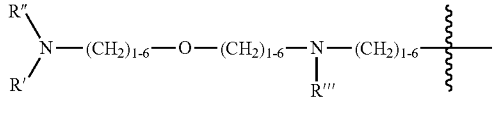

wherein the symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In one embodiment, the rifamycin analog compounds of the disclosure have the structure of formula (IV):

(IV)

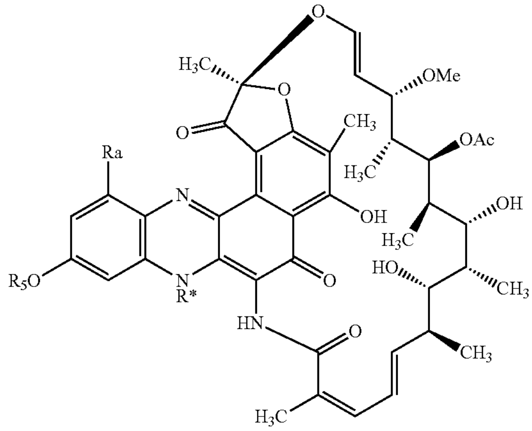

or a pharmaceutically acceptable salt thereof wherein:

$R_a$ is selected from hydrogen and —OR*;

$R_5$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof;

$R_N$ is selected from:

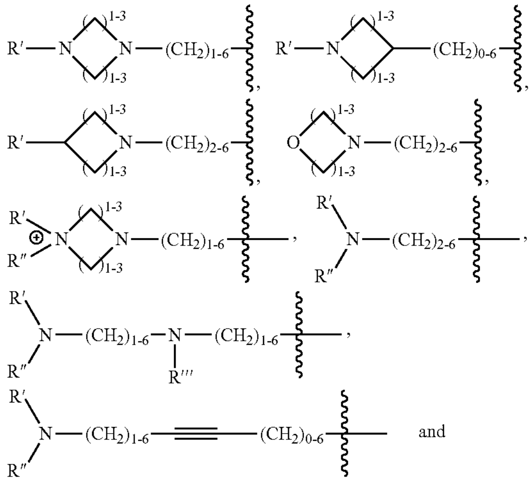

and

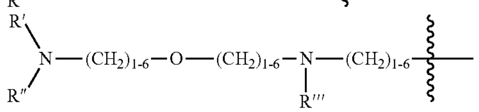

wherein the symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (IV'):

(IV')

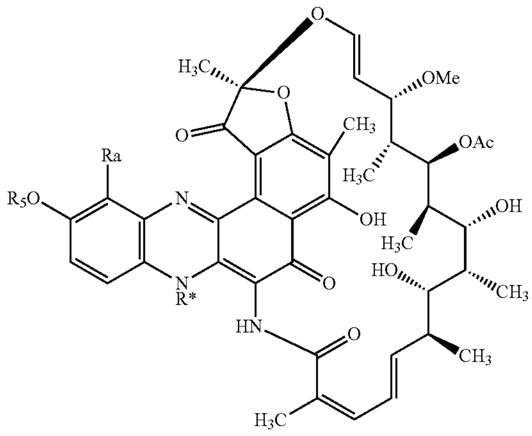

or a pharmaceutically acceptable salt thereof wherein:

$R_a$ is selected from hydrogen and —OR*;

$R_5$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof;

$R_N$ is selected from:

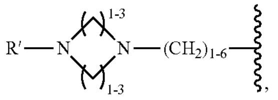

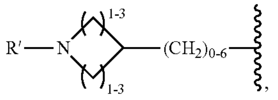

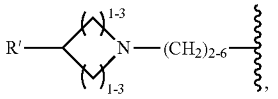

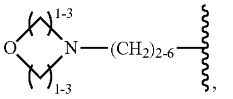

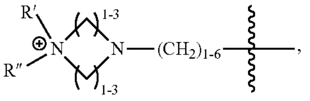

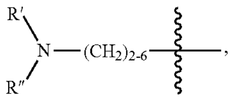

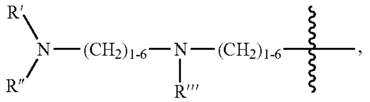

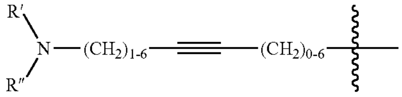

and

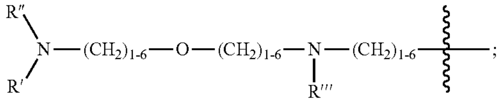

wherein the symbol represents the point of attachment; and R', R'' and R''' are selected from a hydrogen, a $C_1$-$C_6$ aliphatic hydrocarbon, and a protecting group selected from $F_{MOC}$ and $B_{OC}$, or wherein R' and R'' together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (V):

(V)

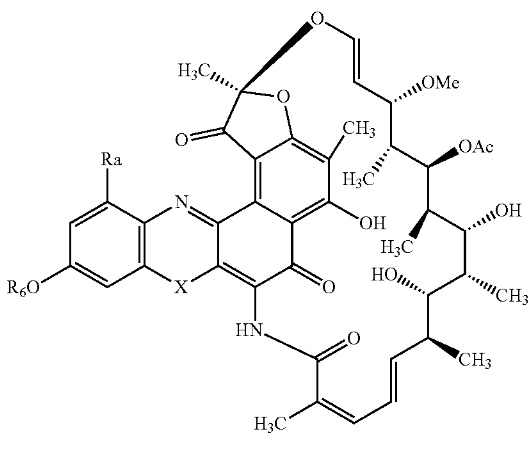

or a pharmaceutically acceptable salt thereof wherein:

X is selected from —O— and —NR*—;

$R_a$ is selected from hydrogen and —OR*;

$R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_6$ is optionally substituted with one or more of —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_6$ is not an n-butyl group;

$R_N$ is selected from:

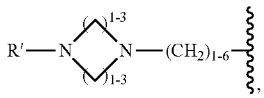

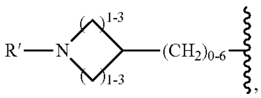

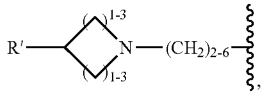

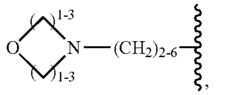

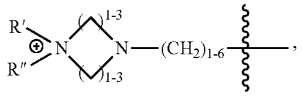

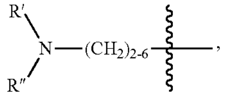

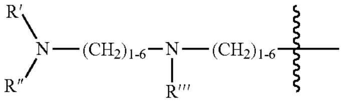

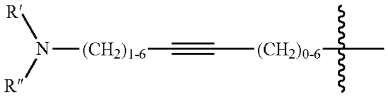

and

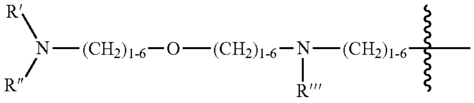

wherein the symbol represents the point of attachment; and R', R'' and R''' are selected from a hydrogen, a $C_1$-$C_6$ aliphatic hydrocarbon, and a protecting group selected from $F_{MOC}$ and $B_{OC}$, or wherein R' and R'' together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (V'):

(V')

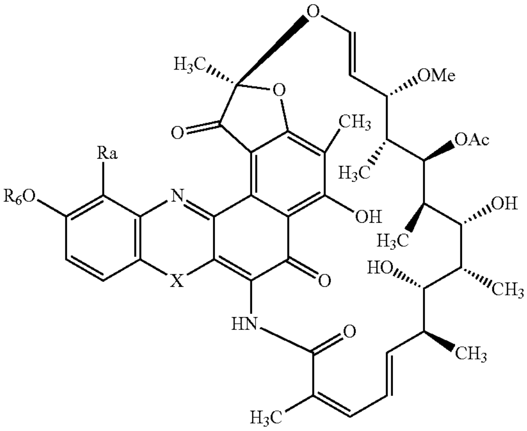

or a pharmaceutically acceptable salt thereof wherein:

X is selected from —O— and —NR*—;

$R_a$ is selected from hydrogen and —OR*;

$R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, each of which further comprises 0-8 heteroatoms selected from halogen, O, N, and S, and wherein $R_6$ is optionally substituted with one or more of —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_6$ is not an n-butyl group;

$R_N$ is selected from:

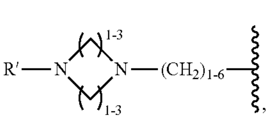

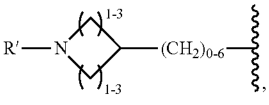

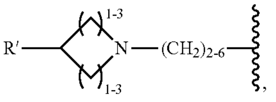

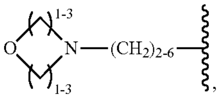

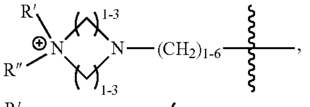

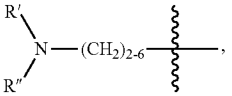

-continued

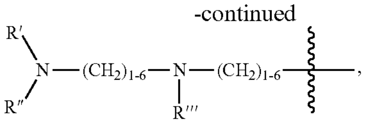

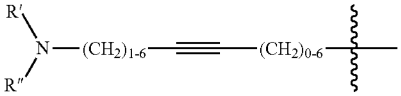

and

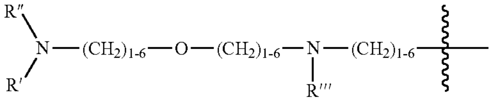

wherein the  symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound, intermediate or precursor thereof having a structure of formula (B):

(B)

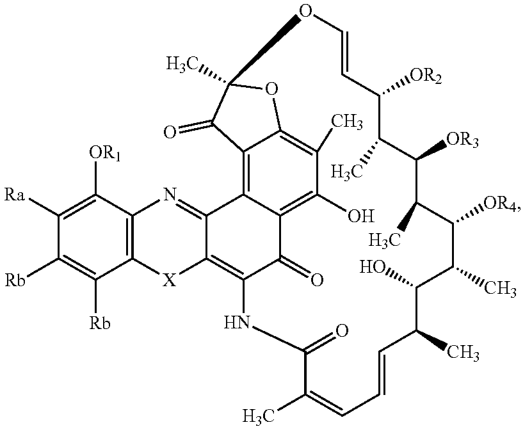

or a pharmaceutically acceptable salt thereof, wherein:

X is selected from —O— and —NR*—;

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

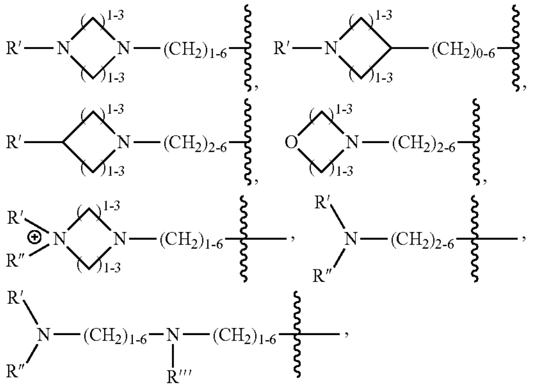

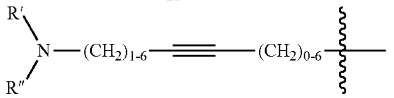

and

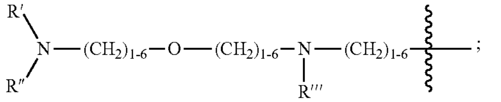

wherein the symbol represents the point of attachment; and R', R'' and R''' are selected from a hydrogen, a $C_1$-$C_6$ aliphatic hydrocarbon, and a protecting group selected from Fluorenylmethyloxycarbonyl ($F_{MOC}$) and tert-Butyloxycarbonyl ($B_{OC}$), or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound having a structure of formula (B-1):

(B-1)

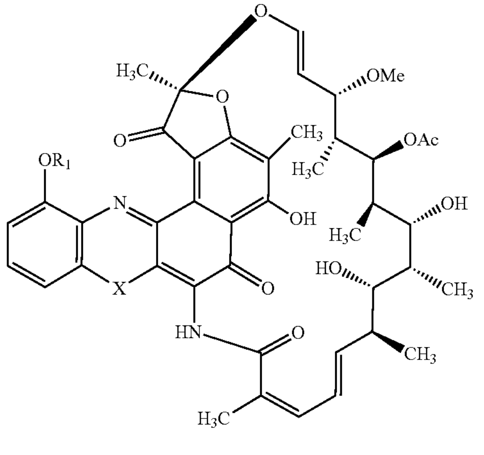

or a pharmaceutically acceptable salt thereof wherein:

X is selected from —O— and —NR*—;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —N2, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—N$(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with a proviso that $R_1$ is not an n-butyl group;

$R_N$ is selected from:

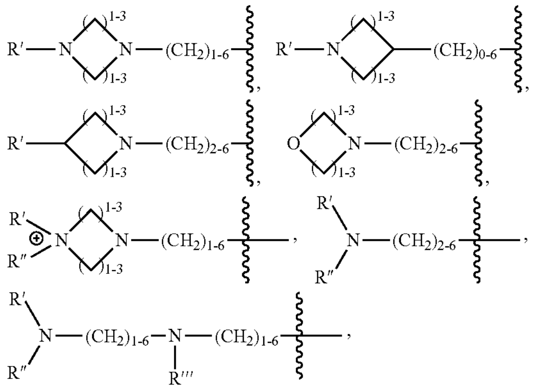

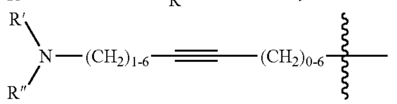

and

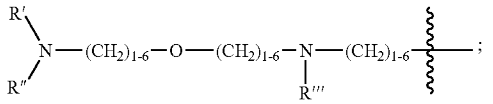

wherein the ∿∿∿ symbol represents the point of attachment; and R', R" and R''' are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound having a structure of formula (B-2):

(B-2)

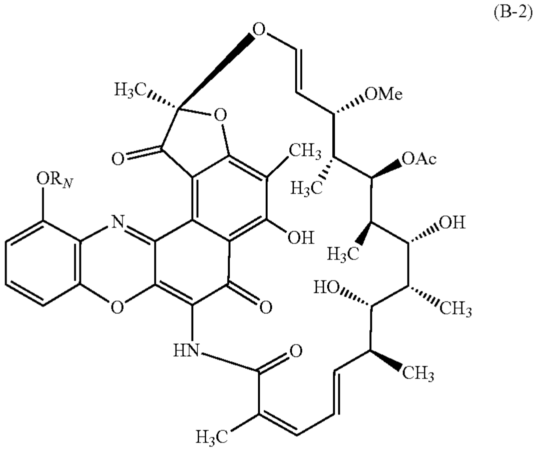

or a pharmaceutically acceptable salt thereof wherein:

$R_N$ is selected from:

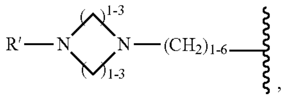

,

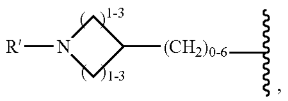

,

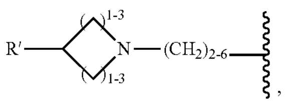

,

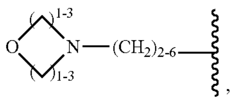

,

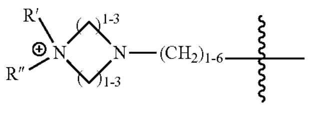

,

-continued

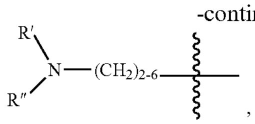

,

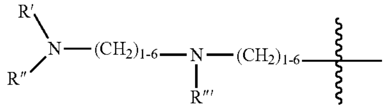

,

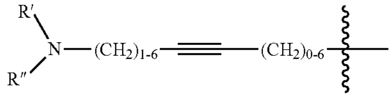

and

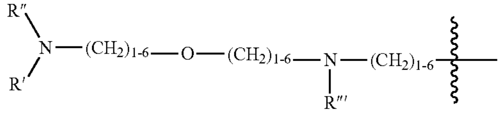

wherein the ∿∿∿ symbol represents the point of attachment; and R', R" and R''' are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In another aspect, the present disclosure provides a rifamycin analog compound having a structure of formula (B-2):

(B-2)

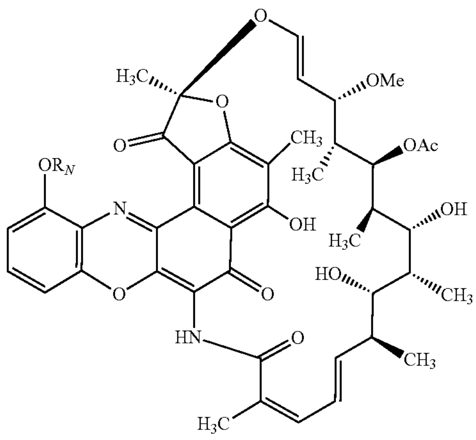

or a pharmaceutically acceptable salt thereof wherein:

$R_N$ is

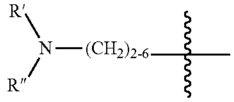

wherein the ∿∿∿ symbol represents the point of attachment; and R' and R" are selected from a hydrogen and a $C_1$-$C_6$ aliphatic hydrocarbon.

In one embodiment, a rifamycin analog compound has a structure according to the following formula:

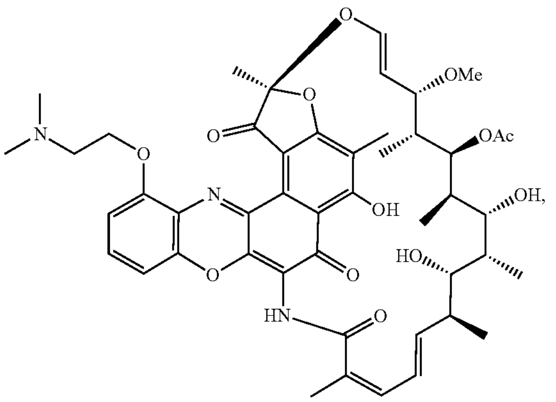 [SMILES: CO[C@H]1/C=C/O[C@@]2(C)Oc3c(C)c(O)c4c(=O)c(c5oc6cccc(OCCN(C)C)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

or a pharmaceutically acceptable salt thereof.

In an embodiment of any of the preceding formulas is provided a compound wherein $R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-3 heteroatoms selected from O and N, and wherein $R_1$ is optionally substituted with one or more of —F, —Cl, —Br, —I, —OH, $C_{1-3}$ alkoxide, $—NH_2$, —NHR*, $—N(R^*)_2$, $—N(R^*)_3^+$, —N(R*)—OH, $—O—N(R^*)_2$, —N(R*)—O—R*, —N(R*)—(C=O)—R*, —(C=O)—R*, —CHO, $—CO_2H$, $—CO_2R^*$, —O—(C=O)—H, —O—(C=O)—R*, $—(C=O)—NH_2$, $—(C=O)—N(R^*)_2$, $—Si(R^*)_3$, $—CF_3$, $—O—CF_3$ and combinations thereof, with the provisos that $R_1$ is not an n-butyl group, and when X is —O—, $R_1$ is not hydrogen.

In an embodiment of any of the preceding formulas is provided a compound wherein $R_1$ is a combination of an aliphatic $C_1$-$C_{20}$ hydrocarbon and an aromatic $C_1$-$C_{20}$ hydrocarbon.

In an embodiment of any of the preceding formulas is provided a compound wherein $R_1$ is a combination of an aliphatic $C_1$-$C_{20}$ hydrocarbon and a heteroaromatic $C_1$-$C_{20}$ hydrocarbon.

In an embodiment of any of the preceding formulas is provided a compound wherein $R_1$ is selected from:

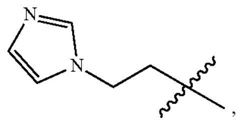

,

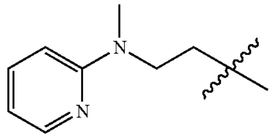

, and

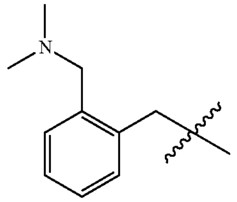

.

In an embodiment of any of the preceding formulas is provided a compound wherein $R_1$ is an aliphatic $C_1$-$C_{20}$ hydrocarbon substituted with one or more of $—NH_2$, —NHR*, $—N(R^*)_2$, or —N(R*)—(C=O)—R*.

In an embodiment of any of the preceding formulas is provided a compound wherein $R_1$ is an aliphatic $C_1$-$C_{20}$ hydrocarbon substituted with $—NH—(C=O)—CH_3$ or $—N(CH_3)—(C=O)—CH_3$.

In an embodiment of any of the preceding formulas is provided a compound wherein $R_a$ is hydrogen.

In an embodiment of any of the preceding formulas is provided a compound wherein $R_a$ is —OH.

In an embodiment of any of the preceding formulas is provided a compound wherein $R_a$ is —Cl.

In an embodiment of any of the preceding formulas is provided a compound wherein $R_a$ is —OR*, and R* is selected from an aliphatic $C_1$-$C_{20}$ hydrocarbon, an aromatic $C_1$-$C_{20}$ hydrocarbon, and combinations thereof.

In an embodiment of any of the preceding formulas is provided a compound wherein $R_N$ is selected from:

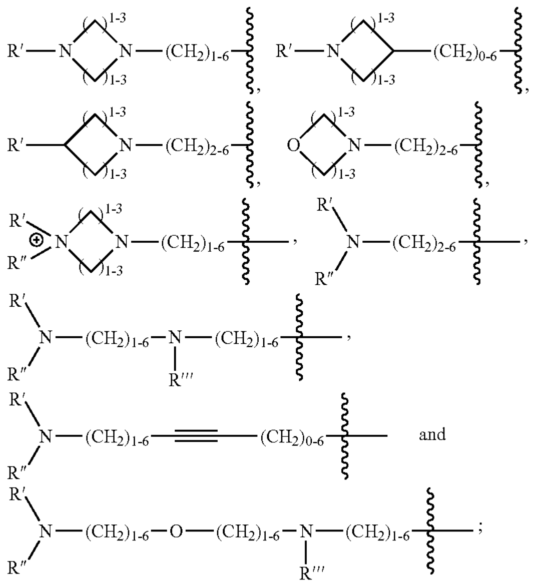

wherein the symbol represents the point of attachment; and R', R'' and R''' are selected from a hydrogen, a $C_1$-$C_6$ aliphatic hydrocarbon, and a protecting group selected from $F_{MOC}$ and $B_{OC}$, or wherein R' and R'' together form an aliphatic monocyclic, an aliphatic bicyclic, or an aliphatic polycyclic structure.

In an embodiment of any of the preceding formulas is provided a compound wherein $R_N$ is selected from:

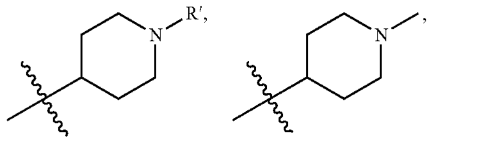

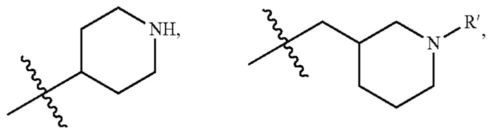

-continued
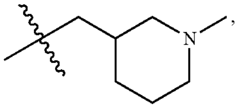, 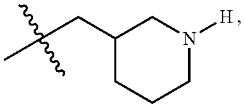,
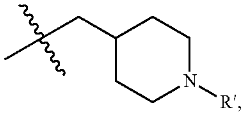, 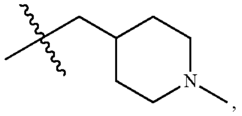,
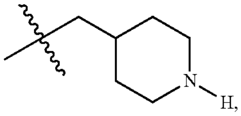,
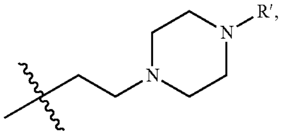,
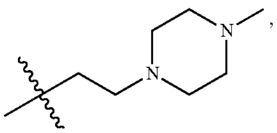,
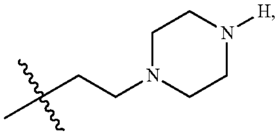, 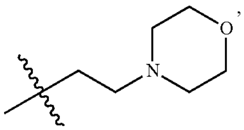,
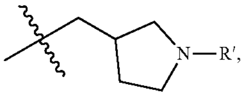, 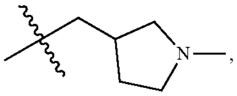,
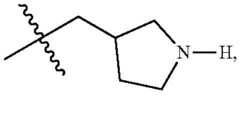, 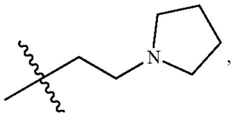,
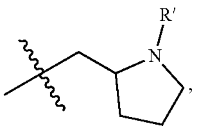, 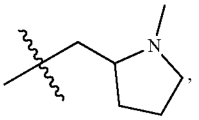,
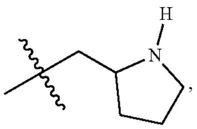, 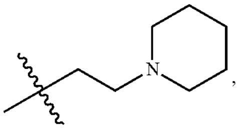,
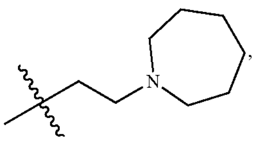, 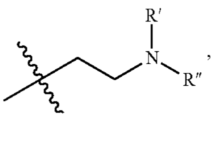,
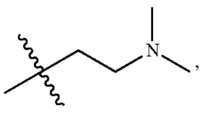, 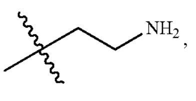,
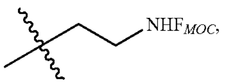, 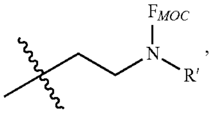,
-continued
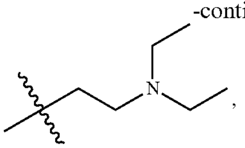, 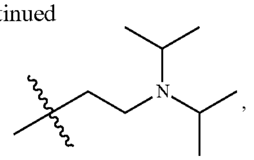,
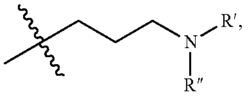, 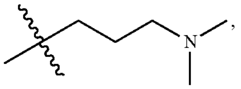,
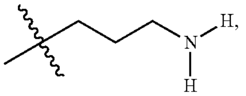, 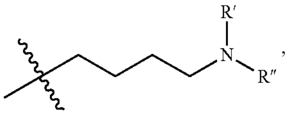,
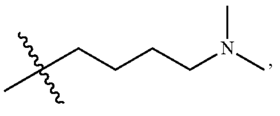,
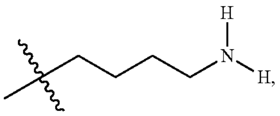,
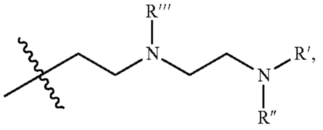,
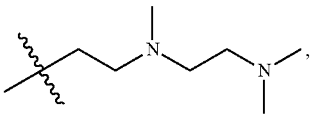,
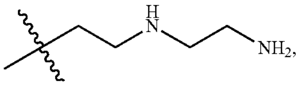,
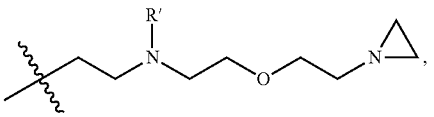,
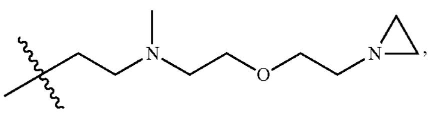,
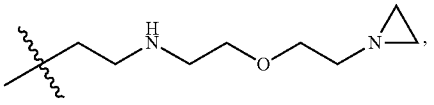,
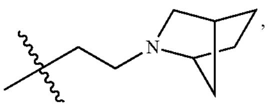, 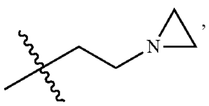, and
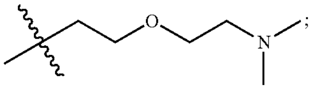;
wherein R' is hydrogen, aliphatic hydrocarbon or a protecting group, and wherein the ∿∿∿ symbol represents the point of attachment.

In an embodiment of a compound of any of the preceding formulas is provided a compound wherein R* is independently at each occurrence selected from hydrogen, an aliphatic $C_1$-$C_6$ hydrocarbon, an aromatic $C_4$-$C_6$ hydrocarbon, and combinations thereof, which optionally comprise 1-3 heteroatoms selected from O, N and combinations thereof.

In one embodiment, a rifamycin analog compound of the disclosure has a structure selected from the group consisting of:

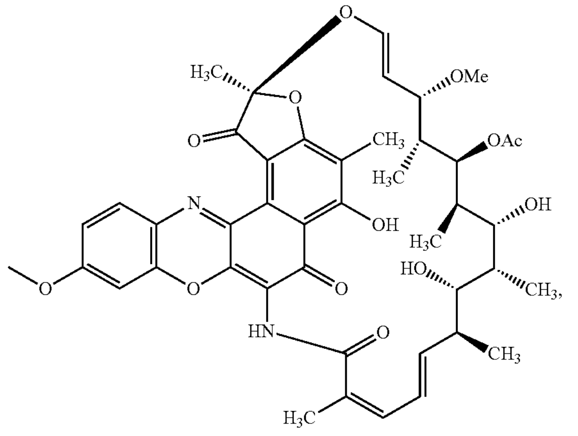

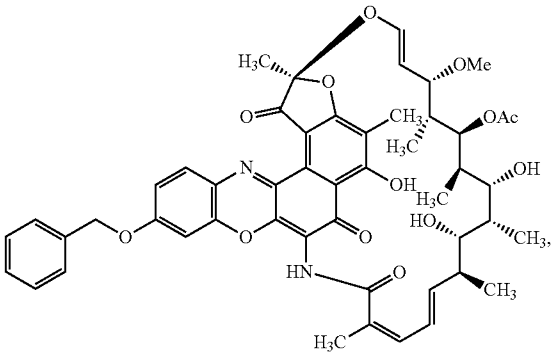

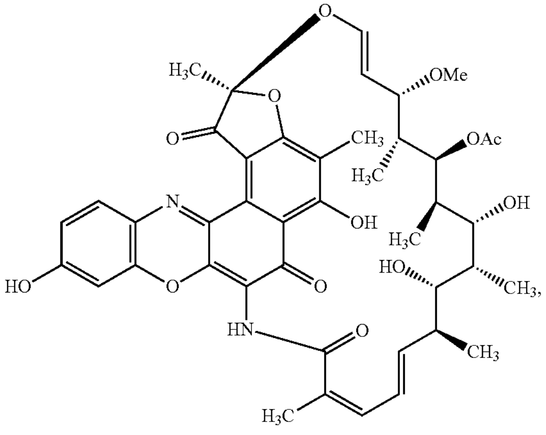

-continued

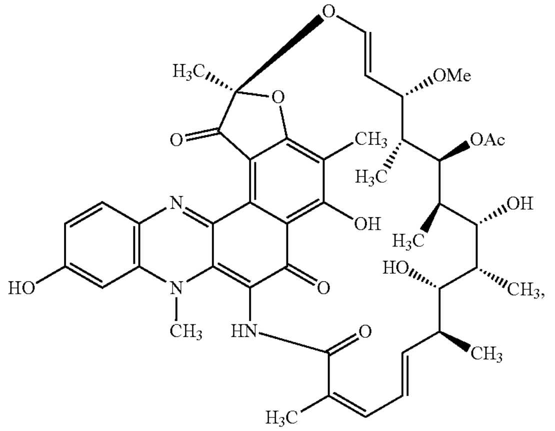

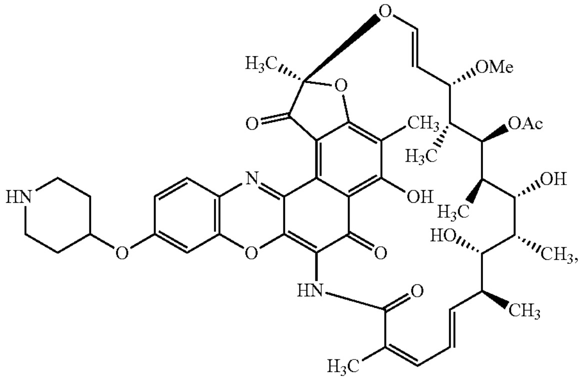

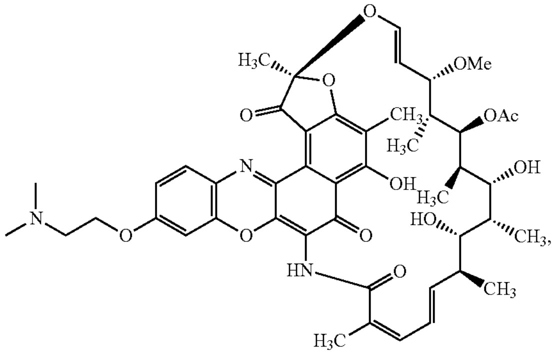

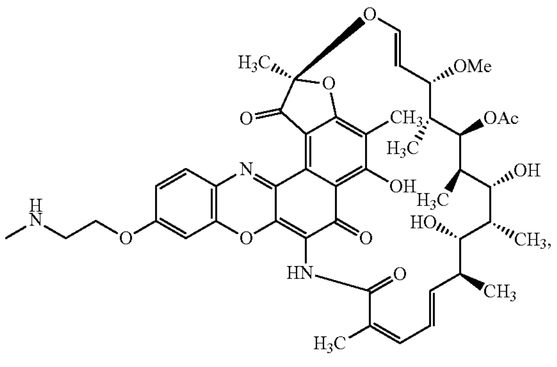

-continued
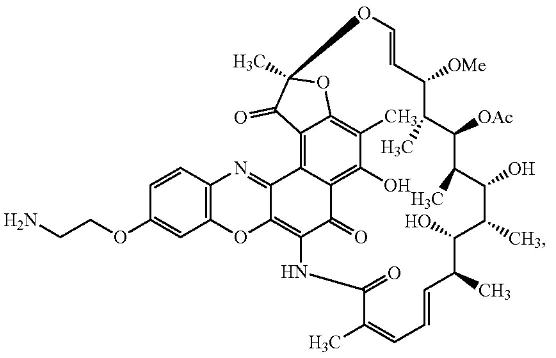
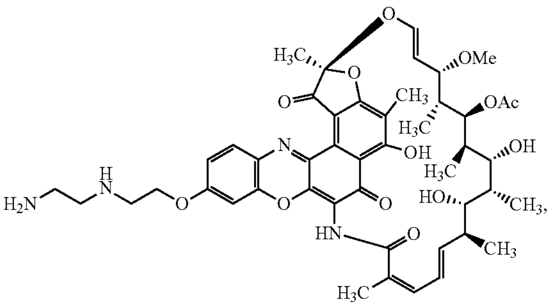
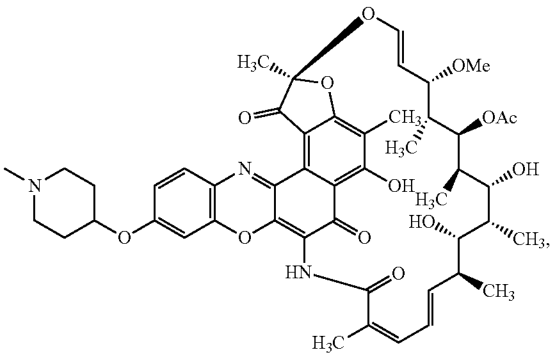
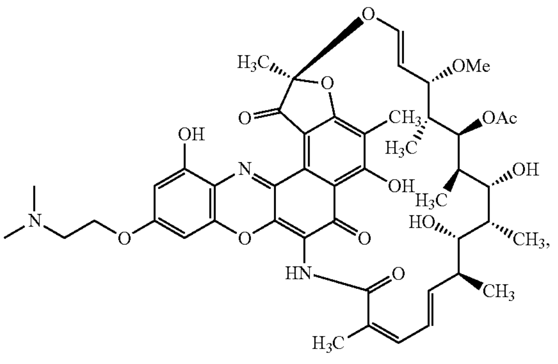
-continued
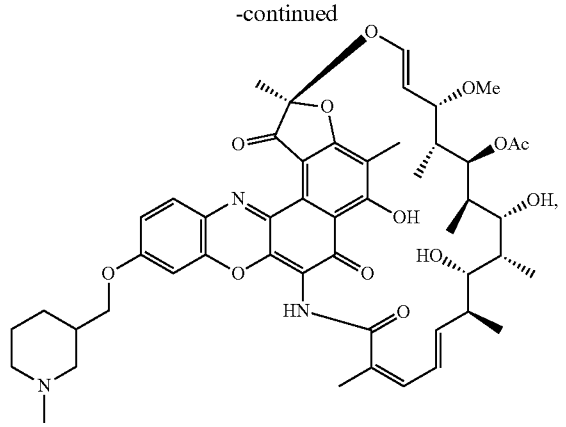
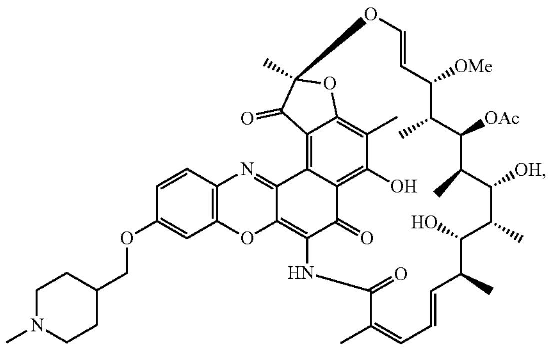
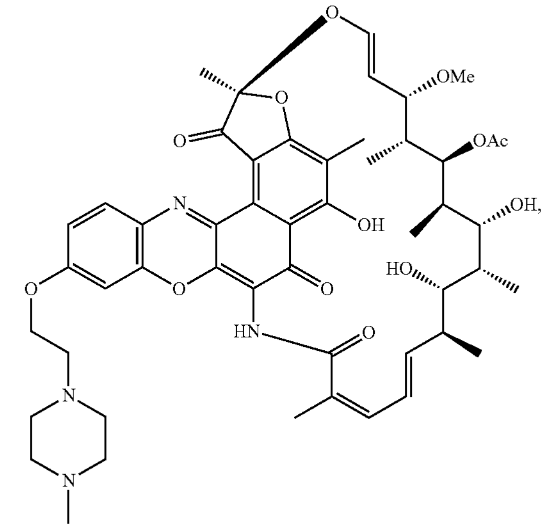

-continued
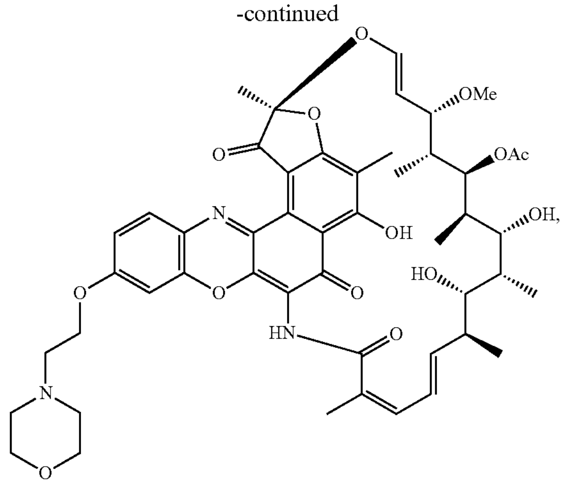
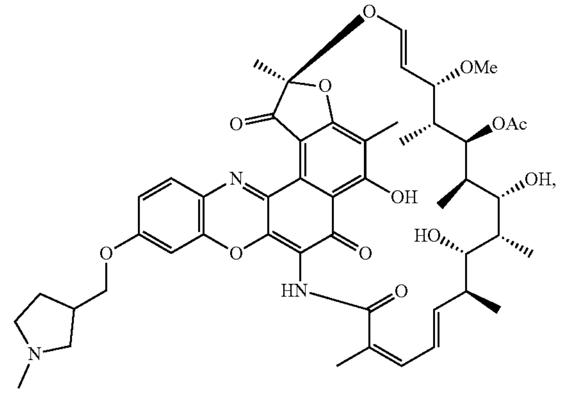
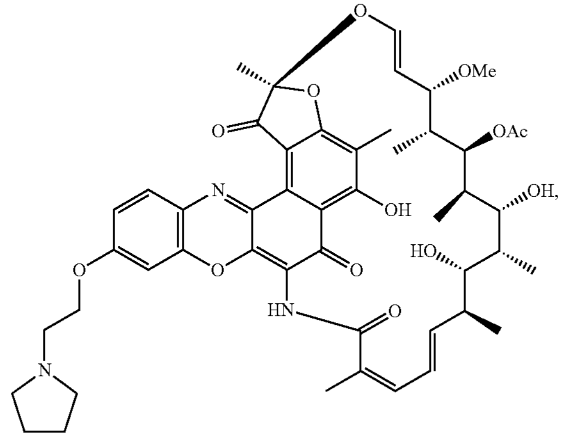
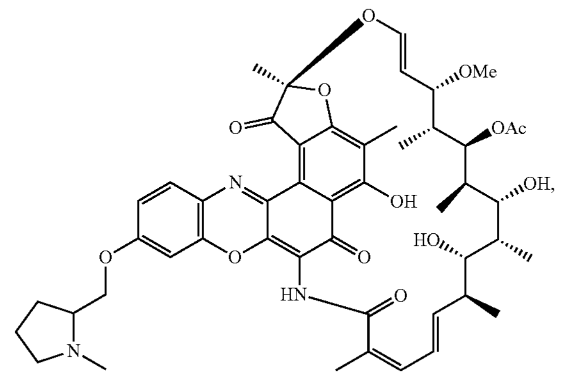
-continued
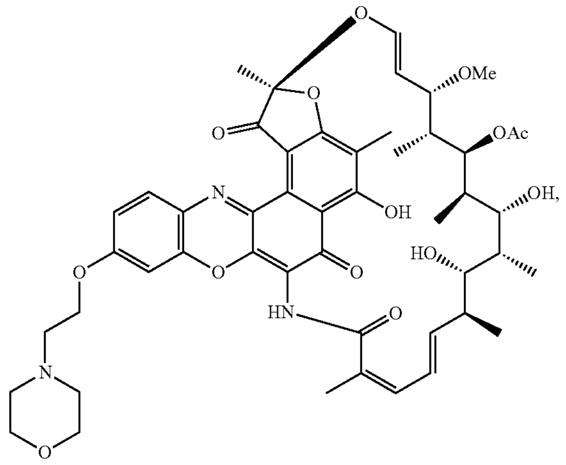
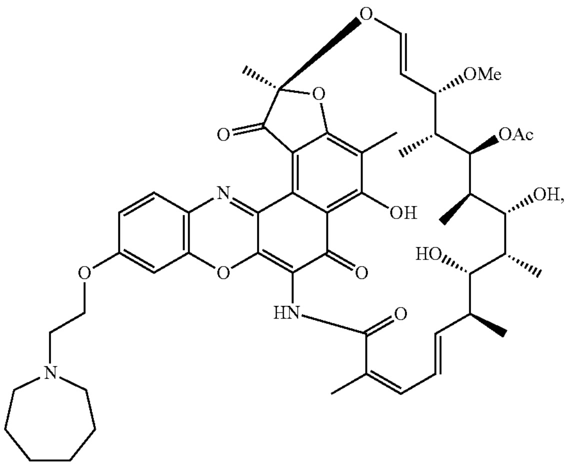
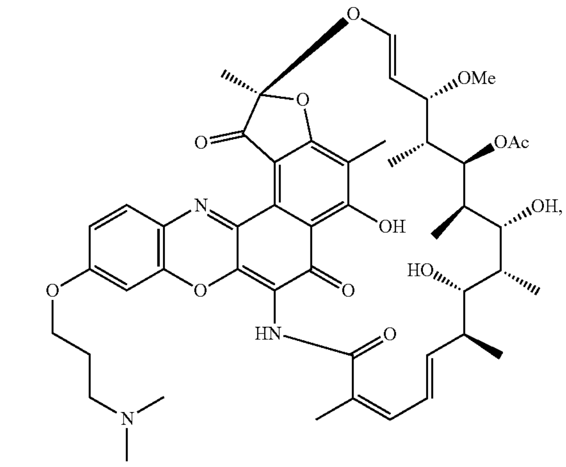

-continued
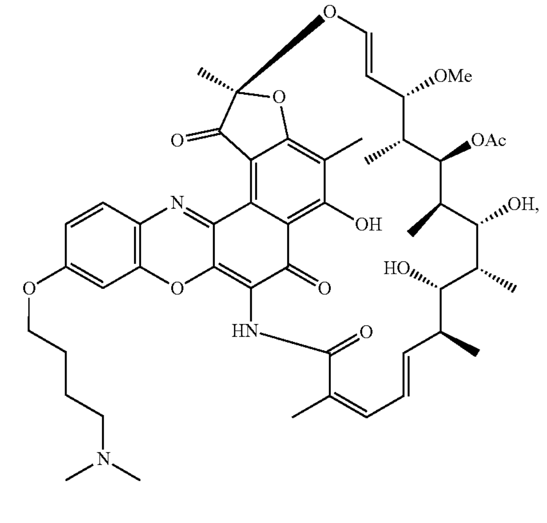
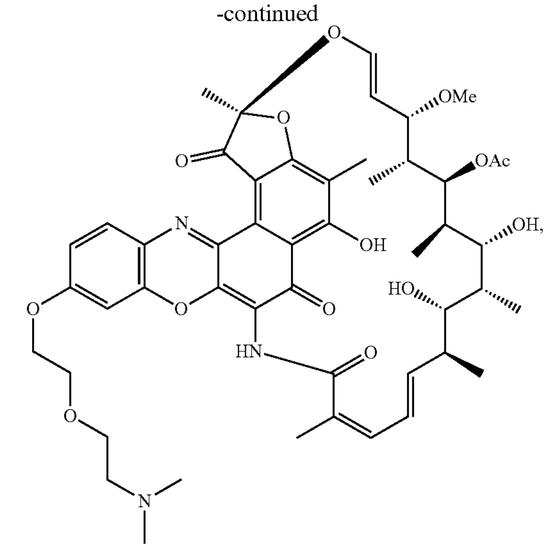
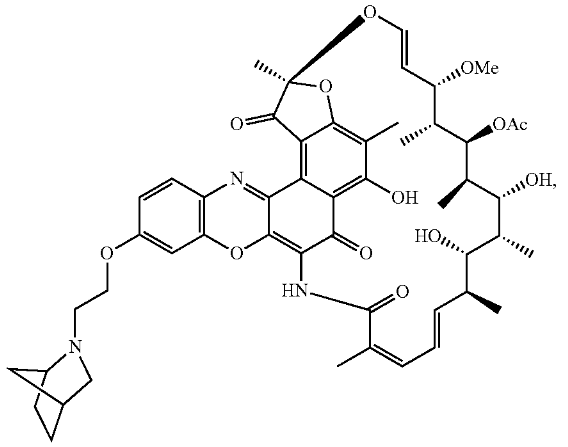
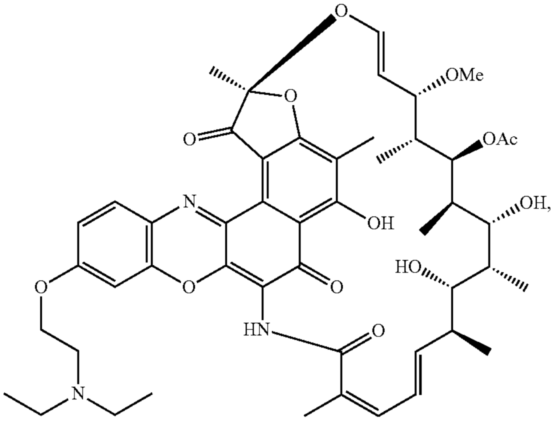
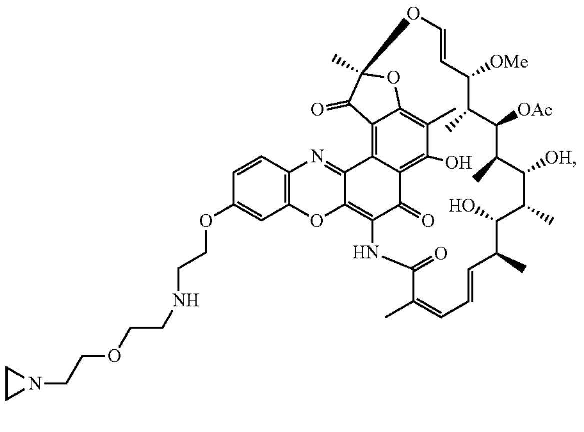
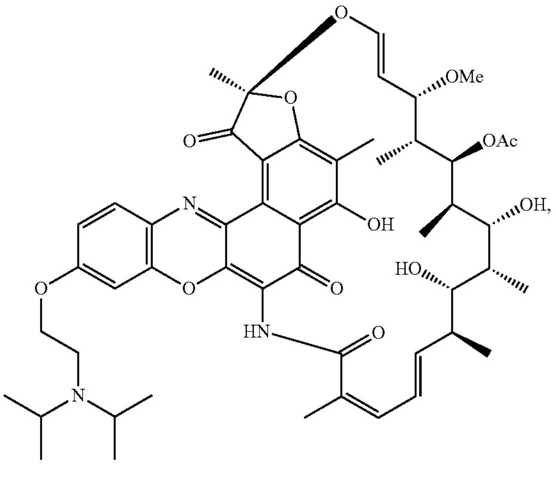

-continued
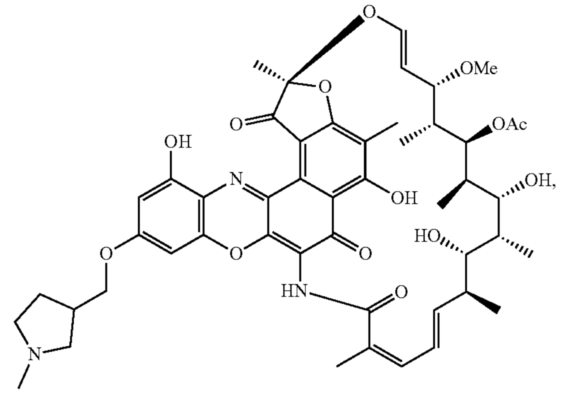
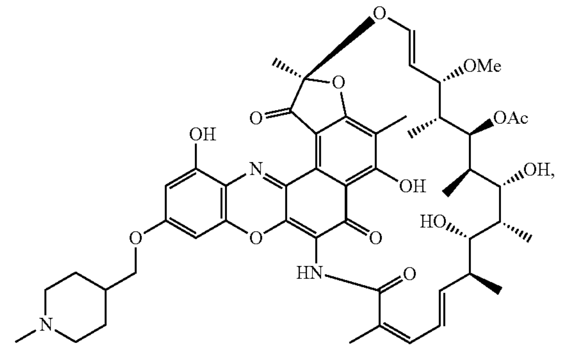
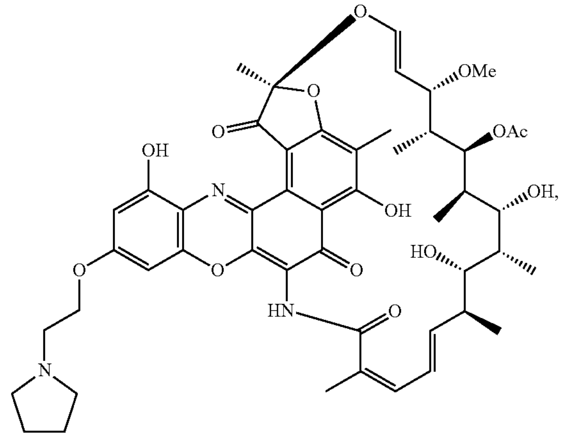
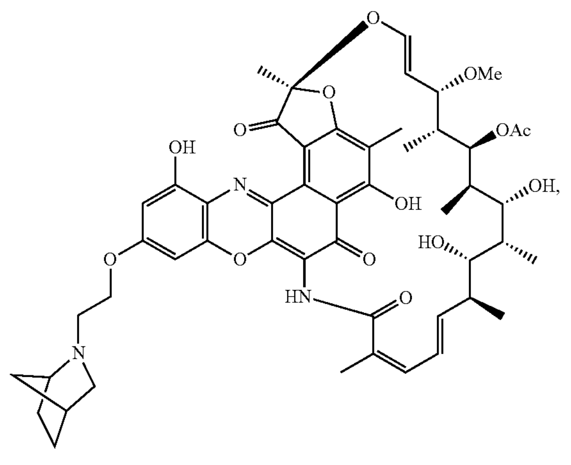
-continued
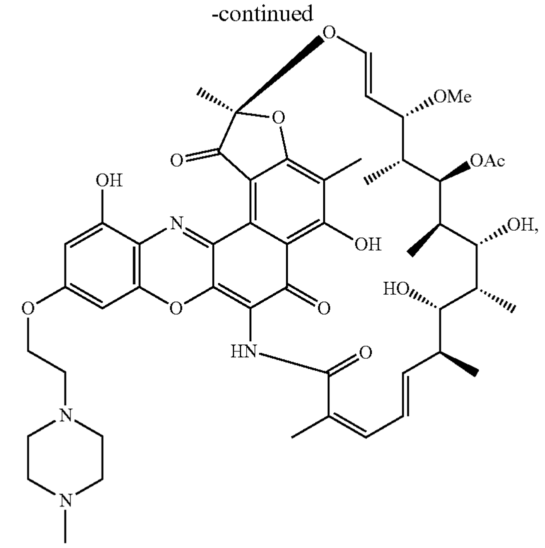
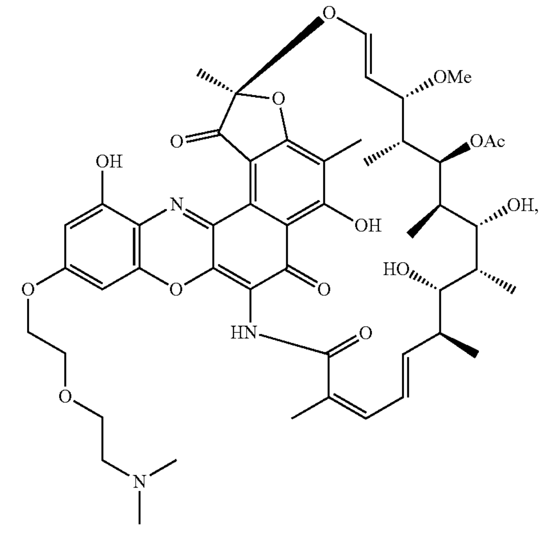
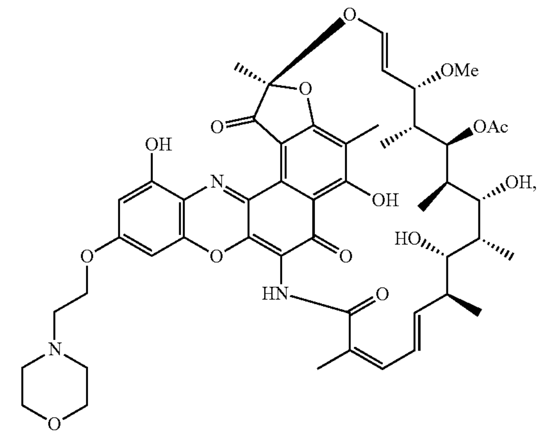

-continued
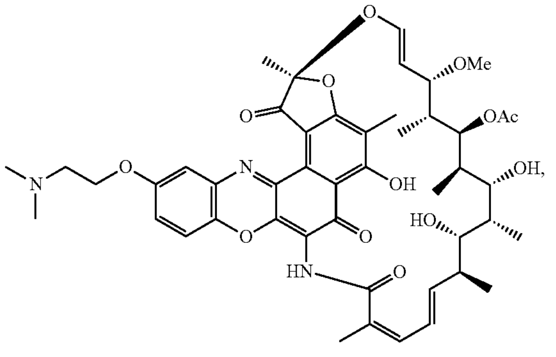
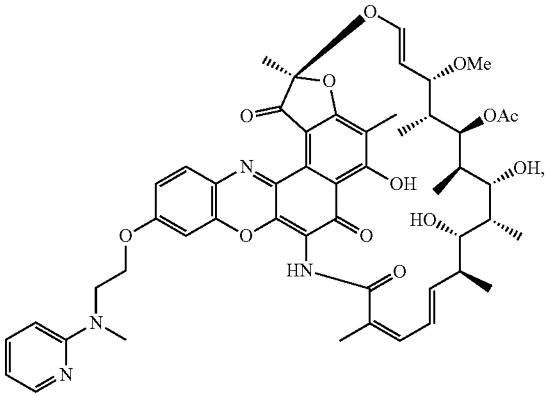
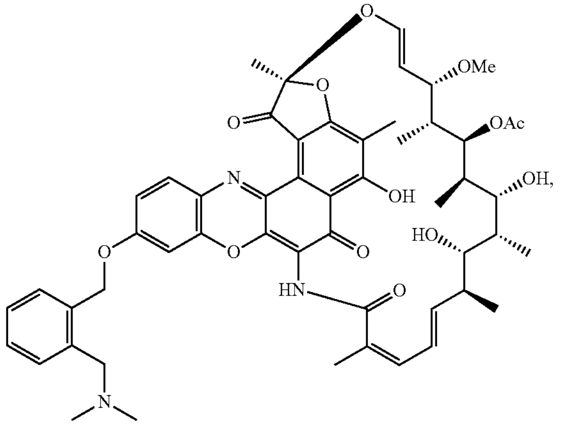
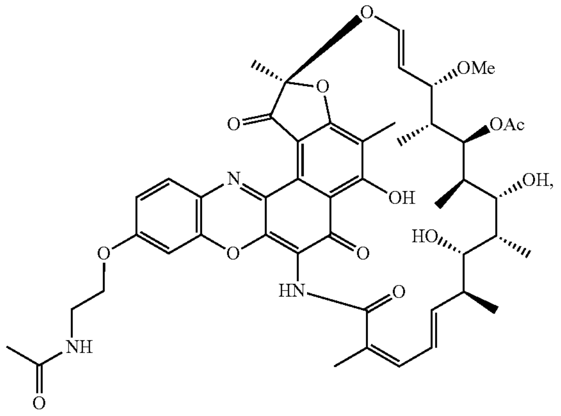
-continued
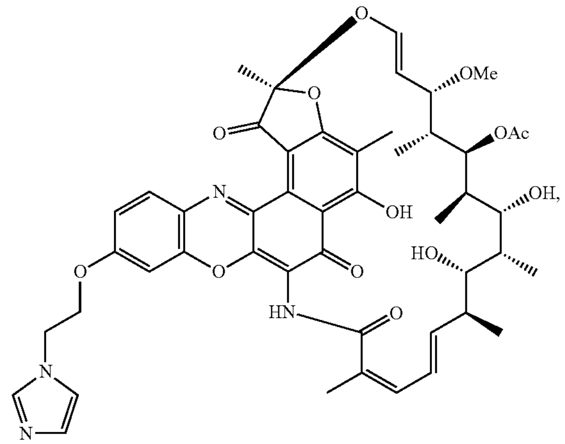
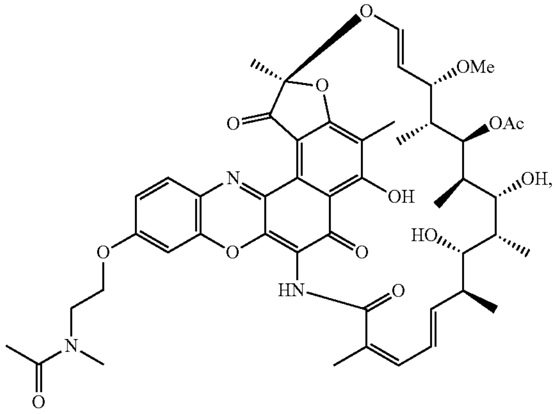
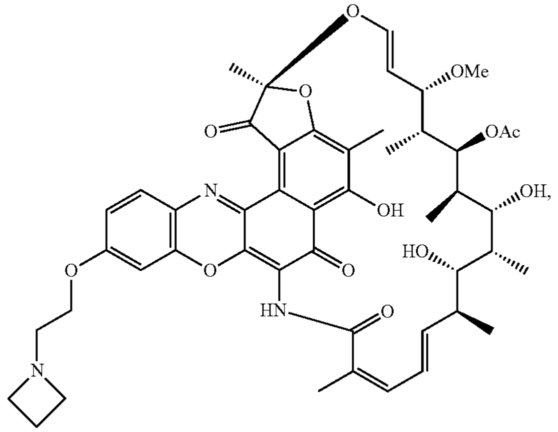
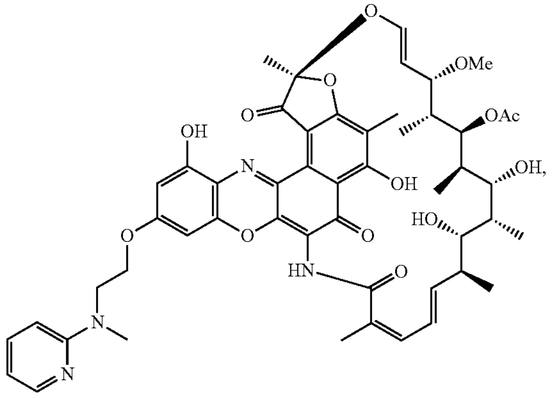

-continued
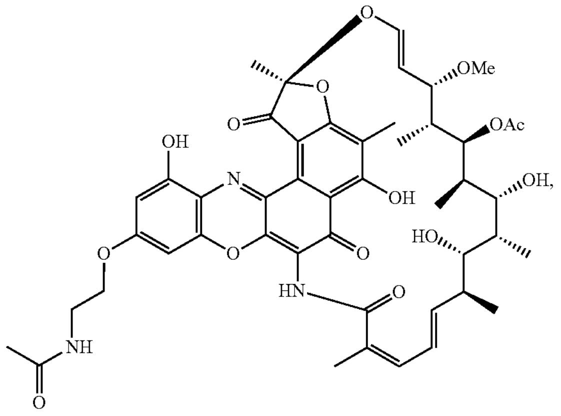
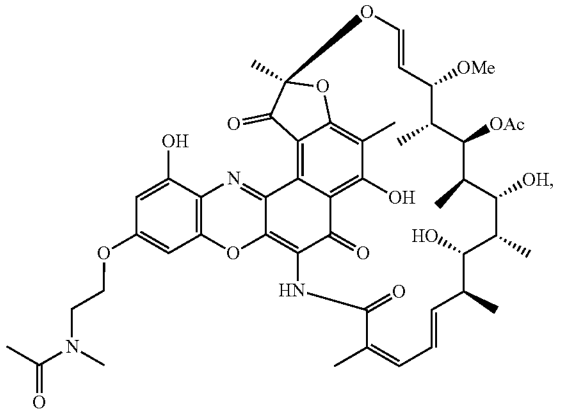
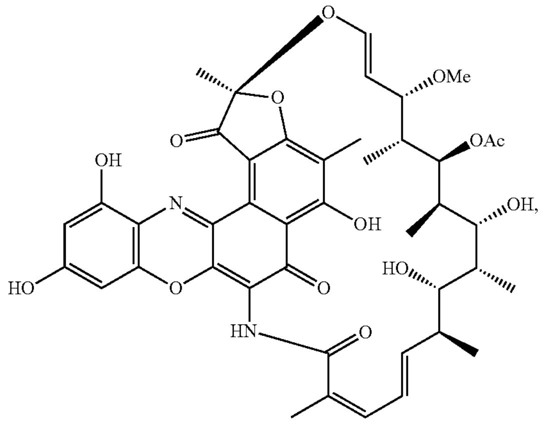
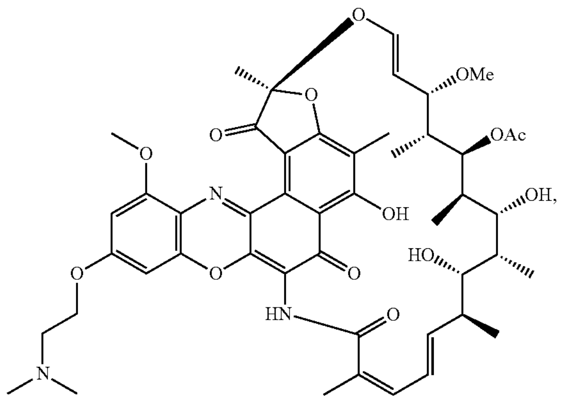
-continued
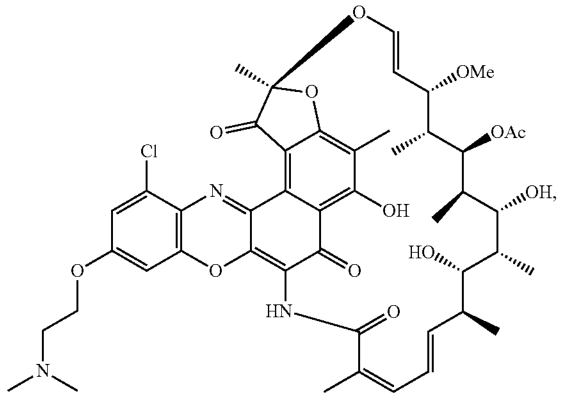
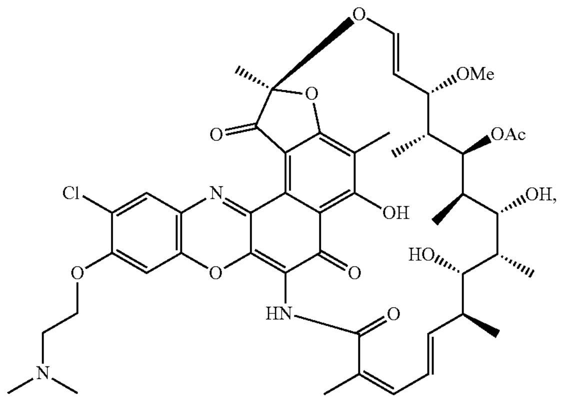
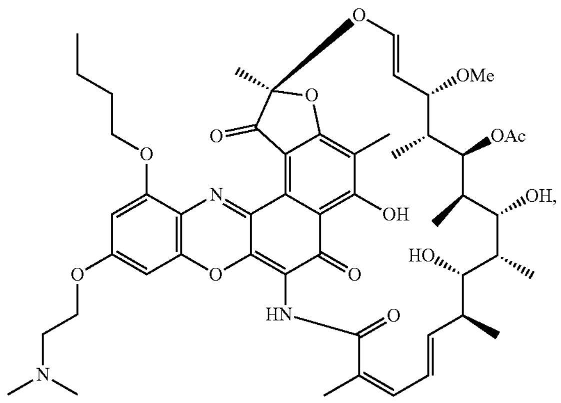
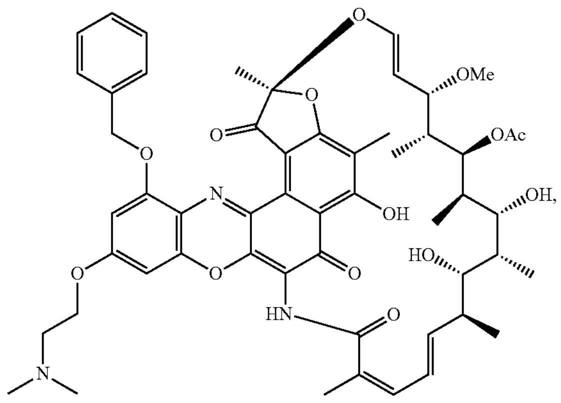

-continued
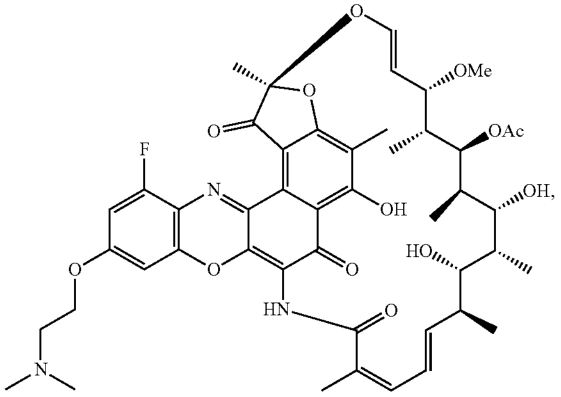
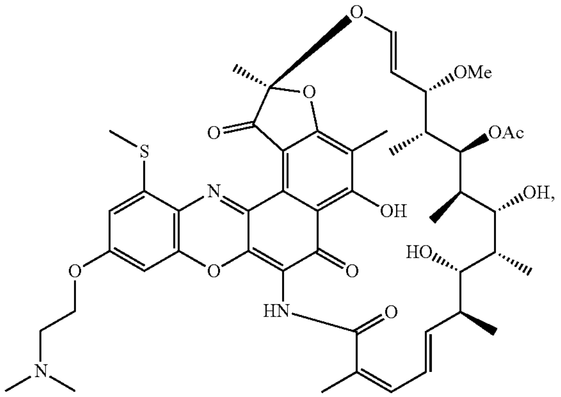
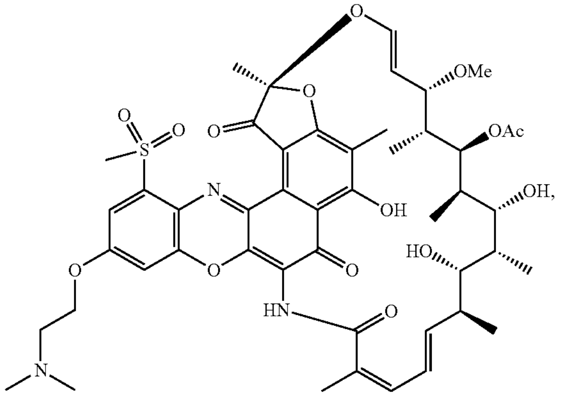
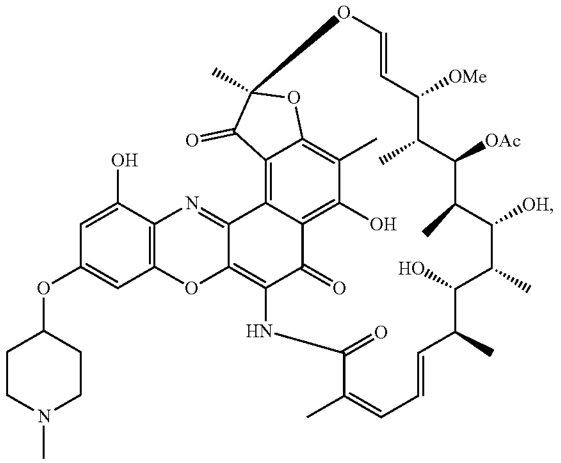
-continued
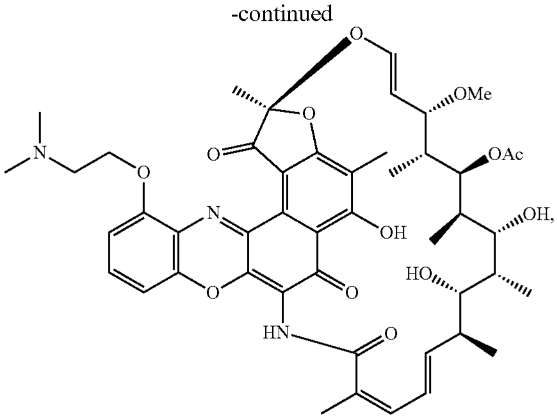
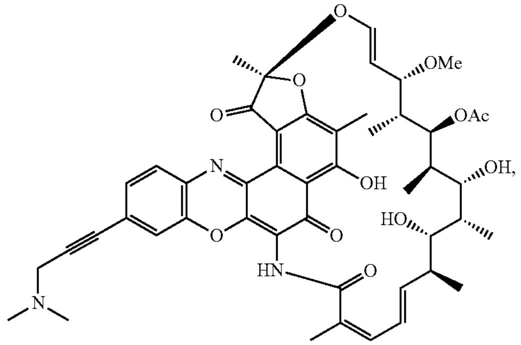
and
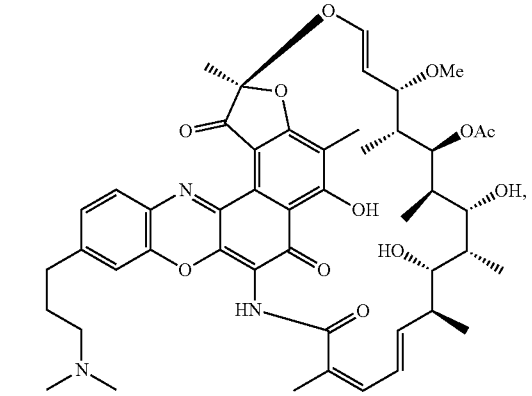
or a pharmaceutically acceptable salt thereof.
In one embodiment, a rifamycin analog compound of the disclosure has a structure selected from the group consisting of:
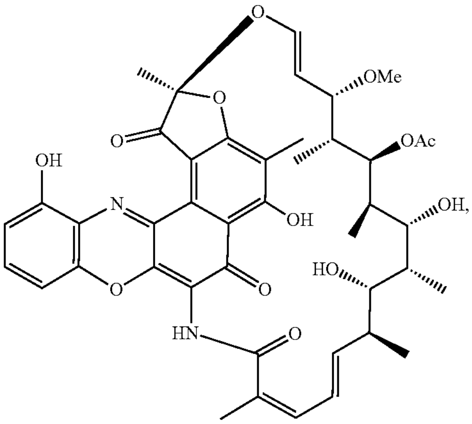

-continued

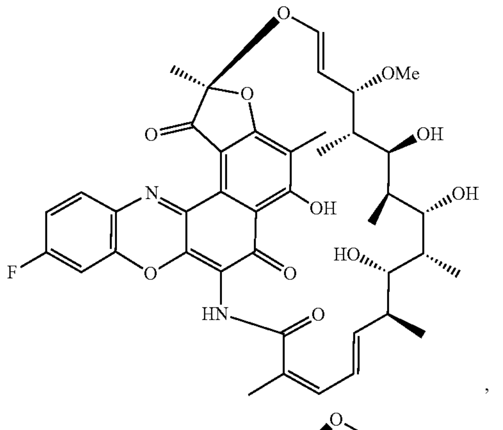

, and

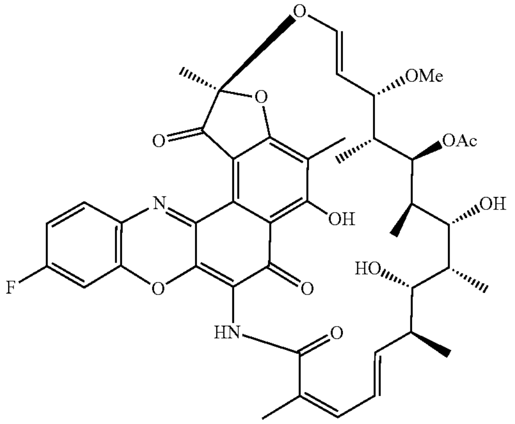

or a pharmaceutically acceptable salt thereof.

In one aspect, the present disclosure provides a method of manufacturing a rifamycin analog compound having the structure of formula (V):

(V)

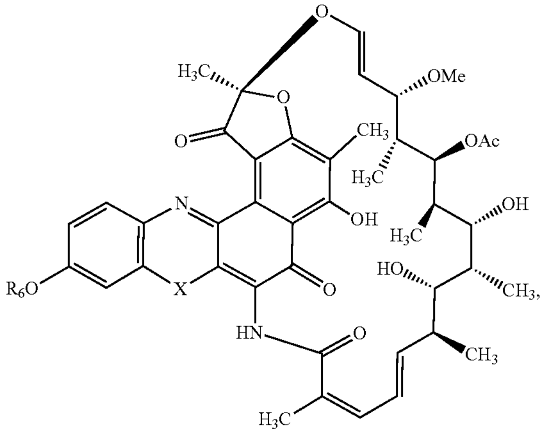

wherein X is selected from —O— and NR*—;

$R_6$ is selected from a $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, $R_N$ is selected from:

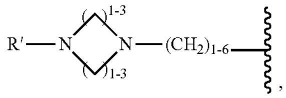

,

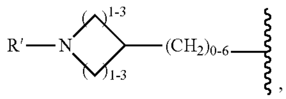

,

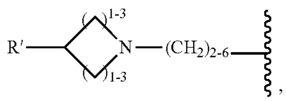

,

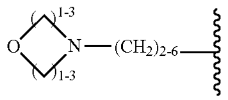

,

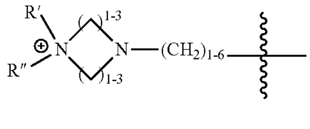

,

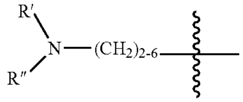

,

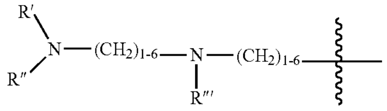

,

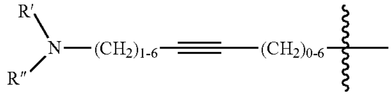

and

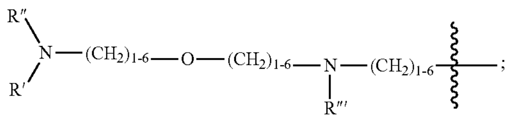

;

wherein the  symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising the steps of:

(a) contacting Rifamycin S having the structure:

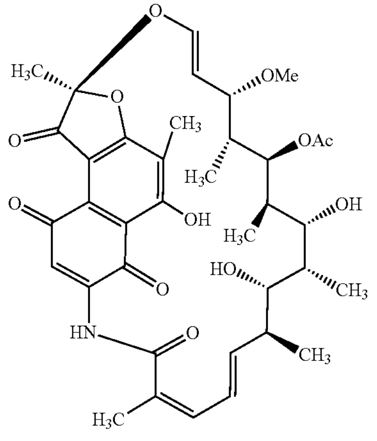 [SMILES: CO[C@H]1/C=C/O[C@@]2(C)Oc3c(C)c(O)c4c(c3C2=O)C(=O)C=C(NC(=O)/C(C)=C\C=C\[C@H](C)[C@H](O)[C@@H](C)[C@@H](O)[C@@H](C)[C@H](OC(C)=O)[C@@H]1C)C4=O]

with a compound having the structure of formula (VI):

(VI)

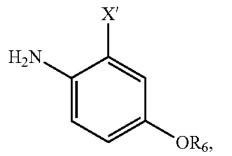

wherein X' is selected from —OH and —NHR*, and (b) treating the product of step (a) with an oxidizing agent.

In one aspect, the present disclosure provides a method of manufacturing a rifamycin analog compound having the structure of formula (V'):

(V')

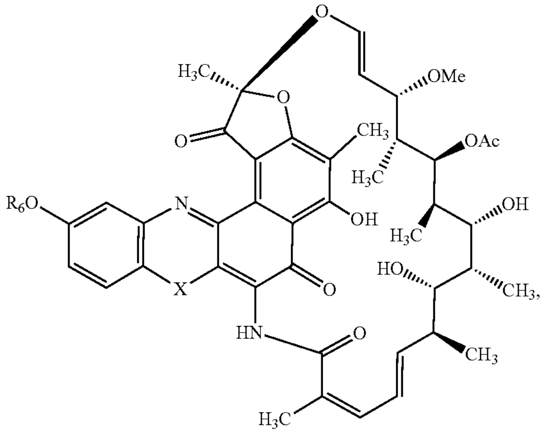

wherein X is selected from —O— and NR*—;

$R_6$ is selected from a $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, $R_N$ is selected from:

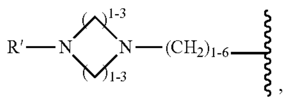
,

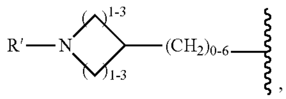
,

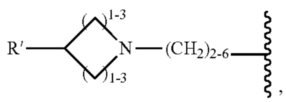
,

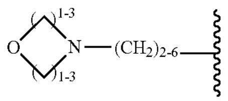
,

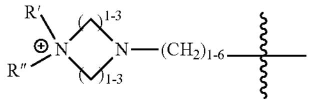
,

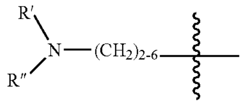
,

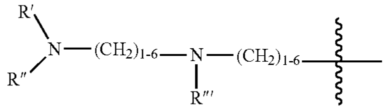
,

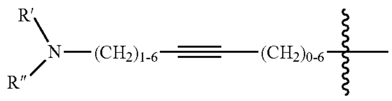
and

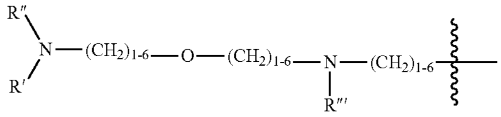

wherein the ∿∿∿ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising the steps of:

(a) contacting Rifamycin S having the structure:

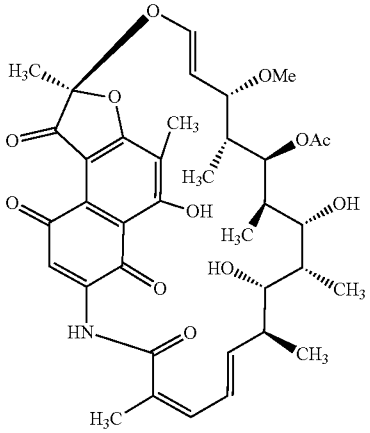 [SMILES: CO[C@H]1/C=C/O[C@@]2(C)Oc3c(C)c(O)c4c(c3C2=O)C(=O)C=C(NC(=O)/C(C)=C\C=C\[C@H](C)[C@H](O)[C@@H](C)[C@@H](O)[C@@H](C)[C@H](OC(C)=O)[C@@H]1C)C4=O]

with a compound having the structure of formula (VI'):

(VI')

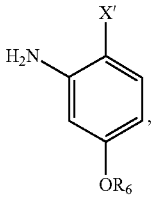

wherein X' is selected from —OH and —NHR*, and (b) treating the product of step (a) with an oxidizing agent.

In one aspect, the present disclosure provides a method of manufacturing a compound having the structure:

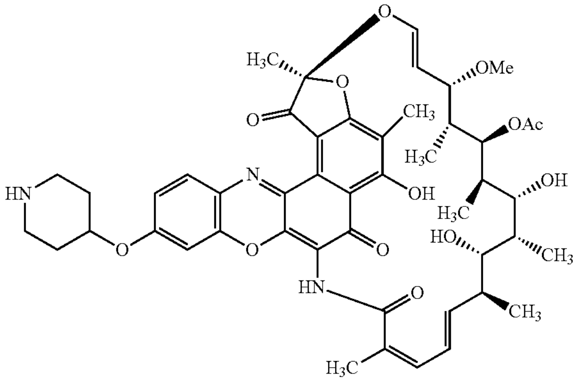 [SMILES: CO[C@H]1/C=C/O[C@@]2(C)Oc3c(C)c(O)c4c(=O)c(c5oc6cc(OC7CCNCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

comprising the steps of:

(a) contacting Rifamycin S with a compound having the structure of formula (VII):

(VII)

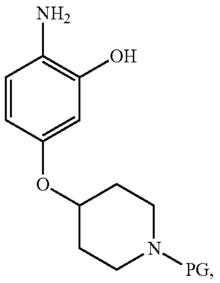

wherein PG is a protecting group;

(b) treating the product of step (a) with an oxidizing agent, and (c) removing the protecting group PG.

In one embodiment, the compound of formula (VII) is prepared by removing protecting group PG' from a compound of formula (VIII):

(VIII)

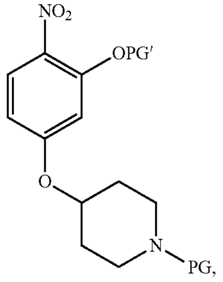

wherein protecting groups PG and PG' may be the same or different from each other.

In one embodiment, the compound of formula (VIII) is prepared by contacting a compound of formula (IX):

(IX)

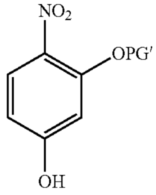

with a compound of formula (X):

(X)

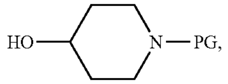

wherein protecting groups PG and PG' may be the same or different from each other.

In one aspect, the present disclosure provides a method of manufacturing a compound having the structure of formula (XI):

(XI)

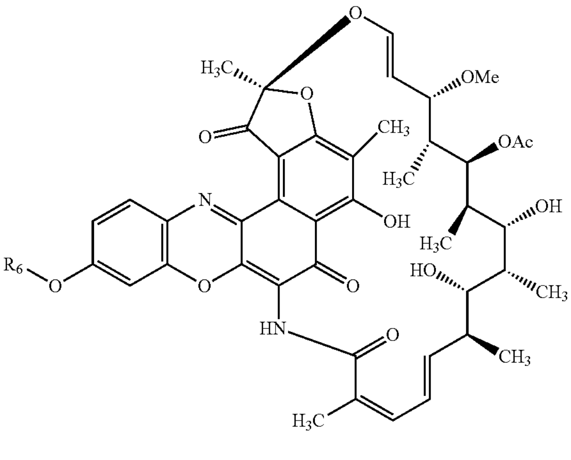

wherein $R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof and wherein $R_6$ is optionally substituted with one or more of —F—Cl, —Br, —I, —OH, —OR*, —NO, —$NO_2$, —$NO_3$, —O—NO, —$N_3$, —$N_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof;

$R_N$ is selected from:

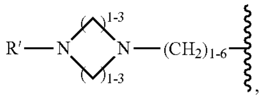,
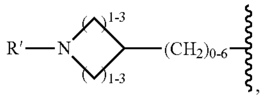,
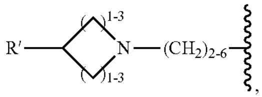,
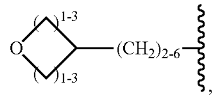,
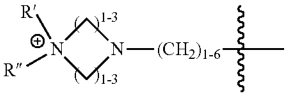,
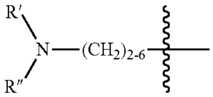,
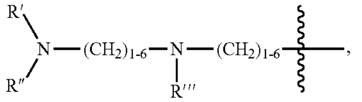,
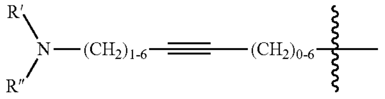 and
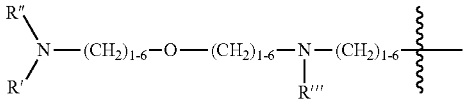

wherein the  symbol represents the point of attachment; and R', R" and R''' are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

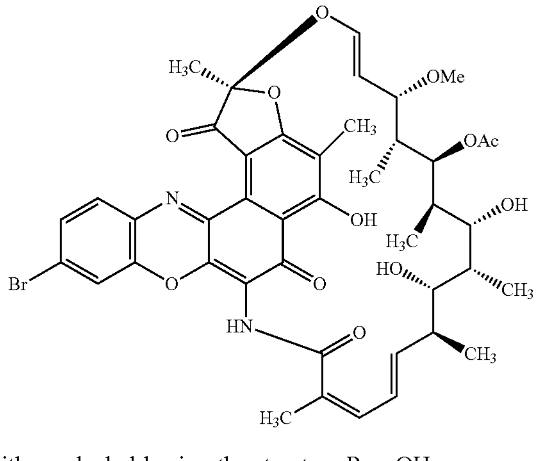

with an alcohol having the structure $R_6$—OH.

In one aspect, the present disclosure provides a method of manufacturing a compound having the structure of formula (XIII):

(XIII)

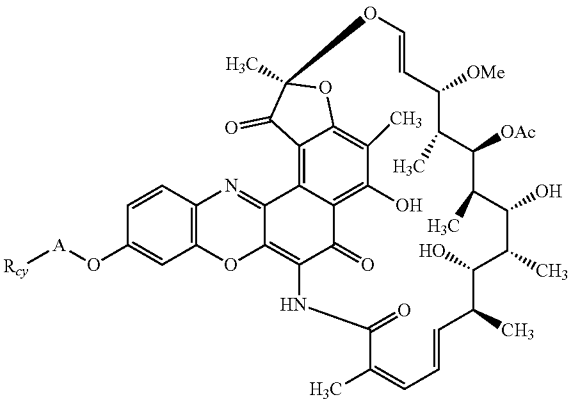

wherein A is selected from a bond (A is absent) or an aliphatic $C_1$-$C_{20}$ hydrocarbon;

$R_{cy}$ is a $C_3$-$C_{14}$ cycloaliphatic hydrocarbon which further comprises 0-8 heteroatoms selected from halogen, O, N, and S and combinations thereof and wherein $R_{cy}$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

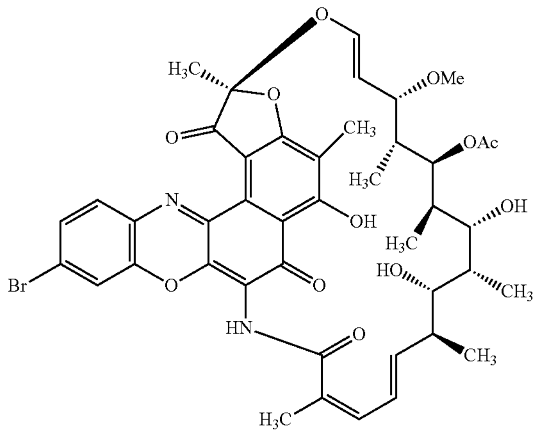

with an alcohol having the structure $R_{cy}$-A-OH.

In one aspect, the present disclosure provides a method of manufacturing a compound having the structure of formula (XIII'):

(XIII')

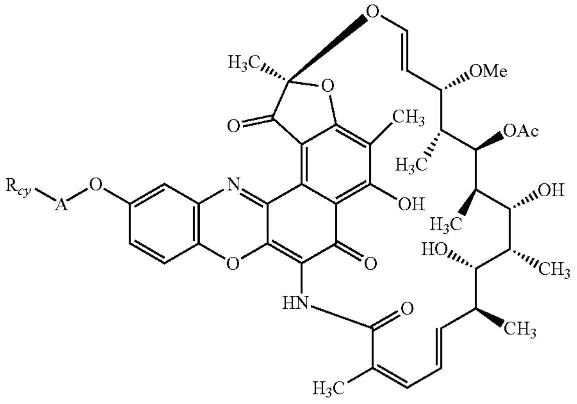

wherein A is selected from a bond (A is absent) or an aliphatic $C_1$-$C_{20}$ hydrocarbon;

$R_{cy}$ is a $C_3$-$C_{14}$ cycloaliphatic hydrocarbon which further comprises 0-8 heteroatoms selected from halogen, O, N, and S and combinations thereof and wherein $R_{cy}$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

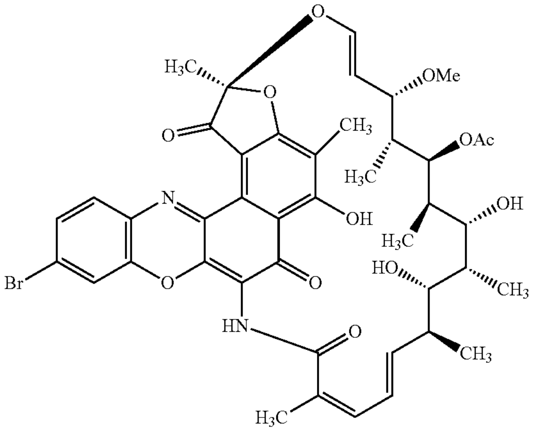

with an alcohol having the structure $R_{cy}$-A-OH.

In one aspect, the present disclosure provides a method of manufacturing a compound having the structure of formula (XIV):

(XIV)

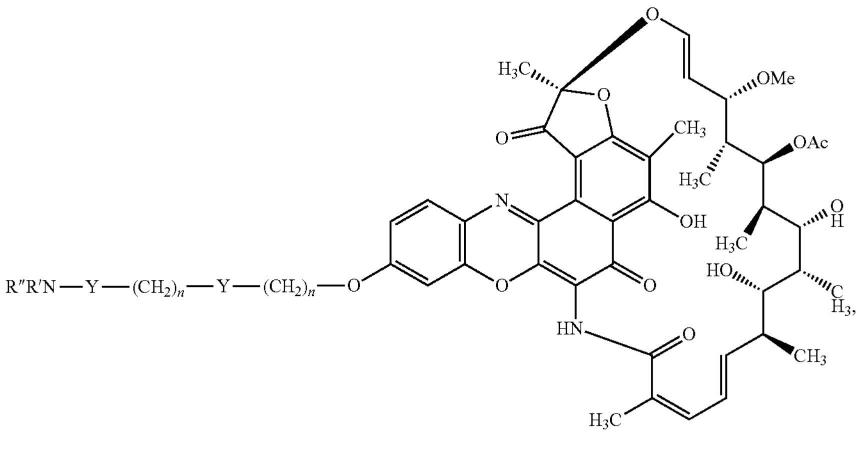

wherein Y is at each occurrence selected from —O— and —NR'R''—; n is independently at each occurrence an integer from 1-6, and R', R'', and R''' are each independently selected from a hydrogen, an aliphatic $C_1$-$C_{20}$ hydrocarbon; said method comprising contacting a compound having the structure of formula (XII):

(XII)

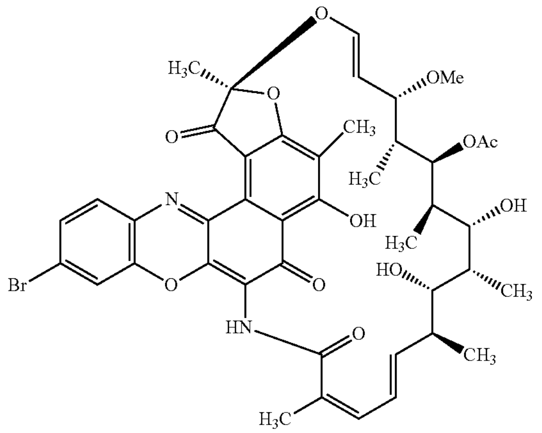

with an alcohol having the structure R''R'N—Y—$(CH_2)_n$—Y—$(CH_2)_n$—OH.

In one aspect, the present disclosure provides a method of manufacturing a compound having the structure of formula (XIV'):

(XIV')

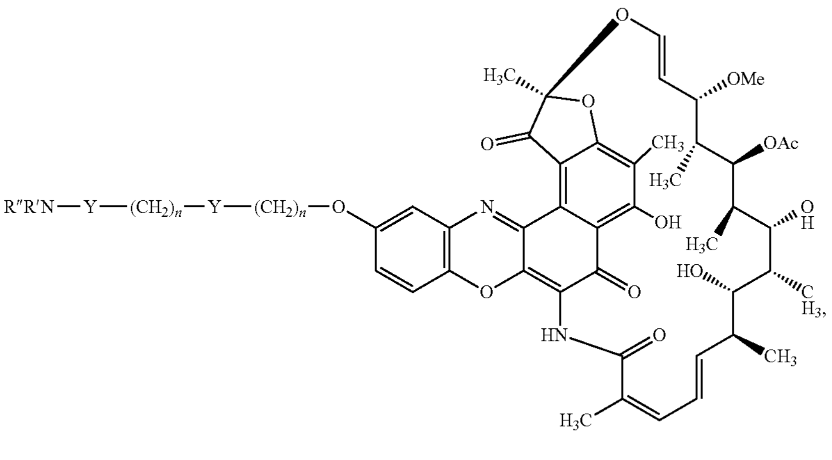

wherein Y is at each occurrence selected from —O— and —NR'R''—; n is independently at each occurrence an integer from 1 to 6, and R', R'', and R''' are each independently selected from a hydrogen and an aliphatic $C_1$-$C_{20}$ hydrocarbon; said method comprising contacting a compound having the structure of formula (XII'):

(XII')

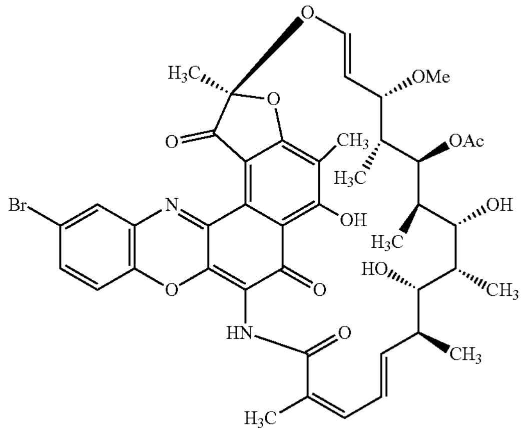

with an alcohol having the structure R"R'N—Y—$(CH_2)_n$—Y—$(CH_2)_n$—OH.

In one embodiment, the compound of formula (XII) is prepared by contacting Rifamycin S with 2-amino-5-bromophenol, and treating the product with an oxidizing agent.

In one embodiment, the compound of formula (XII') is prepared by contacting Rifamycin S with 2-amino-4-bromophenol, and treating the product with an oxidizing agent.

In one aspect, the present disclosure provides a pharmaceutical composition comprising any one or more of compounds as described above, or a pharmaceutically acceptable salt thereof, and a pharmaceutically acceptable carrier.

In another aspect, the present disclosure provides a pharmaceutical dosage form comprising any one or more of compounds as described above, or a pharmaceutically acceptable salt thereof, or a pharmaceutical composition as described above.

In another aspect, the present disclosure provides a method of preventing or inhibiting growth of a bacterium comprising administering an effective amount of a rifamycin analog compound having a structure according to any one of formula (A), (B), (I), (I'), (II), (II'), (III), (III'), (IV), (IV'), (V), (V') as provided herein.

In one embodiment, the bacterium is a Gram-positive bacterium.

In one embodiment, the bacterium is a penicillin-resistant bacterium.

In one embodiment, the bacterium is *Staphylococcus aureus*.

In one embodiment, the bacterium is methicillin-resistant *Staphylococcus aureus* (MRSA).

In one embodiment, the bacterium is vancomycin-resistant *Staphylococcus aureus* (VRSA).

In one embodiment, the bacterium is methicillin-susceptible *Staphylococcus aureus* (MSSA).

In yet another aspect, the present disclosure provides a method of treating a bacterial infection in a subject in need of such treatment comprising administering to the subject an effective amount of a rifamycin analog compound having a structure according to any one of formula (A), (B), (I), (I'), (II), (II'), (III), (III'), (IV), (IV'), (V), (V') as provided herein.

In one embodiment, the bacterial infection is a Gram-positive bacterial infection.

In one embodiment, the bacterial infection is a penicillin-resistant bacterial infection.

In one embodiment, the bacterial infection is a *Staphylococcus aureus* infection.

In one embodiment, the bacterial infection is a methicillin-resistant *Staphylococcus aureus* (MRSA) infection.

In one embodiment, the bacterial infection is a vancomycin-resistant *Staphylococcus aureus* (VRSA) infection.

In one embodiment, wherein the bacterial infection is a methicillin-susceptible *Staphylococcus aureus* (MSSA) infection.

In one embodiment, the bacterial infection is an intracellular bacterial infection.

In one embodiment, the subject is human.

In one embodiment, the method further comprises administering a second therapeutic agent.

In one embodiment, the second therapeutic agent is a second antibiotic.

In one embodiment, the second antibiotic is effective against *Staphylococcus aureus*.

In one embodiment, the second antibiotic is selected from an aminoglycoside, a beta-lactam, a macrolide, a cyclic peptide, a tetracycline, a fluoroquinoline, a fluoroquinolone, and an oxazolidinone.

In one embodiment, the second antibiotic is selected from clindamycin, novobiocin, retapamulin, daptomycin, sitafloxacin, teicoplanin, triclosan, napthyridone, radezolid, doxorubicin, ampicillin, vancomycin, imipenem, doripenem, gemcitabine, dalbavancin, and azithromycin.

In one embodiment, the compound is administered to the subject orally, topically, intranasally, intravenously, intramuscularly, or subcutaneously.

In another aspect, provided herein are antibody-drug conjugates comprising antibodies, or antigen-binding fragments of antibodies, and further comprising a rifamycin analog. In some embodiments of the antibody-drug conjugates of the present invention, the antibodies, or antigen-binding fragments of antibodies, bind to an infectious disease-related target. Infectious disease-related targets useful for the present disclosure include, but are not limited to, Macrophage scavenger receptor 1 (MSR1), wall teichoic acids (WTA), *S. aureus* antigens such as Protein A, IsdA, IsdB, IsdC, IsdE, IsdH, ClfA, ClfB, CP5, CP8, SdrC, SdrD, SdrE, FnBpA, FnBpB, Cna, polysaccharide poly-N-aceytl-glucosamine (PNAG), and SasG.

In some embodiments, the antibodies, or antigen-binding fragments of antibodies bind to MSR1. In some embodiments, the antibodies, or antigen-binding fragments of antibodies bind to WTA. In some embodiments, the antibodies, or antigen-binding fragments of antibodies bind to Protein A.

In another aspect, provided herein are antibody-drug conjugates comprising antibodies, or antigen-binding fragments of antibodies, that bind the membrane glycoprotein receptor known as MSR1, and further comprising a rifamycin analog. The antibodies are useful, inter alia, for targeting cells that express MSR1, such as macrophage cells.

In another aspect, provided herein are antibody-drug conjugates comprising antibodies, or antigen-binding fragments of antibodies, that bind wall teichoic acids (WTA), and further comprising a rifamycin analog.

In another aspect, provided herein are antibody-drug conjugates comprising antibodies, or antigen-binding fragments of antibodies, that bind Protein A, and further comprising a rifamycin analog.

In another aspect, provided herein is a pharmaceutical composition comprising an antibody-drug conjugate comprising a recombinant human antibody or fragment thereof, further comprising a rifamycin analog, and a pharmaceutically acceptable carrier. In some embodiments, the recombinant human antibody or fragment thereof specifically binds an infectious disease-related target. In some embodiments, the recombinant human antibody or fragment thereof specifically binds MSR1, WTA or Protein A. In a related aspect, embodiments relate to a composition which is a combination of an antibody-drug conjugate comprising antibody described herein and further comprising a rifamycin analog, and a second therapeutic agent. In one embodiment, the second therapeutic agent is any agent that is advantageously combined with an antibody-drug conjugate comprising an antibody described herein. In one embodiment, the second therapeutic agent is an antibody-drug conjugate comprising an antibody described herein conjugated to a second drug or a therapeutic agent. Exemplary combination therapies, co-formulations, and ADCs involving the antibodies are disclosed elsewhere herein.

Also provided herein are reactive linker-payloads comprising rifamycin analogs, for example, the compounds having a structure according to any embodiment of formulas (A), (B), (I), (I'), (II), (II'), (III), (III'), (IV), (IV'), (V), (V'), (B-1), (B-2) as provided herein, useful for making the antibody-drug conjugates comprising an antibody. Further provided herein are modified antibodies and modified antigen-binding fragments useful for making the antibody-drug conjugates comprising rifamycin analogs. In some embodiments, the antibody or antigen-binding fragment thereof specifically binds an infectious disease-related target. In some embodiments, the antibody or antigen-binding fragment thereof specifically binds MSR1, WTA or Protein A.

Also provided herein are methods of preventing or inhibiting growth of a bacterium comprising administration of an effective amount of an antibody-drug conjugate (ADC) comprising an antibody or antigen-binding fragment thereof and a rifamycin analog. In some embodiments, the antibody or antigen-binding fragment thereof specifically binds an infectious disease-related target. In some embodiments, the antibody or antigen-binding fragment thereof specifically binds MSR1, WTA or Protein A.

Also provided herein are therapeutic methods comprising administration of an effective amount of an ADC comprising an antibody or antigen-binding fragment thereof and a rifamycin analog, to a subject in need thereof. The therapeutic methods comprise administering a therapeutically effective amount of a pharmaceutical composition comprising an ADC comprising an antibody or antigen-binding fragment thereof and a rifamycin analog to the subject. The disorder treated is any disease or condition which is improved, ameliorated, inhibited or prevented by targeting the infectious disease-related target and/or by the administration of an antibiotic agent. In some embodiments, the disease or condition is a proliferative disease, a metabolic disease, inflammation, a neurodegenerative disease, or disease, disorder, or condition associated with glucocorticoid receptor signaling. In some of such embodiments, the side effects associated with administration of the unconjugated rifamycin analog are reduced. Provided herein is the use of an antibody, an antigen-binding portion thereof, or an ADC comprising an antibody or antigen-binding fragment thereof, described herein, for the treatment of any disease disorder or condition described herein. In some embodiments, the antibody or antigen-binding fragment thereof specifically binds an infectious disease-related target. In some embodiments, the antibody or antigen-binding fragment thereof specifically binds MSR1, WTA or Protein A.

Also provided herein are therapeutic methods for treating, attenuating, or ameliorating a disease or disorder or condition associated with Staphylococcal infection, for example, a *S. aureus* infection and/or for ameliorating at least one symptom associated with such disease, disorder or condition, comprising administration of a rifamycin analog or an ADC comprising an antibody or antigen-binding fragment thereof and a rifamycin analog, to a subject in need thereof. Such disease, disorder or condition may be cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, or septic arthritis. In some embodiments, the subject has a prosthetic joint and the rifamycin analogs or ADCs comprising an antibody or antigen-binding fragment thereof and a rifamycin analog disclosed herein are used for treating and/or preventing *S. aureus* infection of the tissue surrounding the prosthetic joint. In some embodiments, the subject has a catheter and the rifamycin analogs or ADCs comprising an antibody or antigen-binding fragment thereof and a rifamycin analog disclosed herein are used for treating and/or preventing *S. aureus* infection of the catheter and/or the tissue surrounding the catheter. In some embodiments, the subject has a foreign body implanted, and the rifamycin analogs or ADCs comprising an antibody or antigen-binding fragment thereof and a rifamycin analog disclosed herein are used for treating and/or preventing *S. aureus* infection of the foreign body and/or the tissue surrounding the foreign body. In some embodiments, the subject has mastitis, and the antibodies disclosed herein are useful for treating mastitis. The therapeutic methods comprise administering a therapeutically effective amount of a pharmaceutical composition comprising a rifamycin analog or an ADC comprising an antibody or antigen-binding fragment thereof and a rifamycin analog, to a subject in need thereof. In some embodiments, the antibody or antigen-binding fragment thereof specifically binds an infectious disease-related target. In some embodiments, the antibody or antigen-binding fragment thereof specifically binds MSR1, WTA or Protein A.

In another aspect, the present disclosure provides an antibody-drug conjugate comprising an antibody, or an antigen-binding fragment thereof, conjugated to the rifamycin analog compound of any of the embodiments of the disclosure via a linker or through a linker-spacer.

In various embodiments, the antibody, or the antigen-binding fragment thereof, binds macrophage scavenger receptor 1 (MSR1). In various embodiments, the antibody, or the antigen-binding fragment thereof, binds wall teichoic acids (WTA). In various embodiments, the antibody, or the antigen-binding fragment thereof, binds *S. aureus* Protein A.

In one embodiment, the antibody, or the antigen-binding fragment thereof, may comprise: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, may comprise:

(i) a HCDR1 domain comprising an amino acid sequence selected from the group consisting of SEQ ID NOs: 4, 36, 52, 92, and 284;

(ii) a HCDR2 domain comprising an amino acid sequence selected from the group consisting of SEQ ID NOs: 6, 38, 54, 94, and 286;

(iii) a HCDR3 domain comprising an amino acid sequence selected from the group consisting of SEQ ID NOs: 8, 40, 56, 96, and 288;

(iv) a LCDR1 domain comprising an amino acid sequence selected from the group consisting of SEQ ID NOs: 12, 44, 60, 100, and 292;

(v) a LCDR2 domain comprising an amino acid sequence selected from the group consisting of SEQ ID NOs: 14, 46, 62, 102, and 294; and (vi) a LCDR3 domain comprising an amino acid sequence selected from the group consisting of SEQ ID NOs: 16, 48, 64, 104, and 296.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTA antibody, or the antigen-binding fragment thereof, may comprise:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTA antibody, or the antigen-binding fragment thereof, may comprise:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation (EU numbering) in the light chain.

In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

In one embodiment, the linker or linker spacer is selected from

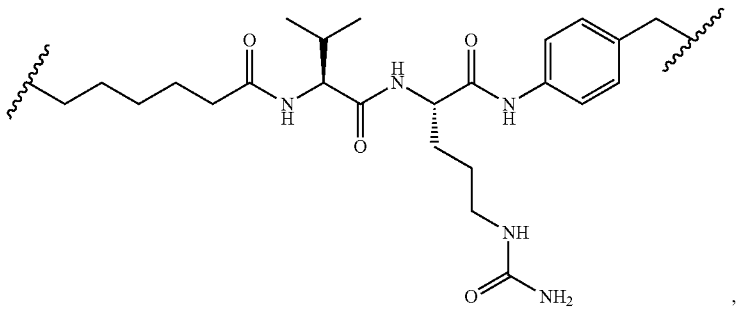

,

-continued

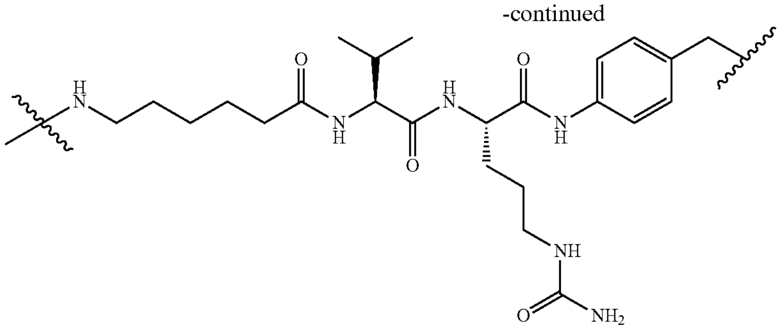

,

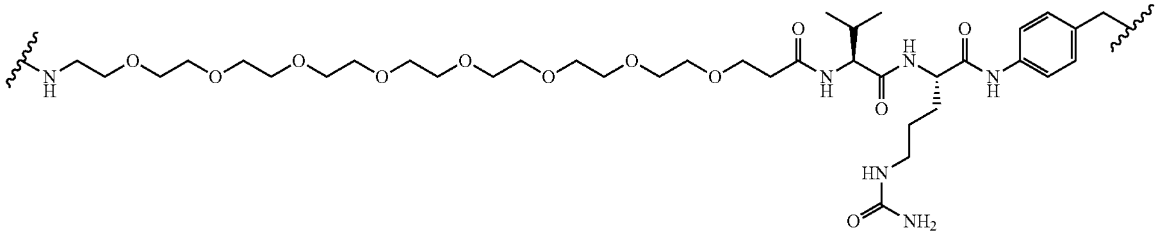

,

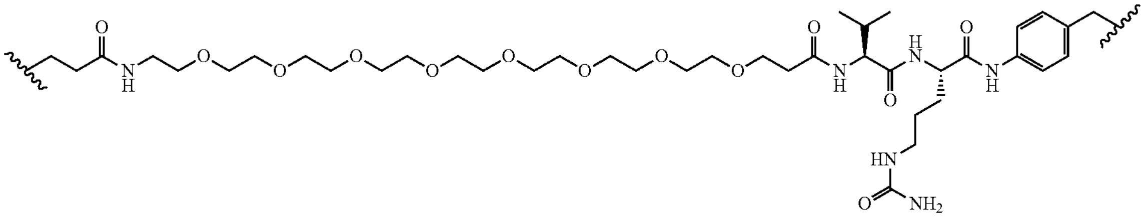

,

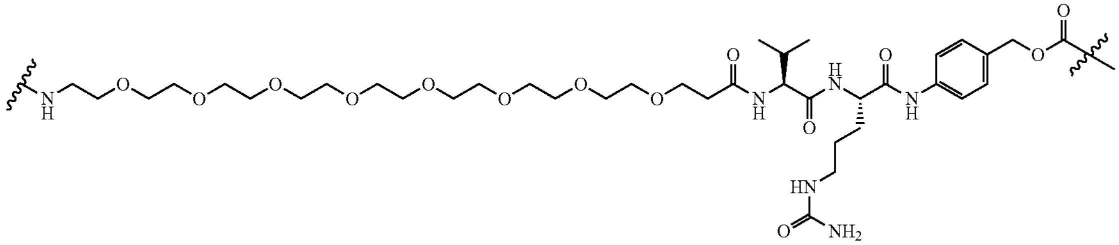

, and

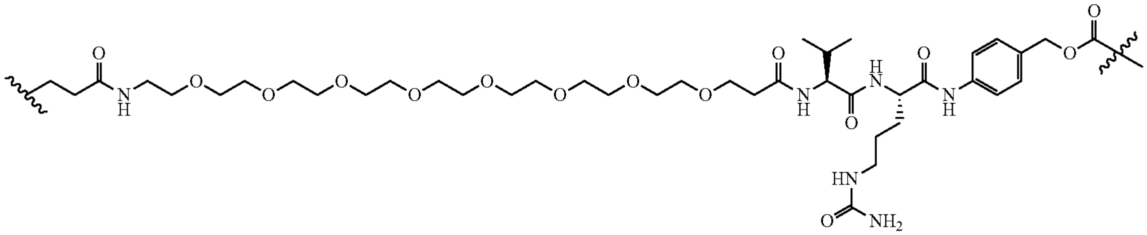

.

In another aspect, the present disclosure provides an antibody-drug conjugate having the structure according to Formula (XVIII):

$$BA-[RG-SP-AA-B-PA]_n, \quad \text{(XVIII)}$$

wherein

BA is an antibody, or an antigen-binding fragment thereof;

RG is a reactive group selected from a maleimide, an N-hydroxy succinimide, or a succinimide;

SP is absent or a spacer group residue selected from the group consisting of $C_{1-6}$ alkyl, —NH—, —C(O)—, —$CH_2$—$CH_2$—C(O)—NH—, —$(CH)_u$—C(O)—NH—, (—$CH_2$—$CH_2$—$O)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, —(CH)—C(O)—NH—($CH_2$—$CH_2$—$O)_e$—(CH)—C(O)—NH—, —$(CH)_2$—C(O)—NH—($CH_2$—$CH_2$—$O)_8$—$(CH)_2$—C(O)—NH—, and combinations thereof, wherein independently at each occurrence subscript e is an integer from 0 to 20, subscript u is an integer from 1 to 8, and subscript v is an integer from 1 to 8;

AA is a linker selected from valine-citrulline; citrulline-valine; valine-alanine; alanine-valine; valine-glycine, or glycine-valine;

B is absent or

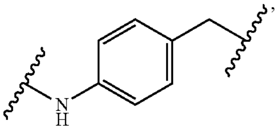 [SMILES: *Cc1ccc(N*)cc1]

, wherein the
indicates the atom through which the B is bonded to the adjacent groups in the formula;
n is an integer from 1 to 30, and
PA is a rifamycin analog according to any of the embodiments of the disclosure.
In one embodiment,
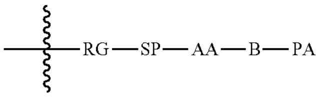
is
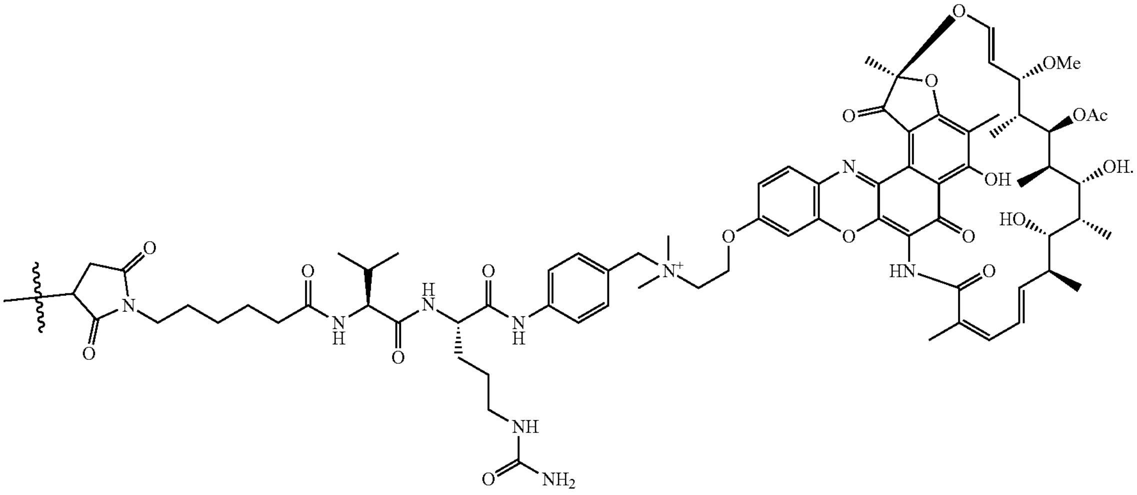 [SMILES: *C1CC(=O)N(CCCCCC(=O)N[C@H](C(=O)N[C@@H](CCCNC(N)=O)C(=O)Nc2ccc(C[N+](C)(C)CCOc3ccc4nc5c6c7c8c(C)c(O)c6c(=O)c(c-5oc4c3)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O8)C7=O)cc2)C(C)C)C1=O]
In one embodiment,
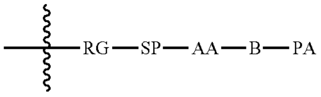
is
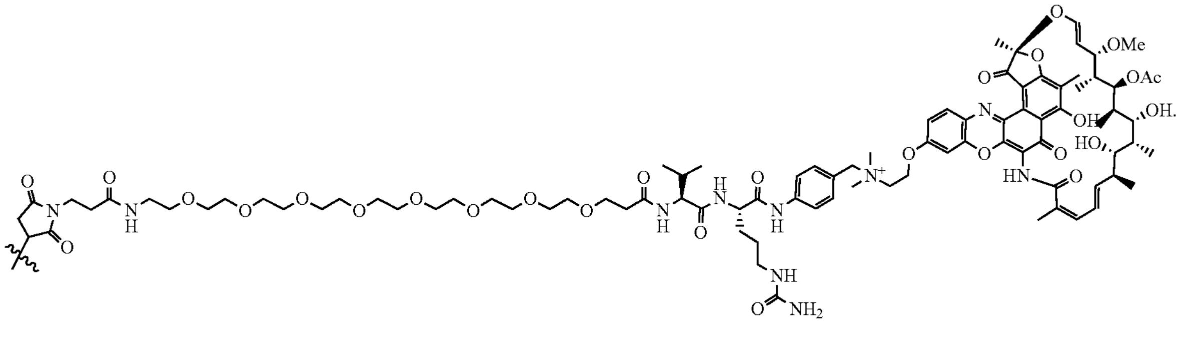
In one embodiment
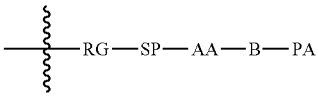
is
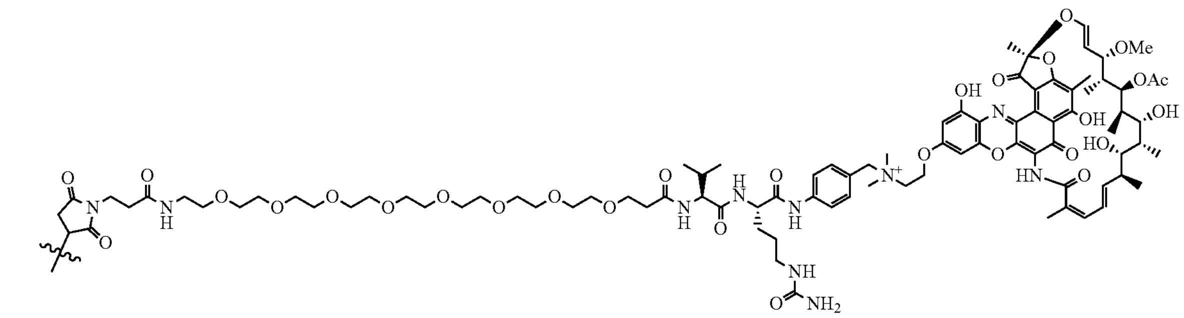

wherein the

is the bond to the antibody or the antigen-binding fragment thereof. In one aspect, the present disclosure provides an antibody-drug conjugate having the structure according to Formula (XIX):

$$BA-[RG-SP^1-(PEG)_m-SP^2-AA-B-PA]_n, \quad \text{(XIX)}$$

wherein

BA is an antibody, or an antigen-binding fragment thereof;

RG is selected from a maleimide, a N-hydroxy succinimide, or a succinimide;

$SP^1$ and $SP^2$ are independently absent or a spacer group selected from the group consisting of $C_{1-6}$ alkyl, —NH—, —C(O)—, —$CH_2$—$CH_2$—C(O)—NH—

(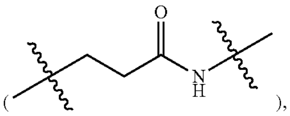 [SMILES: *CCC(=O)N*]),

—$(CH)_u$—C(O)—NH—, (—$CH_2$—$CH_2$—O$)_e$, —NH—$CH_2$—$CH_2$—(—O—$CH_2$—$CH_2$$)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

AA is a linker selected from valine-citrulline; citrulline-valine; valine-alanine; alanine-valine; valine-glycine, or glycine-valine;

PEG is a polyethylene glycol chain comprising between 1 and 30 polyethylene glycol residues;

B is absent or

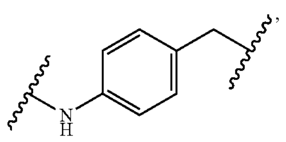 [SMILES: *Cc1ccc(N*)cc1], wherein the

indicates the atom through which the B is bonded to the adjacent groups in the formula;

n is an integer from 1 to 30;

m is an integer from 0 to 20, and PA is a rifamycin analog according to any of the embodiments of the disclosure.

In one embodiment,

$-RG-SP^1-(PEG)_m-SP^2-AA-B-PA$ is

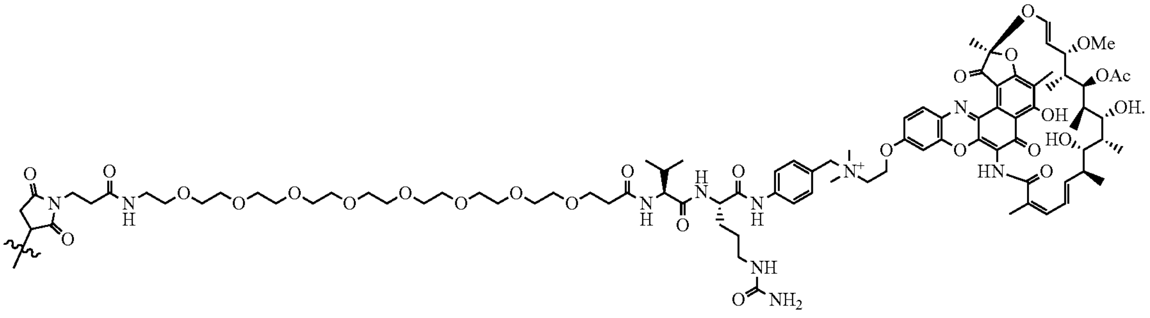

-

In one aspect, the present disclosure provides an antibody-drug conjugate comprising an antibody, or an antigen-binding fragment thereof, conjugated via a linker or through a linker-spacer to a rifamycin analog payload having the structure of Formula (XX):

(XX)

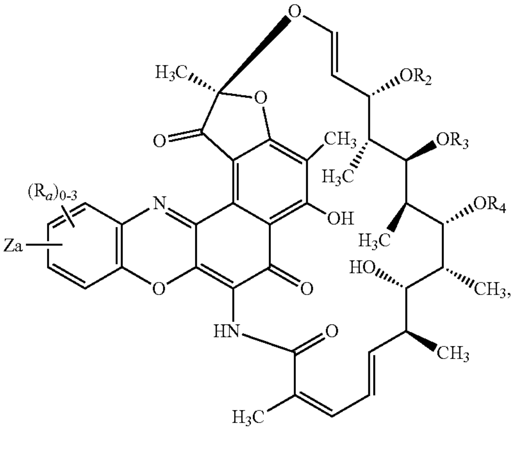

wherein:

X is selected from —O—, —S—, and —NR*—;

Za is selected from —$OR_1$ and —$R_N$;

$R_1$ is selected from a bond; an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F; —Cl; —Br; —I; —OH, —OR*; —NO; —$NO_2$; —$NO_3$; —O—NO; —$N_3$; —$NH_2$; —NHR*; —$N(R^*)_2$; —$N(R^*)_3^+$; —N(R*)—OH; —O—N$(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—$N(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —Si$(R^*)_3$; —$CF_3$; —O—$CF_3$ and combinations thereof;

$R_N$ is selected from:

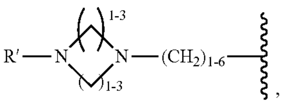
,
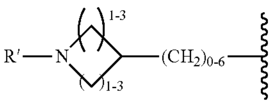
,
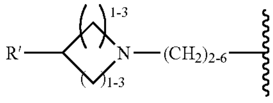
,
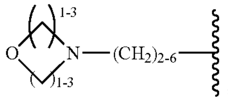
,
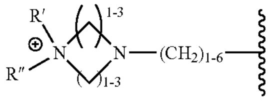
,
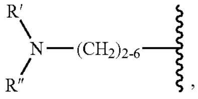
,
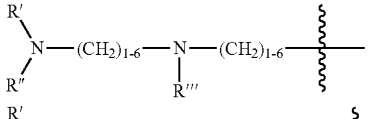
,
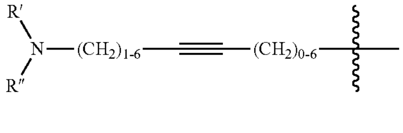
and -continued

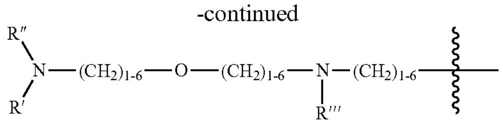

wherein the ∿∿ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is independently at each occurrence selected from hydrogen, —F, —Cl, —Br, —I, —OH, OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and wherein the group Za is bonded to the linker.

It is to be understood that the group $R_1$ is either a bond (i.e., $R_1$ is absent), or a divalent group, i.e. $R_1$ capable of bonding to the —O— of the rifamycin analog as well as to the linker.

In one embodiment, —$OR_1$ is —O— (i.e., $R_1$ is absent),

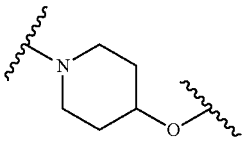
,
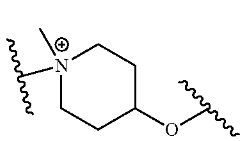
,
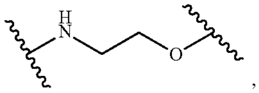
,
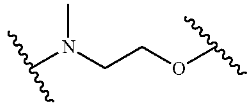
,
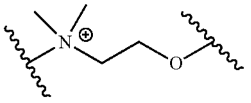
, or
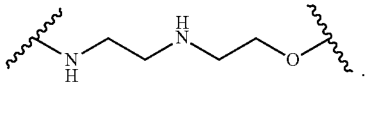
.

In one embodiment, X is —O—, and —$OR_1$ comprises a tertiary amine. In some of such embodiments, —$OR_1$ is

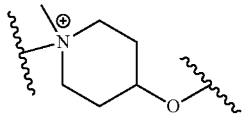
or
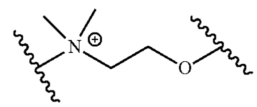
.

In some embodiments, antibody-drug conjugates comprising linker-rifamycin analog payloads comprise ammonium salts having one or more counterions. Any pharmaceutically acceptable counterion may be suitable. For example, in an embodiment of the disclosure a suitable counterion may be an anion selected from $F^-$, $Cl^-$, $Br^-$, $I^-$, $OH^-$, $^-BF_4$, $CF_3SO_3^-$, monobasic sulfate, dibasic sulfate, monobasic phosphate, dibasic phosphate, or tribasic phosphate, $NO_3^-$, $PF_6^-$, $NO_2^-$, carboxylate, $C_eF_fSO_3^-$, (where in e=2-10 and f=2e+1), acetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, glycollyalarsanilate, hexanoate, hydrabamine, hydroxynaphthoate, isthionate, lactate, lactobionate, malate, maleate, mandelate, mesylate, methylbromide, methylnitrate, mucate, napsylate, octanoate, oleate, pamoate, pantothenate, polygalacturonate, propionate, salicylate, stearate, subacetate, succinate, tartrate, teoclate, tosylate, or triethiiodide.

In some embodiments, $R_a$ is absent. In some embodiments, $R_a$ is —OH and is present at one occurrence.

In one aspect, the present disclosure provides an antibody, or an antigen-binding fragment thereof, conjugated via a linker or through a linker-spacer to a rifamycin analog having the structure of Formula (XXI):

(XXI)

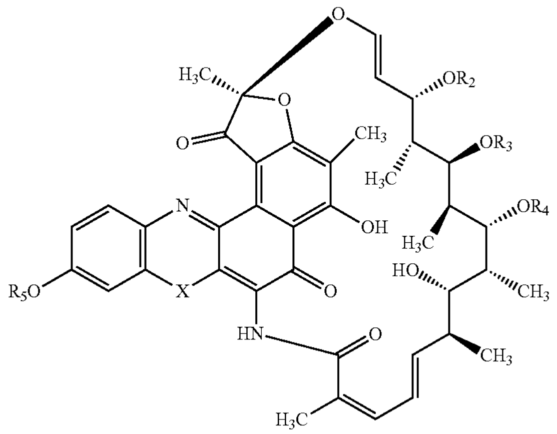

, wherein:

X is selected from —O—, —S—, and —NR*—;

$R_5$ is selected from a bond; an aliphatic $C_1$-$C_{20}$ hydrocarbon which further comprises 0-8 heteroatoms selected from halogen, O, N, and S;

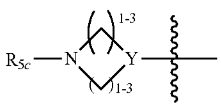

; or

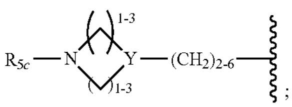

;

wherein Y is C or N;

$R_2$, $R_3$, and $R_4$ are independently selected from a hydrogen, a straight chained, branched or cyclic aliphatic $C_1$-$C_{20}$ hydrocarbon, or —(C═O)—R*, each of which further comprises 0-8 heteroatoms selected from halogen, O, N, and S, and $R_{5c}$ is a bond or an aliphatic $C_1$-$C_8$ hydrocarbon, wherein the group $R_5$ is bonded to the linker.

It is to be understood that the group $R_5$ is either a bond (i.e., $R_5$ is absent), or a divalent group, i.e. $R_5$ capable of bonding to the —O— of rifamycin as well as to the linker.

In one embodiment, —$OR_5$ is —O— (i.e., $R_5$ is absent),

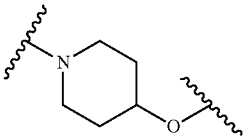

,

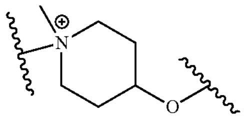

,

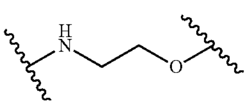

,

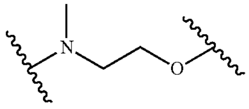

,

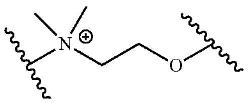

, or

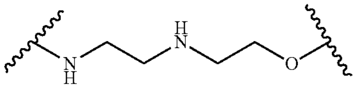

.

In one embodiment, X is O, and —$OR_5$ comprises a tertiary amine. In some of such embodiments, —$OR_5$ is

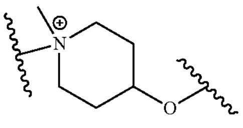

or

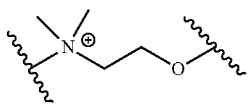

.

In one embodiment of any of the above, $R_2$ is methyl, ethyl, propyl or isopropyl; $R_3$ is $CH_3$—(C═O)— (acetyl) group, $CH_3CH_2$—(C═O)—, $CH_3CH_2CH_2$—(C═O)—, or $(CH_3)_2CH$—(C═O)—, and $R_4$ is hydrogen.

In one embodiment of any of the above, $R_2$ is methyl, $R_3$ is acetyl, and $R_4$ is hydrogen.

In one embodiment of any of the above, the compound is selected from the group consisting of:
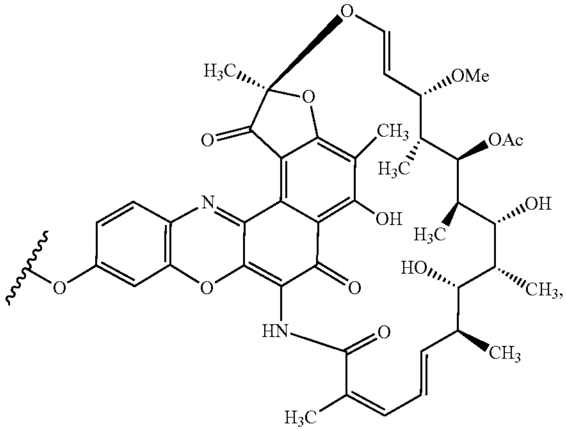
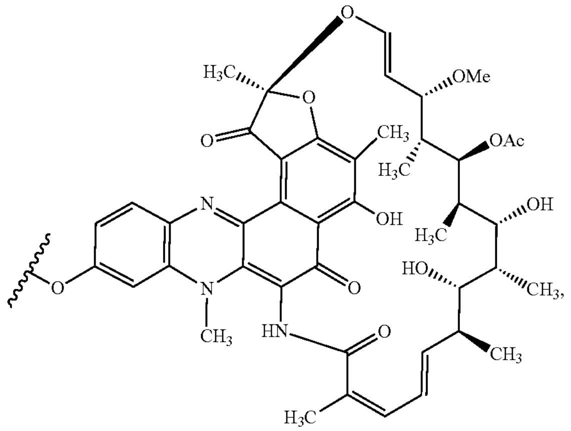
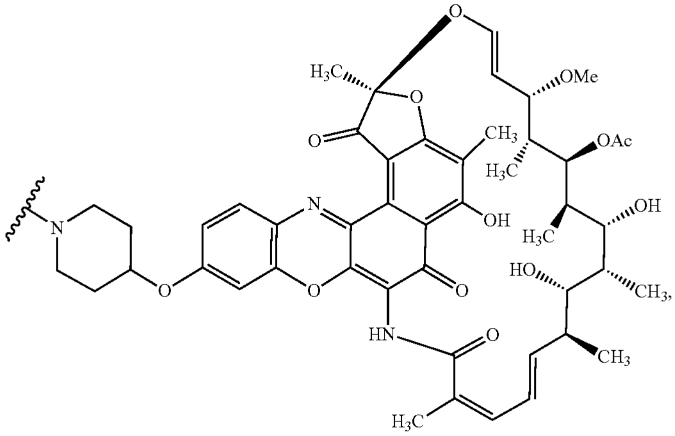
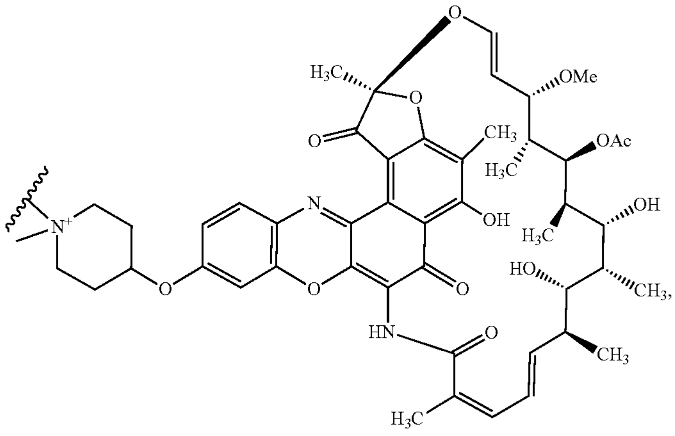

-continued
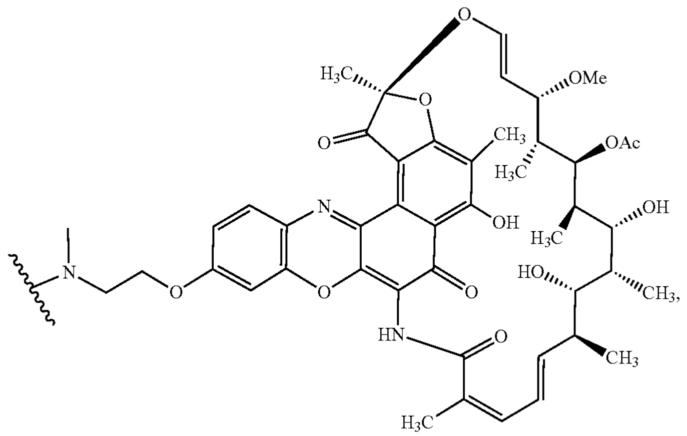
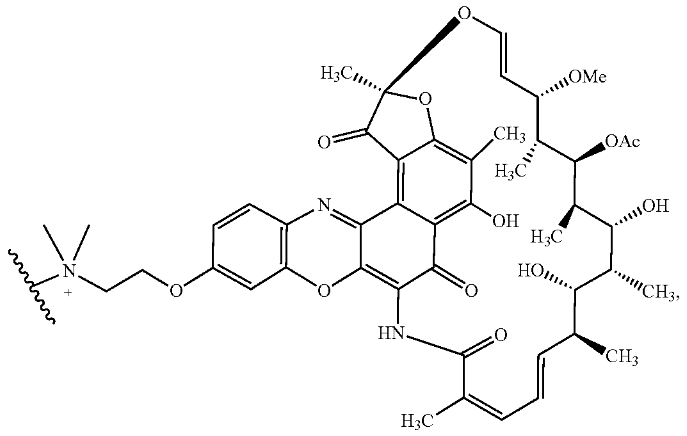
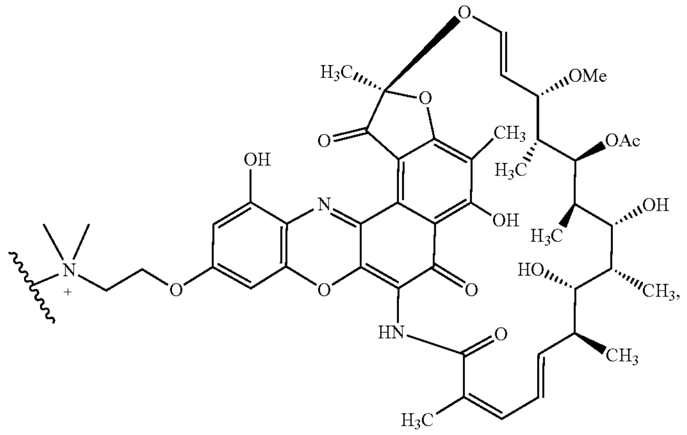

-continued
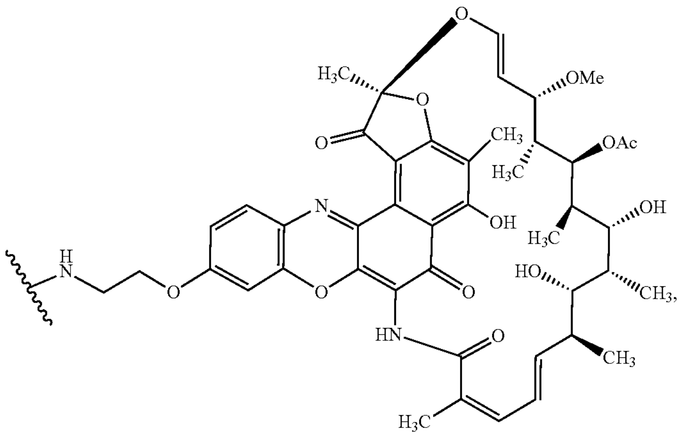
,
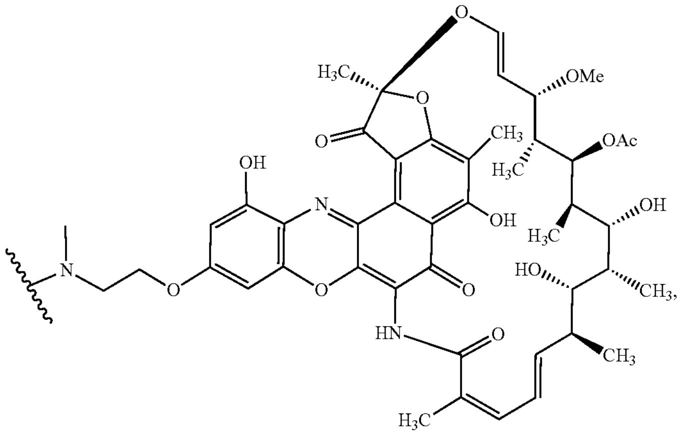
,
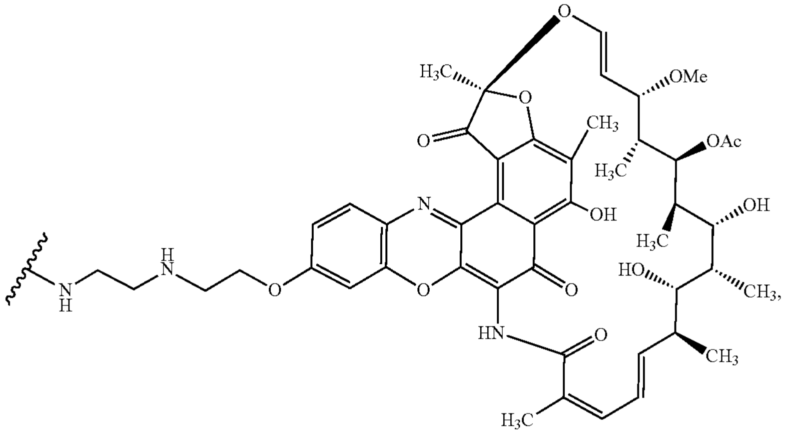
,

-continued
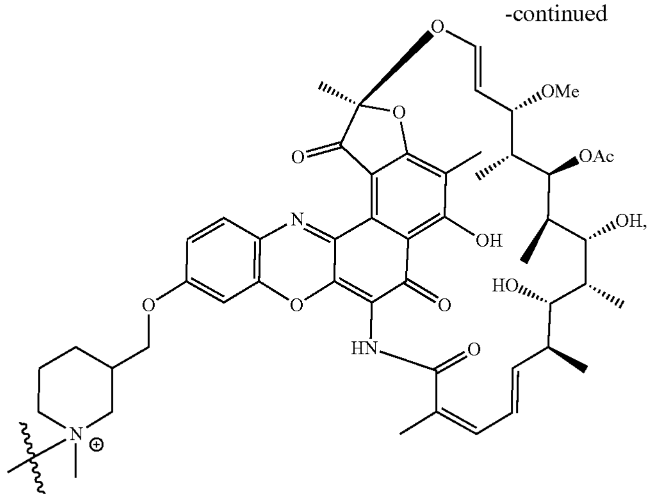
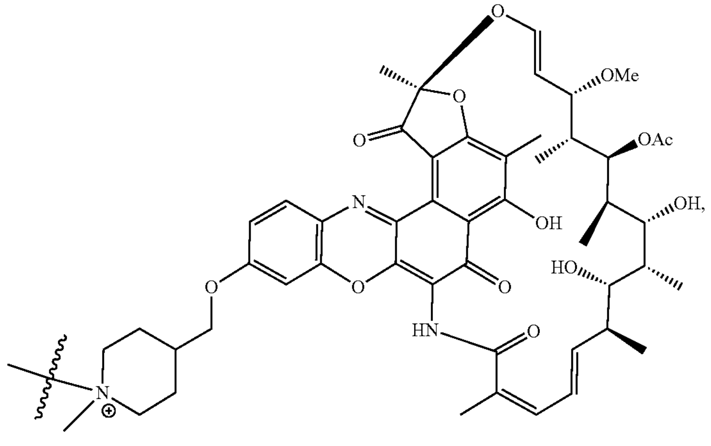
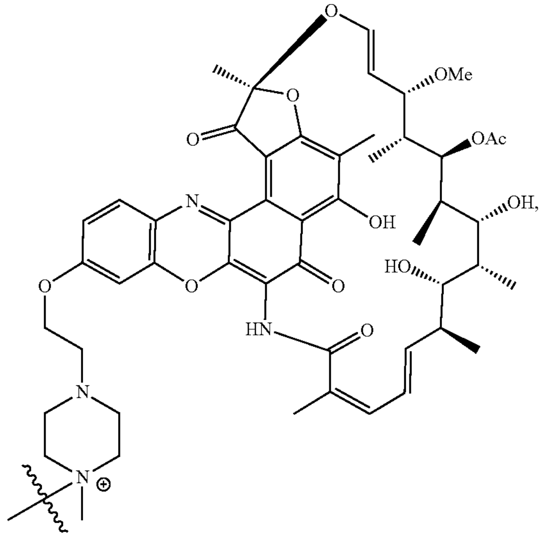

-continued
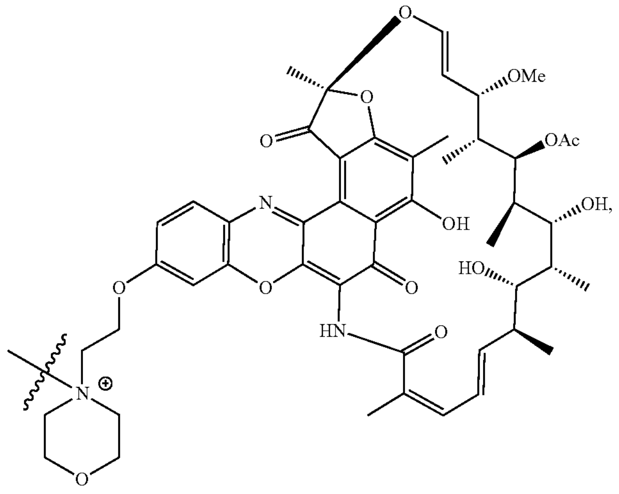
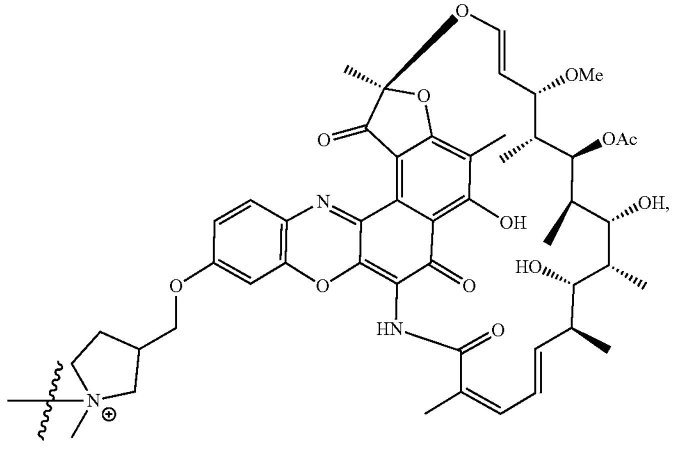
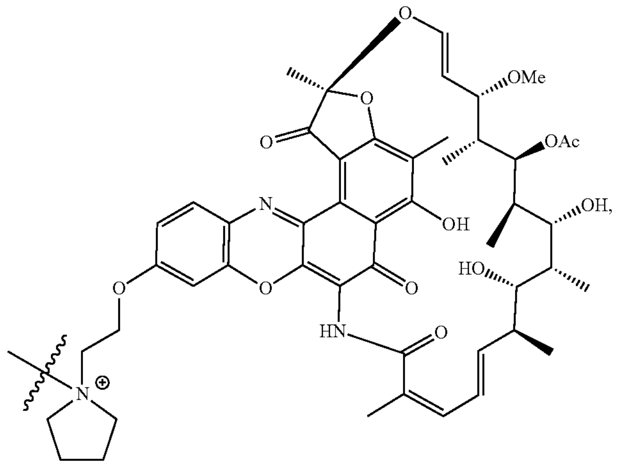

-continued
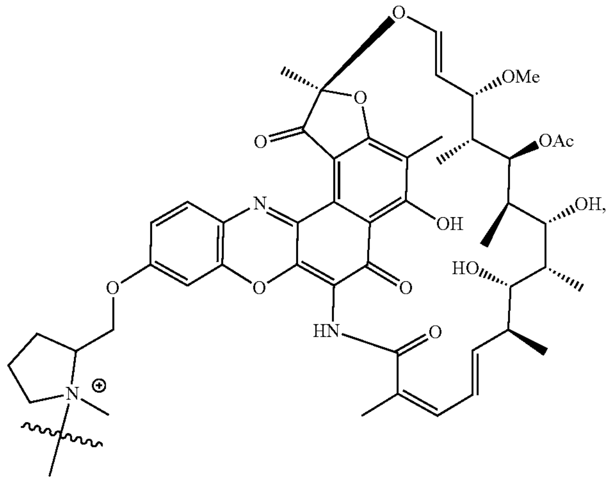
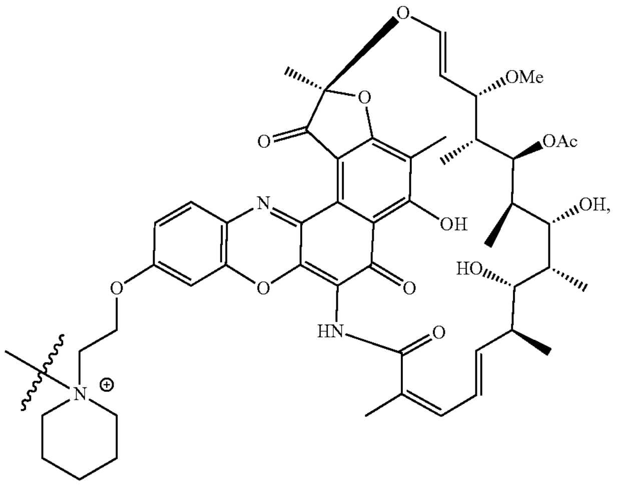
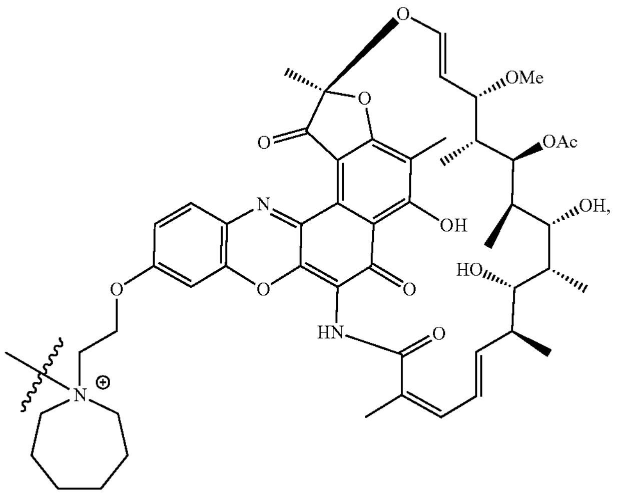

-continued
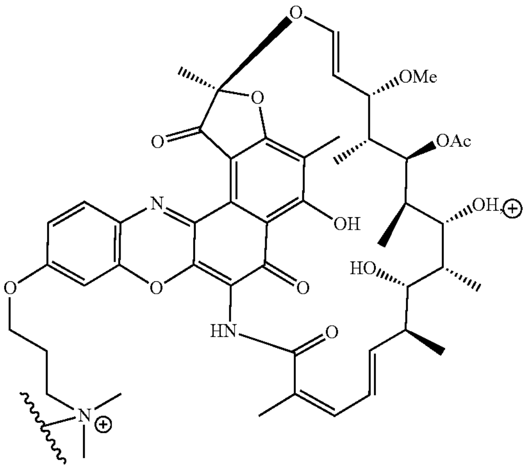
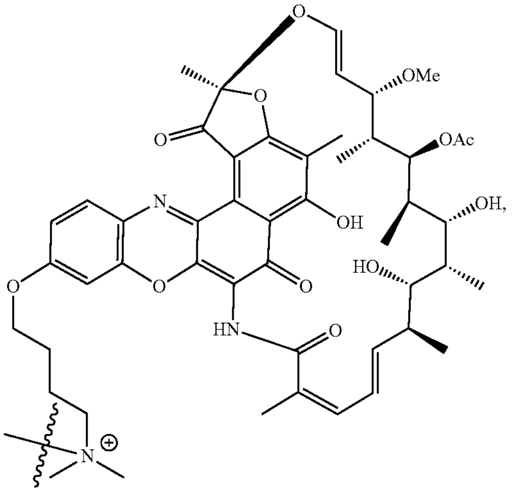
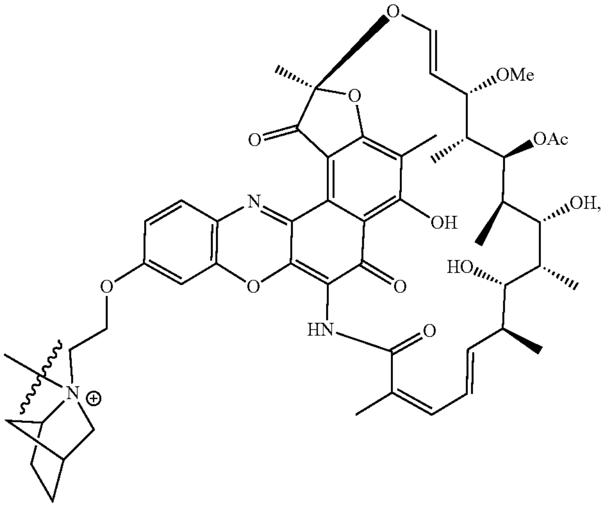

-continued
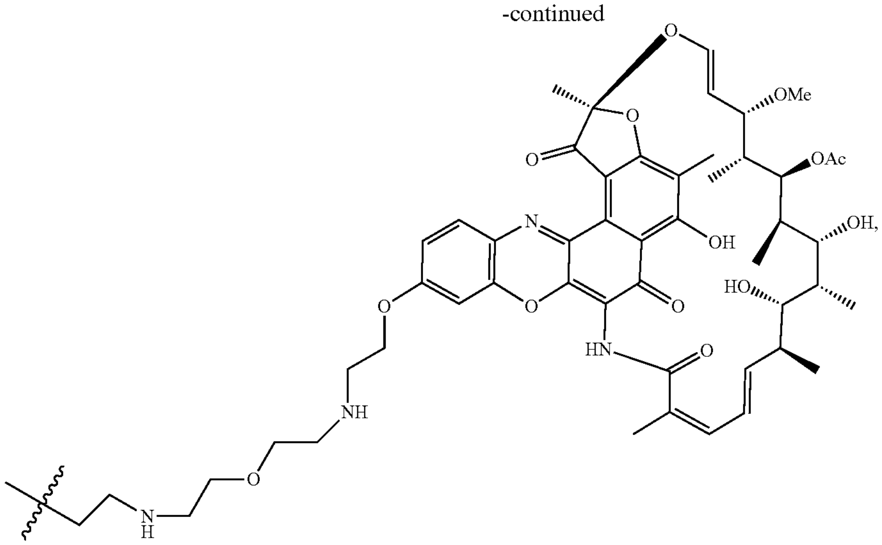
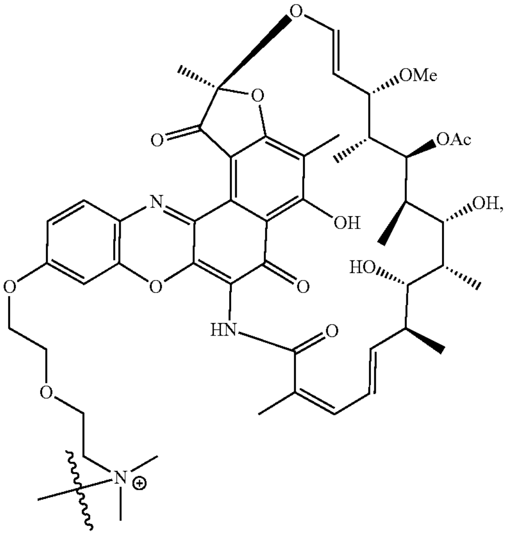
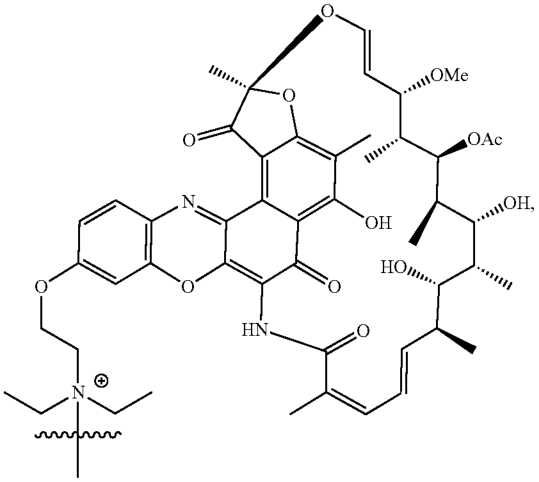
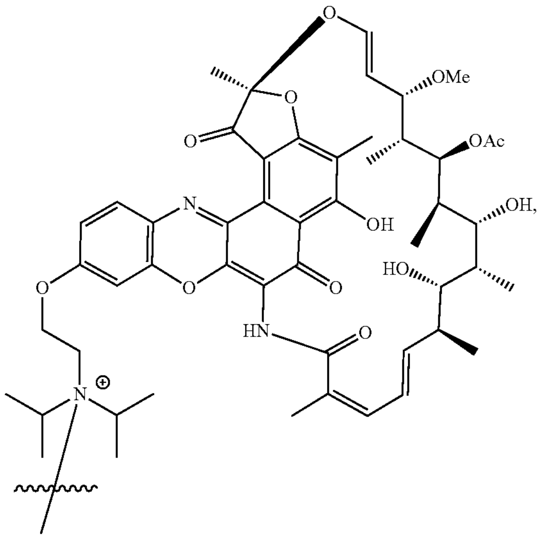

-continued
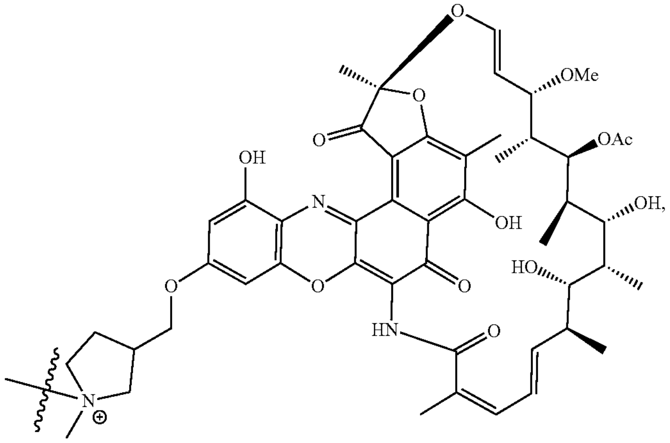
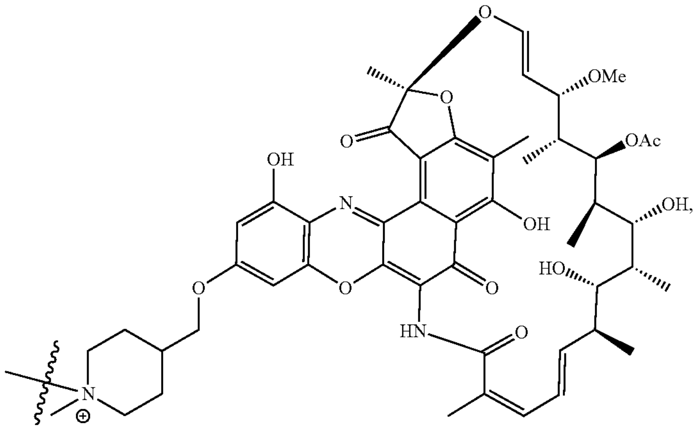
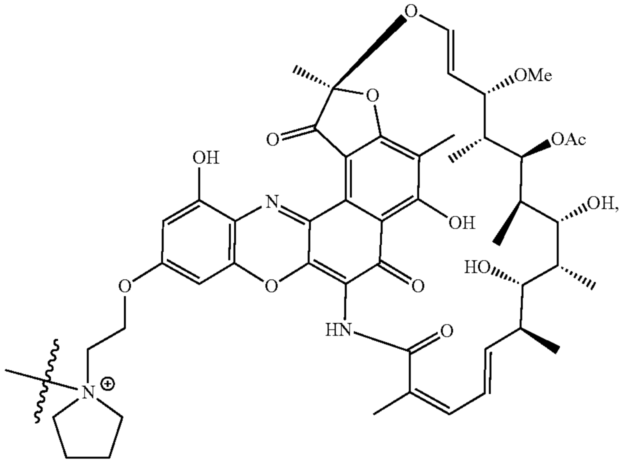

-continued
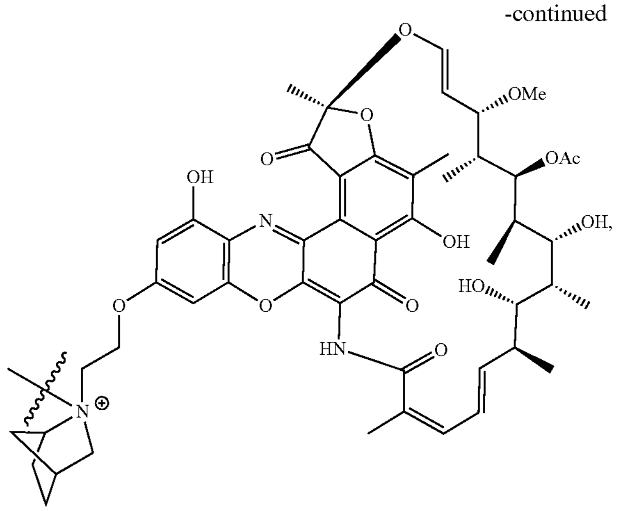
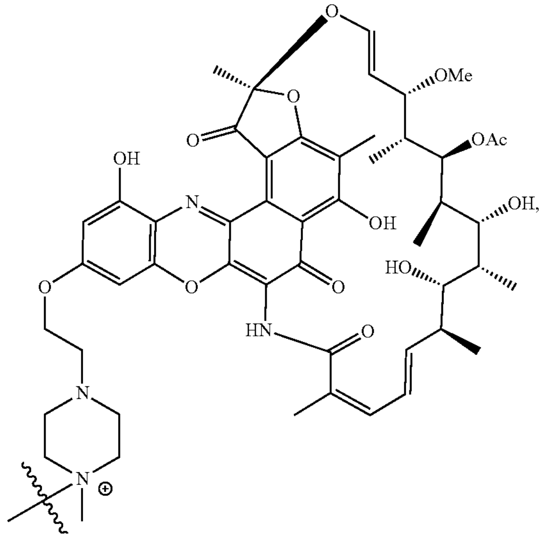
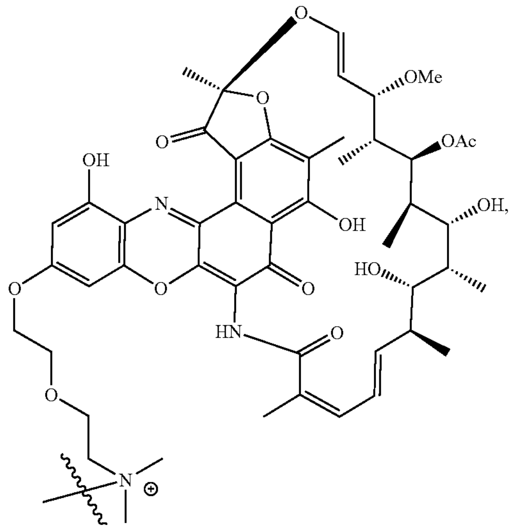

-continued
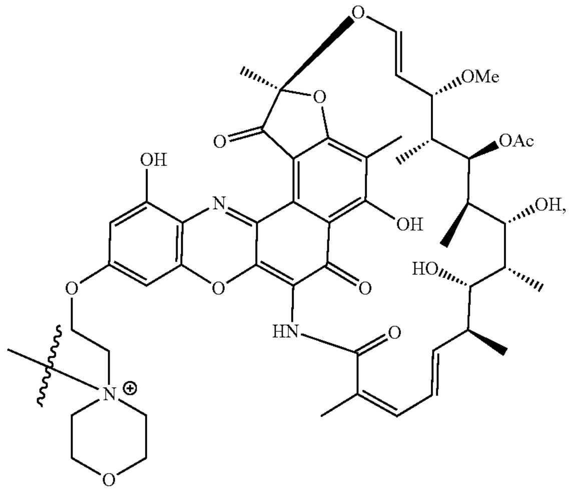
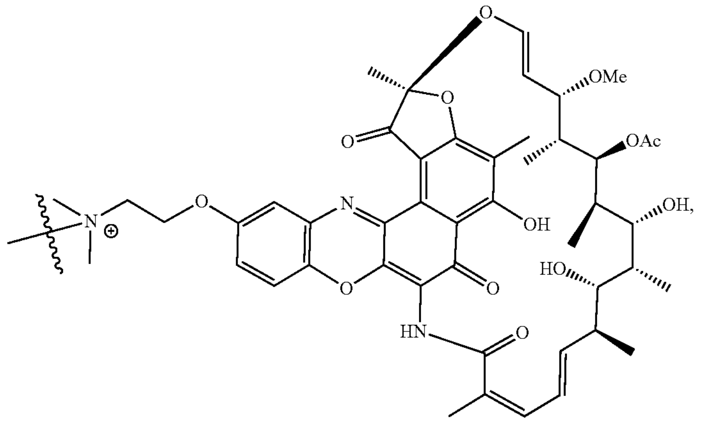
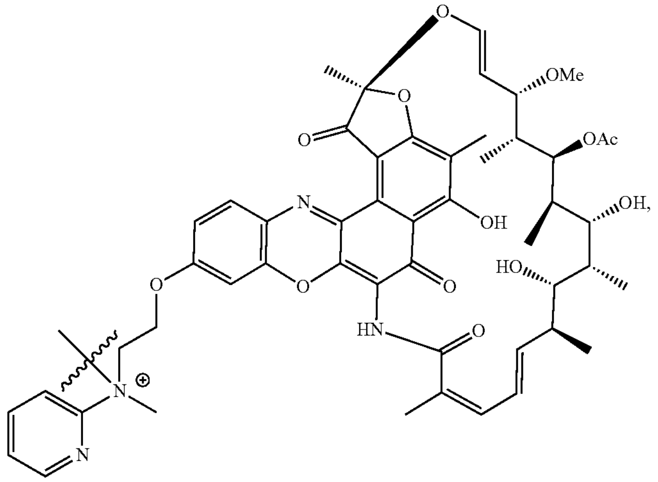

-continued
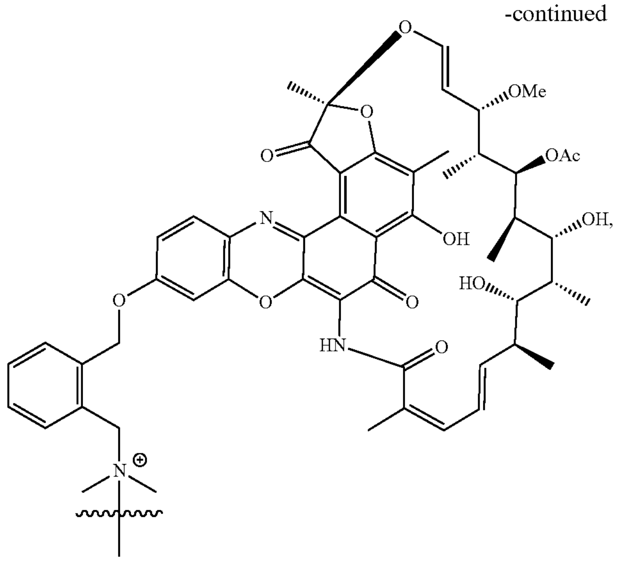
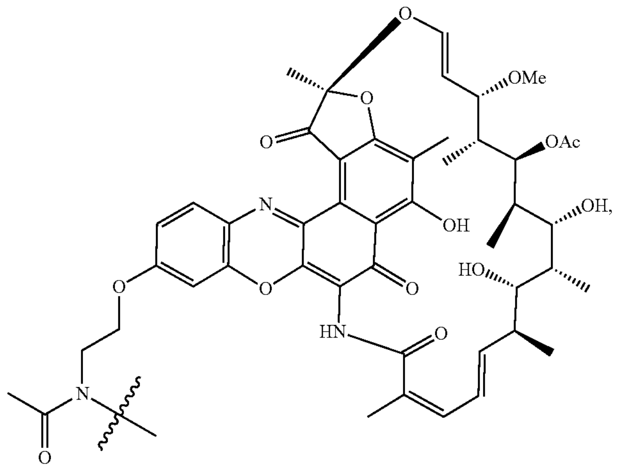
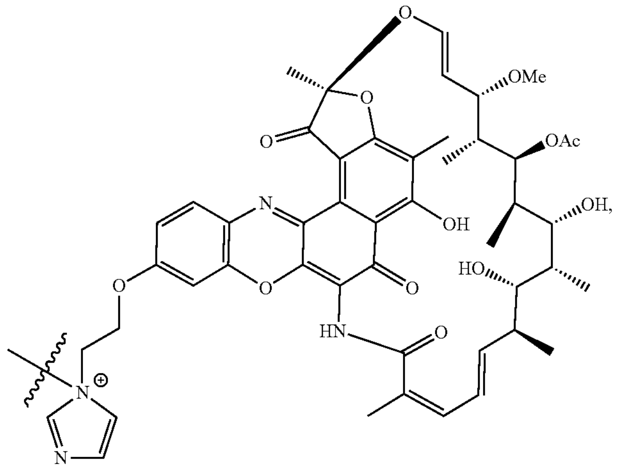

-continued
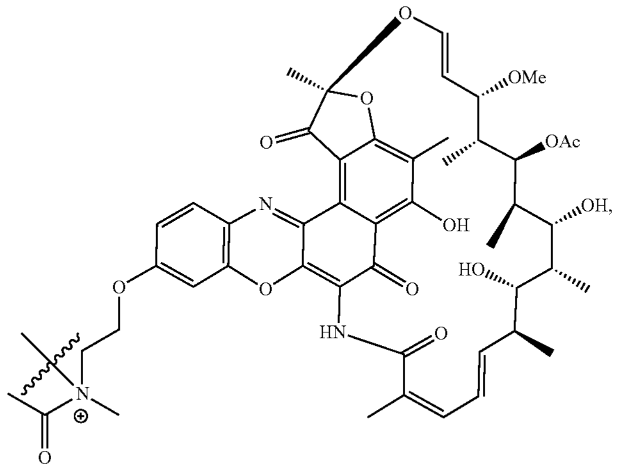
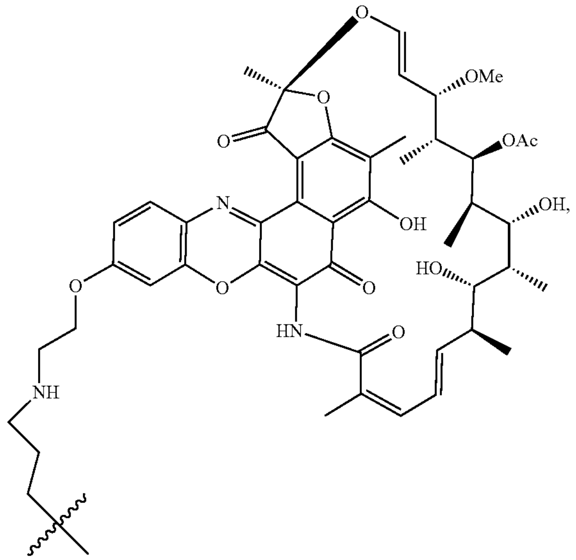
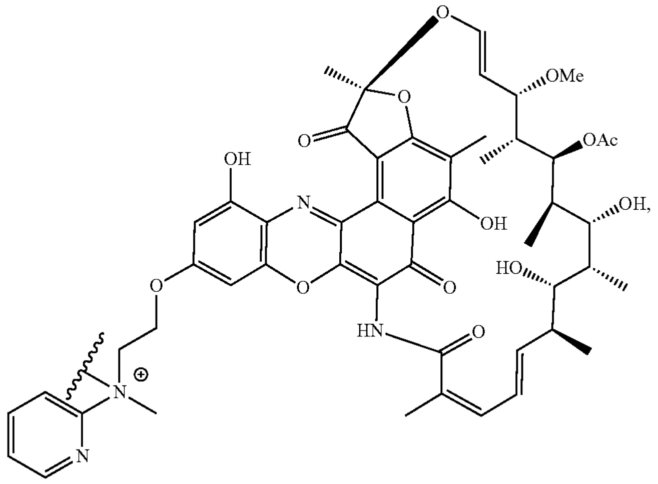

-continued
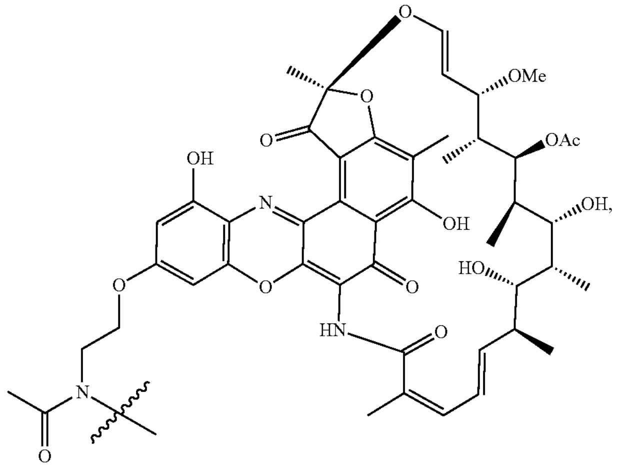
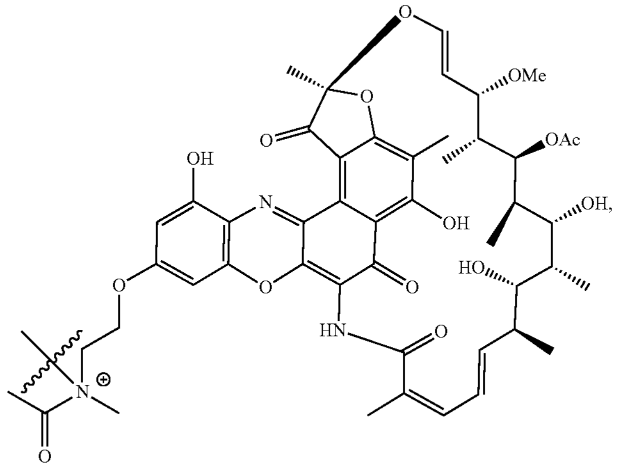
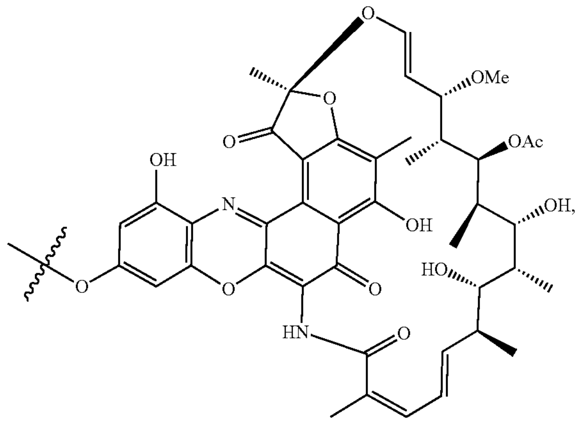

-continued
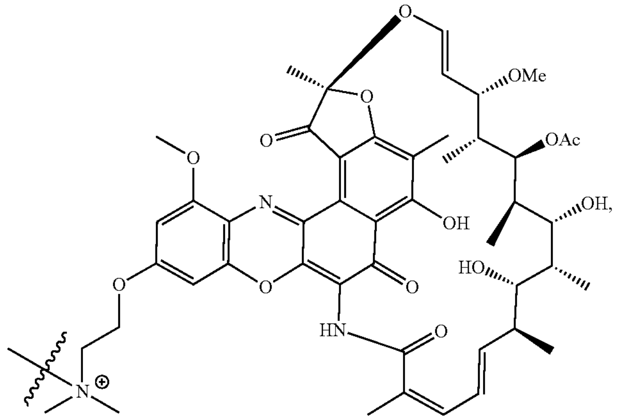
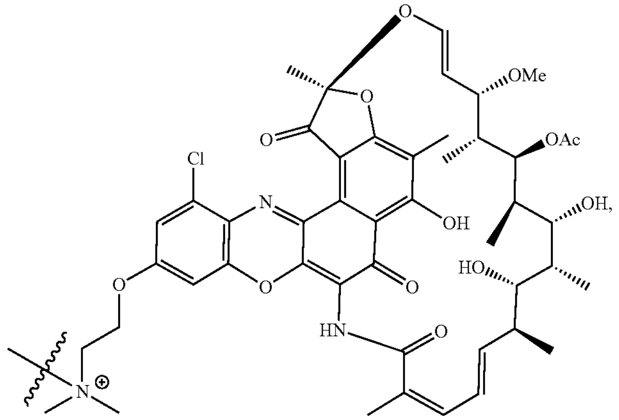
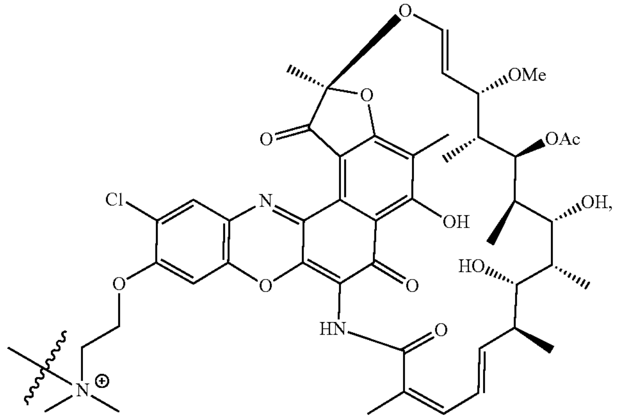
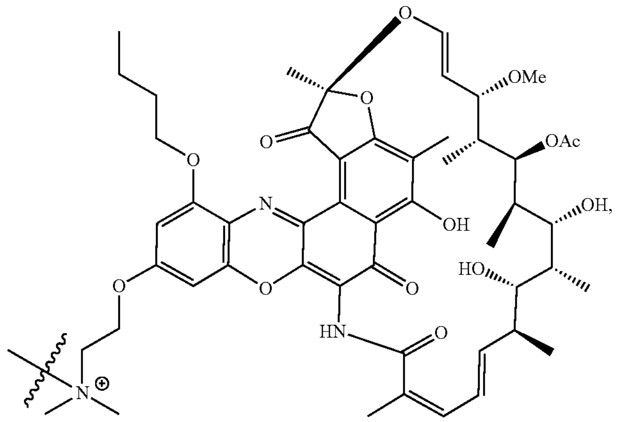

-continued
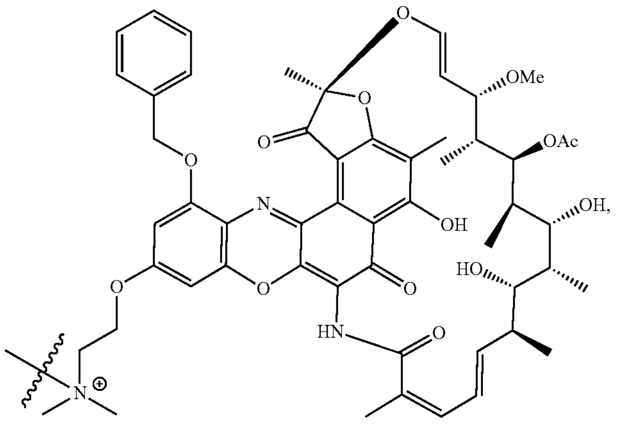
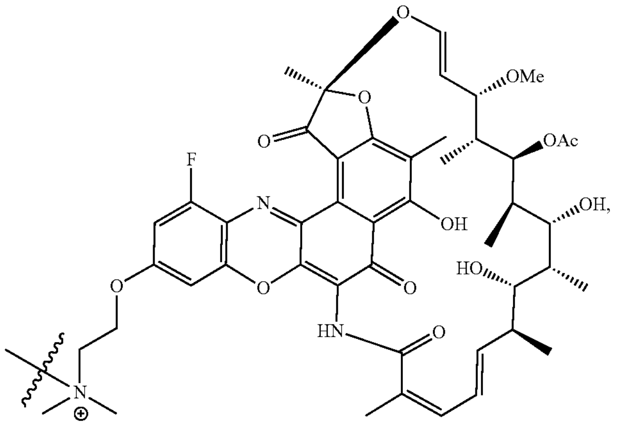
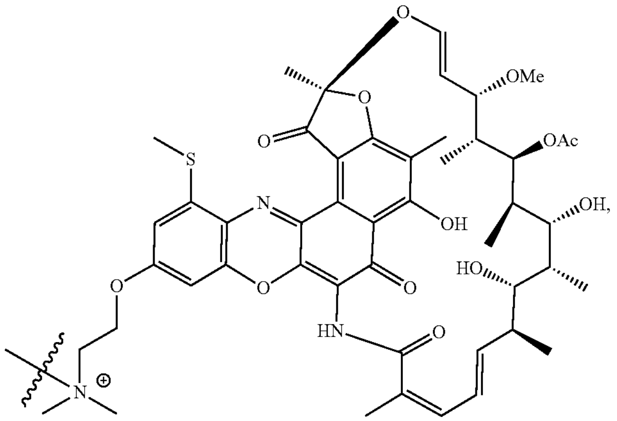
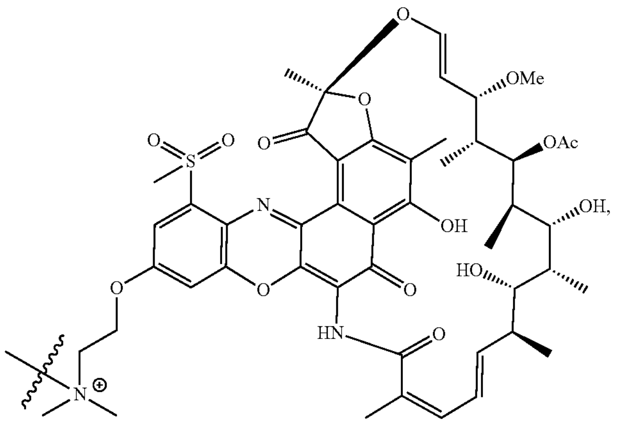

-continued
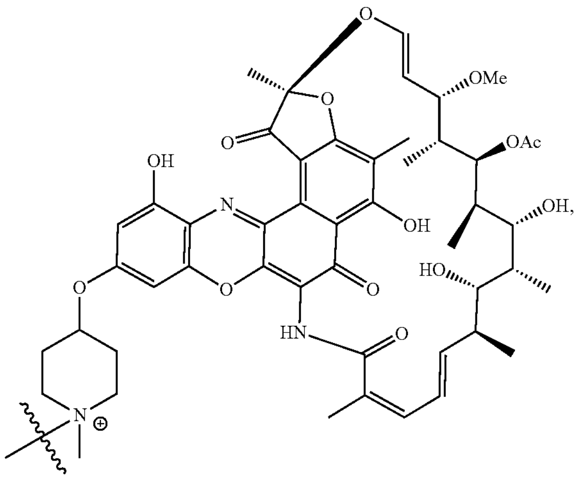
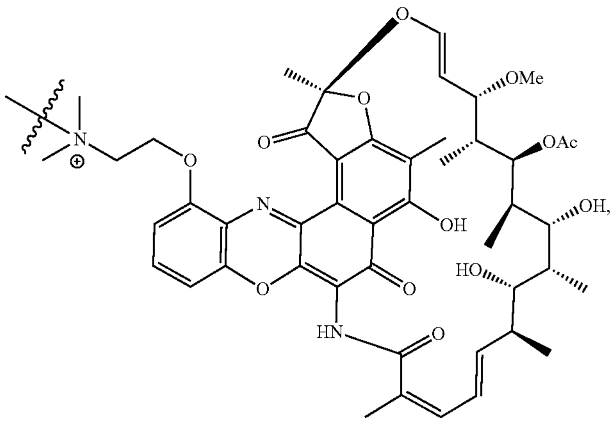
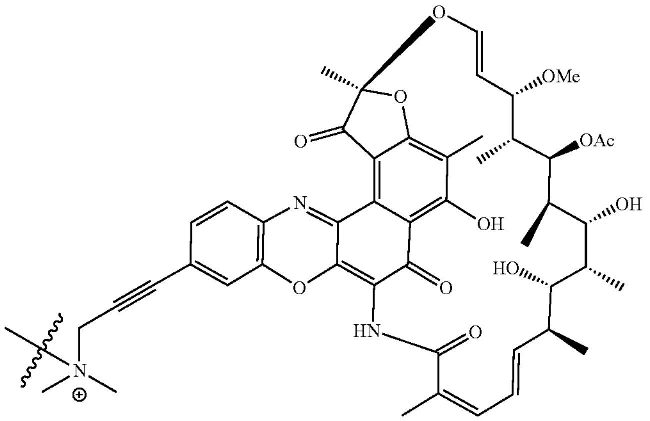
, and

-continued
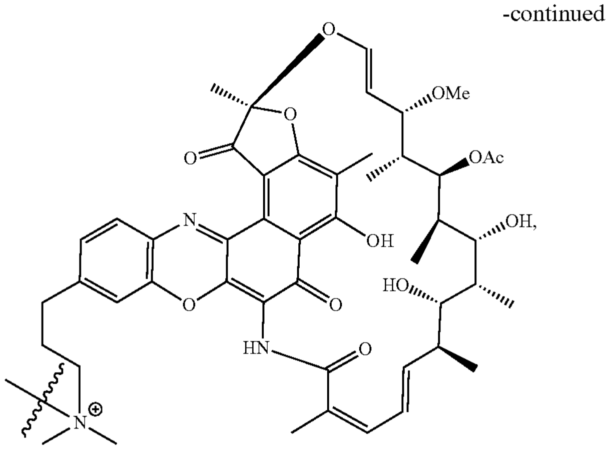
wherein the
is the bond to the linker.
In one aspect, the present disclosure provides an antibody-drug conjugate having the structure of Formula (XXII):
(XXII)
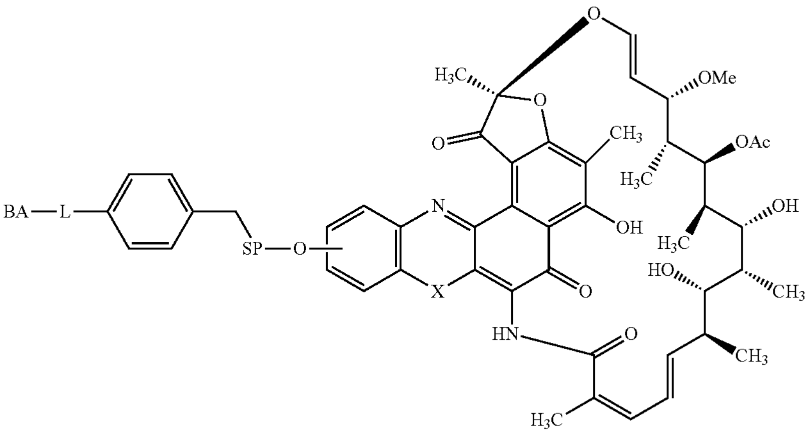
wherein:
BA is an antibody, or an antigen-binding fragment thereof,
L is a linker;
SP is a spacer group selected from
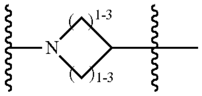
;
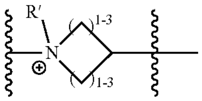
;
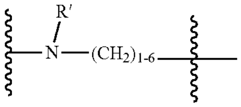
;
-continued
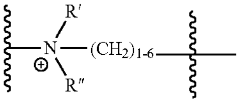
;
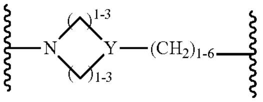
;
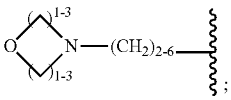
;
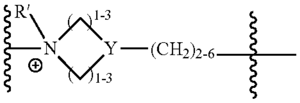
;

-continued

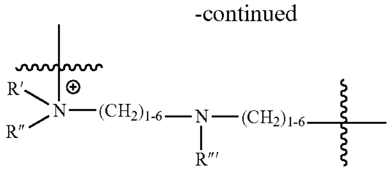

, and

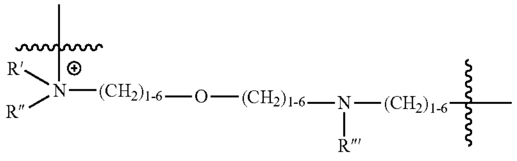

wherein the symbol represents the point of attachment; and R', R" and R"' are selected from a hydrogen, a $C_1$-$C_6$ aliphatic hydrocarbon, and a protecting group selected from Fluorenylmethyloxycarbonyl ($F_{MOC}$) and tert-Butyloxycarbonyl ($B_{OC}$), or wherein R' and R" together form an aliphatic monocyclic, an aliphatic bicyclic, or an aliphatic polycyclic structure;

Y is C or N;

R' and R" are independently at each occurrence selected from a hydrogen and a $C_{1-6}$ alkyl, and X is selected from —O—, —S—, and —NR*.

In one embodiment, the antibody is an anti-MSR1 antibody, or the antigen-binding fragment thereof, comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, comprises:

(i) a HCDR1 domain comprising an amino acid sequence selected from the group consisting of SEQ ID NOs: 4, 36, 52, 92, and 284;

(ii) a HCDR2 domain comprising an amino acid sequence selected from the group consisting of SEQ ID NOs: 6, 38, 54, 94, and 286;

(iii) a HCDR3 domain comprising an amino acid sequence selected from the group consisting of SEQ ID NOs: 8, 40, 56, 96, and 288;

(iv) a LCDR1 domain comprising an amino acid sequence selected from the group consisting of SEQ ID NOs: 12, 44, 60, 100, and 292;

(v) a LCDR2 domain comprising an amino acid sequence selected from the group consisting of SEQ ID NOs: 14, 46, 62, 102, and 294; and (vi) a LCDR3 domain comprising an amino acid sequence selected from the group consisting of SEQ ID NOs: 16, 48, 64, 104, and 296.

In one embodiment, the anti-MSR1 antibody, or the antigen-binding fragment thereof, comprises (i) a HCDR1 domain comprising an amino acid sequence of SEQ ID NO: 52;

(ii) a HCDR2 domain comprising an amino acid sequence of SEQ ID NO: 54;

(iii) a HCDR3 domain comprising an amino acid sequence of SEQ ID NO: 56;

(iv) a LCDR1 domain comprising an amino acid sequence of SEQ ID NO: 60;

(v) a LCDR2 domain comprising an amino acid sequence of SEQ ID NO: 62; and (vi) a LCDR3 domain comprising an amino acid sequence of SEQ ID NO: 64.

In one embodiment, the anti-MSR1 antibody, or the antigen-binding fragment thereof, comprises a N297Q mutation.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTA antibody, or the antigen-binding fragment thereof, may comprise:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTA antibody, or the antigen-binding fragment thereof, may comprise:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation (EU numbering) in the light chain.

In one embodiment, the anti-WTA antibody, or the antigen-binding fragment thereof, is derived from antibody 4497 described in US Patent Application Publication 20140356375 (which is incorporated herein by reference in its entirety). In one embodiment, the anti-WTA antibody is derived from antibody 4497 and further comprises a V205C mutation in the light chain.

In one embodiment, the anti-WTA antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTA antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTA antibody or antigen binding fragment thereof comprises an HCVR amino acid sequence of SEQ ID NOs: 586, and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589. In some embodiments, the anti-WTA antibody, or the antigen-binding fragment thereof comprises a V205C mutation in the light chain.

In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiments, the anti-Protein A antibody, further comprises a H435R and a Y436F mutation (EU numbering) in the heavy chain Fc. In one embodiment, anti-Protein A antibody further comprises a C103S mutation in the light chain. In one embodiment, the anti-Protein A antibody, or antigen-binding fragment thereof, is conjugated to a compound of the present disclosure at light chain position 103.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

In one embodiment, L is a linker having the formula

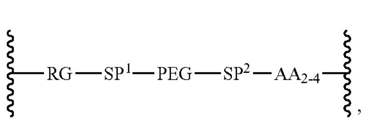

wherein

RG is selected from a maleimide, a N-hydroxy succinimide, or a succinimide;

$SP^1$ and $SP^2$ are independently absent or a spacer group selected from the group consisting of

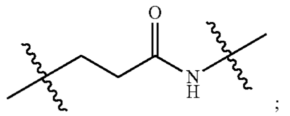 [SMILES: *CCC(=O)N*]

$C_{1-6}$ alkyl, —NH—, —C(O)—, $—CH_2—CH_2—C(O)—NH—$, $—(CH)_u—C(O)—NH—$, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8;

$AA_{2-4}$ is a peptide unit comprising from 2 to 4 amino acids, and

PEG is a polyethylene glycol chain comprising between 1 and 30 polyethylene glycol residues.

In one embodiment, $AA_{2-4}$ is a dipeptide selected from valine-citrulline; citrulline-valine; valine-alanine; alanine-valine; valine-glycine, glycine-valine, or alanine-glycine, alanine-alanine.

In one embodiment, $AA_{2-4}$ is valine-citrulline.

In one embodiment, SP is

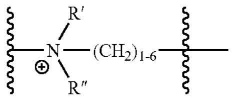

and R' and R" are each a $C_{1-6}$ alkyl.

In one embodiment, SP is

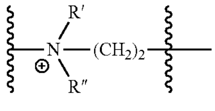

R' and R" are each methyl.

In one embodiment, $SP^1$ and $SP^2$ are each

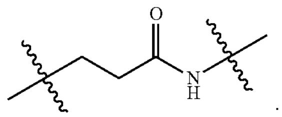 [SMILES: *CCC(=O)N*]

In one embodiment, PEG comprises 8 polyethylene glycol units.

In one embodiment, BA is an antibody, or an antigen-binding fragment thereof;

L is a linker having the formula

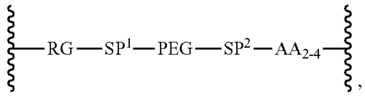

wherein

RG is selected from a maleimide or a succinimide;

$SP^1$ and $SP^2$ are each

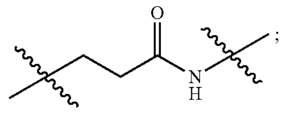

$AA_{2-4}$ is valine-citrulline;

PEG is a polyethylene glycol chain comprising 8 polyethylene glycol residues

SP is

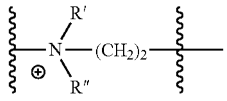

and R" and R' and R" are each methyl, and

X is —O—.

In one embodiment, the antibody-drug conjugate has a structure:

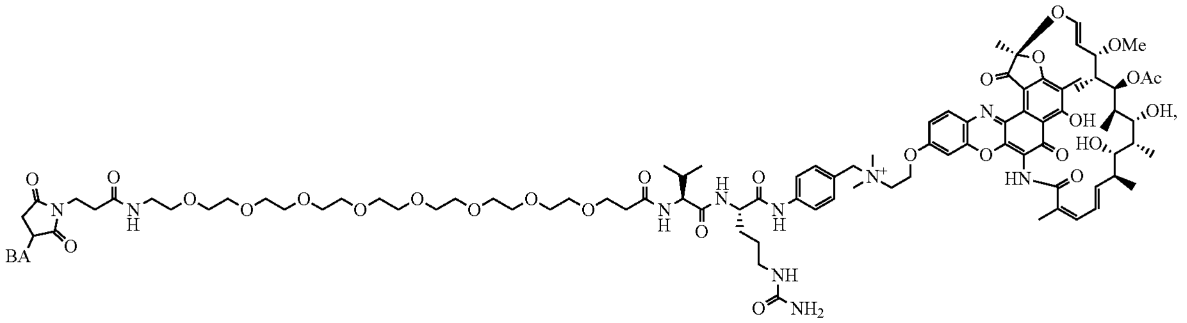

wherein BA is an antibody, or an antigen-binding fragment thereof.

In another aspect, the present disclosure provides an isolated antibody or antigen binding fragment thereof, wherein the antibody or antigen binding fragment thereof is conjugated, directly or through a linker or a linker-spacer, to a payload having the structure selected from the group consisting of:

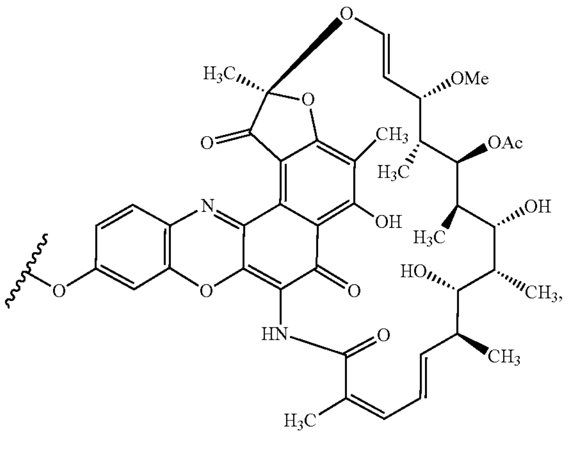

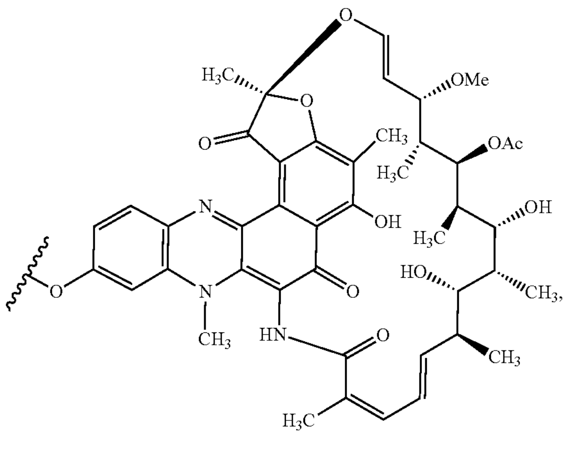

-continued
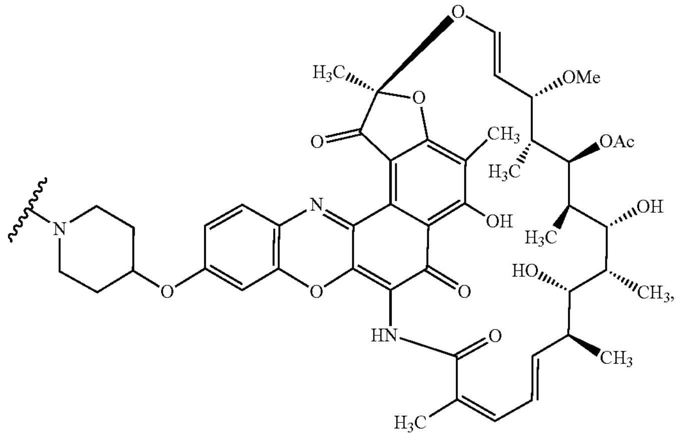
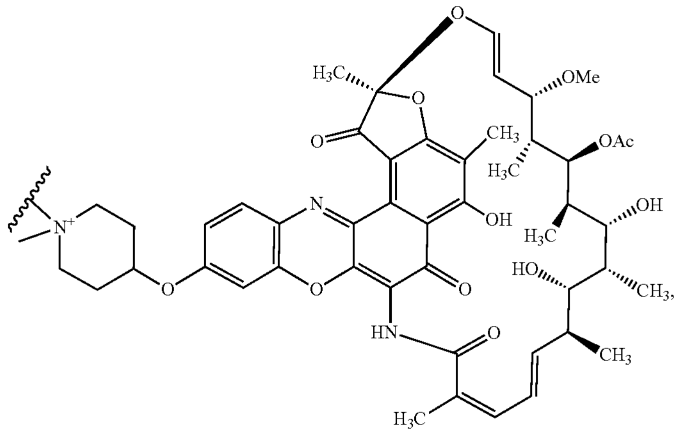
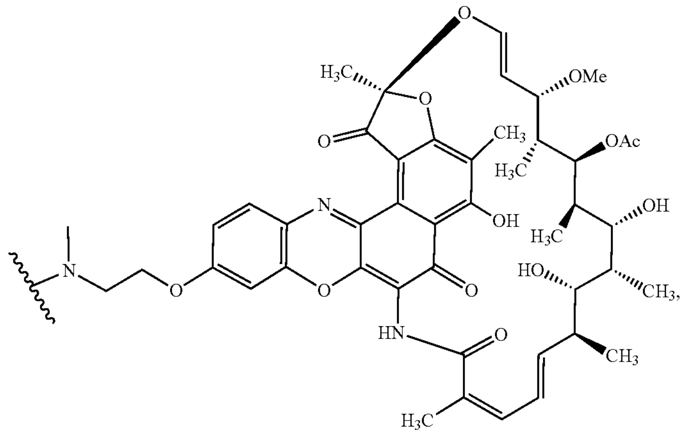

-continued
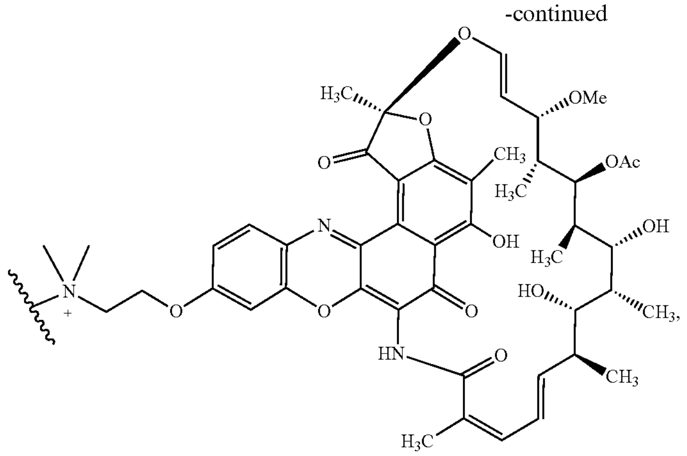
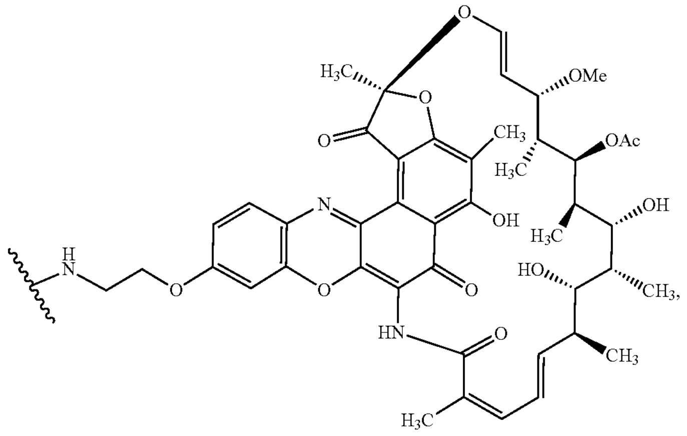
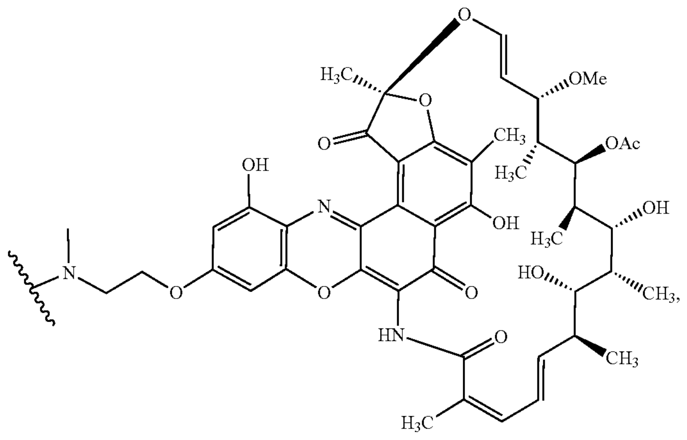

-continued
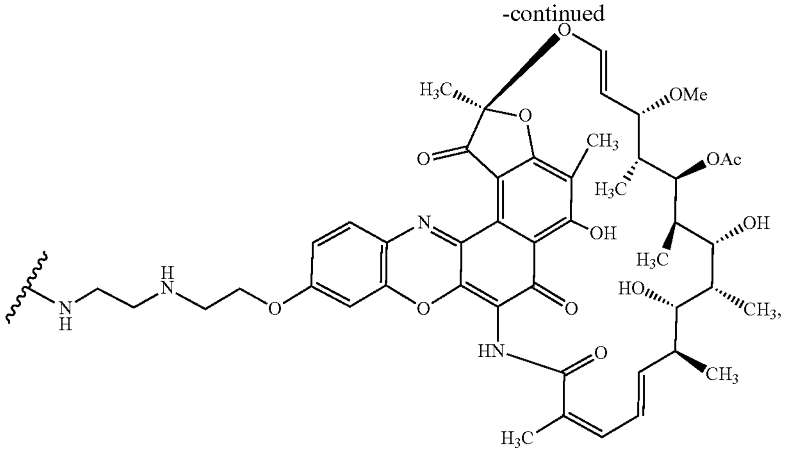
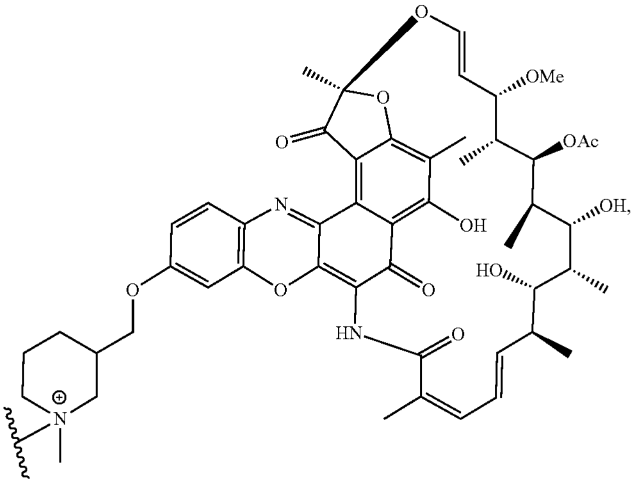
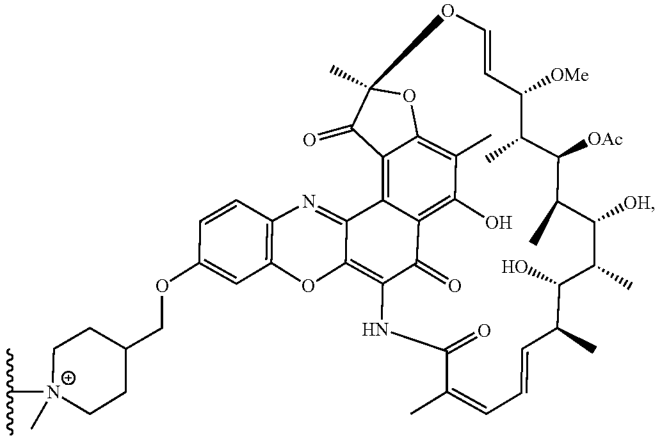

-continued
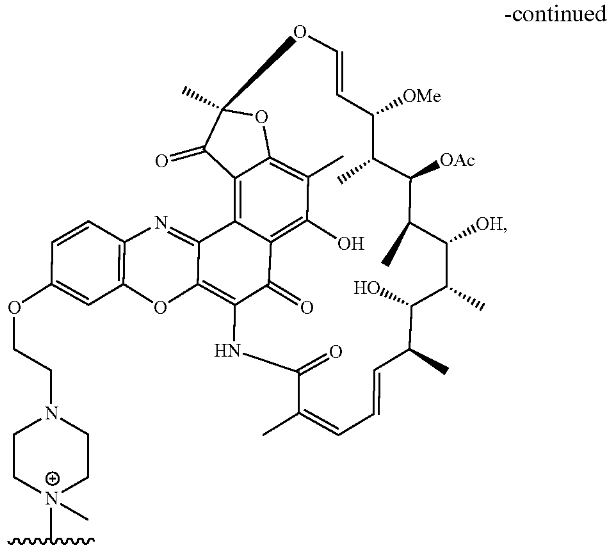
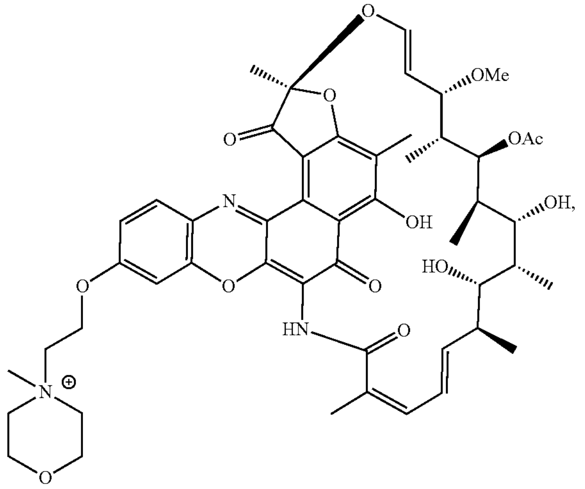
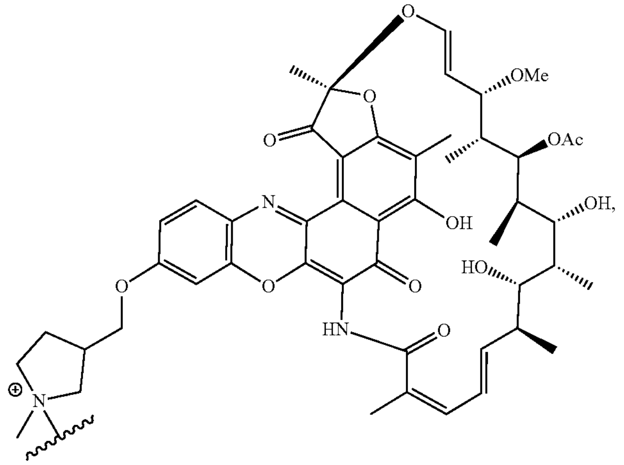

-continued
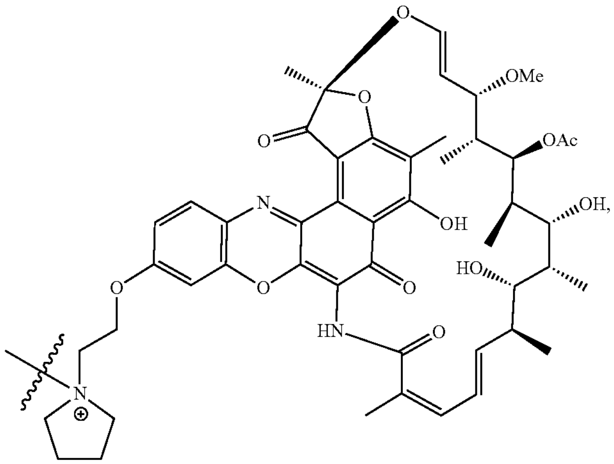
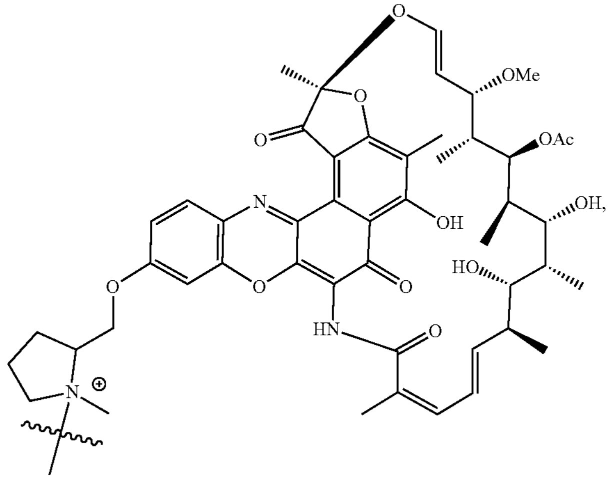
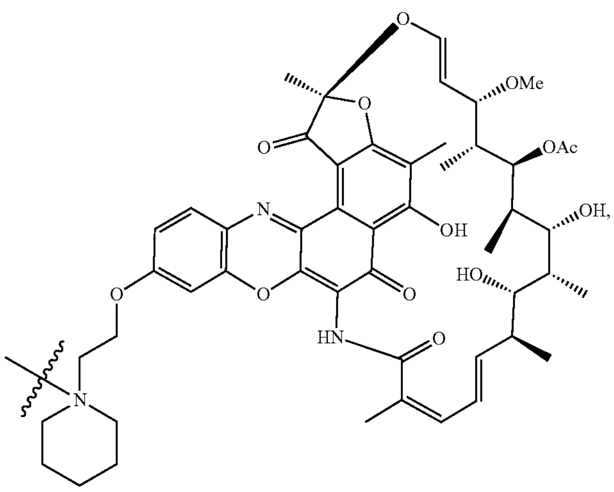

-continued
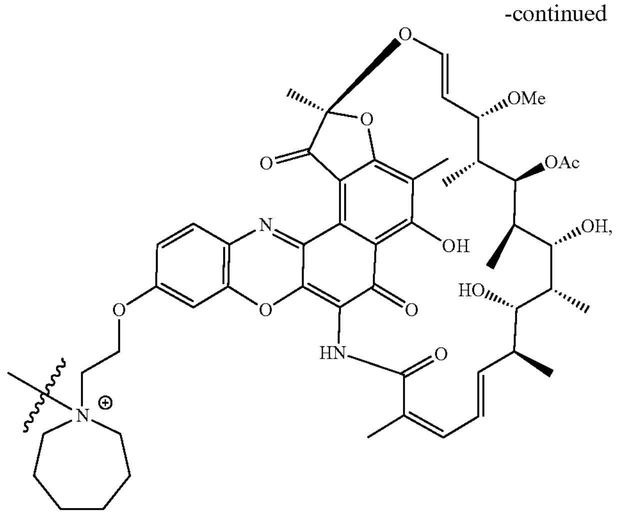
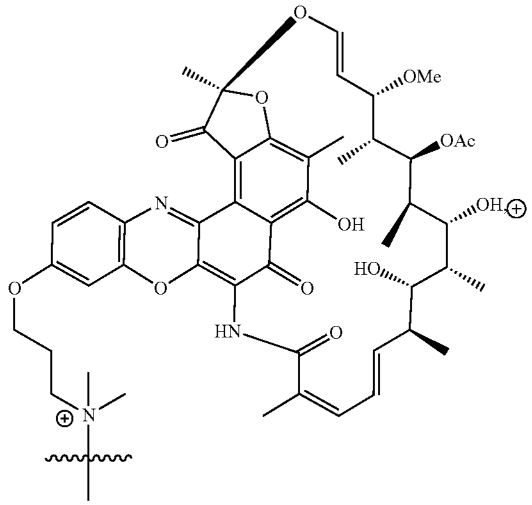
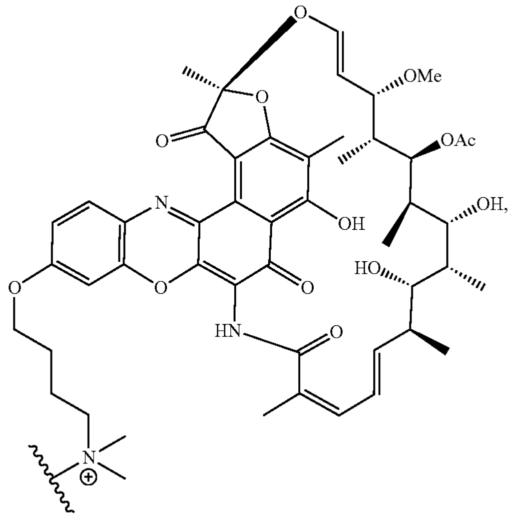

-continued
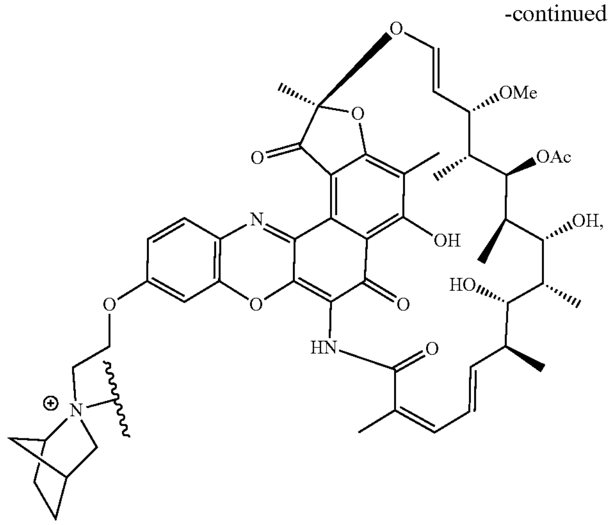
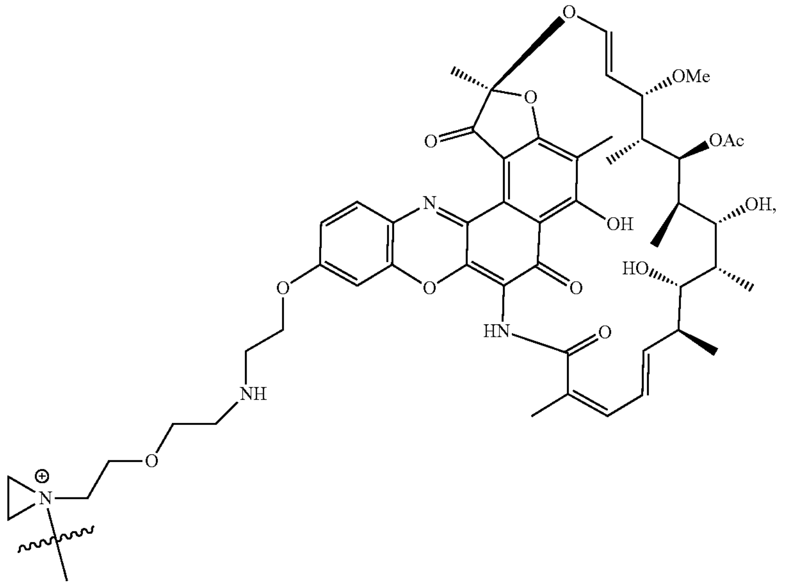
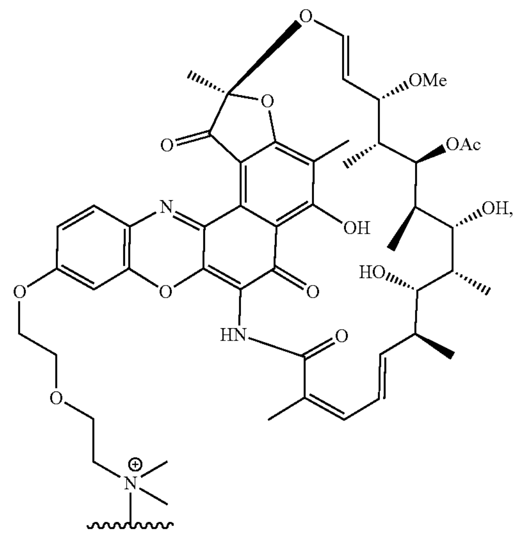
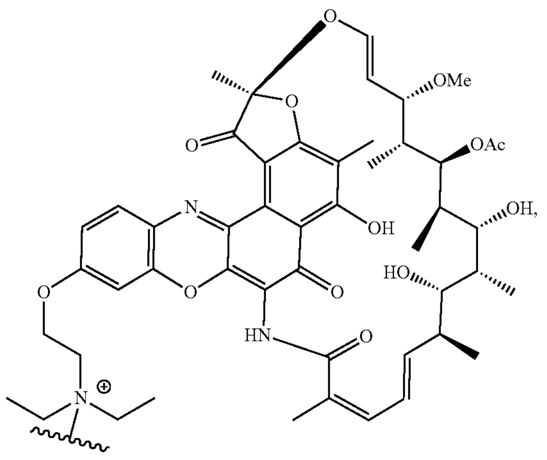

-continued
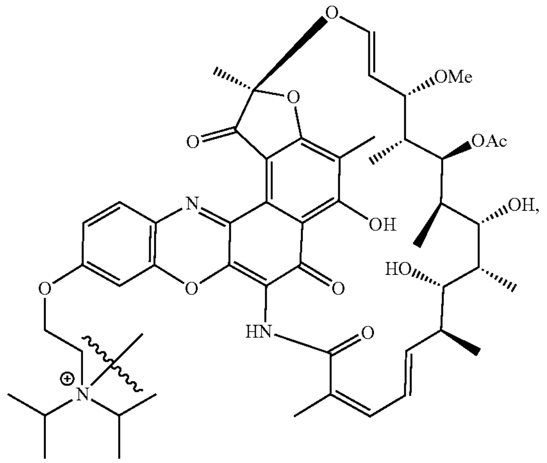
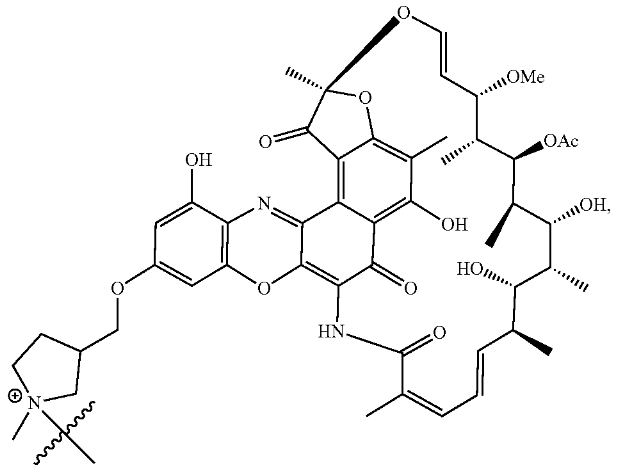
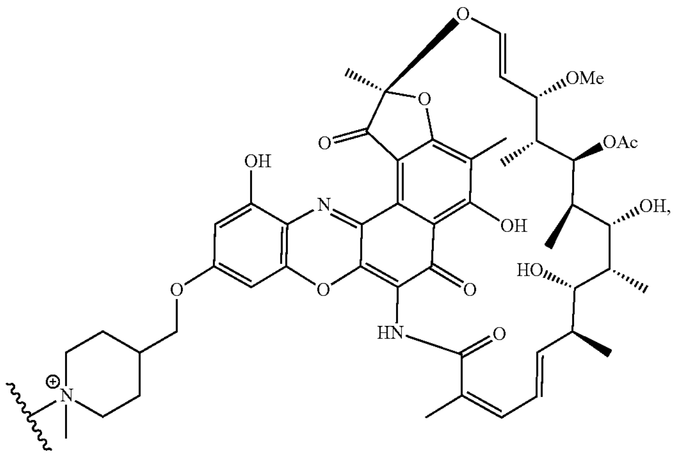

-continued
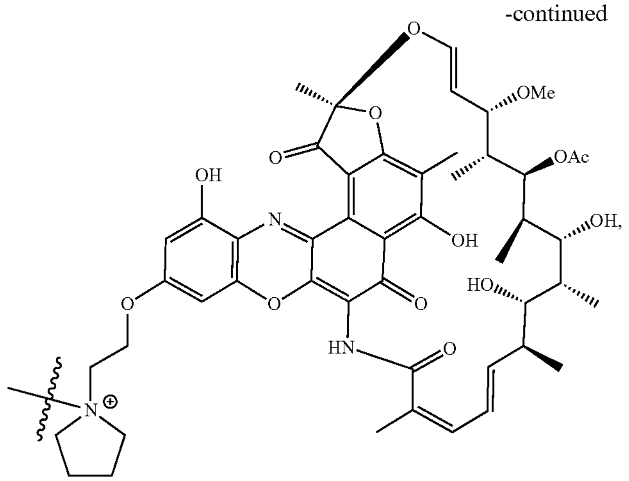
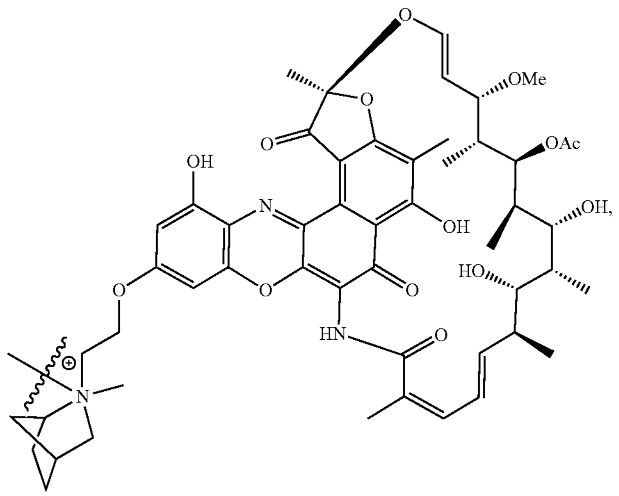
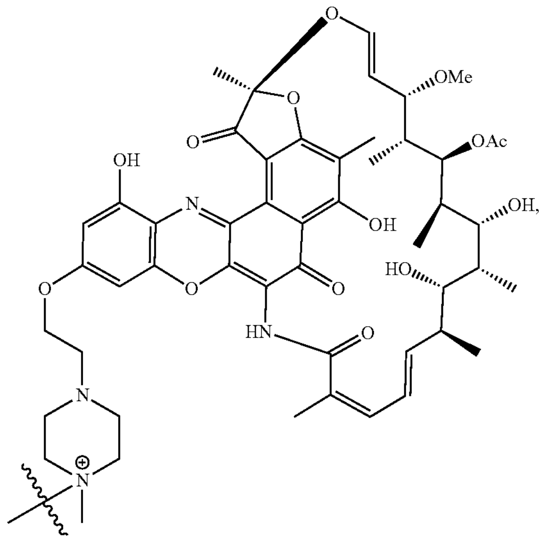

-continued
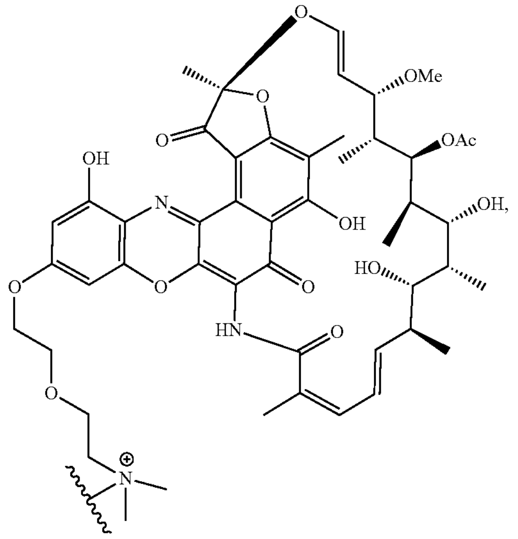
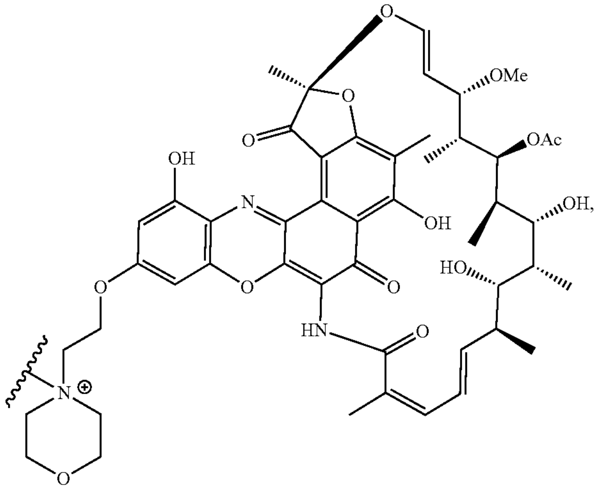
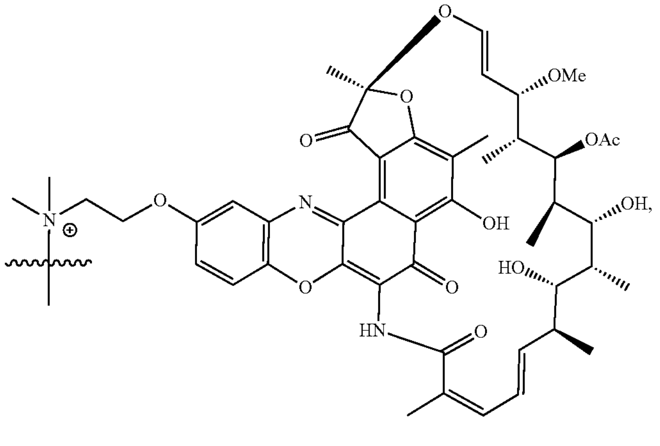

-continued
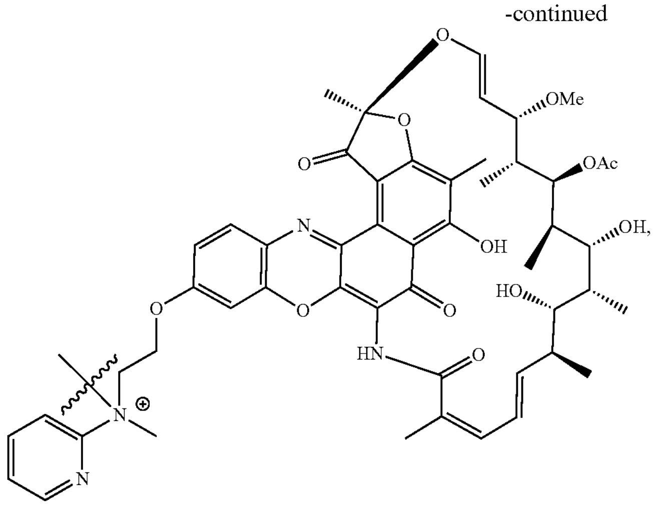
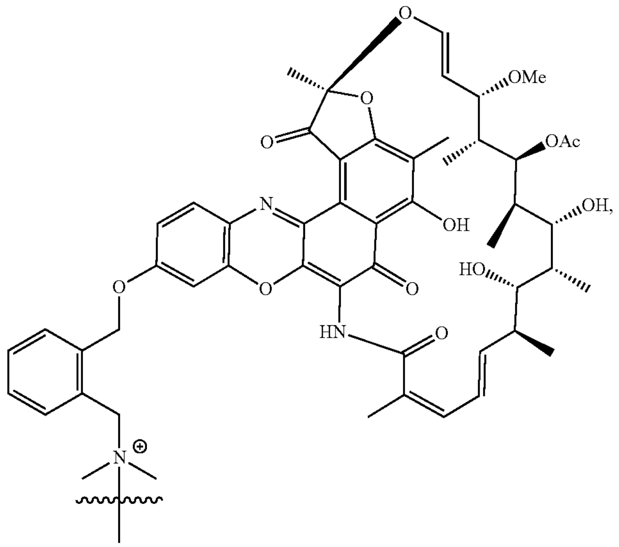
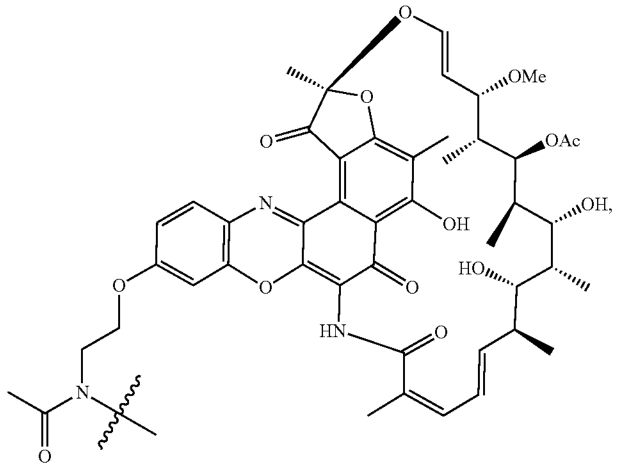

-continued
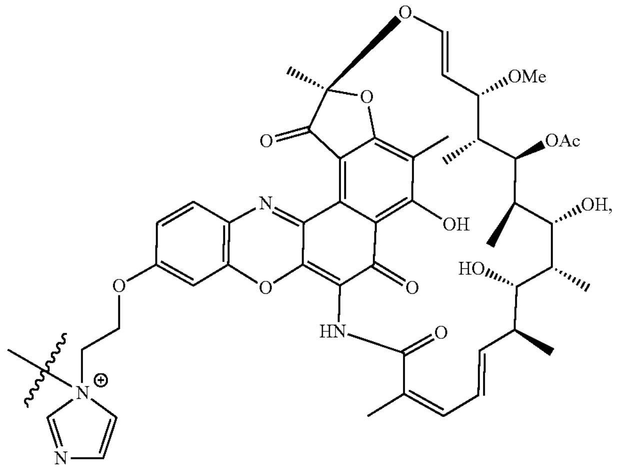
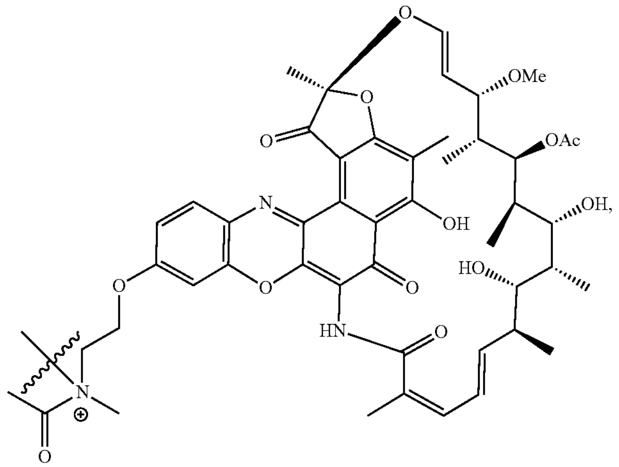
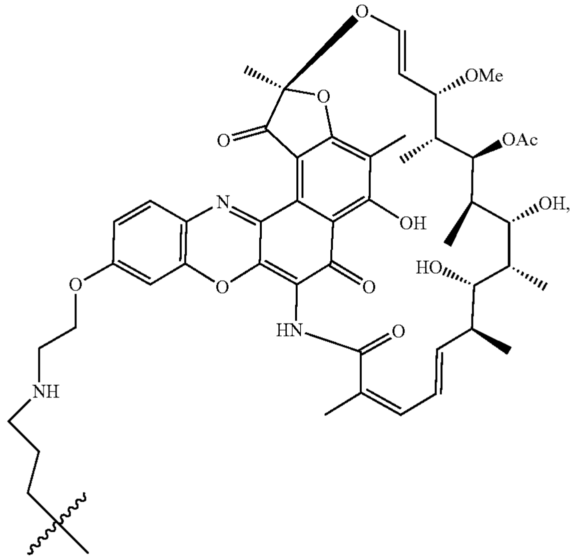

-continued
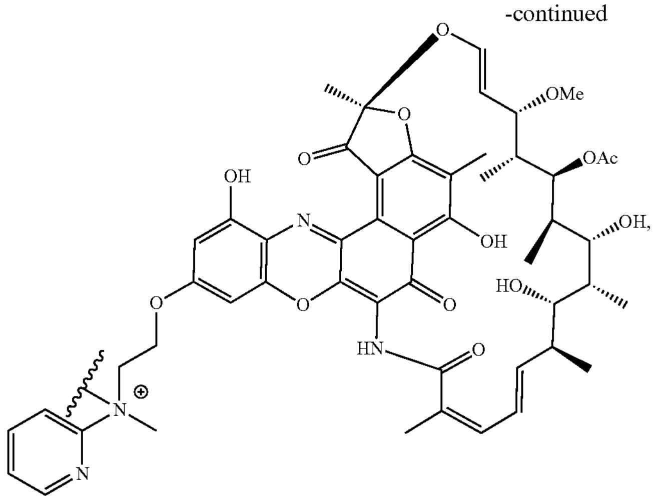
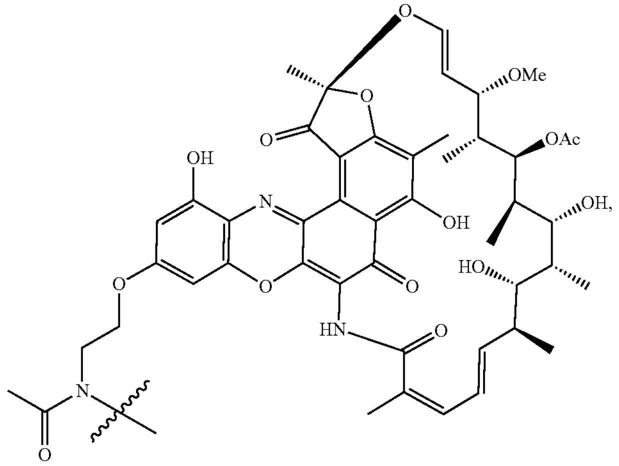
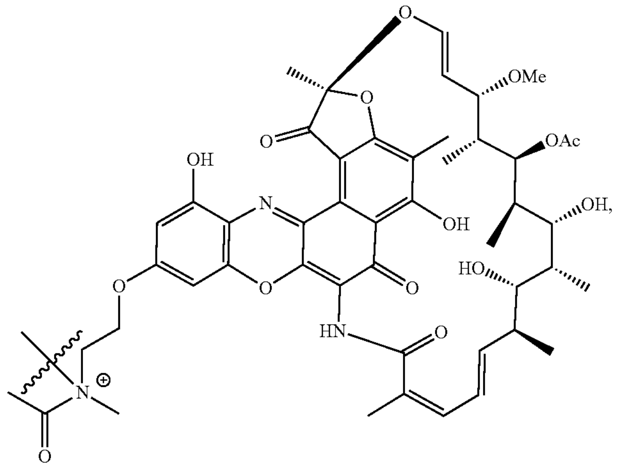

-continued
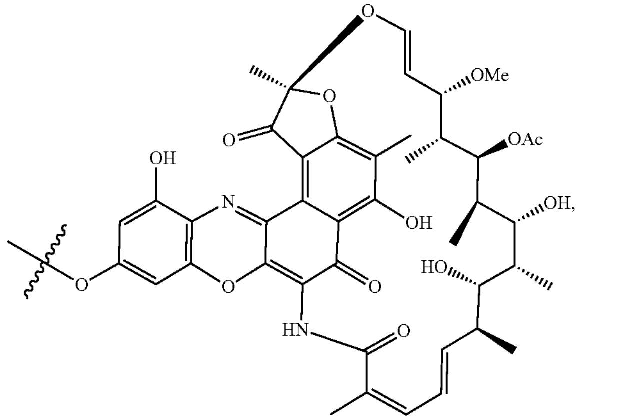
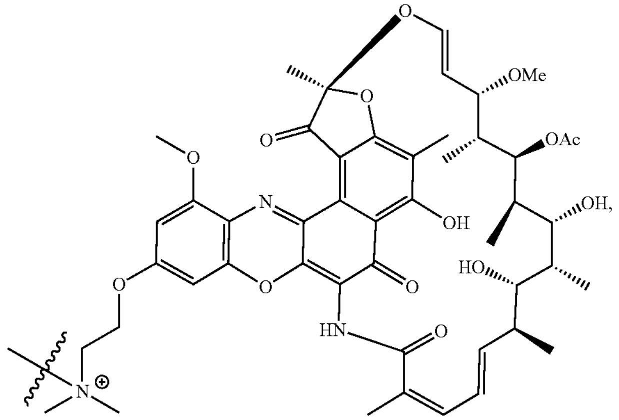
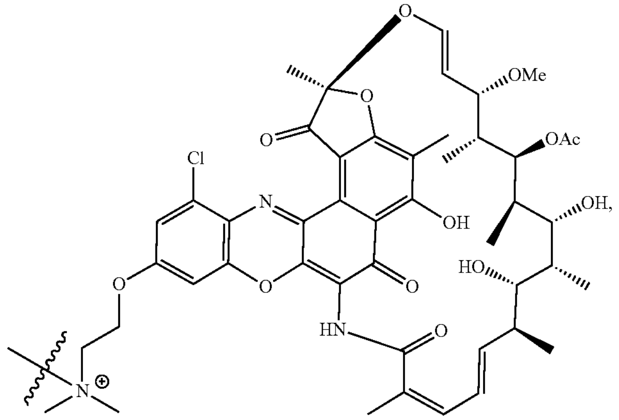
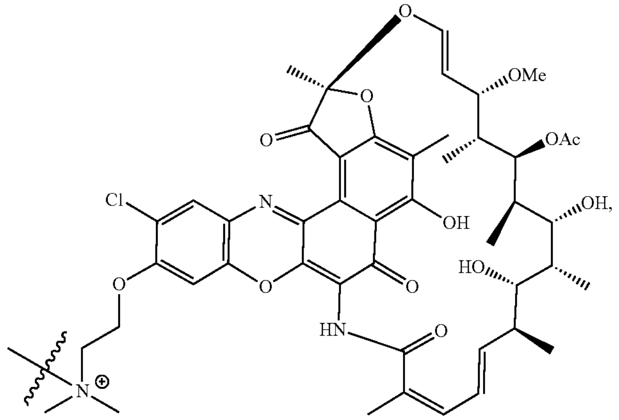

-continued
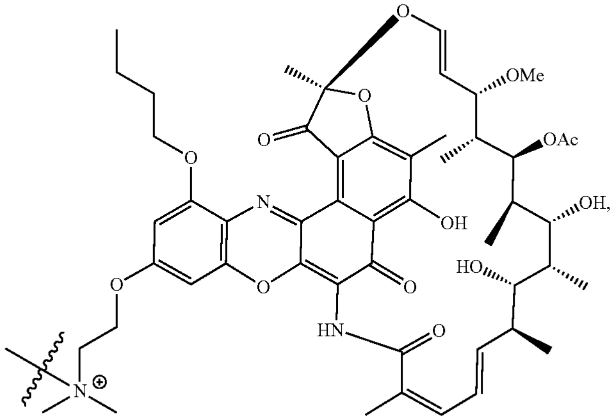
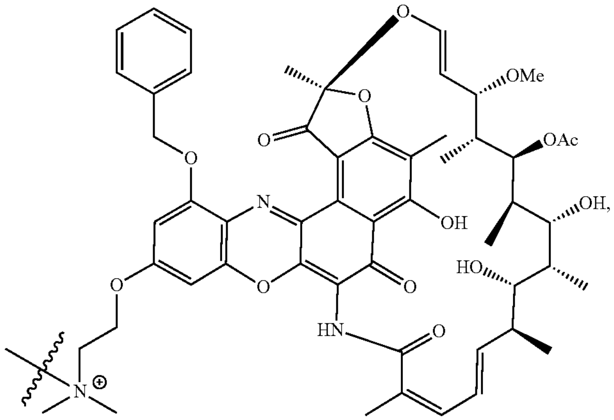
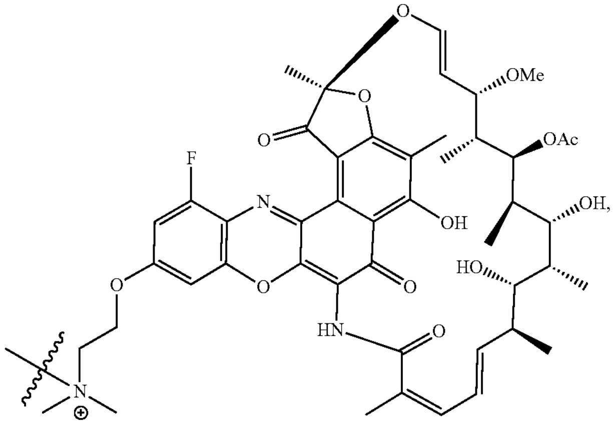

-continued
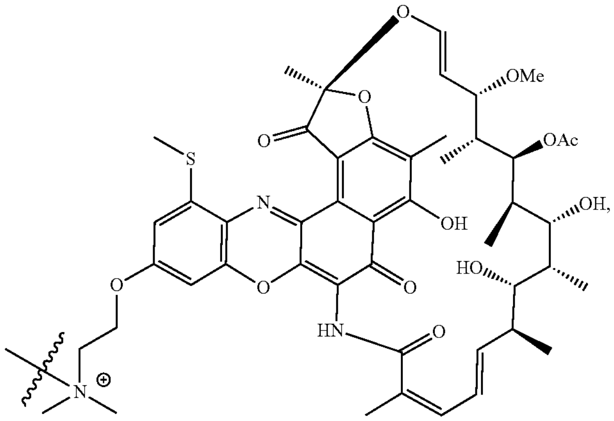
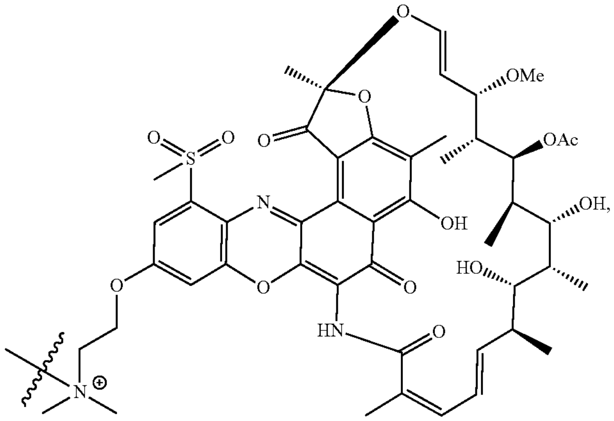
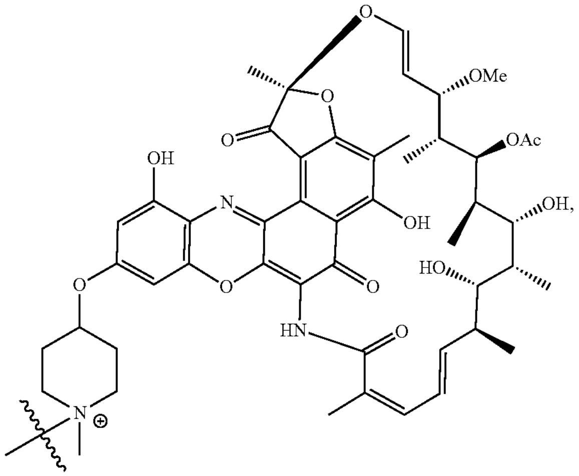

-continued
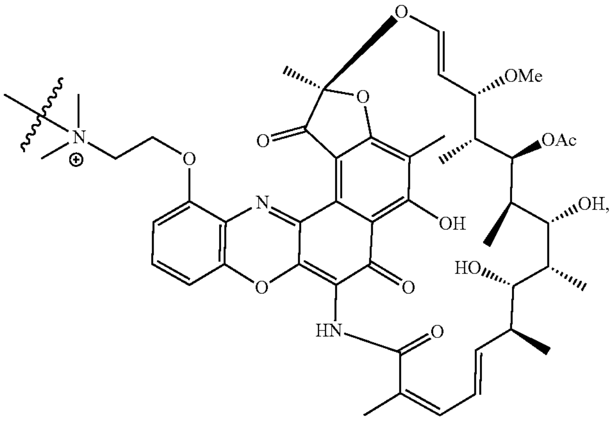
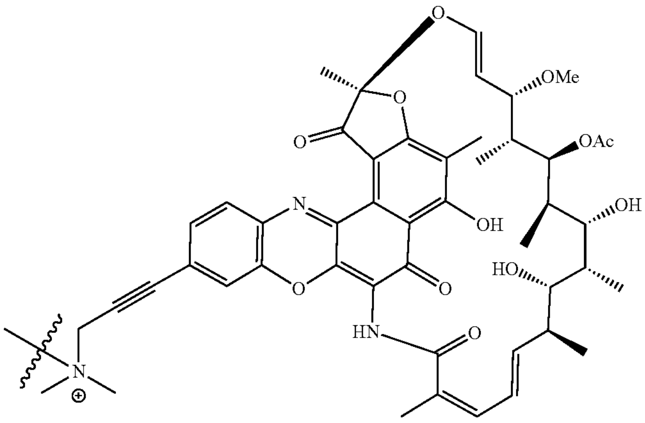
, and
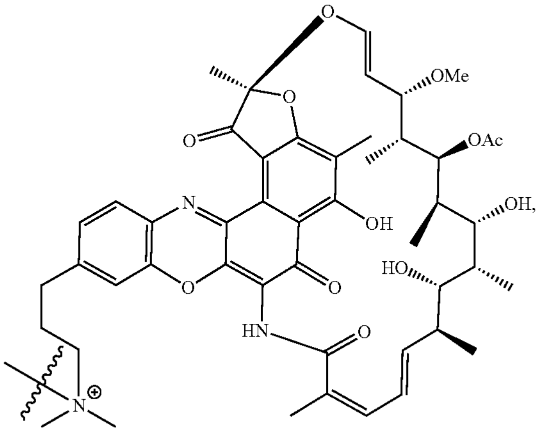

In one embodiment, the payload has the structure selected from:

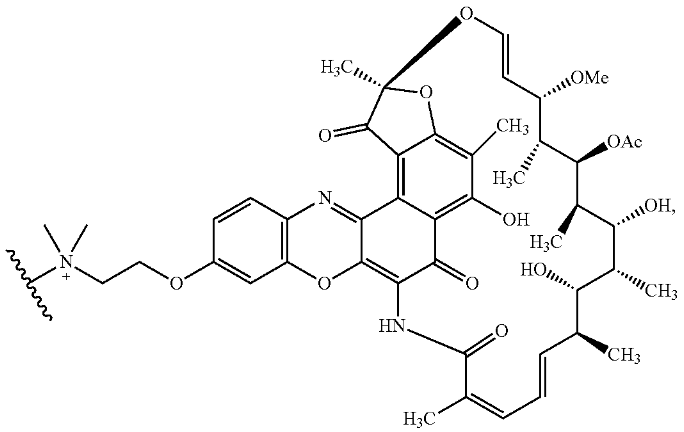

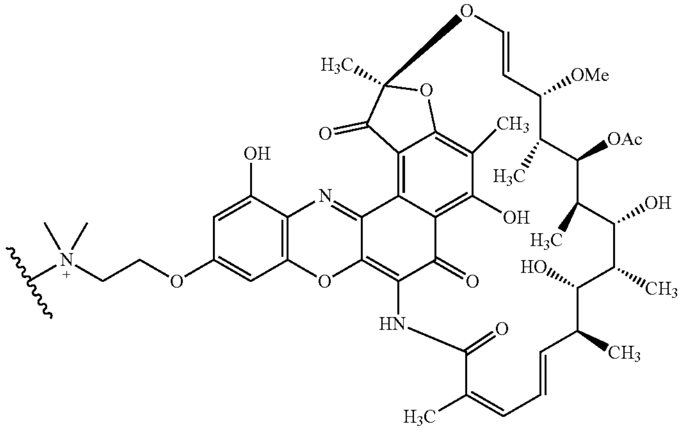

and

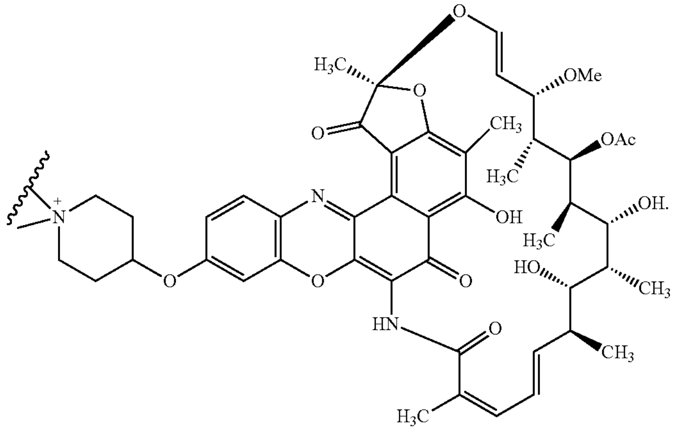

In one embodiment, the payload is conjugated through a linker, the linker having the structure:

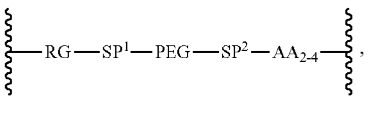

wherein

RG is selected from a maleimide or a succinimide;

$SP^1$ and $SP^2$ are independently absent or a spacer group selected from the group consisting of

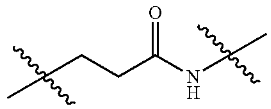

;

$C_{1-6}$ alkyl, —NH—, —C(O)—, —$CH_2$—$CH_2$—C(O)—NH—, —$(CH)_u$—C(O)—NH—, (—$CH_2$—$CH_2$—O$)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

$AA_{2-4}$ is a peptide unit comprising from 2 to 4 amino acids, and

PEG is a polyethylene glycol chain comprising between 1 and 30 polyethylene glycol residues.

In one embodiment, $AA_{2-4}$ is a dipeptide selected from valine-citrulline; citrulline-valine; valine-alanine; alanine-valine; valine-glycine, or glycine-valine.

In one embodiment, $AA_{2-4}$ is valine-citrulline.

In one embodiment, SP is

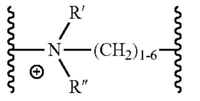

and R' and R" are each a $C_{1-6}$ alkyl.

In one embodiment, SP is

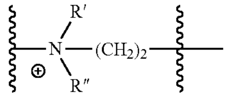

and R' and R" are each methyl.

In one embodiment, $SP^1$ and $SP^2$ are each

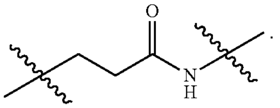

In one embodiment, PEG comprises 8 polyethylene glycol units.

In one embodiment, the payload is conjugated through a linker having the structure:

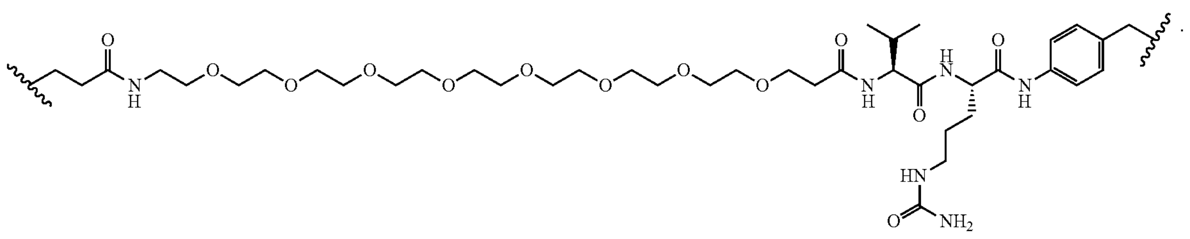

In one embodiment, the payload is conjugated through a linker, the linker-payload having the structure:

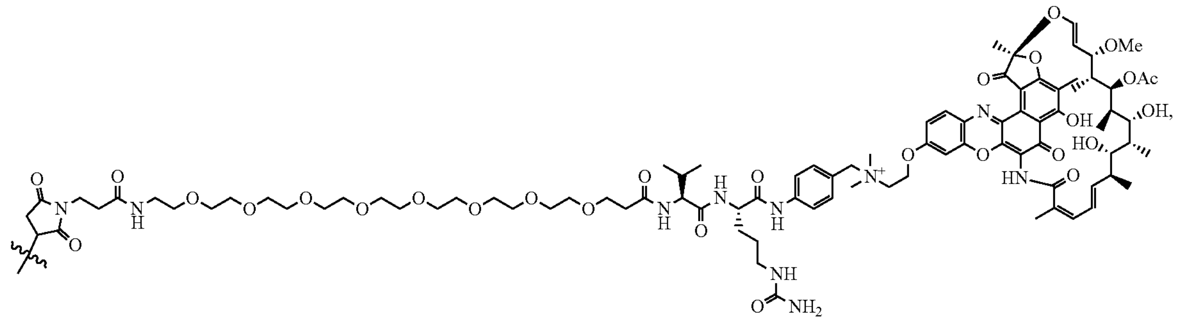

wherein the

is the bond to the antibody or the antigen-binding fragment thereof.

In one embodiment, the payload is conjugated through a linker, the linker-payload having the structure:

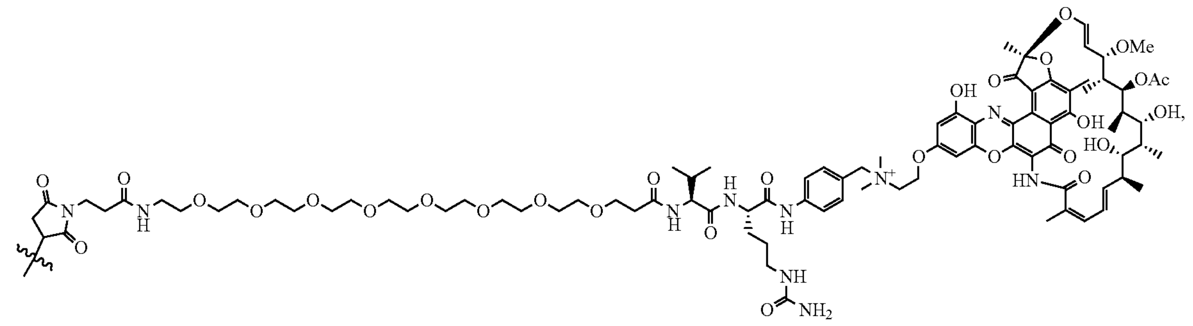

wherein the

is the bond to the antibody or the antigen-binding fragment thereof.

In one embodiment, the antibody, or the antigen-binding fragment thereof, that binds macrophage scavenger receptor 1 (MSR1) comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, comprises:

(i) a HCDR1 domain comprising an amino acid sequence selected from the group consisting of SEQ ID NOs: 4, 36, 52, 92, and 284;

(ii) a HCDR2 domain comprising an amino acid sequence selected from the group consisting of SEQ ID NOs: 6, 38, 54, 94, and 286;

(iii) a HCDR3 domain comprising an amino acid sequence selected from the group consisting of SEQ ID NOs: 8, 40, 56, 96, and 288;

(iv) a LCDR1 domain comprising an amino acid sequence selected from the group consisting of SEQ ID NOs: 12, 44, 60, 100, and 292;

(v) a LCDR2 domain comprising an amino acid sequence selected from the group consisting of SEQ ID NOs: 14, 46, 62, 102, and 294; and (vi) a LCDR3 domain comprising an amino acid sequence selected from the group consisting of SEQ ID NOs: 16, 48, 64, 104, and 296.

In one embodiment, the anti-MSR1 antibody, or the antigen-binding fragment thereof, comprises (i) a HCDR1 domain comprising an amino acid sequence of SEQ ID NO: 52;

(ii) a HCDR2 domain comprising an amino acid sequence of SEQ ID NO: 54;

(iii) a HCDR3 domain comprising an amino acid sequence of SEQ ID NO: 56;

(iv) a LCDR1 domain comprising an amino acid sequence of SEQ ID NO: 60;

(v) a LCDR2 domain comprising an amino acid sequence of SEQ ID NO: 62; and (vi) a LCDR3 domain comprising an amino acid sequence of SEQ ID NO: 64.

In one embodiment, the anti-MSR1 antibody, or the antigen-binding fragment thereof, comprises a N297Q mutation.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTA antibody, or the antigen-binding fragment thereof, may comprise:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In one embodiment, the anti-WTA antibody, or the antigen-binding fragment thereof, may comprise: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTA antibody, or the antigen-binding fragment thereof, may comprise:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation (EU numbering) in the light chain.

In one embodiment, the anti-WTA antibody, or the antigen-binding fragment thereof, is derived from antibody 4497 described in US Patent Application Publication 20140356375 (which is incorporated herein by reference in its entirety). In one embodiment, the anti-WTA antibody is derived from antibody 4497 and further comprises a V205C mutation in the light chain.

In one embodiment, the anti-WTA antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTA antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTA antibody or antigen binding fragment thereof comprises an HCVR amino acid sequence of SEQ ID NOs: 586, and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589. In some embodiments, the anti-WTA antibody, or the antigen-binding fragment thereof comprises a V205C mutation in the light chain.

In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In some embodiments, the anti-Protein A antibody, or the antigen-binding fragment thereof, comprises a H435R and a Y436F mutation (EU numbering) in the heavy chain Fc.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiments, the anti-Protein A antibody, further comprises a H435R and a Y436F mutation (EU numbering) in the heavy chain Fc. In one embodiment, anti-Protein A antibody further comprises a C103S mutation in the light chain. In one embodiment, the anti-Protein A antibody, or antigen-binding fragment thereof, is conjugated to a compound of the present disclosure at light chain position 103.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

In one aspect, the present disclosure provides a method of preventing or inhibiting growth of a bacterium comprising administering an effective amount of an antibody-drug conjugate as described herein.

In one embodiment, the bacterium is a Gram-positive bacterium.

In one embodiment, the bacterium is a penicillin-resistant bacterium.

In one embodiment, the bacterium is *Staphylococcus aureus.*

In one embodiment, the bacterium is selected from methicillin-resistant *Staphylococcus aureus* (MRSA), vancomycin-resistant *Staphylococcus aureus* (VRSA), and methicillin-susceptible *Staphylococcus aureus* (MSSA).

In one aspect, the present disclosure provides a method of treating a bacterial infection in a subject in need of such treatment comprising administering to the subject an effective amount of an antibody-drug conjugate as described herein.

In one embodiment, the bacterial infection is a Gram-positive bacterial infection.

In one embodiment, the bacterial infection is a penicillin-resistant bacterial infection.

In one embodiment, the bacterial infection is a *Staphylococcus aureus* infection.

In one embodiment, the bacterial infection is selected from a methicillin-resistant *Staphylococcus aureus* (MRSA) infection, a vancomycin-resistant *Staphylococcus aureus* (VRSA) infection, and a methicillin-susceptible *Staphylococcus aureus* (MSSA) infection.

In one embodiment, the bacterial infection is an intracellular bacterial infection.

In one embodiment, the subject is human.

In one embodiment, the method further comprises administering a second therapeutic agent.

In one embodiment, the second therapeutic agent is a second antibiotic.

In one embodiment, the second antibiotic is effective against *Staphylococcus aureus*.

In one embodiment, the second antibiotic is selected from an aminoglycoside, a beta-lactam, a macrolide, a cyclic peptide, a tetracycline, a fluoroquinoline, a fluoroquinolone, and an oxazolidinone.

In one embodiment, the second antibiotic is selected from clindamycin, novobiocin, retapamulin, daptomycin, sitafloxacin, teicoplanin, triclosan, napthyridone, radezolid, doxorubicin, ampicillin, vancomycin, imipenem, doripenem, gemcitabine, dalbavancin, and azithromycin.

In one embodiment, the antibody-drug conjugate is administered to the subject orally, topically, intranasally, intravenously, intramuscularly, or subcutaneously.

In yet another aspect, the present disclosure provides a method of preventing or treating cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, septic arthritis, mastitis, infection associated with a prosthetic joint, infection associated with a catheter, or infection associated with an implant, in a subject comprising administering to the subject an effective treatment amount of the compounds, the antibody-drug conjugates, or the pharmaceutical compositions as described herein.

These and other aspects of the present disclosure will become apparent to those skilled in the art after a reading of the following detailed description of the disclosure, including the appended claims.

DETAILED DESCRIPTION

Figure 1:
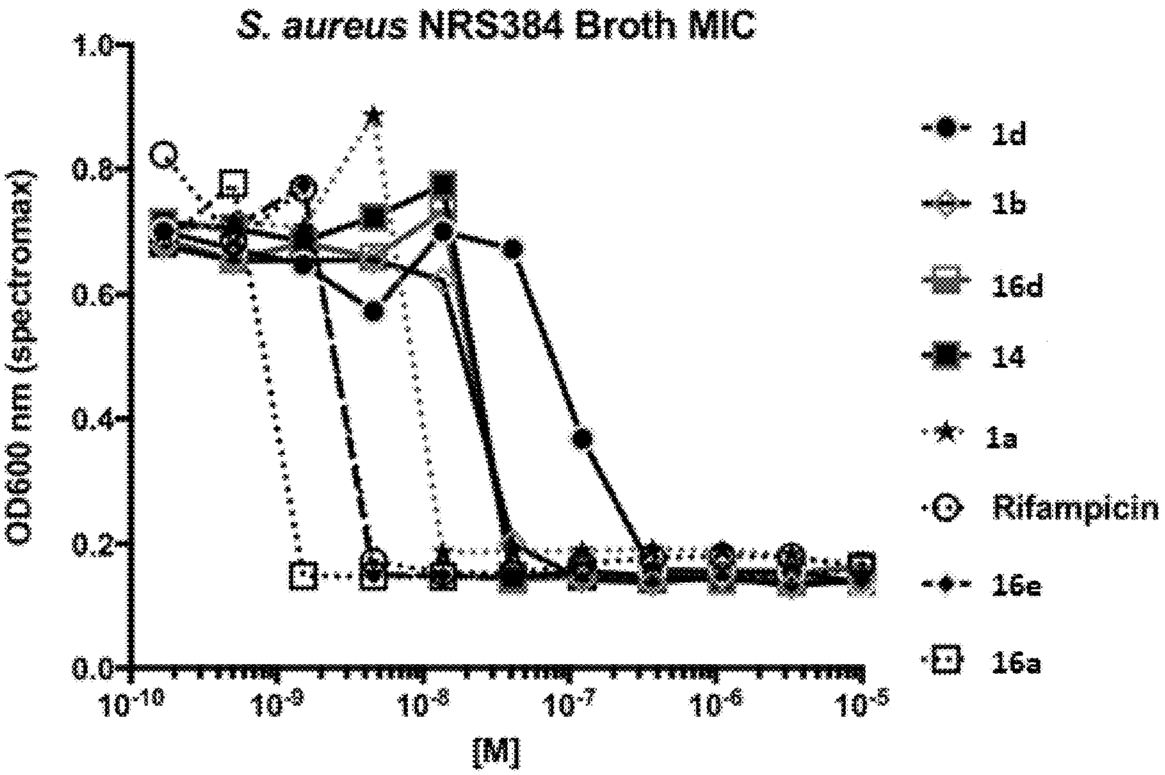
FIG. 1 is a plot of the results of the *S. aureus* growth inhibition assay conducted with rifamycin analogs according to the disclosure.

Detailed embodiments of the present disclosure are disclosed herein; however, it is to be understood that the disclosed embodiments are merely illustrative of the disclosure that may be embodied in various forms. In addition, each of the examples given in connection with the various embodiments of the disclosure is intended to be illustrative, and not restrictive. Therefore, specific structural and functional details disclosed herein are not to be interpreted as limiting, but merely as a representative basis for teaching one skilled in the art to variously employ the present disclosure.

Definitions

Unless defined otherwise, all technical and scientific terms used herein have the same meaning as commonly understood by one of ordinary skill in the art to which this disclosure belongs.

As used in this specification and the appended claims, the singular forms "a", "an", and "the" include plural references unless the context clearly dictates otherwise. Thus, for example, a reference to "a method" includes one or more methods, and/or steps of the type described herein and/or which will become apparent to those persons skilled in the art upon reading this disclosure.

The terms "treat" or "treatment" of a state, disorder or condition include: (1) preventing, delaying, or reducing the incidence and/or likelihood of the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or (2) inhibiting the state, disorder or condition, i.e., arresting, reducing or delaying the development of the disease or a relapse thereof or at least one clinical or sub-clinical symptom thereof, or (3) relieving the disease, i.e., causing regression of the state, disorder or condition or at least one of its clinical or sub-clinical symptoms. The benefit to a subject to be treated is either statistically significant or at least perceptible to the patient or to the physician.

A "subject" or "patient" or "individual" or "animal", as used herein, refers to humans, veterinary animals (e.g., cats, dogs, cows, horses, sheep, pigs, etc.) and experimental animal models of diseases (e.g., mice, rats). In one embodiment, the subject is a human.

As used herein the term "effective" applied to dose or amount refers to that quantity of a compound or pharmaceutical composition that is sufficient to result in a desired activity upon administration to a subject in need thereof. Note that when a combination of active ingredients is administered, the effective amount of the combination may or may not include amounts of each ingredient that would have been effective if administered individually. The exact amount required will vary from subject to subject, depending on the species, age, and general condition of the subject, the severity of the condition being treated, the particular drug or drugs employed, the mode of administration, and the like.

The phrase “pharmaceutically acceptable”, as used in connection with compositions of the disclosure, refers to molecular entities and other ingredients of such compositions that are physiologically tolerable and do not typically produce untoward reactions when administered to a mammal (e.g., a human). Preferably, as used herein, the term “pharmaceutically acceptable” means approved by a regulatory agency of the Federal or a state government or listed in the U.S. Pharmacopeia or other generally recognized pharmacopeia for use in mammals, and more particularly in humans.

The phrase “therapeutically effective amount,” as used herein, refers to an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

Ranges can be expressed herein as from “about” or “approximately” one particular value and/or to “about” or “approximately” another particular value. When such a range is expressed, another embodiment includes from the one particular value and/or to the other particular value.

By “comprising” or “containing” or “including” is meant that at least the named compound, element, particle, or method step is present in the composition or article or method, but does not exclude the presence of other compounds, materials, particles, or method steps, even if the other such compounds, material, particles, or method steps have the same function as what is named.

Compounds of the present disclosure include those described generally herein, and are further illustrated by the classes, subclasses, and species disclosed herein. As used herein, the following definitions shall apply unless otherwise indicated. For purposes of this disclosure, the chemical elements are identified in accordance with the Periodic Table of the Elements, CAS version, Handbook of Chemistry and Physics, 75th Ed. Additionally, general principles of organic chemistry are described in “Organic Chemistry”, Thomas Sorrell, University Science Books, Sausalito: 1999, and “March’s Advanced Organic Chemistry”, 5th Ed., Ed.: Smith, M. B. and March, J., John Wiley & Sons, New York: 2001, the entire contents of which are hereby incorporated by reference. The chemistry of protecting groups can be found, for example, in Wuts and Greene, *Greene’s Protective Groups in Organic Synthesis,* 4th Ed., John Wiley & Sons: New York, 2006.

The term “hydrocarbon” is used herein to encompass hydrocarbon radicals (otherwise referred to as “groups”) that comprise carbon and hydrogen and also encompasses derivatives thereof where in one or more carbons has been replaced by any heteroatom, such as oxygen, nitrogen, sulfur and phosphorus. The hydrocarbon of the instant disclosure is optionally substituted by oxygen, nitrogen, sulfur and phosphorus containing groups or by halogens without limitation. The term hydrocarbon encompasses straight chain, branched, cyclic or multicyclic aliphatic groups as well as aromatic and heteroaromatic groups as discussed in more detail below.

The term “optionally substituted” has the same meaning as wherein the substituted element “further comprises 0-n” of the optional element, where n is an integer, generally from 0-20, or from 0-10, or from 1-3. For example, when an aliphatic hydrocarbon optionally comprises one or more heteroatoms, this would have the same meaning as wherein the aliphatic hydrocarbon further comprises from 0-20 heteroatoms.

The term “aliphatic” or “aliphatic group”, as used herein, mean a straight-chained (i.e., unbranched), branched, substituted or unsubstituted hydrocarbon chain that is completely saturated or that contains one or more units of unsaturation, or a monocyclic hydrocarbon, bicyclic hydrocarbon, or tricyclic hydrocarbon that is completely saturated or that contains one or more units of unsaturation, but which is not aromatic (also referred to herein as “carbocycle,” “cycloaliphatic” or “cycloalkyl”), that has a single point of attachment to the rest of the molecule, and combinations thereof. In some embodiments, aliphatic groups comprise a combination (a hybrid) of a straight-chained and a cyclic aliphatic hydrocarbon. In some embodiments, aliphatic groups comprise a combination of a straight-chained and a cyclic aliphatic hydrocarbon. Unless otherwise specified, aliphatic groups contain 1-30 aliphatic carbon atoms. In some embodiments, aliphatic groups contain 1-20 aliphatic carbon atoms. In other embodiments, aliphatic groups contain 1-10 aliphatic carbon atoms. In still other embodiments, aliphatic groups contain 1-6 aliphatic carbon atoms, and in yet other embodiments, aliphatic groups contain 1, 2, 3, or 4 aliphatic carbon atoms. Suitable aliphatic groups include, but are not limited to, linear or branched, substituted or unsubstituted alkyl, alkenyl, alkynyl groups and combinations/hybrids thereof such as (cycloalkyl)alkyl, (cycloalkenyl)alkyl or (cycloalkyl)alkenyl. Simple aliphatic hydrocarbons include methyl, ethyl, propyl, butyl, t-butyl, n-butyl, pentyl, and so on.

The terms “aliphatic cyclic,” “cyclic aliphatic,” “carbocyclic,” “alicyclic” or “cycloaliphatic,” as used herein, refer to saturated or partially unsaturated cyclic aliphatic monocyclic, bicyclic, or polycyclic ring structures, as described herein, having from 3 to 14 members, wherein the aliphatic ring system is optionally substituted as defined above and described herein. Cycloaliphatic groups include, without limitation, cycyclopropyl, cyclobutyl, cyclopentyl, cyclopentenyl, cyclohexyl, cyclohexenyl, cycloheptyl, cycloheptenyl, cyclooctyl, cyclooctenyl, norbornyl, adamantyl, and cyclooctadienyl. In some embodiments, the cycloalkyl has 3-6 carbons. The aliphatic cyclic structures also include aliphatic rings that are fused to one or more aromatic or nonaromatic rings, such as decahydronaphthyl or tetrahydronaphthyl, where in the radical or point of attachment is on the aliphatic ring. In some embodiments, aliphatic cyclic group is bicyclic. In some embodiments, a ‘carbocyclic group is tricyclic. In some embodiments, an aliphatic cyclic group is polycyclic. In some embodiments, the aliphatic polycyclic group is a spirocyclic structure that presents a twisted structure of two or more rings (a ring system), in which 2 or 3 rings are linked together by one common atom. In another embodiment, the aliphatic polycyclic group is a fused bicyclic structure wherein two rings share two adjacent atoms, that is, the rings share one covalent bond, i.e. the so-called bridgehead atoms are directly connected (e.g. α-thujene and decalin). In some embodiments the aliphatic polycyclic structure is a bridged bicyclic structure where, e.g., two rings share three or more atoms, separating the two bridgehead atoms by a bridge containing at least one atom. For example, norbornane, also known as bicyclo[2.2.1]

heptane, can be thought of as a pair of cyclopentane rings each sharing three of their five carbon atoms. In some embodiments, "aliphatic cyclic" (or "carbocycle" or "cycloalkyl") refers to a monocyclic $C_3$-$C_8$ hydrocarbon, or a $C_6$-$C_{12}$ bicyclic hydrocarbon that is completely saturated or that contains one or more units of unsaturation, but which is not aromatic, that has a single point of attachment to the rest of the molecule, or a $C_9$-$C_{16}$ tricyclic hydrocarbon that is completely saturated or that contains one or more units of unsaturation, but which is not aromatic, that has a single point of attachment to the rest of the molecule.

As used herein, the term "alkyl" is given its ordinary meaning in the art and may include saturated aliphatic groups, including straight-chain alkyl groups, branched-chain alkyl groups, cycloalkyl groups, alkyl substituted cycloalkyl groups, and cycloalkyl substituted alkyl groups. In certain embodiments, a straight chain or branched chain alkyl has about 1-20 carbon atoms in its backbone (e.g., $C_1$-$C_{20}$ for straight chain, $C_2$-$C_{20}$ for branched chain), and alternatively, about 1-10 carbon atoms, or about 1 to 6 carbon atoms. In some embodiments, a cycloalkyl ring has from about 3-10 carbon atoms in their ring structure wherein such rings are monocyclic or bicyclic, and alternatively about 5, 6 or 7 carbons in the ring structure. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more double bonds.

As used herein, the term "alkynyl" refers to an alkyl group, as defined herein, having one or more triple bonds.

The term "heteroalkyl" is given its ordinary meaning in the art and refers to alkyl groups as described herein in which one or more carbon atoms is replaced with a heteroatom (e.g., halogen, oxygen, nitrogen, sulfur, and the like). Examples of heteroalkyl groups include, but are not limited to, alkoxy, poly(ethylene glycol)-, alkyl-substituted amino, tetrahydrofuranyl, piperidinyl, morpholinyl, etc.

As used herein, "aromatic" refers to a monocyclic or polycyclic, aromatic or heteroaromatic ring which may have from 5 to 20 ring atoms, and optionally may have from 1 to 20 heteroatom substituents. In some embodiments, the aromatic groups may optionally have from 1 to 10 heteroatom substituents. In some embodiments, the aromatic groups may optionally have from 1 to 5 heteroatom substituents. In some embodiments, the aromatic groups are monocyclic or polycyclic aromatic rings, such as cyclopentadienyl, phenyl, naphthyl or anthracenyl. In some embodiments, aromatic groups are monocyclic or polycyclic aromatic rings having from 5 to 10 ring atoms. In some embodiments, aromatic groups are monocyclic aromatic rings containing from 5 to 6 carbon atoms, such as phenyl and cyclopentadienyl. In one particular embodiment, an aromatic group is a phenyl group.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present disclosure, "aryl" refers to an aromatic ring system which includes, but not limited to, phenyl, biphenyl, naphthyl, binaphthyl, anthracyi and the like, which may bear one or more substituents. Also included within the scope of the term "aryl," as it is used herein, is a group in which an aromatic ring is fused to one or more nonaromatic rings, such as indanyl, phthalimidyl, naphthimidyl, phenanthridinyl, or tetrahydronaphthyl, and the like.

The terms "heteroaromatic hydrocarbon", "heteroaryl" and "heteroar-," used alone of as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaromatic hydrocarbon or heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. In some embodiments, a heteroaryl is a heterobiaryl group, such as bipyridyl and the like. The terms "heteroaryl" and "heteroar-", as used herein, also include groups in which a heteroaromatic ring is fused to one or more aryl, cycloaliphatic, or heterocyclyl rings, wherein the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be monocyclic, bicyclic, tricyclic, tetracyclic, and/or otherwise polycyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen.

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be monocyclic, bicyclic, tricyclic, tetracyclic, and/or otherwise polycyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring.

The term "unsaturated," as used herein, means that a moiety has one or more units of unsaturation. The term "halogen" means F, Cl, Br, or I; the term "halide" refers to a halogen radical or substituent, namely —F, —Cl, —Br, or —I. As used herein, "haloalkyl" refers to alkyl, as defined above, wherein the alkyl includes at least one substituent selected from a halogen, for example, fluorine (F), chlorine (Cl), bromine (Br), or iodine (I). Examples of haloalkyl include, but are not limited to, $—CF_3$, $—CH_2CF_3$, $—CCl_2F$, and $—CCl_3$.

The term "protecting group" as used in herein refers to groups introduced into a molecule by chemical modification of a functional group such as an amino or alcohol, in order to obtain chemoselectivity in a subsequent chemical reaction. In one non-limiting embodiment, protecting groups may include 1-chloroethyl carbonyl (ACE), acetoyl, benzyl (Bn), benzyloxy carbonyl (CBz), formyl, methyl carbonyl, trifluoroacetyl, t-butoxy carbonyl (Boc), and fluorenylmethyloxycarbonyl (Fmoc). In another non-limiting embodiment, protecting groups include arbobenzyloxy (Cbz), p-Methoxybenzyl carbonyl (Moz or MeOZ), tert-Butyloxycarbonyl (BOC), 9-Fluorenylmethyloxycarbonyl (Fmoc), Acetyl (Ac), Benzoyl (Bz), Benzyl (Bn), p-Methoxybenzyl (PMB), 3,4-Dimethoxybenzyl (DMPM), p-Methoxyphenyl (PMP) group, Tosyl (Ts), Troc (trichloroethyl chloroformate), Sulfonamides such as Nosyl and Nps. In a further non-limiting embodiment, protecting groups include β-Methoxyethoxymethyl ether (MEM), Dimethoxytrityl, [bis-(4-methoxyphenyl)phenylmethyl] (DMT), Methoxymethyl ether (MOM), Methoxytrityl [(4-methoxyphenyl)diphenylmethyl] (MMT), Methylthiomethyl ether, Pivaloyl (Piv), Tetrahydropyranyl (THP), Tetrahydrofuran (THF), Trityl (triphenylmethyl, Tr), Silyl ether (TMS), tert-butyldimethylsilyl (TBDMS), tri-iso-propylsilyloxymethyl (TOM), and triisopropylsilyl (TIPS) ethers), TBDMS and TOM; Methyl ethers and ethoxyethyl ethers (EE).

As used herein, the term "O-amino acid" or "HO-amino acid" designates an amino acid wherein the native amino group at the N-terminus of an amino acid or an amino acid sequence has been replaced with an oxygen or hydroxyl group, respectively. For example, "O—XXXX" or "HO—XXXX" is intended to designate an amino acid sequence (XXXX) wherein the native amino group at the N-terminus has been replaced with an oxygen or hydroxyl group, respectively (e.g.,

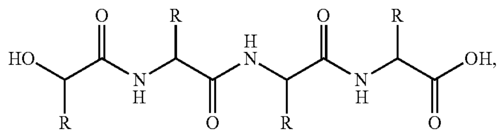

wherein each R is an amino acid side chain). Similarly, the terms "O-amino acid residue" or "HO-amino acid residue" refers to the chemical moiety within a compound that remains after a chemical reaction. For example, "O-amino acid residue" or "HO-amino acid residue" refers to the product of an amide coupling or peptide coupling of an O-amino acid or a HO-amino acid to a suitable coupling partner; wherein, for example, a water molecule is expelled after the amide or peptide coupling of the O-amino acid or a HO-amino acid, resulting in the product having the O-amino acid residue or a HO-amino acid residue incorporated therein.

Designation of an amino acid or amino acid residue without specifying its stereochemistry is intended to encompass the L form of the amino acid, the D form of the amino acid, or a racemic mixture thereof.

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Unless otherwise stated, all tautomeric forms of the compounds of the disclosure are within the scope of the disclosure.

Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}C$-enriched carbon, or the replacement of an oxygen by a $^{17}O$- or $^{18}O$-enriched oxygen, or the replacement of a nitrogen by a $^{15}N$-enriched nitrogen are within the scope of this disclosure.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

Unless otherwise stated, all crystalline forms of the compounds of the disclosure and salts thereof are also within the scope of the disclosure. The compounds of the disclosure may be isolated in various amorphous and crystalline polymorphic forms, including without limitation amorphous and crystalline polymorphic forms which are anhydrous, hydrated, non-solvated, or solvated. Example hydrates include hemihydrates, monohydrates, dihydrates, and the like. In some embodiments, the compounds of the disclosure are anhydrous and non-solvated. By "anhydrous" is meant that the crystalline form of the compound contains essentially no bound water in the crystal lattice structure, i.e., the compound does not form a crystalline hydrate.

As used herein, "crystalline form" is meant to refer to a certain lattice configuration of a crystalline substance. Different crystalline forms (polymorphic forms) of the same substance typically have different crystalline lattices (e.g., unit cells) which are attributed to different physical properties that are characteristic of each of the crystalline forms. In some instances, different lattice configurations have different water or solvent content. The different crystalline lattices can be identified by solid state characterization methods such as by X-ray powder diffraction (PXRD). Other characterization methods such as differential scanning calorimetry (DSC), thermogravimetric analysis (TGA), dynamic vapor sorption (DVS), solid state NMR, and the like further help identify the crystalline form as well as help determine stability and solvent/water content.

Crystalline forms of a substance include both solvated (e.g., hydrated) and non-solvated (e.g., anhydrous) forms. A hydrated form is a crystalline form that includes water in the crystalline lattice. Hydrated forms can be stoichiometric hydrates, where the water is present in the lattice in a certain water/molecule ratio such as for hemihydrates, monohydrates, dihydrates, etc. Hydrated forms can also be non-stoichiometric, where the water content is variable and dependent on external conditions such as humidity.

In some embodiments, the compounds of the disclosure are substantially isolated. By "substantially isolated" is meant that a particular compound is at least partially isolated from impurities. For example, in some embodiments a compound of the disclosure comprises less than about 50%, less than about 40%, less than about 30%, less than about 20%, less than about 15%, less than about 10%, less than about 5%, less than about 2.5%, less than about 1%, or less than about 0.5% of impurities. Impurities generally include anything that is not the substantially isolated compound including, for example, other crystalline forms and other substances.

As used herein, the term "antibiotic" (abx or Abx) includes any molecule that specifically inhibits the growth of or kills micro-organisms, such as bacteria, but is non-lethal to the host at the concentration and dosing interval administered. In a specific aspect, an antibiotic is non-toxic to the host at the administered concentration and dosing intervals. Antibiotics effective against bacteria can be broadly classified as either bactericidal (i.e., directly kills) or bacteriostatic (i.e., prevents division). Anti-bactericidal antibiotics can be further subclassified as narrow-spectrum or broad-spectrum. A broad-spectrum antibiotic is one effective against a broad range of bacteria including both Gram-positive and Gram-negative bacteria, in contrast to a narrow-spectrum antibiotic, which is effective against a smaller range or specific families of bacteria. Examples of antibiotics include: aminoglycosides, e.g., amikacin, gentamicin, kanamycin, neomycin, netilmicin, streptomycin, tobramycin, paromycin, ansamycins, e.g., geldanamycin, herbimycin, carbacephems, e.g., loracarbef, carbapenems, e.g., ertapenum, doripenem, imipenem/cilastatin, meropenem, cephalosporins (first generation), e.g., cefadroxil, cefazolin, cefalotin, cefalexin, cephalosporins (second generation), e.g., ceflaclor, cefamandole, cefoxitin, cefprozil, cefuroxime, cephalosporins (third generation), e.g., cefixime, cefdinir, cefditoren, cefoperazone, cefotaxime, cefpodoxime, ceftazidime, ceftibuten, ceftizoxime, ceftriaxone, cephalosporins (fourth generation), e.g., cefepime, cephalosporins (fifth generation), e.g., ceftobiprole, glycopeptides, e.g., teicoplanin, vancomycin, macrolides, e.g., axithromycin, clarithromycin, dirithromycine, erythromycin, roxithromycin, troleandomycin, telithromycin, spectinomycin, monobactams, e.g., axtreonam, penicilins, e.g., amoxicillin, ampicillin, axlocillin, carbenicillin, cloxacillin, dicloxacillin, flucloxacillin, mezlocillin, meticillin, nafcilin, oxacillin, penicillin, peperacillin, ticarcillin, antibiotic polypeptides, e.g., bacitracin, colistin, polymyxin B, quinolones, e.g., ciprofloxacin, enoxacin, gatifloxacin, levofloxacin, lemefloxacin, moxifloxacin, norfloxacin, orfloxacin, trovafloxacin, sulfonamides, e.g., mafenide, prontosil, sulfacetamide, sulfamethizole, sulfanilamide, sulfasalazine, sulfisoxazole, trimethoprim, trimethoprim-sulfamethoxazole (TMP-SMX), tetracyclines, e.g., demeclocycline, doxycycline, minocycline, oxytetracycline, tetracycline and others such as arspenamine, chloramphenicol, clindamycin, lincomycin, ethambutol, fosfomycin, fusidic acid, furazolidone, isoniazid, linezolid, metronidazole, mupirocin, nitrofurantoin, platensimycin, pyrazinamide, quinupristin/dalfopristin, rifampin/rifampicin or timidazole.

The term "methicillin-resistant *Staphylococcus aureus*" (MRSA), alternatively known as multidrug resistant *Staphylococcus aureus* or oxacillin-resistant *Staphylococcus aureus* (ORSA), refers to any strain of *Staphylococcus aureus* that is resistant to beta-lactam antibiotics, which include the penicillins (e.g., methicillin, dicloxacillin, nafcillin, oxacillin, etc.) and the cephalosporins. "Methicillin-sensitive *Staphylococcus aureus*" (MSSA) refers to any strain of *Staphylococcus aureus* that is sensitive to beta-lactam antibiotics.

The term "minimum inhibitory concentration" ("MIC") refers to the lowest concentration of an antimicrobial that will inhibit the visible growth of a microorganism after overnight incubation. Assay for determining MIC are known. One method is as described in the Examples below.

Drug-to-antibody ratio (DAR) is the average number of drugs conjugated to the antibody or antigen-binding fragment, which has an important effect on the efficacy, potency and pharmacokinetics of the ADC. In various embodiments, the DAR is from 1, 2, 3, 4, 5, 6, 7, or 8 drug molecules per antibody. In some embodiments, the DAR is from 1 to 8. In some embodiments, the DAR is from 1 to 6. In certain embodiments, the DAR is from 2 to 4. In some cases, the DAR is from 2 to 3. In certain cases, the DAR is from 0.5 to 3.5. In some embodiments, the DAR is about 1, or about 1.5, or about 2, or about 2.5, or about 3, or about 3.5.

The expressions "MSR1," "hMSR1" and the like, as used herein, refer to the human single-pass, trimeric type II transmembrane glycoprotein pattern recognition receptor comprising (i) the amino acid sequence as set forth in NCBI accession No. NP_002436.1, (ii) the amino acid sequence as set forth in NCBI accession No. NP_619729.1, and/or (iii) the amino acid sequence as set forth in NCBI accession No. NP_619730.1, which represent the various types and isoforms of class A macrophage scavenger receptors. The expression "MSR1" includes both monomeric and multimeric MSR1 molecules. As used herein, the expression "monomeric human MSR1" means a MSR1 protein or portion thereof that does not contain or possess any multimerizing domains and that exists under normal conditions as a single MSR1 molecule without a direct physical connection to another MSR1 molecule. An exemplary monomeric MSR1 molecule is the molecule referred to herein as "His-hMSR1" comprising the amino acid sequence of SEQ ID NO: 393 (see, e.g., Example 25, herein).

All references to proteins, polypeptides and protein fragments herein are intended to refer to the human version of the respective protein, polypeptide or protein fragment unless explicitly specified as being from a non-human species. Thus, the expression "MSR1" means human MSR1 unless specified as being from a non-human species, e.g., "mouse MSR1," "monkey MSR1," etc.

As used herein, the expression "cell surface-expressed MSR1" means one or more MSR1 protein(s), or the extracellular domain thereof, that is/are expressed on the surface of a cell in vitro or in vivo, such that at least a portion of a MSR protein is exposed to the extracellular side of the cell membrane and is accessible to an antigen-binding portion of an antibody. A "cell surface-expressed MSR1" can comprise or consist of a MSR1 protein expressed on the surface of a cell which normally expresses MSR1 protein. Alternatively, "cell surface-expressed MSR1" can comprise or consist of MSR1 protein expressed on the surface of a cell that normally does not express human MSR1 on its surface but has been artificially engineered to express MSR1 on its surface.

As used herein, the expression "anti-MSR1 antibody" includes monovalent antibodies with a single specificity, as well as bispecific antibodies comprising a first arm that binds MSR1 and a second arm that binds a second (target) antigen, wherein the anti-MSR1 arm comprises any of the HCVR/LCVR or CDR sequences as set forth in Table 9 herein. The expression "anti-MSR1 antibody" also includes antibody-drug conjugates (ADCs) comprising an anti-MSR1 antibody or antigen-binding portion thereof conjugated to a drug or a therapeutic agent. The expression "anti-MSR1 antibody" also includes antibody-radionuclide conjugates (ARCs) comprising an anti-MSR1 antibody or antigen-binding portion thereof conjugated to a radionuclide.

The term "wall teichoic acid" (WTA) refers to anionic glycopolymers that are covalently attached to peptidoglycan via phosphodiester linkage to the $C_6$ hydroxyl of the N-acetyl muramic acid sugars. While the precise chemical structure can vary among organisms, in some embodiments, WTA is a ribitol teichoic acid with repeating units of 1,5-phosphodiester linkages of D-ribitol and D-alanyl ester on position 2 and glycosyl substituents on position 4. The glycosyl groups may be N-acetylglucosaminyl α (alpha) or β (beta) as present in *S. aureus*. The hydroxyls on the alditol/sugar alcohol phosphate repeats may be substituted with cationic D-alanine esters and monosaccharides, such as N-acetylglucosamine. The hydroxyl substituents may include D-alanyl and alpha (α) or beta (β) GlcNHAc. In one specific embodiment, WTA comprises a compound of the formula:

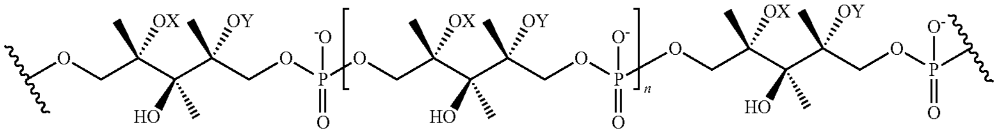

where the wavy lines indicate repeating linkage units or the attachment sites of Polyalditol-P or the peptidoglycan, where X is D-alanyl or H; and Y is α (alpha)-GlcNHAc or β (beta)-GlcNHAc.

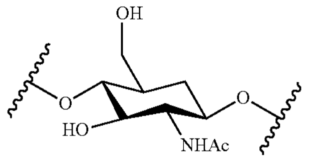

GlcNHAc

As used herein, the term "anti-WTA antibody" refers to any antibody that binds wall teichoic acid (WTA) whether WTA alpha or WTA beta. The terms "anti-wall teichoic acid alpha antibody" or "anti-WTA alpha antibody" or "anti-αWTA" or "anti-αGlcNac WTA antibody" are used interchangeably to refer to an antibody that specifically binds WTA alpha. Similarly, the terms "anti-wall teichoic acid beta antibody" or "anti-WTA beta antibody" or "anti-βWTA" or "anti-βGlcNac WTA antibody" are used interchangeably to refer to an antibody that specifically binds WTA beta. The expression "anti-WTA antibody" includes monovalent antibodies with a single specificity, as well as bispecific antibodies comprising a first arm that binds WTA (whether WTA alpha or WTA beta) and a second arm that binds a second (target) antigen, wherein the anti-WTA arm comprises any of the HCVR/LCVR or CDR sequences as set forth in Tables 2A and 2B herein. The expression "anti-WTA antibody" also includes antibody-drug conjugates (ADCs) comprising an anti-WTA antibody or antigen-binding portion thereof conjugated to a drug or a therapeutic agent.

The term "antibody", as used herein, means any antigen-binding molecule or molecular complex comprising at least one complementarity determining region (CDR) that specifically binds to or interacts with a particular antigen (e.g., MSR1, WTA, or Protein A). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$—$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$—$C_H1$-$C_H2$; (v) $V_H$—$C_H1$-$CH_2$—$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

The antibodies of the present disclosure may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the disclosure in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments, the antibodies disclosed herein are human antibodies. The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies disclosed herein may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG hinge. Embodiments disclosed herein encompass antibodies having one or more mutations in the hinge, $C_H2$ or $C_H3$ region which may be desirable, for example, in production, to improve the yield of the desired antibody form.

The antibodies disclosed herein may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. Embodiments include antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within embodiments disclosed herein.

Embodiments also include antibodies comprising variants of any of the HCVR, LCVR, and/or CDR amino acid sequences disclosed herein having one or more conservative substitutions. For example, embodiments include anti-MSR1 antibodies comprising HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 9 herein. As another example, embodiments include anti-WTA antibodies comprising HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Tables 2A or 2B herein. As yet another example, embodiments include anti-Protein A antibodies comprising HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 3A herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide comprising the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the disclosure to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402.

As used herein, "O-PEG$_n$" refers to a monovalent moiety attached via the terminal oxygen atom, where n is from 1 to 100. For example, when n is 1, then O-PEG$_n$ is $—O—CH_2CH_2OH$; when n is two, then O-PEG$_n$ is $—CH_2CH_2O—CH_2CH_2OH$; and when n is three, then O-PEG$_n$ is $—CH_2CH_2O—CH_2CH_2O—CH_2CH_2OH$.

As used herein, "binding agent" refers to any molecule, e.g., protein or antibody, capable of binding with specificity to a given binding partner, e.g., antigen.

As used herein, "linker" refers to a divalent, trivalent, or multivalent moiety that covalently links the binding agent to one or more compounds described herein, for instance payload compounds and a hydrophilic group, as described herein.

As used herein, "reactive group," or RG, refers to a moiety comprising a portion in its structure that is capable of reacting and forming a covalent bond with another chemical moiety, e.g. reacting with an antibody at its cysteine or lysine residues. Illustrative reactive groups for the present disclosure include, but are not limited to, those that comprise maleimides, succinimides, N-hydroxy succinimides (NHS), terminal primary amines, haloacetyl groups, isothiocyanates, thiols, alcohols, ketones, aldehydes, acids, esters, hydrozides, and anilines. RG also include moieties having the following structure:

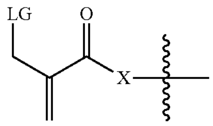
or
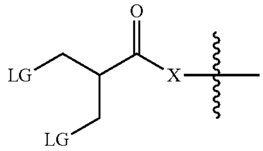
, wherein X is —O— or —NH— and LG is a leaving group, e.g., Br.

As used herein, "amide synthesis conditions" refers to reaction conditions suitable to effect the formation of an amide, e.g., by the reaction of a carboxylic acid, activated carboxylic acid, or acyl halide with an amine. In some examples, amide synthesis conditions refer to reaction conditions suitable to effect the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid and an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy) tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]-1H-1,2,3-triazolo[4,5-b] pyridinium 3-oxid hexafluorophosphate (HATU), N-ethoxycarbonyl-2-ethoxy-1,2-dihydroquinoline (EEDQ), N-ethyl-N'-(3-dimethylaminopropyl)carbodiimide (EDC), 2-chloro-1,3-dimethylimidazolidinium hexafluorophosphate (CIP), 2-chloro-4,6-dimethoxy-1,3,5-triazine (CDMT), (1-Cyano-2-ethoxy-2-oxoethylidenaminooxy)dimethylamino-morpholino-carbenium hexafluorophosphate (COMU), and carbonyldiimidazole (CDI).

In some examples, a carboxylic acid is first converted to an activated carboxylic ester before treating the activated carboxylic ester with an amine to form an amide bond. In certain embodiments, the carboxylic acid is treated with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. The activated carboxylic esters for certain carboxylic acids are subsequently more susceptible to nucleophilic attack by an amine than the carboxylic acid is before it is activated. This results in amide bond formation. As such, the carboxylic acid is described as activated. Exemplary reagents include DCC and DIC.

As used herein, "taurine" refers to the reagent

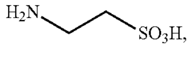

or the group

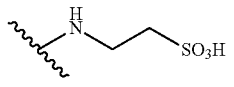 [SMILES: *NCCS(=O)(=O)O]

wherein

indicates the atom through which the taurine is bonded to the adjacent groups in the formula.

Compounds of the Disclosure

In accordance with the foregoing objective and others, the present disclosure provides rifamycin analog compounds, precursors and intermediates thereof, pharmaceutical compositions, and methods for inhibiting bacterial growth and/or treating a bacterial infection in a subject in need of such treatment.

In one aspect, the present disclosure provides a rifamycin analog compound or precursor thereof having a structure of formula (A):

(A)

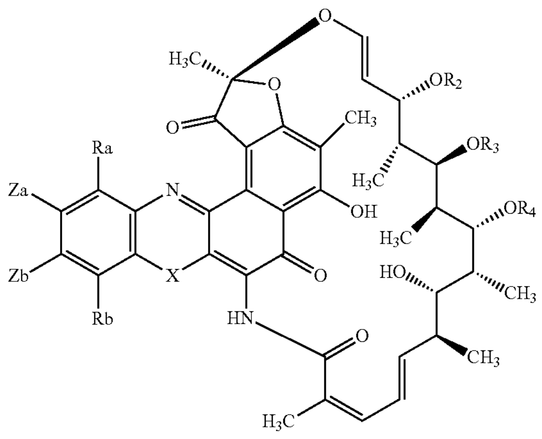

or a pharmaceutically acceptable salt thereof, wherein:

X is selected from —O— and —NR*—;

Za and Zb are independently selected from a hydrogen, —Cl, —Br, —$OR_1$ and —$R_N$; with the proviso that at least one of Za or Zb is not a hydrogen; wherein:

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

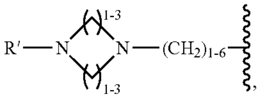
,

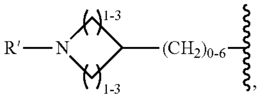
,

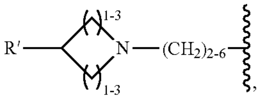
,
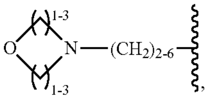
,

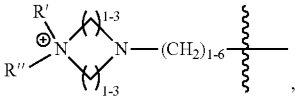
,

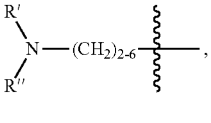
,

-continued

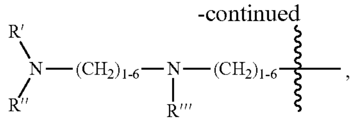

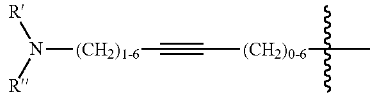

and

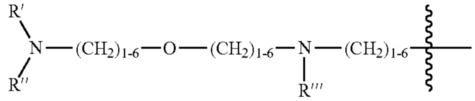

wherein the symbol represents the point of attachment; and R', R'' and R''' are selected from a hydrogen, a $C_1$-$C_6$ aliphatic hydrocarbon, and a protecting group, for example, $F_{MOC}$ and $B_{OC}$, or wherein R' and R'' together form an aliphatic cyclic structure, such as an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S; $R_a$ is selected from hydrogen, —F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one aspect, the present disclosure provides a rifamycin analog compound having a structure of formula (I):

(I)

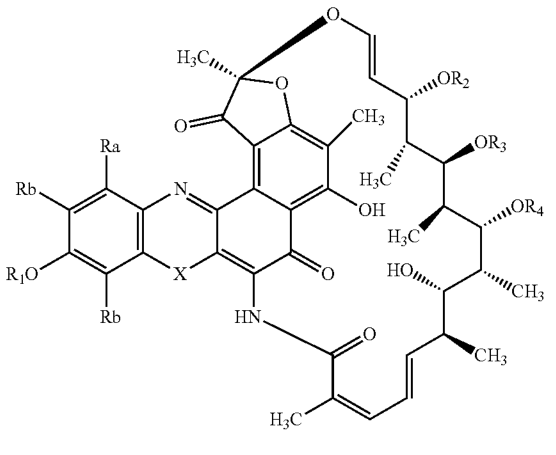

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

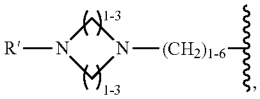

,

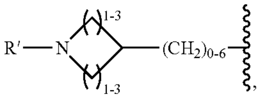

,

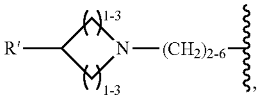

,

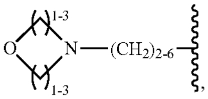

,

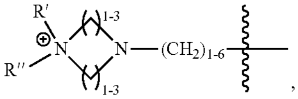

,

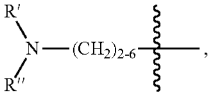

,

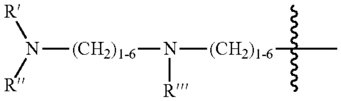

,

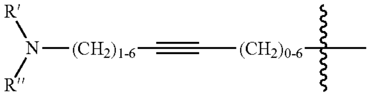

and

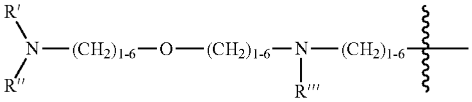

wherein the symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one aspect, the present disclosure provides a rifamycin analog compound having a structure of formula (I'):

(I')

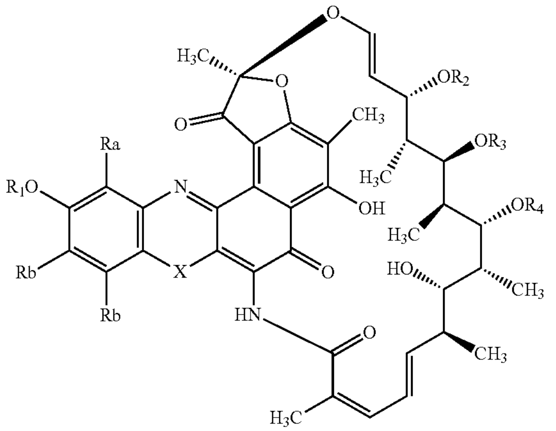

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—N$(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

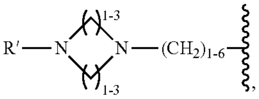

,

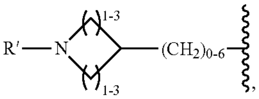

,

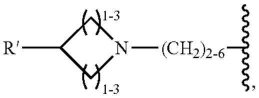

,

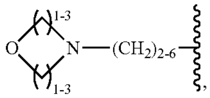

,

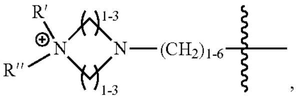

,

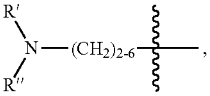

,

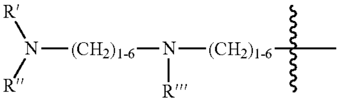

,

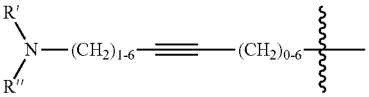

and

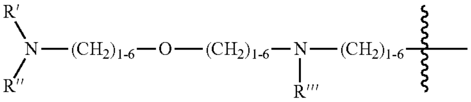

wherein the ∿∿∿ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof. In an embodiment of a compound of the formulas (A), (I) or (I'), X is —O—, $R_1$ is an aliphatic $C_1$-$C_3$ hydrocarbon, $R_2$ is a methyl group, $R_3$ is Ac (—(C═O)—$CH_3$), $R_4$ is a hydrogen, and $R_a$ is a hydrogen.

In an embodiment of a compound of the formulas (A), (I) or (I'), X is —O—, $R_1$ is a benzyl group, $R_2$ is a methyl group, $R_3$ is Ac (—(C═O)—$CH_3$), $R_4$ is a hydrogen; $R_a$ is a hydrogen and $R_b$ is hydrogen.

In an embodiment of a compound of the formulas (A), (I) or (I'), X is —O—, $R_1$ is an aliphatic $C_1$-$C_8$ hydrocarbon comprising 1-8 heteroatoms selected from O and N, $R_2$ is a methyl group, $R_3$ is Ac (—(C═O)—$CH_3$), $R_4$ is a hydrogen; $R_a$ is a hydrogen and $R_b$ is hydrogen.

In an embodiment of a compound of the formulas (A), (I) or (I'), X is —O—; $R_1$ is an aliphatic $C_1$-$C_8$ hydrocarbon substituted with one or more of —$NH_2$, —NHR*, —N(R*)$_2$; R* is H or an aliphatic $C_1$-$C_3$ hydrocarbon; $R_2$ is a methyl group; $R_3$ is Ac (—(C═O)—$CH_3$); $R_4$ is a hydrogen; $R_a$ is a hydrogen and $R_b$ is hydrogen.

In an embodiment of a compound of the formulas (A), (I) or (I'), X is —$NCH_3$—, $R_1$ is —OH, $R_2$ is a methyl group, $R_3$ is Ac (—(C═O)—$CH_3$), $R_4$ is a hydrogen, $R_a$ is a hydrogen and $R_b$ is hydrogen.

In one embodiment, the rifamycin analog compounds of the disclosure have the structure of formula (II):

(II)

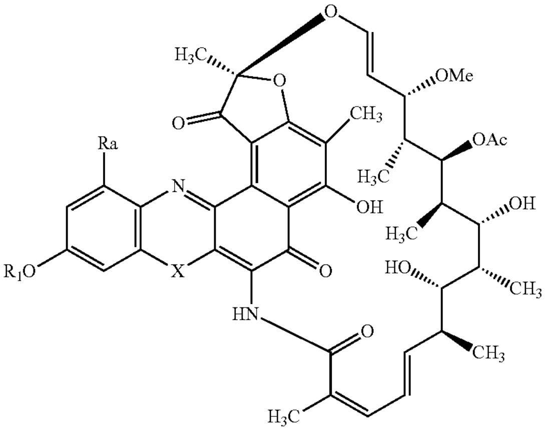

or a pharmaceutically acceptable salt thereof wherein:

X is selected from —O— and —NR*—;

$R_a$ is selected from hydrogen, —Cl, and —OR*;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with a proviso that $R_1$ is not an n-butyl group;

$R_N$ is selected from:

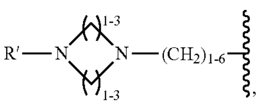
,

-continued

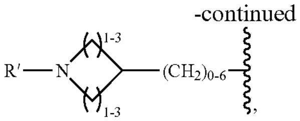
,

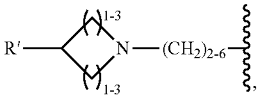
,
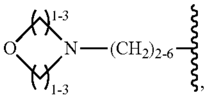
,

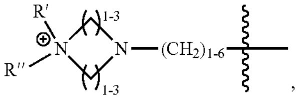
,

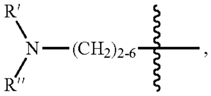
,

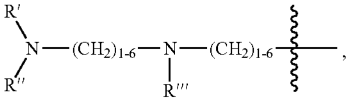
,

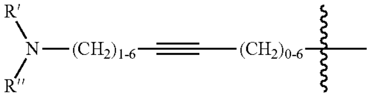
and

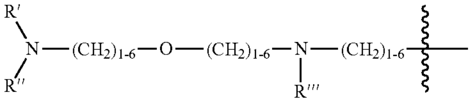

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (II'):

(II')

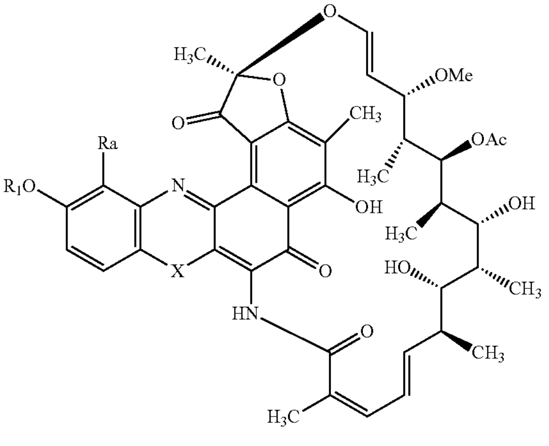

or a pharmaceutically acceptable salt thereof wherein:

X is selected from —O— and —NR*—;

$R_a$ is selected from hydrogen and —OR*;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with a proviso that $R_1$ is not an n-butyl group;

$R_N$ is selected from:

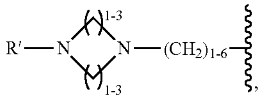,
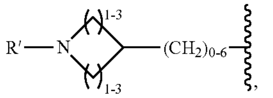,
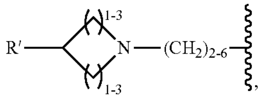, 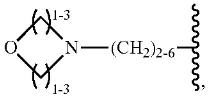,
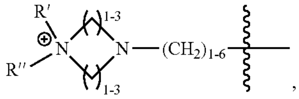,
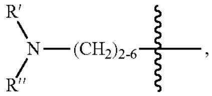,
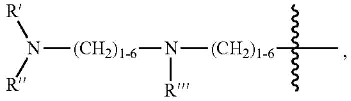,
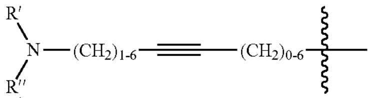 and
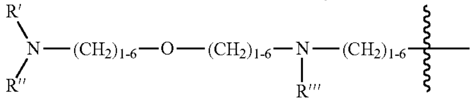

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (III):

(III)

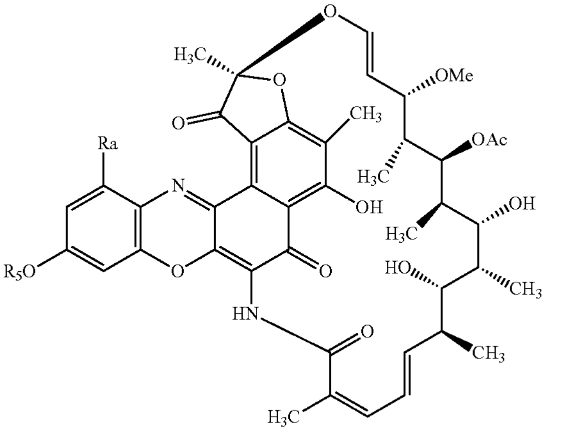

or a pharmaceutically acceptable salt thereof wherein:

$R_a$ is selected from hydrogen and —OR*;

$R_5$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_5$ is not an n-butyl group;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof; and $R_N$ is selected from:

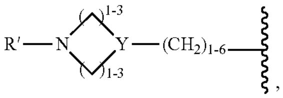,
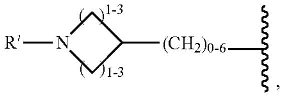,
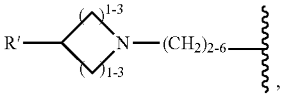,
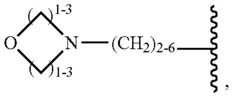,
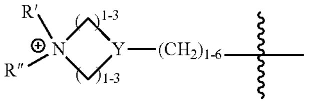,
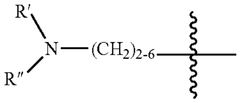,

-continued

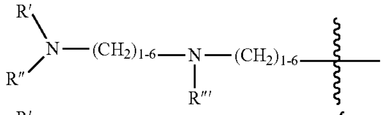

,

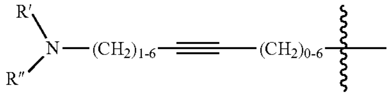

and

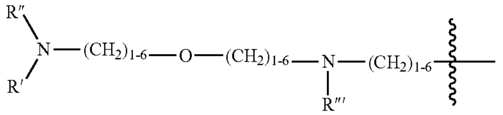

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure.

In one embodiment, the rifamycin analog compounds of the disclosure have the structure of formula (III'):

(III')

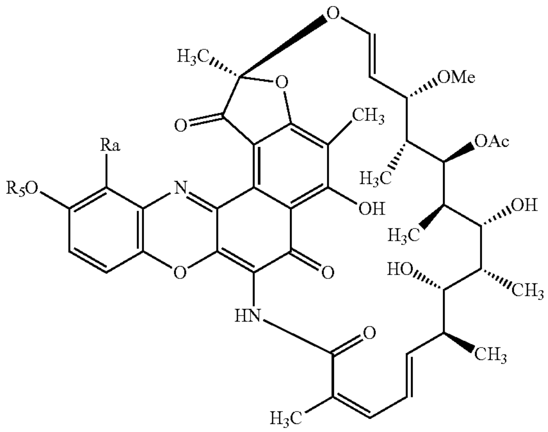

or a pharmaceutically acceptable salt thereof wherein:

$R_a$ is selected from hydrogen and —OR*;

$R_5$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_5$ is not an n-butyl group;

R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof; and $R_N$ is selected from:

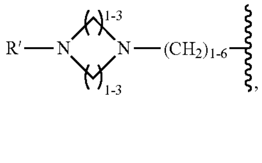

-continued

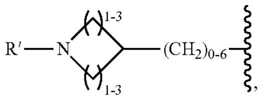

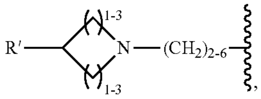

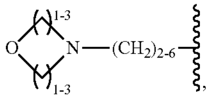

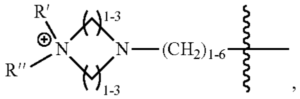

,

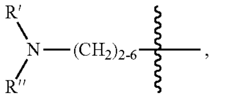

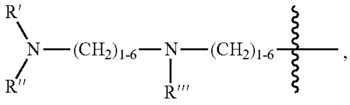

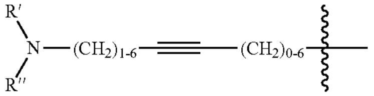

and

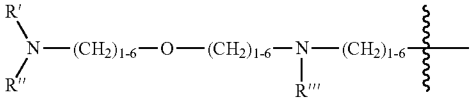

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure.

In one embodiment, the rifamycin analog compounds of the disclosure have the structure of formula (IV):

(IV)

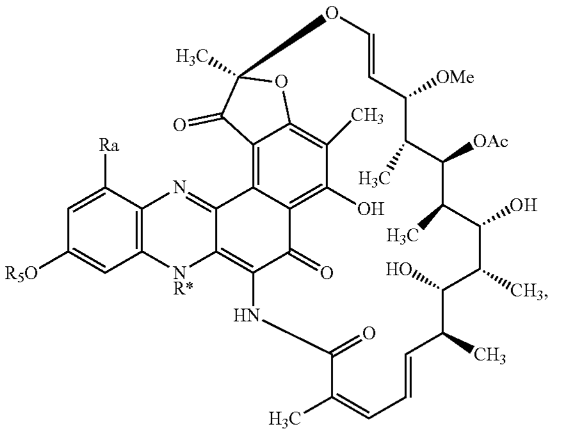

or a pharmaceutically acceptable salt thereof wherein:

$R_a$ is selected from hydrogen and —OR*;

$R_5$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof;

$R_N$ is selected from:

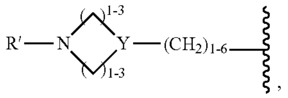,

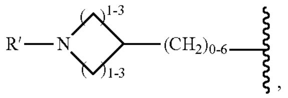,

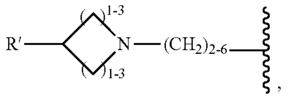,

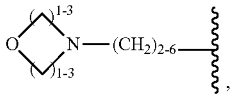,

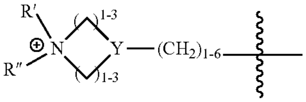,

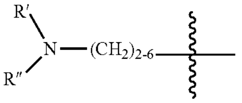,

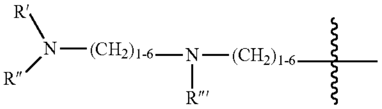,

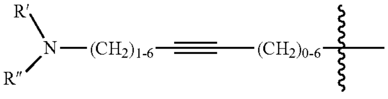 and

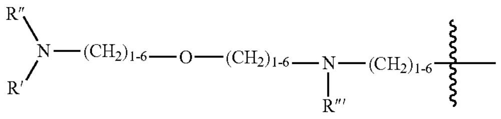

wherein the symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (IV'):

(IV')

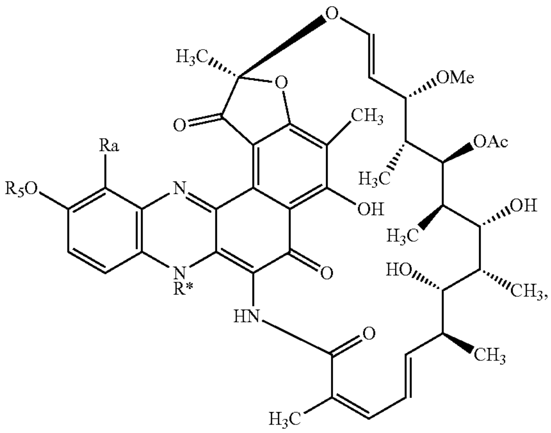

or a pharmaceutically acceptable salt thereof wherein:

$R_a$ is selected from hydrogen and —OR*;

$R_5$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_5$ is optionally substituted with one or more of —F, —Cl, —Br, —I, —OH, —OR*, —$NH_2$, —NHR*, j—N $(R^*)_2$, —$N(R^*)_3^+$, —N(R*)—(C═O)—R*, —(C═O)—R*, —CHO, —$CO_2H$, —$CO_2R^*$ and combinations thereof;

$R_N$ is selected from:

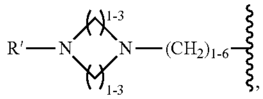,

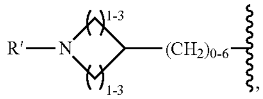,

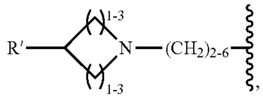, 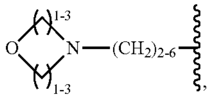,

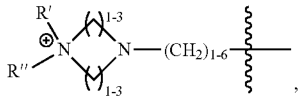,

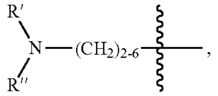,

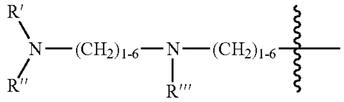,

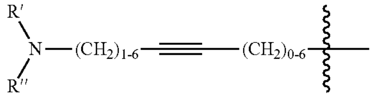 and

-continued

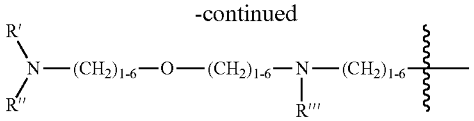

wherein the symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (V):

(V)

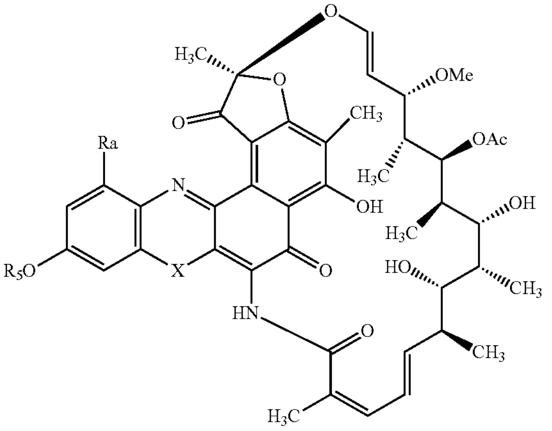

or a pharmaceutically acceptable salt thereof wherein:

X is selected from —O— and —NR*—;

$R_a$ is selected from hydrogen and —OR*;

$R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_6$ is optionally substituted with one or more of —OH, —OR*, —$NH_2$, —NHR*, —$N(R^*)_2$, —$N(R^*)_3^+$, —(C═O)—R*, —CHO, —$CO_2H$, —$CO_2R^*$ and combinations thereof, with a proviso that $R_6$ is not an n-butyl group;

$R_N$ is selected from:

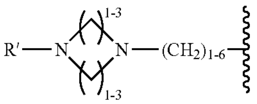,

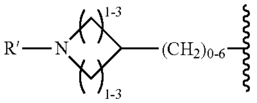,

-continued

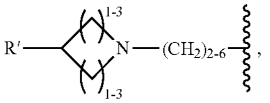, 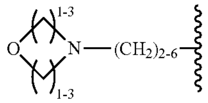,

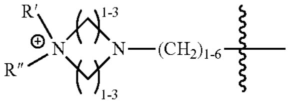,

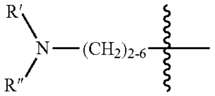,

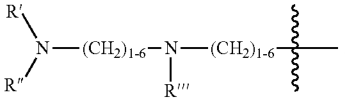,

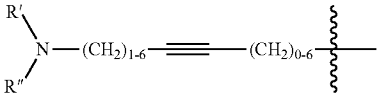 and

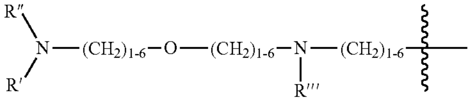

wherein the symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In one embodiment, the rifamycin analog compounds of the disclosure have the structure of formula (V'):

(V')

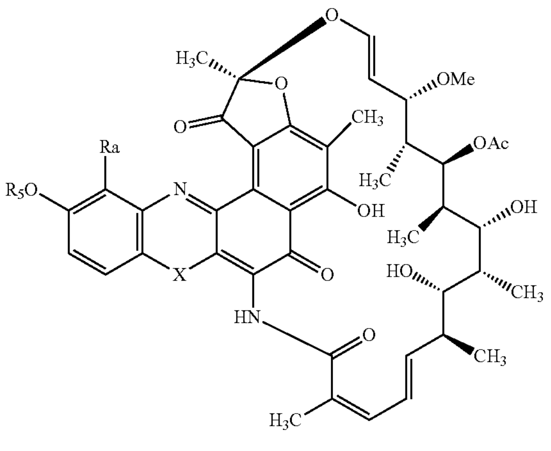

or a pharmaceutically acceptable salt thereof wherein:

X is selected from —O— and —NR*—;

$R_a$ is selected from hydrogen and —OR*;

$R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, each of which further comprises 0-8 heteroatoms selected from halogen, O, N, and S, and wherein $R_6$ is optionally substituted with one or more of —OH, —OR*, —$NH_2$, —NHR*, —$N(R^*)_2$, —$N(R^*)_3^+$, —N(R*)—(C═O)—R*, —(C═O)—R*, —CHO, —$CO_2H$, —$CO_2R^*$ and combinations thereof, with a proviso that $R_6$ is not an n-butyl group;

$R_N$ is selected from:

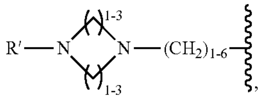,

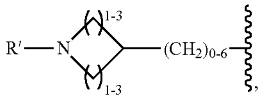,

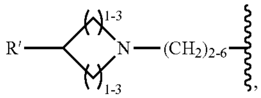, 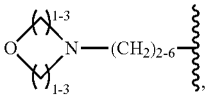,

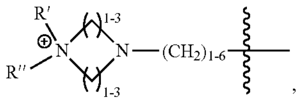,

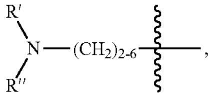,

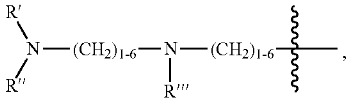,

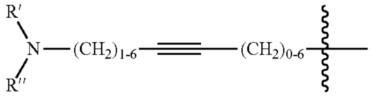 and

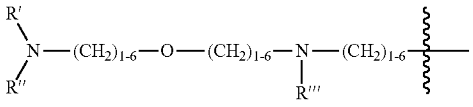

wherein the ∿∿∿ symbol represents the point of attachment; and R', R" and R''' are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound, intermediate or precursor thereof having a structure of formula (B):

(B)

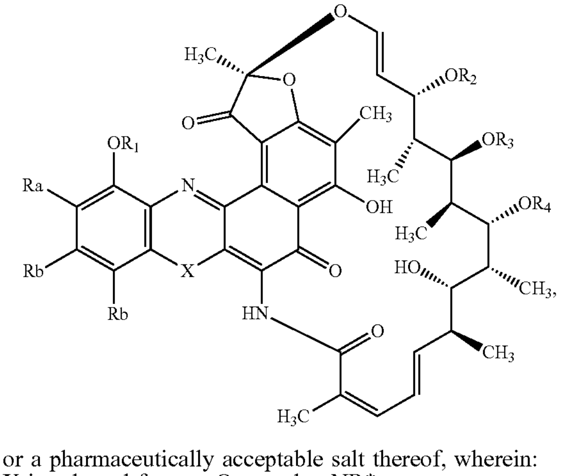

or a pharmaceutically acceptable salt thereof, wherein:

X is selected from —O— and —NR*—;

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

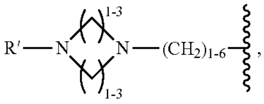,

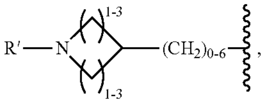,

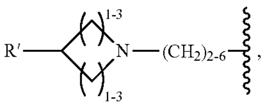, 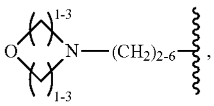,

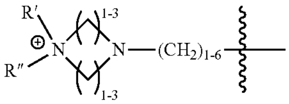,

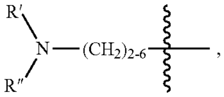,

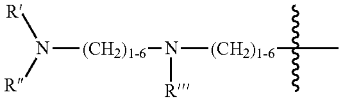,

-continued

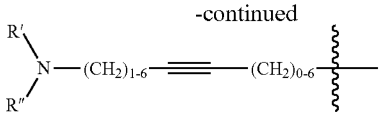

and

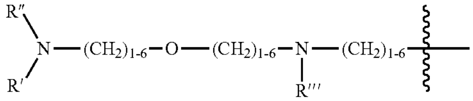

;

wherein the ~~~ symbol represents the point of attachment; and R', R'' and R''' are selected from a hydrogen, a $C_1$-$C_6$ aliphatic hydrocarbon, and a protecting group selected from Fluorenylmethyloxycarbonyl ($F_{MOC}$) and tert-Butyloxycarbonyl (BOC), or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound having a structure of formula (B-1):

(B-1)

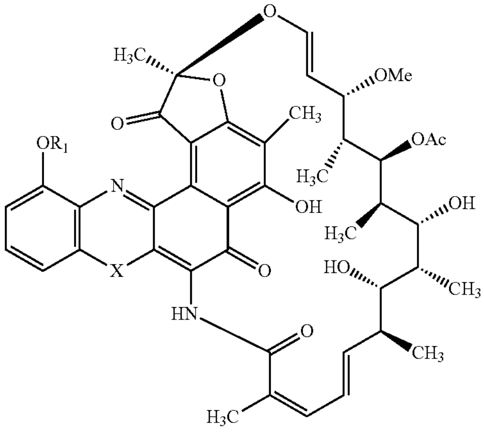

or a pharmaceutically acceptable salt thereof wherein:

X is selected from —O— and —NR*—;

$R_1$ is selected from $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—NHNH$_2$, —O—(C═O)—NHNH$_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with a proviso that $R_1$ is not an n-butyl group;

$R_N$ is selected from:

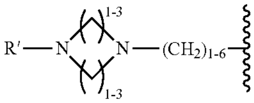

,

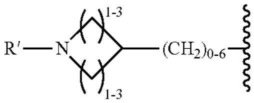

,

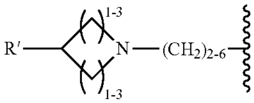

,

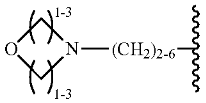

,

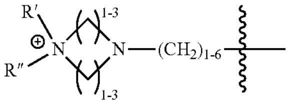

,

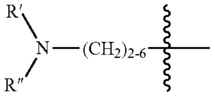

,

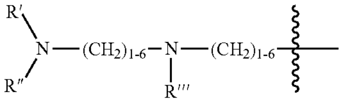

,

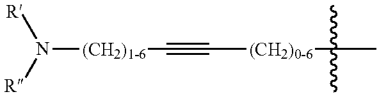

and

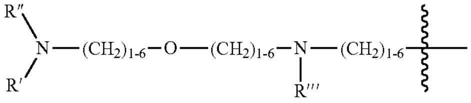

;

wherein the ~~~ symbol represents the point of attachment; and R', R'' and R''' are selected from a hydrogen, a $C_1$-$C_6$ aliphatic hydrocarbon, and a protecting group selected from $F_{MOC}$ and $B_{OC}$, or wherein R' and R'' together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a rifamycin analog compound having a structure of formula (B-2):

(B-2)

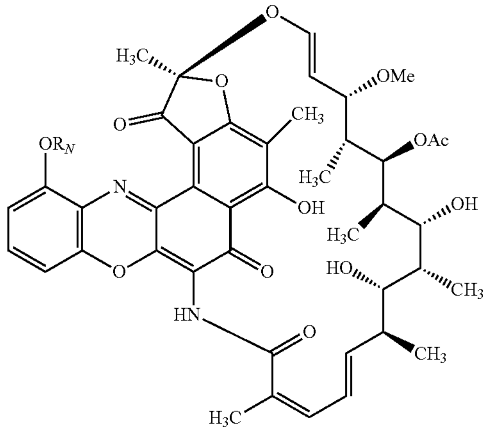

or a pharmaceutically acceptable salt thereof wherein:

$R_N$ is selected from:

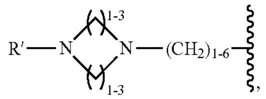
,

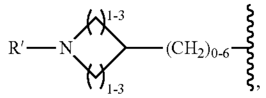
,

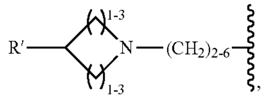
,

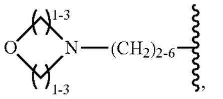
,

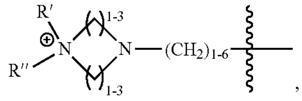
,

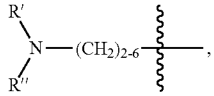
,

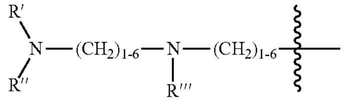
,

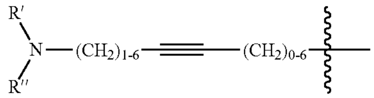
and

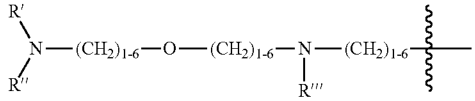

wherein the ∿∿∿ symbol represents the point of attachment; and R', R" and R'" are selected from a hydrogen, a $C_1$-$C_6$ aliphatic hydrocarbon, and a protecting group selected from $F_{MOC}$ and $B_{OC}$, or wherein R' and R" together form an aliphatic monocyclic, an aliphatic bicyclic, or an aliphatic polycyclic structure.

In another aspect, the present disclosure provides a rifamycin analog compound having a structure of formula (B-2):

(B-2)

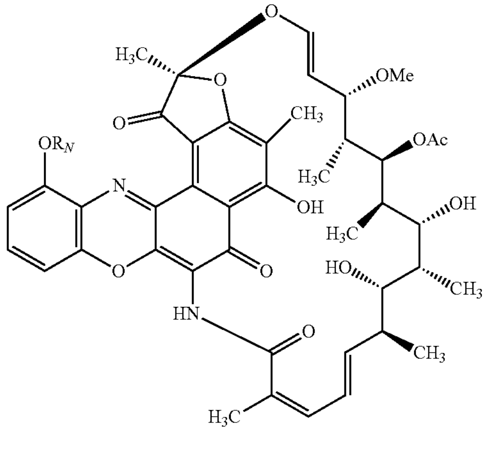

or a pharmaceutically acceptable salt thereof wherein:
$R_N$ is

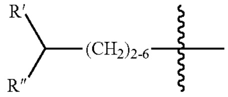

wherein the ∿∿∿ symbol represents the point of attachment; and R' and R" are selected from a hydrogen and a $C_1$-$C_6$ aliphatic hydrocarbon.

In one embodiment, a rifamycin analog compound has a structure according to the following formula:

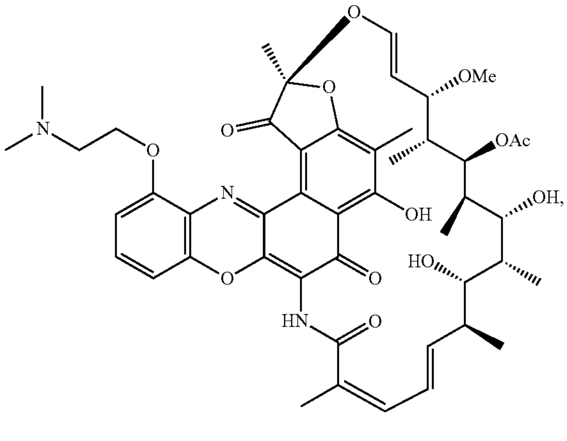 [SMILES: CO[C@H]1/C=C/O[C@@]2(C)Oc3c(C)c(O)c4c(=O)c(c5oc6cccc(OCCN(C)C)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

or a pharmaceutically acceptable salt thereof.

In an embodiment of any of the preceeding formulas is provided a compound wherein $R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-3 heteroatoms selected from O and N, and wherein $R_1$ is optionally substituted with one or more of —F, —Cl, —Br, —I, —OH, $C_{1-3}$ alkoxide, —$NH_2$, —NHR*, —N(R*)$_2$, —N(R*)$_3^+$, —N(R*)—OH, —O—N(R*)$_2$, —N(R*)—O—R*, —N(R*)—(C═O)—R*, —(C═O)—R*, —CHO, —$CO_2$H, —$CO_2$R*, —O—(C═O)—H, —O—(C═O)—R*, —(C═O)—$NH_2$, —(C═O)—$N(R^*)_2$, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen.

In an embodiment of any of the preceeding formulas is provided a compound wherein $R_1$ is a combination of an aliphatic $C_1$-$C_{20}$ hydrocarbon and an aromatic $C_1$-$C_{20}$ hydrocarbon.

In an embodiment of any of the preceeding formulas is provided a compound wherein $R_1$ is a combination of an aliphatic $C_1$-$C_{20}$ hydrocarbon and a heteroaromatic $C_1$-$C_{20}$ hydrocarbon.

an embodiment of any of the preceeding formulas is provided a compound wherein $R_1$ is selected from:

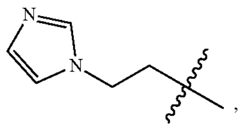

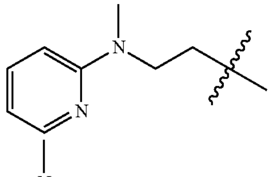

and

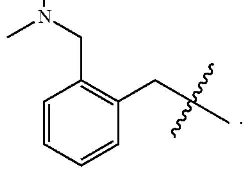

In an embodiment of any of the preceeding formulas is provided a compound wherein $R_1$ is an aliphatic $C_1$-$C_{20}$ hydrocarbon substituted with one or more of —$NH_2$, —$NHR^*$, —$N(R^*)_2$, or —$N(R^*)$—(C═O)—$R^*$.

In an embodiment of any of the preceeding formulas is provided a compound wherein $R_1$ is an aliphatic $C_1$-$C_{20}$ hydrocarbon substituted with —NH—(C═O)—$CH_3$ or —$N(CH_3)$—(C═O)—$CH_3$.

In an embodiment of any of the preceeding formulas is provided a compound wherein $R_a$ is hydrogen.

In an embodiment of any of the preceeding formulas is provided a compound wherein $R_a$ is —OH.

In an embodiment of any of the preceeding formulas is provided a compound wherein $R_a$ is —$C_1$.

In an embodiment of any of the preceeding formulas is provided a compound wherein $R_a$ is —$OR^*$, and $R^*$ is selected from an aliphatic $C_1$-$C_{20}$ hydrocarbon, an aromatic $C_1$-$C_{20}$ hydrocarbon, and combinations thereof.

In an embodiment of any of the preceeding formulas is provided a compound wherein $R_N$ is selected from:

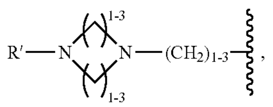

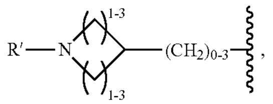

-continued

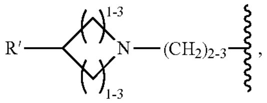

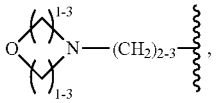

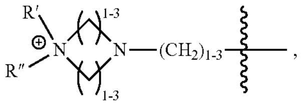

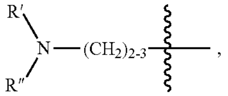

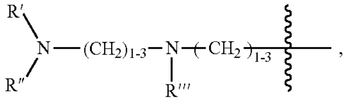

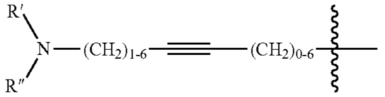

and

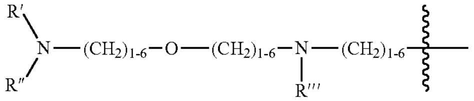

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure.

In an embodiment of any of the preceeding formulas is provided a compound wherein $R_N$ is selected from:

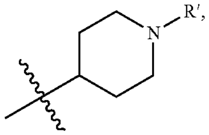

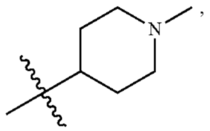

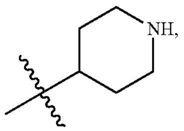

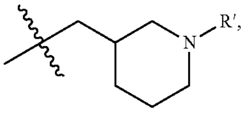

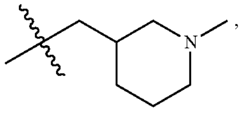

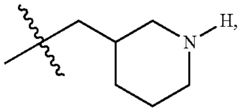

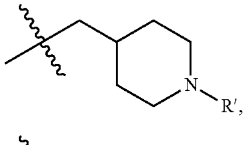

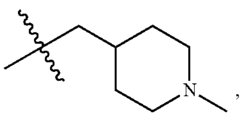

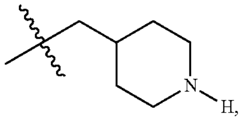

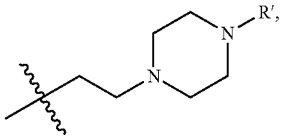

-continued

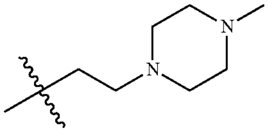,
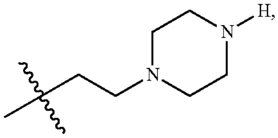
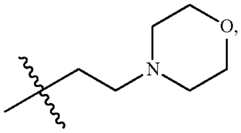
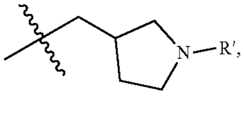
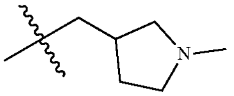,
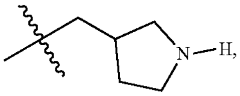
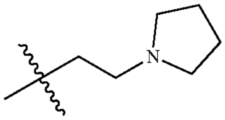,
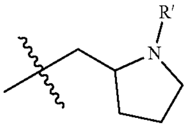,
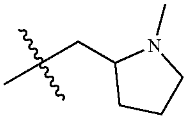,
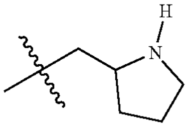,
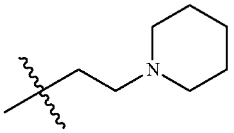,
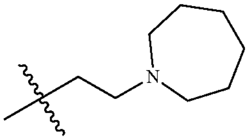,
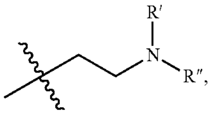
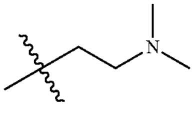,
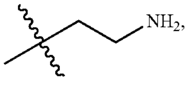
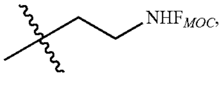
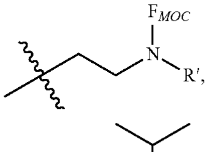
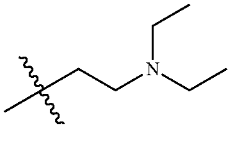,
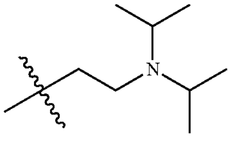,
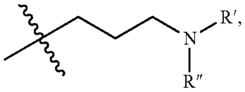
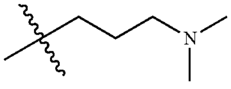,
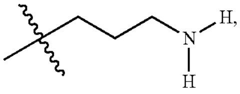

-continued

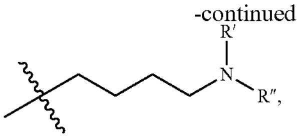
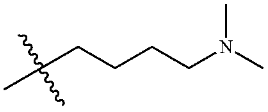,
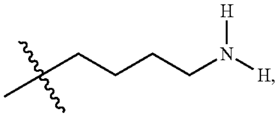
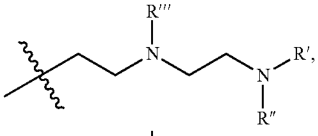
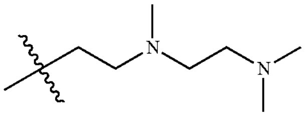,
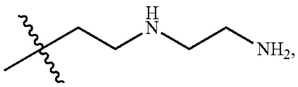
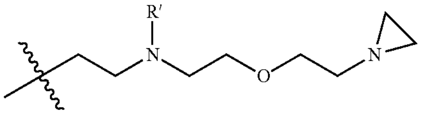,
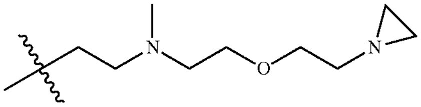,
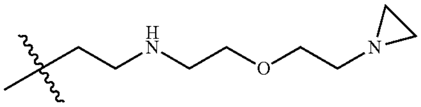,
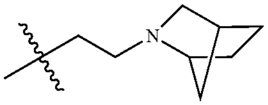,
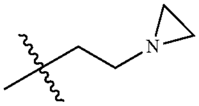, and
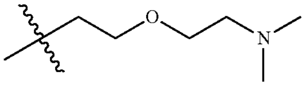;

wherein R' is hydrogen, aliphatic hydrocarbon or a protecting group, and wherein the ∿∿∿ symbol represents the point of attachment;

In an embodiment of any of the preceeding formulas is provided a compound wherein R* is independently at each occurrence selected from hydrogen, an aliphatic $C_1$-$C_6$ hydrocarbon, an aromatic $C_6$-$C_7$ hydrocarbon, and combinations thereof, which further comprise 0-3 heteroatoms selected from O and N, and combinations thereof; an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O and N and combinations thereof.

Some exemplary non-limiting embodiments of the rifamycin analog compounds according to the disclosure are shown in Table 1 below:
TABLE 1
| Select rifamycin analogs according to the disclosure | |
|---|---|
| Rifamycin Analog Compound Structure | Compound Number |
| 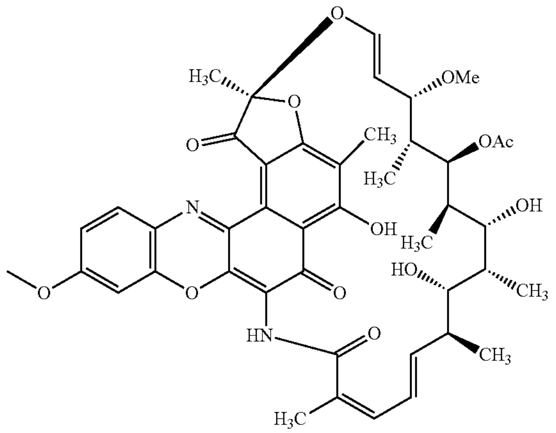 [SMILES: COc1ccc2nc3c4c5c6c(C)c(O)c4c(=O)c(c-3oc2c1)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O] | 1a |
| 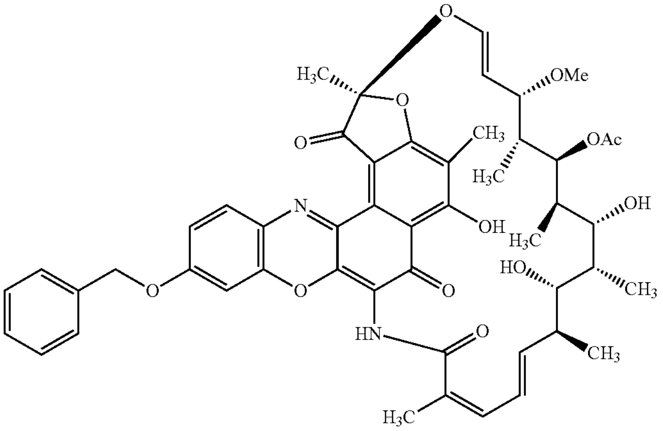 [SMILES: CO[C@H]1/C=C/O[C@@]2(C)Oc3c(C)c(O)c4c(=O)c(c5oc6cc(OCc7ccccc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 1b |
| 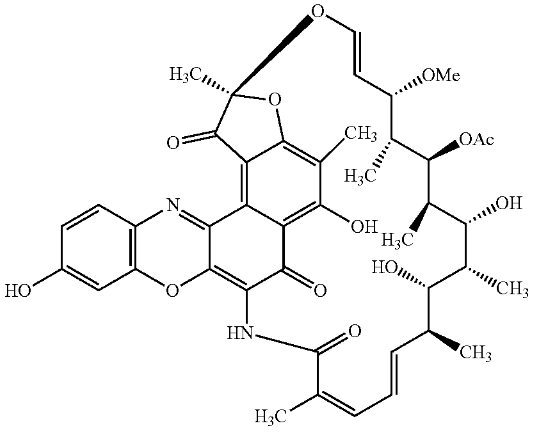 [SMILES: CO[C@H]1/C=C/O[C@@]2(C)Oc3c(C)c(O)c4c(=O)c(c5oc6cc(O)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 1c |

TABLE 1-continued
| Select rifamycin analogs according to the disclosure | |
|---|---|
| Rifamycin Analog Compound Structure | Compound Number |
| 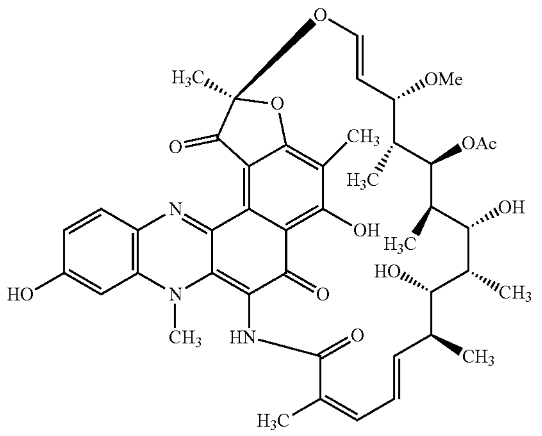 [SMILES: CO[C@H]1/C=C/O[C@@]2(C)Oc3c(C)c(O)c4c(=O)c(c5n(C)c6cc(O)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 1d |
| 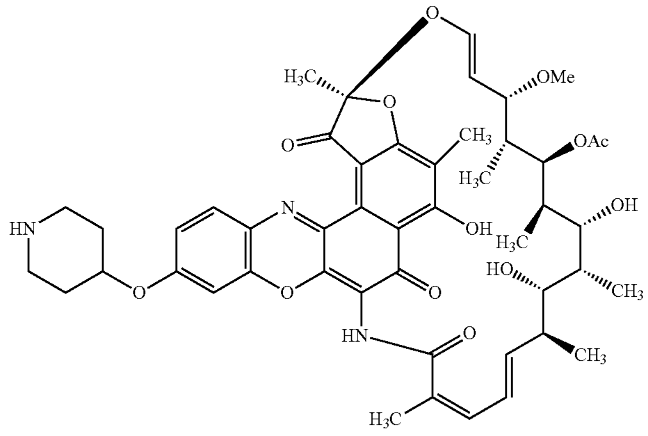 [SMILES: CO[C@H]1/C=C/O[C@@]2(C)Oc3c(C)c(O)c4c(=O)c(c5oc6cc(OC7CCNCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 14 |
| 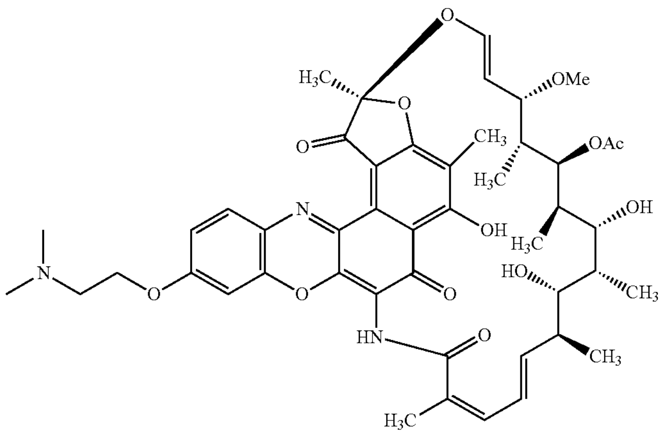 [SMILES: CO[C@H]1/C=C/O[C@@]2(C)Oc3c(C)c(O)c4c(=O)c(c5oc6cc(OCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16a |

TABLE 1-continued
| Select rifamycin analogs according to the disclosure | |
|---|---|
| Rifamycin Analog Compound Structure | Compound Number |
| 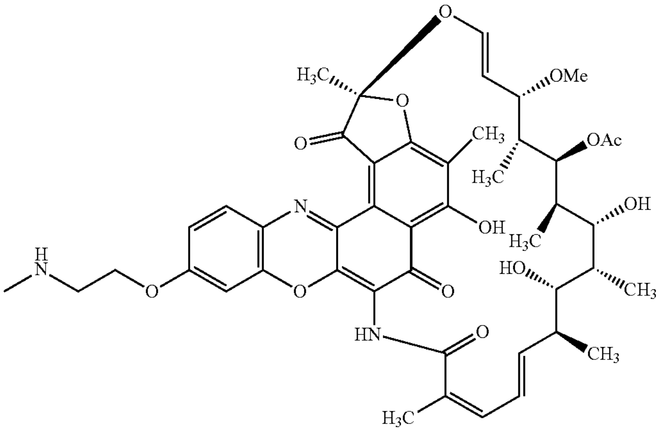 [SMILES: CNCCOc1ccc2nc3c4c5c6c(C)c(O)c4c(=O)c(c-3oc2c1)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O] | 16d |
| 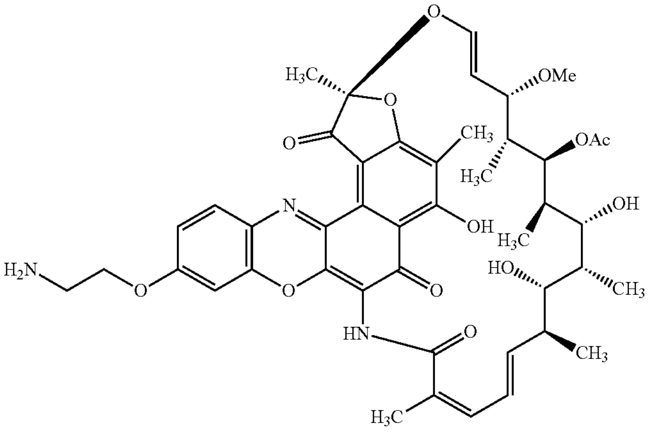 [SMILES: CO[C@H]1/C=C/O[C@@]2(C)Oc3c(C)c(O)c4c(=O)c(c5oc6cc(OCCN)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16e |
| 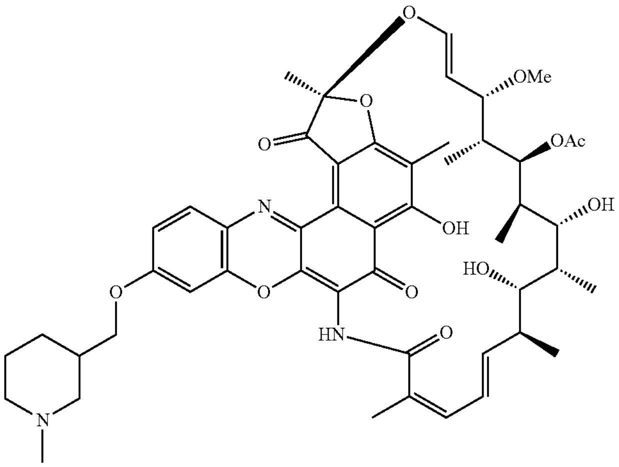 [SMILES: CO[C@H]1/C=C/O[C@@]2(C)Oc3c(C)c(O)c4c(=O)c(c5oc6cc(OCC7CCCN(C)C7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16f |

TABLE 1-continued
| Select rifamycin analogs according to the disclosure | |
|---|---|
| Rifamycin Analog Compound Structure | Compound Number |
| 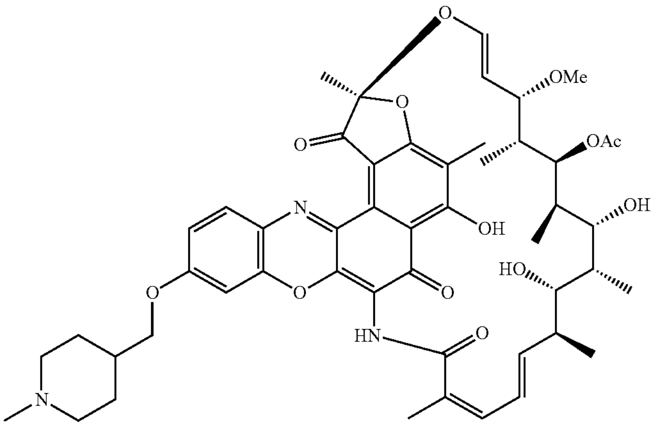 [SMILES: CO[C@H]1/C=C/O[C@@]2(C)Oc3c(C)c(O)c4c(=O)c(c5oc6cc(OCC7CCN(C)CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16g |
| 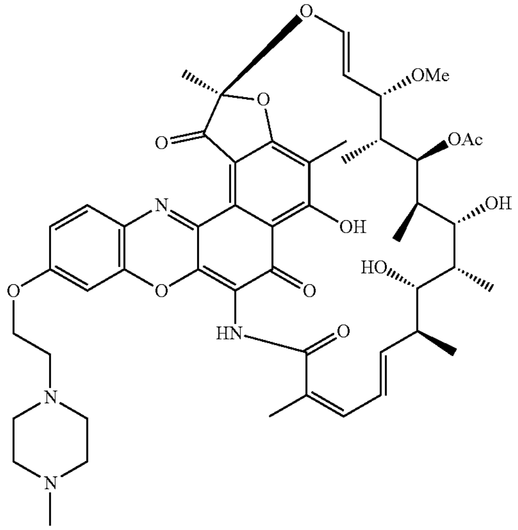 [SMILES: CO[C@H]1/C=C/O[C@@]2(C)Oc3c(C)c(O)c4c(=O)c(c5oc6cc(OCCN7CCN(C)CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16h |
| 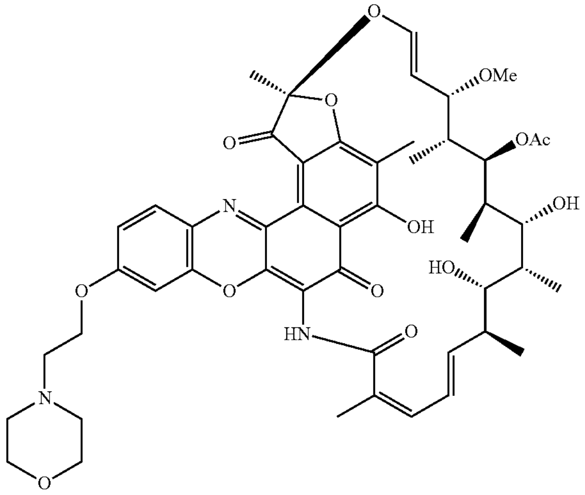 [SMILES: CO[C@H]1/C=C/O[C@@]2(C)Oc3c(C)c(O)c4c(=O)c(c5oc6cc(OCCN7CCOCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16i |

TABLE 1-continued
| Select rifamycin analogs according to the disclosure | |
|---|---|
| Rifamycin Analog Compound Structure | Compound Number |
| 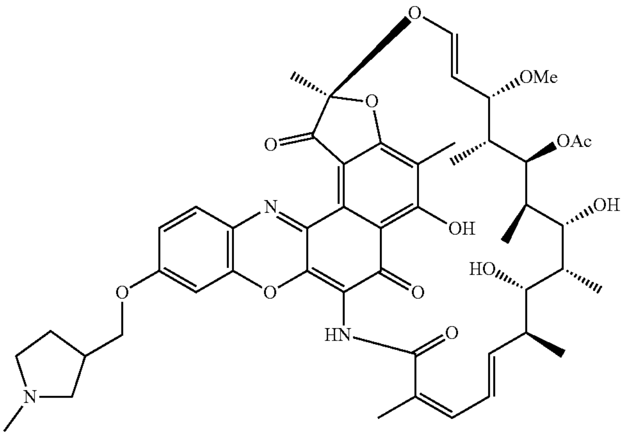 [SMILES: CO[C@H]1/C=C/O[C@@]2(C)Oc3c(C)c(O)c4c(=O)c(c5oc6cc(OCC7CCN(C)C7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16j |
| 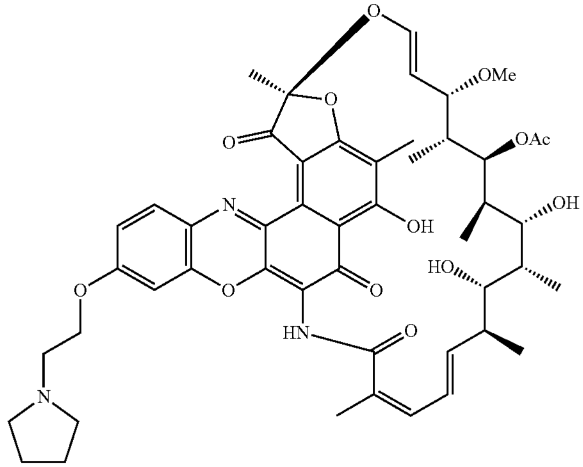 [SMILES: CO[C@H]1/C=C/O[C@@]2(C)Oc3c(C)c(O)c4c(=O)c(c5oc6cc(OCCN7CCCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16k |
| 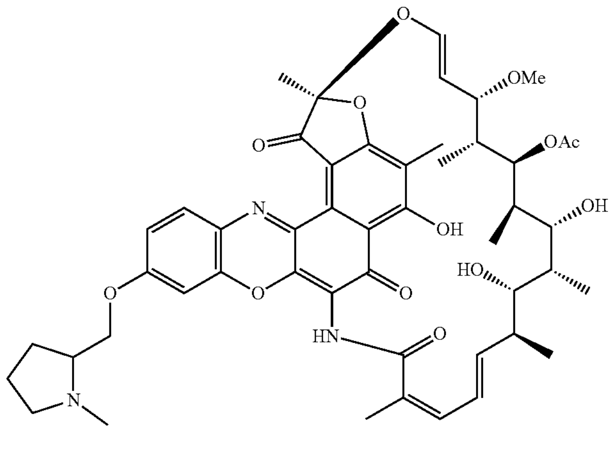 [SMILES: CO[C@H]1/C=C/O[C@@]2(C)Oc3c(C)c(O)c4c(=O)c(c5oc6cc(OCC7CCCN7C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16l |

TABLE 1-continued
| Select rifamycin analogs according to the disclosure | |
|---|---|
| Rifamycin Analog Compound Structure | Compound Number |
| 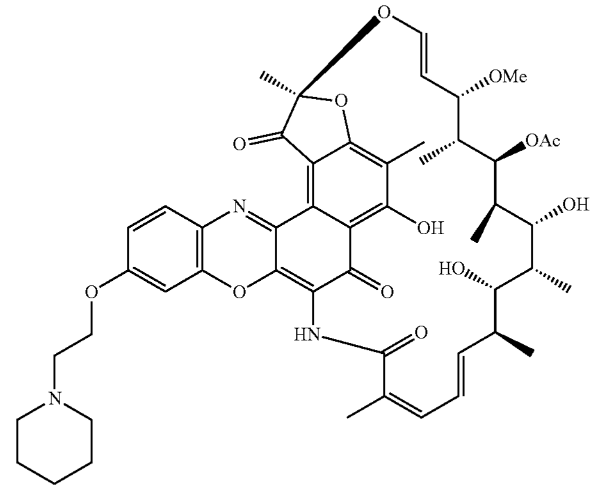 [SMILES: CO[C@H]1/C=C/O[C@@]2(C)Oc3c(C)c(O)c4c(=O)c(c5oc6cc(OCCN7CCCCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16m |
| 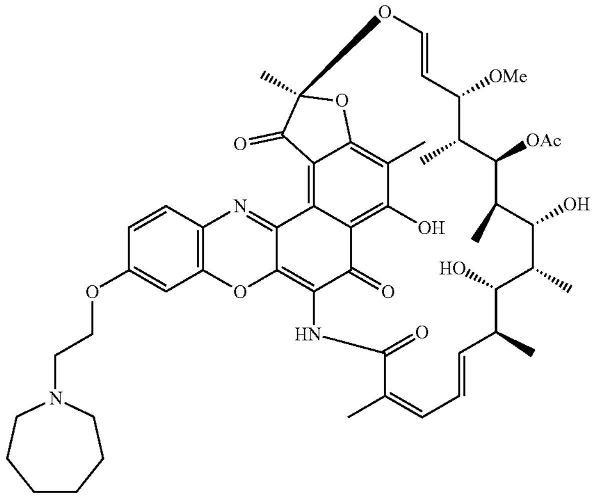 [SMILES: CO[C@H]1/C=C/O[C@@]2(C)Oc3c(C)c(O)c4c(=O)c(c5oc6cc(OCCN7CCCCCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16n |
| 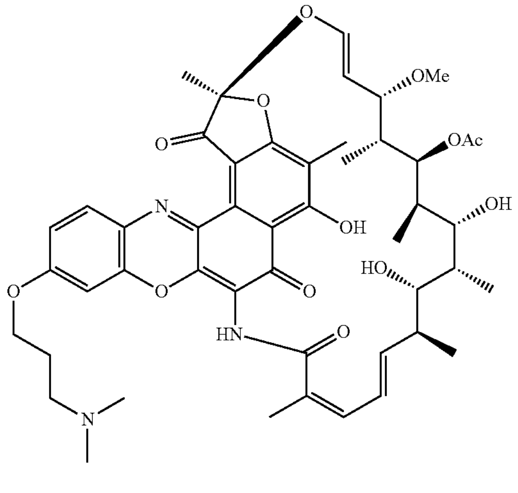 [SMILES: CO[C@H]1/C=C/O[C@@]2(C)Oc3c(C)c(O)c4c(=O)c(c5oc6cc(OCCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16o |

TABLE 1-continued
| Select rifamycin analogs according to the disclosure | |
|---|---|
| Rifamycin Analog Compound Structure | Compound Number |
| 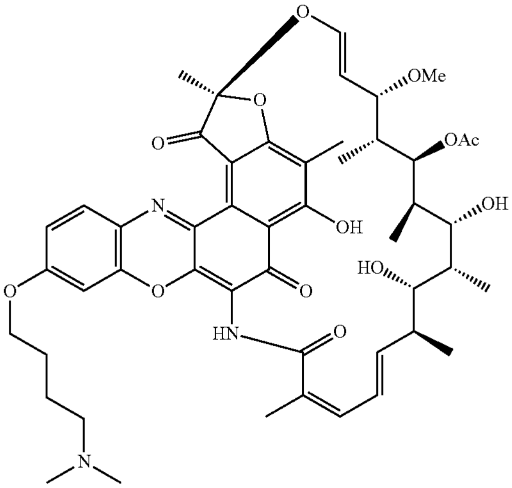 [SMILES: CO[C@H]1/C=C/O[C@@]2(C)Oc3c(C)c(O)c4c(=O)c(c5oc6cc(OCCCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16p |
| 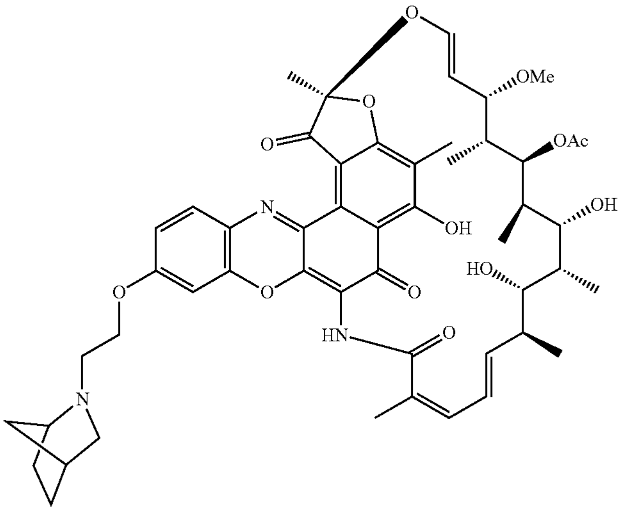 [SMILES: CO[C@H]1/C=C/O[C@@]2(C)Oc3c(C)c(O)c4c(=O)c(c5oc6cc(OCCN7CC8CCC7C8)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16q |
| 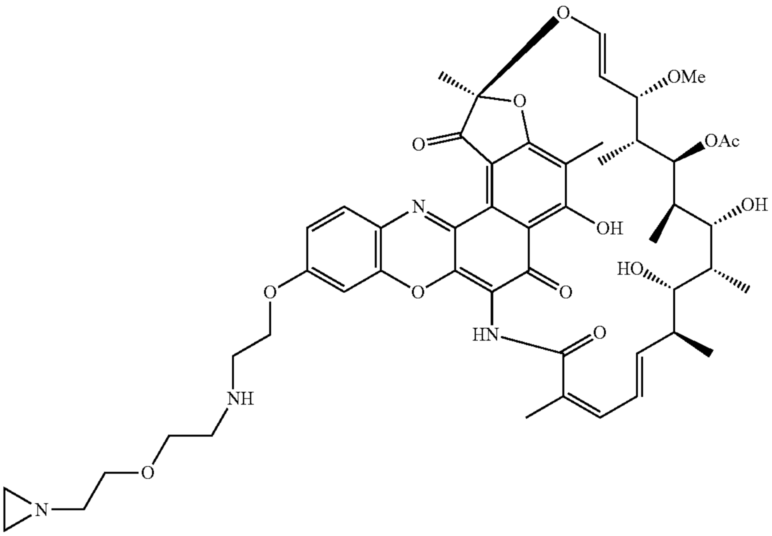 [SMILES: CO[C@H]1/C=C/O[C@@]2(C)Oc3c(C)c(O)c4c(=O)c(c5oc6cc(OCCNCCOCCN7CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16r |

TABLE 1-continued
| Select rifamycin analogs according to the disclosure | |
|---|---|
| Rifamycin Analog Compound Structure | Compound Number |
| 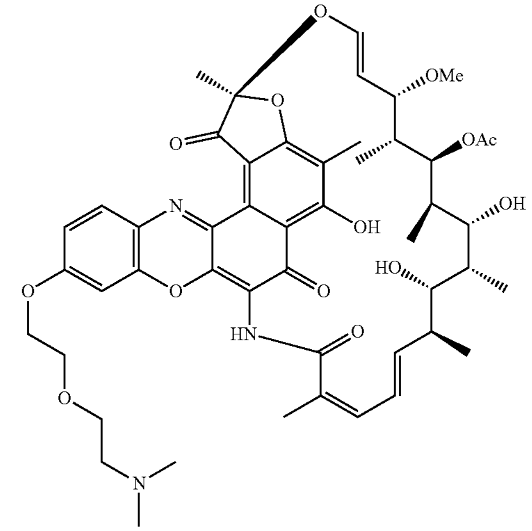 [SMILES: CO[C@H]1/C=C/O[C@@]2(C)Oc3c(C)c(O)c4c(=O)c(c5oc6cc(OCCOCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16s |
| 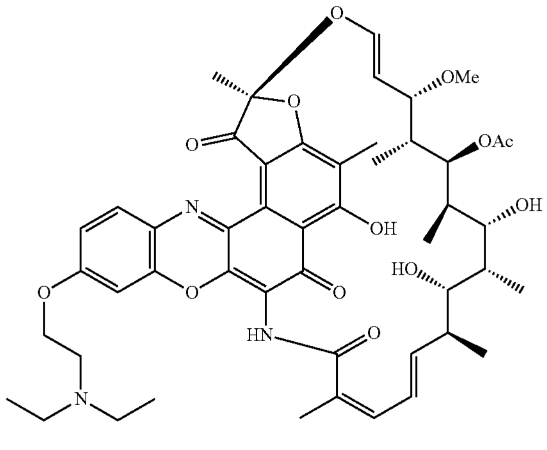 [SMILES: CCN(CC)CCOc1ccc2nc3c4c5c6c(C)c(O)c4c(=O)c(c-3oc2c1)NC(=O)/C(C)=C\C=C\[C@H](C)[C@H](O)[C@@H](C)[C@@H](O)[C@@H](C)[C@H](OC(C)=O)[C@H](C)[C@@H](OC)/C=C/O[C@@](C)(O6)C5=O] | 16t |
| 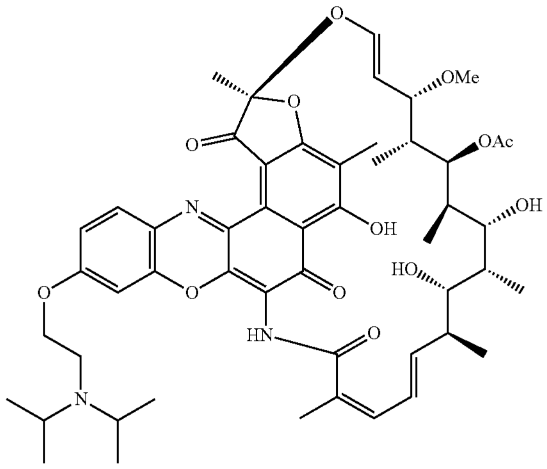 [SMILES: CO[C@H]1/C=C/O[C@@]2(C)Oc3c(C)c(O)c4c(=O)c(c5oc6cc(OCCN(C(C)C)C(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16u |

TABLE 1-continued
Select rifamycin analogs according to the disclosure
| Rifamycin Analog Compound Structure | Compound Number |
| --- | --- |
| 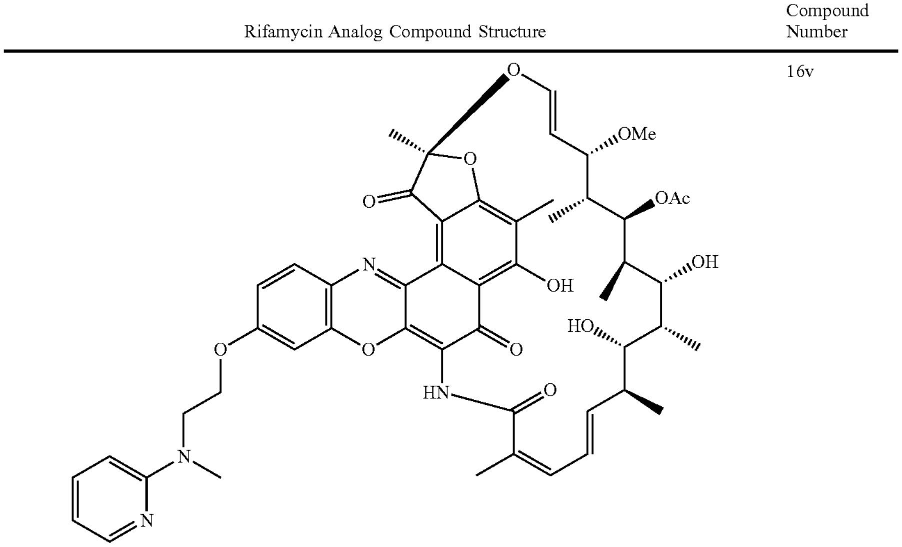 | 16v |
| 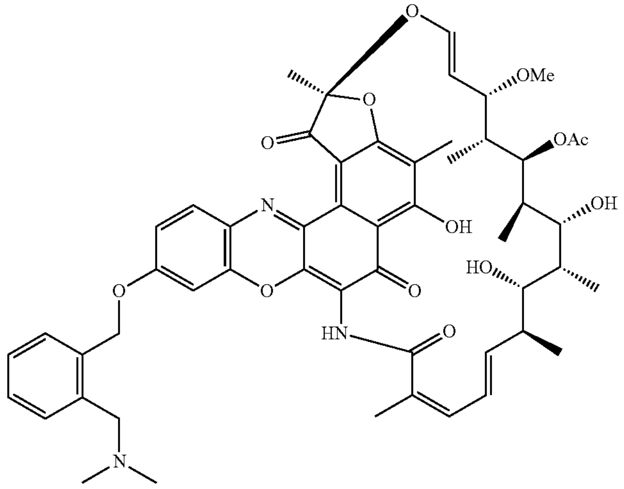 [SMILES: CO[C@H]1/C=C/O[C@@]2(C)Oc3c(C)c(O)c4c(=O)c(c5oc6cc(OCc7ccccc7CN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16w |
| 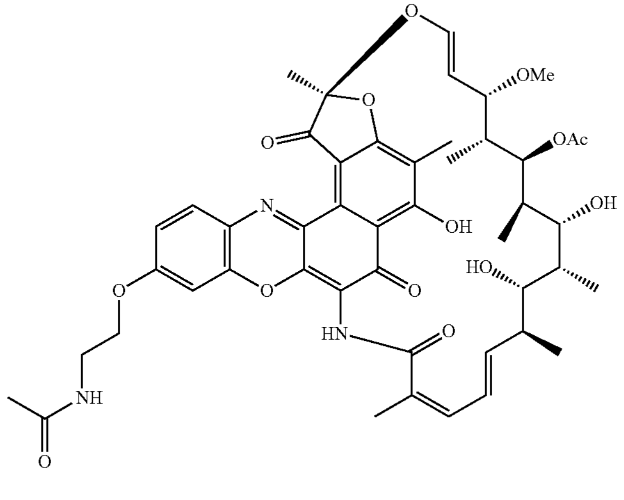 [SMILES: CO[C@H]1/C=C/O[C@@]2(C)Oc3c(C)c(O)c4c(=O)c(c5oc6cc(OCCNC(C)=O)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16x |

TABLE 1-continued
| Select rifamycin analogs according to the disclosure | |
|---|---|
| Rifamycin Analog Compound Structure | Compound Number |
| 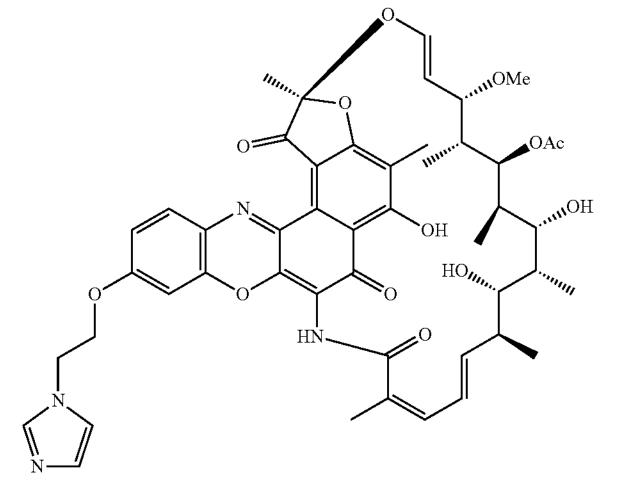 [SMILES: CO[C@H]1/C=C/O[C@@]2(C)Oc3c(C)c(O)c4c(=O)c(c5oc6cc(OCCn7ccnc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16y |
| 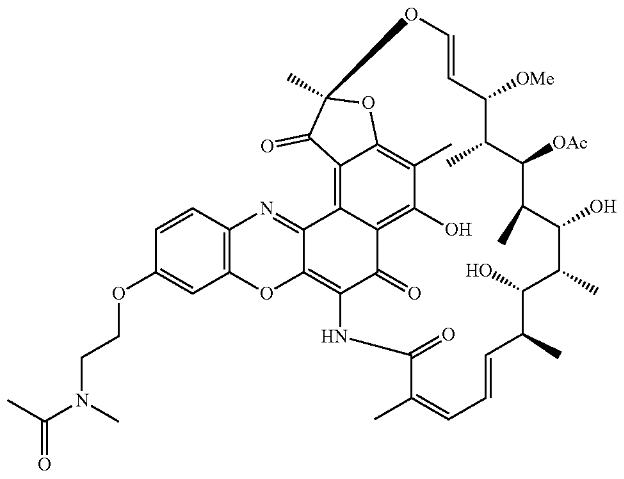 [SMILES: CO[C@H]1/C=C/O[C@@]2(C)Oc3c(C)c(O)c4c(=O)c(c5oc6cc(OCCN(C)C(C)=O)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16z |
| 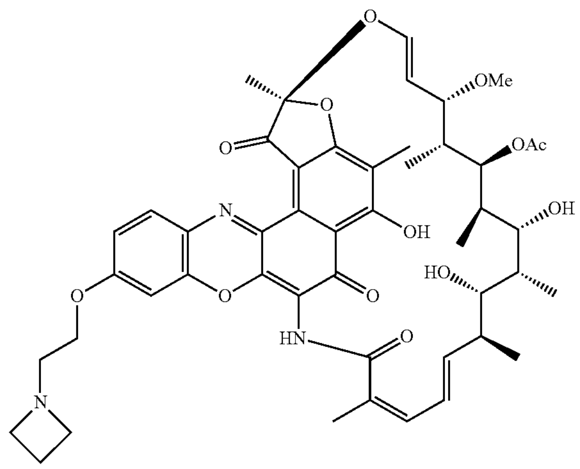 [SMILES: CO[C@H]1/C=C/O[C@@]2(C)Oc3c(C)c(O)c4c(=O)c(c5oc6cc(OCCN7CCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 16z-1 |

TABLE 1-continued
| Select rifamycin analogs according to the disclosure | |
|---|---|
| Rifamycin Analog Compound Structure | Compound Number |
| 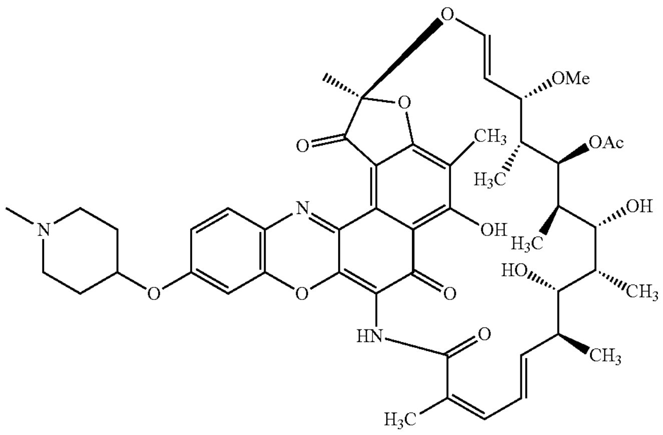 [SMILES: CO[C@H]1/C=C/O[C@@]2(C)Oc3c(C)c(O)c4c(=O)c(c5oc6cc(OC7CCN(C)CC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 17 |
| 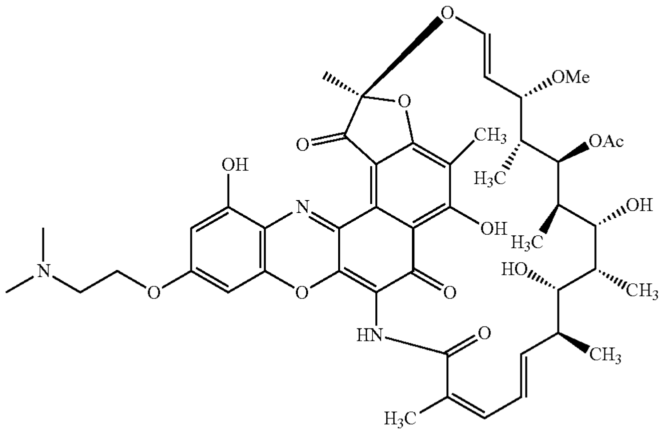 [SMILES: CO[C@H]1/C=C/O[C@@]2(C)Oc3c(C)c(O)c4c(=O)c(c5oc6cc(OCCN(C)C)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29 |
| 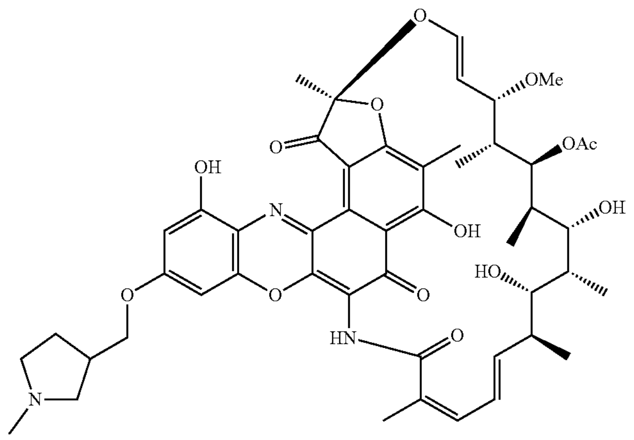 [SMILES: CO[C@H]1/C=C/O[C@@]2(C)Oc3c(C)c(O)c4c(=O)c(c5oc6cc(OCC7CCN(C)C7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29a |

TABLE 1-continued
| Select rifamycin analogs according to the disclosure | |
|---|---|
| Rifamycin Analog Compound Structure | Compound Number |
| 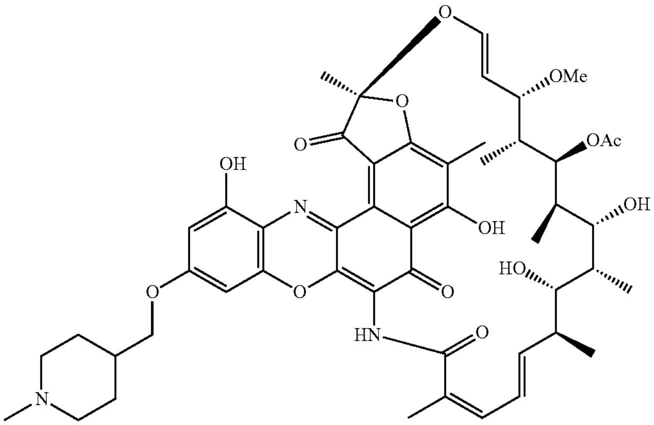 [SMILES: CO[C@H]1/C=C/O[C@@]2(C)Oc3c(C)c(O)c4c(=O)c(c5oc6cc(OCC7CCN(C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29b |
| 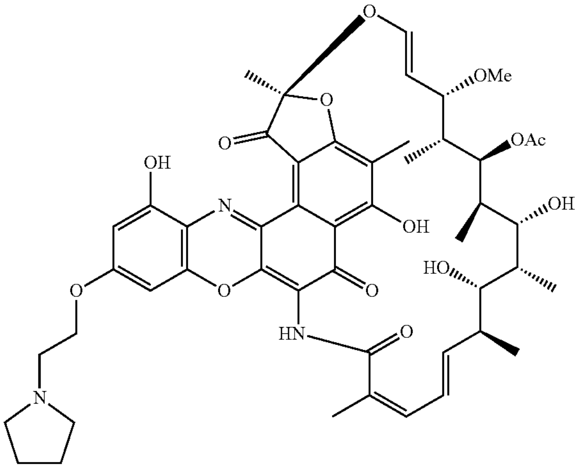 [SMILES: CO[C@H]1/C=C/O[C@@]2(C)Oc3c(C)c(O)c4c(=O)c(c5oc6cc(OCCN7CCCC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29c |
| 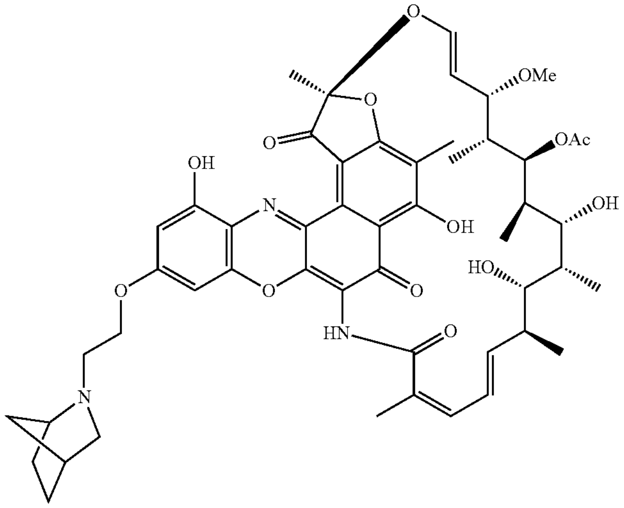 [SMILES: CO[C@H]1/C=C/O[C@@]2(C)Oc3c(C)c(O)c4c(=O)c(c5oc6cc(OCCN7CC8CCC7C8)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29d |

TABLE 1-continued
Select rifamycin analogs according to the disclosure
| Rifamycin Analog Compound Structure | Compound Number |
| --- | --- |
| 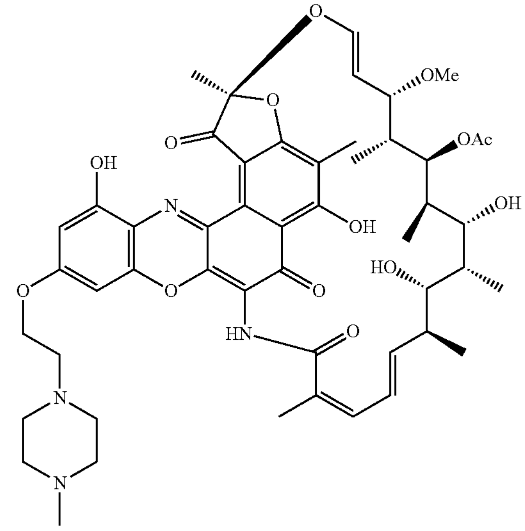 [SMILES: CO[C@H]1/C=C/O[C@@]2(C)Oc3c(C)c(O)c4c(=O)c(c5oc6cc(OCCN7CCN(C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29e |
| 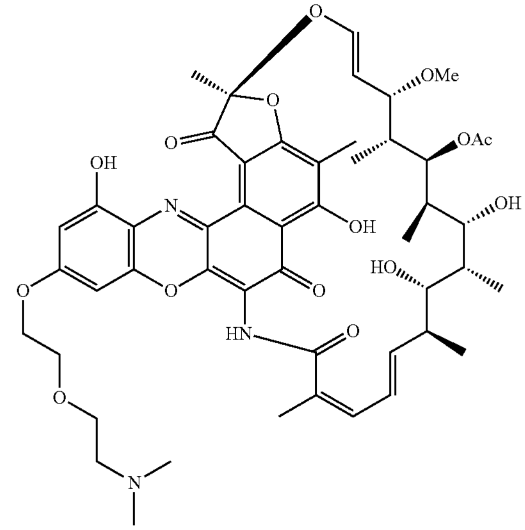 [SMILES: CO[C@H]1/C=C/O[C@@]2(C)Oc3c(C)c(O)c4c(=O)c(c5oc6cc(OCCOCCN(C)C)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29f |
| 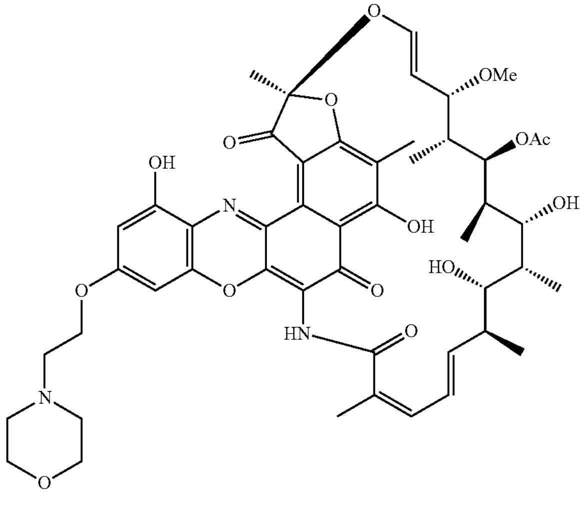 [SMILES: CO[C@H]1/C=C/O[C@@]2(C)Oc3c(C)c(O)c4c(=O)c(c5oc6cc(OCCN7CCOCC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29g |

TABLE 1-continued
| Select rifamycin analogs according to the disclosure | |
|---|---|
| Rifamycin Analog Compound Structure | Compound Number |
| 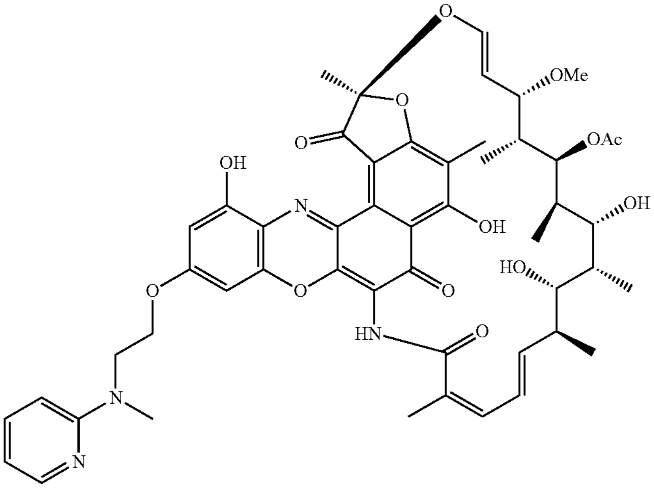 [SMILES: CO[C@H]1/C=C/O[C@@]2(C)Oc3c(C)c(O)c4c(=O)c(c5oc6cc(OCCN(C)c7ccccn7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29h |
| 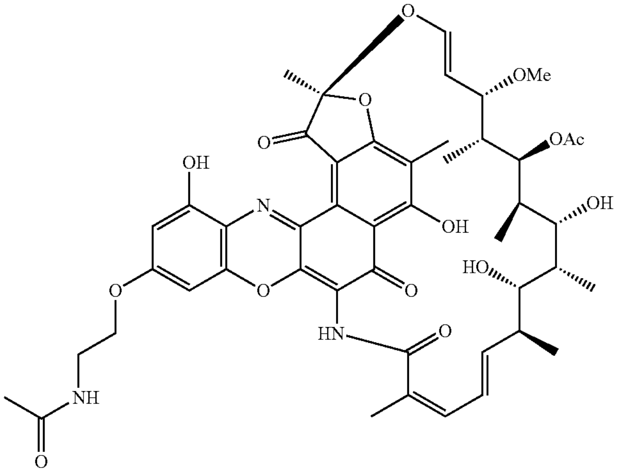 [SMILES: CO[C@H]1/C=C/O[C@@]2(C)Oc3c(C)c(O)c4c(=O)c(c5oc6cc(OCCNC(C)=O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29i |
| 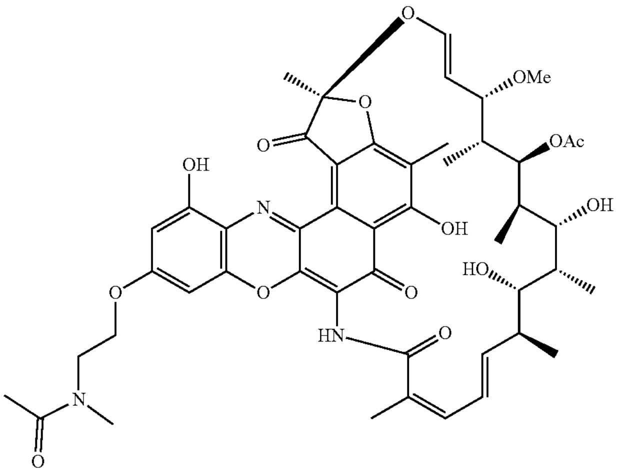 [SMILES: CO[C@H]1/C=C/O[C@@]2(C)Oc3c(C)c(O)c4c(=O)c(c5oc6cc(OCCN(C)C(C)=O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29j |

TABLE 1-continued
| Select rifamycin analogs according to the disclosure | |
|---|---|
| Rifamycin Analog Compound Structure | Compound Number |
| 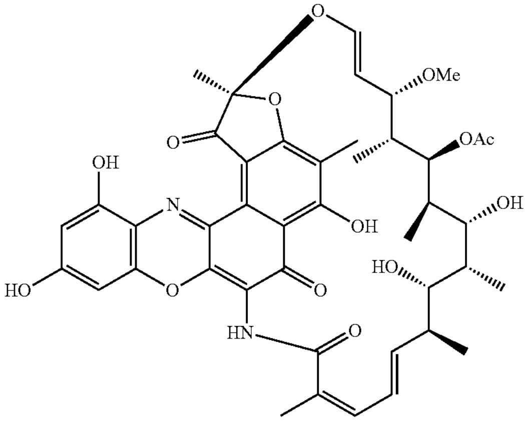 [SMILES: CO[C@H]1/C=C/O[C@@]2(C)Oc3c(C)c(O)c4c(=O)c(c5oc6cc(O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 29k |
| 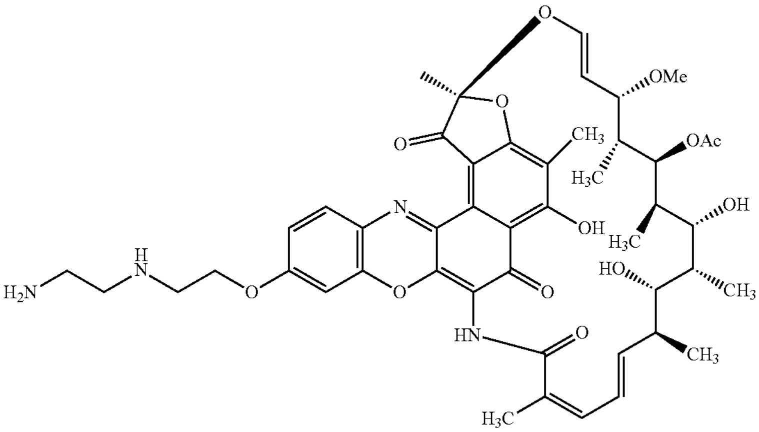 [SMILES: CO[C@H]1/C=C/O[C@@]2(C)Oc3c(C)c(O)c4c(=O)c(c5oc6cc(OCCNCCN)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 35 |
| 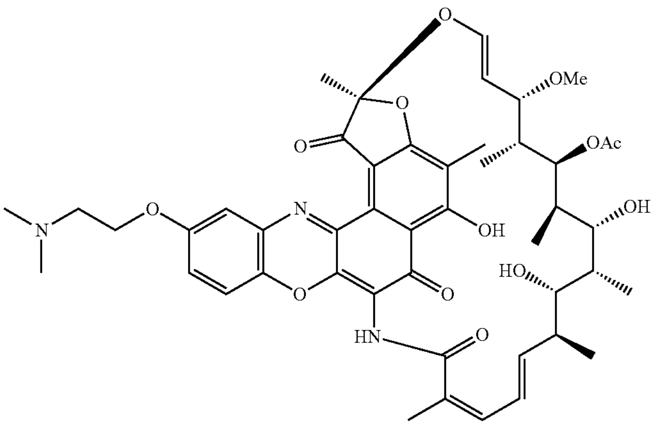 [SMILES: CO[C@H]1/C=C/O[C@@]2(C)Oc3c(C)c(O)c4c(=O)c(c5oc6ccc(OCCN(C)C)cc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 38 |

TABLE 1-continued
| Select rifamycin analogs according to the disclosure | |
|---|---|
| Rifamycin Analog Compound Structure | Compound Number |
| 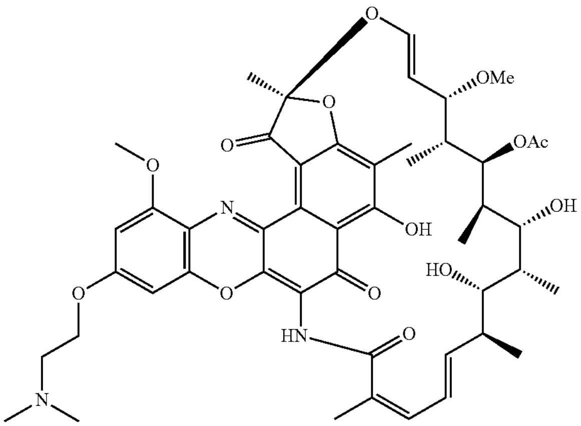 | 43 |
| 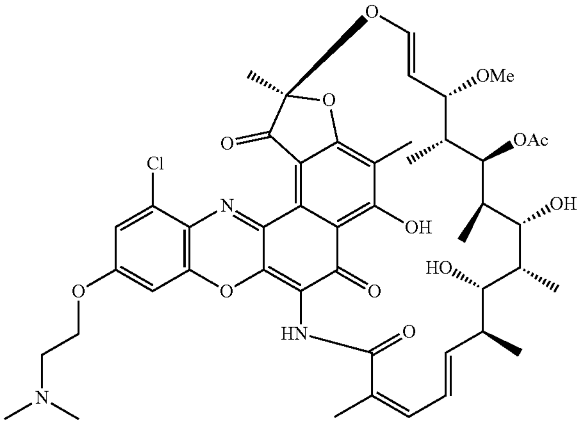 | 45 |
| 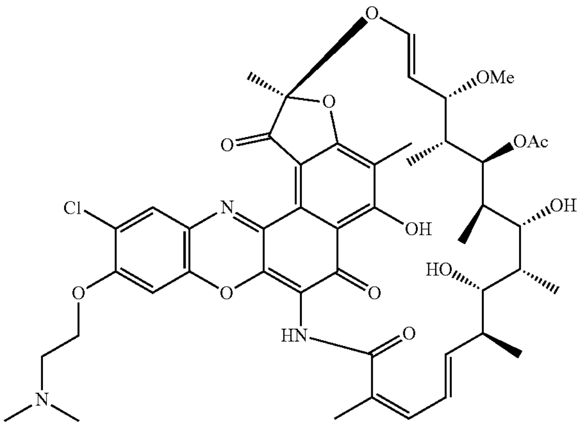 [SMILES: CO[C@H]1/C=C/O[C@@]2(C)Oc3c(C)c(O)c4c(=O)c(c5oc6cc(OCCN(C)C)c(Cl)cc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 48 |

TABLE 1-continued
| Select rifamycin analogs according to the disclosure | |
|---|---|
| Rifamycin Analog Compound Structure | Compound Number |
| 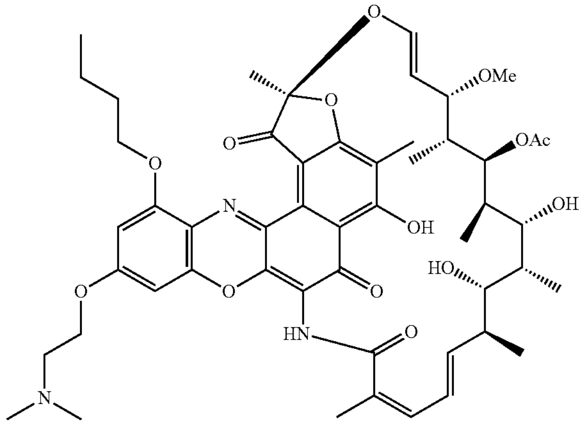 [SMILES: CCCCOc1cc(OCCN(C)C)cc2oc3c4c(=O)c5c(O)c(C)c6c(c5c-3nc12)C(=O)[C@@](C)(O/C=C/[C@H](OC)[C@@H](C)[C@@H](OC(C)=O)[C@H](C)[C@H](O)[C@H](C)[C@@H](O)[C@@H](C)/C=C/C=C(/C)C(=O)N4)O6] | 50 |
| 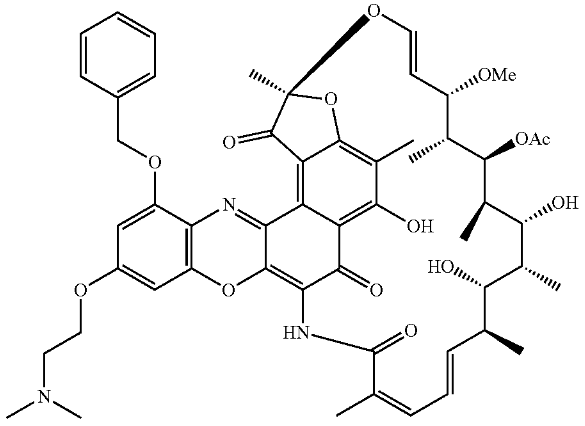 [SMILES: CO[C@H]1/C=C/O[C@@]2(C)Oc3c(C)c(O)c4c(=O)c(c5oc6cc(OCCN(C)C)cc(OCc7ccccc7)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 52 |
| 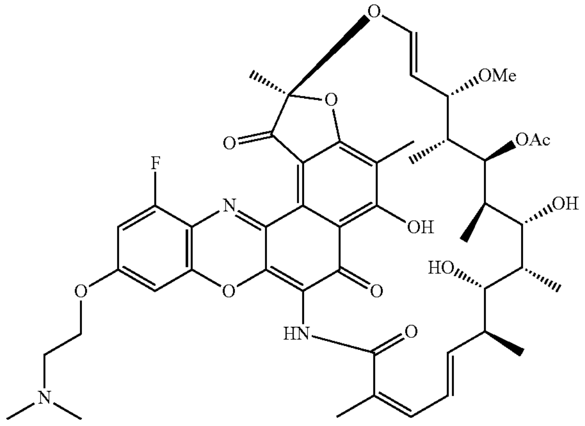 [SMILES: CO[C@H]1/C=C/O[C@@]2(C)Oc3c(C)c(O)c4c(=O)c(c5oc6cc(OCCN(C)C)cc(F)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 55 |

TABLE 1-continued
| Select rifamycin analogs according to the disclosure | |
|---|---|
| Rifamycin Analog Compound Structure | Compound Number |
| 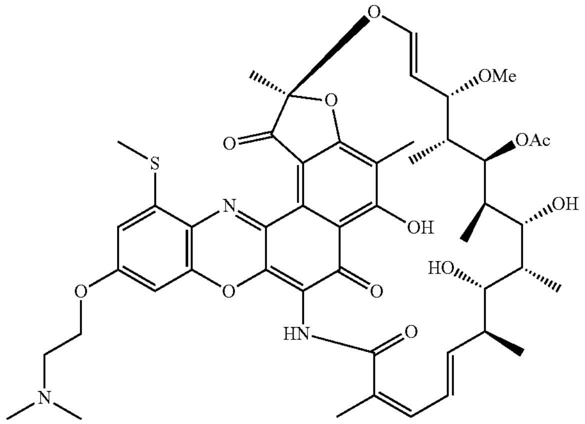 | 60 |
| 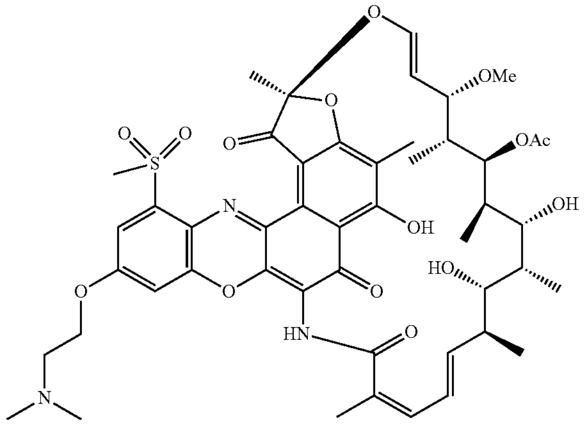 [SMILES: CO[C@H]1/C=C/O[C@@]2(C)Oc3c(C)c(O)c4c(=O)c(c5oc6cc(OCCN(C)C)cc(S(C)(=O)=O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 61 |
| 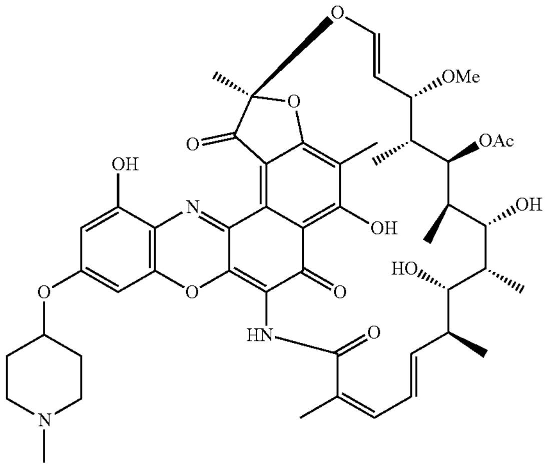 [SMILES: CO[C@H]1/C=C/O[C@@]2(C)Oc3c(C)c(O)c4c(=O)c(c5oc6cc(OC7CCN(C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 68 |

TABLE 1-continued
| Select rifamycin analogs according to the disclosure | |
|---|---|
| Rifamycin Analog Compound Structure | Compound Number |
| 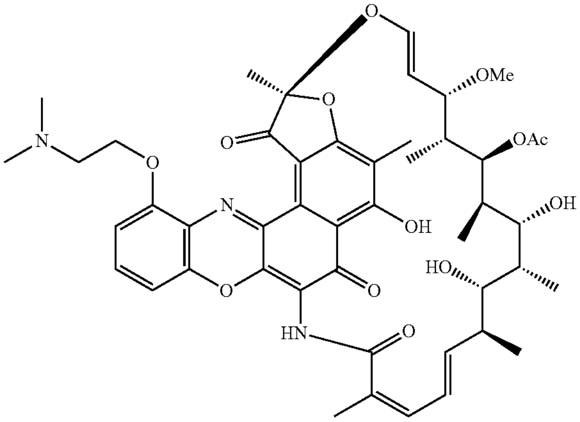 [SMILES: CO[C@H]1/C=C/O[C@@]2(C)Oc3c(C)c(O)c4c(=O)c(c5oc6cccc(OCCN(C)C)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 71 |
| 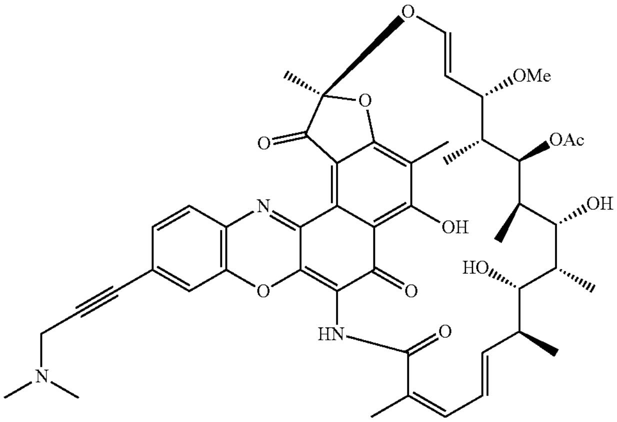 [SMILES: CO[C@H]1/C=C/O[C@@]2(C)Oc3c(C)c(O)c4c(=O)c(c5oc6cc(C#CCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 72 |
| 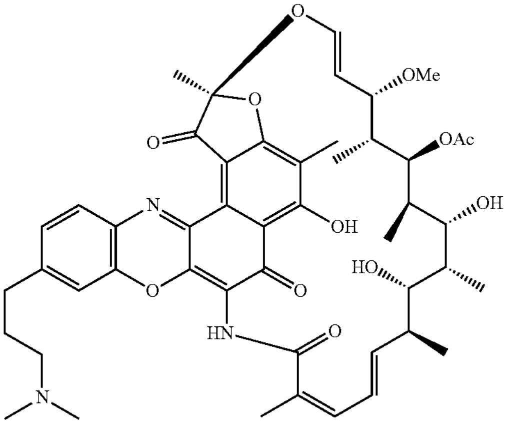 [SMILES: CO[C@H]1/C=C/O[C@@]2(C)Oc3c(C)c(O)c4c(=O)c(c5oc6cc(CCCN(C)C)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C] | 75 |

In one embodiment, a rifamycin analog compound of the disclosure has a structure selected from the group consisting of:

(P1)

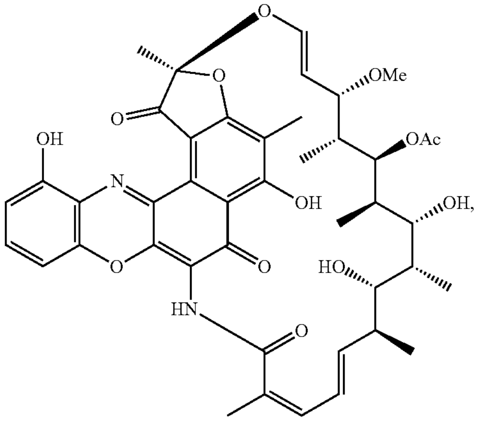

(P2)

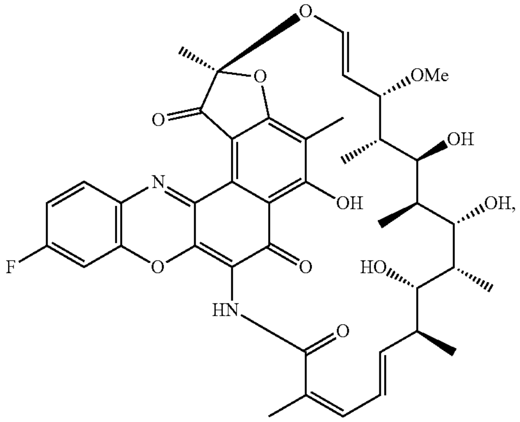

(P3)

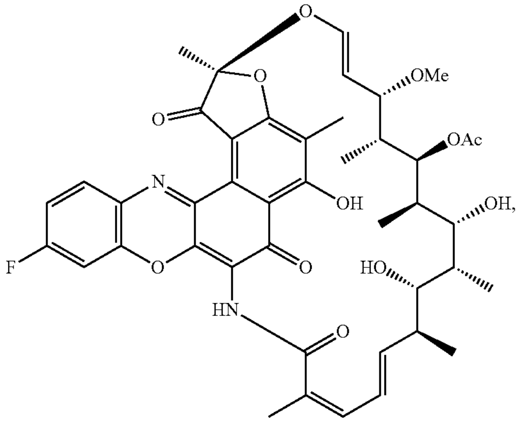

or a pharmaceutically acceptable salt thereof.

In one aspect, the compounds of the disclosure have the structure of Formula (IA):

(IA)

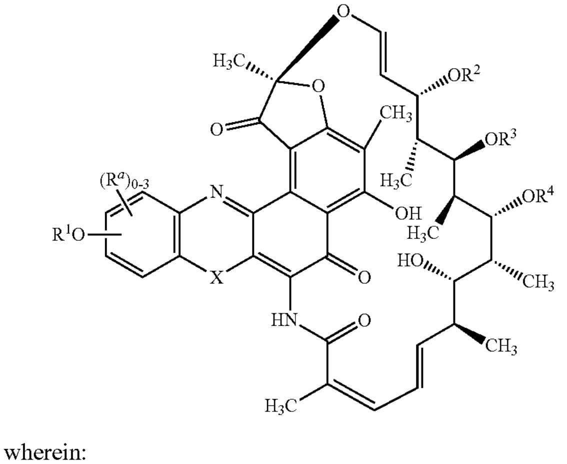

wherein:

X is selected from —O—, —S—, and —NR*—;

$R_1$ is selected from hydrogen, an aliphatic $C_1$-$C_{20}$ hydrocarbon, an aromatic $C_5$-$C_{20}$ hydrocarbon, a heteroaromatic $C_1$-$C_{20}$ hydrocarbon, an aryl $C_6$-$C_{20}$ hydrocarbon, a heteroaryl $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—N$(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —Si$(R^*)_3$, —$CF_3$, —O—$CF_3$ and combinations thereof;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is independently at each occurrence selected from hydrogen, —F, —Cl, —Br, —I, —OH, OR*, —$NH_2$, —NHR*, —$N(R^*)_2$, —$N(R^*)_3^+$, —(C═O)—R*, —CHO, —$CO_2H$, —$CO_2R^*$, —SR*, $SO_2R^*$, and an aliphatic $C_1$-$C_{20}$ hydrocarbon, which further comprises 0-8 heteroatoms selected from halogen, O, N, and S, and wherein $R_a$ and $R_b$ are optionally substituted with one or more of —F, —Cl, —Br, —I, —OH, —OR*;

R* is independently at each occurrence selected from hydrogen, an aliphatic $C_1$-$C_{20}$ hydrocarbon, an aromatic $C_5$-$C_{20}$ hydrocarbon, a heteroaromatic $C_1$-$C_{20}$ hydrocarbon, an aryl $C_6$-$C_{20}$ hydrocarbon, a heteroaryl $C_1$-$C_{20}$ hydrocarbon, and combinations thereof, which further comprises 0-8 heteroatoms selected from halogen, O, N, and S and combinations thereof.

In one embodiment, X is —O—, $R_1$ is an aliphatic $C_1$-$C_3$ hydrocarbon, $R_2$ is a methyl group, $R_3$ is Ac (—(C═O)—$CH_3$), $R_4$ is a hydrogen, and $R_a$ is a hydrogen.

In one embodiment, X is —O—, $R_1$ is a benzyl group, $R_2$ is a methyl group, $R_3$ is Ac (—(C═O)—$CH_3$), $R_4$ is a hydrogen, and $R_a$ is a hydrogen.

In one embodiment, X is —O—, $R_1$ is an aliphatic $C_1$-$C_8$ hydrocarbon comprising 1-8 heteroatoms selected from halogen, O, N, and S, $R_2$ is a methyl group, $R_3$ is Ac (—(C═O)—$CH_3$), $R_4$ is a hydrogen, and $R_a$ is a hydrogen.

In one embodiment, X is —O—, $R_1$ is an aliphatic $C_1$-$C_8$ hydrocarbon substituted with one or more of —$NH_2$, —NHR*, —$N(R^*)_2$, $R_2$ is a methyl group, $R_3$ is Ac (—(C═O)—$CH_3$), $R_4$ is a hydrogen, and $R_a$ is a hydrogen.

In one embodiment, X is —$NCH_3$—, $R_1$ is —OH, $R_2$ is a methyl group, $R_3$ is Ac (—(C═O)—$CH_3$), $R_4$ is a hydrogen, and $R_a$ is a hydrogen.

The present disclosure also includes salts of the compounds described herein. As used herein, "salts" refers to derivatives of the disclosed compounds wherein the parent compound is modified by converting an existing acid or base moiety to its salt form. Examples of salts include, but are not limited to, mineral acid (such as HCl, HBr, $H_2SO_4$) or organic acid (such as acetic acid, benzoic acid, trifluoroacetic acid salts of basic residues such as amines; alkali (such as Li, Na, K, Mg, Ca) or organic (such as trialkylammonium) salts of acidic residues such as carboxylic acids; and the like. The salts of the present application can be synthesized from the parent compound which contains a basic or acidic moiety conventional chemical methods. Generally, such salts can be prepared by reacting the free acid or base forms of these compounds with a stoichiometric amount of the appropriate base or acid in water or in an organic solvent, or in a mixture of the two. In some embodiments, non-aqueous media like ether, ethyl acetate, ethanol, isopropanol, or acetonitrile (ACN) may be used.

The present application also includes pharmaceutically acceptable salts of the compounds described herein. The "pharmaceutically acceptable salts" include a subset of the "salts" described above which are conventional non-toxic salts of the parent compound formed, for example, from non-toxic inorganic or organic acids. Lists of suitable salts are found in Remington's Pharmaceutical Sciences, 17th ed., Mack Publishing Company, Easton, Pa., 1985, p. 1418 and Berge, S M et al, *Journal of Pharmaceutical Science,* 1977, 66, 1, 1-19. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

Preparation of compounds can involve the protection and deprotection of various chemical groups. The need for protection and deprotection, and the selection of appropriate protecting groups can be readily determined by one skilled in the art. The chemistry of protecting groups can be found, for example, in Wuts and Greene, *Greene Protective Groups in Organic Synthesis,* 4th Ed., John Wiley & Sons: New York, 2006. In one non-limiting embodiment, protecting groups may include 1-chloroethyl carbonyl (ACE), acetoyl, benzyl (Bn), benzyloxy carbonyl (CBz), formyl, methyl carbonyl, trifluoroacetyl, t-butoxy carbonyl (Boc), and fluorenylmethyloxycarbonyl (Fmoc).

Rifamycin analog compounds depicted herein include all isomeric (e.g., enantiomeric, diastereomeric, and geometric (or conformational)) forms of the compound; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure. All tautomeric forms of the compounds presented herein are also within the scope of the disclosure.

Rifamycin analog compounds described herein also include all compounds that differ only in the presence of one or more isotopically enriched atoms. For example, compounds having the present structures except for the replacement of hydrogen by deuterium or tritium, or the replacement of a carbon by a $^{11}C$- or $^{13}C$- or $^{14}C$-enriched carbon, or the replacement of an oxygen by a $^{17}O$- or $^{18}O$-enriched oxygen, or the replacement of a nitrogen by a $^{15}N$-enriched nitrogen are within the scope of this disclosure.

Crystalline forms of the compounds of the disclosure and salts thereof are also within the scope of the disclosure. The compounds of the disclosure may be isolated in various amorphous and crystalline polymorphic forms, including without limitation amorphous and crystalline polymorphic forms which are anhydrous, hydrated, non-solvated, or solvated. Example hydrates include hemihydrates, monohydrates, dihydrates, and the like. In some embodiments, the compounds of the disclosure are anhydrous and non-solvated. By "anhydrous" is meant that the crystalline form of the compound contains essentially no bound water in the crystal lattice structure, i.e., the compound does not form a crystalline hydrate.

Methods of Manufacturing

In one aspect, the present disclosure provides a method of manufacturing a rifamycin analog compound having the structure of formula (V):

(V)

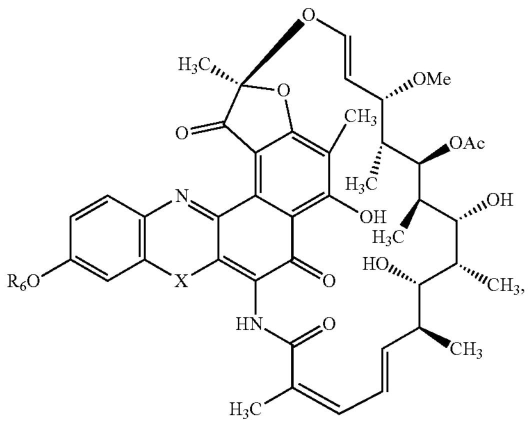

wherein X is selected from —O— and NR*—;

$R_6$ is selected from a $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, $R_N$ is selected from:

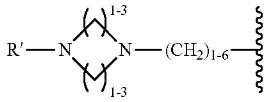

,

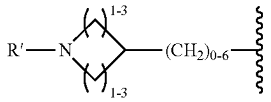

,

-continued

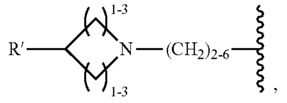

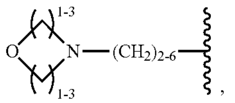

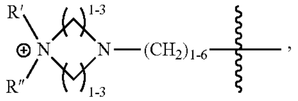

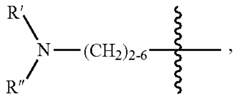

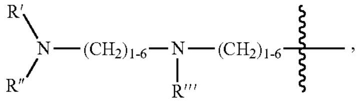

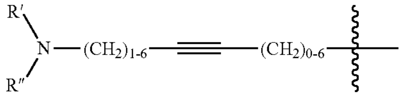

and

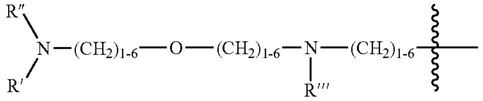

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising the steps of:

(a) contacting Rifamycin S having the structure:

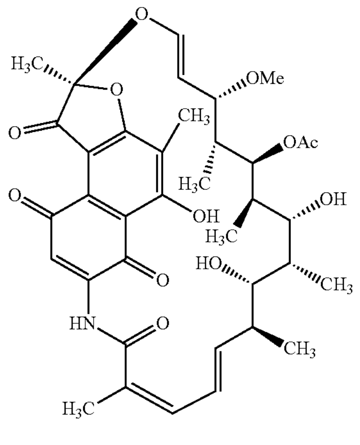 [SMILES: CO[C@H]1/C=C/O[C@@]2(C)Oc3c(C)c(O)c4c(c3C2=O)C(=O)C=C(NC(=O)/C(C)=C\C=C\[C@H](C)[C@H](O)[C@@H](C)[C@@H](O)[C@@H](C)[C@H](OC(C)=O)[C@@H]1C)C4=O]

with a compound having the structure of formula (VI):

(VI)

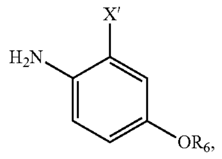

wherein X' is selected from —OH and —NHR*, and (b) treating the product of step (a) with an oxidizing agent.

In one aspect, the present disclosure provides a method of manufacturing a rifamycin analog compound having the structure of formula (V'):

(V')

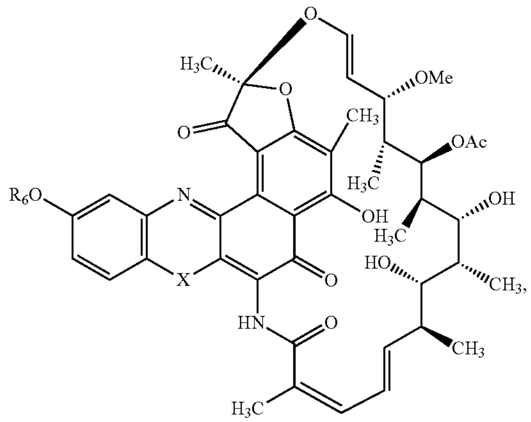

wherein X is selected from —O— and NR*—;

$R_6$ is selected from a $R_N$, hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof;

$R_N$ is selected from:

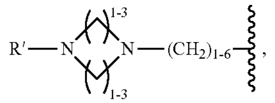

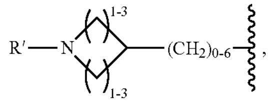

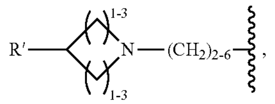

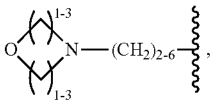

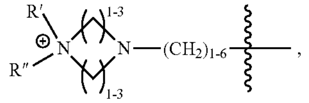

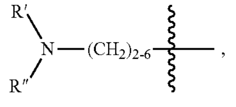

-continued

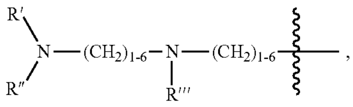

,

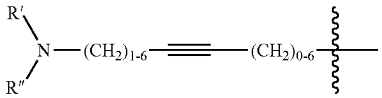

and

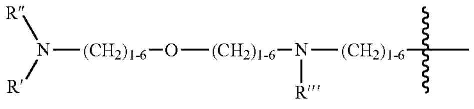

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising the steps of:

(a) contacting Rifamycin S having the structure:

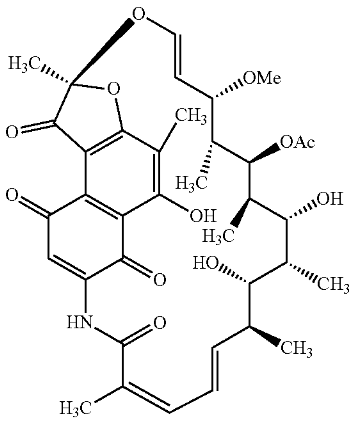 [SMILES: CO[C@H]1/C=C/O[C@@]2(C)Oc3c(C)c(O)c4c(c3C2=O)C(=O)C=C(NC(=O)/C(C)=C\C=C\[C@H](C)[C@H](O)[C@@H](C)[C@@H](O)[C@@H](C)[C@H](OC(C)=O)[C@@H]1C)C4=O]

with a compound having the structure of formula (VI'):

(VI')

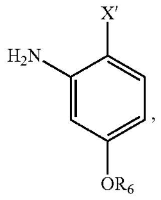

wherein X' is selected from —OH and —NHR*, and (b) treating the product of step (a) with an oxidizing agent.

In one aspect, the present disclosure provides a method of manufacturing a compound having the structure:

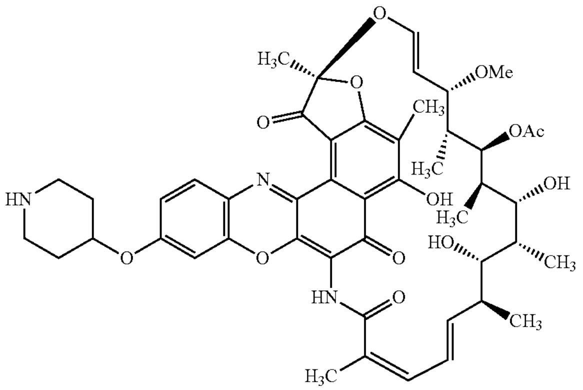 [SMILES: CO[C@H]1/C=C/O[C@@]2(C)Oc3c(C)c(O)c4c(=O)c(c5oc6cc(OC7CCNCC7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

comprising the steps of:

(a) contacting Rifamycin S with a compound having the structure of formula (VII):

(VII)

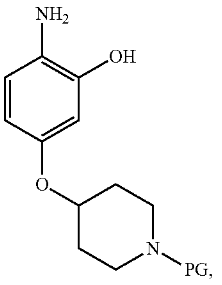

wherein PG is a protecting group;

(b) treating the product of step (a) with an oxidizing agent, and (c) removing the protecting group PG.

In one embodiment, the compound of formula (VII) is prepared by removing protecting group PG' from a compound of formula (VIII):

(VIII)

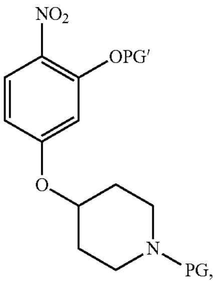

wherein protecting groups PG and PG' may be the same or different from each other.

In one embodiment, the compound of formula (VIII) is prepared by contacting a compound of formula (IX):

(IX)

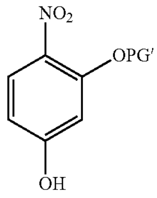

with a compound of formula (X):

(X)

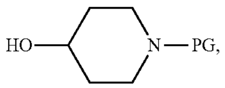

wherein protecting groups PG and PG' may be the same or different from each other.

In one aspect, the present disclosure provides a method of manufacturing a compound having the structure of formula (XI):

(XI)

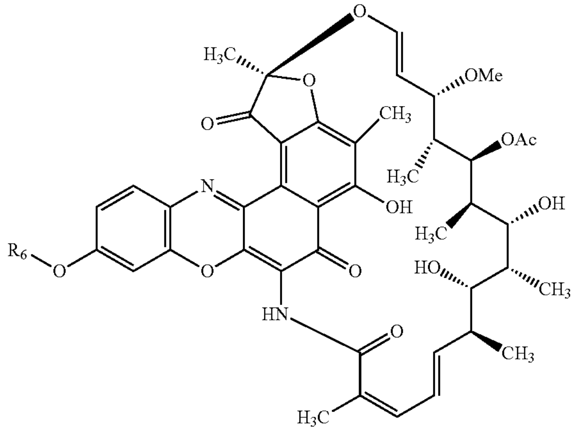

wherein $R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof and wherein $R_6$ is optionally substituted with one or more of —F—Cl, —Br, —I, —OH, —OR*, —NO, —$NO_2$, —$NO_3$, —O—NO, —$N_3$, —$N_2$, —NHR*, —N(R*)$_2$, —N(R*)$_3^+$, —N(R*)—OH, —O—N(R*)$_2$, —N(R*)—O—R*, —CN, —NC, —(C═O)—R*, CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—NHNH$_2$, —O—(C═O)—NHNH$_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof;

$R_N$ is selected from:

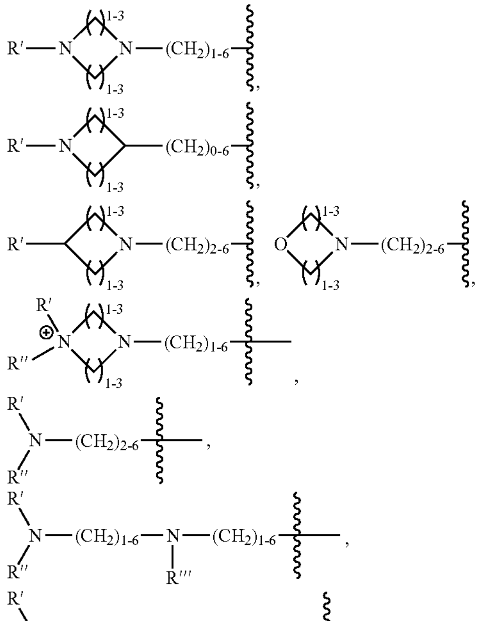

and

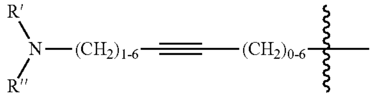

wherein the ∿∿ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

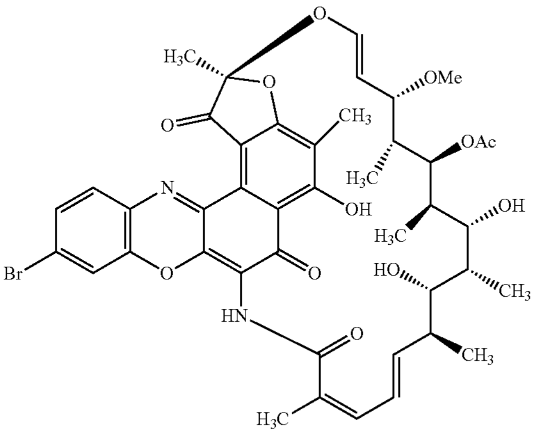

with an alcohol having the structure $R_6$—OH.

In one aspect, the present disclosure provides a method of manufacturing a compound having the structure of formula (XI'):

(XI')

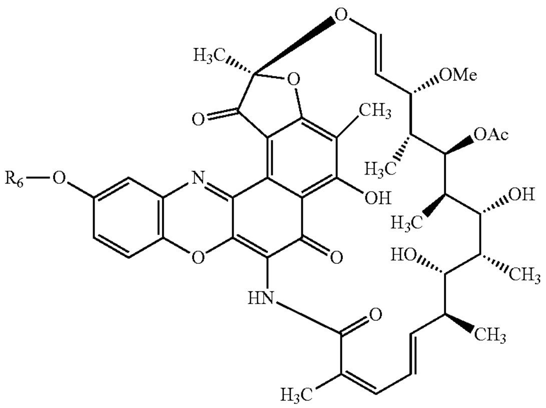

wherein $R_6$ is selected from $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof and wherein $R_6$ is optionally substituted with one or more of —F; —$C_1$; —Br; —I; —OH, —OR*; —NO; —$NO_2$; —$NO_3$; —O—NO; —$N_3$; —$NH_2$; —NHR*; —$N(R^*)_2$; —$N(R^*)_3$; —N(R*)—OH; —O—$N(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—$N(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —$Si(R^*)_3$; —$CF_3$; —O—$CF_3$ and combinations thereof, $R_N$ is selected from:

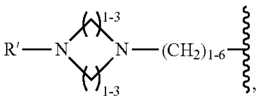,

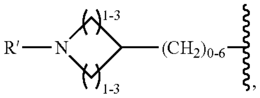,

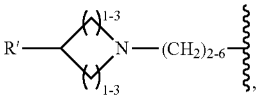, 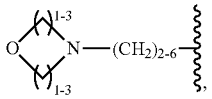,

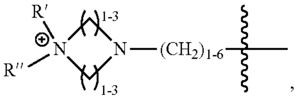,

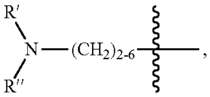,

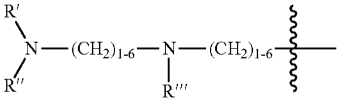,

-continued

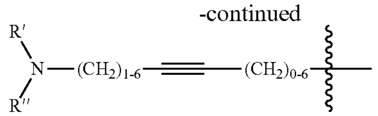 and

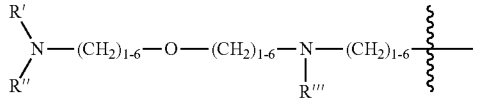

wherein the  symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII')

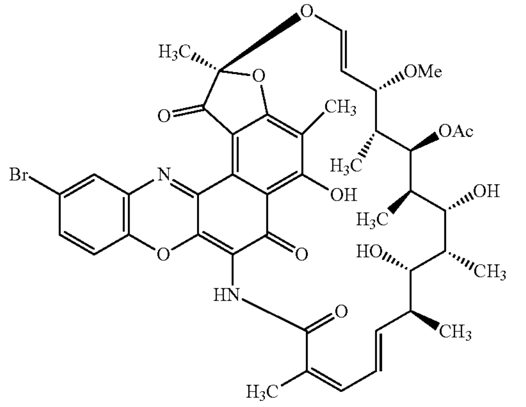

with an alcohol having the structure $R_6$—OH.

In one aspect, the present disclosure provides a method of manufacturing a compound having the structure of formula (XIII):

(XIII)

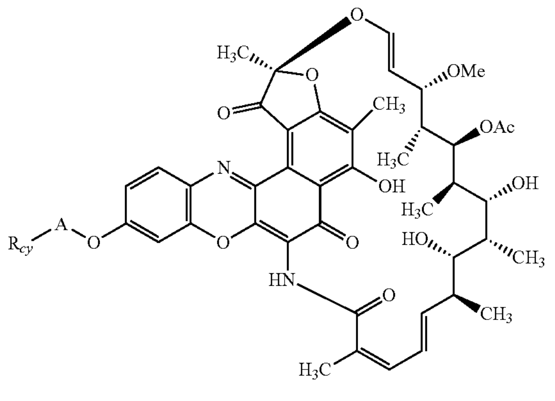

wherein A is selected from a bond (A is absent) or an aliphatic $C_1$-$C_{20}$ hydrocarbon;

$R_{cy}$ is a $C_3$-$C_{14}$ cycloaliphatic hydrocarbon which further comprises 0-8 heteroatoms selected from halogen, O, N, and S and combinations thereof and wherein $R_{cy}$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—N$(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —Si$(R^*)_3$, —$CF_3$, —O—$CF_3$ and combinations thereof; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

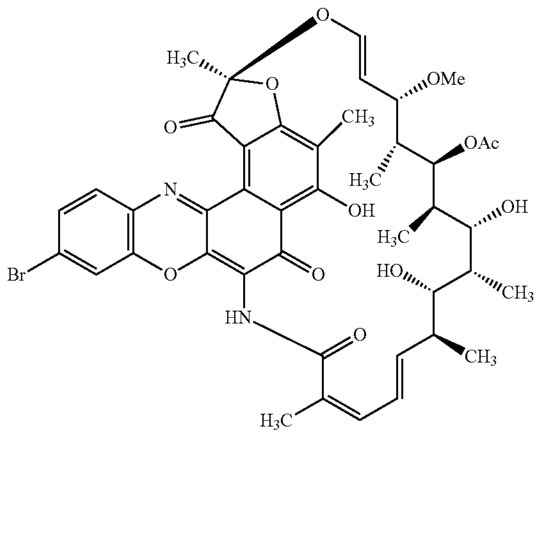

with an alcohol having the structure $R_{cy}$-A-OH.

In one aspect, the present disclosure provides a method of manufacturing a compound having the structure of formula (XIII'):

(XIII')

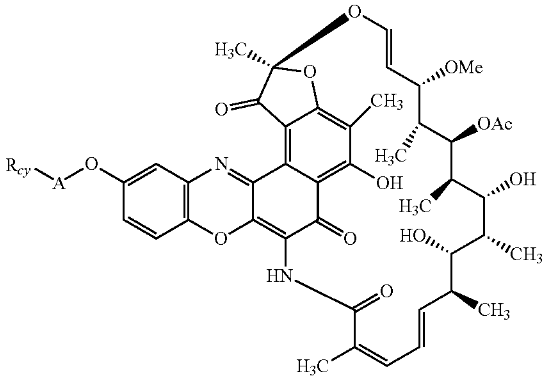

wherein A is selected from a bond (A is absent) or an aliphatic $C_1$-$C_{20}$ hydrocarbon;

$R_{cy}$ is a $C_3$-$C_{14}$ cycloaliphatic hydrocarbon which further comprises 0-8 heteroatoms selected from halogen, O, N, and S and combinations thereof and wherein $R_{cy}$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—N$(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —Si$(R^*)_3$, —$CF_3$, —O—$CF_3$ and combinations thereof; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, comprising contacting a compound having the structure of formula (XII):

(XII)

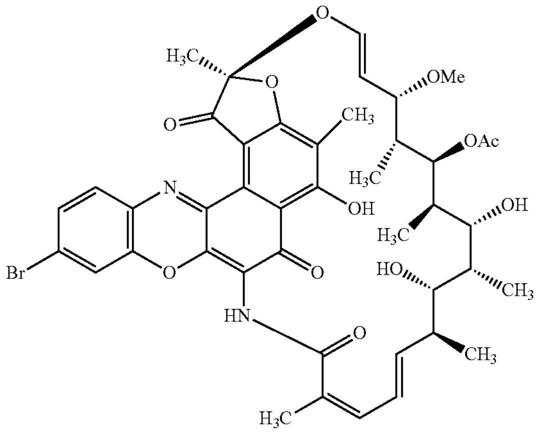

with an alcohol having the structure $R_{cy}$-A-OH.

In one aspect, the present disclosure provides a method of manufacturing a compound having the structure of formula (XIV):

(XIV)

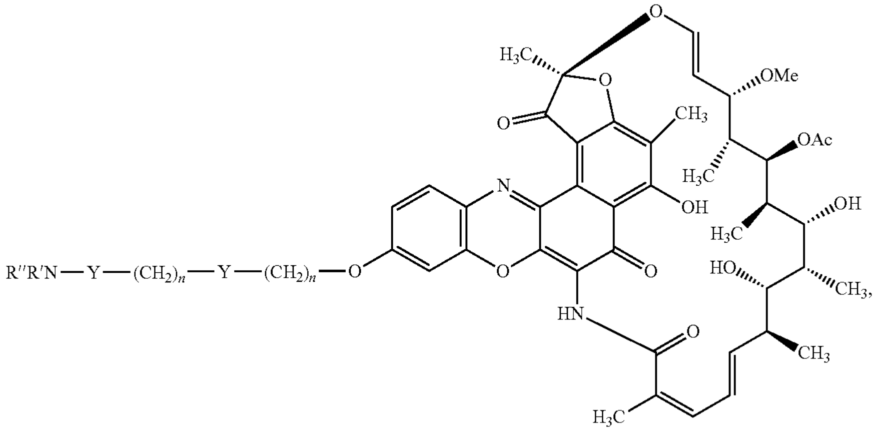

wherein Y is at each occurrence selected from —O— and —NR'R"—; n is independently at each occurrence an integer from 1-6, and R', R", and R'" are each independently selected from a hydrogen, an aliphatic $C_1$-$C_{20}$ hydrocarbon; said method comprising contacting a compound having the structure of formula (XII):

(XII)

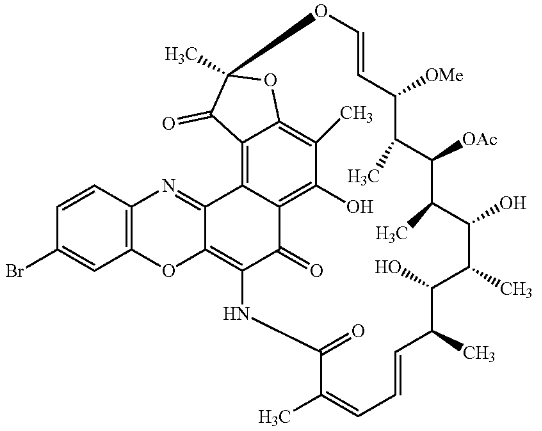

with an alcohol having the structure R"R'N—Y—$(CH_2)_n$—Y—$(CH_2)_n$—OH.

In one aspect, the present disclosure provides a method of manufacturing a compound having the structure of formula (XIV'):

(XIV')

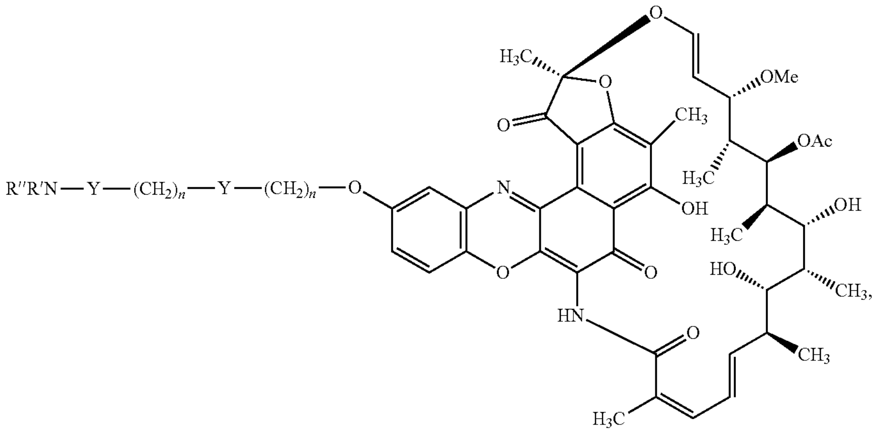

wherein Y is at each occurrence selected from —O— and —NR'R"—; n is independently at each occurrence an integer from 1 to 6, and R', R", and R'" are each independently selected from a hydrogen and an aliphatic $C_1$-$C_{20}$ hydrocarbon; said method comprising contacting a compound having the structure of formula (XII'):

(XII')

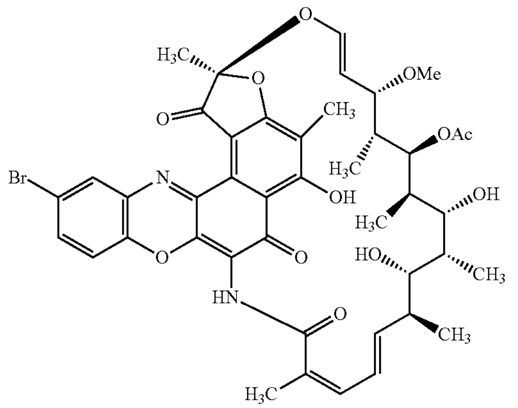

with an alcohol having the structure R"R'N—Y—$(CH_2)_n$—Y—$(CH_2)_n$—OH.

In one embodiment, the compound of formula (XII) is prepared by contacting Rifamycin S with 2-amino-5-bromophenol, and treating the product with an oxidizing agent.

In one embodiment, the compound of formula (XII') is prepared by contacting Rifamycin S with 2-amino-4-bromophenol, and treating the product with an oxidizing agent.

Pharmaceutical Compositions and Dosage Forms

The present disclosure also provides pharmaceutical compositions comprising the compounds described herein. When employed as pharmaceuticals, the compounds of the disclosure can be administered in the form of pharmaceutical compositions which is a combination of the compounds of the disclosure and a pharmaceutically acceptable carrier. These compositions can be prepared in a manner well known in the pharmaceutical art, and can be administered by a variety of routes. Such pharmaceutical compositions can be administered systemically. The term "systemic" as used herein includes parenteral, topical, transdermal, oral, by inhalation/pulmonary, rectal, nasal, buccal, and sublingual administration. The term "parenteral" as used herein includes subcutaneous, intradermal, intravenous, intramuscular, intracranial, and intraperitoneal administration. In some embodiments, the compounds are administered orally, topically, intranasally, intravenously, intramuscularly, or subcutaneously in therapeutically effective amounts to treat bacterial infections (e.g., *S. aureus* infections).

Pharmaceutical compositions containing the compounds of the disclosure can be prepared in combination with one or more pharmaceutically acceptable carriers. In making the compositions of the disclosure, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In some embodiments, the pharmaceutical composition of the disclosure is in liquid form. Liquid forms include, by way of non-limiting example, emulsions, solutions, suspensions, syrups, slurries, dispersions, colloids and the like. In some embodiments, a pharmaceutical composition described herein is in liquid, semi-solid or solid (e.g., powder) form. In specific embodiments, a pharmaceutical composition described herein is in semi-solid form, e.g., a gel, a gel matrix, a cream, a paste, or the like. In some embodiments, semi-solid forms comprise a liquid vehicle. In some embodiments, the pharmaceutical composition of the disclosure is a solid dosage form, such a tablet, a granule, a sachet, or a powder. Also provided are pharmaceutical compositions comprising a compound of the disclosure or a pharmaceutically acceptable salt thereof in the form of a dissolving tablet, a dissolving wafer, a capsule, or a gel capsule. In certain embodiments, solid dosage forms described herein comprise a solid vehicle (e.g., as used in a tablet), and/or a gaseous vehicle (e.g., as used in DPI).

In some embodiments, a composition is in a unit dose formulation for oral, intranasal, intravenous, or other administration to a patient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, a composition or unit dosage form described herein is administered as an emulsion, a solution, a suspension, a syrup, a slurry, a dispersion, a colloid, a dissolving tablet, a dissolving wafer, a capsule, a gel capsule, a semi-solid, a solid forma gel, a gel matrix, a cream, a paste, a tablet, a granule, a sachet, a powder, or the like. In certain aspects, about 0.000001 mg to about 2000 mg, about 0.00001 mg to about 1000 mg, or about 0.0001 mg to about 750 mg, about 0.001 mg to about 500 mg, about 0.01 mg to about 250 mg, about 0.1 mg to about 100 mg, about 0.5 mg to about 75 mg, about 1 mg to about 50 mg, about 2 mg to about 40 mg, about 5 mg to about 20 mg, or about 7.5 mg to about 15 mg of compound of formula (I), or a compound having a structure according to any embodiment of formulas (A), (B), (I), (I'), (II), (II'), (III), (III'), (IV), (IV'), (V), (V') as provided herein, per day or per dose is administered to an individual.

In some embodiments, the compound of the disclosure is present in a composition or a unit dose of a composition described herein in an amount of from about 0.01 mg to about 10 mg (e.g., about 0.1-10 mg, about 0.25-5 mg, about 0.25-2.5 mg, about 1-2 mg or about 2-3 mg, about 0.5 mg to about 2 mg, about 1 to about 2 mg, about 1 mg, or about 2 mg). In some embodiments, the amount of compound administered daily or in a unit dose is between about 0.5 mg and about 3 mg, between about 0.5 mg and about 4 mg, or between about 0.35 mg and about 4 mg. In other embodiments, the amount of the compound present in a unit dose or administered daily is between about 1 and about 3 mg, or between about 1 and about 2 mg, or between about 2 and about 3 mg.

In certain aspects, about 0.05 mg to about 50 mg, about 0.25 mg to about 20 mg, about 0.25 mg to about 15 mg, about 0.25 mg to about 10 mg, or about 0.25 mg to about 5 mg (e.g., about 0.1 to about 5 mg, about 0.25 to about 2.5 mg, about 0.3 mg to about 2 mg, about 0.5 mg to about 1 mg, about 0.7 mg to about 1.5 mg, about 0.375 mg, about 0.75 mg, about 1 mg, about 1.25 mg, about 1.5 mg or about 2 mg) of the compound per day or per dose is administered to a patient.

In some embodiments, the compound is present in a unit dose in an amount of between about 5 mg and about 500 mg. In some embodiments, the amount of the compound administered daily or in a unit dose is between about 5 mg and about 300 mg. In other embodiments, the amount of the compound present in a unit dose or administered daily is between about 5 and about 250 mg, or between about 5 and about 200 mg, between about 5 mg and about 150 mg, between about 5 mg and about 100 mg, or between about 5 and about 50 mg.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g. about 40 mesh. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

For preparing solid compositions such as tablets, the principal active ingredient is mixed with a pharmaceutical excipient to form a solid pre-formulation composition containing a homogeneous mixture of the compound of Formula I. When referring to these pre-formulation compositions as homogeneous, the active ingredient is typically dispersed evenly throughout the composition so that the composition can be readily subdivided into equally effective unit dosage forms such as tablets, pills and capsules. This solid pre-formulation is then subdivided into unit dosage forms of the type described above containing from, for example, 0.000001 to about 2000 mg of the active ingredient of the present application.

The tablets or pills containing the compound of Formula I can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present application can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions in can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9. It will be understood that use of certain of the foregoing excipients, carriers, or stabilizers will result in the formation of pharmaceutical salts.

The therapeutic dosage of the compounds of the disclosure can vary according to, for example, the particular use for which the treatment is made, the manner of administration of the compound, the health and condition of the patient, and the judgment of the prescribing physician. The proportion or concentration of the compounds of the disclosure in a pharmaceutical composition can vary depending upon a number of factors including dosage, chemical characteristics (e.g., hydrophobicity), and the route of administration. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The present application also includes pharmaceutical kits useful, for example, in the treatment of bacterial infections (e.g., *S. aureus* infections), which include one or more containers containing a pharmaceutical composition comprising a therapeutically effective amount of the compounds of the disclosure. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

Delivery devices are important not only for delivering the compounds of the disclosure, but also for providing an appropriate environment for storage. This would include protection from microbial contamination and chemical degradation. The device and formulation should be compatible so as to avoid potential leaching or adsorption. The delivery device (or its packaging) can be optionally provided with a label and/or with instructions for use indicating that the composition should be used intranasally.

Methods of Use

In another aspect, the present disclosure provides a method of preventing or inhibiting growth of a bacterium comprising administering an effective amount of a compound having the structure of formula (A):

(A)

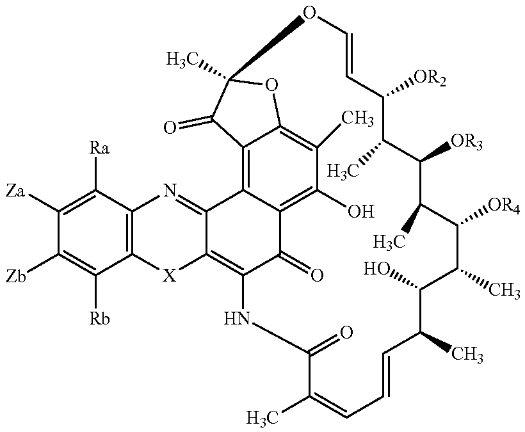

or a pharmaceutically acceptable salt thereof, wherein:

X is selected from —O—, —S— and —NR*—;

Za and Zb are independently selected from a hydrogen, —Cl, —Br, —$OR_1$ and —$R_N$; with the proviso that at least one of Za or Zb is not a hydrogen; wherein:

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—NHNH$_2$, —O—(C═O)—NHNH$_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

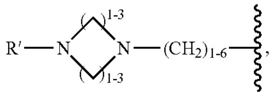,

-continued

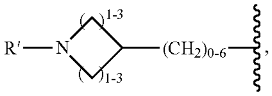,

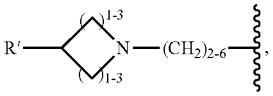, 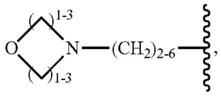,

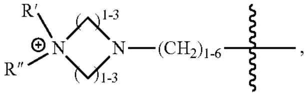,

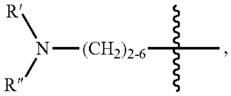,

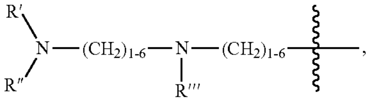,

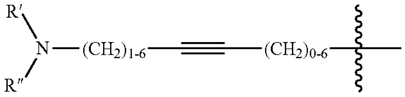 and

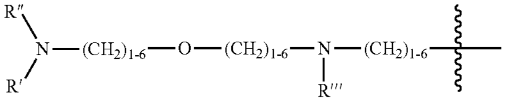

wherein the symbol represents the point of attachment; and R', R" and R'" are selected from a hydrogen, a $C_1$-$C_6$ aliphatic hydrocarbon, and a protecting group, for example, $F_{MOC}$ and $B_{OC}$, or wherein R' and R" together form an aliphatic cyclic structure, such as an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of preventing or inhibiting growth of a bacterium comprising administering an effective amount of a compound having the structure of formula (I):

(I)

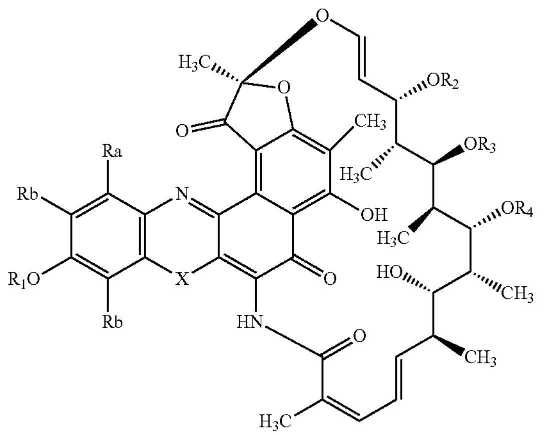

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—N$(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

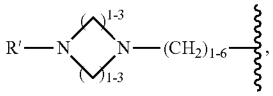
,

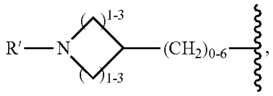
,

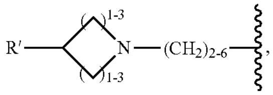
,

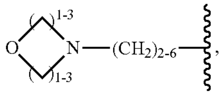
,

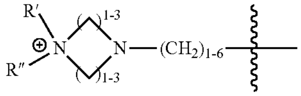
,

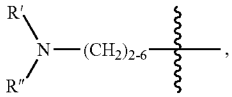
,

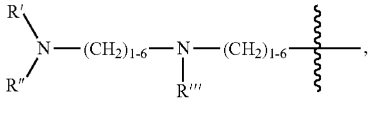
,

-continued

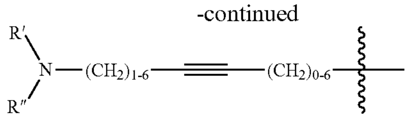

and

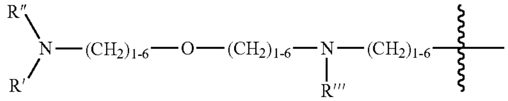

wherein the ∿∿ symbol represents the point of attachment; and R', R" and R'" are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of preventing or inhibiting growth of a bacterium comprising administering an effective amount of a compound having the structure of formula (I'):

(I')

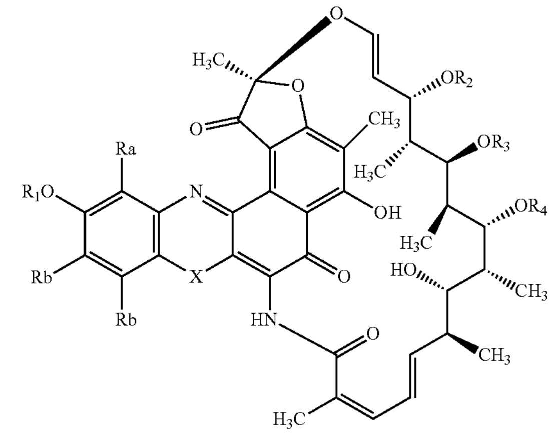

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—NHNH$_2$, —O—(C═O)—NHNH$_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

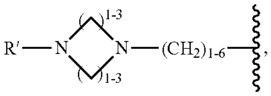
,

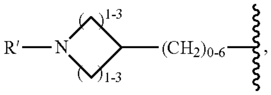
,

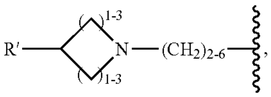
,
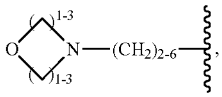
,

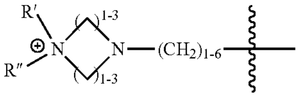
,

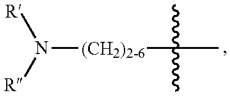
,

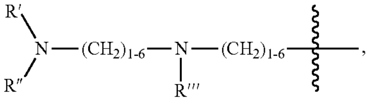
,

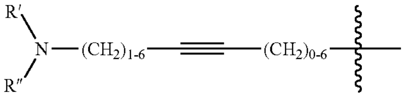
and

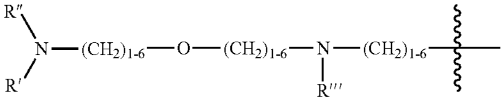

wherein the ∿∿∿ symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —N(R*)$_2$, —N(R*)$_3^+$, —(C═O)—R*, —CHO, —$CO_2$H, —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2$H, —$CO_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of preventing or inhibiting growth of a bacterium comprising administering an effective amount of a compound having the structure of formula (B):

(B)

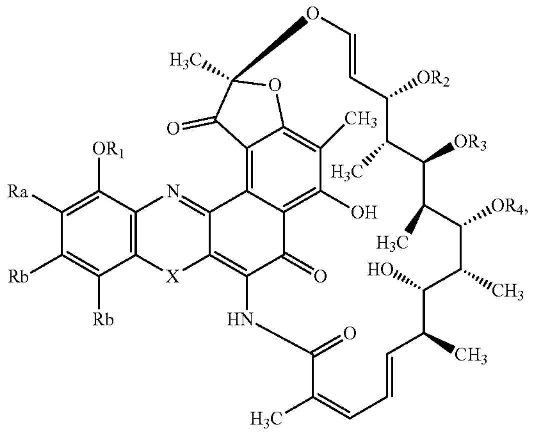

or a pharmaceutically acceptable salt thereof, wherein:

X is selected from —O— and —NR*—;

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—NHNH$_2$, —O—(C═O)—NHNH$_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

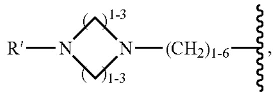
,

-continued

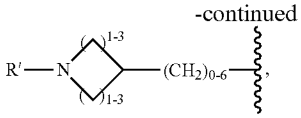,

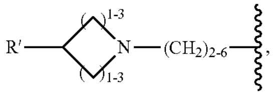, 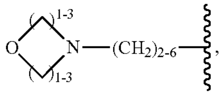,

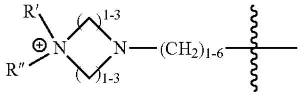,

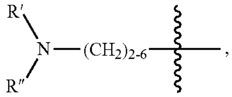,

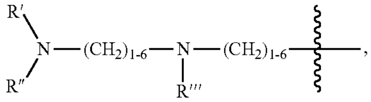,

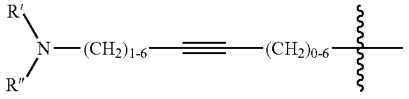 and

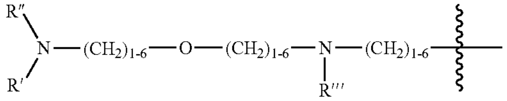

wherein the ∿∿∿ symbol represents the point of attachment; and R', R" and R"' are selected from a hydrogen, a $C_1$-$C_6$ aliphatic hydrocarbon, and a protecting group selected from Fluorenylmethyloxycarbonyl ($F_{MOC}$) and tert-Butyloxycarbonyl (Boc), or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of preventing or inhibiting growth of a bacterium comprising administering an effective amount of a rifamycin analog compound having a structure according to any one of formulas (IA), (II), (II'), (III), (III'), (IV), (IV'), (V), (V'), (B-1), and (B-2) as provided herein. In one embodiment, the bacterium is a Gram-positive bacterium.

In one embodiment, the bacterium is a penicillin-resistant bacterium.

In one embodiment, the bacterium is *Staphylococcus aureus.*

In one embodiment, the bacterium is a resistant *Staphylococcus aureus* strain selected from MRSA and VRSA.

In one embodiment, the bacterium is methicillin-resistant *Staphylococcus aureus* (MRSA).

In one embodiment, the bacterium is vancomycin-resistant *Staphylococcus aureus* (VRSA).

In one embodiment, the bacterium is methicillin-susceptible *Staphylococcus aureus* (MSSA).

In yet another aspect, the present disclosure provides a method of treating a bacterial infection in a subject in need of such treatment, comprising administering to the subject an effective amount of a compound having the structure of formula (A):

(A)

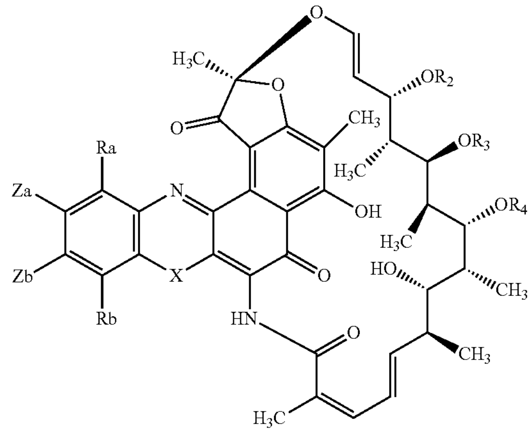

or a pharmaceutically acceptable salt thereof, wherein:

X is selected from —O—, —S— and —NR*—;

Za and Zb are independently selected from a hydrogen, —Cl, —Br, —$OR_1$ and —$R_N$; with the proviso that at least one of Za or Zb is not a hydrogen; wherein:

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—N$(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

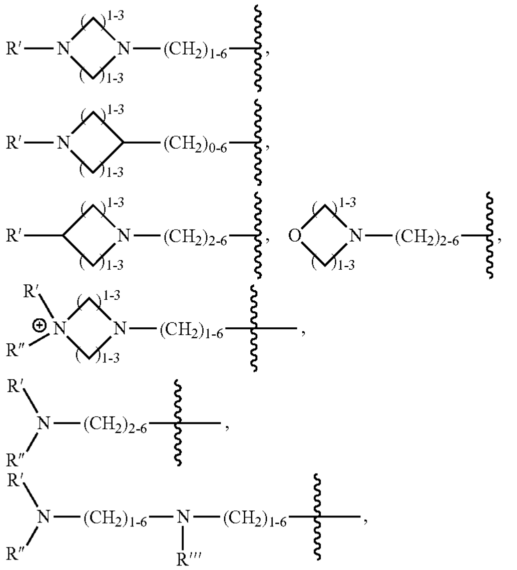

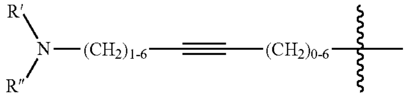

and

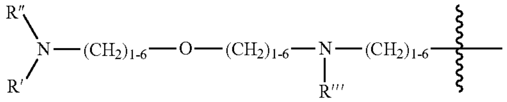

wherein the  symbol represents the point of attachment; and R', R'' and R''' are selected from a hydrogen, a $C_1$-$C_6$ aliphatic hydrocarbon, and a protecting group including $F_{MOC}$ and $B_{OC}$, or wherein R' and R'' together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —$N(R^*)_2$, —$N(R^*)_3^+$, —(C═O)—R*, —CHO, —$CO_2H$, —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2H$, —$CO_2R^*$ and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of treating a bacterial infection in a subject in need of such treatment, comprising administering an effective amount of a compound having the structure of formula (I):

(I)

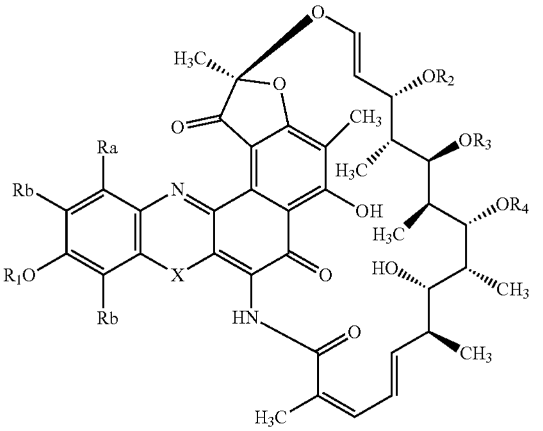

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —$N(R^*)_2$, —$N(R^*)_3^+$, —N(R*)—OH, —O—$N(R^*)_2$, —N(R*)—O—R*, —CN, —NC, —(C═O)—R*, —CHO, —$CO_2H$, —$CO_2R^*$, —(C═O)—S—R*, —O—(C═O)—H, —O—(C═O)—R*, —S—(C═O)—R*, —(C═O)—$NH_2$, —(C═O)—$N(R^*)_2$, —(C═O)—$NHNH_2$, —O—(C═O)—$NHNH_2$, —(C═S)—$NH_2$, —(C═S)—$N(R^*)_2$, —N(R*)—CHO, —N(R*)—(C═O)—R*, —SCN, —NCS, —NSO, —SSR*, —$SO_2R^*$, —$SO_2$—$N(R^*)_2$, —S(═O)—OR*, —S(═O)—R*, —$Si(R^*)_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

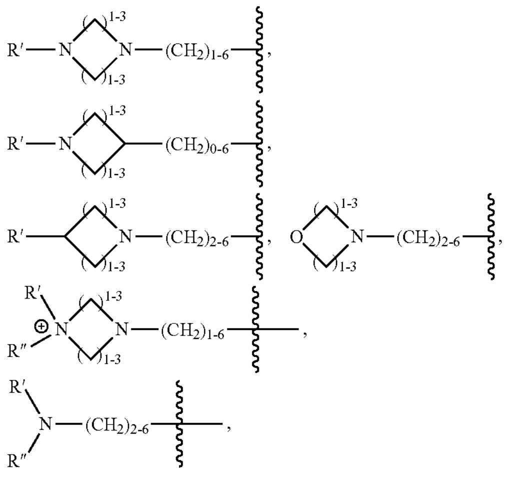

-continued

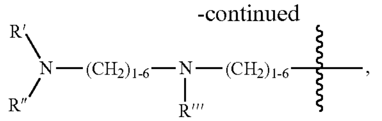,

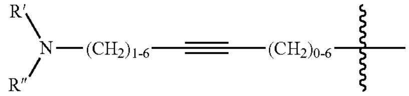 and

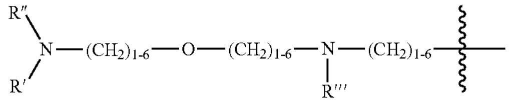

wherein the ∿∿∿ symbol represents the point of attachment; and R', R" and R"' are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —N(R*)$_2$, —N(R*)$_3^+$, —(C═O)—R*, —CHO, —$CO_2$H, —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2$H, —$CO_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of treating a bacterial infection in a subject in need of such treatment, comprising administering an effective amount of a compound having the structure of formula (I'):

(I')

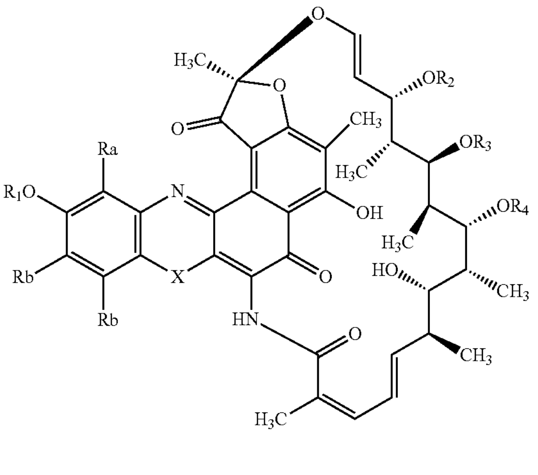

or a pharmaceutically acceptable salt thereof wherein:

X is selected from —O— and —NR*—;

$R_1$ is selected from $R_N$, a hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—NHNH$_2$, —O—(C═O)—NHNH$_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

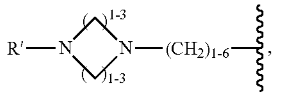,

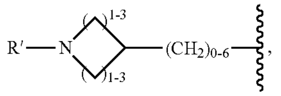,

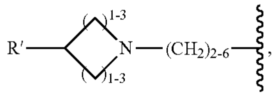, 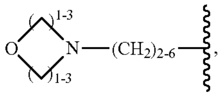,

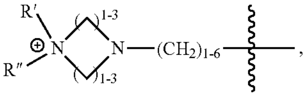,

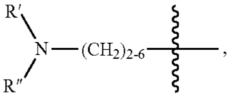,

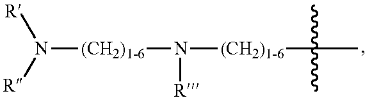,

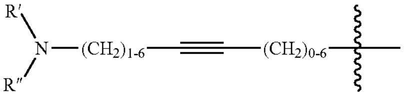 and

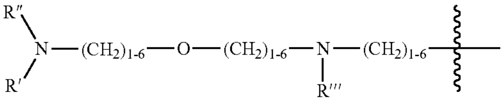

wherein the ∿∿∿ symbol represents the point of attachment; and R', R" and R"' are selected from a hydrogen, a $C_1$-$C_6$ aliphatic hydrocarbon, and a protecting group including $F_{MOC}$ and $B_{OC}$, or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, or —(C═O)—R*, each of which further comprises 0-8 heteroatoms selected from halogen, O, N, and S;

$R_a$ is selected from hydrogen, F, —Cl, —Br, —I, —OH, —OR*, —$NH_2$, —NHR*, —N(R*)$_2$, —N(R*)$_3^+$, —(C═O)—R*, —CHO, —$CO_2$H, —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2$H, —$CO_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*; and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In yet another aspect, the present disclosure provides a method of treating a bacterial infection in a subject in need of such treatment, comprising administering to the subject an effective amount of a compound having the structure of formula (B):

(B)

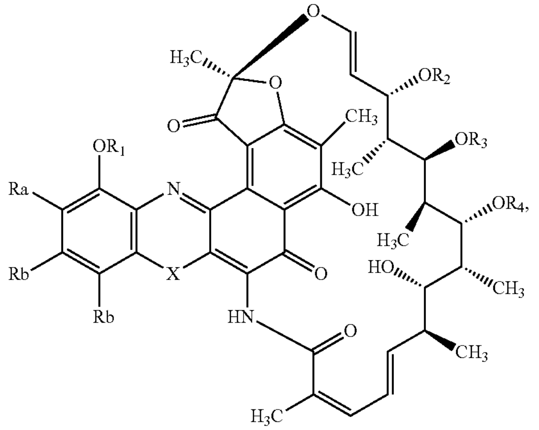

or a pharmaceutically acceptable salt thereof, wherein:

X is selected from —O— and —NR*—;

$R_1$ is selected from a hydrogen, $R_N$, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F, —Cl, —Br, —I, —OH, —OR*, —NO, —$NO_2$, —$NO_3$, —O—NO, —$N_3$, —$NH_2$, —NHR*, —N(R*)$_2$, —N(R*)$_3^+$, —N(R*)—OH, —O—N(R*)$_2$, —N(R*)—O—R*, —CN, —NC, —(C═O)—R*, —CHO, —$CO_2$H, —$CO_2$R*, —(C═O)—S—R*, —O—(C═O)—H, —O—(C═O)—R*, —S—(C═O)—R*, —(C═O)—$NH_2$, —(C═O)—N(R*)$_2$, —(C═O)—$NHNH_2$, —O—(C═O)—$NHNH_2$, —(C═S)—$NH_2$, —(C═S)—N(R*)$_2$, —N(R*)—CHO, —N(R*)—(C═O)—R*, —SCN, —NCS, —NSO, —SSR*, —$SO_2$R*, —$SO_2$—N(R*)$_2$, —S(═O)—OR*, —S(═O)—R*, —Si(R*)$_3$, —$CF_3$, —O—$CF_3$ and combinations thereof, with the provisos that $R_1$ is not an n-butyl group, and when X is —O— and Ra is hydrogen, $R_1$ is not hydrogen;

$R_N$ is selected from:

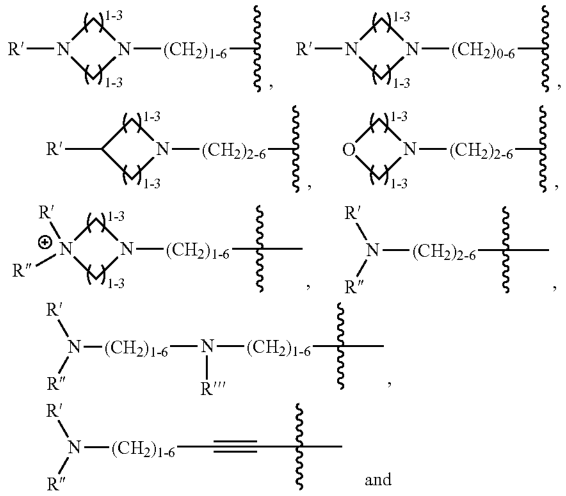

and

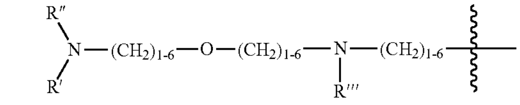

;

wherein the  symbol represents the point of attachment; and R', R" and R'" are selected from a hydrogen, a $C_1$-$C_6$ aliphatic hydrocarbon, and a protecting group selected from Fluorenylmethyloxycarbonyl ($F_{MOC}$) and tert-Butyloxycarbonyl ($B_{OC}$), or wherein R' and R" together form an aliphatic monocyclic, an aliphatic bicyclic, or an aliphatic polycyclic structure;

$R_2$, $R_3$, and $R_4$ are independently selected from hydrogen, an aliphatic $C_1$-$C_{20}$ hydrocarbon, and —(C═O)—R*, each of which further comprises 0-8 heteroatoms selected from halogen, O, N, and S;

$R_a$ is selected from hydrogen, —F, —Cl, —Br, —I, —OH, —OR*, —$NH_2$, —NHR*, —N(R*)$_2$, —N(R*)$_3^+$, —(C═O)—R*, —CHO, —$CO_2$H, —$CO_2$R*, —SR*, —$SO_2$R*, and an aliphatic $C_1$-$C_{20}$ hydrocarbon, which further comprises 0-8 heteroatoms selected from halogen, O, N, and S, and wherein $R_a$ is optionally substituted with one or more of —F, —Cl, —Br, —I, —OH, —OR*;

$R_b$ is selected from hydrogen, —F, —Cl, —Br, —I, —OH, —OR*, —(C═O)—R*, —CHO, —$CO_2$H, —$CO_2$R* and an aliphatic $C_1$-$C_{20}$ hydrocarbon, which further comprises 0-3 heteroatoms selected from halogen, O, and S, and wherein $R_b$ is optionally substituted with one or more of —F, —Cl, —Br, —I, —OH, —OR*, and R* is independently at each occurrence selected from hydrogen, an aliphatic $C_1$-$C_{20}$ hydrocarbon, an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof.

In another aspect, the present disclosure provides a method of treating a bacterial infection in a subject in need of such treatment, comprising administering an effective amount of a rifamycin analog compound having a structure according to any one of formulas (IA) (II), (II'), (III), (III'), (IV), (IV'), (V), (V'), (B-1), and (B-2) as provided herein. In one embodiment, the bacterial infection is a Gram-positive bacterial infection.

In one embodiment, the bacterial infection is a penicillin-resistant bacterial infection.

In one embodiment, the bacterial infection is a *Staphylococcus aureus* infection.

In one embodiment, the bacterial infection is an intracellular bacterial infection.

In one embodiment, the subject is human.

In one embodiment, the method further comprises administering a second therapeutic agent.

In one embodiment, the second therapeutic agent is a second antibiotic.

In one embodiment, the second antibiotic is effective against *Staphylococcus aureus*.

In one embodiment, the second antibiotic is selected from an aminoglycoside, a beta-lactam, a macrolide, a cyclic peptide, a tetracycline, a fluoroquinoline, a fluoroquinolone, and an oxazolidinone.

In one embodiment, the second antibiotic is selected from clindamycin, novobiocin, retapamulin, daptomycin, sitafloxacin, teicoplanin, triclosan, napthyridone, radezolid, doxorubicin, ampicillin, vancomycin, imipenem, doripenem, gemcitabine, dalbavancin, and azithromycin.

In one embodiment, the compound is administered to the subject orally, topically, intranasally, intravenously, intramuscularly, or subcutaneously.

In another aspect, the present disclosure provides a method of preventing or inhibiting growth of a bacterium comprising administering an effective amount of a compound having the structure of formula (I):

(I)

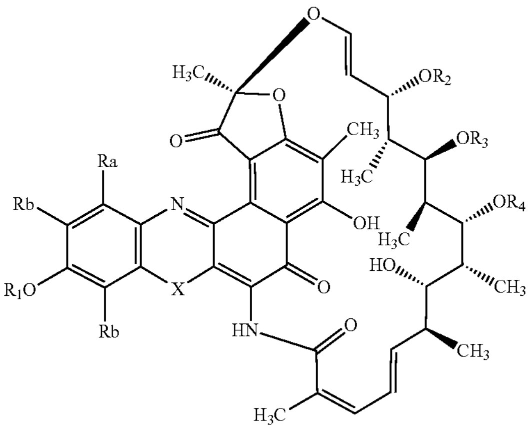

wherein:

X is selected from —O—, —S—, and —NR*—;

$R_1$ is selected from a hydrogen; an aliphatic $C_1$-$C_{20}$ hydrocarbon; an aromatic $C_5$-$C_{20}$ hydrocarbon; a heteroaromatic $C_1$-$C_{20}$ hydrocarbon; a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F; —Cl; —Br; —I; —OH; —OR*; —NO; —$NO_2$; —$NO_3$; —O—NO; —$N_3$; —$NH_2$; —NHR*; —$N(R^*)_2$; —$N(R^*)_3^+$; —N(R*)—OH; —O—$N(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—$N(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —$Si(R^*)_3$; —$CF_3$; —O—$CF_3$ and combinations thereof, with a proviso that $R_1$ is not an n-butyl group;

wherein when X is —O— and Ra is hydrogen, $R_1$ is not hydrogen;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is selected from hydrogen, F; —$C_1$; —Br; —I; —OH; OR*; —$NH_2$; —NHR*; —$N(R^*)_2$; —$N(R^*)_3^+$; —(C═O)—R*; —CHO; —$CO_2H$; —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F; —$C_1$; —Br; —I; —OH; —OR*;

$R_b$ is a hydrogen atom at each occurrence, and

R* is independently at each occurrence selected from hydrogen; an aliphatic $C_1$-$C_{20}$ hydrocarbon; an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, or a pharmaceutically acceptable salt thereof.

In yet another aspect, the present disclosure provides a method of treating a bacterial infection in a subject in need of such treatment, comprising administering to the subject an effective amount of a compound having the structure of Formula (I'):

(I')

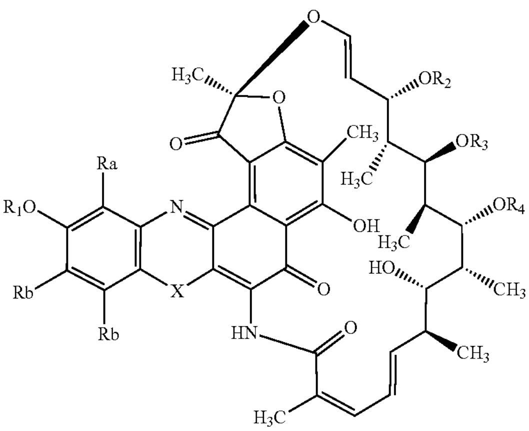

wherein:

X is selected from —O—, —S—, and —NR*—;

$R_1$ is selected from a hydrogen; an aliphatic $C_1$-$C_{20}$ hydrocarbon; an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, each of which further comprises 0-8 heteroatoms selected from halogen, O, N, and S, and wherein $R_1$ is optionally substituted with one or more of —F; —Cl; —Br; —I; —OH, —OR*; —NO; —$NO_2$; —$NO_3$; —O—NO; —$N_3$; —$NH_2$; —NHR*; —$N(R^*)_2$; —$N(R^*)_3^+$; —N(R*)—OH; —O—$N(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—

(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—$N(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —$Si(R^*)_3$; —$CF_3$; —O—$CF_3$ and combinations thereof, with a proviso that $R_1$ is not an n-butyl group;

wherein when X is —O— and Ra is hydrogen, $R_1$ is not hydrogen;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is selected from hydrogen, F; —$C_1$; —Br; —I; —OH; OR*; —$NH_2$; —NHR*; —$N(R^*)_2$; —$N(R^*)_3^+$; —(C═O)—R*; —CHO; —$CO_2H$; —$CO_2R^*$, —SR*, —$SO_2R^*$, and an aliphatic $C_1$-$C_{20}$ hydrocarbon, which further comprises 0-8 heteroatoms selected from halogen, O, N, and S, and wherein $R_a$ is optionally substituted with one or more of —F; —$C_1$; —Br; —I; —OH, —OR*;

$R_b$ is a hydrogen atom at each occurrence, and

R* is independently at each occurrence selected from hydrogen; an aliphatic $C_1$-$C_{20}$ hydrocarbon; an aromatic $C_1$-$C_{20}$ hydrocarbon, a heteroaromatic $C_1$-$C_{20}$ hydrocarbon, a cyclic aliphatic $C_1$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, or a pharmaceutically acceptable salt thereof.

In one aspect, the present disclosure provides a method of preventing or inhibiting growth of a bacterium comprising administering an effective amount of a rifamycin analog compound of the present disclosure, or a pharmaceutical composition comprising a rifamycin analog compound of the present disclosure, or a pharmaceutical dosage form comprising a rifamycin analog compound of the present disclosure.

In another aspect, the present disclosure provides a method of treating a bacterial infection in a subject in need of such treatment comprising administering to said subject an effective amount of a rifamycin analog compound of the present disclosure, or a pharmaceutical composition comprising a rifamycin analog compound of the present disclosure, or a pharmaceutical dosage form comprising a rifamycin analog compound of the present disclosure.

In one embodiment, the compound, the composition, or the dosage form is administered to the subject orally, topically, intranasally, intravenously, intramuscularly, or subcutaneously.

Anti-MSR1 Antibodies Suitable for ADCs

The antibody-drug conjugates described herein may comprise anti-MSR1 antibodies which are full-length (for example, an IgG1 or IgG4 antibody), or may comprise only an antigen-binding portion (for example, a Fab, $F(ab')_2$ or scFv fragment), and may be modified to affect functionality, e.g., to eliminate residual effector functions (Reddy et al., 2000, J. Immunol. 164:1925-1933).

Embodiments of antibody-drug conjugates described herein may comprise anti-MSR1 antibodies listed in Tables 9 and 10. Table 9 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-MSR1 antibodies. Table 10 sets forth the nucleic acid sequence identifiers of the HCVRs, LCVRs, HCDR1, HCDR2 HCDR3, LCDR1, LCDR2 and LCDR3 of the exemplary anti-MSR1 antibodies.

Suitable antibodies or antigen-binding fragments thereof for the antibody-drug conjugates described herein include those that specifically bind MSR1 and comprise an HCVR comprising an amino acid sequence selected from any of the HCVR amino acid sequences listed in Table 9, or a substantially similar sequence thereof having at least 90%, at least 95%, at least 98% or at least 99% sequence identity thereto.

Further suitable antibodies or antigen-binding fragments thereof that specifically bind MSR1 comprise an LCVR comprising an amino acid sequence selected from any of the LCVR amino acid sequences listed in Table 9, or a substantially similar sequence thereof having at least 90%, at least 95%, at least 98% or at least 99% sequence identity thereto.

Further suitable antibodies or antigen-binding fragments thereof that specifically bind MSR1 comprise an HCVR and an LCVR amino acid sequence pair (HCVR/LCVR) comprising any of the HCVR amino acid sequences listed in Table 9 paired with any of the LCVR amino acid sequences listed in Table 9. Certain embodiments relate to antibody-drug conjugates comprising antibodies, or antigen-binding fragments thereof, comprising an HCVR/LCVR amino acid sequence pair contained within any of the exemplary anti-MSR1 antibodies listed in Table 9. In some embodiments, the HCVR/LCVR amino acid sequence pair is selected from the group consisting of: 2/10, 23/42, 50/58; 90/98, and 282/290.

Suitable antibodies or antigen-binding fragments thereof for the antibody-drug conjugates described herein include those that specifically bind MSR1 and comprise a heavy chain CDR1 (HCDR1) comprising an amino acid sequence selected from any of the HCDR1 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise a heavy chain CDR2 (HCDR2) comprising an amino acid sequence selected from any of the HCDR2 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise a heavy chain CDR3 (HCDR3) comprising an amino acid sequence selected from any of the HCDR3 amino acid sequences listed in Table 9 or a substantially similar sequence thereof having at least 90%, at least 95%, at least 98% or at least 99% sequence identity.

Suitable antibodies or antigen-binding fragments thereof for the antibody-drug conjugates described herein include those that specifically bind MSR1 and comprise a light chain CDR1 (LCDR1) comprising an amino acid sequence selected from any of the LCDR1 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise a light chain CDR2 (LCDR2) comprising an amino acid sequence selected from any of the LCDR2 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise a light chain CDR3 (LCDR3) comprising an amino acid sequence selected from any of the LCDR3 amino acid sequences listed in Table 9 or a substantially similar sequence thereof having at least 90%, at least 95%, at least 98% or at least 99% sequence identity.

Further suitable antibodies or antigen-binding fragments thereof that specifically bind MSR1 comprise an HCDR3 and an LCDR3 amino acid sequence pair (HCDR3/LCDR3) comprising any of the HCDR3 amino acid sequences listed in Table 9 paired with any of the LCDR3 amino acid sequences listed in Table 9. Certain embodiments relate to antibodies, or antigen-binding fragments thereof, comprising an HCDR3/LCDR3 amino acid sequence pair contained within any of the exemplary anti-MSR1 antibodies listed in Table 9. In some embodiments, the HCDR3/LCDR3 amino acid sequence pair is selected from the group consisting of: 8/16, 40/48, 56/64; 96/104, and 288/296.

Suitable antibodies or antigen-binding fragments thereof for the antibody-drug conjugates described herein include those that specifically bind MSR1 and comprise a set of six CDRs (i.e., HCDR1-HCDR2-HCDR3-LCDR1-LCDR2-LCDR3) contained within any of the exemplary anti-MSR1 antibodies listed in Table 9. In certain embodiments, the HCDR1-HCDR2-HCDR3-LCDR1-LCDR2-LCDR3 amino acid sequences set is selected from the group consisting of: 4-6-8-12-14-16; 36-38-40-44-46-48; 52-54-56-60-62-64; 92-94-96-100-102-104, and 284-286-288-292-294-296.

In a related embodiment, suitable antibodies, or antigen-binding fragments thereof that specifically bind MSR1 comprise a set of six CDRs (i.e., HCDR1-HCDR2-HCDR3-LCDR1-LCDR2-LCDR3) contained within an HCVR/LCVR amino acid sequence pair as defined by any of the exemplary anti-MSR1 antibodies listed in Table 9. For example, the present disclosure includes suitable antibodies or antigen-binding fragments thereof that specifically bind MSR1 and comprise the HCDR1-HCDR2-HCDR3-LCDR1-LCDR2-LCDR3 amino acid sequences set contained within an HCVR/LCVR amino acid sequence pair selected from the group consisting of: 2/10, 23/42, 50/58, 90/98, and 282/290. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Also provided herein are nucleic acid molecules encoding anti-MSR1 antibodies or portions thereof for the preparation of antibody-drug conjugates described herein. For example, provided herein are nucleic acid molecules encoding any of the HCVR amino acid sequences listed in Table 9; in certain embodiments the nucleic acid molecule may comprise a polynucleotide sequence selected from any of the HCVR nucleic acid sequences listed in Table 10, or a substantially similar sequence thereof having at least 90%, at least 95%, at least 98% or at least 99% sequence identity thereto.

Also provided herein are nucleic acid molecules encoding any of the LCVR amino acid sequences listed in Table 9; in certain embodiments the nucleic acid molecule may comprise a polynucleotide sequence selected from any of the LCVR nucleic acid sequences listed in Table 10, or a substantially similar sequence thereof having at least 90%, at least 95%, at least 98% or at least 99% sequence identity thereto.

Also provided herein are nucleic acid molecules encoding any of the HCDR1 amino acid sequences listed in Table 9; in certain embodiments the nucleic acid molecule may comprise a polynucleotide sequence selected from any of the HCDR1 nucleic acid sequences listed in Table 10, or a substantially similar sequence thereof having at least 90%, at least 95%, at least 98% or at least 99% sequence identity thereto.

Also provided herein are nucleic acid molecules encoding any of the HCDR2 amino acid sequences listed in Table 9; in certain embodiments the nucleic acid molecule may comprise a polynucleotide sequence selected from any of the HCDR2 nucleic acid sequences listed in Table 10, or a substantially similar sequence thereof having at least 90%, at least 95%, at least 98% or at least 99% sequence identity thereto.

Also provided herein are nucleic acid molecules encoding any of the HCDR3 amino acid sequences listed in Table 9; in certain embodiments the nucleic acid molecule may comprise a polynucleotide sequence selected from any of the HCDR3 nucleic acid sequences listed in Table 10, or a substantially similar sequence thereof having at least 90%, at least 95%, at least 98% or at least 99% sequence identity thereto.

Also provided herein are nucleic acid molecules encoding any of the LCDR1 amino acid sequences listed in Table 9; in certain embodiments the nucleic acid molecule may comprise a polynucleotide sequence selected from any of the LCDR1 nucleic acid sequences listed in Table 10, or a substantially similar sequence thereof having at least 90%, at least 95%, at least 98% or at least 99% sequence identity thereto.

Also provided herein are nucleic acid molecules encoding any of the LCDR2 amino acid sequences listed in Table 9; in certain embodiments the nucleic acid molecule may comprise a polynucleotide sequence selected from any of the LCDR2 nucleic acid sequences listed in Table 10, or a substantially similar sequence thereof having at least 90%, at least 95%, at least 98% or at least 99% sequence identity thereto.

Also provided herein are nucleic acid molecules encoding any of the LCDR3 amino acid sequences listed in Table 9; in certain embodiments the nucleic acid molecule may comprise a polynucleotide sequence selected from any of the LCDR3 nucleic acid sequences listed in Table 10, or a substantially similar sequence thereof having at least 90%, at least 95%, at least 98% or at least 99% sequence identity thereto.

Also provided herein are nucleic acid molecules encoding an HCVR, wherein the HCVR may comprise a set of three CDRs (i.e., HCDR1-HCDR2-HCDR3), wherein the HCDR1-HCDR2-HCDR3 amino acid sequence set is as defined by any of the exemplary anti-MSR1 antibodies listed in Table 9.

Also provided herein are nucleic acid molecules encoding an LCVR, wherein the LCVR may comprise a set of three CDRs (i.e., LCDR1-LCDR2-LCDR3), wherein the LCDR1-

LCDR2-LCDR3 amino acid sequence set is as defined by any of the exemplary anti-MSR1 antibodies listed in Table 9.

Also provided herein are nucleic acid molecules encoding both an HCVR and an LCVR, wherein the HCVR may comprise an amino acid sequence of any of the HCVR amino acid sequences listed in Table 9, and wherein the LCVR may comprise an amino acid sequence of any of the LCVR amino acid sequences listed in Table 9. In certain embodiments, the nucleic acid molecule may comprise a polynucleotide sequence selected from any of the HCVR nucleic acid sequences listed in Table 10, or a substantially similar sequence thereof having at least 90%, at least 95%, at least 98% or at least 99% sequence identity thereto, and a polynucleotide sequence selected from any of the LCVR nucleic acid sequences listed in Table 10, or a substantially similar sequence thereof having at least 90%, at least 95%, at least 98% or at least 99% sequence identity thereto. In certain embodiments according to this aspect of the disclosure, the nucleic acid molecule encodes an HCVR and LCVR, wherein the HCVR and LCVR are both derived from the same anti-MSR1 antibody listed in Table 9.

Also provided herein are recombinant expression vectors capable of expressing a polypeptide comprising a heavy or light chain variable region of an anti-MSR1 antibody for the preparation of antibody-drug conjugates described herein. For example, embodiments include recombinant expression vectors comprising any of the nucleic acid molecules mentioned above, i.e., nucleic acid molecules encoding any of the HCVR, LCVR, and/or CDR sequences as set forth in Table 9. Also included within the scope of the present disclosure are host cells into which such vectors have been introduced, as well as methods of producing the antibodies or portions thereof for the preparation of antibody-drug conjugates described herein by culturing the host cells under conditions permitting production of the antibodies or antibody fragments, and recovering the antibodies and antibody fragments so produced.

Suitable anti-MSR1 antibodies for the antibody-drug conjugates described herein include those that have a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

According to certain embodiments, antibody-drug conjugates according to the disclosure comprise anti-MSR1 antibodies comprising an Fc domain comprising one or more mutations which enhance or diminish antibody binding to the FcRn receptor, e.g., at acidic pH as compared to neutral pH. For example, provided herein are antibody-drug conjugates comprising anti-MSR1 antibodies comprising a mutation in the $CH_2$ or a $CH_3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification may comprise a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, embodiments include antibody-drug conjugates comprising anti-MSR1 antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

Biological Characteristics of the Anti-MSR1 Antibodies

Embodiments include antibody-drug conjugates comprising rifamycin analogs and antibodies and antigen-binding fragments thereof that bind human MSR1 with high affinity. For example, the present disclosure includes antibody-drug conjugates comprising anti-MSR1 antibodies that bind human MSR1 extracellular domain expressed with an N-terminal nonahistidine tag (SEQ ID NO: 688) (e.g., His9-hMSR1) with a $K_D$ of less than about 10 nM as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind human MSR1 at 37° C. with a $K_D$ of less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured by surface plasmon resonance, e.g., using an assay format as defined in Example 25 herein, or a substantially similar assay. In some embodiments, the antibody-drug conjugates comprise anti-MSR1 antibodies disclosed herein which bind human MSR1 at 25° C. with a $K_D$ of less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, or less than about 20 pM, as measured by surface plasmon resonance, e.g., using an assay format as defined in Example 25 herein, or a substantially similar assay.

Embodiments also include antibody-drug conjugates comprising antibodies and antigen-binding fragments thereof that bind monkey MSR1 with high affinity. For example, disclosed herein are antibody-drug conjugates comprising anti-MSR1 antibodies that bind monkey MSR1 extracellular domain expressed with an N-terminal mycmyc-hexahistidine tag ("hexahistidine" disclosed as SEQ ID NO: 689) (e.g., HMM-mfMSR1) with a $K_D$ of less than about 20 nM as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind monkey MSR1 at 37° C. with a $K_D$ of less than about 20 nM, less than about 18 pM, less than about 15 nM, less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, less than about 20 pM, or less than about 10 pM, as measured by surface plasmon resonance, e.g., using an assay format as defined in Example 25 herein, or a substantially similar assay. In some embodiments, antibody-drug conjugates comprising the anti-MSR1 antibodies disclosed herein bind monkey MSR1 at 25° C. with a $K_D$ of less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 700 pM, less than about 600 pM, less than about 500 pM, less than about 400 pM, less than about 300 pM, less than about 200 pM, less than about 100 pM, less than about 90 pM, less than about 80 pM, less than about 70 pM, less than about 60 pM, less than about 50 pM, less than about 40 pM, less than about 30 pM, or less than about 20 pM, as measured by surface plasmon resonance, e.g., using an assay format as defined in Example 25 herein, or a substantially similar assay.

The present disclosure also includes antibody-drug conjugates comprising antibodies and antigen-binding fragments thereof that bind human MSR1 extracellular domain expressed with an N-terminal nonahistidine tag (SEQ ID NO: 688) (e.g., His9-hMSR1) with a dissociative half-life (t½) of greater than about 5 minutes as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind human MSR1 at 37° C. with a t1/2 of greater than about 4 minutes, greater than about 5 minutes, greater than about 6 minutes, greater than about 8 minutes, greater than about 10 minutes, greater than about 12 minutes, greater than about 14 minutes, greater than about 16 minutes, greater than about 18 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 120 minutes, greater than about 150 minutes, greater than about 180 minutes, greater than about 210 minutes, greater than about 240 minutes, or longer, as measured by surface plasmon resonance, e.g., using an assay format as defined in Example 25 herein, or a substantially similar assay.

Embodiments also include antibody-drug conjugates comprising antibodies and antigen-binding fragments thereof that can bind monkey MSR1 extracellular domain expressed with an N-terminal myc-myc-hexahistidine tag ("hexahistidine" disclosed as SEQ ID NO: 689) (e.g. HMM-mfMSR1) with high affinity. For example, the present disclosure includes antibody-drug conjugates comprising anti-MSR1 antibodies that bind HMM-mfMSR1 with a $K_D$ of less than about 20 nM as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind HIM-mfMSR1 at 37° C. with a $K_D$ of less than about 20 nM, less than about 15 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 800 pM, less than about 700 pM, less than about 600 pM, less than about 500 pM, less than about 400 pM, less than about 300 pM, less than about 200 pM, less than about 150 pM, less than about 100 pM, less than about 90 pM, less than about 80 pM, less than about 70 pM, less than about 60 pM, or less than about 50 pM, as measured by surface plasmon resonance, e.g., using an assay format as defined in Example 25 herein, or a substantially similar assay. In some embodiments, the anti-MSR1 antibodies disclosed herein bind HMM-mfMSR1 at 25° C. with a $K_D$ of less than about 12 nM, less than about 10 nM, less than about 9 nM, less than about 8 nM, less than about 7 nM, less than about 6 nM, less than about 5 nM, less than about 4 nM, less than about 3 nM, less than about 2 nM, less than about 1 nM, less than about 900 pM, less than about 800 pM, less than about 800 pM, less than about 700 pM, less than about 600 pM, less than about 500 pM, less than about 400 pM, less than about 300 pM, less than about 200 pM, less than about 150 pM, less than about 100 pM, less than about 90 pM, less than about 80 pM, less than about 70 pM, less than about 60 pM, or less than about 50 pM, as measured by surface plasmon resonance, e.g., using an assay format as defined in Example 25 herein, or a substantially similar assay.

Embodiments also include antibody-drug conjugates comprising antibodies and antigen-binding fragments thereof that bind monkey MSR1 extracellular domain expressed with an N-terminal myc-myc-hexahistidine tag ("hexahistidine" disclosed as SEQ ID NO: 689) (e.g. HMM-mfMSR1) with a dissociative half-life (t½) of greater than about 55 minutes as measured by surface plasmon resonance at 25° C. or 37° C., e.g., using an assay format as defined in Example 25 herein, or a substantially similar assay. According to certain embodiments, antibody-drug conjugates comprising anti-MSR1 antibodies are provided that bind dimeric human MSR1 at 37° C. with a t2 of greater than about 1 minute, greater than about 2 minutes, greater than about 3 minutes, greater than about 4 minutes, greater than about 5 minutes, greater than about 6 minutes, greater than about 8 minutes, greater than about 10 minutes, greater than about 12 minutes, greater than about 14 minutes, greater than about 16 minutes, greater than about 18 minutes, greater than about 20 minutes, greater than about 30 minutes, greater than about 40 minutes, greater than about 50 minutes, greater than about 60 minutes, greater than about 70 minutes, greater than about 80 minutes, greater than about 90 minutes, greater than about 120 minutes, greater than about 150 minutes, greater than about 180 minutes, greater than about 210 minutes, or longer, as measured by surface plasmon resonance, e.g., using an assay format as defined in Example 25 herein, or a substantially similar assay.

Embodiments also include antibody-drug conjugates comprising antibodies and antigen-binding fragments thereof that bind engineered cell-surface expressed hMSR1 with binding ratios of engineered hMSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 27 herein, or a substantially similar assay. In some embodiments, provided herein are antibody-drug conjugates comprising antibodies that bind cells with endogenously-expressed hMSR1 with binding ratios of endogenous hMSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, or greater at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 27 herein, or a substantially similar assay. In some embodiments, antibody-drug conjugates comprise an MSR1 antibody or antigen binding fragment disclosed herein which binds engineered cell-surface expressed mouse MSR1 with binding ratios of engineered mouse MSR1-expressing cells to non-expressing cells of at least about 2-fold, at least about 3-fold, at least about 4-fold, at least about 5-fold, at least about 6-fold, at least about 7-fold, at least about 8-fold, at least about 9-fold, at least about 10-fold, at least about 12-fold, at least about 15-fold, at least about 20-fold, at least about 25-fold, at least about 30-fold, at least about 35-fold, at least about 40-fold, at least about 45-fold, at least about 50-fold, or greater, as measured by antibody binding assay, e.g., using an assay format as defined in Example 27 herein, or a substantially similar assay.

The antibody-drug conjugates comprise antibodies disclosed herein which may possess one or more of the aforementioned biological characteristics, or any combination thereof. The foregoing list of biological characteristics of the antibodies disclosed herein is not intended to be exhaustive. Other biological characteristics of the antibodies disclosed herein will be evident to a person of ordinary skill in the art from a review of the present disclosure including the working Examples herein.

Anti-WTA Antibodies Suitable for ADCs

According to certain embodiments, antibody-drug conjugates of the present disclosure may comprise an anti-WTA antibody or an antigen-binding fragment thereof. Such anti-WTA antibodies or antigen-binding fragments thereof bind to wall teichoic acids (WTAs) which are expressed on a number of Gram-positive bacteria including *Staphylococcus aureus*. Anti-WTA antibodies may be selected and produced by the methods taught in, for example, U.S. Pat. No. 8,283,294; Meijer P J et al (2006) J Mol Biol. 358(3):764-72; Lantto J, et al (2011) J Virol. 85(4):1820-33; and WO2016090038, each of which is incorporated herein by reference in its entirety for all purposes.

The chemical structures of WTAs vary among organisms. In *S. aureus*, WTA is covalently linked to the 6-OH of N-acetyl muramic acid (MurNAc) via a disaccharide composed of N-acetylglycosamine (GlcNAc)-1-P and N-acetylmannoseamine (ManNAc), which is followed by about two or three units of glycerol-phosphates. The actual WTA polymer is then composed of about 11-40 ribitol-phosphate (Rbo-P) repeating units. The step-wise synthesis of WTA is first initiated by the enzyme called TagO, and *S. aureus* strains lacking the TagO gene (by deletion of the gene) do not make any WTA. The repeating units can be further tailored with D-alanine (D-Ala) at C2-OH and/or with N-acetylglucosamine (GlcNAc) at the C4-OH position via α-(alpha) or β-(beta) glycosidic linkages. Depending of the *S. aureus* strain, or the growth phase of the bacteria the glycosidic linkages could be α-, β-, or a mixture of the two anomers. These GlcNAc sugar modifications are tailored by two specific *S. aureus*-derived glycosyltransferases (Gtfs): TarM Gtf mediates α-glycosidic linkages, whereas TarS Gtfs mediates β-(beta)glycosidic linkages.

The anti-WTA antibody suitable for ADCs of the present disclosure can be an anti-WTAα or anti-WTAβ antibody. The anti-WTA antibody may be cloned from B cells from *S. aureus* infected patients. In one embodiment, the anti-WTA antibody are human monoclonal antibodies. The ADCs of the present disclosure encompass chimeric antibodies and humanized antibodies comprising the CDRs of the anti-WTA antibodies described herein.

The antibody-drug conjugates of the present disclosure can comprise any one of the anti-WTA antibodies described herein, or antigen-binding fragments thereof. In some embodiments, the anti-WTA antibodies or antigen-binding fragments thereof bind to *Staphylococcus aureus*.

In some embodiments, antibody-drug conjugates of the present disclosure comprise an anti-WTAα monoclonal antibody, or an antigen-binding fragment thereof. As a non-limiting example, the anti-WTAα antibody, or the antigen-binding fragment thereof, comprises: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

TABLE 2A

CDR sequences of exemplary anti-WTAα antibodies

| Anti-WTAα antibody | LCDR1 SEQ ID NO | LCDR2 SEQ ID NO | LCDR3 SEQ ID NO | HCDR1 SEQ ID NO | HCDR2 SEQ ID NO | HCDR3 SEQ ID NO |
|---|---|---|---|---|---|---|
| A1 | 467 | 468 | 469 | 470 | 471 | 472 |
| A2 | 473 | 474 | 475 | 476 | 477 | 478 |
| A3 | 479 | 480 | 481 | 482 | 483 | 484 |
| A4 | 485 | 486 | 487 | 488 | 489 | 490 |

In one embodiment, the anti-WTAα antibody, or an antigen-binding fragment thereof, comprises:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In some embodiments, the anti-WTAα antibody, or the antigen-binding fragment thereof, comprises a heavy chain variable region (HCVR), comprising an amino acid sequence selected from SEQ ID NO: 492, SEQ ID NO: 494, SEQ ID NO: 496, and SEQ ID NO: 498, or a substantially similar sequence thereof having at least 90%, at least 95%, at least 98% or at least 99% sequence identity thereto. The antibodies may further comprise a light chain variable region (LCVR), comprising an amino acid sequence selected from SEQ ID NO: 491, SEQ ID NO: 493, SEQ ID NO: 495, and SEQ ID NO: 497, or a substantially similar sequence thereof having at least 90%, at least 95%, at least 98% or at least 99% sequence identity thereto.

In one embodiment, the anti-WTAα antibody, or the antigen-binding fragment thereof, comprises a LCVR having the amino acid sequence of SEQ ID NO: 491, or a substantially similar sequence thereof having at least 90%, at least 95%, at least 98% or at least 99% sequence identity thereto; and a HCVR having the amino acid sequence of SEQ ID NO: 492, or a substantially similar sequence thereof having at least 90%, at least 95%, at least 98% or at least 99% sequence identity thereto.

In another embodiment, the anti-WTAα antibody, or the antigen-binding fragment thereof, comprises a LCVR having the amino acid sequence of SEQ ID NO: 493, or a substantially similar sequence thereof having at least 90%, at least 95%, at least 98% or at least 99% sequence identity thereto; and a HCVR having the amino acid sequence of SEQ ID NO: 494, or a substantially similar sequence thereof having at least 90%, at least 95%, at least 98% or at least 99% sequence identity thereto.

In another embodiment, the anti-WTAα antibody, or the antigen-binding fragment thereof, comprises a LCVR having the amino acid sequence of SEQ ID NO: 495, or a substantially similar sequence thereof having at least 90%, at least 95%, at least 98% or at least 99% sequence identity thereto; and a HCVR having the amino acid sequence of SEQ ID NO: 496, or a substantially similar sequence thereof having at least 90%, at least 95%, at least 98% or at least 99% sequence identity thereto.

In another embodiment, the anti-WTAα antibody, or the antigen-binding fragment thereof, comprises a LCVR having the amino acid sequence of SEQ ID NO: 497, or a substantially similar sequence thereof having at least 90%, at least 95%, at least 98% or at least 99% sequence identity thereto; and a HCVR having the amino acid sequence of SEQ ID NO: 498, or a substantially similar sequence thereof having at least 90%, at least 95%, at least 98% or at least 99% sequence identity thereto.

In some embodiments, antibody-drug conjugates of the present disclosure comprise an anti-WTAβ monoclonal antibody, or an antigen-binding fragment thereof. Exemplary anti-WTAβ antibodies of the present invention are listed in Table 2B herein. Table 2B sets forth the amino acid sequence identifiers of the heavy chain complementarity determining regions (HCDR1, HCDR2 and HCDR3), and light chain complementarity determining regions (LCDR1, LCDR2 and LCDR3) of the exemplary anti-WTAβ antibodies.

TABLE 2B

CDR sequences of exemplary anti-WTAβ antibodies

| Anti-WTAβ antibody | LCDR1 | LCDR2 | LCDR3 | HCDR1 | HCDR2 | HCDR3 |
|---|---|---|---|---|---|---|
| B1 | 499 | 500 | 501 | 502 | 503 | 504 |
| B2 | 505 | 506 | 507 | 508 | 509 | 510 |
| B3 | 511 | 512 | 513 | 514 | 515 | 516 |
| B4 | 517 | 518 | 519 | 520 | 521 | 522 |
| B5 | 523 | 524 | 525 | 526 | 527 | 528 |
| B6 | 529 | 530 | 531 | 532 | 533 | 534 |
| B7 | 535 | 536 | 537 | 538 | 539 | 540 |
| B8 | 541 | 542 | 543 | 544 | 545 | 546 |
| B9 | 547 | 548 | 549 | 550 | 551 | 552 |
| B10 | 553 | 554 | 555 | 556 | 557 | 558 |
| B11 | 559 | 560 | 561 | 562 | 563 | 564 |
| B12 | 565 | 566 | 567 | 568 | 569 | 570 |
| B13 | 571 | 572 | 573 | 574 | 575 | 576 |
| B12 variant | 565 | 566 | 567 | 568 | 569 | 584 |

In one embodiment, the anti-WTAβ antibody, or an antigen-binding fragment thereof, comprises:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

The present invention also provides anti-WTAβ antibodies, or antigen-binding fragments thereof, comprising a heavy chain CDR1 (HCDR1) comprising an amino acid sequence selected from any of the HCDR1 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a heavy chain CDR2 (HCDR2) comprising an amino acid sequence selected from any of the HCDR2 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a heavy chain CDR3 (HCDR3) comprising an amino acid sequence selected from any of the HCDR3 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a light chain CDR1 (LCDR1) comprising an amino acid sequence selected from any of the LCDR1 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a light chain CDR2 (LCDR2) comprising an amino acid sequence selected from any of the LCDR2 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a light chain CDR3 (LCDR3) comprising an amino acid sequence selected from any of the LCDR3 amino acid sequences listed in Table 2B or a substantially similar sequence thereof having at least 90%, at least 95%, at least 98% or at least 99% sequence identity.

The present invention also provides anti-WTAβ antibodies, or antigen-binding fragments thereof, comprising a set of six CDRs (i.e., HCDR1-HCDR2-HCDR3-LCDR1-LCDR2-LCDR3) contained within any of the exemplary anti-WTAβ antibodies listed in Table 2B. In certain embodiments, the HCDR1-HCDR2-HCDR3-LCDR1-LCDR2-LCDR3 amino acid sequences set is selected from the group consisting of SEQ ID NOs: 502-503-504-499-500-501, 508-509-510-505-506-507, 514-515-516-511-512-513, 520-521-522-517-518-519, 526-527-528-523-524-525, 532-533-534-529-530-531, 538-539-540-535-536-537, 544-545-546-541-542-543, 550-551-552-547-548-549, 556-557-558-553-554-555, 562-563-564-559-560-561, 568-569-570-565-566-567, 574-575-576-571-572-573, and 568-569-584-565-566-567.

In one embodiment, the anti-WTAβ antibody, or the antigen-binding fragment thereof, is derived from antibody 4497 described in US Patent Application Publication 20140356375 (which is incorporated herein by reference in its entirety). In some embodiments, the anti-WTAβ antibody, or the antigen-binding fragment thereof derived from antibody 4497 further comprises a V205C mutation in the light chain.

In one embodiment, the anti-WTAβ antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTAβ antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTAβ antibody or antigen binding fragment thereof comprises an HCVR amino acid sequence of SEQ ID NOs: 586, and an LCVR amino acid sequence of SEQ ID NO: 585.

In some embodiments, the anti-WTAβ antibody comprises a heavy chain amino acid sequence of SEQ ID NOs: 602 and a light chain amino acid sequence of SEQ ID NO: 587 or SEQ ID NO: 589. In some embodiments, the anti-WTAβ antibody, or the antigen-binding fragment thereof comprises a V205C mutation in the light chain.

In some embodiments, the anti-WTAβ antibody, or the antigen-binding fragment thereof, comprises a heavy chain variable region (HCVR), comprising an amino acid sequence corresponding to Kabat positions 1-113 of a full-length heavy chain sequence selected from SEQ ID Nos: 580, 621-628, and 591-594, or a substantially similar sequence thereof having at least 90%, at least 95%, at least 98% or at least 99% sequence identity thereto. The antibodies may further comprise a light chain variable region (LCVR), comprising an amino acid sequence corresponding to Kabat positions 1-107 of a full-length light chain sequence selected from SEQ ID Nos: 579, 610-620, and 587, or a substantially similar sequence thereof having at least 90%, at least 95%, at least 98% or at least 99% sequence identity thereto. Reference of Kabat positions of the full-length heavy chain and full-length light chain can be found, for example, in FIGS. 15A-1, 15A-2, and 15A-3, and FIGS. 15B-1, 15-B 2, 15-B 3, 15-B 4, 15-B 5, and 15-B 6 of US Patent Application Publication No. 20180021450, which is incorporated herein by reference in its entirety for all purposes.

In one embodiment, the anti-WTAβ antibody, or the antigen-binding fragment thereof, comprises a LCVR comprising the amino acid sequence of SEQ ID NO: 577, or a substantially similar sequence thereof having at least 90%, at least 95%, at least 98% or at least 99% sequence identity thereto; and a HCVR comprising the amino acid sequence of SEQ ID NO: 578 wherein X is Q or E and X1 is M, I or V, or a substantially similar sequence thereof having at least 90%, at least 95%, at least 98% or at least 99% sequence identity thereto.

In one embodiment, the anti-WTAβ antibody, or the antigen-binding fragment thereof, comprises a light chain comprising the amino acid sequence of SEQ ID NO: 579, or a substantially similar sequence thereof having at least 90%, at least 95%, at least 98% or at least 99% sequence identity thereto; and a heavy chain comprising the amino acid sequence of SEQ ID NO: 580, or a substantially similar sequence thereof having at least 90%, at least 95%, at least 98% or at least 99% sequence identity thereto.

In a specific embodiment, the anti-WTAβ antibody, or the antigen-binding fragment thereof, comprises a LCVR comprising the amino acid sequence of SEQ ID NO: 577, and a HCVR comprising the amino acid sequence of SEQ ID NO: 578. In a yet more specific embodiment, the anti-WTAβ antibody, or the antigen-binding fragment thereof, comprises a light chain comprising the amino acid sequence of SEQ ID NO: 579, and a heavy chain comprising the amino acid sequence of SEQ ID NO: 580.

In some embodiments, anti-WTAβ antibodies, or the antigen-binding fragments thereof, suitable for ADCs of the present disclosure may contain one or more engineered cysteine in the antibody light chain and/or heavy chain.

In some embodiments, the light chain of the anti-WTAβ antibody, or the antigen-binding fragment thereof, contains an engineered cysteine. In one embodiment, the anti-WTAβ antibody, or the antigen-binding fragment thereof, comprises a light chain comprising the amino acid sequence of SEQ ID NO: 581; and a heavy chain comprising the amino acid sequence of SEQ ID NO: 582 wherein X is M, I or V. In one embodiment, the anti-WTA antibody, or the antigen-binding fragment thereof, comprises a light chain comprising the amino acid sequence of SEQ ID NO: 581; and a heavy chain comprising the amino acid sequence of SEQ ID NO: 580.

In some embodiments, the heavy chain of the anti-WTAβ antibody, or the antigen-binding fragment thereof, contains an engineered cysteine. In one embodiment, the anti-WTAβ antibody, or the antigen-binding fragment thereof, comprises a light chain comprising the amino acid sequence of SEQ ID NO: 579; and a heavy chain comprising the amino acid sequence of SEQ ID NO: 583 wherein X is M, I or V.

In some embodiments, both the light chain and the heavy chain of the anti-WTAβ antibody, or the antigen-binding fragment thereof, contain an engineered cysteine. In one embodiment, the anti-WTAβ antibody, or the antigen-binding fragment thereof, comprises a light chain containing an engineered cysteine and comprising the sequence of SEQ ID NO: 581; a heavy chain containing an engineered cysteine and comprising the amino acid sequence of SEQ ID NO: 583 wherein X is M, I or V.

In some embodiments, the anti-WTAβ antibody, or the antigen-binding fragment thereof, comprises a LCVR having the amino acid sequence of SEQ ID NO: 585, or a substantially similar sequence thereof having at least 90%, at least 95%, at least 98% or at least 99% sequence identity thereto; and a HCVR having the amino acid sequence of SEQ ID NO: 608, or a substantially similar sequence thereof having at least 90%, at least 95%, at least 98% or at least 99% sequence identity thereto. In one embodiment, the anti-WTAβ antibody, or the antigen-binding fragment thereof, comprises a LCVR having the amino acid sequence of SEQ ID NO: 585, and a HCVR having the amino acid sequence of SEQ ID NO: 608.

In one embodiment, the anti-WTAβ antibody, or the antigen-binding fragment thereof, comprises a light chain having the amino acid sequence of SEQ ID NO: 587; and a heavy chain having the amino acid sequence of SEQ ID NO: 590. In one embodiment, the anti-WTAβ antibody, or the antigen-binding fragment thereof, comprises a light chain having the amino acid sequence of SEQ ID NO: 589; and a heavy chain having the amino acid sequence of SEQ ID NO: 609. In one embodiment, the anti-WTAβ antibody, or the antigen-binding fragment thereof, comprises a light chain having the amino acid sequence of SEQ ID NO: 589; and a heavy chain having the amino acid sequence of SEQ ID NO: 590.

In some embodiments, the anti-WTAβ antibody comprises a LCVR having the amino acid sequence of SEQ ID NO:585 and a HCVR having the amino acid sequence of SEQ ID NO: 586 or SEQ ID NO: 608.

In some embodiments, the anti-WTAβ antibody comprises a LCVR having the amino acid sequence of SEQ ID NO: 577 and a HCVR having the amino acid sequence of SEQ ID NO: 578.

In some embodiments of the ADCs of the present disclosure, the anti-WTA antibody binds to the same epitope as any one of the anti-WTA antibodies disclosed herein.

Anti-WTA antibodies or antigen-binding fragments thereof suitable for ADCs of the present invention can be altered at one or more residues, for example to improve the pK, stability, expression, manufacturability, while maintaining substantially about the same or improved binding affinity to the antigen as compared to the wild type, unmodified antibody. Variants of the present anti-WTA antibodies having conservative amino acid substitutions are encompassed by the invention.

In some embodiments, ADCs of the present disclosure may comprise an anti-WTA antigen-binding fragment lacking a Fc region. In some embodiments, the antigen-binding fragment is a F(ab) or F(ab')2. In some embodiments, the antigen-binding fragment further comprises a heavy chain constant region and/or a light chain constant region, wherein the heavy chain constant region and/or the light chain constant region comprise one or more amino acids that are substituted with cysteine residues. In some embodiments, the antigen-binding fragment comprises a heavy chain constant region comprising amino acid substitution A118C and/or S400C, and/or a light chain constant region comprising amino acid substitution V205C. wherein the numbering system is according to EU numbering.

In certain embodiments, it may be desirable to create cysteine engineered anti-WTA antibodies, e.g., "thioMAbs," in which one or more residues of an antibody are substituted with cysteine residues. Any form of antibody may be so engineered, i.e. mutated. For example, a parent Fab antibody fragment may be engineered to form a cysteine engineered Fab, referred to herein as "ThioFab." Similarly, a parent monoclonal antibody may be engineered to form a "ThioMab." It should be noted that a single site mutation yields a single engineered cysteine residue in a ThioFab, while a single site mutation yields two engineered cysteine residues in a ThioMab, due to the dimeric nature of the IgG antibody. In particular embodiments, the substituted residues occur at accessible sites of the antibody. By substituting those residues with cysteine, reactive thiol groups are thereby positioned at accessible sites of the antibody and may be used to conjugate the antibody to other moieties, such as antibiotic moieties (e.g., rifamycin analogs) or linker-antibiotic moieties (e.g., linker-rifamycin analog payload), to create an antibody-drug conjugate, as described further herein. In certain embodiments, any one or more of the following residues may be substituted with cysteine, including V205 (Kabat numbering) of the light chain; A118 (EU numbering) of the heavy chain; and 5400 (EU numbering) of the heavy chain Fc region. Nonlimiting exemplary cysteine engineered heavy chain A118C (SEQ ID NO: 605) and light chain V205C (SEQ ID NO: 607) mutants of an anti-WTA antibody are shown. Cysteine engineered anti-WTA antibodies may be generated as described, for example, in Junutula, et al., 2008b Nature Biotech., 26(8):925-932; U.S. Pat. No. 7,521,541; US-2011/0301334; Lehar et al, *Nature* 2015 527, 323-328, each of which are incorporated herein by reference in its entirety.

The engineered cysteine thiols may react with linker reagents or the linker-drug intermediates of the present invention which have thiol-reactive, electrophilic groups such as maleimide or alpha-halo amides to form ADCs with cysteine engineered antibodies (THIOMAB™ or thioMabs) and the antibiotic moieties (e.g., rifamycin analogs). The location of the antibiotic moiety can thus be designed, controlled, and known. The antibiotic loading can be controlled since the engineered cysteine thiol groups typically react with thiol-reactive linker reagents or linker-antibiotic intermediates in high yield. Engineering an anti-WTA antibody to introduce a cysteine amino acid by substitution at a single site on the heavy or light chain gives two new cysteines on the symmetrical tetramer antibody. An antibiotic loading near 2 can be achieved and near homogeneity of the ADC.

Anti-Protein A Antibodies Suitable for ADCs

According to certain embodiments, antibody-drug conjugates of the present disclosure may comprise an anti-Protein A antibody, or an antigen-binding fragment thereof.

Protein A is a 42-kDa protein that exists in both secreted and membrane-associated forms, possesses two distinct Ig-binding activities: each domain can bind Fcγ, the constant region of IgG involved in effector functions, and Fab, the Ig fragment responsible for antigen recognition. Protein A is covalently anchored in the staphylococcal cell wall through its carboxyl terminal end. The protein is comprised of five repeated domains (E, D, A, B, C) linked to the cell surface by region Xr, and each domain can bind with high affinity to the Fc region of immunoglobulin G and to the Fab region of immunoglobulin of the VH3 subclass. The interaction with IgG Fc hinders effector function. In addition, antibodies bound to Protein A through the Fc region cannot stimulate complement fixation by the classical pathway.

Non-limiting examples of anti-Protein A antibodies suitable for ADCs of the present disclosure are listed in Tables 3A and 3B herein. Table 3A sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-Protein A antibody from which the antibodies of the present disclosure may be derived. Table 3B sets forth the nucleic acid sequence identifiers of the HCVRs, LCVRs, HCDR1, HCDR2 HCDR3, LCDR1, LCDR2 and LCDR3 of the exemplary anti-Protein A antibodies.

In some embodiments, anti-Protein A antibodies suitable for ADCs of the present disclosure have attenuated Fc binding. Such antibodies have HCVR amino acid sequences and LCVR amino acid sequences as shown in Table 3A, and also can comprise an IgG1 heavy chain amino acid sequence of SEQ ID NO: 648. This IgG1 sequence comprises H435R and Y436F mutations in the hIgG1 Fc (EU index numbering; equivalent to H318R and Y319F of SEQ ID NO: 648), which is noted as "*/*" or "**" herein.

TABLE 3A

Amino Acid Sequence Identifiers for Exemplary Anti-Protein A Antibodies

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H1xH15140P*/* | 630 | 632 | 634 | 636 | 638 | 640 | 642 | 644 |
| H1xH15135P*/* | 650 | 652 | 654 | 656 | 658 | 660 | 662 | 664 |
| H1xH15120P*/* | 670 | 672 | 674 | 676 | 678 | 680 | 662 | 683 |

TABLE 3B

Nucleic Acid Sequence Identifiers for Exemplary Anti-Protein A Antibodies

| Antibody | SEQ ID NOs: | | | | | | | |
|---|---|---|---|---|---|---|---|---|
| Designation | HCVR | HCDR1 | HCDR2 | HCDR3 | LCVR | LCDR1 | LCDR2 | LCDR3 |
| H1xH15140P*/* | 629 | 631 | 633 | 635 | 637 | 639 | 641 | 643 |
| H1xH15135P*/* | 649 | 651 | 653 | 655 | 657 | 659 | 661 | 663 |
| H1xH15120P*/* | 669 | 671 | 673 | 675 | 677 | 679 | 681 | 682 |

In one embodiment, the anti-Protein A antibody, or an antigen-binding fragment thereof, comprises:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, antibody-drug conjugates of the present disclosure comprise an antibody or antigen-binding fragment thereof that specifically bind Protein A, comprising an HCVR comprising an amino acid sequence selected from the group consisting of SEQ ID NOs: 630, 650, and 670, or a substantially similar sequence thereof having at least 90%, at least 95%, at least 98% or at least 99% sequence identity thereto.

In some embodiments, antibody-drug conjugates of the present disclosure comprise an antibody or antigen-binding fragment thereof that specifically bind Protein A, comprising an LCVR comprising an amino acid sequence selected from the group consisting of SEQ ID NOs: 638, 658, and 678, or a substantially similar sequence thereof having at least 90%, at least 95%, at least 98% or at least 99% sequence identity thereto.

In some embodiments, antibody-drug conjugates of the present disclosure comprise an antibody or antigen-binding fragment thereof that specifically bind Protein A, comprising an HCVR and an LCVR amino acid sequence pair (HCVR/LCVR) comprising an anti-Protein A HCVR amino acid sequence listed in Table 3A and an anti-Protein A LCVR amino acid sequence listed in Table 3A. According to certain embodiments, antibody-drug conjugates of the present disclosure comprise an antibody or antigen-binding fragment thereof that specifically bind Protein A, comprising an HCVR/LCVR amino acid sequence pair contained within the exemplary anti-Protein A antibody listed in Table 3A. In certain embodiments, the HCVR/LCVR amino acid sequence pair is selected from the group consisting of SEQ ID NOs: 630/638, 650/658, and 670/678.

In some embodiments, antibody-drug conjugates of the present disclosure comprise an antibody or antigen-binding fragment thereof that specifically bind Protein A, comprising a set of six CDRs (i.e., HCDR1-HCDR2-HCDR3-LCDR1-LCDR2-LCDR3) contained within any of the exemplary anti-Protein A antibodies listed in Table 3A. In certain embodiments, the HCDR1-HCDR2-HCDR3-LCDR1-LCDR2-LCDR3 amino acid sequences set comprises SEQ ID NOs: 632-634-636-640-642-644, 652-654-656-660-662-664, or 672-674-676-680-662-683.

In a related embodiment, antibody-drug conjugates of the present disclosure comprise an antibody or antigen-binding fragment thereof that specifically bind Protein A, comprising a set of six CDRs (i.e., HCDR1-HCDR2-HCDR3-LCDR1-LCDR2-LCDR3) contained within an HCVR/LCVR amino acid sequence pair as defined by the exemplary anti-Protein A antibodies listed in Table 3A. For example, the present invention includes antibodies or antigen-binding fragments thereof that specifically bind Protein A, comprising the HCDR1-HCDR2-HCDR3-LCDR1-LCDR2-LCDR3 amino acid sequences set contained within an HCVR/LCVR amino acid sequence pair selected from the group consisting of: SEQ ID NOs: 630/638, 650/658, and 670/678.

In some embodiments, the anti-Protein A antibody, or an antigen-binding fragment thereof, comprises a heavy chain amino acid sequence of SEQ ID NO: 666, or a substantially similar sequence thereof having at least 90%, at least 95%, at least 98% or at least 99% sequence identity thereof. In some aspects, the anti-Protein A antibody, or an antigen-binding fragment thereof, comprises a light chain amino acid sequence of SEQ ID NO: 668, or a substantially similar sequence thereof having at least 90%, at least 95%, at least 98% or at least 99% sequence identity thereof.

In some embodiments, the anti-Protein A antibody, or an antigen-binding fragment thereof, comprises a heavy chain amino acid sequence of SEQ ID NO: 685, or a substantially similar sequence thereof having at least 90%, at least 95%, at least 98% or at least 99% sequence identity thereof. In some embodiments, the anti-Protein A antibody, or an antigen-binding fragment thereof, comprises a light chain amino acid sequence of SEQ ID NO: 687, or a substantially similar sequence thereof having at least 90%, at least 95%, at least 98% or at least 99% sequence identity thereof.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiment, anti-Protein A antibody comprises a light chain mutation at position 103 (C103S). In one embodiment, the anti-Protein A antibody, or antigen-binding fragment thereof, is conjugated to a compound of the present disclosure at light chain position 103.

Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

Nucleic acid molecules encoding anti-Protein A antibodies or portions thereof suitable for ADCs of the present disclosure are also provided. For example, the anti-Protein A HCVR amino acid sequences and anti-Protein A LCVR amino acid sequences listed in Table 3A may be encoded by the nucleic acid molecules listed in Table 3B. In certain embodiments, the nucleic acid molecule comprises a polynucleotide sequence selected from the anti-Protein A HCVR nucleic acid sequences and anti-Protein A LCVR nucleic acid sequences listed in Table 3B, or a substantially similar sequence thereof having at least 90%, at least 95%, at least 98% or at least 99% sequence identity thereto.

For example, the anti-Protein A CDR amino acid sequences listed in Table 3A may be encoded by the nucleic acid molecules listed in Table 3B. In certain embodiments, the nucleic acid molecule comprises a polynucleotide sequence selected from any of the anti-Protein A CDR nucleic acid sequences listed in Table 3B, or a substantially similar sequence thereof having at least 90%, at least 95%, at least 98% or at least 99% sequence identity thereto.

In some embodiments, a nucleic acid molecule encoding anti-Protein A antibody or an antigen-binding fragment thereof may comprise a nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by the exemplary anti-Protein A antibodies listed in Table 3A.

A nucleic acid molecule encoding anti-Protein A antibody or an antigen-binding fragment thereof may comprise a nucleic acid molecule encoding an LCVR, wherein the LCVR comprises a set of three CDRs (i.e., LCDR1-LCDR2-LCDR3), wherein the LCDR1-LCDR2-LCDR3 amino acid sequence set is as defined by the exemplary anti-Protein A antibodies listed in Table 3A.

Also provided are recombinant expression vectors capable of expressing a polypeptide comprising a heavy or light chain variable region of an anti-Protein A antibody. For example, the present disclosure includes recombinant expression vectors comprising any of the nucleic acid molecules mentioned above, i.e., nucleic acid molecules encoding any of the HCVR, LCVR, and/or CDR sequences as set forth in Table 3A. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

Anti-Protein A antibodies suitable for ADCs of the present disclosure may have a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277: 26733). In other applications, modification of galactosylation can be made in order to modify complement dependent cytotoxicity (CDC).

The monoclonal antibodies and antigen-binding fragments thereof that specifically bind a Protein A as provided herein may have attenuated Fc binding to Protein A (and/or SpsQ or other homologous protein). In the present disclosure this is noted as "*/*" or "**", and refers to antibodies, or antigen-binding fragments thereof, comprising H435R and Y436F mutations in the hIgG1 Fc according to EU index numbering. The H435R and Y436F mutations are equivalent to H318R and Y319F of SEQ ID NO: 648, an hIgG1 heavy chain. While the */* mutation position refers to H435R and Y436F according to EU numbering, the */* mutation can be found at different positions in the actual heavy chain for a given antibody (or antigen-binding fragment thereof) depending on the variable domain sequence lengths.

In addition to the */* variants described above, certain additional Fc variants are contemplated herein. According to certain embodiments, speciated antibodies to Protein A will be modified in the Fc region of the antibody to attenuate binding by Protein A or homologous protein appropriate for the respective animal species.

According to certain embodiments, antibodies to Protein A suitable for ADCs of the present disclosure comprise an Fc domain comprising one or more mutations which enhance or diminish antibody binding to the FcRn receptor, e.g., at acidic pH as compared to neutral pH. For example, the present invention includes antibodies to Protein A comprising a mutation in the $CH_2$ or a $CH_3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., H/F or Y); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P).

For example, antibodies to Protein A comprise an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); and 433K and 434F (e.g., H433K and N434F). All possible combinations of the foregoing Fc domain mutations, and other mutations within the antibody variable domains disclosed herein, are contemplated within the scope of the present disclosure.

The antibodies to Protein A suitable for ADCs of the present disclosure may comprise a modified Fc domain having altered effector function, for example, increased or reduced effector function. As used herein, a "modified Fc domain having altered effector function" means any Fc portion of an immunoglobulin that has been modified, mutated, truncated, etc., relative to a wild-type, naturally occurring Fc domain such that a molecule comprising the modified Fc exhibits an increase or reduction in the severity or extent of at least one effect selected from the group consisting of cell killing (e.g., ADCC and/or CDC), complement activation, phagocytosis and opsonization, relative to a comparator molecule comprising the wild-type, naturally occurring version of the Fc portion. In certain embodiments, a "modified Fc domain having altered effector function" is an Fc domain with reduced or attenuated binding to an Fc receptor (e.g., FcγR). Exemplary modified Fc domains are described in US 2006/0024298, incorporated by reference herein in its entirety. In some embodiments, the modification is G236A.

In certain embodiments, the modified Fc domain is a variant IgG1 Fc or a variant IgG4 Fc comprising a substitution in the hinge region. For example, a modified Fc for use in the context of the present invention may comprise a variant IgG1 Fc wherein at least one amino acid of the IgG1 Fc hinge region is replaced with the corresponding amino acid from the IgG2 Fc hinge region. Alternatively, a modified Fc for use in the context of the present invention may comprise a variant IgG4 Fc wherein at least one amino acid of the IgG4 Fc hinge region is replaced with the corresponding amino acid from the IgG2 Fc hinge region. Non-limiting, exemplary modified Fc regions that can be used in the context of the present invention are set forth in US Patent Application Publication No. 2014/0243504, the disclosure of which is hereby incorporated by reference in its entirety, as well as any functionally equivalent variants of the modified Fc regions set forth therein.

Other modified Fc domains and Fc modifications that can be used in the context of the present invention include any of the modifications as set forth in US 2014/0171623; U.S. Pat. No. 8,697,396; US 2014/0134162; WO 2014/043361, the disclosures of which are hereby incorporated by reference in their entireties. Methods of constructing antibodies or other antigen-binding fusion proteins comprising a modified Fc domain as described herein are known in the art.

Antibody-Drug Conjugates (ADCs)

Provided herein are antibody-drug conjugates (ADCs) comprising an antibody or antigen-binding fragment thereof conjugated to a drug or a therapeutic agent. In some embodiments, the therapeutic agent may be a rifamycin analog. Also provided herein are reactive linker-payloads for example, the compounds having a structure according to any embodiment of formulas (A), (B), (I), (I'), (II), (II'), (III), (III'), (IV), (IV'), (V), (V') as provided herein, useful for making the ADCs. Further provided herein are modified antibodies and modified antigen-binding fragments useful for making the ADCs.

In some embodiments, the antibodies, or antigen-binding fragments of antibodies, suitable for making ADCs of the present disclosure, bind to an infectious disease-related target. In some embodiments, the antibodies, or antigen-binding fragments of antibodies bind to MSR1. In some embodiments, the antibodies, or antigen-binding fragments of antibodies bind to WTA. In some embodiments, the antibodies, or antigen-binding fragments of antibodies bind to Protein A.

The ADCs generally have the Formula (XV): BA-[L-PA]$_n$. In the formula, BA is a binding agent, for instance, an antibody, or an antigen-binding fragment thereof. L is a linker, described in detail below. PA is a payload, for instance a rifamycin analog, as described in detail herein. In the formula, n is an integer from 1 to 30, for instance from 1 to 4, e.g., 2 or 4. Each L-PA is covalently bonded to a functional group of PA. In particular embodiments, each L-PA is covalently bonded to a lysine side chain, a cysteine side chain, a glutamine side chain, or an amino terminus of BA.

In some embodiments, L-PA is covalently bonded to a side chain of the binding agent BA, for instance, an antibody, or an antigen-binding fragment thereof, via a reactive group, or RG. Following conjugation to the binding agent, the reactive group becomes part of the linker L of the ADC having the formula (XV): BA-[L-PA]$_n$. Illustrative reactive groups RG useful for the present disclosure include, but are not limited to, those that comprise maleimides, succinimides, N-hydroxy succinimides (NHS), terminal primary amines, haloacetyl groups, isothiocyanates, thiols, alcohols, ketones, aldehydes, acids, esters, hydrozides, and anilines. RG also include moieties having the following structure:

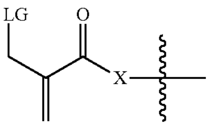
or
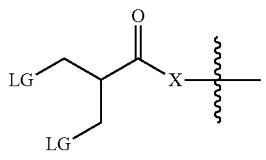
, wherein X is —O— or —NH— and LG is a leaving group, e.g., Br.

In some embodiments, the reactive linker is

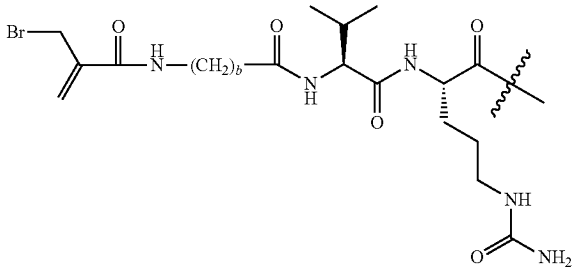

wherein b is an integer from 2 to 8.

In some embodiments, the reactive linker is

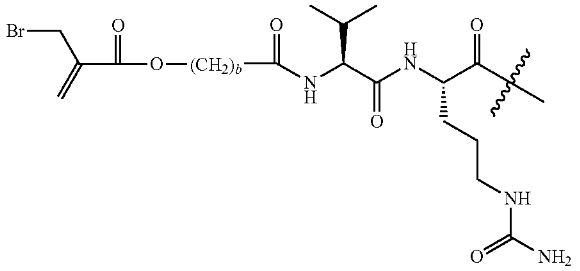

wherein b is an integer from 2 to 8.

In some embodiments, the reactive linker is

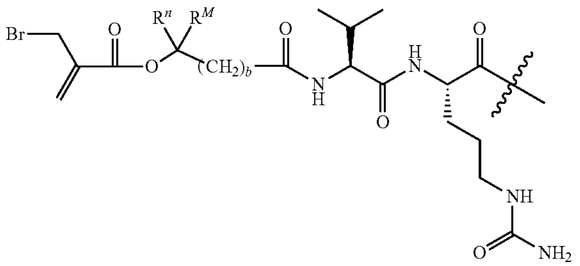

wherein b is an integer from 2 to 8, $R^N$ is a hydrogen atom or an alkyl group, and $R^M$ is an alkyl group.

In some embodiments, the reactive linker is

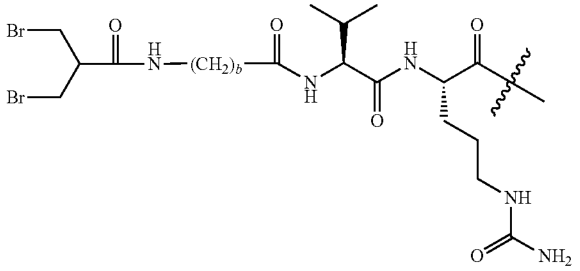

wherein b is an integer from 2 to 8.

In some embodiments, the reactive linker is

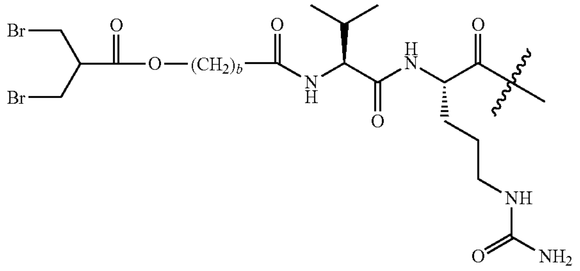

wherein b is an integer from 2 to 8.

In some embodiments, the reactive linker is

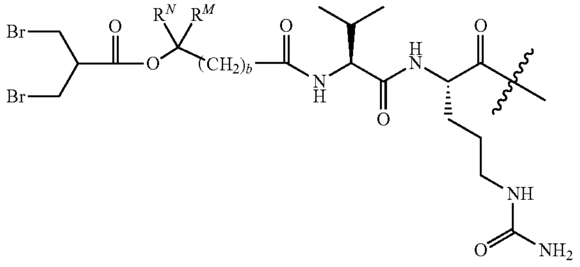

wherein b is an integer from 2 to 8, $R^N$ is a hydrogen atom or an alkyl group, and $R^M$ is an alkyl group.

Techniques and linkers for conjugating to residues of an antibody or antigen binding fragment are known in the art. Exemplary amino acid attachments that can be used in the context of this aspect, e.g., lysine (see, e.g., U.S. Pat. No. 5,208,020; US 2010/0129314; Hollander et al., *Bioconjugate Chem.,* 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Nat. Acad. Sci., USA,* 2008, 105:12451-12456), formyl glycine (see, e.g., Carrico et al., *Nat. Chem. Biol.,* 2007, 3:321-322; Agarwal et al., *Proc. Nat. Acad. Sci., USA,* 2013, 110:46-51, and Rabuka et al., *Nat. Protocols,* 2012, 10:1052-1067), non-natural amino acids (see, e.g., WO 2013/068874, and WO 2012/166559), and acidic amino acids (see, e.g., WO 2012/05982). Lysine conjugation can also proceed through NHS (N-hydroxy succinimide). Linkers can also be conjugated to cysteine residues, including cysteine residues of a cleaved interchain disulfide bond, by forming a carbon bridge between thiols (see, e.g., U.S. Pat. Nos. 9,951,141, and 9,950,076). Linkers can also be conjugated to an antigen-binding protein via attachment to carbohydrates (see, e.g., US 2008/0305497, WO 2014/065661, and Ryan et al., *Food & Agriculture Immunol.,* 2001, 13:127-130) and disulfide linkers (see, e.g., WO 2013/085925, WO 2010/010324, WO 2011/018611, and Shaunak et al., *Nat. Chem. Biol.,* 2006, 2:312-313). Site specific conjugation techniques can also be employed to direct conjugation to particular residues of the antibody or antigen binding protein (see, e.g., Schumacher et al. *J Clin Immunol* (2016) 36(Suppl 1): 100). Site specific conjugation techniques, include, but are not limited to glutamine conjugation via transglutaminase (see e.g., Schibli, Angew Chemie Inter Ed. 2010, 49,9995).

Linkers can be conjugated to one or more glutamine residues via transglutaminase-based chemo-enzymatic conjugation (see, e.g., Dennler et al., *Bioconjugate Chem.* 2014, 25, 569-578, and WO 2017/147542). For example, in the presence of transglutaminase, one or more glutamine residues of an antibody can be coupled to a primary amine compound. Briefly, in some embodiments, an antibody having a glutamine residue (e.g., a Gln295 residue) is treated with a primary amine compound, described in more detail below, in the presence of the enzyme transglutaminase. Primary amine compounds include payloads or linker-payloads, which directly provide antibody drug conjugates via transglutaminase-mediated coupling. Primary amine compounds also include linkers and spacers that are functionalized with reactive groups that can be subsequently reacted with further compounds towards the synthesis of antibody drug conjugates. Antibodies comprising glutamine residues can be isolated from natural sources or engineered to comprise one or more glutamine residues. Techniques for engineering glutamine residues into an antibody polypeptide chain (glutaminyl-modified antibodies or antigen binding molecules) are within the skill of the practitioners in the art. In certain embodiments, the antibody is aglycosylated.

In certain embodiments, the antibody or a glutaminyl-modified antibody or antigen binding molecule may comprise at least one glutamine residue in at least one polypeptide chain sequence. In certain embodiments, the antibody or a glutaminyl-modified antibody or antigen binding molecule may comprise two heavy chain polypeptides, each with one Gln295 residue. In further embodiments, the antibody or a glutaminyl-modified antibody or antigen binding molecule may comprise one or more glutamine residues at a site other than a heavy chain 295. In some embodiments, an antibody can be prepared by site-directed mutagenesis to insert a glutamine residue at a site without resulting in disabled antibody function or binding. For example, included herein are antibodies bearing Asn297Gln (N297Q) mutation(s) as described herein. In some embodiments, an antibody having a Gln295 residue and/or an N297Q mutation contains one or more additional naturally occurring glutamine residues in their variable regions, which can be accessible to transglutaminase and therefore capable of conjugation to a linker or a linker-payload. An exemplary naturally occurring glutamine residue can be found, e.g., at Q55 of the light chain. In such instances, the antibody conjugated via transglutaminase can have a higher than expected DAR value (e.g., a DAR higher than 4). Any such antibodies can be isolated from natural or artificial sources.

In various embodiments, the antibodies, or antigen-binding fragments thereof, suitable for ADCs of the present disclosure, may comprise one or more site-specific cysteine mutations for conjugation. In one embodiment, the antibody, or antigen-binding fragment thereof, comprises a light chain mutation at position 103 (Cys103Ser or C103S). In one embodiment, the antibody, or antigen-binding fragment thereof, is conjugated to a compound of the present disclosure at light chain position 103.

As a non-limiting example, the anti-Protein A antibody, or antigen-binding fragment thereof, may comprise one or more site-specific cysteine mutations for conjugation. In one embodiment, the anti-Protein A antibody, or antigen-binding fragment thereof, comprises a light chain mutation at position 103 (C103S). In one embodiment, the anti-Protein A antibody, or antigen-binding fragment thereof, is conjugated to a compound of the present disclosure at light chain position 103.

The primary amine compound useful for the transglutaminase mediated coupling of an antibody (or antigen binding compound) comprising a glutamine can be any primary amine compound deemed useful by the practitioner of ordinary skill. Generally, the primary amine compound has the formula $H_2N$—R, wherein R can be any group compatible with the antibody and reaction conditions. In certain embodiments, R is alkyl, substituted alkyl, heteroalkyl, or substituted heteroalkyl.

In some embodiments, the primary amine compound may comprise a reactive group or protected reactive group. Useful reactive groups include azides, alkynes, cycloalkynes, thiols, alcohols, ketones, aldehydes, acids, esters, hydrozides, analines, and amines. In certain embodiments, the reactive group is selected from the group consisting of azide, alkyne, sulfhydryl, cycloalkyne, aldehyde, and carboxyl.

In certain embodiments, the primary amine compound is according to the formula $H_2N$-LL-X, wherein LL is a divalent spacer and X is a reactive group or protected reactive group. In particular embodiments, LL is a divalent polyethylene glycol (PEG) group. In certain embodiments, X is selected from the group consisting of —SH, —$N_3$, alkyne, aldehyde, and tetrazole. In particular embodiments, X is —$N_3$.

In certain embodiments, the primary amine compound is according to one of the following formulas:

$H_2N$—$(CH_2)_n$—X;

$H_2N$—$(CH_2CH_2O)_n$—$(CH_2)_p$—X;

$H_2N$—$(CH_2)_n$—N(H)C(O)—$(CH_2)_m$—X;

$H_2N$—$(CH_2CH_2O)_n$—N(H)C(O)—$(CH_2CH_2O)_m$—$(CH_2)_p$—X;

$H_2N$—$(CH_2)_n$—C(O)N(H)—$(CH_2)_m$—X;

$H_2N$—$(CH_2CH_2O)_n$—C(O)N(H)—$(CH_2CH_2O)_m$—$(CH_2)_p$—X;

$H_2N$—$(CH_2)_n$—N(H)C(O)—$(CH_2CH_2O)_m$—$(CH_2)_p$—X;

$H_2N$—$(CH_2CH_2O)_n$—N(H)C(O)—$(CH_2)_m$—X;

$H_2N$—$(CH_2)_n$—C(O)N(H)—$(CH_2CH_2O)_m$—$(CH_2)_p$—X; and $H_2N$—$(CH_2CH_2O)_n$—C(O)N(H)—$(CH_2)_m$—X;

wherein n is an integer selected from 1 to 12; m is an integer selected from 0 to 12; p is an integer selected from 0 to 2; and X is selected from the group consisting of —SH, —$N_3$, —C≡CH, —C(O)H, tetrazole, and any of

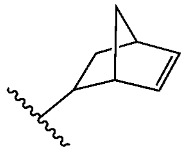

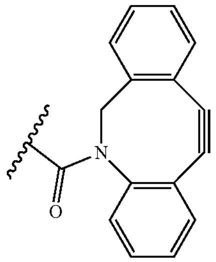

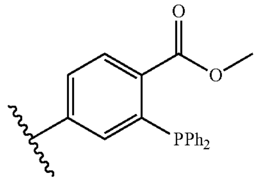

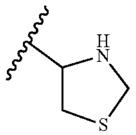

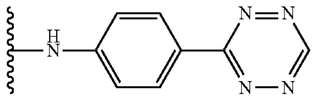

.

In the above, any of the alkyl or alkylene (i.e., —$CH_2$—) groups can optionally be substituted, for example with $C_{1-8}$ alkyl, methylformyl, or —$SO_3H$. In certain embodiments, the alkyl groups are unsubstituted.

In certain embodiments, the primary amine compound is selected from the group consisting of:

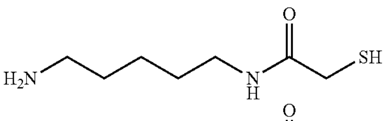

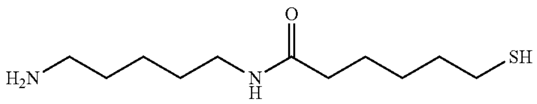

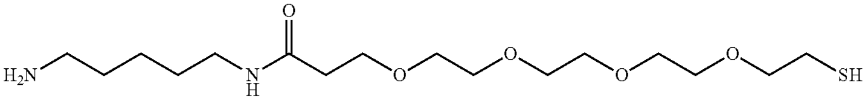

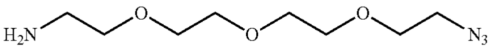

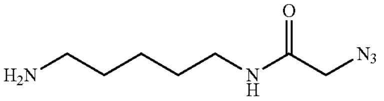

and

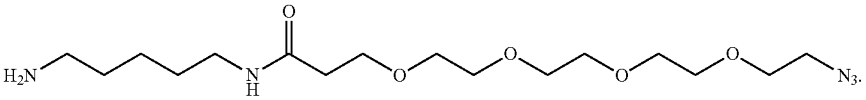

.

In particular embodiments, the primary amine compound is

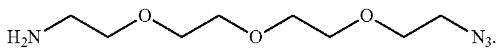

.

Accordingly, provided herein are modified antibodies, and antigen-binding fragments thereof, linked to one or more primary amine compounds. In particular embodiments, provided herein are modified antibodies, and antigen-binding fragments thereof, according to the formula:

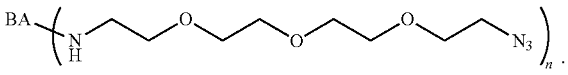

In the formula, BA is an antibody, or an antigen binding fragment thereof. The variable n is an integer from 1 to 30. In certain embodiments, n is from 1 to the number of glutamine residues in BA. In certain embodiments, n is from 1 to 4. In certain embodiments, n is 1, 2, 3, or 4. In some embodiments, n is 2. In some embodiments, n is 4. The modified antibodies, and antigen-binding fragments thereof, are useful, for example, for linking to one or more L-PA molecules to form an ADC.

In certain embodiments, BA may comprise two or four glutamine residues. In certain embodiments, BA may comprise a Q295 residue. In certain embodiments, BA may comprise an N297Q mutation. In certain embodiments, BA may comprise Q295 and N297Q. In such embodiments, because BA can be dimeric, BA has four glutamine residues for conjugation to L-PA moieties.

In the Formula (XV) BA-$[L\text{-}PA]_n$, PA can be any payload deemed useful. In certain embodiments, PA is a rifamycin analog according to the disclosure.

In some embodiments of Formula (XV), L is $-L^1-L^2-(L^3)_{0-1}-$ and $L^2$ may comprise

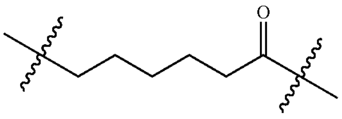, 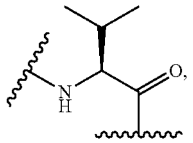 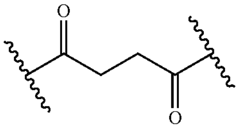,

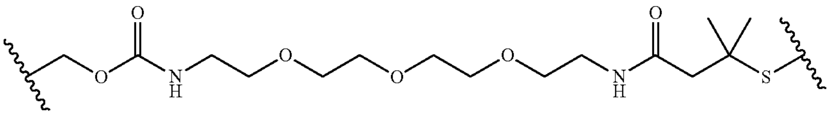, 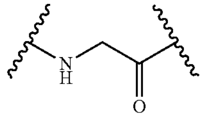,

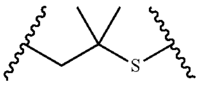, 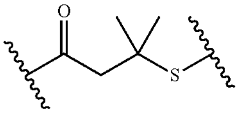, 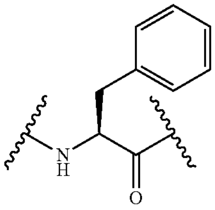, 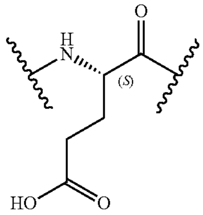,

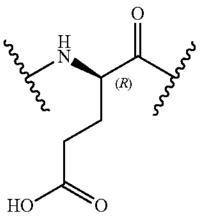, 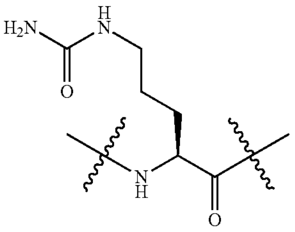, 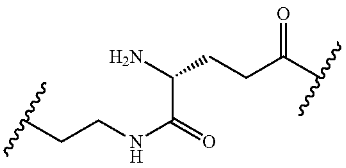,

——C(O)$CH_2CH_2$C(O)NH——, 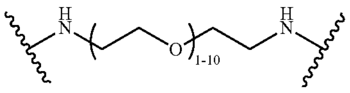, 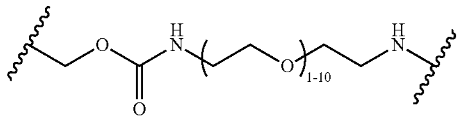,

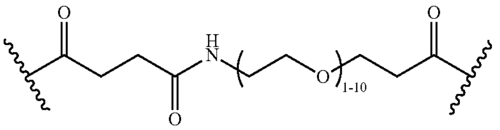, 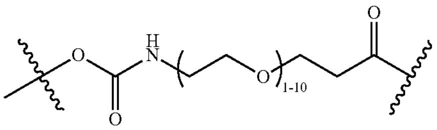,

—$OCH_2C(O)$—, or cyclodextrin residue (CD); or combinations thereof. In some embodiments, L is $-L^1-L^2-(L^3)_{0-1}-$ and $L^2$ may comprise
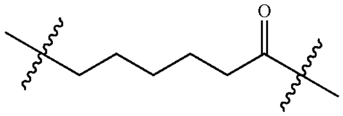
,
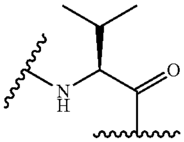
,
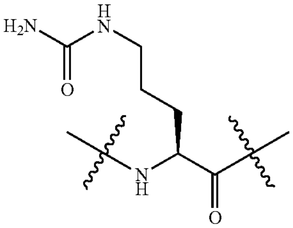
,
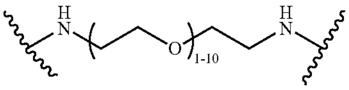
,
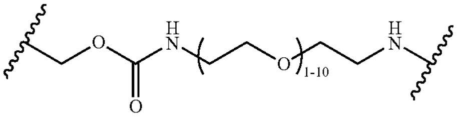
,
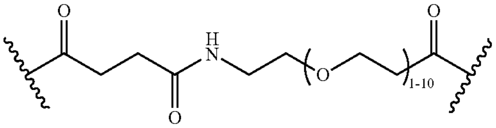
,
or CD, or combinations thereof. In some embodiments, L is $-L^1-L^2-(L^3)_{0-1}-$ and $L^2$ may comprise CD wherein CD is selected from the group consisting of
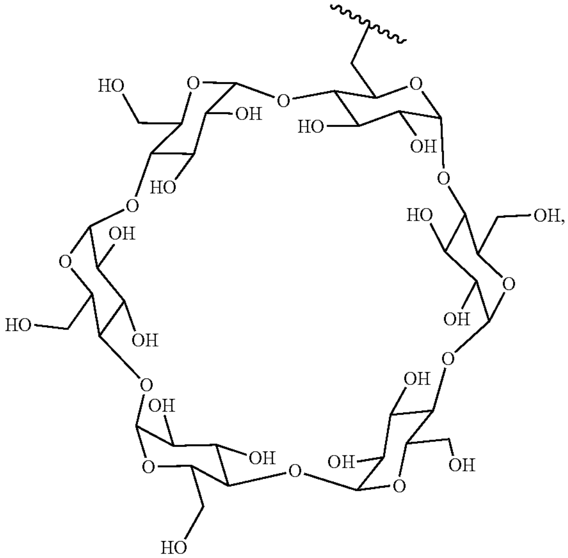
-continued
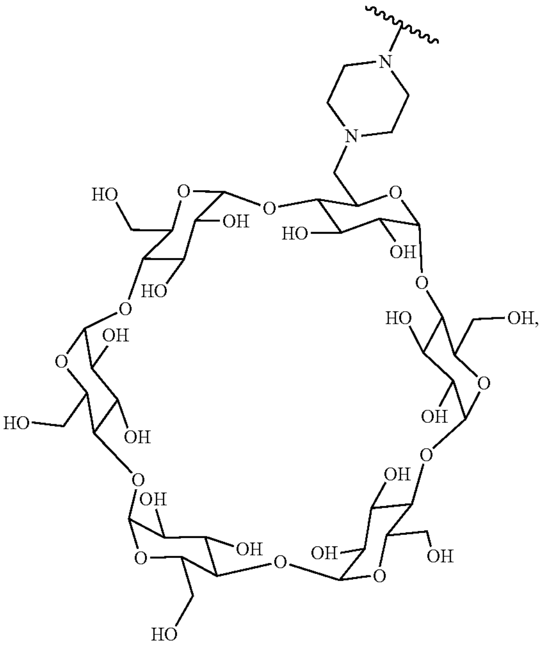
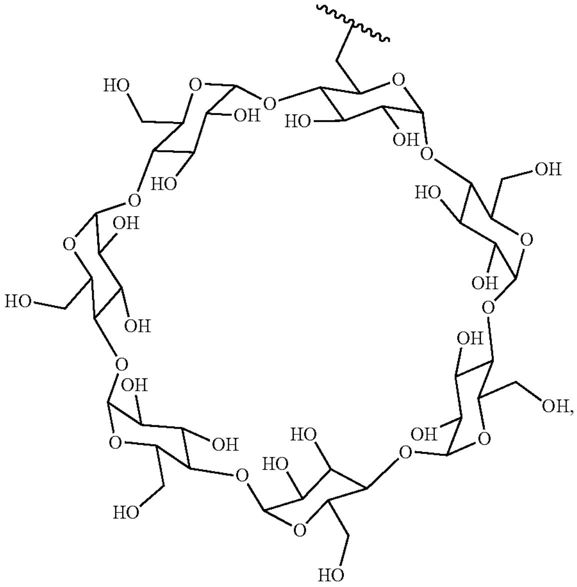

-continued
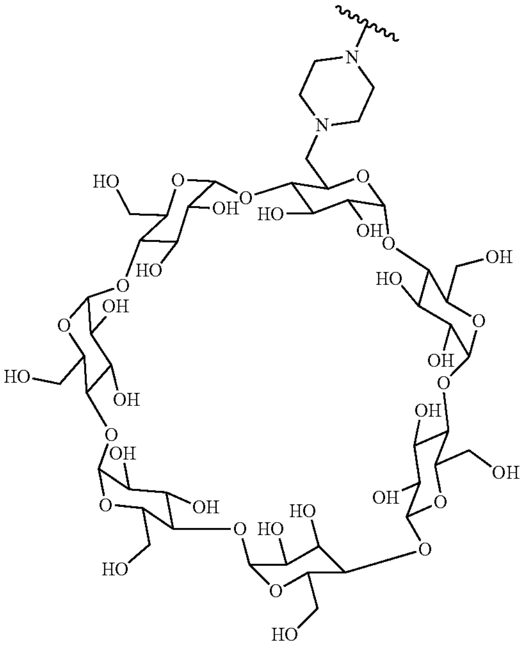
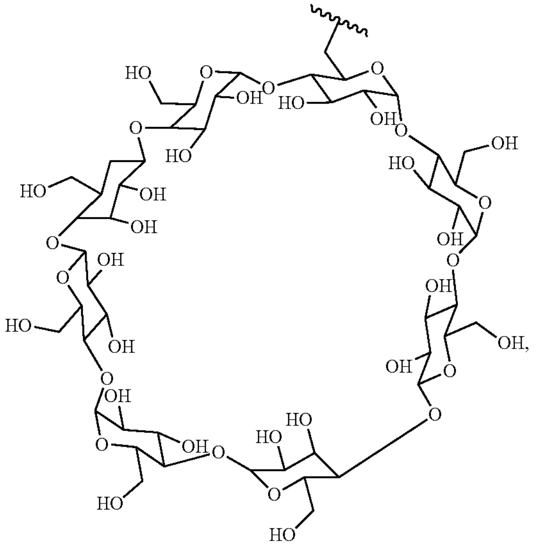
, and
-continued
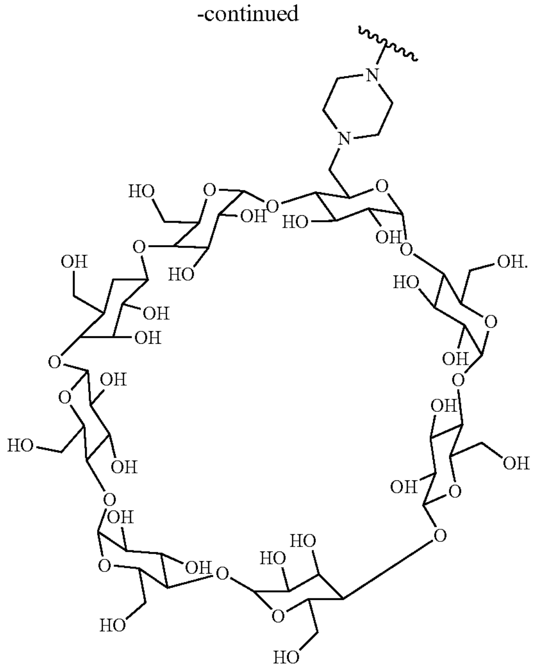
In some embodiments of Formula (XV), L is $-L^1-L^2-(L^3)_{0-1}-$ and $L^2$ may comprise
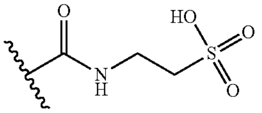
or
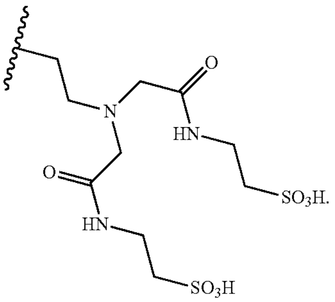
In some embodiments, L is $-L^1-L^2-(L^3)_{0-1}-$ and $-L^1$ may comprise $L^1$ is selected from
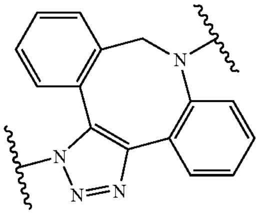 [SMILES: *N1Cc2ccccc2-c2c(nnn2*)-c2ccccc21]
or a regioisomer or mixture of isomers thereof;

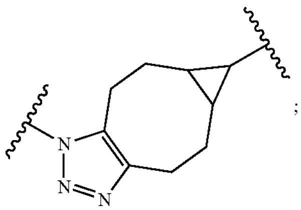
;
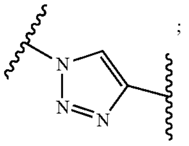
;
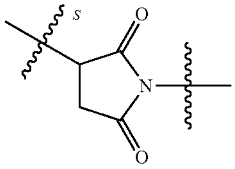
or a stereoisomer or mixture of stereoisomers thereof, wherein S refers to the S atom on a cysteine residue through which the reactive group residue is attached to BA; and
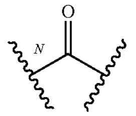
wherein N refers to the N atom on a lysine residue through which the reactive group residue is attached to BA.
In some embodiments, L is $-L^1-L^2-(L^3)_{0-1}-$ and $-L^2-(L^3)_{0-1}-$ may comprise
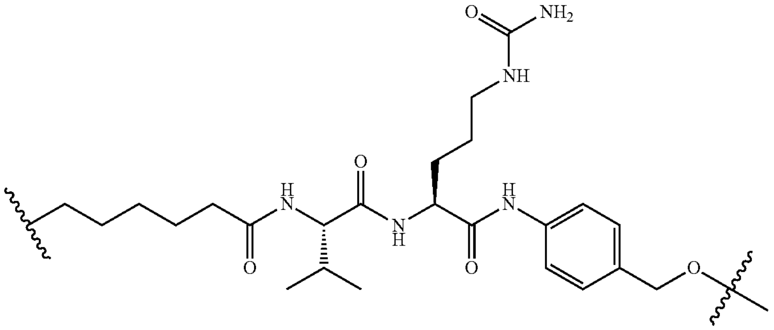
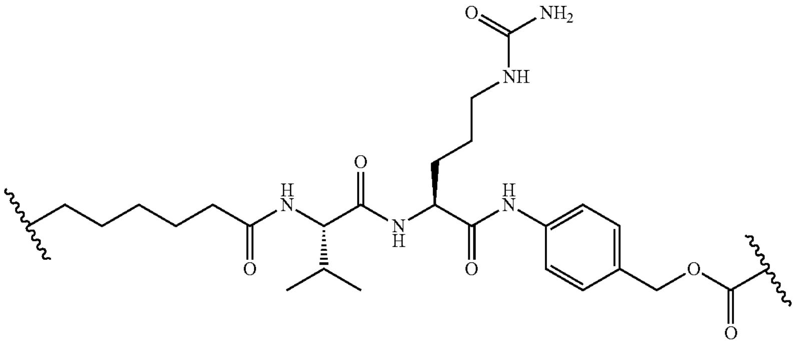
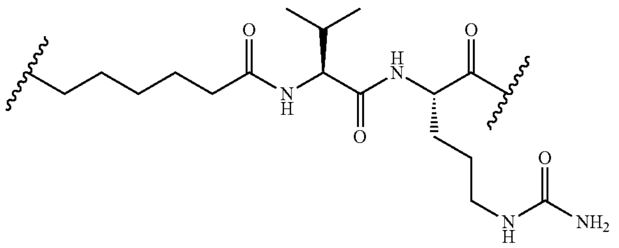
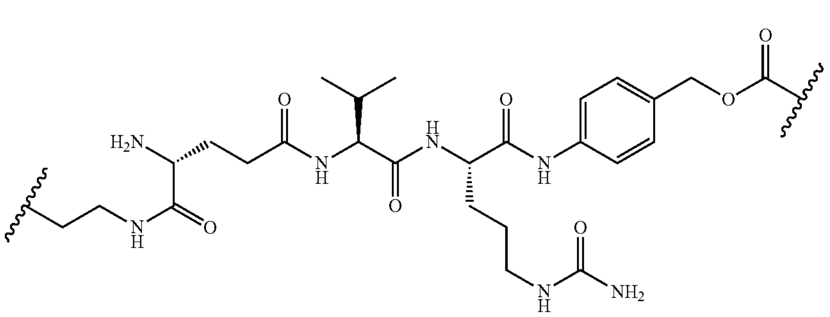

-continued
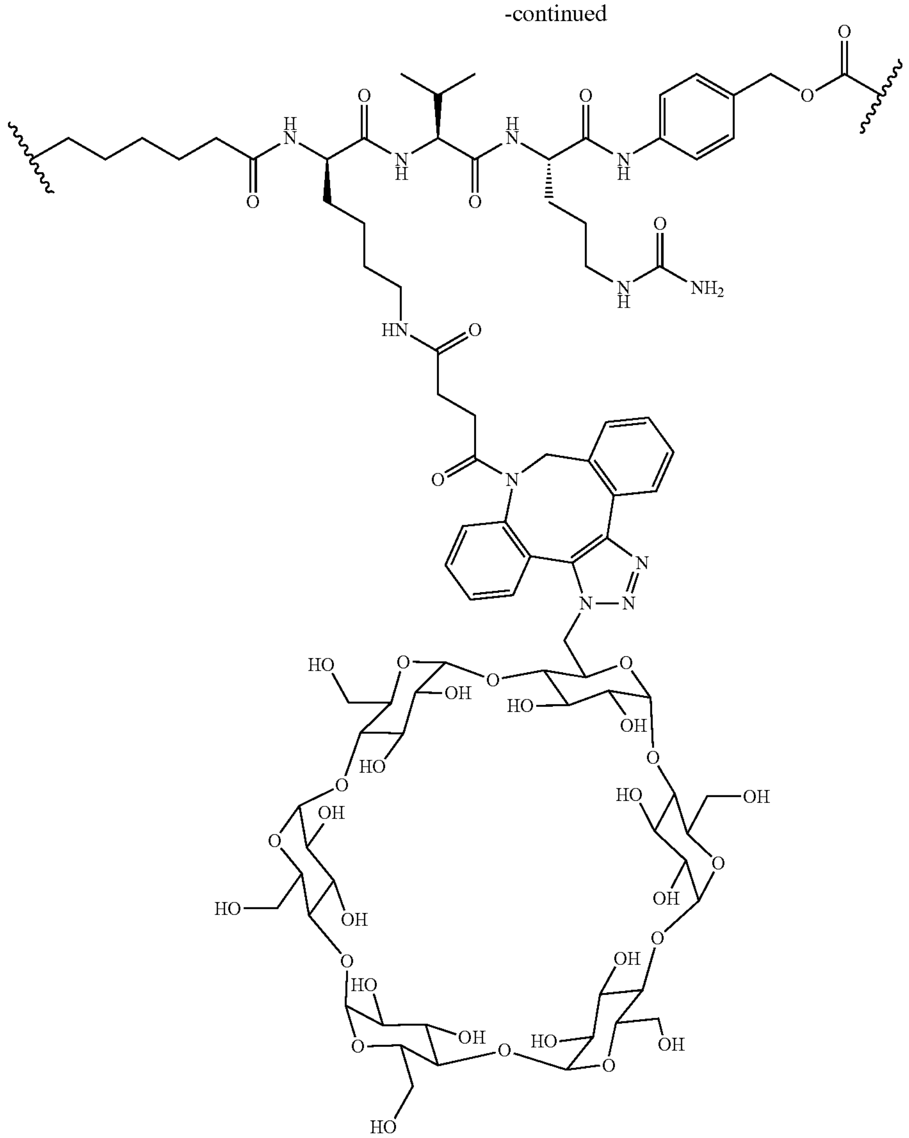
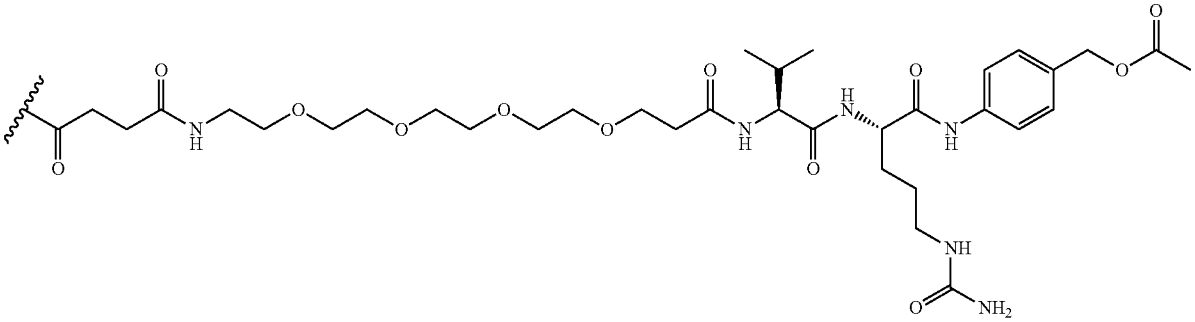
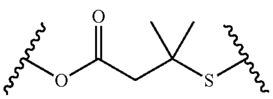 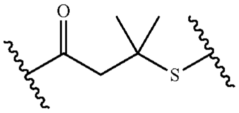 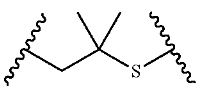
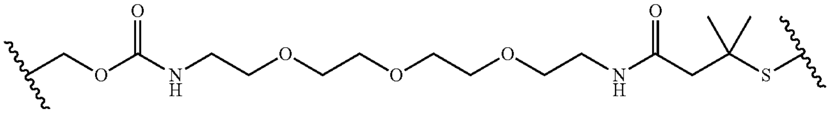

-continued
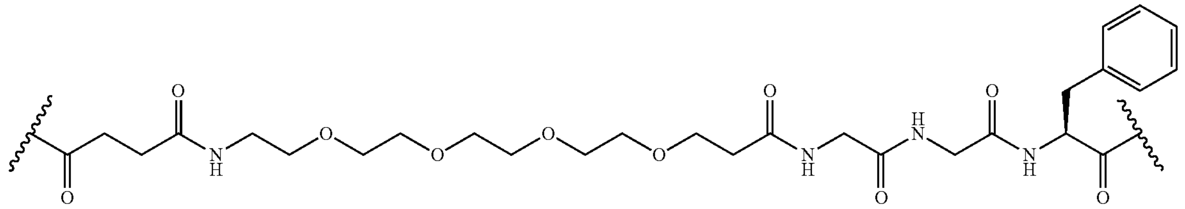
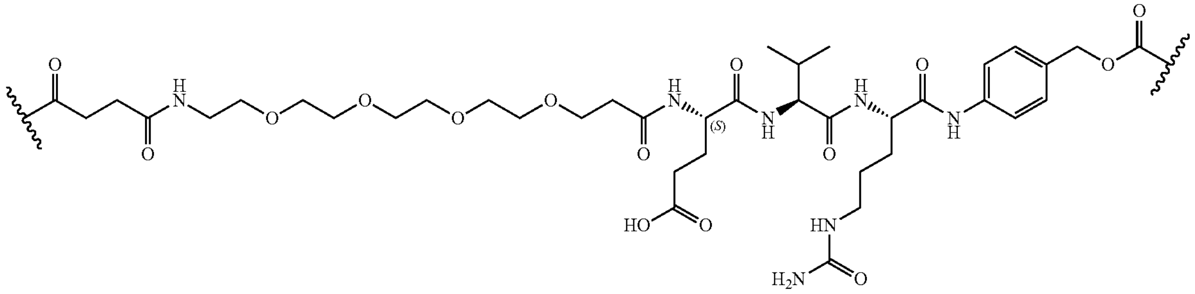
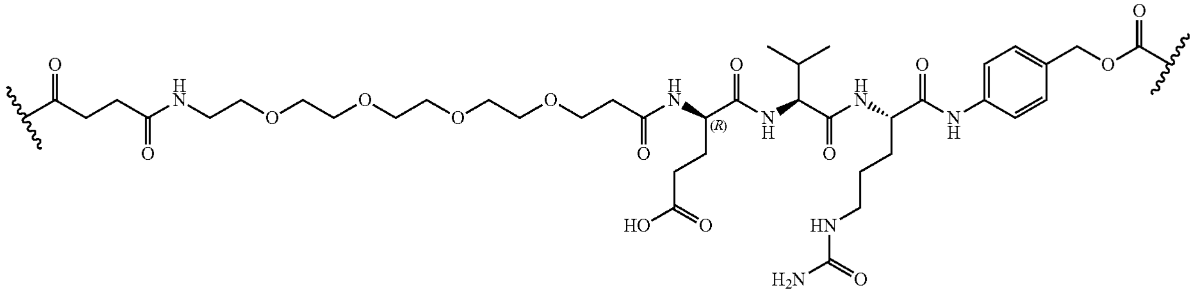
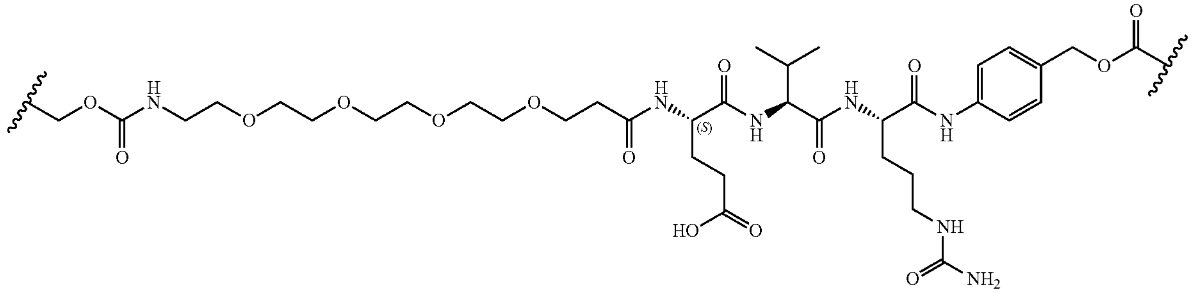
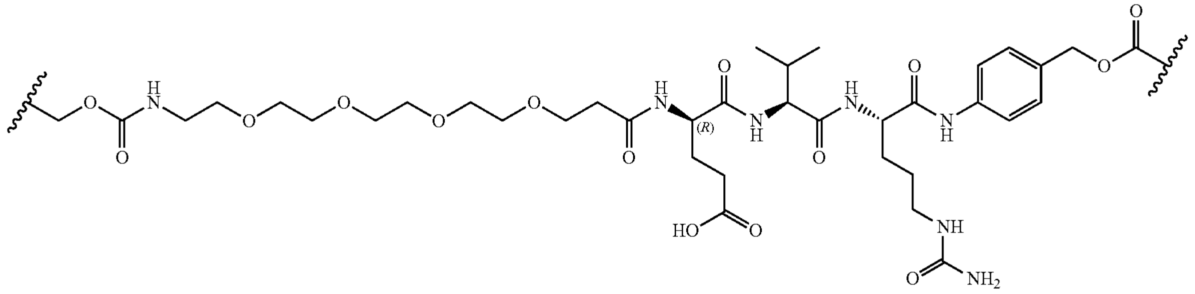
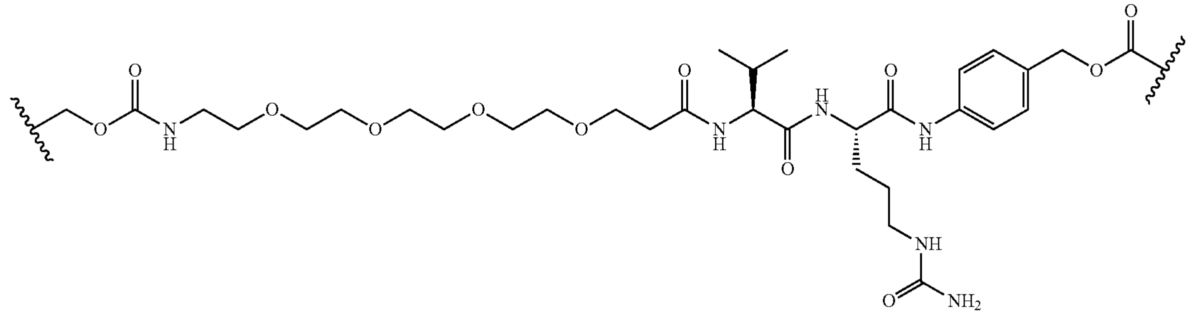

-continued
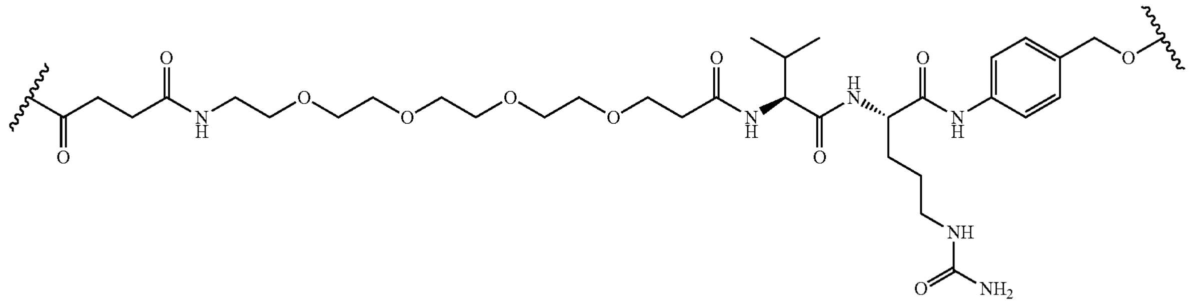
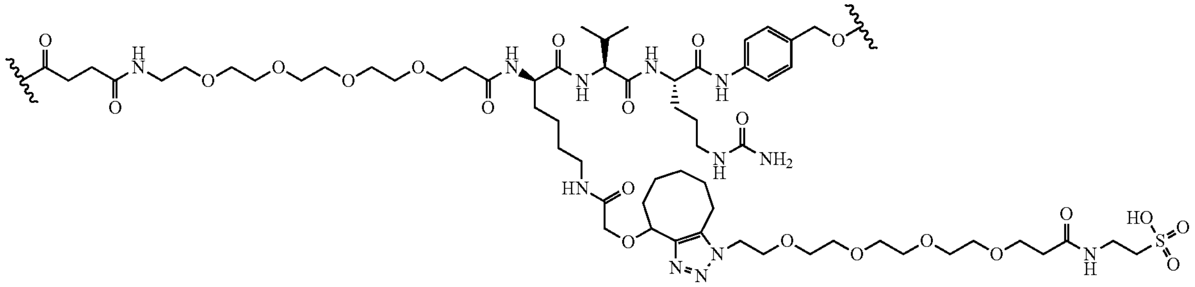
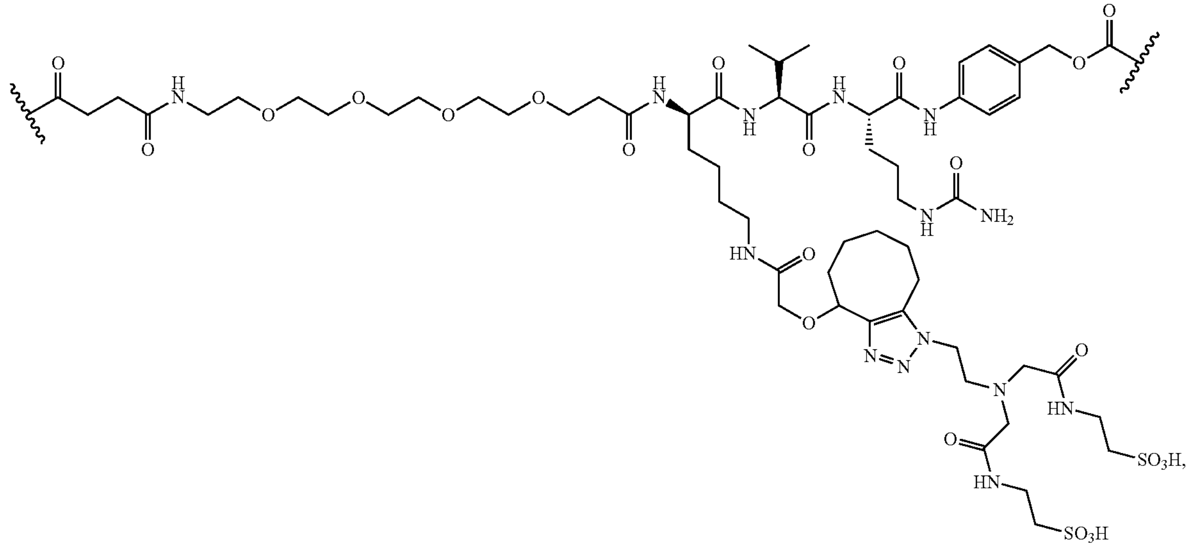
,
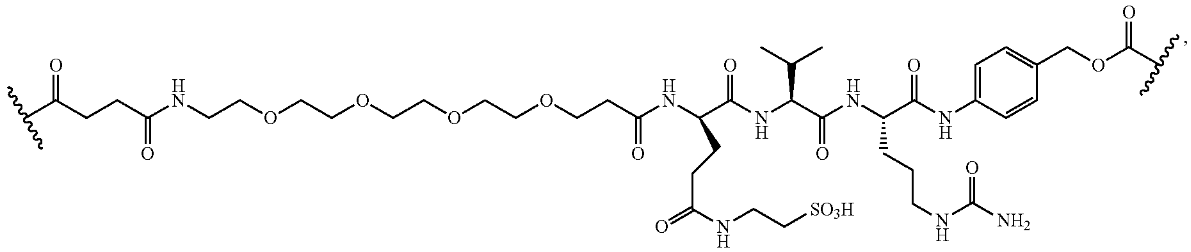
,
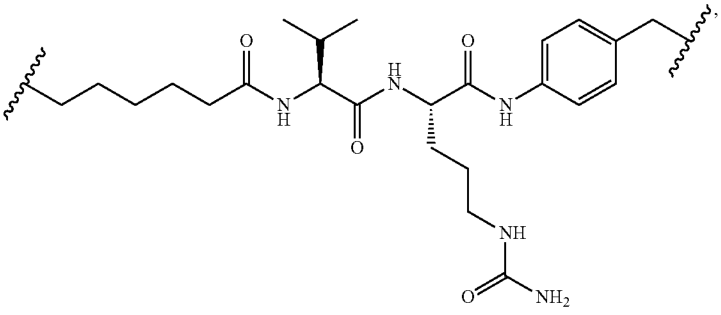
,

-continued

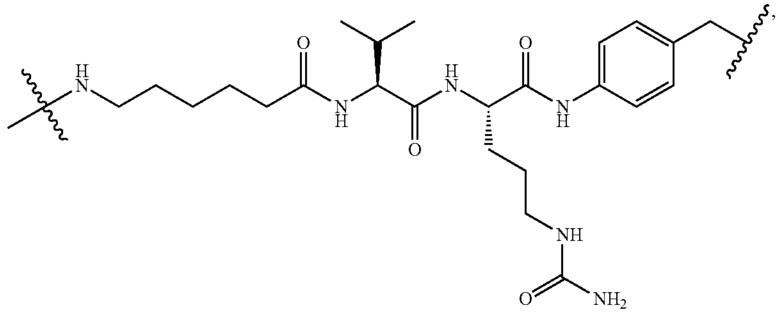

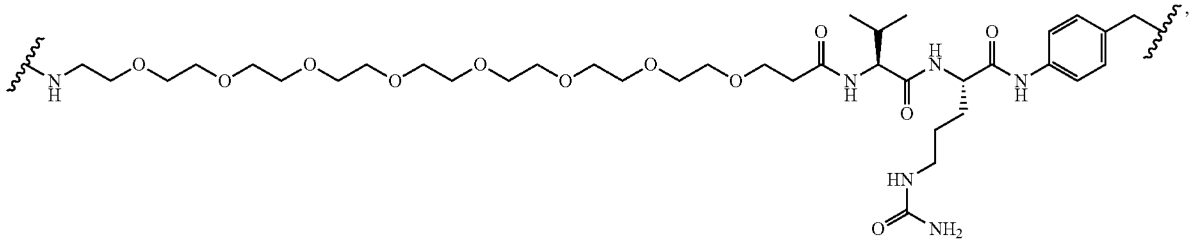

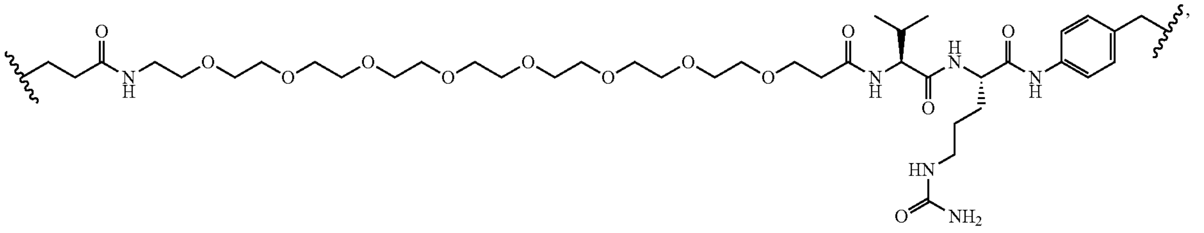

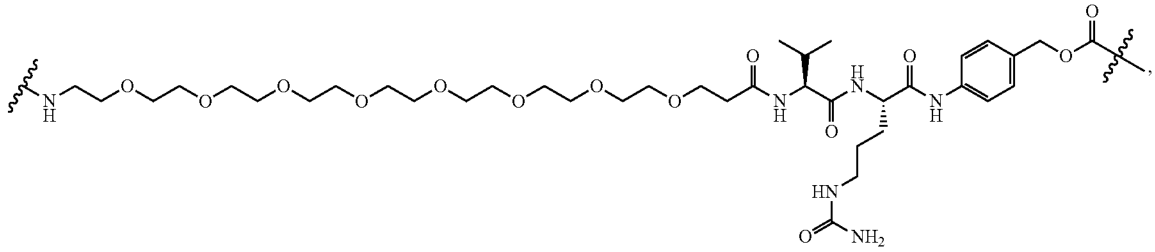

or

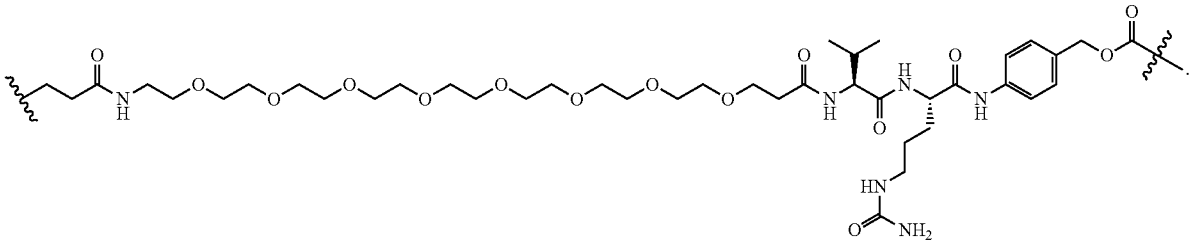

In the Formula (XV), BA-[L-PA]$_n$, PA may be linked to BA with any linker L deemed suitable. Linkers are any group or moiety that links, connects, or bonds the antibody or antigen-binding proteins described herein with a therapeutic moiety, e.g. a rifamycin analog. Suitable linkers may be found, for example, in *Antibody Drug Conjugates and Immunotoxins*; Phillips, G. L., Ed.; Springer Verlag: New York, 2013; *Antibody-Drug Conjugates*; Ducry, L., Ed.; Humana Press, 2013; *Antibody-Drug Conjugates*; Wang, J., Shen, W.-C., and Zaro, J. L., Eds.; Springer International Publishing, 2015, the contents of each incorporated herein in their entirety by reference. Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers include linkers that are cleaved by intracellular metabolism following internalization, e.g., cleavage via hydrolysis, reduction, or enzymatic reaction. Non-cleavable linkers include linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise peptides, glucuronides, succinimide-thioethers, polyethylene glycol (PEG) units, hydrazones, mal-caproyl units, dipeptide units, valine-citruline units, and para-aminobenzyl (PAB) units.

Any linker molecule or linker technology known in the art can be used to create or construct an ADC of the present disclosure. In certain embodiments, the linker is a cleavable linker. According to other embodiments, the linker is a non-cleavable linker. Exemplary linkers that can be used in the context of the present disclosure include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), SIAB (N-Succinimidyl (4-iodo-acetyl)aminobenzoate), and variants and combinations thereof. Additional examples of linkers that can be used in the context of the present disclosure are provided, e.g., in U.S. Pat. No. 7,754,681 and in Ducry, Bioconjugate Chem., 2010, 21:5-13, and the references cited therein, the contents of which are incorporated by reference herein in their entireties.

In certain embodiments, the linkers are stable in physiological conditions. In certain embodiments, the linkers are cleavable, for instance, able to release at least the payload portion in the presence of an enzyme or at a particular pH range or value. In some embodiments, a linker may comprise an enzyme-cleavable moiety. Illustrative enzyme-cleavable moieties include, but are not limited to, peptide bonds, ester linkages, hydrazones, and disulfide linkages. In some embodiments, the linker may comprise a cathepsin-cleavable linker.

In some embodiments, the linker may comprise a non-cleavable moiety.

Suitable linkers also include, but are not limited to, those that are chemically bonded to two cysteine residues of a single binding agent, e.g., antibody. Such linkers can serve to mimic the antibody's disulfide bonds that are disrupted as a result of the conjugation process.

In some embodiments, the linker may comprise one or more amino acids. Suitable amino acids include natural, non-natural, standard, non-standard, proteinogenic, non-proteinogenic, and L- or D-α-amino acids. In some embodiments, the linker may comprise alanine, valine, glycine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or combination thereof. In certain embodiments, one or more side chains of the amino acids is linked to a side chain group, described below. In some embodiments, the linker may comprise valine and citrulline. In some embodiments, the linker may comprise lysine, valine, and citrulline. In some embodiments, the linker may comprise lysine, valine, and alanine. In some embodiments, the linker may comprise valine and alanine.

In some embodiments, the linker may comprise a self-immolative group. The self-immolative group may be any such group known to those of skill. In particular embodiments, the self-immolative group may be p-aminobenzyl (PAB), or a derivative thereof. Useful derivatives include p-aminobenzyloxycarbonyl (PABC). Those of skill will recognize that a self-immolative group is capable of carrying out a chemical reaction which releases the remaining atoms of a linker from a payload.

In some embodiments, the linker may be:

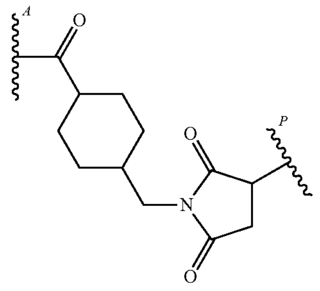

wherein

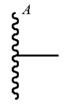

is a bond to the antibody or antigen-binding protein (e.g., via lysine residue) and

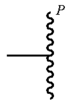

is a bond to the payload. In some embodiments, the linker may be:

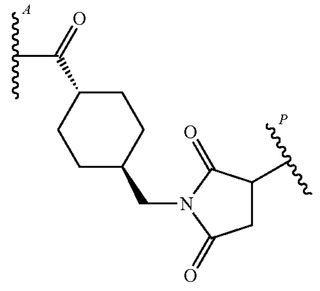

wherein

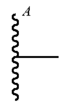

is a bond to the antibody or antigen-binding protein (e.g., via lysine residue) and
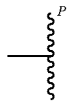
is a bond to the payload. In certain embodiments, the linker may be:
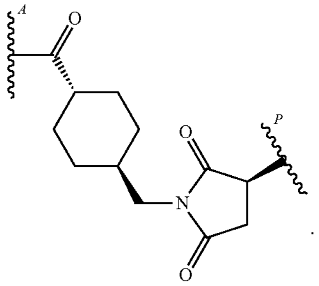
In certain embodiments, the linker may be:
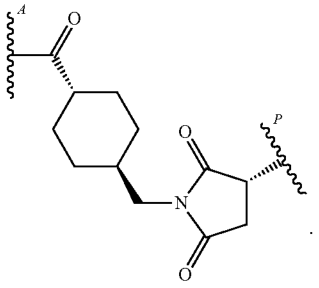
In some embodiments, the linker may be derived from maleimidylmethyl-4-trans-cyclohexanecarboxysuccinate:
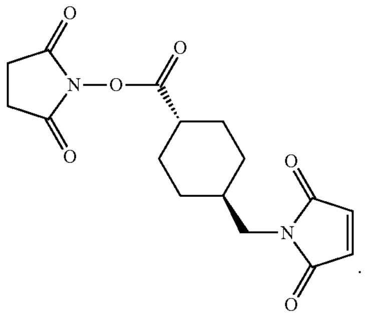 [SMILES: O=C1C=CC(=O)N1C[C@H]1CC[C@H](C(=O)ON2C(=O)CCC2=O)CC1]
In some embodiments, the linker may be:
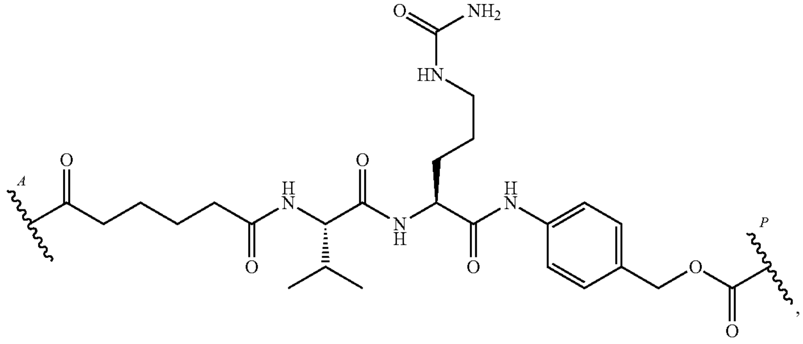
,
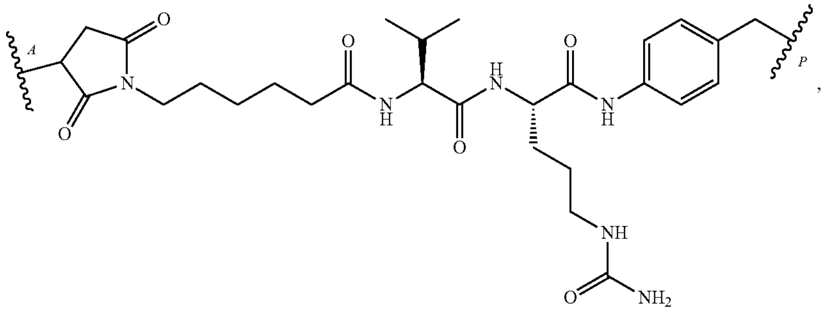
,
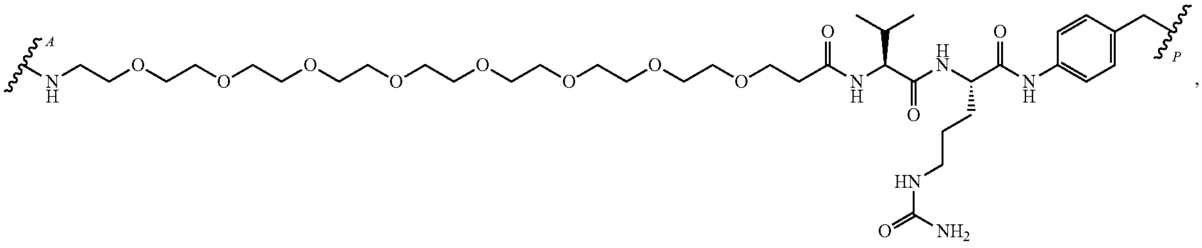
, -continued

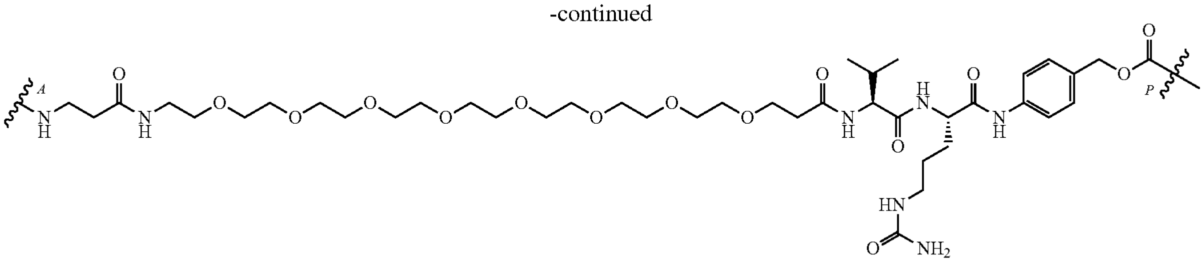

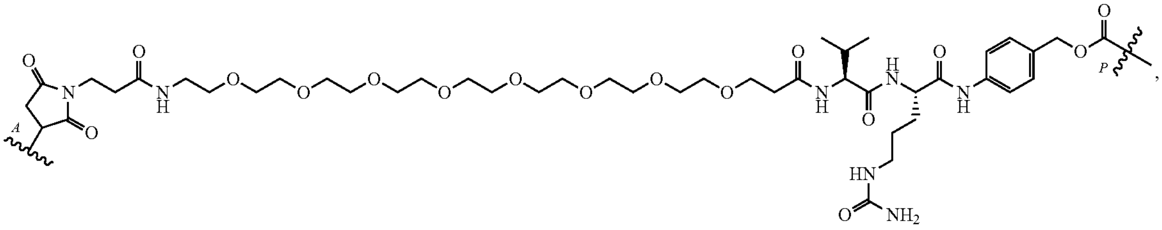

, or

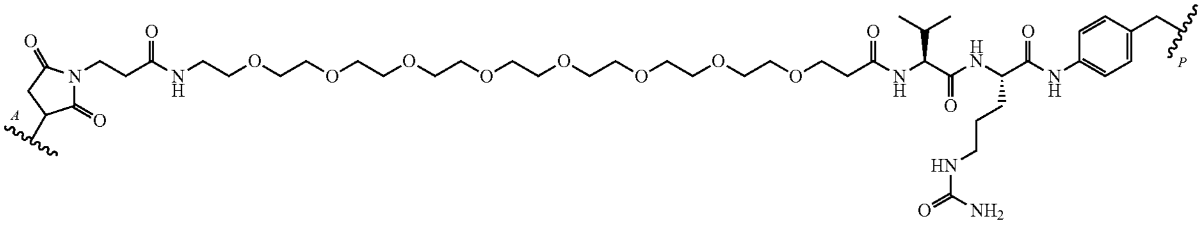

wherein

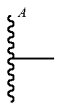

is a bond to the antibody or antigen-binding protein (e.g., via a lysine or a serine residue) and

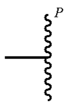

is a bond to the payload.

In some embodiments, L may be a cleavable linker. In some embodiments, L may be a non-cleavable linker. In some embodiments, L may comprise a dipeptide. In some embodiments, L may comprise a

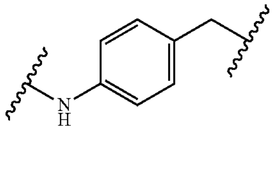 [SMILES: *Cc1ccc(N*)cc1]

moiety.

In some embodiments, L may comprise a moiety having the following structure:

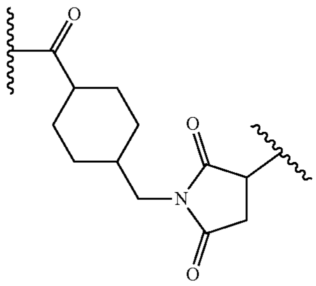

.

In some embodiments, L may comprise a moiety having the following structure:

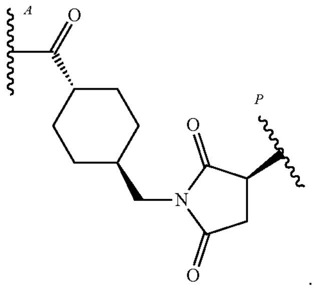

.

In some embodiments, L may comprise a moiety having the following structure:
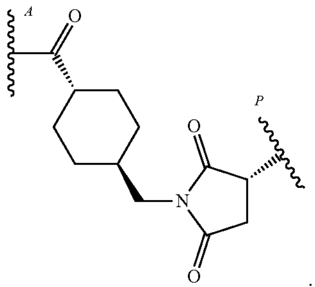
In some embodiments, L may comprise a moiety having a structure selected from:
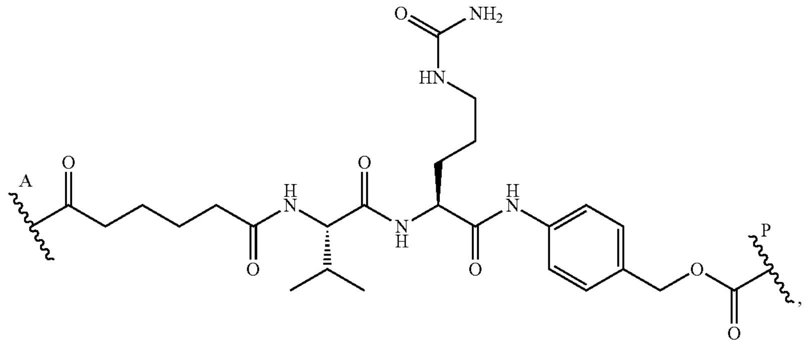
,
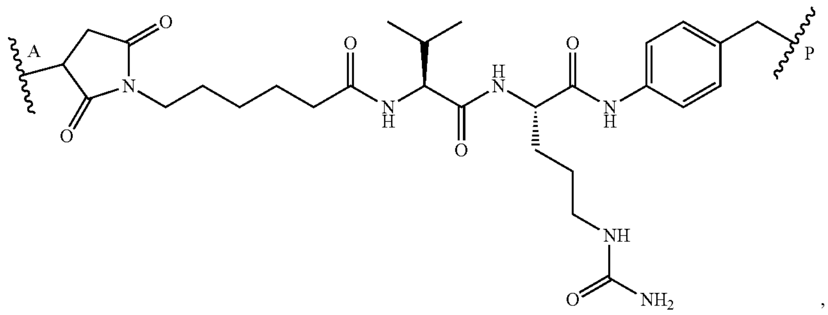
, or
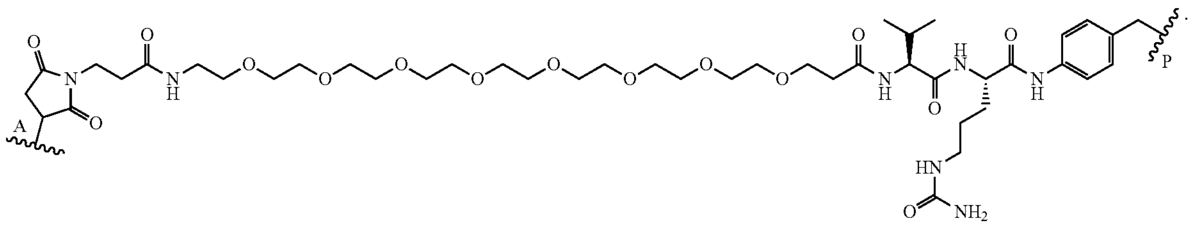
.

In certain embodiments, the linker may comprise a cyclodextrin group. In certain embodiments, the linker provides an ADC according to Formula (XVa):

(XVa)

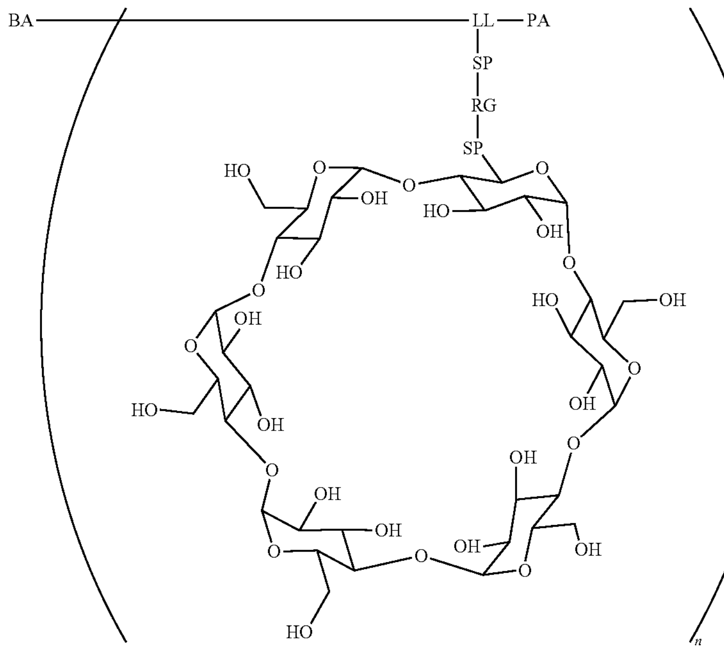

In Formula (XVa), BA is an antibody, or an antigen-binding fragment thereof, LL is a trivalent linker, RG is a reactive linker residue, SP is, independently in each instance, absent or a spacer group, subscript n is an integer from 1 to 30; and PA is a payload. In certain embodiments, n is from 1 to 4. In certain embodiments, n is 4. In certain embodiments, n is 2. In certain embodiments, n is 1. In certain embodiments, n is 3.

In certain embodiments, the linker may comprise a cyclodextrin group. In certain embodiments, the linker provides an ADC according to Formula (XVb):

(XVb)

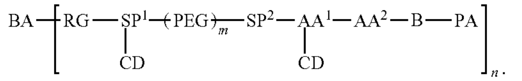

In Formula (XVb), BA is an antibody, or an antigen-binding fragment thereof, RG is a reactive group residue; $SP^1$ and $SP^2$ are each, independently in each instance, absent or a spacer group residue, and wherein $SP^1$ may comprise a trivalent linker; $AA^1$ is a trivalent linker comprising an amino acid residue; $AA^2$ is a di-peptide residue; PEG may comprise between 1 and 30 polyethylene glycol residues; B is absent,

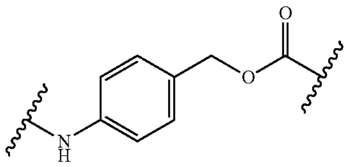

or

-continued

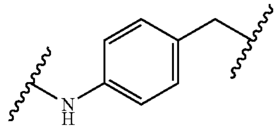

, wherein the

indicates the atom through which the B is bonded to the adjacent groups in the formula, CD is, independently in each instance, absent or a cyclodextrin residue, wherein at least one CD is present, subscript n is an integer from 1 to 30; subscript m is an integer from 0 to 5; and PA is a payload moiety. In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples B is absent. In some examples, B is

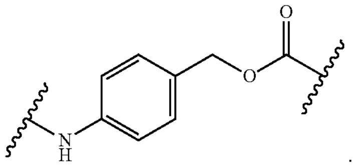 [SMILES: *Nc1ccc(COC(*)=O)cc1]

.

In some examples, B is

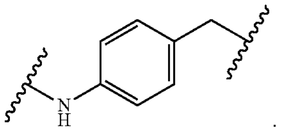 [SMILES: *Cc1ccc(N*)cc1]

.

In some examples, any one of $AA^1$ or $AA^2$ may comprise, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, and combinations thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, and combinations thereof. In certain embodiments, $AA^1$ is lysine. In certain embodiments, $AA^1$ is lysine or a derivative of lysine. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ glutamine-valine-citrulline. In some embodiments, the $AA^1$-$AA^2$ is glutamine-valine-citrulline. In some embodiments, the $AA^1$-$AA^2$ is lysine-valine-alanine. In some embodiments, the $AA^1$-$AA^2$ is lysine-valine-citrulline. In some embodiments, the $AA^1$-$AA^2$ is glutamine-valine-citrulline. In certain embodiments, the lysine is L-lysine. In certain embodiments, the lysine is D-lysine. In some examples, $SP^1$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2—O)_e$, $—NH—CH_2—CH_2—(—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8.

In certain embodiments, the linker may comprise a terminal hydrophilic group (HG). In certain embodiments, the linker may comprise a taurine group. In certain embodiments, the linker may comprise a terminal sulfonic acid group. In certain embodiments, the linker provides an ADC according to Formula (XVI):

(XVI)

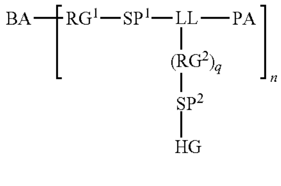

wherein, in Formula (XVI), BA is a binding agent; LL is a trivalent linker; $RG^1$ and $RG^2$ are reactive group residues; $SP^1$ and $SP^2$ are independently, in each instance, absent, or a spacer group residue; HG is a hydrophilic residue; PA is a payload residue; subscript n is an integer from 1 to 30; and subscript q is 0 or 1. In some instances more than one trivalent linker LL may be present. In some instances, n is an integer from 1 to 4. In some instances n is 1. In some instances n is 2. In some instances n is 3. In some instances n is 4. In some instances, HG is a terminal hydrophilic group. In some instances, HG may comprise one terminal sulfonic acid group or a salt thereof. In other instances, HG may comprise more than one terminal sulfonic acid groups or salts thereof. In some instances, HG may comprise one terminal phosphonic acid group or a salt thereof. In other instances, HG may comprise more than one terminal phosphonic acid groups or salts thereof. In some instances, HG may comprise one terminal tertiary amine group or a salt thereof. In other instances, HG may comprise more than one terminal tertiary amine groups or salts thereof. In some instances, HG may comprise one terminal polyol (e.g., glucose, maltose) or a derivative thereof. In other instances, HG may comprise more than one terminal polyol (e.g., glucose, maltose) or derivatives thereof.

In another example, the compound of Formula (XVI) is according to Formula (XVH):

(XVII)

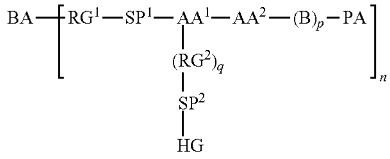

.

In Formula (XVII), BA, $RG^1$, $SP^1$, $RG^2$, $SP^2$ and HG are as defined above, $AA^1$ is a trivalent linker comprising an amino acid residue; $AA^2$ is a dipeptide residue; and B is

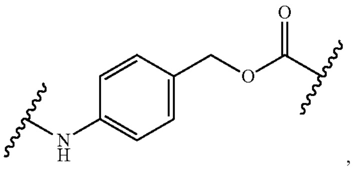 [SMILES: *Nc1ccc(COC(*)=O)cc1]

, wherein the

indicates the atom through which the B is bonded to the adjacent groups in the formula; subscript p is 0 or 1; and subscript q is 0 or 1. In some instances, subscript p is 0 and subscript q is 0. In some instances, subscript p is 1; and subscript q is 0. In some instances, subscript p is 0; and subscript q is 1. In some instances, subscript p is 1; and subscript q is 1. In some instances $SP^1$ may comprise from 0-5 polyethylene glycol (PEG) residues. In some instances $SP^2$ may comprise from 0-5 PEG residues. In some examples, $SP^1$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, any one of $AA^1$ or $AA_2$ may comprise, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, and combinations thereof. In certain embodiments, $AA^1$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, and combinations thereof. In certain embodiments, AA is lysine. In certain embodiments, $AA^1$ is lysine or a derivative of lysine. In certain embodiments, $AA^1$ is glutamic acid. In certain embodiments, the $AA^2$ is valine-citrulline. In some embodiments, the $AA^2$ is citrulline-valine. In some embodiments, the $AA^2$ is valine-alanine. In some embodiments, the $AA^2$ is alanine-valine. In some embodiments, the $AA^2$ is valine-glycine. In some embodiments, the $AA^2$ is glycine-valine. In some embodiments, the $AA^1$-$AA^2$ is glutamine-valine-citrulline. In some embodiments, the $AA^1$-$AA^2$ is lysine-valine-citrulline. In some embodiments, the $AA^1$-$AA^2$ is lysine-valine-alanine. In some embodiments, the $AA^1$-$AA^2$ is glutamine-valine-alanine. In certain embodiments, the lysine is L-lysine. In certain embodiments, the lysine is D-lysine.

In certain embodiments, the linker provides an ADC according to Formula (XVIII):

$$BA\text{—}[RG\text{—}SP\text{—}AA\text{—}B\text{—}PA]_n. \qquad \text{(XVIII)}$$

In Formula (XVIII), BA is an antibody, or an antigen-binding fragment thereof, RG is a reactive group residue, e.g., a maleimide or a succinimide residue; SP is absent or a spacer group residue; AA is a di-peptide residue, e.g. a valine-citrulline linker; B is absent or

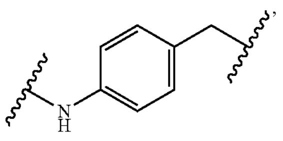 [SMILES: *Cc1ccc(N*)cc1]

wherein the

indicates the atom through which the B is bonded to the adjacent groups in the formula, subscript n is an integer from 1 to 30; and PA is a payload moiety, e.g. a rifamycin analog. In some examples, B is absent. In some examples, B is

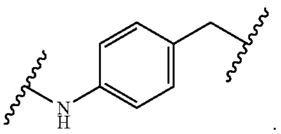 [SMILES: *Cc1ccc(N*)cc1]

In some examples, AA may comprise, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, and combinations thereof. In certain embodiments, the AA is valine-citrulline. In some embodiments, the AA is citrulline-valine. In some embodiments, the AA is valine-alanine. In some embodiments, the AA is alanine-valine. In some embodiments, the AA is valine-glycine. In some embodiments, the AA is glycine-valine. In some examples, SP is selected from the group consisting of $C_{1-6}$ alkyl, —NH—, —C(O)—, $—CH_2—CH_2—C(O)—NH—$, $—(CH)_u—C(O)—NH—$, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, $—(CH)_u—C(O)—NH—(CH_2—CH_2—O)_e—(CH)_u—C(O)—NH—$, $—(CH)_2—C(O)—NH—(CH_2—CH_2—O)_8—(CH)_2—C(O)—NH—$, and combinations thereof, wherein independently at each occurrence subscript e is an integer from 0 to 20, subscript u is an integer from 1 to 8, and subscript v is an integer from 1 to 8.

In certain embodiments, the linker may comprise a cyclodextrin group. In certain embodiments, the linker provides an ADC according to Formula (XIX):

$$BA\text{—}[RG\text{—}SP^1\text{—}(PEG)_m\text{—}SP^2\text{—}AA\text{—}B\text{—}PA]_n$$

(XIX)

In Formula (XIX), BA is an antibody, or an antigen-binding fragment thereof, RG is a reactive group residue, e.g., a maleimide or a succinimide residue; $SP^1$ and $SP^2$ are each, independently in each instance, absent or a spacer group residue, e.g.,

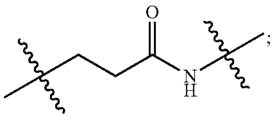 [SMILES: *CCC(=O)N*]

AA is a di-peptide residue, e.g. a valine-citrulline linker; PEG is a polyethylene glycol chain comprising between 1 and 30 polyethylene glycol residues; B is absent or

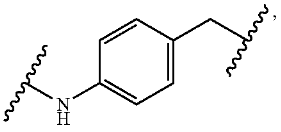 [SMILES: *Cc1ccc(N*)cc1]

wherein the

indicates the atom through which the B is bonded to the adjacent groups in the formula, subscript n is an integer from 1 to 30; subscript m is an integer from 0 to 20; subscript p is 0 or 1; and PA is a payload moiety, e.g. a rifamycin analog. In these examples, subscript m is 0, 1, 2, 3, 4, 5, 6, 7, 8, 9, 10, 11, 12, 13, 14, 15, 16, 17, 18, 19, or 20. In some examples, subscript m is 0. In some examples, subscript m is 1. In some examples, subscript m is 2. In some examples, subscript m is 5. In some examples, subscript m is 8. In some examples, subscript m is 10. In some examples, B is absent. In some examples, B is

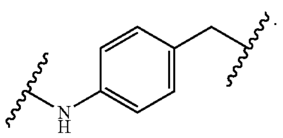 [SMILES: *Cc1ccc(N*)cc1]

In some examples, AA may comprise, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, and combinations thereof. In certain embodiments, the AA is valine-citrulline. In some embodiments, the AA is citrulline-valine. In some embodiments, the AA is valine-alanine. In some embodiments, the AA is alanine-valine. In some embodiments, the AA is valine-glycine. In some embodiments, the AA is glycine-valine. In some examples, $SP^1$ is independently in each instance, selected from the group consisting of $C_{1-6}$ alkyl, —NH—, —C(O)—, $—CH_2—CH_2—C(O)—NH—$, $—(CH)_u—C(O)—NH—$, $(—CH_2—CH_2—O)_e$, $—NH—CH_2—CH_2—(—O—CH_2—CH_2)_e—C(O)—$, $—C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $—CH_2—CH_2—C(O)—NH—$, $—(CH)_u—C(O)—NH—$, $(—CH_2—CH_2—O)_e$, $—NH—CH_2—CH_2—(—O—CH_2—CH_2)_e—C(O)—$, $C(O)—(CH_2)_u—C(O)—$, $—C(O)—NH—(CH_2)_v—$, and combinations thereof, wherein subscript e is an integer from 0 to 4, subscript u is an integer from 1 to 8, and subscript v is an integer from 1 to 8.

Also included in these examples, is a pharmaceutically acceptable salt, solvate, stereoisomeric form thereof, a regioisomer thereof, or mixture of regioisomers thereof, wherein each

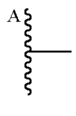

is a bond to the binding agent; and each

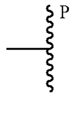

is a bond to the payload.

In some embodiments, antibody-drug conjugates comprising linker-rifamycin analog payloads comprise salts, e.g. ammonium salts, having one or more counterions. Any pharmaceutically acceptable counterion may be suitable. For example, in an embodiment of the disclosure a suitable counterion may be an anion selected from $F^-$, $Cl^-$, $Br^-$, $I^-$, $OH^-$, $^-BF_4$, $CF_3SO_3^-$, monobasic sulfate, dibasic sulfate, monobasic phosphate, dibasic phosphate, or tribasic phosphate, $NO_3^-$, $PF_6^-$, $NO_2^-$, carboxylate, $C_eF_fSO_3^-$, (wherein e=2-10 and f=2e+1), acetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, glycollyalarsanilate, hexanoate, hydrabamine, hydroxynaphthoate, isthionate, lactate, lactobionate, malate, maleate, mandelate, mesylate, methylbromide, methylnitrate, mucate, napsylate, octanoate, oleate, pamoate, pantothenate, polygalacturonate, propionate, salicylate, stearate, subacetate, succinate, tartrate, teoclate, tosylate, or triethiiodide.

The antibody drug conjugates described herein can be prepared using conjugation conditions known to those of ordinary skill in the art, (see, e.g., Doronina et al. *Nature Biotechnology* 2003, 21, 7, 778, which is incorporated herein by reference in its entirety). In some embodiments an ADC is prepared by contacting an antibody or an antigen-binding fragment thereof with a compound comprising the desired linker and payload, wherein said linker possesses a moiety that is reactive with the antibody or antigen-binding protein, e.g., at the desired residue of the antibody or antigen-binding protein. Exemplary conditions are described in the Examples below.

In some aspects, the payloads PA are rifamycin analogs as described in any of the above embodiments of compounds having a structure according to formulas (A), (B), (I), (I'), (II), (II'), (III), (III'), (IV), (IV'), (V), (V') as provided herein.

In one aspect, the payload PA is a rifamycin analog having the structure of Formula (XX):

(XX)

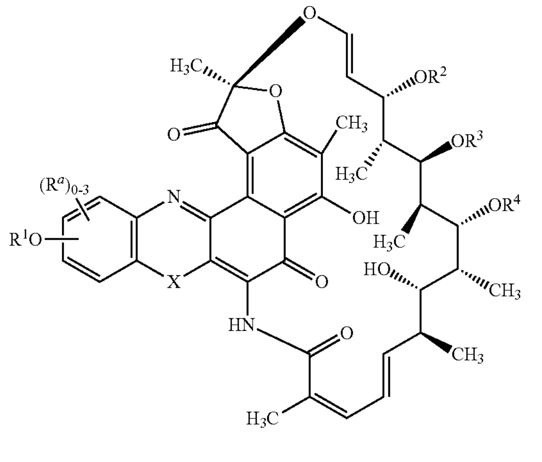

wherein:

X is selected from —O—, —S—, and —NR*—;

$R_1$ is selected from a bond; an aliphatic $C_1$-$C_{20}$ hydrocarbon; an aromatic $C_5$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, and combinations thereof, each of which further comprises 0-8 heteroatoms selected from halogen, O, N, and S, and wherein $R_1$ is optionally substituted with one or more of —F; —$C_1$; —Br; —I; —OH, —OR*; —NO; —$NO_2$; —$NO_3$; —O—NO; —$N_3$; —$NH_2$; —NHR*; —$N(R^*)_2$; —$N(R^*)_3^+$; —N(R*)—OH; —O—N$(R^*)_2$; —N(R*)—O—R*; —CN; —NC; —(C═O)—R*; —CHO; —$CO_2H$; —$CO_2R^*$; —(C═O)—S—R*; —O—(C═O)—H; —O—(C═O)—R*; —S—(C═O)—R*; —(C═O)—$NH_2$; —(C═O)—$N(R^*)_2$; —(C═O)—$NHNH_2$; —O—(C═O)—$NHNH_2$; —(C═S)—$NH_2$; —(C═S)—$N(R^*)_2$; —N(R*)—CHO; —N(R*)—(C═O)—R*; —SCN; —NCS; —NSO; —SSR*; —$SO_2R^*$; —$SO_2$—$N(R^*)_2$; —S(═O)—OR*; —S(═O)—R*; —Si$(R^*)_3$; —$CF_3$; —O—$CF_3$ and combinations thereof;

$R_2$, $R_3$, and $R_4$ are independently selected from hydrogen, a straight chained, branched or cyclic aliphatic $C_1$-$C_{20}$ hydrocarbon, or —(C═O)—R*, each of which further comprises 0-8 heteroatoms selected from halogen, O, N, and S;

$R_a$ is independently at each occurrence selected from hydrogen, —F; —$C_1$; —Br; —I; —OH; OR*; —$NH_2$; —NHR*; —$N(R^*)_2$; —$N(R^*)_3^+$; —(C═O)—R*; —CHO; —$CO_2H$; —$CO_2R^*$ and an aliphatic $C_1$-$C_{20}$ hydrocarbon, which further comprises 0-8 heteroatoms selected from halogen, O, N, and S, and wherein $R_a$ and $R_b$ are optionally substituted with one or more of —F; —Cl; —Br; —I; —OH; —OR*;

R* is independently at each occurrence selected from hydrogen; an aliphatic $C_1$-$C_{20}$ hydrocarbon; an aromatic $C_5$-$C_{20}$ hydrocarbon; a heteroaromatic $C_1$-$C_{20}$ hydrocarbon; an aryl $C_6$-$C_{20}$ hydrocarbon; a heteroaryl $C_1$-$C_{20}$ hydrocarbon, and combinations thereof, which further comprises 0-8 heteroatoms selected from halogen, O, N, and S and combinations thereof, wherein the group $R_1$ is bonded to the linker.

It is to be understood that the group $R_1$ is either a bond (i.e., $R_1$ is absent), or a divalent group, i.e. a In another aspect, the payload PA is a rifamycin analog having the structure of Formula (XXI):

(XXI)

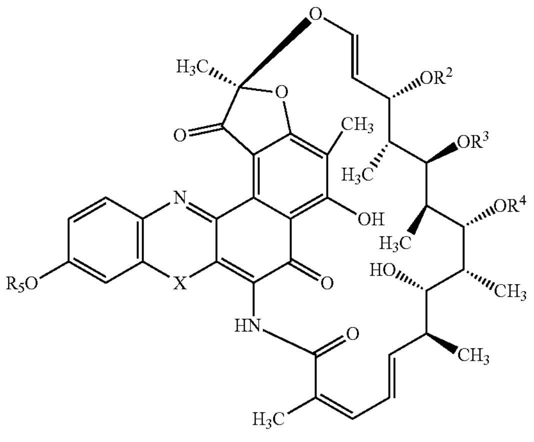

wherein:

X is selected from —O—, —S—, and —NR*—;

$R_5$ is selected from a bond; an aliphatic $C_1$-$C_{20}$ hydrocarbon which further comprises 0-8 heteroatoms selected from halogen, O, N, and S;

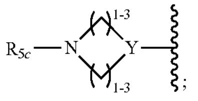 ; or 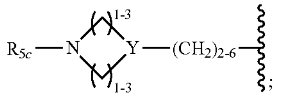 ;

wherein Y is C or N;

$R_2$, $R_3$, and $R_4$ are independently selected from a hydrogen, a straight chained, branched or cyclic aliphatic $C_1$-$C_{20}$ hydrocarbon, or —(C═O)—R*, each of which further comprises 0-8 heteroatoms selected from halogen, O, N, and S, and $R_{5c}$ is a bond or an aliphatic $C_1$—C hydrocarbon;

wherein the group $R_5$ is bonded to the linker.

In another aspect, the payload PA is a rifamycin analog having the structure of Formula (XXI'):

(XXI')

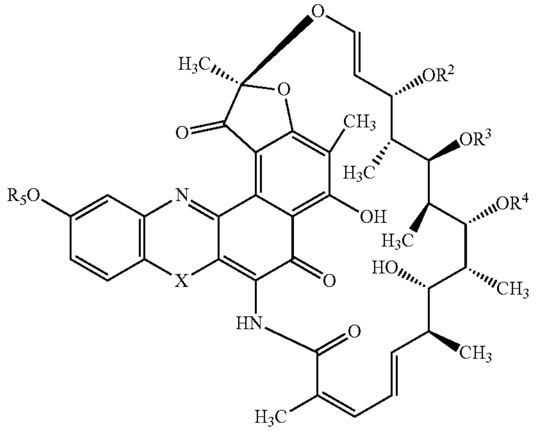

wherein:

X is selected from —O—, —S—, and —NR*—;

$R_5$ is selected from a bond; an aliphatic $C_1$-$C_{20}$ hydrocarbon which further comprises 0-8 heteroatoms selected from halogen, O, N, and S; from

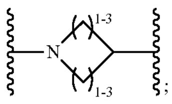 ; 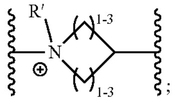 ;

wherein Y is C or N;

$R_2$, $R_3$, and $R_4$ are independently selected from a hydrogen, a straight chained, branched or cyclic aliphatic $C_1$-$C_{20}$ hydrocarbon, or —(C═O)—R*, each of which further comprises 0-8 heteroatoms selected from halogen, O, N, and S, wherein the group $R_5$ is bonded to the linker.

It is to be understood that the group $R_5$ is either a bond (i.e., $R_5$ is absent), or a divalent group, i.e. $R_5$ capable of bonding to the —O— of rifamycin as well as to the linker.

In some or any embodiments of Formulas (A), (B), (I) through (XVI) and (I') through (XVI'), $R_a$ is hydrogen and/or $R_b$ is hydrogen. In some or any embodiments of Formulas (A), (I) through (XVI), and (I') through (XVI') $R_a$ is —OH. In some or any embodiments of Formulas (A), (I) through (XVI) and (I') through (XVI'), $R_2$ is methyl, ethyl, propyl or isopropyl. In one embodiment, $R_2$ is methyl. In some or any embodiments of Formulas (A), (I) through (XVI) and (I') through (XVI'), $R_3$ is $CH_3$—(C═O)— (acetyl group), $CH_3CH_2$—(C═O)— $CH_3CH_2CH_2$—(C═O)—, or $(CH_3)_2$CH—(C═O)—. In one embodiment, $R_3$ is acetyl. In some or any embodiments of Formulas (A), (I) through (XVI) and (I') through (XVI'), $R_4$ is hydrogen.

In some embodiments of Formula (XX) or (XX'), —$OR_1$ is —O— (i.e., $R_1$ is absent),
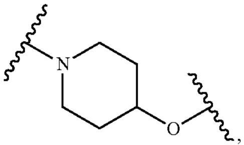,
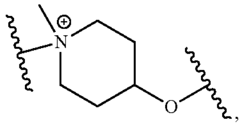,
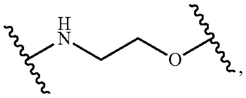,
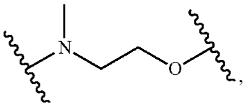,
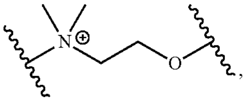,
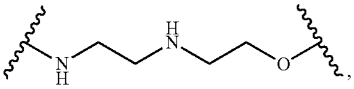,
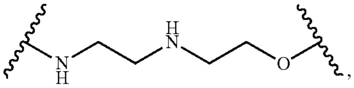,
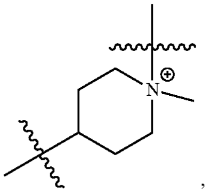,
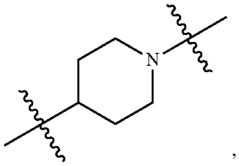,
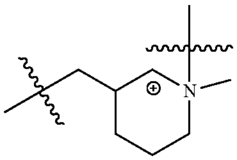,
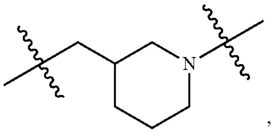,
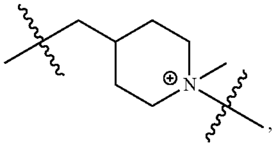,
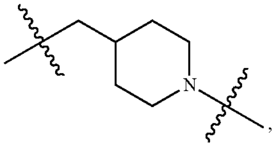,
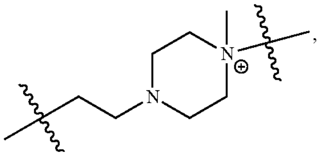,
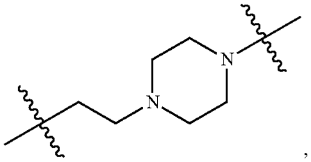,
-continued
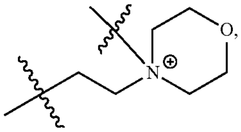,
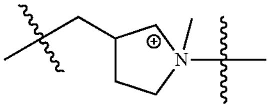,
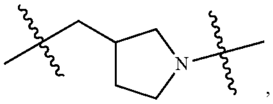,
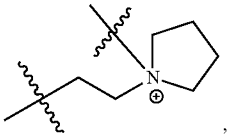,
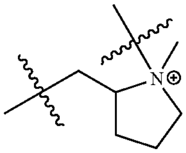,
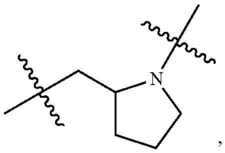,
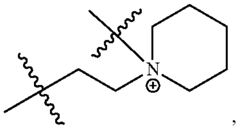,
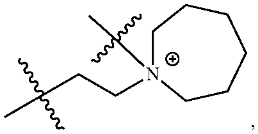,
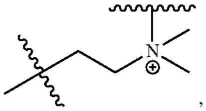,
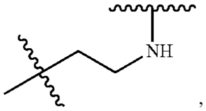,
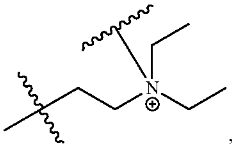,
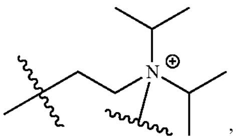,
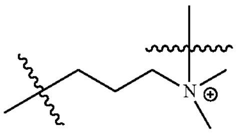,
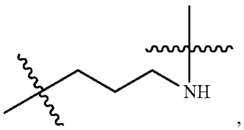,
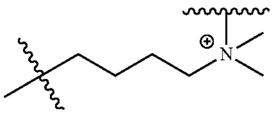,
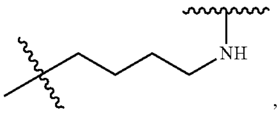,
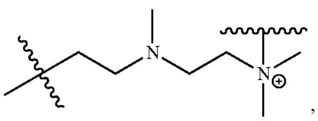,
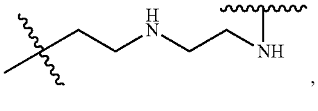,
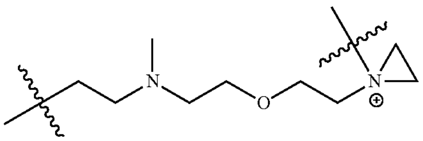, -continued
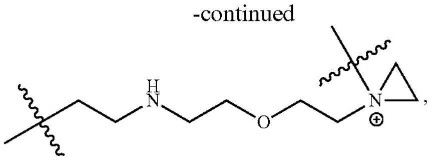,
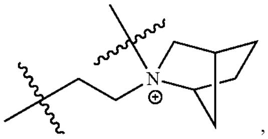, 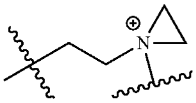, and
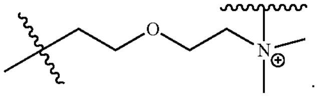.
In some embodiments of Formula (XXI) or (XXI'), —$OR_5$ is —O— i.e. ($R_5$ is absent),
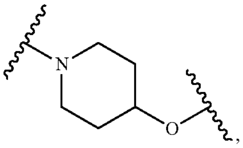, 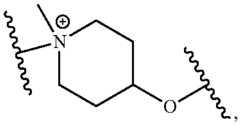,
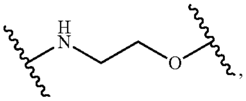, 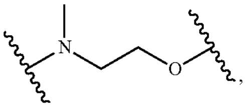,
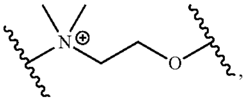,
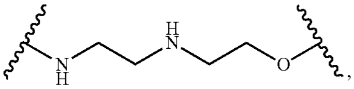,
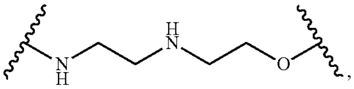,
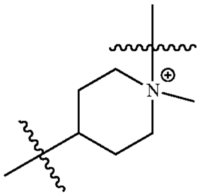, 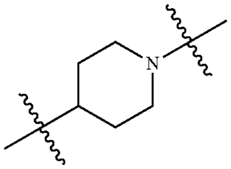,
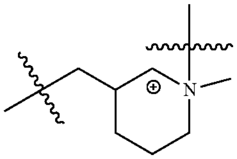, 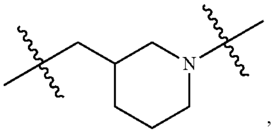,
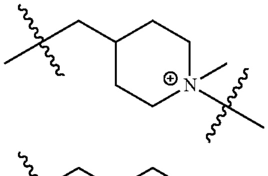,
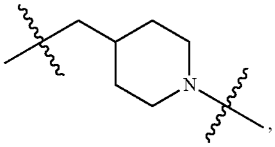,
-continued
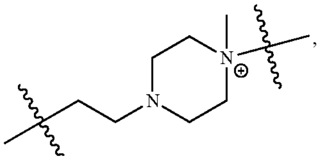,
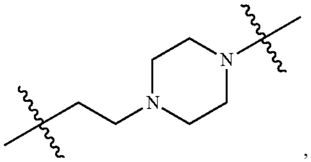,
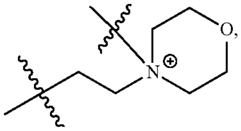
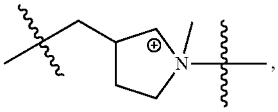,
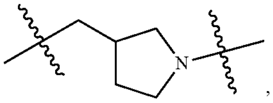, 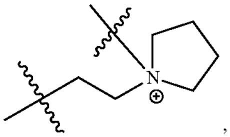,
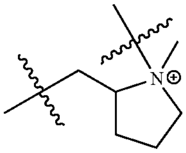, 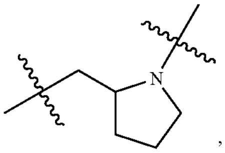,
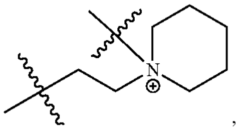, 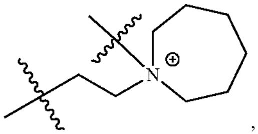,
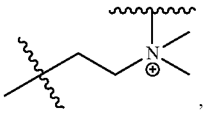, 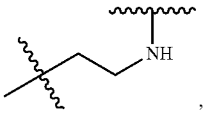,
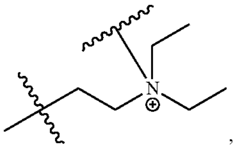, 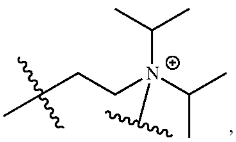,
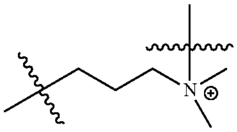, 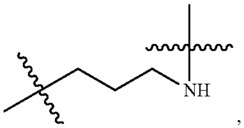,
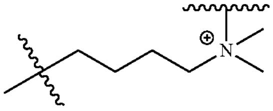, -continued
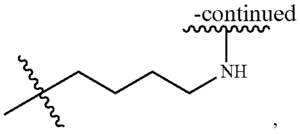
,
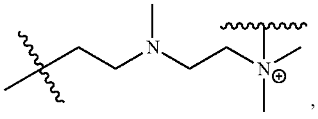
,
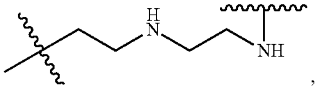
,
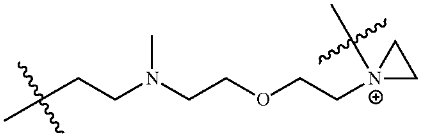
,
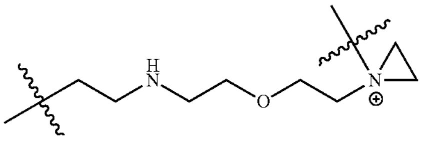
,
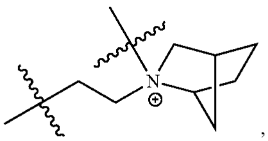
,
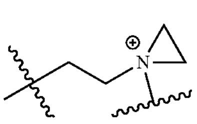
, and
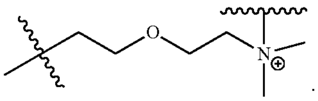
.
In some or any embodiments of Formula (XX), X is —O—, and —$OR_1$ comprises a tertiary amine. In some of such embodiments, —$OR_1$ is
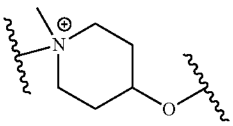
or
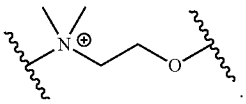
.
In some or any embodiments of Formula (XXI) or (XXI'), X is O, and —$OR_5$ comprises a tertiary amine. In some of such embodiments, —$OR_5$ is
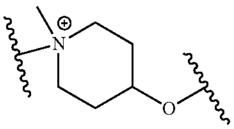
or
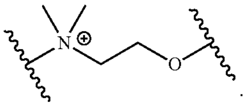
.
In some embodiments. a compound of Formulas (XX), (XXI), (XX') or (XXI') is selected from the group consisting of:
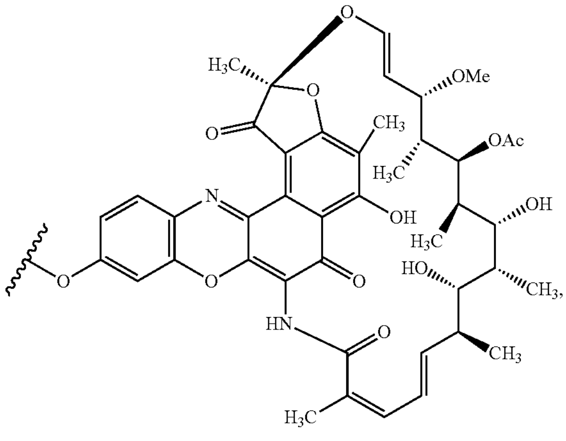
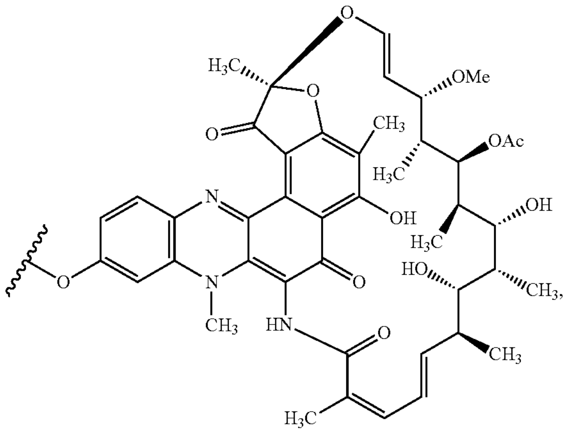
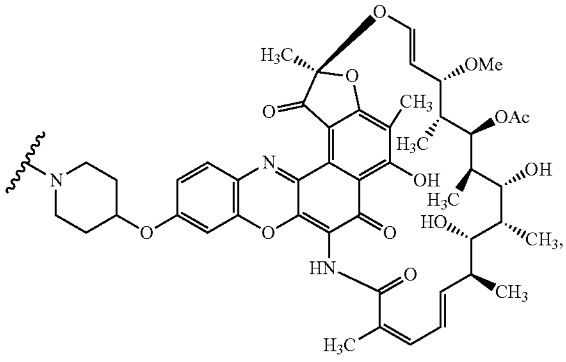
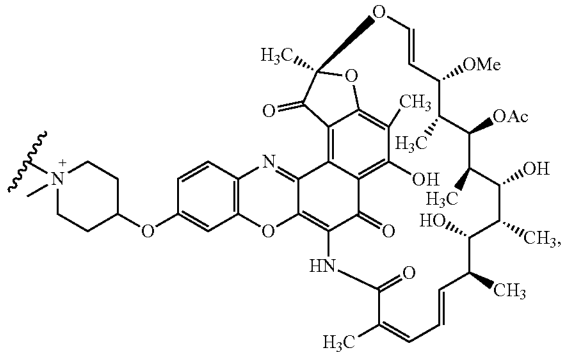

-continued
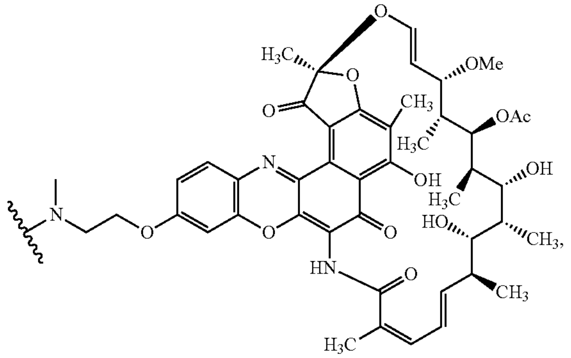
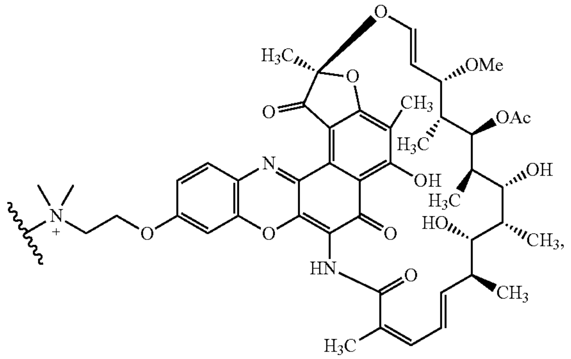
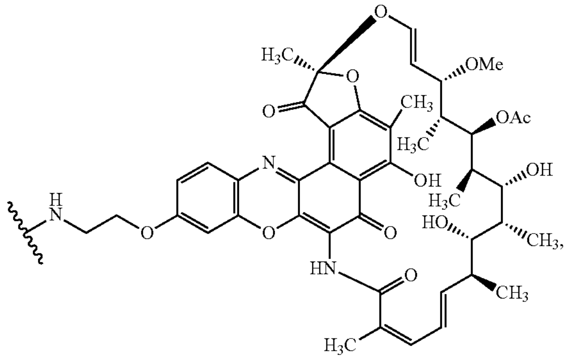
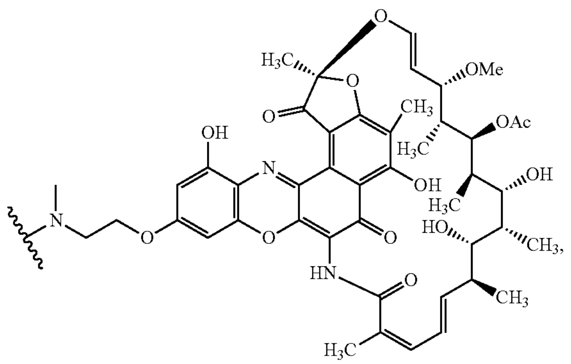
-continued
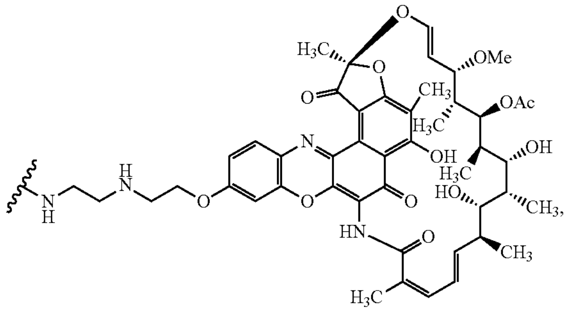
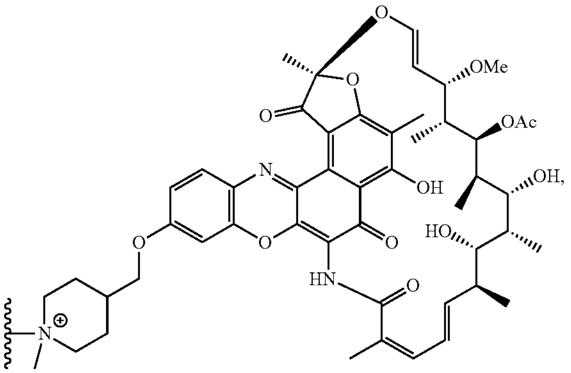
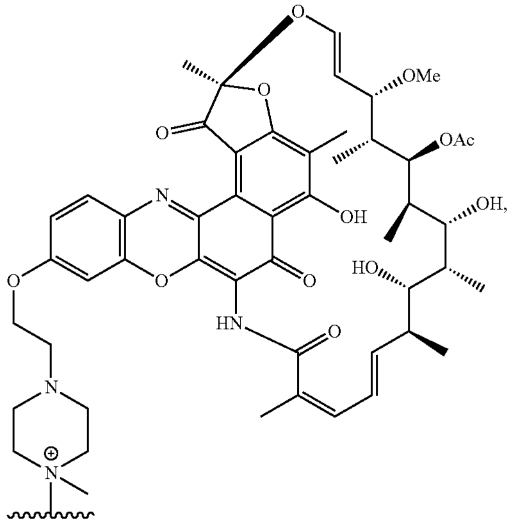
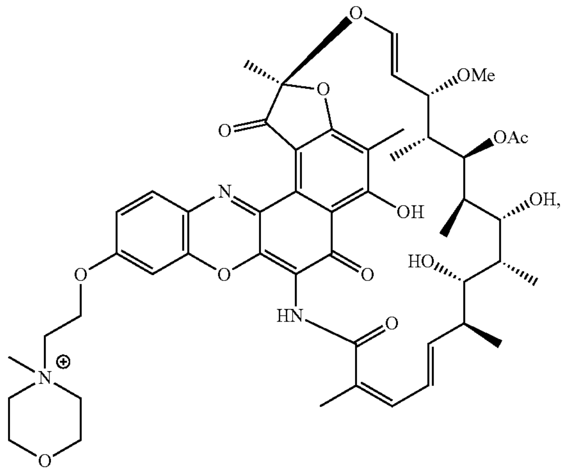

-continued
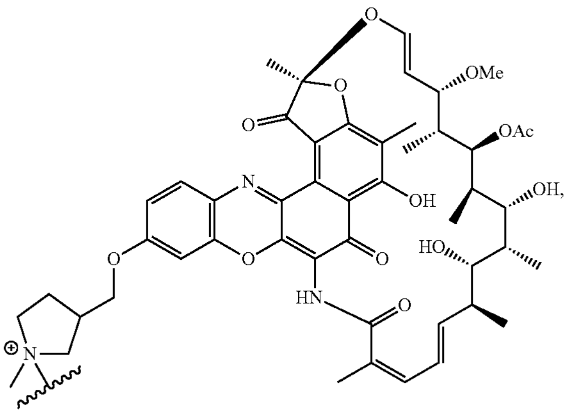
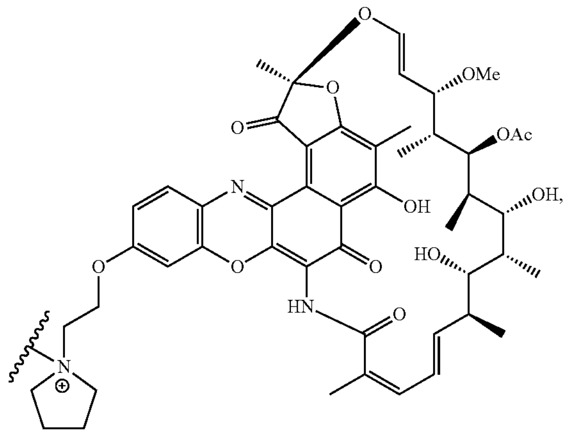
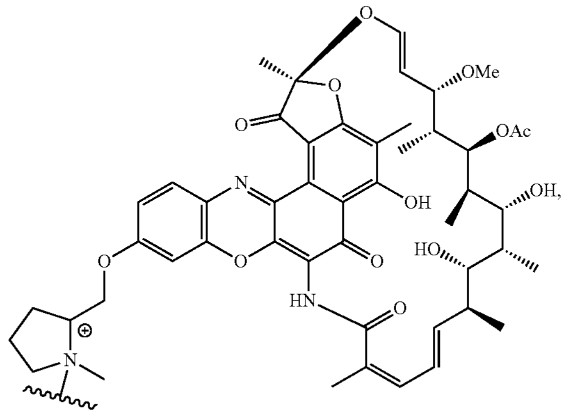
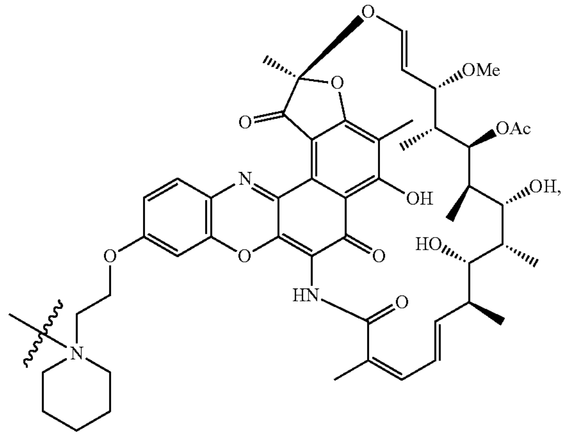
-continued
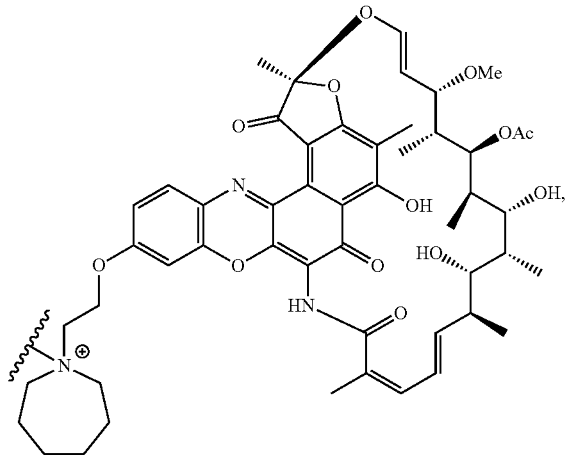
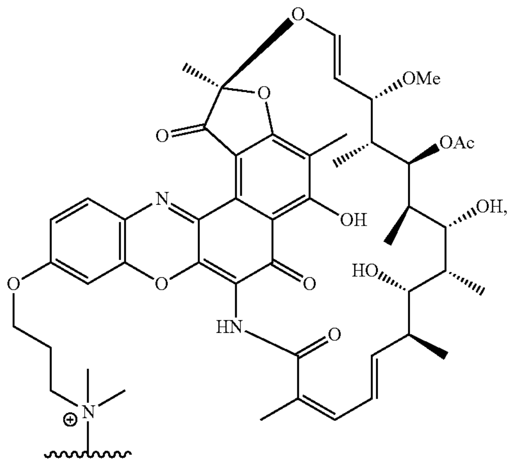
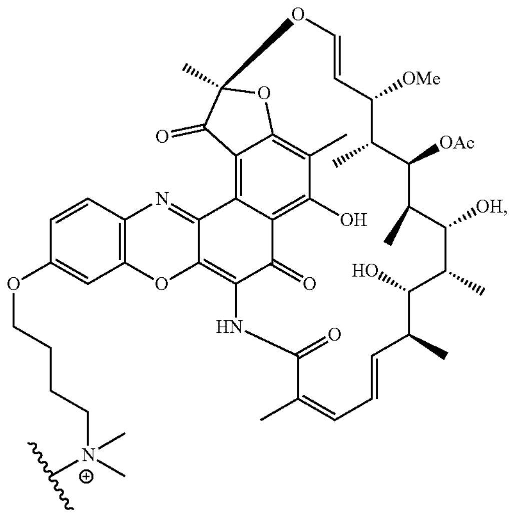

-continued
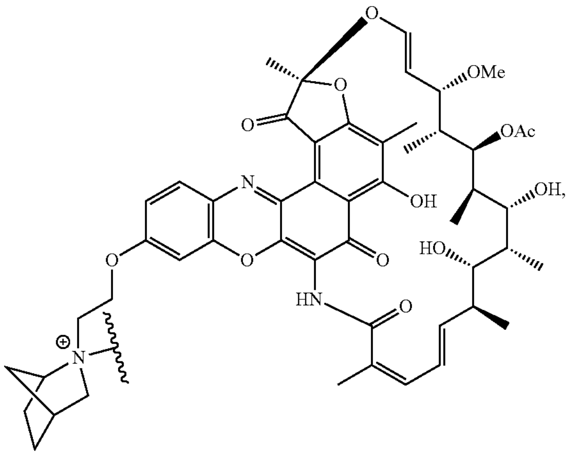
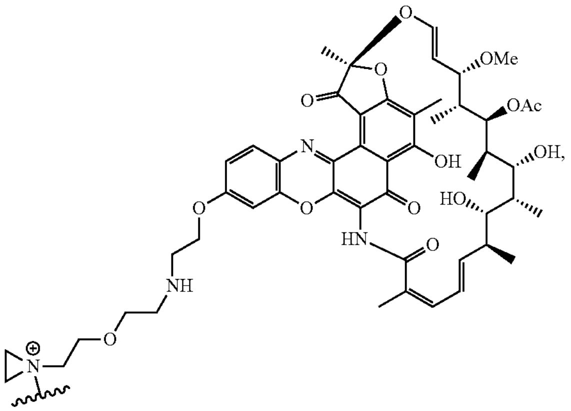
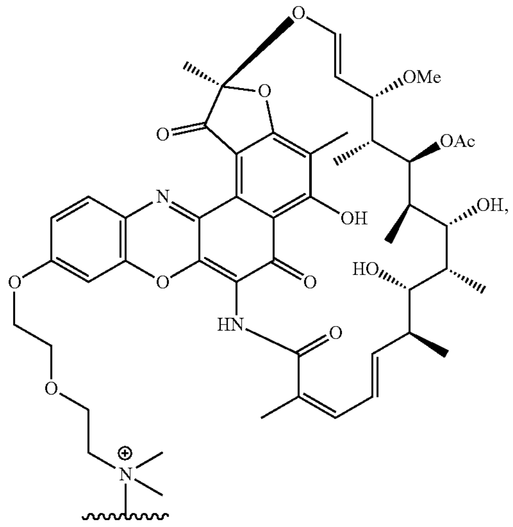
-continued
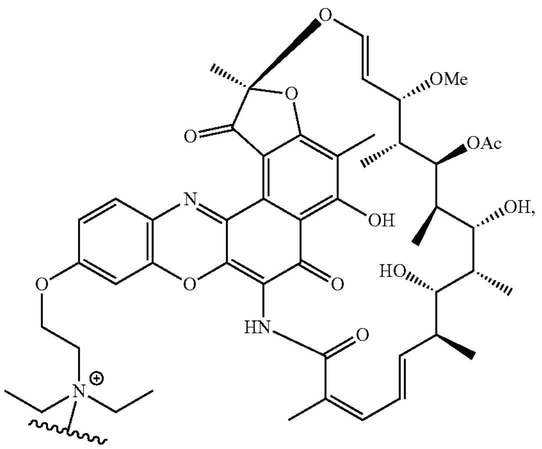
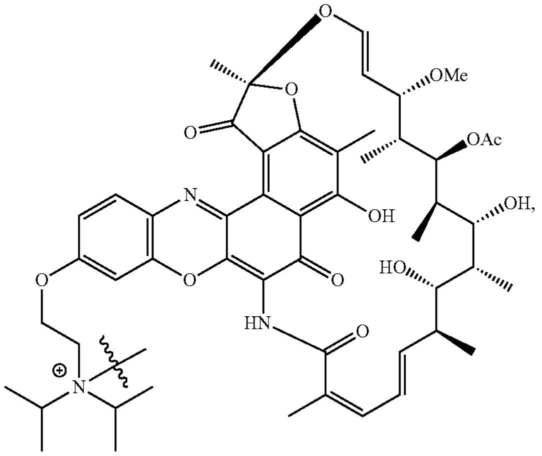
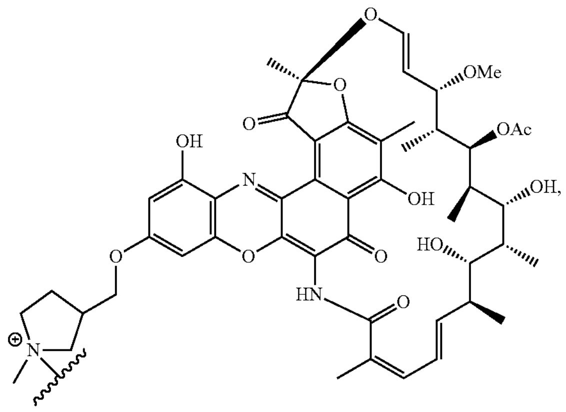
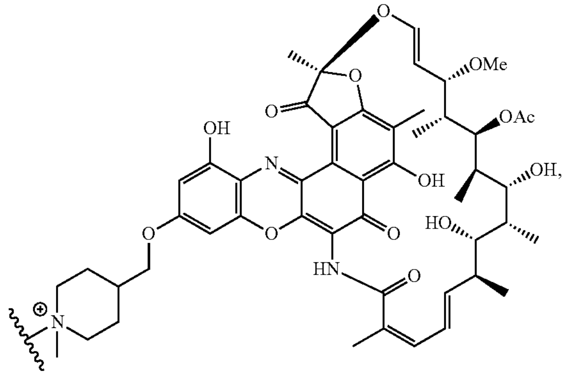

-continued
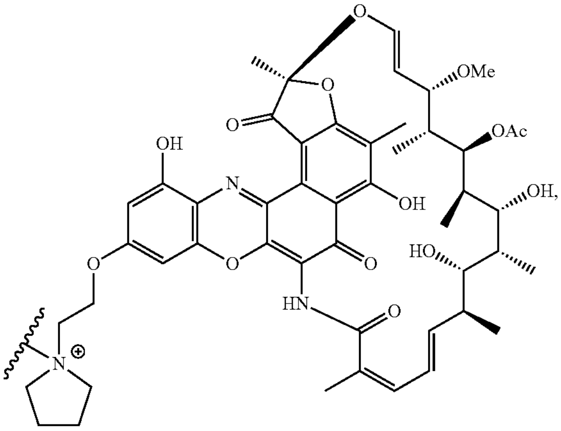
-continued
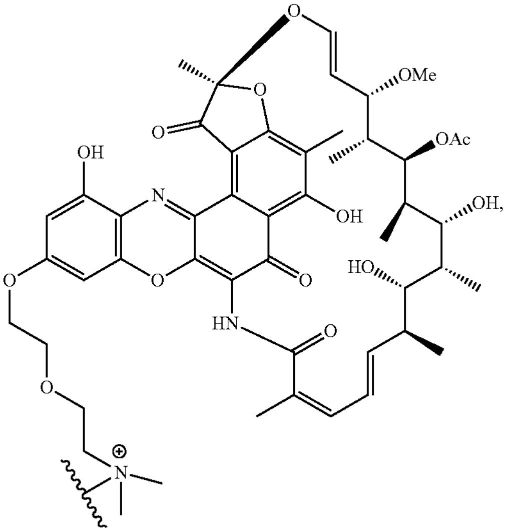
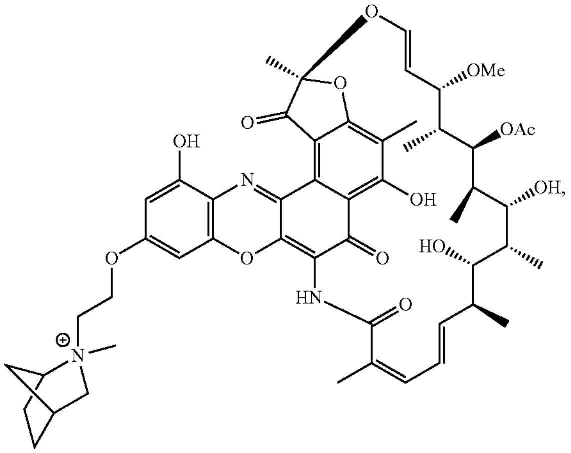
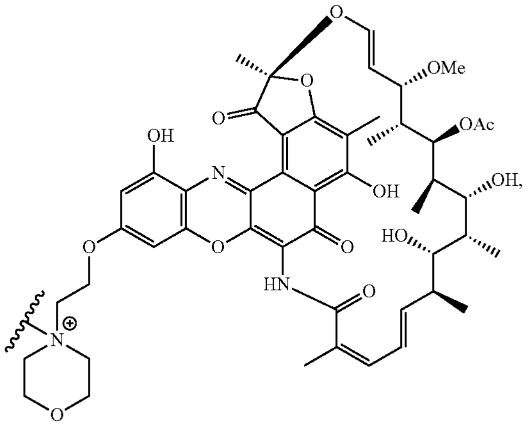
and
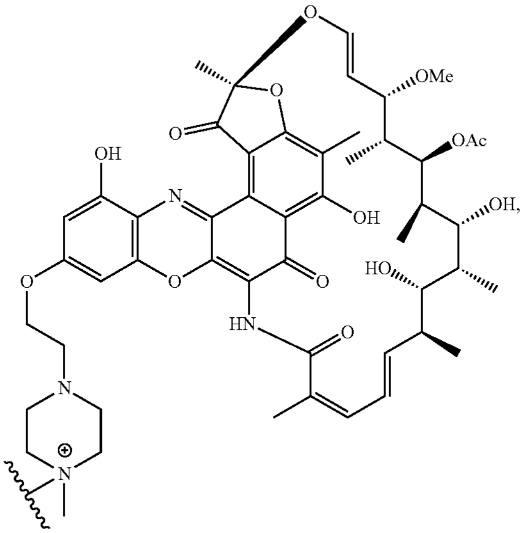
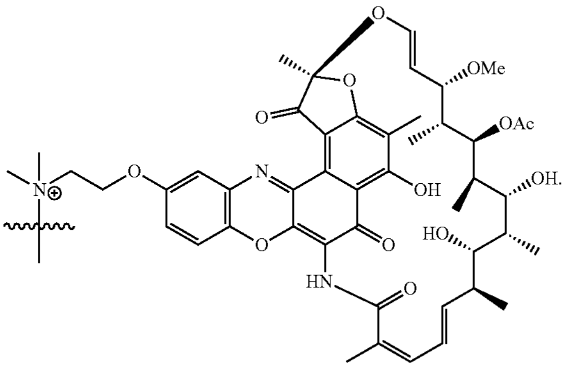
wherein the
is the bond to the linker.

In one aspect, the present disclosure provides an antibody-drug conjugate having the structure of Formula (XXII):

(XXII)

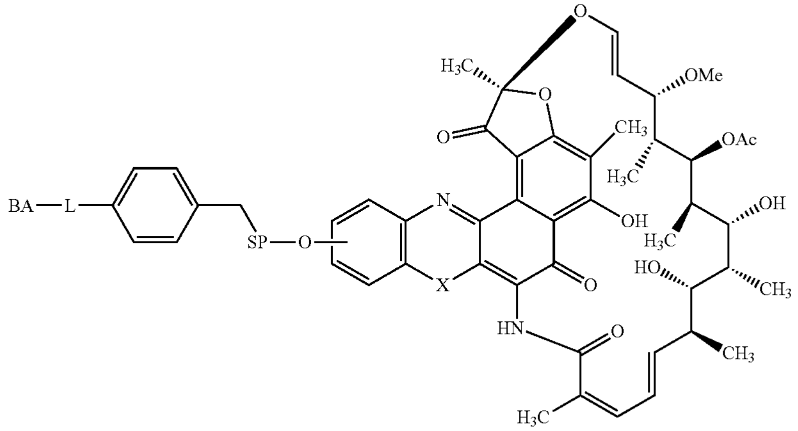

wherein:

BA is an antibody, or an antigen-binding fragment thereof, L is a linker;

SP is a spacer group selected from

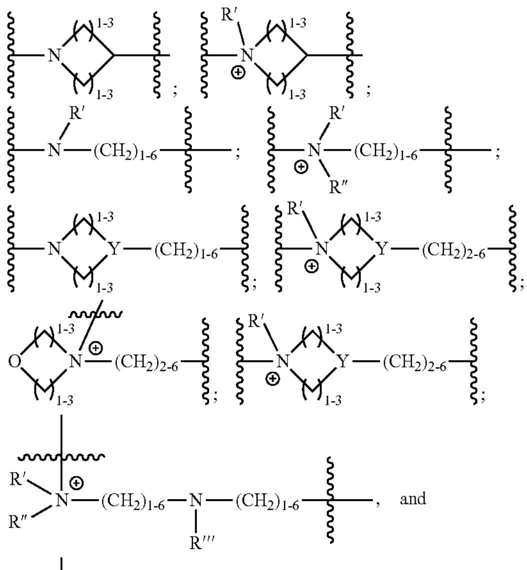

and

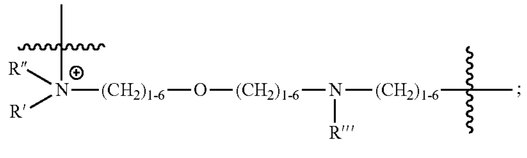

wherein Y is C or N; wherein the symbol represents the point of attachment; and R', R" and R''' are selected from a hydrogen, a $C_1$-$C_6$ aliphatic hydrocarbon, and a protecting group selected from Fluorenylmethyloxycarbonyl (FMOC) and tert-Butyloxycarbonyl (BOC), or wherein R' and R" together form an aliphatic monocyclic, an aliphatic bicyclic, or an aliphatic polycyclic structure;

R' and R" are independently at each occurrence selected from a hydrogen and a $C_{1-6}$ alkyl, and X is selected from —O—, —S—, and —NR*.

In some embodiments, the antibody, or antigen-binding fragment thereof, binds MSR1. In one embodiment, the anti-MSR1 antibody, or the antigen-binding fragment thereof, comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, comprises:

(i) a HCDR1 domain comprising an amino acid sequence selected from the group consisting of SEQ ID NOs: 4, 36, 52, 92, and 284;

(ii) a HCDR2 domain comprising an amino acid sequence selected from the group consisting of SEQ ID NOs: 6, 38, 54, 94, and 286;

(iii) a HCDR3 domain comprising an amino acid sequence selected from the group consisting of SEQ ID NOs: 8, 40, 56, 96, and 288;

(iv) a LCDR1 domain comprising an amino acid sequence selected from the group consisting of SEQ ID NOs: 12, 44, 60, 100, and 292;

(v) a LCDR2 domain comprising an amino acid sequence selected from the group consisting of SEQ ID NOs: 14, 46, 62, 102, and 294; and (vi) a LCDR3 domain comprising an amino acid sequence selected from the group consisting of SEQ ID NOs: 16, 48, 64, 104, and 296.

In one embodiment, the anti-MSR1 antibody, or the antigen-binding fragment thereof, comprises (i) a HCDR1 domain comprising an amino acid sequence of SEQ ID NO: 52;

(ii) a HCDR2 domain comprising an amino acid sequence of SEQ ID NO: 54;

(iii) a HCDR3 domain comprising an amino acid sequence of SEQ ID NO: 56;

(iv) a LCDR1 domain comprising an amino acid sequence of SEQ ID NO: 60;

(v) a LCDR2 domain comprising an amino acid sequence of SEQ ID NO: 62; and (vi) a LCDR3 domain comprising an amino acid sequence of SEQ ID NO: 64.

In one embodiment, the anti-MSR1 antibody, or the antigen-binding fragment thereof, comprises a N297Q mutation.

In some embodiments, the antibody, or antigen-binding fragment thereof, binds WTAα. In one embodiment, the anti-WTAα antibody, or the antigen-binding fragment thereof, comprises: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTAα antibody, or an antigen-binding fragment thereof, comprises:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In some embodiments, the antibody, or antigen-binding fragment thereof, binds WTAβ. In one embodiment, the anti-WTAβ antibody, or the antigen-binding fragment thereof, comprises: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTA antibody, or an antigen-binding fragment thereof, comprises:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation.

In one embodiment, the anti-WTA antibody, or the antigen-binding fragment thereof, is derived from antibody 4497 described in US Patent Application Publication 20140356375 (which is incorporated herein by reference in its entirety). In one embodiment, the anti-WTA antibody is derived from antibody 4497 and further comprises a V205C mutation in the light chain.

In one embodiment, the anti-WTA antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTA antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTA antibody or antigen binding fragment thereof comprises an HCVR amino acid sequence of SEQ ID NOs: 586, and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589. In some embodiments, the anti-WTA antibody, or the antigen-binding fragment thereof comprises a V205C mutation in the light chain.

In some embodiments, the antibody, or antigen-binding fragment thereof, binds Protein A. In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiments, the anti-Protein A antibody, further comprises a H435R and a Y436F mutation (EU numbering) in the heavy chain Fc. In one embodiment, anti-Protein A antibody further comprises a C103S mutation in the light chain. In one embodiment, the anti-Protein A antibody, or antigen-binding fragment thereof, is conjugated to a compound of the present disclosure at light chain position 103.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

In one embodiment, L is a linker having the formula

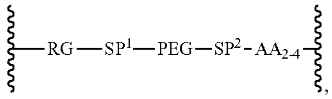, wherein

RG is selected from a maleimide, a N-hydroxysuccinimide, or a succinimide;

$SP^1$ and $SP^2$ are independently absent or a spacer group selected from the group consisting of

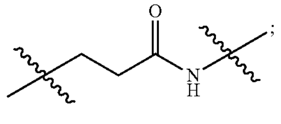 [SMILES: *CCC(=O)N*];

$C_{1-6}$ alkyl, —NH—, —C(O)—, —$CH_2$—$CH_2$—C(O)—NH—, —$(CH)_u$—C(O)—NH—, (—$CH_2$—$CH_2$—O$)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

$AA_{2-4}$ is a peptide unit comprising from 2 to 4 amino acids, and

PEG is a polyethylene glycol chain comprising between 1 and 30 polyethylene glycol residues.

In one embodiment, $AA_{2-4}$ is a dipeptide selected from valine-citrulline; citrulline-valine; valine-alanine; alanine-valine; valine-glycine, or glycine-valine.

In one embodiment, $AA_{2-4}$ is valine-citrulline.

In one embodiment, SP is

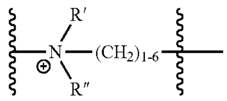

and R' and R" are each a $C_{1-6}$ alkyl.

In one embodiment, SP is

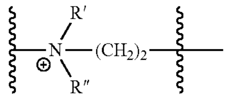

and R' and R" are each methyl.

In one embodiment, $SP^1$ and $SP^2$ are each

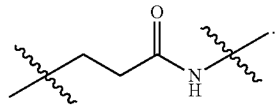 [SMILES: *CCC(=O)N*].

In one embodiment, PEG comprises 8 polyethylene glycol units.

In one embodiment, the antibody-drug conjugate has a structure:

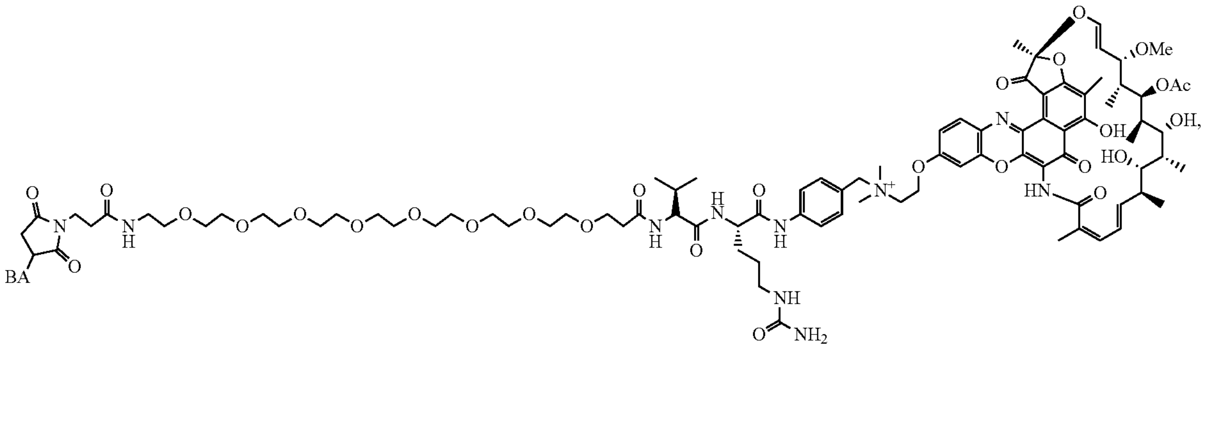

wherein BA is an antibody, or an antigen-binding fragment thereof.

In another aspect, the present disclosure provides an isolated antibody or antigen binding fragment thereof, wherein the antibody or antigen binding fragment thereof is conjugated, directly or through a linker or a linker-spacer, to a payload having the structure selected from the group consisting of:

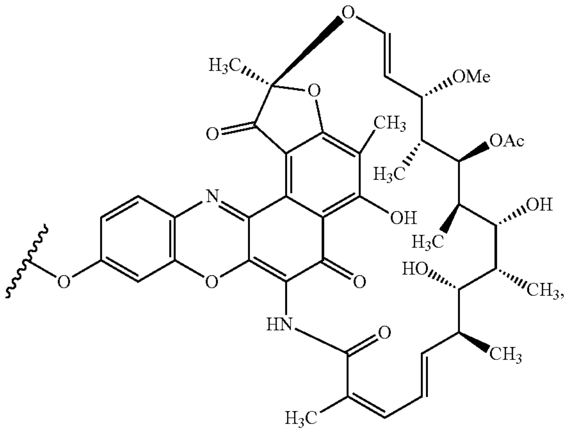

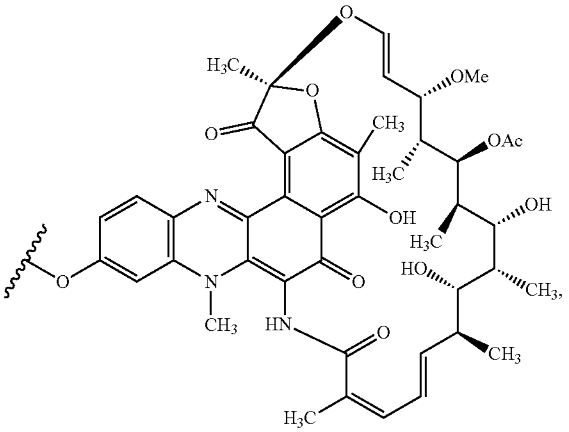

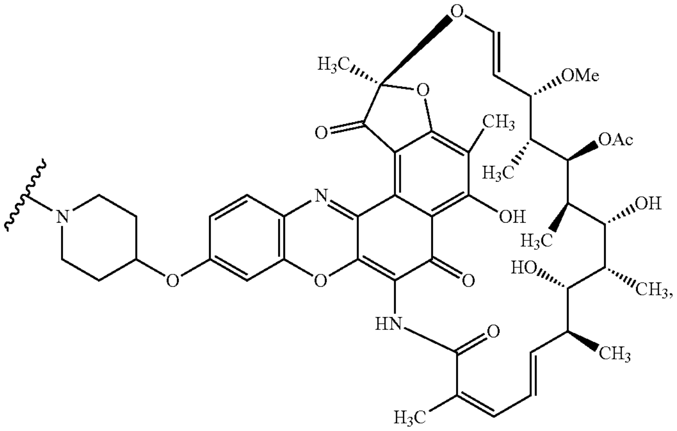

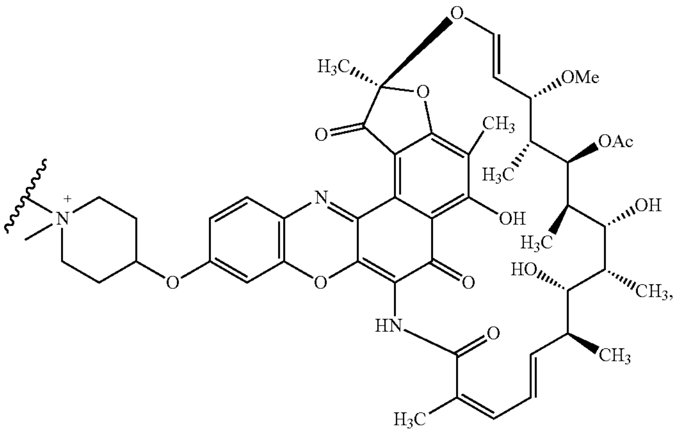

-continued
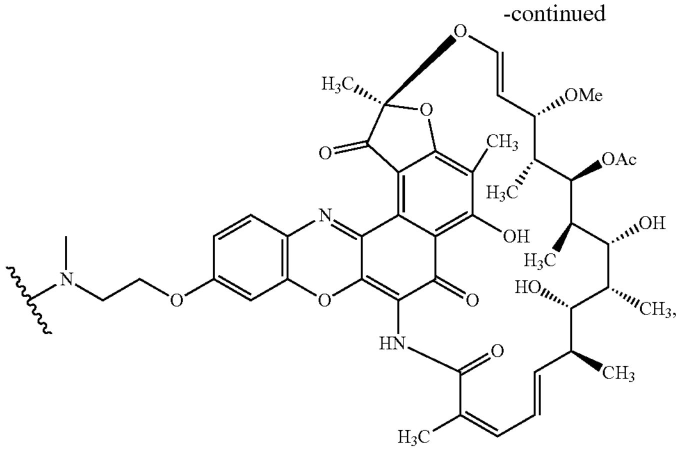
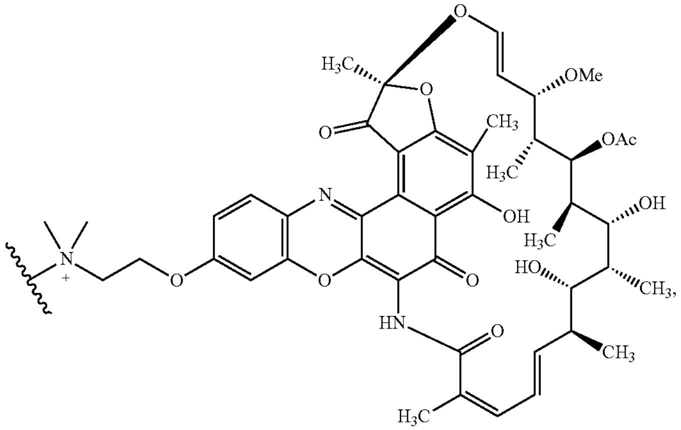
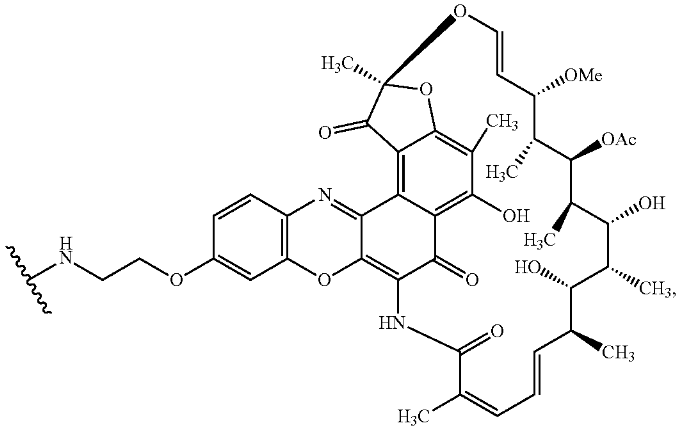
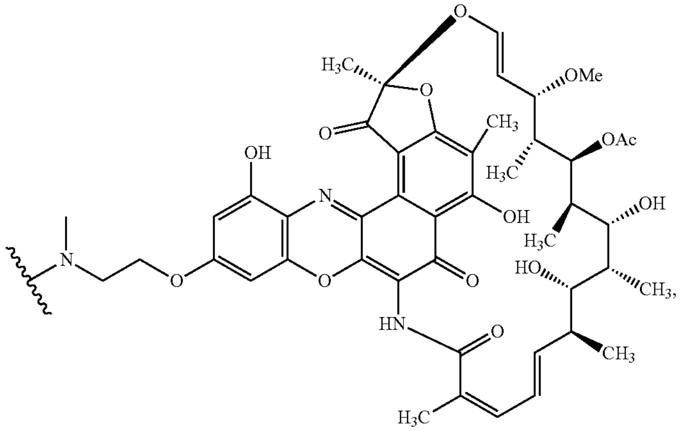

-continued
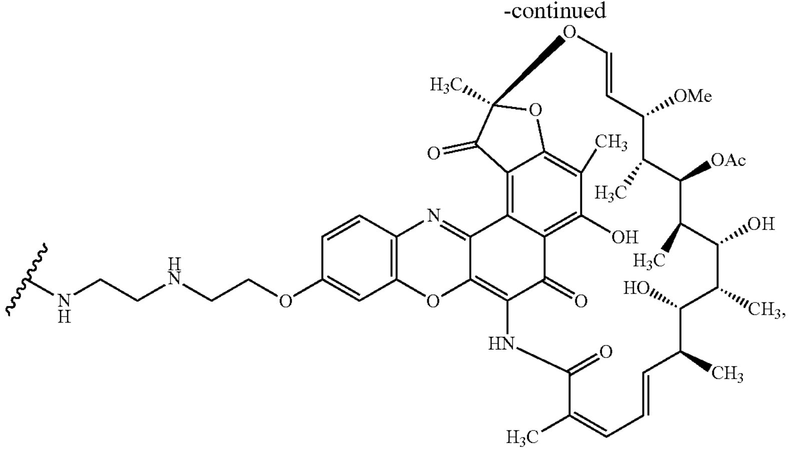
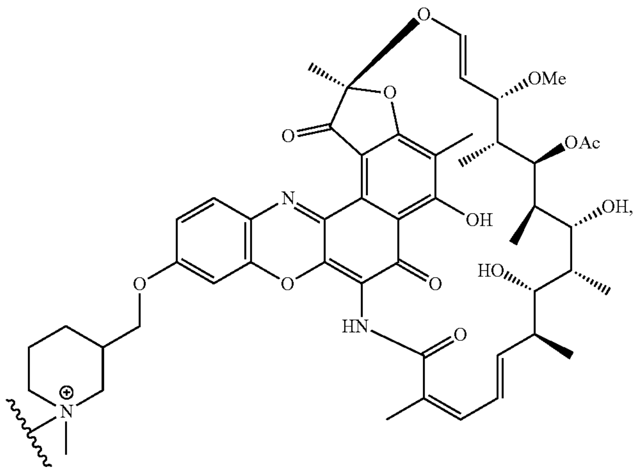
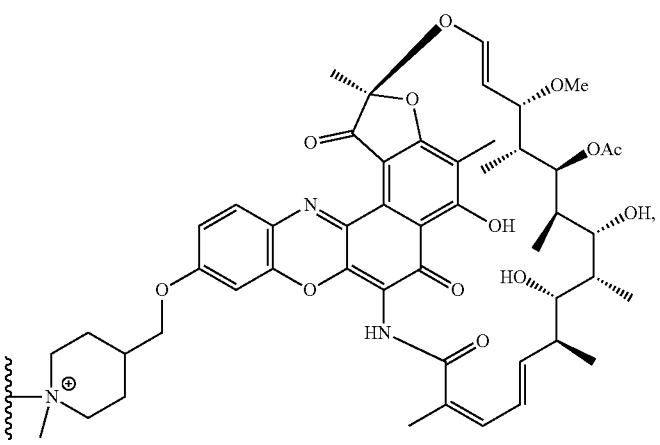

-continued
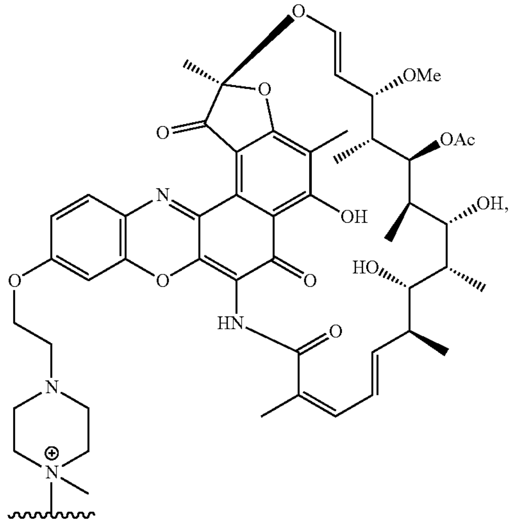
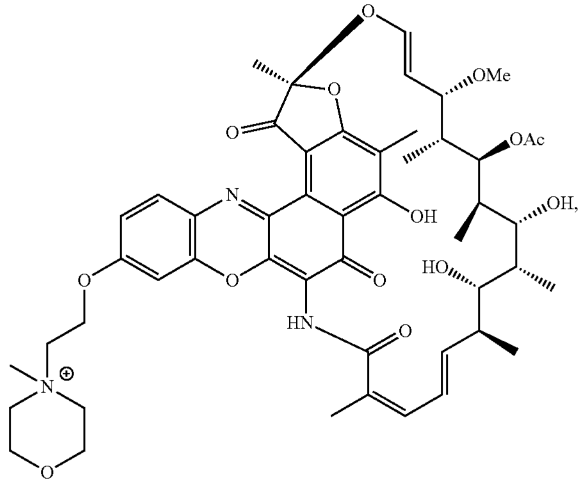
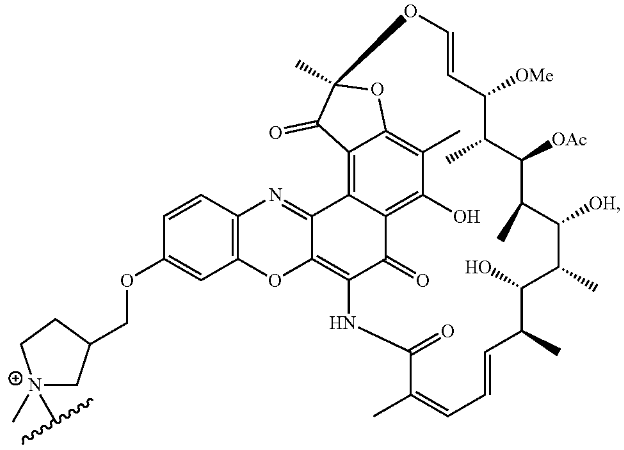
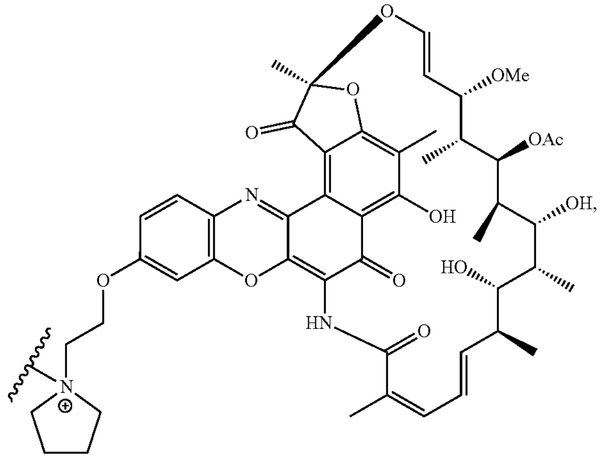

-continued
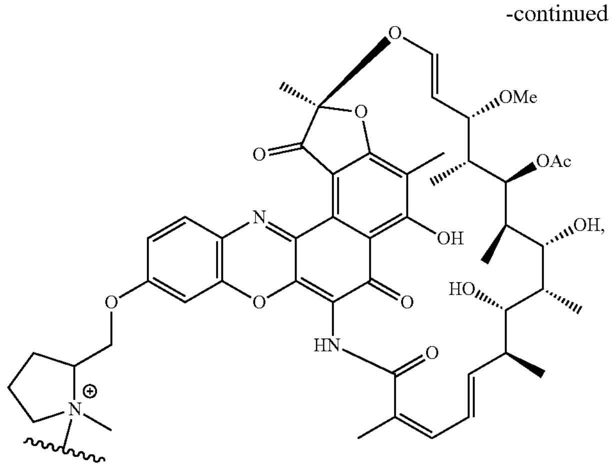
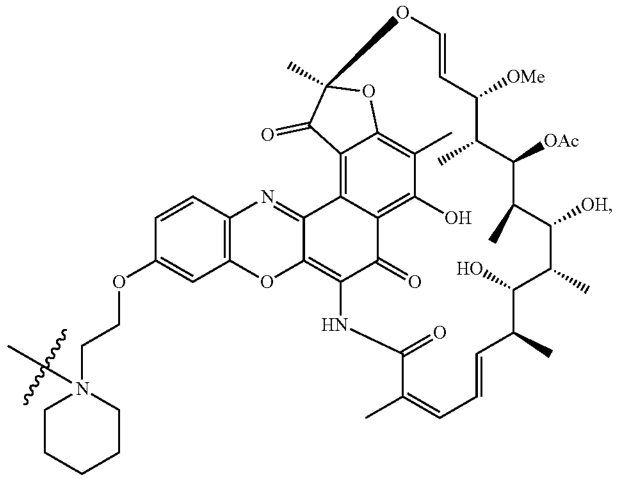
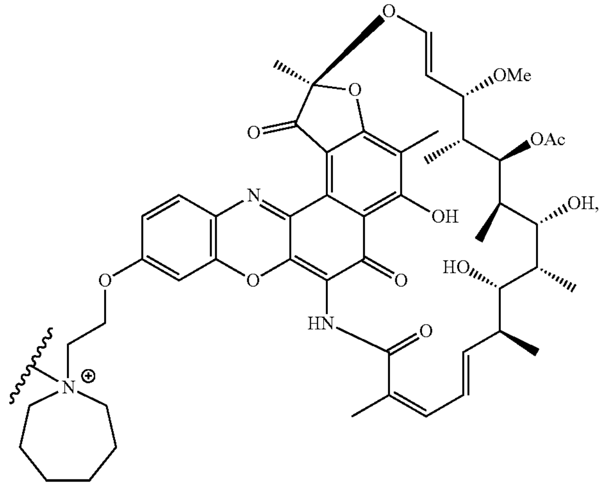
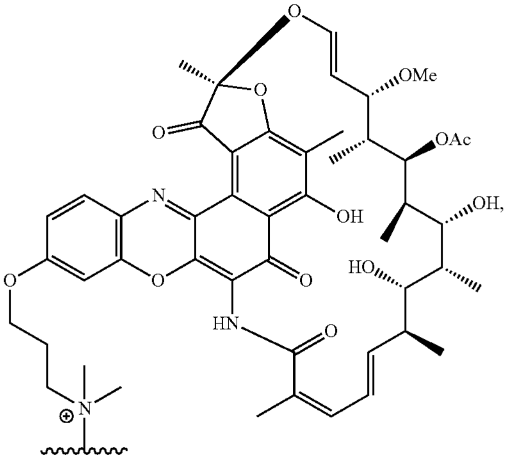

-continued
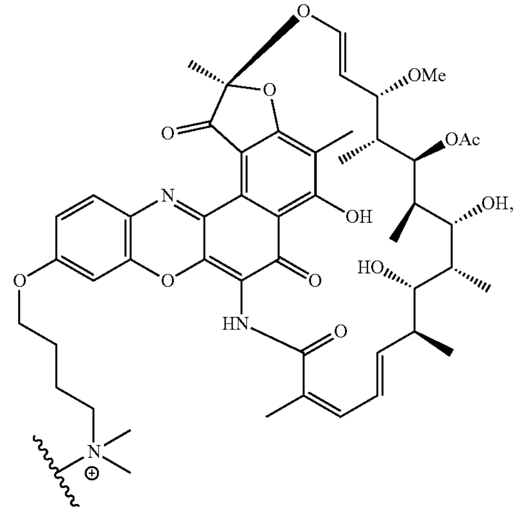
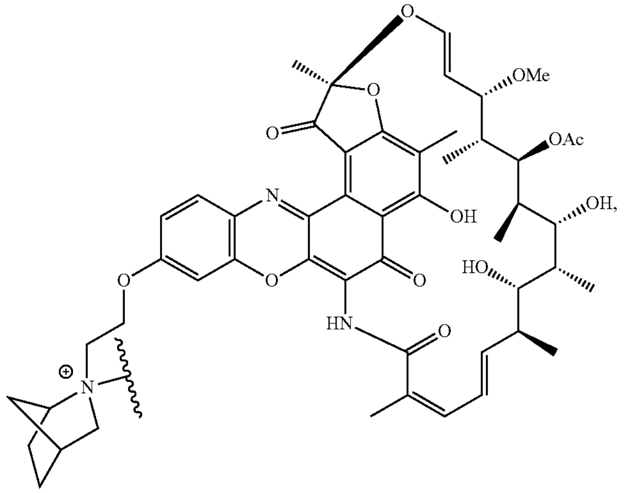
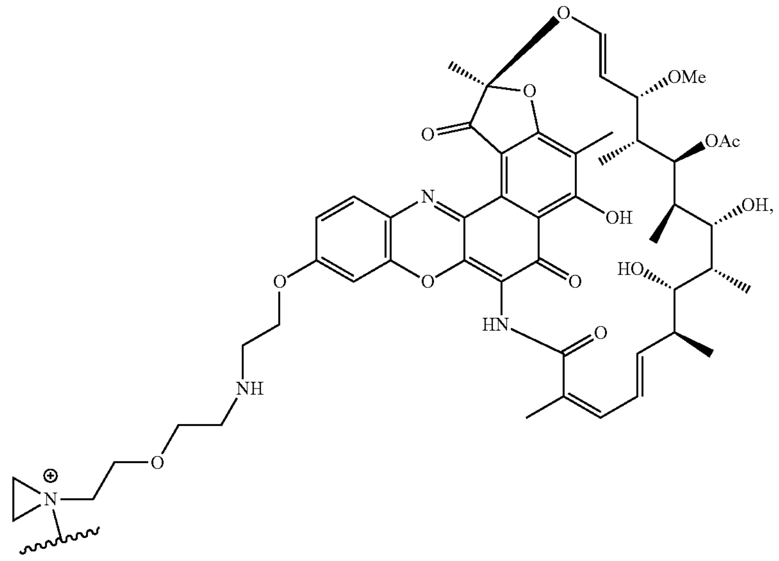
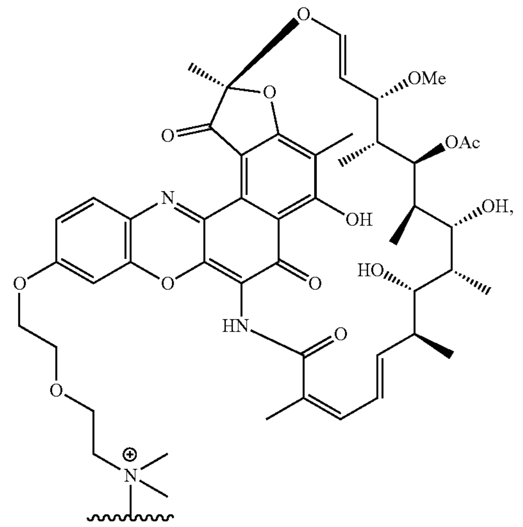
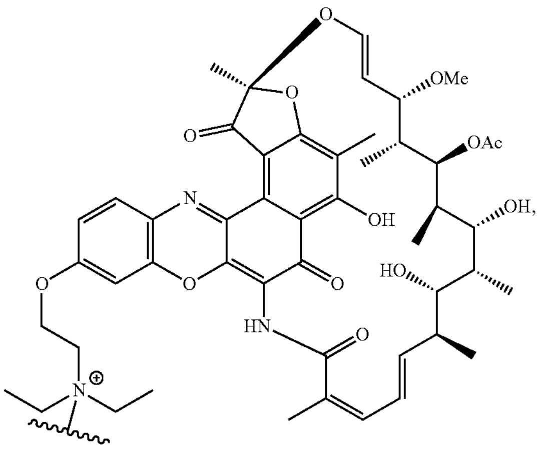

-continued
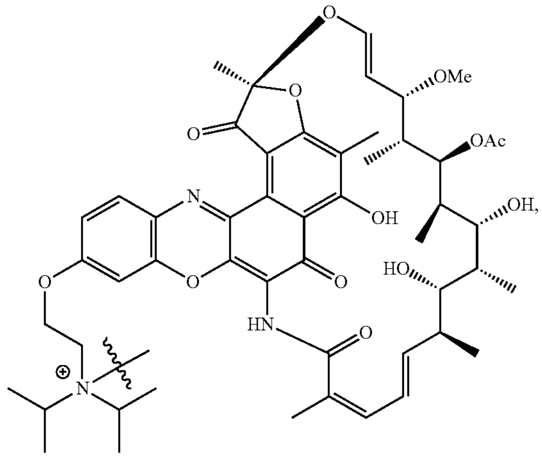
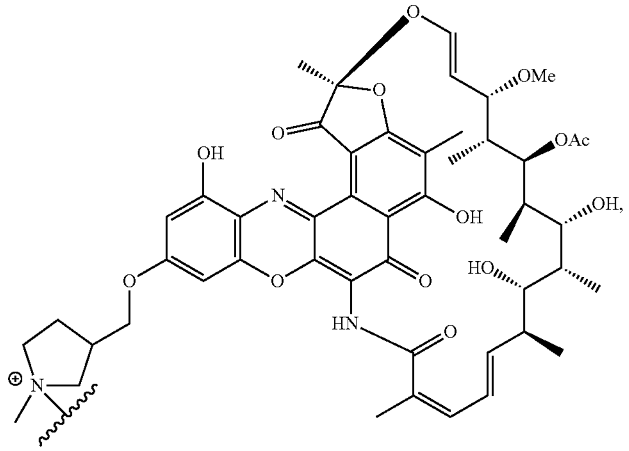
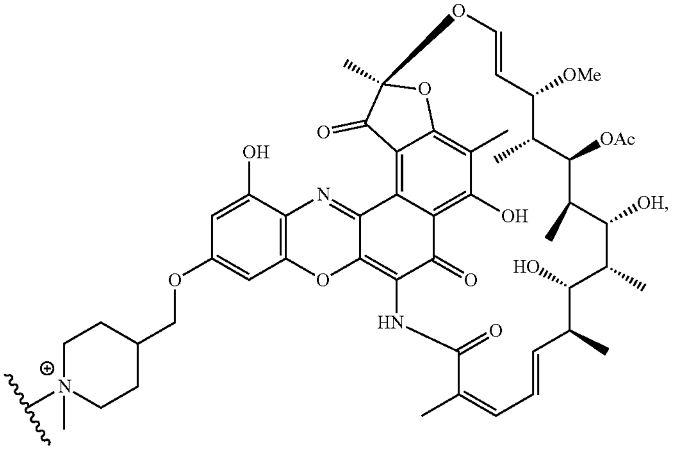

-continued
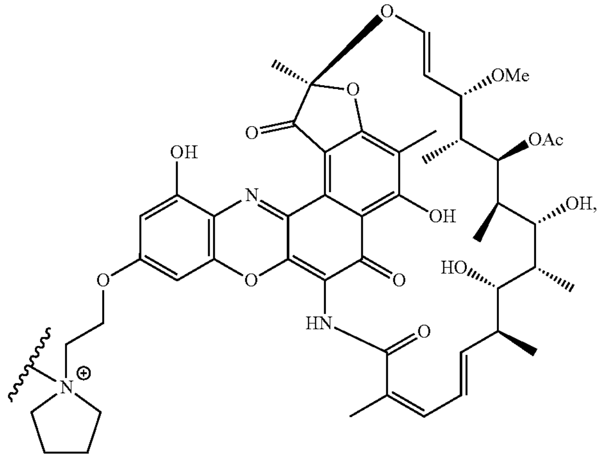
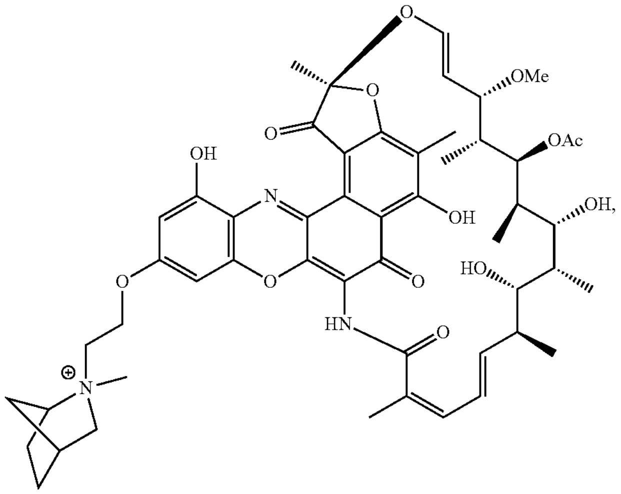
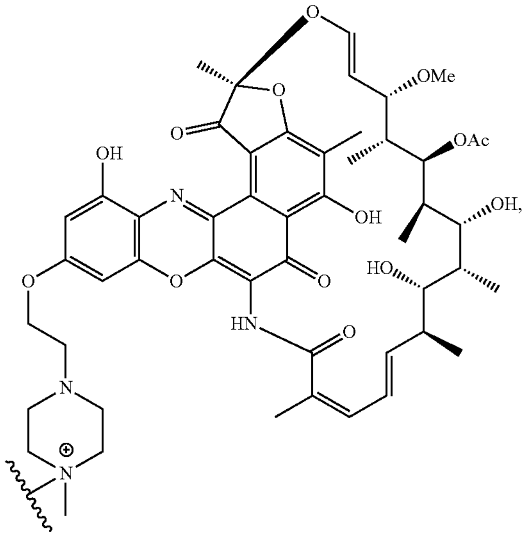
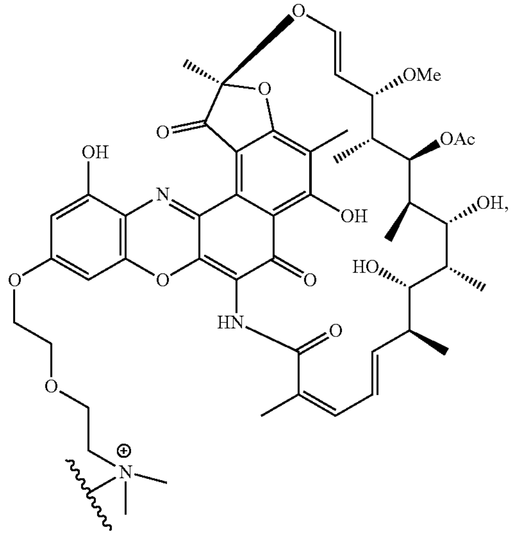
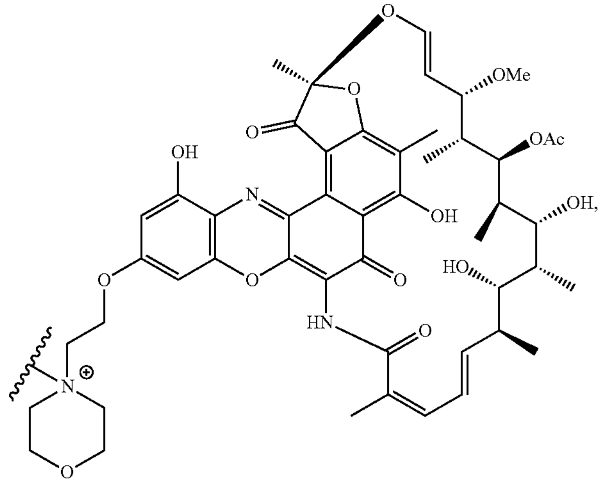

-continued
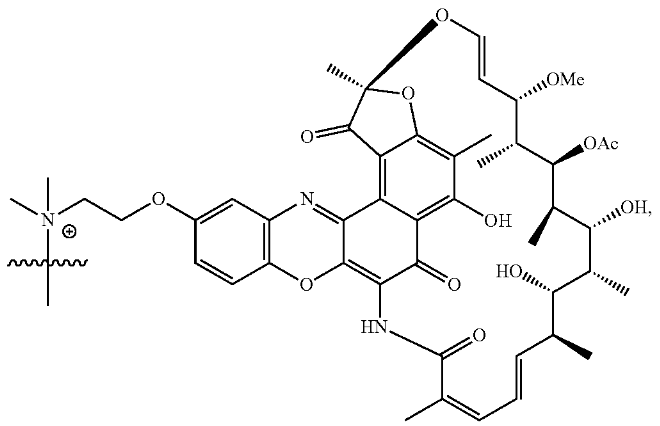
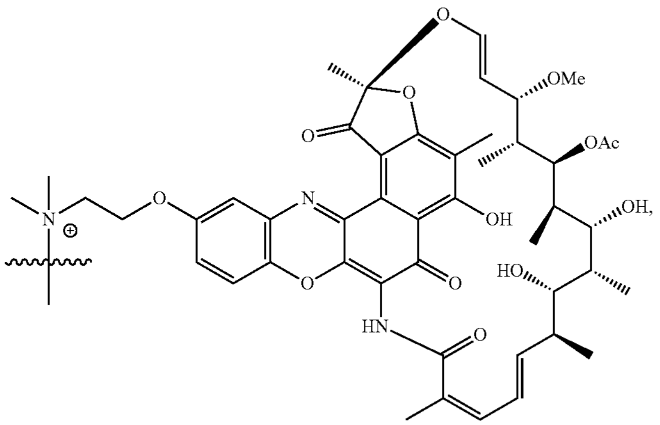
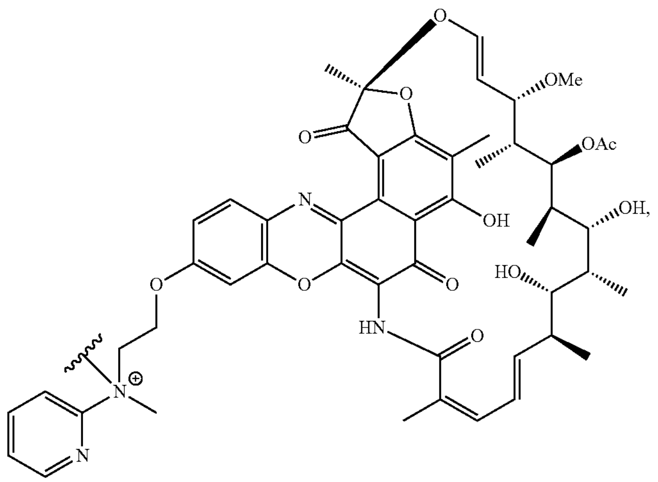

-continued
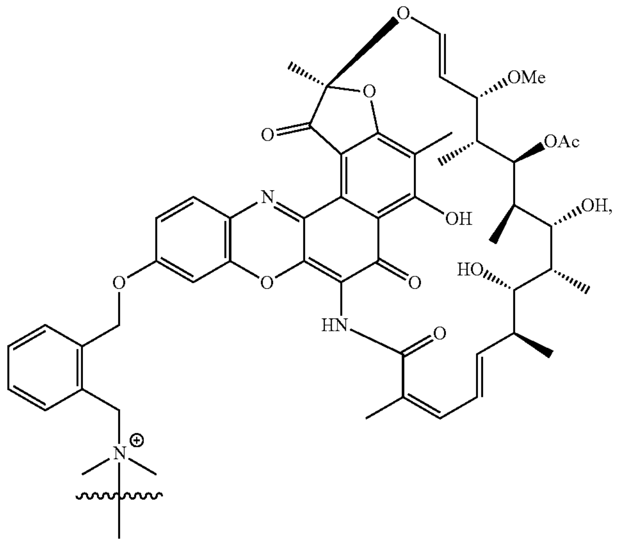
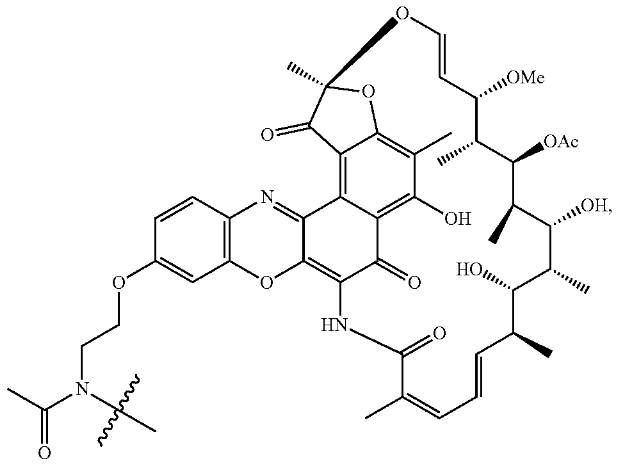
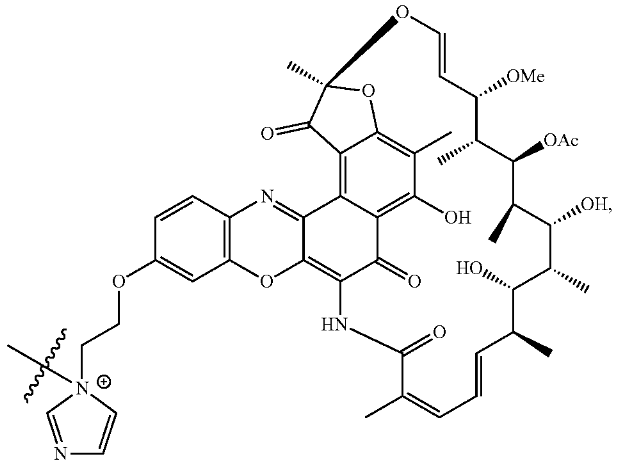

-continued
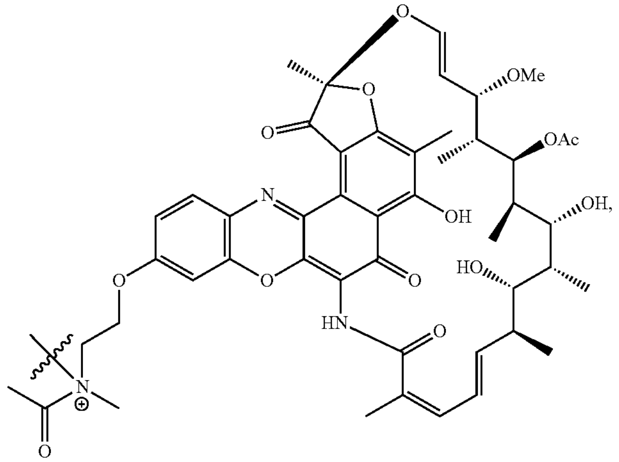
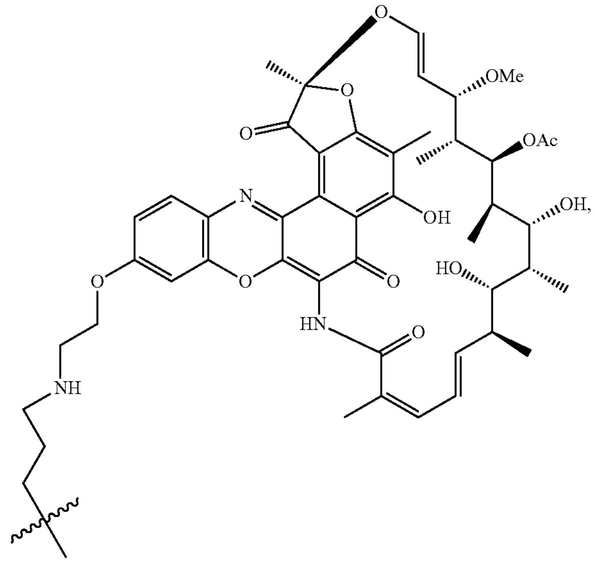
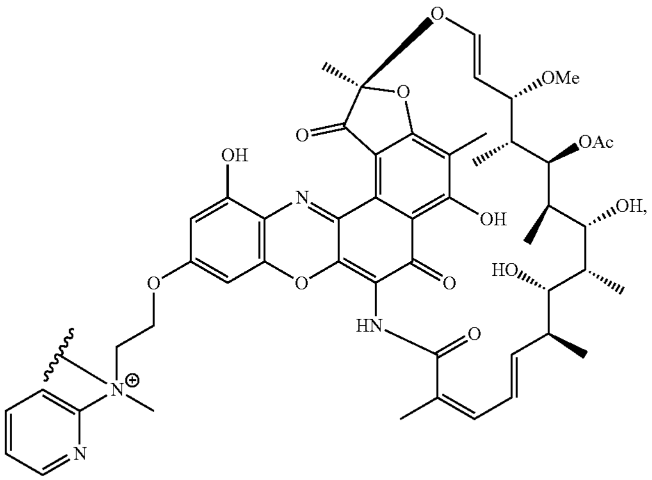

-continued
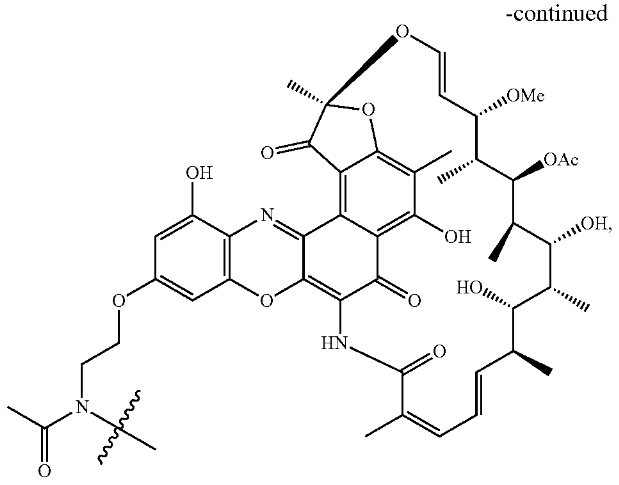
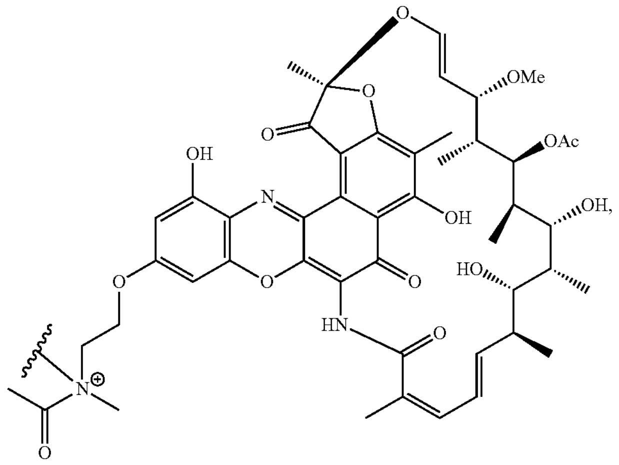
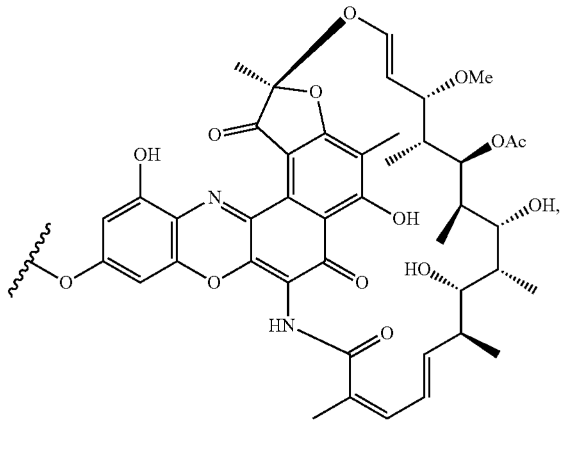

-continued
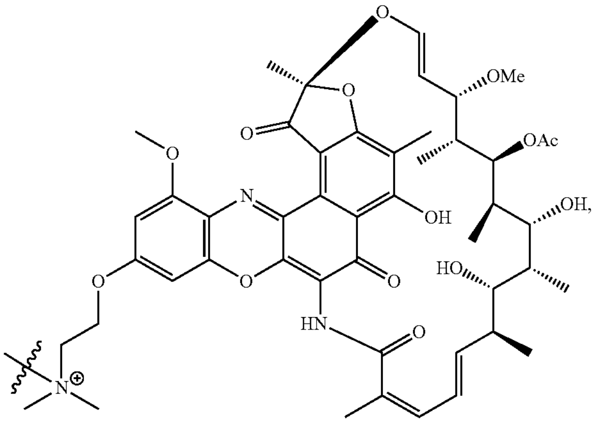
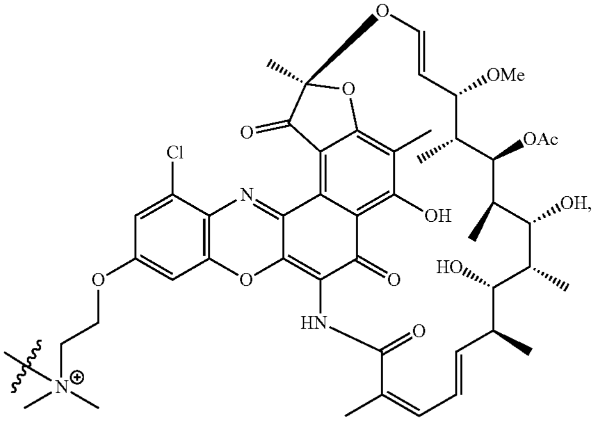
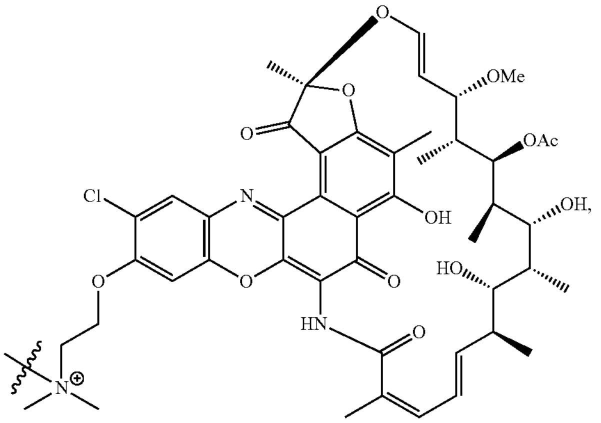
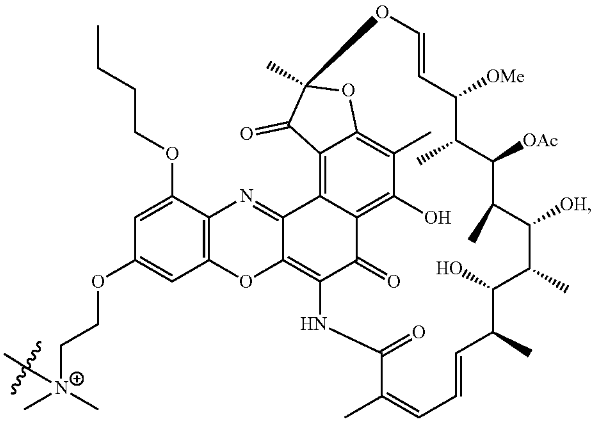

-continued
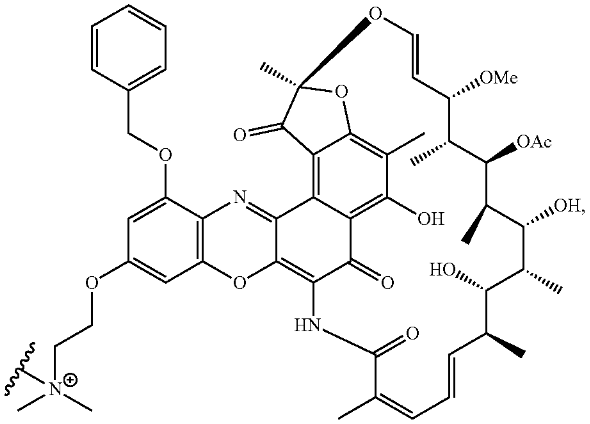
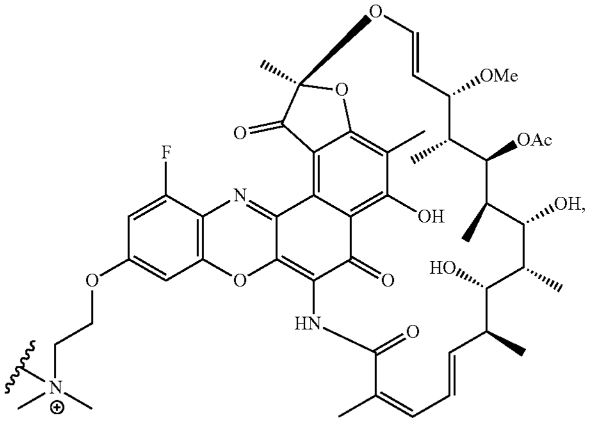
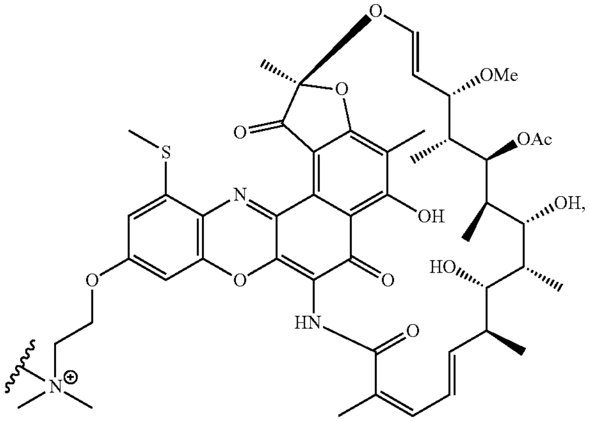
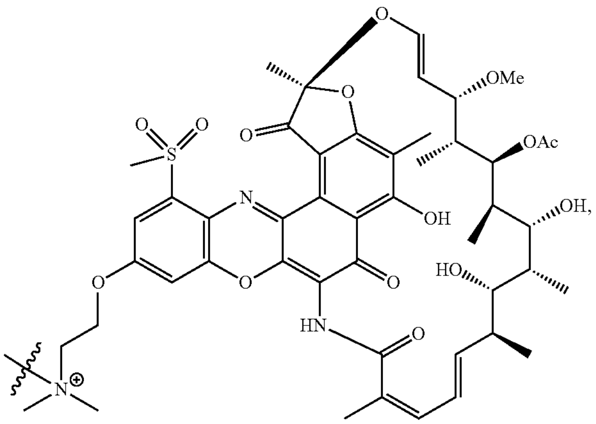

-continued
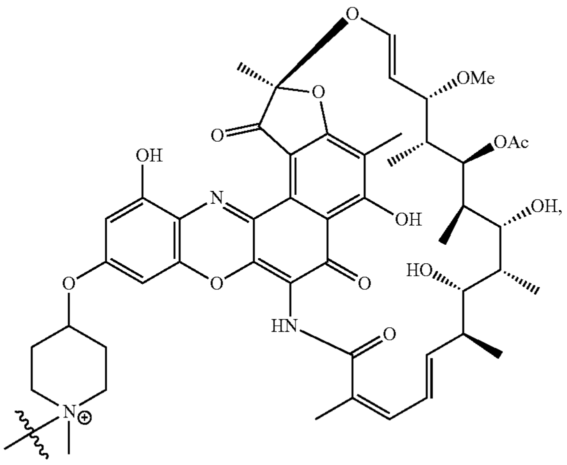
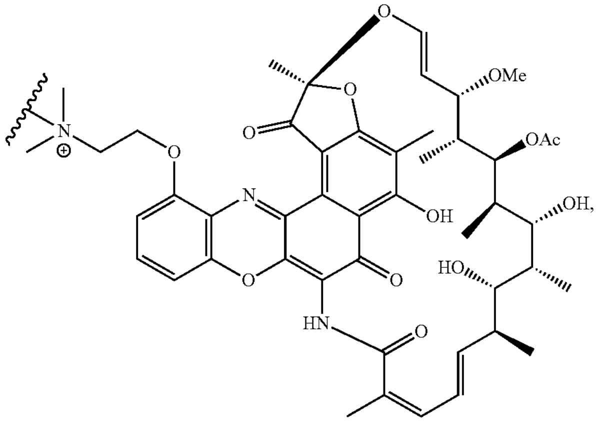
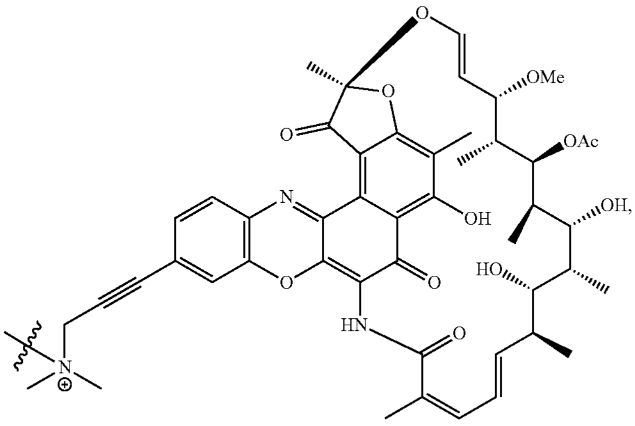
and

-continued

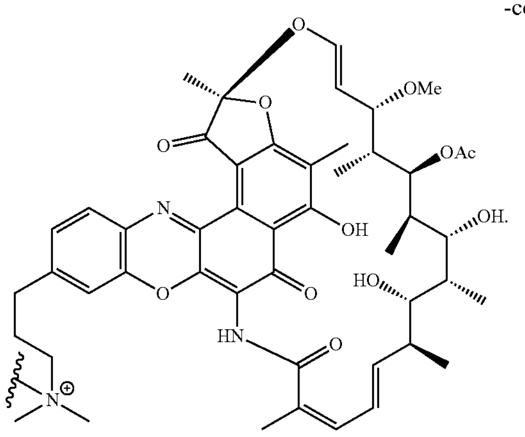

In one embodiment, the payload has the structure selected from:

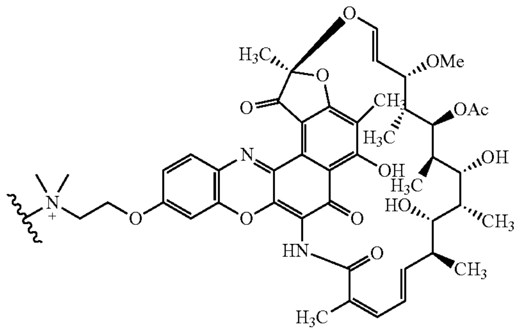

and

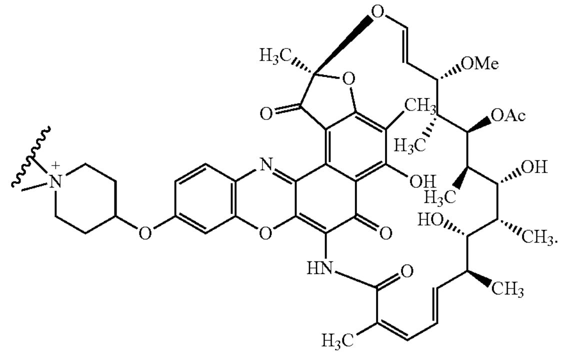

In one embodiment, the payload is conjugated through a linker, the linker having the structure:

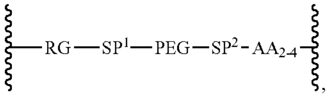

wherein

RG is selected from a maleimide, a N-hydroxysuccinimide, or a succinimide;

$SP^1$ and $SP^2$ are independently absent or a spacer group selected from the group consisting of

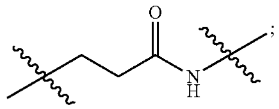 [SMILES: *CCC(=O)N*]

$C_{1-6}$ alkyl, —NH—, —C(O)—, —$CH_2$—$CH_2$—C(O)—NH—, —$(CH)_u$—C(O)—NH—, (—$CH_2$—$CH_2$—O$)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

$AA_{2-4}$ is a peptide unit comprising from 2 to 4 amino acids, and

PEG is a polyethylene glycol chain comprising between 1 and 30 polyethylene glycol residues.

In one embodiment, $AA_{2-4}$ is a dipeptide selected from valine-citrulline; citrulline-valine; valine-alanine; alanine-valine; valine-glycine, or glycine-valine.

In one embodiment, $AA_{2-4}$ is valine-citrulline.

In one embodiment, SP is

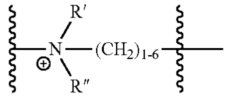

and R' and R" are each a $C_{1-6}$ alkyl.

In one embodiment, SP is

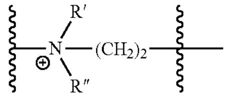

and R' and R" are each methyl.

In one embodiment, $SP^1$ and $SP^2$ are each

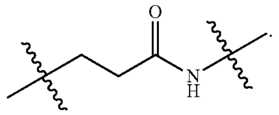 [SMILES: *CCC(=O)N*]

In one embodiment, PEG comprises 8 polyethylene glycol units.

In one embodiment, the payload is conjugated through a linker having the structure:

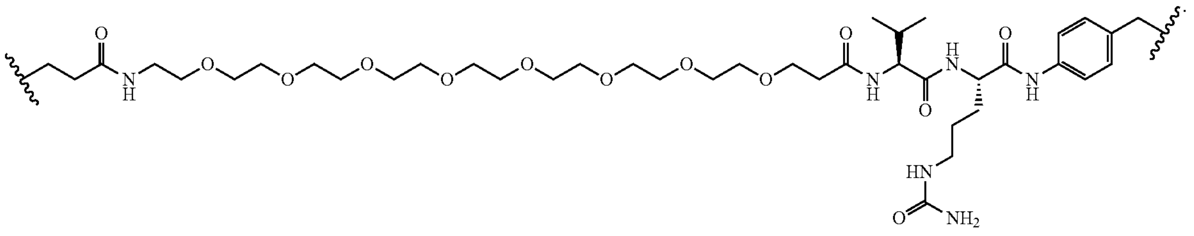 [SMILES: *CCC(=O)NCCOCCOCCOCCOCCOCCOCCOCCOCCC(=O)N[C@H](C(=O)N[C@@H](CCCNC(N)=O)C(=O)Nc1ccc(C*)cc1)C(C)C]

In one embodiment, the payload is conjugated through a linker, the linker-payload having the structure:

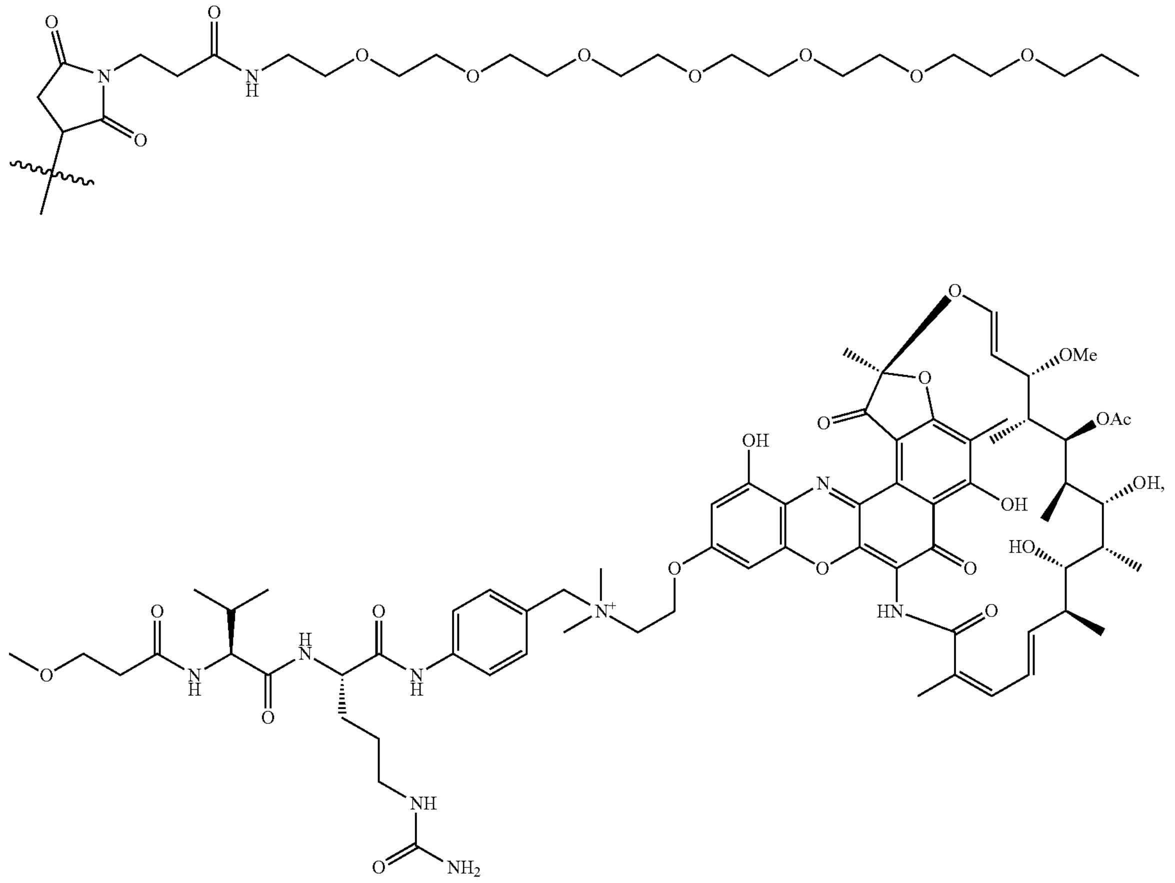

wherein the

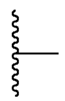

is the bond to the antibody or the antigen-binding fragment thereof.

In one embodiment, the payload is conjugated through a linker, the linker-payload having the structure:

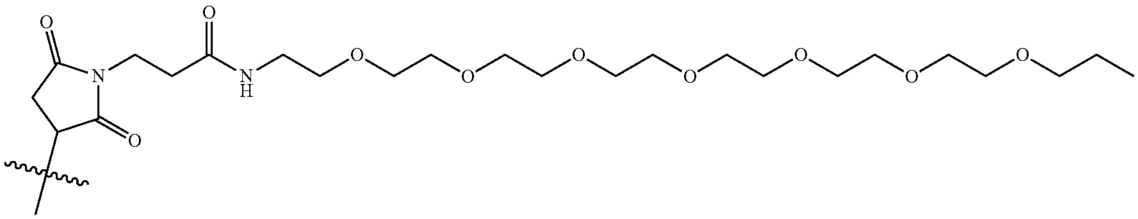
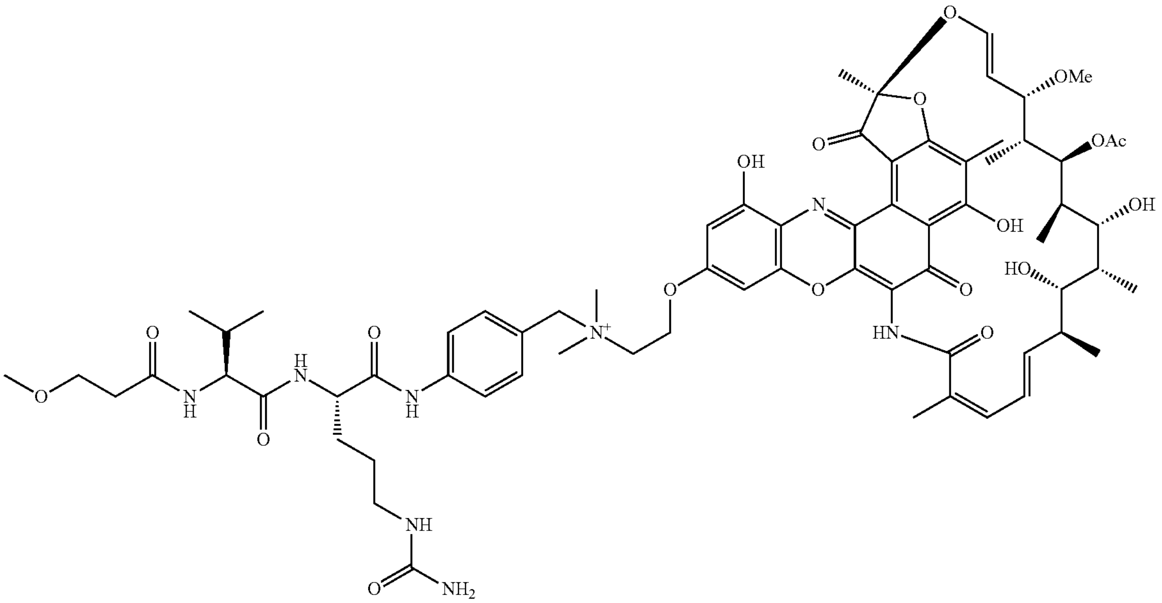
wherein the
is the bond to the antibody or the antigen-binding fragment thereof.
In one embodiment, the payload is conjugated through a linker, the linker-payload having the structure:
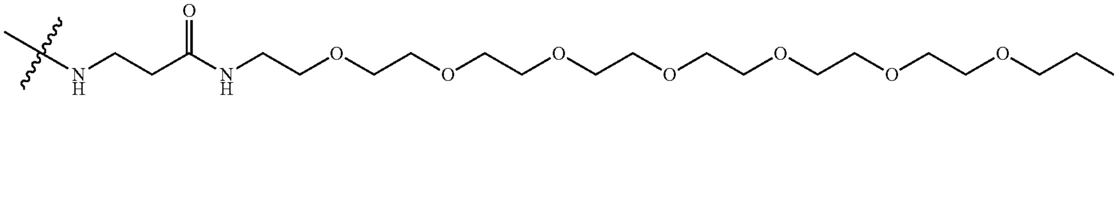

-continued
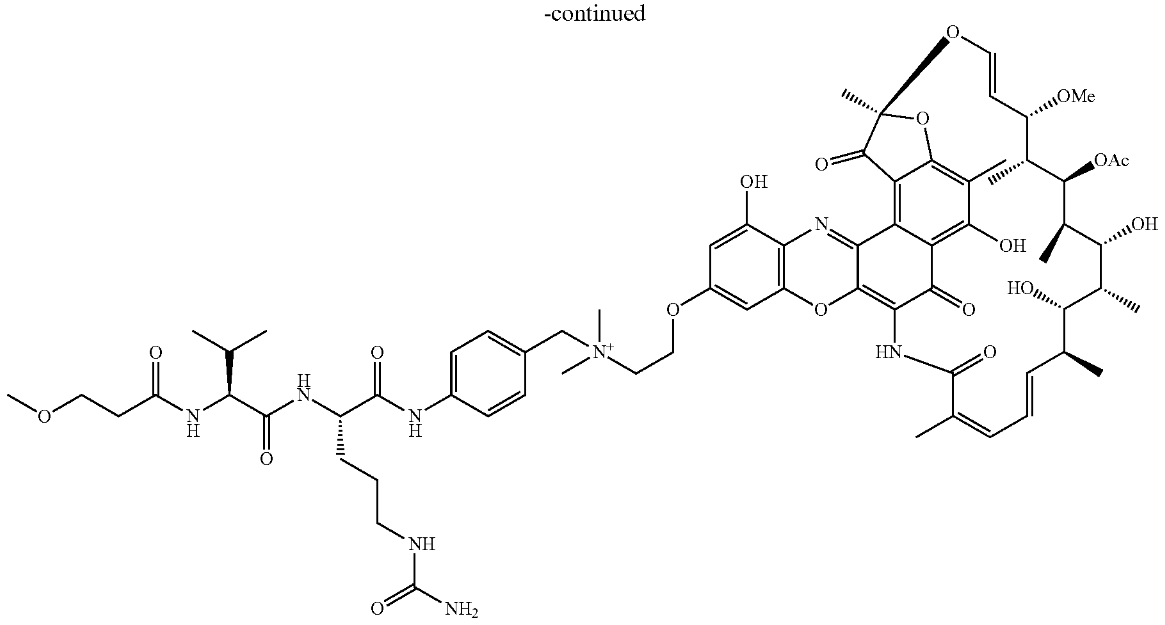
wherein the
is the bond to the antibody or the antigen-binding fragment thereof.
In one embodiment, the payload is conjugated through a linker, the linker-payload having the structure:
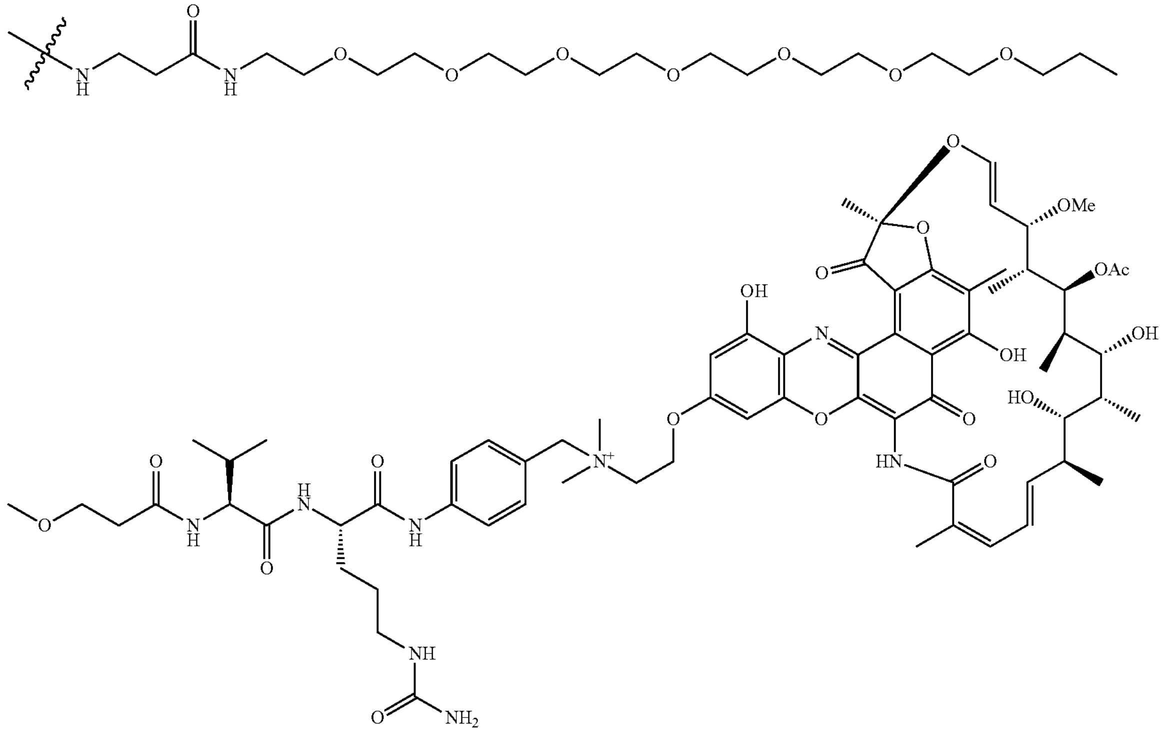

wherein the

is the bond to the antibody or the antigen-binding fragment thereof.

In one embodiment, the antibody, or the antigen-binding fragment thereof, that binds macrophage scavenger receptor 1 (MSR1) comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In some embodiments, the antibody, or antigen-binding fragment thereof, binds MSR1. In one embodiment, the anti-MSR1 antibody, or the antigen-binding fragment thereof, comprises: (a) the complementarity determining regions (CDRs) of a heavy chain variable region (HCVR) comprising an amino acid sequence as set forth in Table 9; and (b) the CDRs of a light chain variable region (LCVR) comprising an amino acid sequence as set forth in Table 9.

In one embodiment, the anti-MSR1 antibody, or the antigen-binding fragment thereof, comprises:

(i) a HCDR1 domain comprising an amino acid sequence selected from the group consisting of SEQ ID NOs: 4, 36, 52, 92, and 284;

(ii) a HCDR2 domain comprising an amino acid sequence selected from the group consisting of SEQ ID NOs: 6, 38, 54, 94, and 286;

(iii) a HCDR3 domain comprising an amino acid sequence selected from the group consisting of SEQ ID NOs: 8, 40, 56, 96, and 288;

(iv) a LCDR1 domain comprising an amino acid sequence selected from the group consisting of SEQ ID NOs: 12, 44, 60, 100, and 292;

(v) a LCDR2 domain comprising an amino acid sequence selected from the group consisting of SEQ ID NOs: 14, 46, 62, 102, and 294; and (vi) a LCDR3 domain comprising an amino acid sequence selected from the group consisting of SEQ ID NOs: 16, 48, 64, 104, and 296.

In one embodiment, the anti-MSR1 antibody, or the antigen-binding fragment thereof, comprises (i) a HCDR1 domain comprising an amino acid sequence of SEQ ID NO: 52;

(ii) a HCDR2 domain comprising an amino acid sequence of SEQ ID NO: 54;

(iii) a HCDR3 domain comprising an amino acid sequence of SEQ ID NO: 56;

(iv) a LCDR1 domain comprising an amino acid sequence of SEQ ID NO: 60;

(v) a LCDR2 domain comprising an amino acid sequence of SEQ ID NO: 62; and (vi) a LCDR3 domain comprising an amino acid sequence of SEQ ID NO: 64.

In one embodiment, the anti-MSR1 antibody, or the antigen-binding fragment thereof, comprises a N297Q mutation.

In some embodiments, the antibody, or antigen-binding fragment thereof, binds WTAα. In one embodiment, the anti-WTAα antibody, or the antigen-binding fragment thereof, comprises: (a) the complementarity determining regions (CDRs) of a heavy chain variable region (HCVR) comprising an amino acid sequence as set forth in Table 2A; and (b) the CDRs of a light chain variable region (LCVR) comprising an amino acid sequence as set forth in Table 2A.

In one embodiment, the anti-WTAα antibody, or an antigen-binding fragment thereof, comprises:

(i) a HCDR1 domain comprising an amino acid sequence selected from the group consisting of SEQ ID NOs: 470, 476, 482, and 488;

(ii) a HCDR2 domain comprising an amino acid sequence selected from the group consisting of SEQ ID NOs: 471, 477, 483, and 489;

(iii) a HCDR3 domain comprising an amino acid sequence selected from the group consisting of SEQ ID NOs: 472, 478, 484, and 490;

(iv) a LCDR1 domain comprising an amino acid sequence selected from the group consisting of SEQ ID NOs: 467, 473, 479, and 485;

(v) a LCDR2 domain comprising an amino acid sequence selected from the group consisting of SEQ ID NOs: 468, 474, 480, and 486; and (vi) a LCDR3 domain comprising an amino acid sequence selected from the group consisting of SEQ ID NOs: 469, 475, 481, and 487.

In some embodiments, the antibody, or antigen-binding fragment thereof, binds WTAβ. In one embodiment, the anti-WTAβ antibody, or the antigen-binding fragment thereof, comprises: (a) the complementarity determining regions (CDRs) of a heavy chain variable region (HCVR) comprising an amino acid sequence as set forth in Table 2B; and (b) the CDRs of a light chain variable region (LCVR) comprising an amino acid sequence as set forth in Table 2B.

In one embodiment, the anti-WTAβ antibody, or an antigen-binding fragment thereof, comprises:

(i) a HCDR1 domain comprising an amino acid sequence selected from the group consisting of SEQ ID NOs: 502, 508, 514, 520, 526, 532, 538, 544, 550, 556, 562, 568, and 574;

(ii) a HCDR2 domain comprising an amino acid sequence selected from the group consisting of SEQ ID NOs: 503, 509, 515, 521, 527, 533, 539, 545, 551, 557, 563, 569, and 575;

(iii) a HCDR3 domain comprising an amino acid sequence selected from the group consisting of SEQ ID NOs: 504, 510, 516, 522, 528, 534, 540, 546, 552, 558, 564, 570, 576, and 584;

(iv) a LCDR1 domain comprising an amino acid sequence selected from the group consisting of SEQ ID NOs: 499, 505, 511, 517, 523, 529, 535, 541, 547, 553, 559, 565, and 571;

(v) a LCDR2 domain comprising an amino acid sequence selected from the group consisting of SEQ ID NOs: 500, 506, 512, 518, 524, 530, 536, 542, 548, 554, 560, 566, and 572; and (vi) a LCDR3 domain comprising an amino acid sequence selected from the group consisting of SEQ ID NOs: 501, 507, 513, 519, 525, 531, 537, 543, 549, 555, 561, 567, and 573.

In some embodiments, the anti-WTA antibody, or the antigen-binding fragment thereof, comprises a V205C mutation.

In one embodiment, the anti-WTA antibody, or the antigen-binding fragment thereof, is derived from antibody 4497 described in US Patent Application Publication 20140356375 (which is incorporated herein by reference in its entirety). In one embodiment, the anti-WTA antibody is derived from antibody 4497 and further comprises a V205C mutation in the light chain.

In one embodiment, the anti-WTA antibody, or the antigen-binding fragment thereof, comprises the HCDR1-HCDR2-HCDR3-LCDR1-LCDR2-LCDR3 of SEQ ID Nos: 568-569-570-565-566-567.

In some embodiments, the anti-WTA antibody or antigen binding fragment thereof comprises three heavy chain complementarity determining regions (HCDR1, HCDR2, and HCDR3) within a heavy chain variable region (HCVR) amino acid sequence of SEQ ID NOs: 586; and three light chain complementarity determining regions (LCDR1, LCDR2, and LCDR3) within a light chain variable region (LCVR) amino acid sequence of SEQ ID NO: 585.

In some embodiments, the anti-WTA antibody or antigen binding fragment thereof comprises an HCVR amino acid sequence of SEQ ID NOs: 586; and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589. In some embodiments, the anti-WTA antibody, or the antigen-binding fragment thereof comprises a V205C mutation in the light chain.

In some embodiments, the antibody, or antigen-binding fragment thereof, binds Protein A. In one embodiment, the anti-Protein A antibody, or the antigen-binding fragment thereof, may comprise: (a) the complementarity determining regions (CDRs) of a heavy chain variable region (HCVR) comprising an amino acid sequence as set forth in Table 3A; and (b) the CDRs of a light chain variable region (LCVR) comprising an amino acid sequence as set forth in Table 3A.

In one embodiment, the anti-Protein A antibody, or the antigen-binding fragment thereof, may comprise:

(i) a HCDR1 domain comprising an amino acid sequence selected from the group consisting of SEQ ID NOs: 632, 652, and 672;

(ii) a HCDR2 domain comprising an amino acid sequence selected from the group consisting of SEQ ID NOs: 634, 654, and 674;

(iii) a HCDR3 domain comprising an amino acid sequence selected from the group consisting of SEQ ID NOs: 636, 656, and 676;

(iv) a LCDR1 domain comprising an amino acid sequence selected from the group consisting of SEQ ID NOs: 640, 660, and 680;

(v) a LCDR2 domain comprising an amino acid sequence selected from the group consisting of SEQ ID NOs: 642 and 662; and (vi) a LCDR3 domain comprising an amino acid sequence selected from the group consisting of SEQ ID NOs: 644, 664, and 683.

In some embodiments, the anti-Protein A antibody, or the antigen-binding fragment thereof, comprises a H435R and a Y436F mutation (EU numbering) in the heavy chain Fc.

In one embodiment, the anti-Protein A antibody or antigen binding fragment thereof comprises three heavy chain complementarity determining regions (HCDR1, HCDR2, and HCDR3) within a heavy chain variable region (HCVR) amino acid sequence of SEQ ID NOs: 630; and three light chain complementarity determining regions (LCDR1, LCDR2, and LCDR3) within a light chain variable region (LCVR) amino acid sequence of SEQ ID NO: 638. In one embodiment, the anti-Protein A antibody or antigen binding fragment thereof comprises a set of six CDRs (HCDR1-HCDR2-HCDR3-LCDR1-LCDR2-LCDR3) comprising SEQ ID NOs: 632-634-636-640-642-644.

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668. In one embodiments, the anti-Protein A antibody, further comprises a H435R and a Y436F mutation (EU numbering) in the heavy chain Fc. In one embodiment, anti-Protein A antibody further comprises a C103S mutation in the light chain. In one embodiment, the anti-Protein A antibody, or antigen-binding fragment thereof, is conjugated to a compound of the present disclosure at light chain position 103.

In various embodiments, the antibody, or antigen-binding fragment thereof, comprises a C103S mutation in the light chain.

The various embodiments, the antibody, or the antigen-binding fragment thereof, is conjugated to a compound of the present disclosure at position 103 of the light chain.

Exemplary Antibody-Drug Conjugates of the Disclosure

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

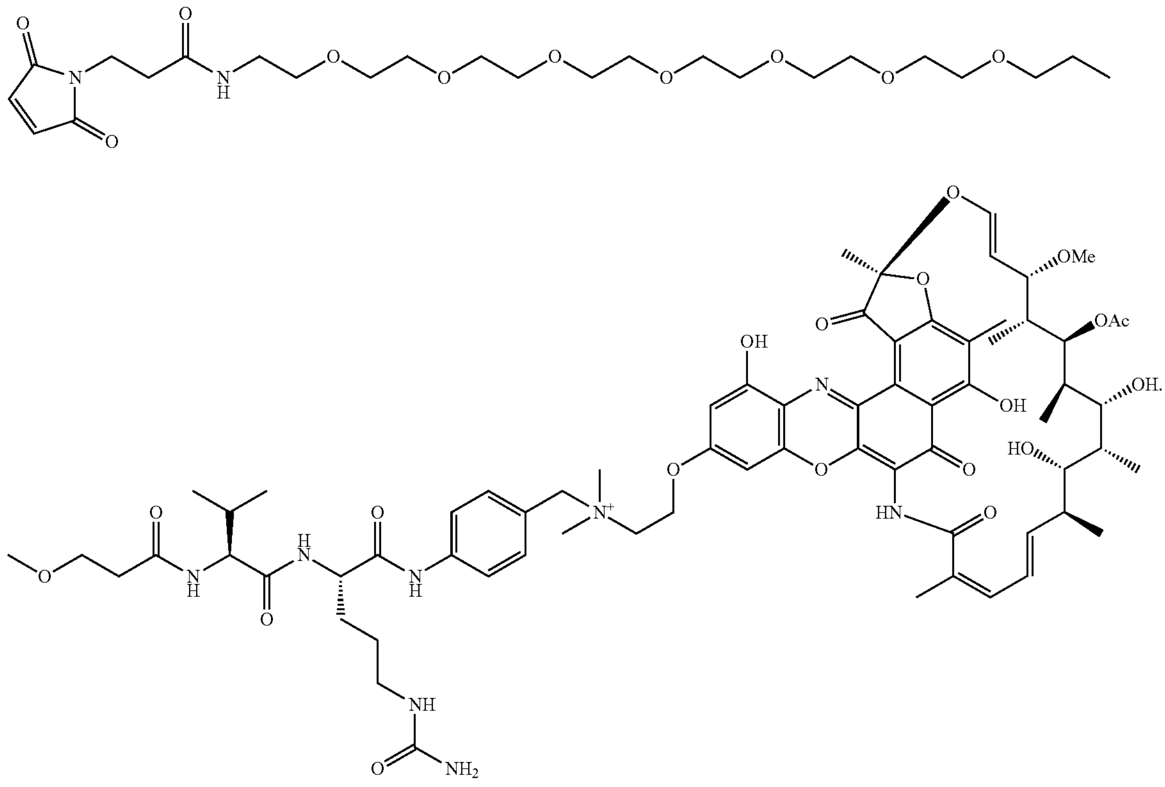
In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of
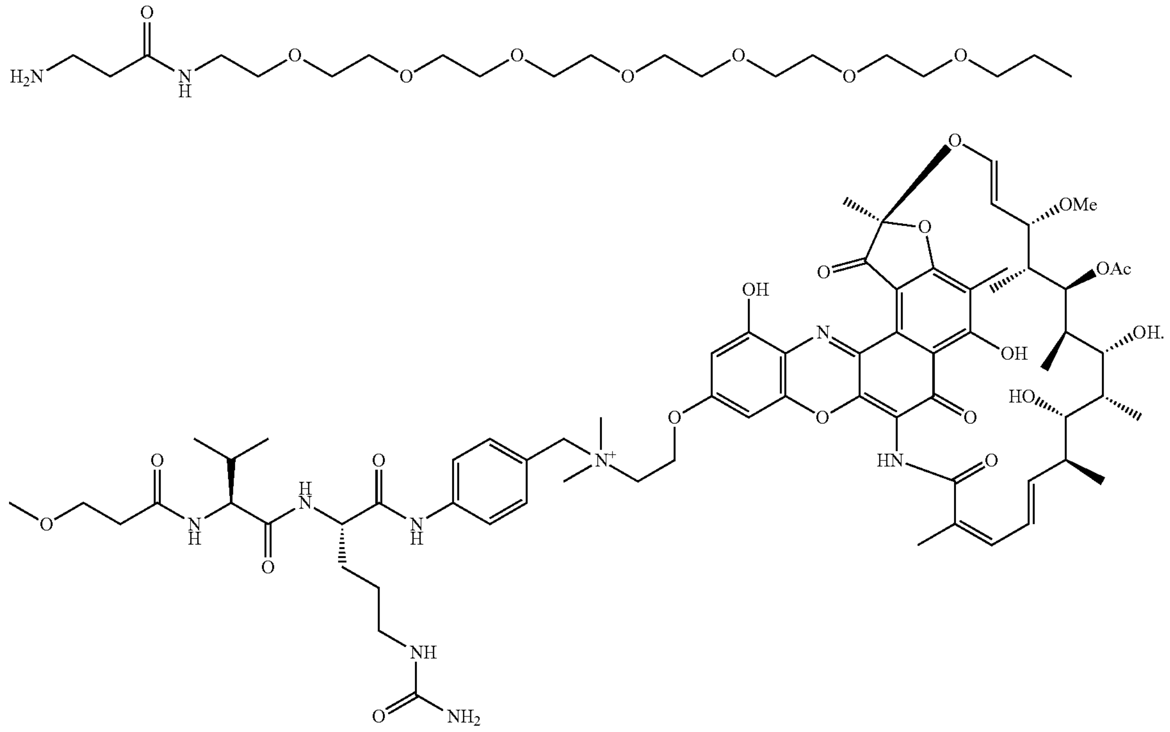

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

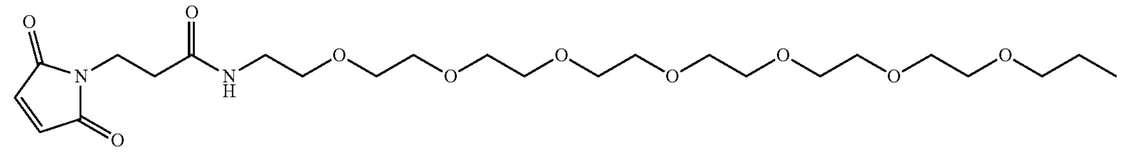

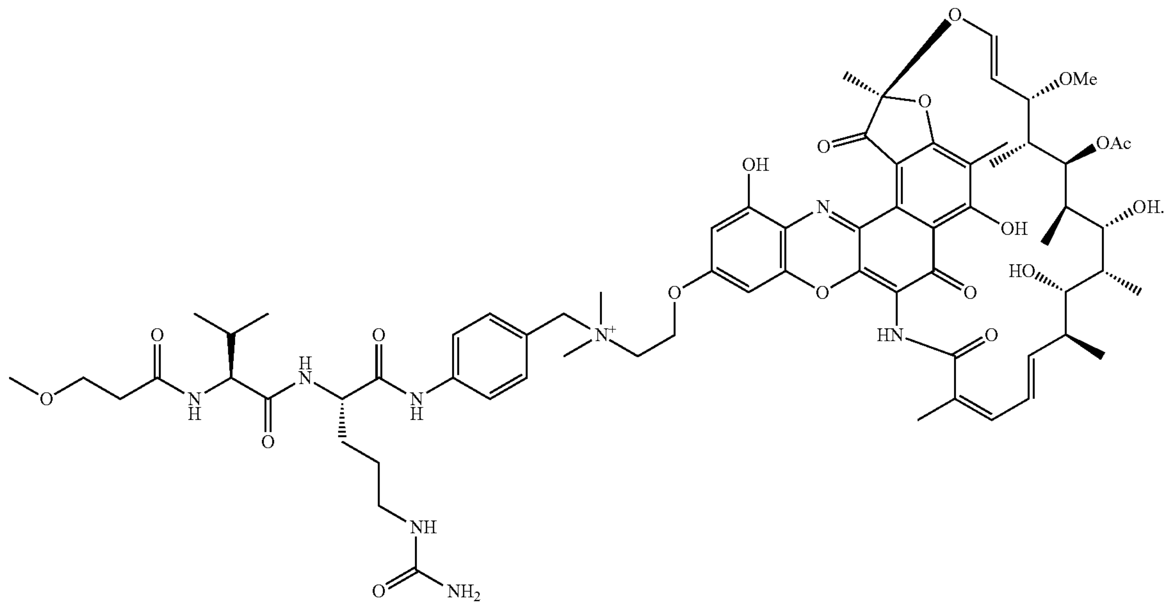

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

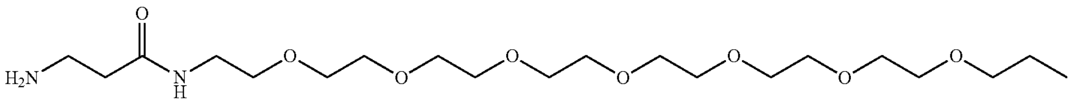

-continued

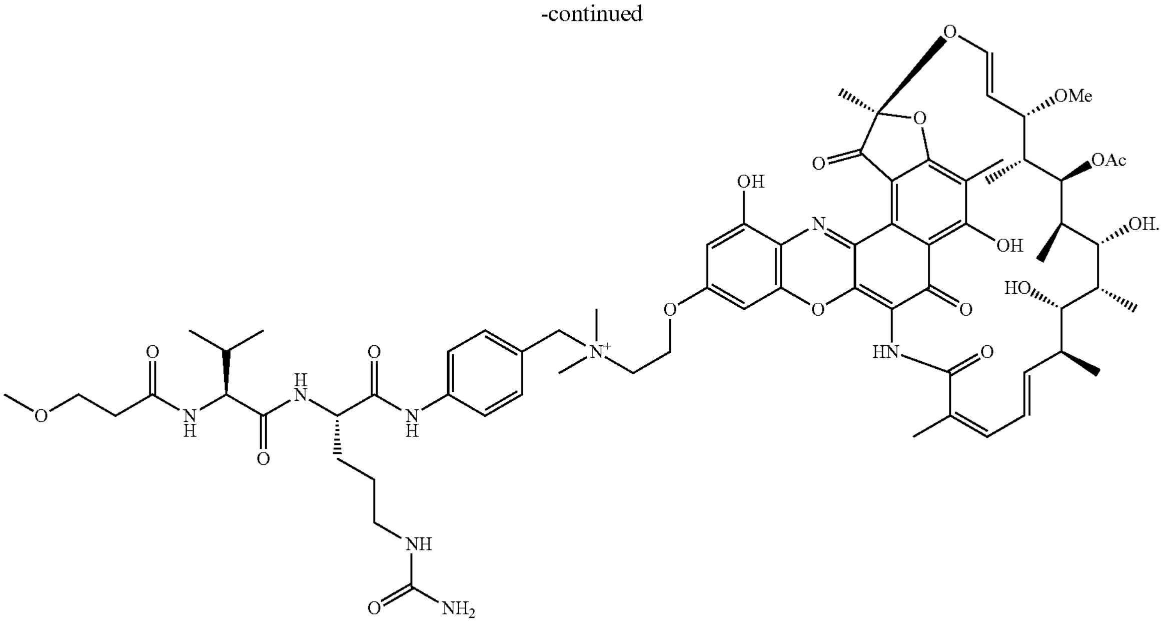

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

80

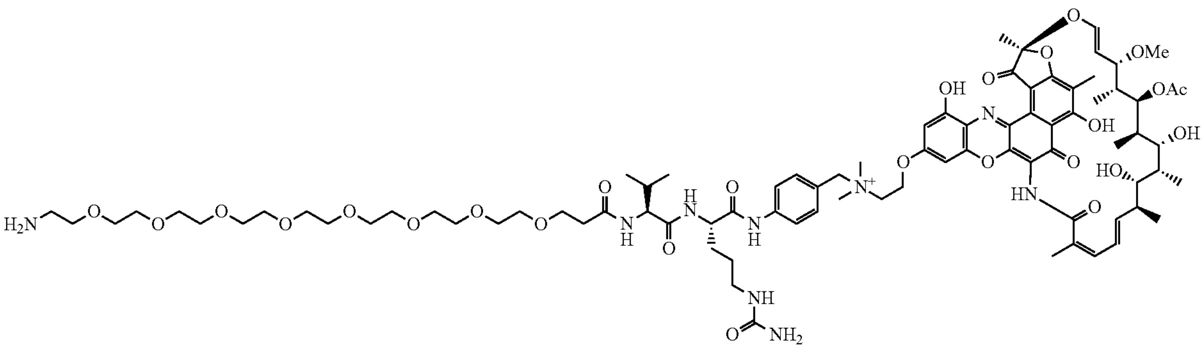

In one embodiment, the antibody-drug conjugate of the present disclosure comprises an anti-MSR1 antibody, or antigen-binding fragment thereof, comprising a set of six CDRs (HCDR1-HCDR2-HCDR3-LCDR1-LCDR2-LCDR3) comprising SEQ ID NOs: 52-54-56-60-62-64, and a N297Q mutation, said anti-MSR1 antibody, or antigen-binding fragment thereof, is conjugated to a compound having the structure of

82

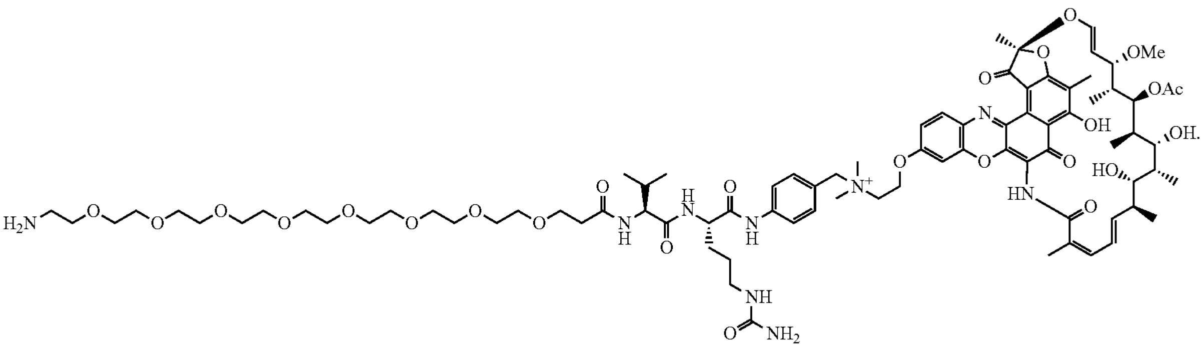

In some embodiments, the anti-MSR1 antibody or antigen binding fragment thereof comprises an HCVR amino acid sequence of SEQ ID NOs: 50; and an LCVR amino acid sequence of SEQ ID NO: 58.

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

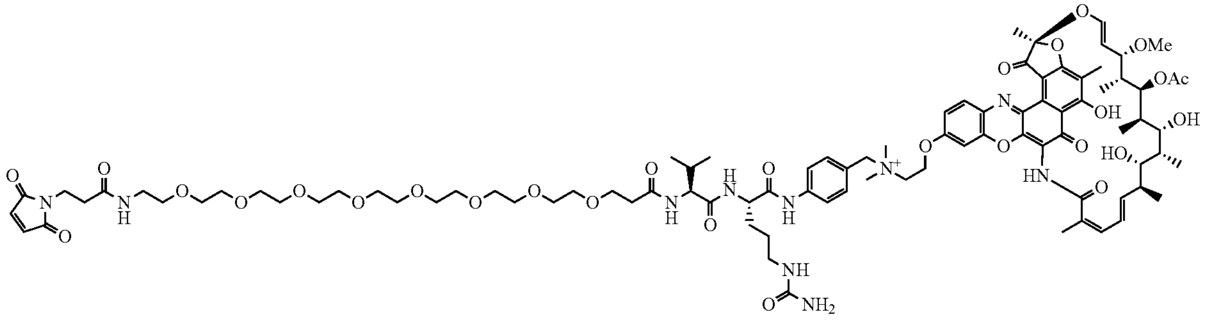 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCNC(=O)CCN8C(=O)C=CC8=O)C(C)C)cc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

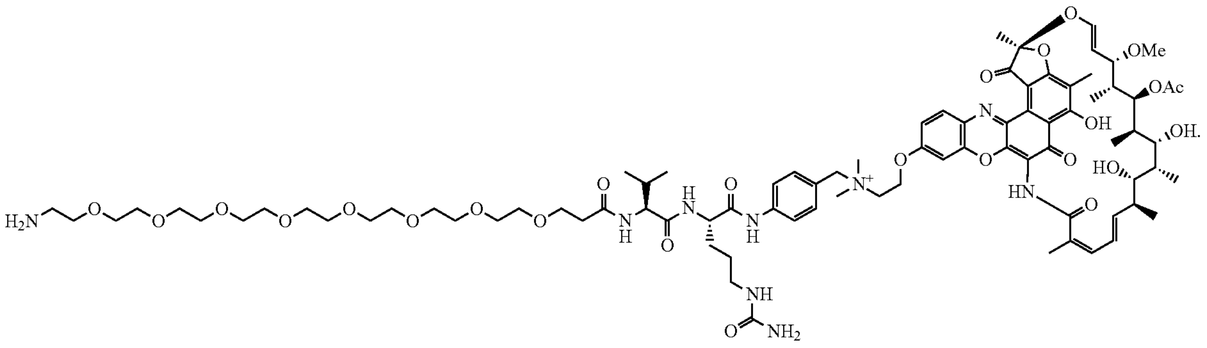

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

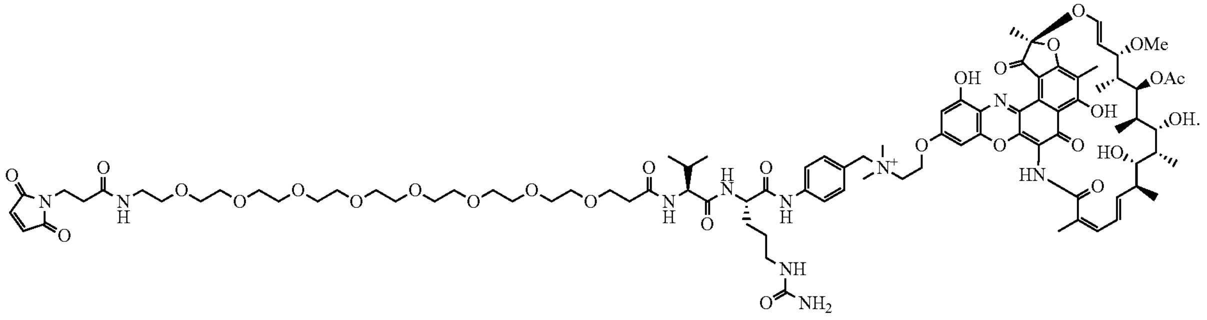 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCNC(=O)CCN8C(=O)C=CC8=O)C(C)C)cc7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

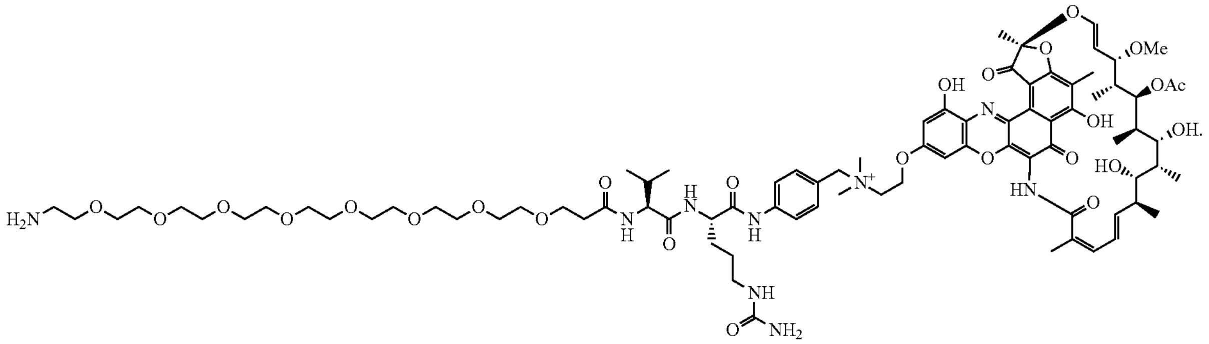 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCN)C(C)C)cc7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-WTA antibody, or antigen-binding fragment thereof, comprising a set of six CDRs (HCDR1-HCDR2-HCDR3-LCDR1-LCDR2-LCDR3) comprising SEQ ID NOs: 568-569-570-565-566-567, and a V205C mutation in the light chain, said anti-WTA antibody, or antigen-binding fragment thereof, is conjugated to a compound having the structure of

21

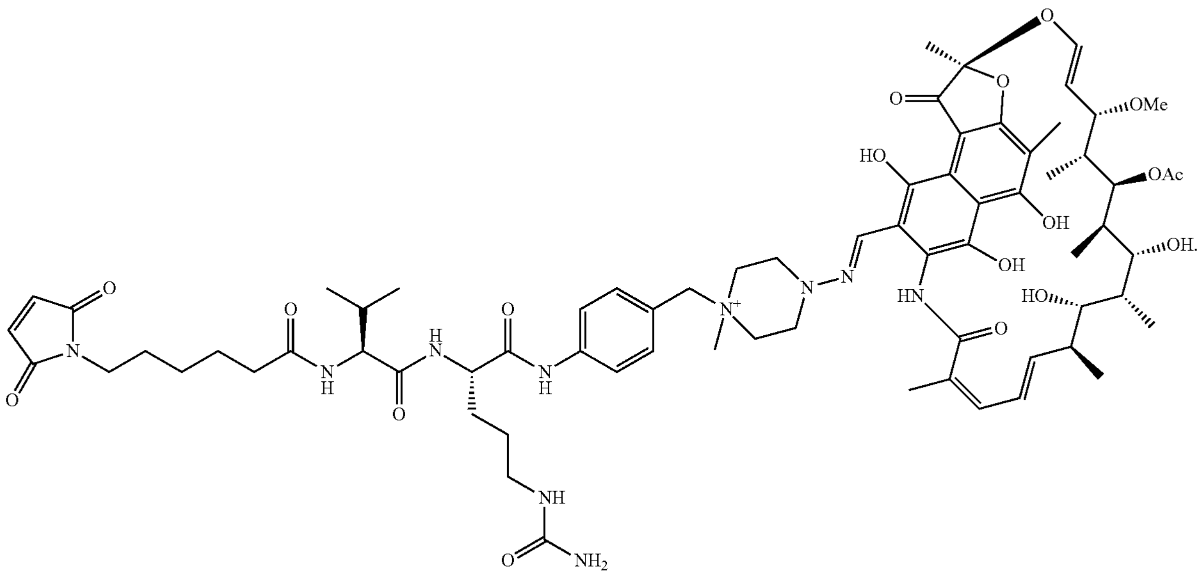

In some embodiments, the anti-WTA antibody or antigen binding fragment thereof comprises an HCVR amino acid sequence of SEQ ID NOs: 586, and an LCVR amino acid sequence of SEQ ID NO: 585.

In some embodiments, the anti-WTA antibody comprises a heavy chain amino acid sequence of SEQ ID NOs: 602 and a light chain amino acid sequence of SEQ ID NO: 587 or SEQ ID NO: 589.

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a C103S mutation in the light chain, said anti-Protein A antibody, or antigen-binding fragment thereof, is conjugated to a compound having the structure of

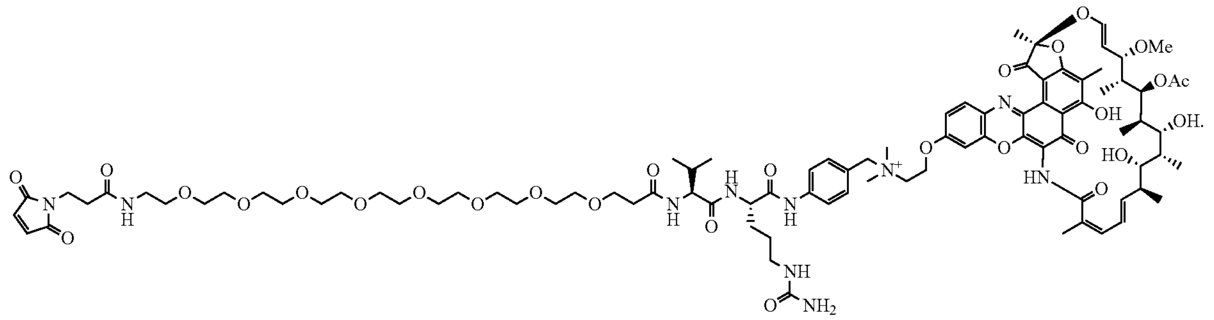 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCNC(=O)CCN8C(=O)C=CC8=O)C(C)C)cc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a C103S mutation in the light chain, said anti-Protein A antibody, or antigen-binding fragment thereof, is conjugated to a compound having the structure of

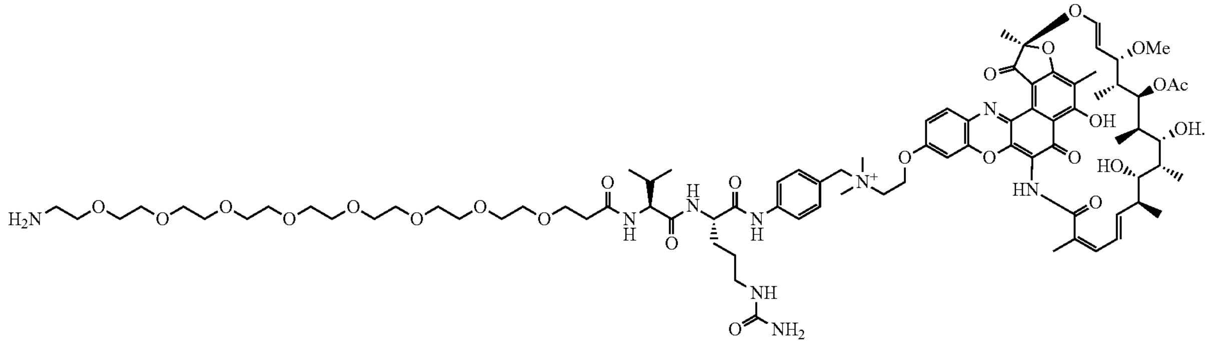 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCN)C(C)C)cc7)ccc6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a C103S mutation in the light chain, said anti-Protein A antibody, or antigen-binding fragment thereof, is conjugated to a compound having the structure of

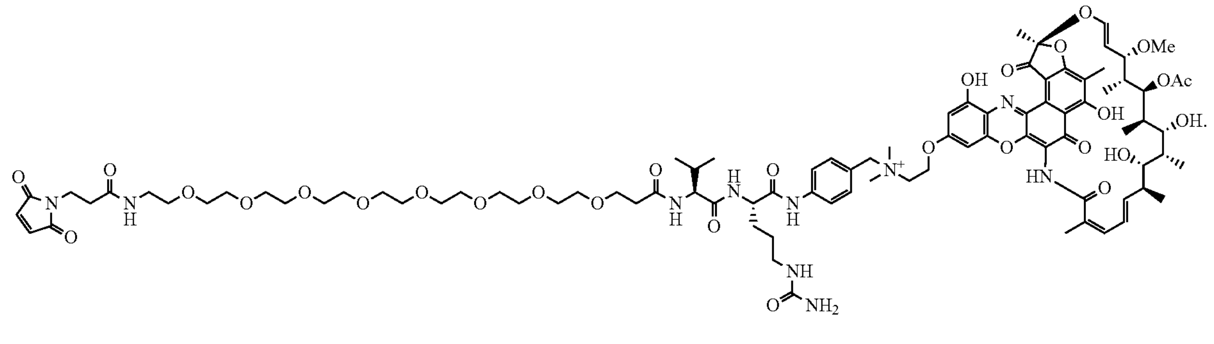 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCNC(=O)CCN8C(=O)C=CC8=O)C(C)C)cc7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a C103S mutation in the light chain, said anti-Protein A antibody, or antigen-binding fragment thereof, is conjugated to a compound having the structure of amino acids located within the antigen (e.g., an MSR1 protein or Protein A) (e.g. a linear epitope in a domain). Alternatively, the epitope may consist of a plurality of non-contiguous amino acids (or amino acid sequences) of MSR1. In some embodiments, the epitope is located on or near the modified LDL-binding domain of MSR1. In other embodiments, the epitope is located outside of the modified LDL-binding domain of MSR1, e.g., at a location on the surface of MSR1 at which an antibody, when bound to such

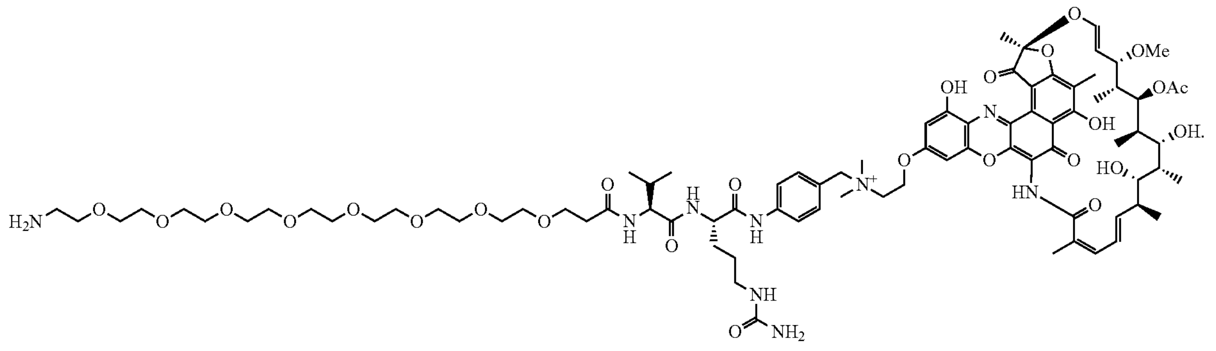

In one embodiment, the antibody-drug conjugate of the present disclosure comprises an anti-Protein A antibody, or antigen-binding fragment thereof, comprising a set of six CDRs (HCDR1-HCDR2-HCDR3-LCDR1-LCDR2-LCDR3) comprising SEQ ID NOs: 632-634-636-640-642-644, and a H435R and a Y436F mutation in the heavy chain Fc, and a C103S mutation in the light chain, said anti-Protein A antibody, or antigen-binding fragment thereof, is conjugated to a compound having the structure of an epitope, does not interfere with modified-LDL binding to the antigen (e.g. a conformational epitope).

Various techniques known to persons of ordinary skill in the art can be used to determine whether an antibody "interacts with one or more amino acids" within a polypeptide or protein. Exemplary techniques include, e.g., routine cross-blocking assay such as that described *Antibodies*, Harlow and Lane (Cold Spring Harbor Press, Cold Spring Harb., N.Y.), alanine scanning mutational analysis, peptide

80

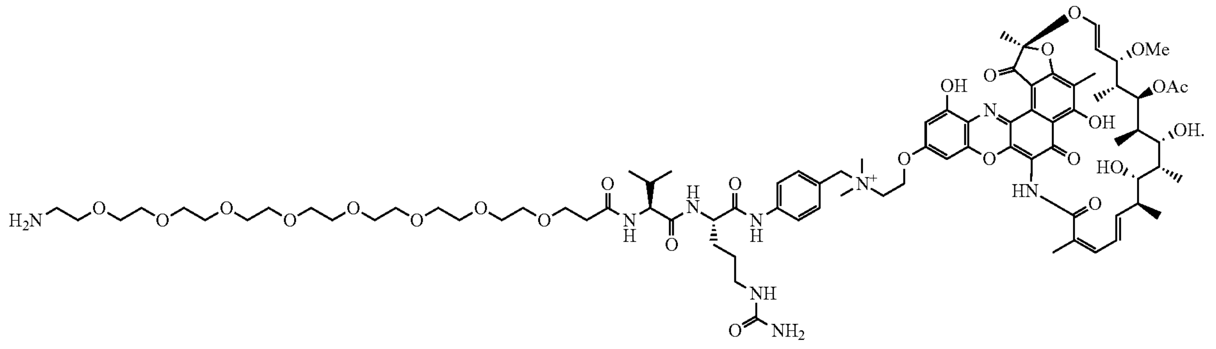 [SMILES: CO[C@H]1/C=C/O[C@@]2(C)Oc3c(C)c(O)c4c(=O)c(c5oc6cc(OCC[N+](C)(C)Cc7ccc(NC(=O)[C@H](CCCNC(N)=O)NC(=O)[C@@H](NC(=O)CCOCCOCCOCCOCCOCCOCCOCCOCCN)C(C)C)cc7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

In one embodiment, the anti-Protein A antibody or antigen binding fragment thereof comprises an HCVR amino acid sequence of SEQ ID NOs: 630; and an LCVR amino acid sequence of SEQ ID NO: 638.

In one embodiment, the anti-Protein A antibody comprises a heavy chain amino acid sequence of SEQ ID NOs: 666 and a light chain amino acid sequence of SEQ ID NO: 668.

Epitope Mapping and Related Technologies

The epitope to which the antibody-drug conjugates comprising antibodies of the present disclosure bind may consist of a single contiguous sequence of 3 or more (e.g., 3, 4, 5, 6, 7, 8, 9, 10, 11, 12, 13, 14, 15, 16, 17, 18, 19, 20 or more)

blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A.

Embodiments include antibody-drug conjugates comprising anti-MSR1 antibodies that bind to the same epitope as any of the specific exemplary antibodies described herein (e.g. anti-MSR1 antibodies comprising any of the amino acid sequences as set forth in Table 9 herein; anti-WTA antibodies comprising any of the amino acid sequences as set forth in Tables 2A and 2B herein; or anti-Protein A antibodies comprising any of the amino acid sequences as set forth in Table 3A herein). Likewise, embodiments also include antibody-drug conjugates comprising anti-MSR1 antibodies that compete for binding to the same antigen with any of the specific exemplary antibodies described herein (e.g. anti-MSR1 antibodies comprising any of the amino acid sequences as set forth in Table 9 herein; anti-WTA antibodies comprising any of the amino acid sequences as set forth in Tables 2A and 2B herein; or anti-Protein A antibodies comprising any of the amino acid sequences as set forth in Table 3A herein).

One can easily determine whether an antibody binds to the same epitope as, or competes for binding with, a reference antibody by using routine methods known in the art and exemplified herein at, e.g., Example 29. For example, to determine if a test antibody binds to the same epitope as a reference anti-MSR1 antibody disclosed herein, the reference antibody is allowed to bind to a MSR1 protein. Next, the ability of a test antibody to bind to the MSR1 molecule is assessed. If the test antibody is able to bind to MSR1 following saturation binding with the reference anti-MSR1 antibody, it can be concluded that the test antibody binds to a different epitope than the reference anti-MSR1 antibody. On the other hand, if the test antibody is not able to bind to the MSR1 molecule following saturation binding with the reference anti-MSR1 antibody, then the test antibody may bind to the same epitope as the epitope bound by the reference anti-MSR1 antibody of the disclosure. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present disclosure, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine, for example, if an antibody competes for binding (or cross-competes for binding) with a reference anti-MSR1 antibody, the above-described binding methodology is performed in two orientations. In a first orientation, the reference antibody is allowed to bind to a MSR1 protein under saturating conditions followed by assessment of binding of the test antibody to the MSR1 molecule. In a second orientation, the test antibody is allowed to bind to a MSR1 molecule under saturating conditions followed by assessment of binding of the reference antibody to the MSR1 molecule. If, in both orientations, only the first (saturating) antibody is capable of binding to the MSR1 molecule, then it is concluded that the test antibody and the reference antibody compete for binding to MSR1. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies Suitable for ADCs

Suitable antibodies for antibody-drug conjugates disclosed herein can be fully human antibodies. Methods for generating monoclonal antibodies, including fully human monoclonal antibodies are known in the art. Any such known methods can be used in the context of the present disclosure to make human antibodies that specifically bind to a target antigen, such as an infectious disease-related target (e.g., MSR1, WTA or Protein A).

Using VELOCIMMUNE™ technology, for example, or any other similar known method for generating fully human monoclonal antibodies, high affinity chimeric antibodies to MSR1 are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human antibody. While the constant region selected may vary according to specific use, high affinity antigen-binding and target specificity characteristics reside in the variable region. In certain instances, fully human antibodies are isolated directly from antigen-positive B cells.

Bioequivalents

The antibody-drug conjugates comprising antibodies and antibody fragments disclosed herein encompass proteins having amino acid sequences that vary from those of the described antibodies but that retain the ability to bind to a target antigen, such as an infectious disease-related target (e.g., MSR1, WTA or Protein A). Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences disclosed herein encompass sequences that comprise one or more additions, deletions, or substitutions of nucleotides when compared to the disclosed sequence, but that encode an antibody or antibody fragment that is essentially bioequivalent to an antibody or antibody fragment disclosed herein. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single dose or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of antibodies suitable for antibody-drug conjugates disclosed herein may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes which modify the glycosylation characteristics of the antibodies, e.g., mutations which eliminate or remove glycosylation.

Species Selectivity and Species Cross-Reactivity

According to certain embodiments, provided herein are antibody-drug conjugates comprising anti-MSR1 antibodies that bind to human MSR1 but not to MSR1 from other species. Embodiments also include antibody-drug conjugates comprising anti-MSR1 antibodies that bind to human MSR1 and to MSR1 from one or more non-human species. For example, the antibody-drug conjugates comprising anti-MSR1 antibodies disclosed herein may bind to human MSR1 and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee MSR1. According to certain exemplary embodiments, antibody-drug conjugates comprising anti-MSR1 antibodies are provided which specifically bind human MSR1 and cynomolgus monkey (e.g., *Macaca fascicularis*) MSR1. Other antibody-drug conjugates comprising anti-MSR1 antibodies disclosed herein bind human MSR1 but do not bind, or bind only weakly, to cynomolgus monkey MSR1.

Multispecific Antibodies

The antibodies suitable for antibody-drug conjugates disclosed herein may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, *J. Immunol.* 147:60-69; Kufer et al., 2004, *Trends Biotechnol.* 22:238-244. The antibodies disclosed herein can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bispecific or a multispecific antibody with a second binding specificity.

Embodiments include antibody-drug conjugates comprising bispecific antibodies wherein one arm of an immunoglobulin binds a first antigen, and the other arm of the immunoglobulin is specific for a second antigen. The antigen may be an infectious disease-related target. As a non-limiting example, antibody-drug conjugates may comprise bispecific antibodies wherein one arm of an immunoglobulin binds human MSR1, and the other arm of the immunoglobulin is specific for WTA or Protein A. As another non-limiting example, antibody-drug conjugates may comprise bispecific antibodies wherein one arm of an immunoglobulin binds WTA, and the other arm of the immunoglobulin is specific for Protein A.

For example, the MSR1-binding arm can comprise any of the HCVR/LCVR or CDR amino acid sequences as set forth in Table 9 herein. In certain embodiments, the MSR1-binding arm binds human MSR1 and blocks modified LDL binding to MSR1. In other embodiments, the MSR1-binding arm binds human MSR1 but does not block modified LDL binding to MSR1. In some embodiments, the MSR1 binding arm binds human MSR1 and activates MSR1 signaling. In other embodiments, the MSR1 binding arm blocks MSR1-mediated receptor stimulation. Embodiments also include bispecific antibodies wherein one arm of an antibody binds a first epitope of human MSR1, and the other arm of said antibody binds a second distinct epitope of human MSR1.

An exemplary bispecific antibody format that can be used in the context of the antibody-drug conjugates according to the present disclosure involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bispecific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present disclosure.

Other exemplary bispecific formats that can be used in the context of the present disclosure include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and $Mab^2$ bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [*Epub: Dec.* 4, 2012]).

Combination Treatment

In one embodiment of any of the above methods, the method further comprises administering a second therapeutic agent.

In one embodiment, the second therapeutic agent is a second antibiotic.

In one embodiment, the second therapeutic agent is an antibiotic including an antibiotic against *S. aureus* in general and/or MRSA in particular.

In one embodiment, the second therapeutic agent is a second antibiotic selected from an aminoglycoside, a beta-lactam, a macrolide, a cyclic peptide, a tetracycline, a fluoroquinoline, a fluoroquinolone, and an oxazolidinone.

In one embodiment, the second therapeutic agent is a second antibiotic selected from clindamycin, novobiocin, retapamulin, daptomycin, sitafloxacin, teicoplanin, triclosan, napthyridone, radezolid, doxorubicin, ampicillin, vancomycin, imipenem, doripenem, gemcitabine, dalbavancin, and azithromycin.

Embodiments include compositions and therapeutic formulations comprising any of the antibodies or ADCs described herein in combination with one or more additional therapeutically active components, and methods of treatment comprising administering such combinations to subjects in need thereof.

The antibodies or ADCs disclosed herein may be co-formulated with and/or administered in combination with one or more additional therapeutically active component(s) selected from the group consisting of: cytokine inhibitors, including small-molecule cytokine inhibitors and antibodies that bind to cytokines such as IL-1, IL-2, IL-3, IL-4, IL-5, IL-6, IL-8, IL-9, IL-11, IL,-12, IL-13, IL-17, IL-18, or to their respective receptors.

The antibodies or ADCs disclosed herein may also be administered and/or co-formulated in combination with anti-inflammatory agents, immunomodulatory agents, analgesics, corticosteroids, steroids, antioxidants, COX inhibitors, cardioprotectants, metal chelators, IFN-gamma, and/or NSAIDs. In some embodiments, the antibodies or ADCs can be administered and/or co-formulated in combination with anti-PCSK9 antibodies, anti-ANGPTL3 antibodies, statins, ezetimibe and other lipid lowering therapies.

The additional therapeutically active component(s), e.g., any of the agents listed above or derivatives thereof, may be administered just prior to, concurrent with, or shortly after the administration of an antibody or ADC disclosed herein; (for purposes of the present disclosure, such administration regimens are considered the administration of an antibody or ADC "in combination with" an additional therapeutically active component). Embodiments include pharmaceutical compositions in which an antibody or ADC disclosed herein is co-formulated with one or more of the additional therapeutically active component(s) as described else wherein herein.

EXAMPLES

The following examples illustrate specific aspects of the instant description. The examples should not be construed as limiting, as the examples merely provide specific understanding and practice of the embodiments and their various aspects.

As used herein, the symbols and conventions used in the processes, and Examples, herein, are consistent with those used in the contemporary scientific literature, for example, the Journal of the American Chemical Society or the Journal of Biological Chemistry unless specified otherwise to the contrary. Specifically, but without limitation, the following abbreviations may be used in the Examples and throughout the specification:

| Abbreviation | Term |
|---|---|
| ADC | Antibody-drug conjugate |
| Aglycosylated antibody | Antibody does not have any glycan |
| aq | Aqueous |
| BARAC | Biarylazacyclooctynone |
| BCN | (1R,8S,9s)-Bicyclo[6.1.0]non-4-yn-9-yl |
| Boc | N-tert-butoxycarbonyl |
| BupHTM | Thermo Scientific Prod# 28372, containing 100 mM sodium phosphate and 150 mM sodium chloride, potassium free, pH was adjusted from 7.2 to 7.6-7.8 MQ, unless otherwise noted. |
| CD | Cyclodextrin |
| COT | Cyclooctynol |
| Da | Dalton |
| DAR | Drug to antibody ratio. |
| DCM | Dichloromethane |
| DIBAC | Dibenz[b,f]azocine,11,12-didehydro-5,6-dihydro- or Dibenzocyclooctyne or Dibenz[b,f]azocine-5(6H)-butanoic acid,11,12-didehydro |

-continued

| Abbreviation | Term |
|---|---|
| DIBAC-Suc | Dibenz[b,f]azocine-5(6H)-butanoic acid,11,12-didehydro |
| DIBACT | 3H-Benzo[c]-1,2,3-triazolo[4,5-e][1]benzazocine,8,9-dihydro- |
| DIBO | Dibenzocyclooctyne |
| DIFO | Difluorinated cyclooctyne |
| DIPEA | Diisopropylethylamine |
| DMF | N,N-dimethylformamide |
| DMSO | Dimethylsulfoxide |
| ESI | Electrospray ionization |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr or hrs | Hours |
| LC | Light chain of immunoglobulin |
| LC | Liquid chromatography |
| MC | Maleimidocaproyl |
| mg | Milligrams |
| min | Minutes |
| mL | Milliliters |
| mM | Millimolar |
| MMAE | Monomethyl auristatin E |
| MS | Mass spectrometry |
| MSD | Mass-selective detector |
| MTG | Microbial transglutaminase |
| MW | Molecular weight |
| ncADC | Non-Cytotoxic antibody drug conjugation |
| NHS | N-hydroxy succinimide |
| nM | nanomolar |
| NMR | Nuclear magnetic resonance |
| NOESY | Nuclear Overhauser effect spectroscopy |
| PAB | Para-aminobezyloxy(carbonyl) |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| ppm | Parts per million (chemical shift) |
| RP | Reversed phase |
| RT or rt | Room temperature |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TFA | Trifluoroacetic acid |
| TG | Transglutaminase |
| THF | Tetrahydrofuran |
| TOF | Time-of-flight |
| UPLC | Ultra-Performance Liquid Chromatography |
| UV | Ultraviolet |
| VA | Valine-Aniline |
| VC | Valine-citrulline |
| μL | Microliters |
| μM | micromolar |

As use herein, the symbols an conventions use in these processes, schemes, an examples, regardless of whether a particular abbreviation is specifically defined, are consistent with those used in the contemporary scientific literature, for example, the Journal of the American Chemical Society or the Journal of Biological Chemistry.

General Methods

All the solvents used were purchased either from Sigma Aldrich or Fisher Scientific and were used without further purification. Rifamycin S was purchased from Bosche Scientific. $^1$H-NMR spectra were recorded on a Varian Inova 300 MHz and 500 MHz NMR instruments. The chemical shifts (δ) are reported in ppm with respect to the NMR solvents used for analysis and are reported as s—singlet, d—doublet, t—triplet, q—quartet, dd—doublet of doublet, dt—doublet of triplet, dq—doublet of quartet, and m—multiplet. Coupling constants (J) are reported in hertz (Hz). Chromatographic purities were determined on an Agilent 1100, 1260 Infinity, or 1200 Series LC/MS systems using Chromolith©FastGradient RP-18e analytical columns (50×2 mm, Merck KGaA, P/N 1.52007.0001) and the following analytical HPLC method: injection volume 5 or 10 μL; flow rate 1 mL/min; 5-95% acetonitrile in water over 4 min; Agilent diode array detector at k=254 nm; room temperature. Low resolution mass spectrometry was performed on an Agilent system using electrospray ionization sources and analyzed with either single quadrupole or ion trap mass detectors.

Example 1: Synthesis of Analogs 1a-1d According to the Disclosure

Scheme 1, below, depicts the synthesis of exemplary compounds 1a-1d according to the disclosure from commercially available starting materials.

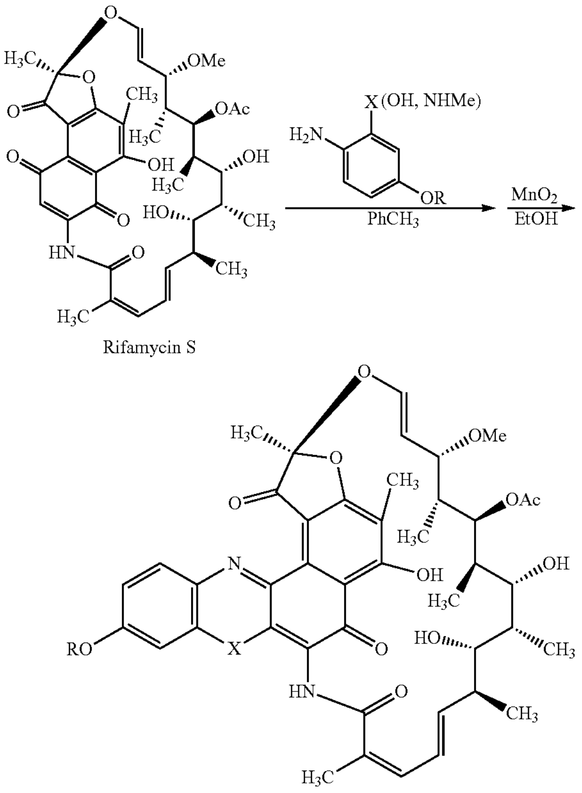

Rifamycin S

1a, R = Me X = O
1b, R = Bn X = O
1c, R = H X = O
1d, R = H X = NHMe

Example 1A: Rifamycin 4-MeO-Phenol Analogs (1a)

The General Coupling Procedure of Example 1 is Used to Prepare the Title Compound:

To a stirring solution under argon of rifamycin S (200 mg, 0.287 mmol) in 15 mL of toluene at room temperature was added 2-amino-5-methoxyphenol (44 mg, 0.316 mmol). The mixture solution was stirred for 3 days at room temperature. The progress of reaction was monitored by LC/MS, then the mixture was evaporated to dryness. The dark residue was dissolved in 10 mL of ethanol, and 100 mg (1.14 mmol) of manganese oxide ($MnO_2$) was added in one portion to the ethanol solution. The sluggish mixture was stirred for 15 h at room temperature. After filtration of insoluble materials using a Celite pad, the filtrate was evaporated under reduced pressure. The dark residue was purified on a 40 g HP silica gel Gold RediSep column via ISCO (gradient elution: 5→95% EA in hexanes) and the pure fractions evaporated and dried in vacuo giving the title compound 1a as a dark reddish solid (85 mg, 37%). MS (ESI, pos.): calc'd for $C_{44}H_{50}N_2O_{13}$, 814.33; found 815.3 (M+H), 837.3 (M+Na). $^1$H NMR (500 MHz; $CDCl_3$) δ 7.96 (d, J=9.0 Hz, 1H), 7.47 (s, 1H), 7.05-7.01 (m, 2H), 6.86 (s, 1H), 5.99 (s, 2H), 4.97 (dd, J=12.4, 7.4 Hz, 2H), 3.93 (s, 3H), 3.08 (s, 3H), 3.00-2.99 (m, 1H), 2.30 (s, 3H), 2.13 (s, 3H), 2.03 (d, J=18.1 Hz, 3H), 1.81 (s, 3H), 1.70-1.67 (m, 1H), 1.59-1.54 (m, 16H), 1.53 (s, 3H), 0.96-0.95 (m, 3H).

Example 1B: Rifamycin 4-BnO-Phenol Analogs (1b)

Analog 1b was prepared using intermediate 2, the synthesis of which is depicted in Scheme 2, below.

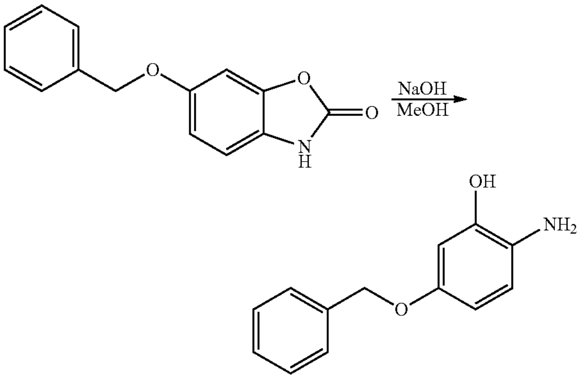

2

Synthesis of Compound 2.

The mixture of 6-(benzyloxy)benzo[d]oxazol-2(3H)-one (500 mg, 2.07 mmol) and methanol (6 mL) was treated with a solution of 1.2 g of NaOH in 6 mL of water. The suspension was heated at 90° C. overnight. After cooling at room temperature, the mixture was treated with 6N HCl (5 mL) then filtered. The filtrate was adjusted to afford pH=8-9 with sat. aq. $NaHCO_3$ and the precipitate was filtered, washed with water to give a dark solid, which was purified by 40 g HP silica gel Gold RediSep column (0→90% EA in hexanes) to afford 220 mg (49%) of compound 2. MS (ESI, pos.): calc'd for $C_{13}H_{13}NO_2$, 215.09; found 216.1 (M+H). $^1$H NMR (500 MHz; DMSO-$d_6$) δ 7.39-7.37 (m, 5H), 7.31 (d, J=7.0 Hz, 1H), 6.49 (d, J=8.4 Hz, 1H), 6.37 (d, J=2.7 Hz, 1H), 6.25 (dd, J=8.4, 2.7 Hz, 1H), 4.91 (s, 2H).

Synthesis of Analog 1b.

To a stirred solution of rifamycin S (20 mg, 0.0287 mmol) under argon in 1 mL of toluene at room temperature was treated with 2-amino-5-(benzyloxy)phenol 2 (6.8 mg, 0.0316 mmol). The solution was stirred for 3 days at room temperature and additional 2-amino-5-(benzyloxy)phenol (6.8 mg) was added. The progress of reaction was monitored by LC/MS. After 5 days, the mixture was evaporated to dryness. The dark residue was dissolved in 3.5 mL of ethanol and 10 mg (0.11 mmol) of manganese oxide ($MnO_2$) was added in one portion to the ethanol solution. The sluggish mixture was stirred for 3 h at room temperature. After filtration of insoluble materials using a Celite pad, the filtrate was evaporated under reduced pressure. The dark residue was purified on a 24 g HP silica gel Gold RediSep column via ISCO (gradient elution: 5→98% EA in hexanes) and the pure fractions evaporated and dried in vacuo giving the title compound 1b as a dark reddish solid (8.5 mg, 33%). MS (ESI, pos.): calc'd for $C_{50}H_{54}N_2O_{13}$, 890.36; found 891.3 (M+H). $^1$H NMR (500 MHz; $CDCl_3$) δ 7.97 (s, 1H), 7.49 (s, 1H), 7.44-7.41 (m, 5H), 7.14-7.11 (m, 2H), 7.07 (s, 1H), 6.94 (s, 1H), 5.32 (s, 1H), 5.23 (s, 1H), 5.18 (d, J=11.9 Hz, 2H), 4.99 (s, 2H), 3.11 (s, 3H), 3.04 (dd, J=2.0, 0.6 Hz, 1H), 2.32 (s, 3H), 2.07 (s, 6H), 1.83 (s, 3H), 1.71-1.69 (m, 1H), 1.61 (d, J=0.4 Hz, 9H), 1.58-1.52 (m, 6H), 1.28 (s, 1H), 0.97 (td, J=1.9, 1.2 Hz, 3H), 0.79 (t, J=0.8 Hz, 1H).

Example 1C: Rifamycin 4-OH-Phenol Analogs (1c)

Analog 1c was prepared using intermediate 4, the synthesis of which is depicted in Scheme 3, below.

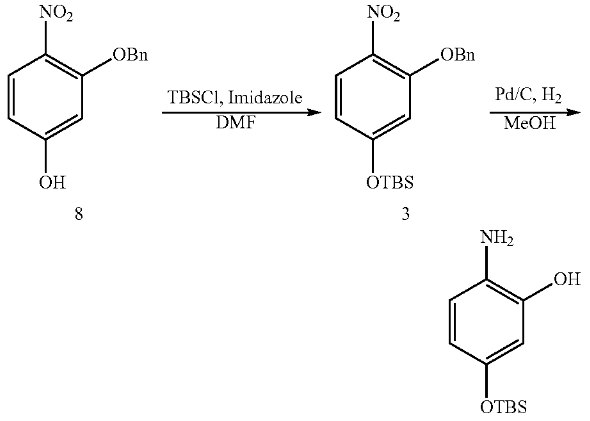

8 3 4

2-amino-5-((tert-butyldimethylsilyl) oxy)phenol (4)

Synthesis of Compound 3.

Compound 8 was prepared from the product in Example 1B. To the solution of 3-benzyloxy-4-nitrophenol 8 (400 mg, 1.63 mmol) under argon in DMF (2 mL) was added TBSCl (0.247 mL, 2.44 mmol), imidazole (222 mg, 3.26 mmol), and DMAP (0.5 mg). The mixture was stirred at room temperature overnight then diluted with ethyl acetate (25 mL), washed with water (2×10 mL), brine solution (10 mL), and dried over sodium sulfate. The crude was purified by 40 g HP silica gel Gold RediSep column via ISCO (gradient elution: 0-20% EA in hexanes) and the pure fractions evaporated to afford the desired compound 3 (540 mg, 92%). MS (ESI, pos.): calc'd for $C_{19}H_{25}N_{204}Si$, 359.16; found 382.1 (M+Na).

Synthesis of Compound 4.

To the solution under argon of compound 3 (120 mg, 0.33 mmol) in 3 mL of methanol (degassed with argon three times) was added 10% Pd/C (10 mg). The mixture was again degassed and bubbled with hydrogen from a balloon. A hydrogen balloon was inserted through the septa and the mixture was aged for overnight. The mixture was filtered through Celite and concentrated to give a dark greenish solid (71 mg, 90%). MS (ESI, pos.): calc'd for $C_{12}H_{21}NO_2Si$, 239.13; found 240.2 (M+H).

Synthesis of Analog 1c.

To a stirring solution under argon of rifamycin S (120 mg, 0.172 mmol) in 10 mL of toluene at room temperature was added compound 4 (46 mg, 0.192 mmol). The mixture solution was stirred for 3 days at room temperature. The progress of the reaction was monitored by LC/MS, then the mixture was evaporated to dryness. The dark residue was dissolved in 10 mL of ethanol, and 50 mg (0.6 mmol) of manganese oxide ($MnO_2$) was added in one portion to the ethanol solution. The sluggish mixture was stirred for 12 h at room temperature. After filtration of insoluble materials using a Celite pad, the filtrate was evaporated under reduced pressure. The dark residue was purified on a 24 g HP silica gel Gold RediSep column via ISCO (gradient elution: 5→95% EA in hexanes). The pure fractions were evaporated and dried in vacuo giving the title compound 1c as a dark reddish solid (48 mg, 35%). MS: calc'd for $C_{43}H_{48}N_2O_{13}$, 800.32; found 801.3 (M+H), 799.2 (M−H). $^1H$ NMR (500 MHz; DMSO-$d_6$) δ 11.43 (d, J=1.7 Hz, 1H), 9.33-9.32 (m, 1H), 7.82 (dt, J=2.0, 1.0 Hz, 1H), 7.02-7.01 (m, 1H), 6.89 (t, J=1.3 Hz, 1H), 6.04 (dd, J=2.5, 0.9 Hz, 1H), 5.83 (dt, J=1.9, 1.0 Hz, 1H), 5.25-5.24 (m, 1H), 4.78-4.77 (m, 1H), 4.14-4.14 (m, 1H), 3.52 (d, J=0.8 Hz, 1H), 3.07 (d, J=0.7 Hz, 1H), 3.03 (t, J=0.6 Hz, 3H), 2.89 (s, 1H), 2.78 (t, J=2.7 Hz, 1H), 2.19 (d, J=16.7 Hz, 3H), 1.99 (d, J=12.2 Hz, 4H), 1.95 (t, J=0.5 Hz, 4H), 1.67 (d, J=1.9 Hz, 3H), 1.24 (s, 2H), 0.89 (dd, J=2.5, 1.1 Hz, 2H), 0.85 (d, J=6.5 Hz, 6H), 0.69 (d, J=1.5 Hz, 3H).

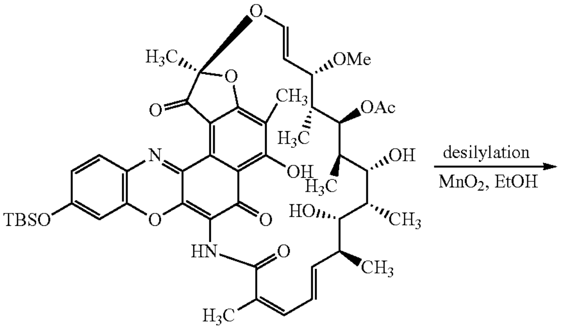

1c-TBS

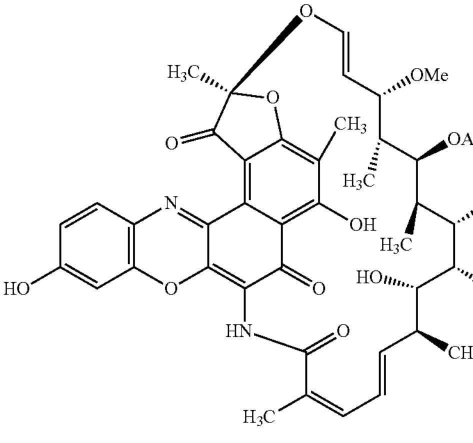

1c

Example 1D: Rifamycin 4-OH-Phenol N-Methyl analogs (1d)

Analog 1d was prepared using intermediate 7, the synthesis of which is depicted in Scheme 4, below.

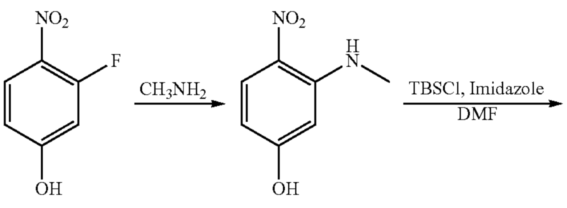

5

-continued

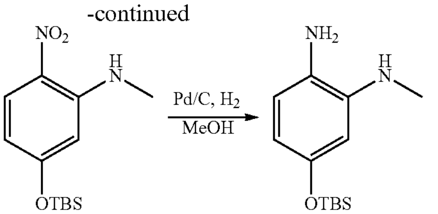

6 7

5-((tert-butyldimethylsilyl)oxy)-N1-methylbenzene-1,2-diamine (7)

Synthesis of Compound 5.

The title compound was prepared using the method disclosed in PTC *Int. Appl.* 2008051805. In a sealed tube were placed a mixture of 3-fluoro-4-nitrophenyl (1 g, 6.36 mmol) and 2 mL of a 40% methylamine aqueous solution. The flask was sealed via septum, purged with argon, and heated at 80° C. in an oil-bath for 18 h. The reaction was complete by LCMS analysis and cooled to room temperature. The solution was dissolved by the addition of water (15-20 mL) and extracted using ethyl acetate (3×30 mL). The combined organic layer was then washed with water, brine, dried ($Na_2SO_4$), and then concentrated to give a crude product, brown white solid (900 mg, 84%) of 5, which was used in the next step without further purification. MS (ESI, pos.): calc'd for $C_7H_8N_2O_3$, 168.05; found 169.1 (M+H).

Synthesis of Compound 6.

Under argon 3-(methylamino)-4-nitrophenol 5 (200 mg, 1.19 mmol) and imidazole (162 mg, 2.38 mmol) were dissolved in anhydrous DMF in the presence of catalytic DMAP (0.7 mg). The stirred yellow solution was cooled in an ice-bath and TBSCl (269 mg, 1.79 mmol) was added in one portion to the yellow solution. After 5 min the bath was removed and the solution was allowed to warm to room temperature overnight. The mixture was quenched by saturated $NaHCO_3$ solution and extracted with ethyl acetate (2×25 mL). The combine organics were dried by addition of $Na_2SO_4$ and then concentrated to give a crude product. The residue was purified on a 24 g HP silica gel Gold RediSep column via ISCO (gradient elution: 0→90% EA in hexanes) and the pure fractions evaporated then dried in vacuo giving the title compound 6 as a yellow solid (220 mg, 66%). MS: calc'd for $C_{13}H_{22}N_2O_3Si$, 282.14; found 283.1 (M+H).

Synthesis of Compound 7.

Under argon 5-((tert-butyldimethylsilyl)oxy)-$N_1$-methylbenzene-1,2-diamine 6 (50 mg, 0.177 mmol) was dissolved in 2 mL of methanol. The solution was degassed with argon three times followed by addition of Pd/C (5 mg). The mixture was further degassed with argon and connected to a hydrogen balloon via septum. After 2.5 h, the analysis by LC/MS from an in-process aliquot indicated the reaction was complete. The mixture was filtered through Celite and concentrated to afford 46 mg of compound 7 quantitatively, which was used in the next step instantly without further purification. MS: calc'd for $C_{13}H_{24}N_2OSi$, 252.17; found 253.2 (M+H).

Synthesis of Analog 1d.

To a stirring solution under argon of rifamycin S (58 mg, 0.083 mmol) in 3 mL of toluene at room temperature was added compound 7 (21 mg, 0.083 mmol). The solution was stirred for 2 days at room temperature. The progress of the reaction was monitored by LC/MS, then the solution was evaporated to dryness. The dark residue was dissolved in 5 mL of ethanol and 10 mg of manganese oxide ($MnO_2$) was added in one portion to the ethanol solution. The sluggish mixture was stirred for 12 h at room temperature. After filtration of insoluble materials using a Celite pad, the filtrate was evaporated under reduced pressure. The dark residue was purified on a 12 g HP silica gel Gold RediSep column via ISCO (gradient elution: 5→95% EA in hexanes) and the pure fractions evaporated then dried in vacuo giving the title compound 1d as a dark reddish solid (22.3 mg, 33%). This was found to be impure by LC/MS, so it was dissolved in MeCN/water and repurified on a 15.5 g C18 Aq Gold column (gradient elution: 10-95% MeCN in water, 0.05% acetic acid in both, over 20 min). The product fractions were combined, frozen on dry ice, and lyophilized giving the title compound 1d as a white solid (13.5 mg, 20%). MS: calc'd for $C_{44}H_{51}N_3O_{12}$, 813.35; found 814.3 (M+H), 812.3 (M−H). $^1H$ NMR (500 MHz; DMSO-$d_6$) δ 11.31 (b, J=0.8 Hz, 2H), 9.41 (s, 1H), 9.22 (s, 1H), 8.86 (s, 1H), 8.01-7.95 (m, 2H), 7.19-7.13 (m, 2H), 7.04 (s, 2H), 6.79-6.74 (m, 1H), 6.39-6.37 (m, 1H), 6.19 (t, J=11.4 Hz, 2H), 6.08 (d, J=12.4 Hz, 1H), 6.02-5.92 (m, 1H), 5.73 (d, J=26.4 Hz, 1H), 5.49 (d, J=11.2 Hz, 1H), 5.28 (d, J=0.6 Hz, 1H), 5.09-5.02 (m, 2H), 4.82 (dd, J=11.5, 10.2 Hz, 1H), 4.54 (d, J=6.6 Hz, 1H), 4.36 (d, J=2.6 Hz, 1H), 3.96 (d, J=4.4 Hz, 1H), 3.88 (s, 1H), 3.83 (s, 1H), 3.79 (s, 1H), 3.70 (s, 1H), 3.09 (s, 1H), 2.91 (s, 3H), 2.21 (s, 3H), 2.15 (d, J=5.9 Hz, 1H), 1.97 (s, 2H), 1.72 (s, 2H), 1.64 (s, 2H), 1.59 (s, 2H), 0.90 (d, J=7.0 Hz, 1H), 0.70 (d, J=6.6 Hz, 1H), 0.62 (d, J=6.8 Hz, 1H), 0.20-0.18 (m, 1H), 0.07 (d, J=0.7 Hz, 1H).

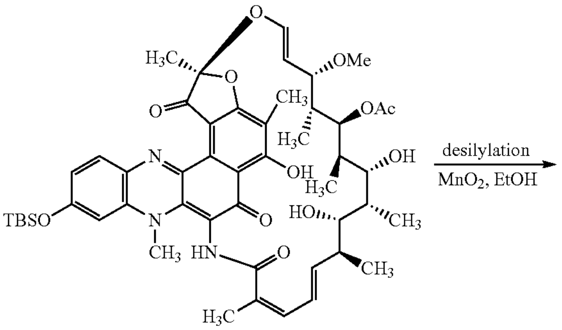

1d-TBS

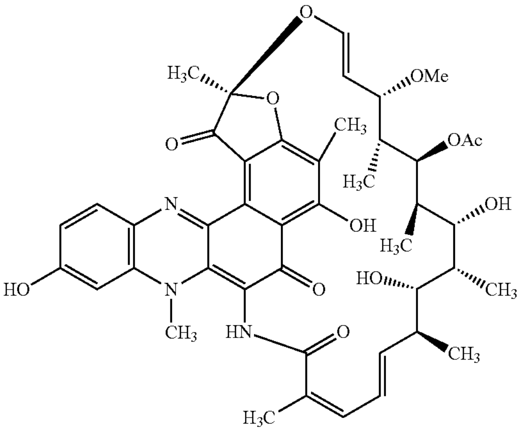

1d

Example 2: Synthesis of Analog 14 According to the Disclosure
Rifamycin analog 14 was synthesized from rifamycin S as shown in Scheme 5, below, and as described below.
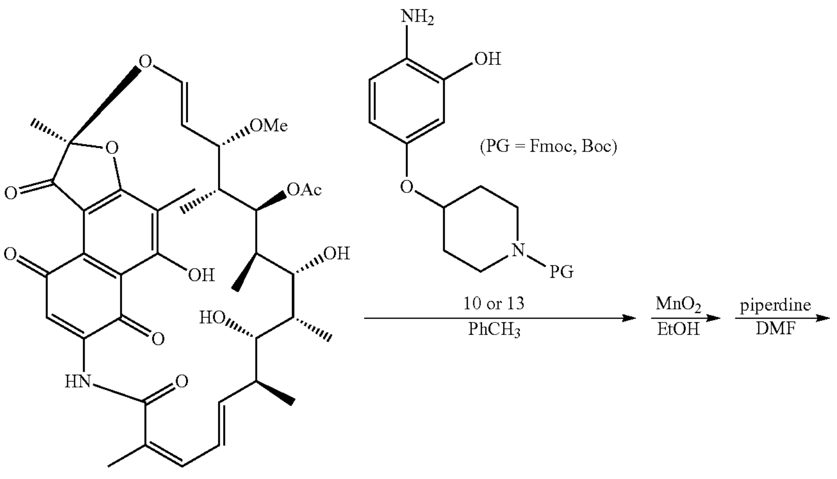
Rifamycin S
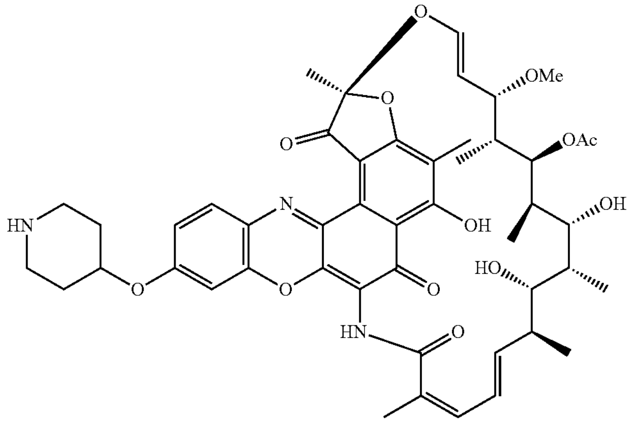
14
Example 2A: Preparation of Compounds (10 and 13)
Intermediates 10 and 13 were prepared according to Scheme 6, shown below.
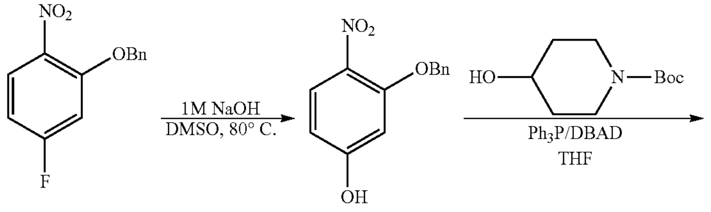
8

-continued

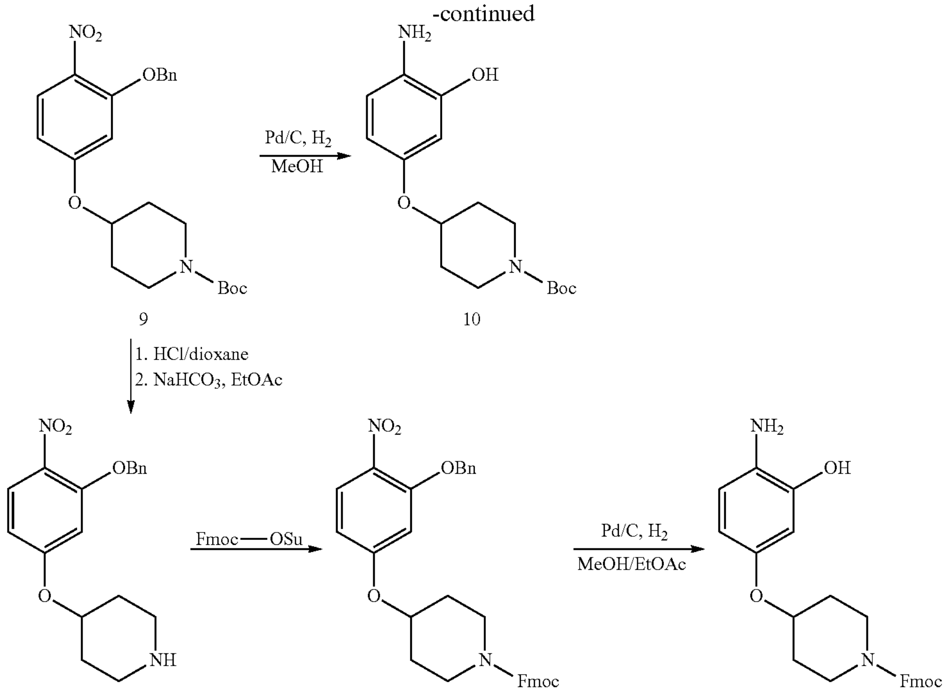

9 10

11 12 13

Synthesis of Compound 8.

The title compound was prepared using a slightly modified method reported by Otten et. al. (*Bioconjugate Chem.* 2001, 12, 76-83). To a solution of 3-fluoro-4-nitrophenyl (2.09 g, 8.45 mmol) in DMSO (10 mL) was added 1M NaOH (10 mL) and heated to 80° C. on a heating block for 18 h. The reaction was complete by LCMS and cooled to room temperature. The reaction was acidified with 1M HCl (15-20 mL) until the pH=3-4 and the resultant solution was extracted using ethyl acetate (3×30 mL). The combined organic layers were washed with water, brine, dried ($Na_2SO_4$), and concentrated in vacuo. The crude oil was then purified on an 80 g HP silica gel Gold RediSep column via ISCO (gradient elution: 0→100% ethyl acetate in hexanes) and the pure fractions evaporated then dried in vacuo giving the title compound 8 as a yellowish white solid (1.51 g, 73%). MS (ESI, pos.): calc'd for $C_{13}H_{11}NO_4$, 245.1; found 268.1 (M+Na), 244.1 (M−H).

Synthesis of Compound 9.

To a stirring solution under argon of compound 8 (1.51 g, 6.157 mmol) in THF (16 mL) at room temperature were added the BOC-piperidin-4-ol (1.61 g, 8.005 mmol) and $PPh_3$ (2.91 g, 11.083 mmol). A solution of DBAD (2.55 g, 11.083 mmol) in THF (9 mL) was added to the reaction mixture dropwise. After stirring for 16 h, the mixture was evaporated to dryness and the residue was purified on a 40 g HP silica gel Gold RediSep column via ISCO (gradient elution: 0→100% ethyl acetate in hexanes) and the pure fractions evaporated then dried in vacuo giving the title compound 9 as a yellowish white solid (2.41 g, 91%). MS: calc'd for $C_{23}H_{28}N_2O_6$, 428.2; found 451.1 (M+Na).

Synthesis of Compound 10.

To a degassed solution under argon of compound 9 (100 mg, 0.233 mmol) in 3 mL of methanol was added 5 mg of 10% Pd/C. The mixture was further degassed and connected to a hydrogen balloon. After 2.5 h, the analysis by LC/MS from in-process aliquot indicated the reaction was complete. The mixture was filtered through Celite and concentrated to afford 75 mg of compound 10 quantitatively, which was used in the next step instantly without further purification. MS: calc'd for $C_{16}H_{24}N_2O_4$, 308.17; found 331.2 (M+Na), 307.1 (M−H).

Synthesis of Compound 11.

To a solution of compound 9 (1100 mg, 2.561 mmol) in 1,4-dioxane (15 mL) was added 4 M HCl in 1,4-dioxane (5 mL). After stirring for 15 h an in-process aliquot indicated the reaction was complete. To the solution was added diethyl ether (50 mL), then the mixture was stirred vigorously for 1 h until a white precipitate formed. The solid was filtered and washed with ether to afford the HCl salt of 11. To the white solid was added EtOAc (10 mL) and sat. $NaHCO_3$(15 mL) until pH=8-9 and stirred for 15 min. The two layers were separated and the aqueous layer was extracted with EtOAc (3×30 mL). The combined organic layers were dried ($Na_2SO_4$) and concentrated in vacuo to give compound 11 (372 mg, 44%) which was used in the next step instantly without further purification. MS: calc'd for $C_{18}H_{21}N_2O_4$, 328.1; found 329.1 (M+H).

Synthesis of Compound 12.

To a solution under argon of compound 11 (372 mg, 1.128 mmol) in 1,4-dioxane/water (v/v, 10:1, 11 mL) was added Fmoc-OSu (399 mg, 1.184 mmol). After stirring for 15 h an in-process LC/MS analysis indicated the reaction was complete. The reaction mixture was concentrated in vacuo to give compound 12 which was used in the next step instantly without further purification. MS: calc'd for $C_{33}H_{30}N_2O_6$, 550.2; found 551.2 (M+H).

Synthesis of Compound 13.

To a solution under argon of compound 12 (72 mg, 0.131 mmol) in 2 mL of methanol and degassed with argon was added 9 mg of 10% Pd/C. The mixture was further degassed with argon and connected to a hydrogen balloon. After 45 min, analysis by LC/MS from an in-process aliquot indicated the reaction was complete. The mixture was filtered through Celite and concentrated in vacuo to afford 55 mg of compound 13 quantitatively, which was used in the next step instantly without further purification. MS: calc'd for $C_{26}H_{26}N_2O_4$, 430.1; found 431.2 (M+H).

Example 2B: Preparation of Analog 14 from Intermediate 10

Synthesis of Compound 14-Boc:

To a stirring solution of rifamycin S (100 mg, 0.143 mmol) in 5 mL of toluene at room temperature was added compound 10 (44 mg, 0.143 mmol). The mixture solution was stirred for 4 days at room temperature. The progress of the reaction was monitored by LC/MS until complete, then the mixture was evaporated to dryness. The dark residue was dissolved in 10 mL of ethanol and 62 mg (0.715 mmol) of manganese oxide ($MnO_2$) was added at one portion to the ethanol solution. The sluggish mixture was stirred for 15 h at room temperature. After filtration of insoluble materials using Celite pad, the filtrate was evaporated under reduced pressure. The dark residue was purified on a 12 g HP silica gel Gold RediSep column via ISCO (gradient elution: 5%→95% ethyl acetate in hexanes). After concentrating under reduced pressure the crude product (ca. 85% pure) was repurified on a 50 g C18 Aq Gold column (gradient elution: 10-95% MeCN in water, 0.05% acetic acid in both). The pure fractions were combined, frozen on dry ice, and lyophilized to afford 14-Boc as a dark reddish solid (36 mg, 26%). MS: calc'd for $C_{53}H_{65}N_3O_{15}$, 983.44; found 984.4 (M+H).

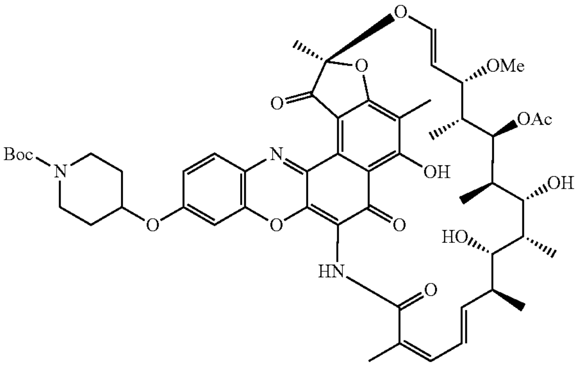

14-Boc

Synthesis of Compound 14:

14-Boc (30 mg, 0.03 mmol) was treated with a mixture of TFA/acetonitrile/water (0.25 mL/5 mL/5 mL) at room temperature for 20 h to afford compound 14. The reaction mixture was purified on a 15.5 g C18 Aq. Gold column via ISCO system (gradient elution: 10%-100% MeCN in water, 0.05% acetic acid in both, over 30 min). The product-containing fractions were combined, frozen on dry ice, and lyophilized overnight giving the title compound 14 (10 mg, 37%) as dark reddish solid. MS: calc'd for $C_{48}H_{57}N_3O_{13}$, 883.4; found 884.3 (M+H).

Example 2C: Preparation of Analog 14 from Intermediate 13

Synthesis of Compound 14:

To a round-bottom flask with hydroxyaniline 13 (55 mg, 0.1278 mmol) were added toluene (1.5 mL) and rifamycin S (67 mg, 0.0956 mmol). The reaction mixture was sonicated for 1 min to dissolve the reaction mixture, sealed via rubber septum, purged with argon, and the reaction stirred at ambient temperature. After 2 days another portion of hydroxyaniline (45 mg, 0.1045 mmol) was added and stirred for 1 d. The reaction was concentrated in vacuo to remove toluene, dissolved in EtOH (6 mL) and $MnO_2$ (20 mg) was added. After stirring for 3 d, the reaction was concentrated in vacuo and purified by chromatography on a 40 g HP silica gel Gold RediSep column via ISCO (gradient elution: 0-100% ethyl acetate in hexanes). The pure fractions were evaporated and dried in vacuo giving the title compound 14-Fmoc as a dark reddish solid (35 mg, 33%). MS (ESI, pos.): calc'd for $C_{63}H_{67}N_3O_{15}$, 1105.4; found 1106.5 (M+H), 1128.5 (M+Na).

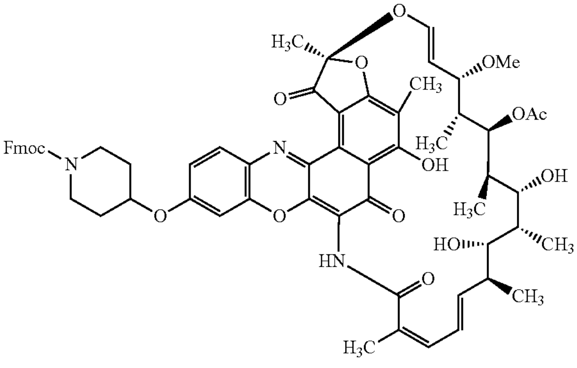

14-Fmoc

To a stirred solution under argon of Fmoc-rifamycin-piperidine-O-phenol 14-Fmoc of the preceding step (35 mg, 0.0361 mmol) in N,N-dimethylformamide (DMF, 1 mL), was treated with a solution of 2% piperidine (3.5 mg, 0.2 mL, 0.0411 mmol) in DMF and the reaction stirred at ambient temperature. After 2 h, the reaction was purified directly on a 50 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the title compound 14 as dark reddish solid (12 mg, 43%). MS: calc'd for $C_{48}H_{57}N_3O_{13}$, 883.4; found 884.3 (M+H). $^1H$ NMR (500 MHz; DMSO-$d_6$) δ 9.40 (s, 1H), 7.87 (d, J=8.9 Hz, 1H), 7.16-7.23 (m, 4H), 5.99-6.05 (m, 2H), 5.76-5.85 (m, 2H), 5.18-5.23 (m, 2H), 4.83-4.95 (m, 2H), 4.80 (br. s, 2H), 4.12 (br. S., 1H), 2.91-3.18 (m, 13H), 2.88 (s, 1H), 2.78 (t, J=0.9 Hz, 2H), 2.67 (s, 2H), 2.22 (d, J=3.7 Hz, 4H), 2.15 (s, 2H), 2.02 (s, 2H), 1.96 (d, J=1.2 Hz, 2H), 1.90 (s, 1H), 1.68 (s, 2H), 0.85-0.92 (m, 12H), 0.69 (br. s, 9H).

Example 3: Synthesis of Analogs 16a-16z-1 According to the Disclosure

Rifamycin analogs 16a-16z-1 were synthesized from rifamycin S as shown in Scheme 7 and Scheme 7a, below, and as described below.

Scheme 7

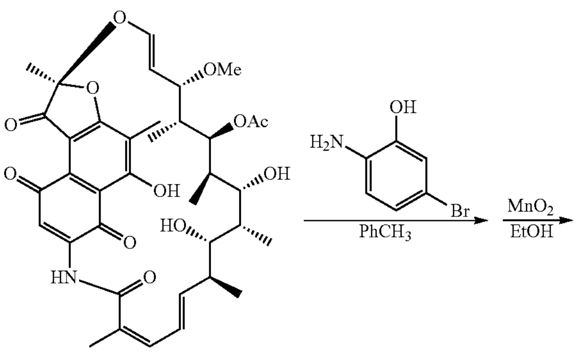

Rifamycin S

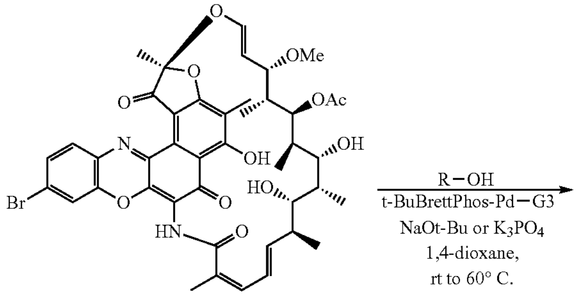

15

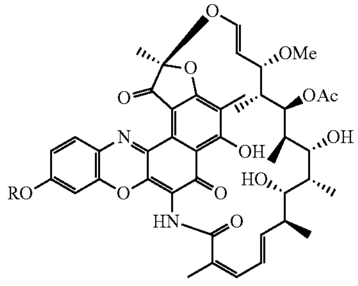

16

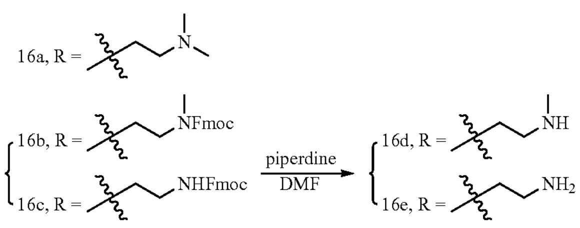

Pd-Catalyzed O-Alkylation (16a-16z-1):

Synthesis of Compound 15.

To a stirring solution under argon of rifamycin S (2.0 g, 2.87 mmol) in 80 mL of toluene at room temperature was added 2-amino-5-bromophenol (0.54 g, 2.87 mmol). The solution was stirred for 2 days at room temperature. The reaction mixture was then evaporated to dryness and the dark residue dissolved in 20 mL of ethanol and 300 mg of manganese oxide ($MnO_2$) was added in one portion to the ethanol solution. The sluggish mixture was stirred under argon for 15 h at room temperature. After filtration of insoluble materials using a Celite pad, the filtrate was evaporated under reduced pressure. The dark residue was purified on a 120 g HP silica gel Gold RediSep column via ISCO (gradient elution: 5→95% EA in hexanes). The pure fractions were evaporated and dried in vacuo giving the title compound 15 as a dark reddish solid (1.6 g, 65%). MS (ESI, pos.): calc'd for $C_{43}H_{47}BrN_2O_{13}$, 862.23; found 863.1 and 865.1 (M+H), 885.1 and 888.0 (M+Na). $^1H$ NMR (500 MHz; DMSO-$d_6$): δ 9.49 (d, J=6.0 Hz, 1H), 7.92 (ddd, J=3.6, 2.9, 1.8 Hz, 1H), 7.86-7.85 (m, 1H), 7.75-7.74 (m, 1H), 6.06-6.05 (m, 1H), 5.84 (dt, J=2.6, 1.4 Hz, 2H), 5.25-5.23 (m, 2H), 4.80 (dt, J=2.5, 1.0 Hz, 1H), 4.23 (td, J=2.4, 1.0 Hz, 1H), 3.49 (d, J=1.1 Hz, 1H), 3.10-3.09 (m, 2H), 3.03 (s, 3H), 2.79 (s, 1H), 2.19 (s, 3H), 2.01 (s, 4H), 1.96 (s, 4H), 1.81 (d, J=2.2 Hz, 1H), 1.68 (s, 3H), 1.60 (dq, J=2.8, 0.9 Hz, 1H), 1.48 (t, J=1.4 Hz, 1H), 0.90 (dt, J=2.1, 1.1 Hz, 2H), 0.84 (d, J=7.1 Hz, 4H), 0.69 (dd, J=2.2, 1.2 Hz, 5H).

Synthesis of Compound 16a.

Using a similar method reported by Buchwald S. L. et al. (*Org. Lett.* 2018, 20, 1580), a palladium-catalyzed C—O coupling of primary alcohols with compound 15 was employed for title compounds 16a-16c. To a 2 dram screw-top oven-dried test tube, equipped with a stir bar, and sealed with a screw cap was charged compound 15 (40 mg, 0.0463 mmol, 1.00 eq.), 2-(dimethylamino)ethan-1-ol (42 mg, 0.462 mmol, 10 eq.), tBuBrettPhos Pd G3-palladacycle (11.8 mg, 30 mol %), and NaOt-Bu (5 mg, 0.051 mmol, 1.1 eq.). The reaction tube was recapped with a septum and pierced with a needle attached to evacuate and backfilled with argon (this process was repeated twice) followed by addition of 1,4-dioxane (2.0 mL) via syringe. The reaction was heated at 55° C.±5 in an oil bath under argon pressure for 15 h, the reaction was allowed to cool to room temperature before filtration through a pad of Celite® and rinsed with EtOAc. The crude material was concentrated in vacuo and purified on a 15.5 g C18 Aq Gold column (gradient elution: 10-95% MeCN in water, 0.05% acetic acid in both). The product fractions were combined, frozen on dry ice, and lyophilized giving the title compound 16a as a dark reddish solid (12.5 mg, 32%). MS: calc'd for $C_{47}H_{57}N_3O_{13}$, 871.39; found 872.3 (M+H), 870.2 (M−H). $^1H$ NMR (300 MHz; DMSO-$d_6$) δ 9.40 (s, 1H), 7.87 (d, J=8.9 Hz, 1H), 7.23-7.16 (m, 2H), 6.83 (dt, J=2.3, 1.1 Hz, 1H), 6.23 (d, J=4.6 Hz, 1H), 6.06 (dd, J=5.9, 1.1 Hz, 1H), 5.82 (dd, J=2.3, 1.5 Hz, 2H), 5.24 (dt, J=1.4, 0.7 Hz, 1H), 4.83-4.75 (m, 1H), 4.24 (d, J=29.9 Hz, 3H), 3.80 (d, J=1.3 Hz, 1H), 3.03 (t, J=0.5 Hz, 3H), 2.88 (s, 1H), 2.78 (t, J=0.9 Hz, 2H), 2.67 (s, 2H), 2.22 (d, J=3.7 Hz, 4H), 2.15 (s, 2H), 2.02 (s, 2H), 1.96 (d, J=1.2 Hz, 2H), 1.90 (s, 1H), 1.68 (s, 2H), 0.85 (d, J=6.7 Hz, 3H), 0.69 (t, J=1.2 Hz, 3H).

Synthesis of Compound 16b.

To a 8 mL screw-top oven-dried vial, equipped with a stir bar, and sealed with a screw cap was charged compound 15 (40 mg, 0.0463 mmol, 1.00 eq.), Fmoc-glycinol (131 mg, 0.463 mmol, 10 eq.), t-BuBrettPhos-Pd-G3-palladacycle (16 mg, 0.4 eq.), and $K_3PO_4$ (20 mg, 0.0942 mmol, 2.0 eq.). The reaction vial was capped with a rubber septum, pierced with a needle attached to evacuate and backfilled with argon (this process was repeated twice), followed by the addition of 1,4-dioxane (2.0 mL). The reaction was heated at 60° C. in a heating block under argon pressure for 15 h, the reaction was allowed to cool to room temperature before filtration through a pad of Celite® and rinsed with MeOH. The crude material was concentrated in vacuo and purified on a 50 g C18 Aq Gold column (gradient elution: 5-100% MeCN in water, 0.05% acetic acid in both). The product fractions were combined, frozen on dry ice, and lyophilized giving the title compound 16b as a dark reddish solid (19 mg, 38%). MS (ESI, pos.): calc'd for $C_{60}H_{63}N_3O_{15}$, 1065.4; found 1066.4 (M+H).

Synthesis of Compound 16d.

Compound 16b of the preceding step (26 mg, 0.0244 mmol) was dissolved in DMF (1 mL), treated with a solution of 2% piperidine (3.1 mg, 0.2 mL, 0.0366 mmol) in DMF and the reaction stirred under argon at ambient temperature. After 2 h, the reaction was purified directly on a 50 g C18 Aq Gold column via ISCO system (gradient elution: 0-100% MeCN in water, 0.05% acetic acid in both, over 30 min). The product-containing fractions were combined, frozen on dry ice, and lyophilized overnight giving the title compound 16d as dark blue solid (9 mg, 44%). MS: calc'd for $C_{45}H_{53}N_3O_{13}$, 843.4; found 844.4 (M+H), 842.3 (M−H). $^1H$ NMR (500 MHz; $CD_3OD$): δ 7.83 (d, J=8.8 Hz, 1H), 6.91-7.03 (m, 2H), 6.55 (s, 1H), 6.43 (d, J=11.2 Hz, 1H), 6.21-6.30 (m, 2H), 4.98-5.08 (m, 2H), 3.76 (br. s, 3H), 3.43-3.47 (m, 1H), 3.41 (d, J=5.37 Hz, 2H), 3.12 (br. s, 1H), 2.97-3.04 (m, 4H), 2.39 (br. s, 1H), 2.19-2.32 (m, 4H), 2.09-2.14 (m, 4H), 1.95-2.07 (m, 4H), 1.78 (s, 4H), 1.67 (d, J=6.84 Hz, 1H), 1.31 (br. s., 2H), 0.97 (br. s, 8H), 0.66-0.85 (m, 4H), 0.08 (d, J=5.5 Hz, 3H), −0.26 (d, J=6.5 Hz, 3H).

Synthesis of Compound 16c.

To a 8 mL screw-top oven-dried vial, equipped with a stir bar and sealed with a screw cap was charged compound 15 (80 mg, 0.0926 mmol, 1.00 eq.), Fmoc-sarcosinol (275 mg, 0.9262 mmol, 10 eq.), t-BuBrettPhos-Pd-G3-palladacycle (40 mg, 0.5 eq.), and $K_3PO_4$ (39 mg, 0.1852 mmol, 2 eq.). The reaction vial was capped with a rubber septum, pierced with a needle attached to evacuate and backfilled with argon (this process was repeated twice) followed by addition of 1,4-dioxane (3.0 mL) via syringe. The reaction was heated at 60° C. in a heating block under argon pressure for 15 h, the reaction was allowed to cool to room temperature before filtration through a pad of Celite® and rinsed with MeOH. The crude material was concentrated in vacuo and purified on a 50 g C18 Aq Gold column (gradient elution: 5-100% MeCN in water, 0.05% acetic acid in both). The product fractions were combined, frozen on dry ice, and lyophilized to give the title compound 16c as a dark reddish solid (49 mg, 49%). MS: calc'd for $C_{61}H_{65}N_3O_{15}$, 1079.4; found 1080.5 (M+H).

Synthesis of Compound 16e.

Compound 16c of the preceding step (49 mg, 0.045 mmol) was dissolved in DMF (1 mL), treated with a solution of 2% piperidine (7.7 mg, 0.45 mL, 0.091 mmol) in DMF and the reaction stirred under argon at ambient temperature. After 2 h, the reaction was purified directly on a 50 g C18 Aq Gold column via ISCO system (gradient elution: 0-100% MeCN in water, 0.05% acetic acid in both, over 30 min). The product-containing fractions were combined, frozen on dry ice, and lyophilized overnight giving the title compound 16e as a dark blue solid (18 mg, 46%). MS: calc'd for $C_{46}H_{55}N_3O_{13}$, 857.3; found 858.3 (M+H). $^1H$ NMR (500 MHz; $CD_3OD$): δ 7.84 (d, J=8.79 Hz, 1H), 7.11-7.20 (m, 1H), 6.88-6.96 (m, 1H), 6.64 (s, 1H), 6.42 (d, J=10.26 Hz, 1H), 6.17-6.28 (m, 2H), 4.93-5.06 (m, 2H), 3.86 (br. s, 1H), 3.66-3.84 (m, 8H), 3.18-3.31 (m, 7H), 3.10 (br. s, 2H), 2.94-3.05 (m, 6H), 2.37 (br. s, 1H), 2.25 (d, J=4.88 Hz, 4H), 2.05-2.22 (m, 7H), 1.85-2.05 (m, 7H), 1.78 (s, 6H), 1.65 (br. s, 1H), 1.30 (br. s., 2H), 0.95 (br. s, 8H), 0.82-0.92 (m, 4H), 0.78 (br. s., 1H), 0.70 (br. s, 1H), 0.03 (d, J=5.86 Hz, 3H), −0.28 (d, J=5.86 Hz, 3H).

Scheme 7a

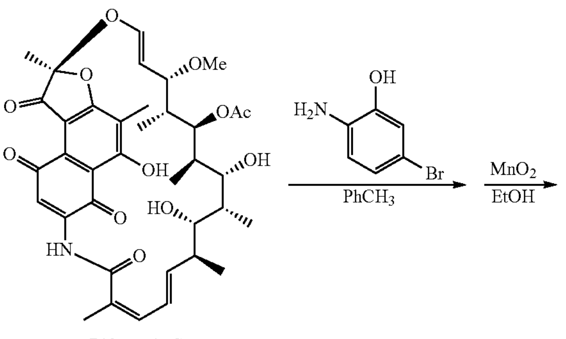

Rifamycin S

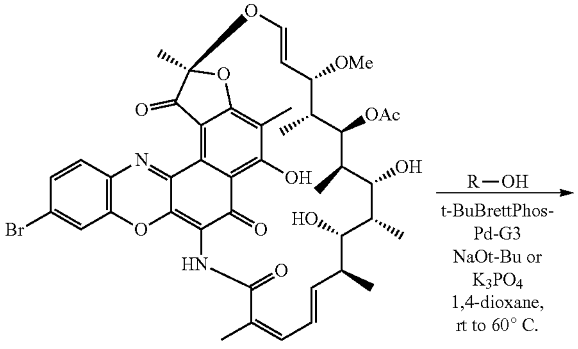

15

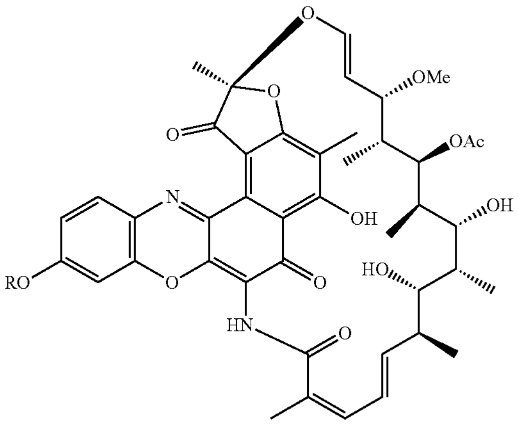

16

16f, R =

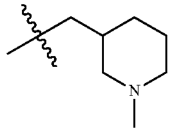

16g, R =

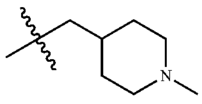

16h, R =

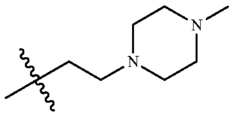

16i, R =

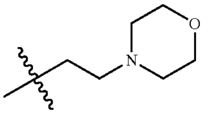

-continued

16j, R =

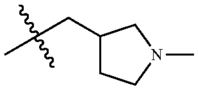

16k, R =

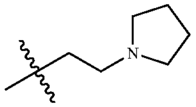

16l, R =

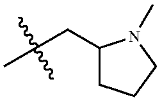

16m, R =

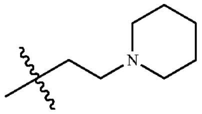

16n, R =

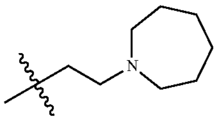

16o, R =

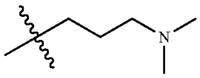

16p, R =

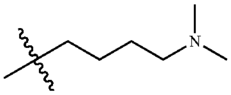

16q, R =

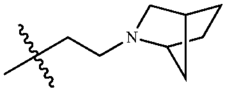

16r, R =

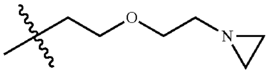

16s, R =

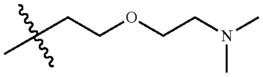

16t, R =

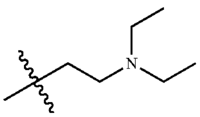

16u, R =

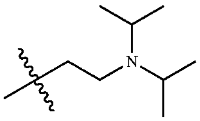

16v, R =

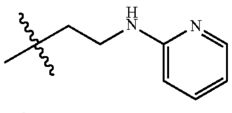

16w, R =

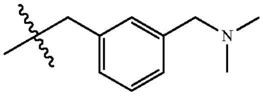

16x, R =

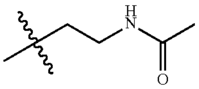

16y, R =

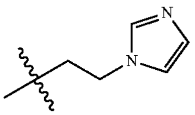

16z, R =

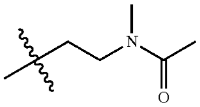

-continued 16z-1, R =

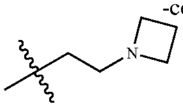

Compound 16f:

To a 8 mL screw-top oven-dried vial, equipped with a stir bar and sealed with a screw cap was charged with compound 15 (40 mg, 0.0463 mmol, 1.00 eq.), (1-methylpiperidin-3-yl)methanol (60 mg, 0.463 mmol, 10 eq.), t-BuBrettPhos-Pd-G3-palladacycle (19 mg, 0.0222 mmol, 0.5 eq.), and $K_3PO_4$ (20 mg, 0.0942 mmol, 2.0 eq.). The reaction vial was capped with a rubber septum. The septum was pierced with a needle attached to evacuate and backfilled with argon (this process was repeated twice) followed by the addition of 1,4-dioxane (2.0 mL). The reaction was heated at 60° C. in a heating block under argon pressure for 15 h, the reaction was allowed to cool to room temperature before filtration through a pad of Celite® and rinsed with MeOH. The crude material was concentrated in vacuo and purified on a 50 g C18 Aq Gold column (gradient elution: 5-100% MeCN in water, 0.05% acetic acid in both). Pure fractions were combined, frozen on dry ice, and lyophilized giving the title compound 16f as a dark reddish solid (16.2 mg, 39%). MS: calc'd for $C_{50}H_{61}N_3O_{13}$, 911.4; found 912.4 (M+H). $^1$H-NMR (500 MHz; DMSO-$d_6$): δ 9.38 (s, 1H), 7.86-7.84 (m, 1H), 7.19-7.18 (m, 2H), 6.06 (td, J=2.9, 1.9 Hz, 1H), 5.86-5.80 (m, 1H), 5.24-5.21 (m, 1H), 4.80-4.76 (m, 1H), 4.08-4.07 (m, 2H), 3.51 (ddq, J=5.7, 2.9, 1.0 Hz, 1H), 3.09 (t, J=0.6 Hz, 2H), 3.02-3.01 (m, 3H), 2.77 (d, J=0.7 Hz, 3H), 2.61-2.59 (m, 1H), 2.14 (s, 6H), 2.00 (s, 3H), 1.95-1.94 (m, 3H), 1.83-1.76 (m, 2H), 1.66 (s, 9H), 1.50-1.47 (m, 3H), 1.37 (d, J=15.9 Hz, 3H), 1.27-1.20 (m, 2H), 1.07 (d, J=6.5 Hz, 2H), 0.85 (d, J=6.5 Hz, 6H), 0.70-0.67 (m, 3H).

Compound 16g:

16 g was prepared using the general procedure as described for 16b: Compound 15 (40 mg, 0.0463 mmol, 1.00 eq.), (1-methylpiperidin-4-yl)-methanol (90 mg, 0.719 mmol, 15 eq.), t-BuBrettPhos-Pd-G3-palladacycle (21 mg, 0.0245 mmol, 0.5 eq.), and $K_3PO_4$ (23 mg, 0.108 mmol, 2.3 eq.) to afford the title compound 16g (5.6 mg, 13%). MS: calc'd for $C_{50}H_{61}N_3O_{13}$, 911.4; found 912.4 (M+H). $^1$H NMR (500 MHz, $CD_3OD$): δ 8.01 (br. s., 1H), 7.18 (br. s., 1H), 6.94 (br. s., 2H), 6.43 (br. s., 1H), 6.23 (br. s., 2H), 5.06 (br. s., 1H), 5.01 (br. s., 1H), 4.01-4.19 (m, 1H), 3.93 (br. s., 1H), 3.75 (br. s., 1H), 3.07 (br. s., 1H), 2.86-3.05 (m, 7H), 2.33-2.45 (m, 4H), 2.30 (br. s., 4H), 2.11-2.20 (m, 5H), 1.98 (br. s., 4H), 1.83-1.93 (m, 4H), 1.78 (br. s., 4H), 1.48 (d, J=11.72 Hz, 2H), 1.32 (d, J=18.07 Hz, 1H), 0.95 (br. s., 8H), 0.80 (br. s., 2H), 0.03 (br. s., 2H), −0.23 (br. s., 2H).

Compound 16h:

16 h was prepared using the general procedure as described for 16b: Compound 15 (40 mg, 0.0463 mmol, 1.00 eq.), 2-(4-methylpiperazin-1-yl)ethan-1-ol (80 mg, 0.554 mmol, 12 eq.), t-BuBrettPhos-Pd-G3-palladacycle (20 mg, 0.0234 mmol, 0.5 eq.), and $K_3PO_4$ (23 mg, 0.108 mmol, 2.3 eq.) to afford the title compound 16h (9.6 mg, 22%). MS: calc'd for $C_{50}H_{62}N_4O_{13}$, 926.4; found 927.4 (M+H), 925.3 (M−H). $^1$H NMR (500 MHz; DMSO-$d_6$): δ 9.36-9.41 (m, 1H), 7.87 (br. s., 1H), 7.19 (br. s., 2H), 5.81 (br. s., 1H), 5.25 (br. s., 1H), 4.78 (br. s., 1H), 4.31 (br. s., 1H), 4.23 (br. s., 1H), 4.16 (br. s., 1H), 3.51 (br. s., 1H), 3.03 (br. s., 2H), 2.86 (d, J=10.75 Hz, 1H), 2.78 (br. s., 1H), 2.72 (br. s., 3H), 2.31 (br. s., 5H), 2.14 (br. s., 7H), 2.10 (br. s., 1H), 2.01 (br. s., 5H), 1.95 (br. s., 3H), 1.90 (br. s., 2H), 1.67 (br. s., 3H), 1.59

(br. s., 1H), 1.51 (br. s., 1H), 1.26-1.46 (m, 1H), 1.23 (br. s., 1H), 0.85 (br. s., 8H), 0.79 (br. s., 2H), 0.69-0.67 (m, 5H).

Compound 16i:

16i was prepared using the general procedure as described for 16b: Compound 15 (30 mg, 0.0347 mmol, 1.00 eq.), 2-morpholinoethan-1-ol (46 mg, 0.347 mmol, 10 eq.), t-BuBrettPhos-Pd-G3-palladacycle (15 mg, 0.0173 mmol, 0.5 eq.), and $K_3PO_4$ (15 mg, 0.0704 mmol, 2.0 eq.) to afford 69% (22 mg). MS: calc'd for $C_{49}H_{59}N_3O_{14}$, 913.40; found 914.3 (M+H). $^1$H NMR (500 MHz; DMSO-$d_6$): δ 9.41-9.40 (m, 1H), 7.86 (dd, J=5.2, 2.0 Hz, 1H), 7.23-7.18 (m, 2H), 6.06-6.03 (m, 1H), 5.83-5.81 (m, 1H), 5.25-5.24 (m, 1H), 4.79-4.78 (m, 1H), 4.33-4.31 (m, 1H), 4.33-4.16 (m, 3H), 3.58 (s, 5H), 3.09-3.03 (m, 4H), 2.73 (s, 2H), 2.16 (s, 4H), 1.99 (d, J=29.4 Hz, 8H), 1.67 (s, 3H), 1.52 (d, J=4.2 Hz, 2H), 1.13 (d, J=13.8 Hz, 1H), 0.85 (d, J=6.5 Hz, 10H), 0.69-0.67 (m, 8H).

Compound 16j:

16j was prepared using the general procedure as described for 16b: Compound 15 (30 mg, 0.0347 mmol, 1.00 eq.), (1-methylpyrrolidin-3-yl)methanol (40 mg, 0.347 mmol, 10 eq.), t-BuBrettPhos-Pd-G3-palladacycle (15 mg, 0.0173 mmol, 0.5 eq.), and $K_3PO_4$ (15 mg, 0.0704 mmol, 2.0 eq.) to afford 23% (7.0 mg). MS: calc'd for $C_{49}H_{59}N_3O_{13}$, 897.40; found 898.4 (M+H). $^1$H NMR (500 MHz; DMSO-$d_6$): δ 9.39-9.38 (m, 1H), 7.89-7.86 (m, 1H), 7.19 (t, J=7.0 Hz, 2H), 6.05-6.03 (m, 1H), 5.86-5.80 (m, 1H), 5.25-5.23 (m, 1H), 4.80-4.78 (m, 1H), 4.17-4.15 (m, 1H), 4.14-4.09 (m, 1H), 3.99 (s, 1H), 3.52-3.49 (m, 1H), 3.09-3.03 (m, 3H), 2.78-2.77 (m, 1H), 2.37 (dt, J=5.5, 2.7 Hz, 2H), 2.21 (d, J=35.5 Hz, 6H), 1.98 (d, J=31.1 Hz, 7H), 1.67-1.59 (m, 3H), 1.60-1.58 (m, 1H), 1.53-1.47 (m, 2H), 1.39-1.34 (m, 2H), 0.84 (d, J=6.8 Hz, 11H), 0.67 (t, J=2.9 Hz, 7H).

Compound 16k:

16k was prepared using the general procedure as described for 16b: Compound 15 (50 mg, 0.0579 mmol, 1.00 eq.), 2-(pyrrolidin-1-yl)ethan-1-ol (67 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 46% (23.6 mg). MS: calc'd for $C_{49}H_{59}N_3O_{13}$, 897.40; found 898.4 (M+H), 896.3 (M−H). $^1$H NMR (500 MHz; DMSO-$d_6$): δ 9.38 (d, J=1.2 Hz, 1H), 7.88-7.87 (m, 1H), 7.21 (s, 1H), 6.05-6.03 (m, 1H), 5.82 (dd, J=1.3, 0.7 Hz, 1H), 5.25-5.20 (m, 1H), 4.81-4.79 (m, 1H), 4.33-4.30 (m, 1H), 4.24-4.15 (m, 1H), 3.54-3.50 (m, 2H), 3.09-3.03 (m, 6H), 2.85-2.78 (m, 6H), 2.18 (s, 4H), 1.99 (d, J=31.9 Hz, 5H), 1.70 (s, 6H), 1.15-1.05 (m, 1H), 0.85 (d, J=6.7 Hz, 11H), 0.68 (dt, J=3.6, 0.9 Hz, 9H).

Compound 16l:

16l was prepared using the general procedure as described for 16b: Compound 15 (50 mg, 0.0579 mmol, 1.00 eq.), (1-methylpyrrolidin-2-yl)methanol (67 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 35% (17.7 mg). MS: calc'd for $C_{49}H_{59}N_3O_{13}$, 897.40; found 898.4 (M+H), 896.3 (M−H). $^1$H NMR (500 MHz; DMSO-$d_6$): δ 9.38-9.37 (m, 1H), 7.88-7.87 (m, 1H), 7.20-7.18 (m, 1H), 6.06-6.04 (m, 1H), 5.84-5.82 (m, 1H), 5.25-5.24 (m, 1H), 4.81-4.79 (m, 1H), 4.19-4.11 (m, 2H), 3.54-3.50 (m, 1H), 3.10-3.07 (m, 1H), 3.03 (s, 2H), 2.97-2.96 (m, 1H), 2.79-2.78 (m, 3H), 2.64-2.61 (m, 6H), 2.37 (s, 3H), 2.18 (s, 3H), 1.99 (d, J=32.7 Hz, 6H), 1.68 (s, 3H), 1.68-1.57 (m, 3H), 1.55-1.45 (m, 1H), 0.85 (d, J=6.7 Hz, 11H), 0.69-0.67 (m, 7H).

Compound 16m:

16m was prepared using the general procedure as described for 16b: Compound 15 (50 mg, 0.0579 mmol, 1.00 eq.), 2-(piperidin-1-yl)ethan-1-ol (75 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 54% (28.3 mg). MS: calc'd for $C_{50}H_{61}N_3O_{13}$, 911.42; found 912.4 (M+H), 910.3 (M−H). $^1$H NMR (500 MHz; DMSO-$d_6$): δ 9.38-9.36 (m, 1H), 7.88-7.86 (m, 1H), 7.22 (dt, J=1.7, 0.8 Hz, 1H), 6.07-6.05 (m, 1H), 5.83-5.82 (m, 1H), 5.26-5.22 (m, 1H), 4.81-4.78 (m, 1H), 4.31 (dd, J=2.5, 1.0 Hz, 1H), 4.23-4.15 (m, 1H), 3.54-3.50 (m, 1H), 3.10-3.01 (m, 3H), 2.79-2.77 (m, 1H), 2.69 (s, 2H), 2.44 (d, J=0.7 Hz, 6H), 2.17 (s, 6H), 1.99 (d, J=32.3 Hz, 5H), 1.68 (s, 6H), 1.50 (s, 3H), 1.38-1.37 (m, 2H), 0.85 (d, J=6.7 Hz, 9H), 0.69-0.67 (m, 7H).

Compound 16n:

16n was prepared using the general procedure as described for 16b: Compound 15 (50 mg, 0.0579 mmol, 1.00 eq.), 2-(azepan-1-yl)ethan-1-ol (83 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 53% (28.4 mg). MS: calc'd for $C_{51}H_{63}N_3O_{13}$, 925.44; found 926.5 (M+H), 924.3 (M−H). $^1$H NMR (500 MHz; DMSO-$d_6$): δ 9.42-9.34 (m, 1H), 7.85-7.84 (m, 1H), 7.16 (td, J=1.8, 0.5 Hz, 2H), 6.07-6.04 (m, 1H), 5.84-5.82 (m, 1H), 5.24 (s, 1H), 4.81-4.77 (m, 1H), 4.26-4.25 (m, 1H), 4.19-4.13 (m, 2H), 3.57-3.48 (m, 1H), 3.12-3.10 (m, 2H), 3.02-2.99 (m, 4H), 2.89 (s, 6H), 2.89-2.76 (m, 3H), 2.69 (s, 3H), 2.15-2.14 (m, 3H), 2.01 (s, 3H), 1.95 (s, 3H), 1.90 (s, 3H), 1.67 (s, 3H), 1.58-1.54 (m, 6H), 0.86 (d, J=6.5 Hz, 8H), 0.71-0.67 (m, 6H).

Compound 16o:

16o was prepared using the general procedure as described for 16b: Compound 15 (30 mg, 0.0347 mmol, 1.0 eq.), N,N-dimethylaminopropan-1-ol (35 mg, 0.339 mmol, 10 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 55% (17 mg). MS: calc'd for $C_{48}H_9N_3O_{13}$, 885.4; found 886.4 (M+H). $^1$H NMR (500 MHz, $CD_3OD$) δ 7.86-8.10 (m, 1H), 7.16 (s, 1H), 6.93 (br. s., 1H), 6.43 (br. s., 1H), 6.22 (br. s., 2H), 5.06 (br. s., 1H), 4.98 (br. s., 1H), 4.24 (br. s., 1H), 4.15 (br. s., 1H), 3.75 (br. s., 1H), 2.90-3.13 (m, 5H), 2.58 (br. s., 2H), 2.34 (br. s., 7H), 2.26 (br. s., 3H), 2.09-2.17 (m, 4H), 2.05 (br. s., 3H), 1.98 (br. s., 3H), 1.82-1.95 (m, 3H), 1.79 (s, 3H), 1.73 (s, 1H), 0.77-1.00 (m, 8H), 0.03 (s, 2H), −0.25 (s, 2H).

Compound 16p:

16p was prepared using the general procedure as described for 16b: Compound 15 (30 mg, 0.0347 mmol, 1.0 eq.), N,N-dimethylaminobutan-1-ol (40 mg, 0.341 mmol, 10 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 35% (11 mg). MS: calc'd for $C_{49}H_{61}N_3O_{13}$, 899.42; found 900.4 (M+H). $^1$H NMR (500 MHz, $CD_3OD$) δ 7.98 (br. s., 1H), 7.18 (br. s., 1H), 6.93 (br. s., 1H), 6.22 (br. s., 2H), 5.06 (br. s., 1H), 4.99 (br. s., 1H), 4.93 (br. s., 1H), 4.22 (br. s., 2H), 4.12 (br. s., 1H), 3.83-3.96 (m, 1H), 3.63-3.83 (m, 2H), 3.08 (br. s., 2H), 3.01 (d, J=8.79 Hz, 5H), 2.51 (br. s., 3H), 2.35 (br. s., 6H), 2.28 (br. s., 3H), 2.09-2.17 (m, 3H), 2.07 (br. s., 1H), 1.98 (br. s., 3H), 1.81-1.92 (m, 3H), 1.68-1.81 (m, 2H), 1.52-1.65 (m, 2H), 1.36-1.52 (m, 3H), 1.32 (d, J=18.56 Hz, 2H), 0.95 (br. s., 3H), 0.88 (d, J=6.84 Hz, 4H) 0.04 (s, 2H), −0.24 (s, 2H).

Compound 16q:

16q was prepared using the general procedure as described for 16b: Compound 15 (50 mg, 0.0579 mmol, 1.00 eq.), 2-(2-azabicyclo[2.2.1]heptan-2-yl)ethan-1-ol (82 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 55% (29 mg). MS: calc'd for $C_{51}H_{61}N_3O_{13}$, 923.42; found 924.4 (M+H), 922.3 (M−H). $^1H$ NMR (500 MHz; DMSO-$d_6$): δ 9.34-9.32 (m, 1H), 7.88-7.86 (m, 1H), 7.18-7.17 (m, 2H), 6.06-6.03 (m, 1H), 5.84-5.81 (m, 1H), 5.25-5.22 (m, 1H), 4.82-4.78 (m, 1H), 4.21-4.13 (m, 3H), 3.46-3.39 (m, 1H), 3.13 (t, J=2.6 Hz, 3H), 3.02-3.01 (m, 3H), 2.81-2.79 (m, 3H), 2.29 (d, J=0.8 Hz, 3H), 2.18 (s, 3H), 2.02 (s, 3H), 1.95 (s, 3H), 1.68 (s, 5H), 1.55-1.50 (m, 3H), 1.40 (s, 3H), 1.22 (d, J=9.2 Hz, 6H), 0.86 (d, J=6.8 Hz, 8H), 0.69-0.68 (m, 5H).

Compound 16r:

16r was prepared using the general procedure as described for 16b: Compound 15 (50 mg, 0.0579 mmol, 1.00 eq.), 2-(aziridin-1-yl)ethan-1-ol (50.4 mg, 0.579 mmol, 10 eq.), t-BuBrettPhos-Pd-G3-palladacycle (25 mg, 0.0289 mmol, 0.5 eq.), and $K_3PO_4$ (25 mg, 0.1158 mmol, 2.0 eq.) to afford 11% (5.6 mg). MS: calc'd for $C_{51}H_{64}N_4O_{14}$, 956.44; found 957.4 (M+H), 955.3 (M−H). $^1H$ NMR (500 MHz; DMSO-$d_6$): δ 9.37-9.35 (m, 1H), 7.87-7.84 (m, 1H), 7.20-7.18 (m, 1H), 6.07-6.03 (m, 1H), 5.83-5.81 (m, 1H), 5.25-5.21 (m, 1H), 4.78 (dq, J=2.8, 0.9 Hz, 1H), 4.34-4.31 (m, 2H), 4.23-4.15 (m, 1H), 3.47 (d, J=5.8 Hz, 5H), 3.09-3.08 (m, 2H), 3.02 (dddd, J=3.6, 2.6, 2.4, 1.3 Hz, 3H), 2.78-2.77 (m, 1H), 2.71-2.70 (m, 2H), 2.63 (d, J=1.2 Hz, 2H), 2.41-2.34 (m, 8H), 2.17-2.15 (m, 3H), 2.01 (t, J=0.4 Hz, 3H), 1.94 (t, J=0.9 Hz, 3H), 1.89 (s, 2H), 1.66 (d, J=0.4 Hz, 3H), 1.61-1.53 (m, 1H), 1.38 (d, J=15.9 Hz, 2H), 0.86-0.84 (m, 9H), 0.69-0.67 (m, 6H).

Compound 16s:

16s was prepared using the general procedure as described for 16b: Compound 15 (30 mg, 0.0347 mmol, 1.0 eq.), 2-(2-(dimethylamino)ethoxy)ethan-1-ol (50 mg, 0.375 mmol, 10 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 35% (11 mg). MS: calc'd for $C_{49}H_{61}N_3O_{14}$, 915.4; found 916.4 (M+H). $^1H$ NMR (500 MHz, $CD_3OD$) δ 8.01 (d, J=15.1 Hz, 1H), 7.20 (br. s., 1H), 6.96 (br. s., 1H), 6.44 (br. s., 1H), 6.15-6.32 (m, 2H), 5.07 (d, J=16.2 Hz, 1H), 4.34 (br. s., 2H), 4.24 (br. s., 1H), 3.86 (br. s., 3H), 3.78 (d, J=11.7 Hz, 1H), 3.69 (br. s., 3H), 3.18 (br. s., 1H), 3.06-3.15 (m, 2H), 3.02 (d, J=9.77 Hz, 5H), 2.51-2.70 (m, 2H), 2.32 (d, J=11.7 Hz, 6H), 2.11 (s., 3H), 1.94-2.07 (m, 6H), 1.90 (br. s., 1H), 1.75-1.86 (m, 5H), 1.73 (br. s., 1H), 1.67 (br. s., 2H), 1.24-1.45 (m, 3H), 0.89-0.96 (m, 8H), 0.06 (s, 2H), −0.20 (s, 2H).

Compound 16t:

16t was prepared using the general procedure as described for 16b: Compound 15 (30 mg, 0.0347 mmol, 1.0 eq.), 2-diethylaminoethan-1-ol (45 mg, 0.383 mmol, 11 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 14% (4.5 mg). MS: calc'd for $C_{49}H_{61}N_3O_{13}$, 899.4; found 900.4 (M+H), 898.3 (M−H). $^1H$ NMR (500 MHz, $CD_3OD$) δ 8.06 (br. s., 1H), 7.26 (br. s., 1H), 7.02 (br. s., 1H), 6.44 (br. s., 1H), 6.23 (br. s., 2H), 5.10 (br. s., 1H), 5.00 (br. s., 2H), 4.48 (br. s., 1H), 4.38 (br. s., 1H), 3.77 (br. s., 1H), 3.46 (br. s., 2H), 3.15 (s, 4H), 3.18 (s, 3H), 3.03 (d, J=9.28 Hz, 6H), 2.32 (br. s., 4H), 2.09-2.16 (m, 4H), 1.99 (br. s., 4H), 1.78 (br. s., 4H), 1.38 (br. s., 1H), 1.30 (br. s., 10H), 0.96 (br. s., 8H), 0.11 (s, 2H), −0.20 (s, 2H).

Compound 16u:

16u was prepared using the general procedure as described for 16b: Compound 15 (30 mg, 0.0347 mmol, 1.0 eq.), 2-diisopropylaminoethan-1-ol (45 mg, 0.383 mmol, 11 eq.), t-BuBrettPhos-Pd-G3-palladacycle (15 mg, 0.0176 mmol, 0.5 eq.), and $K_3PO_4$ (15 mg, 0.0707 mmol, 2.0 eq.) to afford 31% (10 mg). MS: calc'd for $C_{51}H_{65}N_3O_{13}$, 927.45; found 928.4 (M+H), 926.3 (M−H). $^1H$ NMR (500 MHz, $CD_3OD$) δ 8.03 (br. s., 1H), 7.10-7.29 (m, 1H), 6.94 (br. s., 1H), 6.23 (br. s., 1H), 5.01-5.06 (m, 2H), 4.23 (br. s., 1H), 3.18 (br. s., 1H), 3.12 (br. s., 2H), 2.91-3.06 (m, 4H), 2.31 (br. s., 4H), 2.11 (s, 4H), 1.98 (br. s., 4H), 1.78 (br. s., 4H), 1.64 (br. s., 1H), 1.28-1.41 (m, 2H), 1.18 (br. s., 14H), 1.06 (d, J=6.84 Hz, 1H), 0.95 (s, 9H), 0.81 (s, 2H), 0.07-0.13 (m, 1H), 0.04 (s, 2H), −0.23 (s, 2H).

Compound 16v:

16v was prepared using general procedure as described for 16b: Compound 15 (40 mg, 0.0463 mmol, 1.0 eq.), 2-(methyl(pyridin-2-yl)amino)ethan-1-ol (75 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16v (15.6 mg, 36%). MS: calc'd for $C_{51}H_{58}N_4O_{13}$, 934.40; found 935.3 (M+H), 933.3 (M−H). $^1H$ NMR (500 MHz, $CD_3OD$): δ 8.09 (t, J=1.4 Hz, 1H), 8.02-8.00 (m, 1H), 7.56-7.53 (m, 1H), 7.19-7.17 (m, 1H), 7.07 (s, 1H), 6.86-6.84 (m, 1H), 6.70-6.68 (m, 2H), 6.61 (td, J=1.8, 0.7 Hz, 2H), 6.42-6.41 (m, 1H), 6.22-6.20 (m, 2H), 5.04-5.02 (m, 1H), 4.59 (s, 2H), 4.39-4.36 (m, 1H), 4.32-4.29 (m, 1H), 4.01 (s, 2H), 3.72-3.68 (m, 1H), 3.15 (s, 7H), 3.00-2.99 (m, 4H), 2.31 (s, 4H), 2.11 (s, 4H), 1.95 (d, J=22.7 Hz, 3H), 1.77 (s, 3H), 1.63-1.60 (m, 1H), 1.30 (s, 2H), 0.94 (d, J=6.6 Hz, 4H), 0.80-0.79 (m, 4H), −0.03 (dd, J=2.4, 0.5 Hz, 2H), −0.24 (dd, J=2.3, 1.1 Hz, 2H).

Compound 16w:

16w was prepared using general procedure as described for 16b: Compound 15 (40 mg, 0.0463 mmol, 1.0 eq.), (2-((dimethylamino)methyl)phenyl)methanol (76 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16w (5.6 mg, 18%). MS: calc'd for $C_{53}H_{61}N_3O_{13}$, 947.42; found 948.4 (M+H), 946.3 (M−H). $^1H$ NMR (500 MHz, $CD_3OD$): δ 8.05-8.04 (m, 1H), 7.46-7.44 (m, 1H), 7.34-7.33 (m, 1H), 7.07-7.05 (m, 1H), 6.80 (d, J=4.2 Hz, 1H), 6.53-6.48 (m, 1H), 6.24-6.22 (m, 1H), 5.51 (d, J=12.1 Hz, 1H), 5.44-5.42 (m, 1H), 5.07-5.00 (m, 1H), 4.59 (s, 1H), 3.82-3.69 (m, 2H), 3.55 (d, J=8.6 Hz, 1H), 3.31-3.11 (m, 12H), 3.03-3.01 (m, 4H), 2.33 (s, 3H), 2.24 (s, 5H), 2.09 (dd, J=1.9, 1.0 Hz, 3H), 1.99 (s, 3H), 1.92 (s, 1H), 1.77 (d, J=0.5 Hz, 4H), 1.67-1.61 (m, 1H), 1.30 (d, J=0.3 Hz, 1H), 0.96-0.87 (m, 5H), 0.11 (d, J=2.8 Hz, 1H), 0.06-0.04 (m, 3H), −0.20-0.22 (m, 2H).

Compound 16x:

16x was prepared using general procedure as described for 16b: Compound 15 (40 mg, 0.0463 mmol, 1.0 eq.), N-(2-hydroxyethyl)acetamide (48 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16x (20 mg, 41%). MS: calc'd for $C_{47}H_{55}N_3O_{14}$, 885.37; found 886.3 (M+H). $^1H$ NMR (500 MHz, $CD_3OD$) δ 7.98 (br. s., 1H), 7.18 (s, 2H), 6.94 (br. s., 1H), 6.23 (br. s., 1H), 5.01-5.06 (m, 2H), 4.14 (br. s., 1H), 3.62 (br. s., 4H), 2.94-3.18 (m, 5H), 2.31 (br. s., 5H), 2.11 (s, 5H), 1.98 (br. s., 10H), 1.78 (br. s., 5H), 1.64 (br. s., 1H), 1.28-1.41 (m, 2H), 1.06 (d, J=6.84 Hz, 1H), 0.95 (s, 8H), 0.07-0.13 (m, 1H), 0.04 (s, 2H), −0.23 (s, 2H).

Compound 16y:

16y was prepared using general procedure as described for 16b: Compound 15 (40 mg, 0.0463 mmol, 1.0 eq.), 2-(1H-imidazol-1-yl)ethan-1-ol (52 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16y (8 mg, 8%). MS: calc'd for $C_{48}H_{54}N_4O_{13}$, 894.37; found 895.3 (M+H). $^1H$ NMR (500 MHz, $CD_3OD$) δ 7.75 (br. s., 1H), 7.16-7.26 (m, 2H), 6.98

(s, 1H), 6.94 (s, 1H), 4.58 (br. s., 5H), 4.44-4.54 (m, 3H), 4.31-4.35 (m, 1H), 3.83-3.90 (m, 2H), 3.72 (br. s., 1H), 3.66 (s, 1H), 3.55 (s, 1H), 3.33-3.36 (m, 1H), 3.00 (d, J=8.30 Hz, 3H), 2.30 (br. s., 3H), 2.00-2.11 (m, 4H), 1.92-2.00 (m, 3H), 1.90 (s, 2H), 1.76 (br. s., 3H), 1.70 (d, J=6.84 Hz, 1H), 1.52-1.65 (m, 2H), 1.49 (d, J=15.14 Hz, 2H), 1.32-1.41 (m, 2H), 1.11-1.32 (m, 3H), 0.83-1.00 (m, 6H), 0.09-0.10 (m, 1H), 0.00 (br. s., 2H), −0.23 (br. s., 1H).

Compound 16z:

16z was prepared using general procedure as described for 16b: Compound 15 (40 mg, 0.0463 mmol, 1.0 eq.), N-(2-hydroxyethyl)-N-methylacetamide (54 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16z (6.5 mg, 16%). MS: calc'd for $C_{48}H_{57}N_3O_{14}$, 899.38; found 900.4 (M+H). $^1$H NMR (500 MHz, $CD_3OD$) δ 8.03 (br. s., 1H), 7.20 (br. s., 2H), 6.42 (br. s., 1H), 6.22 (br. s., 1H), 5.06 (br. s., 1H), 4.99 (br. s., 2H), 4.58 (s, 3H), 4.38 (d, J=3.91 Hz, 1H), 4.31 (br. s., 2H), 4.23 (br. s., 2H), 3.86 (br. s., 2H), 3.80 (br. s., 2H), 3.74 (br. s., 1H), 3.19 (s, 3H), 2.96-3.06 (m, 5H), 2.31 (br. s., 2H), 2.20 (s, 2H), 2.11 (d, J=6.84 Hz, 3H), 2.04 (s, 1H), 1.97 (br. s., 6H), 1.93 (s, 2H), 1.76 (br. s., 3H), 1.65 (br. s., 2H), 1.29 (s, 1H), 0.94 (br. s., 3H), 0.10 (d, J=2.93 Hz, 1H), 0.03 (br. s., 2H), −0.23 (br. s., 2H).

Compound 16z-1:

16z-1 was prepared using general procedure as described for 16b: Compound 15 (40 mg, 0.0463 mmol, 1.0 eq.), 2-(azetidin-1-yl)ethan-1-ol (47 mg, 0.463 mmol, 10 eq.), t-BuBrettPhos-Pd-G3-palladacycle (20 mg, 0.0213 mmol, 0.5 eq.), and $K_3PO_4$ (20 mg, 0.094 mmol, 2.0 eq.) to afford the title compound 16z-1 (8.7 mg, 21%). MS: calc'd for $C_{48}H_{57}N_3O_{13}$, 883.39; found 884.4 (M+H). $^1$H NMR (500 MHz, $CD_3OD$) δ 7.19 (br. s., 1H), 4.58 (br. s., 2H), 4.19 (br. s., 1H), 3.83-3.89 (m, 1H), 3.73-3.82 (m, 1H), 3.52 (s, 1H), 3.46 (br. s., 6H), 3.00 (br. s., 1H), 2.30 (br. s., 4H), 2.13-2.22 (m, 3H), 2.10 (br. s., 3H), 1.97 (br. s., 3H), 1.92 (s, 8H), 1.76 (br. s., 4H), 1.56-1.69 (m, 2H), 1.43 (s, 2H), 1.46 (s, 2H), 1.31-1.39 (m, 2H), 1.29 (br. s., 1H), 1.24 (d, J=14.17 Hz, 1H), 1.15 (d, J=5.86 Hz, 1H), 0.95 (br. s., 3H), 0.10 (d, J=2.44 Hz, 2H), 0.03 (br. s., 2H), −0.23 (br. s., 1H).

Example 4: Reductive Amination

Rifamycin analog (17) was synthesized from compound 14 by use of reductive amination as shown in Scheme 8, below.

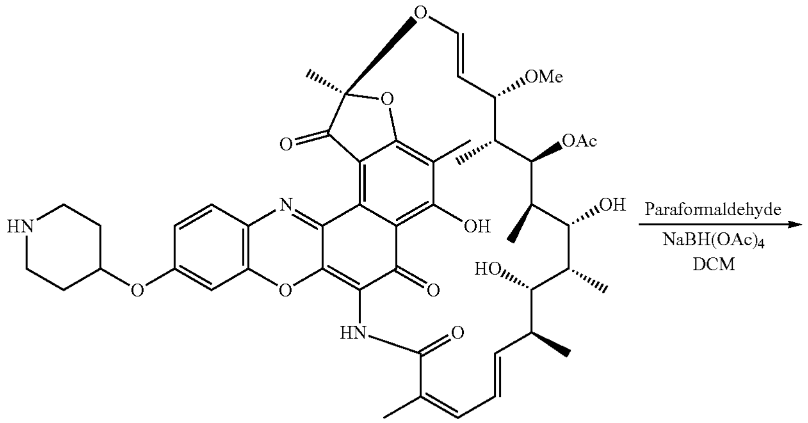

14

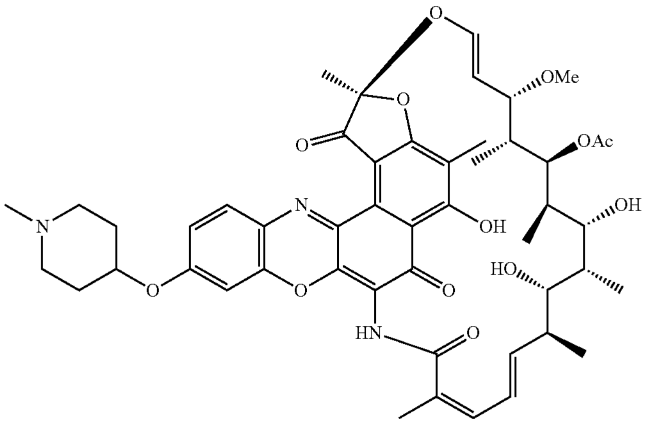

17

To a solution of compound 14 (9 mg, 0.0102 mmol) and paraformaldehyde (1.52 mg, 0.051 mmol) in 1.0 mL of anhydrous DCM at room temperature was added NaBH$(OAc)_3$ (4.3 mmol, 0.0204 mmol). The mixture was stirred for 1 h. The reaction progress was monitored by LC/MS to afford the desired product. The crude reaction mixture was quenched by addition of 2-3 drops of water. All volatiles were removed under reduced pressure, then diluted with DMSO (0.5 mL). The crude mixture was purified by preparative HPLC (Gemini, 5 μm, 150 mm×30 mm, eluents: 10-95% MeCN in water, 0.05% AcOH) pure fractions combined and lyophilized to give 6 mg (66%) of 17 as a reddish solid. MS (ESI, pos.): calc'd for $C_{49}H_{59}N_3O_{13}$, 897.40; found 898.4 (M+H). $^1$H NMR (500 MHz; DMSO-$d_6$): δ 9.38 (br. s., 1H), 7.86 (br. s., 1H), 7.17-7.25 (m, 4H), 6.04 (d, J=6.35 Hz, 1H), 5.81 (br. s., 2H), 4.79 (br. s., 2H), 4.70 (br. s., 2H), 4.15 (br. s., 1H), 3.53 (br. s., 1H), 3.30 (br. s., 5H), 3.09 (br. s., 3H), 3.03 (br. s., 4H), 2.87 (s, 1H), 2.78 (br. s., 2H), 2.58-2.66 (m, 6H), 2.54 (br. s., 8H), 2.37 (d, J=1.47 Hz, 2H), 2.15-2.27 (m, 20H), 2.12 (br. s., 1H), 2.03-2.09 (m, 3H), 2.00 (s, 9H), 1.95 (br. s., 10H), 1.91 (s, 3H), 1.72 (br. s., 3H), 1.67 (br. s., 8H), 1.58 (s, 1H), 1.50 (br. s., 1H), 1.24 (br. s., 2H), 0.81-0.94 (m, 15H), 0.78 (d, J=6.84 Hz, 3H), 0.69 (br. s., 9H).

Example 5: Preparation of Compound 29

Rifamycin analog 29 was prepared as shown in Scheme 9, below, and described below.

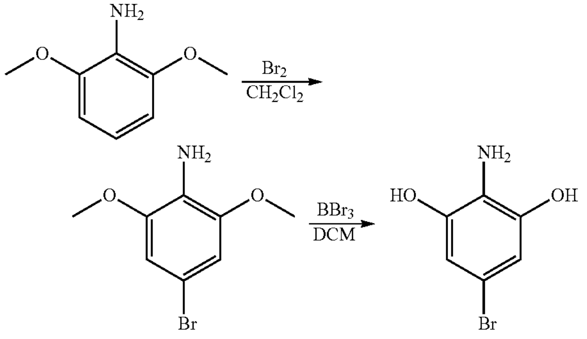

26 27

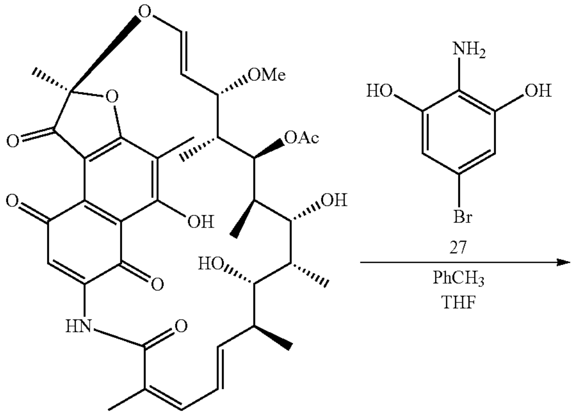

Rifamycin S

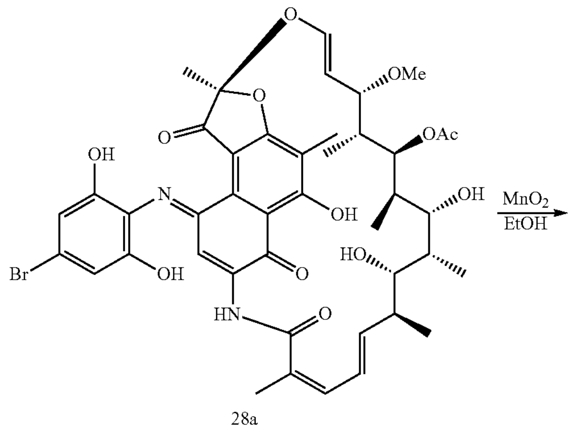

28a

-continued

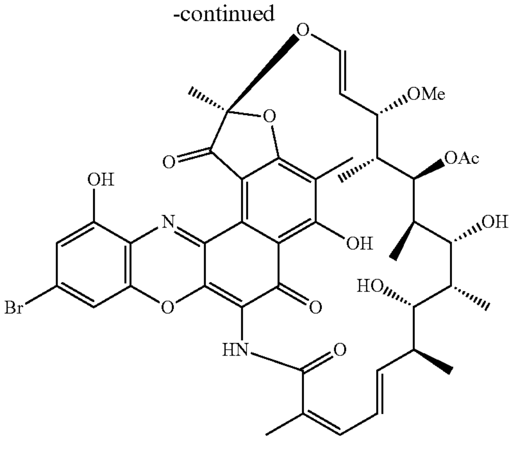

28

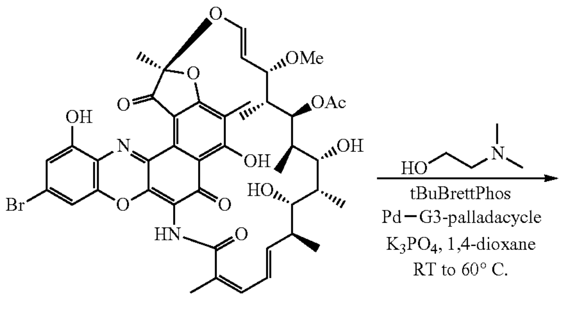

28

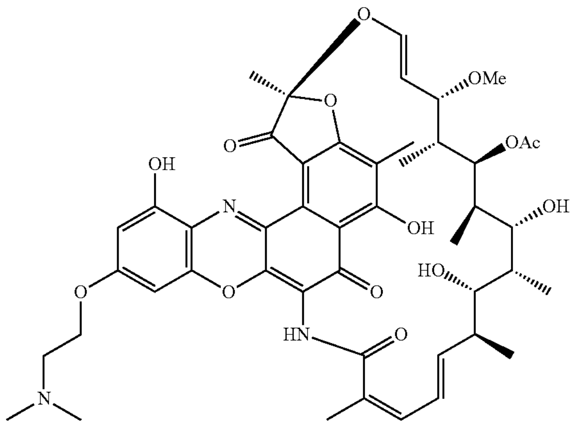

29

Synthesis of Compound 26.

To a stirred solution of 2,6-dimethoxyaniline (9.0 g, 58.7 mmol, 1.0 eq) in 350 mL of anhydrous DCM was dropwise added over 30 min a $Br_2$ solution in 50 mL of anhydrous DCM at 4° C. An additional 200 mL was added to the slurry to achieve a semi-homogeneous solution. The reaction mixture was stirred overnight at room temperature. The dark brown mixture was cooled to 4° C. and basified by addition of 1.0 M NaOH solution (ca. 100 mL) to pH=10-11. The mixture was diluted with 200 mL of DCM and the layers are separated. The aqueous layer was extracted with DCM (200 mL total). The combined DCM layers were washed with water, brine, and dried over $Na_2SO_4$. After concentration in vacuo, the crude product was obtained as a slightly reddish solid. The residue was dissolved in DCM (8 mL) and loaded onto a 220 g HP silica gel Gold RediSep column and purified via ISCO (gradient elution: 5-95% EA in hexanes), pure fractions combined, and the solvent evaporated in vacuo.

The solid was triturated with DCM and hexanes and filtered. The off-while solid was dried in vacuo giving the title compound 26 as an off-white solid (9.4 g, 70%). MS (ESI, pos.): calc'd for $C_8H_{10}BrNO_2$, 230.99; found 231.9 and 234.0 (M+H). 1H NMR (500 MHz; $CDCl_3$) δ 6.66 (s, 2H), 3.84 (s, 6H).

Synthesis of Compound 27.

Compound 26 (2.2 g, 9.47 mmol, 1.0 eq) was dissolved in 10 mL of anhydrous DCM and a $BBr_3$ solution was added dropwise over 10 min (10 mL, 1.0 M solution in DCM) at 4° C. The reaction was exothermic and produced a precipitate. An additional amount of $BBr_3$ (9 mL, 94.7 mmol, 10 eq) was added and the reaction mixture was stirred at room temperature overnight. The reddish suspension was checked by LC/MS to confirm the desired product. The reaction mixture was transferred to a 250 mL flask and cooled to 4° C. The mixture was carefully quenched with water followed by treatment with aqueous saturated $NaHCO_3$ solution to give a pH=7-8. The mixture was extracted with DCM and the aqueous layer cooled to 4° C. to afford a dark brown precipitate. The mixture was filtered and the brown solid was dissolved in 10 mL of methanol and dried over $Na_2SO_4$ to provide the desired product 27 (1.9 g, 100%). MS (ESI, pos.): calc'd for $C_6H_6BrNO_2$, 202.96; found 204.0 and 206.1 (M+H). $^1H$ NMR (500 MHz; $CD_3OD$) δ 6.45 (s, 2H), 4.87 (s, 2H).

Synthesis of Compound 28.

To a stirred solution of compound 27 (0.146 g, 0.72 mmol) in a mixture of toluene (20 mL) and THE (20 mL) at room temperature was added rifamycin S (0.5 g, 0.72 mmol). The solution was stirred for 3 days at room temperature to afford the desired product. The solvents were removed in vacuo, the dark residue was dissolved in 10 mL of ethanol followed by 100 mg of manganese dioxide ($MnO_2$). The sluggish mixture was stirred for 5 h at room temperature. After filtration of insoluble materials using a Celite pad, the filtrate was evaporated in vacuo. The dark residue was purified on a 120 g HP silica gel Gold RediSep column via ISCO (gradient elution: 5-95% EA in hexanes). The pure fractions combined and evaporated in vacuo giving the title compound 28 as a dark reddish solid (270 mg, 43%). MS (ESI, pos.): calc'd for $C_{43}H_{47}BrN_2O_{13}$, 878.23; found 879.2 and 880.2 (M+H), 878.1 and 879.1 (M−1). $^1H$ NMR (500 MHz; DMSO-$d_6$) δ 10.22 (br. s., 1H), 9.52 (br. s., 1H), 7.43 (br. s., 1H), 7.35 (br. s., 1H), 6.04 (br. s., 1H), 5.83 (br. s., 2H), 5.21 (d, J=6.35 Hz, 2H), 4.89 (t, J=10.50 Hz, 1H), 4.16 (br. s., 1H), 3.51 (br. s., 1H), 3.15 (br. s., 2H), 3.02 (br. s., 4H), 2.80 (t, J=8.55 Hz, 1H), 2.21 (br. s., 3H), 2.08 (br. s., 1H), 1.96 (s, 4H), 1.99 (s, 4H), 1.78 (br. s., 1H), 1.71 (br. s., 3H), 1.60 (br. s., 1H), 1.47 (br. s., 1H), 0.84 (d, J=6.84 Hz, 6H), 0.69 (br. s., 6H).

Synthesis of Compound 29.

To a 8 mL screw-top oven-dried vial, equipped with a stir bar was charged with compound 15 (60 mg, 0.069 mmol, 1.00 eq), 2-(dimethylamino)ethan-1-ol (61 mg, 0.69 mmol, 10 eq), t-BuBrettPhos-Pd-G3-palladacycle (31 mg, 0.0345 mmol, 0.5 eq), and $K_3PO_4$ (30 mg, 0.141 mmol, 2.0 eq.). The reaction vial was capped with a rubber septum. The septum was pierced with a needle attached to evacuate and back-filled with argon (this process was repeated twice) followed by the addition of 1,4-dioxane (1.5 mL). The reaction was heated at 60° C. under argon pressure for 15 h, the reaction was allowed to cool to room temperature, filtered through a pad of Celite®, and rinsed with MeOH. The crude material was concentrated in vacuo and purified on a 50 g C18 Aq column (gradient elution: 10-95% MeCN in water, 0.05% acetic acid in both). The product fractions were combined and lyophilized giving the title compound 29 as a dark reddish solid (21 mg, 35%). MS (ESI, pos.): calc'd for $C_{47}H_{57}N_3O_{14}$, 887.38; found 888.3 (M+H). $^1H$ NMR (500 MHz; DMSO-$d_6$) δ 10.12 (br. s., 1H), 9.39 (br. s., 1H), 6.75 (br. s., 1H), 6.70 (br. s., 1H), 6.03 (br. s., 1H), 5.77 (d, J=15.14 Hz, 1H), 5.21 (br. s., 1H), 4.83-4.90 (m, 1H), 4.15-4.30 (m, 2H), 4.08 (br. s., 1H), 3.53 (br. s., 1H), 3.29 (s, 1H), 3.16 (br. s., 1H), 3.03 (br. s., 3H), 2.87 (br. s., 1H), 2.79 (br. s., 1H), 2.62-2.71 (m, 2H), 2.36 (s, 1H), 2.23 (s, 6H), 2.19 (br. s., 3H), 1.93-2.11 (m, 7H), 1.91 (s, 1H), 1.76 (br. s., 1H), 1.69 (br. s., 3H), 1.53-1.65 (m, 1H), 1.50 (br. s., 1H), 1.32-1.45 (m, 1H), 0.76-0.94 (m, 6H), 0.68 (br. s., 5H).

29a

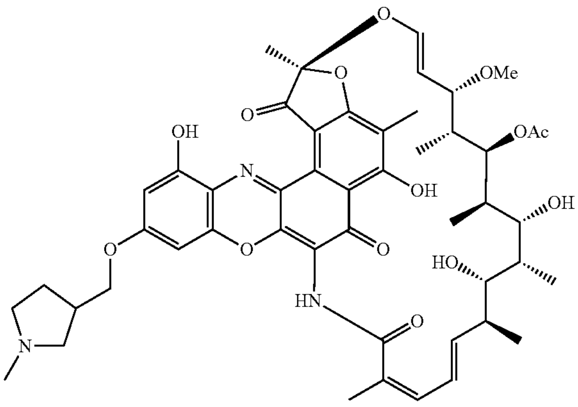

Compound 29a:

29a was prepared using the general procedure as described for 29: Compound 28 (50 mg, 0.0568 mmol, 1.00 eq.), (1-methylpyrrolidin-3-yl)methanol (65 mg, 0.568 mmol, 10 eq.), t-BuBrettPhos-Pd-G3-palladacycle (24 mg, 0.0284 mmol, 0.5 eq.), and $K_3PO_4$ (24 mg, 0.115 mmol, 2.0 eq.) to afford 19% (9.8 mg). MS: calc'd for $C_{49}H_{59}N_3O_{14}$, 913.40; found 914.4 (M+H), 912.3 (M−H). $^1H$ NMR (500 MHz; DMSO-$d_6$): δ 9.38-9.34 (m, 1H), 6.74-6.64 (m, 1H), 6.26 (s, 1H), 6.02-6.00 (m, 1H), 5.80-5.78 (m, 1H), 5.23-5.19 (m, 1H), 4.87-4.82 (m, 1H), 4.06-4.03 (m, 2H), 3.55-3.51 (m, 1H), 3.17-3.15 (m, 1H), 3.03 (dd, J=3.2, 1.1 Hz, 2H), 2.87 (s, 3H), 2.78 (tdd, J=2.8, 1.5, 0.6 Hz, 3H), 2.64-2.58 (m, 1H), 2.37 (s, 1H), 2.30 (s, 6H), 2.18 (s, 6H), 1.97 (d, J=16.7 Hz, 5H), 1.69 (t, J=0.4 Hz, 3H), 1.53-1.51 (m, 2H), 0.85 (dt, J=2.6, 1.3 Hz, 11H), 0.69-0.67 (m, 4H).

29b

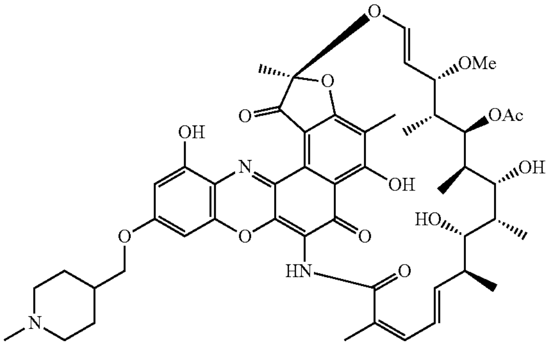

Compound 29b:

29b was prepared using the general procedure as described for 29: Compound 28 (60 mg, 0.068 mmol, 1.00 eq.), (1-methylpiperidin-4-yl)methanol (88 mg, 0.683 mmol, 10 eq.), t-BuBrettPhos-Pd-G3-palladacycle (29 mg, 0.034 mmol, 0.5 eq.), and $K_3PO_4$ (29 mg, 0.136 mmol, 2.0 eq.) to afford 9.5% (6.0 mg). MS: calc'd for $C_{50}H_{61}N_3O_{14}$, 927.42; found 928.4 (M+H), 926.3 (M−H). $^1$H NMR (500 MHz; DMSO-$d_6$): δ 8.84 (dd, J=1.5, 0.9 Hz, 1H), 7.13 (dd, J=1.7, 0.9 Hz, 1H), 6.92-6.88 (m, 1H), 6.29-6.26 (m, 1H), 6.21-6.18 (m, 1H), 5.67 (t, J=0.6 Hz, 1H), 5.00-4.99 (m, 1H), 4.75-4.73 (m, 1H), 3.92-3.90 (m, 1H), 3.81-3.79 (m, 4H), 2.85 (d, J=2.5 Hz, 2H), 2.75-2.72 (m, 1H), 2.63 (s, 2H), 2.36 (s, 3H), 2.12 (t, J=5.7 Hz, 6H), 1.93 (d, J=9.7 Hz, 4H), 1.81 (ddd, J=3.6, 3.0, 1.4 Hz, 2H), 1.72 (s, 6H), 1.66 (s, 6H), 1.37-1.34 (m, 5H), 0.88-0.85 (m, 7H), 0.69-0.64 (m, 4H).

29c

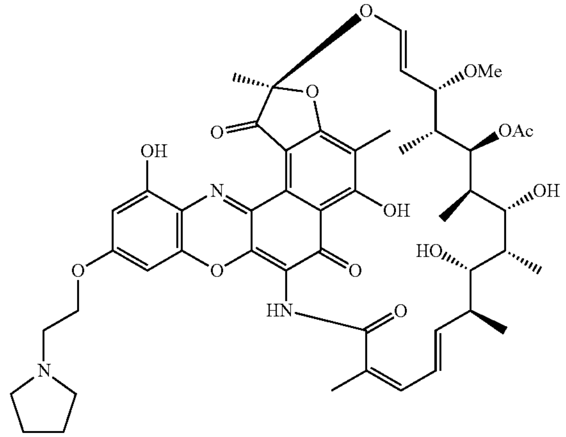

Compound 29c:

29c was prepared using the general procedure as described for 29: Compound 28 (60 mg, 0.068 mmol, 1.00 eq.), 2-(pyrrolidin-1-yl)ethan-1-ol (88 mg, 0.682 mmol, 10 eq.), t-BuBrettPhos-Pd-G3-palladacycle (29 mg, 0.034 mmol, 0.5 eq.), and $K_3PO_4$ (29 mg, 0.136 mmol, 2.0 eq.) to afford 26% (16.2 mg). MS: calc'd for $C_{49}H_{59}N_3O_{14}$, 913.40; found 914.4 (M+H), 912.3 (M−H). $^1$H NMR (500 MHz; DMSO-$d_6$): δ 9.40-9.39 (m, 1H), 6.77-6.76 (m, 1H), 6.67-6.65 (m, 1H), 6.02-6.00 (m, 1H), 5.78-5.76 (m, 1H), 5.21-5.19 (m, 1H), 4.86 (t, J=10.6 Hz, 1H), 4.27-4.20 (m, 2H), 4.08-4.06 (m, 1H), 3.54-3.50 (m, 1H), 3.17-3.14 (m, 1H), 3.03 (d, J=0.8 Hz, 3H), 2.86 (d, J=0.4 Hz, 3H), 2.79-2.77 (m, 1H), 2.64-2.57 (m, 4H), 2.18 (s, 8H), 1.97 (d, J=18.7 Hz, 7H), 1.70 (s, 7H), 1.60-1.56 (m, 1H), 1.51-1.46 (m, 1H), 0.84 (d, J=5.8 Hz, 7H), 0.67 (dt, J=1.5, 0.7 Hz, 5H).

29d

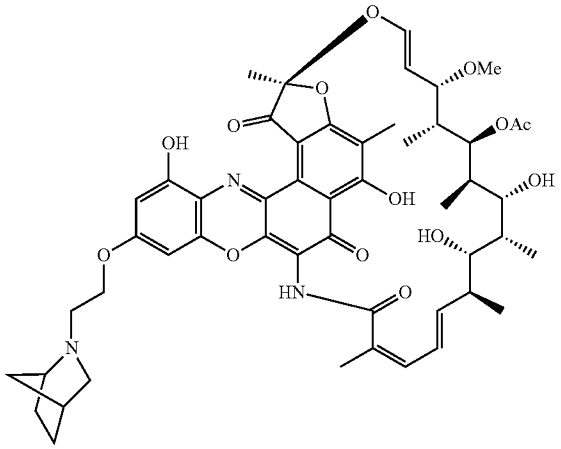

Compound 29d:

29d was prepared using the general procedure as described for 29: Compound 28 (60 mg, 0.068 mmol, 1.00 eq.), 2-(2-azabicyclo[2.2.1]heptan-2-yl)ethan-1-ol (96 mg, 0.682 mmol, 10 eq.), t-BuBrettPhos-Pd-G3-palladacycle (29 mg, 0.034 mmol, 0.5 eq.), and $K_3PO_4$ (29 mg, 0.136 mmol, 2.0 eq.) to afford 37% (23.7 mg). MS: calc'd for $C_{51}H_{61}$N3014, 939.42; found 940.5 (M+H), 938.3 (M−H). $^1$H NMR (500 MHz; DMSO-$d_6$): δ 9.37-9.35 (m, 1H), 6.72-6.65 (m, 1H), 6.04-6.00 (m, 1H), 5.79 (tdd, J=3.6, 1.8, 1.1 Hz, 1H), 5.22-5.19 (m, 1H), 4.86-4.82 (m, 1H), 4.19-4.16 (m, 2H), 4.07-4.05 (m, 2H), 3.54-3.52 (m, 1H), 3.17-3.14 (m, 1H), 3.07-3.02 (m, 2H), 2.86-2.80 (m, 3H), 2.80-2.77 (m, 1H), 2.32 (d, J=1.2 Hz, 3H), 2.18 (s, 7H), 1.98-1.91 (m, 8H), 1.69 (d, J=0.5 Hz, 3H), 1.58 (ddd, J=5.0, 2.0, 0.9 Hz, 1H), 1.52-1.43 (m, 2H), 1.42-1.40 (m, 2H), 1.27-1.24 (m, 2H), 0.85 (dt, J=2.2, 1.1 Hz, 9H), 0.68-0.67 (m, 5H).

29e

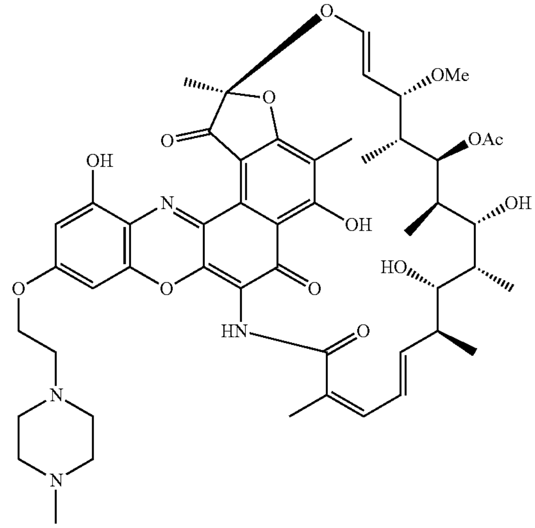

Compound 29e:

29e was prepared using the general procedure as described for 29: Compound 28 (60 mg, 0.068 mmol, 1.00 eq.), 2-(4-methylpiperazin-1-yl)ethan-1-ol (100 mg, 0.693 mmol, 10 eq.), t-BuBrettPhos-Pd-G3-palladacycle (30 mg, 0.0351 mmol, 0.5 eq.), and $K_3PO_4$ (30 mg, 0.141 mmol, 2.0 eq.) to afford 15% (9.8 mg). MS: calc'd for $C_{50}H_{62}N_4O_{14}$, 942.43; found 943.4 (M+H). $^1$H NMR (500 MHz, $CD_3OD$) δ 6.53-6.63 (m, 2H), 6.24 (br. s., 1H), 4.99-5.11 (m, 2H), 4.27-4.40 (m, 2H), 3.67 (s, 1H), 3.01 (d, J=8.30 Hz, 4H), 2.89 (br. s., 2H), 2.56-2.68 (m, 6H), 2.46 (br. s., 1H), 2.32 (s, 8H), 2.12 (br. s., 3H), 2.06 (s, 1H), 1.92-2.04 (m, 3H), 1.83 (s, 3H), 1.65 (d, J=8.79 Hz, 2H), 1.56 (s, 1H), 1.31 (br. s., 3H), 1.03 (br. s., 1H), 0.95 (s, 8H), 0.81 (s, 4H), 0.01 (s, 2H), −0.28 (s, 2H).

29f

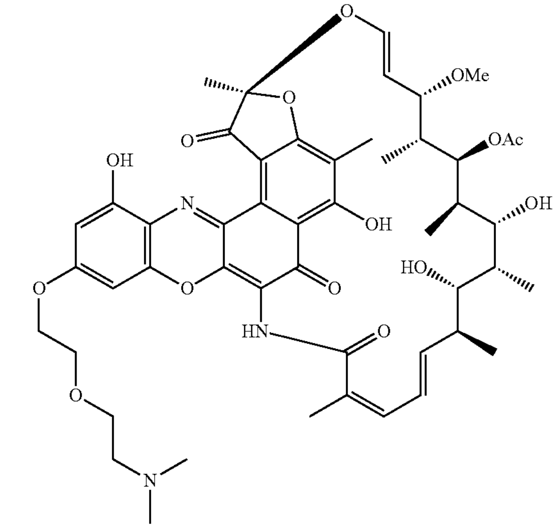

Compound 29f:

29f was prepared using the general procedure as described for 29: Compound 28 (60 mg, 0.068 mmol, 1.00 eq.), 2-(2-(dimethylamino)ethoxy)ethan-1-ol (100 mg, 0.693 mmol, 10 eq.), t-BuBrettPhos-Pd-G3-palladacycle (30 mg, 0.0351 mmol, 0.5 eq.), and $K_3PO_4$ (30 mg, 0.141 mmol, 2.0 eq.) to afford 11% (7.1 mg). MS: calc'd for $C_{49}H_{61}N_3O_{15}$, 931.41; found 932.3 (M+H). $^1$H NMR (500 MHz, $CD_3OD$) δ 6.49-6.59 (m, 2H), 6.21 (br. s., 1H), 4.95-5.07 (m, 2H), 4.24-4.40 (m, 2H), 3.87 (br. s., 3H), 3.72 (br. s., 3H), 3.00 (d, J=8.79 Hz, 5H), 2.67 (d, J=4.88 Hz, 3H), 2.36 (s, 10H), 2.30 (s, 5H), 2.11 (s, 5H), 1.99 (s, 5H), 1.82 (s, 4H), 1.30 (s, 2H), 0.93 (s, 6H), 0.00 (s, 2H), −0.30 (s, 2H).

29g

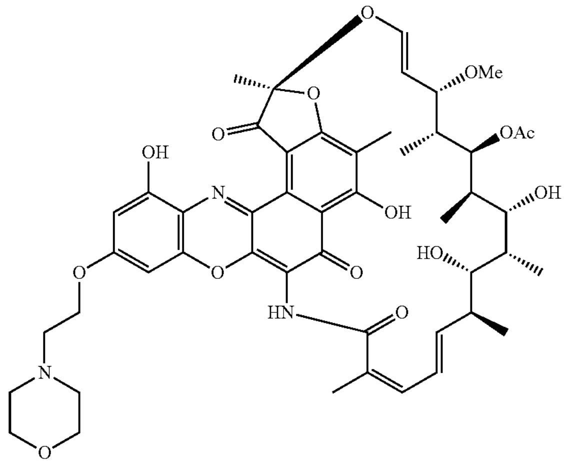

Compound 29g:

29 g was prepared using the general procedure as described for 29: Compound 28 (50 mg, 0.0568 mmol, 1.00 eq.), 2-morpholinoethan-1-ol (75 mg, 0.568 mmol, 10 eq.), t-BuBrettPhos-Pd-G3-palladacycle (24 mg, 0.028 mmol, 0.5 eq.), and $K_3PO_4$ (24 mg, 0.115 mmol, 2.0 eq.) to afford 12% (5.8 mg). MS: calc'd for $C_{49}H_{59}N_3O_{15}$, 929.39; found 930.4 (M+H). $^1$H NMR (500 MHz; DMSO-$d_6$): δ 10.14-10.11 (m, 1H), 9.38-9.31 (m, 1H), 6.76-6.59 (m, 1H), 6.34-6.20 (m, 1H), 6.04-6.01 (m, 1H), 5.79-5.76 (m, 2H), 5.21 (td, J=2.0, 1.1 Hz, 1H), 4.83 (t, J=0.8 Hz, 1H), 4.27-4.22 (m, 1H), 4.06-4.05 (m, 1H), 3.57 (s, 6H), 3.15 (d, J=0.7 Hz, 3H), 3.03 (d, J=1.5 Hz, 4H), 2.86 (s, 1H), 2.71 (dt, J=2.0, 1.5 Hz, 4H), 2.17 (s, 3H), 1.97 (d, J=15.3 Hz, 6H), 1.69 (s, 3H), 1.60-1.59 (m, 3H), 1.50-1.44 (m, 3H), 1.37 (s, 1H), 1.24 (d, J=1.0 Hz, 2H), 1.15-1.14 (m, 1H), 0.85 (td, J=1.9, 0.8 Hz, 6H), 0.67 (dtd, J=4.1, 2.1, 0.9 Hz, 4H).

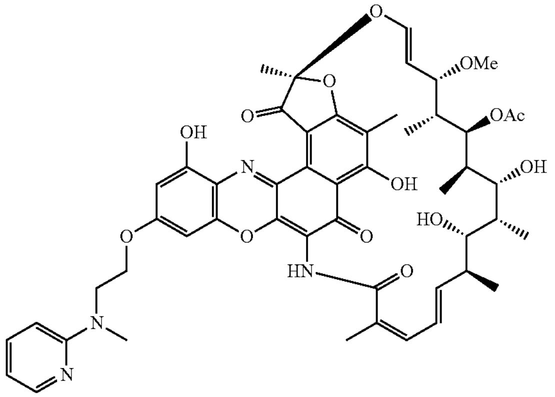 [SMILES: CO[C@H]1/C=C/O[C@@]2(C)Oc3c(C)c(O)c4c(=O)c(c5oc6cc(OCCN(C)c7ccccn7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 29h:

29 h was prepared using general procedure as described for 29: Compound 28 (40 mg, 0.0454 mmol, 1.0 eq.), 2-(methyl(pyridin-2-yl)amino)ethan-1-ol (69 mg, 0.454 mmol, 10 eq.), t-BuBrettPhos-Pd-G3-palladacycle (20 mg, 0.0223 mmol, 0.5 eq.), and $K_3PO_4$ (20 mg, 0.0921 mmol, 2.0 eq.) to afford 29 h (5.6 mg, 13%). MS: calc'd for $C_{51}H_{58}N_4O_{14}$, 950.39; found 951.3 (M+H). $^1$H NMR (500 MHz, $CD_3OD$): δ 8.07 (d, J=3.91 Hz, 1H), 7.53 (t, J=7.08 Hz, 1H), 6.69 (d, J=8.79 Hz, 1H), 6.59-6.66 (m, 2H), 6.44 (d, J=1.95 Hz, 1H), 6.22 (d, J=10.26 Hz, 1H), 5.95 (d, J=1.95 Hz, 1H), 5.74 (d, J=11.72 Hz, 1H), 5.13-5.18 (m, 2H), 4.58 (s, 5H), 4.30 (d, J=6.35 Hz, 2H), 4.22 (dd, J=2.93, 5.86 Hz, 1H), 4.00 (t, J=5.62 Hz, 2H), 3.86 (d, J=10.26 Hz, 1H), 3.35 (br. s., 2H), 3.13 (s, 2H), 2.95-3.03 (m, 3H), 2.11-2.17 (m, 2H), 2.03-2.11 (m, 4H), 1.92-2.00 (m, 8H), 1.71 (br. s., 1H), 1.42 (d, J=2.93 Hz, 1H), 1.35 (d, J=6.35 Hz, 2H), 1.22-1.32 (m, 5H), 0.85-1.00 (m, 3H), 0.33 (d, J=6.84 Hz, 2H), 0.09-0.10 (m, 1H), −0.33 (d, J=7.33 Hz, 2H).

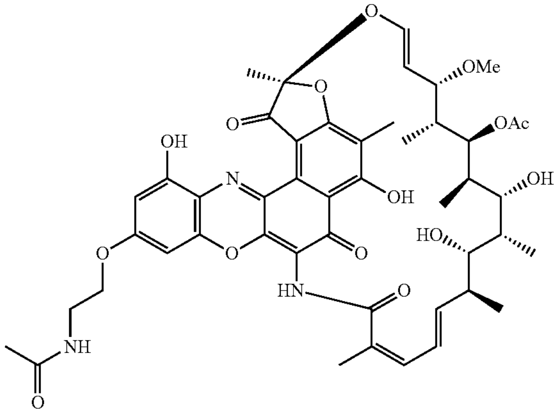 [SMILES: CO[C@H]1/C=C/O[C@@]2(C)Oc3c(C)c(O)c4c(=O)c(c5oc6cc(OCCNC(C)=O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 29i:

29i was prepared using general procedure as described for 29: Compound 28 (40 mg, 0.0454 mmol, 1.0 eq.), 2N-(2-hydroxyethyl)acetamide (47 mg, 0.454 mmol, 10 eq.), t-Bu-BrettPhos-Pd-G3-palladacycle (20 mg, 0.0227 mmol, 0.5 eq.), and $K_3PO_4$ (20 mg, 0.0939 mmol, 2.0 eq.) to afford 29i (12.2 mg, 31%). MS: calc'd for $C_{47}H_{55}N_3O_{15}$, 901.36; found 902.3 (M+H), 900.3 (M−H). $^1$H NMR (500 MHz; $CD_3OD$): 6.65-6.84 (m, 1H), 6.43-6.64 (m, 3H), 6.31-6.43 (m, 1H), 6.07-6.28 (m, 2H), 4.92-5.10 (m, 2H), 4.08-4.24 (m, 4H), 3.62 (br. s., 5H), 2.91-3.09 (m, 4H), 2.29 (s, 5H), 2.11 (br. s., 5H), 2.04 (s, 2H), 1.90-2.02 (m, 7H), 1.82 (s, 5H), 0.91 (br. s., 5H), 0.10 (s, 3H), −0.34 (s, 2H).

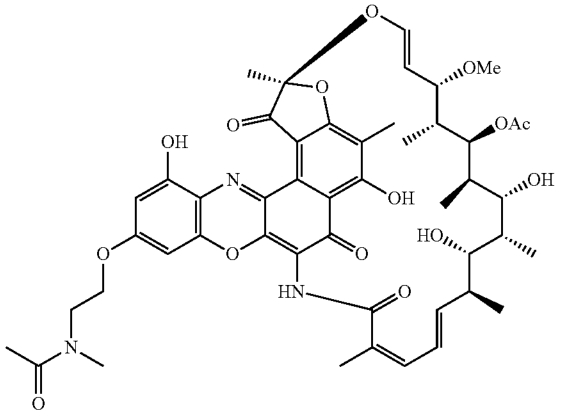 [SMILES: CO[C@H]1/C=C/O[C@@]2(C)Oc3c(C)c(O)c4c(=O)c(c5oc6cc(OCCN(C)C(C)=O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 29j:

29j was prepared using general procedure as described for 29: Compound 28 (40 mg, 0.0454 mmol, 1.0 eq.), N-(2-hydroxyethyl)-N-methylacetamide (53 mg, 0.454 mmol, 10 eq.), t-BuBrettPhos-Pd-G3-palladacycle (20 mg, 0.0227 mmol, 0.5 eq.), and $K_3PO_4$ (20 mg, 0.0939 mmol, 2.0 eq.) to afford 29j (7 mg, 17%). MS: calc'd for $C_{48}H_{57}N_3O_{15}$, 915.38; found 916.3 (M+H). $^1$H NMR (500 MHz; $CD_3OD$): δ 6.45-6.68 (m, 2H), 6.30-6.45 (m, 1H), 6.11-6.30 (m, 1H), 5.09-5.34 (m, 1H), 4.95-5.09 (m, 5H), 4.58 (s, 3H), 4.18-4.40 (m, 2H), 3.73-3.90 (m, 2H), 3.14-3.23 (m, 2H), 2.99 (d, J=9.28 Hz, 6H), 2.31 (br. s., 5H), 2.10 (s, 5H), 2.13 (s, 2H), 2.04 (s, 1H), 1.98 (br. s., 3H), 1.93 (s, 1H), 1.81 (s, 6H), 0.79-1.02 (m, 6H), −0.10-0.04 (m, 2H), −0.21-0.41 (m, 2H).

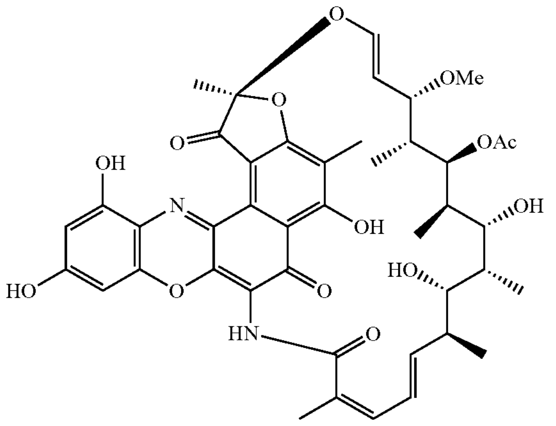 [SMILES: CO[C@H]1/C=C/O[C@@]2(C)Oc3c(C)c(O)c4c(=O)c(c5oc6cc(O)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 29k:

29k was the byproduct for all the C—O cross coupling reaction starting with compound 28. MS: calc'd for $C_{43}H_{48}N_2O_{14}$, 816.3; found 817.3 (M+H), 839.3 (M+Na). $^1$H NMR (500 MHz; DMSO-$d_6$): δ 10.09 (s, 1H), 9.31 (s, 1H), 6.44 (s, 2H), 6.00 (s, 1H), 5.77 (br. s., 2H), 5.20 (br. s., 1H), 4.81-4.88 (m, 2H), 4.05 (br. s., 1H), 3.48-3.54 (m, 1H), 3.16 (br. s., 1H), 3.02 (br. s., 3H), 2.97 (br. s., 1H), 2.77 (br. s., 1H), 2.51-2.54 (m, 1H), 2.12-2.21 (m, 4H), 2.00 (br. s., 1H), 1.92-1.98 (m, 5H), 1.90 (s, 1H), 1.74 (s, 3H), 1.61-1.71 (m, 6H), 1.43-1.61 (m, 3H), 1.22-1.24 (m, 1H), 0.83 (d, J=6.35 Hz, 2H), 0.66 (br. s., 3H), 0.06 (d, J=0.98 Hz, 1H).

Example 6: Preparation of Compound 35

Rifamycin analog 35 was synthesized from rifamycin S as shown in Scheme 10, below, and described below.

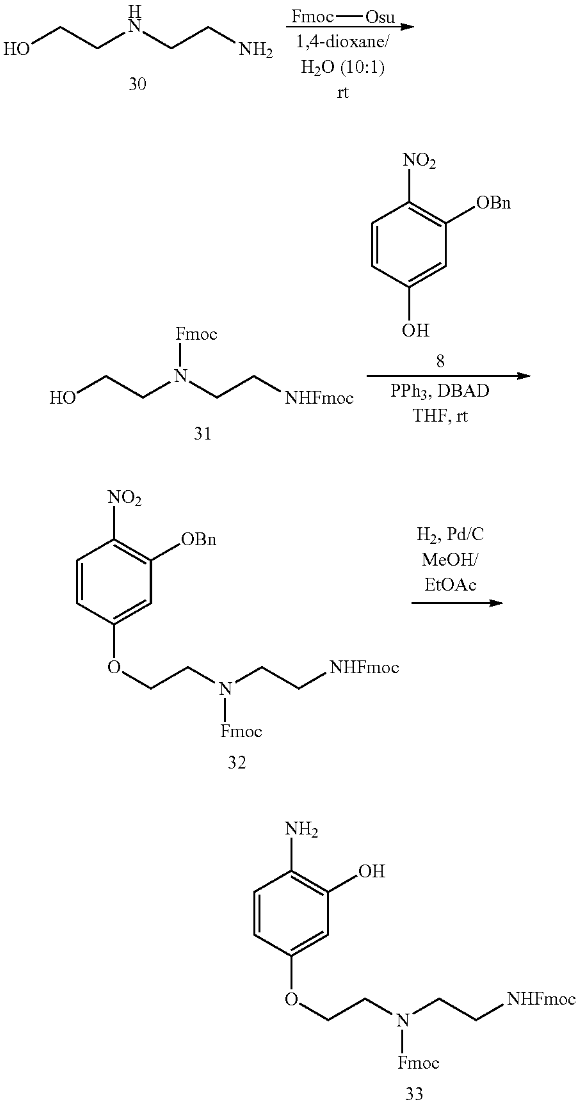

-continued

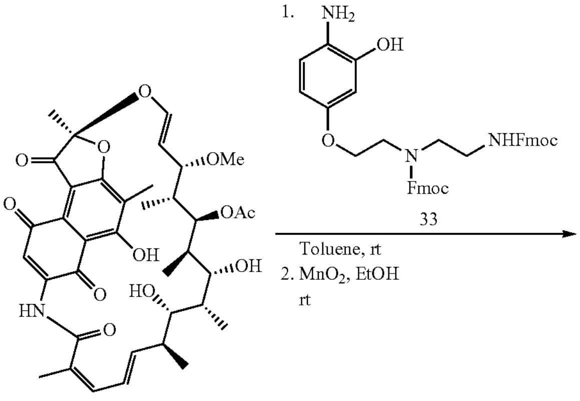

33 rifamycin S

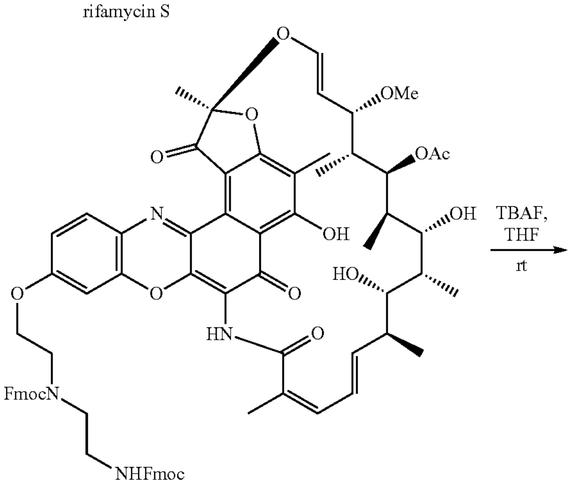

34

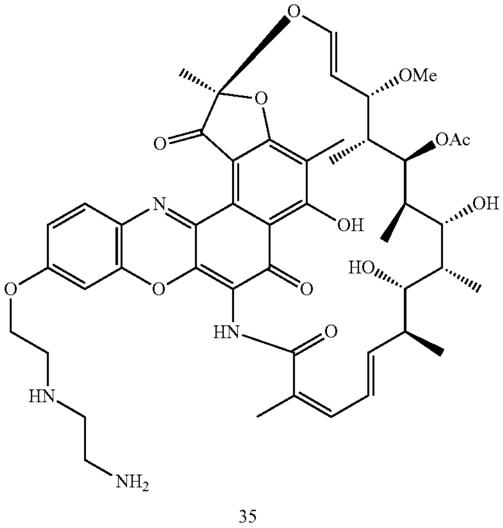

35

Synthesis of Compound 31.

To a solution of compound 30 (200 mg, 1.920 mmol) under argon in 1,4-dioxane/water (v/v, 10:1, 11 mL) was added Fmoc-OSu (1360 mg, 4.032 mmol). After stirring for 5 h an LC/MS analysis indicated the reaction was complete. The reaction mixture was treated with sat. $NaHCO_3$(5 mL) and extracted with EtOAc (3×15 mL). The combined organic layer was then treated with brine (10 mL), dried ($Na_2SO_4$) and concentrated in vacuo to give crude compound 31 as a white foam (800 mg, 76%), which was used in the next step instantly without further purification. MS: calc'd for $C_{34}H_{32}N_2O_5$, 548.2; found 549.2 (M+H).

Synthesis of Compound 32.

To a stirring solution of compound 8 (160 mg, 0.652 mmol) under argon in THF (2 mL) at room temperature were added the alcohol 31 (432 mg, 0.788 mmol) and $PPh_3$ (308 mg, 1.174 mmol). Then a solution of DBAD (270 mg, 1.174 mmol) in THF (1 mL) was added to the reaction mixture dropwise. After stirring for 15 h, the mixture was evaporated to dryness and the residue was purified on a 40 g HP silica gel Gold RediSep column via ISCO (gradient elution: 0-100% ethyl acetate in hexanes), and the pure fractions evaporated and dried in vacuo giving the title compound 32 as a yellowish white solid (286 mg, 56%). MS: calc'd for $C_{47}H_{41}N_3O$, 775.3; found 776.3 (M+H), 798.2 (M+Na).

Synthesis of Compound 33.

To a solution under argon of compound 32 (220 mg, 0.284 mmol) in 5 mL of methanol/EtOAc (2:3) and degassed with argon was added 31 mg of 10% Pd/C. The mixture was further degassed with argon and connected to a hydrogen balloon. After 2 h, analysis by LC/MS from an in-process aliquot indicated the reaction was complete. The mixture was filtered through Celite and concentrated to afford 150 mg of compound 33 (85% pure by LC/MS) as yellowish oil, which was used in the next step instantly without further purification. MS: calc'd for $C_{40}H_{37}N_3O_6$, 655.3; found 656.3 (M+H).

Synthesis of Compound 34.

To a round-bottom flask with hydroxyaniline 33 (150 mg, 0.194 mmol, 85% pure), were added toluene (2 mL) and rifamycin S (129 mg, 0.185 mmol). The reaction mixture was sonicated for 1 min to dissolve the reaction mixture, sealed via rubber septum, purged with argon, and the reaction stirred at ambient temperature. After 1 day another portion of hydroxyaniline 33 (45 mg, 0.059 mmol, 86% pure, synthesized using same procedure describe before) in toluene (2 mL) was added and stirred for 5 d. The reaction was concentrated in vacuo to remove toluene, dissolved in EtOH (4 mL) and $MnO_2$ (20 mg) was added. After stirring for 4 d, the reaction was concentrated in vacuo and purified by chromatography on a 40 g HP silica gel Gold RediSep column via ISCO (gradient elution: 0-100% ethyl acetate in hexanes). The pure fractions were evaporated and dried in vacuo giving the title compound 34 as a dark reddish solid (65 mg, 26%). MS (ESI, pos.): calc'd for $C_{77}H_{78}N_4O_{17}$, 1330.5; found, 1353.5 (M+Na).

Synthesis of Compound 35.

To a stirred solution of compound 34 (28 mg, 0.021 mmol) under argon in THF (1 mL), was treated with a solution of TBAF (13 mg, 0.05 mL, 0.050 mmol, 1M in THF) and the reaction was stirred at ambient temperature. After 2 h, the reaction was purified directly on a 50 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the title compound 35 as dark reddish solid (9 mg, 48%). MS: calc'd for $C_{47}H_{58}N_4O_{13}$, 886.4; found 887.3 (M+H). $^1$H-NMR (500 MHz; $CD_3OD$): δ 7.86-7.74 (m, 1H), 7.18-7.08 (m, 1H), 6.98-6.84 (m, 1H), 6.78-6.68 (m, 1H), 6.53-6.40 (m, 1H), 6.23-6.15 (m, 1H), 6.23-6.15 (m, 1H), 6.00-5.79 (m, 1H), 6.00-5.79 (m, 1H), 5.30-4.95 (m, 2H), 3.81-3.65 (m, 6H), 3.35 (s, 3H), 3.09-2.93 (m, 7H), 2.25-2.20 (m, 2H), 2.17-2.03 (m, 4H), 2.00-1.87 (m, 5H), 1.76-1.68 (m, 4H), 1.03-0.85 (m, 7H), 0.78-0.65 (m, 2H), 0.14-0.03 (m, 4H), 0.13-0.00 (m, 3H), −0.30 (m, 2H).

Example 7: Synthesis of Analog 38 According to the Disclosure

Rifamycin analog 38 was synthesized from rifamycin S as shown in Scheme 11 below, and as described below.

Scheme 11

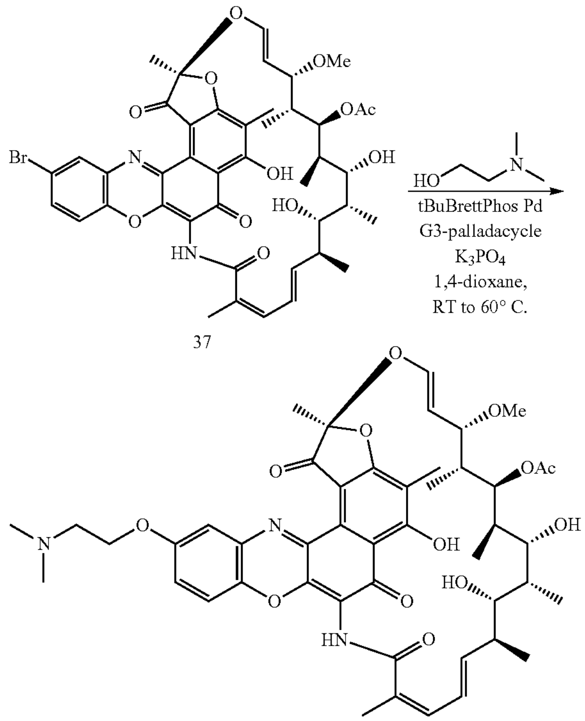

37

38

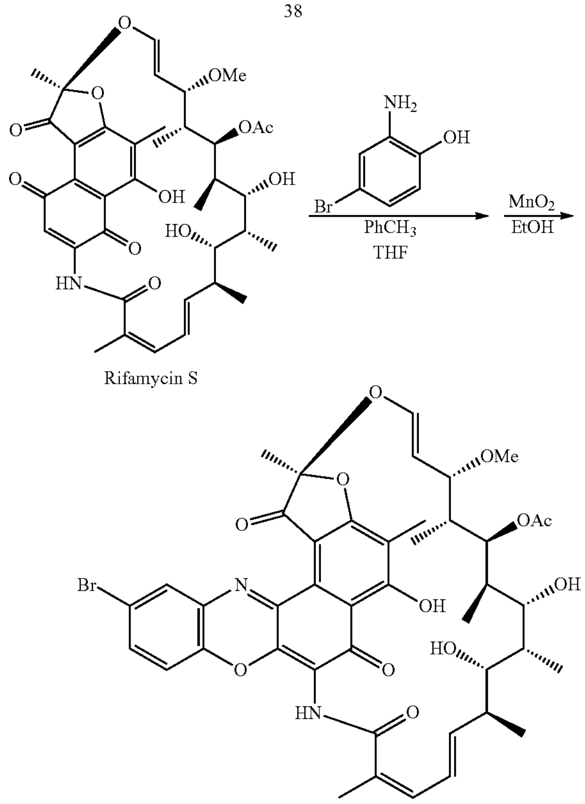

Rifamycin S

37

Example 6A: Pd-Catalyzed O-Alkylation (37)

Compound 37:

As described in the Example 3, rifamycin S (2.0 g, 2.87 mmol) in 80 mL of toluene at room temperature was treated with 2-amino-4-bromophenol (0.54 g, 2.87 mmol). The mixture solution was stirred for 2 days at room temperature. The mixture was then evaporated to dryness and the residue dissolved in 20 mL of ethanol and 300 mg of manganese oxide ($MnO_2$) was added in one portion to the ethanol solution. The mixture was stirred under argon for 15 h at room temperature. After filtration of insoluble materials using a Celite pad, the filtrate was evaporated under reduced pressure. The dark residue was purified on a 120 g HP silica gel Gold RediSep column via ISCO (gradient elution: 5-95% EA in hexanes). The pure fractions were evaporated and dried in vacuo giving the title compound 37 as a dark reddish solid (1.5 g, 60%). MS (ESI, pos.): calc'd for $C_{43}H_{47}BrN_2O_2$, 862.23; found 863.1 and 865.1 (M+H), 885.1 and 888.0 (M+Na). $^1$H NMR $^1$H-NMR (500 MHz; $CDCl_3$): δ 8.19-8.19 (m, 1H), 7.66-7.64 (m, 1H), 7.48 (s, 2H), 7.06 (s, 1H), 6.23-6.18 (m, 1H), 6.01 (d, J=12.3 Hz, 2H), 5.06-5.05 (m, 1H), 4.98 (dd, J=12.2, 7.1 Hz, 2H), 3.11 (s, 3H), 3.03-3.00 (m, 2H), 2.33 (s, 6H), 2.13 (s, 3H), 2.07 (s, 6H), 1.83 (s, 6H), 1.70 (s, 2H), 1.54 (s, 1H), 0.97 (d, J=6.6 Hz, 3H), 0.80 (d, J=5.2 Hz, 6H), 0.58-0.57 (m, 4H).

Compound 38:

A palladium-catalyzed C—O coupling of primary alcohols similar to title compounds 15 and 29 was employed. To compound 37 (60 mg, 0.069 mmol, 1.00 eq) was added 2-(dimethylamino)ethan-1-ol (62 mg, 0.69 mmol, 10 eq), t-BuBrettPhos-Pd-G3-palladacycle (30 mg, 0.0345 mmol, 0.5 eq), and $K_3PO_4$ (30 mg, 0.141 mmol, 2.0 eq.). The septum was pierced with a needle to evacuate and backfill with argon (this process was repeated twice) followed by the addition of 1,4-dioxane (1.5 mL). The reaction was heated at 60° C. in an oil bath under argon pressure for 15 h. The crude material was concentrated in vacuo and purified on a 50 g C18 Aq column (gradient elution: 10-95% MeCN in water, 0.05% acetic acid in both). The product fractions were combined, frozen on dry ice, and lyophilized giving the title compound 38 as a dark reddish solid (6.8 mg, 12%). Another purification by preparative HPLC (Gemini, 5 μm, 150 mm×30 mm, eluents: 10-95% MeCN in water, 0.05% AcOH) was conducted and lyophilized to afford pure product (4.5 mg). MS (ESI, pos.): calc'd for $C_{47}H_{57}N_3O_{13}$, 871.39; found 872.4 (M+H). $^1$H NMR (500 MHz; DMSO-$d_6$) δ 9.48-9.32 (m, 2H), 7.68-7.49 (m, 2H), 7.44-7.27 (m, 1H), 6.11-5.95 (m, 1H), 5.88-5.76 (m, 2H), 5.28-5.16 (m, 2H), 4.84-4.71 (m, 1H), 4.21-4.18 (m, 1H), 3.57-3.43 (m, 2H), 3.09-3.01 (m, 1H), 2.82-2.75 (m, 1H), 2.67 (dd, J=15.5, 10.1 Hz, 3H), 2.29-2.23 (m, 13H), 2.19 (d, J=0.6 Hz, 9H), 1.99-1.91 (m, 1H), 1.69 (s, 1H), 1.64-1.56 (m, 1H), 1.55-1.43 (m, 1H), 1.24 (s, 1H), 0.85-0.84 (m, 7H), 0.69-0.68 (m, 4H).

Example 8: Preparation of Compound 43

Rifamycin analog 43 was synthesized from rifamycin S as shown in Scheme 12 below, and as described below.

Scheme 12

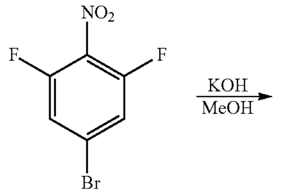

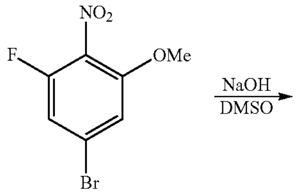

39

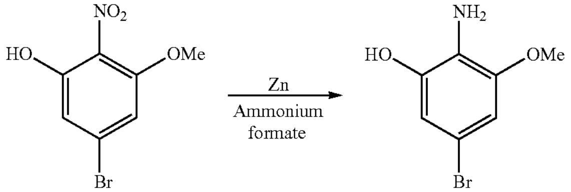

40

41

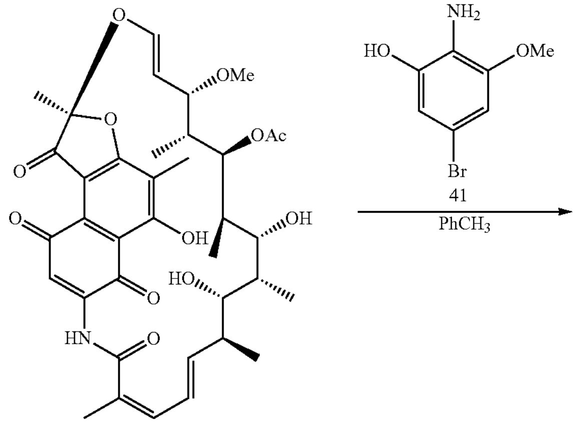

rifamycin S

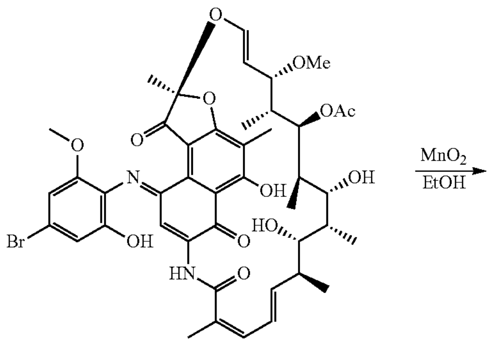

42a

-continued

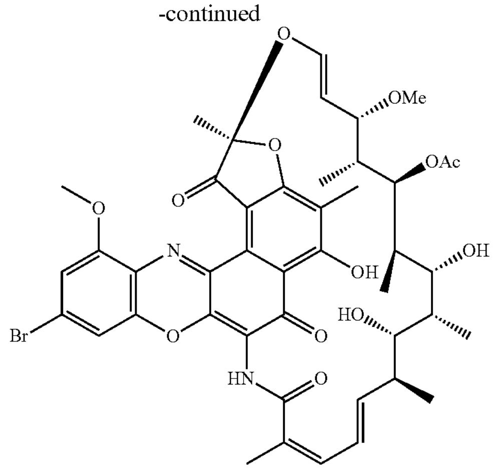

42

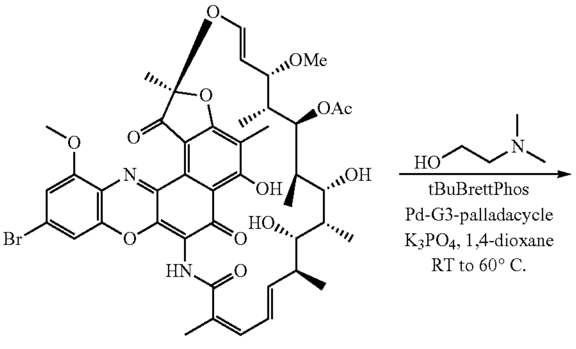

42

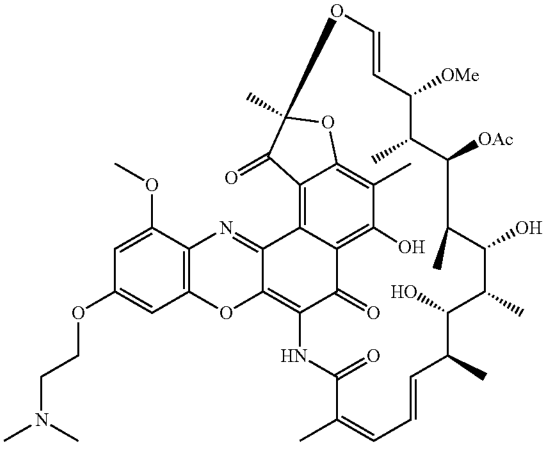

43

Compound 39:

To a stirred solution of 5-bromo-1,3-difluoro-2-nitrobenzene (2.0 g, 8.40 mmol, 1.0 eq.) in 15 mL of methanol at room temperature was added KOH (504 mg, 8.98 mmol, 1.07 eq.). The resulting mixture was refluxed at 90° C. for 1 h. After reaction completion, the mixture was cooled at room temperature and concentrated under reduced pressure. The residue was diluted with ethyl acetate (20 mL) and washed with water, brine, and dried over $Na_2SO_4$. After concentration in vacuo, the crude product was obtained as a dark solid. The residue was dissolved in DCM (5 mL) and loaded on a 80 g HP silica gel Gold RediSep column via ISCO (gradient elution: hexanes–90% EA in hexanes), and the pure fractions evaporated to afford light yellow solid of 39 (1.48 g, 70%). MS (ESI, pos.): calc'd for $C_7H_5BrFNO_3$, 250.02; found 273.2 (M+Na). $^1$H-NMR (500 MHz; $CDCl_3$): δ 7.06 (dd, J=8.6, 1.5 Hz, 1H), 7.02 (s, 1H), 3.95 (s, 3H).

Compound 40:

To a stirred solution of 5-bromo-1-fluoro-3-methoxy-2-nitrobenzene 39 (400 mg, 1.56 mmol) in DMSO (3 mL) was added 1M NaOH (2 mL, 2 mmol) and heated to 85° C. in an oil bath for 15 h. The reaction was complete by LCMS and cooled to room temperature then acidified with 1M HCl until the pH=2-3. The resultant solution was extracted using ethyl acetate (2×10 mL). The combined organic layers were washed with water, brine, dried ($Na_2SO_4$), and then concentrated. The crude oil was then purified on a 24 g HP silica gel Gold RediSep column via ISCO (gradient elution: 0-100% ethyl acetate in hexanes), and the pure fractions evaporated and dried in vacuo giving 40 as a yellowish white solid (0.35 g, 89%). MS (ESI, pos.): calc'd for $C_7H_6BrNO_4$, 248.03; found 247.9 and 248.9 isotopes (M+H). H-NMR (500 MHz; $CDCl_3$): δ 10.50 (t, J=0.4 Hz, 1H), 6.94 (s, 1H), 6.71 (s, 1H), 3.97 (s, 3H).

Compound 41:

To a stirred solution of 5-bromo-3-methoxy-2-nitrophenol 40 (150 mg, 0.605 mmol, 1.0 eq.) and ammonium acetate (114 mg, 1.814 mmol, 3.0 eq.) in anhydrous THE (3 mL) at room temperature was added Zn dust (593 mg, 9.07 mmol, 15 eq.) and degassed by nitrogen. The mixture was heated to 50° C. in an oil bath for overnight. The reaction was complete by LCMS. The reaction was cooled to room temperature and the crude was filtered through a Celite pad and concentrated. The crude oil was then purified on a 24 g HP silica gel Gold RediSep column via ISCO (gradient elution: 0-20% DCM in methanol), and the pure fractions evaporated and dried in vacuo giving 41 as a brown solid (40 mg, 31%). MS (ESI, pos.): calc'd for $C_7HBrNO_2$, 218.05; found 219.9 and 220.9 isotopes (M+H). $^1$H-NMR (500 MHz; $CDCl_3$): δ 6.65 (s, 1H), 6.62 (s, 1H), 3.85 (s, 3H), 1.45 (s, 2H).

Compound 42:

Following the general procedure in Example 3, To a stirring solution under argon of rifamycin S (118 mg, 0.169 mmol) in 4 mL of toluene at room temperature was added 2-amino-5-bromo-3-methoxyphenol 41 (37 mg, 0.169 mmol). The mixture solution was stirred for 2 days at room temperature. The mixture was then evaporated to dryness and the dark residue dissolved in 5 mL of ethanol and 30 mg of manganese oxide ($MnO_2$) was added at one portion to the ethanol solution. The sluggish mixture was stirred under argon for 15 h at room temperature. After filtration of insoluble materials using a Celite pad, the filtrate was evaporated under reduced pressure. The dark residue was purified on a 24 g HP silica gel Gold RediSep column via ISCO (gradient elution: 5-95% EA in hexanes). The pure fractions were evaporated and dried in vacuo giving the title compound 42 as a dark reddish solid (70 mg, 47%). MS (ESI, pos.): calc'd for $C_{44}H_{49}BrN_2O_{13}$, 893.78; found 893.7 and 895.7 (M+H), 891.3 and 893.1 (M−H). $^1$H-NMR (500 MHz; $CDCl_3$): δ 7.06 (d, J=9.8 Hz, 1H), 6.00-5.98 (m, 1H), 5.32 (s, 1H), 5.10-5.05 (m, 1H), 5.00-4.96 (m, 1H), 4.13 (s, 4H), 3.11 (s, 3H), 3.03-3.01 (m, 1H), 2.32 (s, 3H), 2.13 (s, 3H), 2.07 (d, J=4.3 Hz, 4H), 1.85 (s, 3H), 1.74 (dtd, J=6.2, 1.7, 1.2 Hz, 1H), 1.67-1.65 (m, 1H), 1.54 (s, 2H), 1.29-1.26 (m, 1H), 0.99-0.97 (m, 3H), 0.85-0.80 (m, 3H), 0.63-0.59 (m, 3H).

Compound 43:

43 was prepared using general procedure as described for 16b: Compound 42 (37 mg, 0.0447 mmol, 1.0 eq.), 2-(dimethylamino)ethan-1-ol (40 mg, 0.447 mmol, 10 eq.), t-BuBrettPhos-Pd-G3-palladacycle (20 mg, 0.0223 mmol, 0.5 eq.), and $K_3PO_4$ (20 mg, 0.091 mmol, 2.0 eq.) to afford the title compound 43 (15.0 mg, 40%). MS: calc'd for $C_{48}H_9N_3O_{14}$, 901.40; found 902.3 (M+H), 900.3 (M−H). $^1$H-NMR (500 MHz; DMSO-$d_6$): δ 9.31-9.30 (m, 1H), 6.79-6.76 (m, 1H), 6.70 (d, J=6.2 Hz, 2H), 6.05-6.03 (m, 1H), 5.81-5.80 (m, 2H), 5.25-5.22 (m, 2H), 4.77-4.77 (m, 2H), 4.29 (dt, J=1.9, 1.0 Hz, 2H), 4.21-4.13 (m, 3H), 4.00 (s, 3H), 3.57-3.54 (m, 1H), 3.04 (t, J=0.9 Hz, 4H), 2.96-2.87 (m, 1H), 2.80-2.76 (m, 2H), 2.66 (s, 6H), 2.22 (s, 2H), 2.15 (s, 3H), 2.00 (s, 3H), 1.95 (s, 3H), 1.80-1.78 (m, 1H), 1.66-1.59 (m, 3H), 0.85-0.84 (m, 6H), 0.69-0.66 (m, 6H).

Example 9: Preparation of Compound 45

Rifamycin analog 45 was synthesized from rifamycin S as shown in Scheme 13 below, and as described below.

Scheme 13

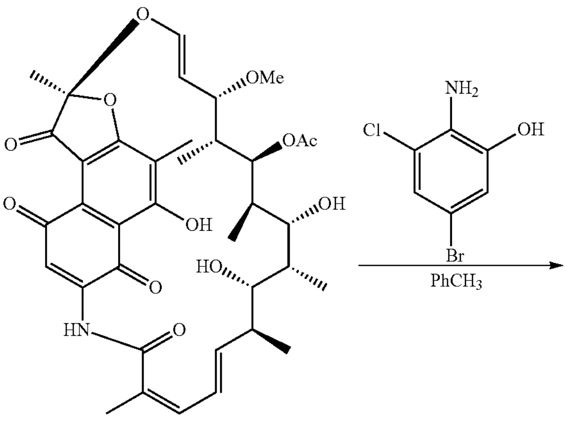

rifamycin S

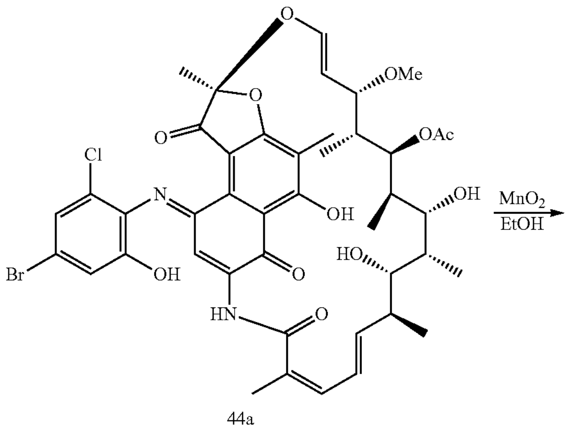

44a

-continued

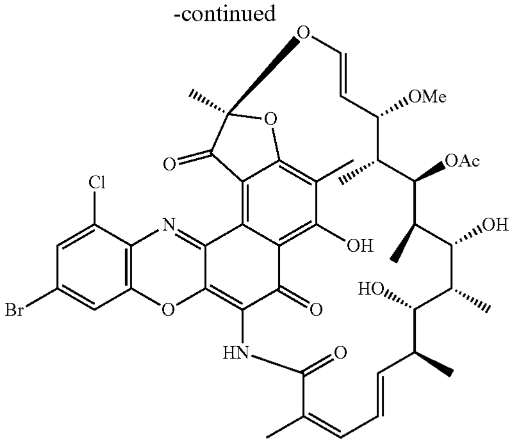

44

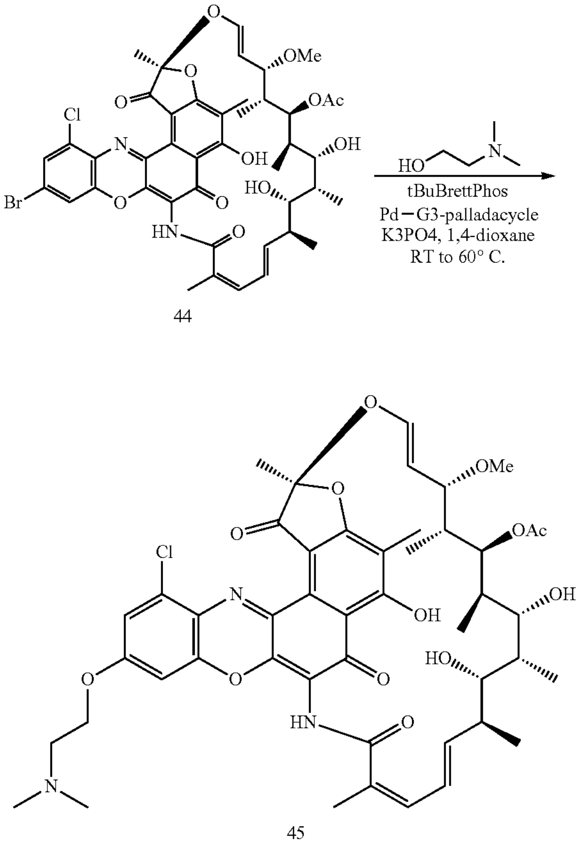

44

45

Compound 44:

Following the general procedure in Example 3, To a stirring solution under argon of rifamycin S (250 mg, 0.359 mmol) in 5 mL of toluene at room temperature was added commercially available 2-amino-5-bromo-3-chlorophenol (80 mg, 0.359 mmol). The mixture solution was stirred overnight at room temperature. The mixture was then evaporated to dryness and the dark reddish residue dissolved in 15 mL of ethanol and 300 mg of manganese oxide ($MnO_2$) was added in one portion to the ethanol solution. The sluggish mixture was stirred under argon for 15 h at room temperature. After filtration of insoluble materials using a Celite pad, the filtrate was evaporated under reduced pressure. The dark residue was purified on a 40 g HP silica gel Gold RediSep column via ISCO (gradient elution: hexanes–95% EA in hexanes). The pure fractions were evaporated and dried in vacuo giving the title compound 44 as a dark reddish solid (161 mg, 50%). MS (ESI, pos.): calc'd for $C_{43}H_{46}BrClN_2O_{12}$, 898.19; found 899.1 (M+H). $^1$H-NMR (500 MHz; $CDCl_3$): δ 13.81 (s, 1H), 7.65 (d, J=1.7 Hz, 1H), 7.44 (s, 1H), 6.24-6.22 (m, 1H), 6.01 (d, J=12.2 Hz, 1H), 5.07-5.05 (m, 1H), 4.99 (dd, J=12.3, 6.8 Hz, 1H), 3.11 (s, 3H), 3.04-3.02 (m, 1H), 2.32 (s, 3H), 2.13 (s, 3H), 2.08 (s, 4H), 1.84 (s, 3H), 1.74-1.71 (m, 1H), 1.71-1.66 (m, 1H), 1.60 (s, 9H), 0.98 (d, J=6.5 Hz, 4H), 0.82-0.81 (m, 4H), 0.63 (d, J=0.5 Hz, 4H).

Compound 45:

45 was prepared using general procedure as described for 16b: Compound 44 (20 mg, 0.0222 mmol, 1.0 eq.), 2-(dimethylamino)ethan-1-ol (20 mg, 0.222 mmol, 10 eq.), t-BuBrettPhos-Pd-G3-palladacycle (9.5 mg, 0.0111 mmol, 0.5 eq.), and $K_3PO_4$ (9.6 mg, 0.045 mmol, 2.0 eq.) to afford the title compound 45 (6.8 mg, 34%). MS: calc'd for $C_{47}H_{56}ClN_3O_{13}$, 905.35; found 906.3 (M+H). H-NMR (500 MHz; $CD_3OD$): δ 7.30 (d, J=0.4 Hz, 1H), 6.93-6.92 (m, 1H), 6.78-6.76 (m, 1H), 6.39-6.37 (m, 1H), 6.20 (dd, J=12.5, 0.4 Hz, 2H), 5.09-5.07 (m, 1H), 4.58 (dq, J=2.2, 0.6 Hz, 1H), 4.30 (dd, J=9.1, 4.5 Hz, 1H), 4.21 (dtd, J=2.8, 1.4, 0.7 Hz, 1H), 3.04 (d, J=9.5 Hz, 6H), 2.83 (s, 3H), 2.36 (s, 6H), 2.31 (s, 3H), 2.11 (s, 1H), 2.00 (s, 2H), 1.91 (s, 4H), 1.76 (s, 3H), 1.73-1.62 (m, 2H), 1.30 (s, 1H), 0.96 (d, J=5.4 Hz, 6H), 0.88 (d, J=6.4 Hz, 4H), 0.25 (d, J=6.6 Hz, 1H), 0.11 (s, 2H), −0.16-0.19 (m, 2H).

Example 10: Preparation of Compound 48

Rifamycin analog 48 was synthesized from rifamycin S as shown in Scheme 14 below, and as described below.

Scheme 14

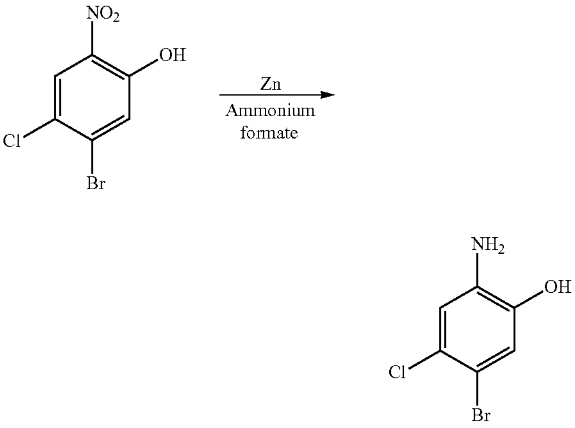

46

-continued

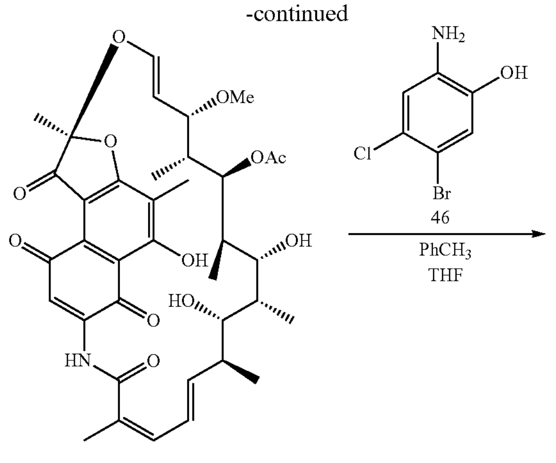

Rifamycin S

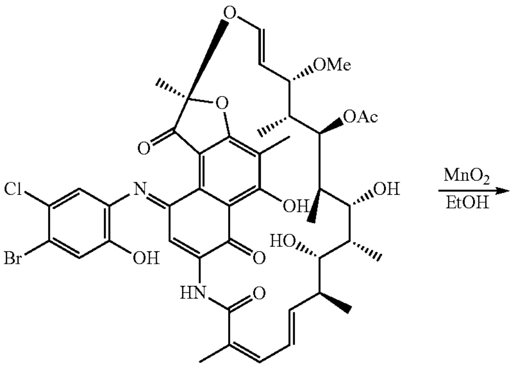

47a

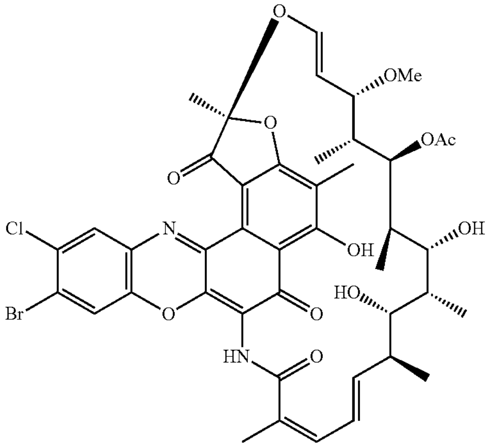

47

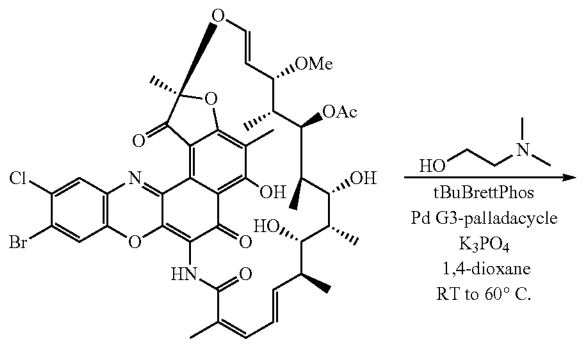

47

-continued

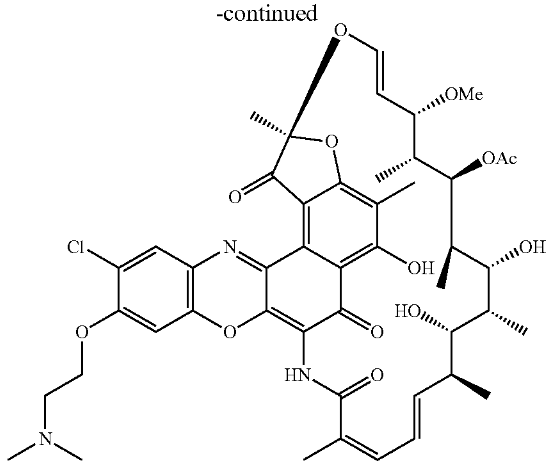

48

Compound 46:

To a stirred solution of commercially available 5-bromo-4-chloro-2-nitrophenol (100 mg, 0.396 mmol, 1.0 eq.) and ammonium acetate (75 mg, 1.188 mmol, 3.0 eq.) in anhydrous THE (5 mL) at room temperature was added Zn dust (388 mg, 5.94 mmol, 15 eq.) and degassed by nitrogen. The mixture was heated to 50° C. in an oil bath for 2 h. The reaction was complete by LCMS and cooled to room temperature. The crude was filtered through Celite pad and concentrated. The crude oil was then purified on a 24 g HP silica gel Gold RediSep column via ISCO (gradient elution: 0-20% DCM in methanol), and the pure fractions evaporated and dried in vacuo giving 46 as a brown solid (37 mg, 42%). MS (ESI, pos.): calc'd for $C_6H_5BrClNO$, 222.47; found 222.9 and 223.9 isotopes (M+H). $^1$H-NMR (500 MHz; $CD_3OD$): δ 6.89 (s, 1H), 6.81 (s, 1H) $NH_2$ and OH not seen.

Compound 47:

Following the general procedure in Example 3, To a stirring solution under argon of rifamycin S (62 mg, 0.0899 mmol) in 1.5 mL of toluene and 0.25 mL of THE at room temperature was added 2-amino-5-bromo-4-chlorophenol 46 (20 mg, 0.0899 mmol). The mixture solution was stirred for 7 days at room temperature. The mixture was then evaporated to dryness and the dark reddish residue dissolved in 10 mL of ethanol and 100 mg of manganese oxide ($MnO_2$) was added at one portion to the ethanol solution. The sluggish mixture was stirred under argon for 15 h at room temperature. After filtration of insoluble materials using a Celite pad, the filtrate was evaporated under reduced pressure. The dark residue was purified on a 40 g HP silica gel Gold RediSep column via ISCO (gradient elution: hexanes–95% EA in hexanes). The pure fractions were evaporated and dried in vacuo giving the title compound 47 as a dark reddish solid (40 mg, 51%). MS (ESI, pos.): calc'd for $C_{43}H_{46}BrClN_2O_{12}$, 898.19; found 899.1 (M+H). $^1$H-NMR (500 MHz; $CDCl_3$): δ 13.87 (s, 1H), 8.11 (s, 1H), 7.67 (s, 1H), 6.32 (s, 1H), 6.01 (d, J=12.4 Hz, 2H), 5.04-5.04 (m, 1H), 4.98 (dd, J=12.2, 6.5 Hz, 2H), 3.11 (s, 6H), 3.03-3.01 (m, 2H), 2.34 (s, 6H), 2.14 (s, 7H), 2.07 (s, 6H), 1.83 (s, 6H), 1.73 (dt, J=6.4, 0.6 Hz, 3H), 1.65-1.56 (m, 17H), 0.99 (d, J=6.2 Hz, 6H), 0.83-0.82 (m, 6H), 0.60 (t, J=0.7 Hz, 5H).

Compound 48:

48 was prepared using general procedure as described for 16b: Compound 47 (20 mg, 0.0222 mmol, 1.0 eq.), 2-(dimethylamino)ethan-1-ol (20 mg, 0.222 mmol, 10 eq.), t-Bu-BrettPhos-Pd-G3-palladacycle (9.5 mg, 0.0111 mmol, 0.5 eq.), and $K_3PO_4$ (9.6 mg, 0.045 mmol, 2.0 eq.) to afford the title compound 48 (2.8 mg, 12%). MS: calc'd for $C_{47}H_{56}ClN_3O_{13}$, 905.35; found 906.3 (M+H). H-NMR (500 MHz; $CD_3OD$): δ 8.04 (t, J=0.6 Hz, 1H), 7.15-7.14 (m, 1H), 6.90-6.89 (m, 2H), 6.42-6.41 (m, 2H), 6.22-6.20 (m, 1H), 5.02-4.99 (m, 1H), 4.59 (s, 1H), 4.42-4.41 (m, 1H), 4.24-4.21 (m, 1H), 3.77-3.74 (m, 1H), 3.04-3.02 (m, 1H), 2.94 (d, J=0.4 Hz, 1H), 2.43 (s, 6H), 2.31 (s, 5H), 2.12 (s, 6H), 1.99 (s, 5H), 1.92 (s, 4H), 1.79 (s, 1H), 1.69 (t, J=1.4 Hz, 1H), 1.31 (s, 1H), 0.96 (t, J=0.5 Hz, 6H), 0.85-0.70 (m, 4H), 0.11 (s, 1H), −0.22 (td, J=2.3, 1.2 Hz, 1H).

Example 11: Preparation of Compound 50

Rifamycin analog 50 was synthesized from compound 28 as shown in Scheme 15 below, and as described below.

Scheme 15

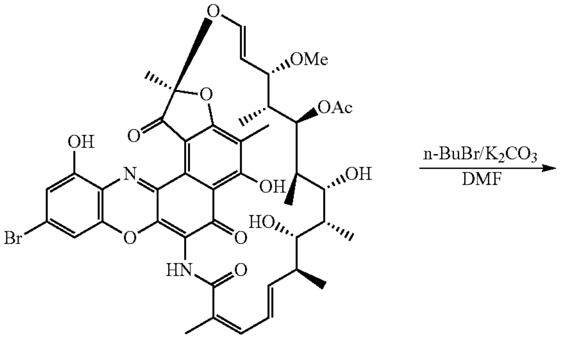

28

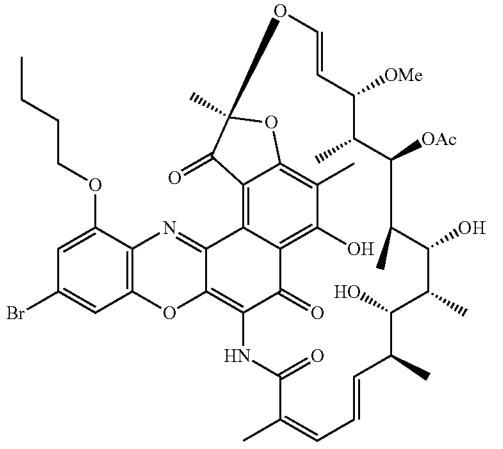

49

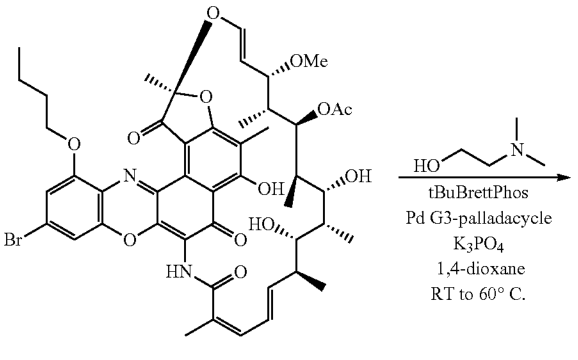

49

-continued

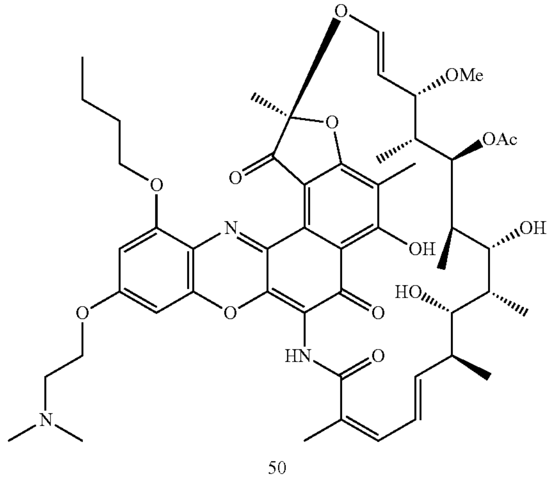

50

Compound 49:

To a stirred solution of compound 28 (50 mg, 0.0568 mmol, 1.0 eq.) in 1.5 mL of anhydrous DMF at room temperature was added $K_2CO_3$ (12 mg, 0.0852 mmol, 1.5 eq.) followed by addition of n-BuBr (15.5 mg, 0.1136 mmol, 2.0 eq.) The resulting mixture was refluxed at 50° C. for overnight. The crude product was diluted with acetonitrile/water and purified on an ISCO system by an EZ preparative column (eluents: 10-95% MeCN in water, 0.05% in AcOH). Pure fractions by LC/MS were collected, frozen at dry-ice/acetone bath, and lyophilized for 30 h to afford 34 mg (65%) of 49. MS (ESI, pos.): calc'd for $C_{47}H_{55}BrN_2O_{13}$, 935.85; found 935.2 and 937.2 (M+H). $^1$H-NMR (500 MHz; $CDCl_3$): δ 7.48 (s, 2H), 7.13 (s, 1H), 7.07 (s, 2H), 7.02 (s, 1H), 5.92-6.07 (m, 1H), 4.98 (dd, J=6.84, 12.21 Hz, 1H), 4.18-4.25 (m, 2H), 3.11 (s, 3H), 3.02 (br. s., 1H), 2.31 (s, 3H), 2.13 (s, 3H), 2.07 (s, 4H), 1.95-2.03 (m, 2H), 1.80 (s, 4H), 1.74 (br. s., 2H), 1.60-1.71 (m, 2H), 1.50-1.59 (m, 12H), 1.05 (t, J=7.33 Hz, 4H), 0.98 (br. s., 3H), 0.81 (br. s., 2H), 0.62 (br. s., 2H)

Compound 50:

50 was prepared using general procedure as described for 16b: Compound 49 (20 mg, 0.0213 mmol, 1.0 eq.), 2-(dimethylamino)ethan-1-ol (19 mg, 0.213 mmol, 10 eq.), t-Bu-BrettPhos-Pd-G3-palladacycle (9.1 mg, 0.01065 mmol, 0.5 eq.), and $K_3PO_4$ (9.2 mg, 0.043 mmol, 2.0 eq.) to afford the title compound 50 (6.1 mg, 30%). An ISCO EZ preparative column (Gemini) was used to purify the desired product (eluents: 10-95% MeCN in water, 0.05% in AcOH). MS: calc'd for $C_{51}H_{65}N_3O_{14}$, 943.45; found 944.4 (M+H), 942.3 (M−H). $^1$H-NMR (500 MHz; $CD_3OD$): δ 6.82-6.81 (m, 2H), 6.70 (s, 1H), 6.58-6.55 (m, 1H), 6.38-6.37 (m, 2H), 6.23 (ddd, J=3.0, 1.6, 0.8 Hz, 2H), 5.07 (bs, 2H), 4.59 (s, 6H), 4.29 (t, J=5.3 Hz, 4H), 4.20-4.14 (m, 2H), 3.74-3.71 (m, 2H), 3.03 (s, 6H), 2.83 (d, J=0.3 Hz, 2H), 2.36 (s, 6H), 2.31 (s, 1H), 2.11 (s, 3H), 1.98 (s, 2H), 1.76 (s, 3H), 1.69-1.60 (m, 1H), 1.30 (s, 2H), 1.08 (s, 6H), 0.97-0.91 (m, 4H), 0.11 (s, 3H), −0.21 (dd, J=2.2, 0.9 Hz, 2H).

Example 12: Preparation of Compound 52

Rifamycin analog 52 was synthesized from compound 28 as shown in Scheme 16 below, and as described below.

Scheme 16

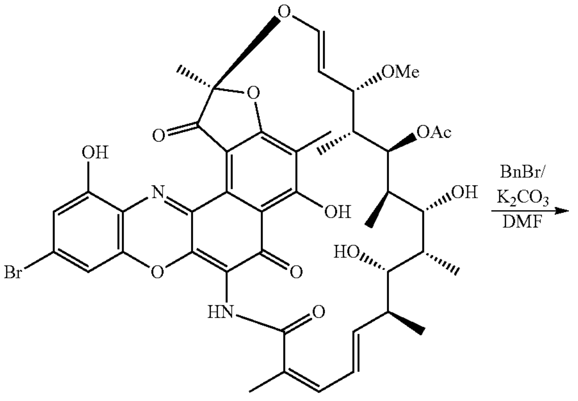

28

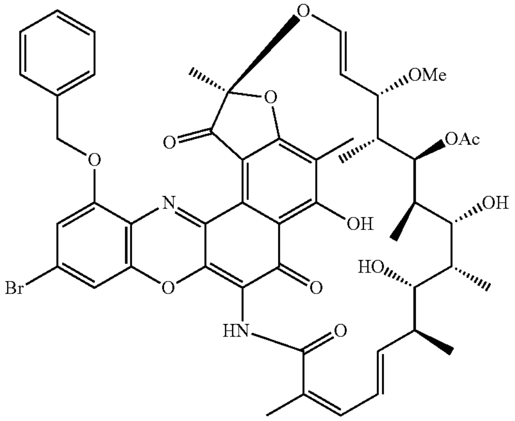

51

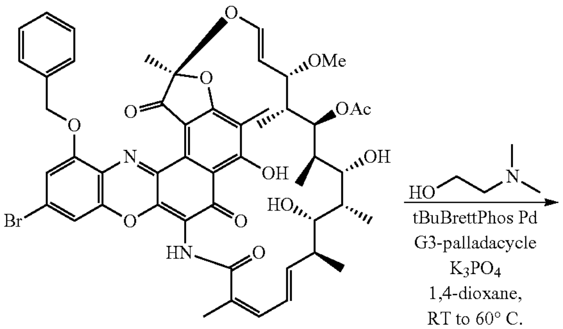

51

-continued

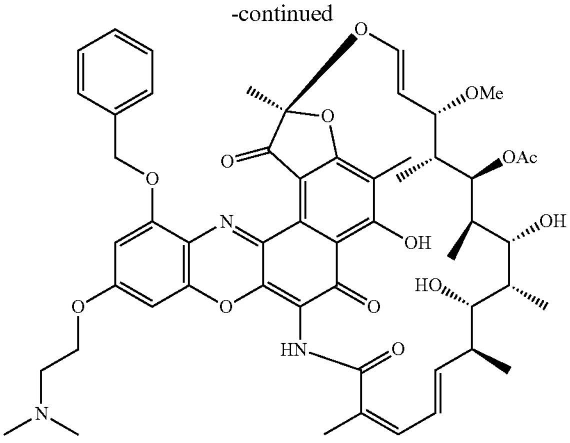

52

Compound 51:

To a stirred solution of compound 28 (50 mg, 0.0568 mmol, 1.0 eq.) in 1.5 mL of anhydrous DMF at room temperature was added $K_2CO_3$ (12 mg, 0.0852 mmol, 1.5 eq.) followed by addition of benzyl bromide (19.4 mg, 0.1136 mmol, 2.0 eq.) The resulting mixture was stirred at room temperature overnight. An ISCO system EZ preparative column was used to purify the desired product (eluents: 10-95% MeCN in water, 0.05% in AcOH). Pure fractions by LC/MS were collected, frozen at dry-ice/acetone bath, and lyophilized for 30 h to afford 25 mg (45%) of 51. MS (ESI, pos.): calc'd for $C_{50}H_{53}BrN_2O_{13}$, 969.88; found 969.2 and 971.2 (M+H). $^1$H-NMR (500 MHz; $CDCl_3$): δ 7.68-7.66 (m, 1H), 7.45-7.42 (m, 2H), 7.39-7.37 (m, 2H), 7.19 (dt, J=1.0, 0.5 Hz, 2H), 7.14 (t, J=0.4 Hz, 2H), 5.99 (dd, J=12.2, 0.4 Hz, 1H), 5.44-5.38 (m, 1H), 5.29-5.22 (m, 2H), 5.00-4.96 (m, 2H), 3.10 (s, 3H), 3.03-3.01 (m, 1H), 2.31 (s, 6H), 2.14 (s, 3H), 2.07 (s, 3H), 1.78 (d, J=0.4 Hz, 3H), 1.66-1.64 (m, 3H), 1.54 (s, 3H), 1.27 (s, 3H), 1.00-0.98 (m, 3H), 0.90 (dd, J=8.5, 4.8 Hz, 3H), 0.83 (dddd, J=2.9, 2.1, 1.5, 0.7 Hz, 2H), 0.63-0.61 (m, 1H), 0.14 (s, 1H).

Compound 52:

52 was prepared using general procedure as described for 16b: Compound 51 (26 mg, 0.0268 mmol, 1.0 eq.), 2-(dimethylamino)ethan-1-ol (24 mg, 0.268 mmol, 10 eq.), t-BuBrettPhos-Pd-G3-palladacycle (11.4 mg, 0.0134 mmol, 0.5 eq.), and $K_3PO_4$ (11.5 mg, 0.054 mmol, 2.0 eq.) to afford the title compound 52 (7.0 mg, 27%). An ISCO EZ preparative column (Gemini) was used to purify the desired product (eluents: 10-95% MeCN in water, 0.05% in AcOH). MS: calc'd for $C_{54}H_{63}N_3O_{14}$, 977.43; found 978.4 (M+H), 976.3 (M−H). $^1$H-NMR (500 MHz; $CD_3OD$): δ 7.73 (d, J=7.0 Hz, 2H), 7.43 (d, J=4.3 Hz, 2H), 7.38-7.37 (m, 1H), 6.81 (s, 2H), 6.58 (d, J=0.9 Hz, 1H), 6.42-6.40 (m, 1H), 6.21-6.18 (m, 1H), 6.03 (d, J=12.6 Hz, 1H), 5.41-5.36 (m, 2H), 5.05-5.01 (m, 1H), 4.59 (s, 1H), 4.29 (d, J=5.1 Hz, 1H), 4.18 (dt, J=2.6, 1.3 Hz, 1H), 3.72-3.70 (m, 1H), 3.00 (d, J=9.9 Hz, 4H), 2.83 (s, 2H), 2.37 (s, 7H), 2.29 (s, 3H), 2.11 (s, 3H), 2.03 (d, J=18.5 Hz, 6H), 1.74 (s, 4H), 1.64-1.63 (m, 1H), 1.30 (s, 1H), 0.96-0.90 (m, 10H), 0.11-0.09 (m, 2H), −0.25 (t, J=0.6 Hz, 2H).

Example 13: Preparation of Compound 55

Rifamycin analog 55 was synthesized from Rifamycin S as shown in Scheme 17 below, and as described below.

Scheme 17

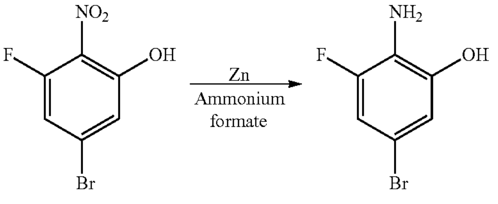

53

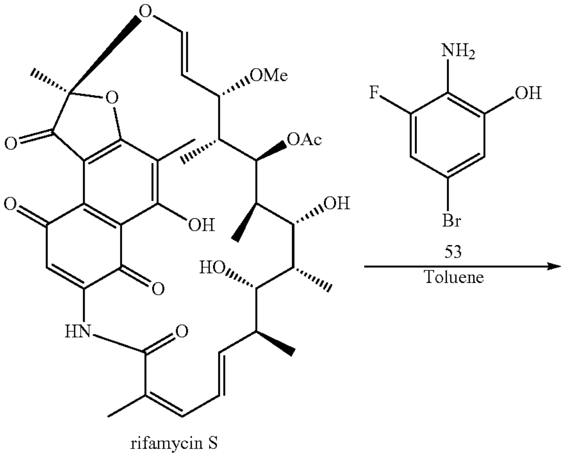

rifamycin S

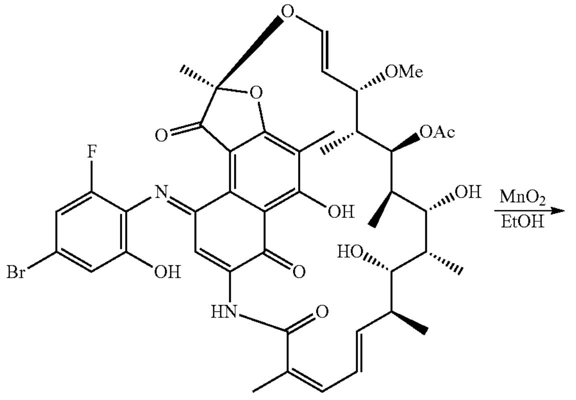

54a

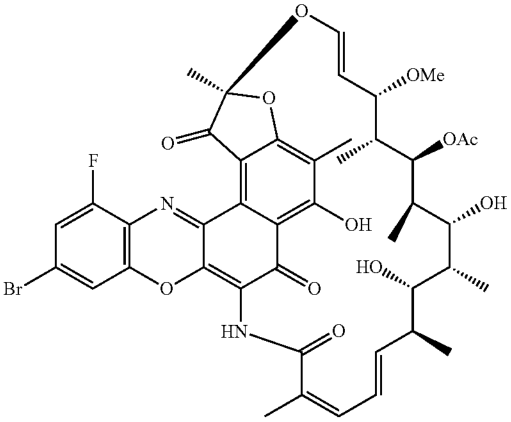

54

-continued

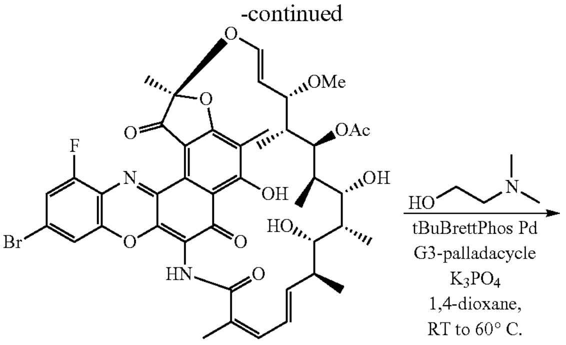

54

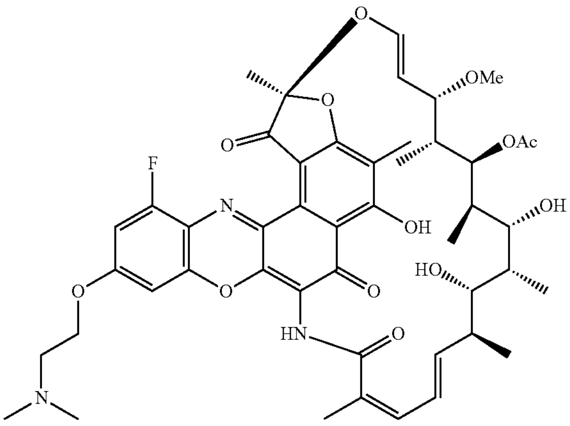

55

Compound 53:

To a solution of commercially available 5-bromo-3-fluoro-2-nitrophenol (150 mg, 0.635 mmol, 1.0 eq.) and ammonium acetate (120 mg, 1.906 mmol, 3.0 eq.) in anhydrous THE (5 mL) at room temperature, degassed with nitrogen, was added Zn dust (622 mg, 9.52 mmol, 15 eq.). The mixture was heated to 50° C. in an oil bath for 2 h. The reaction was complete by LCMS and cooled to room temperature. The crude was filtered through a Celite pad and concentrated. The crude oil was then purified on a 24 g HP silica gel Gold RediSep column via ISCO system (gradient elution: 0-20% DCM in methanol), and the pure fractions evaporated and dried in vacuo giving 53 as a brown solid (67 mg, 52%). MS (ESI, pos.): calc'd for $C_6H_5BrFNO$, 206.01; found 205.9 and 207.9 isotopes (M+H). $^1$H-NMR (500 MHz; $CD_3OD$): δ 6.71-6.67 (m, 2H). $NH_2$ and OH not seen.

Compound 54:

Following the general procedure in Example 9, To a stirring solution under argon of rifamycin S (120 mg, 0.172 mmol) in 1.5 mL of toluene at room temperature was added compound 53 (36 mg, 0.172 mmol) to afford the title compound 54 as a dark reddish solid (92 mg, 61%). MS (ESI, pos.): calc'd for $C_{43}H_{46}BrFN_2O_{12}$, 881.75; found 882.1 and 883.2 (M+H), 880.1 and 881.1 (M−H). $^1$H-NMR (500 MHz; DMSO-$d_6$): δ 9.54 (s, 1H), 7.80-7.79 (m, 2H), 6.04-6.01 (m, 1H), 5.74 (s, 1H), 5.22 (s, 2H), 4.80-4.76 (m, 1H), 4.23 (dt, J=1.4, 0.6 Hz, 1H), 3.09-3.02 (m, 5H), 2.78 (td, J=10.0, 1.8 Hz, 1H), 2.16 (s, 3H), 1.99 (s, 4H), 1.95 (s, 4H), 1.65 (s, 3H), 1.60-1.59 (m, 2H), 1.46 (dt, J=1.9, 0.9 Hz, 1H), 0.88-0.85 (m, 2H), 0.83 (t, J=7.8 Hz, 4H), 0.67 (s, 5H).

Compound 55:

55 was prepared using general procedure as described for 16b: Compound 54 (40 mg, 0.0453 mmol, 1.0 eq.), 2-(dimethylamino)ethan-1-ol (40 mg, 0.453 mmol, 10 eq.), t-BuBrettPhos-Pd-G3-palladacycle (19.3 mg, 0.0226 mmol, 0.5 eq.), and $K_3PO_4$ (19.6 mg, 0.0919 mmol, 2.0 eq.) to afford the title compound 55 (16.8 mg, 42%). MS: calc'd for $C_{47}H_{56}FN_3O_{13}$, 889.38; found 890.4 (M+H), 888.3 (M−H). $^1$H-NMR (500 MHz; DMSO-$d_6$): δ 9.43-9.42 (m, 1H), 7.15-7.12 (m, 1H), 7.05-7.03 (m, 1H), 6.04 (dtd, J=4.5, 2.2, 1.1 Hz, 1H), 5.85-5.80 (m, 1H), 5.23 (dtd, J=3.5, 1.8, 1.0 Hz, 1H), 4.79-4.75 (m, 1H), 4.27 (s, 1H), 4.19-4.18 (m, 2H), 3.52-3.51 (m, 1H), 3.09-2.99 (m, 4H), 2.80-2.75 (m, 1H), 2.64-2.63 (m, 2H), 2.15 (s, 9H), 1.99 (s, 3H), 1.94 (s, 2H), 1.64 (s, 2H), 1.48-1.44 (m, 1H), 1.36-1.33 (m, 1H), 1.23-1.22 (m, 1H), 1.14-1.13 (m, 1H), 1.05 (d, J=12.0 Hz, 1H), 0.83 (d, J=6.8 Hz, 6H), 0.68-0.66 (m, 5H).

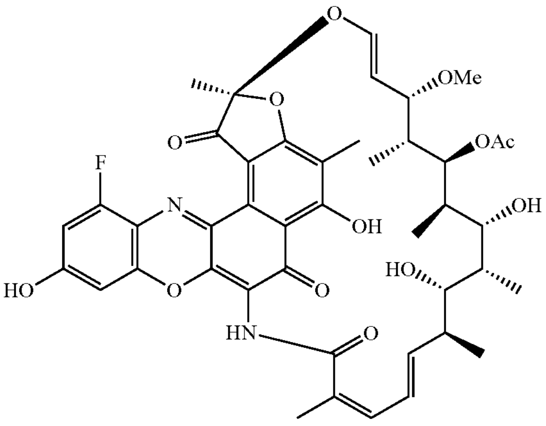 [SMILES: CO[C@H]1/C=C/O[C@@]2(C)Oc3c(C)c(O)c4c(=O)c(c5oc6cc(O)cc(F)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Compound 55a:

55a was the byproduct for the C—O cross coupling reaction starting with compound 54. MS: calc'd for $C_{43}H_{47}N_2O_{13}$, 818.3; found 819.3 (M+H), 817.2 (M−H). $^1$H NMR (500 MHz; DMSO-$d_6$): δ 9.31 (s, 1H), 5.82 (s, 2H), 4.76 (s, 2H), 4.13 (br. s., 1H), 3.52 (d, J=5.86 Hz, 1H), 3.08 (br. s., 2H), 3.02 (br. s., 3H), 2.97 (s, 1H), 2.88 (s, 1H), 2.77 (br. s., 2H), 2.72 (s, 1H), 2.52 (d, J=8.79 Hz, 1H), 2.19 (br. s., 1H), 2.14 (br. s., 3H), 1.92-2.01 (m, 7H), 1.90 (s, 1H), 1.64 (br. s., 3H), 1.58 (br. s., 2H), 1.22 (s, 1H), 0.72-0.95 (m, 6H), 0.67 (br. s., 3H), 0.06 (s, 2H).

Example 14: Preparation of Compounds 60 and 61

Rifamycin analogs 60 and 61 were synthesized from Rifamycin S as shown in Scheme 18 below, and as described below.

Scheme 18

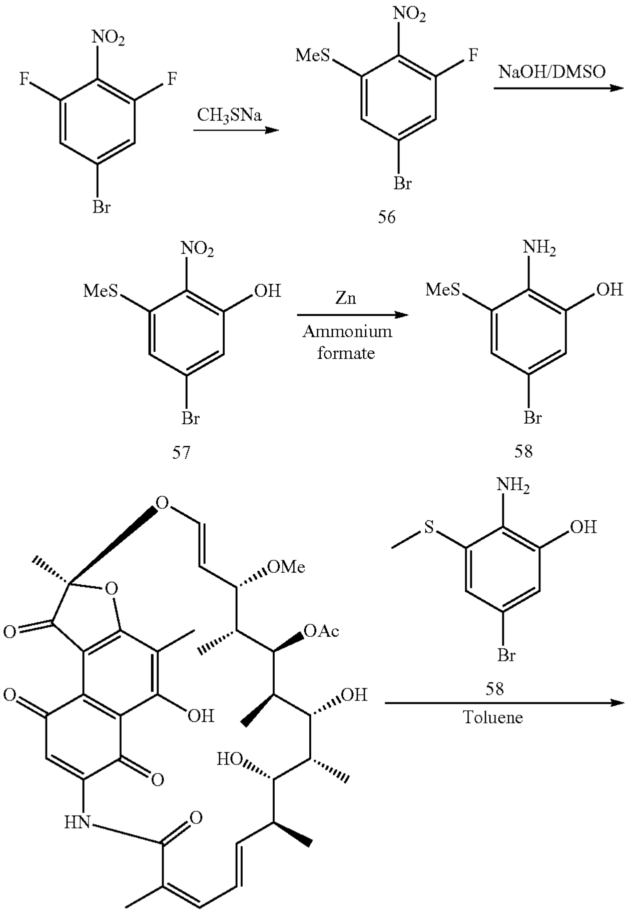

56

57

58

58 rifamycin S

-continued
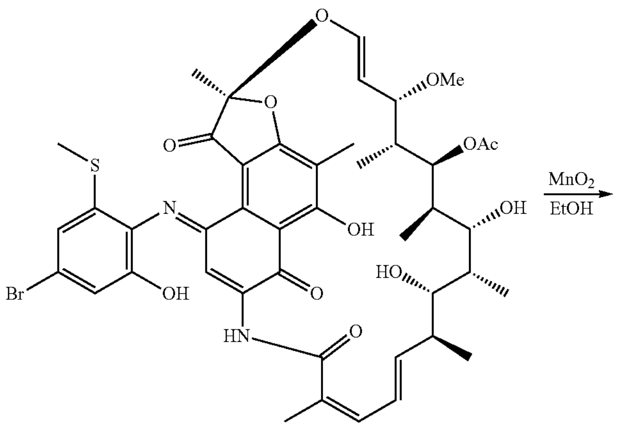
59a
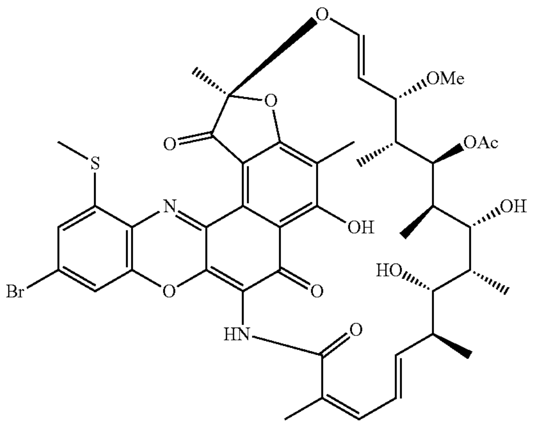
59
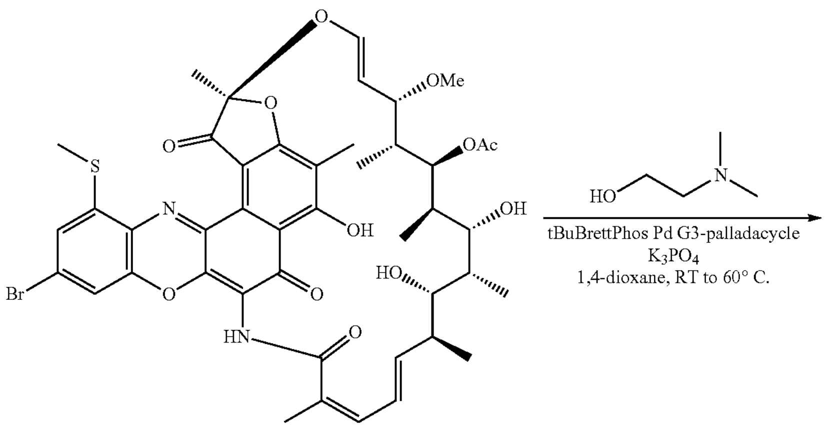
59

-continued

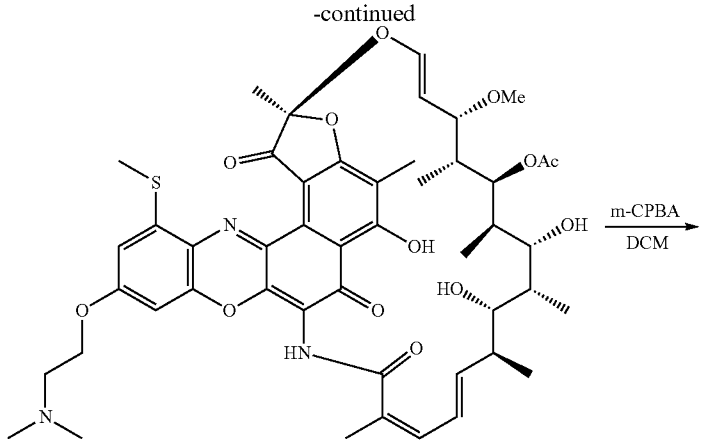

60

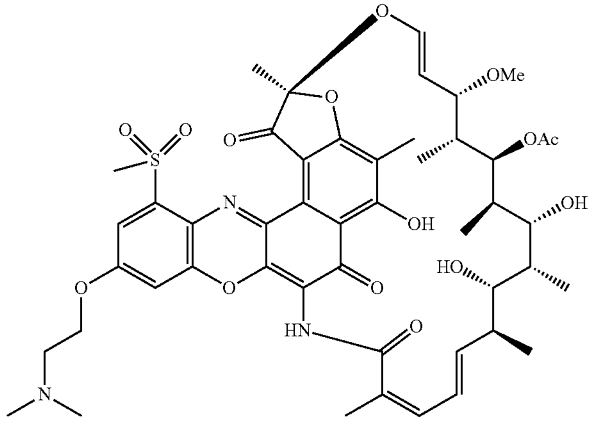

61

Compound 56:

To a stirred solution of 5-bromo-1,3-difluoro-2-nitrobenzene (1.0 g, 4.2 mmol, 1.0 eq.) in 7.5 mL of DMF in an ice-bath was added $CH_3SNa$ (320 mg, 4.6 mmol, 1.1 eq.) in 2.5 mL of water. The resulting mixture was stirred at room temperature for 1 h. The yellow suspension was diluted with water (5 mL) and filtered to obtain yellow solid (0.91 g) with an impurity of di-sulfide byproducts. MS (ESI, pos.): calc'd for $C_7H_5BrFNO_2S$, 266.08; found 299.1 (M+Na).

Compound 57:

The crude 56 (900 mg) in DMSO (10 mL) was treated with 1M NaOH (6 mL, 6 mmol) and heated to 85° C. in oil bath for 1.5 h. The reaction was complete by LCMS and cooled to room temperature. The reaction was acidified with 1M HCl until the pH=2-3 and the resultant solution was extracted using ethyl acetate (2×10 mL). The combined organic layers were washed with water, brine, dried ($Na_2SO_4$), and then concentrated. The crude product was then purified on a 24 g HP silica gel Gold RediSep column via ISCO system (gradient elution: 0-100% ethyl acetate in hexanes), and the pure fractions evaporated and dried in vacuo giving 57 as a yellowish white solid (0.51 g, 46%). MS (ESI, pos.): calc'd for $C_7H_6BrNO_3S$, 264.09; found 263.9 and 262.9 isotopes (M−H). $^1$H-NMR (500 MHz; $CDCl_3$): δ 11.40 (s, 1H), 7.10 (dd, J=2.0, 1.1 Hz, 1H), 6.91 (d, J=1.1 Hz, 1H), 6.91 (d, J=1.1 Hz, 1H), 2.48 (s, 3H).

Compound 58:

To a solution of compound 57 (200 mg, 0.757 mmol, 1.0 eq.) and ammonium acetate (143 mg, 2.271 mmol, 3.0 eq.) in anhydrous THF (7 mL) at room temperature was added Zn dust (495 mg, 7.57 mmol, 10 eq.) and degassed by nitrogen. The mixture was heated to 50° C. in an oil bath for 2 h. The reaction was complete by LCMS and cooled to room temperature. The crude was filtered through a Celite pad and concentrated. The crude was then purified on a 24 g HP silica gel Gold RediSep column via ISCO system (gradient elution: 0-20% DCM in methanol), and the pure fractions evaporated and dried in vacuo giving 58 as a pale brown solid (120 mg, 68%). MS (ESI, pos.): calc'd for $C_7H_8BrNOS$, 234.11; found 235.9 and 236.9 isotopes (M+H), 232.9 and 231.9 isotopes (M−H). $^1$H-NMR (300 MHz; $CDCl_3$): δ 7.09 (d, J=2.0 Hz, 1H), 6.84 (d, J=2.1 Hz, 1H), 5.07-5.06 (m, 1H), 4.15-4.09 (m, 2H), 2.42 (s, 3H).

Compound 59:

Following the general procedure in Example 9, to a stirred solution under argon of rifamycin S (267 mg, 0.384 mmol) in 5 mL of toluene at room temperature was added compound 58 (90 mg, 0.384 mmol). After 2 days, the reaction was concentrated in vacuo to remove toluene, dissolved in EtOH (10 mL) and $MnO_2$ (30 mg) was added. After stirring for 1 day, the reaction was concentrated in vacuo. The crude was purified on a 40 g HP silica gel Gold RediSep column via ISCO system (gradient elution: 0-100% ethyl acetate in hexanes) to afford the title compound 59 as a dark reddish solid (181 mg, 52%). MS (ESI, pos.): calc'd for $C_{44}H_{49}BrN_2O_{12}S$, 909.84; found 910.2 and 911.2 (M+H), 908.1 and 907.1 (M−H). $^1$H-NMR (500 MHz; $CD_3OD$): δ 7.35 (s, 1H), 7.25-7.23 (m, 1H), 6.74 (dt, J=1.7, 0.9 Hz, 1H), 6.37-6.35 (m, 1H), 6.26-6.22 (m, 2H), 5.20 (ddt, J=7.1, 2.9, 1.1 Hz, 1H), 5.09-5.08 (m, 1H), 3.70-3.68 (m,), 3.05-3.03 (m, 4H), 2.57 (s, 3H), 2.30 (s, 3H), 2.09 (s, 3H), 1.99 (s, 3H), 1.75 (s, 3H), 1.67-1.64 (m, 1H), 0.94 (d, J=6.9 Hz, 3H), 0.87-0.86 (m, 3H), 0.07-0.06 (m, 2H), −0.17-0.18 (m, 1H).

Compound 60:

60 was prepared using general procedure as described for 16b: Compound 59 (40 mg, 0.044 mmol, 1.0 eq.), 2-(dimethylamino)ethan-1-ol (40 mg, 0.439 mmol, 10 eq.), t-Bu-BrettPhos-Pd-G3-palladacycle (19 mg, 0.022 mmol, 0.5 eq.), and $K_3PO_4$ (19 mg, 0.089 mmol, 2.0 eq.) to afford the title compound 60 (22 mg, 55%). MS: calc'd for $C_{48}H_{59}N_3O_{13}S$, 917.38; found 918.4 (M+H), 916.3 (M−H). $^1$H-NMR (500 MHz; $CD_3OD$): δ 6.85-6.81 (m, 2H), 6.68-6.67 (m, 1H), 6.41-6.39 (m, 1H), 6.27 (dt, J=1.5, 0.7 Hz, 1H), 6.19-6.16 (m, 1H), 5.25-5.22 (m, 1H), 5.03-5.02 (m, 1H), 4.30 (t, J=5.1 Hz, 1H), 4.19-4.17 (m, 1H), 3.68 (ddd, J=5.5, 2.2, 1.0 Hz, 1H), 3.48-3.44 (m, 1H), 3.02 (d, J=8.9 Hz, 6H), 2.81 (d, J=4.9 Hz, 3H), 2.56 (s, 3H), 2.43-2.37 (m, 6H), 2.29 (s, 4H), 2.14-2.04 (m, 3H), 1.98 (s, 3H), 1.79-1.71 (m, 3H), 1.63-1.59 (m, 2H), 1.25-1.22 (m, 2H), 1.08-1.05 (m, 2H), 0.94 (d, J=7.0 Hz, 6H), 0.89-0.87 (m, 3H), 0.05-0.03 (m, 2H), −0.24 (ddt, J=2.8, 2.2, 1.4 Hz, 2H).

Compound 61:

To a stirring solution of compound 60 (12 mg, 0.013 mmol) in 3 mL of anhydrous DCM in an ice-bath was added m-CPBA (6.8 mg, 0.039 mmol). The resulting solution was allowed to warm to room temperature for 3 h to afford the title compound 61. The crude was concentrated and purified by ISCO system EZ preparative HPLC column (Gemini, 5 μm, 150 mm×30 mm, eluents: 10-95% MeCN in water, 0.05% AcOH). Pure fractions were collected, frozen in a dry-ice/acetone bath, and dried by lyophilizer for 30 h to afford 6.5 mg (52%) of 61 as a red purple solid. MS (ESI, pos.): calc'd for $C_{48}H_{59}N_3O_{15}S$, 949.37; found 950.37 (M+H), 948.2 (M−H). $^1$H-NMR (500 MHz; $CD_3OD$): δ 7.94-7.85 (m, 1H), 7.59 (d, J=0.7 Hz, 1H), 7.42 (d, J=7.9 Hz, 1H), 7.37 (dd, J=7.2, 0.6 Hz, 1H), 7.18-7.15 (m, 1H), 6.85-6.81 (m, 1H), 6.41-6.36 (m, 1H), 6.23-6.21 (m, 1H), 5.11-5.08 (m, 1H), 4.74-4.72 (m, 2H), 3.83-3.81 (m, 4H), 3.14-3.06 (m, 2H), 3.03 (dd, J=10.2, 2.1 Hz, 6H), 2.33 (s, 6H), 2.11 (d, J=5.2 Hz, 4H), 2.04 (s, 3H), 1.98 (s, 3H), 1.77 (d, J=10.6 Hz, 2H), 1.70-1.65 (m, 1H), 1.29 (s, 1H), 0.94 (d, J=6.9 Hz, 6H), 0.87-0.86 (m, 3H), 0.10 (d, J=2.8 Hz, 3H), 0.05-0.02 (m, 2H), −0.17-0.19 (m, 2H).

Example 15: Preparation of Compound 68

Rifamycin analog 68 was synthesized from Rifamycin S as shown in Scheme 19 below, and as described below.

Scheme 19

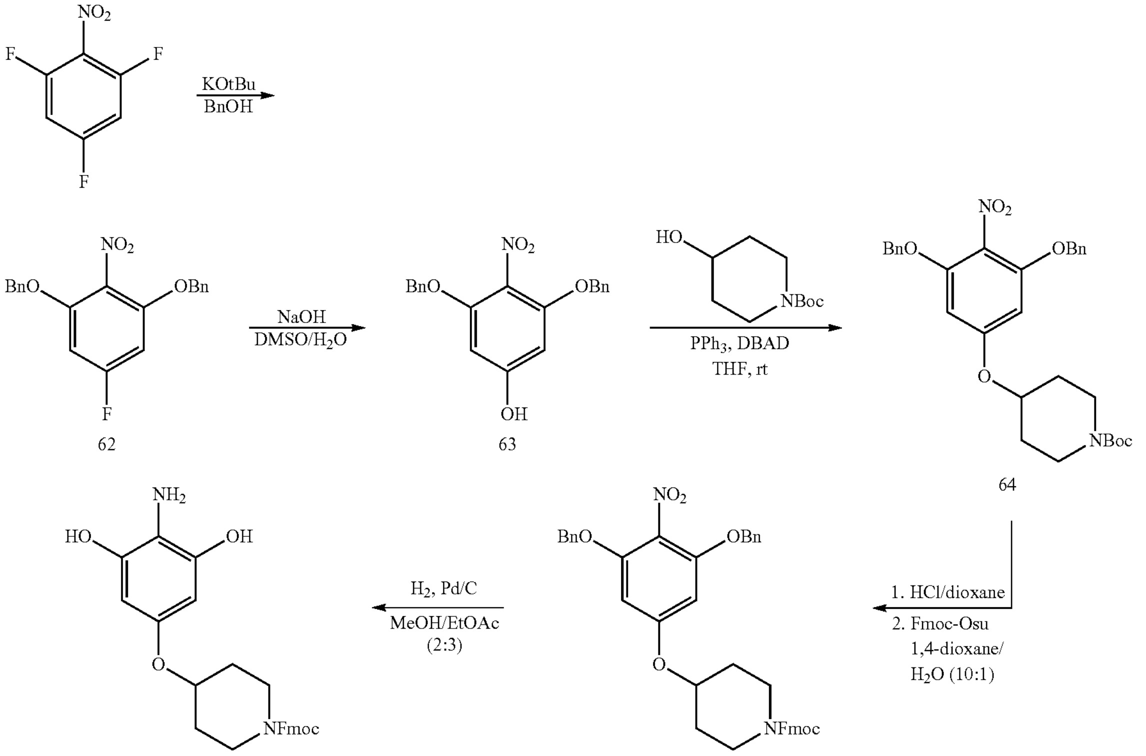

62

63

64

66

65

-continued
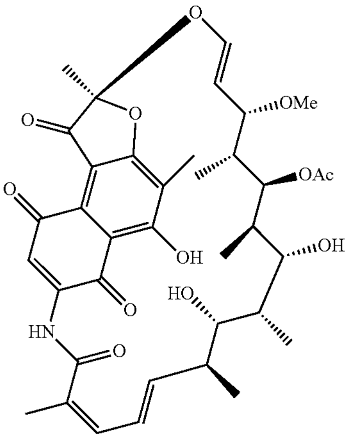
rifamycin S
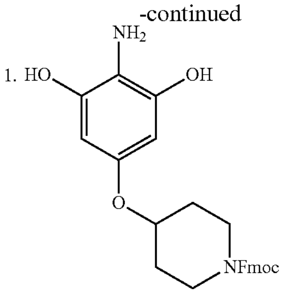
66
Toluene/THF (5:1), rt
2. $MnO_2$, EtOH
rt
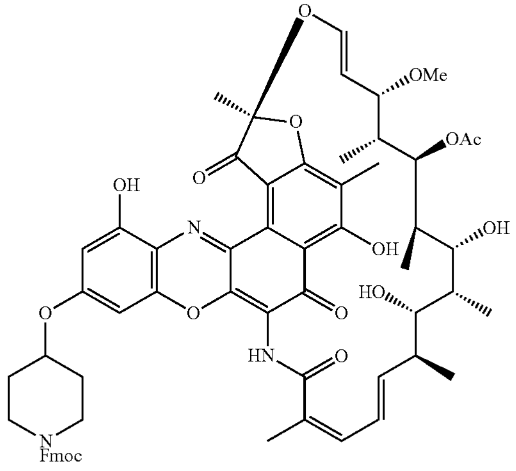
67
1. 2% piperidine
in DMF
DMF, rt
2. paraformaldehyde
$Na(OAc)_3BH$
DCM, rt
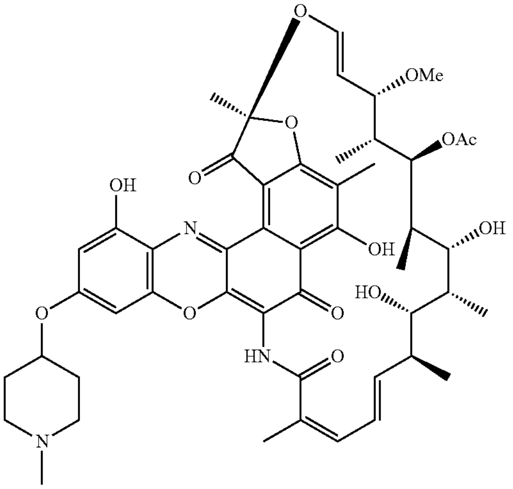
68

Compound 62:

To a stirred solution of 1,3,5-trifluoro-2-nitrobenzene (1.0 g, 5.65 mmol, 1.0 eq.) in 5 mL of anhydrous THF in an ice-bath was dropwise added a solution of benzyl alcohol (1.34 g, 12.42 mmol, 2.2 eq.) in 7 mL of THF, which was then treated with a solution of $KO^tBu$ (12 mL, 11.86 mmol, 2.1 eq.) in THF under Argon. The resulting mixture was stirred at room temperature for 4 h. The resultant solution was extracted using ethyl acetate (2×40 mL). The combined organic layers were washed with water, brine, dried ($Na_2SO_4$), and then concentrated. The crude product was recrystallized by THF/ethanol to afford an off-white solid of compound 62 (1.63 g, 82%). MS (ESI, pos.): calc'd for $C_{20}H_{16}FNO_4$, 353.35; found 376.1 (M+Na). $^1$H-NMR (500 MHz; $CDCl_3$): δ 7.40-7.35 (m, 10H), 6.40 (d, J=10.1 Hz, 2H), 5.16 (s, 4H).

Compound 63:

Compound 62 (1.4 g, 3.96 mmol) in DMSO (7 mL) was treated with 2M NaOH (5 mL, 10 mmol) and heated to 85° C. in oil bath overnight. The reaction was complete by LCMS and cooled to room temperature. The reaction was acidified with 1M HCl until the pH=2-3 and the resultant solution was extracted using ethyl acetate (2×30 mL). The combined organic layers were washed with water, brine, dried ($Na_2SO_4$), and then concentrated. The crude product was then purified on a 80 g HP silica gel Gold RediSep column via ISCO system (gradient elution: 0-100% ethyl acetate in hexanes), and the pure fractions evaporated and dried in vacuo giving 63 as a yellow solid (1.29 g, 82%). MS (ESI, pos.): calc'd for $C_{20}H_{17}NO_5$, 351.11; found 374.1 (M+H) and 350.1 (M−H). $^1$H-NMR (300 MHz; $CDCl_3$): δ 7.40-7.35 (m, 10H), 6.20 (d, J=10.1 Hz, 2H), 5.15 (s, 4H).

Compound 64:

The title compound was prepared using the same method reported in Example 2. To a stirred solution under argon of compound 63 (200 mg, 0.569 mmol) in THE (5 mL) at room temperature were added BOC-piperidin-4-ol (115 mg, 0.569 mmol) and $PPh_3$ (224 mg, 0.853 mmol) followed by a dropwise addition of DBAD (157 mg, 0.682 mmol) in THF (2 mL). After stirring overnight, the mixture was evaporated to dryness and the residue was purified on a 40 g HP silica gel Gold RediSep column via ISCO system (gradient elution: 0-100% ethyl acetate in hexanes), and the pure fractions evaporated and dried in vacuo giving the title compound 64 as an off-white solid (285 mg, 93%). MS: calc'd for $C_{30}H_{34}N_2O_7$, 534.24; found 557.2 (M+Na). $^1$H-NMR (500 MHz; $CDCl_3$): δ 7.39 (d, J=4.3 Hz, 6H), 7.34 (d, J=4.7 Hz, 4H), 6.14 (s, 2H), 5.15 (s, 4H), 4.29 (dd, J=3.6, 3.0 Hz, 1H), 3.67-3.63 (m, 2H), 3.28-3.26 (m, 2H), 1.79-1.76 (m, 2H), 1.63-1.56 (m, 2H), 1.49 (d, J=2.0 Hz, 9H.

Compound 65:

To a solution of compound 64 (285 mg, 0.54 mmol) in 1,4-dioxane (2.0 mL) was added 4 M HCl in 1,4-dioxane (1.4 mL). After stirring for 15 h an in-process aliquot indicated the reaction was complete. To the solution was added diethyl ether (50 mL), then the mixture was stirred vigorously for 1 h until a white precipitate formed. The solid was filtered and washed with ether to afford the HCl salt of corresponding amine, which was used in the next step instantly without further purification. MS: calc'd for $C_{25}H_{26}N_2O_5$, 434.18; found 435.2 (M+H).

To the solution of HCl salt in 1,4-dioxane/water (v/v, 1:1, 6 mL) was added $NaHCO_3$(182 mg, 2.17 mmol, 4.0 eq.) followed by addition of Fmoc-OSu (219 mg, 0.65 mmol, 1.2 eq.). After stirring for 5 h an in-process LC/MS analysis indicated the reaction was complete. The reaction mixture was treated with water (5 mL) and extracted with EtOAc (3×15 mL). The combined organic layers were then treated with brine (10 mL), dried ($Na_2SO_4$) and concentrated in vacuo. The crude compound was purified on a 24 g HP silica gel Gold RediSep column via ISCO system (gradient elution: 0-100% ethyl acetate in hexanes), and the pure fractions evaporated to afford off-white foam (250 mg, 70%). MS: calc'd for $C_{40}H_{36}N_2O_7$, 656.25; found 657.2 (M+H), 689.3 (M+Na). $^1$H-NMR (500 MHz; $CDCl_3$): δ 7.79 (d, J=7.5 Hz, 2H), 7.59 (d, J=7.4 Hz, 2H), 7.40 (quintet, J=5.6 Hz, 10H), 7.34 (t, J=6.9 Hz, 4H), 6.13 (s, 2H), 5.15 (s, 4H), 4.48-4.47 (m, 2H), 4.31-4.30 (m, 1H), 4.26 (t, J=6.5 Hz, 1H), 3.63 (dddt, J=5.1, 2.7, 1.7, 0.9 Hz, 2H), 3.35-3.32 (m, 2H), 1.74-1.72 (m, 2H), 1.62-1.58 (m, 2H).

Compound 66:

To a solution of compound 65 (220 mg, 0.304 mmol) in 5 mL of methanol/EtOAc (2:3), degassed with argon, was added 28 mg of 10% Pd/C. The mixture was further degassed with argon and connected to a hydrogen balloon. After 2 h, analysis by LC/MS from an in-process aliquot indicated the reaction was complete. The mixture was filtered through Celite, washed with MeOH (2×10 mL) and EtOAc (10 mL) and concentrated to afford 130 mg of compound 66 (70% pure by LC/MS) as yellowish oil which was used in the next step instantly without further purification. MS: calc'd for $C_{26}H_{26}N_2O_5$, 446.1; found 447.1 (M+H).

Compound 67:

To a round-bottom flask with hydroxyaniline 66 (130 mg, 0.204 mmol, 70% pure), was added THE (1 mL) and sonicated for 1 min. Then rifamycin S (135 mg, 0.194 mmol) and toluene (5 mL) were added and the reaction mixture was sonicated for 2 min to dissolve the dark yellow solid, sealed via rubber septum, purged with argon, and the reaction stirred vigorously at ambient temperature. After 10 days, the reaction was concentrated in vacuo to remove toluene/THF, dissolved in EtOH (10 mL) and $MnO_2$ (70 mg, 0.805 mmol) was added. After stirring for 4 days, the reaction was concentrated in vacuo and purified by chromatography on a 24 g HP silica gel Gold RediSep column via ISCO system (gradient elution: 0-50% MeOH/DCM). The relatively pure fractions were evaporated and dried in vacuo giving the title compound 67 as a dark reddish solid (120 mg, 38%). Compound 67 did not ionize in the LCMS.

Compound 68:

To a stirred solution of crude compound 67 (120 mg, 0.041 mmol, 38% pure) under argon in DMF (2 mL), was treated with a solution of piperidine (0.5 mL, 2% in DMF) and the reaction was stirred at ambient temperature. After 1 h, the reaction was purified directly on a 50 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the Fmoc deprotected product as dark reddish solid (9 mg, 25%). MS: calc'd for $C_{48}H_{57}N_3O_{14}$, 899.4; found 900.4 (M+H).

To a stirred solution of the product (7 mg, 0.0078 mmol) under argon in DCM (2 mL), was added paraformaldehyde (3.5 mg, 0.1167 mmol) and $Na(OAc)_3BH$ (6.6 mg, 0.0312 mmol) at ambient temperature. After 4 h, another portion of paraformaldehyde (3.5 mg, 0.1167 mmol) and $Na(OAc)_3BH$ (6.0 mg, 0.0283 mmol) was added to the reaction mixture. After 1 h, the reaction was filtered through Celite, washed with MeOH (2×10 mL), concentrated and purified directly on a 15.5 g C18 RediSep Gold column via ISCO system (gradient elution: 0-100% MeCN in water, 0.05% acetic acid in both, over 30 min). The product-containing fractions were combined, frozen on dry ice, and lyophilized overnight giving the title compound 68. The compound was re-purified by EZ preparative HPLC column (Gemini, 5 μm, 150 mm×30 mm, eluents: 10-95% MeCN in water, 0.05% AcOH). Pure fractions were combined, frozen on dry ice/Acetone, and lyophilized overnight giving the title compound 68 as dark reddish solid. (2 mg, 28%). MS: calc'd for $C_{49}H_{59}N_3O_{14}$, 913.4; found 914.4 (M+H). $^1$H-NMR (500 MHz; $CD_3OD$): δ 6.68 (br. s., 1H), 6.47-6.58 (m, 1H), 6.32-6.46 (m, 1H), 6.13-6.32 (m, 1H), 4.64-4.75 (m, 1H), 4.59 (br. s., 1H), 3.46 (s, 1H), 3.18 (br. s., 1H), 2.91-3.12 (m, 4H), 2.76 (br. s., 2H), 2.51 (br. s., 2H), 2.35-2.42 (m, 3H), 2.31 (br. s., 2H), 2.22 (br. s., 2H), 2.04-2.17 (m, 3H), 1.97-2.04 (m, 3H), 1.94 (s, 6H), 1.90 (br. s., 2H), 1.72-1.83 (m, 6H), 1.55-1.71 (m, 3H), 1.39-1.52 (m, 3H), 1.25-1.37 (m, 3H), 0.76-1.06 (m, 4H), 0.02 (br. s., 2H), −0.25 (br. s., 3H).
Example 16: Preparation of Compound 71
Rifamycin analog 71 was synthesized from Rifamycin S as shown in Scheme 20 below, and as described below.
Scheme 20
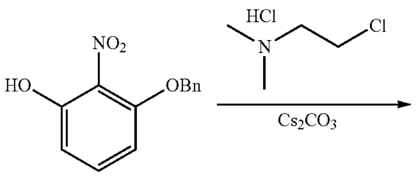
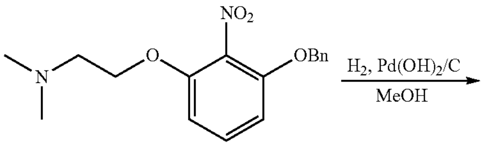
69
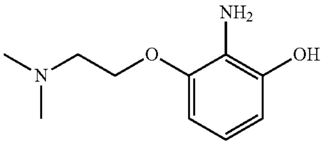
70
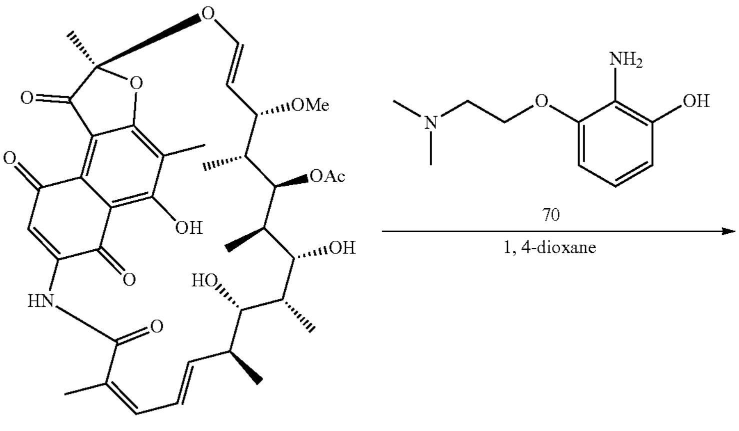
rifamycin S
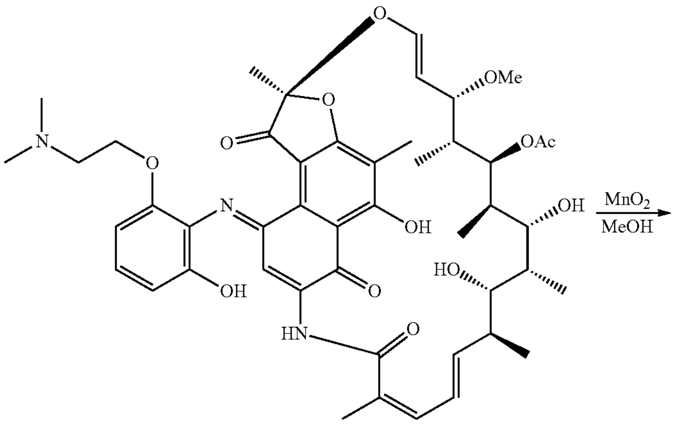
71a -continued

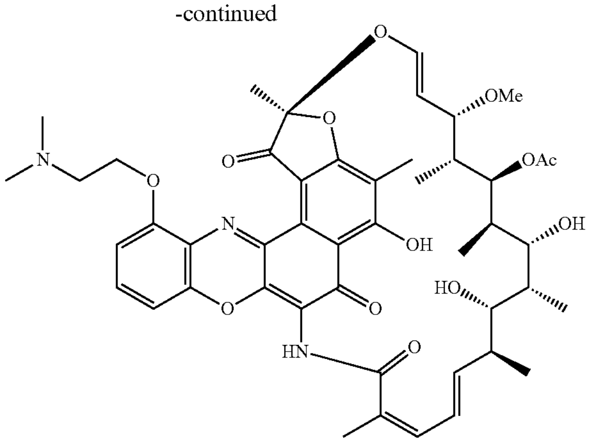

71

Compound 69:

To a stirred mixture of 3-(benzyloxy)-2-nitrophenol (500 mg, 2.03 mmol, 1.0 eq.), 2-chloro-N,N-dimethylethan-1-amine HCl salt (380 mg, 2.65 mmol, 1.3 eq.), and $Cs_2CO_3$ (1.65 g, 5.07 mmol, 2.5 eq.) was added anhydrous acetone (7 mL) and heated at 50° C. overnight. The reaction was complete by LC/MS and cooled to room temperature. The crude was filtered through a Celite pad and concentrated. The crude was then purified on a 40 g HP silica gel Gold RediSep column via ISCO (gradient elution: 0-20% DCM in methanol), and the pure fractions evaporated and dried in vacuo giving 69 as a dark oil (428 mg, 67%). MS (ESI, pos.): calc'd for $C_{17}H_2N_2O_4$, 316.36; found 317.2 (M+H). $^1$H-NMR (500 MHz; $CDCl_3$): δ 7.39-7.29 (m, 6H), 6.65 (t, J=8.5 Hz, 2H), 5.18 (s, 2H), 4.17 (t, J=5.9 Hz, 2H), 2.75 (t, J=5.9 Hz, 2H), 2.33 (s, 6H).

Compound 70:

To a stirred solution, under argon, of compound 69 (185 mg, 0.585 mmol) in methanol (3 mL) was added 37 mg of 20% $Pd(OH)_2/C$ (contains 50% water). The mixture was further degassed with argon and connected to a hydrogen balloon. After 2 h, analysis by LC/MS from an in-process aliquot indicated the reaction was complete. The mixture was filtered through Celite and concentrated to afford 110 mg of the title compound 70 (85% pure by LC/MS) as dark yellow oil, which was used in the next step instantly without further purification. MS: calc'd for $C_{10}H_{16}N_2O_2$, 196.1; found 197.1 (M+H).

Compound 71:

To a round-bottom flask with hydroxyaniline 70 (110 mg, 0.476 mmol, 85% pure), were added 1,4-dioxane (6.8 mL) and rifamycin S (663 mg, 0.953 mmol). The reaction mixture was sealed via rubber septum, purged with argon, and the reaction stirred vigorously at ambient temperature. After 7 days, the reaction was concentrated in vacuo, dissolved in MeOH (10 mL) and $MnO_2$ (104 mg, 1.191 mmol) was added. After stirring for 4 weeks, the reaction was filtered through Celite, washed with MeOH (2×20 mL) concentrated in vacuo and purified by chromatography on a 40 g HP silica gel Gold RediSep column via ISCO system (gradient elution: 0-10% then 10-50% MeOH/DCM). The pure fractions were evaporated and dried in vacuo. The concentrated fractions were dissolved in $MeCN/H_2O$ (1:1), frozen on dry ice/Acetone, and lyophilized overnight to give the title compound 71 as a dark reddish solid (48 mg, 12%). MS (ESI, pos.): calc'd for $C_{47}H_{57}N_3O_{13}$, 871.4; found, 872.4 (M+H). $^1$H-NMR (500 MHz; DMSO-$d_6$): δ 9.37 (s, 1H), 7.65 (t, J=8.55 Hz, 1H), 7.15 (d, J=8.30 Hz, 1H), 5.23 (br. s., 1H), 4.33 (br. s., 2H), 4.28 (br. s., 1H), 3.13 (br. s., 1H), 3.01 (br. s., 4H), 2.95 (br. s., 1H), 2.91 (br. s., 3H), 2.78 (t, J=9.28 Hz, 1H), 2.31 (br. s., 9H), 2.17 (br. s., 4H), 1.98 (s, 5H), 1.94 (br. s., 4H), 1.67 (br. s., 3H), 1.59 (br. s., 1H), 0.80-0.93 (m, 8H), 0.78 (br. s., 1H), 0.67 (br. s., 6H).

Example 17: Preparation of Compound 72

Rifamycin analog 72 was synthesized from compound 15 as shown in Scheme 21 below, and as described below.

Scheme 21

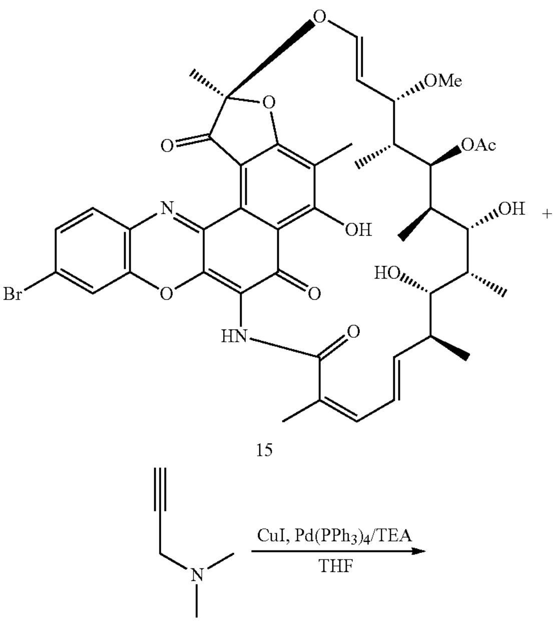

15

-continued

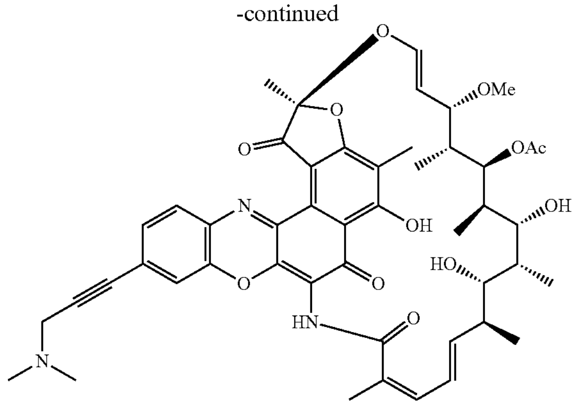

72

Compound 72:

The title compound was prepared using a Sonogashira coupling reaction. A mixture of compound 15 (100 mg, 0.115 mmol, 1.0 eq.), N,N-dimethylprop-2-yn-1-amine (19 μL, 0.173 mmol, 1.5 eq.), CuI (1.1 mg, 0.00575 mmol, 0.05 eq.), $Pd(PPh_3)_4$ (3.3 mg, 0.00287 mmol, 0.025 eq.), and triethylamine (64 μL, 0.46 mmol, 4.0 eq.) in anhydrous THE (3 mL), degassed, at room temperature, was stirred overnight. The progress of the reaction was monitored by LC/MS and additional catalyst (10 mg) was added. The mixture was heated to 40° C. in an oil bath for overnight. The reaction was complete by LC/MS. The crude was filtered through a Celite pad and concentrated. The crude was then purified by a C18 50 g column followed by another purification by ISCO EZ preparative HPLC column (Gemini, 5 μm, 150 mm×30 mm, eluents: 10-95% MeCN in water, 0.05% AcOH). Pure fractions were collected, frozen in a dry-ice/acetone bath, and dried by lyophilizer for 20 h to afford 12 mg (9%) of 72 as a reddish solid. MS (ESI, pos.): calc'd for $C_{48}H_{55}N_3O_{12}$, 865.38; found 866.4 (M+H), 864.4 (M−H). $^{1}$H-NMR (500 MHz; $CD_3OD$): δ 7.97-7.94 (m, 1H), 7.54 (t, J=1.7 Hz, 1H), 7.39-7.35 (m, 1H), 6.89-6.86 (m, 1H), 6.38-6.35 (m, 1H), 6.17-6.15 (m, 2H), 5.12-5.09 (m, 1H), 4.95-4.93 (m, 2H), 3.82-3.79 (m, 1H), 3.58 (s, 2H), 3.02 (s, 6H), 2.40 (s, 3H), 2.27-2.27 (m, 4H), 2.12-2.01 (m, 3H), 1.97 (d, J=10.6 Hz, 8H), 1.74 (s, 4H), 1.72-1.68 (m, 2H), 1.54-1.49 (m, 1H), 1.29 (d, J=2.3 Hz, 1H), 0.95 (s, 3H), 0.89 (dd, J=5.2, 1.5 Hz, 3H), 0.21-0.17 (m, 2H), −0.08-0.12 (m, 2H).

Example 18: Preparation of Compound 75

Rifamycin analog 75 was synthesized from Rifamycin S as shown in Scheme 22 below, and as described below.

Scheme 22

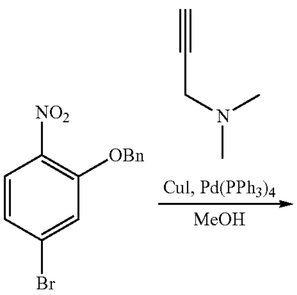

-continued

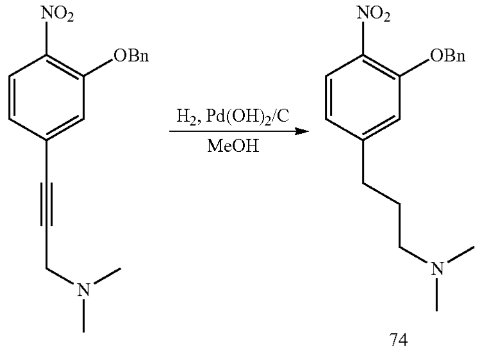

73

74

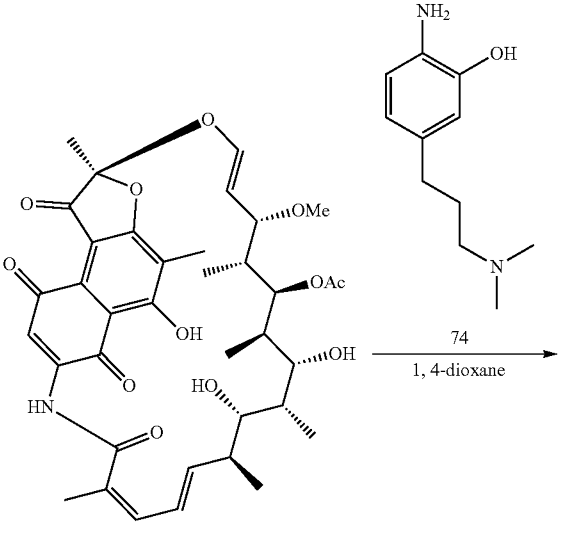

rifamycin S

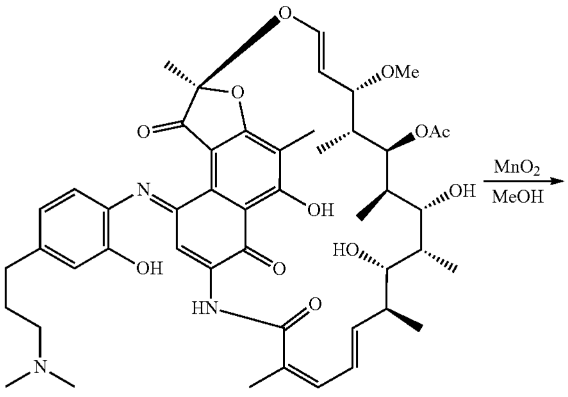

75a

-continued

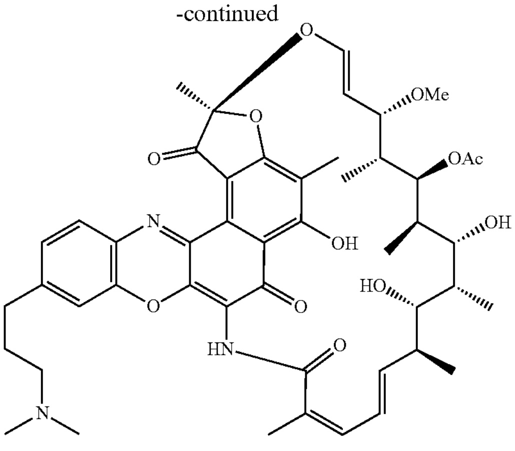

75

Compound 73:

The mixture of 2-(benzyloxy)-4-bromo-1-nitrobenzene (500 mg, 1.622 mmol, 1.0 eq.), N,N-dimethylprop-2-yn-1-amine (262 μL, 2.433 mmol, 1.5 eq.), CuI (15.4 mg, 0.0811 mmol, 0.05 eq.), $Pd(PPh_3)_4$ (47 mg, 0.0405 mmol, 0.025 eq.), and triethylamine (904 L, 6.488 mmol, 4.0 eq.) in anhydrous THE (15 mL) at room temperature, was degassed and stirred for 5 h. The progress of reaction was monitored by LC/MS. The crude was filtered through a Celite pad and concentrated. The crude was then purified on a 40 g HP silica gel Gold RediSep column via ISCO system (gradient elution: 0-20% DCM in methanol), and the pure fractions evaporated and dried in vacuo giving 73 (492 mg, 98%). MS (ESI, pos.): calc'd for $C_{18}H_{18}N_2O_3$, 310.13; found 311.2 (M+H). $^1$H-NMR (500 MHz; $CD_3OD$): δ 7.81 (d, J=8.3 Hz, 1H), 7.47 (d, J=7.6 Hz, 2H), 7.38 (dd, J=8.4, 1.4 Hz, 4H), 7.14 (dd, J=8.3, 1.5 Hz, 1H), 5.28 (s, 2H), 3.52 (s, 2H), 2.36 (dd, J=1.3, 0.6 Hz, 6H).

Compound 74:

To a solution of compound 73 (100 mg, 0.322 mmol) under argon in methanol (4 mL) was added 20 mg of 20% $Pd(OH)_2$/C. The mixture was further degassed with argon and connected to a hydrogen balloon. After 16 h, analysis by LC/MS from an in-process aliquot indicated the reaction was complete. The mixture was filtered through Celite, washed with MeOH (2×10 mL) and concentrated to afford 72 mg of the title compound 74 as reddish yellow oil, which was used in the next step instantly without further purification. MS: calc'd for $C_{11}H_{18}N_2O$, 194.1; found 195.2 (M+H).

Compound 75:

To a round-bottom flask with hydroxyaniline 74 (72 mg, 0.304 mmol, 82% pure), were added 1,4-dioxane (3 mL) and rifamycin S (423 mg, 0.608 mmol). The reaction mixture was sealed via rubber septum, purged with argon, and the reaction stirred vigorously at ambient temperature. After 12 days, the reaction was concentrated in vacuo to remove dioxane, dissolved in MeOH (6 mL) and $MnO_2$ (106 mg, 1.216 mmol) was added. After stirring for 20 h, the reaction was filtered through Celite, washed with MeOH (2×10 mL), concentrated in vacuo and purified directly on a 50 g C18 RediSep Gold column via ISCO system (gradient elution: 0-100% MeCN in water, 0.05% acetic acid in both). The product-containing fractions were combined, frozen on dry ice/acetone, and lyophilized overnight giving the title compound 75. The compound was re-purified by EZ preparative HPLC column (Gemini, 5 μm, 150 mm×30 mm, eluents: 10-95% MeCN in water, 10 mM $NH_4OAc$ in both). Pure fractions were combined, frozen on dry ice/acetone, and lyophilized overnight giving the title compound 75 as a reddish brown solid (6 mg, 2.2%). MS: calc'd for $C_{48}H_{59}N_3O_{12}$, 869.4; found 870.4 (M+H). $^1$H-NMR (500 MHz; $CD_3OD$): δ 8.46 (s, 1H), 7.67 (s, 1H), 7.00 (s, 1H), 6.28 (d, J=8.79 Hz, 1H), 6.20 (s, 1H), 5.98-6.11 (m, 2H), 5.21 (dd, J=6.11, 12.46 Hz, 1H), 5.11 (d, J=10.26 Hz, 1H), 3.85-3.99 (m, 2H), 3.76 (s, 3H), 3.65-3.70 (m, 3H), 3.58 (s, 3H), 3.45 (br. s., 3H), 3.04-3.15 (m, 3H), 2.35 (br. s., 3H), 2.03 (s, 3H), 1.99 (s, 3H), 1.77 (s, 3H), 1.61-1.69 (m, 3H), 1.29 (s, 3H), 1.00 (d, J=6.84 Hz, 3H), 0.92 (d, J=7.33 Hz, 3H), 0.75-0.89 (m, 3H), 0.63 (d, J=6.84 Hz, 3H), 0.10 (s, 3H), 0.00 (d, J=6.84 Hz, 2H).

Example 19: Preparation of Linker-Payload Compounds

The linker-payload chemistry is used to prepare compound 20, as shown in Scheme 23, below, and described below.

Scheme 23

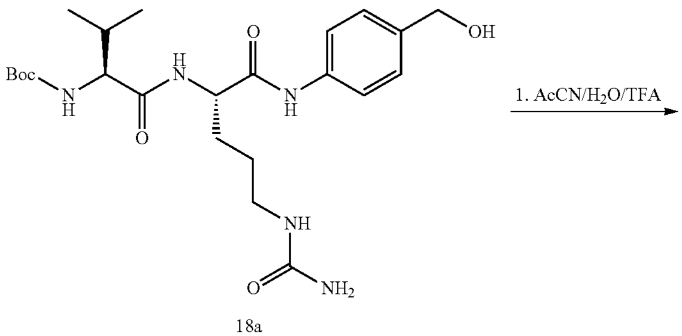

18a

-continued
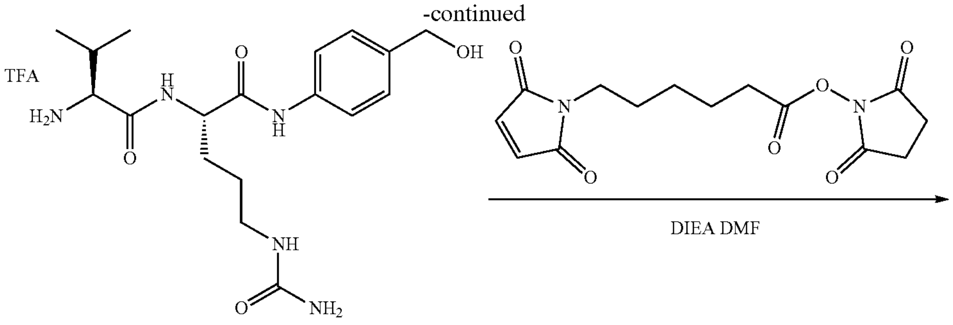
18b
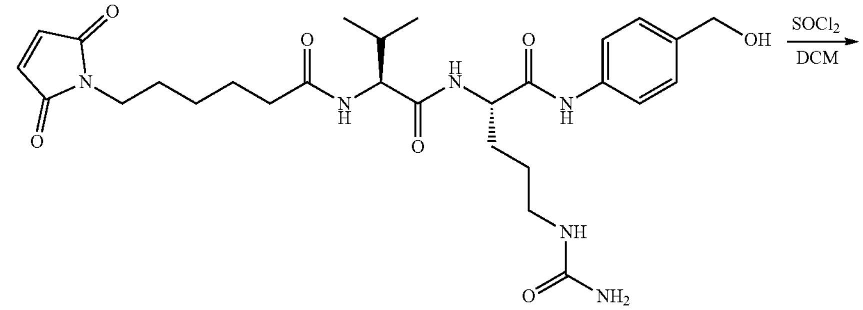
18
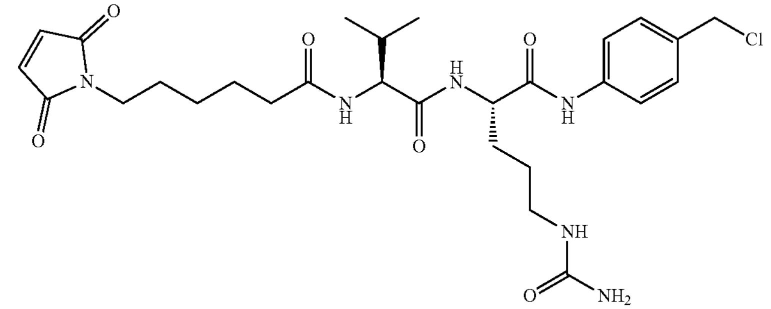
+
19
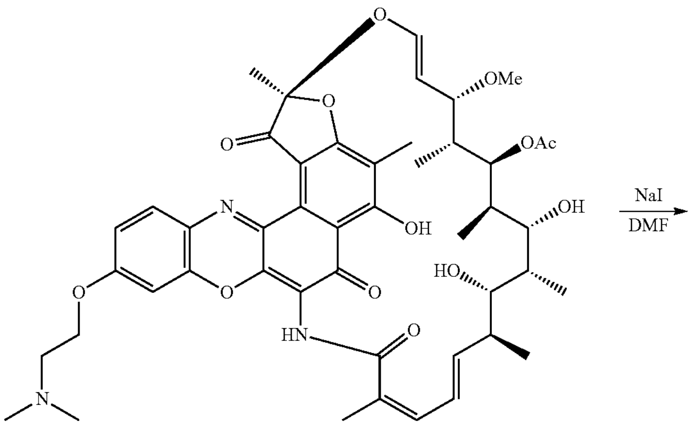
16a

-continued

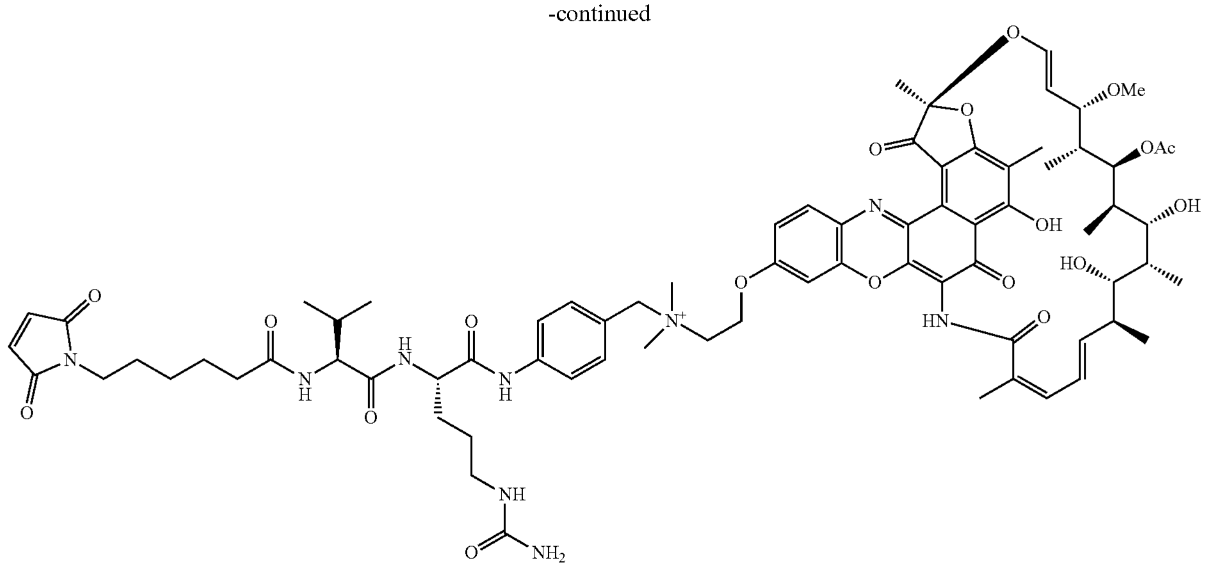

Synthesis of Compound 18.

The title compound was prepared using a procedure in PCT Int. Appl., 2014145090. tert-butyl ((S)-1-(((S)-1-((4-(hydroxymethyl) phenyl)amino)-1-oxo-5-ureidopentan-2-yl)amino)-3-methyl-1-oxobutan-2-yl)carbamate 18a, (500 mg, 1.04 mmol) was dissolved in a mixture of $CH_3CN/H_2O/$TFA (3:1:1=v/v/v, 12 mL/4 mL/4 mL). The reaction mixture was stirred at room temperature for 48 h. The progress of the reaction was determined to be complete by LCMS. After concentrating in vacuo, the crude product 18b (0.9 g wet) was used directly for the next step without further purification. MS (ESI, pos.): calc'd for $C_{18}H_{29}N_5O_4$, 379.22; found 380.2 (M+H).

A solution of 18b (700 mg, 1.47 mmol, 1.0 eq) in water (8 mL) was diluted with 2 mL of aqueous $NaHCO_3$ solution at 4° C. and the mixture (pH=8.0) was treated with commercially available 2,5-dioxopyrrolidin-1-yl 6-(2,5-dioxo-2,5-dihydro-1H-pyrrol-1-yl)hexanoate (408 mg, 0.9 eq) in 10 mL of acetonitrile. The suspension was stirred at room temperature for 16 h until the reaction was complete. The crude product was concentrated under reduced pressure and diluted with DMSO (5 mL). The crude product was purified by an ISCO 150 g C18 column (eluents: 10-95% MeCN in water, 0.05% in AcOH). Pure fractions were combined and lyophilized to afford 368 mg (44%) of compound 18 as a white solid. MS (ESI, pos.): calc'd for $C_{28}H_{40}N_6O_7$, 572.30; found 573.6 (M+H), (2M+H), 1145.9. $^1$H NMR (500 MHz; DMSO-$d_6$): δ 9.89 (s, 1H), 8.05 (d, J=7.33 Hz, 1H), 7.81 (d, J=8.79 Hz, 1H), 7.52-7.57 (m, J=8.79 Hz, 2H), 7.21-7.26 (m, J=8.79 Hz, 2H), 6.99-7.02 (m, 2H), 5.98 (br. s., 1H), 5.40 (s, 2H), 5.10 (t, J=5.62 Hz, 1H), 4.35-4.45 (m, 3H), 4.18 (dd, J=6.84, 8.30 Hz, 1H), 3.26-3.33 (m, 2H), 2.91-3.06 (m, 2H), 2.08-2.22 (m, 2H), 1.93-2.01 (m, 1H), 1.66-1.74 (m, 1H), 1.59 (dd, J=4.40, 9.28 Hz, 1H), 1.43-1.55 (m, 5H), 1.32-1.43 (m, 1H), 1.19 (quin, J=7.57 Hz, 2H), 0.84 (d, J=8.30 Hz, 3H), 0.80-0.89 (m, 3H).

Synthesis of Compound 19.

To a stirred suspension of 18 (100 mg, 0.174 mmol, 1.0 eq) at room temperature was slowly added $SOCl_2$ (14 μL, 0.192 mmol, 1.1 eq) using a micro syringe. The slurry reaction mixture was stirred for 1.5 h and an aliquot analyzed by LC/MS indicated the formation of the desired. The crude mixture was concentrated to remove all volatiles under reduced pressure. The mixture was diluted with 2 mL of DMSO and loaded on to an ISCO C18 Aq 50 g column for purification (10-95% MeCN in water, 0.05% AcOH). The pure fractions were combined and lyophilized to give 72 mg (71%) of 19 as an off-white solid. MS (ESI, pos.): calc'd for $C_{28}H_{39}ClN_6O_6$, 590.26; found 591.3 (M+H), 1181.5 (2M+H). $^1$H NMR (500 MHz; DMSO-$d_6$) δ 10.03 (s, 1H), 8.03-8.11 (m, 1H), 7.79 (d, J=8.30 Hz, 1H), 7.57-7.63 (m, J=8.79 Hz, 2H), 7.34-7.38 (m, J=8.79 Hz, 2H), 6.99-7.02 (m, 2H), 5.97 (br. s., 1H), 5.40 (br. s., 2H), 4.71 (s, 2H), 4.34-4.43 (m, 2H), 4.16-4.21 (m, 1H), 3.36-3.42 (m, 3H), 2.90-3.06 (m, 3H), 2.07-2.22 (m, 3H), 1.91-2.00 (m, 1H), 1.66-1.73 (m, 1H), 1.31-1.41 (m, 1H), 1.18 (quin, J=7.69 Hz, 3H), 0.79-0.89 (m, 7H).

Synthesis of Compound 20.

The mixture of 19 (13.5 mg, 0.0228 mmol, 1.2 eq), 16a (16.6 mg, 0.0190 mmol, 1.0 eq), and NaI (14.2 mg, 0.095 mmol) in a 2 dram vial was dissolved in 1 mL of anhydrous DMF. A catalytic amount (10 μL) of 0.5 M DIPEA solution in DMF was added by syringe. The mixture was heated at 55° C. in an oil bath overnight. The reaction was complete by LC/MS to afford the desired product. The mixture was cooled to 4° C. and diluted with 1 mL of water. After filtration, the dark crude mixture was purified by an EZ preparative HPLC column (Gemini, 5 μm, 150 mm×30 mm, eluents: 10-95% MeCN in water, 0.05% AcOH). Pure fractions were combined and lyophilized to afford 14.6 mg (55%) of 20 as a dark red solid. MS (ESI, pos.): calc'd for $C_{75}H_{96}N_9O_{19}^+$, 1426.68; found 1427.3 (M+1) and 1425.5 (M−1). $^1$H NMR (500 MHz; DMSO-$d_6$) δ 10.25 (s, 1H), 8.19 (d, J=6.84 Hz, 1H), 7.82 (d, J=8.30 Hz, 2H), 7.76 (d, J=8.79 Hz, 3H), 7.50 (d, J=8.30 Hz, 3H), 7.00 (s, 2H), 6.12 (d, J=12.70 Hz, 1H), 6.03 (br. s., 1H), 5.43 (s, 2H), 4.70-4.80 (m, 2H), 4.58 (br. s., 3H), 4.36-4.41 (m, 1H), 4.18 (t, J=7.82 Hz, 1H), 3.77 (br. s., 2H), 3.36-3.45 (m, 8H), 3.13 (d, J=8.30 Hz, 1H), 2.89-3.06 (m, 12H), 2.78 (t, J=9.04 Hz, 1H), 2.06-2.22 (m, 3H), 2.03 (br. s., 1H), 1.91-2.00 (m, 10H), 1.85 (s, 3H), 1.66-1.74 (m, 1H), 1.56-1.64 (m, 6H), 1.42-1.56 (m, 8H), 1.38 (d, J=6.84 Hz, 2H), 1.15-1.25 (m, 3H), 0.75-0.88 (m, 14H), 0.07 (s, 1H).

Linker-payload compound 25 was prepared as shown in Scheme 24, below, and described below.

Scheme 24
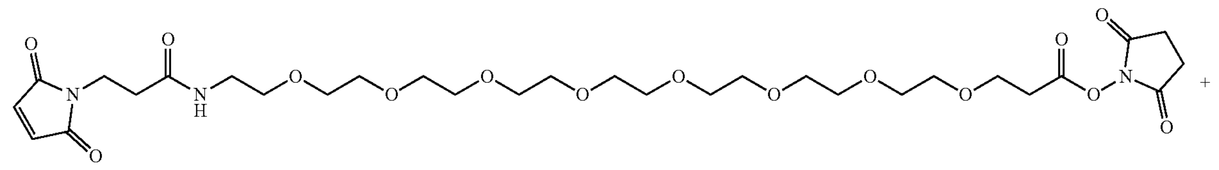
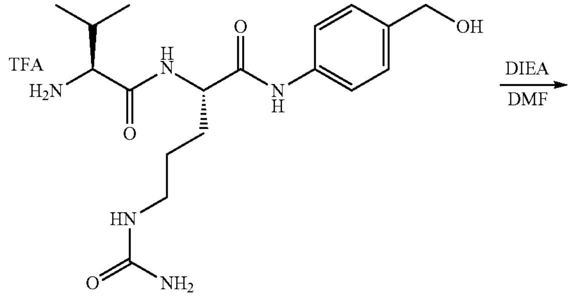
18b
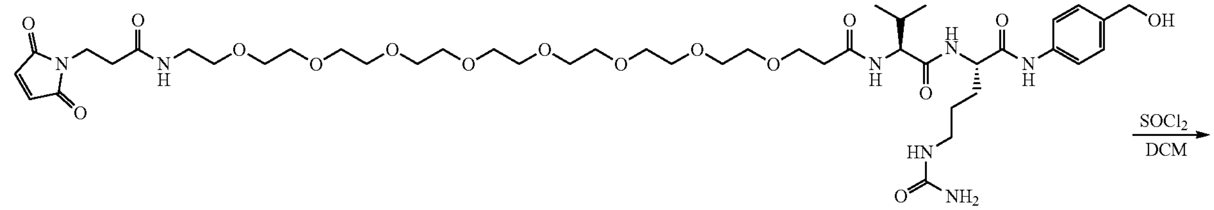
23
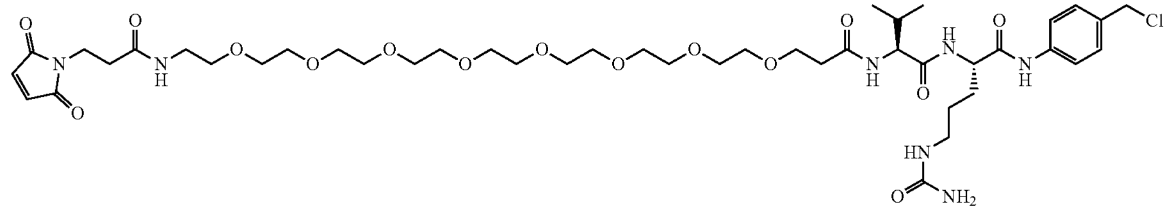
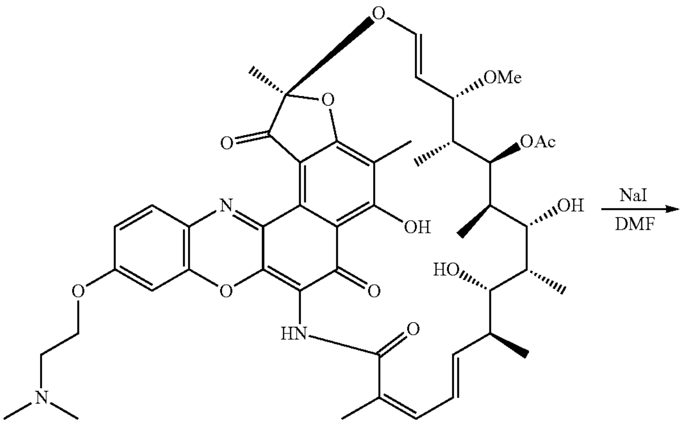
16a -continued

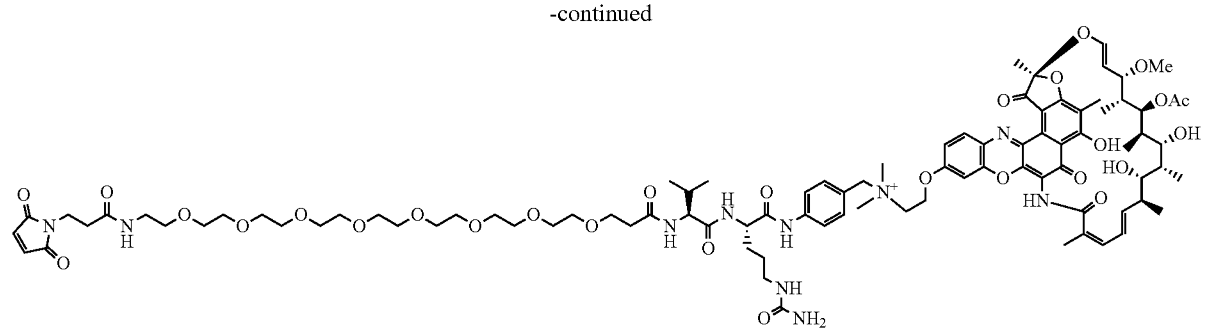

25

Synthesis of Compound 23.

To a mixture of 22 (100 mg, 0.144 mmol) and 18b (82 mg, 0.217 mmol) in anhydrous DMF (1.5 mL) was then treated with DIEA (50 μL, 0.288 mmol) via micro syringe. The reaction mixture was stirred for 2 h at room temperature and determined to afford 23 by LC/MS. The crude mixture was purified by an ISCO C18 100 g Aq column (eluents: 10-95% MeCN in water, 0.05% in AcOH), pure factions combined and lyophilized to yield 84.4 mg (62%) of 23. MS (ESI, pos.): calc'd for $C_{44}H_{71}N_7O_{16}$, 953.50; found 954.4 (M+H), 976.4 (M+Na), 952.4 (M−H). $^1$H NMR (500 MHz; DMSO-$d_6$) δ 9.88 (s, 1H), 8.08 (d, J=7.2 Hz, 1H), 8.00 (s, 1H), 7.86 (d, J=8.5 Hz, 1H), 7.55 (d, J=8.4 Hz, 2H), 7.23 (d, J=8.3 Hz, 2H), 7.00 (s, 2H), 5.98 (s, 1H), 5.40 (s, 1H), 4.43 (s, 2H), 4.39 (d, J=5.4 Hz, 1H), 4.23 (dd, J=8.3, 6.8 Hz, 2H), 3.60 (d, J=6.9 Hz, 6H), 3.44-3.54 (m, 30H), 3.37 (t, J=5.8 Hz, 3H), 3.15 (d, J=5.7 Hz, 2H), 2.99 (d, J=29.6 Hz, 2H), 2.33 (t, J=7.3 Hz, 3H), 1.98 (d, J=6.7 Hz, 1H), 1.71-1.70 (m, 1H), 1.61-1.58 (m, 1H), 1.44-1.36 (m, 2H), 0.85 (dd, J=15.5, 6.7 Hz, 7H).

Synthesis of Compound 24.

To a stirred suspension of 23 (15 mg, 0.0157 mmol, 1.0 eq) in a vial at room temperature was slowly added $SOCl_2$ (1.3 μL, 0.0173 mmol, 1.1 eq) via a micro syringe. After 1 h, an aliquot analyzed by LC/MS indicated the formation of the desired product. The crude mixture was concentrated to remove all volatiles under reduced pressure. The crude mixture was diluted with 0.8 mL of MeCN and loaded onto an EZ preparative HPLC column and eluted (Gemini, 5 μm, 150 mm×30 mm, eluents: 10-95% MeCN in water, 0.05% AcOH). Pure fractions were combined and lyophilized to afford 9.5 mg (63%) of 24 as an off-white solid. MS (ESI, pos.): calc'd for $C_{44}H_{70}ClN_7O_{15}$, 971.46; found 972.4 (M+H), 994.4 (M+Na), 970.3 (M−1).

Synthesis of Linker-Payload Compound 25.

To a mixture of 24 (9.5 mg, 0.00976 mmol, 1.0 eq), 16a (8.51 mg, 0.00976 mmol, 1.0 eq), and NaI (7.3 mg, 0.0488 mmol) in a 1 dram vial was dissolved in 1 mL of anhydrous DMF. A catalytic amount (20 μL) of 0.5M DIEA solution in DMF was added by syringe. The mixture was heated at 55° C. in an oil bath overnight. The reaction was complete by LC/MS to afford the desired product. The mixture was cooled in an ice-bath and diluted with 1 mL of water. After filtration, the dark crude mixture was purified by an EZ preparative HPLC column (Gemini, 5 μm, 150 mm×30 mm, eluents: 10-95% MeCN in water, 0.05% AcOH). Pure fractions were combined and lyophilized to afford 7.4 mg (42%) of 25 as a dark red solid. MS (ESI, pos.): calc'd for $C_{91}H_{127}N_{10}O_{28}^+$, 1807.88; found 1808.8 (M+H) and 1806.5 (M−1). 1H NMR (500 MHz; DMSO-$d_6$) δ 10.23 (s, 1H), 8.22-8.17 (m, 1H), 8.03-7.98 (m, 1H), 7.86 (d, J=8.3 Hz, 1H), 7.75 (d, J=8.2 Hz, 4H), 7.50 (d, J=8.3 Hz, 3H), 7.00 (s, 2H), 6.01 (s, 1H), 5.76 (s, 1H), 5.43 (s, 1H), 4.80-4.80 (m, 1H), 4.58 (s, 1H), 4.43-4.41 (m, 1H), 4.27-4.23 (m, 1H), 3.76 (t, J=0.6 Hz, 2H), 3.59 (t, J=7.3 Hz, 5H), 3.49 (d, J=2.9 Hz, 54H), 3.14 (d, J=5.8 Hz, 4H), 3.03 (s, 8H), 2.90 (t, J=0.7 Hz, 3H), 2.77 (d, J=0.7 Hz, 1H), 2.33 (t, J=7.3 Hz, 4H), 2.08 (d, J=6.1 Hz, 4H), 1.94 (d, J=18.9 Hz, 10H), 1.83 (s, 5H), 1.59 (s, 8H), 0.85 (dd, J=16.1, 6.7 Hz, 8H).

Linker-payload compound 36 was prepared as shown in Scheme 25, below, and described below.

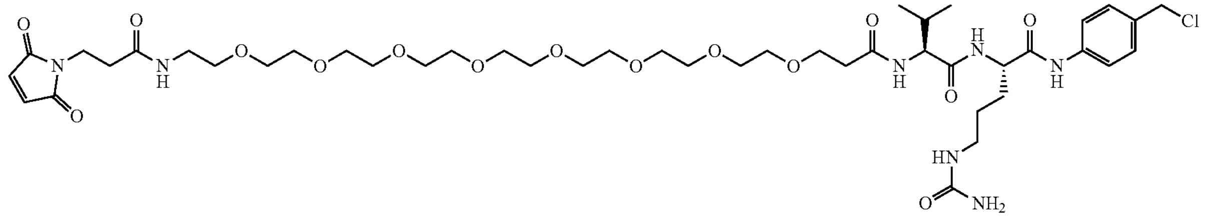

24

-continued

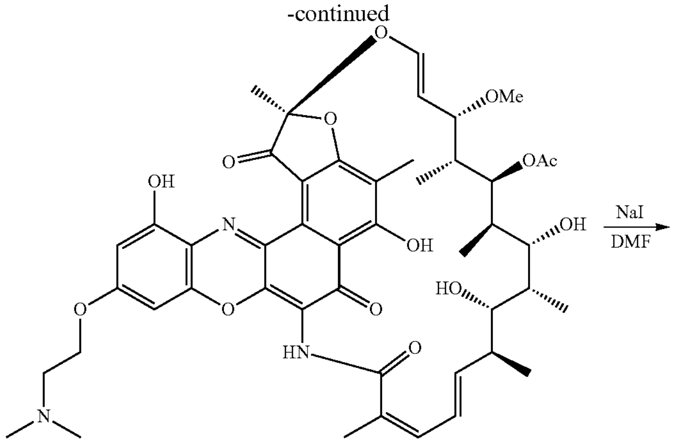

29

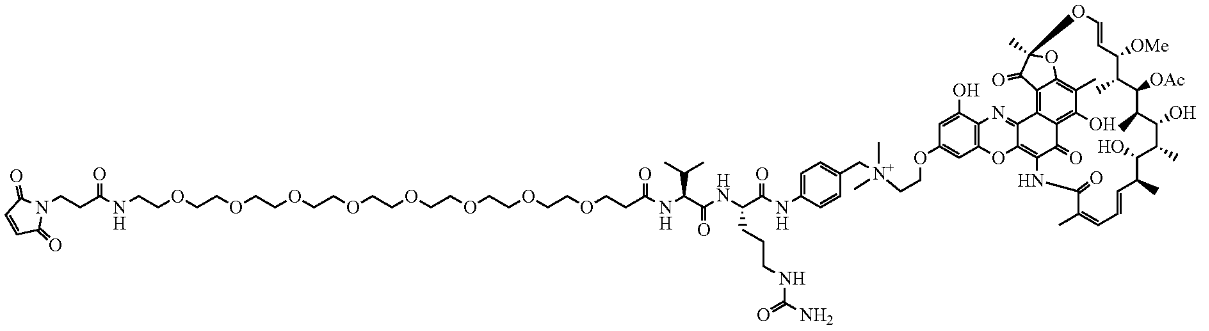

36

Compound 36:

The mixture of 24 (14.4 mg, 0.00149 mmol, 1.2 eq), 16a (11.0 mg, 0.00123 mmol, 1.0 eq), and NaI (9.1 mg, 0.0615 mmol) in a 1 dram vial was dissolved in 1 mL of anhydrous DMF. A catalytic amount of 0.5M DIEA solution in DMF (10 μL) was added via a syringe. The mixture was heated at 55° C. in an oil bath overnight. The reaction was complete when assayed by LC/MS to afford the desired product. The mixture was cooled in an ice-bath and diluted with 0.5 mL of water. After filtration, the dark crude mixture was purified by EZ preparative HPLC column (Gemini, 5 μm, 150 mm×30 mm, eluents: 10-95% MeCN in water, 0.05% AcOH). Pure fractions were collected, frozen, and lyophilized to afford 11.7 mg (53%) of 36 as a dark red solid. MS (ESI, pos.): calc'd for $C_{91}H_{127}N_{10}O_{29}^+$, 1823.88; found 1824.8 (M+H) and 1821.7 (M−1). $^1H$ NMR (500 MHz; DMSO-$d_6$): δ 10.22 (s, 1H), 8.85 (d, J=0.8 Hz, 1H), 8.18-8.17 (m, 1H), 8.01 (s, 1H), 7.86 (d, J=8.1 Hz, 1H), 7.75-7.73 (m, 2H), 7.49-7.47 (m, 2H), 7.00 (s, 2H), 6.28 (dd, J=9.9, 0.9 Hz, 1H), 6.21 (dd, J=12.4, 0.6 Hz, 1H), 6.00-5.98 (m, 1H), 5.86 (s, 1H), 5.48 (s, 1H), 5.42 (d, J=8.4 Hz, 2H), 5.04-4.99 (m, 1H), 4.72-4.69 (m, 1H), 4.58-4.50 (m, 3H), 4.40-4.38 (m, 1H), 4.25-4.22 (m, 1H), 3.89-3.87 (m, 1H), 3.73-3.70 (m, 4H), 3.62-3.58 (m, 7H), 3.54-3.47 (m, 29H), 3.36 (t, J=5.8 Hz, 7H), 3.15 (d, J=5.7 Hz, 4H), 3.03-2.98 (m, 4H), 2.85 (s, 3H), 2.66 (d, J=23.9 Hz, 3H), 2.34 (dd, J=16.4, 9.2 Hz, 4H), 2.12-2.05 (m, 3H), 1.92 (d, J=18.7 Hz, 13H), 1.67 (s, 3H), 1.61 (t, J=0.6 Hz, 3H), 1.47-1.37 (m, 3H), 1.24 (d, J=0.6 Hz, 1H), 0.88-0.78 (m, 8H), 0.78-0.65 (m, 4H), 0.17-0.16 (m, 1H), 0.07 (s, 1H), −0.41 (td, J=2.5, 0.9 Hz, 1H).

Linker-payload compound 25a was prepared as shown in Scheme 26, below, and described below.

Scheme 26

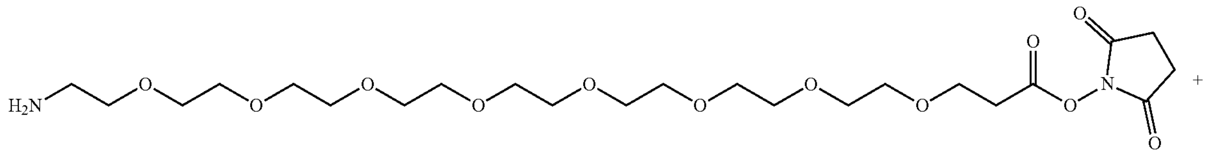

22a

-continued
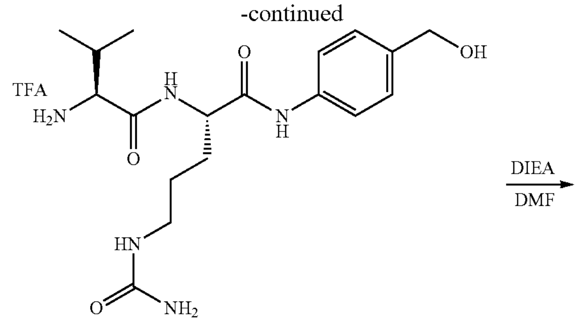
18b
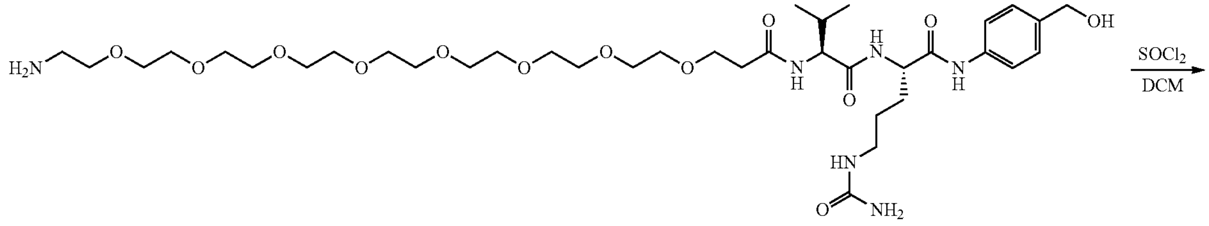
23a
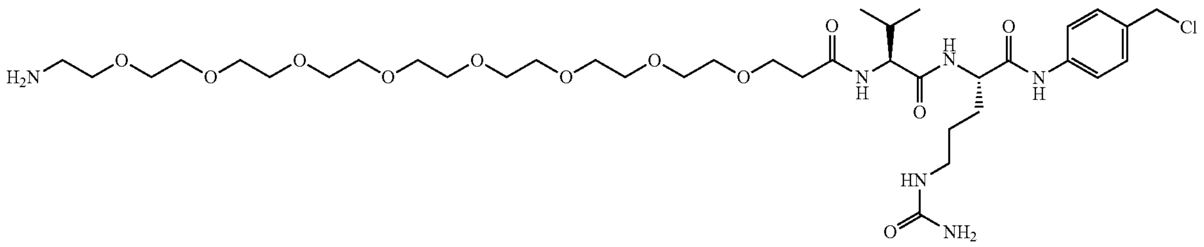
24a
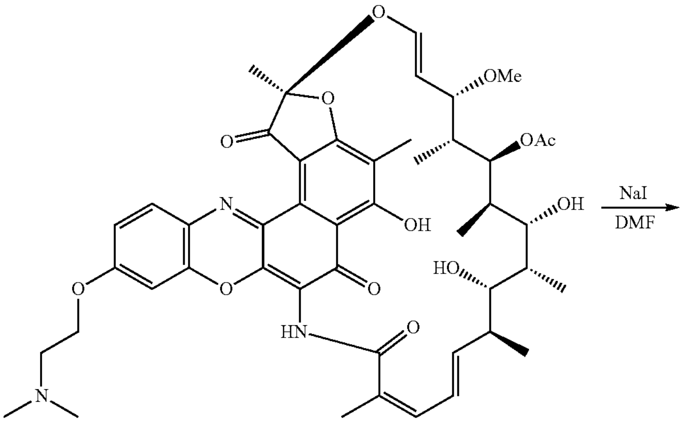
16a

-continued

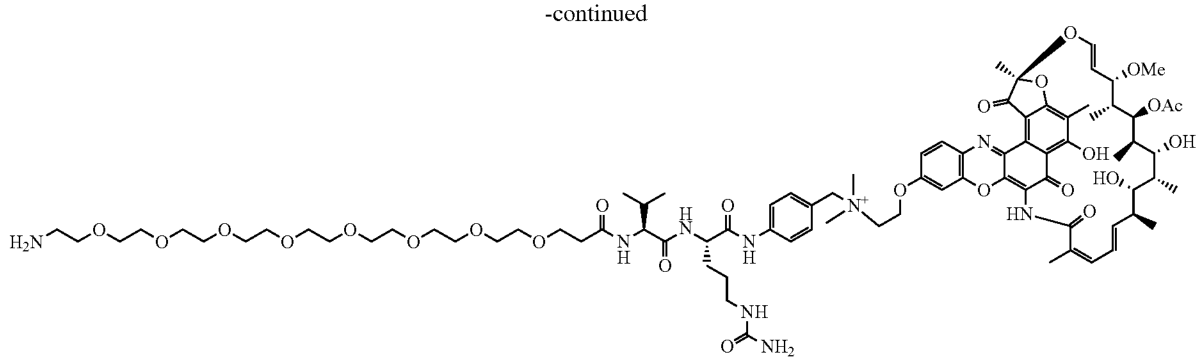

25a

Synthesis of Compound 23a.

To a mixture of 22a (100 mg, 0.144 mmol) and 18b (82 mg, 0.217 mmol) in anhydrous DMF (1.5 mL) was then treated with DIEA (50 μL, 0.288 mmol) via micro syringe. The reaction mixture was stirred for 2 h at room temperature and determined to afford 23a by LC/MS. The crude mixture was purified by an ISCO C18 100 g Aq column (eluents: 10-95% MeCN in water, 0.05% in AcOH), pure factions combined and lyophilized to yield 84.4 mg (62%) of 23. MS (ESI, pos.): calc'd for $C_{44}H_{71}N_7O_{16}$, 953.50; found 954.4 (M+H), 976.4 (M+Na), 952.4 (M−H). 1H NMR (500 MHz; DMSO-$d_6$) δ 9.88 (s, 1H), 8.08 (d, J=7.2 Hz, 1H), 8.00 (s, 1H), 7.86 (d, J=8.5 Hz, 1H), 7.55 (d, J=8.4 Hz, 2H), 7.23 (d, J=8.3 Hz, 2H), 7.00 (s, 2H), 5.98 (s, 1H), 5.40 (s, 1H), 4.43 (s, 2H), 4.39 (d, J=5.4 Hz, 1H), 4.23 (dd, J=8.3, 6.8 Hz, 2H), 3.60 (d, J=6.9 Hz, 6H), 3.44-3.54 (m, 30H), 3.37 (t, J=5.8 Hz, 3H), 3.15 (d, J=5.7 Hz, 2H), 2.99 (d, J=29.6 Hz, 2H), 2.33 (t, J=7.3 Hz, 3H), 1.98 (d, J=6.7 Hz, 1H), 1.71-1.70 (m, 1H), 1.61-1.58 (m, 1H), 1.44-1.36 (m, 2H), 0.85 (dd, J=15.5, 6.7 Hz, 7H).

Synthesis of Compound 24a.

To a stirred suspension of 23a (15 mg, 0.0157 mmol, 1.0 eq) in a vial at room temperature was slowly added $SOCl_2$ (1.3 μL, 0.0173 mmol, 1.1 eq) via a micro syringe. After 1 h, an aliquot analyzed by LC/MS indicated the formation of the desired product. The crude mixture was concentrated to remove all volatiles under reduced pressure. The crude mixture was diluted with 0.8 mL of MeCN and loaded onto an EZ preparative HPLC column and eluted (Gemini, 5 μm, 150 mm×30 mm, eluents: 10-95% MeCN in water, 0.05% AcOH). Pure fractions were combined and lyophilized to afford 9.5 mg (63%) of 24 as an off-white solid. MS (ESI, pos.): calc'd for $C_{44}H_{70}ClN_7O_{15}$, 971.46; found 972.4 (M+H), 994.4 (M+Na), 970.3 (M−1).

Synthesis of Linker-Payload Compound 25a.

To a mixture of 24a (9.5 mg, 0.00976 mmol, 1.0 eq), 16a (8.51 mg, 0.00976 mmol, 1.0 eq), and NaI (7.3 mg, 0.0488 mmol) in a 1 dram vial was dissolved in 1 mL of anhydrous DMF. A catalytic amount (20 μL) of 0.5M DIEA solution in DMF was added by syringe. The mixture was heated at 55° C. in an oil bath overnight. The reaction was complete by LC/MS to afford the desired product. The mixture was cooled in an ice-bath and diluted with 1 mL of water. After filtration, the dark crude mixture was purified by an EZ preparative HPLC column (Gemini, 5 μm, 150 mm×30 mm, eluents: 10-95% MeCN in water, 0.05% AcOH). Pure fractions were combined and lyophilized to afford 7.4 mg (42%) of 25 as a dark red solid. MS (ESI, pos.): calc'd for $C_{91}H_{127}N_{10}O_{28}^{+}$, 1807.88; found 1808.8 (M+H) and 1806.5 (M−1). $^1$H NMR (500 MHz; DMSO-$d_6$) δ 10.23 (s, 1H), 8.22-8.17 (m, 1H), 8.03-7.98 (m, 1H), 7.86 (d, J=8.3 Hz, 1H), 7.75 (d, J=8.2 Hz, 4H), 7.50 (d, J=8.3 Hz, 3H), 7.00 (s, 2H), 6.01 (s, 1H), 5.76 (s, 1H), 5.43 (s, 1H), 4.80-4.80 (m, 1H), 4.58 (s, 1H), 4.43-4.41 (m, 1H), 4.27-4.23 (m, 1H), 3.76 (t, J=0.6 Hz, 2H), 3.59 (t, J=7.3 Hz, 5H), 3.49 (d, J=2.9 Hz, 54H), 3.14 (d, J=5.8 Hz, 4H), 3.03 (s, 8H), 2.90 (t, J=0.7 Hz, 3H), 2.77 (d, J=0.7 Hz, 1H), 2.33 (t, J=7.3 Hz, 4H), 2.08 (d, J=6.1 Hz, 4H), 1.94 (d, J=18.9 Hz, 10H), 1.83 (s, 5H), 1.59 (s, 8H), 0.85 (dd, J=16.1, 6.7 Hz, 8H).

Linker-payload compound 36a was prepared as shown in Scheme 27, below, and described below.

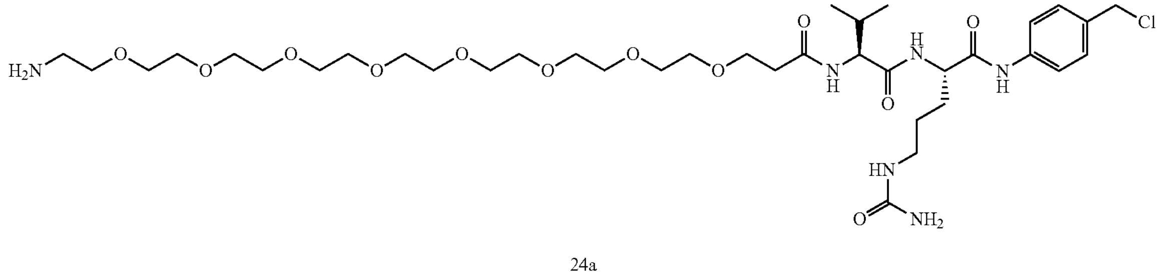

+

24a

-continued

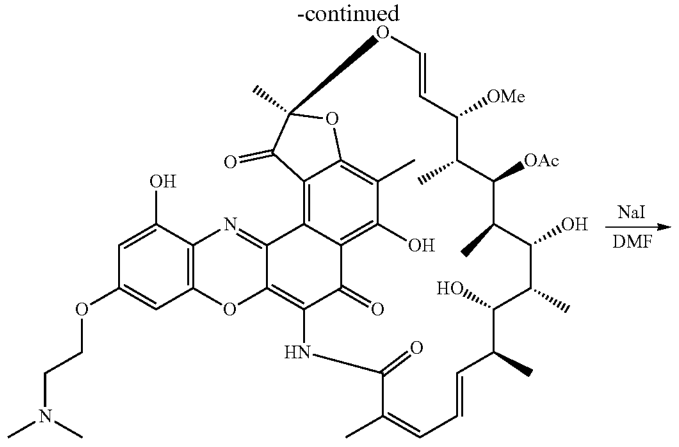

29

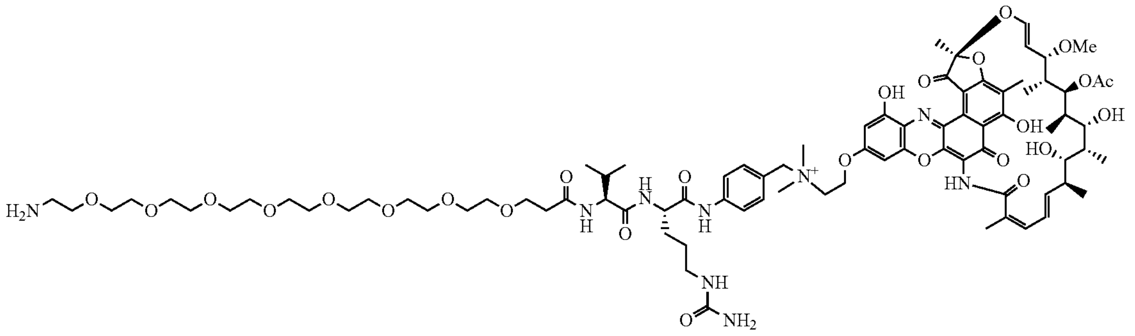

36a

Compound 36a:

The mixture of 24a (14.4 mg, 0.00149 mmol, 1.2 eq), 16a (11.0 mg, 0.00123 mmol, 1.0 eq), and NaI (9.1 mg, 0.0615 mmol) in a 1 dram vial was dissolved in 1 mL of anhydrous DMF. A catalytic amount of 0.5M DIEA solution in DMF (10 μL) was added via a syringe. The mixture was heated at 55° C. in an oil bath overnight. The reaction was complete when assayed by LC/MS to afford the desired product. The mixture was cooled in an ice-bath and diluted with 0.5 mL of water. After filtration, the dark crude mixture was purified by EZ preparative HPLC column (Gemini, 5 μm, 150 mm×30 mm, eluents: 10-95% MeCN in water, 0.05% AcOH). Pure fractions were collected, frozen, and lyophilized to afford 11.7 mg (53%) of 36 as a dark red solid. MS (ESI, pos.): calc'd for $C_{91}H_{127}N_{10}O_{29}^{+}$, 1823.88; found 1824.8 (M+H) and 1821.7 (M−1). $^1$H NMR (500 MHz; DMSO-d$_6$): δ 10.22 (s, 1H), 8.85 (d, J=0.8 Hz, 1H), 8.18-8.17 (m, 1H), 8.01 (s, 1H), 7.86 (d, J=8.1 Hz, 1H), 7.75-7.73 (m, 2H), 7.49-7.47 (m, 2H), 7.00 (s, 2H), 6.28 (dd, J=9.9, 0.9 Hz, 1H), 6.21 (dd, J=12.4, 0.6 Hz, 1H), 6.00-5.98 (m, 1H), 5.86 (s, 1H), 5.48 (s, 1H), 5.42 (d, J=8.4 Hz, 2H), 5.04-4.99 (m, 1H), 4.72-4.69 (m, 1H), 4.58-4.50 (m, 3H), 4.40-4.38 (m, 1H), 4.25-4.22 (m, 1H), 3.89-3.87 (m, 1H), 3.73-3.70 (m, 4H), 3.62-3.58 (m, 7H), 3.54-3.47 (m, 29H), 3.36 (t, J=5.8 Hz, 7H), 3.15 (d, J=5.7 Hz, 4H), 3.03-2.98 (m, 4H), 2.85 (s, 3H), 2.66 (d, J=23.9 Hz, 3H), 2.34 (dd, J=16.4, 9.2 Hz, 4H), 2.12-2.05 (m, 3H), 1.92 (d, J=18.7 Hz, 13H), 1.67 (s, 3H), 1.61 (t, J=0.6 Hz, 3H), 1.47-1.37 (m, 3H), 1.24 (d, J=0.6 Hz, 1H), 0.88-0.78 (m, 8H), 0.78-0.65 (m, 4H), 0.17-0.16 (m, 1H), 0.07 (s, 1H), −0.41 (td, J=2.5, 0.9 Hz, 1H).

Linker-payload compound 80 was prepared as shown in Scheme 28, below, and described below.

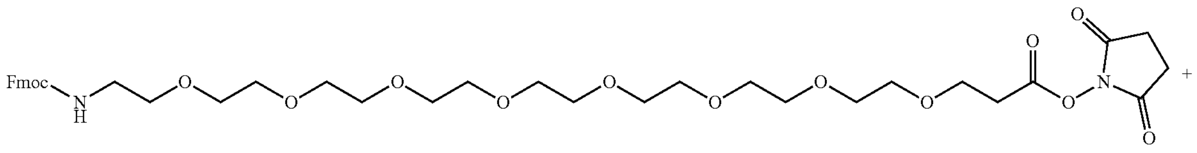

-continued
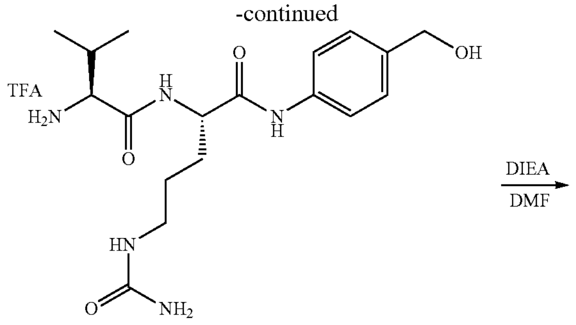
18b
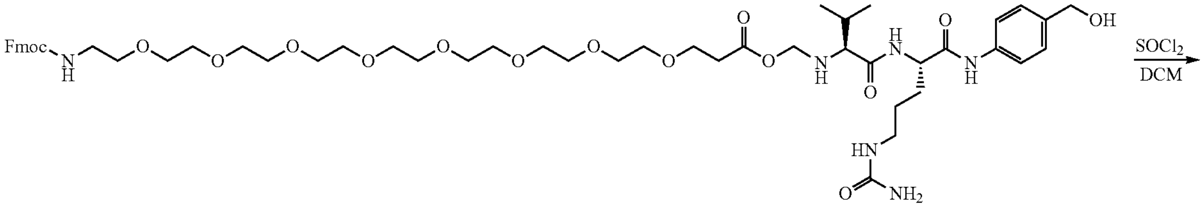
77
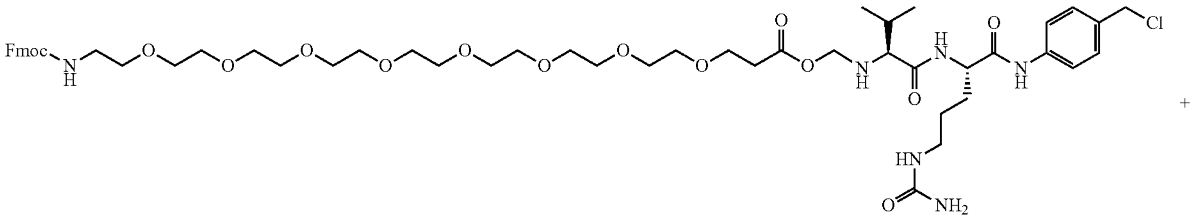
78
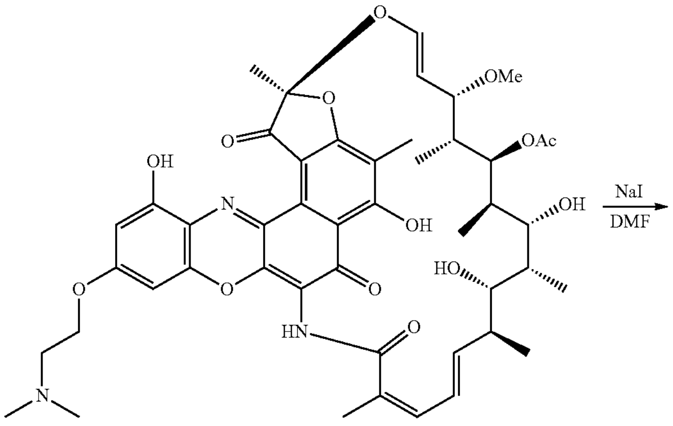
29
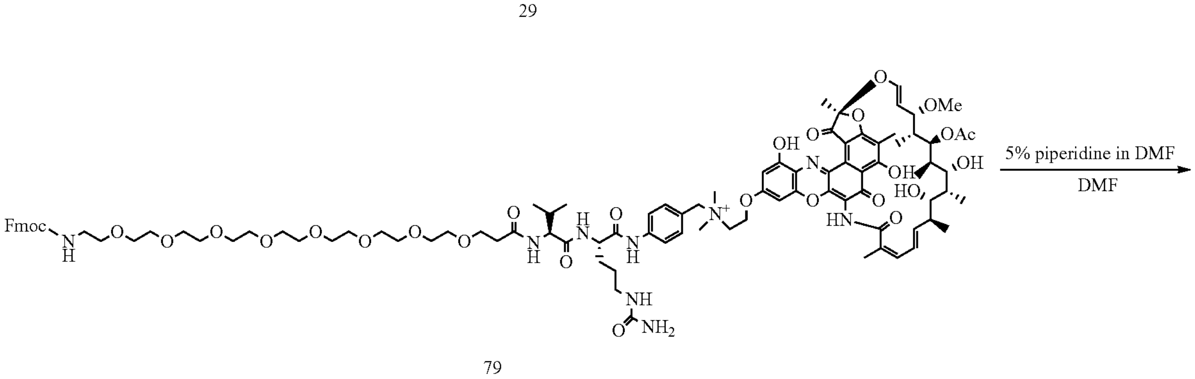
79

-continued

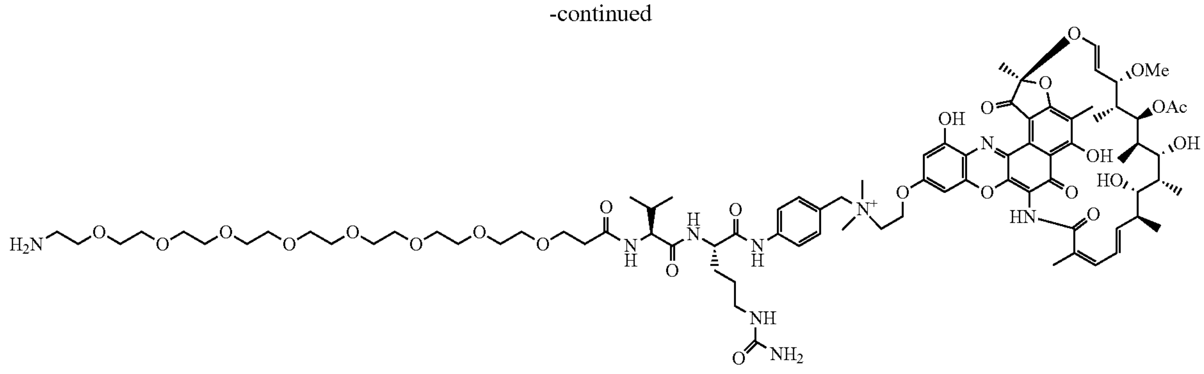

80

Compound 77:

To a solution of commercially available compound 76 (100 mg, 0.131 mmol) and 18b (71 mg, 0.144 mmol) in anhydrous DMF (1.5 mL) was added DIEA (34 μL, 0.197 mmol) via micro syringe. The reaction mixture was stirred for 1 h at room temperature. The reaction was complete by LC/MS and concentrated in vacuo. The crude product was purified by ISCO system using a C18 100 g Aq column (eluents: 10-95% MeCN in water, 0.05% in AcOH). Pure fractions by LC/MS were collected, frozen in a dry-ice/acetone bath, and lyophilized for 24 h to afford 114 mg (85%) of 77. MS (ESI, pos.): calc'd for $C_{52}H_{76}N_6O_{15}$, 1024.54; found 1025.5 (M+H), 1047.4 (M+Na).

Compound 78:

To a stirred suspension of 77 (46 mg, 0.0448 mmol, 1.0 eq) in 1.5 mL of anhydrous DCM at room temperature was slowly added $SOCl_2$ (3.6 μL, 0.0493 mmol, 1.1 eq) using a micro syringe. After 30 min, an in process aliquot was analyzed by LC/MS to indicate the formation of desired product. The crude mixture was concentrated in vacuo and diluted with 1 mL of MeCN. The solution was loaded on to a ISCO system C18 50 g Ag column (eluents: 10-95% MeCN in water, 0.05% AcOH). Pure fractions were collected, frozen in a dry-ice/acetone bath, and lyophilized to afford 40 mg (85%) of 77 as an off-white solid. MS (ESI, pos.): calc'd for $C_{52}H_{75}ClN_6O_{14}$, 1042.50; found 1043.4 (M+H), 1065.4 (M+Na).

Compound 79:

To a mixture of 78 (35 mg, 0.0337 mmol, 1.2 eq), 29 (25 mg, 0.0281 mmol, 1.0 eq), and NaI (21 mg, 0.145 mmol, 5.0 eq.) in 2 dram vial was added 1.5 mL of anhydrous DMF. A catalytic amount of 0.5M DIEA solution in DMF (20 μL) was added by syringe via septa. The mixture was heated at 55° C. in an oil bath for overnight. The reaction was complete by LC/MS to afford the desired product. The mixture was cooled with an ice-bath and diluted with 1 mL of water. After filtration, the dark crude mixture was purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 42 mg (79%) of 79 as a dark red solid. MS (ESI, pos.): calc'd for $C_{99}H_{132}N_9O_{28}^+$, 1894.92; found 1895.9 (M+H). $^1$H-NMR (500 MHz; DMSO-$d_6$): δ 10.22 (s, 1H), 8.85 (s, 1H), 8.19-8.17 (m, 1H), 7.89-7.84 (m, 2H), 7.74-7.73 (m, 2H), 7.70-7.68 (m, 2H), 7.48-7.46 (m, 2H), 7.41 (t, J=7.5 Hz, 2H), 7.32 (t, J=7.4 Hz, 2H), 6.91-6.87 (m, 1H), 6.28-6.26 (m, 1H), 6.20 (dd, J=12.8, 0.7 Hz, 1H), 6.09-6.07 (m, 1H), 6.06-5.97 (m, 2H), 5.85 (t, J=0.7 Hz, 1H), 5.72-5.65 (m, 1H), 5.48 (d, J=0.7 Hz, 1H), 5.42 (s, 3H), 5.23-5.22 (m, 1H), 5.04-4.98 (m, 2H), 4.71-4.69 (m, 1H), 4.51 (t, J=0.8 Hz, 6H), 4.39-4.38 (m, 12H), 4.29 (d, J=6.9 Hz, 3H), 4.23-4.20 (m, 2H), 3.87 (dd, J=8.2, 1.1 Hz, 1H), 3.70 (dd, J=1.7, 0.9 Hz, 4H), 3.59 (d, J=5.7 Hz, 4H), 3.46 (s, 12H), 3.40 (d, J=5.8 Hz, 3H), 3.13-3.11 (m, 2H), 3.03-2.97 (m, 6H), 2.85 (s, 3H), 2.68 (dd, J=1.3, 0.8 Hz, 2H), 2.63 (d, J=1.7 Hz, 5H), 2.36 (dd, J=3.5, 1.7 Hz, 4H), 2.22-2.18 (m, 1H), 2.12 (s, 3H), 2.05 (dd, J=1.4, 0.7 Hz, 1H), 1.98-1.93 (m, 3H), 1.86 (s, 1H), 1.67 (s, 1H), 1.60 (t, J=0.8 Hz, 3H), 1.45-1.44 (m, 2H), 1.38-1.37 (m, 1H), 1.24-1.20 (m, 1H), 0.85 (dd, J=16.5, 6.6 Hz, 2H), 0.78-0.76 (m, 3H), 0.70-0.60 (m, 2H), 0.17-0.16 (m, 2H), −0.42 (dd, J=5.2, 0.8 Hz, 2H).

Compound 80:

To a stirred solution of compound 79 (25 mg, 0.0131 mmol) in 2 mL of DMF was added a solution of 5% piperidine (400 μL) in DMF and the reaction stirred at ambient temperature. After 1 h, the reaction was complete by LC/MS. The crude was then purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 18.6 mg (82%) of 80 as a reddish solid. MS (ESI, pos.): calc'd for $C_{84}H_{22}N_9O_{26}^+$, 1672.85 (free base); found 1673.8 (M+H). $^1$H-NMR (500 MHz; DMSO-$d_6$): δ 10.26 (s, 1H), 8.85 (d, J=0.9 Hz, 1H), 8.23 (dd, J=6.3, 0.4 Hz, 1H), 7.89-7.87 (m, 1H), 7.75-7.74 (m, 2H), 7.48-7.47 (m, 2H), 6.90-6.87 (m, 1H), 6.28-6.26 (m, 1H), 6.21-6.19 (m, 1H), 6.04 (t, J=10.3 Hz, 2H), 5.88-5.85 (m, 1H), 5.74-5.72 (m, 1H), 5.50 (ddt, J=3.3, 1.0, 0.8 Hz, 1H), 5.43 (s, 2H), 5.03-4.98 (m, 1H), 4.71-4.69 (m, 1H), 4.52 (s, 4H), 4.38 (d, J=5.4 Hz, 1H), 4.23 (t, J=7.6 Hz, 1H), 3.89-3.87 (m, 1H), 3.70 (d, J=0.7 Hz, 3H), 3.60 (d, J=5.2 Hz, 4H), 3.48 (s, 24H), 3.00-2.97 (m, 12H), 2.85 (s, 2H), 2.64 (s, 2H), 2.39-2.36 (m, 1H), 2.23-2.20 (m, 1H), 2.11 (d, J=0.4 Hz, 3H), 1.93 (s, 9H), 1.83 (s, 3H), 1.67-1.60 (m, 6H), 1.46-1.38 (m, 3H), 1.24 (s, 1H), 0.85 (dd, J=16.2, 6.6 Hz, 12H), 0.76 (d, J=8.3 Hz, 5H), 0.15-0.15 (m, 2H), 0.07 (s, 1H), −0.40 (d, J=1.9 Hz, 1H).

Linker-payload compound 82 was prepared as shown in Scheme 29, below, and described below.
Scheme 29
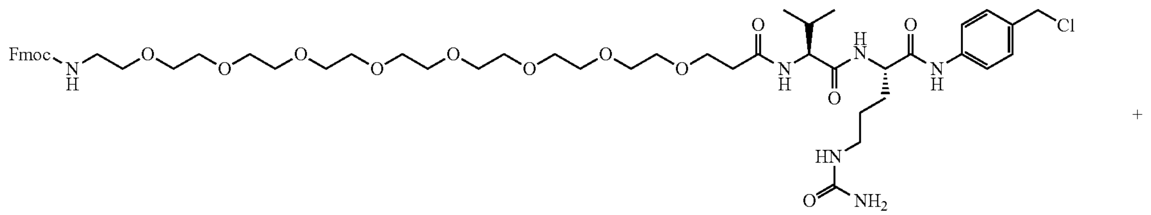
78
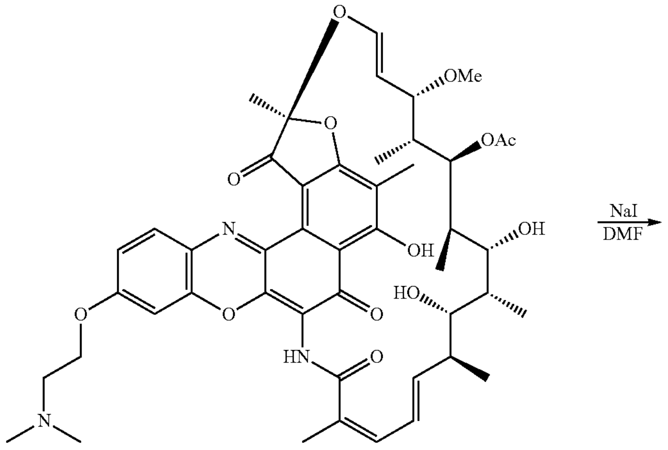
16a
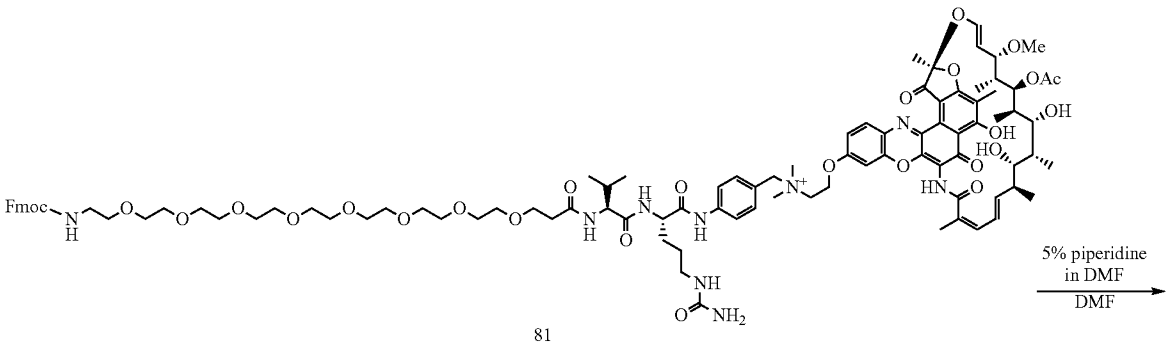
81
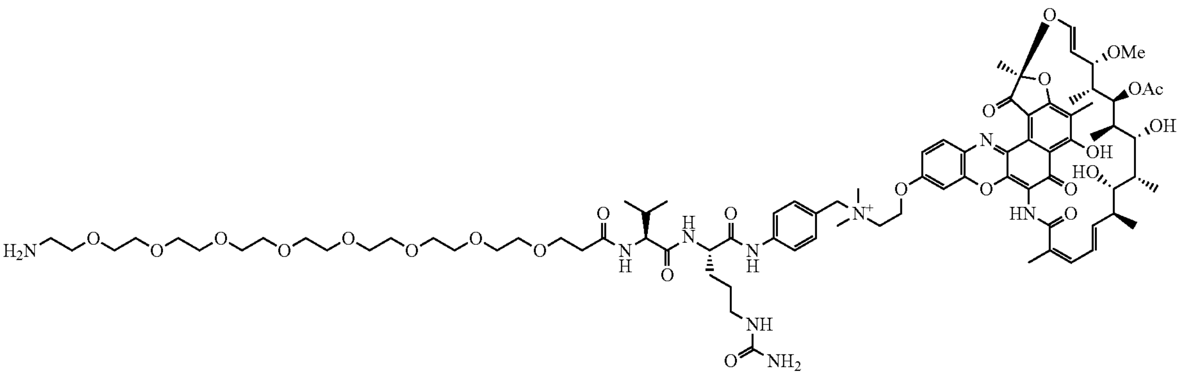
82

Compound 81:

The mixture of 78 (43 mg, 0.0414 mmol, 1.0 eq), 16a (36 mg, 0.0412 mmol, 1.0 eq), and NaI (30 mg, 0.206 mmol, 5.0 eq.) in 2 dram vial was dissolved in 2 mL of anhydrous DMF. A catalytic amount (20 μL) of 0.5M DIEA solution in DMF was added via syringe. The mixture was heated at 55° C. in an oil bath overnight. The reaction was complete by LC/MS. The mixture was cooled in an ice-bath and diluted with 1 mL of water. After filtration, the dark crude mixture was purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 48 mg (62%) of 81 as a dark red solid. MS (ESI, pos.): calc'd for $C_{99}H_{132}N_9O_{27}^+$, 1878.92; found 1879.9 (M+H). $^1$H-NMR (500 MHz; DMSO-$d_6$): δ 10.35 (s, 1H), 8.86-8.81 (m, 1H), 8.34-8.33 (m, 1H), 7.93 (d, J=8.7 Hz, 1H), 7.89 (t, J=12.9 Hz, 3H), 7.75 (d, J=8.7 Hz, 3H), 7.68 (d, J=7.5 Hz, 2H), 7.48 (d, J=8.6 Hz, 2H), 7.40 (t, J=7.4 Hz, 2H), 7.31 (td, J=7.4, 0.8 Hz, 3H), 7.05-7.03 (m, 1H), 6.81-6.74 (m, 1H), 6.70-6.67 (m, 1H), 6.22-6.19 (m, 1H), 6.13-6.08 (m, 2H), 5.44 (s, 2H), 5.12-5.09 (m, 1H), 4.75 (dd, J=12.8, 8.4 Hz, 1H), 4.71-4.68 (m, 1H), 4.56 (s, 3H), 4.37-4.35 (m, 1H), 4.28 (d, J=6.9 Hz, 2H), 4.20 (dd, J=9.5, 2.8 Hz, 2H), 3.75 (s, 3H), 3.58 (d, J=5.5 Hz, 4H), 3.49-3.46 (m, 32H), 3.12 (d, J=6.0 Hz, 4H), 3.02 (s, 8H), 2.88 (d, J=0.4 Hz, 3H), 2.78-2.74 (m, 1H), 2.62 (quintet, J=1.8 Hz, 1H), 2.37-2.34 (m, 1H), 1.95-1.91 (m, 10H), 1.74 (s, 5H), 1.58 (s, 5H), 1.45-1.43 (m, 2H), 1.37-1.34 (m, 1H), 0.83 (dd, J=16.3, 6.8 Hz, 13H), 0.29 (s, 1H), 0.21-0.16 (m, 2H), 0.03-0.02 (m, 1H).

Compound 82:

To a stirred solution of compound 81 (26 mg, 0.0138 mmol) of the preceding step in 1.5 mL of DMF was added a solution of 5% piperidine (500 μL) in DMF and the reaction was stirred at ambient temperature. After 50 min, the reaction was complete by LC/MS. The crude was then purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 17.6 mg (77%) of 82 as a reddish solid. MS (ESI, pos.): calc'd for $C_{84}H_{122}N_9O_{25}^+$, 1656.85 (free base); found 1658.7 (M+H), 1655.7 (M−H). $^1$H-NMR (500 MHz; DMSO-$d_6$): δ 10.25 (d, J=1.1 Hz, 1H), 8.26-8.17 (m, 1H), 7.89-7.87 (m, 1H), 7.75 (d, J=8.4 Hz, 3H), 7.49 (d, J=8.4 Hz, 2H), 7.08-7.05 (m, 1H), 6.12-6.09 (m, 1H), 6.04-6.01 (m, 1H), 5.42 (s, 2H), 5.13-5.09 (m, 1H), 4.76 (dd, J=12.6, 8.7 Hz, 1H), 4.70 (dq, J=3.2, 1.0 Hz, 1H), 4.57 (s, 3H), 4.37-4.36 (m, 1H), 4.23-4.20 (m, 1H), 3.75 (s, 2H), 3.58 (t, J=5.5 Hz, 3H), 3.48 (t, J=1.9 Hz, 32H), 3.14-3.07 (m, 3H), 3.02 (d, J=9.5 Hz, 10H), 2.96-2.93 (m, 4H), 2.91-2.87 (m, 4H), 2.78-2.76 (m, 1H), 2.63-2.62 (m, 3H), 2.38-2.35 (m, 1H), 1.95 (dd, J=3.4, 0.7 Hz, 8H), 1.92 (s, 3H), 1.83 (s, 3H), 1.68 (dd, J=2.2, 1.6 Hz, 1H), 1.59 (s, 5H), 1.45-1.43 (m, 2H), 1.38-1.35 (m, 1H), 1.22 (s, 1H), 0.84 (dt, J=12.6, 5.0 Hz, 10H), 0.79-0.77 (m, 2H), 0.06-0.01 (m, 1H).

Linker-payload compound 84 was prepared as shown in Scheme 30, below, and described below.

Scheme 30

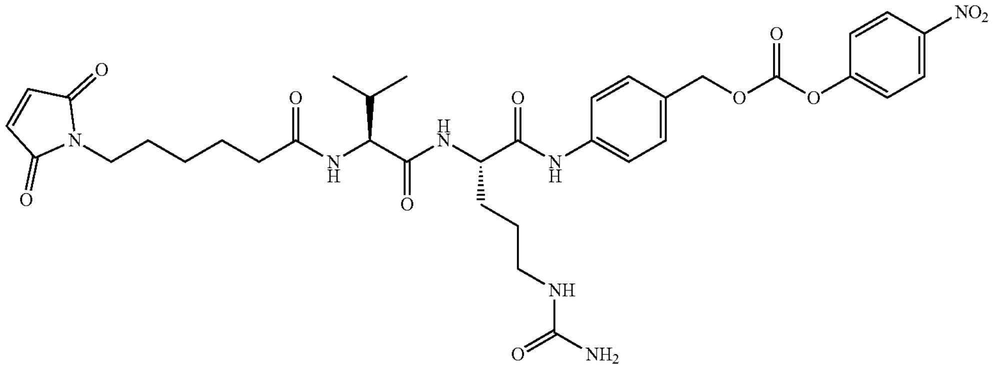

83

+

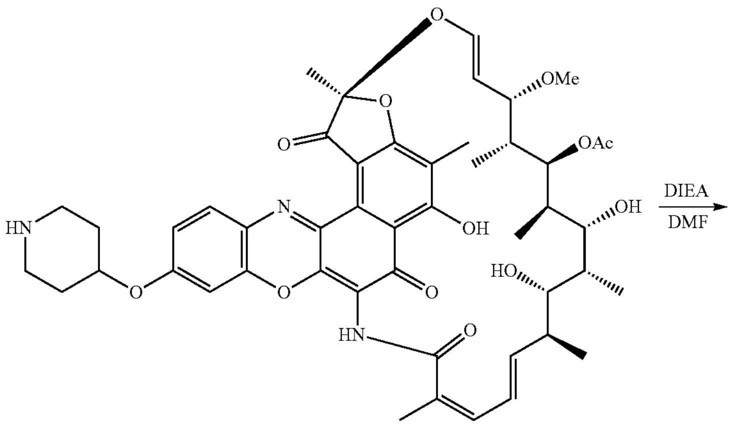

14

-continued

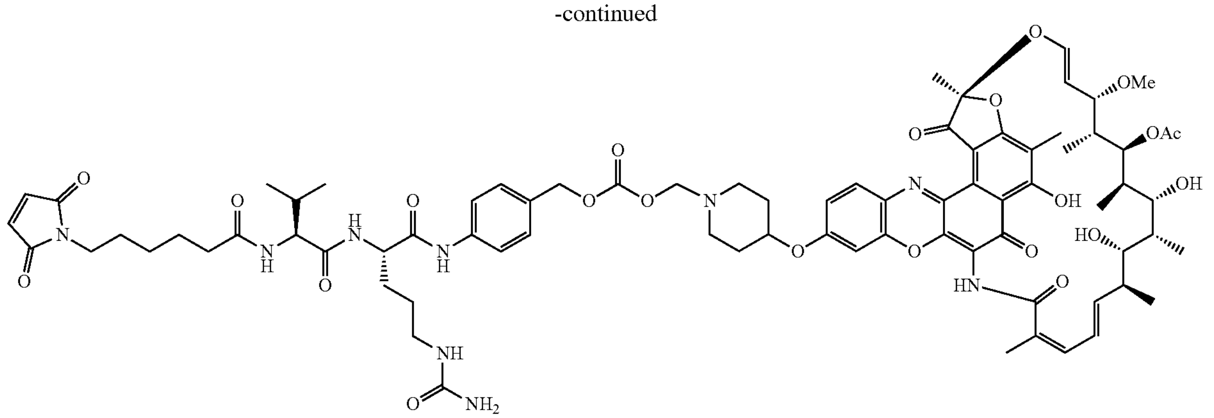

84

Compound 84:

To a stirred solution of commercially available compound 83 (14 mg, 0.0186 mmol, 1.5 eq.) and compound 14 (11 mg, 0.0124 mmol, 1.0 eq.) in anhydrous 2.5 mL DMF was added DIEA (4.3 μL, 0.0248 mmol, 2.0 eq.) and the reaction was stirred at ambient temperature. After 15 min, the reaction was complete by LC/MS. The crude was then purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 11.4 mg (64%) of 84 as a reddish solid. MS (ESI, pos.): calc'd for $C_{77}H_{95}N_9O_{21}$, 1481.66; found 1482.6 (M+H), 1480.6 (M−H). $^1$H-NMR (500 MHz; DMSO-$d_6$): δ 9.99 (s, 1H), 8.08 (d, J=7.33 Hz, 1H), 7.87 (br. s., 1H), 7.80 (d, J=8.30 Hz, 1H), 7.60 (d, J=8.30 Hz, 2H), 7.24-7.34 (m, 3H), 7.21 (d, J=8.79 Hz, 1H), 7.00 (s, 2H), 5.95-6.00 (m, 1H), 5.81 (br. s., 1H), 5.40 (s, 2H), 5.02 (s, 2H), 4.91 (br. s., 1H), 4.79 (br. s., 1H), 4.35-4.41 (m, 1H), 4.19 (t, J=7.57 Hz, 2H), 3.73 (br. s., 2H), 3.38 (br. s., 2H), 3.08 (s, 3H), 3.10 (s, 3H), 2.82-3.05 (m, 6H), 2.78 (br. s., 1H), 2.64 (br. s., 1H), 2.54 (br. s., 1H), 2.37 (d, J=4.40 Hz, 6H), 2.25 (br. s., 1H), 2.02-2.23 (m, 6H), 1.93-2.02 (m, 9H), 1.90 (s, 2H), 1.67 (br. s., 5H), 1.60 (br. s., 4H), 1.43-1.55 (m, 6H), 1.28-1.43 (m, 2H), 1.14-1.28 (m, 3H), 0.72-0.95 (m, 6H), 0.67 (br. s., 2H), 0.07 (s, 1H).

Linker-payload compound 86 was prepared as shown in Scheme 31, below, and described below.

Scheme 31

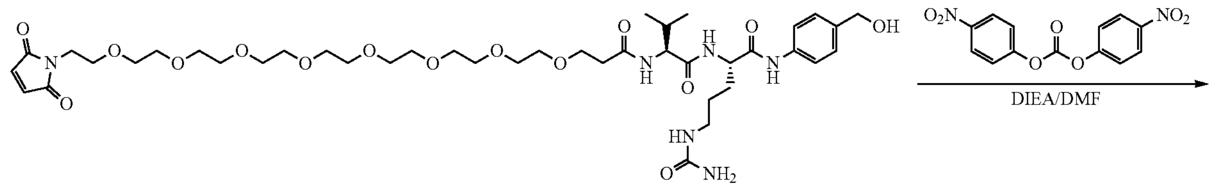

23

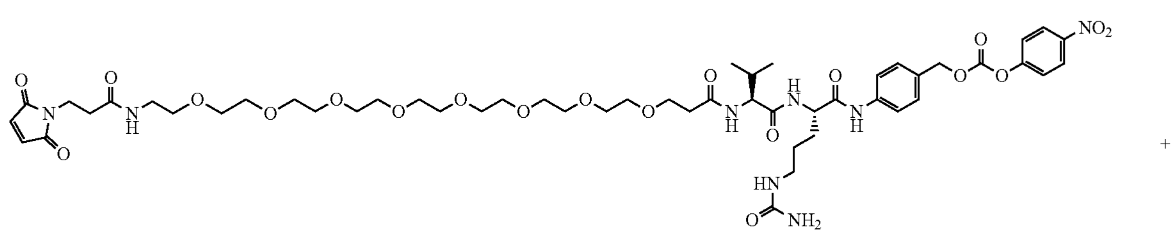

85

-continued

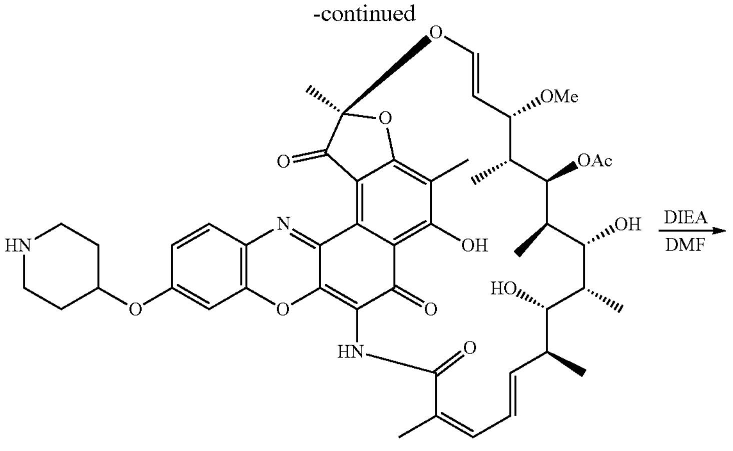

14

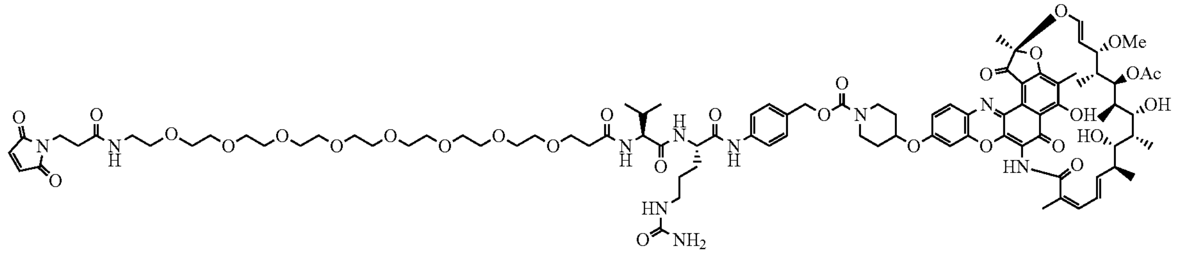

86

Compound 85:

To a stirred solution of compound 23 (85 mg, 0.0894 mmol, 1.0 eq.) and bis(4-nitrophenyl) carbonate (82 mg, 0.2682 mmol, 3.0 eq.) under argon in anhydrous DMF (2.5 mL), was added DIEA (31 μL, 0.1788 mmol, 2.0 eq.) and the reaction was stirred at ambient temperature overnight. The reaction was complete by LC/MS analysis. The resulting mixture was purified directly on a 100 g C18 Aq. column via ISCO system (gradient elution: 10-100% MeCN in water, 0.05% acetic acid in both, over 30 min). The product-containing fractions were combined, frozen on dry ice, and lyophilized overnight giving the title compound 85 as a dark reddish solid. (68 mg, 69%). MS: calc'd for $C_{51}H_{74}N_8O_{20}$, 1118.50; found 1120.0 (M+H).

Compound 86:

The title compound was prepared using linker-payload chemistry described in compound 84. To a stirred solution of compound 85 (12 mg, 0.01085 mmol, 1.2 eq.) and compound 14 (8 mg, 0.00905 mmol, 1.0 eq.) in anhydrous DMF (1.5 mL), was added with DIEA (3.2 μL, 0.0180 mmol, 2.0 eq.) and the reaction was stirred at ambient temperature. After 30 min, the reaction was complete to afford a desired product by LC/MS. The crude was then purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized to afford 12.5 mg (74%) of 86 as a reddish solid. MS (ESI, pos.): calc'd for $C_{93}H_{26}N_{10}O_{30}$, 1862.86; found 1863.8 (M+H), 1886.8 (M+Na). $^1$H-NMR (500 MHz; DMSO-$d_6$): δ δ 9.99 (s, 1H), 9.38 (s, 1H), 8.11 (d, J=7.33 Hz, 1H), 8.00 (t, J=5.37 Hz, 1H), 7.86 (d, J=8.79 Hz, 2H), 7.60 (d, J=8.30 Hz, 2H), 7.25-7.34 (m, 3H), 7.21 (d, J=8.79 Hz, 1H), 7.00 (s, 2H), 5.97 (t, J=5.62 Hz, 1H), 5.81 (br. s., 1H), 5.40 (s, 2H), 5.24 (br. s., 1H), 5.02 (s, 2H), 4.91 (br. s., 1H), 4.78 (br. s., 1H), 4.35-4.41 (m, 1H), 4.21-4.25 (m, 1H), 3.74 (br. s., 2H), 3.53-3.69 (m, 5H), 3.43-3.53 (m, 38H), 3.34-3.39 (m, 3H), 3.29 (br. s., 1H), 3.06-3.18 (m, 4H), 2.84-3.06 (m, 5H), 2.78 (br. s., 1H), 2.45-2.49 (m, 1H), 2.30-2.40 (m, 3H), 2.17 (br. s., 2H), 1.93-2.05 (m, 9H), 1.90 (s, 1H), 1.72 (br. s., 1H), 1.53-1.69 (m, 7H), 1.42-1.53 (m, 1H), 1.33-1.42 (m, 1H), 0.86 (d, J=6.84 Hz, 6H), 0.82 (d, J=6.84 Hz, 6H), 0.67 (br. s., 4H).

Linker-payload compound 89 was prepared as shown in Scheme 32, below, and described below.

Scheme 32

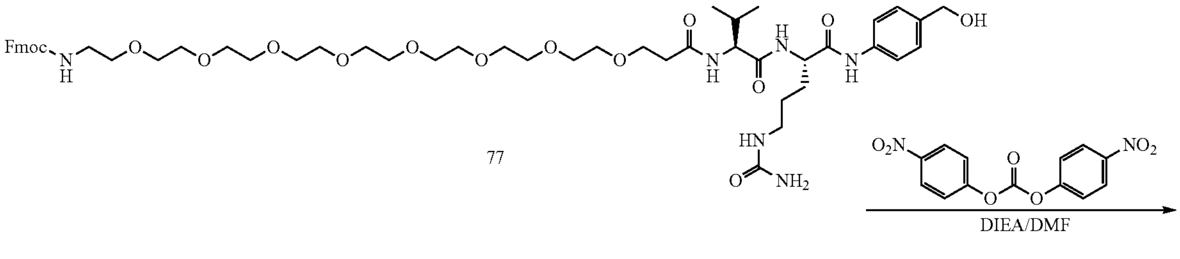

77

-continued

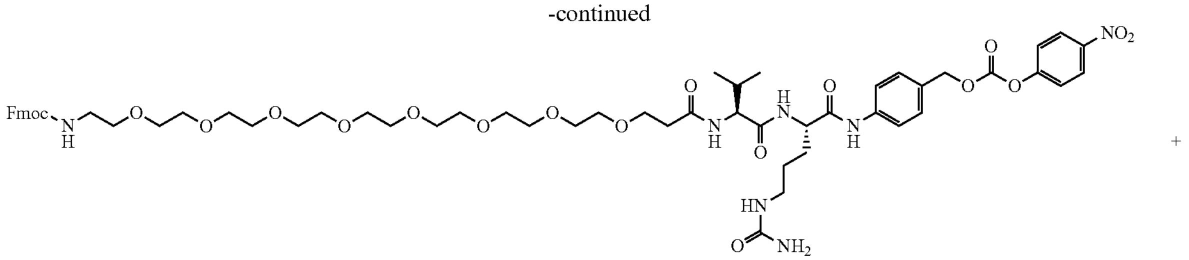

87

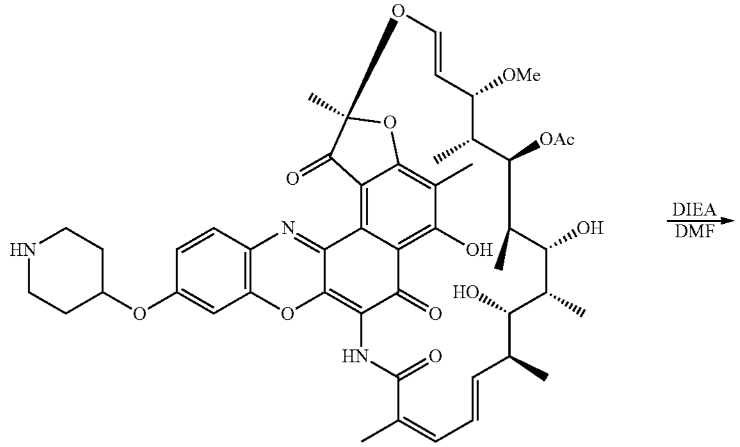

14

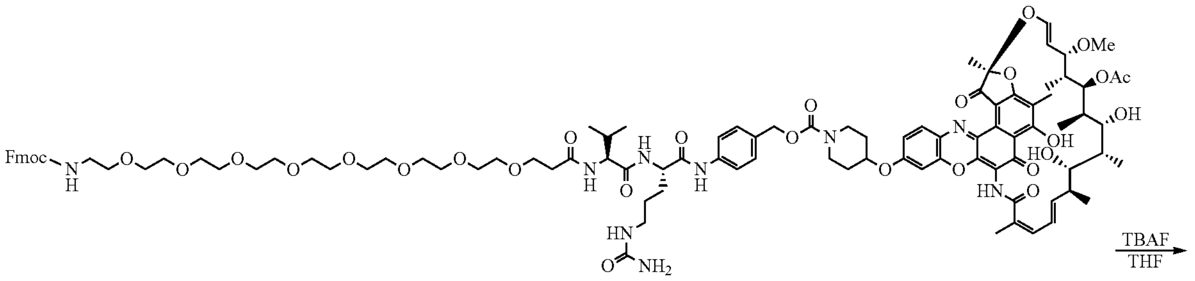

88

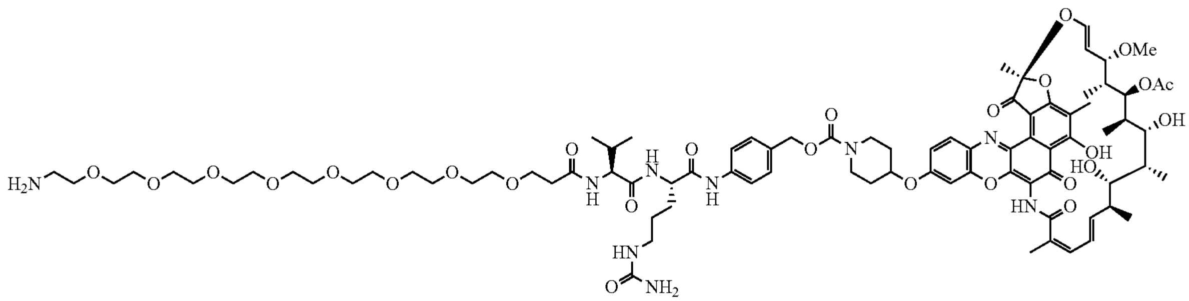

89

Compound 87:

The title compound was prepared using the same procedure described for compound 85. To a stirred solution of compound 77 (56 mg, 0.0546 mmol, 1.0 eq.) and bis(4-nitrophenyl) carbonate (50 mg, 0.1638 mmol, 3.0 eq.) under argon in anhydrous DMF (1.5 mL), was added DIEA (19 μL, 0.1092 mmol, 2.0 eq.) to afford a dark reddish solid. (43 mg, 67%). MS: calc'd for $C_{59}H_{79}N_7O_{19}$, 1189.54; found 1190.5 (M+H), 1212.5 (M+Na).

Compound 88:

The title compound was prepared using linker-payload chemistry described for compound 86. The solution of compound 87 (40.3 mg, 0.0339 mmol, 1.0 eq.) and compound 14 (30 mg, 0.0339 mmol, 1.0 eq.) in anhydrous DMF (3 mL) was stirred at room temperature to afford 50.7 mg (77%) of 88 as a reddish solid. MS: calc'd for $C_{101}H_{131}N_9O_{29}$, 1933.91; found 1935.7 (M+H), 1957.8 (M+Na).

Compound 89:

To a stirred solution of compound 88 (34 mg, 0.0175 mmol, 1.0 eq.) in anhydrous THE (2.5 mL) was added TBAF (1.0 M solution in THF, 35 μL, 0.0351 mmol, 2.0 eq.) and the reaction was stirred at ambient temperature. After 30 min, the reaction was complete by LC/MS. The crude was purified by EZ preparative HPLC column (Gemini, 5 μm, 150 mm×30 mm, eluents: 10-95% MeCN in water, 0.05% AcOH). Pure fractions were collected, frozen in a dry-ice/acetone bath, and lyophilized for 30 h to afford 23.5 mg (79%) of 89 as a reddish solid. MS (ESI, pos.): calc'd for $C_{86}H_{121}N_9O_{27}$, 1711.84; found 1713.7 (M+H), 1711.6 (M−H). $^1$H-NMR (500 MHz; DMSO-$d_6$): 9.99 (s, 1H), 8.11 (d, J=7.33 Hz, 1H), 7.83-7.89 (m, 2H), 7.58-7.62 (m, J=8.79 Hz, 2H), 7.29-7.33 (m, J=8.30 Hz, 2H), 7.18 (br. s., 1H), 5.97 (t, J=5.37 Hz, 1H), 5.40 (s, 2H), 5.02 (s, 2H), 4.89 (br. s., 1H), 4.76-4.83 (m, 1H), 4.35-4.41 (m, 1H), 4.21-4.25 (m, 1H), 3.73 (br. s., 2H), 3.44-3.68 (m, 39H), 3.38 (t, J=5.62 Hz, 3H), 3.29 (br. s., 2H), 2.90-3.14 (m, 7H), 2.75-2.81 (m, 1H), 2.68 (t, J=5.62 Hz, 2H), 2.64 (d, J=1.95 Hz, 1H), 2.45-2.48 (m, 1H), 2.35-2.41 (m, 2H), 2.15 (br. s., 3H), 1.92-2.02 (m, 10H), 1.90 (s, 1H), 1.63-1.72 (m, 5H), 1.59 (d, J=9.28 Hz, 3H), 1.45 (d, J=6.84 Hz, 1H), 1.37 (dd, J=6.35, 16.12 Hz, 1H), 0.73-0.93 (m, 13H), 0.68 (br. s., 3H).

Example 20: Broth Minimum Inhibitory Concentration (MIC) Assay 1

To test the potency of rifamycin analogs of the disclosure in vitro, a broth growth inhibition assay was developed. For the assay, *S. aureus* NRS384 was grown in Tryptic Soy Broth (TSB) overnight, then sub-cultured 1:50 in fresh TSB and grown for an additional two hours. The culture was then pelleted via centrifugation and washed twice in PBS. The culture was then diluted to $1\times10^4$ cfu/mL in TSB and 50 μL of the suspension was added per well to a 96 well microtiter dish in duplicate. A dilution series of the indicated antibiotic (an analog according to the disclosure or a previously known analog Rifampicin) was added 1:1 for a final starting concentration of $1\times10^{-5}$ M with 1:3 dilutions. The plates were incubated at 37° C. with shaking for 24 h and then the OD600 nm was read on a Spectramax i3 Minimax 300.

The reagents used and lot numbers are shown in Table 4, below.

TABLE 4

Reagents and Lot Numbers for MIC Assay

| Reagent | Vendor | Catalogue # | Lot |
|---|---|---|---|
| PBS | Gibco | 20012-043 | 2003838 |
| *S. aureus* NRS384 | BEI resources | NR-46070 | |
| Tryptic Soy Broth (TSB) | Teknova | T1525 | T014420G1801 |
| Dilution plates | Greiner Bio one | 780261 | B17073CP |

The lowest concentrations that inhibited growth of *S. aureus* (minimum inhibitory concentration, MIC) are listed in Table 5. A plot of the *S. aureus* inhibition assay conducted with rifamycin analogs according to the disclosure is shown as FIG. 1.

TABLE 5

Minimum inhibitory concentration (MIC) of antibiotics in a broth growth inhibition assay.

| Rifamycin analog tested | Mol. Wt. (Da) | *S. aureus* Broth MIC (M) |
|---|---|---|
| Rifampicin | 823 | 4.6E−09 |
| 1a | 815 | 1.4E−08 |
| 1b | 890 | 1.2E−07 |
| 1d | 813 | 3.7E−07 |
| 14 | 883 | 4.1E−08 |
| 16a | 823 | 1.5E−09 |
| 16d | 843 | 4.1E−08 |
| 16e | 858 | 4.6E−09 |

As shown in Table 5, all rifamycin analogs according to the disclosure are effective at inhibiting growth of *S. aureus* at sub-micromolar to nanomolar concentrations. Analog 16a inhibited growth of *S. aureus* more potently than rifampicin with an MIC of $1.5\times10^{-9}$M.

Example 21: Intracellular Killing Assay 1

The rifamycin analog compounds' activity against *S. aureus* was tested in an intracellular "killing" assay.

The reagents used and lot numbers are shown in Table 6, below.

TABLE 6

Reagents and Lot Numbers for Intracellular Assay

| Reagent | Vendor | Catalogue # | Lot |
|---|---|---|---|
| TSB | Teknova | T1525 | T152517E1701 |
| PBS | Gibco | 20012-043 | 1951145 |
| Triton X-100 | Sigma | TX1568-1 | |
| RPMI | Gibco | 11875-093 | 1989237 |
| FBS | Gibco | 172667 | 138252-100 |
| PMA | Sigma | P8139 | MkBV849TV |
| Costa 96 well plate | Corning | 3904 | 16618025 |
| TSA plates | Teknova | T0144 | T014420G1801 |
| Pen/Strep | Gibco | 15140-122 | 1953095 |
| Dilution plates | Greiner Bio one | 780261 | B17073CP |
| Gentamicin | Gibco | 10131-035 | 1729122 |

THP-1 monocytic cell line was grown in media (RMPI+10% FBS+1% Penicillin/Streptomycin), then seeded at a density of 1e5 cells/well in a 96 well plate and differentiated into macrophages for three days prior to infection using 200 nM PMA. An overnight culture of *S. aureus* NRS384 was grown in RPMI, washed twice with PBS and resuspended at 1e7 cfu/mL in PBS. THP-1 were washed with warm media (RMPI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing 2× with warm media and remaining extracellular *S. aureus* were killed by addition of media containing gentamicin (50 ug/mL). After 1 h, media was aspirated and the indicated compound was added to infected macrophages in media containing 50 pg/mL gentamicin to prevent extracellular growth of *S. aureus*. After 2 h, plates were washed 2× with warm RPMI without FBS, and 100 ul of THP-1 lysis buffer (0.1% Triton in PBS) was added to each well. *S. aureus* survival was enumerated by colony forming units through serial dilution and plating onto TSA.

Figure 2:
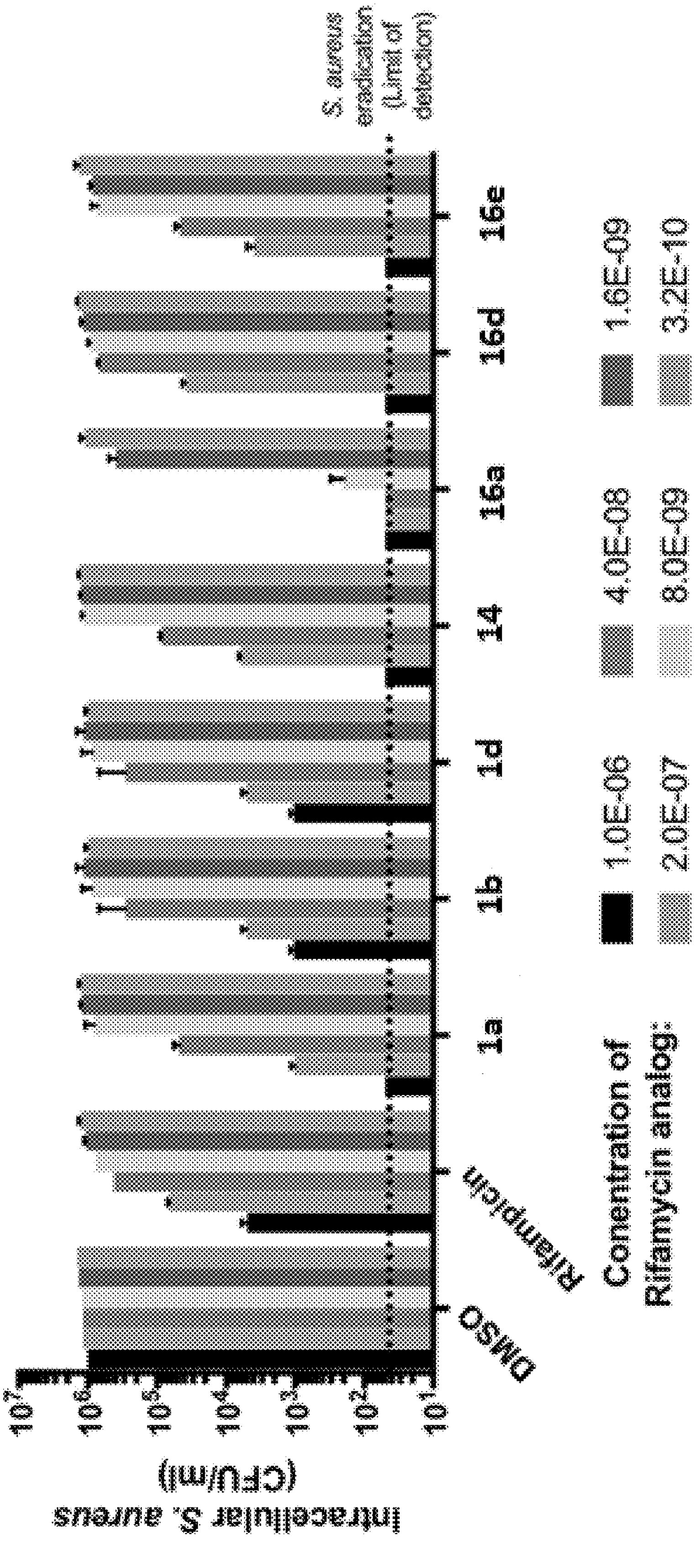
FIG. 2 is a bar graph of the results of the *S. aureus* intracellular killing assay conducted with rifamycin analogs according to the disclosure.
Figure 3:
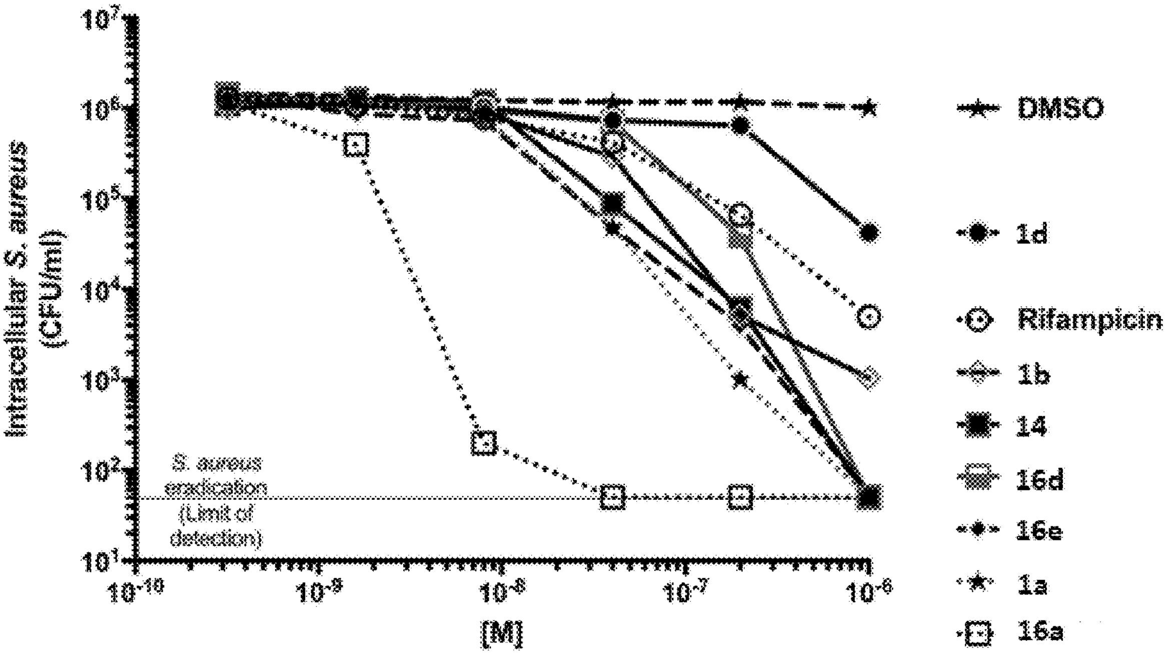
FIG. 3 is a plot of the results of the *S. aureus* intracellular killing assay conducted with rifamycin analogs according to the disclosure.

The results of the intracellular killing assay are shown in Table 7 and FIGS. 2 and 3. The minimum inhibitory concentration (MIC) corresponds to the lowest concentration of each compound that resulted in intracellular *S. aureus* eradication.

TABLE 7

| Results of Intracellular Killing Assay | |
|---|---|
| Rifamycin Analog Tested | Intracellular killing MIC |
| Rifampicin | >1.0E−06 |
| 1a | 1.0E−06 |
| 1b | >1.0E−06 |
| 1d | >1.0E−06 |
| 14 | 1.0E−06 |
| 16a | 4.0E−08 |
| 16d | 1.0E−06 |
| 16e | 1.0E−06 |

As the above table and FIGS. 2 and 3 demonstrate, compounds 1a, 14, 16a, 16d, and 16e had increased intracellular *S. aureus* killing capacity compared to rifampicin, with compound 16a having the highest activity.

Example 22: MSR1 Antibody-Drug Conjugation

The MSR1 antibody (1-10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative compound 25 (1.2 equivalents/SH group) in DMSO (10 mg/ml) was added to the reduced antibody and the mixture adjusted to pH 7.0 with 1 M HEPES (pH 7.4). After 1 h the reaction was quenched with excess N-ethyl maleimide. The conjugates were purified using PBS with 5% glycerol by size exclusion chromatography and sterile filtered. Protein concentrations and payload to antibody ratios were determined by UV spectral analysis. Size-exclusion HPLC established that all conjugates used were >90% monomeric, and RP-HPLC established that there was <1% unconjugated linker payload. All conjugated antibodies were analyzed by HIC for linker payload loading values. Payload to antibody ratios are reported in Table 8.

TABLE 8

| Percent yield and payload to antibody ratios for each of the antibody drug conjugates | | |
|---|---|---|
| Antibody | Yield (%) | DAR (HIC) |
| MSR1 ncADC H1H21234N-N297Q-25 | 50 | 3 |
| Isotype Control Antibody N297Q-25 | 50 | 2 |

Characterization of Conjugates by Hydrophobic Interaction Chromatography (HIC)

To determine the loading of the linker-payloads on the antibody, the conjugates were run on Agilent 1260 using a TSK-NPR Butyl HIC column using a linear gradient of 1M potassium phosphate pH 8.5 to water over 60 min. The payload loading was determined by integration of peak areas corresponding to the species of conjugated and unconjugated antibody.

Example 23: Generation of Anti-MSR1 Antibodies

Anti-MSR1 antibodies were obtained by immunizing a genetically engineered mouse comprising DNA encoding human immunoglobulin heavy and kappa light chain variable regions with an immunogen comprising recombinant human MSR1 extracellular domain fused to an N-terminal nonahistidine tag (SEQ ID NO: 688) (R&D Systems, Catalog #2708-MS-050, Minneapolis, Minn.). The mice used for the immunizations were Velocimmune mice or mice which expressed a "universal light chain" ("ULC" mice). Antibodies produced ULC mouse have different heavy chain variable regions but essentially identical light chain variable domains.

The antibody immune response was monitored by a MSR1-specific immunoassay. When a desired immune response was achieved splenocytes were harvested and fused with mouse myeloma cells to preserve their viability and form hybridoma cell lines. The hybridoma cell lines were screened and selected to identify cell lines that produce MSR1-specific antibodies. Using this technique several anti-MSR1 chimeric antibodies (i.e., antibodies possessing human variable domains and mouse constant domains) were obtained. In addition, several fully human anti-MSR1 antibodies were isolated directly from antigen-positive B cells without fusion to myeloma cells, as described in US 2007/0280945A1.

Certain biological properties of the exemplary anti-MSR1 antibodies generated in accordance with the methods of this Example are described in detail in the Examples set forth below.

Example 24: Heavy and Light Chain Variable Region Amino Acid and Nucleic Acid Sequences Table 9 sets forth the amino acid sequence identifiers of the heavy and light chain variable regions and CDRs of selected anti-MSR1 antibodies described herein. The corresponding nucleic acid sequence identifiers are set forth in Table 10.

TABLE 9

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H21227N | 2 | 4 | 6 | 8 | 10 | 12 | 14 | 16 |
| H1H21228N | 18 | 20 | 22 | 24 | 26 | 28 | 30 | 32 |
| H1H21231N | 34 | 36 | 38 | 40 | 42 | 44 | 46 | 48 |
| H1H21234N | 50 | 52 | 54 | 56 | 58 | 60 | 62 | 64 |
| H1H21235N | 66 | 68 | 70 | 72 | 74 | 76 | 78 | 80 |
| H1H25685N | 82 | 84 | 86 | 88 | 90 | 92 | 94 | 96 |

TABLE 9-continued

| Amino Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H25690N | 98 | 100 | 102 | 104 | 106 | 108 | 110 | 112 |
| H1H25695N | 114 | 116 | 118 | 120 | 122 | 124 | 126 | 128 |
| H1H25700N | 130 | 132 | 134 | 136 | 138 | 140 | 142 | 144 |
| H1H27729P | 146 | 148 | 150 | 152 | 154 | 156 | 158 | 160 |
| H1H27731P | 162 | 164 | 166 | 168 | 170 | 172 | 174 | 176 |
| H1H27732P | 178 | 180 | 182 | 184 | 186 | 188 | 190 | 192 |
| H1H27734P | 194 | 196 | 198 | 200 | 202 | 204 | 206 | 208 |
| H1H27736P | 210 | 212 | 214 | 216 | 218 | 220 | 222 | 224 |
| H1H27739P | 226 | 228 | 230 | 232 | 234 | 236 | 238 | 240 |
| H1H27747P | 242 | 244 | 246 | 248 | 250 | 252 | 254 | 256 |
| H1H27749P | 258 | 260 | 262 | 264 | 266 | 268 | 270 | 272 |
| H1H27751P | 274 | 276 | 278 | 280 | 282 | 284 | 286 | 288 |
| H1H27754P | 290 | 292 | 294 | 296 | 298 | 300 | 302 | 304 |
| H1H27756P | 306 | 308 | 310 | 312 | 314 | 316 | 318 | 320 |
| H1H27760P2 | 322 | 324 | 326 | 328 | 90 | 92 | 94 | 96 |
| H1H27761P2 | 330 | 332 | 334 | 336 | 90 | 92 | 94 | 96 |
| H1H27762P2 | 338 | 340 | 342 | 344 | 90 | 92 | 94 | 96 |
| H1H27766P2 | 346 | 348 | 350 | 352 | 90 | 92 | 94 | 96 |
| H1H27771P2 | 354 | 356 | 358 | 360 | 362 | 364 | 366 | 368 |
| H1xH27759P2 | 370 | 372 | 374 | 376 | 90 | 92 | 94 | 96 |
| H1xH27773P2 | 378 | 380 | 382 | 384 | 362 | 364 | 366 | 368 |
| H1xH27778P2 | 386 | 388 | 390 | 392 | 362 | 364 | 366 | 368 |
| H1xH29273P2 | 394 | 396 | 397 | 400 | 90 | 92 | 94 | 96 |
| H1xH29282P2 | 402 | 404 | 406 | 408 | 90 | 92 | 94 | 96 |
| H1xH29283P2 | 410 | 412 | 414 | 416 | 90 | 92 | 94 | 96 |
| H2M21229N | 420 | 422 | 424 | 426 | 428 | 430 | 432 | 434 |
| H2M21230N | 436 | 438 | 440 | 442 | 444 | 446 | 448 | 450 |
| H2M21232N | 452 | 454 | 456 | 458 | 460 | 462 | 464 | 466 |

TABLE 10

| Nucleic Acid Sequence Identifiers | | | | | | | | |
|---|---|---|---|---|---|---|---|---|
| Antibody | SEQ ID NOs: | | | | | | | |
| Designation | HCVR | HCDR1 | HCDR2 | HCDR3 | LCVR | LCDR1 | LCDR2 | LCDR3 |
| H1H21227N | 1 | 3 | 5 | 7 | 9 | 11 | 13 | 15 |
| H1H21228N | 17 | 19 | 21 | 23 | 25 | 27 | 29 | 31 |
| H1H21231N | 33 | 35 | 37 | 39 | 41 | 43 | 45 | 47 |
| H1H21234N | 49 | 51 | 53 | 55 | 57 | 59 | 61 | 63 |
| H1H21235N | 65 | 67 | 69 | 71 | 73 | 75 | 77 | 79 |
| H1H25685N | 81 | 83 | 85 | 87 | 89 | 91 | 93 | 95 |
| H1H25690N | 97 | 99 | 101 | 103 | 105 | 107 | 109 | 111 |
| H1H25695N | 113 | 115 | 117 | 119 | 121 | 123 | 125 | 127 |
| H1H25700N | 129 | 131 | 133 | 135 | 137 | 139 | 141 | 143 |
| H1H27729P | 145 | 147 | 149 | 151 | 153 | 155 | 157 | 159 |
| H1H27731P | 161 | 163 | 165 | 167 | 169 | 171 | 173 | 175 |
| H1H27732P | 177 | 179 | 181 | 183 | 185 | 187 | 189 | 191 |
| H1H27734P | 193 | 195 | 197 | 199 | 201 | 203 | 205 | 207 |
| H1H27736P | 209 | 211 | 213 | 215 | 217 | 219 | 221 | 223 |
| H1H27739P | 225 | 227 | 229 | 231 | 233 | 235 | 237 | 239 |
| H1H27747P | 241 | 243 | 245 | 247 | 249 | 251 | 253 | 255 |
| H1H27749P | 257 | 259 | 261 | 263 | 265 | 267 | 269 | 271 |
| H1H27751P | 273 | 275 | 277 | 279 | 281 | 283 | 285 | 287 |
| H1H27754P | 289 | 291 | 293 | 295 | 297 | 299 | 301 | 303 |
| H1H27756P | 305 | 307 | 309 | 311 | 313 | 315 | 317 | 319 |
| H1H27760P2 | 321 | 323 | 325 | 327 | 89 | 91 | 93 | 95 |
| H1H27761P2 | 329 | 331 | 333 | 335 | 89 | 91 | 93 | 95 |
| H1H27762P2 | 337 | 339 | 341 | 343 | 89 | 91 | 93 | 95 |
| H1H27766P2 | 345 | 347 | 349 | 351 | 89 | 91 | 93 | 95 |
| H1H27771P2 | 353 | 355 | 357 | 359 | 361 | 363 | 365 | 367 |
| H1xH27759P2 | 369 | 371 | 373 | 375 | 89 | 91 | 93 | 95 |
| H1xH27773P2 | 377 | 379 | 381 | 383 | 361 | 363 | 365 | 367 |
| H1xH27778P2 | 385 | 387 | 389 | 391 | 361 | 363 | 365 | 367 |
| H1xH29273P2 | 393 | 395 | 397 | 399 | 89 | 91 | 93 | 95 |
| H1xH29282P2 | 401 | 403 | 405 | 407 | 89 | 91 | 93 | 95 |
| H1xH29283P2 | 409 | 411 | 413 | 415 | 89 | 91 | 93 | 95 |
| H2M21229N | 419 | 421 | 423 | 425 | 427 | 429 | 431 | 433 |
| H2M21230N | 435 | 437 | 439 | 441 | 443 | 445 | 447 | 449 |
| H2M21232N | 451 | 453 | 455 | 457 | 459 | 461 | 463 | 465 |

Antibodies are typically referred to herein according to the following nomenclature: Fc prefix (e.g. "H1H," "H2aM," etc.), followed by a numerical identifier (e.g. "21227," "21228," "21231," etc.), followed by a "P," "N," or "P2" suffix, as shown in Tables 9 and 10. Thus, according to this nomenclature, an antibody may be referred to herein as, e.g., "H1H21227N," "H2aM21228N," "H1H27729P," "H1H27760P2," etc. The prefix on the antibody designations used herein indicate the particular Fc region isotype of the antibody. In particular, an "H1H" antibody has a human IgG1 Fc (all variable regions are fully human as denoted by the first 'H' in the antibody designation), while an "H2aM" antibody has a mouse IgG2a Fc. As will be appreciated by a person of ordinary skill in the art, an antibody having a particular Fc isotype can be converted to an antibody with a different Fc isotype (e.g., an antibody with a mouse IgG4 Fc can be converted to an antibody with a human IgG1, etc.), but in any event, the variable domains (including the CDRs)—which are indicated by the numerical identifiers shown in Tables 9 and 10—will remain the same, and the binding properties are expected to be identical or substantially similar regardless of the nature of the Fc domain.

Antibody Modifications.

Three anti-MSR1 antibodies described in Example 23 (21227N, 21231N, 21234N) were produced with the original human Fcγ portion, as well as a version with an N297Q single point mutation for all three anti-MSR1 antibodies. All other antibodies described herein were made with an N297Q single point mutation in human Fcγ portion. A third version, an N297D mutation was produced for the 21227N antibody only.

Example 25: Surface Plasmon Resonance Derived Binding Affinities and Kinetic Constants of Human Monoclonal Anti-MSR1 Antibodies Binding affinities and kinetic constants of human anti-MSR1 antibodies for different MSR1 reagents were determined by real-time surface plasmon resonance (Biacore 4000). All binding studies were performed in 10 mM HEPES, 150 mM NaCl, 3 mM EDTA, and 0.05% v/v Surfactant Tween-20, pH 7.4 (HBS-ET) running buffer at 25° C. and 37° C. The Biacore CM4 sensor chip surface was first derivatized by amine coupling with the goat anti-human Fcγ specific polyclonal antibody (Jackson ImmunoResearch Laboratories, Cat #BR-1008-39) to capture anti-MSR1 monoclonal antibodies. Binding studies were performed on human MSR1 extracellular domain expressed with a N-terminal nonahistidine tag (SEQ ID NO: 688) (His9-hMSR1; R&D Systems, Cat #2708-MS), and monkey MSR1 extracellular domain expressed with a N-terminal hexahistidine-myc-myc tag ("hexahistidine" disclosed as SEQ ID NO: 689) (HMM-mfMSR1; SEQ ID NO: 418). Different concentrations of His9-hMSR1 and HMM-mfMSR1 (100 nM-3.7 nM; 3-fold serial dilution) were first prepared in HBS-ET running buffer and were injected over anti-human Fcγ captured anti-MSR1 monoclonal antibody surface for 3 minutes at a flow rate of 30 μL/minute, while the dissociation of monoclonal antibody bound MSR1 reagent was monitored for 10 minutes in HBS-ET running buffer.

The association rate ($k_a$) and dissociation rate ($k_d$) were determined by fitting the real-time binding sensorgrams to a 1:1 binding model with mass transport limitation using Scrubber 2.0 c curve-fitting software. Binding dissociation equilibrium constant ($K_D$) and dissociative half-life (t½) were calculated from the kinetic rates as:

$$K_D(M) = \frac{kd}{ka}, \text{ and } t\frac{1}{2}\text{ (min)} = \frac{\ln(2)}{60 * kd}$$

Binding kinetics parameters for His9-hMSR1 or HMM-mfMSR1 binding to different anti-MSR1 monoclonal antibodies at 25° C. and 37° C. are shown in Tables 11 and 12, respectively.

TABLE 11

Biacore Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H21227N- | His9-hMSR1 | 1.23E+06 | 4.89E−05 | 3.97E−11 | 236 |
| N297Q | HMM-mfMSR1 | 1.36E+06 | 7.51E−05 | 5.53E−11 | 154 |
| H1H21227N- | His9-hMSR1 | 1.14E+06 | 3.79E−05 | 3.33E−11 | 305 |
| N297D | HMM-mfMSR1 | 1.35E+06 | 4.03E−05 | 2.99E−11 | 287 |
| H1H21231N- | His9-hMSR1 | 3.99E+05 | 5.88E−05 | 1.47E−10 | 196 |
| N297Q | HMM-mfMSR1 | 2.40E+05 | 9.03E−05 | 3.76E−10 | 128 |
| H1H21234N- | His9-hMSR1 | 4.97E+05 | 1.00E−05* | 2.01E−11 | 1155 |
| N297Q | HMM-mfMSR1 | 4.08E+05 | 1.95E−05 | 4.66E−11 | 593 |
| H1H27729P- | His9-hMSR1 | 1.97E+05 | 1.07E−03 | 5.45E−09 | 11 |
| N297Q | HMM-mfMSR1 | 2.69E+05 | 2.12E−03 | 7.90E−09 | 5 |
| H1H27731P- | His9-hMSR1 | 1.29E+05 | 2.24E−05 | 1.74E−10 | 515 |
| N297Q | HMM-mfMSR1 | 9.82E+04 | 4.69E−05 | 4.77E−10 | 247 |
| H1H27732P- | His9-hMSR1 | 1.25E+05 | 1.00E−05* | 8.01E−11 | 1155 |
| N297Q | HMM-mfMSR1 | 1.28E+05 | 3.17E−05 | 2.48E−10 | 364 |
| H1H27734P- | His9-hMSR1 | 4.20E+05 | 1.11E−03 | 2.64E−09 | 10 |
| N297Q | HMM-mfMSR1 | 4.23E+05 | 2.91E−03 | 6.88E−09 | 4 |
| H1H27736P- | His9-hMSR1 | 5.15E+05 | 2.31E−04 | 4.48E−10 | 50 |
| N297Q | HMM-mfMSR1 | 4.64E+05 | 5.87E−04 | 1.27E−09 | 20 |
| H1H27739P- | His9-hMSR1 | 3.75E+05 | 1.03E−03 | 2.74E−09 | 11 |
| N297Q | HMM-mfMSR1 | 3.52E+05 | 1.44E−04 | 4.10E−10 | 80 |
| H1H27747P- | His9-hMSR1 | 2.43E+05 | 6.52E−04 | 2.69E−09 | 18 |
| N297Q | HMM-mfMSR1 | 2.31E+05 | 8.74E−04 | 3.78E−09 | 13 |
| H1H27749P- | His9-hMSR1 | 3.18E+05 | 1.76E−05 | 5.54E−11 | 656 |
| N297Q | HMM-mfMSR1 | 2.49E+05 | 4.27E−05 | 1.71E−10 | 271 |
| H1H27751P- | His9-hMSR1 | 1.78E+06 | 3.05E−04 | 1.72E−10 | 38 |
| N297Q | HMM-mfMSR1 | 7.44E+05 | 7.49E−04 | 1.01E−09 | 15 |
| H1H27754P- | His9-hMSR1 | 2.90E+05 | 1.00E−05* | 3.44E−11 | 1155 |
| N297Q | HMM-mfMSR1 | 2.35E+05 | 1.76E−05 | 7.50E−11 | 657 |

TABLE 11-continued

Biacore Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H27756P- | His9-hMSR1 | 3.00E+05 | 1.22E−04 | 4.06E−10 | 94 |
| N297Q | HMM-mfMSR1 | 3.58E+05 | 2.44E−03 | 6.81E−09 | 5 |
| H1H27760P- | His9-hMSR1 | 4.54E+05 | 9.09E−04 | 2.00E−09 | 13 |
| N297Q | HMM-mfMSR1 | 3.63E+05 | 7.01E−04 | 1.93E−09 | 16 |
| H1H27759P- | His9-hMSR1 | 5.99E+05 | 1.22E−03 | 2.03E−09 | 9 |
| N297Q | HMM-mfMSR1 | 4.17E+05 | 9.19E−04 | 2.20E−09 | 13 |
| H1H27761P- | His9-hMSR1 | 3.12E+05 | 5.10E−04 | 1.63E−09 | 23 |
| N297Q | HMM-mfMSR1 | 3.18E+05 | 5.97E−04 | 1.88E−09 | 19 |
| H1H27762P- | His9-hMSR1 | 9.89E+05 | 1.83E−03 | 1.85E−09 | 6 |
| N297Q | HMM-mfMSR1 | 1.25E+06 | 1.99E−03 | 1.59E−09 | 6 |
| H1H27766P- | His9-hMSR1 | 2.34E+05 | 1.86E−05 | 7.96E−11 | 620 |
| N297Q | HMM-mfMSR1 | 1.57E+05 | 7.94E−05 | 5.06E−10 | 145 |
| H1H27771P- | His9-hMSR1 | 6.86E+05 | 9.58E−04 | 1.40E−09 | 12 |
| N297Q | HMM-mfMSR1 | 5.19E+05 | 5.26E−03 | 1.01E−08 | 2.2 |
| H1H27773P- | His9-hMSR1 | 6.58E+05 | 2.63E−03 | 3.99E−09 | 4 |
| N297Q | HMM-mfMSR1 | 6.43E+05 | 1.96E−03 | 3.05E−09 | 6 |
| H1H27778P- | His9-hMSR1 | 5.75E+05 | 3.94E−04 | 6.85E−10 | 29 |
| N297Q | HMM-mfMSR1 | 4.67E+05 | 1.36E−03 | 2.91E−09 | 8 |
| H1H21234N | His9-hMSR1 | 6.04E+05 | 1.00E−05* | 1.66E−11 | 1155 |
| | HMM-mfMSR1 | 3.36E+05 | 1.00E−05* | 2.98E−11 | 1155 |
| H1H21231N | His9-hMSR1 | 4.77E+05 | 1.00E−05* | 2.10E−11 | 1155 |
| | HMM-mfMSR1 | 2.74E+05 | 6.39E−05 | 2.33E−10 | 181 |
| H1H21227N | His9-hMSR1 | 1.20E+06 | 1.44E−05 | 1.20E−11 | 800 |
| | HMM-mfMSR1 | 1.27E+06 | 4.41E−05 | 3.48E−11 | 262 |
| Non-binding | His9-hMSR1 | NB$ | NB$ | NB$ | NB$ |
| Control | HMM-mfMSR1 | NB$ | NB$ | NB$ | NB$ |

*indicates that no dissociation of His9-hMSR1 or HMM-mfMSR1 was observed under the current experimental conditions and the $k_d$ value was manually fixed at 1.00E−05 while fitting the data
$indicates that no binding was observed under the current experimental conditions.

TABLE 12

Biacore Binding Affinities of Anti-MSR1 mAbs at 37° C.
Binding at 37° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H21227N- | His9-hMSR1 | 2.67E+06 | 1.23E−05 | 4.60E−12 | 941 |
| N297Q | HMM-mfMSR1 | 2.74E+06 | 1.08E−05 | 3.95E−12 | 1069 |
| H1H21227N- | His9-hMSR1 | 2.73E+06 | 1.00E−05* | 3.66E−12 | 1155 |
| N297D | HMM-mfMSR1 | 2.68E+06 | 2.42E−05 | 9.03E−12 | 477 |
| H1H21231N- | His9-hMSR1 | 5.34E+05 | 1.15E−04 | 2.15E−10 | 101 |
| N297Q | HMM-mfMSR1 | 5.87E+05 | 1.09E−04 | 1.86E−10 | 106 |
| H1H21234N- | His9-hMSR1 | 7.87E+05 | 1.00E−05* | 1.27E−11 | 1155 |
| N297Q | HMM-mfMSR1 | 7.50E+05 | 1.00E−05* | 1.33E−11 | 1155 |
| H1H27729P- | His9-hMSR1 | 2.39E+05 | 2.04E−03 | 8.53E−09 | 6 |
| N297Q | HMM-mfMSR1 | 4.07E+05 | 3.49E−03 | 8.58E−09 | 3.3 |
| H1H27731P- | His9-hMSR1 | 2.86E+05 | 1.32E−04 | 4.62E−10 | 88 |
| N297Q | HMM-mfMSR1 | 2.78E+05 | 1.87E−04 | 6.74E−10 | 62 |
| H1H27732P- | His9-hMSR1 | 2.81E+05 | 3.12E−05 | 1.11E−10 | 370 |
| N297Q | HMM-mfMSR1 | 3.34E+05 | 1.06E−04 | 3.17E−10 | 109 |
| H1H27734P- | His9-hMSR1 | 1.09E+06 | 1.90E−03 | 1.74E−09 | 6 |
| N297Q | HMM-mfMSR1 | 9.49E+05 | 3.20E−03 | 3.37E−09 | 4 |
| H1H27736P- | His9-hMSR1 | 1.02E+06 | 7.33E−04 | 7.17E−10 | 16 |
| N297Q | HMM-mfMSR1 | 2.01E+06 | 1.28E−03 | 6.37E−10 | 9 |
| H1H27739P- | His9-hMSR1 | 7.76E+05 | 2.88E−03 | 3.72E−09 | 4 |
| N297Q | HMM-mfMSR1 | 2.25E+06 | 8.42E−04 | 3.74E−10 | 14 |
| H1H27747P- | His9-hMSR1 | 5.13E+05 | 2.76E−03 | 5.37E−09 | 4 |
| N297Q | HMM-mfMSR1 | 6.57E+05 | 2.28E−03 | 3.47E−09 | 5 |
| H1H27749P- | His9-hMSR1 | 4.97E+05 | 2.42E−04 | 4.86E−10 | 48 |
| N297Q | HMM-mfMSR1 | 4.77E+05 | 1.72E−04 | 3.61E−10 | 67 |
| H1H27751P- | His9-hMSR1 | 1.45E+06 | 9.43E−04 | 6.50E−10 | 12 |
| N297Q | HMM-mfMSR1 | 1.17E+06 | 1.80E−03 | 1.55E−09 | 6 |
| H1H27754P- | His9-hMSR1 | 6.63E+05 | 2.53E−05 | 3.81E−11 | 457 |
| N297Q | HMM-mfMSR1 | 7.01E+05 | 3.53E−05 | 5.04E−11 | 327 |
| H1H27756P- | His9-hMSR1 | 6.63E+05 | 7.71E−04 | 1.16E−09 | 15 |
| N297Q | HMM-mfMSR1 | 8.02E+05 | 3.19E−03 | 3.97E−09 | 4 |
| H1H27760P- | His9-hMSR1 | 1.08E+06 | 1.89E−03 | 1.74E−09 | 6 |
| N297Q | HMM-mfMSR1 | 1.52E+06 | 1.59E−03 | 1.05E−09 | 7 |
| H1H27759P- | His9-hMSR1 | 1.03E+06 | 2.30E−03 | 2.24E−09 | 5 |
| N297Q | HMM-mfMSR1 | 1.46E+06 | 1.88E−03 | 1.28E−09 | 6 |
| H1H27761P- | His9-hMSR1 | 6.81E+05 | 2.22E−03 | 3.26E−09 | 5 |
| N297Q | HMM-mfMSR1 | 9.20E+05 | 2.14E−03 | 2.32E−09 | 5 |

TABLE 12-continued

Biacore Binding Affinities of Anti-MSR1 mAbs at 37° C.
Binding at 37° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H1H27762P- | His9-hMSR1 | 3.06E+06 | 1.96E−03 | 6.40E−10 | 6 |
| N297Q | HMM-mfMSR1 | 2.82E+06 | 1.97E−03 | 6.98E−10 | 6 |
| H1H27766P- | His9-hMSR1 | 3.40E+05 | 7.72E−05 | 2.27E−10 | 150 |
| N297Q | HMM-mfMSR1 | 3.43E+05 | 5.89E−04 | 1.72E−09 | 20 |
| H1H27771P- | His9-hMSR1 | 1.35E+06 | 2.04E−03 | 1.51E−09 | 6 |
| N297Q | HMM-mfMSR1 | 4.94E+05 | 9.07E−03 | 1.84E−08 | 1.3 |
| H1H27773P- | His9-hMSR1 | 9.19E+05 | 3.07E−03 | 3.34E−09 | 4 |
| N297Q | HMM-mfMSR1 | 9.60E+05 | 5.06E−03 | 5.27E−09 | 2.3 |
| H1H27778P- | His9-hMSR1 | 1.19E+06 | 6.55E−04 | 5.49E−10 | 18 |
| N297Q | HMM-mfMSR1 | 1.19E+06 | 1.25E−03 | 1.05E−09 | 9 |
| H1H21234N | His9-hMSR1 | 6.76E+05 | 1.00E−05* | 1.48E−11 | 1155 |
| | HMM-mfMSR1 | 7.26E+05 | 1.00E−05* | 1.38E−11 | 1155 |
| H1H21231N | His9-hMSR1 | 7.02E+05 | 9.09E−05 | 1.30E−10 | 127 |
| | HMM-mfMSR1 | 7.12E+05 | 7.82E−05 | 1.10E−10 | 148 |
| H1H21227N | His9-hMSR1 | 2.56E+06 | 1.85E−05 | 7.24E−12 | 624 |
| | HMM-mfMSR1 | 2.76E+06 | 1.00E−05* | 3.62E−12 | 1155 |
| Non-binding | His9-hMSR1 | NB$ | NB$ | NB$ | NB$ |
| Control | HMM-mfMSR1 | NB$ | NB$ | NB$ | NB$ |

*indicates that no dissociation of His9-hMSR1 or HMM-mfMSR1 was observed under the current experimental conditions and the $k_d$ value was manually fixed at 1.00E−05 while fitting the data
$indicates that no binding was observed under the current experimental conditions.

At 25° C., all of the anti-MSR1 monoclonal antibodies according to the disclosure bound to His9-hMSR1 with $K_D$ values ranging from 12 pM to 5.45 nM, as shown in Table 11. At 37° C., all of the anti-MSR1 monoclonal antibodies of the disclosure bound to His9-hMSR1 with $K_D$ values ranging from 3.66 pM to 8.53 nM, as shown in Table 12.

At 25° C., all of the anti-MSR1 monoclonal antibodies according to the disclosure bound to HMM-mfMSR1 with $K_D$ values ranging from 29.9 pM to 10.1 nM, as shown in Table 11. At 37° C., all of the anti-MSR1 monoclonal antibodies of the disclosure bound to HMM-mfMSR1 with $K_D$ values ranging from 3.62 pM to 18.4 nM, as shown in Table 12.

Example 26: Octet-Derived Binding Affinities and Kinetic Constants of Human Monoclonal Anti-MSR1 Antibodies Binding affinities and kinetic constants of human anti-MSR1 antibodies for different MSR1 reagents were determined using a real time, label-free bio-layer interferometry assay on an OCTET® HTX biosensor platform (Pall FortéBio Corp., Menlo Park, Calif.). The experiment was performed at 25° C. in 10 mM HEPES, 150 mM NaCl, 3 mM EDTA, 0.05% v/v Surfactant Tween-20, and 1 mg/mL BSA, pH7.4 (HBS-EBT) buffer with the plate shaking at the speed of 1000 rpm. Binding studies were performed on human MSR1 extracellular domain expressed with a N-terminal nonahistidine tag (SEQ ID NO: 688) (His9-hMSR1; R&D Systems, Cat #2708-MS), monkey MSR1 extracellular domain expressed with a N-terminal myc-myc-hexahistidine tag (HMM-mfMSR1; SEQ ID NO: 418), and mouse MSR1 extracellular domain expressed with a N-terminal nonahistidine tag (SEQ ID NO: 688) ("hexahistidine" disclosed as SEQ ID NO: 689) (His9-mMSR1; R&D Systems, Cat #1797-MS). The anti-MSR1 monoclonal antibodies were captured by dipping either anti-human Fc (AHC) or anti-mouse Fc (AMC) Octet biosensors in wells containing 5 g/mL or 10 g/mL of anti-MSR1 monoclonal antibody for 45-90 seconds. The AHC captured anti-MSR1 monoclonal antibodies were then dipped in wells containing 50 nM of His9-mMSR1, while the AMC captured anti-MSR1 monoclonal antibodies were dipped in wells containing different concentrations of His9-hMSR1 or HMM-mfMSR1 (100 nM, 25 nM) or 100 nM His9-mMSR1. The binding of different MSR1 reagents to the captured anti-MSR1 monoclonal antibody was measured for 4 minutes and the dissociation of monoclonal antibody bound MSR1 reagent was monitored for 8-10 minutes in HBS-EBT buffer.

The association rate ($k_a$) and dissociation rate ($k_d$) were determined by fitting the real-time binding sensorgrams to a 1:1 binding model with mass transport limitation using Scrubber 2.0 c curve-fitting software. Binding dissociation equilibrium constant ($K_D$) and dissociative half-life (t½) were calculated from the kinetic rates as:

$$K_D(M) = \frac{kd}{ka}, \text{ and } t\frac{1}{2} \text{ (min)} = \frac{\ln(2)}{60 * kd}$$

Binding kinetics parameters for His9-hMSR1, HMM-mfMSR1 or His9-mMSR1 binding to different anti-MSR1 monoclonal antibodies of the disclosure at 25° C. are shown in Tables 13 and 14.

TABLE 13

OCTET ® Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H2aM21228N | His9-hMSR1 | 1.22E+05 | 1.16E−04 | 9.54E−10 | 100 |
| | HMM-mfMSR1 | 1.00E+05 | 1.46E−04 | 1.45E−09 | 79 |

TABLE 13-continued

OCTET ® Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H2aM21229N | His9-hMSR1 | 3.00E+05 | 2.10E−04 | 7.00E−10 | 55 |
| | HMM-mfMSR1 | 1.35E+05 | 2.22E−03 | 1.64E−08 | 5 |
| H2aM21230N | His9-hMSR1 | 6.47E+05 | 2.87E−04 | 4.43E−10 | 40 |
| | HMM-mfMSR1 | 2.37E+05 | 3.76E−04 | 1.59E−09 | 31 |
| H2aM21232N | His9-hMSR1 | 1.30E+05 | 2.86E−04 | 2.20E−09 | 40 |
| | HMM-mfMSR1 | 9.75E+04 | 3.27E−04 | 3.35E−09 | 35 |
| H2aM21235N | His9-hMSR1 | 1.21E+05 | 4.58E−05 | 3.78E−10 | 252 |
| | HMM-mfMSR1 | 1.02E+05 | 6.27E−05 | 6.12E−10 | 184 |
| H2aM25700N | His9-hMSR1 | 5.58E+05 | 1.14E−04 | 2.05E−10 | 101 |
| | HMM-mfMSR1 | 5.53E+05 | 1.15E−04 | 2.08E−10 | 100 |
| H2aM25690N | His9-hMSR1 | 2.29E+05 | 3.11E−04 | 1.36E−09 | 37 |
| | HMM-mfMSR1 | 1.64E+05 | 5.47E−04 | 3.35E−09 | 21 |
| H2aM25695N | His9-hMSR1 | 3.60E+05 | 5.27E−04 | 1.46E−09 | 22 |
| | HMM-mfMSR1 | 3.12E+05 | 5.71E−04 | 1.83E−09 | 20 |
| H2aM25685N | His9-hMSR1 | 2.01E+05 | 3.97E−04 | 1.98E−09 | 29 |
| | HMM-mfMSR1 | 6.49E+04 | 1.28E−03 | 1.97E−08 | 9 |
| mIgG Isotype | His9-hMSR1 | NB$ | NB$ | NB$ | NB$ |
| Control | HMM-mfMSR1 | NB$ | NB$ | NB$ | NB$ |

$indicates that no binding was observed under the current experimental conditions.

TABLE 14

OCTET ® Binding Affinities of Anti-MSR1 mAbs at 25° C.
Binding at 25° C./Antibody-Capture Format

| Antibody | Analyte | ka ($M^{-1}s^{-1}$) | kd ($s^{-1}$) | $K_D$ (Molar) | t½ (min) |
|---|---|---|---|---|---|
| H2aM21228N | His9-mMSR1 | NB$ | NB$ | NB$ | NB$ |
| H2aM21229N | His9-mMSR1 | NB$ | NB$ | NB$ | NB$ |
| H2aM21230N | His9-mMSR1 | NB$ | NB$ | NB$ | NB$ |
| H2aM21232N | His9-mMSR1 | NB$ | NB$ | NB$ | NB$ |
| H2aM21235N | His9-mMSR1 | NB$ | NB$ | NB$ | NB$ |
| H2aM25700N | His9-mMSR1 | 3.60E+04 | 1.85E−04 | 5.20E−09 | 63 |
| H2aM25690N | His9-mMSR1 | NB$ | NB$ | NB$ | NB$ |
| H2aM25695N | His9-mMSR1 | NB$ | NB$ | NB$ | NB$ |
| H2aM25685N | His9-mMSR1 | NB$ | NB$ | NB$ | NB$ |
| mIgG Isotype Control | His9-mMSR1 | NB$ | NB$ | NB$ | NB$ |
| H1H21227N-N297Q | His9-mMSR1 | 3.74E+05 | 7.08E−04 | 1.89E−09 | 16 |
| H1H21227N-N297D | His9-mMSR1 | 4.6IE+05 | 7.86E−04 | 1.71E−09 | 15 |
| H1H21231N-N297Q | His9-mMSR1 | IC# | IC# | IC# | IC# |
| H1H21234N-N297Q | His9-mMSR1 | 3.82E+04 | 5.00E−05* | 1.31E−09 | 231 |
| H1H27729P-N297Q | His9-mMSR1 | NB$ | NB$ | NB$ | NB$ |
| H1H27731P-N297Q | His9-mMSR1 | NB$ | NB$ | NB$ | NB$ |
| H1H27732P-N297Q | His9-mMSR1 | NB$ | NB$ | NB$ | NB$ |
| H1H27734P-N297Q | His9-mMSR1 | NB$ | NB$ | NB$ | NB$ |
| H1H27736P-N297Q | His9-mMSR1 | IC# | IC# | IC# | IC# |
| H1H27739P-N297Q | His9-mMSR1 | NB$ | NB$ | NB$ | NB$ |
| H1H27747P-N297Q | His9-mMSR1 | NB$ | NB$ | NB$ | NB$ |
| H1H27749P-N297Q | His9-mMSR1 | IC# | IC# | IC# | IC# |
| H1H27751P-N297Q | His9-mMSR1 | NB$ | NB$ | NB$ | NB$ |
| H1H27754P-N297Q | His9-mMSR1 | NB$ | NB$ | NB$ | NB$ |
| H1H27756P-N297Q | His9-mMSR1 | NB$ | NB$ | NB$ | NB$ |
| H1H27760P-N297Q | His9-mMSR1 | NB$ | NB$ | NB$ | NB$ |
| H1H27759P-N297Q | His9-mMSR1 | NB$ | NB$ | NB$ | NB$ |
| H1H27761P-N297Q | His9-mMSR1 | IC# | IC# | IC# | IC# |
| H1H27762P-N297Q | His9-mMSR1 | NB$ | NB$ | NB$ | NB$ |
| H1H27766P-N297Q | His9-mMSR1 | NB$ | NB$ | NB$ | NB$ |
| H1H27771P-N297Q | His9-mMSR1 | IC# | IC# | IC# | IC# |
| H1H27773P-N297Q | His9-mMSR1 | NB$ | NB$ | NB$ | NB$ |
| H1H27778P-N297Q | His9-mMSR1 | NB$ | NB$ | NB$ | NB$ |
| H1H21234N | His9-mMSR1 | 4.60E+04 | 5.00E−05* | 1.09E−09 | 231 |
| H1H21231N | His9-mMSR1 | IC# | IC# | IC# | IC# |
| H1H21227N | His9-mMSR1 | 4.15E+05 | 8.16E−04 | 1.97E−09 | 14 |
| Non-binding Control | His9-mMSR1 | NB$ | NB$ | NB$ | NB$ |

*indicates that no dissociation of His9-mMSR1 was observed under the current experimental conditions and the $k_d$ value was manually fixed at 5.00E−05 while fitting the data $indicates that no binding was observed under the current experimental conditions.

#indicates that the binding data is inconclusive (IC)

The anti-MSR1 monoclonal antibodies bound to His9-hMSR1 with $K_D$ values ranging from 205 pM to 2.2 nM, as shown in Table 13. The anti-MSR1 monoclonal antibodies bound to HMM-mfMSR1 with $K_D$ values ranging from 208 pM to 19.7 nM, as shown in Table 13.

As shown in Table 14, 23 out of 35 anti-MSR1 monoclonal antibodies did not bind to His9-mMSR1, while the binding data for 6 anti-MSR1 monoclonal antibodies was inconclusive. Six (6) out of 35 anti-MSR1 monoclonal antibodies bound to His9-mMSR1 with $K_D$ values ranging from 1.09 nM to 5.2 nM, as shown in Table 14.

Example 27: Anti-MSR1 Antibodies Display Specific Binding to Cell Surface-Expressed Human and Monkey MSR1

The ability of anti-MSR1 monoclonal antibodies to bind to human or monkey MSR1 expressing cells was determined using electrochemiluminescence (ECL) based detection.

Generation of MSR1-Expressing Cell Lines.

Two cell lines overexpressing either human or monkey MSR1 were generated. To generate the human MSR1 overexpressing cell line, human embryonic kidney (HEK) 293 cells were engineered by transduction with hygromycin resistant lentiviral vector encoding full length human MSR1 (hMSR1, amino acids M1-L451 of accession number NP_619729.1) with a C-terminal Myc tag. The resulting cell line is referred to as HEK293.Myc.hMSR1. Similarly, to generate the monkey MSR1 overexpressing cell line, HEK293 cells were engineered by transfection with the geneticin resistant expression plasmid encoding full length monkey MSR1 (*Macaca fascicularis*, mfMSR1, amino acids M1-L451 of accession number XP_005562705.1). The resulting cell line is referred to as HEK293.mfMSR1 cells. To measure the ability of antibodies to bind to endogenously expressed human MSR1, THP-1 human monocytic cells were treated with 200 nM of phorbol 12-myristate 13-acetate (PMA; Sigma, Cat #P8139) for 72 hours to induce high MSR1 expression prior to antibody binding. Non-transfected HEK293 cells were included as non-specific binding controls as they have no detectable expression of MSR1 by next-generation sequencing of gene expression (data not shown).

Antibody Binding Assay.

To perform the antibody binding assay, cells from each of the cell lines described above were rinsed once in PBS buffer without $Ca^{2+}/Mg^{2+}$ and incubated for 5 minutes at 37° C. with Enzyme Free Cell Dissociation Solution (Millipore, Cat. #S-004-C, Burlington, Mass.) to detach cells from a flask. All cells were washed once with 1×PBS with $Ca^{2+}/Mg^{2+}$ and counted with a Cellometer™ Auto T4 cell counter (Nexcelom Bioscience). Approximately $1.0\times10^4$ cells were seeded separately onto 96-well carbon electrode plates [MULTI-ARRAY high bind plate, Meso Scale Diagnostics] and incubated for 1 hour at 37° C. Non-specific binding sites were then blocked by 2% BSA (w/v) in PBS with $Ca^{2+}/Mg^{2+}$ for 1 hour at room temperature. THP-1 cells were pre-incubated for 0.5 hours at room temperature in sample dilution buffer with: 1) 1 mg/mL Fc receptor block reagents to block Fc gamma receptors on THP-1 cell surface [whole molecule human IgG (Jackson Immunoresearch, Cat #009-000-003) for wells being tested with anti-MSR1-mFc antibodies or 2) whole molecule mIgG (Jackson Immunoresearch, Cat #015-000-003) for wells being tested with anti-MSR1-hFc antibodies. Antibody binding on HEK293.Myc.hMSR1, HEK293.mfMSR1 and HEK293 cells was tested without Fc receptor block reagents. To the plate-bound HEK293.Myc.hMSR1, HEK293.mfMSR1 and HEK293 cells or THP-1+Fc block, solutions of anti-MSR1 or control antibodies in serial dilutions ranging from 1.7 pM to 100 nM, and solutions without the presence of antibodies were added in duplicate, and the plates were incubated for 1 hour at room temperature. Plates were then washed to remove unbound antibodies an AquaMax2000 plate washer with a cell washing head (MDS Analytical Technologies). The plate-bound antibodies were detected with either a SULFO-TAG™-conjugated goat polyclonal anti-human IgG antibody specific for Fcγ fragment (Jackson Immunoresearch, Cat #109-005-098) or a SULFO-TAG™-conjugated goat polyclonal anti-mouse IgG antibody specific for Fcγ fragment (Jackson Immunoresearch, Cat #115-005-164) for 1 hour at room temperature. Plates were washed and developed with Read Buffer (Meso Scale Diagnostics, Cat #R92TD-2) according to manufacturer's recommended procedure and luminescent signals were recorded with a SECTOR Imager 600 (Meso Scale Diagnostics). Luminescence intensity, measured in relative light units (RLU), was recorded to indicate the binding intensity of each antibody at the range of concentrations. The ratio of signal detected for cell-surface binding of each anti-MSR antibody compared to isotype control antibody (both at 11 nM) was reported as an indication of specificity of MSR1 binding. Antibodies with the binding ratio on MSR-1 expressing cells of greater than or equal to 2-fold compared to the ratio on parental HEK293 cells were classified as specific binders. Antibodies with a binding ratio of less than 2-fold compared to the ratio on parental HEK293 cells were classified as non-binders as shown in. (See Table 15).

TABLE 15

Binding of Anti-MSR1 Antibodies to MSR1-Expressing Cells

| Antibody | Ratio of 11 nM Antibody Binding Signal (RLU) on MSR1-expressing cells and parental HEK293 to isotype control: HEK293.Myc.hMSR1 | PMA-treated THP-1 | HEK293.mfMSR1 | HEK293 |
|---|---|---|---|---|
| Specific Human and monkey MSR1 binders | | | | |
| H1H21227N-N297Q | 37 | 5 | 23 | 1 |
| H1H21227N-N297D | 34 | 6 | 25 | 1 |
| H1H21227N | 37 | 7 | 26 | 1 |
| H1H21231N-N297Q | 64 | 45 | 69 | 4 |
| H1H21231N | 61 | 42 | 75 | <1 |
| H1H21234N-N297Q | 43 | 25 | 35 | 9 |
| H1H21234N | 32 | 18 | 31 | 3 |
| H1H27729P-N297Q | 17 | 8 | 6 | 3 |

TABLE 15-continued

Binding of Anti-MSR1 Antibodies to MSR1-Expressing Cells

| Antibody | Ratio of 11 nM Antibody Binding Signal (RLU) on MSR1-expressing cells and parental HEK293 to isotype control | | | |
|---|---|---|---|---|
| | HEK293.Myc.h MSR1 | PMA-treated THP-1 | HEK293.mf MSR1 | HEK293 |
| H1H27731P-N297Q | 48 | 38 | 43 | 7 |
| H1H27732P-N297Q | 72 | 56 | 46 | 6 |
| H1H27734P-N297Q | 40 | 21 | 28 | 14 |
| H1H27736P-N297Q | 58 | 48 | 45 | 12 |
| H1H27739P-N297Q | 22 | 9 | 20 | 1 |
| H1H27747P-N297Q | 26 | 13 | 21 | 5 |
| H1H27749P-N297Q | 27 | 33 | 24 | 3 |
| H1H27751P-N297Q | 63 | 54 | 49 | 15 |
| H1H27754P-N297Q | 55 | 66 | 53 | 18 |
| H1H27756P-N297Q | 38 | 21 | 20 | 6 |
| H1H27759P2-N297Q | 23 | 9 | 25 | 2 |
| H1H27760P2-N297Q | 29 | 15 | 25 | 3 |
| H1H27761P2-N297Q | 23 | 10 | 15 | 3 |
| H1H27762P2-N297Q | 33 | 11 | 25 | 3 |
| H1H27771P2-N297Q | 42 | 21 | 7 | 2 |
| H1H27773P2-N297Q | 5 | 3 | 10 | 2 |
| H1H27778P2-N297Q | 51 | 32 | 29 | 4 |
| H1xH27759P2 | 22 | 6 | 21 | <1 |
| H1xH29283P2 | 26 | 9 | 24 | 1 |
| H2aM25685N | 75 | 11 | 25 | 2 |
| H2aM25690N | 166 | 25 | 77 | 5 |
| H2aM25695N | 35 | 8 | 45 | 5 |
| H2aM25700N | 46 | 3 | 39 | 1 |
| H2aM21228N | 66 | 16 | 60 | 2 |
| H2aM21230N | 78 | 21 | 55 | 5 |
| H2aM21232N | 86 | 21 | 51 | 1 |
| H2aM21235N | 68 | 20 | 40 | 6 |
| Specific Human MSR1 only binders | | | | |
| H2aM21229N | 78 | 56 | 27 | 36 |
| H1xH29282P2 | 9 | 3 | 1 | <1 |
| H1H27766P2-N297Q | 20 | 9 | 13 | 8 |
| Non-specific binder | | | | |
| H1xH29273P2 | 20 | 24 | 27 | |
| Isotype controls | | | | |
| hIgG1 Isotype Control | 1 | 1 | 1 | 1 |
| mIgG Isotype Control | 1 | 1 | 1 | 1 |

As illustrated in Table 15, thirty-eight of thirty-nine tested anti-MSR1 antibodies bound specifically to HEK293.Myc.hMSR1 cells with binding ratios ranging from 5- to 166-fold above isotype control at 11 nM anti-MSR1 antibody concentration. Thirty-three of these anti-MSR1 antibodies specifically bound to THP-1 cells endogenously expressing human MSR1 after PMA cell differentiation with cell binding ratios ranging from 3- to 66-fold above isotype control at 11 nM. Thirty-five anti-MSR1 antibodies that bound to engineered hMSR1 cells also bound specifically to mfMSR1 engineered cells with cell binding ratios ranging from 6- to 77-fold above isotype control at 11 nM. Twelve anti-MSR1 antibodies (H1H21234N-N297Q, H1H27731P-N297Q, H1H27732P-N297Q, H1H27734P-N297Q, H1H27736P-N297Q, H1H27751P-N297Q, H1H27754P-N297Q, H1H27756P-N297Q, H2aM25695N, H2aM21235N, H2aM21229N, H1H27766P2-N297Q) bound to parental HEK293 cells with ratios 5-fold or greater above isotype control. Anti-MSR1 antibodies produced with a human IgG1 containing a N297Q or a N297D single point mutation bound cells comparable to their corresponding unmodified parental antibodies.

One anti-MSR1 antibody, H1xH29273P2, was characterized as a non-specific binder, as it bound to MSR1 cells with ratios less than 2 compared to the HEK293 cells at 11 nM antibody concentration. The hIgG1 and mIgG1 isotype controls were not specific, as expected.

Example 28: Relative Binding of Anti-MSR1 Antibodies to Cell Surface-Expressed Mouse MSR1

Relative cell surface binding of the anti-MSR1 antibodies to mouse MSR1 expressing cells was determined by flow cytometry using MSR1 positive RAW264.7 cells (ATCC, Catalog #TIB-71) and MSR1 negative B16F10.9 cells (Lin et al. 1998. *PNAS* 95:8829-8834). For the assay, cells were plated in PBS without calcium and magnesium (VWR Cat #45000-446) and 2% FBS (Saradigm Cat #1500-500) (Staining Buffer) in 96 well V-bottom plates (Axygen Scientific, Cat #P-96-450-V-C-S). To block binding to Fc receptors, RAW264.7 cells were incubated for 30 minutes at 4° C. with 500 μg/mL mouse IgG (Jackson ImmunoResearch, Cat #015-000-003) diluted in staining buffer, while B16F10.9 cells remained in staining buffer. Following Fc receptor blocking, 10 μg/mL of anti-MSR1 antibodies or an isotype control antibody were added to the cells and were subsequently incubated for 30 minutes on ice. For a positive control, a commercial anti-mouse MSR1 (Sino Biological, Cat #50129-R004) antibody was used, while a rabbit IgG antibody (Thermo Scientific, Cat #26102) was used as a negative control. The cells were then washed once with staining buffer and were incubated with either an APC conjugated anti-human Fc secondary antibody (Jackson ImmunoResearch, Cat #109-136-170) or an Alexa-Flour 647 conjugated anti-rabbit Fc secondary antibody [Jackson ImmunoResearch Cat #111-606-046] at 10 g/mL for 30 minutes at 4° C. Cells were subsequently washed and fixed using a 50% solution of Cytofix (BD Biosciences, Cat #554655) diluted in PBS. Samples were run on the Beckman Coulter Cytoflex and results were analyzed in Flowjo 10.2 software (BD) to calculate the mean fluorescent intensity (MFI; Table 16). The signal to noise (S/N) was determined by calculating the ratio of the anti-MSR1 antibodies or the control antibodies MFI to the unstained sample MFI (Table 16).

TABLE 16

Binding of Anti-MSR1 Antibodies to RAW264.7 Cells (Flow Cytometry)

| Antibody | RAW264.7 MFI | B16F10.9 MFI | RAW264.7 S/N | B16F10.9 S/N |
|---|---|---|---|---|
| Unstained | 2524 | 3657 | 1 | 1 |
| Anti-human IgG secondary antibody only | 3095 | 3174 | 1 | 1 |
| Non-binding control | 3402 | 3829 | 1 | 1 |
| H1H21227N-N297Q | 12810 | 3287 | 5 | 1 |
| H1H21231N-N297Q | 3582 | 3374 | 1 | 1 |
| H1H21234N-N297Q | 7052 | 3499 | 3 | 1 |
| Anti-mouse MSR antibody | 245149 | 6161 | 97 | 2 |
| Anti-rabbit IgG secondary antibody only | 8720 | 5389 | 3 | 1 |
| H1H27729P-N297Q | 3484 | 3459 | 1 | 1 |
| H1H27731P-N297Q | 3510 | 3688 | 1 | 1 |
| H1H27732P-N297Q | 3425 | 3730 | 1 | 1 |
| H1H27734P-N297Q | 4783 | 4505 | 1 | 1 |
| H1H27736P-N297Q | 3554 | 3759 | 1 | 1 |
| H1H27739P-N297Q | 3271 | 3580 | 1 | 1 |
| H1H27747P-N297Q | 3630 | 3875 | 1 | 1 |
| H1H27749P-N297Q | 3789 | 3693 | 1 | 1 |
| H1H27751P-N297Q | 3823 | 4992 | 1 | 1 |
| H1H27754P-N297Q | 5406 | 4091 | 1 | 1 |
| H1H27756P-N297Q | 4573 | 3782 | 1 | 1 |
| H1H27759P-N297Q | 3288 | 3425 | 1 | 1 |
| H1H27760P-N297Q | 3429 | 3521 | 1 | 1 |
| H1H27761P-N297Q | 3837 | 3734 | 1 | 1 |
| H1H27762P-N297Q | 3519 | 3608 | 1 | 1 |
| H1H27766P-N297Q | 3812 | 3793 | 1 | 1 |
| H1H27771P-N297Q | 4055 | 3865 | 1 | 1 |
| H1H27773P-N297Q | 3367 | 3735 | 1 | 1 |
| H1H27778P-N297Q | 3648 | 4138 | 1 | 1 |

As illustrated in Table 16, two anti-MSR1 antibodies (H1H21227N-N297Q and H1H21234N-N297Q) bound weakly to RAW264.7 cells with S/N values of 5 and 3, respectively. The non-binding control antibody did not bind RAW264.7 cells. None of the 22 anti-MSR1 antibodies bound to B16F10.9 cells. A reference positive control (mouse MSR1/CD204 antibody, Sino Biological, Cat. #50129-R004) bound Raw 264.7 cells with a S/N of 97.

Example 29: Anti-MSR1 Antibodies Bind to Distinct Epitopes on MSR1 Receptor/Cross-Competition Between Anti-MSR1 Antibodies Binding competition between different anti-MSR1 antibodies was assessed using a real time, label-free bio-layer interferometry assay on an OCTET® HTX biosensor platform (Pall ForteBio Corp., Menlo Park, Calif.). The experiment was performed at 25° C. in 10 mM HEPES, 150 mM NaCl, 3 mM EDTA, 0.05% v/v Surfactant Tween-20, and 1 mg/mL BSA, pH 7.4 (HBS-EBT) buffer with the plate shaking at the speed of 1000 rpm.

To assess whether different antibodies are able to compete with one another for binding to their respective epitopes on the recombinant human MSR1 extracellular domain expressed with a N-terminal nonahistidine tag (SEQ ID NO: 688) (His9-hMSR1; R&D Systems, Cat #2708-MS), around 0.59-0.79 nM of His9-hMSR1 was first captured onto anti-Penta-His antibody coated OCTET® biosensor tips ("Penta-His" disclosed as SEQ ID NO: 690) (Pall ForteBio Corp., #18-5122) by submerging the biosensor tips for 45 seconds into wells containing a 20 pg/mL solution of His9-hMSR1. The antigen-captured biosensor tips were then saturated with a first anti-MSR1 monoclonal antibody (subsequently referred to as "mAb-1") by immersion into wells containing a 50 pg/mL solution of mAb-1 for 4 minutes. The biosensor tips were then submerged into wells containing a 50 pg/mL solution of a second anti-MSR1 monoclonal antibody (subsequently referred to as "mAb-2") for 4 minutes. All of the biosensor tips were washed in HBS-EBT buffer in between each step of the experiment. The real-time binding response was monitored during the course of the experiment and the binding response at the end of each step was recorded. The response of mAb-2 binding to His9-hMSR1 pre-complexed with mAb-1 was compared, and the competitive/non-competitive behavior of the different anti-MSR1 monoclonal antibodies was determined using a 50% inhibition threshold. Table 17 explicitly defines the relationships of antibodies competing in both directions, independent of the order of binding.

TABLE 17

Cross-competition of Anti-MSR1 Antibodies for Binding to His9-hMSR1

| First mAb (mAb-1) Captured using Anti-Penta-His Octet Biosensors ("Penta-His" disclosed as SEQ ID NO: 690) | mAb-2 antibodies which Compete with mAb-1 |
|---|---|
| H1H27756P-N297Q | H1H21231N |
| | H1H27760P-N297Q |
| | H1H27762P-N297Q |
| | H1H21231N-N297Q |
| | H1H27747P-N297Q |
| | H1H27749P-N297Q |
| H1H21231N | H1H27756P-N297Q |
| | H1H27760P-N297Q |
| | H1H27762P-N297Q |
| | H1H21231N-N297Q |
| | H1H27747P-N297Q |
| | H1H27749P-N297Q |
| H1H27760P-N297Q | H1H27756P-N297Q |
| | H1H21231N |
| | H1H27762P-N297Q |
| | H1H21231N-N297Q |
| | H1H27747P-N297Q |
| | H1H27749P-N297Q |
| H1H27762P-N297Q | H1H27756P-N297Q |
| | H1H21231N |
| | H1H27760P-N297Q |
| | H1H21231N-N297Q |
| | H1H27747P-N297Q |
| | H1H27749P-N297Q |
| | H1H27766P-N297Q |
| H1H21231N-N297Q | H1H27756P-N297Q |
| | H1H21231N |
| | H1H27760P-N297Q |
| | H1H27762P-N297Q |
| | H1H27747P-N297Q |
| | H1H27749P-N297Q |
| H1H27747P-N297Q | H1H27760P-N297Q |
| | H1H27762P-N297Q |
| | H1H21231N-N297Q |
| H1H27749P-N297Q | H1H27760P-N297Q |
| | H1H27762P-N297Q |
| | H1H21231N-N297Q |
| H1H21234N-N297Q | H1H21234N |
| H1H21234N | H1H21234N-N297Q |
| H1H27734P-N297Q | H1H21234N-N297Q |
| | H1H27751P-N297Q |
| | H1H27732P-N297Q |
| | H1H27731P-N297Q |
| | H1H27754P-N297Q |
| | H1H27766P-N297Q |
| | H1H21227N-N297D |
| H1H27766P-N297Q | No mAb* |
| H1H21227N-N297D | H1H21234N-N297Q |
| | H1H21234N |
| | H1H27766P-N297Q |
| H1H27739P-N297Q | H1H27759P-N297Q |
| H1H21227N | Data Inconclusive** |
| H1H27751P-N297Q | H1H21234N-N297Q |
| | H1H27734P-N297Q |
| | H1H27732P-N297Q |
| | H1H27731P-N297Q |
| | H1H27754P-N297Q |
| | H1H27766P-N297Q |
| | H1H21227N-N297D |
| H1H27732P-N297Q | H1H27734P-N297Q |
| | H1H27751P-N297Q |
| | H1H27731P-N297Q |
| | H1H27754P-N297Q |
| H1H27731P-N297Q | H1H27734P-N297Q |
| | H1H27751P-N297Q |
| | H1H27732P-N297Q |
| | H1H27754P-N297Q |

TABLE 17-continued

Cross-competition of Anti-MSR1 Antibodies for Binding to His9-hMSR1

| First mAb (mAb-1) Captured using Anti-Penta-His Octet Biosensors ("Penta-His" disclosed as SEQ ID NO: 690) | mAb-2 antibodies which Compete with mAb-1 |
|---|---|
| H1H27754P-N297Q | H1H27734P-N297Q |
| | H1H27751P-N297Q |
| | H1H27732P-N297Q |
| | H1H27731P-N297Q |
| H1H27761P-N297Q | H1H27736P-N297Q |
| | H1H27771P-N297Q |
| | H1H27778P-N297Q |
| | H1H27773P-N297Q |
| | H1H27739P-N297Q |
| H1H27736P-N297Q | H1H27761P-N297Q |
| | H1H27771P-N297Q |
| | H1H27778P-N297Q |
| | H1H27759P-N297Q |
| | H1H27773P-N297Q |
| | H1H27773P-N297Q |
| H1H27771P-N297Q | H1H27761P-N297Q |
| | H1H27736P-N297Q |
| | H1H27778P-N297Q |
| | H1H27759P-N297Q |
| | H1H27773P-N297Q |
| | H1H27739P-N297Q |
| H1H27778P-N297Q | H1H27761P-N297Q |
| | H1H27736P-N297Q |
| | H1H27771P-N297Q |
| | H1H27759P-N297Q |
| | H1H27773P-N297Q |
| | H1H27739P-N297Q |
| H1H27759P-N297Q | H1H27736P-N297Q |
| | H1H27771P-N297Q |
| | H1H27778P-N297Q |
| | H1H27773P-N297Q |
| | H1H27739P-N297Q |
| H1H27773P-N297Q | H1H27749P-N297Q |
| | H1H27766P-N297Q |
| | H1H21227N-N297D |
| H1H27729P-N297Q | Data Inconclusive** |
| H1H21227N-N297Q | Data Inconclusive** |

*Does not cross compete with any other mAb for binding to MSR1 when captured as 'mAb-1'

**mAb failed to saturate MSR1 surface or did not bind to MSR1 surface

Example 30: Ligand Uptake of Anti-MSR1 Antibodies

MSR1 can binds and internalize chemically modified or altered polyanionic molecules, including modified low density lipoproteins (LDL) (Platt, N. and S. Gordon. 2001. *J Clin Invest.* 108(5):649-654). A bioassay was generated to assess the ability of the exemplary anti-MSR1 antibodies to regulate the uptake of certain MSR1 ligands.

Generation of MSR1-Expressing Cell Lines for Assay.

Human embryonic kidney cells (HEK293) were transduced to stably express human MSR1 (amino acids 1-451 of UniProtKB accession number NP_619729.1) with a C-terminal Myc tag. The resulting cell line, referred to here as "HEK293.Myc.hMSR1", was selected and maintained in DMEM containing 10% FBS, NEAA, penicillin/streptomycin, L-glutamine, and 100 μg/mL hygromycin.

Ligand Uptake Assay.

For the bioassay, HEK293.Myc.hMSR1 cells were plated onto 96-well poly-D-lysine-coated assay plates (Greiner Bio One, Cat #655946) at 20,000 cells per well in Opti-MEM containing 0.1% FBS, penicillin/streptomycin, and L-Glutamine (assay media) and incubated at 37° C. in 5% $CO_2$ overnight. The following day, antibodies were serially diluted from 300 nM to 5.08 pM (1:3 serial dilution) and pre-incubated with the cells, along with a negative control consisting of assay media alone, for 30 minutes at 37° C. in 5% $CO_2$. After 30 minutes, either oxidized or acetylated low-density lipoprotein (LDL) labeled with 1,1' dioctadecyl-3,3,3',3'-tetramethylindocarbocyanine perchlorate (referred to as "DiI-OxLDL" or "DiI-AcLDL," respectively) was added to the cells at a constant concentration of 10 μg/mL. To determine the dose response of ligand uptake, DiI-OxLDL or DiI-AcLDL was serially diluted from 25 μg/mL to 24.4 pg/mL (plus assay media alone without LDL) and added to cells not with antibodies. After an overnight incubation at 37° C. in 5% $CO_2$, cells were fixed with BD CytoFix™ (BD Biosciences, Cat #554655) for 2 hours at 4° C., and ligand uptake was evaluated using a Flexstation3 plate reader (Molecular Devices) with excitation at 514 nm and emission at 565 nm. Results were analyzed using nonlinear regression (4-parameter logistics) with the Prism 7 program to obtain $EC_{50}$ and $IC_{50}$ values. The percentage of inhibition was calculated with the Relative Fluorescent Unit (RFU) values by using the following equation:

$$\text{Max \% Inhibition} = 100 \times \frac{RLU_{Baseline} - RLU_{Inhibition}}{RLU_{Baseline} - RLU_{Background}}$$

In the equation, "$RFU_{Baseline}$" is the fluorescence value from the cells treated with 10 μg/mL ligand without antibodies, "$RFU_{Inhibition}$" is the minimum fluorescence value with for a particular antibody with 10 μg/mL ligand, and "$RFU_{Background}$" is the fluorescence value from cells without any ligand or antibodies. The results and calculated values of the ligand uptake assay are provided in Table 18.

TABLE 18

Antibody Inhibition of Dil-OxLDL and Dil-AcLDL Uptake in HEK293.Myc.hMSR1 Cells

| | | Dil-Oxidized LDL | | Dil-Acetylated LDL | |
|---|---|---|---|---|---|
| Row | Antibodies | % Inhibition | $IC_{50}$ (M) | % Inhibition | $IC_{50}$ (M) |
| 1 | H2aM21227N | 90 | 3.1E−09 | 62 | 3.7E−09 |
| 2 | H2aM21228N | 79 | 3.1E−09 | 10 | >1.0E−07 |
| 3 | H2aM21229N | 26 | >1.0E−07 | no inhibition | no inhibition |
| 4 | H2aM21230N | 70 | 2.3E−09 | 47 | >1.0E−08 |
| 5 | H1M21231N | 79 | 3.7E−09 | 50 | >2.0E−08 |
| 6 | H2aM21232N | 79 | 4.8E−09 | 54 | >1.0E−08 |
| 7 | H2bM21234N | 61 | 4.5E−09 | 19 | 1.8E−09 |
| 8 | H2aM21235N | 64 | 3.2E−09 | 24 | >1.0E−07 |
| 9 | Mouse IgG2a Isotype control mAb 1 | no inhibition | no inhibition | no inhibition | no inhibition |
| 10 | Mouse IgG1 Isotype control mAb | no inhibition | no inhibition | no inhibition | no inhibition |
| 11 | H2aM25685N | 43 | >1.0E−07 | 22 | >1.0E−07 |
| 12 | H2aM25690N | 83 | 1.7E−09 | 53 | 2.1E−09 |
| 13 | H2aM25695N | 69 | >1.6E−08 | 40 | >1.7E−07 |
| 14 | H2aM25700N | 91 | 2.2E−09 | 79 | 2.4E−09 |
| 15 | Mouse IgG2a isotype control mAb 2 | no inhibition | no inhibition | no inhibition | no inhibition |
| 16 | H1H21227N-N297Q | 94 | 1.8E−09 | 65 | 2.4E−09 |
| 17 | H1H21231N-N297Q | 88 | 3.7E−09 | 62 | 3.7E−09 |
| 18 | H1H21234N-N297Q | 52 | 6.1E−09 | 34 | 1.3E−09 |
| 19 | H1H21227N | 89 | 2.0E−09 | 65 | 2.1E−09 |
| 20 | H1H21231N | 78 | 3.6E−09 | 63 | 3.5E−09 |
| 21 | H1H21234N | 64 | 4.3E−09 | 36 | 7.1E−10 |
| 22 | H1H27729P-N297Q | no inhibition | no inhibition | 28 | 1.2E−09 |
| 23 | H1H27731P-N297Q | 62 | >1.0E−08 | 37 | 1.8E−09 |
| 24 | H1H27732P-N297Q | 86 | 1.7E−09 | 62 | 2.2E−09 |
| 25 | H1H27734P-N297Q | 22 | 5.5E−09 | no inhibition | no inhibition |
| 26 | H1H27736P-N297Q | 83 | 3.2E−09 | 49 | 3.4E−09 |
| 27 | H1H27739P-N297Q | 55 | >1.0E−07 | no inhibition | no inhibition |
| 28 | H1H27747P-N297Q | 42 | >1.0E−07 | 26 | >1.0E−07 |
| 29 | H1H27749P-N297Q | 42 | 1.7E−09 | 35 | 4.2E−10 |
| 30 | H1H27751P-N297Q | 85 | 2.9E−09 | 59 | 1.6E−09 |
| 31 | H1H27754P-N297Q | 73 | 4.6E−09 | 38 | 1.8E−09 |
| 32 | H1H27756P-N297Q | 76 | 3.4E−09 | 42 | >1.0E−07 |
| 33 | H1H27759P-N297Q | 74 | >1.0E−08 | 48 | >1.0E−07 |
| 34 | H1H27760P-N297Q | 70 | 4.9E−09 | 46 | 2.6E−09 |
| 35 | H1H27761P-N297Q | 43 | 9.5E−09 | 29 | >1.0E−07 |
| 36 | H1H27762P-N297Q | 78 | 4.0E−09 | 38 | 2.9E−09 |
| 37 | H1H27766P-N297Q | 72 | 3.7E−09 | 38 | 3.5E−09 |
| 38 | H1H27771P-N297Q | 73 | 3.0E−09 | 49 | 1.9E−09 |
| 39 | H1H27773P-N297Q | 41 | >1.0E−07 | 31 | >1.0E−07 |
| 40 | H1H27778P-N297Q | 88 | 2.2E−09 | 54 | 1.5E−09 |
| 41 | Human IgG1-N297Q, Isotype Control mAb | no inhibition | no inhibition | no inhibition | no inhibition |
| 42 | Human IgG1 Isotype Control mAb | no inhibition | no inhibition | no inhibition | no inhibition |

Suitable antibody candidates illustrate relatively efficient inhibition (e.g., an $IC_{50}$ value of less than about 10 nM). In some embodiments, suitable antibody candidates also illustrate less than about 6500 maximum inhibition of ligand uptake.

As shown in Table 18 (rows 1-10), eight antibodies showed inhibition of DiI-OxLDL uptake on the HEK293.Myc.hMSR1 cells with maximum inhibition ranging from 2600 to 90% and $IC_{50}$ values ranging from 2.3 nM to >100 nM. Seven of the 8 antibodies showed inhibition of DiI-AcLDL uptake with maximum inhibition ranging from 10% to 62% and $IC_{50}$ values ranging from 1.8 nM to >100 nM. Antibody H2aM21229N showed no inhibition of DiI-AcLDL uptake.

As shown in Table 18 (rows 11-15), four antibodies showed inhibition of MSR1-mediated DiI-OxLDL uptake with maximum inhibition ranging from 43% to 91% and $IC_{50}$ values ranging from 1.7 nM to >100 nM. Four antibodies of the disclosure showed inhibition of MSR1-mediated DiI-AcLDL uptake with maximum inhibition ranging from 22% to 79% and $IC_{50}$ values ranging from 2.1 nM to >100 nM.

As shown in Table 18 (rows 16-42), twenty-four out of 25 antibodies showed inhibition of MSR1-mediated uptake of DiI-OxLDL with maximum inhibition ranging from 22% to 94% and $IC_{50}$ values ranging from 1.7 nM to >100 nM. Twenty-three of the 25 antibodies showed inhibition of DiI-AcLDL uptake with maximum inhibition ranging from 26% to 65% and $IC_{50}$ values ranging from 0.42 nM to >100 nM. Antibody H1H27729P-N297Q showed no inhibition of DiI-OxLDL uptake while antibodies H1H27739P-N297Q and H1H27734P-N297Q showed no inhibition of DiI-AcLDL uptake on HEK293.Myc.hMSR1 cells.

Human and mouse Isotype control antibodies did not show inhibition of DiI-OxLDL and DiI-AcLDL uptake by HEK293.Myc.hMSR1 cells in any of the assays.

Example 31: Binding and Internalization of Cell-Surface Expressed MSR1 by Anti-MSR1 Antibodies Exemplary anti-MSR1 antibodies were assessed for their ability to bind and internalize MSR1 on MSR1-expressing cells.

For the assay, THP-1 cells [ATCC, Cat #TIB-202] were seeded into 96 well PDL coated plates (Perkin Elmer, Cat #6055500) in RPMI (Irvine Scientific, Cat #9160) containing 10% FBS (ATCC, Cat #30-2020), pencillin/streptomycin/L-glutamine (Gibco, Cat #10378-016), 50 pM Beta-Mercaptoethanol (Sigma, Cat #M7522) (growth media) plus 200 nM Phorbol Myristate Acetate (PMA; Sigma, Cat #P1585). The THP-1 cells were allowed to differentiate for 4 days at 37° C. in 5% $CO_2$. To stain, quadruplicate plates of cells were incubated with 10 µg/mL of anti-MSR1 antibodies diluted in 2% FBS in PBS, without Calcium and Magnesium (Irving, Cat #9240) (staining buffer) for 30 minutes at 4° C. Cells were washed twice with staining buffer incubated with an Alexa-Flour 488 conjugated secondary Ab (Jackson Immunoresearch, Cat #115-547-003 or Jackson Immunoresearch, Cat #109-547-003) at 10 g/mL for 30 minutes at 4° C., and subsequently washed twice more with staining buffer. Two plates were immediately fixed and stained with 4% paraformaldehyde (PFA; ThermoFisher, Cat #28908)+5 M DRAQ5 (ThermoFisher, Cat #62251) in PBS for 20 minutes (non-internalization plates). The remaining two plates were incubated at 37° C. for 1 hour followed by fixation and staining for 20 minutes using a solution of 4% PFA+5 µM DRAQ5 diluted in PBS (internalization plates). After fixation, all plates were washed once with PBS. One non-internalization plate and one internalization plate were incubated with an anti-Alexa Fluor 488 antibody (Regeneron) at 50 g/mL in PBS overnight at 4° C. to quench surface Alexa Fluor 488 fluorescence. The remaining plates were incubated with PBS only. Confocal images were acquired on the Opera Phenix (Perkin Elmer) at 40× magnification. Harmony analysis software (Perkin Elmer) was utilized to identify DRAQ5-labeled cells and the total Alexa-Fluor 488 relative fluorescent units (RFU) per cell was determined. The total binding at 4° C. (RFU values of 4° C. unquenched wells), total binding at 37° C. (RFU values of 37° C. unquenched wells), the total internalized RFU, and % Internalization were determined for each antibody as shown in Table 19.

For all calculations, background fluorescence from unstained wells was subtracted from every well. Total internalized RFU was calculated as follows: Total RFU of 37° C. unquenched samples—Surface RFU at 37° C. Surface RFU is defined as unquenched RFU at 37° C.-quenched RFU at 37° C.)/QE. QE (quenching efficiency) is defined as: 1-(Total RFU of 4° C. quenched sample/Total RFU of 4° C. unquenched sample). The % Internalization was determined from the following formula: (Total internalized RFU at 37° C./Total RFU at 37° C.)*100.

TABLE 19

Internalization and Surface Binding of Anti-MSR1 Antibodies in Differentiated THP-1 Cells

| Antibody | Total Binding at 4° C. | Total Binding at 37° C. | Total Internalized RFU | % Internalization |
|---|---|---|---|---|
| H1H27729P-N297Q | 1930685 | 6607625 | 3763127 | 57.0 |
| H1H27731P-N297Q | 1215319 | 1802404 | 977543 | 54.2 |
| H1H27732P-N297Q | 2513511 | 4924734 | 2414132 | 49.0 |
| H1H27734P-N297Q | 482859 | 1151348 | 737425 | ND* |
| H1H27736P-N297Q | 9514681 | 12267400 | 14468087 | 117.9** |
| H1H27739P-N297Q | 3702857 | 5608380 | 4016378 | 71.6 |
| H1H27747P-N297Q | 2518361 | 5917858 | 3444330 | 58.2 |
| H1H27749P-N297Q | 4478384 | 12799899 | 5704834 | 44.6 |

TABLE 19-continued

Internalization and Surface Binding of Anti-MSR1 Antibodies in Differentiated THP-1 Cells

| Antibody | Total Binding at 4° C. | Total Binding at 37° C. | Total Internalized RFU | % Internalization |
|---|---|---|---|---|
| H1H27751P-N297Q | 5831744 | 7998767 | 6787876 | 84.9 |
| H1H27754P-N297Q | 3077308 | 7161570 | 6446236 | 90.0 |
| H1H27756P-N297Q | 6691792 | 11904608 | 9039171 | 75.9 |
| H1H27759P-N297Q | 4028970 | 2480463 | 1861578 | 75.0 |
| H1H27760P-N297Q | 1297337 | 6011876 | 3707164 | 61.7 |
| H1H27761P-N297Q | 1940392 | 2764577 | 1625899 | 58.8 |
| H1H27762P-N297Q | 2529645 | 3856573 | 3767717 | 97.7 |
| H1H27766P-N297Q | 1877240 | 3224247 | 2062539 | 64.0 |
| H1H27771P-N297Q | 6272656 | 7535203 | 6991358 | 92.8 |
| H1H27773P-N297Q | 490905 | 962752 | −67811 | ND* |
| H1H27778P-N297Q | 9910952 | 16552831 | 12518725 | 75.6 |
| H1H21227N-N297Q | 1800012 | 4110990 | 3226161 | 78.5 |
| H1H21234N-N297Q | 1953248 | 5451125 | 722651 | 13.3 |
| Isotype control | 185971 | 1087469 | 1704047 | ND* |

ND*: % internalization could not be determined due to weak binding and/or inability to determine quenching efficiency

**A % internalized value >100% is due to the total internalized values being slightly higher than total values at 37° C. An internalization of 100% was confirmed visually by the appearance of all Alex488 fluorescence into vesicular structures at 37° C.

As shown in Table 19, 19 of 21 assayed anti-MSR1 antibodies demonstrated internalization into differentiated THP-1 cells ranging from 13.3% to 117.9% internalization. For two of the 21 anti-MSR1 antibodies, internalization could not be determined due to weak binding and/or inability to determine quenching efficiency. As a control, the isotype control did not demonstrate any measurable internalization.

Example 32: Assessing Blocking Ability of Anti-MSR1 Antibodies for Human MSR1

The ability of anti-MSR1 antibodies disclosed herein to block the binding of various ligands to human MSR1 was measured using three competition sandwich ELISA assays. The ligands used in the assays were: (1) acetylated LDL (Ac-LDL), (2) oxidized LDL (Ox-LDL), and (3) advanced glycation end-products of bovine serum albumin (AGE-BSA).

For the assay, recombinant monomeric human MSR1 protein comprised of a portion of the human MSR1 extracellular domain expressed with a N-terminal 9-Histidine tag (SEQ ID NO: 688) (His9-hMSR1; R&D Systems, Cat #2708-MS) was coated at a concentration of 2 g/mL in PBS on a 96-well microtiter plate overnight at 4° C. for use in competition ELISA assays with Ac-LDL, Ox-LDL, or biotinylated-AGE-BSA ("biot-AGE-BSA"). Nonspecific binding sites were subsequently blocked using a 0.5% (w/v) solution of bovine serum albumin (BSA) in phosphate-buffered saline (PBS). Anti-MSR1 antibodies or isotype control antibodies were serially diluted as appropriate for each tested ligand and added in duplicate for each serial dilution set to microtiter plates coated with His9-hMSR1. Buffer alone was also added to wells on each coat. After 1 hour incubation at room temperature, without wash, a final constant concentration of 50 pM Ac-LDL (Life Technologies/ThermoFisher Scientific, Cat #L-35354), 5 nM or 10 nM Ox-LDL (Alfa Aesar, Cat #J65591), or 400 pM biot-AGE-BSA (R&D Systems, Cat #BT4127) were added to plates with His9-hMSR1, and the plates were incubated for an additional 1 hour at room temperature. (Concentrations of Ac-LDL, Ox-LDL and biot-AGE-BSA for antibody inhibition assays were selected from the approximate midway point within the linear portion of individual binding curves of Ac-LDL, Ox-LDL or biot-AGE-BSA to plate-coated His9-hMSR1.) Wells were washed, and plate-bound Ac-LDL or Ox-LDL were detected with anti-LDL rabbit antibody (Alfa Aesar, Cat #J64398) in combination with anti-rabbit IgG (H+L) specific donkey polyclonal antibodies conjugated with horseradish peroxidase (HRP) (JacksonImmunoResearch, Cat #711-035-152) and biot-AGE-BSA was detected with a streptavidin-HRP (ThermoFisher Scientific, Cat #N200). Plates were developed using TMB substrate solution (BD Biosciences, Cat #51-2606KC & Cat #51-2607KC) according to manufacturer's recommendation and absorbance at 450 nm was measured on a Victor™ Multilabel Plate Reader (PerkinElmer™). This assay was conducted in four different assay runs.

Data analysis was performed using a sigmoidal dose-response model within Prism™ software (GraphPad). Percent blockade at maximum concentration of the antibody tested in each assay was calculated as an indicator of the ability of the antibodies to block the binding of Ac-LDL, Ox-LDL or biot-AGE-BSA to His9-hMSR1 on the plate relative to the baseline of the assay. In the calculation, binding signal of the same concentrations of Ac-LDL, Ox-LDL, or biot-AGE-BSA used for the assays in the absence of antibody was referenced as 100% binding or 0% blocking, while the baseline of the assay, defined as binding signal of the sample of buffer without MSR1 ligands or antibody, was referenced as 0% binding or 100% blocking. The maximum percent blockade at the highest concentration of antibody tested in each assay are reported for all antibodies. Negative percent blockade numbers reflected higher MSR1 ligands binding to plate coated His9-hMSR1 in the presence of antibodies. The blocking results are summarized in Table 20.

TABLE 20

Blocking Ability of Anti-MSR1 Antibodies in Competition ELISA Assays

| Antibody | anti-MSR1 antibody blocking of Ox-LDL binding to His9-hMSR1: anti-MSR1 antibody concentration | Ox-LDL concentration | % Blocking | Anti-MSR1 antibody (100 nM) blocking of Ac-LDL binding to His9-hMSR1 % Blocking | Anti-MSR1 antibody (300 nM) blocking of biot-AGE-BSA binding to His9-hMSR1 % Blocking |
|---|---|---|---|---|---|
| Blocked >50% in all assay formats | | | | | |
| H2aM25700N | 500 nM | 10 nM | 98 | 104 | 101 |
| H1H21227N-N297Q | 500 nM | 10 nM | 97 | 105 | 96 |
| H1H21227N-N297D | 500 nM | 10 nM | 99 | 101 | 97 |
| H1H21227N | 500 nM | 10 nM | 100 | 105 | 99 |
| Blocked >50% in some assay formats | | | | | |
| H2aM25695N | 500 nM | 10 nM | 96 | 65 | 16 |
| H1H27766P2-N297Q | 1 µM | 10 nM | 54 | 52 | 27 |
| H1H21234N-N297Q | 500 nM | 10 nM | 49 | 75 | −27 |
| H1H21234N | 500 nM | 10 nM | 98 | 70 | 21 |
| Blocked <50% in all assay formats | | | | | |
| H2aM21228N | 500 nM | 5 nM | 41 | −32 | −1 |
| H2aM21229N | 500 nM | 5 nM | 38 | −11 | 3 |
| H2aM21230N | 500 nM | 5 nM | 45 | −14 | 9 |
| H2aM21232N | 500 nM | 5 nM | 16 | 25 | −50 |
| H2aM21235N | 500 nM | 5 nM | −4 | 24 | −24 |
| H2aM25685N | 500 nM | 10 nM | 28 | −33 | −86 |
| H2aM25690N | 500 nM | 10 nM | 8 | −76 | −96 |
| H1H21231N-N297Q | 500 nM | 10 nM | 26 | −60 | −50 |
| H1H21231N | 500 nM | 10 nM | 22 | −62 | −44 |
| H1H27729P-N297Q | 1 µM | 10 nM | 36 | 8 | 15 |
| H1H27731P-N297Q | 1 µM | 10 nM | −1 | −41 | 4 |
| H1H27732P-N297Q | 1 µM | 10 nM | −60 | −61 | −9 |
| H1H27734P-N297Q | 1 µM | 10 nM | −15 | −38 | −4 |
| H1H27736P-N297Q | 1 µM | 10 nM | 3 | −31 | −3 |
| H1H27739P-N297Q | 1 µM | 10 nM | −41 | −47 | −9 |
| H1H27747P-N297Q | 1 µM | 10 nM | −31 | −44 | −2 |
| H1H27749P-N297Q | 1 µM | 10 nM | −21 | −51 | −1 |
| H1H27751P-N297Q | 1 µM | 10 nM | −31 | −51 | −11 |
| H1H27754P-N297Q | 1 µM | 10 nM | −44 | −42 | −9 |
| H1H27756P-N297Q | 1 µM | 10 nM | −45 | −54 | −8 |
| H1H27759P2-N297Q | 1 µM | 10 nM | −62 | −45 | −19 |
| H1H27760P2-N297Q | 1 µM | 10 nM | −47 | −43 | −4 |
| H1H27761P2-N297Q | 1 µM | 10 nM | −21 | −36 | −4 |
| H1H27762P2-N297Q | 1 µM | 10 nM | −65 | −58 | −16 |
| H1H27771P2-N297Q | 1 µM | 10 nM | −23 | −21 | −1 |
| H1H27773P2-N297Q | 1 µM | 10 nM | 2 | −11 | 1 |
| H1H27778P2-N297Q | 1 µM | 10 nM | −59 | −40 | −8 |
| Isotype control antibodies | | | | | |
| hIgG1 isotype control | 1 µM | 10 nM | 3 | −8 | 4 |
| mIgG1 isotype control | 1 µM | 10 nM | 16 | −4 | 7 |

Four of 35 assayed anti-MSR1 antibodies were identified as blocking >50% of Ac-LDL, Ox-LDL, and biot-AGE-BSA binding to hMSR1. These four anti-MSR1 antibodies blocked greater than 95% of 50 pM Ac-LDL, 10 nM Ox-LDL and 400 pM biot-AGE-BSA binding to His9-hMSR1.

At the maximum concentration of antibody tested, four of the 35 anti-MSR1 antibodies blocked >50% Ac-LDL and/or Ox-LDL binding to hMSR1 but did not block biot-AGE-BSA binding to hMSR1. Three of these antibodies blocked both 50 pM Ac-LDL and 10 nM Ox-LDL binding to hMSR1 with 52% to 98% blockade. One antibody (H1H21234N-N297Q) blocked only 50 pM Ac-LDL binding to hMSR1 with 75% blockade.

Twenty-seven (27) of the 35 anti-MSR1 antibodies and the irrelevant isotype control antibodies blocked <50% of Ac-LDL, Ox-LDL, and biot-AGE-BSA binding to hMSR1.

Three anti-MSR1 antibodies (21227N, 21231N, 21234N) were produced both with the original human Fcγ portion and a version with a N297Q single point mutation. The 21227N antibody was also produced as a third version with a N297D mutation. The modified versions of 21227N (H1H21227N-N297Q and H1H21227N-N297D) and 21231N (H1H21231N-N297Q) anti-MSR1 antibodies retained parental characteristics. Antibodies H1H21227N-N297Q and H1H21227N-N297D blocked >50% of Ac-LDL, Ox-LDL, and biot-AGE-BSA binding to hMSR1, while antibody H1H21231N-N297Q blocked <50% of Ac-LDL, Ox-LDL, and biot-AGE-BSA binding to hMSR1. Anti-MSR1 modified antibody H1H21234N-N297Q blocked only 50 pM Ac-LDL binding to hMSR1 in comparison to unmodified H1H21234N antibody, which blocked >50% for both Ac-LDL and Ox-LDL binding to hMSR1.

Example 33: Intracellular *S. aureus* Antibody-Drug Conjugate Killing Assay 1 (MSR1)

The reagents used are shown in Table 21, below.

TABLE 21

Reagents for Intracellular Assay

| Reagent | Vendor | Catalogue # |
|---|---|---|
| RPMI | Gibco | 11835-030 |
| PBS | Gibco | 20012-043 |
| Triton X-100 | Sigma | TX1568-1 |
| RPMI | Gibco | 11875-093 |
| FBS | Gibco | 10082-147 |
| PMA | Sigma | P8139 |
| Costa 48 well plate | Corning | 3548 |
| TSA plates | Teknova | T0144 |
| Pen/Strep | Gibco | 15140-122 |
| Dilution plates | Greiner Bio one | 780271-FD |
| Gentamicin | BioWhittaker | 17-519Z |

To test the efficacy of an anti-MSR1 Ab-antibiotic ncADC according to the disclosure in vitro, an intracellular *S. aureus* killing assay was utilized. For the assay, a THP-1 monocytic cell line was grown in media comprised of RPMI containing 10% FBS and 1% Penicillin/Streptomycin, then was seeded at a density of $1\times10^5$ cells/well in a 96 well plate and differentiated into macrophages for three days prior to infection using 200 nM Phorbol Myristate Acetate (PMA). An overnight culture of *S. aureus* MRSA strain NRS384 was grown in RPMI, washed twice with PBS and subsequently resuspended at $1\times10^7$ cfu/mL in PBS. THP-1 cells were washed with warm media (RPMI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing twice with warm media and remaining extracellular *S. aureus* were killed by addition of media containing 100 pg/mL of gentamicin. After 1 hour, media was aspirated and the anti-MSR1 Ab-antibiotic ncADCs (H1H21234N-N297Q-25 and H1H21234N-N297Q-80), which is an anti-MSR1 antibody according to the disclosure conjugated to the maleimido linker payload derivative compounds 25 and 80 according to the disclosure via interchain cysteines, at different doses (10 pg/mL, 3.3 pg/mL, 1.1 pg/mL, 0.4 pg/mL, 0.1 pg/mL, and 0.04 pg/mL) and the isotype control-antibiotic ncADC (Isotype control-N297Q-25 and Isotype control-N297Q-80) at 10 pg/mL were added to infected macrophages in media containing 50 pg/mL gentamicin to prevent extracellular growth of *S. aureus*. A sample without any ncADC was also included for reference. After 24 hours, plates were washed twice with warm RPMI without FBS, and then 100 μL of 0.1% Triton X-100 in PBS was added and incubated for 10 minutes to lyse the THP-1. *S. aureus* survival was enumerated by colony forming units through serial dilution in PBS and plating onto trypticase soy agar plates.

The DARs are summarized in Table 22, below.

TABLE 22

Drug-antibody-ratios for the antibody-drug conjugates used

| Antibody | DAR |
|---|---|
| MSR1 ncADC H1H21234N-N297Q-25 | 3 (HIC) |
| Isotype Control-N297Q-25 | 2 (HIC) |
| MSR1 ncADC H1H21234N-N297Q-80 | 3 (HIC) |
| Isotype Control-N297Q-80 | 3 (HIC) |

The results are summarized in Table 23, below.

TABLE 23

Average colony forming units of anti-MSR1 Ab-Antibiotic

| | ncADC dose (ug/mL) | Average cfu/mL | Standard Deviation |
|---|---|---|---|
| *S. aureus* control | none | 1,350,000 | 139,194 |
| Isotype Control-N297Q-25 | 10 | 608,333 | 52,042 |
| MSR1 ncADC | 10 | 1,325 | 87 |
| H1H21234N-N297Q-25 | 3.3 | 4,917 | 722 |
| | 1.1 | 13,250 | 1,887 |
| | 0.4 | 56,667 | 7,638 |
| | 0.1 | 82,500 | 17,500 |
| | 0.04 | 1,025,000 | 43,301 |
| Isotype Control-N297Q-80 | 10 | 1,208,333 | 94,648 |
| MSR1 ncADC | 10 | 50 (limit of detection) | 0 |
| H1H21234N-N297Q-80 | 3.3 | 50 (limit of detection) | 0 |
| | 1.1 | 50 (limit of detection) | 0 |
| | 0.4 | 7,417 | 2,876 |
| | 0.1 | 75,833 | 15,275 |
| | 0.04 | 758,333 | 230,940 |

As shown in Table 23, the anti-MSR1 Ab-antibiotic ncADCs (H1H21234N-N297Q-25 and H1H21234N-N297Q-80) demonstrated the ability to reduce intracellular *S. aureus* from infected macrophages in vitro in a dose-dependent manner compared to the untreated control. Macrophages treated with the isotype control-antibiotic ncADC (Isotype control-N297Q-25 and Isotype control-N297Q-80) at 10 pg/mL harbored intracellular *S. aureus* at a similar level to the untreated control. These data demonstrate that an anti-MSR1 Ab-antibiotic ncADC according to the disclosure can be used to effectively kill pathogens residing within a macrophage reservoir.

Example 34: *S. aureus* IV Disseminated Infection Mouse Model

To test the efficacy of an anti-MSR1 Ab-antibiotic ncADC according to the disclosure in vivo, an intravenous disseminated infection model was utilized. *S. aureus* MRSA strain NRS384 was grown overnight in trypic soy broth (TSB) and sub-cultured to mid-logarithmic phase. Bacteria were then washed twice with PBS and resuspended in PBS at a concentration of $1.2\times10^{8}$ cfu/mL. Mice homozygously expressing human MSR1 extracellular domain and transmembrane domain in place of mouse MSR1 extracellular and transmembrane domains (humanized MSR, MAID 7343-MSR1 HumIn delHyg) were then infected intravenously through the tail vein with 100 μL of the bacterial suspension, for a final infectious dose of $1.2\times10^{7}$ cfu/mouse. From one to three days post infection, mice were treated with 110 mg/kg vancomycin subcutaneously twice daily wherein indicated. Either the anti-MSR1 monoclonal antibody (H1H21234N-N297Q), anti-MSR1 Ab-antibiotic ncADC (H1H21234N-N297Q-25), which is an anti-MSR1 antibody according to the disclosure conjugated to the maleimido linker payload derivative compound 25 according to the disclosure via interchain cysteines, the Isotype control antibody or the ncADC Isotype control conjugated to the maleimido linker payload derivative compound 25, was administered subcutaneously at the indicated dose, as described in Table 24, one day after infection. Mice were monitored for weight loss and body conditioning score throughout the infection. At four days post infection, mice were euthanized and the *S. aureus* kidney burden was quantified by tissue homogenization followed by enumeration of colony forming units through serial dilution in PBS and plating onto trypicase soy agar plates.

TABLE 24

Average *S. aureus* kidney burden in mice treated with anti-MSR1 Ab-Antibiotic ncADC in combination with vancomycin

| Treatment | Vancomycin treatment | mAb or conjugate dose (mg/kg) | Average cfu/kidney pair | # of mice with *S. aureus* below the limit of detection | Standard Deviation |
|---|---|---|---|---|---|
| Infected Control | − | (—) | 4.33E+08 | 0/5 | 2.32E+08 |
| Vancomycin | + | (—) | 2.07E+06 | 0/6 | 2.76E+06 |
| Isotype Control 1 mg/kg | + | 1 | 2.44E+06 | 0/4 | 1.51E+06 |
| ncADC Isotype control (Isotype control-25) | + | 1 | 4.01E+05 | 1/5 | 6.49E+05 |
| anti-MSR1 Ab (H1H21234N-N297Q) | + | 1 | 1.55E+05 | 4/8 | 2.72E+05 |
| anti-MSR1 Ab (H1H21234N-N297Q) | + | 0.1 | 2.43E+05 | 0/6 | 2.64E+05 |
| anti-MSR1 Ab-antibiotic ncADC (H1H21234N-N297Q-25) | + | 1 | 6.17E+03 | 7/9 | 1.69E+04 |
| anti-MSR1 Ab-antibiotic ncADC (H1H21234N-N297Q-25) | + | 0.1 | 1.16E+03 | 6/8 | 1.78E+03 |

Limit of detection = 250 colony forming units (cfu)

As shown in Table 24, above, intravenous infection with *S. aureus* MRSA strain NRS384 results in high bacterial burden in the kidneys, and treatment of mice with the standard of care antibiotic vancomycin reduces the *S. aureus* kidney burden by approximately 2 logs, but none of the mice had levels of *S. aureus* reduced below the limit of detection (LOD). The anti-MSR1 Ab-antibiotic ncADC (H1H21234N-N297Q-25) at doses of 1 and 0.1 mg/kg in combination with vancomycin resulted in 77% and 75% of mice with *S. aureus* levels below the LOD, demonstrating a marked improvement in *S. aureus* clearance in mice treated with the Ab-antibiotic ncADC combination therapy. *S. aureus* clearance was less pronounced in mice treated with the isotype control ncADC conjugate (Isotype Control-N297Q-25) plus vancomycin, demonstrating the benefit of payload targeting to macrophages.

Example 35: Conjugation Method for Aglycosylated Antibodies to Amino-Linker-Payloads Bacterial Transglutaminase Conjugation of Compound 80 and 82

An anti-MSR1 antibody H1H21234N containing a N297Q mutation, which eliminates N-linked glycosylation of the Fc at this site, was used. The mutation allowed the antibodies to be conjugated to a maximum loading of 4 at 295Q and 297Q of the heavy chains. A nontargeting antibody control, containing the same N297Q mutation, was used as a non-binding isotype control.

Deglycosylated control and MSR1 antibodies were conjugated at 1 mg/mL in PBS pH 7.4. Compound 80 or 82 was added in a 10-40 fold molar excess over antibody and the enzymatic reaction was initiated by addition of 12 units of bacterial transglutaminase (Zedira, T1001) per mg antibody and incubated at 37° C. for 4-16 hours. Samples were purified by SEC into PBS. The conjugates were analyzed by ESI-MS for the determination of the drug to antibody ratio (DAR) and by hydrophobic interaction chromatography (HIC). The results are listed in Table 25.

TABLE 25

Percent yield and payload to antibody ratios for each of the antibody drug conjugates

| Antibody | Purity (by SEC) | Yield (%) | DAR (HIC) | DAR (ESI-MS) |
|---|---|---|---|---|
| H1H21234N-82 | >95% | 50 | 3 | 3.6 |
| Nontargeting Antibody Control-82 | >95% | 50 | 3 | 3.5 |
| H1H21234N-80 | >95% | 50 | 2 | 3.4 |
| Nontargeting Antibody Control-80 | >95% | 50 | 2 | 3.0 |

Characterization of Conjugates by Hydrophobic Interaction Chromatography (HIC)

To determine the loading of the linker-payloads on the antibody, the conjugates were run on an Agilent 1260 using a TSK-NPR Butyl HIC column using a linear gradient of 1M potassium phosphate pH 8.5 in water over 60 min. The payload loading was determined by integration of peak areas corresponding to the species of conjugated and unconjugated antibody.

Characterization of Conjugates by ESI-MS

The chromatographic separation was achieved on a C4 column (0.3×50 mm ACQUITY UPLC BEH protein C4, 1.7 um, 300 A) in a 10 min gradient (minute: percentage of mobile phase B; 0:5%, 2:50%, 2.1:26%, 6.5:40%, 6.6:90%, 8.5:90%, 8.6:5%, 10:5%, 10.5:90%, 12.5:90%, 12.9:5%, 15:5%). The mobile phase A was 0.1% formic acid in water and mobile phase B was 0.1% formic acid in acetonitrile. The flow rate was set at 8 μL/min. The detector TOF scan was set from m/z 500-4500 with major parameters as listed (Capillary voltage 3.0 kV; Sampling Cone 80V; Source Offset at 100V; Source temperatures 150° C.; Desolvation temperature 400° C.; Cone gas 0 L/hr; Desolvation gas 600 L/hr). The spectra were deconvoluted with MaxEnt function within MassLynx software.

Average drug to antibody ratio (DAR) calculation based on deconvoluted mass spectra peak intensity using the following equation, where PI=Peak Intensity and D=Individual DAR.

$$DAR = \frac{\sum(PI_o + PI_1 * D_1 + PI_2 * D_2 + PI_n * D_n)}{\sum(PI_o + PI_1 + PI_2 + PI_n)}$$

Example 36: Antibody Engineered Cysteine Deblocking

Anti-Protein A (H1xH15140P*/*) and a nontargeting antibody control engineered antibodies were created by mutating the interchain disulfide forming heavy chain C103S. The antibodies are expressed in CHO cells and need to be deblocked on the native light chain cysteine using mild reduction in PBS at room temperature by the addition of a thirty fold molar excess of reducing agent, TCEP followed by buffer exchange. To reform the two heavy interchain disulfide bonds, the antibody was incubated for three hours at room temperature with $CuSO_4$ or with dhAA at a two to twenty fold molar excess. The reduced and oxidized antibody was buffer exchanged into PBS to remove oxidizing agent. This process produces two free thiols that reside on the light chain and are available for maleimide conjugation.

The anti-WTA engineered antibody was taken from the literature (Lehar et al, *Nature* 2015 527, 323-328; antibody 4497 described in US20140356375 and WO2016090038, the content of which is incorporated herein by reference in its entirety) and has a light chain mutation V205C to provide 2 sites for maleimide conjugation. The same procedure above was used to deblock the engineered cysteines.

Conjugation of Antibody Engineered Deblocked Cysteine to Linker Payload

To the reduced and oxidized antibody (1-10 mg/ml) in PBS pH7.5, the maleimido linker payload (2 equivalents/SH group, Lehar et al, *Nature* 527, 323-328), or the linker payloads of this filing, in DMSO (10 mg/ml) was added. The reaction proceeded for 2 hrs. The conjugates were purified into PBS by size exclusion chromatography and sterile filtered. Protein concentrations and payload to antibody ratios were determined by UV spectral analysis. Size-exclusion HPLC established that all conjugates used were >95% monomeric, and RP-HPLC established that there was <1% unconjugated linker payload. All conjugated antibodies were analyzed by HIC for linker payload loading values. Payload to antibody ratios are reported in Table 26.

Conjugation Method for Aglycosylated Antibodies (H1H21234N and a Nontargeting Antibody Control The antibody (1-10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative compound 25 (1.2 equivalents/SH group) in DMSO (10 mg/ml) was added to the reduced antibody and the mixture adjusted to pH 7.0 with 1 M HEPES (pH 7.4). The conjugates were purified using PBS with 5% glycerol by size exclusion chromatography and sterile filtered. Protein concentrations and payload to antibody ratios were determined by UV spectral analysis. Size-exclusion HPLC established that all conjugates used were >95% monomeric. All conjugated antibodies were analyzed by HIC for linker payload loading values. Payload to antibody ratios are reported in Table 26.

TABLE 26

Purity and drug to antibody ratios (DAR) of conjugates.

| Antibody Drug Conjugate | DAR (by HIC) | DAR (by ESI-MS) | Purity (by SEC) | Yield (%) |
|---|---|---|---|---|
| Anti-WTA-rifalog | 1.8 | 1.8 | >95% | 53% |
| Anti-WTA-21 (rifampicin control) | 2.0 | 1.5 | >95% | 70% |
| Anti-WTA-compound 25 | 1.7 | 1.6 | >95% | 50% |
| Anti-WTA-compound 36 | 1.8 | 1.4 | >95% | 40% |
| Anti-Protein A-rifalog | 1.9 | Not available | >95% | 30% |

TABLE 26-continued

| Purity and drug to antibody ratios (DAR) of conjugates. | | | | |
|---|---|---|---|---|
| Antibody Drug Conjugate | DAR (by HIC) | DAR (by ESI-MS) | Purity (by SEC) | Yield (%) |
| Anti-Protein A-compound 36 | 1.1 | 1.1 | >95% | 40% |
| H1H21234N-compound 25 | 3 | 3.2 | >95% | 50% |
| Nontargeting antibody control 1-rifalog | 1.7 | 1.6 | >95% | 60% |
| Nontargeting antibody control 1-rifampicin | 2.0 | 1.7 | >95% | 70% |
| Nontargeting antibody control 1- 25 | 1.3 | 0.6 | >95% | 50% |
| Nontargeting antibody control 1- 36 | 1.2 | 0.7 | >95% | 40% |
| Nontargeting antibody control 2- 25 | 2 | 2.0 | >95% | 50% |

Rifalog (Lehar et al, *Nature* 2015 527, 323-328; WO2016090038):

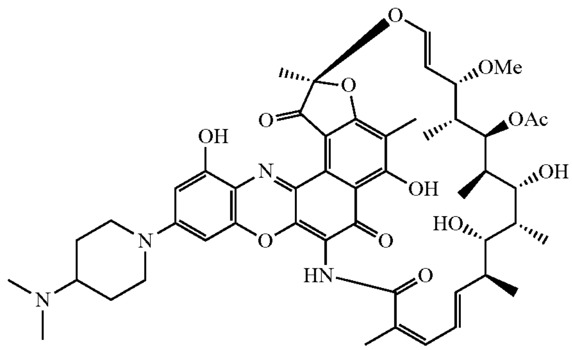 [SMILES: CO[C@H]1/C=C/O[C@@]2(C)Oc3c(C)c(O)c4c(=O)c(c5oc6cc(N7CCC(N(C)C)CC7)cc(O)c6nc-5c4c3C2=O)NC(=O)/C(C)=C\C=C\[C@H](C)[C@H](O)[C@@H](C)[C@@H](O)[C@@H](C)[C@H](OC(C)=O)[C@@H]1C]

Characterization of Conjugates by Hydrophobic Interaction Chromatography (HIC)

To determine the loading of the linker-payloads on the antibody, the conjugates were run on Agilent 1260 using a TSK-NPR Butyl HIC column using a linear gradient of 1M potassium phosphate pH 8.5 to water over 60 min. The payload loading was determined by integration of peak areas corresponding to the species of conjugated and unconjugated antibody.

Characterization of Conjugates by ESI-MS

To determine the loading of the linker-payloads on the antibody (cysteine conjugates), the conjugates were deglycosylated, reduced, and analyzed by LC-MS.

For the assay, 50 μg of the conjugate was diluted with mili-Q water to a final concentration of 1 mg/mL. Ten μL of PNGase F solution [PNGase F solution was prepared by adding 150 μL of PNGase F stock (New England Biolabs, Cat #P0704L) and 850 μL of mili-Q water and mixed well] was added to the diluted conjugate solution and then incubated at 37° C. overnight. 2.4 μL of 0.5 M TCEP was added to the sample such that the resulting material had a final TCEP concentration of 20 mM and this was then incubated at 50° C. for 30 minutes. Injections of 10 μL of each sample were made onto LC-MS (Waters Synat G2-Si) and eluted with 0.1 mL/minute of a gradient mobile phase 20-40% of mobile phase B over 25 minutes (Mobile Phase A: 0.1% v/v FA in H2O; Mobile Phase B: 0.1% v/v FA in Acetonitrile). The LC separation was achieved on Waters Acquity BEH C18 column (1.0×50 mM, 1.7 μM).

The mass spectrometry spectra were deconvoluted and the identified light and heavy chain peaks represent the light chain (L) with linker-payload values=0 and 1, heavy chain (H) with linker-payload values=0, 1, 2, and 3. From the intensity values of each species, the drug to antibody ratio (DAR) was calculated using the equation below for a homo-dimer antibody conjugate.

$$DAR = 2*\left[\frac{L1}{L0+L1} + \frac{H1+2*H2+3*H3}{H0+H1+H2+H3}\right]$$

Example 37: Broth Minimum Inhibitory Concentration (MIC) Assay 2

To test the potency of rifamycin analogs of the disclosure in vitro, a broth growth inhibition assay was developed. For the assay, *S. aureus* NRS384 was grown in Tryptic Soy Broth (TSB) overnight, then sub-cultured 1:50 in fresh TSB and grown for an additional two hours. The culture was then pelleted via centrifugation and washed twice in PBS. The culture was then diluted to $1\times10^{6}$ cfu/mL in TSB and 100 μL of the suspension was added per well to a 2 mL dilution plate in triplicate. A dilution series of the indicated antibiotic (an analog according to the disclosure or a previously known analog Rifampicin) was added 1:1 for a final starting concentration of $1\times10^{-5}$ M, then a 1:10 dilution for $1\times10^{-6}$ M followed with 1:4 dilutions to include $2.5\times10^{-7}$ M, $6.25\times10^{-8}$ M, $1.56\times10^{-8}$ M, $3.91\times10^{-9}$ M, $9.77\times10^{-10}$ M, $2.44\times10^{-10}$ M, $6.1\times10^{-11}$ M, $1.53\times10^{-11}$ M, and $3.81\times10^{-12}$ M for a total of 11 points. The plates were sealed and incubated at 37° C. with shaking for 24 hours, then 150 μL of each sample was added to 96 well microtiter plates and the OD600 nm was read on a Spectramax i3 Minimax 300.

The reagents used are shown in Table 27, below.

TABLE 27

| Reagents for MIC Assay | | |
|---|---|---|
| Reagent | Vendor | Catalogue # |
| PBS | Gibco | 20012-043 |
| *S. aureus* NRS384 | BEI resources | NR-46070 |
| Tryptic Soy Broth (TSB) | Teknova | T1525 |
| Dilution plates | Greiner Bio one | 780261 |
| 250 mL Flask | Thermo Scientific | 4116-0250 |
| 50 mL bioreactor tube | TPP | 87050 |
| Tryptic Soy agar (TSA) | Teknova | T0144 |
| DMSO | VWR | WN182 |
| Reagent Reservoir | VWR | 89094-658 |
| Costa 96 well plate | Corning | 3904 |

The lowest concentrations that inhibited growth of *S. aureus* (minimum inhibitory concentration, MIC) are listed in Table 28. As shown in Table 28, all rifamycin analogs according to the disclosure are effective at inhibiting growth of *S. aureus* at sub-micromolar to nanomolar concentrations. The broth MIC experiments were assessed in at least two independent experiments and the median value is captured below unless indicated otherwise.

TABLE 28

Minimum inhibitory concentration (MIC) of antibiotics in a broth growth inhibition assay.

| Antibiotic tested | *S. aureus* Broth MIC (M) |
|---|---|
| Rifampicin | 3.91E−09 |
| Rifalog | 9.77E−10 |
| P1 | 6.25E−08 |
| P2 | 6.25E−08 |
| P3 | 1.56E−08 |
| 16f | 1.56E−08 |
| 16g | 1.56E−08 |
| 16h | 1.56E−08 |
| 16i | 1.56E−08 |
| 16j | 6.25E−08 |
| 16k | 9.77E−10 |
| 16l | 3.91E−09 |
| 16m | 3.91E−09 |
| 16n | 1.56E−08 |
| 16o | 3.91E−09 |
| 16p | 1.56E−08 |
| 16q | 3.91E−09 |
| 16r | 1.56E−08 |
| 16s | 6.25E−08 |
| 16t | 6.25E−08 |
| 16u | 1.00E−06 |
| 16v | 6.25E−08 |
| 16w | 6.25E−08 |
| 16x | 9.77E−10 |
| 16y | 1.56E−08 |
| 16z | 3.91E−09 |
| 16z-1 | 3.91E−09 |
| 17 | 1.56E−08 |
| 29 | 3.91E−09 |
| 29a | 3.91E−09 |
| 29b | 3.91E−09 |
| 29c | 3.91E−09 |
| 29d | 3.91E−09 |
| 29e | 1.56E−08 |
| 29f | 1.56E−08 |
| 29g | 3.91E−09 |
| 29h | 6.25E−08 |
| 29i | 2.44E−09 |
| 29j | 9.77E−10 |
| 29k | 6.25E−08 |
| 35 | 2.50E−07 |
| 38 | 6.25E−08 |
| 43 | 3.91E−09 |
| 45 | 3.91E−09 |
| 48 | 1.56E−08 |
| 50 | 1.56E−08 |
| 52 | 6.25E−08 |
| 55 | 1.56E−08 |
| 55a | 6.25E−08 |
| 60 | 3.91E−09 |
| 68 | 1.56E−08 |
| 71 | 1.56E−08 |
| 72 | 6.25E−08 |
| 75 | 2.90E−07 |

Example 38: Intracellular Killing Assay 2

The rifamycin analog compounds' activity against *S. aureus* was tested in an intracellular "killing" assay.

The reagents used are shown in Table 29, below.

TABLE 29

Reagents for Intracellular Assay

| Reagent | Vendor | Catalogue # |
|---|---|---|
| RPMI | Gibco | 11835-030 |
| PBS | Gibco | 20012-043 |
| Triton X-100 | Sigma | TX1568-1 |
| RPMI | Gibco | 11875-093 |
| FBS | Gibco | 10082-147 |
| PMA | Sigma | P8139 |
| Costa 96 well plate | Corning | 3904 |
| TSA plates | Teknova | T0144 |
| Pen/Strep | Gibco | 15140-122 |
| Dilution plates | Greiner Bio one | 780271-FD |
| DMSO | VWR | WN182 |
| Rifampicin | Sigma | R3501 |
| Gentamicin | BioWhittaker | 17-519Z |

THP-1 monocytic cell line was grown in media (RMPI+10% FBS+1% Penicillin/Streptomycin), then seeded at a density of 1e5 cells/well in a 96 well plate and differentiated into macrophages for three days prior to infection using 200 nM PMA. An overnight culture of *S. aureus* NRS384 was grown in RPMI, washed twice with PBS and resuspended at 1e7 cfu/mL in PBS. THP-1 were washed with warm media (RMPI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing 2× with warm media and remaining extracellular *S. aureus* were killed by addition of media containing gentamicin (50 ug/mL). After 1 hour, media was aspirated and the indicated compound was added to infected macrophages in a dilution series starting at 1e-6 M, with 1:5 dilutions for 6 points ($1.0\times10^{-6}$ M, $2.0\times10^{-7}$ M, $4.0\times10^{-8}$ M, $8.0\times10^{-9}$ M, $1.6\times10^{-9}$ M, and $3.2\times10^{-10}$ M). The compounds were added in media containing 50 pg/mL gentamicin to prevent extracellular growth of *S. aureus*. After 2 hours, plates were washed 2× with warm RPMI without FBS, and 100 ul of THP-1 lysis buffer (0.1% Triton in PBS) was added to each well. *S. aureus* survival was enumerated by colony forming units through serial dilution and plating onto TSA.

The results of the intracellular killing assay are shown in Table 30. The minimum inhibitory concentration (MIC) corresponds to the lowest concentration of each compound that resulted in intracellular *S. aureus* below the limit of detection (50 cfu/mL). The intracellular MIC value indicated represents the median value of at least two independent experiments, unless indicated otherwise.

TABLE 30

Minimum inhibitory concentration (MIC) of antibiotics of the invention in an intracellular killing assay using THP cells

| Antibiotic tested | *S. aureus* Intracellular killing MIC (M) |
|---|---|
| Rifampicin | 1.0E−06 |
| P1 | 2.0E−07 |
| P2 | >1.0E−06 |
| 16f | 1.0E−06 |
| 16g | 2.0E−07 |
| 16h | 1.0E−06 |
| 16i | 1.0E−06 |
| 16j | 1.0E−06 |
| 16k | 1.0E−06 |
| 16l | 1.0E−06 |

TABLE 30-continued

| Minimum inhibitory concentration (MIC) of antibiotics of the invention in an intracellular killing assay using THP cells | |
|---|---|
| Antibiotic tested | *S. aureus* Intracellular killing MIC (M) |
| 16m | 1.0E−06 |
| 16n | 1.0E−06 |
| 16o | 2.0E−07 |
| 16p | 1.0E−06 |
| 16q | 1.0E−06 |
| 16r | 1.0E−06 |
| 16s | 1.0E−06 |
| 16t | 1.0E−06 |
| 16u | 1.0E−06 |
| 16v | 1.0E−06 |
| 16w | >1.0E−06 |
| 16x | >1.0E−06 |
| 16y | >1.0E−06 |
| 16z | >1.0E−06 |
| 16z-1 | 1.0E−06 |
| 17 | 2.0E−07 |
| 29 | 4.0E−08 |
| 29a | 4.0E−08 |
| 29b | 4.0E−08 |
| 29c | 4.0E−08 |
| 29d | 4.0E−08 |
| 29e | 4.0E−08 |
| 29f | 2.0E−07 |
| 29g | 2.0E−07 |
| 29h | 1.0E−06 |
| 29i | 2.0E−07 |
| 29j | 4.0E−08 |
| 29k | >1.0E−06 |
| 35 | >1.0E−06 |
| 38 | 1.0E−06 |
| 43 | 4.0E−08 |
| 45 | 1.0E−06 |
| 48 | 1.0E−06 |
| 50 | 1.0E−06 |
| 52 | 1.0E−06 |
| 55 | 2.0E−07 |
| 55a | >1.0E−06 |
| 60 | 2.0E−07 |
| 68 | 2.0E−07 |
| 71 | >1.0E−06 |
| 72 | >1.0E−06 |
| 75 | >1.0E−06 |

As Table 30 demonstrates, the intracellular killing MIC for rifamycin analogs according to the disclosure (and rifampicin) ranged from >1e-6 M to 4e-8 M, with 8 novel rifamycin analogs exhibiting potent intracellular killing activity.

Example 39: Intracellular *S. aureus* Antibody-Drug Conjugate Killing Assay 2 (Anti-WTA and Anti-Protein A)

The reagents used are shown in Table 31, below.

TABLE 31

| Reagents for Intracellular Assay | | |
|---|---|---|
| Reagent | Vendor | Catalogue # |
| RPMI | Gibco | 11835-030 |
| PBS | Gibco | 20012-043 |
| Triton X-100 | Sigma | TX1568-1 |
| RPMI | Gibco | 11875-093 |
| FBS | Gibco | 10082-147 |
| PMA | Sigma | P8139 |
| Costa 48 well plate | Corning | 3548 |
| TSA plates | Teknova | T0144 |
| Pen/Strep | Gibco | 15140-122 |
| Dilution plates | Greiner Bio one | 780271-FD |
| Gentamicin | BioWhittaker | 17-519Z |

Rifamycin analog compounds of the disclosure were conjugated to either an anti-WTA antibody (Anti-WTA mAb, hIgG1), an anti-Protein A antibody (anti-Protein A mAb, hIgG1 C103S), or a control antibody (Non-targeting isotype control, hIgG1).

To test the efficacy of Anti-*Staphylococcus aureus* antibody-drug conjugates (ADCs) of the present disclosure in vitro, an *S. aureus* intracellular killing assay was developed. For the assay, THP-1 monocytic cell line was grown in media (RMPI+10% FBS+1% Penicillin/Streptomycin), then seeded at a density of 1e5 cells/well in a 48 well plate and differentiated into macrophages for three days prior to infection using 200 nM PMA. An overnight culture of *S. aureus* NRS384 was grown in RPMI, washed twice with PBS and resuspended at 1e7 cfu/mL in PBS. The *S. aureus* suspension was preincubated with the indicated anti-*S. aureus* ADC in a dilution series starting at 10 ug/mL, with 1:3 dilutions for 6 points (10, 3.3, 1.1, 0.37, 0.12, and 0.041 pg/mL final concentrations) and the isotype control ADCs were tested at the highest concentration only. THP-1 were washed with warm media (RMPI without FBS) to remove the Penicillin/Streptomycin and then infected with the pre-incubated *S. aureus* suspension and the ADC, naked antibody or no mAb at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing 2× with warm media and remaining extracellular *S. aureus* were killed by addition of media containing gentamicin (50 μg/mL). After 24 hours, media was aspirated and wells washed 2× with warm RPMI without FBS, and 100 μl of THP-1 lysis buffer (0.1% Triton in PBS) and 150 μl of PBS were added to each well. *S. aureus* survival was enumerated by colony forming units through serial dilution and plating onto TSA.

Figure 5:
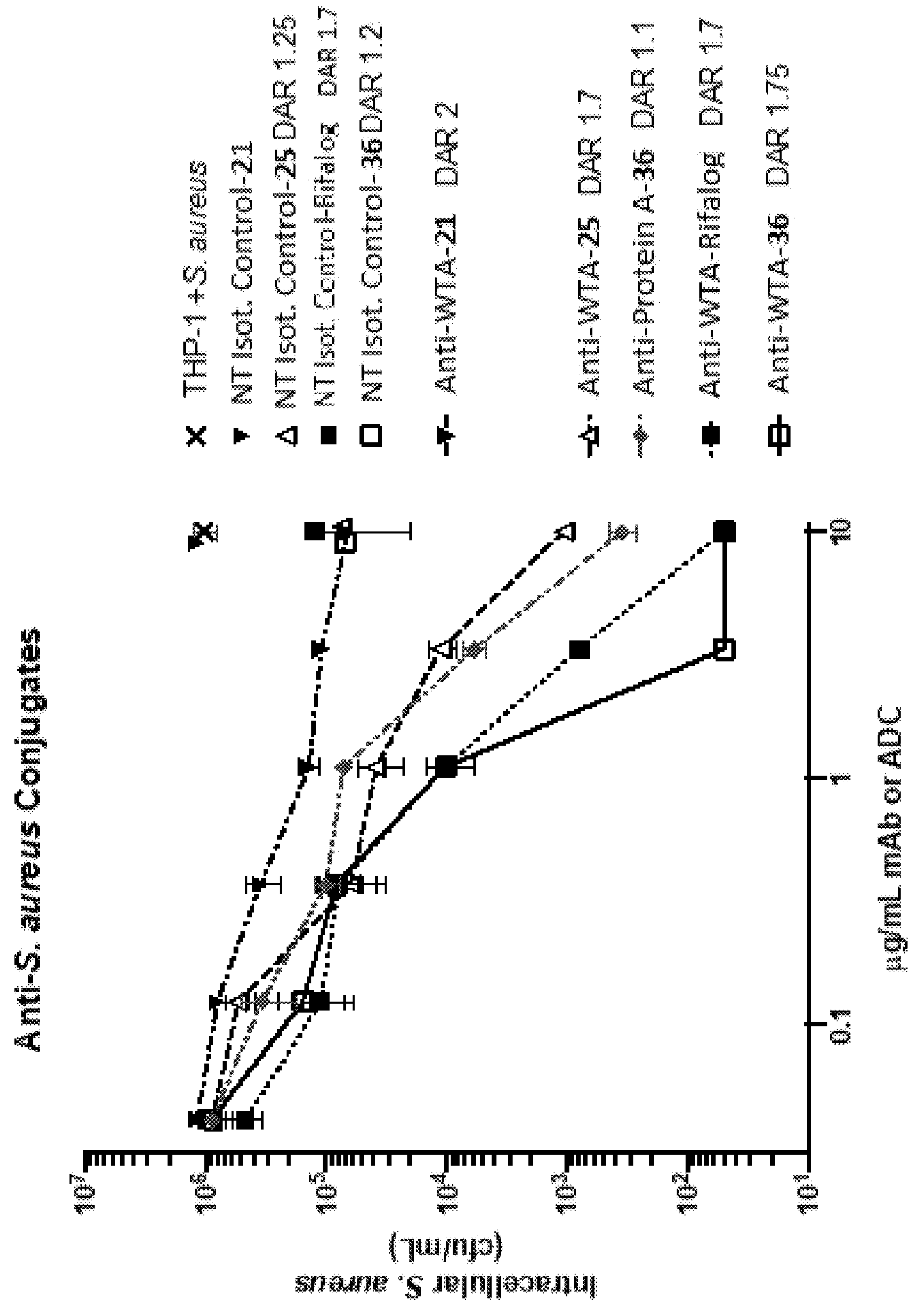
FIG. 5 is a plot of colony forming units of Anti-*Staphylococcus aureus* ADCs according to the disclosure in an intracellular killing assay using THP cells.

The results of the intracellular killing assay are shown in FIG. 5 and Table 32, with a limit of detection of 50 cfu/mL.

TABLE 32

| Colony forming units of Anti-*Staphylococcus aureus* ADCs of the disclosure in an intracellular killing assay using THP cells | | | | |
|---|---|---|---|---|
| | ncADC or mAb dose (ug/mL) | Average cfu/mL | Standard Deviation | Fold Reduction compared to *S. aureus* control |
| *S. aureus* control | none | 1,025,000 | 212,132 | 1 |
| Non-targeting isotype control | 10 | 600,000 | 141,421 | 2 |
| Anti-Protein A mAb | 10 | 500,000 | 70,711 | 2 |
| Anti-WTA mAb | 10 | 750,000 | 70,711 | 1 |
| Non-targeting isotype control-21 | 10 | 1,175,000 | 70,711 | 1 |
| Non-targeting isotype control-25 | 10 | 73,750 | 8,839 | 14 |
| Non-targeting isotype control-Rifalog | 10 | 128,750 | 22,981 | 8 |

TABLE 32-continued

Colony forming units of Anti-*Staphylococcus aureus* ADCs of the disclosure in an intracellular killing assay using THP cells

| | ncADC or mAb dose (ug/mL) | Average cfu/mL | Standard Deviation | Fold Reduction compared to *S. aureus* control |
|---|---|---|---|---|
| Non-targeting isotype control-36 | 10 | 70,000 | 0 | 15 |
| Anti-WTA mAb-21 | 10 | 65,833 | 46,256 | 16 |
| | 3.3 | 109,167 | 3,819 | 9 |
| | 1.1 | 138,333 | 26,732 | 7 |
| | 0.4 | 350,000 | 108,972 | 3 |
| | 0.1 | 800,000 | 108,972 | 1 |
| | 0.04 | 1,175,000 | 139,194 | 1 |
| Anti-WTA mAb-25 | 10 | 1,067 | 113 | 961 |
| | 3.3 | 11,250 | 2,883 | 91 |
| | 1.1 | 38,333 | 16,073 | 27 |
| | 0.4 | 61,667 | 28,976 | 17 |
| | 0.1 | 533,333 | 152,753 | 2 |
| | 0.04 | 883,333 | 289,756 | 1 |
| Anti-WTA mAb-Rifalog | 10 | 50 | 0 | 20,500 |
| | 3.3 | 808 | 138 | 1,268 |
| | 1.1 | 10,250 | 4,265 | 100 |
| | 0.4 | 78,333 | 40,646 | 13 |
| | 0.1 | 110,833 | 39,713 | 9 |
| | 0.04 | 466,667 | 125,831 | 2 |
| Anti-Protein A mAb-36 | 10 | 350 | 87 | 2,929 |
| | 3.3 | 5,917 | 1,258 | 173 |
| | 1.1 | 71,667 | 8,780 | 14 |
| | 0.4 | 100,000 | 22,220 | 10 |
| | 0.1 | 341,667 | 166,458 | 3 |
| | 0.04 | 883,333 | 128,290 | 1 |
| Anti-WTA mAb-36 | 10 | 50 | 0 | 20,500 |
| | 3.3 | 50 | 0 | 20,500 |
| | 1.1 | 10,250 | 1,521 | 100 |
| | 0.4 | 82,500 | 32,692 | 12 |
| | 0.1 | 156,667 | 97,511 | 7 |
| | 0.04 | 883,333 | 189,297 | 1 |

Control ADCs (Non-targeting isotype control conjugates), which are a human IgG1 isotype and therefore able to bind to Protein A on *S. aureus*, reduced intracellular *S. aureus* viability by ~1 log or less compared to the untreated control. Anti-WTA mAb-21, which releases a rifampicin payload, reduced the bacterial burden similarly to the control ADCs. Anti-*S. aureus* ADCs which delivered a payload with potent intracellular killing activity (Anti-WTA mAb-25, Anti-Protein A mAb-36, Anti-WTA mAb-Rifalog, and Anti-WTA mAb-36), were more effective than the rifampicin conjugate (Anti-WTA mAb-21) at reducing intracellular *S. aureus*, with reductions of 3 log or greater compared to the untreated control. Anti-WTA mAb-36 consistently reduced *S. aureus* viability more than Anti-WTA mAb-Rifalog in multiple experiments.

Example 40: Intracellular *S. aureus* Antibody-Drug Conjugate Killing Assay 3 (MSR1)

The reagents used are shown in Table 33, below.

TABLE 33

Reagents for Intracellular Assay

| Reagent | Vendor | Catalogue # |
|---|---|---|
| RPMI | Gibco | 11835-030 |
| PBS | Gibco | 20012-043 |
| Triton X-100 | Sigma | TX1568-1 |
| RPMI | Gibco | 11875-093 |
| FBS | Gibco | 10082-147 |
| PMA | Sigma | P8139 |
| Costa 48 well plate | Corning | 3548 |
| TSA plates | Teknova | T0144 |
| Pen/Strep | Gibco | 15140-122 |
| Dilution plates | Greiner Bio one | 780271-FD |
| Gentamicin | BioWhittaker | 17-519Z |

To test the efficacy of an anti-MSR1 Ab-antibiotic ncADC of the disclosure in vitro, an intracellular *S. aureus* killing assay was utilized. For the assay, a THP-1 monocytic cell line was grown in media comprised of RPMI containing 10% FBS and 1% Penicillin/Streptomycin, then was seeded at a density of $1\times10^5$ cells/well in a 48 well plate and differentiated into macrophages for three days prior to infection using 200 nM Phorbol Myristate Acetate (PMA). An overnight culture of *S. aureus* MRSA strain NRS384 was grown in RPMI, washed twice with PBS and subsequently resuspended at $1\times10^7$ cfu/mL in PBS. THP-1 cells were washed with warm media (RPMI without FBS) to remove the Penicillin/Streptomycin and then infected with the *S. aureus* suspension at a multiplicity of infection of 10:1 (*S. aureus*: macrophages). Plates were spun at 300×g for 5 minutes to synchronize adhesion of the bacteria, then incubated at 37° C. for 2 hours. Free-floating bacteria were removed by washing twice with warm media and remaining extracellular *S. aureus* were killed by addition of media containing 50 pg/mL of gentamicin. After 1 hour, media was aspirated and the anti-MSR1 Ab-antibiotic ncADCs (H1H21234N-N297Q-25 and H1H21234N-N297Q-80) at different doses (10 pg/mL, 3.3 pg/mL, 1.1 pg/mL, 0.4 pg/mL, 0.1 pg/mL and 0.04 pg/mL) and the isotype control-antibiotic ncADC (Isotype control-N297Q-25 and Isotype Control-N297Q-80) at 10 pg/mL were added to infected macrophages in media containing 50 pg/mL gentamicin to prevent extracellular growth of *S. aureus*. A sample without any ncADC was also included for reference. After 24 hours, plates were washed twice with warm RPMI without FBS and then 100 μL of 0.1% Triton X-100 in PBS was added and incubated for 10 minutes to lyse the THP-1. *S. aureus* survival was enumerated by colony forming units through serial dilution in PBS and plating onto trypticase soy agar plates.

The results are summarized in Table 34, below.

TABLE 34

Average colony forming units of anti-MSRl Ab-Antibiotic

| | ncADC dose (μg/mL) | Average cfu/mL | Standard Deviation | Fold Reduction compared to *S. aureus* control |
|---|---|---|---|---|
| *S. aureus* control | none | 1,350,000 | 139,194 | 1 |
| Isotype Control-N297Q-25 | 10 | 608,333 | 52,042 | 2 |
| MSR1 ncADC H1H21234N-N297Q-25 | 10 | 1,325 | 87 | 1,019 |
| | 3.3 | 4,917 | 722 | 275 |
| | 1.1 | 13,250 | 1,887 | 102 |
| | 0.4 | 56,667 | 7,638 | 24 |
| | 0.1 | 82,500 | 17,500 | 16 |
| | 0.04 | 1,025,000 | 43,301 | 1 |
| Isotype Control-N297Q-80 | 10 | 1,208,333 | 94,648 | 1 |
| MSR1 ncADC | 10 | 50 | 0 | 27,000 |

TABLE 34-continued

| Average colony forming units of anti-MSRl Ab-Antibiotic | | | | |
|---|---|---|---|---|
| | ncADC dose (μg/mL) | Average cfu/mL | Standard Deviation | Fold Reduction compared to *S. aureus* control |
| H1H21234N-N297Q-80 | 3.3 | 50 | 0 | 27,000 |
| | 1.1 | 50 | 0 | 27,000 |
| | 0.4 | 7,417 | 2,876 | 182 |
| | 0.1 | 75,833 | 15,275 | 18 |
| | 0.04 | 758,333 | 230,940 | 2 |

As shown in Table 34, the anti-MSR1 Ab-antibiotic ncADCs (H1H21234N-N297Q-25 and H1H21234N-N297Q-80) demonstrated the ability to reduce intracellular *S. aureus* in macrophages in vitro in a dose-dependent manner compared to the untreated control. Macrophages treated with the isotype control-antibiotic ncADC (Isotype control-N297Q-25 and Isotype control-N297Q-80) at 10 μg/mL harbored intracellular *S. aureus* at a similar level to the untreated control. These data demonstrate that an anti-MSR1 Ab-antibiotic ncADC according to the disclosure can be used to effectively kill pathogens residing within a macrophage reservoir.

Example 41: *S. aureus* IV Disseminated Infection Mouse Model (4 Day Model)

Figure 4:
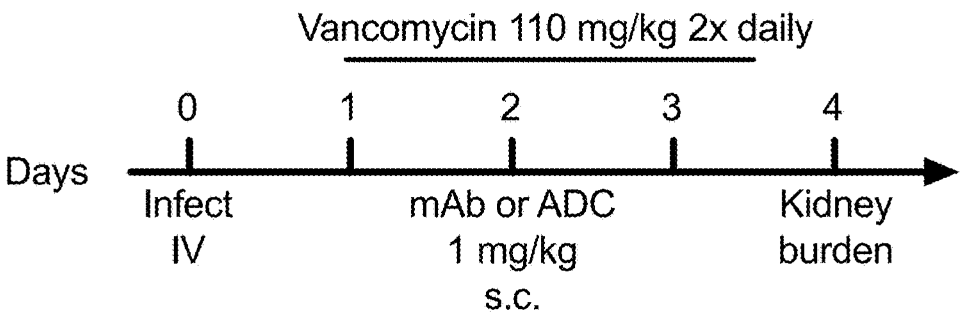
FIG. 4 is a schematic of four day *S. aureus* infection model.

To test the efficacy of an anti-*S. aureus* Ab-antibiotic ncADC of the disclosure alone and in combination with the standard of care MRSA antibiotic vancomycin in vivo, a four day intravenous disseminated infection model was utilized. *S. aureus* MSRA strain NRS384 was grown overnight in Tryptic soy broth (TSB) and sub-cultured to mid-logarithmic phase. Bacteria were then washed twice with PBS and resuspended in PBS at a concentration of 1.5×10^8 cfu/mL. Balb/c mice were then infected intravenously through the tail vein with 100 μL of the bacterial suspension, for a final infectious dose of 1.5×10∂cfu/mouse. In the study, mice were treated with either vancomycin alone, an isotype control Ab-Antibiotic ncADC (Isotype control Ab-Antibiotic ncADC-Rifalog), which is an anti-WTA antibody conjugated to Rifalog, an anti-WTA antibody, an anti-WTA Ab-Antibiotic ncADC (anti-WTA Ab-Antibiotic ncADC-36), which is an anti-WTA antibody conjugated to compound 36 according to the disclosure, a second anti-WTA Ab-Antibiotic ncADC (anti-WTA Ab-Antibiotic ncADC-25), which is an anti-WTA antibody conjugated to compound 25 according to the disclosure, or a third anti-WTA Ab-Antibiotic ncADC (anti-WTA Ab-Antibiotic ncADC-Rifalog), an isotype control Ab-Antibiotic ncADC (Isotype control Ab-Antibiotic ncADC-Rifalog) plus vancomycin, an anti-WTA antibody plus vancomycin, an anti-WTA Ab-Antibiotic ncADC (anti-WTA Ab-Antibiotic ncADC-36), a second anti-WTA Ab-Antibiotic ncADC (anti-WTA Ab-Antibiotic ncADC-25) plus vancomycin, or a third anti-WTA Ab-Antibiotic ncADC (anti-WTA Ab-Antibiotic ncADC-Rifalog) plus vancomycin. For treatment groups that included vancomycin, it was dosed from 1 day to 3 days post infection at 110 mg/kg subcutaneously twice daily. For treatment groups that included antibodies and ncADCs, they were administered 2 days after infection subcutaneously at 1 mg/kg. A no treatment infected control and an uninfected control were included in the study. Mice were monitored for weight loss and body conditioning score throughout the infection. At four days post infection, mice were euthanized, and the *S. aureus* kidney burden was quantified. For quantification, the kidneys were homogenized followed by enumeration of colony forming units through serial dilution in PBS and plating onto trypticase soy agar plates. Infection scheme is represented in FIG. 4. Data is represented in Table 35 as median *S. aureus* kidney burden in mice.

TABLE 35

Median *S. aureus* kidney burden in mice treated with anti-*S. aureus* Ab-Antibiotic ncADC at 1 mg/kg alone and in combination with vancomycin (4 day infection model).

| mAb or conjugate dose (1 mg/kg) | Vancomycin treatment | Median cfu/kidney pair | Standard Deviation | Mortality (n) |
|---|---|---|---|---|
| Uninfected Control | – | 250 (limit of detection) | — | 0/1 |
| Infected Control | – | 3.63E+07 | 3.72E+07 | 2/5 |
| Non-targeting Isotype Control Ab-Antibiotic ncADC-Rifalog | – | 1.50E+08 | 8.32E+07 | 2/5 |
| Anti-WTA mAb | – | 2.19E+08 | 3.78E+08 | 1/5 |
| Anti-WTA Ab-Antibiotic ncADC-Rifalog | – | 5.38E+07 | 1.34E+08 | 0/5 |
| Anti-WTA Ab-Antibiotic ncADC-25 | – | 1.06E+06 | 2.77E+06 | 1/5 |
| Anti-WTA Ab-Antibiotic ncADC-36 | – | 1.61E+06 | 8.10E+07 | 1/5 |
| Vancomycin control | + | 4.38E+05 | 6.92E+05 | 0/5 |
| Non-targeting Isotype Control Ab-Antibiotic ncADC-Rifalog | + | 3.13E+06 | 5.70E+06 | 0/5 |
| Anti-WTA mAb | + | 4.50E+05 | 8.12E+06 | 0/5 |
| Anti-WTA Ab-Antibiotic ncADC-Rifalog | + | 2.50E+02 | 3.24E+06 | 0/5 |
| Anti-WTA Ab-Antibiotic ncADC-25 | + | 3.75E+02 | 1.55E+04 | 0/5 |
| Anti-WTA Ab-Antibiotic ncADC-36 | + | 2.50E+02 | 2.21E+05 | 0/5 |

Limit of detection = 250 colony forming units (cfu)

As shown in Table 35, intravenous infection with *S. aureus* MRSA strain NRS384 results in high median bacterial burden in the kidneys of 3.63E+07 cfus/kidney pair. As a monotherapy, anti-WTA Ab Antibiotic ncADC-25 and anti-WTA Ab Antibiotic ncADC-36 reduced the kidney bacterial burden by ~2 logs. When the anti-WTA Ab antibiotic ncADCs tested were administered in combination with vancomycin, all treatment groups had a further reduction in kidney bacterial burden by ~3 logs compared to the vancomycin treated control.

Example 42: *S. aureus* IV Advanced Disseminated Infection Mouse Model (8 Day Model)

To test the efficacy of anti-*S. aureus* Ab-antibiotic ncADCs of the disclosure in combination therapy with standard of care vancomycin in vivo, two different 8 day intravenous disseminated infection models was performed. In this model, treatment was initiated at an advanced infection stage where abscesses have already formed. *S. aureus* MSRA strain NRS384 was grown overnight in Tryptic soy broth (TSB) and sub-cultured to mid-logarithmic phase. Bacteria were then washed twice with PBS and resuspended in PBS at a concentration of 1.5×10^8 cfu/mL. Balb/c mice were then infected intravenously through the tail vein with 100 uL of the bacterial suspension, for a final infectious dose of 1.5×10⑧cfu/mouse. In the first study, mice were treated either vancomycin alone, an isotype control antibody plus vancomycin, an isotype control Ab-ncADC (Isotype control-36) plus vancomycin, an anti-WTA antibody plus vancomycin, an anti-WTA Ab-Antibiotic ncADC (anti-WTA Ab-Antibiotic ncADC-36), or a different anti-WTA Ab-Antibiotic ncADC (anti-WTA Ab-Antibiotic ncADC-25) plus vancomycin. Mice were also treated either vancomycin alone, an isotype control antibody plus vancomycin, an isotype control Ab-Antibiotic ncADC (Isotype control Ab-Antibiotic ncADC-36) plus vancomycin, an anti-Protein A antibody plus vancomycin, or an anti-Protein A Ab-Antibiotic ncADC (anti-Protein A Ab-Antibiotic ncADC-36).

In the second study, mice were treated either vancomycin alone, an isotype control antibody plus vancomycin, an isotype control Ab-Antibiotic ncADC (Isotype control Ab-Antibiotic ncADC-36) plus vancomycin, a second isotype control Ab-Antibiotic ncADC (Isotype control Ab-Antibiotic ncADC-25) plus vancomycin, a third isotype control Ab-Antibiotic ncADC (Isotype control Ab-Antibiotic ncADC-21) plus vancomycin, an anti-WTA antibody plus vancomycin, an anti-WTA Ab-Antibiotic ncADC (anti-WTA Ab-Antibiotic ncADC-36), a second anti-WTA Ab-Antibiotic ncADC (anti-WTA Ab-Antibiotic ncADC-25) plus vancomycin, or a third anti-WTA Ab-Antibiotic ncADC (anti-WTA Ab-Antibiotic ncADC-21) plus vancomycin. In all studies, for treatment groups that included vancomycin, it was dosed from three to seven days post infection at 110 mg/kg subcutaneously twice daily. For treatment groups that included antibodies and ncADCs, they were administered four days after infection subcutaneously at 2 mg/kg for the first study or 5 mg/kg for the second study. A no treatment infected control and an uninfected control were included in each of the studies. Mice were monitored for weight loss and body conditioning score throughout the infection. At eight days post infection, mice were euthanized, and the *S. aureus* kidney burden was quantified. For quantification, the kidneys were homogenized followed by enumeration of colony forming units through serial dilution in PBS and plating onto trypticase soy agar plates. Data points represent the kidney burden from individual mice tested.

TABLE 36

Average *S. aureus* kidney burden in mice treated with isotype control and anti-WTA Ab-Antibiotic ncADC at 2 mg/kg in combination with vancomycin

| mAb or conjugate dose (2 mg/kg) | Vancomycin treatment | Median cfu/kidney pair | Standard Deviation | Mortality (n) |
|---|---|---|---|---|
| Uninfected Control | – | 2.50E+02 (limit of detection) | 0.00E+00 | 0/5 |
| Infected Control | – | 4.63E+08 | 2.56E+08 | 3/6 |
| Vancomycin Control | + | 7.25E+06 | 1.83E+07 | 7/11 |
| Isotype Control mAb | + | 6.50E+06 | 1.12E+08 | 1/6 |
| Non-targeting Isotype Control Ab-Antibiotic ncADC-Rifalog | + | 1.56E+06 | 1.12E+06 | 1/5 |
| Non-targeting Isotype Control Ab-Antibiotic ncADC-36 | + | 4.56E+06 | 1.21E+07 | 2/7 |
| anti-WTA mAb | + | 3.50E+06 | 8.78E+06 | 0/5 |
| Anti-WTA Ab-Antibiotic ncADC-Rifalog | + | 2.25E+05 | 1.45E+06 | 1/6 |
| Anti-WTA Ab-Antibiotic ncADC-25 | + | 2.50E+02 | 1.84E+05 | 0/6 |
| Anti-WTA Ab-Antibiotic ncADC-36 | + | 4.13E+04 | 1.25E+05 | 0/5 |

Figure 6:
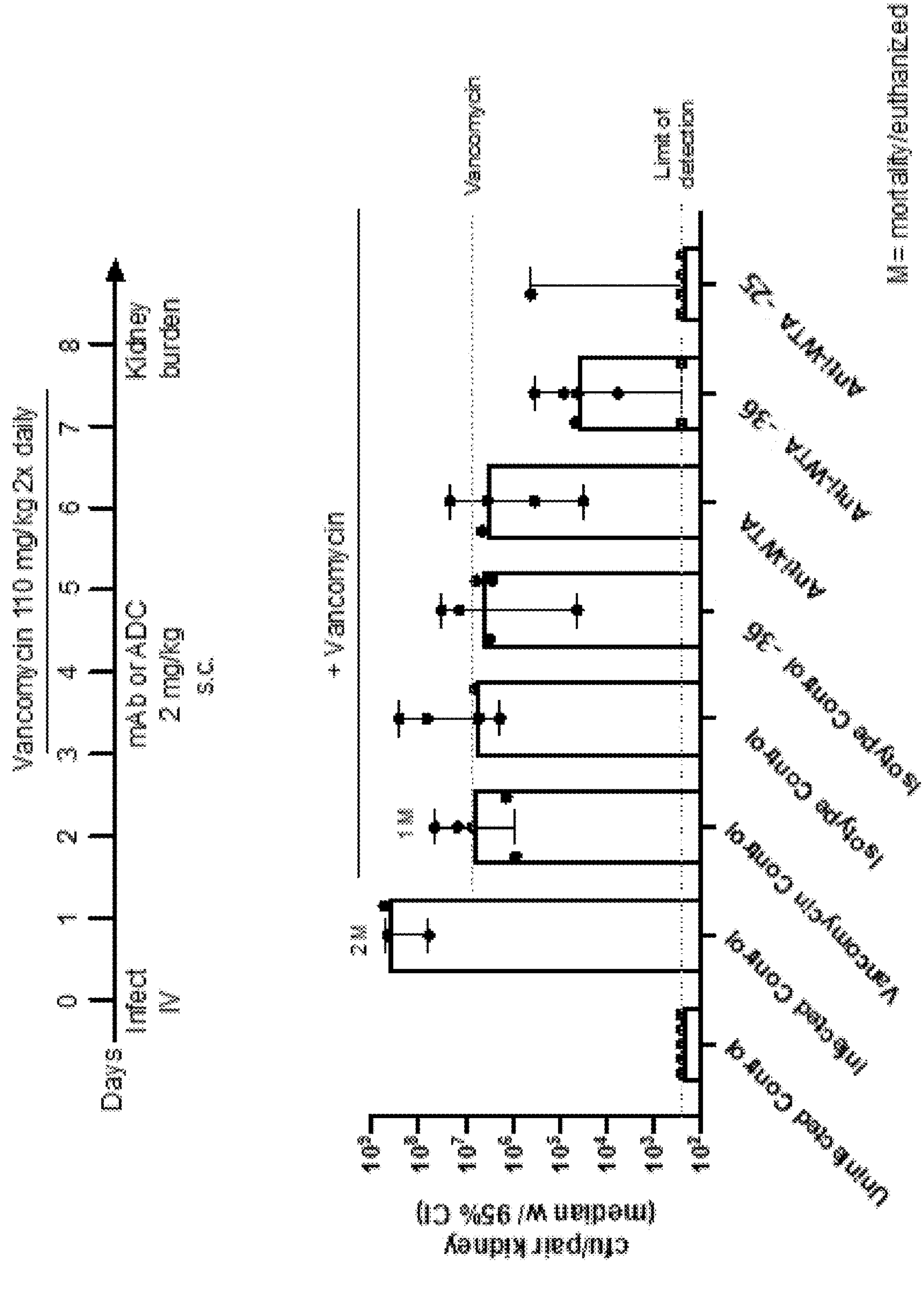
FIG. 6 depicts the average *S. aureus* kidney burden in mice treated with isotype control and anti-WTA Ab-Antibiotic ncADC (antibody-drug conjugates) according to the disclosure at 2 mg/kg in combination with vancomycin.

For the first study, as shown in FIG. 6 and Table 36, intravenous infection with *S. aureus* MRSA strain NRS384 results in high median bacterial burden in the kidneys of 4.63E+08 cfu/kidney pair. Vancomycin treatment alone reduced *S. aureus* kidney burden by 1-2 logs. Combination treatment of vancomycin with the isotype control mAb, anti-WTA monoclonal mAb, and isotype control Ab-Antibiotic ncADC-36 did not result in a further reduction in kidney bacterial burden compared to vancomycin treated mice. When the anti-WTA Ab-Antibiotic ncADC-36 and anti-WTA Ab-Antibiotic ncADC-25 were administered in combination with vancomycin, there was a further ~100 and ~10,000 times reduction in median kidney bacterial burden, respectively.

TABLE 37

Average *S. aureus* kidney burden in mice treated with isotype control and anti-Protein A Ab-Antibiotic ncADC at 2 mg/kg in combination with vancomycin

| mAb or conjugate dose (2 mg/kg) | Vancomycin treatment | Median cfu/kidney pair | Standard Deviation | Mortality (n) |
|---|---|---|---|---|
| Uninfected Control | – | 2.50E+02 | 0.00E+00 | 0/5 |
| Infected Control | – | 4.63E+08 | 2.56E+08 | 3/6 |
| Vancomycin Control | + | 7.25E+06 | 1.83E+07 | 7/11 |
| Non-targeting Isotype Control mAb | + | 6.50E+06 | 1.12E+08 | 1/6 |
| Non-targeting Isotype Control Ab-Antibiotic ncADC 36 | + | 4.56E+06 | 1.21E+07 | 2/7 |
| Anti-Protein A Ab | + | 5.69E+04 | 1.22E+07 | 0/6 |
| Anti-Protein A Ab-Antibiotic ncADC - Rifalog | + | 7.08E+04 | 2.13E+05 | 0/6 |
| Anti-Protein A Ab-Antibiotic ncADC - 36 | + | 6.25E+03 | 3.64E+05 | 1/6 |

Figure 7:
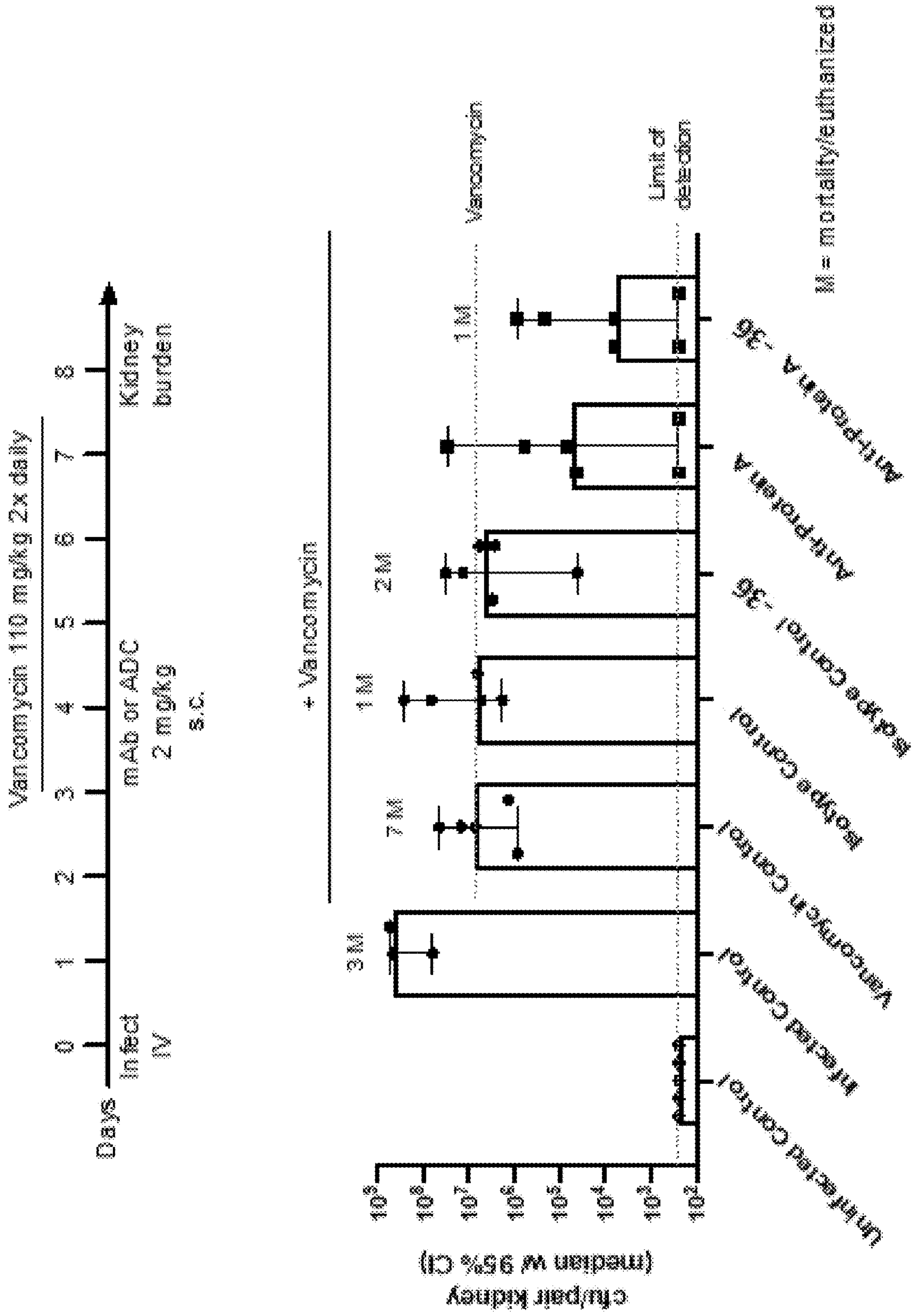
FIG. 7 depicts the average *S. aureus* kidney burden in mice treated with isotype control and anti-Protein A Ab-Antibiotic ncADC according to the disclosure at 2 mg/kg in combination with vancomycin.

Also in the first study, as shown in FIG. 7 and Table 37, intravenous infection with *S. aureus* MRSA strain NRS384 results in high median bacterial burden in the kidneys of 4.63E+08 cfu/kidney pair. Vancomycin treatment alone reduced *S. aureus* kidney bacterial burden by 1-2 logs. Combination treatment of vancomycin with the isotype control mAb and isotype control Ab-Antibiotic ncADC-36 did not result in a further reduction in kidney bacterial burden compared to vancomycin treated mice. When anti-Protein A mAb and anti-Protein A Ab-Antibiotic ncADC-36 were administered in combination with vancomycin, there was a further ~100 and ~1,000 times reduction in median kidney bacterial burden, respectively.

TABLE 38

Average *S. aureus* kidney burden in mice treated with isotype control and anti-WTA Ab-Antibiotic ncADC at 5 mg/kg in combination with vancomycin

| mAb or conjugate dose (5 mg/kg) | Vancomycin treatment | Median cfu/kidney pair | Standard Deviation | Mortality (n) |
|---|---|---|---|---|
| Uninfected Control | – | 2.50E+02 | 0.00E+00 | 0/2 |
| Infected Control | – | 2.50E+07 | 1.00E+07 | 2/5 |
| Vancomycin Control | + | 1.88E+06 | 6.17E+05 | 2/5 |
| Non-targeting Isotype Control mAb | + | 3.13E+06 | 1.28E+07 | 1/4 |
| Non-targeting Isotype Control Ab-Antibiotic ncADC-Rifalog | + | 2.77E+06 | 1.28E+07 | 1/4 |
| Non-targeting Isotype Control Ab-Antibiotic ncADC-36 | + | 1.50E+06 | 5.78E+06 | 0/5 |
| Non-targeting Isotype Control Ab-Antibiotic ncADC 25 | + | 4.13E+05 | 1.68E+06 | 0/5 |
| Non-targeting Isotype Control Ab-Antibiotic ncADC-21 | + | 2.50E+06 | 1.56E+07 | 0/5 |
| Anti-WTA mAb | + | 2.13E+06 | 1.95E+06 | 0/5 |
| Anti-WTA mAb-Antibiotic ncADC-Rifalog | + | 3.50E+04 | 1.99E+04 | 2/5 |
| Anti-WTA mAb-Antibiotic ncADC-36 | + | 2.25E+06 | 3.21E+06 | 0/5 |
| Anti-WTA mAb-Antibiotic ncADC 25 | + | 8.56E+03 | 2.02E+04 | 1/5 |
| Anti-WTA mAb-Antibiotic ncADC 21 | + | 2.13E+06 | 1.48E+07 | 0/5 |

Figure 8:
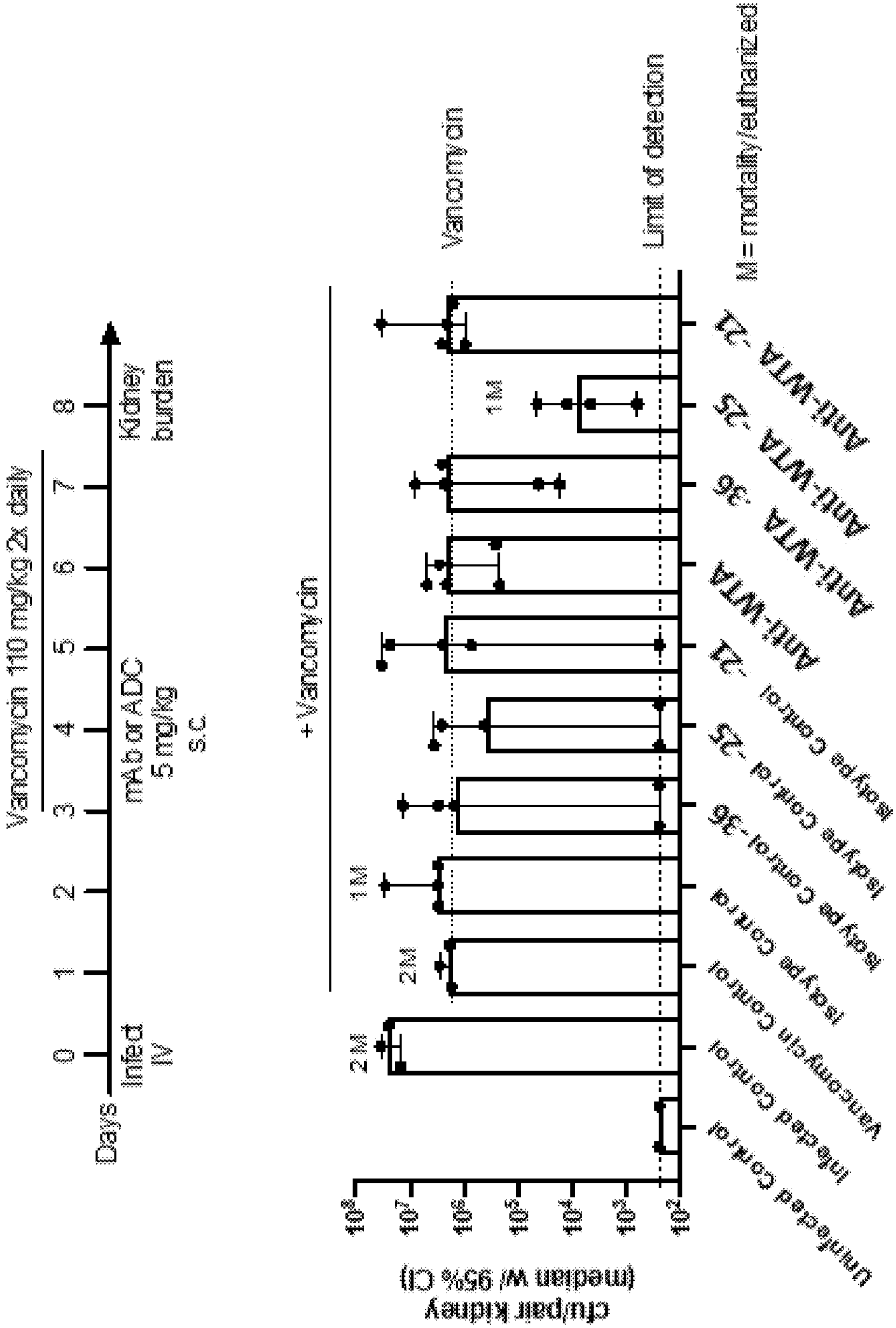
FIG. 8 depicts the average *S. aureus* kidney burden in mice treated with isotype control and anti-WTA Ab-Antibiotic ncADC according to the disclosure at 5 mg/kg in combination with vancomycin.

For the second study, as shown in FIG. 8 and Table 38, intravenous infection with *S. aureus* MRSA strain NRS384 results in high median bacterial burden in the kidneys of 2.50E+07 cfus/kidney pair. Vancomycin treatment alone reduced *S. aureus* kidney bacterial burden by 1-2 logs. Combination treatments with vancomycin and isotype control mAb, anti-WTA mAb, isotype control Ab-antibiotic ncADCs, anti-WTA Ab-antibiotic ncADC-36, or anti-WTA-Ab-antibiotic ncADC-21 (Rifampicin ADC) did not result in a further reduction in kidney bacterial burden compared to vancomycin treated mice. However, when the anti-WTA Ab-Antibiotic ncADC-25 tested were administered in combination with vancomycin, there was a further ~100 times reduction in median kidney bacterial burden.

Example 43: Antibody Engineered Cysteine Deblocking

Anti-Protein A (H1xH15140P*/*) and a nontargeting antibody control engineered antibodies were created by mutating the interchain disulfide forming heavy chain C103S. The antibodies are expressed in CHO cells and need to be deblocked on the native light chain cysteine using mild reduction in PBS at room temperature by the addition of a thirty fold molar excess of reducing agent, TCEP followed by buffer exchange. To reform the two heavy interchain disulfide bonds, the antibody was incubated for three hours at room temperature with $CuSO_4$ or with dhAA at a two to twenty fold molar excess. The reduced and oxidized antibody was buffer exchanged into PBS to remove oxidizing agent. This process produces two free thiols that reside on the light chain and are available for maleimide conjugation.

The anti-WTA engineered antibody was taken from the literature (Lehar et al, Nature 2015 527, 323-328; antibody 4497 described in US20140356375 and WO2016090038, the content of which is incorporated herein by reference in its entirety) and has a light chain mutation V205C to provide 2 sites for maleimide conjugation. The same procedure above was used to deblock the engineered cysteines.

Conjugation of Antibody Engineered Deblocked Cysteine to Linker Payload

To the reduced and oxidized antibody (1-10 mg/ml) in PBS pH7.5, the maleimido linker payload (2 equivalents/SH group, Lehar et al, Nature 527, 323-328), or the linker payloads of this filing, in DMSO (10 mg/ml) was added. The reaction proceeded for 2 hrs. The conjugates were purified into PBS by size exclusion chromatography and sterile filtered. Protein concentrations and payload to antibody ratios were determined by UV spectral analysis. Size-exclusion HPLC established that all conjugates used were >95% monomeric, and RP-HPLC established that there was <1% unconjugated linker payload. All conjugated antibodies were analyzed by HIC for linker payload loading values. Payload to antibody ratios are reported in Table 39.

Conjugation Method for Aglycosylated Antibodies (H1H21234N and Nontargeting Antibody Control 2)

The antibody (1-10 mg/ml) in 50 mM HEPES, 150 mM NaCl, pH 7.5, was treated with 1 mM dithiothreitol at 37° C. for 30 min. After gel filtration (G-25, pH 4.5 sodium acetate), the maleimido linker payload derivative compound 25 (Rifanalog M2767) (1.2 equivalents/SH group) in DMSO (10 mg/ml) was added to the reduced antibody and the mixture adjusted to pH 7.0 with 1 M HEPES (pH 7.4). The conjugates were purified using PBS with 5% glycerol by size exclusion chromatography and sterile filtered. Protein concentrations and payload to antibody ratios were determined by UV spectral analysis. Size-exclusion HPLC established that all conjugates used were >95% monomeric. All conjugated antibodies were analyzed by HIC for linker payload loading values. Payload to antibody ratios are reported in Table 39.

TABLE 39

Purity and drug to antibody ratios (DAR) of conjugates.

| Antibody Drug Conjugate | DAR (by HIC) | DAR (by ESI-MS) | Purity (by SEC) | Yield |
|---|---|---|---|---|
| z | | z | z | z |
| Anti-WTA-rifalog | 1.8 | | >95% | 53% |
| Anti-WTA-21 (rifampicin control) | 2.0 | | >95% | 70% |
| Anti-WTA-25 | 1.7 | | >95% | 50% |
| Anti-WTA-36 | 1.8 | | >95% | 40% |
| Anti-Protein A-rifalog | 1.9 | | >95% | 30% |
| Anti-Protein A-36 | 1.1 | | >95% | 40% |
| H1H21234N-25 | 3 | | >95% | 50% |
| nontargeting antibody control 1- rifalog | 1.7 | | >95% | 60% |
| nontargeting antibody control 1-21 (Rifampicin) | 2.0 | | >95% | 70% |
| nontargeting antibody control 1-25 | 1.3 | | >95% | 50% |
| nontargeting antibody control 1-36 | 1.2 | | >95% | 40% |
| nontargeting antibody control 2-25 | 2 | | >95% | 50% |

Characterization of Conjugates by Hydrophobic Interaction Chromatography (HIC)

To determine the loading of the linker-payloads on the antibody, the conjugates were run on Agilent 1260 using a TSK-NPR Butyl HIC column using a linear gradient of 1M potassium phosphate pH 8.5 to water over 60 min. The payload loading was determined by integration of peak areas corresponding to the species of conjugated and unconjugated antibody.

Characterization of Conjugates by ESI-MS

To determine the loading of the linker-payloads on the antibody (cysteine conjugates), the conjugates were deglycosylated, reduced, and analyzed by LC-MS.

For the assay, 50 pg of the conjugate was diluted with mili-Q water to a final concentration of 1 mg/mL. Ten μL of PNGase F solution [PNGase F solution was prepared by adding 150 μL of PNGase F stock (New England Biolabs, Cat #P0704L) and 850 μL of mili-Q water and mixed well] was added to the diluted conjugate solution and then incubated at 37° C. overnight. 2.4 μL of 0.5 M TCEP was added to the sample such that the resulting material had a final TCEP concentration of 20 mM and this was then incubated at 50° C. for 30 minutes. Injections of 10 μL of each sample were made onto LC-MS (Waters Synat G2-Si) and eluted with 0.1 mL/minute of a gradient mobile phase 20-40% of mobile phase B over 25 minutes (Mobile Phase A: 0.1% v/v FA in $H_2O$; Mobile Phase B: 0.1% v/v FA in Acetonitrile). The LC separation was achieved on Waters Acquity BEH C18 column (1.0×50 mM, 1.7 μM).

The mass spectrometry spectra were deconvoluted and the identified light and heavy chain peaks represent the light chain (L) with linker-payload values=0 and 1, heavy chain (H) with linker-payload values=0, 1, 2, and 3. From the intensity values of each species, the drug to antibody ratio (DAR) was calculated using equation below for a homodimer antibody conjugate.

$$DAR = 2*\left[\frac{L1}{L0+L1} + \frac{H1+2*H2+3*H3}{H0+H1+H2+H3}\right]$$

As various changes can be made in the above-described subject matter without departing from the scope and spirit of the present disclosure, it is intended that all subject matter contained in the above description, or defined in the appended claims, be interpreted as descriptive and illustrative of the present disclosure. Many modifications and variations of the present disclosure are possible in light of the above teachings. Accordingly, the present description is intended to embrace all such alternatives, modifications, and variances which fall within the scope of the appended claims.

All patents, applications, publications, test methods, literature, and other materials cited herein are hereby incorporated by reference in their entirety as if physically present in this specification.

What is claimed is:

1. An antibody-drug conjugate comprising an antibody, or an antigen-binding fragment thereof, conjugated via a linker or through a linker-spacer to a rifamycin analog having the structure of Formula (XXI):

(XXI)

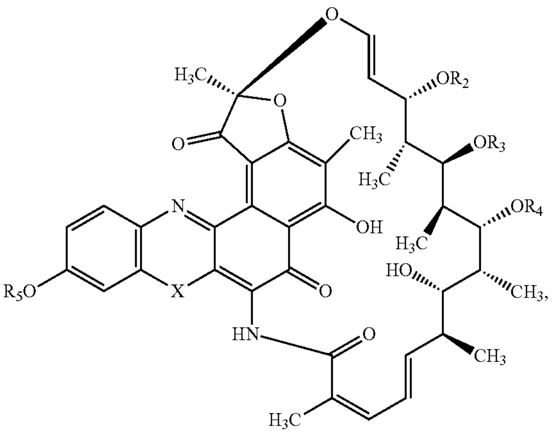

wherein:

X is selected from —O—, —S—, and —NR*—;

$R_5$ is selected from a bond; an aliphatic $C_1$-$C_{20}$ hydrocarbon which further comprises 0-8 heteroatoms selected from halogen, O, N, and S;

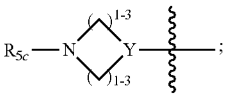

or

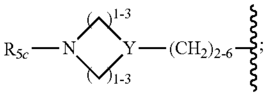

wherein Y is C or N;

$R_2$, $R_3$, and $R_4$ are independently selected from a hydrogen, a straight chained, branched or cyclic aliphatic $C_3$-$C_{20}$ hydrocarbon, or —(C═O)—R*, each of which further comprises 0-8 heteroatoms selected from halogen, O, N, and S;

R* is independently at each occurrence selected from hydrogen, an aliphatic $C_1$-$C_{20}$ hydrocarbon, an aromatic $C_5$-$C_{20}$ hydrocarbon, a heteroaromatic $C_1$-$C_{20}$ hydrocarbon, a cyclic aliphatic $C_3$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and $R_{5c}$ is a bond or an aliphatic $C_1$-$C_8$ hydrocarbon;

wherein the group $R_5$ is bonded to the linker.

2. The antibody-drug conjugate of claim 1, wherein —$OR_5$ is —O—,

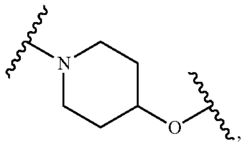,
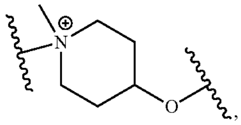,
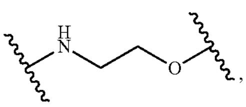,
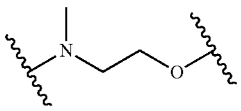,
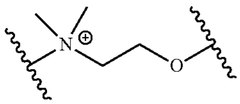,
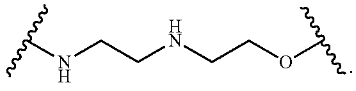.
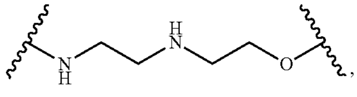, -continued

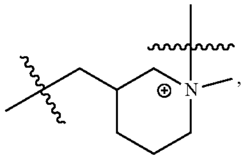, 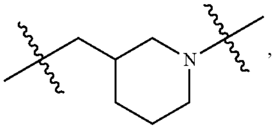,

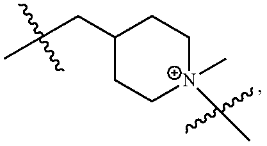, 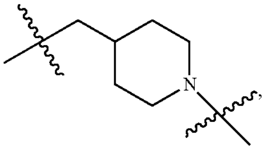,

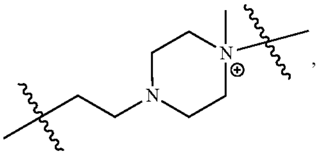,

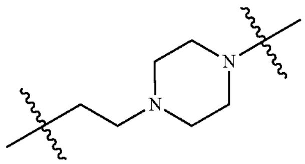,

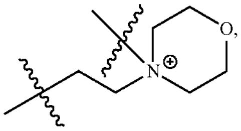 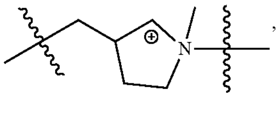,

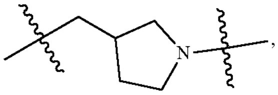, 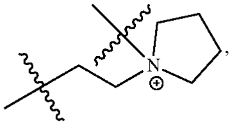,

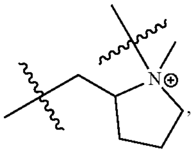, 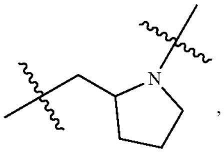,

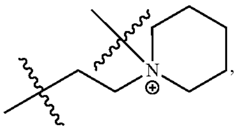, 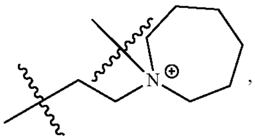,

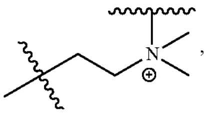, 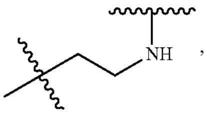,

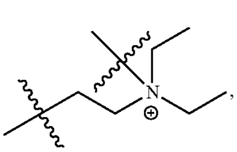, 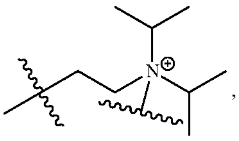,

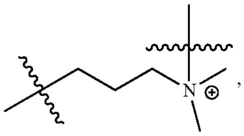, 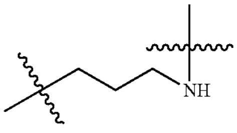,

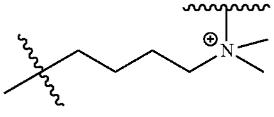,

-continued

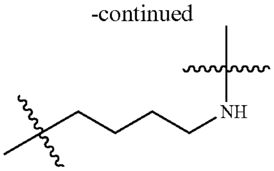,

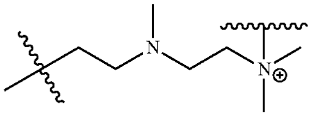,

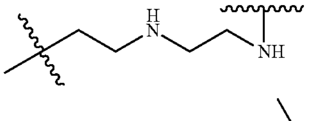,

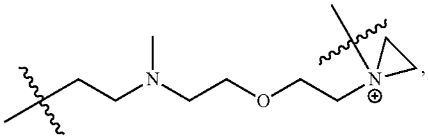,

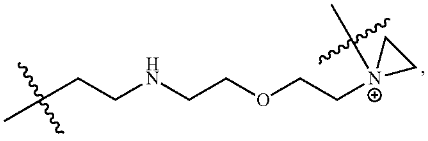,

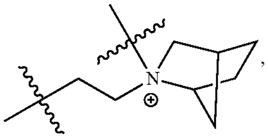, 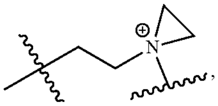, or

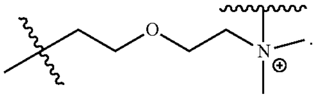.

3. The antibody-drug conjugate of claim 1, wherein X is O, and —$OR_5$ comprises a tertiary amine.

4. The antibody-drug conjugate of claim 1, wherein —$OR_5$ is

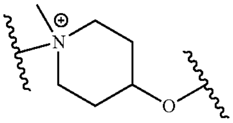 or 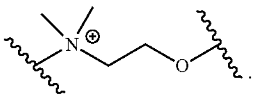.

5. The antibody-drug conjugate of claim 1, wherein $R_2$ is methyl, ethyl, propyl or isopropyl; $R_3$ is $CH_3$—(C═O)-(acetyl), $CH_3CH_2$—(C═O)—, $CH_3CH_2CH_2$—(C═O)—, or $(CH_3)_2CH$—(C═O)—, and $R_4$ is hydrogen.

6. The antibody-drug conjugate of claim 1, wherein $R_2$ is methyl, $R_3$ is acetyl, and $R_4$ is hydrogen.

7. An antibody-drug conjugate comprising an antibody, or an antigen-binding fragment thereof, conjugated via a linker or through a linker-spacer to a compound selected from the group consisting of:

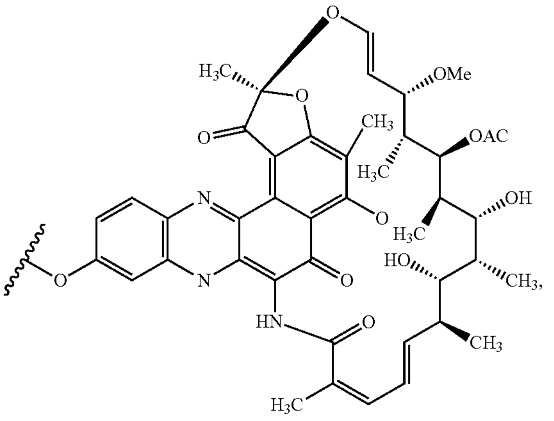
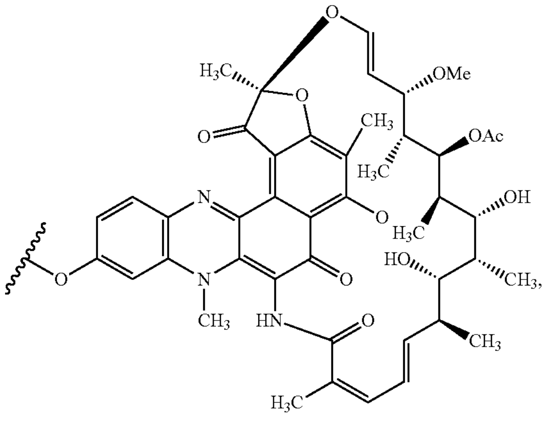
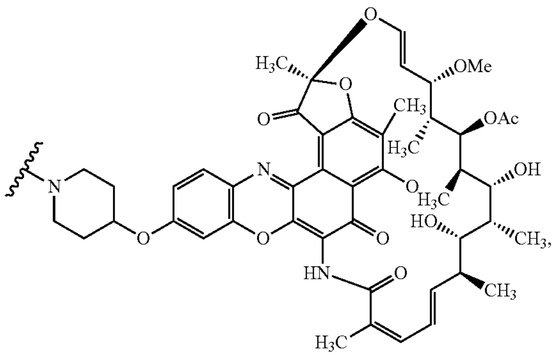
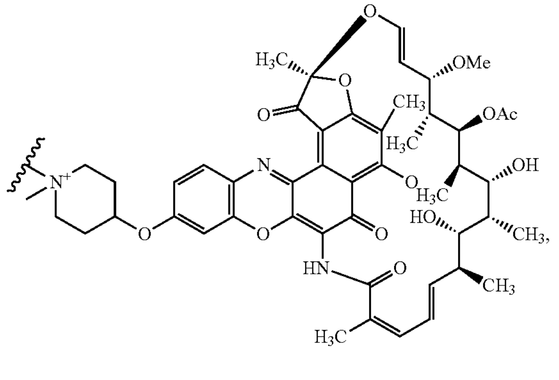
-continued
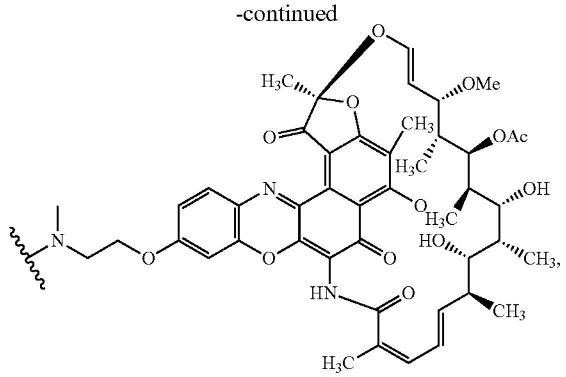
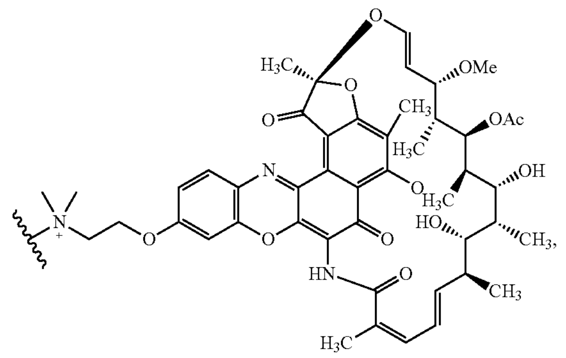
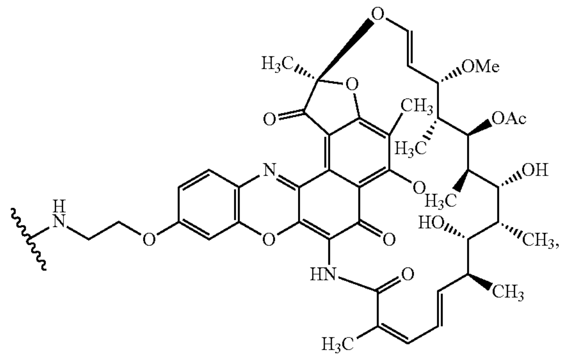
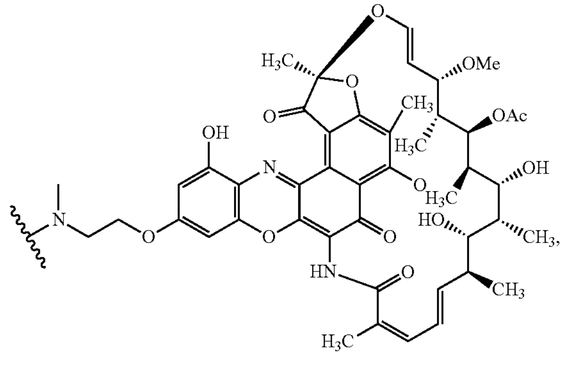

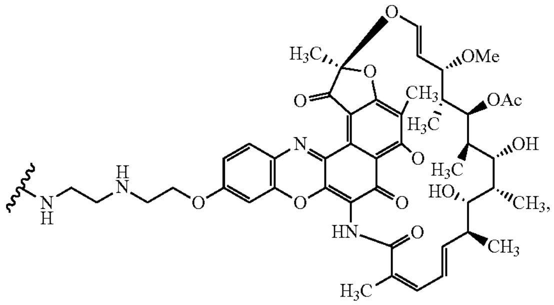
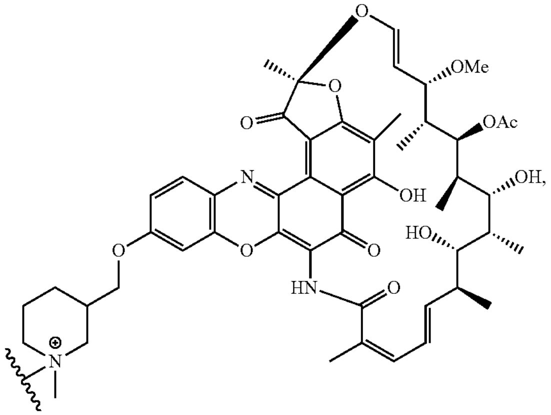
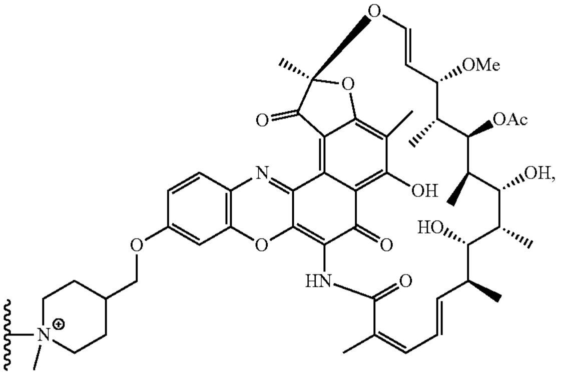
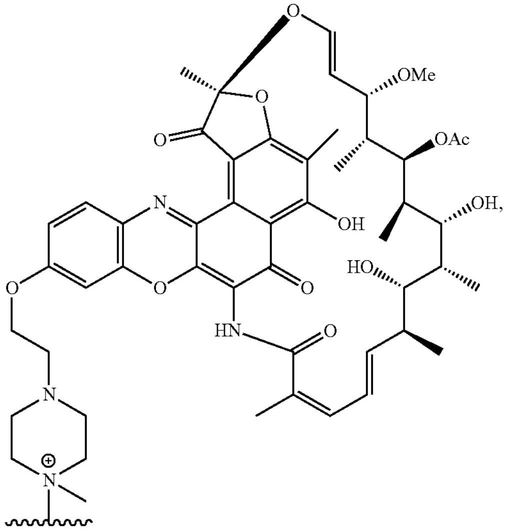
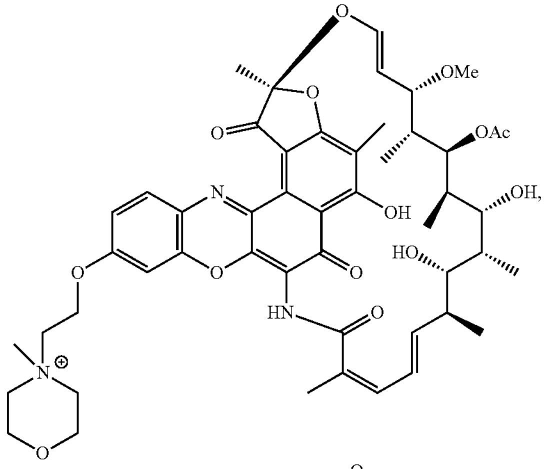
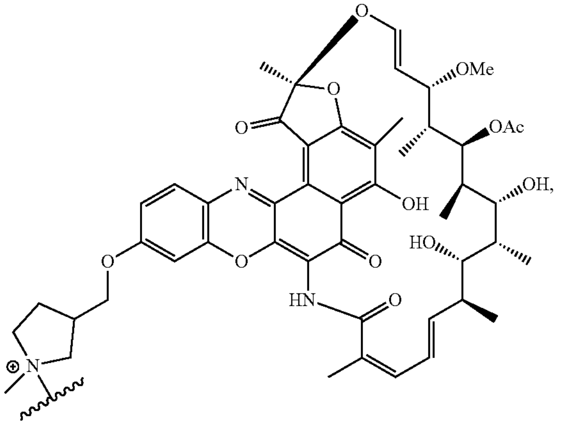
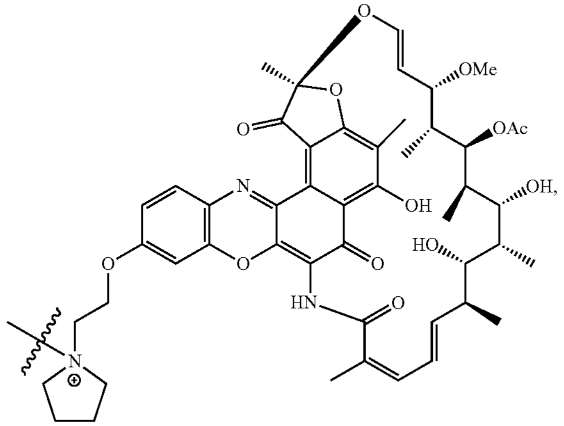
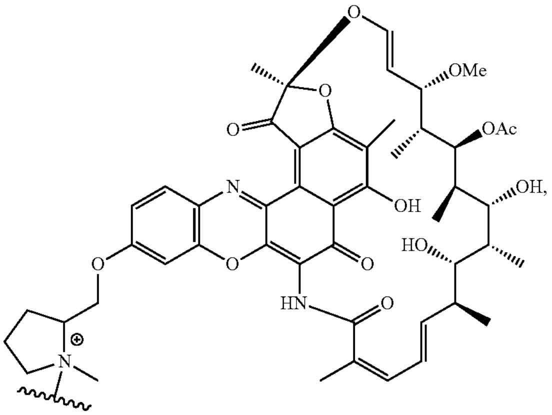

-continued
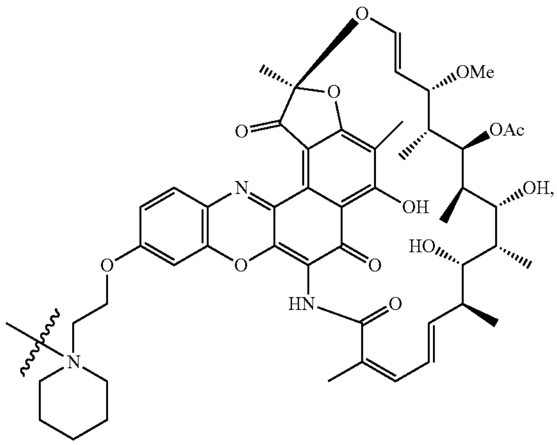
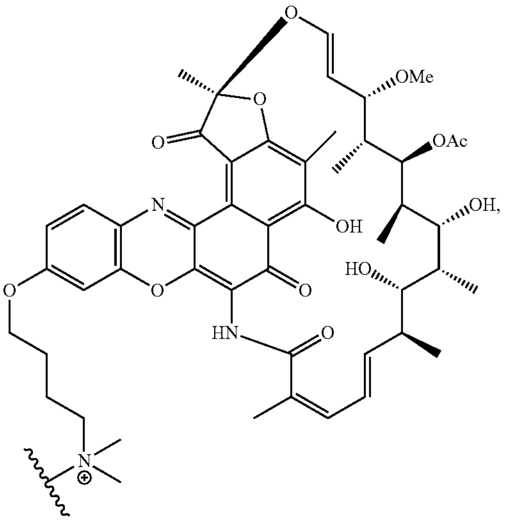
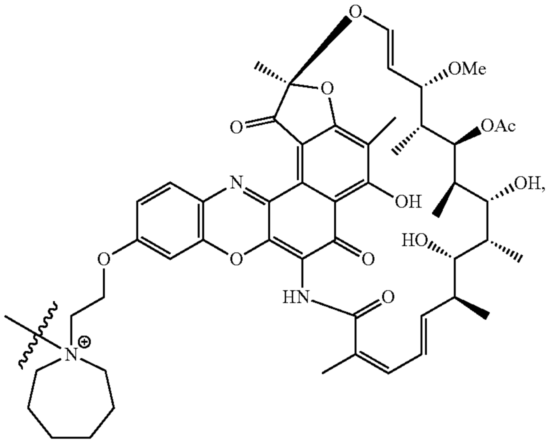
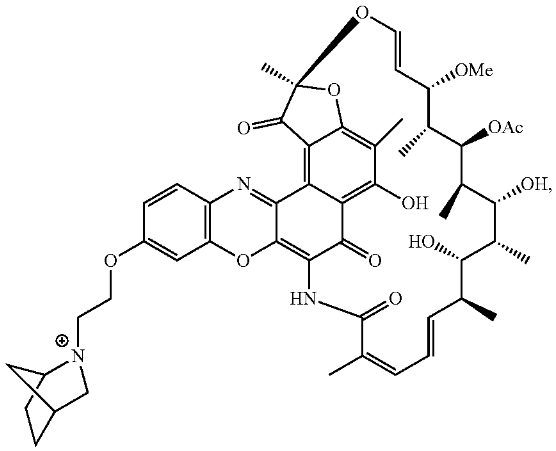
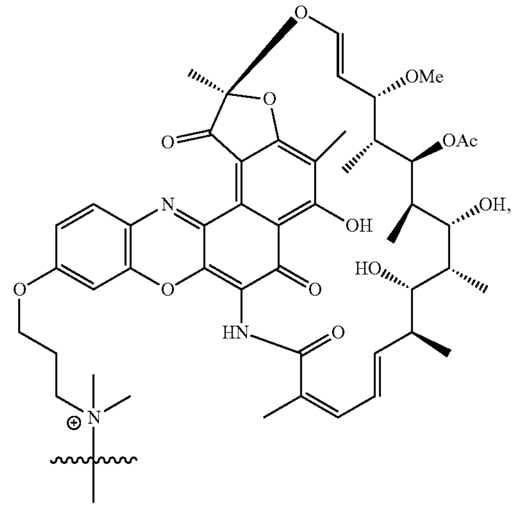
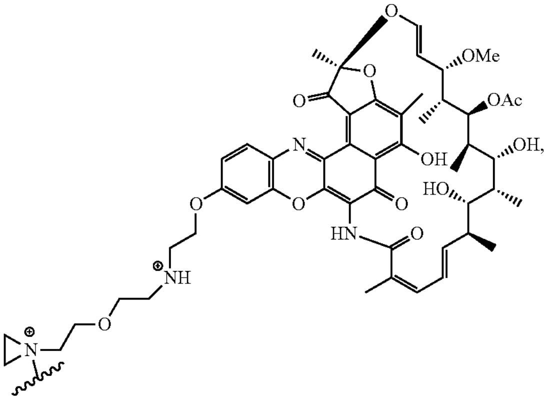

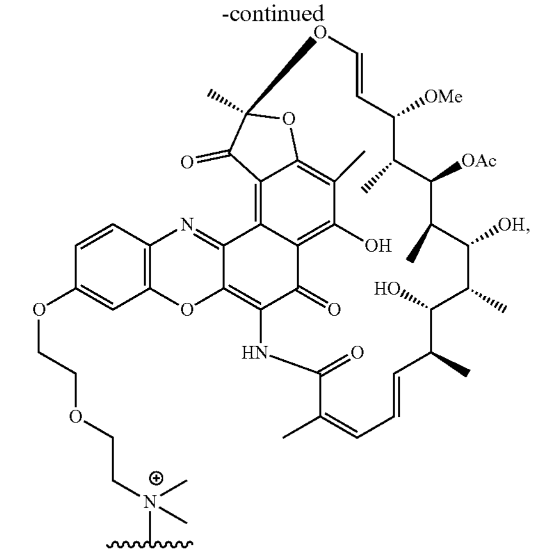
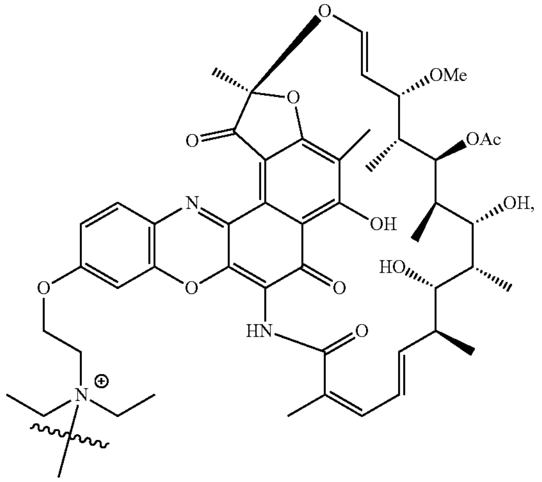
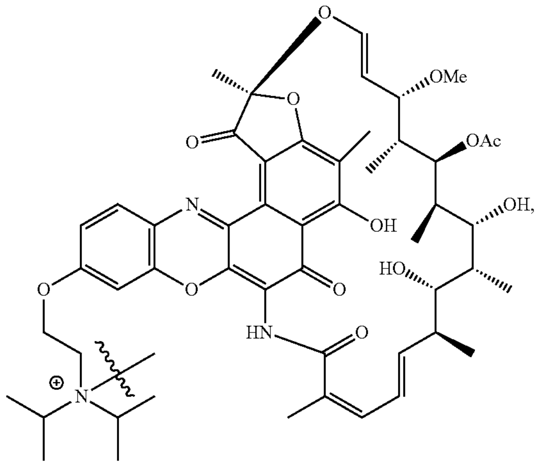
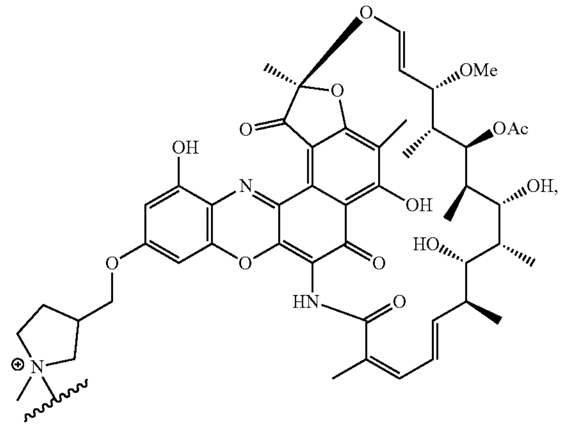
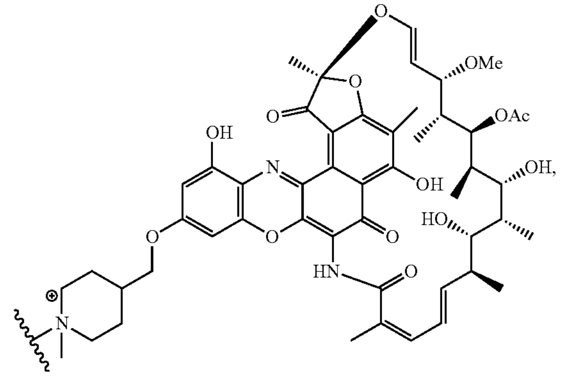
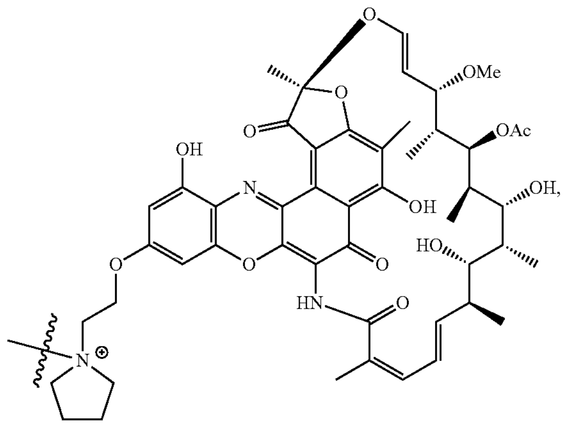
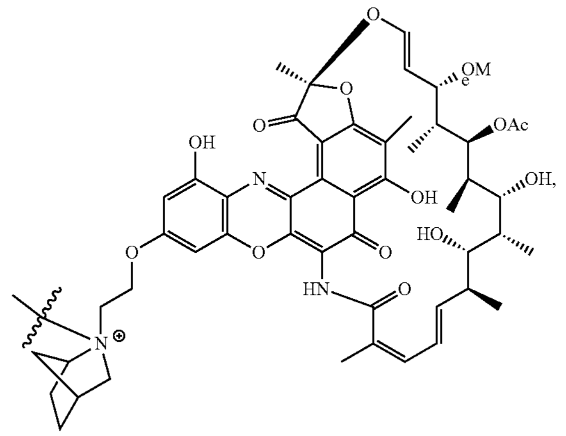

-continued
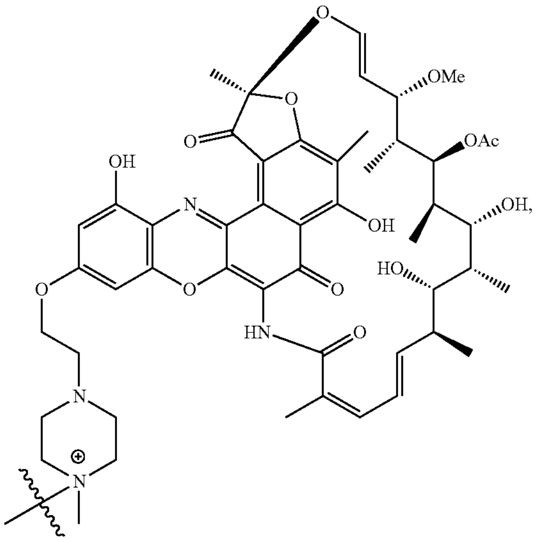
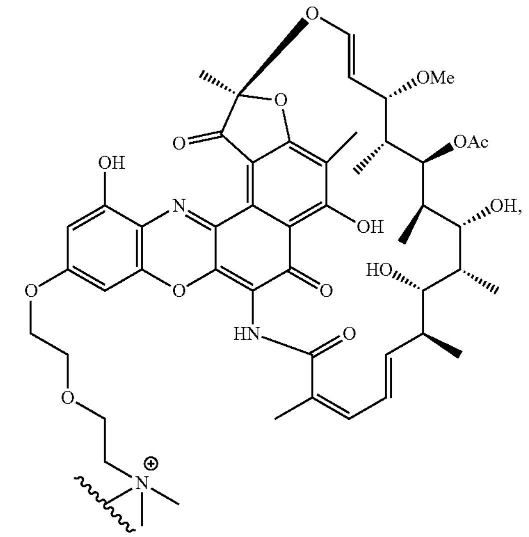
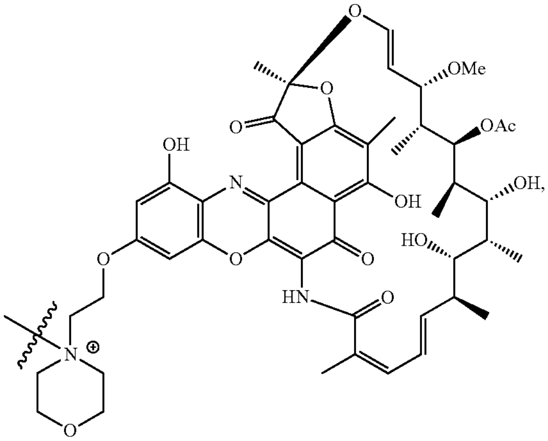
-continued
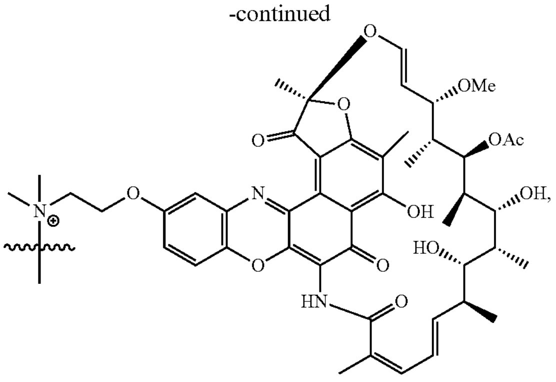
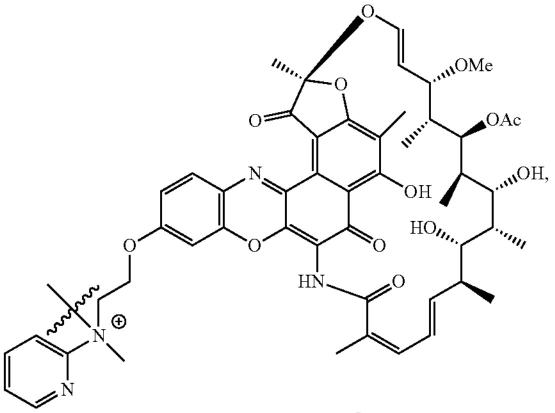
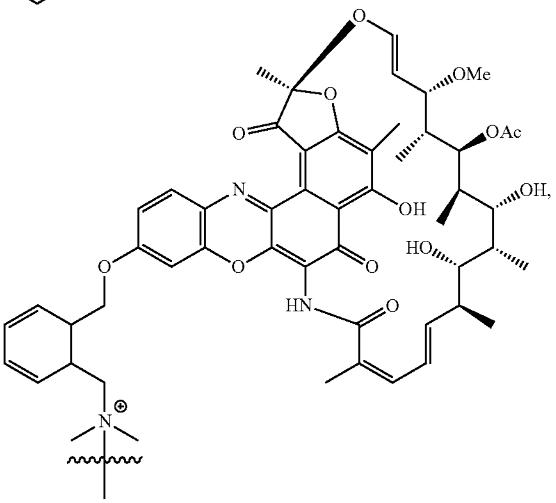
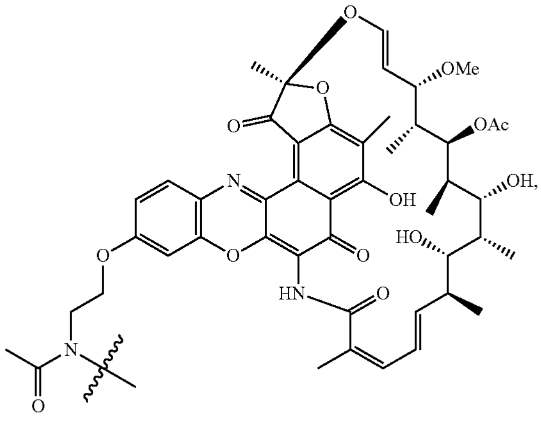

-continued
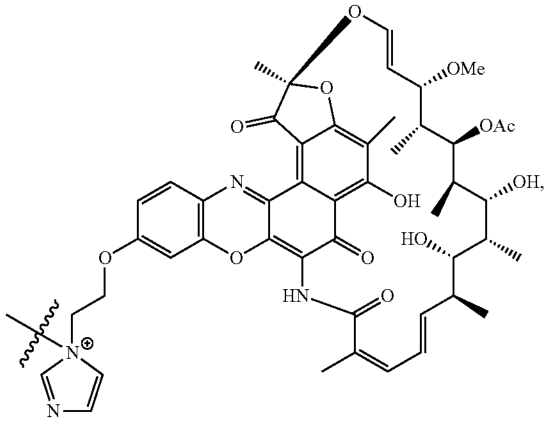
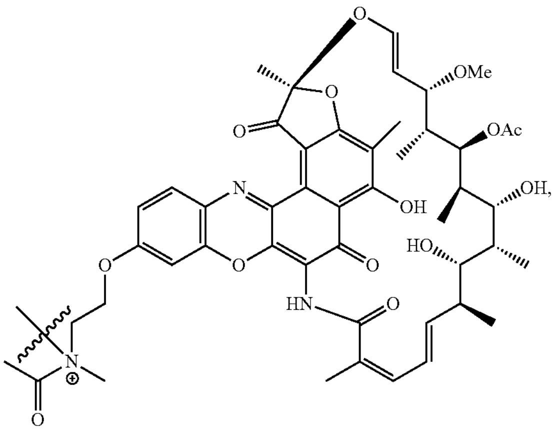
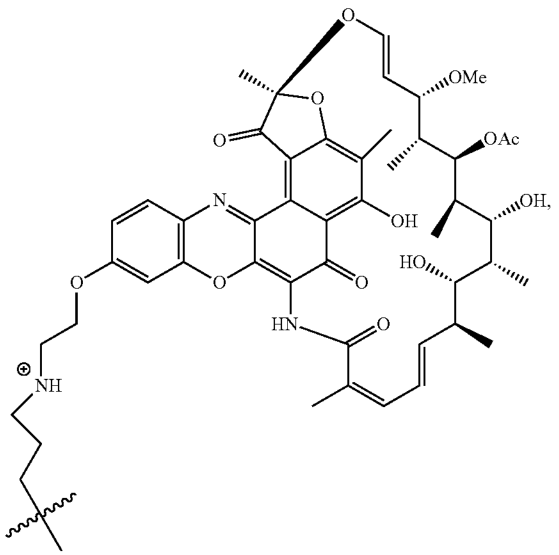
-continued
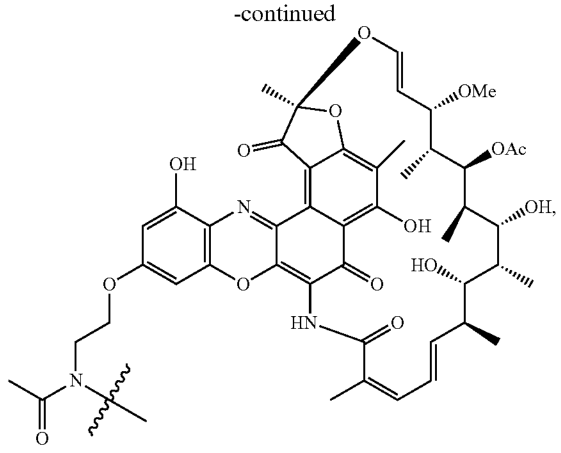
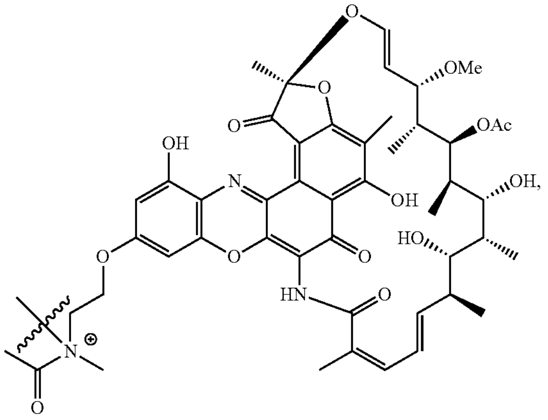
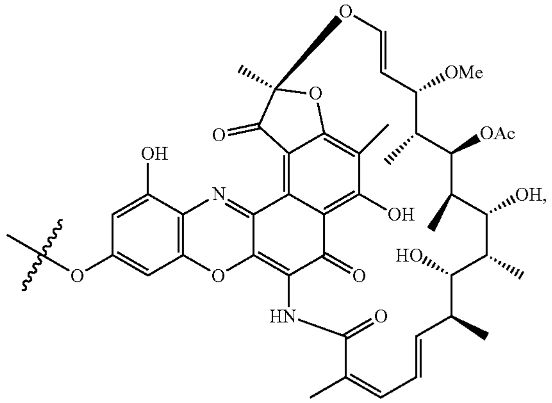
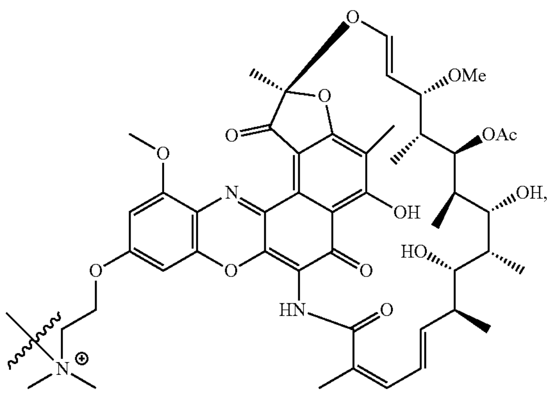

-continued
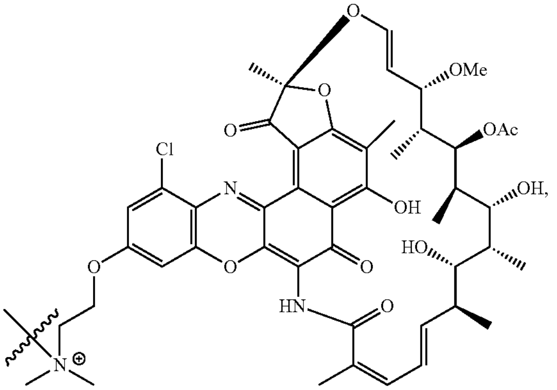
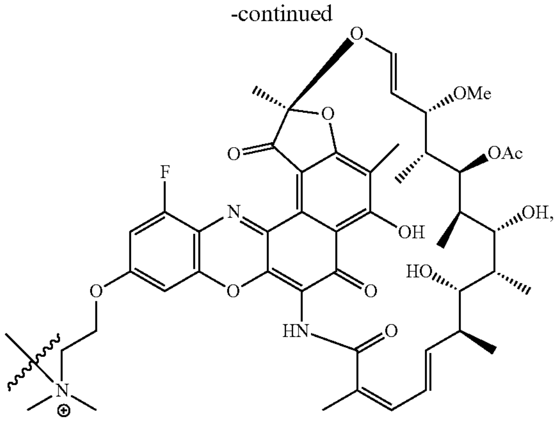
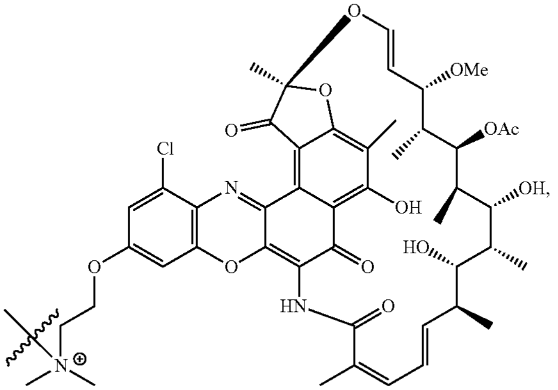
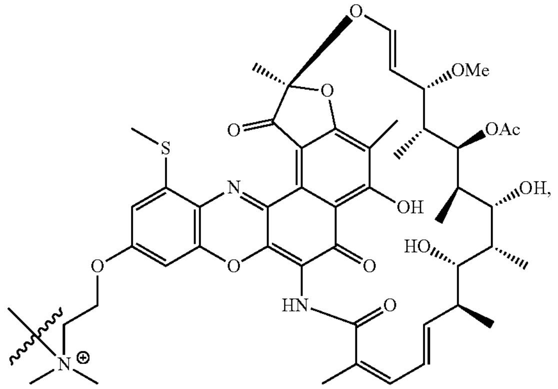
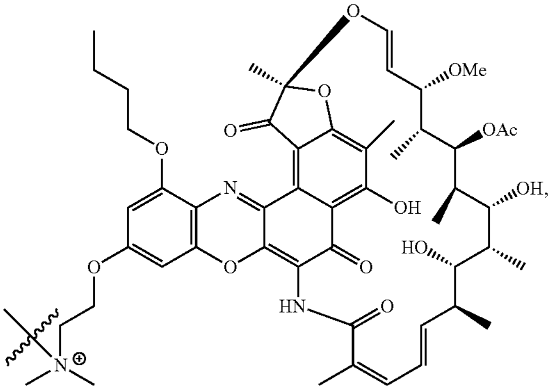
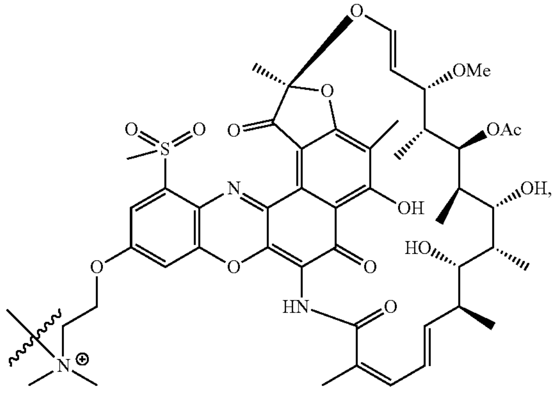
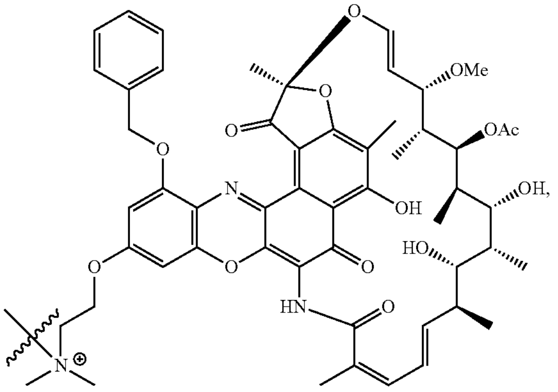
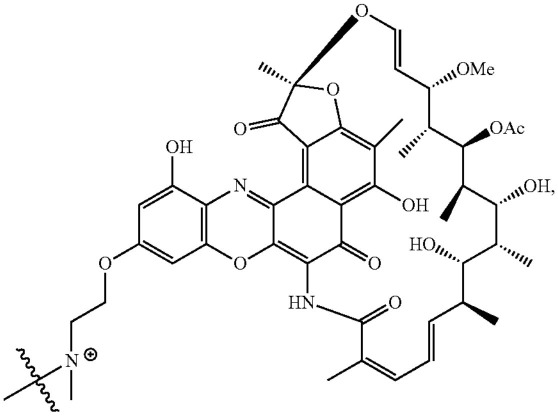

-continued

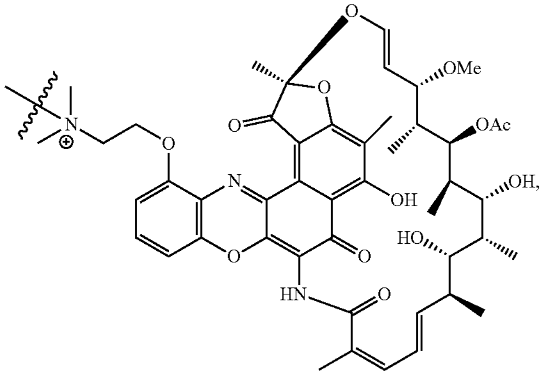

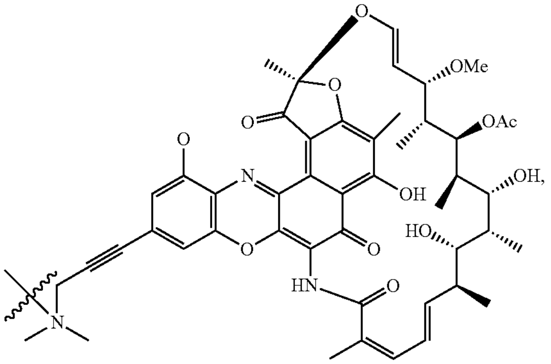

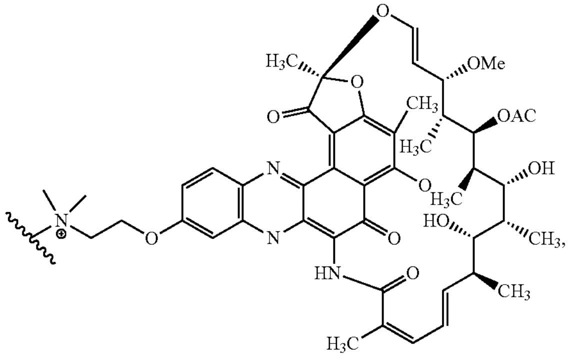

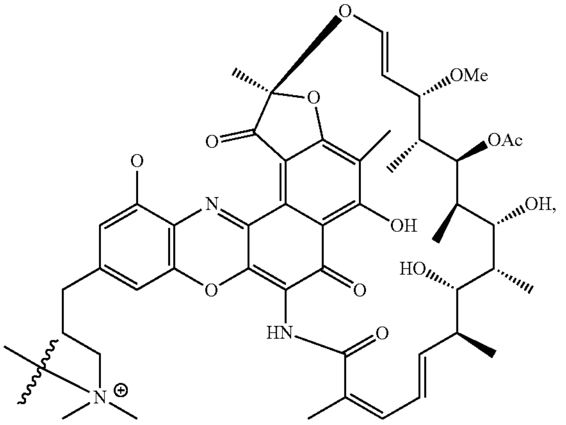

wherein the

is the bond to the linker, and when the compound comprises an ammonium salt, the counterion is an anion selected from $F^-$, $Cl^-$, $Br^-$, $I^-$, $OH^-$, $^-BF_4$, $CF_3SO_3^-$, monobasic sulfate, dibasic sulfate, monobasic phosphate, dibasic phosphate, or tribasic phosphate, $NO_3^-$, $PF_6^-$, $NO_2^-$, carboxylate, $C_eF_f$, wherein e=2-10 and f=2e+1, acetate, aspartate, benzenesulfonate, benzoate, besylate, bicarbonate, bitartrate, camsylate, carbonate, citrate, decanoate, edetate, esylate, fumarate, gluceptate, gluconate, glutamate, glycolate, glycollyalarsanilate, hexanoate, hydrabamine, hydroxynaphthoate, isthionate, lactate, lactobionate, malate, maleate, mandelate, mesylate, methylbromide, methylnitrate, mucate, napsylate, octanoate, oleate, pamoate, pantothenate, polygalacturonate, propionate, salicylate, stearate, subacetate, succinate, tartrate, teoclate, tosylate, or triethiiodide.

8. An antibody-drug conjugate having the structure of Formula (XXII):

(XXII)

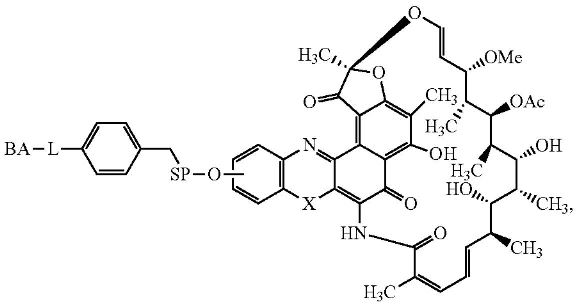

wherein:

BA is an antibody, or an antigen-binding fragment thereof;

L is a linker having the formula

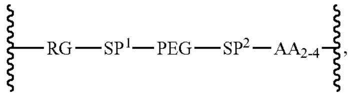

wherein

RG is selected from a maleimide, a N-hydroxysuccinimide, or a succinimide;

$SP^1$ and $SP^2$ are independently absent or a spacer group selected from the group consisting of

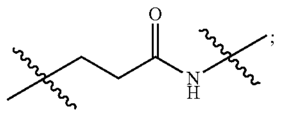 [SMILES: *CCC(=O)N*]

$C_{1-6}$ alkyl, —NH—, —C(O)—, —$CH_2$—$CH_2$—C(O)—NH—, —$(CH)_u$—C(O)—NH—, (—$CH_2$—$CH_2$—O$)_e$, —NH—$CH_2$—$CH_2$—(—O—$CH_2$—$CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8;

$AA_{2-4}$ is a dipeptide selected from valine-citrulline; citrulline-valine; valine-alanine; alanine-valine; valine-glycine, or glycine-valine, and PEG is a polyethylene glycol chain comprising between 1 and 30 polyethylene glycol residues;

SP is a spacer group selected from

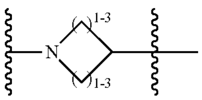 ; 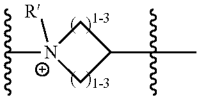 ;

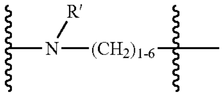 ; 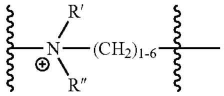 ;

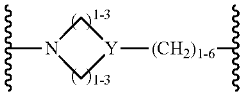 ;

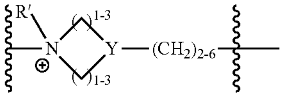 ;

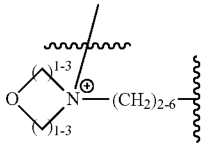 ; 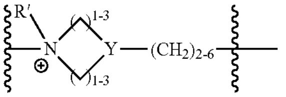 ;

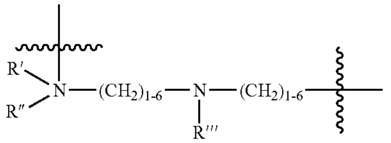 ,

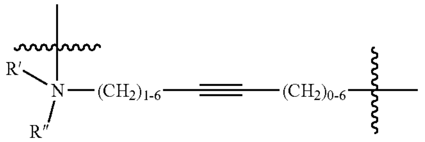 and

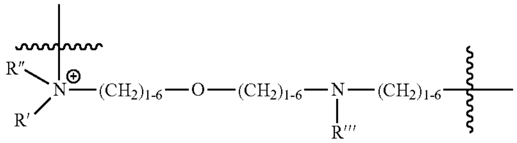 ;

Y is C or N; wherein the ~ symbol represents the point of attachment; and R', R" and R''' are selected from a hydrogen, a $C_1$-$C_6$ aliphatic hydrocarbon, and a protecting group selected from Fluorenylmethyloxycarbonyl ($F_{MOC}$) and tert-Butyloxycarbonyl ($B_{OC}$), or wherein R' and R" together form an aliphatic monocyclic, an aliphatic bicyclic, or an aliphatic polycyclic structure; or wherein the

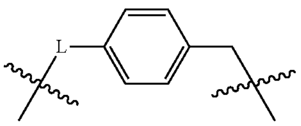

has a structure:

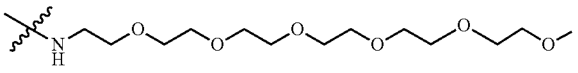

-continued

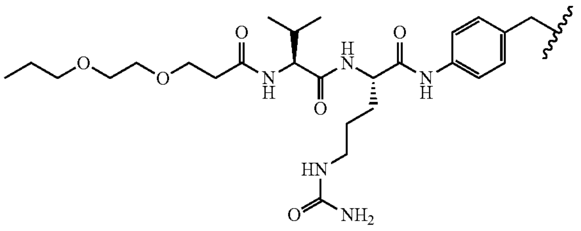

or,

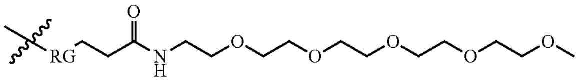

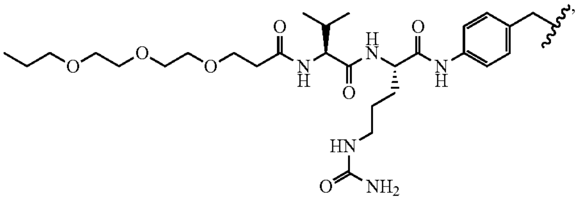

R* is independently at each occurrence selected from hydrogen, an aliphatic $C_1$-$C_{20}$ hydrocarbon, an aromatic $C_5$-$C_{20}$ hydrocarbon, a heteroaromatic $C_1$-$C_{20}$ hydrocarbon, a cyclic aliphatic $C_3$-$C_{20}$ hydrocarbon, a heterocyclic $C_1$-$C_{20}$ hydrocarbon, and combinations thereof, which further comprises 0-8 heteroatoms selected from halogen, O, N, and S and combinations thereof, and X is selected from —O—, —S—, and —NR*.

9. The antibody-drug conjugate of claim 8, wherein $AA_{2-4}$ is valine-citrulline.

10. The antibody-drug conjugate of claim 8, wherein SP is

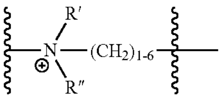

and R' and R" are each a $C_{1-6}$ alkyl.

11. The antibody-drug conjugate of claim 10, wherein SP is

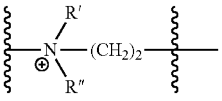

and R' and R" are each methyl.

12. The antibody-drug conjugate of claim 8, wherein $SP^1$ and $SP^2$ are each

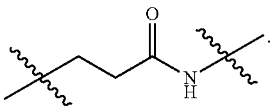 [SMILES: *CCC(=O)N*]

13. The antibody-drug conjugate of claim 8, wherein PEG comprises 8 polyethylene glycol units.

14. The antibody-drug conjugate of claim 8, wherein the antibody-drug conjugate has a structure selected from the group consisting of:

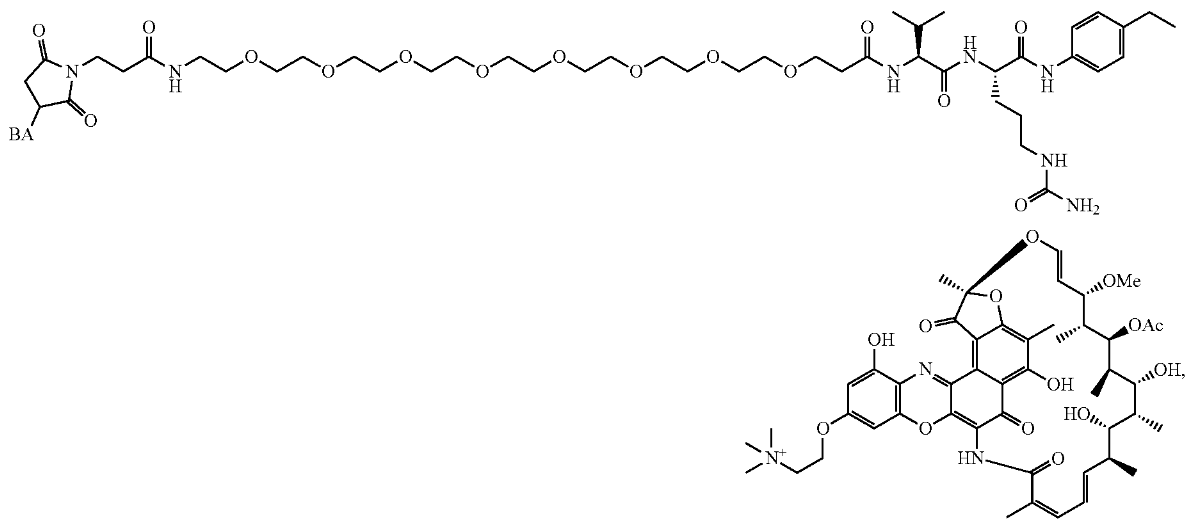
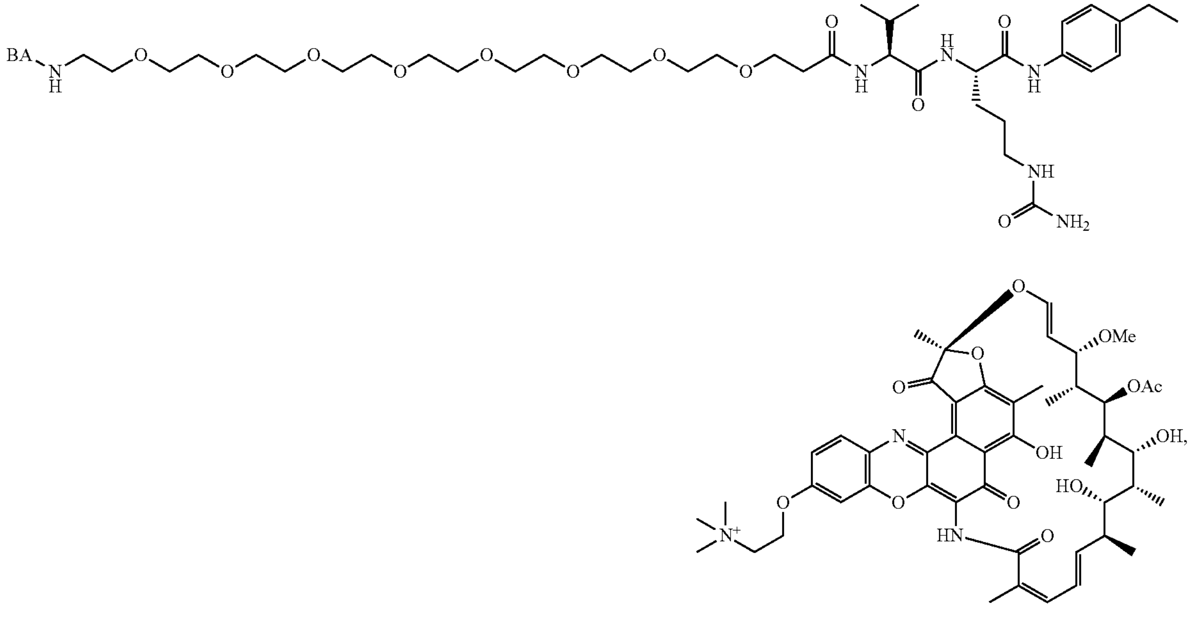
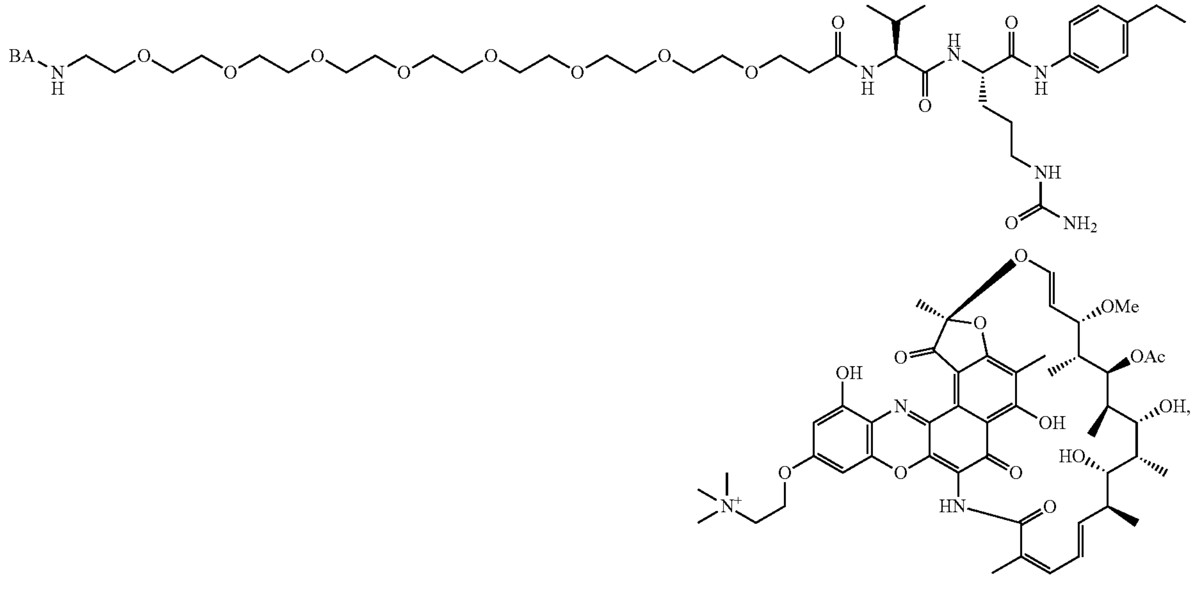

wherein BA is an antibody, or an antigen-binding fragment thereof.

15. The antibody-drug conjugate of claim 1, wherein the antibody, or an antigen-binding fragment thereof, binds an infectious disease-related target.

16. A method of inhibiting growth of a bacterium comprising administering an effective amount of the antibody-drug conjugate of claim 1.

17. A method of treating a bacterial infection in a subject in need of such treatment comprising administering to the subject an effective amount of the antibody-drug conjugate of claim 1.

18. A method of preventing or treating cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, septic arthritis, mastitis, infection associated with a prosthetic joint, infection associated with a catheter, or infection associated with an implant, in a subject comprising administering to the subject an effective treatment amount of the antibody-drug conjugate of claim 1.

19. A pharmaceutical composition comprising the antibody-drug conjugate of claim 1 or a pharmaceutically acceptable salt thereof and a pharmaceutically acceptable carrier.

20. A pharmaceutical dosage form comprising the antibody-drug conjugate of claim 1 or a pharmaceutically acceptable salt thereof.

21. The antibody-drug conjugate of claim 7, wherein the antibody, or an antigen-binding fragment thereof, binds an infectious disease-related target.

22. A method of preventing or inhibiting growth of a bacterium comprising administering an effective amount of the antibody-drug conjugate of claim 7.

23. A method of treating a bacterial infection in a subject in need of such treatment comprising administering to the subject an effective amount of the antibody-drug conjugate of claim 7.

24. A method of treating cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, septic arthritis, mastitis, infection associated with a prosthetic joint, infection associated with a catheter, or infection associated with an implant, in a subject comprising administering to the subject an effective treatment amount of the antibody-drug conjugate of claim 7.

25. A pharmaceutical composition comprising the antibody-drug conjugate of claim 7 or a pharmaceutically acceptable salt thereof and a pharmaceutically acceptable carrier.

26. A pharmaceutical dosage form comprising the antibody-drug conjugate of claim 7 or a pharmaceutically acceptable salt thereof.

27. The antibody-drug conjugate of claim 8, wherein the antibody, or an antigen-binding fragment thereof, binds an infectious disease-related target.

28. A method of preventing or inhibiting growth of a bacterium comprising administering an effective amount of the antibody-drug conjugate of claim 8.

29. A method of treating a bacterial infection in a subject in need of such treatment comprising administering to the subject an effective amount of the antibody-drug conjugate of claim 8.

30. A method of treating cellulitis, bacteremia, dermonecrosis, eyelid infection, eye infection, neonatal conjunctivitis, osteomyelitis, impetigo, boils, scalded skin syndrome, food poisoning, pneumonia, surgical infection, urinary tract infection, burn infection, meningitis, endocarditis, septicemia, toxic shock syndrome, septic arthritis, mastitis, infection associated with a prosthetic joint, infection associated with a catheter, or infection associated with an implant, in a subject comprising administering to the subject an effective treatment amount of the antibody-drug conjugate of claim 8.

31. A pharmaceutical composition comprising the antibody-drug conjugate of claim 8 or a pharmaceutically acceptable salt thereof and a pharmaceutically acceptable carrier.

32. A pharmaceutical dosage form comprising the antibody-drug conjugate of claim 8 or a pharmaceutically acceptable salt thereof.

* * * * *

UNITED STATES PATENT AND TRADEMARK OFFICE

CERTIFICATE OF CORRECTION

PATENT NO. : 11,666,658 B2
APPLICATION NO. : 16/722958
DATED : June 6, 2023
INVENTOR(S) : Thomas Nittoli et al.

It is certified that error appears in the above-identified patent and that said Letters Patent is hereby corrected as shown below:

On the Title Page

Page 1, Column 1, Item (73): “Regeneran Pharmaceuticals, Inc.” should read:
-- Regeneron Pharmaceuticals, Inc. --

Signed and Sealed this
Eighteenth Day of July, 2023

Katherine Kelly Vidal

Katherine Kelly Vidal
*Director of the United States Patent and Trademark Office*

SEQUENCE LISTING

<160> NUMBER OF SEQ ID NOS: 690

<210> SEQ ID NO 1
<211> LENGTH: 363
<212> TYPE: DNA
<213> ORGANISM: Artificial Sequence -continued
<220> FEATURE:
<223> OTHER INFORMATION: Synthetic

<400> SEQUENCE: 1

```
caggtccaat tggtacagtc tggggctgag gtgaagaagc ctggggcctc agtgaaggtg    60
tcctgcaagg tttccggata caccctcact gaattatcca tacactgggt gcgccaggtt   120
cctggaaaag gacttgagtg gatgggaggt tttgatcctg aagagggtga aacaatcttc   180
gcacaggagt tccgggacag agtcaccttg accgaggaca catctccaga cacagcctac   240
atggagttga gcagcctgaa atctgaggac gcggccgtat attactgtac aaccccccga   300
tattgtaata atggtatatg ttatgactac tggggccagg gaaccctggt caccgtctct   360
tca                                                                 363
```

<210> SEQ ID NO 2
<211> LENGTH: 121
<212> TYPE: PRT
<213> ORGANISM: Artificial Sequence
<220> FEATURE:
<223> OTHER INFORMATION: Synthetic

<400> SEQUENCE: 2

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Ile His Trp Val Arg Gln Val Pro Gly Lys Gly Leu Glu Trp Met
        35                  40                  45

Gly Gly Phe Asp Pro Glu Glu Gly Glu Thr Ile Phe Ala Gln Glu Phe
    50                  55                  60

Arg Asp Arg Val Thr Leu Thr Glu Asp Thr Ser Pro Asp Thr Ala Tyr
65                  70                  75                  80

Met Glu Leu Ser Ser Leu Lys Ser Glu Asp Ala Ala Val Tyr Tyr Cys
                85                  90                  95

Thr Thr Pro Arg Tyr Cys Asn Asn Gly Ile Cys Tyr Asp Tyr Trp Gly
            100                 105                 110

Gln Gly Thr Leu Val Thr Val Ser Ser
        115                 120
```

<210> SEQ ID NO 3
<211> LENGTH: 24
<212> TYPE: DNA
<213> ORGANISM: Artificial Sequence
<220> FEATURE:
<223> OTHER INFORMATION: Synthetic

<400> SEQUENCE: 3

```
ggatacaccc tcactgaatt atcc                                           24
```

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

```
Gly Tyr Thr Leu Thr Glu Leu Ser
1               5
```

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
tttgatcctg aagagggtga aaca 24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Phe Asp Pro Glu Glu Gly Glu Thr
1 5

<210> SEQ ID NO 7
<211> LENGTH: 42
<212> TYPE: DNA
<213> ORGANISM: Artificial Sequence
<220> FEATURE:
<223> OTHER INFORMATION: Synthetic

<400> SEQUENCE: 7
acaacccccc gatattgtaa taatggtata tgttatgact ac 42

<210> SEQ ID NO 8
<211> LENGTH: 14
<212> TYPE: PRT
<213> ORGANISM: Artificial Sequence
<220> FEATURE:
<223> OTHER INFORMATION: Synthetic

<400> SEQUENCE: 8

Thr Thr Pro Arg Tyr Cys Asn Asn Gly Ile Cys Tyr Asp Tyr
1 5 10

<210> SEQ ID NO 9
<211> LENGTH: 327
<212> TYPE: DNA
<213> ORGANISM: Artificial Sequence
<220> FEATURE:
<223> OTHER INFORMATION: Synthetic

<400> SEQUENCE: 9
gacatccaga tgacccagtc gccttcctcc ctgtctgcat ctgtgggaga cagagtcacc 60
atcacttgcc gggcaagtca gagcattagc aactatttaa attggtatca gcagaaacca 120
gggaaagccc ctaagctcct gatctatact gcatccagtt tgcaaagtgg ggtcccatca 180
aggttcagtg gcagtggatc tgggacagat ttcactctca ccatcagcag tcttcaaact 240
gaagattttg caacttacta ttgtcaacag agttacagta attttccgat caccttcggc 300
caagggacac gactggagat taaacga 327

<210> SEQ ID NO 10
<211> LENGTH: 109
<212> TYPE: PRT
<213> ORGANISM: Artificial Sequence
<220> FEATURE:
<223> OTHER INFORMATION: Synthetic

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
            20                  25                  30

Leu Asn Trp Tyr Gln Gln Lys Pro Gly Lys Ala Pro Lys Leu Leu Ile
        35                  40                  45

Tyr Thr Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Thr
65                  70                  75                  80

Glu Asp Phe Ala Thr Tyr Tyr Cys Gln Gln Ser Tyr Ser Asn Phe Pro
                85                  90                  95

Ile Thr Phe Gly Gln Gly Thr Arg Leu Glu Ile Lys Arg
            100                 105

<210> SEQ ID NO 11
<211> LENGTH: 18
<212> TYPE: DNA
<213> ORGANISM: Artificial Sequence
<220> FEATURE:
<223> OTHER INFORMATION: Synthetic

<400> SEQUENCE: 11
cagagcatta gcaactat 18

<210> SEQ ID NO 12
<211> LENGTH: 6
<212> TYPE: PRT
<213> ORGANISM: Artificial Sequence
<220> FEATURE:
<223> OTHER INFORMATION: Synthetic

<400> SEQUENCE: 12

Gln Ser Ile Ser Asn Tyr
1               5

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 actgcatcc 9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Thr Ala Ser
1

<210> SEQ ID NO 15
<211> LENGTH: 30
<212> TYPE: DNA
<213> ORGANISM: Artificial Sequence
<220> FEATURE:

<223> OTHER INFORMATION: Synthetic

<400> SEQUENCE: 15
caacagagtt acagtaattt tccgatcacc 30

<210> SEQ ID NO 16
<211> LENGTH: 10
<212> TYPE: PRT
<213> ORGANISM: Artificial Sequence
<220> FEATURE:
<223> OTHER INFORMATION: Synthetic

<400> SEQUENCE: 16

Gln Gln Ser Tyr Ser Asn Phe Pro Ile Thr
1 5 10

<210> SEQ ID NO 17
<211> LENGTH: 360
<212> TYPE: DNA
<213> ORGANISM: Artificial Sequence
<220> FEATURE:
<223> OTHER INFORMATION: Synthetic

<400> SEQUENCE: 17
gtgcagctgg tggagtctgg gggaggcttg gtccagcctg gagggtccct gagactctcc 60
tgtgcagcct ctggattcac cttcagtgac cactacatgg actgggtccg tcaggctcct 120
gggaaggggc tggagtgggt tggccgaacc agaaacaaag ctaatagtca caccacagaa 180
tacgccgcgt ctgtgagtgg cagattcacc atctcaagag atgattcaaa gaactcattg 240
tatctgcaaa tgaacagcct gaaaaccgag gacacggccg tgtattattg cactagagcc 300
ggtataattg gaaccctctt tgactactgg ggccagggaa ccctggtcac cgtctcctca 360

<210> SEQ ID NO 18
<211> LENGTH: 120
<212> TYPE: PRT
<213> ORGANISM: Artificial Sequence
<220> FEATURE:
<223> OTHER INFORMATION: Synthetic

<400> SEQUENCE: 18

Val Gln Leu Val Glu Ser Gly Gly Gly Leu Val Gln Pro Gly Gly Ser
1 5 10 15

Leu Arg Leu Ser Cys Ala Ala Ser Gly Phe Thr Phe Ser Asp His Tyr
20 25 30

Met Asp Trp Val Arg Gln Ala Pro Gly Lys Gly Leu Glu Trp Val Gly
35 40 45

Arg Thr Arg Asn Lys Ala Asn Ser His Thr Thr Glu Tyr Ala Ala Ser
50 55 60

Val Ser Gly Arg Phe Thr Ile Ser Arg Asp Asp Ser Lys Asn Ser Leu
65 70 75 80

Tyr Leu Gln Met Asn Ser Leu Lys Thr Glu Asp Thr Ala Val Tyr Tyr
85 90 95

Cys Thr Arg Ala Gly Ile Ile Gly Thr Leu Phe Asp Tyr Trp Gly Gln
100 105 110

Gly Thr Leu Val Thr Val Ser Ser
115 120

<210> SEQ ID NO 19
<211> LENGTH: 24
<212> TYPE: DNA

<213> ORGANISM: Artificial Sequence
<220> FEATURE:
<223> OTHER INFORMATION: Synthetic

<400> SEQUENCE: 19
ggattcacct tcagtgacca ctac 24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Thr Phe Ser Asp His Tyr
1 5

<210> SEQ ID NO 21
<211> LENGTH: 30
<212> TYPE: DNA
<213> ORGANISM: Artificial Sequence
<220> FEATURE:
<223> OTHER INFORMATION: Synthetic

<400> SEQUENCE: 21
accagaaaca aagctaatag tcacaccaca 30

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Thr Arg Asn Lys Ala Asn Ser His Thr Thr
1 5 10

<210> SEQ ID NO 23
<211> LENGTH: 36
<212> TYPE: DNA
<213> ORGANISM: Artificial Sequence
<220> FEATURE:
<223> OTHER INFORMATION: Synthetic

<400> SEQUENCE: 23
actagagccg gtataattgg aaccctcttt gactac 36

<210> SEQ ID NO 24
<211> LENGTH: 12
<212> TYPE: PRT
<213> ORGANISM: Artificial Sequence
<220> FEATURE:
<223> OTHER INFORMATION: Synthetic

<400> SEQUENCE: 24

Thr Arg Ala Gly Ile Ile Gly Thr Leu Phe Asp Tyr
1 5 10

<210> SEQ ID NO 25
<211> LENGTH: 327
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccgtca 180
aggttcagtg gcagtggatc tgggacagat ttcactctca ccatcagcag tctgcaacct 240
gaagattttg caacttacta ctgtcaacag agttacagta cccctccgat caccttcggc 300
caagggacac gactggagat taaacga 327

<210> SEQ ID NO 26
<211> LENGTH: 109
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Ile Thr Phe Gly Gln Gly Thr Arg Leu Glu Ile Lys Arg
100 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagagcatta gcagctat 18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Ser Ile Ser Ser Tyr
1 5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc 9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
caacagagtt acagtacccc tccgatcacc 30

<210> SEQ ID NO 32
<211> LENGTH: 10
<212> TYPE: PRT
<213> ORGANISM: Artificial Sequence
<220> FEATURE:
<223> OTHER INFORMATION: Synthetic

<400> SEQUENCE: 32

Gln Gln Ser Tyr Ser Thr Pro Pro Ile Thr
1 5 10

<210> SEQ ID NO 33
<211> LENGTH: 363
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaggc ttggtccagc ctggagggtc cctgagactc 60
tcctgtgcag cctctggatt caccttcagt gaccactata tggactgggt ccgccaggct 120
ccagggaagg ggctggaatg ggttggccgt actcgaaaca aagctaatag tcacaccaca 180
gaatacaccg cgtctgtgac aggcagattc accatctcaa gagatgattc aagaaactca 240
ctatatctgc aaatgaacag cctgaaaacc gaggacacgg ccgtatatta ctgtgttaga 300
gccggtataa ttggaaccct ctttgactat tggggccagg gaaccctggt caccgtctcc 360
tca 363

<210> SEQ ID NO 34
<211> LENGTH: 121
<212> TYPE: PRT
<213> ORGANISM: Artificial Sequence
<220> FEATURE:
<223> OTHER INFORMATION: Synthetic

<400> SEQUENCE: 34

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp His

```
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser His Thr Thr Glu Tyr Thr Ala
    50                  55                  60

Ser Val Thr Gly Arg Phe Thr Ile Ser Arg Asp Asp Ser Arg Asn Ser
65                  70                  75                  80

Leu Tyr Leu Gln Met Asn Ser Leu Lys Thr Glu Asp Thr Ala Val Tyr
                85                  90                  95

Tyr Cys Val Arg Ala Gly Ile Ile Gly Thr Leu Phe Asp Tyr Trp Gly
            100                 105                 110

Gln Gly Thr Leu Val Thr Val Ser Ser
        115                 120


<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35

ggattcacct tcagtgacca ctat                                            24


<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

Gly Phe Thr Phe Ser Asp His Tyr
1               5


<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37

actcgaaaca aagctaatag tcacaccaca                                      30


<210> SEQ ID NO 38
<211> LENGTH: 10
<212> TYPE: PRT
<213> ORGANISM: Artificial Sequence
<220> FEATURE:
<223> OTHER INFORMATION: Synthetic

<400> SEQUENCE: 38

Thr Arg Asn Lys Ala Asn Ser His Thr Thr
1               5                   10


<210> SEQ ID NO 39
<211> LENGTH: 36
<212> TYPE: DNA
<213> ORGANISM: Artificial Sequence
<220> FEATURE:
<223> OTHER INFORMATION: Synthetic

<400> SEQUENCE: 39
```

gttagagccg gtataattgg aaccctcttt gactat 36

<210> SEQ ID NO 40
<211> LENGTH: 12
<212> TYPE: PRT
<213> ORGANISM: Artificial Sequence
<220> FEATURE:
<223> OTHER INFORMATION: Synthetic

<400> SEQUENCE: 40

Val Arg Ala Gly Ile Ile Gly Thr Leu Phe Asp Tyr
1 5 10

<210> SEQ ID NO 41
<211> LENGTH: 327
<212> TYPE: DNA
<213> ORGANISM: Artificial Sequence
<220> FEATURE:
<223> OTHER INFORMATION: Synthetic

<400> SEQUENCE: 41
gacatccaga tgacccagtt tccatcctcc ctgtctgcat ctgtaggaga cagagtcacc 60
atcacttgcc gggcaagtca gagcattagc agctttttaa attggtttca gcagaaacca 120
gggaaagccc ctaagttcct gatctatgct gcatccagtt tgcaaagtgg ggtcccatca 180
aggttcagtg gcagtgggtc tgggacagat ttcactctca ccatcagcag tctacaacct 240
gaagattttg caacttacta ctgtcaacag agttacagtt cccctccgat caccttcggc 300
caagggacac gactggagat taaacga 327

<210> SEQ ID NO 42
<211> LENGTH: 109
<212> TYPE: PRT
<213> ORGANISM: Artificial Sequence
<220> FEATURE:
<223> OTHER INFORMATION: Synthetic

<400> SEQUENCE: 42

Asp Ile Gln Met Thr Gln Phe Pro Ser Ser Leu Ser Ala Ser Val Gly
1 5 10 15

Asp Arg Val Thr Ile Thr Cys Arg Ala Ser Gln Ser Ile Ser Ser Phe
20 25 30

Leu Asn Trp Phe Gln Gln Lys Pro Gly Lys Ala Pro Lys Phe Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Ser Pro Pro
85 90 95

Ile Thr Phe Gly Gln Gly Thr Arg Leu Glu Ile Lys Arg
100 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagagcatta gcagcttt 18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Ser Ile Ser Ser Phe
1 5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc 9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
1

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
caacagagtt acagttcccc tccgatcacc 30

<210> SEQ ID NO 48
<211> LENGTH: 10
<212> TYPE: PRT
<213> ORGANISM: Artificial Sequence
<220> FEATURE:
<223> OTHER INFORMATION: Synthetic

<400> SEQUENCE: 48

Gln Gln Ser Tyr Ser Ser Pro Pro Ile Thr
1 5 10

<210> SEQ ID NO 49
<211> LENGTH: 357
<212> TYPE: DNA
<213> ORGANISM: Artificial Sequence
<220> FEATURE:
<223> OTHER INFORMATION: Synthetic

<400> SEQUENCE: 49
caggtgcagc tgcaggagtc gggcccagga ctggtgaagc cttcggagac cctgtccctc 60
acctgcactg tcactggtgg ctccatcagt aggaactact ggagttggat ccggcagccc 120

```
ccagggaagg gactggaatg gattggatat atctattaca gtgggagtat cgactacaat    180

ccctccctca agagtcgagt caccatatca gtagacacgt ccaagaacca gttctccctg    240

aagctgagtt ctatgaccgc tgcggacacg gccgtatact actgtgcgag agatcggtgg    300

aactggaaat acggtatgga cgtctggggc caagggacca cggtcatcgt ctcgtca       357
```

<210> SEQ ID NO 50
<211> LENGTH: 119
<212> TYPE: PRT
<213> ORGANISM: Artificial Sequence
<220> FEATURE:
<223> OTHER INFORMATION: Synthetic

<400> SEQUENCE: 50

```
Gln Val Gln Leu Gln Glu Ser Gly Pro Gly Leu Val Lys Pro Ser Glu
1               5                   10                  15

Thr Leu Ser Leu Thr Cys Thr Val Thr Gly Gly Ser Ile Ser Arg Asn
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Ile Asp Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Met Thr Ala Ala Asp Thr Ala Val Tyr Tyr Cys Ala
                85                  90                  95

Arg Asp Arg Trp Asn Trp Lys Tyr Gly Met Asp Val Trp Gly Gln Gly
            100                 105                 110

Thr Thr Val Ile Val Ser Ser
        115
```

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51

```
ggtggctcca tcagtaggaa ctac                                            24
```

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

```
Gly Gly Ser Ile Ser Arg Asn Tyr
1               5
```

<210> SEQ ID NO 53
<211> LENGTH: 21
<212> TYPE: DNA
<213> ORGANISM: Artificial Sequence
<220> FEATURE:
<223> OTHER INFORMATION: Synthetic

<400> SEQUENCE: 53

```
atctattaca gtgggagtat c                                               21
```

<210> SEQ ID NO 54
<211> LENGTH: 7
<212> TYPE: PRT
<213> ORGANISM: Artificial Sequence
<220> FEATURE:
<223> OTHER INFORMATION: Synthetic

<400> SEQUENCE: 54

Ile Tyr Tyr Ser Gly Ser Ile
1               5

<210> SEQ ID NO 55
<211> LENGTH: 39
<212> TYPE: DNA
<213> ORGANISM: Artificial Sequence
<220> FEATURE:
<223> OTHER INFORMATION: Synthetic

<400> SEQUENCE: 55
gcgagagatc ggtggaactg gaaatacggt atggacgtc 39

<210> SEQ ID NO 56
<211> LENGTH: 13
<212> TYPE: PRT
<213> ORGANISM: Artificial Sequence
<220> FEATURE:
<223> OTHER INFORMATION: Synthetic

<400> SEQUENCE: 56

Ala Arg Asp Arg Trp Asn Trp Lys Tyr Gly Met Asp Val
1               5                   10

<210> SEQ ID NO 57
<211> LENGTH: 327
<212> TYPE: DNA
<213> ORGANISM: Artificial Sequence
<220> FEATURE:
<223> OTHER INFORMATION: Synthetic

<400> SEQUENCE: 57
gaaattgtgt tgacgcagtc tccaggcacc ctgtctttgt ctccagggga aagagccacc 60
ctctcctgca gggccagtca gactgttaga aacaactact tagcctggta ccaccagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttacagtgta ttactgtcac cagtatggta actcaccttg gacgttcggc 300
caagggacca aaatggaaat caaacga 327

<210> SEQ ID NO 58
<211> LENGTH: 109
<212> TYPE: PRT
<213> ORGANISM: Artificial Sequence
<220> FEATURE:
<223> OTHER INFORMATION: Synthetic

<400> SEQUENCE: 58

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Thr Val Arg Asn Asn
            20                  25                  30

Tyr Leu Ala Trp Tyr His Gln Lys Pro Gly Gln Ala Pro Arg Leu Leu
        35                  40                  45

```
Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Thr Val Tyr Tyr Cys His Gln Tyr Gly Asn Ser Pro
                85                  90                  95

Trp Thr Phe Gly Gln Gly Thr Lys Met Glu Ile Lys Arg
            100                 105


<210> SEQ ID NO 59
<211> LENGTH: 21
<212> TYPE: DNA
<213> ORGANISM: Artificial Sequence
<220> FEATURE:
<223> OTHER INFORMATION: Synthetic

<400> SEQUENCE: 59

cagactgtta gaaacaacta c                                              21


<210> SEQ ID NO 60
<211> LENGTH: 7
<212> TYPE: PRT
<213> ORGANISM: Artificial Sequence
<220> FEATURE:
<223> OTHER INFORMATION: Synthetic

<400> SEQUENCE: 60

Gln Thr Val Arg Asn Asn Tyr
1               5


<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61

ggtgcatcc                                                             9


<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Gly Ala Ser
1


<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63

caccagtatg gtaactcacc ttggacg                                        27


<210> SEQ ID NO 64
<211> LENGTH: 9
<212> TYPE: PRT
<213> ORGANISM: Artificial Sequence
```

<220> FEATURE:
<223> OTHER INFORMATION: Synthetic

<400> SEQUENCE: 64

His Gln Tyr Gly Asn Ser Pro Trp Thr
1 5

<210> SEQ ID NO 65
<211> LENGTH: 363
<212> TYPE: DNA
<213> ORGANISM: Artificial Sequence
<220> FEATURE:
<223> OTHER INFORMATION: Synthetic

<400> SEQUENCE: 65
gaggtgcagc tggtggagtc tgggggaggc ttggtccagc ctggagggtc cctgagactc 60
tcctgtgcag cctctggatt caccttcagt gaccactaca tggactgggt ccgccaggct 120
cctgggaagg ggctggagtg ggttggccga actagaaaca aagctaatag ttacaccaca 180
gaatacgccg cgtctgtgag tggcagattc accatctcaa gagatgattc aaagaactca 240
ttatatctgc aaatgaacag cctgaaaacc gaggacacgg ccgtgtatta ttgcactaga 300
gccggtataa ttggaaccct ctttgactac tggggccagg gaaccctggt caccgtctcc 360
tca 363

<210> SEQ ID NO 66
<211> LENGTH: 121
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asp His
20 25 30

Tyr Met Asp Trp Val Arg Gln Ala Pro Gly Lys Gly Leu Glu Trp Val
35 40 45

Gly Arg Thr Arg Asn Lys Ala Asn Ser Tyr Thr Thr Glu Tyr Ala Ala
50 55 60

Ser Val Ser Gly Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Thr Arg Ala Gly Ile Ile Gly Thr Leu Phe Asp Tyr Trp Gly
100 105 110

Gln Gly Thr Leu Val Thr Val Ser Ser
115 120

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcacct tcagtgacca ctac 24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Ser Asp His Tyr
1 5

<210> SEQ ID NO 69
<211> LENGTH: 30
<212> TYPE: DNA
<213> ORGANISM: Artificial Sequence
<220> FEATURE:
<223> OTHER INFORMATION: Synthetic

<400> SEQUENCE: 69
actagaaaca aagctaatag ttacaccaca 30

<210> SEQ ID NO 70
<211> LENGTH: 10
<212> TYPE: PRT
<213> ORGANISM: Artificial Sequence
<220> FEATURE:
<223> OTHER INFORMATION: Synthetic

<400> SEQUENCE: 70

Thr Arg Asn Lys Ala Asn Ser Tyr Thr Thr
1 5 10

<210> SEQ ID NO 71
<211> LENGTH: 36
<212> TYPE: DNA
<213> ORGANISM: Artificial Sequence
<220> FEATURE:
<223> OTHER INFORMATION: Synthetic

<400> SEQUENCE: 71
actagagccg gtataattgg aaccctcttt gactac 36

<210> SEQ ID NO 72
<211> LENGTH: 12
<212> TYPE: PRT
<213> ORGANISM: Artificial Sequence
<220> FEATURE:
<223> OTHER INFORMATION: Synthetic

<400> SEQUENCE: 72

Thr Arg Ala Gly Ile Ile Gly Thr Leu Phe Asp Tyr
1 5 10

<210> SEQ ID NO 73
<211> LENGTH: 327
<212> TYPE: DNA
<213> ORGANISM: Artificial Sequence
<220> FEATURE:
<223> OTHER INFORMATION: Synthetic

<400> SEQUENCE: 73
gacatccaga tgacccagtc tccatcctcc ctgtctgcat ctgtaggaga cagagtcacc 60
atcacttgcc gggcaagtca gatcattggt agatatttaa attggtttca gcagaaacca 120
gggaaagtcc ctaagctcct gatctatgct gcatccagtt tgcaacgtgg ggtcccatca 180
aggttcagtg gcagtggatc tgggacagat ttcactctca ccatcagcag tctgcaacct 240
gaagattttg caacttacta ctgtcaacag agttacaata cccctccgat caccttcggc 300
caagggacac gactggagat taaacga 327

<210> SEQ ID NO 74
<211> LENGTH: 109
<212> TYPE: PRT
<213> ORGANISM: Artificial Sequence
<220> FEATURE:
<223> OTHER INFORMATION: Synthetic

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ile Ile Gly Arg Tyr
            20                  25                  30

Leu Asn Trp Phe Gln Gln Lys Pro Gly Lys Val Pro Lys Leu Leu Ile
        35                  40                  45

Tyr Ala Ala Ser Ser Leu Gln Arg Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Asn Thr Pro Pro
                85                  90                  95

Ile Thr Phe Gly Gln Gly Thr Arg Leu Glu Ile Lys Arg
            100                 105
```

<210> SEQ ID NO 75
<211> LENGTH: 18
<212> TYPE: DNA
<213> ORGANISM: Artificial Sequence
<220> FEATURE:
<223> OTHER INFORMATION: Synthetic

<400> SEQUENCE: 75
cagatcattg gtagatat 18

<210> SEQ ID NO 76
<211> LENGTH: 6
<212> TYPE: PRT
<213> ORGANISM: Artificial Sequence
<220> FEATURE:
<223> OTHER INFORMATION: Synthetic

<400> SEQUENCE: 76

```
Gln Ile Ile Gly Arg Tyr
1               5
```

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 gctgcatcc 9

<210> SEQ ID NO 78
<211> LENGTH: 3
<212> TYPE: PRT
<213> ORGANISM: Artificial Sequence
<220> FEATURE:

<223> OTHER INFORMATION: Synthetic

<400> SEQUENCE: 78

Ala Ala Ser
1

<210> SEQ ID NO 79
<211> LENGTH: 30
<212> TYPE: DNA
<213> ORGANISM: Artificial Sequence
<220> FEATURE:
<223> OTHER INFORMATION: Synthetic

<400> SEQUENCE: 79
caacagagtt acaataccc tccgatcacc 30

<210> SEQ ID NO 80
<211> LENGTH: 10
<212> TYPE: PRT
<213> ORGANISM: Artificial Sequence
<220> FEATURE:
<223> OTHER INFORMATION: Synthetic

<400> SEQUENCE: 80

Gln Gln Ser Tyr Asn Thr Pro Pro Ile Thr
1 5 10

<210> SEQ ID NO 81
<211> LENGTH: 363
<212> TYPE: DNA
<213> ORGANISM: Artificial Sequence
<220> FEATURE:
<223> OTHER INFORMATION: Synthetic

<400> SEQUENCE: 81
caggtccagc tggtgcagtc tggggctgag gtgagggagc ctggggcctc agtgaagctc 60
tcctgcaagg tttccggata caccctcact gaattatcca tccactgggt gcgacaggct 120
cctggaaaag gacttgagtg gatgggaggt tttgatcctg aagagggtga aacagtctac 180
gcacagaagt tccggggcag agtcaccctg accgaggaca taagtccaga cacggcctac 240
atggagctga gcagcctgac ctctgaggac acggccgtat attattgtgc aaccccccgc 300
tattgtaata atggtatatg ttatgactac tggggccagg gaaccctaat caccgtctcc 360
tca 363

<210> SEQ ID NO 82
<211> LENGTH: 121
<212> TYPE: PRT
<213> ORGANISM: Artificial Sequence
<220> FEATURE:
<223> OTHER INFORMATION: Synthetic

<400> SEQUENCE: 82

Gln Val Gln Leu Val Gln Ser Gly Ala Glu Val Arg Glu Pro Gly Ala
1 5 10 15

Ser Val Lys Leu Ser Cys Lys Val Ser Gly Tyr Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Glu Gly Glu Thr Val Tyr Ala Gln Lys Phe
50 55 60

Arg Gly Arg Val Thr Leu Thr Glu Asp Ile Ser Pro Asp Thr Ala Tyr

```
65                  70                  75                  80

Met Glu Leu Ser Ser Leu Thr Ser Glu Asp Thr Ala Val Tyr Tyr Cys
                85                  90                  95

Ala Thr Pro Arg Tyr Cys Asn Asn Gly Ile Cys Tyr Asp Tyr Trp Gly
            100                 105                 110

Gln Gly Thr Leu Ile Thr Val Ser Ser
        115                 120


<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83

ggatacaccc tcactgaatt atcc                                            24


<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

Gly Tyr Thr Leu Thr Glu Leu Ser
1               5


<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85

tttgatcctg aagagggtga aaca                                            24


<210> SEQ ID NO 86
<211> LENGTH: 8
<212> TYPE: PRT
<213> ORGANISM: Artificial Sequence
<220> FEATURE:
<223> OTHER INFORMATION: Synthetic

<400> SEQUENCE: 86

Phe Asp Pro Glu Glu Gly Glu Thr
1               5


<210> SEQ ID NO 87
<211> LENGTH: 42
<212> TYPE: DNA
<213> ORGANISM: Artificial Sequence
<220> FEATURE:
<223> OTHER INFORMATION: Synthetic

<400> SEQUENCE: 87

gcaaccccc gctattgtaa taatggtata tgttatgact ac                         42


<210> SEQ ID NO 88
<211> LENGTH: 14
<212> TYPE: PRT
<213> ORGANISM: Artificial Sequence
<220> FEATURE:
```

<223> OTHER INFORMATION: Synthetic

<400> SEQUENCE: 88

Ala Thr Pro Arg Tyr Cys Asn Asn Gly Ile Cys Tyr Asp Tyr
1 5 10

<210> SEQ ID NO 89
<211> LENGTH: 324
<212> TYPE: DNA
<213> ORGANISM: Artificial Sequence
<220> FEATURE:
<223> OTHER INFORMATION: Synthetic

<400> SEQUENCE: 89
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccgtca 180
aggttcagtg gcagtggatc tgggacagat ttcactctca ccatcagcag tctgcaacct 240
gaagattttg caacttacta ctgtcaacag agttacagta cccctccgat caccttcggc 300
caagggacac gactggagat taaa 324

<210> SEQ ID NO 90
<211> LENGTH: 108
<212> TYPE: PRT
<213> ORGANISM: Artificial Sequence
<220> FEATURE:
<223> OTHER INFORMATION: Synthetic

<400> SEQUENCE: 90

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Thr Pro Pro
85 90 95

Ile Thr Phe Gly Gln Gly Thr Arg Leu Glu Ile Lys
100 105

<210> SEQ ID NO 91
<211> LENGTH: 18
<212> TYPE: DNA
<213> ORGANISM: Artificial Sequence
<220> FEATURE:
<223> OTHER INFORMATION: Synthetic

<400> SEQUENCE: 91
cagagcatta gcagctat 18

<210> SEQ ID NO 92
<211> LENGTH: 6
<212> TYPE: PRT
<213> ORGANISM: Artificial Sequence
<220> FEATURE:
<223> OTHER INFORMATION: Synthetic

<400> SEQUENCE: 92

Gln Ser Ile Ser Ser Tyr
1 5

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 gctgcatcc 9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Ala Ala Ser
1

<210> SEQ ID NO 95
<211> LENGTH: 30
<212> TYPE: DNA
<213> ORGANISM: Artificial Sequence
<220> FEATURE:
<223> OTHER INFORMATION: Synthetic

<400> SEQUENCE: 95
caacagagtt acagtacccc tccgatcacc 30

<210> SEQ ID NO 96
<211> LENGTH: 10
<212> TYPE: PRT
<213> ORGANISM: Artificial Sequence
<220> FEATURE:
<223> OTHER INFORMATION: Synthetic

<400> SEQUENCE: 96

Gln Gln Ser Tyr Ser Thr Pro Pro Ile Thr
1 5 10

<210> SEQ ID NO 97
<211> LENGTH: 363
<212> TYPE: DNA
<213> ORGANISM: Artificial Sequence
<220> FEATURE:
<223> OTHER INFORMATION: Synthetic

<400> SEQUENCE: 97
gaggtgcagc tgttggagtc tgggggaggc ttggtacagc ctggggggtc cctgagactc 60
tcctgtgcag cctctggatt cacctttagt aattatgcca tgacctgggt ccgccaggct 120
ccagggacgg ggctggagtg ggtctcagct attagtggtc gtggtagtaa cacatactac 180
acagactccg tgaagggccg gttcaccatc tccagagaca attccaagaa catgctgtat 240
ctgcaaatga acagcctgag agccgaggac acggcctcat attactgtgc gaaagatcgt 300
tttactacag tggggaactg gttcgacccc tggggccagg gaaccctggt caccgtctcc 360
tca 363

<210> SEQ ID NO 98
<211> LENGTH: 121
<212> TYPE: PRT
<213> ORGANISM: Artificial Sequence
<220> FEATURE:
<223> OTHER INFORMATION: Synthetic

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Thr Trp Val Arg Gln Ala Pro Gly Thr Gly Leu Glu Trp Val
        35                  40                  45

Ser Ala Ile Ser Gly Arg Gly Ser Asn Thr Tyr Tyr Thr Asp Ser Val
    50                  55                  60

Lys Gly Arg Phe Thr Ile Ser Arg Asp Asn Ser Lys Asn Met Leu Tyr
65                  70                  75                  80

Leu Gln Met Asn Ser Leu Arg Ala Glu Asp Thr Ala Ser Tyr Tyr Cys
                85                  90                  95

Ala Lys Asp Arg Phe Thr Thr Val Gly Asn Trp Phe Asp Pro Trp Gly
            100                 105                 110

Gln Gly Thr Leu Val Thr Val Ser Ser
        115                 120

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99
ggattcacct ttagtaatta tgcc                                            24

<210> SEQ ID NO 100
<211> LENGTH: 8
<212> TYPE: PRT
<213> ORGANISM: Artificial Sequence
<220> FEATURE:
<223> OTHER INFORMATION: Synthetic

<400> SEQUENCE: 100

Gly Phe Thr Phe Ser Asn Tyr Ala
1               5

<210> SEQ ID NO 101
<211> LENGTH: 24
<212> TYPE: DNA
<213> ORGANISM: Artificial Sequence
<220> FEATURE:
<223> OTHER INFORMATION: Synthetic

<400> SEQUENCE: 101
attagtggtc gtggtagtaa caca                                            24

<210> SEQ ID NO 102
<211> LENGTH: 8
<212> TYPE: PRT
<213> ORGANISM: Artificial Sequence
<220> FEATURE:
<223> OTHER INFORMATION: Synthetic

<400> SEQUENCE: 102

Ile Ser Gly Arg Gly Ser Asn Thr
1 5

<210> SEQ ID NO 103
<211> LENGTH: 42
<212> TYPE: DNA
<213> ORGANISM: Artificial Sequence
<220> FEATURE:
<223> OTHER INFORMATION: Synthetic

<400> SEQUENCE: 103
gcgaaagatc gttttactac agtggggaac tggttcgacc cc 42

<210> SEQ ID NO 104
<211> LENGTH: 14
<212> TYPE: PRT
<213> ORGANISM: Artificial Sequence
<220> FEATURE:
<223> OTHER INFORMATION: Synthetic

<400> SEQUENCE: 104

Ala Lys Asp Arg Phe Thr Thr Val Gly Asn Trp Phe Asp Pro
1 5 10

<210> SEQ ID NO 105
<211> LENGTH: 327
<212> TYPE: DNA
<213> ORGANISM: Artificial Sequence
<220> FEATURE:
<223> OTHER INFORMATION: Synthetic

<400> SEQUENCE: 105
gacatccaga tgacccagtc tccatcctcc ctgtctgcat ctgtaggaga cagagtcacc 60
atcacttgcc gggcaagtca gagtattagc agctatttaa attggtatca gcagaaacca 120
gggaaagccc ctaagctcct gatctatgct gcgtccagtt tgcaaaatgg ggtcccatca 180
aggttcagtg gcagtggatc tgggacagat ttcactctca ccatcagcag tctgcagcct 240
gaagattttg caacttacta ctgtcaacag agttacagta gtcttccgat caccttcggc 300
caagggacac gactggatat taaacga 327

<210> SEQ ID NO 106
<211> LENGTH: 109
<212> TYPE: PRT
<213> ORGANISM: Artificial Sequence
<220> FEATURE:
<223> OTHER INFORMATION: Synthetic

<400> SEQUENCE: 106

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Asn Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Tyr Ser Ser Leu Pro

```
                85                  90                  95

Ile Thr Phe Gly Gln Gly Thr Arg Leu Asp Ile Lys Arg
            100                 105


<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107

cagagtatta gcagctat                                                    18


<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Ser Ile Ser Ser Tyr
1               5


<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109

gctgcgtcc                                                               9


<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Ala Ser
1


<210> SEQ ID NO 111
<211> LENGTH: 30
<212> TYPE: DNA
<213> ORGANISM: Artificial Sequence
<220> FEATURE:
<223> OTHER INFORMATION: Synthetic

<400> SEQUENCE: 111

caacagagtt acagtagtct tccgatcacc                                       30


<210> SEQ ID NO 112
<211> LENGTH: 10
<212> TYPE: PRT
<213> ORGANISM: Artificial Sequence
<220> FEATURE:
<223> OTHER INFORMATION: Synthetic

<400> SEQUENCE: 112

Gln Gln Ser Tyr Ser Ser Leu Pro Ile Thr
1               5                   10
```

<210> SEQ ID NO 113
<211> LENGTH: 357
<212> TYPE: DNA
<213> ORGANISM: Artificial Sequence
<220> FEATURE:
<223> OTHER INFORMATION: Synthetic

<400> SEQUENCE: 113
caggtgcagc tgcaggagtc gggcccagga ctggtgaagc cttcggagac cctgtccctc 60
acctgcactg tcactggtgg ctccatcagt aggaactact ggagttggat ccggcagccc 120
ccagggaagg gactggaatg gattggatat atctattaca gtgggagtat caactacaat 180
ccctccctca agagtcgagt caccatatca gtggacatgt ctaagaacca gttctcccta 240
aagctgaatt ctgtgaccgc tgcggacacg gccgtgtact actgtgcgag agatcgatgg 300
aactggaaat acggtatgga cgtctggggc caagggacca cggtcatcgt ctcgtca 357

<210> SEQ ID NO 114
<211> LENGTH: 119
<212> TYPE: PRT
<213> ORGANISM: Artificial Sequence
<220> FEATURE:
<223> OTHER INFORMATION: Synthetic

<400> SEQUENCE: 114

Gln Val Gln Leu Gln Glu Ser Gly Pro Gly Leu Val Lys Pro Ser Glu
1 5 10 15

Thr Leu Ser Leu Thr Cys Thr Val Thr Gly Gly Ser Ile Ser Arg Asn
20 25 30

Tyr Trp Ser Trp Ile Arg Gln Pro Pro Gly Lys Gly Leu Glu Trp Ile
35 40 45

Gly Tyr Ile Tyr Tyr Ser Gly Ser Ile Asn Tyr Asn Pro Ser Leu Lys
50 55 60

Ser Arg Val Thr Ile Ser Val Asp Met Ser Lys Asn Gln Phe Ser Leu
65 70 75 80

Lys Leu Asn Ser Val Thr Ala Ala Asp Thr Ala Val Tyr Tyr Cys Ala
85 90 95

Arg Asp Arg Trp Asn Trp Lys Tyr Gly Met Asp Val Trp Gly Gln Gly
100 105 110

Thr Thr Val Ile Val Ser Ser
115

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggtggctcca tcagtaggaa ctac 24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

Gly Gly Ser Ile Ser Arg Asn Tyr
1               5

<210> SEQ ID NO 117
<211> LENGTH: 21
<212> TYPE: DNA
<213> ORGANISM: Artificial Sequence
<220> FEATURE:
<223> OTHER INFORMATION: Synthetic

<400> SEQUENCE: 117
atctattaca gtgggagtat c 21

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

Ile Tyr Tyr Ser Gly Ser Ile
1               5

<210> SEQ ID NO 119
<211> LENGTH: 39
<212> TYPE: DNA
<213> ORGANISM: Artificial Sequence
<220> FEATURE:
<223> OTHER INFORMATION: Synthetic

<400> SEQUENCE: 119
gcgagagatc gatggaactg gaaatacggt atggacgtc 39

<210> SEQ ID NO 120
<211> LENGTH: 13
<212> TYPE: PRT
<213> ORGANISM: Artificial Sequence
<220> FEATURE:
<223> OTHER INFORMATION: Synthetic

<400> SEQUENCE: 120

Ala Arg Asp Arg Trp Asn Trp Lys Tyr Gly Met Asp Val
1               5                   10

<210> SEQ ID NO 121
<211> LENGTH: 327
<212> TYPE: DNA
<213> ORGANISM: Artificial Sequence
<220> FEATURE:
<223> OTHER INFORMATION: Synthetic

<400> SEQUENCE: 121
gaaattgtgt tgacgcagtc tccaggcacc ctgtctttgt ctccagggga aagagccacc 60
ctctcctgca gggccagtca gactgttaga aacagctact tagcctggta ccaccagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gttcatattg gacgttcggc 300
caagggacca aaatggaaat caaacga 327

<210> SEQ ID NO 122
<211> LENGTH: 109
<212> TYPE: PRT

<213> ORGANISM: Artificial Sequence
<220> FEATURE:
<223> OTHER INFORMATION: Synthetic

<400> SEQUENCE: 122

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Thr Val Arg Asn Ser
20 25 30

Tyr Leu Ala Trp Tyr His Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Tyr
85 90 95

Trp Thr Phe Gly Gln Gly Thr Lys Met Glu Ile Lys Arg
100 105

<210> SEQ ID NO 123
<211> LENGTH: 21
<212> TYPE: DNA
<213> ORGANISM: Artificial Sequence
<220> FEATURE:
<223> OTHER INFORMATION: Synthetic

<400> SEQUENCE: 123
cagactgtta gaaacagcta c 21

<210> SEQ ID NO 124
<211> LENGTH: 7
<212> TYPE: PRT
<213> ORGANISM: Artificial Sequence
<220> FEATURE:
<223> OTHER INFORMATION: Synthetic

<400> SEQUENCE: 124

Gln Thr Val Arg Asn Ser Tyr
1 5

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 ggtgcatcc 9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Gly Ala Ser
1

<210> SEQ ID NO 127

<211> LENGTH: 27
<212> TYPE: DNA
<213> ORGANISM: Artificial Sequence
<220> FEATURE:
<223> OTHER INFORMATION: Synthetic

<400> SEQUENCE: 127
cagcagtatg gtagttcata ttggacg 27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Gln Gln Tyr Gly Ser Ser Tyr Trp Thr
1 5

<210> SEQ ID NO 129
<211> LENGTH: 363
<212> TYPE: DNA
<213> ORGANISM: Artificial Sequence
<220> FEATURE:
<223> OTHER INFORMATION: Synthetic

<400> SEQUENCE: 129
caggtccagc tggtgcagtc tgggtctgag gtgaagaagc ctggggcctc agtgaaggtc 60
tcctgcaagg tttccggata caccctcact gaattatcca tacactgggt gcgacaggct 120
cctggaaaag gacttgagtg gatgggaggt tttgatcctg aagatggtga aacaatctac 180
gcacagaagt tccggggcag agtcaccatg accgaggaca tatctccaga cacagcctac 240
atggagctga gcagcctgag atctgaagac acggccgtat attactgtgc aaccccccgc 300
tattgtaata atggtatatg ttatgactat tggggccagg gaaccctggt caccgtctcc 360
tca 363

<210> SEQ ID NO 130
<211> LENGTH: 121
<212> TYPE: PRT
<213> ORGANISM: Artificial Sequence
<220> FEATURE:
<223> OTHER INFORMATION: Synthetic

<400> SEQUENCE: 130

Gln Val Gln Leu Val Gln Ser Gly Ser Glu Val Lys Lys Pro Gly Ala
1 5 10 15

Ser Val Lys Val Ser Cys Lys Val Ser Gly Tyr Thr Leu Thr Glu Leu
20 25 30

Ser Ile His Trp Val Arg Gln Ala Pro Gly Lys Gly Leu Glu Trp Met
35 40 45

Gly Gly Phe Asp Pro Glu Asp Gly Glu Thr Ile Tyr Ala Gln Lys Phe
50 55 60

Arg Gly Arg Val Thr Met Thr Glu Asp Ile Ser Pro Asp Thr Ala Tyr
65 70 75 80

Met Glu Leu Ser Ser Leu Arg Ser Glu Asp Thr Ala Val Tyr Tyr Cys
85 90 95

Ala Thr Pro Arg Tyr Cys Asn Asn Gly Ile Cys Tyr Asp Tyr Trp Gly
100 105 110

Gln Gly Thr Leu Val Thr Val Ser Ser

-continued 115 120

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggatacaccc tcactgaatt atcc 24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Tyr Thr Leu Thr Glu Leu Ser
1 5

<210> SEQ ID NO 133
<211> LENGTH: 24
<212> TYPE: DNA
<213> ORGANISM: Artificial Sequence
<220> FEATURE:
<223> OTHER INFORMATION: Synthetic

<400> SEQUENCE: 133
tttgatcctg aagatggtga aaca 24

<210> SEQ ID NO 134
<211> LENGTH: 8
<212> TYPE: PRT
<213> ORGANISM: Artificial Sequence
<220> FEATURE:
<223> OTHER INFORMATION: Synthetic

<400> SEQUENCE: 134

Phe Asp Pro Glu Asp Gly Glu Thr
1 5

<210> SEQ ID NO 135
<211> LENGTH: 42
<212> TYPE: DNA
<213> ORGANISM: Artificial Sequence
<220> FEATURE:
<223> OTHER INFORMATION: Synthetic

<400> SEQUENCE: 135
gcaacccccc gctattgtaa taatggtata tgttatgact at 42

<210> SEQ ID NO 136
<211> LENGTH: 14
<212> TYPE: PRT
<213> ORGANISM: Artificial Sequence
<220> FEATURE:
<223> OTHER INFORMATION: Synthetic

<400> SEQUENCE: 136

Ala Thr Pro Arg Tyr Cys Asn Asn Gly Ile Cys Tyr Asp Tyr
1 5 10

<210> SEQ ID NO 137

<211> LENGTH: 327
<212> TYPE: DNA
<213> ORGANISM: Artificial Sequence
<220> FEATURE:
<223> OTHER INFORMATION: Synthetic

<400> SEQUENCE: 137
gacatccaga tgacccagtc tccatcctcc ctgtctgcat ctataggaga cagagtcacc 60
atcacttgcc gggcaagtca gagcattagc agctatttaa attggtatca gcagaaacca 120
gggaaagccc ctatgctcct gatctatgct gcatccagtt tgcaaagtgg ggtcccatca 180
aggttcagtg gcagtggatc tgggacagat ttcactctca ccatcagcag tctgcaaact 240
gaagattttg caacttacta ctgtcaacag agttacagta cccctccgat caccttcggc 300
caagggacac gactggagat taaacga 327

<210> SEQ ID NO 138
<211> LENGTH: 109
<212> TYPE: PRT
<213> ORGANISM: Artificial Sequence
<220> FEATURE:
<223> OTHER INFORMATION: Synthetic

<400> SEQUENCE: 138

Asp Ile Gln Met Thr Gln Ser Pro Ser Ser Leu Ser Ala Ser Ile Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Met Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Thr
65 70 75 80

Glu Asp Phe Ala Thr Tyr Tyr Cys Gln Gln Ser Tyr Ser Thr Pro Pro
85 90 95

Ile Thr Phe Gly Gln Gly Thr Arg Leu Glu Ile Lys Arg
100 105

<210> SEQ ID NO 139
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagagcatta gcagctat 18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Ser Ile Ser Ser Tyr
1 5

<210> SEQ ID NO 141
<211> LENGTH: 9

<212> TYPE: DNA
<213> ORGANISM: Artificial Sequence
<220> FEATURE:
<223> OTHER INFORMATION: Synthetic

<400> SEQUENCE: 141 gctgcatcc 9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Ala Ser
1

<210> SEQ ID NO 143
<211> LENGTH: 30
<212> TYPE: DNA
<213> ORGANISM: Artificial Sequence
<220> FEATURE:
<223> OTHER INFORMATION: Synthetic

<400> SEQUENCE: 143
caacagagtt acagtacccc tccgatcacc 30

<210> SEQ ID NO 144
<211> LENGTH: 10
<212> TYPE: PRT
<213> ORGANISM: Artificial Sequence
<220> FEATURE:
<223> OTHER INFORMATION: Synthetic

<400> SEQUENCE: 144

Gln Gln Ser Tyr Ser Thr Pro Pro Ile Thr
1 5 10

<210> SEQ ID NO 145
<211> LENGTH: 345
<212> TYPE: DNA
<213> ORGANISM: Artificial Sequence
<220> FEATURE:
<223> OTHER INFORMATION: Synthetic

<400> SEQUENCE: 145
caggtgcagc tggtggagtc tgggggaggc ttggtcaagc ctggagggtc cctgagactc 60
tcctgtgcag cctctggatt catttttagt gactactaca tgagctggat ccgccaggct 120
ccagggaagg ggctggagtg ggtttcatac attagtagta gtggtactac catatatgga 180
gactctgtga agggccgatt caccatgtcc agggacaacg ccaagaactc actgtatctg 240
caaatgaaca gcctgagagc cgaggacacg gccgtgtatt actgtgcgag gaactacgct 300
ctctttgact actggggcca gggaaccctg gtcaccgtct cctca 345

<210> SEQ ID NO 146
<211> LENGTH: 115
<212> TYPE: PRT
<213> ORGANISM: Artificial Sequence
<220> FEATURE:
<223> OTHER INFORMATION: Synthetic

<400> SEQUENCE: 146

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Ile Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Thr Thr Ile Tyr Gly Asp Ser Val Lys
    50                  55                  60

Gly Arg Phe Thr Met Ser Arg Asp Asn Ala Lys Asn Ser Leu Tyr Leu
65                  70                  75                  80

Gln Met Asn Ser Leu Arg Ala Glu Asp Thr Ala Val Tyr Tyr Cys Ala
                85                  90                  95

Arg Asn Tyr Ala Leu Phe Asp Tyr Trp Gly Gln Gly Thr Leu Val Thr
            100                 105                 110

Val Ser Ser
        115


<210> SEQ ID NO 147
<211> LENGTH: 24
<212> TYPE: DNA
<213> ORGANISM: Artificial Sequence
<220> FEATURE:
<223> OTHER INFORMATION: Synthetic

<400> SEQUENCE: 147

ggattcattt ttagtgacta ctac                                            24


<210> SEQ ID NO 148
<211> LENGTH: 8
<212> TYPE: PRT
<213> ORGANISM: Artificial Sequence
<220> FEATURE:
<223> OTHER INFORMATION: Synthetic

<400> SEQUENCE: 148

Gly Phe Ile Phe Ser Asp Tyr Tyr
1               5


<210> SEQ ID NO 149
<211> LENGTH: 24
<212> TYPE: DNA
<213> ORGANISM: Artificial Sequence
<220> FEATURE:
<223> OTHER INFORMATION: Synthetic

<400> SEQUENCE: 149

attagtagta gtggtactac cata                                            24


<210> SEQ ID NO 150
<211> LENGTH: 8
<212> TYPE: PRT
<213> ORGANISM: Artificial Sequence
<220> FEATURE:
<223> OTHER INFORMATION: Synthetic

<400> SEQUENCE: 150

Ile Ser Ser Ser Gly Thr Thr Ile
1               5


<210> SEQ ID NO 151
<211> LENGTH: 27
<212> TYPE: DNA
<213> ORGANISM: Artificial Sequence
```

<220> FEATURE:
<223> OTHER INFORMATION: Synthetic

<400> SEQUENCE: 151
gcgaggaact acgctctctt tgactac 27

<210> SEQ ID NO 152
<211> LENGTH: 9
<212> TYPE: PRT
<213> ORGANISM: Artificial Sequence
<220> FEATURE:
<223> OTHER INFORMATION: Synthetic

<400> SEQUENCE: 152

Ala Arg Asn Tyr Ala Leu Phe Asp Tyr
1 5

<210> SEQ ID NO 153
<211> LENGTH: 324
<212> TYPE: DNA
<213> ORGANISM: Artificial Sequence
<220> FEATURE:
<223> OTHER INFORMATION: Synthetic

<400> SEQUENCE: 153
gacatccaga tgacccagtc tccatcctcc ctgtctgcat ctgtaggaga cagagtcacc 60
atcacttgcc aggcgagtca ggacattagc aaatatttaa attggtatca gcagaaacca 120
gggaaagccc ctaagctcct gatctactat acatccaatt tggaaacagg ggtcccatca 180
aggttcagtg gaagtggatc tgggacagat tttactttca ccatcagcag cctgcagcct 240
gaagatattg caacatatta ctgtcaccag tctgattatc tcccattcac tttcggccct 300
gggaccaaag tggatatcaa acga 324

<210> SEQ ID NO 154
<211> LENGTH: 108
<212> TYPE: PRT
<213> ORGANISM: Artificial Sequence
<220> FEATURE:
<223> OTHER INFORMATION: Synthetic

<400> SEQUENCE: 154

Asp Ile Gln Met Thr Gln Ser Pro Ser Ser Leu Ser Ala Ser Val Gly
1 5 10 15

Asp Arg Val Thr Ile Thr Cys Gln Ala Ser Gln Asp Ile Ser Lys Tyr
20 25 30

Leu Asn Trp Tyr Gln Gln Lys Pro Gly Lys Ala Pro Lys Leu Leu Ile
35 40 45

Tyr Tyr Thr Ser Asn Leu Glu Thr Gly Val Pro Ser Arg Phe Ser Gly
50 55 60

Ser Gly Ser Gly Thr Asp Phe Thr Phe Thr Ile Ser Ser Leu Gln Pro
65 70 75 80

Glu Asp Ile Ala Thr Tyr Tyr Cys His Gln Ser Asp Tyr Leu Pro Phe
85 90 95

Thr Phe Gly Pro Gly Thr Lys Val Asp Ile Lys Arg
100 105

<210> SEQ ID NO 155
<211> LENGTH: 18
<212> TYPE: DNA
<213> ORGANISM: Artificial Sequence
<220> FEATURE:

<223> OTHER INFORMATION: Synthetic

<400> SEQUENCE: 155
caggacatta gcaaatat 18

<210> SEQ ID NO 156
<211> LENGTH: 6
<212> TYPE: PRT
<213> ORGANISM: Artificial Sequence
<220> FEATURE:
<223> OTHER INFORMATION: Synthetic

<400> SEQUENCE: 156

Gln Asp Ile Ser Lys Tyr
1 5

<210> SEQ ID NO 157
<211> LENGTH: 9
<212> TYPE: DNA
<213> ORGANISM: Artificial Sequence
<220> FEATURE:
<223> OTHER INFORMATION: Synthetic

<400> SEQUENCE: 157 tatacatcc 9

<210> SEQ ID NO 158
<211> LENGTH: 3
<212> TYPE: PRT
<213> ORGANISM: Artificial Sequence
<220> FEATURE:
<223> OTHER INFORMATION: Synthetic

<400> SEQUENCE: 158

Tyr Thr Ser
1

<210> SEQ ID NO 159
<211> LENGTH: 27
<212> TYPE: DNA
<213> ORGANISM: Artificial Sequence
<220> FEATURE:
<223> OTHER INFORMATION: Synthetic

<400> SEQUENCE: 159
caccagtctg attatctccc attcact 27

<210> SEQ ID NO 160
<211> LENGTH: 9
<212> TYPE: PRT
<213> ORGANISM: Artificial Sequence
<220> FEATURE:
<223> OTHER INFORMATION: Synthetic

<400> SEQUENCE: 160

His Gln Ser Asp Tyr Leu Pro Phe Thr
1 5

<210> SEQ ID NO 161
<211> LENGTH: 363
<212> TYPE: DNA
<213> ORGANISM: Artificial Sequence
<220> FEATURE:
<223> OTHER INFORMATION: Synthetic

<400> SEQUENCE: 161

```
cagctgcagc tgcaggagtc gggcccagga ctggtgaagc cttcggagac cctgtccctc      60

acctgcactg tctctggtgg ctccatcagc cgtattagtt actactgggg ctggatccgc     120

cagcccccag ggaaggggct ggagtggatt gggagtatct atgatagtgg gagtacctac     180

tacaacccgt ccctcaagag tcgagtcacc atatccatag acacgtccaa gaaccagttc     240

tccctgaagc tgagctctgt gaccgccgca gacacggctg tgtattactg tgtgagatat     300

agcagttcgt ccgccttcgc ttttgactac tggggccagg gaaccctggt caccgtctcc     360

tca                                                                   363
```

<210> SEQ ID NO 162
<211> LENGTH: 121
<212> TYPE: PRT
<213> ORGANISM: Artificial Sequence
<220> FEATURE:
<223> OTHER INFORMATION: Synthetic

<400> SEQUENCE: 162

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Arg Ile
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Asp Ser Gly Ser Thr Tyr Tyr Asn Pro Ser
    50                  55                  60

Leu Lys Ser Arg Val Thr Ile Ser Ile Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Val Arg Tyr Ser Ser Ser Ser Ala Phe Ala Phe Asp Tyr Trp Gly
            100                 105                 110

Gln Gly Thr Leu Val Thr Val Ser Ser
        115                 120
```

<210> SEQ ID NO 163
<211> LENGTH: 30
<212> TYPE: DNA
<213> ORGANISM: Artificial Sequence
<220> FEATURE:
<223> OTHER INFORMATION: Synthetic

<400> SEQUENCE: 163

```
ggtggctcca tcagccgtat tagttactac                                       30
```

<210> SEQ ID NO 164
<211> LENGTH: 10
<212> TYPE: PRT
<213> ORGANISM: Artificial Sequence
<220> FEATURE:
<223> OTHER INFORMATION: Synthetic

<400> SEQUENCE: 164

```
Gly Gly Ser Ile Ser Arg Ile Ser Tyr Tyr
1               5                   10
```

<210> SEQ ID NO 165
<211> LENGTH: 21
<212> TYPE: DNA
<213> ORGANISM: Artificial Sequence
<220> FEATURE:

<223> OTHER INFORMATION: Synthetic

<400> SEQUENCE: 165
atctatgata gtgggagtac c 21

<210> SEQ ID NO 166
<211> LENGTH: 7
<212> TYPE: PRT
<213> ORGANISM: Artificial Sequence
<220> FEATURE:
<223> OTHER INFORMATION: Synthetic

<400> SEQUENCE: 166

Ile Tyr Asp Ser Gly Ser Thr
1 5

<210> SEQ ID NO 167
<211> LENGTH: 39
<212> TYPE: DNA
<213> ORGANISM: Artificial Sequence
<220> FEATURE:
<223> OTHER INFORMATION: Synthetic

<400> SEQUENCE: 167
gtgagatata gcagttcgtc cgccttcgct tttgactac 39

<210> SEQ ID NO 168
<211> LENGTH: 13
<212> TYPE: PRT
<213> ORGANISM: Artificial Sequence
<220> FEATURE:
<223> OTHER INFORMATION: Synthetic

<400> SEQUENCE: 168

Val Arg Tyr Ser Ser Ser Ser Ala Phe Ala Phe Asp Tyr
1 5 10

<210> SEQ ID NO 169
<211> LENGTH: 324
<212> TYPE: DNA
<213> ORGANISM: Artificial Sequence
<220> FEATURE:
<223> OTHER INFORMATION: Synthetic

<400> SEQUENCE: 169
gacatccaga tgacccagtc tccatcttcc gtgtctgcat ctgtaggaga cagagtcacc 60
atcacttgtc gggcgagtca gggtattagc agttggttag cctggtatca gcagaaacca 120
gggaaagccc ctaagctcct gatctatgct gcatccagtt tgcaaagtgg ggtcccatca 180
aggttcagcg gcagtggatc tgggacagat ttcactctca ccatcagcag cctgcagcct 240
gaagattttg caacttacta ttgtcaacag gctaacagtt tcccattcac tttcggccct 300
gggaccaaag tggatatcaa acga 324

<210> SEQ ID NO 170
<211> LENGTH: 108
<212> TYPE: PRT
<213> ORGANISM: Artificial Sequence
<220> FEATURE:
<223> OTHER INFORMATION: Synthetic

<400> SEQUENCE: 170

Asp Ile Gln Met Thr Gln Ser Pro Ser Ser Val Ser Ala Ser Val Gly
1 5 10 15

```
Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys Arg
            100                 105


<210> SEQ ID NO 171
<211> LENGTH: 18
<212> TYPE: DNA
<213> ORGANISM: Artificial Sequence
<220> FEATURE:
<223> OTHER INFORMATION: Synthetic

<400> SEQUENCE: 171

cagggtatta gcagttgg                                                    18


<210> SEQ ID NO 172
<211> LENGTH: 6
<212> TYPE: PRT
<213> ORGANISM: Artificial Sequence
<220> FEATURE:
<223> OTHER INFORMATION: Synthetic

<400> SEQUENCE: 172

Gln Gly Ile Ser Ser Trp
1               5


<210> SEQ ID NO 173
<211> LENGTH: 9
<212> TYPE: DNA
<213> ORGANISM: Artificial Sequence
<220> FEATURE:
<223> OTHER INFORMATION: Synthetic

<400> SEQUENCE: 173

gctgcatcc                                                               9


<210> SEQ ID NO 174
<211> LENGTH: 3
<212> TYPE: PRT
<213> ORGANISM: Artificial Sequence
<220> FEATURE:
<223> OTHER INFORMATION: Synthetic

<400> SEQUENCE: 174

Ala Ala Ser
1


<210> SEQ ID NO 175
<211> LENGTH: 27
<212> TYPE: DNA
<213> ORGANISM: Artificial Sequence
<220> FEATURE:
<223> OTHER INFORMATION: Synthetic

<400> SEQUENCE: 175

caacaggcta acagtttccc attcact                                          27
```

<210> SEQ ID NO 176
<211> LENGTH: 9
<212> TYPE: PRT
<213> ORGANISM: Artificial Sequence
<220> FEATURE:
<223> OTHER INFORMATION: Synthetic

<400> SEQUENCE: 176

```
Gln Gln Ala Asn Ser Phe Pro Phe Thr
1               5
```

<210> SEQ ID NO 177
<211> LENGTH: 360
<212> TYPE: DNA
<213> ORGANISM: Artificial Sequence
<220> FEATURE:
<223> OTHER INFORMATION: Synthetic

<400> SEQUENCE: 177

```
cagctgcagc tgcaggagtc gggcccagga ctggtgaagc cttcggagac cctgtccctc     60

acctgcactg tctctggtgg ctccatcagc agtagtactt actactgggg ctggatccgc    120

cagcccccag ggaaggggct ggagtggatt gggagtttct attatagtgg gagcacctac    180

tacaacccgt ccctcaagag tcgagtcacc atatccgtag gcacgtccaa gaaccagttc    240

tccctgaagc tgagctctgt gaccgccgca gacacggctg tttatttctg tgcgagaggg    300

gggctcctgg ggagaccttt tgttatctgg ggccaaggga caatggtcac cgtctcttca    360
```

<210> SEQ ID NO 178
<211> LENGTH: 120
<212> TYPE: PRT
<213> ORGANISM: Artificial Sequence
<220> FEATURE:
<223> OTHER INFORMATION: Synthetic

<400> SEQUENCE: 178

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Thr Tyr Tyr Trp Gly Trp Ile Arg Gln Pro Pro Gly Lys Gly Leu Glu
        35                  40                  45

Trp Ile Gly Ser Phe Tyr Tyr Ser Gly Ser Thr Tyr Tyr Asn Pro Ser
    50                  55                  60

Leu Lys Ser Arg Val Thr Ile Ser Val Gly Thr Ser Lys Asn Gln Phe
65                  70                  75                  80

Ser Leu Lys Leu Ser Ser Val Thr Ala Ala Asp Thr Ala Val Tyr Phe
                85                  90                  95

Cys Ala Arg Gly Gly Leu Leu Gly Arg Pro Phe Val Ile Trp Gly Gln
            100                 105                 110

Gly Thr Met Val Thr Val Ser Ser
        115                 120
```

<210> SEQ ID NO 179
<211> LENGTH: 30
<212> TYPE: DNA
<213> ORGANISM: Artificial Sequence
<220> FEATURE:
<223> OTHER INFORMATION: Synthetic

<400> SEQUENCE: 179
ggtggctcca tcagcagtag tacttactac 30

<210> SEQ ID NO 180
<211> LENGTH: 10
<212> TYPE: PRT
<213> ORGANISM: Artificial Sequence
<220> FEATURE:
<223> OTHER INFORMATION: Synthetic

<400> SEQUENCE: 180

Gly Gly Ser Ile Ser Ser Ser Thr Tyr Tyr
1               5                   10

<210> SEQ ID NO 181
<211> LENGTH: 21
<212> TYPE: DNA
<213> ORGANISM: Artificial Sequence
<220> FEATURE:
<223> OTHER INFORMATION: Synthetic

<400> SEQUENCE: 181
ttctattata gtgggagcac c 21

<210> SEQ ID NO 182
<211> LENGTH: 7
<212> TYPE: PRT
<213> ORGANISM: Artificial Sequence
<220> FEATURE:
<223> OTHER INFORMATION: Synthetic

<400> SEQUENCE: 182

Phe Tyr Tyr Ser Gly Ser Thr
1               5

<210> SEQ ID NO 183
<211> LENGTH: 36
<212> TYPE: DNA
<213> ORGANISM: Artificial Sequence
<220> FEATURE:
<223> OTHER INFORMATION: Synthetic

<400> SEQUENCE: 183
gcgagagggg ggctcctggg gagacctttt gttatc 36

<210> SEQ ID NO 184
<211> LENGTH: 12
<212> TYPE: PRT
<213> ORGANISM: Artificial Sequence
<220> FEATURE:
<223> OTHER INFORMATION: Synthetic

<400> SEQUENCE: 184

Ala Arg Gly Gly Leu Leu Gly Arg Pro Phe Val Ile
1               5                   10

<210> SEQ ID NO 185
<211> LENGTH: 324
<212> TYPE: DNA
<213> ORGANISM: Artificial Sequence
<220> FEATURE:
<223> OTHER INFORMATION: Synthetic

<400> SEQUENCE: 185
gacatccaga tgacccagtc tccatcctcc ctgtctgcat ctgtaggaga cagagtcacc 60
atcacttgcc gggcaagtca gggcattaga aatgatttag gctggtatca gcagaaacca 120

-continued

```
gggaaagccc ctaagcgcct gatctatgct gcatccagtt tgcaaagtgg ggtcccatca    180

aggttcagcg gcagtggatc tgggacagaa ttcactctca caatcagcag cctgcagcct    240

gaagattttg caacttatta ctgtctacag cataatagtt acccgctcac tttcggcgga    300

gggaccaagg tggagatcaa acga                                           324
```

<210> SEQ ID NO 186
<211> LENGTH: 108
<212> TYPE: PRT
<213> ORGANISM: Artificial Sequence
<220> FEATURE:
<223> OTHER INFORMATION: Synthetic

<400> SEQUENCE: 186

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys Arg
            100                 105
```

<210> SEQ ID NO 187
<211> LENGTH: 18
<212> TYPE: DNA
<213> ORGANISM: Artificial Sequence
<220> FEATURE:
<223> OTHER INFORMATION: Synthetic

<400> SEQUENCE: 187

```
cagggcatta gaaatgat                                                   18
```

<210> SEQ ID NO 188
<211> LENGTH: 6
<212> TYPE: PRT
<213> ORGANISM: Artificial Sequence
<220> FEATURE:
<223> OTHER INFORMATION: Synthetic

<400> SEQUENCE: 188

```
Gln Gly Ile Arg Asn Asp
1               5
```

<210> SEQ ID NO 189
<211> LENGTH: 9
<212> TYPE: DNA
<213> ORGANISM: Artificial Sequence
<220> FEATURE:
<223> OTHER INFORMATION: Synthetic

<400> SEQUENCE: 189

```
gctgcatcc                                                              9
```

<210> SEQ ID NO 190

<211> LENGTH: 3
<212> TYPE: PRT
<213> ORGANISM: Artificial Sequence
<220> FEATURE:
<223> OTHER INFORMATION: Synthetic

<400> SEQUENCE: 190

Ala Ala Ser
1

<210> SEQ ID NO 191
<211> LENGTH: 27
<212> TYPE: DNA
<213> ORGANISM: Artificial Sequence
<220> FEATURE:
<223> OTHER INFORMATION: Synthetic

<400> SEQUENCE: 191
ctacagcata atagttaccc gctcact 27

<210> SEQ ID NO 192
<211> LENGTH: 9
<212> TYPE: PRT
<213> ORGANISM: Artificial Sequence
<220> FEATURE:
<223> OTHER INFORMATION: Synthetic

<400> SEQUENCE: 192

Leu Gln His Asn Ser Tyr Pro Leu Thr
1 5

<210> SEQ ID NO 193
<211> LENGTH: 366
<212> TYPE: DNA
<213> ORGANISM: Artificial Sequence
<220> FEATURE:
<223> OTHER INFORMATION: Synthetic

<400> SEQUENCE: 193
gaggtgcagc tggtggagtc taggggaggc ttggtacagc ctggggggtc cctgagactc 60
tcctgtgcag cctctggatt cacttttagc agctatgcca tgagctgggt ccgccaggct 120
ccagggaagg ggctggagtg ggtctcagct attagtggta gtggtggtag cacattctac 180
gcagactccg tgaagggccg gttcaccatc tccagagaca attccaagaa cacggtatat 240
ctgcaaatga acagcctgag agccgaggac acggccgtat attactgtgc gaaagccctc 300
gtattgcgat tttggagtg gttaggggac tactggggcc agggaaccct ggtcaccgtc 360
tcctca 366

<210> SEQ ID NO 194
<211> LENGTH: 122
<212> TYPE: PRT
<213> ORGANISM: Artificial Sequence
<220> FEATURE:
<223> OTHER INFORMATION: Synthetic

<400> SEQUENCE: 194

Glu Val Gln Leu Val Glu Ser Arg Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

-continued

```
Ser Ala Ile Ser Gly Ser Gly Gly Ser Thr Phe Tyr Ala Asp Ser Val
    50                  55                  60

Lys Gly Arg Phe Thr Ile Ser Arg Asp Asn Ser Lys Asn Thr Val Tyr
65                  70                  75                  80

Leu Gln Met Asn Ser Leu Arg Ala Glu Asp Thr Ala Val Tyr Tyr Cys
                85                  90                  95

Ala Lys Ala Leu Val Leu Arg Phe Leu Glu Trp Leu Gly Asp Tyr Trp
            100                 105                 110

Gly Gln Gly Thr Leu Val Thr Val Ser Ser
        115                 120


<210> SEQ ID NO 195
<211> LENGTH: 24
<212> TYPE: DNA
<213> ORGANISM: Artificial Sequence
<220> FEATURE:
<223> OTHER INFORMATION: Synthetic

<400> SEQUENCE: 195

ggattcactt ttagcagcta tgcc                                            24


<210> SEQ ID NO 196
<211> LENGTH: 8
<212> TYPE: PRT
<213> ORGANISM: Artificial Sequence
<220> FEATURE:
<223> OTHER INFORMATION: Synthetic

<400> SEQUENCE: 196

Gly Phe Thr Phe Ser Ser Tyr Ala
1               5


<210> SEQ ID NO 197
<211> LENGTH: 24
<212> TYPE: DNA
<213> ORGANISM: Artificial Sequence
<220> FEATURE:
<223> OTHER INFORMATION: Synthetic

<400> SEQUENCE: 197

attagtggta gtggtggtag caca                                            24


<210> SEQ ID NO 198
<211> LENGTH: 8
<212> TYPE: PRT
<213> ORGANISM: Artificial Sequence
<220> FEATURE:
<223> OTHER INFORMATION: Synthetic

<400> SEQUENCE: 198

Ile Ser Gly Ser Gly Gly Ser Thr
1               5


<210> SEQ ID NO 199
<211> LENGTH: 45
<212> TYPE: DNA
<213> ORGANISM: Artificial Sequence
<220> FEATURE:
<223> OTHER INFORMATION: Synthetic

<400> SEQUENCE: 199

gcgaaagccc tcgtattgcg atttttggag tggttagggg actac                     45


<210> SEQ ID NO 200
```

<211> LENGTH: 15
<212> TYPE: PRT
<213> ORGANISM: Artificial Sequence
<220> FEATURE:
<223> OTHER INFORMATION: Synthetic

<400> SEQUENCE: 200

Ala Lys Ala Leu Val Leu Arg Phe Leu Glu Trp Leu Gly Asp Tyr
1               5                   10                  15

<210> SEQ ID NO 201
<211> LENGTH: 321
<212> TYPE: DNA
<213> ORGANISM: Artificial Sequence
<220> FEATURE:
<223> OTHER INFORMATION: Synthetic

<400> SEQUENCE: 201
gacatccaga tgacccagtc tccttccacc ctgtctgcat ctgtaggaga cagagtcacc 60
atcacttgtc gggccagtca gagtattagt agctggttgg cctggtttca gcagaaacca 120
gggaaagccc ctaagctcct gatctataag gcgtctagtt tagaaagtgg ggtcccatca 180
aggttcagcg gcagtggatc tgggacagaa ttcactctca ccatcagcag cctgcagcct 240
gatgattttg caacttatta ctgtcaacag tataaaagtt attggacgtt cggccaaggg 300
accaaggtgg aaatcaaacg a 321

<210> SEQ ID NO 202
<211> LENGTH: 107
<212> TYPE: PRT
<213> ORGANISM: Artificial Sequence
<220> FEATURE:
<223> OTHER INFORMATION: Synthetic

<400> SEQUENCE: 202

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Phe Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Lys Ser Tyr Trp Thr
                85                  90                  95

Phe Gly Gln Gly Thr Lys Val Glu Ile Lys Arg
            100                 105

<210> SEQ ID NO 203
<211> LENGTH: 18
<212> TYPE: DNA
<213> ORGANISM: Artificial Sequence
<220> FEATURE:
<223> OTHER INFORMATION: Synthetic

<400> SEQUENCE: 203
cagagtatta gtagctgg 18

<210> SEQ ID NO 204
<211> LENGTH: 6

<212> TYPE: PRT
<213> ORGANISM: Artificial Sequence
<220> FEATURE:
<223> OTHER INFORMATION: Synthetic

<400> SEQUENCE: 204

Gln Ser Ile Ser Ser Trp
1 5

<210> SEQ ID NO 205
<211> LENGTH: 9
<212> TYPE: DNA
<213> ORGANISM: Artificial Sequence
<220> FEATURE:
<223> OTHER INFORMATION: Synthetic

<400> SEQUENCE: 205 aaggcgtct 9

<210> SEQ ID NO 206
<211> LENGTH: 3
<212> TYPE: PRT
<213> ORGANISM: Artificial Sequence
<220> FEATURE:
<223> OTHER INFORMATION: Synthetic

<400> SEQUENCE: 206

Lys Ala Ser
1

<210> SEQ ID NO 207
<211> LENGTH: 24
<212> TYPE: DNA
<213> ORGANISM: Artificial Sequence
<220> FEATURE:
<223> OTHER INFORMATION: Synthetic

<400> SEQUENCE: 207
caacagtata aaagttattg gacg 24

<210> SEQ ID NO 208
<211> LENGTH: 8
<212> TYPE: PRT
<213> ORGANISM: Artificial Sequence
<220> FEATURE:
<223> OTHER INFORMATION: Synthetic

<400> SEQUENCE: 208

Gln Gln Tyr Lys Ser Tyr Trp Thr
1 5

<210> SEQ ID NO 209
<211> LENGTH: 372
<212> TYPE: DNA
<213> ORGANISM: Artificial Sequence
<220> FEATURE:
<223> OTHER INFORMATION: Synthetic

<400> SEQUENCE: 209
gaggtgcagc tggtggagtc tgggggaggc ctggtacagc ctggggggtc cctgagactc 60
tcctgtgcag cctctggatt cacctttagc agctatgcca tgagctgggt ccgccaggct 120
ccagggaagg ggctggagtg ggtctcaagt attagtggta gtggtgatag cacattctac 180
acagactccg tgaagggccg gttcaccatc tccagagaca tttccaagaa cacgctgtat 240
ctgcaaatga acagcctgag agccgaggac acggccgtat attactgtgc gaaagatcgt 300
cttctatggt tcggggactt aatatccccc tttcactact ggggccaggg aaccctggtc 360
accgtctcct ca 372

<210> SEQ ID NO 210
<211> LENGTH: 124
<212> TYPE: PRT
<213> ORGANISM: Artificial Sequence
<220> FEATURE:
<223> OTHER INFORMATION: Synthetic

<400> SEQUENCE: 210

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ser Ile Ser Gly Ser Gly Asp Ser Thr Phe Tyr Thr Asp Ser Val
50 55 60

Lys Gly Arg Phe Thr Ile Ser Arg Asp Ile Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Arg Leu Leu Trp Phe Gly Asp Leu Ile Ser Pro Phe His
100 105 110

Tyr Trp Gly Gln Gly Thr Leu Val Thr Val Ser Ser
115 120

<210> SEQ ID NO 211
<211> LENGTH: 24
<212> TYPE: DNA
<213> ORGANISM: Artificial Sequence
<220> FEATURE:
<223> OTHER INFORMATION: Synthetic

<400> SEQUENCE: 211
ggattcacct ttagcagcta tgcc 24

<210> SEQ ID NO 212
<211> LENGTH: 8
<212> TYPE: PRT
<213> ORGANISM: Artificial Sequence
<220> FEATURE:
<223> OTHER INFORMATION: Synthetic

<400> SEQUENCE: 212

Gly Phe Thr Phe Ser Ser Tyr Ala
1 5

<210> SEQ ID NO 213
<211> LENGTH: 24
<212> TYPE: DNA
<213> ORGANISM: Artificial Sequence
<220> FEATURE:
<223> OTHER INFORMATION: Synthetic

<400> SEQUENCE: 213
attagtggta gtggtgatag caca 24

<210> SEQ ID NO 214
<211> LENGTH: 8

<212> TYPE: PRT
<213> ORGANISM: Artificial Sequence
<220> FEATURE:
<223> OTHER INFORMATION: Synthetic

<400> SEQUENCE: 214

Ile Ser Gly Ser Gly Asp Ser Thr
1 5

<210> SEQ ID NO 215
<211> LENGTH: 51
<212> TYPE: DNA
<213> ORGANISM: Artificial Sequence
<220> FEATURE:
<223> OTHER INFORMATION: Synthetic

<400> SEQUENCE: 215
gcgaaagatc gtcttctatg gttcggggac ttaatatccc cctttcacta c 51

<210> SEQ ID NO 216
<211> LENGTH: 17
<212> TYPE: PRT
<213> ORGANISM: Artificial Sequence
<220> FEATURE:
<223> OTHER INFORMATION: Synthetic

<400> SEQUENCE: 216

Ala Lys Asp Arg Leu Leu Trp Phe Gly Asp Leu Ile Ser Pro Phe His
1 5 10 15

Tyr

<210> SEQ ID NO 217
<211> LENGTH: 327
<212> TYPE: DNA
<213> ORGANISM: Artificial Sequence
<220> FEATURE:
<223> OTHER INFORMATION: Synthetic

<400> SEQUENCE: 217
gaaattgtgt tgacgcagtc tccaggcacc ctgtctttgt ctccagggga aagagccacc 60
ctctcctgca gggccagtca gagtgttagc aacatctact tagcctggta ccagcagaaa 120
cctgcccagg ctcccaggct cctcatctat ggtgcatcca gcagggccac tggcatccca 180
gacaggttta gtgtcagtgg gtctgggaca gacttcactc tcaccatcag cagactggag 240
cctgaagatt ttgcagtgta ttactgtcag cagtatggta gctcacctcg gacgttcggc 300
caagggacca aggtggaaat caaacga 327

<210> SEQ ID NO 218
<211> LENGTH: 109
<212> TYPE: PRT
<213> ORGANISM: Artificial Sequence
<220> FEATURE:
<223> OTHER INFORMATION: Synthetic

<400> SEQUENCE: 218

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Asn Ile
20 25 30

Tyr Leu Ala Trp Tyr Gln Gln Lys Pro Ala Gln Ala Pro Arg Leu Leu
35 40 45

Ile Tyr Gly Ala Ser Ser Arg Ala Thr Gly Ile Pro Asp Arg Phe Ser

```
    50                  55                  60

Val Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Arg Thr Phe Gly Gln Gly Thr Lys Val Glu Ile Lys Arg
            100                 105


<210> SEQ ID NO 219
<211> LENGTH: 21
<212> TYPE: DNA
<213> ORGANISM: Artificial Sequence
<220> FEATURE:
<223> OTHER INFORMATION: Synthetic

<400> SEQUENCE: 219

cagagtgtta gcaacatcta c                                               21


<210> SEQ ID NO 220
<211> LENGTH: 7
<212> TYPE: PRT
<213> ORGANISM: Artificial Sequence
<220> FEATURE:
<223> OTHER INFORMATION: Synthetic

<400> SEQUENCE: 220

Gln Ser Val Ser Asn Ile Tyr
1               5


<210> SEQ ID NO 221
<211> LENGTH: 9
<212> TYPE: DNA
<213> ORGANISM: Artificial Sequence
<220> FEATURE:
<223> OTHER INFORMATION: Synthetic

<400> SEQUENCE: 221

ggtgcatcc                                                              9


<210> SEQ ID NO 222
<211> LENGTH: 3
<212> TYPE: PRT
<213> ORGANISM: Artificial Sequence
<220> FEATURE:
<223> OTHER INFORMATION: Synthetic

<400> SEQUENCE: 222

Gly Ala Ser
1


<210> SEQ ID NO 223
<211> LENGTH: 27
<212> TYPE: DNA
<213> ORGANISM: Artificial Sequence
<220> FEATURE:
<223> OTHER INFORMATION: Synthetic

<400> SEQUENCE: 223

cagcagtatg gtagctcacc tcggacg                                         27


<210> SEQ ID NO 224
<211> LENGTH: 9
<212> TYPE: PRT
<213> ORGANISM: Artificial Sequence
<220> FEATURE:
```

<223> OTHER INFORMATION: Synthetic

<400> SEQUENCE: 224

Gln Gln Tyr Gly Ser Ser Pro Arg Thr
1 5

<210> SEQ ID NO 225
<211> LENGTH: 366
<212> TYPE: DNA
<213> ORGANISM: Artificial Sequence
<220> FEATURE:
<223> OTHER INFORMATION: Synthetic

<400> SEQUENCE: 225
gaggtgcagc tggtggagtc tgggggaggc ttggtacagc ctgggggtc cctgagactc 60 tcctgtacag cctctggatt cacctttagc agctatgcca tgagttgggt ccgccaggct 120
ccagggaagg ggctggaatg ggtctcagct attagtggga ctggtagtag tacatacttc 180
acagactccg tgaagggccg gttcgccatc tccagagaca attccaagaa cacgctgtat 240
ctgcaaatga acagcctgag agccgaggac acggccgtat attactgtgc gaaagatgga 300
gagtggctct ctacggtgac cctttttgac tactggggcc agggaaccct ggtcaccgtc 360
tcctca 366

<210> SEQ ID NO 226
<211> LENGTH: 122
<212> TYPE: PRT
<213> ORGANISM: Artificial Sequence
<220> FEATURE:
<223> OTHER INFORMATION: Synthetic

<400> SEQUENCE: 226

Glu Val Gln Leu Val Glu Ser Gly Gly Gly Leu Val Gln Pro Gly Gly
1 5 10 15

Ser Leu Arg Leu Ser Cys Thr Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Ala Ile Ser Gly Thr Gly Ser Ser Thr Tyr Phe Thr Asp Ser Val
50 55 60

Lys Gly Arg Phe Ala Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Gly Glu Trp Leu Ser Thr Val Thr Leu Phe Asp Tyr Trp
100 105 110

Gly Gln Gly Thr Leu Val Thr Val Ser Ser
115 120

<210> SEQ ID NO 227
<211> LENGTH: 24
<212> TYPE: DNA
<213> ORGANISM: Artificial Sequence
<220> FEATURE:
<223> OTHER INFORMATION: Synthetic

<400> SEQUENCE: 227
ggattcacct ttagcagcta tgcc 24

<210> SEQ ID NO 228

-continued

<211> LENGTH: 8
<212> TYPE: PRT
<213> ORGANISM: Artificial Sequence
<220> FEATURE:
<223> OTHER INFORMATION: Synthetic

<400> SEQUENCE: 228

Gly Phe Thr Phe Ser Ser Tyr Ala
1               5

<210> SEQ ID NO 229
<211> LENGTH: 24
<212> TYPE: DNA
<213> ORGANISM: Artificial Sequence
<220> FEATURE:
<223> OTHER INFORMATION: Synthetic

<400> SEQUENCE: 229
attagtggga ctggtagtag taca 24

<210> SEQ ID NO 230
<211> LENGTH: 8
<212> TYPE: PRT
<213> ORGANISM: Artificial Sequence
<220> FEATURE:
<223> OTHER INFORMATION: Synthetic

<400> SEQUENCE: 230

Ile Ser Gly Thr Gly Ser Ser Thr
1               5

<210> SEQ ID NO 231
<211> LENGTH: 45
<212> TYPE: DNA
<213> ORGANISM: Artificial Sequence
<220> FEATURE:
<223> OTHER INFORMATION: Synthetic

<400> SEQUENCE: 231
gcgaaagatg gagagtggct ctctacggtg accctttttg actac 45

<210> SEQ ID NO 232
<211> LENGTH: 15
<212> TYPE: PRT
<213> ORGANISM: Artificial Sequence
<220> FEATURE:
<223> OTHER INFORMATION: Synthetic

<400> SEQUENCE: 232

Ala Lys Asp Gly Glu Trp Leu Ser Thr Val Thr Leu Phe Asp Tyr
1               5                   10                  15

<210> SEQ ID NO 233
<211> LENGTH: 330
<212> TYPE: DNA
<213> ORGANISM: Artificial Sequence
<220> FEATURE:
<223> OTHER INFORMATION: Synthetic

<400> SEQUENCE: 233
gaaattgtga tgacgcagtc tccagccacc ctgtctgtgt ctccagggga aagagccacc 60
ctctcctgca gggccagtca gagtgttagc agcaacttag cctggtacca gcagaaacct 120
ggccaggctc ccaggctcct catctatggt gcatccacca gggccactgg tatcccagcc 180
aggttcagtg gcagtgggtc tgggacagat ttcactctca ccatcagcag cctgcagtct 240

-continued

```
gaagattttg cactttatta ctgtcagcag tattttatct ggcctccgca tcccactttc    300

ggccctggga ccaaagtgga tatcaaacga                                     330


<210> SEQ ID NO 234
<211> LENGTH: 110
<212> TYPE: PRT
<213> ORGANISM: Artificial Sequence
<220> FEATURE:
<223> OTHER INFORMATION: Synthetic

<400> SEQUENCE: 234

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Asp Phe Thr Leu Thr Ile Ser Ser Leu Gln Ser
65                  70                  75                  80

Glu Asp Phe Ala Leu Tyr Tyr Cys Gln Gln Tyr Phe Ile Trp Pro Pro
                85                  90                  95

His Pro Thr Phe Gly Pro Gly Thr Lys Val Asp Ile Lys Arg
            100                 105                 110


<210> SEQ ID NO 235
<211> LENGTH: 18
<212> TYPE: DNA
<213> ORGANISM: Artificial Sequence
<220> FEATURE:
<223> OTHER INFORMATION: Synthetic

<400> SEQUENCE: 235

cagagtgtta gcagcaac                                                   18


<210> SEQ ID NO 236
<211> LENGTH: 6
<212> TYPE: PRT
<213> ORGANISM: Artificial Sequence
<220> FEATURE:
<223> OTHER INFORMATION: Synthetic

<400> SEQUENCE: 236

Gln Ser Val Ser Ser Asn
1               5


<210> SEQ ID NO 237
<211> LENGTH: 9
<212> TYPE: DNA
<213> ORGANISM: Artificial Sequence
<220> FEATURE:
<223> OTHER INFORMATION: Synthetic

<400> SEQUENCE: 237

ggtgcatcc                                                              9


<210> SEQ ID NO 238
<211> LENGTH: 3
<212> TYPE: PRT
<213> ORGANISM: Artificial Sequence
<220> FEATURE:
<223> OTHER INFORMATION: Synthetic
```

<400> SEQUENCE: 238

Gly Ala Ser
1

<210> SEQ ID NO 239
<211> LENGTH: 33
<212> TYPE: DNA
<213> ORGANISM: Artificial Sequence
<220> FEATURE:
<223> OTHER INFORMATION: Synthetic

<400> SEQUENCE: 239
cagcagtatt ttatctggcc tccgcatccc act 33

<210> SEQ ID NO 240
<211> LENGTH: 11
<212> TYPE: PRT
<213> ORGANISM: Artificial Sequence
<220> FEATURE:
<223> OTHER INFORMATION: Synthetic

<400> SEQUENCE: 240

Gln Gln Tyr Phe Ile Trp Pro Pro His Pro Thr
1 5 10

<210> SEQ ID NO 241
<211> LENGTH: 363
<212> TYPE: DNA
<213> ORGANISM: Artificial Sequence
<220> FEATURE:
<223> OTHER INFORMATION: Synthetic

<400> SEQUENCE: 241
caggtgcagc tggtggagtc tgggggagcc gtggtccagc ctgggaggtc cctgagactc 60
tcctgtgcag cctctggatt caccttcagt tactatggca tgcactgggt ccgccaggct 120
ccaggcaagg ggctggagtg ggtggcagtt atatcatatg atggaagtaa aaaatactat 180
gcagactccg tgaagggccg attcaccatc tccagagaca attccaagaa cacgctgtat 240
ctgcaaatga acagcctgag agctgaggac acggctgtgt attactgtgc gaaagatctg 300
acagtagact tctactacgg tatggacgtc tggggccaag ggaccacggt caccgtctcc 360
tca 363

<210> SEQ ID NO 242
<211> LENGTH: 121
<212> TYPE: PRT
<213> ORGANISM: Artificial Sequence
<220> FEATURE:
<223> OTHER INFORMATION: Synthetic

<400> SEQUENCE: 242

Gln Val Gln Leu Val Glu Ser Gly Gly Ala Val Val Gln Pro Gly Arg
1 5 10 15

Ser Leu Arg Leu Ser Cys Ala Ala Ser Gly Phe Thr Phe Ser Tyr Tyr
20 25 30

Gly Met His Trp Val Arg Gln Ala Pro Gly Lys Gly Leu Glu Trp Val
35 40 45

Ala Val Ile Ser Tyr Asp Gly Ser Lys Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Leu Thr Val Asp Phe Tyr Tyr Gly Met Asp Val Trp Gly
100 105 110

Gln Gly Thr Thr Val Thr Val Ser Ser
115 120

<210> SEQ ID NO 243
<211> LENGTH: 24
<212> TYPE: DNA
<213> ORGANISM: Artificial Sequence
<220> FEATURE:
<223> OTHER INFORMATION: Synthetic

<400> SEQUENCE: 243
ggattcacct tcagttacta tggc 24

<210> SEQ ID NO 244
<211> LENGTH: 8
<212> TYPE: PRT
<213> ORGANISM: Artificial Sequence
<220> FEATURE:
<223> OTHER INFORMATION: Synthetic

<400> SEQUENCE: 244

Gly Phe Thr Phe Ser Tyr Tyr Gly
1 5

<210> SEQ ID NO 245
<211> LENGTH: 24
<212> TYPE: DNA
<213> ORGANISM: Artificial Sequence
<220> FEATURE:
<223> OTHER INFORMATION: Synthetic

<400> SEQUENCE: 245
atatcatatg atggaagtaa aaaa 24

<210> SEQ ID NO 246
<211> LENGTH: 8
<212> TYPE: PRT
<213> ORGANISM: Artificial Sequence
<220> FEATURE:
<223> OTHER INFORMATION: Synthetic

<400> SEQUENCE: 246

Ile Ser Tyr Asp Gly Ser Lys Lys
1 5

<210> SEQ ID NO 247
<211> LENGTH: 42
<212> TYPE: DNA
<213> ORGANISM: Artificial Sequence
<220> FEATURE:
<223> OTHER INFORMATION: Synthetic

<400> SEQUENCE: 247
gcgaaagatc tgacagtaga cttctactac ggtatggacg tc 42

<210> SEQ ID NO 248
<211> LENGTH: 14
<212> TYPE: PRT
<213> ORGANISM: Artificial Sequence
<220> FEATURE:
<223> OTHER INFORMATION: Synthetic

<400> SEQUENCE: 248

```
Ala Lys Asp Leu Thr Val Asp Phe Tyr Tyr Gly Met Asp Val
1               5                   10
```

<210> SEQ ID NO 249
<211> LENGTH: 324
<212> TYPE: DNA
<213> ORGANISM: Artificial Sequence
<220> FEATURE:
<223> OTHER INFORMATION: Synthetic

<400> SEQUENCE: 249

```
gacatccaga tgacccagtc tccatcttcc gtgtctgcat ctgtaggaga cagagtcacc     60

atcacttgtc gggcgagtca gggtattagc agctggttag cctggtatca gcagaaacca    120

gggaaagccc ctaagctcct gatctatgct acatccagtt tgcaaagtgg ggccccatca    180

aggttcagcg gcagtggatc tgggacagat ttcactctca ccatcagcag cctgcagcct    240

gaagattttg caacttactt ttgtcaacag gctaacagtt tcccatacac ttttggccag    300

gggaccaagc tggagatcaa acga                                            324
```

<210> SEQ ID NO 250
<211> LENGTH: 108
<212> TYPE: PRT
<213> ORGANISM: Artificial Sequence
<220> FEATURE:
<223> OTHER INFORMATION: Synthetic

<400> SEQUENCE: 250

```
Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Thr Ser Ser Leu Gln Ser Gly Ala Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Ala Asn Ser Phe Pro Tyr
                85                  90                  95

Thr Phe Gly Gln Gly Thr Lys Leu Glu Ile Lys Arg
            100                 105
```

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251

```
cagggtatta gcagctgg                                                    18
```

<210> SEQ ID NO 252
<211> LENGTH: 6
<212> TYPE: PRT
<213> ORGANISM: Artificial Sequence
<220> FEATURE:
<223> OTHER INFORMATION: Synthetic

<400> SEQUENCE: 252

Gln Gly Ile Ser Ser Trp
1               5

<210> SEQ ID NO 253
<211> LENGTH: 9
<212> TYPE: DNA
<213> ORGANISM: Artificial Sequence
<220> FEATURE:
<223> OTHER INFORMATION: Synthetic

<400> SEQUENCE: 253 gctacatcc 9

<210> SEQ ID NO 254
<211> LENGTH: 3
<212> TYPE: PRT
<213> ORGANISM: Artificial Sequence
<220> FEATURE:
<223> OTHER INFORMATION: Synthetic

<400> SEQUENCE: 254

Ala Thr Ser
1

<210> SEQ ID NO 255
<211> LENGTH: 27
<212> TYPE: DNA
<213> ORGANISM: Artificial Sequence
<220> FEATURE:
<223> OTHER INFORMATION: Synthetic

<400> SEQUENCE: 255
caacaggcta acagtttccc atacact 27

<210> SEQ ID NO 256
<211> LENGTH: 9
<212> TYPE: PRT
<213> ORGANISM: Artificial Sequence
<220> FEATURE:
<223> OTHER INFORMATION: Synthetic

<400> SEQUENCE: 256

Gln Gln Ala Asn Ser Phe Pro Tyr Thr
1               5

<210> SEQ ID NO 257
<211> LENGTH: 342
<212> TYPE: DNA
<213> ORGANISM: Artificial Sequence
<220> FEATURE:
<223> OTHER INFORMATION: Synthetic

<400> SEQUENCE: 257
caggtgcagc tgcaggagtc gggcccagga ctggtgaagc cttcggagac cctgtccctc 60
acctgcactg tctctgatgg ctccatcagt agttactact ggagctggat ccggcagccc 120
ccagggaggg gactggagtg gattgggttt atctattaca gtgggagcac cagctacaac 180
ccctccctca agagtcgagt caccatttca gtagacacgt ccatgagcca gttctccctg 240
aagctgaggt ctgtgaccgc cgcagacacg gccgtgtatt actgtgcgcg tgggagcccc 300
tttgactact ggggcccggg aaccctggtc accgtctcct ca 342

<210> SEQ ID NO 258

<211> LENGTH: 114
<212> TYPE: PRT
<213> ORGANISM: Artificial Sequence
<220> FEATURE:
<223> OTHER INFORMATION: Synthetic

<400> SEQUENCE: 258

```
Gln Val Gln Leu Gln Glu Ser Gly Pro Gly Leu Val Lys Pro Ser Glu
1               5                   10                  15

Thr Leu Ser Leu Thr Cys Thr Val Ser Asp Gly Ser Ile Ser Ser Tyr
            20                  25                  30

Tyr Trp Ser Trp Ile Arg Gln Pro Pro Gly Arg Gly Leu Glu Trp Ile
        35                  40                  45

Gly Phe Ile Tyr Tyr Ser Gly Ser Thr Ser Tyr Asn Pro Ser Leu Lys
    50                  55                  60

Ser Arg Val Thr Ile Ser Val Asp Thr Ser Met Ser Gln Phe Ser Leu
65                  70                  75                  80

Lys Leu Arg Ser Val Thr Ala Ala Asp Thr Ala Val Tyr Tyr Cys Ala
                85                  90                  95

Arg Gly Ser Pro Phe Asp Tyr Trp Gly Pro Gly Thr Leu Val Thr Val
            100                 105                 110

Ser Ser
```

<210> SEQ ID NO 259
<211> LENGTH: 24
<212> TYPE: DNA
<213> ORGANISM: Artificial Sequence
<220> FEATURE:
<223> OTHER INFORMATION: Synthetic

<400> SEQUENCE: 259
gatggctcca tcagtagtta ctac 24

<210> SEQ ID NO 260
<211> LENGTH: 8
<212> TYPE: PRT
<213> ORGANISM: Artificial Sequence
<220> FEATURE:
<223> OTHER INFORMATION: Synthetic

<400> SEQUENCE: 260

```
Asp Gly Ser Ile Ser Ser Tyr Tyr
1               5
```

<210> SEQ ID NO 261
<211> LENGTH: 21
<212> TYPE: DNA
<213> ORGANISM: Artificial Sequence
<220> FEATURE:
<223> OTHER INFORMATION: Synthetic

<400> SEQUENCE: 261
atctattaca gtgggagcac c 21

<210> SEQ ID NO 262
<211> LENGTH: 7
<212> TYPE: PRT
<213> ORGANISM: Artificial Sequence
<220> FEATURE:
<223> OTHER INFORMATION: Synthetic

<400> SEQUENCE: 262

Ile Tyr Tyr Ser Gly Ser Thr 1 5

<210> SEQ ID NO 263
<211> LENGTH: 24
<212> TYPE: DNA
<213> ORGANISM: Artificial Sequence
<220> FEATURE:
<223> OTHER INFORMATION: Synthetic

<400> SEQUENCE: 263
gcgcgtggga gcccctttga ctac 24

<210> SEQ ID NO 264
<211> LENGTH: 8
<212> TYPE: PRT
<213> ORGANISM: Artificial Sequence
<220> FEATURE:
<223> OTHER INFORMATION: Synthetic

<400> SEQUENCE: 264

Ala Arg Gly Ser Pro Phe Asp Tyr
1 5

<210> SEQ ID NO 265
<211> LENGTH: 327
<212> TYPE: DNA
<213> ORGANISM: Artificial Sequence
<220> FEATURE:
<223> OTHER INFORMATION: Synthetic

<400> SEQUENCE: 265
gaaattgtgt tgacgcagtc tccaggcacc ctgtctttgt ctccagggga aagagccacc 60
ctctcctgca gggccagtca gagtgttagc agcagctact tagcctggta ccagcaaaga 120
cctggccagg ctcccagcct cctcatctct ggtgcatcca ggagggccac tggcatccca 180
gacaggttca gtggcagtgg gtctgggaca gacttcactc tcaccatcag aagactggag 240
cctgaagatt ttgcaatgta ttactgtcag cagtatggta gttcacctcc cactttcggc 300
ggagggacca aggtggagat caaacga 327

<210> SEQ ID NO 266
<211> LENGTH: 109
<212> TYPE: PRT
<213> ORGANISM: Artificial Sequence
<220> FEATURE:
<223> OTHER INFORMATION: Synthetic

<400> SEQUENCE: 266

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Arg Pro Gly Gln Ala Pro Ser Leu Leu
35 40 45

Ile Ser Gly Ala Ser Arg Arg Ala Thr Gly Ile Pro Asp Arg Phe Ser
50 55 60

Gly Ser Gly Ser Gly Thr Asp Phe Thr Leu Thr Ile Arg Arg Leu Glu
65 70 75 80

Pro Glu Asp Phe Ala Met Tyr Tyr Cys Gln Gln Tyr Gly Ser Ser Pro
85 90 95

Pro Thr Phe Gly Gly Gly Thr Lys Val Glu Ile Lys Arg
100 105

<210> SEQ ID NO 267
<211> LENGTH: 21
<212> TYPE: DNA
<213> ORGANISM: Artificial Sequence
<220> FEATURE:
<223> OTHER INFORMATION: Synthetic

<400> SEQUENCE: 267
cagagtgtta gcagcagcta c 21

<210> SEQ ID NO 268
<211> LENGTH: 7
<212> TYPE: PRT
<213> ORGANISM: Artificial Sequence
<220> FEATURE:
<223> OTHER INFORMATION: Synthetic

<400> SEQUENCE: 268

Gln Ser Val Ser Ser Ser Tyr
1 5

<210> SEQ ID NO 269
<211> LENGTH: 9
<212> TYPE: DNA
<213> ORGANISM: Artificial Sequence
<220> FEATURE:
<223> OTHER INFORMATION: Synthetic

<400> SEQUENCE: 269 ggtgcatcc 9

<210> SEQ ID NO 270
<211> LENGTH: 3
<212> TYPE: PRT
<213> ORGANISM: Artificial Sequence
<220> FEATURE:
<223> OTHER INFORMATION: Synthetic

<400> SEQUENCE: 270

Gly Ala Ser
1

<210> SEQ ID NO 271
<211> LENGTH: 27
<212> TYPE: DNA
<213> ORGANISM: Artificial Sequence
<220> FEATURE:
<223> OTHER INFORMATION: Synthetic

<400> SEQUENCE: 271
cagcagtatg gtagttcacc tcccact 27

<210> SEQ ID NO 272
<211> LENGTH: 9
<212> TYPE: PRT
<213> ORGANISM: Artificial Sequence
<220> FEATURE:
<223> OTHER INFORMATION: Synthetic

<400> SEQUENCE: 272

Gln Gln Tyr Gly Ser Ser Pro Pro Thr
1 5

<210> SEQ ID NO 273
<211> LENGTH: 363

<212> TYPE: DNA
<213> ORGANISM: Artificial Sequence
<220> FEATURE:
<223> OTHER INFORMATION: Synthetic

<400> SEQUENCE: 273
gaggtgcagc tggtggagtc tgggggaggc ttggtccagc ctgggggtc cctgagactc 60 tcctgtgcag cctctggatt cacgttcagt aactatgcta tgcactgggt ccgccaggct 120
ccagggaagg gactggaata tgtttcagct attagtagta atgggggtag tacatattat 180
gcagactctg tgaagggcag aatcaccatc tccagagaca attccaagaa cacgctgtat 240
cttcaaatgg gcagcctgag agctgaggat atggctgtgt attactgtgc gagagggcga 300
ccgtactact actacttcgg tatggacgtc tggggccaag ggaccacggt caccgtctcc 360
tca 363

<210> SEQ ID NO 274
<211> LENGTH: 121
<212> TYPE: PRT
<213> ORGANISM: Artificial Sequence
<220> FEATURE:
<223> OTHER INFORMATION: Synthetic

<400> SEQUENCE: 274

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Asn Tyr
20 25 30

Ala Met His Trp Val Arg Gln Ala Pro Gly Lys Gly Leu Glu Tyr Val
35 40 45

Ser Ala Ile Ser Ser Asn Gly Gly Ser Thr Tyr Tyr Ala Asp Ser Val
50 55 60

Lys Gly Arg Ile Thr Ile Ser Arg Asp Asn Ser Lys Asn Thr Leu Tyr
65 70 75 80

Leu Gln Met Gly Ser Leu Arg Ala Glu Asp Met Ala Val Tyr Tyr Cys
85 90 95

Ala Arg Gly Arg Pro Tyr Tyr Tyr Tyr Phe Gly Met Asp Val Trp Gly
100 105 110

Gln Gly Thr Thr Val Thr Val Ser Ser
115 120

<210> SEQ ID NO 275
<211> LENGTH: 24
<212> TYPE: DNA
<213> ORGANISM: Artificial Sequence
<220> FEATURE:
<223> OTHER INFORMATION: Synthetic

<400> SEQUENCE: 275
ggattcacgt tcagtaacta tgct 24

<210> SEQ ID NO 276
<211> LENGTH: 8
<212> TYPE: PRT
<213> ORGANISM: Artificial Sequence
<220> FEATURE:
<223> OTHER INFORMATION: Synthetic

<400> SEQUENCE: 276

Gly Phe Thr Phe Ser Asn Tyr Ala
1 5

<210> SEQ ID NO 277
<211> LENGTH: 24
<212> TYPE: DNA
<213> ORGANISM: Artificial Sequence
<220> FEATURE:
<223> OTHER INFORMATION: Synthetic

<400> SEQUENCE: 277
attagtagta atgggggtag taca 24

<210> SEQ ID NO 278
<211> LENGTH: 8
<212> TYPE: PRT
<213> ORGANISM: Artificial Sequence
<220> FEATURE:
<223> OTHER INFORMATION: Synthetic

<400> SEQUENCE: 278

Ile Ser Ser Asn Gly Gly Ser Thr
1 5

<210> SEQ ID NO 279
<211> LENGTH: 42
<212> TYPE: DNA
<213> ORGANISM: Artificial Sequence
<220> FEATURE:
<223> OTHER INFORMATION: Synthetic

<400> SEQUENCE: 279
gcgagagggc gaccgtacta ctactacttc ggtatggacg tc 42

<210> SEQ ID NO 280
<211> LENGTH: 14
<212> TYPE: PRT
<213> ORGANISM: Artificial Sequence
<220> FEATURE:
<223> OTHER INFORMATION: Synthetic

<400> SEQUENCE: 280

Ala Arg Gly Arg Pro Tyr Tyr Tyr Tyr Phe Gly Met Asp Val
1 5 10

<210> SEQ ID NO 281
<211> LENGTH: 339
<212> TYPE: DNA
<213> ORGANISM: Artificial Sequence
<220> FEATURE:
<223> OTHER INFORMATION: Synthetic

<400> SEQUENCE: 281
gatattgtga tgactcagac tccagtctcc tcacctgtca cccttggaca gccggcctcc 60
atctcctgca ggtctagtca aagcctcgta cacagtgatg gaaacaccta cttgagttgg 120
tttcagcaga ggccgggcca gcctccaaga ctcctaattt ataagatttc taaccggttc 180
tctggggtcc cagacagatt cagtggcagt ggggcaggga cagatttcac actgaaaatc 240
agcagggtgg aagctgagga tgtcggggtt tattactgca tgcaagctac acaatttcct 300
ctcaatttcg gcggagggac caaggtggag atcaaacga 339

<210> SEQ ID NO 282
<211> LENGTH: 113
<212> TYPE: PRT
<213> ORGANISM: Artificial Sequence
<220> FEATURE:

<223> OTHER INFORMATION: Synthetic

<400> SEQUENCE: 282

Asp Ile Val Met Thr Gln Thr Pro Val Ser Ser Pro Val Thr Leu Gly
1 5 10 15

Gln Pro Ala Ser Ile Ser Cys Arg Ser Ser Gln Ser Leu Val His Ser
20 25 30

Asp Gly Asn Thr Tyr Leu Ser Trp Phe Gln Gln Arg Pro Gly Gln Pro
35 40 45

Pro Arg Leu Leu Ile Tyr Lys Ile Ser Asn Arg Phe Ser Gly Val Pro
50 55 60

Asp Arg Phe Ser Gly Ser Gly Ala Gly Thr Asp Phe Thr Leu Lys Ile
65 70 75 80

Ser Arg Val Glu Ala Glu Asp Val Gly Val Tyr Tyr Cys Met Gln Ala
85 90 95

Thr Gln Phe Pro Leu Asn Phe Gly Gly Gly Thr Lys Val Glu Ile Lys
100 105 110

Arg

<210> SEQ ID NO 283
<211> LENGTH: 33
<212> TYPE: DNA
<213> ORGANISM: Artificial Sequence
<220> FEATURE:
<223> OTHER INFORMATION: Synthetic

<400> SEQUENCE: 283
caaagcctcg tacacagtga tggaaacacc tac 33

<210> SEQ ID NO 284
<211> LENGTH: 11
<212> TYPE: PRT
<213> ORGANISM: Artificial Sequence
<220> FEATURE:
<223> OTHER INFORMATION: Synthetic

<400> SEQUENCE: 284

Gln Ser Leu Val His Ser Asp Gly Asn Thr Tyr
1 5 10

<210> SEQ ID NO 285
<211> LENGTH: 9
<212> TYPE: DNA
<213> ORGANISM: Artificial Sequence
<220> FEATURE:
<223> OTHER INFORMATION: Synthetic

<400> SEQUENCE: 285 aagatttct 9

<210> SEQ ID NO 286
<211> LENGTH: 3
<212> TYPE: PRT
<213> ORGANISM: Artificial Sequence
<220> FEATURE:
<223> OTHER INFORMATION: Synthetic

<400> SEQUENCE: 286

Lys Ile Ser
1

<210> SEQ ID NO 287

<211> LENGTH: 27
<212> TYPE: DNA
<213> ORGANISM: Artificial Sequence
<220> FEATURE:
<223> OTHER INFORMATION: Synthetic

<400> SEQUENCE: 287
atgcaagcta cacaatttcc tctcaat 27

<210> SEQ ID NO 288
<211> LENGTH: 9
<212> TYPE: PRT
<213> ORGANISM: Artificial Sequence
<220> FEATURE:
<223> OTHER INFORMATION: Synthetic

<400> SEQUENCE: 288

Met Gln Ala Thr Gln Phe Pro Leu Asn
1 5

<210> SEQ ID NO 289
<211> LENGTH: 366
<212> TYPE: DNA
<213> ORGANISM: Artificial Sequence
<220> FEATURE:
<223> OTHER INFORMATION: Synthetic

<400> SEQUENCE: 289
gaggtgcagc tggtggagtc tgggggaggc ttggtacagc ctggggggtc cctgagactc 60
tcctgtgcag cctctggatt cacctttagg acctatgcca tgacctgggt ccgccaggct 120
ccagggaagg ggctagactg ggtctcagct attactggtg atggtggtaa tacatactac 180
gcagactccg tgaagggccg gttcaccatt tccagagaca attccaagaa cacgctgtat 240
ctgcaaatga acagcctgag agccgaggac acggccatct attactgtgc gaaagatcag 300
agattcagct ttgctctata ctactttgac tactggggcc agggaaccct ggtcactgtc 360
tcctca 366

<210> SEQ ID NO 290
<211> LENGTH: 122
<212> TYPE: PRT
<213> ORGANISM: Artificial Sequence
<220> FEATURE:
<223> OTHER INFORMATION: Synthetic

<400> SEQUENCE: 290

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Arg Thr Tyr
20 25 30

Ala Met Thr Trp Val Arg Gln Ala Pro Gly Lys Gly Leu Asp Trp Val
35 40 45

Ser Ala Ile Thr Gly Asp Gly Gly Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Ile Tyr Tyr Cys
85 90 95

Ala Lys Asp Gln Arg Phe Ser Phe Ala Leu Tyr Tyr Phe Asp Tyr Trp
100 105 110

Gly Gln Gly Thr Leu Val Thr Val Ser Ser 115 120

<210> SEQ ID NO 291
<211> LENGTH: 24
<212> TYPE: DNA
<213> ORGANISM: Artificial Sequence
<220> FEATURE:
<223> OTHER INFORMATION: Synthetic

<400> SEQUENCE: 291
ggattcacct ttaggaccta tgcc 24

<210> SEQ ID NO 292
<211> LENGTH: 8
<212> TYPE: PRT
<213> ORGANISM: Artificial Sequence
<220> FEATURE:
<223> OTHER INFORMATION: Synthetic

<400> SEQUENCE: 292

Gly Phe Thr Phe Arg Thr Tyr Ala
1 5

<210> SEQ ID NO 293
<211> LENGTH: 24
<212> TYPE: DNA
<213> ORGANISM: Artificial Sequence
<220> FEATURE:
<223> OTHER INFORMATION: Synthetic

<400> SEQUENCE: 293
attactggtg atggtggtaa taca 24

<210> SEQ ID NO 294
<211> LENGTH: 8
<212> TYPE: PRT
<213> ORGANISM: Artificial Sequence
<220> FEATURE:
<223> OTHER INFORMATION: Synthetic

<400> SEQUENCE: 294

Ile Thr Gly Asp Gly Gly Asn Thr
1 5

<210> SEQ ID NO 295
<211> LENGTH: 45
<212> TYPE: DNA
<213> ORGANISM: Artificial Sequence
<220> FEATURE:
<223> OTHER INFORMATION: Synthetic

<400> SEQUENCE: 295
gcgaaagatc agagattcag ctttgctcta tactactttg actac 45

<210> SEQ ID NO 296
<211> LENGTH: 15
<212> TYPE: PRT
<213> ORGANISM: Artificial Sequence
<220> FEATURE:
<223> OTHER INFORMATION: Synthetic

<400> SEQUENCE: 296

Ala Lys Asp Gln Arg Phe Ser Phe Ala Leu Tyr Tyr Phe Asp Tyr
1 5 10 15

<210> SEQ ID NO 297

<211> LENGTH: 324
<212> TYPE: DNA
<213> ORGANISM: Artificial Sequence
<220> FEATURE:
<223> OTHER INFORMATION: Synthetic

<400> SEQUENCE: 297
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaacgccc ctaagctcct gatctatgct gcattcagtt tgcaaagtgg ggtcccgtca 180
aggttcagcg gcagtggatc tgggacagat ttcactctca ccatcagcag cctgcagcct 240
gaagattttg caacttacta ttgtcaacag gctaacaatt tcccgtggac gttcggccaa 300
gggaccaagg tggaaatcaa acga 324

<210> SEQ ID NO 298
<211> LENGTH: 108
<212> TYPE: PRT
<213> ORGANISM: Artificial Sequence
<220> FEATURE:
<223> OTHER INFORMATION: Synthetic

<400> SEQUENCE: 298

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Asn Ala Pro Lys Leu Leu Ile
35 40 45

Tyr Ala Ala Phe Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ala Asn Asn Phe Pro Trp
85 90 95

Thr Phe Gly Gln Gly Thr Lys Val Glu Ile Lys Arg
100 105

<210> SEQ ID NO 299
<211> LENGTH: 18
<212> TYPE: DNA
<213> ORGANISM: Artificial Sequence
<220> FEATURE:
<223> OTHER INFORMATION: Synthetic

<400> SEQUENCE: 299
cagggtatta gcagctgg 18

<210> SEQ ID NO 300
<211> LENGTH: 6
<212> TYPE: PRT
<213> ORGANISM: Artificial Sequence
<220> FEATURE:
<223> OTHER INFORMATION: Synthetic

<400> SEQUENCE: 300

Gln Gly Ile Ser Ser Trp
1 5

<210> SEQ ID NO 301
<211> LENGTH: 9

<212> TYPE: DNA
<213> ORGANISM: Artificial Sequence
<220> FEATURE:
<223> OTHER INFORMATION: Synthetic

<400> SEQUENCE: 301 gctgcattc 9

<210> SEQ ID NO 302
<211> LENGTH: 3
<212> TYPE: PRT
<213> ORGANISM: Artificial Sequence
<220> FEATURE:
<223> OTHER INFORMATION: Synthetic

<400> SEQUENCE: 302

Ala Ala Phe
1

<210> SEQ ID NO 303
<211> LENGTH: 27
<212> TYPE: DNA
<213> ORGANISM: Artificial Sequence
<220> FEATURE:
<223> OTHER INFORMATION: Synthetic

<400> SEQUENCE: 303
caacaggcta acaatttccc gtggacg 27

<210> SEQ ID NO 304
<211> LENGTH: 9
<212> TYPE: PRT
<213> ORGANISM: Artificial Sequence
<220> FEATURE:
<223> OTHER INFORMATION: Synthetic

<400> SEQUENCE: 304

Gln Gln Ala Asn Asn Phe Pro Trp Thr
1 5

<210> SEQ ID NO 305
<211> LENGTH: 354
<212> TYPE: DNA
<213> ORGANISM: Artificial Sequence
<220> FEATURE:
<223> OTHER INFORMATION: Synthetic

<400> SEQUENCE: 305
caggtgcagc tggtggagtc tgggggaggc gtggtccagc ctgggaggtc cctgagactc 60
tcctgtgcag cctctggatt caccttcagt aactatgaca tgcactgggt ccgccaggct 120
ccaggcaagg ggctggagtg gatggcagtt atatcatatg atggaattaa taaatattat 180
gcagactccg tgaagggccg attcaccatc tccagagaca attccaagaa cacgctgtat 240
ctgcaaatga acagcctgag agctgaggac acggctgtgt attactgtgc gaaaggtact 300
tactcctggt acttcgatct ctggggccgt ggcaccctgg tcactgtctc ctca 354

<210> SEQ ID NO 306
<211> LENGTH: 118
<212> TYPE: PRT
<213> ORGANISM: Artificial Sequence
<220> FEATURE:
<223> OTHER INFORMATION: Synthetic

<400> SEQUENCE: 306

-continued

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Asp Met His Trp Val Arg Gln Ala Pro Gly Lys Gly Leu Glu Trp Met
        35                  40                  45

Ala Val Ile Ser Tyr Asp Gly Ile Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Thr Tyr Ser Trp Tyr Phe Asp Leu Trp Gly Arg Gly Thr
            100                 105                 110

Leu Val Thr Val Ser Ser
        115


<210> SEQ ID NO 307
<211> LENGTH: 24
<212> TYPE: DNA
<213> ORGANISM: Artificial Sequence
<220> FEATURE:
<223> OTHER INFORMATION: Synthetic

<400> SEQUENCE: 307

ggattcacct tcagtaacta tgac                                            24


<210> SEQ ID NO 308
<211> LENGTH: 8
<212> TYPE: PRT
<213> ORGANISM: Artificial Sequence
<220> FEATURE:
<223> OTHER INFORMATION: Synthetic

<400> SEQUENCE: 308

Gly Phe Thr Phe Ser Asn Tyr Asp
1               5


<210> SEQ ID NO 309
<211> LENGTH: 24
<212> TYPE: DNA
<213> ORGANISM: Artificial Sequence
<220> FEATURE:
<223> OTHER INFORMATION: Synthetic

<400> SEQUENCE: 309

atatcatatg atggaattaa taaa                                            24


<210> SEQ ID NO 310
<211> LENGTH: 8
<212> TYPE: PRT
<213> ORGANISM: Artificial Sequence
<220> FEATURE:
<223> OTHER INFORMATION: Synthetic

<400> SEQUENCE: 310

Ile Ser Tyr Asp Gly Ile Asn Lys
1               5


<210> SEQ ID NO 311
<211> LENGTH: 33
<212> TYPE: DNA
<213> ORGANISM: Artificial Sequence
```

<220> FEATURE:
<223> OTHER INFORMATION: Synthetic

<400> SEQUENCE: 311
gcgaaaggta cttactcctg gtacttcgat ctc 33

<210> SEQ ID NO 312
<211> LENGTH: 11
<212> TYPE: PRT
<213> ORGANISM: Artificial Sequence
<220> FEATURE:
<223> OTHER INFORMATION: Synthetic

<400> SEQUENCE: 312

Ala Lys Gly Thr Tyr Ser Trp Tyr Phe Asp Leu
1 5 10

<210> SEQ ID NO 313
<211> LENGTH: 324
<212> TYPE: DNA
<213> ORGANISM: Artificial Sequence
<220> FEATURE:
<223> OTHER INFORMATION: Synthetic

<400> SEQUENCE: 313
gacatccaga tgacccagtc tccttccacc ctgtctacat ctgtaggaga cagagtcacc 60
atcacttgcc gggccagtca gactattagt agctggttgg cctggtatca gcagaaacca 120
gggaaagccc ctaagctcct gatctataag gcgtctcgtt tagaaagtgg ggtcccatca 180
aggttcagcg gcagtggatc tgggacagaa ttcactctca ccatcagcag cctgcagcct 240
gatgattttg caacttatta ctgccaacag tataatagtt attcgtggac gttcggccaa 300
gggaccaagg tggaaatcaa acga 324

<210> SEQ ID NO 314
<211> LENGTH: 108
<212> TYPE: PRT
<213> ORGANISM: Artificial Sequence
<220> FEATURE:
<223> OTHER INFORMATION: Synthetic

<400> SEQUENCE: 314

Asp Ile Gln Met Thr Gln Ser Pro Ser Thr Leu Ser Thr Ser Val Gly
1 5 10 15

Asp Arg Val Thr Ile Thr Cys Arg Ala Ser Gln Thr Ile Ser Ser Trp
20 25 30

Leu Ala Trp Tyr Gln Gln Lys Pro Gly Lys Ala Pro Lys Leu Leu Ile
35 40 45

Tyr Lys Ala Ser Arg Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Ala Thr Tyr Tyr Cys Gln Gln Tyr Asn Ser Tyr Ser Trp
85 90 95

Thr Phe Gly Gln Gly Thr Lys Val Glu Ile Lys Arg
100 105

<210> SEQ ID NO 315
<211> LENGTH: 18
<212> TYPE: DNA
<213> ORGANISM: Artificial Sequence
<220> FEATURE:

-continued

```
<223> OTHER INFORMATION: Synthetic

<400> SEQUENCE: 315

cagactatta gtagctgg                                                    18


<210> SEQ ID NO 316
<211> LENGTH: 6
<212> TYPE: PRT
<213> ORGANISM: Artificial Sequence
<220> FEATURE:
<223> OTHER INFORMATION: Synthetic

<400> SEQUENCE: 316

Gln Thr Ile Ser Ser Trp
1               5


<210> SEQ ID NO 317
<211> LENGTH: 9
<212> TYPE: DNA
<213> ORGANISM: Artificial Sequence
<220> FEATURE:
<223> OTHER INFORMATION: Synthetic

<400> SEQUENCE: 317

aaggcgtct                                                               9


<210> SEQ ID NO 318
<211> LENGTH: 3
<212> TYPE: PRT
<213> ORGANISM: Artificial Sequence
<220> FEATURE:
<223> OTHER INFORMATION: Synthetic

<400> SEQUENCE: 318

Lys Ala Ser
1


<210> SEQ ID NO 319
<211> LENGTH: 27
<212> TYPE: DNA
<213> ORGANISM: Artificial Sequence
<220> FEATURE:
<223> OTHER INFORMATION: Synthetic

<400> SEQUENCE: 319

caacagtata atagttattc gtggacg                                          27


<210> SEQ ID NO 320
<211> LENGTH: 9
<212> TYPE: PRT
<213> ORGANISM: Artificial Sequence
<220> FEATURE:
<223> OTHER INFORMATION: Synthetic

<400> SEQUENCE: 320

Gln Gln Tyr Asn Ser Tyr Ser Trp Thr
1               5


<210> SEQ ID NO 321
<211> LENGTH: 366
<212> TYPE: DNA
<213> ORGANISM: Artificial Sequence
<220> FEATURE:
<223> OTHER INFORMATION: Synthetic

<400> SEQUENCE: 321
```

-continued

```
gaagtgcagc tggtggagtc tgggggaggc ttggtacagc ctggcaggtc cctgagactc      60

tcctgtgcag cctctggatt cacctttgat gcttatgcca tgcactgggt ccggcaagct     120

ccagggaagg gcctggagtg ggtctcaggt attagttgga atagtggtag cataggctat     180

gcggactctg tgaagggccg attcaccatt tccagagaca acgccaagaa ctccctgtat     240

ctgcaaatga acagtctgag agaagaggac acggccttgt attactgtgc aaaagataaa     300

attttggaac tttactacta cggtatggac gtctggggcc aagggaccac ggtcaccgtc     360

tcctca                                                                366
```

<210> SEQ ID NO 322
<211> LENGTH: 122
<212> TYPE: PRT
<213> ORGANISM: Artificial Sequence
<220> FEATURE:
<223> OTHER INFORMATION: Synthetic

<400> SEQUENCE: 322

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Ala Tyr
            20                  25                  30

Ala Met His Trp Val Arg Gln Ala Pro Gly Lys Gly Leu Glu Trp Val
        35                  40                  45

Ser Gly Ile Ser Trp Asn Ser Gly Ser Ile Gly Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Glu Glu Asp Thr Ala Leu Tyr Tyr Cys
                85                  90                  95

Ala Lys Asp Lys Ile Leu Glu Leu Tyr Tyr Tyr Gly Met Asp Val Trp
            100                 105                 110

Gly Gln Gly Thr Thr Val Thr Val Ser Ser
        115                 120
```

<210> SEQ ID NO 323
<211> LENGTH: 24
<212> TYPE: DNA
<213> ORGANISM: Artificial Sequence
<220> FEATURE:
<223> OTHER INFORMATION: Synthetic

<400> SEQUENCE: 323

```
ggattcacct ttgatgctta tgcc                                             24
```

<210> SEQ ID NO 324
<211> LENGTH: 8
<212> TYPE: PRT
<213> ORGANISM: Artificial Sequence
<220> FEATURE:
<223> OTHER INFORMATION: Synthetic

<400> SEQUENCE: 324

```
Gly Phe Thr Phe Asp Ala Tyr Ala
1               5
```

<210> SEQ ID NO 325
<211> LENGTH: 24
<212> TYPE: DNA
<213> ORGANISM: Artificial Sequence
<220> FEATURE:

<223> OTHER INFORMATION: Synthetic

<400> SEQUENCE: 325
attagttgga atagtggtag cata 24

<210> SEQ ID NO 326
<211> LENGTH: 8
<212> TYPE: PRT
<213> ORGANISM: Artificial Sequence
<220> FEATURE:
<223> OTHER INFORMATION: Synthetic

<400> SEQUENCE: 326

Ile Ser Trp Asn Ser Gly Ser Ile
1 5

<210> SEQ ID NO 327
<211> LENGTH: 45
<212> TYPE: DNA
<213> ORGANISM: Artificial Sequence
<220> FEATURE:
<223> OTHER INFORMATION: Synthetic

<400> SEQUENCE: 327
gcaaaagata aaattttgga actttactac tacggtatgg acgtc 45

<210> SEQ ID NO 328
<211> LENGTH: 15
<212> TYPE: PRT
<213> ORGANISM: Artificial Sequence
<220> FEATURE:
<223> OTHER INFORMATION: Synthetic

<400> SEQUENCE: 328

Ala Lys Asp Lys Ile Leu Glu Leu Tyr Tyr Tyr Gly Met Asp Val
1 5 10 15

<210> SEQ ID NO 329
<211> LENGTH: 369
<212> TYPE: DNA
<213> ORGANISM: Artificial Sequence
<220> FEATURE:
<223> OTHER INFORMATION: Synthetic

<400> SEQUENCE: 329
gaggtgcagc tggtggagtc tgggggagac ttggtacagc ctggggggtc cctgagactc 60
tcctgttcag cctctggatt cacctttaac atctatgcca tgagctgggt ccgccaggct 120
ccagggaagg ggctggagtg ggtctcaggt attagtggta gtggtggtag cacatactac 180
gcagactccg tgaagggccg gttcaccatc tccagagaca attcaaagaa cacgctgtat 240
ttccaaatga atagcctgag agtcgaggac acggccgtat attactgtgc gaaaaaaata 300
agcagctcgt cctactacta ctacgctatg gacgtctggg gccaagggac cacggtcacc 360
gtctcctca 369

<210> SEQ ID NO 330
<211> LENGTH: 123
<212> TYPE: PRT
<213> ORGANISM: Artificial Sequence
<220> FEATURE:
<223> OTHER INFORMATION: Synthetic

<400> SEQUENCE: 330

Glu Val Gln Leu Val Glu Ser Gly Gly Asp Leu Val Gln Pro Gly Gly

-continued

```
1               5                   10                  15

Ser Leu Arg Leu Ser Cys Ser Ala Ser Gly Phe Thr Phe Asn Ile Tyr
            20                  25                  30

Ala Met Ser Trp Val Arg Gln Ala Pro Gly Lys Gly Leu Glu Trp Val
        35                  40                  45

Ser Gly Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Phe Gln Met Asn Ser Leu Arg Val Glu Asp Thr Ala Val Tyr Tyr Cys
                85                  90                  95

Ala Lys Lys Ile Ser Ser Ser Ser Tyr Tyr Tyr Tyr Ala Met Asp Val
            100                 105                 110

Trp Gly Gln Gly Thr Thr Val Thr Val Ser Ser
        115                 120
```

<210> SEQ ID NO 331
<211> LENGTH: 24
<212> TYPE: DNA
<213> ORGANISM: Artificial Sequence
<220> FEATURE:
<223> OTHER INFORMATION: Synthetic

<400> SEQUENCE: 331
ggattcacct ttaacatcta tgcc 24

<210> SEQ ID NO 332
<211> LENGTH: 8
<212> TYPE: PRT
<213> ORGANISM: Artificial Sequence
<220> FEATURE:
<223> OTHER INFORMATION: Synthetic

<400> SEQUENCE: 332

```
Gly Phe Thr Phe Asn Ile Tyr Ala
1               5
```

<210> SEQ ID NO 333
<211> LENGTH: 24
<212> TYPE: DNA
<213> ORGANISM: Artificial Sequence
<220> FEATURE:
<223> OTHER INFORMATION: Synthetic

<400> SEQUENCE: 333
attagtggta gtggtggtag caca 24

<210> SEQ ID NO 334
<211> LENGTH: 8
<212> TYPE: PRT
<213> ORGANISM: Artificial Sequence
<220> FEATURE:
<223> OTHER INFORMATION: Synthetic

<400> SEQUENCE: 334

```
Ile Ser Gly Ser Gly Gly Ser Thr
1               5
```

<210> SEQ ID NO 335
<211> LENGTH: 48
<212> TYPE: DNA
<213> ORGANISM: Artificial Sequence
<220> FEATURE:

<223> OTHER INFORMATION: Synthetic

<400> SEQUENCE: 335
gcgaaaaaaa taagcagctc gtcctactac tactacgcta tggacgtc 48

<210> SEQ ID NO 336
<211> LENGTH: 16
<212> TYPE: PRT
<213> ORGANISM: Artificial Sequence
<220> FEATURE:
<223> OTHER INFORMATION: Synthetic

<400> SEQUENCE: 336

Ala Lys Lys Ile Ser Ser Ser Ser Tyr Tyr Tyr Tyr Ala Met Asp Val
1 5 10 15

<210> SEQ ID NO 337
<211> LENGTH: 355
<212> TYPE: DNA
<213> ORGANISM: Artificial Sequence
<220> FEATURE:
<223> OTHER INFORMATION: Synthetic

<400> SEQUENCE: 337
caggtgcagc tggtgcagtc tggggctgag gtgaagaagc ctgggtcctc ggtgaaggtc 60
tcctgcaagg cttctggagg caccttcagc agatatgata tcagctgggt gcgacaggcc 120
cctggacaag gacttgagtg gatgggaggg atcatcccta tctttggtac atcaaactac 180
gcacagaagt tccagggcag agtcacgatt accacggacg aatccacgag tacagtctac 240
atggagctga gcagtctgag atctgaagac acggccgtgt attattgtgc gagaggaggt 300
cgatatggct ggttcgaccc ctggggccag ggaaccctgg tcaccgtctc ctcag 355

<210> SEQ ID NO 338
<211> LENGTH: 118
<212> TYPE: PRT
<213> ORGANISM: Artificial Sequence
<220> FEATURE:
<223> OTHER INFORMATION: Synthetic

<400> SEQUENCE: 338

Gln Val Gln Leu Val Gln Ser Gly Ala Glu Val Lys Lys Pro Gly Ser
1 5 10 15

Ser Val Lys Val Ser Cys Lys Ala Ser Gly Gly Thr Phe Ser Arg Tyr
20 25 30

Asp Ile Ser Trp Val Arg Gln Ala Pro Gly Gln Gly Leu Glu Trp Met
35 40 45

Gly Gly Ile Ile Pro Ile Phe Gly Thr Ser Asn Tyr Ala Gln Lys Phe
50 55 60

Gln Gly Arg Val Thr Ile Thr Thr Asp Glu Ser Thr Ser Thr Val Tyr
65 70 75 80

Met Glu Leu Ser Ser Leu Arg Ser Glu Asp Thr Ala Val Tyr Tyr Cys
85 90 95

Ala Arg Gly Gly Arg Tyr Gly Trp Phe Asp Pro Trp Gly Gln Gly Thr
100 105 110

Leu Val Thr Val Ser Ser
115

<210> SEQ ID NO 339
<211> LENGTH: 24
<212> TYPE: DNA

<213> ORGANISM: Artificial Sequence
<220> FEATURE:
<223> OTHER INFORMATION: Synthetic

<400> SEQUENCE: 339
ggaggcacct tcagcagata tgat 24

<210> SEQ ID NO 340
<211> LENGTH: 8
<212> TYPE: PRT
<213> ORGANISM: Artificial Sequence
<220> FEATURE:
<223> OTHER INFORMATION: Synthetic

<400> SEQUENCE: 340

Gly Gly Thr Phe Ser Arg Tyr Asp
1 5

<210> SEQ ID NO 341
<211> LENGTH: 24
<212> TYPE: DNA
<213> ORGANISM: Artificial Sequence
<220> FEATURE:
<223> OTHER INFORMATION: Synthetic

<400> SEQUENCE: 341
atcatcccta tctttggtac atca 24

<210> SEQ ID NO 342
<211> LENGTH: 8
<212> TYPE: PRT
<213> ORGANISM: Artificial Sequence
<220> FEATURE:
<223> OTHER INFORMATION: Synthetic

<400> SEQUENCE: 342

Ile Ile Pro Ile Phe Gly Thr Ser
1 5

<210> SEQ ID NO 343
<211> LENGTH: 33
<212> TYPE: DNA
<213> ORGANISM: Artificial Sequence
<220> FEATURE:
<223> OTHER INFORMATION: Synthetic

<400> SEQUENCE: 343
gcgagaggag gtcgatatgg ctggttcgac ccc 33

<210> SEQ ID NO 344
<211> LENGTH: 11
<212> TYPE: PRT
<213> ORGANISM: Artificial Sequence
<220> FEATURE:
<223> OTHER INFORMATION: Synthetic

<400> SEQUENCE: 344

Ala Arg Gly Gly Arg Tyr Gly Trp Phe Asp Pro
1 5 10

<210> SEQ ID NO 345
<211> LENGTH: 375
<212> TYPE: DNA
<213> ORGANISM: Artificial Sequence
<220> FEATURE:
<223> OTHER INFORMATION: Synthetic

<400> SEQUENCE: 345

```
gaggtgcagc tggtggagtc tgggggaggc ttggtacagc ctggggggtc cctgagactc      60
tcctgtgcag cctctggatt cacctttagc agctttgcca tgagctgggt ccgccaggct     120
ccagggaagg aactggagtg ggtctcatct attagtggtc gtggtggtag cacatactac     180
gcagactccg tgaggggccg gttcaccatc tccagagaca attccaagat cacgctgtat     240
ctgcaaatga acagcctgag agccgaggac acggccgtat attactgtgc gaaagatatt     300
gtcttccggt ataccagctc ggcctactgg tacttcgatc tctggggccg tggcaccctg     360
gtcaccgtct cctca                                                      375
```

<210> SEQ ID NO 346
<211> LENGTH: 125
<212> TYPE: PRT
<213> ORGANISM: Artificial Sequence
<220> FEATURE:
<223> OTHER INFORMATION: Synthetic

<400> SEQUENCE: 346

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ala Met Ser Trp Val Arg Gln Ala Pro Gly Lys Glu Leu Glu Trp Val
        35                  40                  45

Ser Ser Ile Ser Gly Arg Gly Gly Ser Thr Tyr Tyr Ala Asp Ser Val
    50                  55                  60

Arg Gly Arg Phe Thr Ile Ser Arg Asp Asn Ser Lys Ile Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Val Phe Arg Tyr Thr Ser Ser Ala Tyr Trp Tyr Phe
            100                 105                 110

Asp Leu Trp Gly Arg Gly Thr Leu Val Thr Val Ser Ser
        115                 120                 125
```

<210> SEQ ID NO 347
<211> LENGTH: 24
<212> TYPE: DNA
<213> ORGANISM: Artificial Sequence
<220> FEATURE:
<223> OTHER INFORMATION: Synthetic

<400> SEQUENCE: 347

```
ggattcacct ttagcagctt tgcc                                            24
```

<210> SEQ ID NO 348
<211> LENGTH: 8
<212> TYPE: PRT
<213> ORGANISM: Artificial Sequence
<220> FEATURE:
<223> OTHER INFORMATION: Synthetic

<400> SEQUENCE: 348

```
Gly Phe Thr Phe Ser Ser Phe Ala
1               5
```

<210> SEQ ID NO 349
<211> LENGTH: 24
<212> TYPE: DNA

<213> ORGANISM: Artificial Sequence
<220> FEATURE:
<223> OTHER INFORMATION: Synthetic

<400> SEQUENCE: 349
attagtggtc gtggtggtag caca 24

<210> SEQ ID NO 350
<211> LENGTH: 8
<212> TYPE: PRT
<213> ORGANISM: Artificial Sequence
<220> FEATURE:
<223> OTHER INFORMATION: Synthetic

<400> SEQUENCE: 350

Ile Ser Gly Arg Gly Gly Ser Thr
1 5

<210> SEQ ID NO 351
<211> LENGTH: 54
<212> TYPE: DNA
<213> ORGANISM: Artificial Sequence
<220> FEATURE:
<223> OTHER INFORMATION: Synthetic

<400> SEQUENCE: 351
gcgaaagata ttgtcttccg gtataccagc tcggcctact ggtacttcga tctc 54

<210> SEQ ID NO 352
<211> LENGTH: 18
<212> TYPE: PRT
<213> ORGANISM: Artificial Sequence
<220> FEATURE:
<223> OTHER INFORMATION: Synthetic

<400> SEQUENCE: 352

Ala Lys Asp Ile Val Phe Arg Tyr Thr Ser Ser Ala Tyr Trp Tyr Phe
1 5 10 15

Asp Leu

<210> SEQ ID NO 353
<211> LENGTH: 375
<212> TYPE: DNA
<213> ORGANISM: Artificial Sequence
<220> FEATURE:
<223> OTHER INFORMATION: Synthetic

<400> SEQUENCE: 353
gaggtgcagc tggtggagtc tgggggaggc ttggtacagc ctggggggtc cctgagactc 60
tcctgtgcag cctctggatt cacctttagc agctatggca tgaactgggt ccgccaggct 120
ccagggaagg ggctggagtg ggtctcagtt attagtggta gtggtggtag cacatactac 180
gcagactccg tgaagggccg gttcaccatc tccagagaca attccaagaa cacgctgtat 240
ctgcaaatga acagcctgag agccgaggac acggccgtat attactgtgc gaaagatcgt 300
tggacgtatt actatgatag tagtggttcc ccctttgact actggggcca gggaaccctg 360
gtcaccgtct cctca 375

<210> SEQ ID NO 354
<211> LENGTH: 125
<212> TYPE: PRT
<213> ORGANISM: Artificial Sequence
<220> FEATURE:
<223> OTHER INFORMATION: Synthetic

<400> SEQUENCE: 354

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Gly Met Asn Trp Val Arg Gln Ala Pro Gly Lys Gly Leu Glu Trp Val
35 40 45

Ser Val Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Lys Asp Arg Trp Thr Tyr Tyr Tyr Asp Ser Ser Gly Ser Pro Phe
100 105 110

Asp Tyr Trp Gly Gln Gly Thr Leu Val Thr Val Ser Ser
115 120 125

<210> SEQ ID NO 355
<211> LENGTH: 24
<212> TYPE: DNA
<213> ORGANISM: Artificial Sequence
<220> FEATURE:
<223> OTHER INFORMATION: Synthetic

<400> SEQUENCE: 355
ggattcacct ttagcagcta tggc 24

<210> SEQ ID NO 356
<211> LENGTH: 8
<212> TYPE: PRT
<213> ORGANISM: Artificial Sequence
<220> FEATURE:
<223> OTHER INFORMATION: Synthetic

<400> SEQUENCE: 356

Gly Phe Thr Phe Ser Ser Tyr Gly
1 5

<210> SEQ ID NO 357
<211> LENGTH: 24
<212> TYPE: DNA
<213> ORGANISM: Artificial Sequence
<220> FEATURE:
<223> OTHER INFORMATION: Synthetic

<400> SEQUENCE: 357
attagtggta gtggtggtag caca 24

<210> SEQ ID NO 358
<211> LENGTH: 8
<212> TYPE: PRT
<213> ORGANISM: Artificial Sequence
<220> FEATURE:
<223> OTHER INFORMATION: Synthetic

<400> SEQUENCE: 358

Ile Ser Gly Ser Gly Gly Ser Thr
1 5

<210> SEQ ID NO 359

<211> LENGTH: 54
<212> TYPE: DNA
<213> ORGANISM: Artificial Sequence
<220> FEATURE:
<223> OTHER INFORMATION: Synthetic

<400> SEQUENCE: 359
gcgaaagatc gttggacgta ttactatgat agtagtggtt ccccctttga ctac 54

<210> SEQ ID NO 360
<211> LENGTH: 18
<212> TYPE: PRT
<213> ORGANISM: Artificial Sequence
<220> FEATURE:
<223> OTHER INFORMATION: Synthetic

<400> SEQUENCE: 360

Ala Lys Asp Arg Trp Thr Tyr Tyr Tyr Asp Ser Ser Gly Ser Pro Phe
1 5 10 15

Asp Tyr

<210> SEQ ID NO 361
<211> LENGTH: 324
<212> TYPE: DNA
<213> ORGANISM: Artificial Sequence
<220> FEATURE:
<223> OTHER INFORMATION: Synthetic

<400> SEQUENCE: 361
gaaattgtgt tgacgcagtc tccaggcacc ctgtctttgt ctccagggga aagagccacc 60
ctctcctgca gggccagtca gagtgttagc agcagctact tagcctggta ccagcagaaa 120
cctggccagg ctcccaggct cctcatctat ggtgcatcca gcagggccac tggcatccca 180
gacaggttca gtggcagtgg gtctgggaca gacttcactc tcaccatcag cagactggag 240
cctgaagatt ttgcagtgta ttactgtcag cagtatggta gctcaccttg gacgttcggc 300
caagggacca aggtggaaat caaa 324

<210> SEQ ID NO 362
<211> LENGTH: 108
<212> TYPE: PRT
<213> ORGANISM: Artificial Sequence
<220> FEATURE:
<223> OTHER INFORMATION: Synthetic

<400> SEQUENCE: 362

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Arg Leu Leu
35 40 45

Ile Tyr Gly Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Gln Tyr Gly Ser Ser Pro
85 90 95

Trp Thr Phe Gly Gln Gly Thr Lys Val Glu Ile Lys
100 105

<210> SEQ ID NO 363
<211> LENGTH: 21
<212> TYPE: DNA
<213> ORGANISM: Artificial Sequence
<220> FEATURE:
<223> OTHER INFORMATION: Synthetic

<400> SEQUENCE: 363
cagagtgtta gcagcagcta c 21

<210> SEQ ID NO 364
<211> LENGTH: 7
<212> TYPE: PRT
<213> ORGANISM: Artificial Sequence
<220> FEATURE:
<223> OTHER INFORMATION: Synthetic

<400> SEQUENCE: 364

Gln Ser Val Ser Ser Ser Tyr
1 5

<210> SEQ ID NO 365
<211> LENGTH: 9
<212> TYPE: DNA
<213> ORGANISM: Artificial Sequence
<220> FEATURE:
<223> OTHER INFORMATION: Synthetic

<400> SEQUENCE: 365 ggtgcatcc 9

<210> SEQ ID NO 366
<211> LENGTH: 3
<212> TYPE: PRT
<213> ORGANISM: Artificial Sequence
<220> FEATURE:
<223> OTHER INFORMATION: Synthetic

<400> SEQUENCE: 366

Gly Ala Ser
1

<210> SEQ ID NO 367
<211> LENGTH: 27
<212> TYPE: DNA
<213> ORGANISM: Artificial Sequence
<220> FEATURE:
<223> OTHER INFORMATION: Synthetic

<400> SEQUENCE: 367
cagcagtatg gtagctcacc ttggacg 27

<210> SEQ ID NO 368
<211> LENGTH: 9
<212> TYPE: PRT
<213> ORGANISM: Artificial Sequence
<220> FEATURE:
<223> OTHER INFORMATION: Synthetic

<400> SEQUENCE: 368

Gln Gln Tyr Gly Ser Ser Pro Trp Thr
1 5

<210> SEQ ID NO 369
<211> LENGTH: 363
<212> TYPE: DNA
<213> ORGANISM: Artificial Sequence
<220> FEATURE:
<223> OTHER INFORMATION: Synthetic

<400> SEQUENCE: 369
gaggtgcagc tggtggagtc tgggggaggc tttgtacagc ctgggggtc cctgagactc 60 tcctgtgcag cctctggatt cacttttagc agttatgcca tgagttgggt ccgccaggct 120
ccaggtaagg ggctggagtg ggtctcagct attagtggta ctggtagtaa cacatactac 180
gcagactccg tgaagggccg gttcaccatc tccagagaca attccaagaa cacgctgtat 240
ctgcaaatga acagcctgag agccgaggac acggccgttt actactgtgc gaaagatcgc 300
gtgactacag taacctacta ctttgactac tggggccagg gaaccctggt caccgtctcc 360
tca 363

<210> SEQ ID NO 370
<211> LENGTH: 121
<212> TYPE: PRT
<213> ORGANISM: Artificial Sequence
<220> FEATURE:
<223> OTHER INFORMATION: Synthetic

<400> SEQUENCE: 370

Glu Val Gln Leu Val Glu Ser Gly Gly Gly Phe Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Thr Gly Ser Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Val Thr Thr Val Thr Tyr Tyr Phe Asp Tyr Trp Gly
            100                 105                 110

Gln Gly Thr Leu Val Thr Val Ser Ser
        115                 120

<210> SEQ ID NO 371
<211> LENGTH: 24
<212> TYPE: DNA
<213> ORGANISM: Artificial Sequence
<220> FEATURE:
<223> OTHER INFORMATION: Synthetic

<400> SEQUENCE: 371
ggattcactt ttagcagtta tgcc 24

<210> SEQ ID NO 372
<211> LENGTH: 8
<212> TYPE: PRT
<213> ORGANISM: Artificial Sequence
<220> FEATURE:
<223> OTHER INFORMATION: Synthetic

<400> SEQUENCE: 372

Gly Phe Thr Phe Ser Ser Tyr Ala
1               5

<210> SEQ ID NO 373
<211> LENGTH: 24
<212> TYPE: DNA
<213> ORGANISM: Artificial Sequence
<220> FEATURE:
<223> OTHER INFORMATION: Synthetic

<400> SEQUENCE: 373
attagtggta ctggtagtaa caca                                              24

<210> SEQ ID NO 374
<211> LENGTH: 8
<212> TYPE: PRT
<213> ORGANISM: Artificial Sequence
<220> FEATURE:
<223> OTHER INFORMATION: Synthetic

<400> SEQUENCE: 374

Ile Ser Gly Thr Gly Ser Asn Thr
1               5

<210> SEQ ID NO 375
<211> LENGTH: 42
<212> TYPE: DNA
<213> ORGANISM: Artificial Sequence
<220> FEATURE:
<223> OTHER INFORMATION: Synthetic

<400> SEQUENCE: 375
gcgaaagatc gcgtgactac agtaacctac tactttgact ac                          42

<210> SEQ ID NO 376
<211> LENGTH: 14
<212> TYPE: PRT
<213> ORGANISM: Artificial Sequence
<220> FEATURE:
<223> OTHER INFORMATION: Synthetic

<400> SEQUENCE: 376

Ala Lys Asp Arg Val Thr Thr Val Thr Tyr Tyr Phe Asp Tyr
1               5                   10

<210> SEQ ID NO 377
<211> LENGTH: 372
<212> TYPE: DNA
<213> ORGANISM: Artificial Sequence
<220> FEATURE:
<223> OTHER INFORMATION: Synthetic

<400> SEQUENCE: 377
gaggtgcagc tggtggagtc tgggggaggc ttggtacagc ctggggggtc cctgagactc        60
tcctgtgcag cctctggttt cacctttagc agctatgcca tgaactgggt ccgccaggct       120
ccagggaagg gactggagtg ggtctcagct attagtggta gtggtgatag cacatactac       180
gcagactccg tgaagggccg gttcaccatc tccagagaca attccaggac cacgctgtct       240
ctgcaattga acagcctgag agccgaggac acggccgtat attactgtgc gaaagatcga       300
ctactatggt tcggggaatt aggatcccca tttcactact ggggccaggg aaccctggtc       360
accgtctcct ca                                                          372

<210> SEQ ID NO 378
<211> LENGTH: 124
<212> TYPE: PRT
<213> ORGANISM: Artificial Sequence
<220> FEATURE:

<223> OTHER INFORMATION: Synthetic

<400> SEQUENCE: 378

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Ser Gly Ser Gly Asp Ser Thr Tyr Tyr Ala Asp Ser Val
    50                  55                  60

Lys Gly Arg Phe Thr Ile Ser Arg Asp Asn Ser Arg Thr Thr Leu Ser
65                  70                  75                  80

Leu Gln Leu Asn Ser Leu Arg Ala Glu Asp Thr Ala Val Tyr Tyr Cys
                85                  90                  95

Ala Lys Asp Arg Leu Leu Trp Phe Gly Glu Leu Gly Ser Pro Phe His
            100                 105                 110

Tyr Trp Gly Gln Gly Thr Leu Val Thr Val Ser Ser
        115                 120

<210> SEQ ID NO 379
<211> LENGTH: 24
<212> TYPE: DNA
<213> ORGANISM: Artificial Sequence
<220> FEATURE:
<223> OTHER INFORMATION: Synthetic

<400> SEQUENCE: 379
ggtttcacct ttagcagcta tgcc                                              24

<210> SEQ ID NO 380
<211> LENGTH: 8
<212> TYPE: PRT
<213> ORGANISM: Artificial Sequence
<220> FEATURE:
<223> OTHER INFORMATION: Synthetic

<400> SEQUENCE: 380

Gly Phe Thr Phe Ser Ser Tyr Ala
1               5

<210> SEQ ID NO 381
<211> LENGTH: 24
<212> TYPE: DNA
<213> ORGANISM: Artificial Sequence
<220> FEATURE:
<223> OTHER INFORMATION: Synthetic

<400> SEQUENCE: 381
attagtggta gtggtgatag caca                                              24

<210> SEQ ID NO 382
<211> LENGTH: 8
<212> TYPE: PRT
<213> ORGANISM: Artificial Sequence
<220> FEATURE:
<223> OTHER INFORMATION: Synthetic

<400> SEQUENCE: 382

Ile Ser Gly Ser Gly Asp Ser Thr
1               5

<210> SEQ ID NO 383
<211> LENGTH: 51
<212> TYPE: DNA
<213> ORGANISM: Artificial Sequence
<220> FEATURE:
<223> OTHER INFORMATION: Synthetic

<400> SEQUENCE: 383
gcgaaagatc gactactatg gttcggggaa ttaggatccc catttcacta c 51

<210> SEQ ID NO 384
<211> LENGTH: 17
<212> TYPE: PRT
<213> ORGANISM: Artificial Sequence
<220> FEATURE:
<223> OTHER INFORMATION: Synthetic

<400> SEQUENCE: 384

Ala Lys Asp Arg Leu Leu Trp Phe Gly Glu Leu Gly Ser Pro Phe His
1 5 10 15

Tyr

<210> SEQ ID NO 385
<211> LENGTH: 363
<212> TYPE: DNA
<213> ORGANISM: Artificial Sequence
<220> FEATURE:
<223> OTHER INFORMATION: Synthetic

<400> SEQUENCE: 385
gaggtgcagc tggtggagtc tgggggaggc ttggaacagc ctgggggtc cctgagactc 60 tcctgtgcag cctctggatt cacctttagc agctatgcca tgagctgggt ccgccaggct 120
ccagggaagg ggctggagtg ggtctcagtc attagtggta gtggtggtta cacaaactac 180
gcagactccg tgaagggccg gttcaccatc tccagagaca attccaagaa cacgctgtat 240
ctgcaaatga accgcctgag agccgaggac tcggccgttt attactgtgc gaggcataat 300
tggaactacg actattacgg tatggacgtc tggggccagg ggaccacggt caccgtctcc 360
tca 363

<210> SEQ ID NO 386
<211> LENGTH: 121
<212> TYPE: PRT
<213> ORGANISM: Artificial Sequence
<220> FEATURE:
<223> OTHER INFORMATION: Synthetic

<400> SEQUENCE: 386

Glu Val Gln Leu Val Glu Ser Gly Gly Gly Leu Glu Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Val Ile Ser Gly Ser Gly Gly Tyr Thr Asn Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Arg Leu Arg Ala Glu Asp Ser Ala Val Tyr Tyr Cys
85 90 95

Ala Arg His Asn Trp Asn Tyr Asp Tyr Tyr Gly Met Asp Val Trp Gly 100 105 110

Gln Gly Thr Thr Val Thr Val Ser Ser
115 120

<210> SEQ ID NO 387
<211> LENGTH: 24
<212> TYPE: DNA
<213> ORGANISM: Artificial Sequence
<220> FEATURE:
<223> OTHER INFORMATION: Synthetic

<400> SEQUENCE: 387
ggattcacct ttagcagcta tgcc 24

<210> SEQ ID NO 388
<211> LENGTH: 8
<212> TYPE: PRT
<213> ORGANISM: Artificial Sequence
<220> FEATURE:
<223> OTHER INFORMATION: Synthetic

<400> SEQUENCE: 388

Gly Phe Thr Phe Ser Ser Tyr Ala
1 5

<210> SEQ ID NO 389
<211> LENGTH: 24
<212> TYPE: DNA
<213> ORGANISM: Artificial Sequence
<220> FEATURE:
<223> OTHER INFORMATION: Synthetic

<400> SEQUENCE: 389
attagtggta gtggtggtta caca 24

<210> SEQ ID NO 390
<211> LENGTH: 8
<212> TYPE: PRT
<213> ORGANISM: Artificial Sequence
<220> FEATURE:
<223> OTHER INFORMATION: Synthetic

<400> SEQUENCE: 390

Ile Ser Gly Ser Gly Gly Tyr Thr
1 5

<210> SEQ ID NO 391
<211> LENGTH: 42
<212> TYPE: DNA
<213> ORGANISM: Artificial Sequence
<220> FEATURE:
<223> OTHER INFORMATION: Synthetic

<400> SEQUENCE: 391
gcgaggcata attggaacta cgactattac ggtatggacg tc 42

<210> SEQ ID NO 392
<211> LENGTH: 14
<212> TYPE: PRT
<213> ORGANISM: Artificial Sequence
<220> FEATURE:
<223> OTHER INFORMATION: Synthetic

<400> SEQUENCE: 392

Ala Arg His Asn Trp Asn Tyr Asp Tyr Tyr Gly Met Asp Val
1 5 10

<210> SEQ ID NO 393
<211> LENGTH: 360
<212> TYPE: DNA
<213> ORGANISM: Artificial Sequence
<220> FEATURE:
<223> OTHER INFORMATION: Synthetic

<400> SEQUENCE: 393
caggtgcagc tggtggagtc tgggggaggc gtggtccagt ctgggaggtc cctgagactc 60
tcctgtgcag ccgctggatt caccttcagt aattatggca tgcactgggt ccgccaggct 120
ccaggcaagg ggctggagtg ggtggcactt atgtcatttg atggaagtga taaatactat 180
gcagactccg tgaagggccg attcaccatc tccagagaca attccaagaa cacgttgtat 240
ctgcaaatga acagcctgag agctgaggac acggctctgt attactgtgc gaaaggatac 300
gatttttgga gtggttattg ggactactgg ggccagggaa ccctggtcac cgtctcctca 360

<210> SEQ ID NO 394
<211> LENGTH: 120
<212> TYPE: PRT
<213> ORGANISM: Artificial Sequence
<220> FEATURE:
<223> OTHER INFORMATION: Synthetic

<400> SEQUENCE: 394

Gln Val Gln Leu Val Glu Ser Gly Gly Gly Val Val Gln Ser Gly Arg
1 5 10 15

Ser Leu Arg Leu Ser Cys Ala Ala Ala Gly Phe Thr Phe Ser Asn Tyr
20 25 30

Gly Met His Trp Val Arg Gln Ala Pro Gly Lys Gly Leu Glu Trp Val
35 40 45

Ala Leu Met Ser Phe Asp Gly Ser Asp Lys Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Leu Tyr Tyr Cys
85 90 95

Ala Lys Gly Tyr Asp Phe Trp Ser Gly Tyr Trp Asp Tyr Trp Gly Gln
100 105 110

Gly Thr Leu Val Thr Val Ser Ser
115 120

<210> SEQ ID NO 395
<211> LENGTH: 24
<212> TYPE: DNA
<213> ORGANISM: Artificial Sequence
<220> FEATURE:
<223> OTHER INFORMATION: Synthetic

<400> SEQUENCE: 395
ggattcacct tcagtaatta tggc 24

<210> SEQ ID NO 396
<211> LENGTH: 8
<212> TYPE: PRT
<213> ORGANISM: Artificial Sequence
<220> FEATURE:
<223> OTHER INFORMATION: Synthetic

<400> SEQUENCE: 396

```
Gly Phe Thr Phe Ser Asn Tyr Gly
1               5


<210> SEQ ID NO 397
<211> LENGTH: 24
<212> TYPE: DNA
<213> ORGANISM: Artificial Sequence
<220> FEATURE:
<223> OTHER INFORMATION: Synthetic

<400> SEQUENCE: 397

atgtcatttg atggaagtga taaa                                              24


<210> SEQ ID NO 398
<211> LENGTH: 8
<212> TYPE: PRT
<213> ORGANISM: Artificial Sequence
<220> FEATURE:
<223> OTHER INFORMATION: Synthetic

<400> SEQUENCE: 398

Met Ser Phe Asp Gly Ser Asp Lys
1               5


<210> SEQ ID NO 399
<211> LENGTH: 39
<212> TYPE: DNA
<213> ORGANISM: Artificial Sequence
<220> FEATURE:
<223> OTHER INFORMATION: Synthetic

<400> SEQUENCE: 399

gcgaaaggat acgatttttg gagtggttat tgggactac                              39


<210> SEQ ID NO 400
<211> LENGTH: 13
<212> TYPE: PRT
<213> ORGANISM: Artificial Sequence
<220> FEATURE:
<223> OTHER INFORMATION: Synthetic

<400> SEQUENCE: 400

Ala Lys Gly Tyr Asp Phe Trp Ser Gly Tyr Trp Asp Tyr
1               5                   10


<210> SEQ ID NO 401
<211> LENGTH: 351
<212> TYPE: DNA
<213> ORGANISM: Artificial Sequence
<220> FEATURE:
<223> OTHER INFORMATION: Synthetic

<400> SEQUENCE: 401

gaggtgcagc tggtggagtc tgggggaggc ttggtacaac ctggggggtc cctgagactc       60

tcctgtgcag cctctggatt cacctttagc acctatgcca tgagctgggt ccgccaggct      120

ccagggaagg ggcttgagtg ggtctcaact attagtggtc gttctgatat tacatacttc      180

gcagactccg tgaagggccg gtttaccgtc tccagagaca attccaagac cacgctatat      240

ctccaaatga acagtctgag agccgaggac acggccgtat attactgtgc gacagatgac      300

gacctgcccc ttgactactg gggccaggga accctggtca ccgtctcctc a               351


<210> SEQ ID NO 402
<211> LENGTH: 117
<212> TYPE: PRT
```

```
<213> ORGANISM: Artificial Sequence
<220> FEATURE:
<223> OTHER INFORMATION: Synthetic

<400> SEQUENCE: 402

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Thr Ile Ser Gly Arg Ser Asp Ile Thr Tyr Phe Ala Asp Ser Val
    50                  55                  60

Lys Gly Arg Phe Thr Val Ser Arg Asp Asn Ser Lys Thr Thr Leu Tyr
65                  70                  75                  80

Leu Gln Met Asn Ser Leu Arg Ala Glu Asp Thr Ala Val Tyr Tyr Cys
                85                  90                  95

Ala Thr Asp Asp Asp Leu Pro Leu Asp Tyr Trp Gly Gln Gly Thr Leu
            100                 105                 110

Val Thr Val Ser Ser
        115


<210> SEQ ID NO 403
<211> LENGTH: 24
<212> TYPE: DNA
<213> ORGANISM: Artificial Sequence
<220> FEATURE:
<223> OTHER INFORMATION: Synthetic

<400> SEQUENCE: 403

ggattcacct ttagcaccta tgcc                                            24


<210> SEQ ID NO 404
<211> LENGTH: 8
<212> TYPE: PRT
<213> ORGANISM: Artificial Sequence
<220> FEATURE:
<223> OTHER INFORMATION: Synthetic

<400> SEQUENCE: 404

Gly Phe Thr Phe Ser Thr Tyr Ala
1               5


<210> SEQ ID NO 405
<211> LENGTH: 24
<212> TYPE: DNA
<213> ORGANISM: Artificial Sequence
<220> FEATURE:
<223> OTHER INFORMATION: Synthetic

<400> SEQUENCE: 405

attagtggtc gttctgatat taca                                            24


<210> SEQ ID NO 406
<211> LENGTH: 8
<212> TYPE: PRT
<213> ORGANISM: Artificial Sequence
<220> FEATURE:
<223> OTHER INFORMATION: Synthetic

<400> SEQUENCE: 406

Ile Ser Gly Arg Ser Asp Ile Thr
1               5
```

<210> SEQ ID NO 407
<211> LENGTH: 30
<212> TYPE: DNA
<213> ORGANISM: Artificial Sequence
<220> FEATURE:
<223> OTHER INFORMATION: Synthetic

<400> SEQUENCE: 407
gcgacagatg acgacctgcc ccttgactac 30

<210> SEQ ID NO 408
<211> LENGTH: 10
<212> TYPE: PRT
<213> ORGANISM: Artificial Sequence
<220> FEATURE:
<223> OTHER INFORMATION: Synthetic

<400> SEQUENCE: 408

Ala Thr Asp Asp Asp Leu Pro Leu Asp Tyr
1 5 10

<210> SEQ ID NO 409
<211> LENGTH: 354
<212> TYPE: DNA
<213> ORGANISM: Artificial Sequence
<220> FEATURE:
<223> OTHER INFORMATION: Synthetic

<400> SEQUENCE: 409
caggtgcagc tggtgcagtc tgggactgag gtgaagaagc ctgggtcctc ggtgaaggtc 60
tcctgcaagg cttctggagg caccttcagc agatatactt tcagctgggt gcgacaggcc 120
cctggacaag ggcttgagtg gatgggaggg atcatcccta tctttggtac aacaaactac 180
gcacagaagt tccagggcag agtcacgatt accacggacg aatccacgag cacagtctac 240
atggagctga gcagcctgag atctgaggac acggccgtgt attattgtac cagaggaggt 300
cgatatggct ggttcgaccc ctggggccag ggaaccctgg tcaccgtctc ctca 354

<210> SEQ ID NO 410
<211> LENGTH: 118
<212> TYPE: PRT
<213> ORGANISM: Artificial Sequence
<220> FEATURE:
<223> OTHER INFORMATION: Synthetic

<400> SEQUENCE: 410

Gln Val Gln Leu Val Gln Ser Gly Thr Glu Val Lys Lys Pro Gly Ser
1 5 10 15

Ser Val Lys Val Ser Cys Lys Ala Ser Gly Gly Thr Phe Ser Arg Tyr
20 25 30

Thr Phe Ser Trp Val Arg Gln Ala Pro Gly Gln Gly Leu Glu Trp Met
35 40 45

Gly Gly Ile Ile Pro Ile Phe Gly Thr Thr Asn Tyr Ala Gln Lys Phe
50 55 60

Gln Gly Arg Val Thr Ile Thr Thr Asp Glu Ser Thr Ser Thr Val Tyr
65 70 75 80

Met Glu Leu Ser Ser Leu Arg Ser Glu Asp Thr Ala Val Tyr Tyr Cys
85 90 95

Thr Arg Gly Gly Arg Tyr Gly Trp Phe Asp Pro Trp Gly Gln Gly Thr
100 105 110

Leu Val Thr Val Ser Ser
        115

<210> SEQ ID NO 411
<211> LENGTH: 24
<212> TYPE: DNA
<213> ORGANISM: Artificial Sequence
<220> FEATURE:
<223> OTHER INFORMATION: Synthetic

<400> SEQUENCE: 411
ggaggcacct tcagcagata tact 24

<210> SEQ ID NO 412
<211> LENGTH: 8
<212> TYPE: PRT
<213> ORGANISM: Artificial Sequence
<220> FEATURE:
<223> OTHER INFORMATION: Synthetic

<400> SEQUENCE: 412

Gly Gly Thr Phe Ser Arg Tyr Thr
1               5

<210> SEQ ID NO 413
<211> LENGTH: 24
<212> TYPE: DNA
<213> ORGANISM: Artificial Sequence
<220> FEATURE:
<223> OTHER INFORMATION: Synthetic

<400> SEQUENCE: 413
atcatcccta tctttggtac aaca 24

<210> SEQ ID NO 414
<211> LENGTH: 8
<212> TYPE: PRT
<213> ORGANISM: Artificial Sequence
<220> FEATURE:
<223> OTHER INFORMATION: Synthetic

<400> SEQUENCE: 414

Ile Ile Pro Ile Phe Gly Thr Thr
1               5

<210> SEQ ID NO 415
<211> LENGTH: 33
<212> TYPE: DNA
<213> ORGANISM: Artificial Sequence
<220> FEATURE:
<223> OTHER INFORMATION: Synthetic

<400> SEQUENCE: 415
accagaggag gtcgatatgg ctggttcgac ccc 33

<210> SEQ ID NO 416
<211> LENGTH: 11
<212> TYPE: PRT
<213> ORGANISM: Artificial Sequence
<220> FEATURE:
<223> OTHER INFORMATION: Synthetic

<400> SEQUENCE: 416

Thr Arg Gly Gly Arg Tyr Gly Trp Phe Asp Pro
1               5                   10

<210> SEQ ID NO 417
<211> LENGTH: 403
<212> TYPE: PRT
<213> ORGANISM: Homo sapiens
<220> FEATURE:
<223> OTHER INFORMATION: His-myc tagged human MSR1 antibody
(extracellular domain)

<400> SEQUENCE: 417

```
His His His His His His Glu Gln Lys Leu Ile Ser Glu Glu Asp Leu
1               5                   10                  15

Gly Gly Glu Gln Lys Leu Ile Ser Glu Glu Asp Leu Lys Trp Glu Thr
            20                  25                  30

Lys Asn Cys Ser Val Ser Ser Thr Asn Ala Asn Asp Ile Thr Gln Ser
        35                  40                  45

Leu Thr Gly Lys Gly Asn Asp Ser Glu Glu Glu Met Arg Phe Gln Glu
    50                  55                  60

Val Phe Met Glu His Met Ser Asn Met Glu Lys Arg Ile Gln His Ile
65                  70                  75                  80

Leu Asp Met Glu Ala Asn Leu Met Asp Thr Glu His Phe Gln Asn Phe
                85                  90                  95

Ser Met Thr Thr Asp Gln Arg Phe Asn Asp Ile Leu Leu Gln Leu Ser
            100                 105                 110

Thr Leu Phe Ser Ser Val Gln Gly His Gly Asn Ala Ile Asp Glu Ile
        115                 120                 125

Ser Lys Ser Leu Ile Ser Leu Asn Thr Thr Leu Leu Asp Leu Gln Leu
    130                 135                 140

Asn Ile Glu Asn Leu Asn Gly Lys Ile Gln Glu Asn Thr Phe Lys Gln
145                 150                 155                 160

Gln Glu Glu Ile Ser Lys Leu Glu Glu Arg Val Tyr Asn Val Ser Ala
                165                 170                 175

Glu Ile Met Ala Met Lys Glu Glu Gln Val His Leu Glu Gln Glu Ile
            180                 185                 190

Lys Gly Glu Val Lys Val Leu Asn Asn Ile Thr Asn Asp Leu Arg Leu
        195                 200                 205

Lys Asp Trp Glu His Ser Gln Thr Leu Arg Asn Ile Thr Leu Ile Gln
    210                 215                 220

Gly Pro Pro Gly Pro Pro Gly Glu Lys Gly Asp Arg Gly Pro Thr Gly
225                 230                 235                 240

Glu Ser Gly Pro Arg Gly Phe Pro Gly Pro Ile Gly Pro Pro Gly Leu
                245                 250                 255

Lys Gly Asp Arg Gly Ala Ile Gly Phe Pro Gly Ser Arg Gly Leu Pro
            260                 265                 270

Gly Tyr Ala Gly Arg Pro Gly Asn Ser Gly Pro Lys Gly Gln Lys Gly
        275                 280                 285

Glu Lys Gly Ser Gly Asn Thr Leu Thr Pro Phe Thr Lys Val Arg Leu
    290                 295                 300

Val Gly Gly Ser Gly Pro His Glu Gly Arg Val Glu Ile Leu His Ser
305                 310                 315                 320

Gly Gln Trp Gly Thr Ile Cys Asp Asp Arg Trp Glu Val Arg Val Gly
                325                 330                 335

Gln Val Val Cys Arg Ser Leu Gly Tyr Pro Gly Val Gln Ala Val His
            340                 345                 350

Lys Ala Ala His Phe Gly Gln Gly Thr Gly Pro Ile Trp Leu Asn Glu
        355                 360                 365
```

-continued

```
Val Phe Cys Phe Gly Arg Glu Ser Ser Ile Glu Glu Cys Lys Ile Arg
    370                 375                 380

Gln Trp Gly Thr Arg Ala Cys Ser His Ser Glu Asp Ala Gly Val Thr
385                 390                 395                 400

Cys Thr Leu


<210> SEQ ID NO 418
<211> LENGTH: 403
<212> TYPE: PRT
<213> ORGANISM: Macaca fascicularis
<220> FEATURE:
<223> OTHER INFORMATION: His-myc tagged monkey MSR1 antibody
      (extracellular domain)

<400> SEQUENCE: 418

His His His His His His Glu Gln Lys Leu Ile Ser Glu Glu Asp Leu
1               5                   10                  15

Gly Gly Glu Gln Lys Leu Ile Ser Glu Glu Asp Leu Lys Trp Glu Thr
            20                  25                  30

Lys Asn Cys Ser Ile Gly Ser Thr Asn Ala Asp Asp Ile Thr Gln Ser
        35                  40                  45

Leu Thr Gly Lys Gly Asn Asp Ser Glu Ala Glu Thr Arg Phe Gln Glu
    50                  55                  60

Val Phe Met Glu His Met Ser Asn Met Glu Lys Arg Ile Gln His Ile
65                  70                  75                  80

Ser Asp Met Glu Ala Asn Leu Ile Asp Ala Glu His Phe Gln Asn Phe
                85                  90                  95

Ser Met Thr Thr Asp Gln Arg Phe Asn Asp Ile Leu Leu Gln Leu Ser
            100                 105                 110

Thr Leu Phe Ser Ser Val Gln Gly His Gly Asn Thr Ile Asp Glu Ile
        115                 120                 125

Ser Lys Ser Leu Ile Ser Leu Asn Thr Thr Leu Leu Asp Leu Gln Leu
    130                 135                 140

Asn Ile Glu Lys Leu Asn Gly Lys Ile Gln Glu Lys Thr Phe Lys Gln
145                 150                 155                 160

Gln Glu Glu Ile Ser Lys Leu Glu Glu His Val Tyr Asn Val Ser Ala
                165                 170                 175

Glu Ile Met Ala Met Lys Glu Glu Gln Val His Leu Glu Gln Glu Ile
            180                 185                 190

Lys Gly Glu Val Lys Val Leu Asn Asn Ile Thr Asn Asp Leu Arg Leu
        195                 200                 205

Lys Asp Trp Glu His Ser Gln Thr Leu Arg Asn Ile Thr Leu Ile Gln
    210                 215                 220

Gly Pro Pro Gly Pro Pro Gly Glu Lys Gly Asp Arg Gly Pro Thr Gly
225                 230                 235                 240

Glu Ser Gly Pro Arg Gly Phe Pro Gly Pro Val Gly Pro Pro Gly Leu
                245                 250                 255

Lys Gly Asp Arg Gly Ala Ile Gly Phe Pro Gly Ser Arg Gly Leu Pro
            260                 265                 270

Gly Tyr Ala Gly Arg Pro Gly Asn Ser Gly Pro Lys Gly Gln Lys Gly
        275                 280                 285

Glu Lys Gly Ser Gly Asn Thr Leu Thr Ser Phe Lys Lys Val Arg Leu
    290                 295                 300

Val Gly Gly Ser Gly Pro His Glu Gly Arg Val Glu Ile Leu His Ser
305                 310                 315                 320
```

-continued

```
Gly Gln Trp Gly Thr Ile Cys Asp Asp Arg Trp Glu Val Arg Val Gly
                325                 330                 335

Gln Val Ile Cys Arg Ser Leu Gly Tyr Pro Gly Val Gln Ala Val His
            340                 345                 350

Lys Ala Ala His Phe Gly Gln Gly Thr Gly Pro Ile Trp Leu Asn Glu
        355                 360                 365

Val Tyr Cys Phe Gly Arg Glu Ser Ser Ile Glu Glu Cys Lys Ile Arg
    370                 375                 380

Gln Trp Gly Thr Arg Thr Cys Ser His Ser Glu Asp Ala Gly Val Thr
385                 390                 395                 400

Cys Thr Leu
```

<210> SEQ ID NO 419
<211> LENGTH: 360
<212> TYPE: DNA
<213> ORGANISM: Artificial Sequence
<220> FEATURE:
<223> OTHER INFORMATION: Synthetic

<400> SEQUENCE: 419

```
gaggtgcagc tggtggagtc tgggggaggc ctggtcaagc cggggggggtc cctgagactc      60

tcctgtgcag cctctggatt cactttcagt agatatagta tgaactgggt ccgccaggct     120

ccagggaagg ggctggagtg ggtctcatcc attagcagta gcagtagtta catatactac     180

ggagacacag tgaagggccg attcaccatc tccagagaca acgccaagaa gtcactgtat     240

ctgcaaatga acagcctgag agccgaggac acggctgtct attactgtgt gagagatcga     300

ggacagctcg tcctctactt tgactactgg ggccagggaa ccctggtcac cgtctcctca     360
```

<210> SEQ ID NO 420
<211> LENGTH: 120
<212> TYPE: PRT
<213> ORGANISM: Artificial Sequence
<220> FEATURE:
<223> OTHER INFORMATION: Synthetic

<400> SEQUENCE: 420

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Arg Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Ser Tyr Ile Tyr Tyr Gly Asp Thr Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Val Tyr Tyr Cys
                85                  90                  95

Val Arg Asp Arg Gly Gln Leu Val Leu Tyr Phe Asp Tyr Trp Gly Gln
            100                 105                 110

Gly Thr Leu Val Thr Val Ser Ser
        115                 120
```

<210> SEQ ID NO 421
<211> LENGTH: 24
<212> TYPE: DNA
<213> ORGANISM: Artificial Sequence
<220> FEATURE:

-continued

<223> OTHER INFORMATION: Synthetic

<400> SEQUENCE: 421
ggattcactt tcagtagata tagt 24

<210> SEQ ID NO 422
<211> LENGTH: 8
<212> TYPE: PRT
<213> ORGANISM: Artificial Sequence
<220> FEATURE:
<223> OTHER INFORMATION: Synthetic

<400> SEQUENCE: 422

Gly Phe Thr Phe Ser Arg Tyr Ser
1 5

<210> SEQ ID NO 423
<211> LENGTH: 24
<212> TYPE: DNA
<213> ORGANISM: Artificial Sequence
<220> FEATURE:
<223> OTHER INFORMATION: Synthetic

<400> SEQUENCE: 423
attagcagta gcagtagtta cata 24

<210> SEQ ID NO 424
<211> LENGTH: 8
<212> TYPE: PRT
<213> ORGANISM: Artificial Sequence
<220> FEATURE:
<223> OTHER INFORMATION: Synthetic

<400> SEQUENCE: 424

Ile Ser Ser Ser Ser Ser Tyr Ile
1 5

<210> SEQ ID NO 425
<211> LENGTH: 39
<212> TYPE: DNA
<213> ORGANISM: Artificial Sequence
<220> FEATURE:
<223> OTHER INFORMATION: Synthetic

<400> SEQUENCE: 425
gtgagagatc gaggacagct cgtcctctac tttgactac 39

<210> SEQ ID NO 426
<211> LENGTH: 13
<212> TYPE: PRT
<213> ORGANISM: Artificial Sequence
<220> FEATURE:
<223> OTHER INFORMATION: Synthetic

<400> SEQUENCE: 426

Val Arg Asp Arg Gly Gln Leu Val Leu Tyr Phe Asp Tyr
1 5 10

<210> SEQ ID NO 427
<211> LENGTH: 324
<212> TYPE: DNA
<213> ORGANISM: Artificial Sequence
<220> FEATURE:
<223> OTHER INFORMATION: Synthetic

<400> SEQUENCE: 427

```
gacatccaga tgacccagtc tccagcctcc ctgtctacat ctataagaga cagagtcacc     60

atcacttgcc gggcaagtct gagcattagc agctttttaa attggtttca gcagagacca    120

gggaaagccc ctaaactcct gatctatgtt gcatccaatt tgcaaagtgg ggtcccatca    180

agattcagtg acagtggatc tgggacagat ttcactctca ccatcagcag tctgcaacct    240

gaagattttg caacttacta ctgtcaacag aattacagta cccctccgat caccttcggc    300

caagggacac gactggagat taaa                                           324


<210> SEQ ID NO 428
<211> LENGTH: 108
<212> TYPE: PRT
<213> ORGANISM: Artificial Sequence
<220> FEATURE:
<223> OTHER INFORMATION: Synthetic

<400> SEQUENCE: 428

Asp Ile Gln Met Thr Gln Ser Pro Ala Ser Leu Ser Thr Ser Ile Arg
1               5                   10                  15

Asp Arg Val Thr Ile Thr Cys Arg Ala Ser Leu Ser Ile Ser Ser Phe
            20                  25                  30

Leu Asn Trp Phe Gln Gln Arg Pro Gly Lys Ala Pro Lys Leu Leu Ile
        35                  40                  45

Tyr Val Ala Ser Asn Leu Gln Ser Gly Val Pro Ser Arg Phe Ser Asp
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Asn Tyr Ser Thr Pro Pro
                85                  90                  95

Ile Thr Phe Gly Gln Gly Thr Arg Leu Glu Ile Lys
            100                 105


<210> SEQ ID NO 429
<211> LENGTH: 18
<212> TYPE: DNA
<213> ORGANISM: Artificial Sequence
<220> FEATURE:
<223> OTHER INFORMATION: Synthetic

<400> SEQUENCE: 429

ctgagcatta gcagcttt                                                   18


<210> SEQ ID NO 430
<211> LENGTH: 6
<212> TYPE: PRT
<213> ORGANISM: Artificial Sequence
<220> FEATURE:
<223> OTHER INFORMATION: Synthetic

<400> SEQUENCE: 430

Leu Ser Ile Ser Ser Phe
1               5


<210> SEQ ID NO 431
<211> LENGTH: 9
<212> TYPE: DNA
<213> ORGANISM: Artificial Sequence
<220> FEATURE:
<223> OTHER INFORMATION: Synthetic

<400> SEQUENCE: 431

gttgcatcc                                                              9
```

-continued

<210> SEQ ID NO 432
<211> LENGTH: 3
<212> TYPE: PRT
<213> ORGANISM: Artificial Sequence
<220> FEATURE:
<223> OTHER INFORMATION: Synthetic

<400> SEQUENCE: 432

Val Ala Ser
1

<210> SEQ ID NO 433
<211> LENGTH: 30
<212> TYPE: DNA
<213> ORGANISM: Artificial Sequence
<220> FEATURE:
<223> OTHER INFORMATION: Synthetic

<400> SEQUENCE: 433
caacagaatt acagtacccc tccgatcacc 30

<210> SEQ ID NO 434
<211> LENGTH: 10
<212> TYPE: PRT
<213> ORGANISM: Artificial Sequence
<220> FEATURE:
<223> OTHER INFORMATION: Synthetic

<400> SEQUENCE: 434

Gln Gln Asn Tyr Ser Thr Pro Pro Ile Thr
1 5 10

<210> SEQ ID NO 435
<211> LENGTH: 369
<212> TYPE: DNA
<213> ORGANISM: Artificial Sequence
<220> FEATURE:
<223> OTHER INFORMATION: Synthetic

<400> SEQUENCE: 435
caggtgcagc tggtggagtc tgggggaggc gtggtccagc ctgggaggtc cctgagactc 60
tcctgtgcgg gctctggatt caccttcagt agctatggct tgcactgggt ccgccaggct 120
ccaggcaagg ggctggagtg ggtggcagtt atatcatatg atggaagtaa taaatattat 180
gcagactccg tgaagggccg attcaccatc tccagagaca attccaagaa cacgctgtat 240
ctgcaaatga gcagcctgag agctgaggac acggctgtgt attactgtgc gaaagatcga 300
cttgtacgat attctgactg gccattcttt gactattggg gccagggaac cctggtcacc 360
gtctcctca 369

<210> SEQ ID NO 436
<211> LENGTH: 123
<212> TYPE: PRT
<213> ORGANISM: Artificial Sequence
<220> FEATURE:
<223> OTHER INFORMATION: Synthetic

<400> SEQUENCE: 436

Gln Val Gln Leu Val Glu Ser Gly Gly Gly Val Val Gln Pro Gly Arg
1 5 10 15

Ser Leu Arg Leu Ser Cys Ala Gly Ser Gly Phe Thr Phe Ser Ser Tyr
20 25 30

Gly Leu His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Lys Asp Arg Leu Val Arg Tyr Ser Asp Trp Pro Phe Phe Asp Tyr
            100                 105                 110

Trp Gly Gln Gly Thr Leu Val Thr Val Ser Ser
        115                 120

<210> SEQ ID NO 437
<211> LENGTH: 24
<212> TYPE: DNA
<213> ORGANISM: Artificial Sequence
<220> FEATURE:
<223> OTHER INFORMATION: Synthetic

<400> SEQUENCE: 437
ggattcacct tcagtagcta tggc                                              24

<210> SEQ ID NO 438
<211> LENGTH: 8
<212> TYPE: PRT
<213> ORGANISM: Artificial Sequence
<220> FEATURE:
<223> OTHER INFORMATION: Synthetic

<400> SEQUENCE: 438

Gly Phe Thr Phe Ser Ser Tyr Gly
1               5

<210> SEQ ID NO 439
<211> LENGTH: 24
<212> TYPE: DNA
<213> ORGANISM: Artificial Sequence
<220> FEATURE:
<223> OTHER INFORMATION: Synthetic

<400> SEQUENCE: 439
atatcatatg atggaagtaa taaa                                              24

<210> SEQ ID NO 440
<211> LENGTH: 8
<212> TYPE: PRT
<213> ORGANISM: Artificial Sequence
<220> FEATURE:
<223> OTHER INFORMATION: Synthetic

<400> SEQUENCE: 440

Ile Ser Tyr Asp Gly Ser Asn Lys
1               5

<210> SEQ ID NO 441
<211> LENGTH: 48
<212> TYPE: DNA
<213> ORGANISM: Artificial Sequence
<220> FEATURE:
<223> OTHER INFORMATION: Synthetic

<400> SEQUENCE: 441
gcgaaagatc gacttgtacg atattctgac tggccattct ttgactat                    48

<210> SEQ ID NO 442
<211> LENGTH: 16
<212> TYPE: PRT
<213> ORGANISM: Artificial Sequence
<220> FEATURE:
<223> OTHER INFORMATION: Synthetic

<400> SEQUENCE: 442

Ala Lys Asp Arg Leu Val Arg Tyr Ser Asp Trp Pro Phe Phe Asp Tyr
1 5 10 15

<210> SEQ ID NO 443
<211> LENGTH: 324
<212> TYPE: DNA
<213> ORGANISM: Artificial Sequence
<220> FEATURE:
<223> OTHER INFORMATION: Synthetic

<400> SEQUENCE: 443
gacatccaga tgacccagtc tccatcctcc ctgtctgcat ctgtaggaga cagagtcacc 60
atcacttgcc gggcaagtca aaacattacc agctatttga attgctatca gcagaaacca 120
gggaaagccc ctaaactcct gatctatgct gcatccagtt tgyaaagtgg ggtcccatca 180
aggttcagtg gcagtggatc tgggacagat ttcactctca ccatcagcag tctgcaacct 240
gaagattttg caacttacta ctgtcaacag agtttcagta gtcctccgat caccttcggc 300
caagggacac gactggagat taca 324

<210> SEQ ID NO 444
<211> LENGTH: 108
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (55)..(55)
<223> OTHER INFORMATION: Any amino acid

<400> SEQUENCE: 444

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asn Ile Thr Ser Tyr
20 25 30

Leu Asn Cys Tyr Gln Gln Lys Pro Gly Lys Ala Pro Lys Leu Leu Ile
35 40 45

Tyr Ala Ala Ser Ser Leu Xaa Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Ser Phe Ser Ser Pro Pro
85 90 95

Ile Thr Phe Gly Gln Gly Thr Arg Leu Glu Ile Thr
100 105

<210> SEQ ID NO 445
<211> LENGTH: 18
<212> TYPE: DNA
<213> ORGANISM: Artificial Sequence
<220> FEATURE:
<223> OTHER INFORMATION: Synthetic

<400> SEQUENCE: 445
caaaacatta ccagctat 18

<210> SEQ ID NO 446
<211> LENGTH: 6
<212> TYPE: PRT
<213> ORGANISM: Artificial Sequence
<220> FEATURE:
<223> OTHER INFORMATION: Synthetic

<400> SEQUENCE: 446

Gln Asn Ile Thr Ser Tyr
1 5

<210> SEQ ID NO 447
<211> LENGTH: 9
<212> TYPE: DNA
<213> ORGANISM: Artificial Sequence
<220> FEATURE:
<223> OTHER INFORMATION: Synthetic

<400> SEQUENCE: 447 gctgcatcc 9

<210> SEQ ID NO 448
<211> LENGTH: 3
<212> TYPE: PRT
<213> ORGANISM: Artificial Sequence
<220> FEATURE:
<223> OTHER INFORMATION: Synthetic

<400> SEQUENCE: 448

Ala Ala Ser
1

<210> SEQ ID NO 449
<211> LENGTH: 30
<212> TYPE: DNA
<213> ORGANISM: Artificial Sequence
<220> FEATURE:
<223> OTHER INFORMATION: Synthetic

<400> SEQUENCE: 449
caacagagtt tcagtagtcc tccgatcacc 30

<210> SEQ ID NO 450
<211> LENGTH: 10
<212> TYPE: PRT
<213> ORGANISM: Artificial Sequence
<220> FEATURE:
<223> OTHER INFORMATION: Synthetic

<400> SEQUENCE: 450

Gln Gln Ser Phe Ser Ser Pro Pro Ile Thr
1 5 10

<210> SEQ ID NO 451
<211> LENGTH: 348
<212> TYPE: DNA
<213> ORGANISM: Artificial Sequence
<220> FEATURE:
<223> OTHER INFORMATION: Synthetic

<400> SEQUENCE: 451
caggtgcagc tgcaggagtc gggcccagga ctggtgaagc cttcggagac cctgtccctc 60

-continued

```
acctgcactg tctctggtgg ctccatcagt agttactact ggagctggat ccggcagccc    120

ccagggaagg gactggaatg gattgggtac atctattaca gtgggagcgc caactacaac    180

ccctccctca agagtcgagt caccatatca gtagacacgt ccaagaacca gttctccctg    240

aagctaagct ctgtgaccgc tgcggacacg gccgtgtatt actgtgtgag agaccgggac    300

ctactccttg accactgggg ccagggaacc ctggtcaccg tctcctca                 348
```

```
<210> SEQ ID NO 452
<211> LENGTH: 116
<212> TYPE: PRT
<213> ORGANISM: Artificial Sequence
<220> FEATURE:
<223> OTHER INFORMATION: Synthetic

<400> SEQUENCE: 452

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Ala Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Val
                85                  90                  95

Arg Asp Arg Asp Leu Leu Leu Asp His Trp Gly Gln Gly Thr Leu Val
            100                 105                 110

Thr Val Ser Ser
        115
```

```
<210> SEQ ID NO 453
<211> LENGTH: 24
<212> TYPE: DNA
<213> ORGANISM: Artificial Sequence
<220> FEATURE:
<223> OTHER INFORMATION: Synthetic

<400> SEQUENCE: 453

ggtggctcca tcagtagtta ctac                                            24
```

```
<210> SEQ ID NO 454
<211> LENGTH: 8
<212> TYPE: PRT
<213> ORGANISM: Artificial Sequence
<220> FEATURE:
<223> OTHER INFORMATION: Synthetic

<400> SEQUENCE: 454

Gly Gly Ser Ile Ser Ser Tyr Tyr
1               5
```

```
<210> SEQ ID NO 455
<211> LENGTH: 21
<212> TYPE: DNA
<213> ORGANISM: Artificial Sequence
<220> FEATURE:
<223> OTHER INFORMATION: Synthetic

<400> SEQUENCE: 455
```

atctattaca gtgggagcgc c 21

<210> SEQ ID NO 456
<211> LENGTH: 7
<212> TYPE: PRT
<213> ORGANISM: Artificial Sequence
<220> FEATURE:
<223> OTHER INFORMATION: Synthetic

<400> SEQUENCE: 456

Ile Tyr Tyr Ser Gly Ser Ala
1 5

<210> SEQ ID NO 457
<211> LENGTH: 30
<212> TYPE: DNA
<213> ORGANISM: Artificial Sequence
<220> FEATURE:
<223> OTHER INFORMATION: Synthetic

<400> SEQUENCE: 457
gtgagagacc gggacctact ccttgaccac 30

<210> SEQ ID NO 458
<211> LENGTH: 10
<212> TYPE: PRT
<213> ORGANISM: Artificial Sequence
<220> FEATURE:
<223> OTHER INFORMATION: Synthetic

<400> SEQUENCE: 458

Val Arg Asp Arg Asp Leu Leu Leu Asp His
1 5 10

<210> SEQ ID NO 459
<211> LENGTH: 324
<212> TYPE: DNA
<213> ORGANISM: Artificial Sequence
<220> FEATURE:
<223> OTHER INFORMATION: Synthetic

<400> SEQUENCE: 459
gacatccaga tgacccagtc tccatcctcc ctgtctgcat ctgtaggaga cagagtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
aggttcagtg gcagtggatc tgggacagat ttcactctca ccatcagcag tctgcaacct 240
gaagattttg caacttacta ctgtcaacag agttacagta cccctccgat caccttcggc 300
caagggacac gactggagat taaa 324

<210> SEQ ID NO 460
<211> LENGTH: 108
<212> TYPE: PRT
<213> ORGANISM: Artificial Sequence
<220> FEATURE:
<223> OTHER INFORMATION: Synthetic

<400> SEQUENCE: 460

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile

```
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105


<210> SEQ ID NO 461
<211> LENGTH: 18
<212> TYPE: DNA
<213> ORGANISM: Artificial Sequence
<220> FEATURE:
<223> OTHER INFORMATION: Synthetic

<400> SEQUENCE: 461

cagagcatta gcagctat                                                18


<210> SEQ ID NO 462
<211> LENGTH: 6
<212> TYPE: PRT
<213> ORGANISM: Artificial Sequence
<220> FEATURE:
<223> OTHER INFORMATION: Synthetic

<400> SEQUENCE: 462

Gln Ser Ile Ser Ser Tyr
1               5


<210> SEQ ID NO 463
<211> LENGTH: 9
<212> TYPE: DNA
<213> ORGANISM: Artificial Sequence
<220> FEATURE:
<223> OTHER INFORMATION: Synthetic

<400> SEQUENCE: 463

gctgcatcc                                                           9


<210> SEQ ID NO 464
<211> LENGTH: 3
<212> TYPE: PRT
<213> ORGANISM: Artificial Sequence
<220> FEATURE:
<223> OTHER INFORMATION: Synthetic

<400> SEQUENCE: 464

Ala Ala Ser
1


<210> SEQ ID NO 465
<211> LENGTH: 30
<212> TYPE: DNA
<213> ORGANISM: Artificial Sequence
<220> FEATURE:
<223> OTHER INFORMATION: Synthetic

<400> SEQUENCE: 465

caacagagtt acagtacccc tccgatcacc                                   30


<210> SEQ ID NO 466
<211> LENGTH: 10
```

<212> TYPE: PRT
<213> ORGANISM: Artificial Sequence
<220> FEATURE:
<223> OTHER INFORMATION: Synthetic

<400> SEQUENCE: 466

Gln Gln Ser Tyr Ser Thr Pro Pro Ile Thr
1 5 10

<210> SEQ ID NO 467
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 467

Lys Ser Ser Gln Ser Val Leu Ser Arg Ala Asn Asn Asn Tyr Tyr Val
1 5 10 15

Ala

<210> SEQ ID NO 468
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 468

Trp Ala Ser Thr Arg Glu Phe
1 5

<210> SEQ ID NO 469
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 469

Gln Gln Tyr Tyr Thr Ser Arg Arg Thr
1 5

<210> SEQ ID NO 470
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 470

Asp Tyr Tyr Met His
1 5

<210> SEQ ID NO 471
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 471

-continued

Trp Ile Asn Pro Lys Ser Gly Gly Thr Asn Tyr Ala Gln Arg Phe Gln
1 5 10 15

Gly

<210> SEQ ID NO 472
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 472

Asp Cys Gly Ser Gly Gly Leu Arg Asp Phe
1 5 10

<210> SEQ ID NO 473
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 473

Arg Ser Asn Gln Asn Leu Leu Ser Ser Ser Asn Asn Asn Tyr Leu Ala
1 5 10 15

<210> SEQ ID NO 474
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 474

Trp Ala Ser Thr Arg Glu Ser
1 5

<210> SEQ ID NO 475
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 475

Gln Gln Tyr Tyr Ala Asn Pro Arg Thr
1 5

<210> SEQ ID NO 476
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 476

Asp Tyr Tyr Ile His
1 5

<210> SEQ ID NO 477
<211> LENGTH: 17
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 477

Trp Ile Asn Pro Asn Thr Gly Gly Thr Tyr Tyr Ala Gln Lys Phe Arg
1 5 10 15

Asp

<210> SEQ ID NO 478
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 478

Asp Cys Gly Arg Gly Gly Leu Arg Asp Ile
1 5 10

<210> SEQ ID NO 479
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 479

Lys Ser Asn Gln Asn Val Leu Ala Ser Ser Asn Asp Lys Asn Tyr Leu
1 5 10 15

Ala

<210> SEQ ID NO 480
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 480

Trp Ala Ser Ile Arg Glu Ser
1 5

<210> SEQ ID NO 481
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 481

Gln Gln Tyr Tyr Thr Asn Pro Arg Thr
1 5

<210> SEQ ID NO 482
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 482

Asp Tyr Tyr Ile His
1 5

<210> SEQ ID NO 483
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 483

Trp Ile Asn Pro Asn Thr Gly Gly Thr Asn Tyr Ala Gln Lys Phe Gln
1 5 10 15

Gly

<210> SEQ ID NO 484
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 484

Asp Cys Gly Asn Ala Gly Leu Arg Asp Ile
1 5 10

<210> SEQ ID NO 485
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 485

Lys Ser Ser Gln Asn Val Leu Tyr Ser Ser Asn Asn Lys Asn Tyr Leu
1 5 10 15

Ala

<210> SEQ ID NO 486
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 486

Trp Ala Ser Thr Arg Glu Ser
1 5

<210> SEQ ID NO 487
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 487

Gln Gln Tyr Tyr Thr Ser Pro Pro Tyr Thr
1 5 10

<210> SEQ ID NO 488
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 488

```
Ser Tyr Trp Ile Gly
1               5
```

<210> SEQ ID NO 489
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 489

```
Ile Ile His Pro Gly Asp Ser Lys Thr Arg Tyr Ser Pro Ser Phe Gln
1               5                   10                  15

Gly
```

<210> SEQ ID NO 490
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 490

```
Leu Tyr Cys Ser Gly Gly Ser Cys Tyr Ser Asp Arg Ala Phe Ser Ser
1               5                   10                  15

Leu Gly Ala Gly Gly Tyr Tyr Tyr Tyr Gly Met Gly Val
            20                  25
```

<210> SEQ ID NO 491
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 491

```
Asp Ile Gln Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Ser Arg
            20                  25                  30

Ala Asn Asn Asn Tyr Tyr Val Ala Trp Tyr Gln His Lys Pro Gly Gln
        35                  40                  45

Pro Pro Lys Leu Leu Ile Tyr Trp Ala Ser Thr Arg Glu Phe Gly Val
    50                  55                  60

Pro Asp Arg Phe Ser Gly Ser Gly Ser Gly Thr Asp Phe Thr Leu Thr
65                  70                  75                  80

Ile Asn Ser Leu Gln Ala Glu Asp Val Ala Val Tyr Tyr Cys Gln Gln
                85                  90                  95

Tyr Tyr Thr Ser Arg Arg Thr Phe Gly Gln Gly Thr Lys Val Glu Ile
            100                 105                 110
```

Lys

<210> SEQ ID NO 492
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 492

```
Gln Val Gln Leu Val Gln Ser Gly Ala Glu Val Arg Lys Pro Gly Ala
1               5                   10                  15

Ser Val Lys Val Ser Cys Lys Ala Ser Gly Tyr Ser Phe Thr Asp Tyr
            20                  25                  30

Tyr Met His Trp Val Arg Gln Ala Pro Gly Gln Gly Leu Glu Trp Met
        35                  40                  45

Gly Trp Ile Asn Pro Lys Ser Gly Gly Thr Asn Tyr Ala Gln Arg Phe
    50                  55                  60

Gln Gly Arg Val Thr Met Thr Gly Asp Thr Ser Ile Ser Ala Ala Tyr
65                  70                  75                  80

Met Asp Leu Ala Ser Leu Thr Ser Asp Asp Thr Ala Val Tyr Tyr Cys
                85                  90                  95

Val Lys Asp Cys Gly Ser Gly Gly Leu Arg Asp Phe Trp Gly Gln Gly
            100                 105                 110

Thr Thr Val Thr Val Ser Ser
        115
```

<210> SEQ ID NO 493
<211> LENGTH: 112
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 493

```
Asp Ile Gln Met Thr Gln Ser Pro Asp Ser Leu Ser Val Ser Leu Gly
1               5                   10                  15

Glu Arg Ala Thr Ile Asn Cys Arg Ser Asn Gln Asn Leu Leu Ser Ser
            20                  25                  30

Ser Asn Asn Asn Tyr Leu Ala Trp Tyr Gln Gln Lys Pro Gly Gln Pro
        35                  40                  45

Leu Lys Leu Leu Ile Tyr Trp Ala Ser Thr Arg Glu Ser Gly Val Pro
    50                  55                  60

Asp Arg Phe Ser Gly Ser Gly Ser Gly Thr Asp Phe Thr Leu Thr Ile
65                  70                  75                  80

Ser Ser Leu Gln Ala Glu Asp Val Ala Val Tyr Tyr Cys Gln Gln Tyr
                85                  90                  95

Tyr Ala Asn Pro Arg Thr Phe Gly Gln Gly Thr Lys Val Glu Ile Lys
            100                 105                 110
```

<210> SEQ ID NO 494
<211> LENGTH: 119
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 494

```
Gln Val Gln Leu Gln Gln Ser Arg Val Glu Val Lys Arg Pro Gly Thr
1               5                   10                  15

Ser Val Lys Val Ser Cys Lys Thr Ser Gly Tyr Thr Phe Ser Asp Tyr
            20                  25                  30

Tyr Ile His Trp Val Arg Leu Ala Pro Gly Gln Gly Leu Glu Leu Met
        35                  40                  45

Gly Trp Ile Asn Pro Asn Thr Gly Gly Thr Tyr Tyr Ala Gln Lys Phe
    50                  55                  60

Arg Asp Arg Val Thr Met Thr Arg Asp Thr Ser Ile Ala Thr Ala Tyr
65                  70                  75                  80

Leu Glu Met Ser Ser Leu Thr Ser Asp Asp Thr Ala Val Tyr Tyr Cys
                85                  90                  95

Ala Lys Asp Cys Gly Arg Gly Gly Leu Arg Asp Ile Trp Gly Pro Gly
            100                 105                 110

Thr Met Val Thr Val Ser Ser
        115


<210> SEQ ID NO 495
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 495

Glu Ile Val Leu Thr Gln Ser Pro Asp Ser Leu Ala Val Ser Leu Gly
1               5                   10                  15

Glu Arg Ala Thr Ile Asn Cys Lys Ser Asn Gln Asn Val Leu Ala Ser
            20                  25                  30

Ser Asn Asp Lys Asn Tyr Leu Ala Trp Phe Gln His Lys Pro Gly Gln
        35                  40                  45

Pro Leu Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Arg Ala Glu Asp Val Ala Val Tyr Tyr Cys Gln Gln
                85                  90                  95

Tyr Tyr Thr Asn Pro Arg Thr Phe Gly Gln Gly Thr Lys Val Glu Phe
            100                 105                 110

Asn


<210> SEQ ID NO 496
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 496

Glu Val Gln Leu Val Gln Ser Gly Ala Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Tyr Ile His Trp Val Arg Leu Ala Pro Gly Gln Gly Leu Glu Leu Met
        35                  40                  45
```

Gly Trp Ile Asn Pro Asn Thr Gly Gly Thr Asn Tyr Ala Gln Lys Phe
50 55 60

Gln Gly Arg Val Thr Met Thr Arg Asp Thr Ser Ile Ala Thr Ala Tyr
65 70 75 80

Met Glu Leu Ser Ser Leu Thr Ser Asp Asp Thr Ala Val Tyr Tyr Cys
85 90 95

Ala Lys Asp Cys Gly Asn Ala Gly Leu Arg Asp Ile Trp Gly Gln Gly
100 105 110

Thr Thr Val Thr Val Ser Ser
115

<210> SEQ ID NO 497
<211> LENGTH: 114
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 497

Asp Ile Gln Leu Thr Gln Ser Pro Asp Ser Leu Ala Val Ser Leu Gly
1 5 10 15

Glu Arg Ala Thr Ile Asn Cys Lys Ser Ser Gln Asn Val Leu Tyr Ser
20 25 30

Ser Asn Asn Lys Asn Tyr Leu Ala Trp Tyr Gln Gln Lys Pro Gly Gln
35 40 45

Pro Pro Lys Leu Leu Ile Tyr Trp Ala Ser Thr Arg Glu Ser Gly Val
50 55 60

Pro Asp Arg Phe Ser Gly Ser Gly Ser Gly Thr Asp Phe Thr Leu Thr
65 70 75 80

Ile Ser Ser Leu Gln Ala Glu Asp Val Ala Val Tyr Tyr Cys Gln Gln
85 90 95

Tyr Tyr Thr Ser Pro Pro Tyr Thr Phe Gly Gln Gly Thr Lys Leu Glu
100 105 110

Ile Glu

<210> SEQ ID NO 498
<211> LENGTH: 138
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 498

Glu Val Gln Leu Val Gln Ser Gly Ala Glu Val Lys Lys Pro Gly Glu
1 5 10 15

Ser Leu Lys Ile Ser Cys Lys Gly Ser Gly Tyr Ser Phe Thr Ser Tyr
20 25 30

Trp Ile Gly Trp Val Arg Gln Met Pro Gly Lys Gly Leu Glu Trp Met
35 40 45

Gly Ile Ile His Pro Gly Asp Ser Lys Thr Arg Tyr Ser Pro Ser Phe
50 55 60

Gln Gly Gln Val Thr Ile Ser Ala Asp Lys Ser Ile Ser Thr Ala Tyr
65 70 75 80

Leu Gln Trp Asn Ser Leu Lys Ala Ser Asp Thr Ala Met Tyr Tyr Cys
85 90 95

Ala Arg Leu Tyr Cys Ser Gly Gly Ser Cys Tyr Ser Asp Arg Ala Phe 100 105 110

Ser Ser Leu Gly Ala Gly Gly Tyr Tyr Tyr Tyr Gly Met Gly Val Trp
115 120 125

Gly Gln Gly Thr Thr Val Thr Val Ser Ser
130 135

<210> SEQ ID NO 499
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 499

Arg Ala Ser Gln Thr Ile Ser Gly Trp Leu Ala
1 5 10

<210> SEQ ID NO 500
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 500

Lys Ala Ser Thr Leu Glu Ser
1 5

<210> SEQ ID NO 501
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 501

Gln Gln Tyr Lys Ser Tyr Ser Phe Asn
1 5

<210> SEQ ID NO 502
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 502

Ser Tyr Asp Ile Asn
1 5

<210> SEQ ID NO 503
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 503

Trp Met Asn Ala Asn Ser Gly Asn Thr Gly Tyr Ala Gln Lys Phe Gln
1 5 10 15

Gly

<210> SEQ ID NO 504
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 504

Ser Ser Ile Leu Val Arg Gly Ala Leu Gly Arg Tyr Phe Asp Leu
1 5 10 15

<210> SEQ ID NO 505
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 505

Arg Ala Ser Gln Thr Ile Ser Gly Trp Leu Ala
1 5 10

<210> SEQ ID NO 506
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 506

Lys Ala Ser Thr Leu Glu Ser
1 5

<210> SEQ ID NO 507
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 507

Gln Gln Tyr Lys Ser Tyr Ser Phe Asn
1 5

<210> SEQ ID NO 508
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 508

Ser Tyr Asp Ile Asn
1 5

<210> SEQ ID NO 509
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 509

Trp Met Asn Ala Asn Ser Gly Asn Thr Gly Tyr Ala Gln Lys Phe Gln
1               5                   10                  15

Gly

<210> SEQ ID NO 510
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 510

Ser Ser Ile Leu Val Arg Gly Ala Leu Gly Arg Tyr Phe Asp Leu
1               5                   10                  15

<210> SEQ ID NO 511
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 511

Arg Ala Ser Gln Phe Val Ser Arg Thr Ser Leu Ala
1               5                   10

<210> SEQ ID NO 512
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 512

Glu Thr Ser Ser Arg Ala Thr
1               5

<210> SEQ ID NO 513
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 513

His Lys Tyr Gly Ser Gly Pro Arg Thr
1               5

<210> SEQ ID NO 514
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 514

Asn Tyr Asp Phe Ile
1               5

```
<210> SEQ ID NO 515
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 515

Trp Met Asn Pro Asn Ser Tyr Asn Thr Gly Tyr Gly Gln Lys Phe Gln
1               5                   10                  15

Gly


<210> SEQ ID NO 516
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 516

Ala Val Arg Gly Gln Leu Leu Ser Glu Tyr
1               5                   10


<210> SEQ ID NO 517
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 517

Arg Ala Ser Gln Ser Val Ser Ser Ser Tyr Leu Ala
1               5                   10


<210> SEQ ID NO 518
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 518

Asp Ala Ser Ser Arg Ala Thr
1               5


<210> SEQ ID NO 519
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 519

Gln Lys Tyr Gly Ser Thr Pro Arg Pro
1               5


<210> SEQ ID NO 520
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 520

Ser Tyr Asp Ile Asn
1               5

<210> SEQ ID NO 521
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 521

Trp Met Asn Pro Asn Ser Gly Asn Thr Asn Tyr Ala Gln Arg Phe Gln
1               5                   10                  15

Gly

<210> SEQ ID NO 522
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 522

Glu Arg Trp Ser Lys Asp Thr Gly His Tyr Tyr Tyr Tyr Gly Met Asp
1               5                   10                  15

Val

<210> SEQ ID NO 523
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 523

Arg Ala Ser Leu Asp Ile Thr Asn His Leu Ala
1               5                   10

<210> SEQ ID NO 524
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 524

Glu Ala Ser Ile Leu Gln Ser
1               5

<210> SEQ ID NO 525
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 525

Glu Lys Cys Asn Ser Thr Pro Arg Thr
1               5

<210> SEQ ID NO 526
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 526

Asn Tyr Asp Ile Asn
1               5

<210> SEQ ID NO 527
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 527

Trp Met Asn Pro Ser Ser Gly Arg Thr Gly Tyr Ala Pro Lys Phe Arg
1               5                   10                  15

Gly

<210> SEQ ID NO 528
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 528

Gly Gly Gly Tyr Tyr Asp Ser Ser Gly Asn Tyr His Ile Ser Gly Leu
1               5                   10                  15

Asp Val

<210> SEQ ID NO 529
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 529

Arg Ala Ser Gln Ser Val Gly Ala Ile Tyr Leu Ala
1               5                   10

<210> SEQ ID NO 530
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 530

Gly Val Ser Asn Arg Ala Thr
1               5

<210> SEQ ID NO 531
<211> LENGTH: 10
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 531

Gln Leu Tyr Thr Ser Ser Arg Ala Leu Thr
1 5 10

<210> SEQ ID NO 532
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 532

Ala Tyr Ala Met Asn
1 5

<210> SEQ ID NO 533
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 533

Ser Ile Thr Lys Asn Ser Asp Ser Leu Tyr Tyr Ala Asp Ser Val Lys
1 5 10 15

Gly

<210> SEQ ID NO 534
<211> LENGTH: 10
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 534

Leu Ala Ala Arg Ile Met Ala Thr Asp Tyr
1 5 10

<210> SEQ ID NO 535
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 535

Arg Ala Ser Gln Gly Ile Arg Asn Gly Leu Gly
1 5 10

<210> SEQ ID NO 536
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 536

```
Pro Ala Ser Thr Leu Glu Ser
1               5


<210> SEQ ID NO 537
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 537

Leu Gln Asp His Asn Tyr Pro Pro Thr
1               5


<210> SEQ ID NO 538
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 538

Tyr Tyr Ser Met Ile
1               5


<210> SEQ ID NO 539
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 539

Ser Ile Asp Ser Ser Ser Arg Tyr Leu Tyr Tyr Ala Asp Ser Val Lys
1               5                   10                  15

Gly


<210> SEQ ID NO 540
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 540

Asp Gly Asp Asp Ile Leu Ser Val Tyr Arg Gly Ser Gly Arg Pro Phe
1               5                   10                  15

Asp Tyr


<210> SEQ ID NO 541
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 541

Arg Ala Ser Gln Gly Ile Arg Asn Gly Leu Gly
1               5                   10


<210> SEQ ID NO 542
```

<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 542

Pro Ala Ser Thr Leu Glu Ser
1 5

<210> SEQ ID NO 543
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 543

Leu Gln Asp His Asn Tyr Pro Pro Ser
1 5

<210> SEQ ID NO 544
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 544

Tyr Tyr Ser Met Ile
1 5

<210> SEQ ID NO 545
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 545

Ser Ile Asp Ser Ser Ser Arg Tyr Arg Tyr Tyr Thr Asp Ser Val Lys
1 5 10 15

Gly

<210> SEQ ID NO 546
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 546

Asp Gly Asp Asp Ile Leu Ser Val Tyr Gln Gly Ser Gly Arg Pro Phe
1 5 10 15

Asp Tyr

<210> SEQ ID NO 547
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 547

Arg Ala Ser Gln Ser Val Arg Thr Asn Val Ala
1 5 10

<210> SEQ ID NO 548
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 548

Gly Ala Ser Thr Arg Ala Ser
1 5

<210> SEQ ID NO 549
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 549

Leu Gln Tyr Asn Thr Trp Pro Arg Thr
1 5

<210> SEQ ID NO 550
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 550

Thr Asn Asp Met Ser
1 5

<210> SEQ ID NO 551
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 551

Thr Ile Ile Gly Ile Asp Asp Thr Thr His Tyr Ala Asp Ser Val Arg
1 5 10 15

Gly

<210> SEQ ID NO 552
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 552

Asn Ser Gly Ile Tyr Ser Phe
1 5

<210> SEQ ID NO 553
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 553

Arg Ala Ser Gln Asp Ile Gly Ser Ser Leu Ala
1 5 10

<210> SEQ ID NO 554
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 554

Ala Thr Ser Thr Leu Gln Ser
1 5

<210> SEQ ID NO 555
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 555

Gln Gln Leu Asn Asn Tyr Val His Ser
1 5

<210> SEQ ID NO 556
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 556

Asp Tyr Ala Met Gly
1 5

<210> SEQ ID NO 557
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 557

Val Val Thr Gly His Ser Tyr Arg Thr His Tyr Ala Asp Ser Val Lys
1 5 10 15

Gly

<210> SEQ ID NO 558
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 558

Arg Ile Trp Ser Tyr Gly Asp Asp Ser Phe Asp Val
1 5 10

<210> SEQ ID NO 559
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 559

Arg Ala Ser Gln Ser Ile Gly Asp Arg Leu Ala
1 5 10

<210> SEQ ID NO 560
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 560

Trp Ala Ser Asn Leu Glu Gly
1 5

<210> SEQ ID NO 561
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 561

Gln Gln Tyr Lys Ser Gln Trp Ser
1 5

<210> SEQ ID NO 562
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 562

Ser Tyr Ala Met Asn
1 5

<210> SEQ ID NO 563
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 563

Tyr Ile Ser Ser Ile Glu Thr Ile Tyr Tyr Ala Asp Ser Val Lys Gly
1 5 10 15

<210> SEQ ID NO 564

<211> LENGTH: 13
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 564

Asp Arg Leu Val Asp Val Pro Leu Ser Ser Pro Asn Ser
1 5 10

<210> SEQ ID NO 565
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 565

Lys Ser Ser Gln Ser Ile Phe Arg Thr Ser Arg Asn Lys Asn Leu Leu
1 5 10 15

Asn

<210> SEQ ID NO 566
<211> LENGTH: 7
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 566

Trp Ala Ser Thr Arg Lys Ser
1 5

<210> SEQ ID NO 567
<211> LENGTH: 9
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 567

Gln Gln Tyr Phe Ser Pro Pro Tyr Thr
1 5

<210> SEQ ID NO 568
<211> LENGTH: 5
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 568

Ser Phe Trp Met His
1 5

<210> SEQ ID NO 569
<211> LENGTH: 17
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 569

Phe Thr Asn Asn Glu Gly Thr Thr Thr Ala Tyr Ala Asp Ser Val Arg
1 5 10 15

Gly

<210> SEQ ID NO 570
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 570

Gly Asp Gly Gly Leu Asp Asp
1 5

<210> SEQ ID NO 571
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 571

Arg Ala Ser Gln Phe Thr Asn His Tyr Leu Asn
1 5 10

<210> SEQ ID NO 572
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 572

Val Ala Ser Asn Leu Gln Ser
1 5

<210> SEQ ID NO 573
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 573

Gln Gln Ser Tyr Arg Thr Pro Tyr Thr
1 5

<210> SEQ ID NO 574
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 574

Ser Gly Tyr Tyr Asn
1 5

<210> SEQ ID NO 575

<211> LENGTH: 16
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 575

Tyr Ile Leu Ser Gly Ala His Thr Asp Ile Lys Ala Ser Leu Gly Ser
1 5 10 15

<210> SEQ ID NO 576
<211> LENGTH: 11
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 576

Ser Gly Val Tyr Ser Lys Tyr Ser Leu Asp Val
1 5 10

<210> SEQ ID NO 577
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 577

Asp Ile Val Met Thr Gln Ser Pro Ser Ile Leu Ser Ala Ser Val Gly
1 5 10 15

Asp Arg Val Thr Ile Thr Cys Arg Ala Ser Gln Thr Ile Ser Gly Trp
20 25 30

Leu Ala Trp Tyr Gln Gln Lys Pro Ala Glu Ala Pro Lys Leu Leu Ile
35 40 45

Tyr Lys Ala Ser Thr Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Gly Ile Tyr Tyr Cys Gln Gln Tyr Lys Ser Tyr Ser Phe
85 90 95

Asn Phe Gly Gln Gly Thr Lys Val Glu Ile Lys
100 105

<210> SEQ ID NO 578
<211> LENGTH: 124
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (1)..(1)
<223> OTHER INFORMATION: Gln or Glu
<220> FEATURE:
<221> NAME/KEY: MOD_RES
<222> LOCATION: (2)..(2)
<223> OTHER INFORMATION: Met, Ile or Val

<400> SEQUENCE: 578

Xaa Xaa Gln Leu Val Gln Ser Gly Ala Glu Val Lys Lys Pro Gly Ala
1 5 10 15

Ser Val Lys Val Ser Cys Glu Ala Ser Gly Tyr Thr Leu Thr Ser Tyr
20 25 30

Asp Ile Asn Trp Val Arg Gln Ala Thr Gly Gln Gly Pro Glu Trp Met
35 40 45

Gly Trp Met Asn Ala Asn Ser Gly Asn Thr Gly Tyr Ala Gln Lys Phe
50 55 60

Gln Gly Arg Val Thr Leu Thr Gly Asp Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Ser Ser Ile Leu Val Arg Gly Ala Leu Gly Arg Tyr Phe Asp
100 105 110

Leu Trp Gly Arg Gly Thr Leu Val Thr Val Ser Ser
115 120

<210> SEQ ID NO 579
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 579

Asp Ile Val Met Thr Gln Ser Pro Ser Ile Leu Ser Ala Ser Val Gly
1 5 10 15

Asp Arg Val Thr Ile Thr Cys Arg Ala Ser Gln Thr Ile Ser Gly Trp
20 25 30

Leu Ala Trp Tyr Gln Gln Lys Pro Ala Glu Ala Pro Lys Leu Leu Ile
35 40 45

Tyr Lys Ala Ser Thr Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Gly Ile Tyr Tyr Cys Gln Gln Tyr Lys Ser Tyr Ser Phe
85 90 95

Asn Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 580
<211> LENGTH: 453
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 580

Gln Met Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380
```

-continued

```
Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 581
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 581

Asp Ile Val Met Thr Gln Ser Pro Ser Ile Leu Ser Ala Ser Val Gly
1               5                   10                  15

Asp Arg Val Thr Ile Thr Cys Arg Ala Ser Gln Thr Ile Ser Gly Trp
            20                  25                  30

Leu Ala Trp Tyr Gln Gln Lys Pro Ala Glu Ala Pro Lys Leu Leu Ile
        35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Gly Ile Tyr Tyr Cys Gln Gln Tyr Lys Ser Tyr Ser Phe
                85                  90                  95

Asn Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Cys Thr Lys Ser
        195                 200                 205

Phe Asn Arg Gly Glu Cys
    210


<210> SEQ ID NO 582
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (2)..(2)
```

<223> OTHER INFORMATION: Met, Ile or Val

<400> SEQUENCE: 582

```
Glu Xaa Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400
```

```
Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 583
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (2)..(2)
<223> OTHER INFORMATION: Met, Ile or Val

<400> SEQUENCE: 583

```
Glu Xaa Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Cys Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
```

```
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 584
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 584

Gly Glu Gly Gly Leu Asp Asp
1               5


<210> SEQ ID NO 585
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 585

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Ile Phe Arg Thr
            20                  25                  30

Ser Arg Asn Lys Asn Leu Leu Asn Trp Tyr Gln Gln Arg Pro Gly Gln
        35                  40                  45

Pro Pro Arg Leu Leu Ile His Trp Ala Ser Thr Arg Lys Ser Gly Val
    50                  55                  60

Pro Asp Arg Phe Ser Gly Ser Gly Phe Gly Thr Asp Phe Thr Leu Thr
65                  70                  75                  80

Ile Thr Ser Leu Gln Ala Glu Asp Val Ala Ile Tyr Tyr Cys Gln Gln
                85                  90                  95

Tyr Phe Ser Pro Pro Tyr Thr Phe Gly Gln Gly Thr Lys Leu Glu Ile
```

100 105 110

Lys

<210> SEQ ID NO 586
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 586

Glu Val Gln Leu Val Glu Ser Gly Gly Gly Leu Val Gln Pro Gly Gly
1 5 10 15

Ser Leu Arg Leu Ser Cys Ser Ala Ser Gly Phe Ser Phe Asn Ser Phe
20 25 30

Trp Met His Trp Val Arg Gln Val Pro Gly Lys Gly Leu Val Trp Ile
35 40 45

Ser Phe Thr Asn Asn Glu Gly Thr Thr Thr Ala Tyr Ala Asp Ser Val
50 55 60

Arg Gly Arg Phe Ile Ile Ser Arg Asp Asn Ala Lys Asn Thr Leu Tyr
65 70 75 80

Leu Glu Met Asn Asn Leu Arg Gly Glu Asp Thr Ala Val Tyr Tyr Cys
85 90 95

Ala Arg Gly Asp Gly Gly Leu Asp Asp Trp Gly Gln Gly Thr Leu Val
100 105 110

Thr Val Ser Ser
115

<210> SEQ ID NO 587
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 587

Asp Ile Gln Leu Thr Gln Ser Pro Asp Ser Leu Ala Val Ser Leu Gly
1 5 10 15

Glu Arg Ala Thr Ile Asn Cys Lys Ser Ser Gln Ser Ile Phe Arg Thr
20 25 30

Ser Arg Asn Lys Asn Leu Leu Asn Trp Tyr Gln Gln Arg Pro Gly Gln
35 40 45

Pro Pro Arg Leu Leu Ile His Trp Ala Ser Thr Arg Lys Ser Gly Val
50 55 60

Pro Asp Arg Phe Ser Gly Ser Gly Phe Gly Thr Asp Phe Thr Leu Thr
65 70 75 80

Ile Thr Ser Leu Gln Ala Glu Asp Val Ala Ile Tyr Tyr Cys Gln Gln
85 90 95

Tyr Phe Ser Pro Pro Tyr Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

Glu Gln Leu Lys Ser Gly Thr Ala Ser Val Val Cys Leu Leu Asn Asn
130 135 140

Phe Tyr Pro Arg Glu Ala Lys Val Gln Trp Lys Val Asp Asn Ala Leu
145 150 155 160

```
Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220


<210> SEQ ID NO 588
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 588

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Glu Gly Gly Leu Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
```

```
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445


<210> SEQ ID NO 589
<211> LENGTH: 220
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 589

Asp Ile Gln Leu Thr Gln Ser Pro Asp Ser Leu Ala Val Ser Leu Gly
1               5                   10                  15

Glu Arg Ala Thr Ile Asn Cys Lys Ser Ser Gln Ser Ile Phe Arg Thr
            20                  25                  30

Ser Arg Asn Lys Asn Leu Leu Asn Trp Tyr Gln Gln Arg Pro Gly Gln
        35                  40                  45

Pro Pro Arg Leu Leu Ile His Trp Ala Ser Thr Arg Lys Ser Gly Val
    50                  55                  60

Pro Asp Arg Phe Ser Gly Ser Gly Phe Gly Thr Asp Phe Thr Leu Thr
65                  70                  75                  80

Ile Thr Ser Leu Gln Ala Glu Asp Val Ala Ile Tyr Tyr Cys Gln Gln
                85                  90                  95

Tyr Phe Ser Pro Pro Tyr Thr Phe Gly Gln Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205
```

```
Ser Pro Val Thr Lys Ser Phe Asn Arg Gly Glu Cys
    210                 215                 220


<210> SEQ ID NO 590
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 590

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Glu Gly Gly Leu Asp Asp Trp Gly Gln Gly Thr Leu Val
            100                 105                 110

Thr Val Ser Ser Cys Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350
```

Arg Glu Glu Met Thr Lys Asn Gln Val Ser Leu Thr Cys Leu Val Lys
355 360 365

Gly Phe Tyr Pro Ser Asp Ile Ala Val Glu Trp Glu Ser Asn Gly Gln
370 375 380

Pro Glu Asn Asn Tyr Lys Thr Thr Pro Pro Val Leu Asp Ser Asp Gly
385 390 395 400

Ser Phe Phe Leu Tyr Ser Lys Leu Thr Val Asp Lys Ser Arg Trp Gln
405 410 415

Gln Gly Asn Val Phe Ser Cys Ser Val Met His Glu Ala Leu His Asn
420 425 430

His Tyr Thr Gln Lys Ser Leu Ser Leu Ser Pro Gly
435 440

<210> SEQ ID NO 591
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 591

Gln Met Gln Leu Gln Glu Ser Gly Pro Gly Leu Val Lys Pro Ser Glu
1 5 10 15

Thr Leu Ser Leu Ser Cys Ser Val Ser Gly Ala Ser Ala Ser Ser Gly
20 25 30

Tyr Tyr Asn Trp Val Arg Gln Thr Pro Gly Gly Gly Leu Glu Trp Ile
35 40 45

Ala Tyr Ile Leu Ser Gly Ala His Thr Asp Ile Lys Ala Ser Leu Gly
50 55 60

Ser Arg Val Ala Val Ser Val Asp Thr Ser Lys Asn Gln Val Thr Leu
65 70 75 80

Arg Leu Ser Ser Val Thr Ala Ala Asp Thr Ala Thr Tyr Tyr Cys Ala
85 90 95

Arg Ser Gly Val Tyr Ser Lys Tyr Ser Leu Asp Val Trp Gly Gln Gly
100 105 110

Thr Thr Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro
195 200 205

Ser Asn Thr Lys Val Asp Lys Lys Val Glu Pro Lys Ser Cys Asp Lys
210 215 220

Thr His Thr Cys Pro Pro Cys Pro Ala Pro Glu Leu Leu Gly Gly Pro
225 230 235 240

Ser Val Phe Leu Phe Pro Pro Lys Pro Lys Asp Thr Leu Met Ile Ser
245 250 255

Arg Thr Pro Glu Val Thr Cys Val Val Val Asp Val Ser His Glu Asp

```
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 592
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 592

Glu Val Gln Leu Val Gln Ser Gly Gly Asp Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Gly Trp Val Arg Gln Ala Pro Gly Lys Gly Leu Glu Trp Leu
        35                  40                  45

Ser Val Val Thr Gly His Ser Tyr Arg Thr His Tyr Ala Asp Ser Val
    50                  55                  60

Lys Gly Arg Phe Ile Ile Ser Arg Asp Asn Ser Lys Asn Thr Leu Phe
65                  70                  75                  80

Leu Gln Met Asn Ser Leu Arg Ala Glu Asp Thr Ala Val Tyr Tyr Cys
                85                  90                  95

Ala Lys Arg Ile Trp Ser Tyr Gly Asp Asp Ser Phe Asp Val Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

-continued

```
Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450


<210> SEQ ID NO 593
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 593

Glu Val Gln Leu Val Gln Ser Gly Gly Gly Val Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Tyr Ile Ser Ser Ile Glu Thr Ile Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80
```

```
Gln Met Asn Ser Leu Arg Asp Glu Asp Thr Ala Val Tyr Tyr Cys Ala
                85                  90                  95

Arg Asp Arg Leu Val Asp Val Pro Leu Ser Ser Pro Asn Ser Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly
    450
```

<210> SEQ ID NO 594
<211> LENGTH: 445
<212> TYPE: PRT
<213> ORGANISM: Artificial Sequence
<220> FEATURE:

<223> OTHER INFORMATION: Description of Artificial Sequence: Synthetic polypeptide

<400> SEQUENCE: 594

Glu Val Gln Leu Val Glu Ser Gly Gly Gly Leu Val Gln Pro Gly Gly
1 5 10 15

Ser Leu Arg Leu Ser Cys Ser Ala Ser Gly Phe Ser Phe Asn Ser Phe
20 25 30

Trp Met His Trp Val Arg Gln Val Pro Gly Lys Gly Leu Val Trp Ile
35 40 45

Ser Phe Thr Asn Asn Glu Gly Thr Thr Thr Ala Tyr Ala Asp Ser Val
50 55 60

Arg Gly Arg Phe Ile Ile Ser Arg Asp Asn Ala Lys Asn Thr Leu Tyr
65 70 75 80

Leu Glu Met Asn Asn Leu Arg Gly Glu Asp Thr Ala Val Tyr Tyr Cys
85 90 95

Ala Arg Gly Asp Gly Gly Leu Asp Asp Trp Gly Gln Gly Thr Leu Val
100 105 110

Thr Val Ser Ser Ala Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly
435 440 445

<210> SEQ ID NO 595
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 595

Glu Met Gln Leu Val Gln Ser Gly Ala Glu Val Lys Lys Pro Gly Ala
1 5 10 15

Ser Val Lys Val Ser Cys Glu Ala Ser Gly Tyr Thr Leu Thr Ser Tyr
20 25 30

Asp Ile Asn Trp Val Arg Gln Ala Thr Gly Gln Gly Pro Glu Trp Met
35 40 45

Gly Trp Met Asn Ala Asn Ser Gly Asn Thr Gly Tyr Ala Gln Lys Phe
50 55 60

Gln Gly Arg Val Thr Leu Thr Gly Asp Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Ser Ser Ile Leu Val Arg Gly Ala Leu Gly Arg Tyr Phe Asp
100 105 110

Leu Trp Gly Arg Gly Thr Leu Val Thr Val Ser Ser Cys Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp

```
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 596
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 596

Glu Met Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205
```

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Glu Glu Met Thr Lys Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

Leu Thr Val Asp Lys Ser Arg Trp Gln Gln Gly Asn Val Phe Ser Cys
420 425 430

Ser Val Met His Glu Ala Leu His Asn His Tyr Thr Gln Lys Ser Leu
435 440 445

Ser Leu Ser Pro Gly
450

<210> SEQ ID NO 597
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 597

Glu Ile Gln Leu Val Gln Ser Gly Ala Glu Val Lys Lys Pro Gly Ala
1 5 10 15

Ser Val Lys Val Ser Cys Glu Ala Ser Gly Tyr Thr Leu Thr Ser Tyr
20 25 30

Asp Ile Asn Trp Val Arg Gln Ala Thr Gly Gln Gly Pro Glu Trp Met
35 40 45

Gly Trp Met Asn Ala Asn Ser Gly Asn Thr Gly Tyr Ala Gln Lys Phe
50 55 60

Gln Gly Arg Val Thr Leu Thr Gly Asp Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Ser Ser Ile Leu Val Arg Gly Ala Leu Gly Arg Tyr Phe Asp
100 105 110

```
Leu Trp Gly Arg Gly Thr Leu Val Thr Val Ser Ser Cys Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450
```

<210> SEQ ID NO 598
<211> LENGTH: 453
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 598

```
Glu Ile Gln Leu Val Gln Ser Gly Ala Glu Val Lys Lys Pro Gly Ala
```

-continued

```
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430
```

```
Ser Val Met His Glu Ala Leu His Asn His Tyr Thr Gln Lys Ser Leu
        435                 440                 445

Ser Leu Ser Pro Gly
    450


<210> SEQ ID NO 599
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 599

Glu Val Gln Leu Val Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Ile Leu Val Arg Gly Ala Leu Gly Arg Tyr Phe Asp
            100                 105                 110

Leu Trp Gly Arg Gly Thr Leu Val Thr Val Ser Ser Cys Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
```

325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Glu Glu Met Thr Lys Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

Leu Thr Val Asp Lys Ser Arg Trp Gln Gln Gly Asn Val Phe Ser Cys
420 425 430

Ser Val Met His Glu Ala Leu His Asn His Tyr Thr Gln Lys Ser Leu
435 440 445

Ser Leu Ser Pro Gly
450

<210> SEQ ID NO 600
<211> LENGTH: 453
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 600

Glu Val Gln Leu Val Gln Ser Gly Ala Glu Val Lys Lys Pro Gly Ala
1 5 10 15

Ser Val Lys Val Ser Cys Glu Ala Ser Gly Tyr Thr Leu Thr Ser Tyr
20 25 30

Asp Ile Asn Trp Val Arg Gln Ala Thr Gly Gln Gly Pro Glu Trp Met
35 40 45

Gly Trp Met Asn Ala Asn Ser Gly Asn Thr Gly Tyr Ala Gln Lys Phe
50 55 60

Gln Gly Arg Val Thr Leu Thr Gly Asp Thr Ser Ile Ser Thr Ala Tyr
65 70 75 80

Met Glu Leu Ser Ser Leu Arg Ser Glu Asp Thr Ala Val Tyr Tyr Cys
85 90 95

Ala Arg Ser Ser Ile Leu Val Arg Gly Ala Leu Gly Arg Tyr Phe Asp
100 105 110

Leu Trp Gly Arg Gly Thr Leu Val Thr Val Ser Ser Ala Ser Thr Lys
115 120 125

Gly Pro Ser Val Phe Pro Leu Ala Pro Ser Ser Lys Ser Thr Ser Gly
130 135 140

Gly Thr Ala Ala Leu Gly Cys Leu Val Lys Asp Tyr Phe Pro Glu Pro
145 150 155 160

Val Thr Val Ser Trp Asn Ser Gly Ala Leu Thr Ser Gly Val His Thr
165 170 175

Phe Pro Ala Val Leu Gln Ser Ser Gly Leu Tyr Ser Leu Ser Ser Val
180 185 190

Val Thr Val Pro Ser Ser Ser Leu Gly Thr Gln Thr Tyr Ile Cys Asn
195 200 205

Val Asn His Lys Pro Ser Asn Thr Lys Val Asp Lys Lys Val Glu Pro
210 215 220

Lys Ser Cys Asp Lys Thr His Thr Cys Pro Pro Cys Pro Ala Pro Glu
225 230 235 240

Leu Leu Gly Gly Pro Ser Val Phe Leu Phe Pro Pro Lys Pro Lys Asp
245 250 255

Thr Leu Met Ile Ser Arg Thr Pro Glu Val Thr Cys Val Val Val Asp
260 265 270

Val Ser His Glu Asp Pro Glu Val Lys Phe Asn Trp Tyr Val Asp Gly
275 280 285

Val Glu Val His Asn Ala Lys Thr Lys Pro Arg Glu Glu Gln Tyr Asn
290 295 300

Ser Thr Tyr Arg Val Val Ser Val Leu Thr Val Leu His Gln Asp Trp
305 310 315 320

Leu Asn Gly Lys Glu Tyr Lys Cys Lys Val Ser Asn Lys Ala Leu Pro
325 330 335

Ala Pro Ile Glu Lys Thr Ile Ser Lys Ala Lys Gly Gln Pro Arg Glu
340 345 350

Pro Gln Val Tyr Thr Leu Pro Pro Ser Arg Glu Glu Met Thr Lys Asn
355 360 365

Gln Val Ser Leu Thr Cys Leu Val Lys Gly Phe Tyr Pro Ser Asp Ile
370 375 380

Ala Val Glu Trp Glu Ser Asn Gly Gln Pro Glu Asn Asn Tyr Lys Thr
385 390 395 400

Thr Pro Pro Val Leu Asp Ser Asp Gly Ser Phe Phe Leu Tyr Ser Lys
405 410 415

Leu Thr Val Asp Lys Ser Arg Trp Gln Gln Gly Asn Val Phe Ser Cys
420 425 430

Ser Val Met His Glu Ala Leu His Asn His Tyr Thr Gln Lys Ser Leu
435 440 445

Ser Leu Ser Pro Gly
450

<210> SEQ ID NO 601
<211> LENGTH: 220
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 601

Asp Ile Gln Leu Thr Gln Ser Pro Asp Ser Leu Ala Val Ser Leu Gly
1 5 10 15

Glu Arg Ala Thr Ile Asn Cys Lys Ser Ser Gln Ser Ile Phe Arg Thr
20 25 30

Ser Arg Asn Lys Asn Leu Leu Asn Trp Tyr Gln Gln Arg Pro Gly Gln
35 40 45

Pro Pro Arg Leu Leu Ile His Trp Ala Ser Thr Arg Lys Ser Gly Val
50 55 60

Pro Asp Arg Phe Ser Gly Ser Gly Phe Gly Thr Asp Phe Thr Leu Thr
65 70 75 80

Ile Thr Ser Leu Gln Ala Glu Asp Val Ala Ile Tyr Tyr Cys Gln Gln
85 90 95

Tyr Phe Ser Pro Pro Tyr Thr Phe Gly Gln Gly Thr Lys Leu Glu Ile
100 105 110

Lys Arg Thr Val Ala Ala Pro Ser Val Phe Ile Phe Pro Pro Ser Asp
115 120 125

```
Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Cys Thr Lys Ser Phe Asn Arg Gly Glu Cys
    210                 215                 220


<210> SEQ ID NO 602
<211> LENGTH: 445
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 602

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Asp Gly Gly Leu Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
```

260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly
435 440 445

<210> SEQ ID NO 603
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 603

Glu Val Gln Leu Val Glu Ser Gly Gly Gly Leu Val Gln Pro Gly Gly
1 5 10 15

Ser Leu Arg Leu Ser Cys Ser Ala Ser Gly Phe Ser Phe Asn Ser Phe
20 25 30

Trp Met His Trp Val Arg Gln Val Pro Gly Lys Gly Leu Val Trp Ile
35 40 45

Ser Phe Thr Asn Asn Glu Gly Thr Thr Thr Ala Tyr Ala Asp Ser Val
50 55 60

Arg Gly Arg Phe Ile Ile Ser Arg Asp Asn Ala Lys Asn Thr Leu Tyr
65 70 75 80

Leu Glu Met Asn Asn Leu Arg Gly Glu Asp Thr Ala Val Tyr Tyr Cys
85 90 95

Ala Arg Gly Glu Gly Gly Leu Asp Asp Trp Gly Gln Gly Thr Leu Val
100 105 110

Thr Val Ser Ser Cys Ser Thr Lys Gly Pro Ser Val Phe Pro Leu Ala
115 120 125

Pro Ser Ser Lys Ser Thr Ser Gly Gly Thr Ala Ala Leu Gly Cys Leu
130 135 140

Val Lys Asp Tyr Phe Pro Glu Pro Val Thr Val Ser Trp Asn Ser Gly
145 150 155 160

Ala Leu Thr Ser Gly Val His Thr Phe Pro Ala Val Leu Gln Ser Ser
165 170 175

Gly Leu Tyr Ser Leu Ser Ser Val Val Thr Val Pro Ser Ser Ser Leu
180 185 190

Gly Thr Gln Thr Tyr Ile Cys Asn Val Asn His Lys Pro Ser Asn Thr
195 200 205

Lys Val Asp Lys Lys Val Glu Pro Lys Ser Cys Asp Lys Thr His Thr
210 215 220

Cys Pro Pro Cys Pro Ala Pro Glu Leu Leu Gly Gly Pro Ser Val Phe
225 230 235 240

Leu Phe Pro Pro Lys Pro Lys Asp Thr Leu Met Ile Ser Arg Thr Pro
245 250 255

Glu Val Thr Cys Val Val Val Asp Val Ser His Glu Asp Pro Glu Val
260 265 270

Lys Phe Asn Trp Tyr Val Asp Gly Val Glu Val His Asn Ala Lys Thr
275 280 285

Lys Pro Arg Glu Glu Gln Tyr Asn Ser Thr Tyr Arg Val Val Ser Val
290 295 300

Leu Thr Val Leu His Gln Asp Trp Leu Asn Gly Lys Glu Tyr Lys Cys
305 310 315 320

Lys Val Ser Asn Lys Ala Leu Pro Ala Pro Ile Glu Lys Thr Ile Ser
325 330 335

Lys Ala Lys Gly Gln Pro Arg Glu Pro Gln Val Tyr Thr Leu Pro Pro
340 345 350

Ser Arg Glu Glu Met Thr Lys Asn Gln Val Ser Leu Thr Cys Leu Val
355 360 365

Lys Gly Phe Tyr Pro Ser Asp Ile Ala Val Glu Trp Glu Ser Asn Gly
370 375 380

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly
435 440 445

<210> SEQ ID NO 604
<211> LENGTH: 330
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 604

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

```
Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

<210> SEQ ID NO 605
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 605

```
Cys Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
```

```
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330


<210> SEQ ID NO 606
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 606

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105


<210> SEQ ID NO 607
<211> LENGTH: 107
<212> TYPE: PRT
<213> ORGANISM: Artificial Sequence
<220> FEATURE:
```

<223> OTHER INFORMATION: Description of Artificial Sequence: Synthetic polypeptide

<400> SEQUENCE: 607

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Cys Thr Lys Ser Phe Asn Arg Gly Glu Cys
            100                 105
```

<210> SEQ ID NO 608
<211> LENGTH: 116
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 608

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Glu Gly Gly Leu Asp Asp Trp Gly Gln Gly Thr Leu Val
            100                 105                 110

Thr Val Ser Ser
        115
```

<210> SEQ ID NO 609
<211> LENGTH: 445
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 609

```
Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Ser Phe Asn Ser Phe
            20                  25                  30

Trp Met His Trp Val Arg Gln Val Pro Gly Lys Gly Leu Val Trp Ile
```

```
        35                  40                  45

Ser Phe Thr Asn Asn Glu Gly Thr Thr Thr Ala Tyr Ala Asp Ser Val
    50                  55                  60

Arg Gly Arg Phe Ile Ile Ser Arg Asp Asn Ala Lys Asn Thr Leu Tyr
65                  70                  75                  80

Leu Glu Met Asn Asn Leu Arg Gly Glu Asp Thr Ala Val Tyr Tyr Cys
                85                  90                  95

Ala Arg Gly Glu Gly Gly Leu Asp Asp Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly
        435                 440                 445
```

<210> SEQ ID NO 610

<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 610

Asp Ile Gln Leu Thr Gln Ser Pro Ser Ile Leu Ser Ala Ser Val Gly
1 5 10 15

Asp Arg Val Thr Ile Thr Cys Arg Ala Ser Gln Thr Ile Ser Gly Trp
20 25 30

Leu Ala Trp Tyr Gln Gln Lys Pro Ala Glu Ala Pro Lys Leu Leu Ile
35 40 45

Tyr Lys Ala Ser Thr Leu Glu Ser Gly Val Pro Ser Arg Phe Ser Gly
50 55 60

Ser Gly Ser Gly Thr Glu Phe Thr Leu Thr Ile Ser Ser Leu Gln Pro
65 70 75 80

Asp Asp Phe Gly Ile Tyr Tyr Cys Gln Gln Tyr Lys Ser Tyr Ser Phe
85 90 95

Asn Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 611
<211> LENGTH: 215
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 611

Glu Ile Val Leu Thr Gln Ser Pro Gly Thr Leu Ser Leu Ser Pro Gly
1 5 10 15

Glu Arg Ala Thr Leu Ser Cys Arg Ala Ser Gln Phe Val Ser Arg Thr
20 25 30

Ser Leu Ala Trp Phe Gln Gln Lys Pro Gly Gln Pro Pro Arg Leu Leu
35 40 45

Ile Tyr Glu Thr Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Met Tyr Tyr Cys His Lys Tyr Gly Ser Gly Pro
85 90 95

Arg Thr Phe Gly Gln Gly Thr Lys Val Glu Val Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 612
<211> LENGTH: 215
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 612

Glu Thr Thr Leu Thr Gln Ser Pro Gly Thr Leu Ser Leu Ser Pro Gly
1 5 10 15

Glu Arg Ala Thr Leu Ser Cys Arg Ala Ser Gln Ser Val Ser Ser Ser
20 25 30

Tyr Leu Ala Trp Tyr Gln Gln Lys Pro Gly Gln Ala Pro Lys Val Leu
35 40 45

Ile Tyr Asp Ala Ser Ser Arg Ala Thr Gly Ile Pro Asp Arg Phe Ser
50 55 60

Gly Ser Gly Ser Gly Thr Asp Phe Thr Leu Thr Ile Ser Arg Leu Glu
65 70 75 80

Pro Glu Asp Phe Ala Val Tyr Tyr Cys Gln Lys Tyr Gly Ser Thr Pro
85 90 95

Arg Pro Phe Gly Gln Gly Thr Lys Val Glu Ile Lys Arg Thr Val Ala
100 105 110

Ala Pro Ser Val Phe Ile Phe Pro Pro Ser Asp Glu Gln Leu Lys Ser
115 120 125

Gly Thr Ala Ser Val Val Cys Leu Leu Asn Asn Phe Tyr Pro Arg Glu
130 135 140

Ala Lys Val Gln Trp Lys Val Asp Asn Ala Leu Gln Ser Gly Asn Ser
145 150 155 160

Gln Glu Ser Val Thr Glu Gln Asp Ser Lys Asp Ser Thr Tyr Ser Leu
165 170 175

Ser Ser Thr Leu Thr Leu Ser Lys Ala Asp Tyr Glu Lys His Lys Val
180 185 190

Tyr Ala Cys Glu Val Thr His Gln Gly Leu Ser Ser Pro Val Thr Lys
195 200 205

Ser Phe Asn Arg Gly Glu Cys
210 215

<210> SEQ ID NO 613
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 613

Asp Val Val Met Thr Gln Ser Ser Ser Ser Leu Ser Ala Ser Val Gly
1 5 10 15

Asp Arg Val Thr Ile Thr Cys Arg Ala Ser Leu Asp Ile Thr Asn His
20 25 30

Leu Ala Trp Tyr Gln Gln Lys Pro Gly Glu Leu Pro Lys Leu Leu Ile
35 40 45

Tyr Glu Ala Ser Ile Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Val Ala Thr Tyr Tyr Cys Glu Lys Cys Asn Ser Thr Pro Arg
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 614
<211> LENGTH: 216
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 614

Glu Ile Val Met Thr Gln Ser Pro Gly Thr Leu Ser Leu Ser Pro Gly
1 5 10 15

Glu Arg Ala Thr Leu Ser Cys Arg Ala Ser Gln Ser Val Gly Ala Ile
20 25 30

Tyr Leu Ala Trp Tyr Gln Gln Glu Pro Gly Arg Ala Pro Thr Leu Leu
35 40 45

Phe Tyr Gly Val Ser Asn Arg Ala Thr Gly Ile Pro Asp Arg Phe Ser
50 55 60

Cys Ser Gly Ser Gly Thr Asp Phe Thr Leu Thr Ile Ser Arg Leu Glu
65 70 75 80

Pro Glu Asp Phe Ala Val Tyr Tyr Cys Gln Leu Tyr Thr Ser Ser Arg

```
                85                  90                  95

Ala Leu Thr Phe Gly Gly Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 615
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 615

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Gly
            20                  25                  30

Leu Gly Trp Tyr Gln Gln Thr Pro Gly Lys Ala Pro Lys Leu Leu Ile
        35                  40                  45

Tyr Pro Ala Ser Thr Leu Glu Ser Gly Val Pro Ser Arg Phe Ser Gly
    50                  55                  60

Ser Gly Ser Asp Arg Asp Phe Thr Leu Thr Ile Thr Ser Leu Gln Pro
65                  70                  75                  80

Glu Asp Phe Ala Thr Tyr Tyr Cys Leu Gln Asp His Asn Tyr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 616
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 616

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Gly
            20                  25                  30

Leu Gly Trp Tyr Gln Gln Ile Pro Gly Lys Ala Pro Lys Leu Leu Ile
        35                  40                  45

Tyr Pro Ala Ser Thr Leu Glu Ser Gly Val Pro Ser Arg Phe Ser Gly
    50                  55                  60

Ser Gly Ser Asp Arg Asp Phe Thr Leu Thr Ile Thr Ser Leu Gln Pro
65                  70                  75                  80

Glu Asp Phe Ala Thr Tyr Tyr Cys Leu Gln Asp His Asn Tyr Pro Pro
                85                  90                  95

Ser Phe Ser Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 617
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 617

```
Asp Ile Gln Met Thr Gln Ser Pro Ala Thr Leu Ser Val Ser Pro Gly
1               5                   10                  15

Glu Thr Val Thr Leu Ser Cys Arg Ala Ser Gln Ser Val Arg Thr Asn
            20                  25                  30

Val Ala Trp Tyr Arg His Lys Ala Gly Gln Ala Pro Met Ile Leu Val
        35                  40                  45

Ser Gly Ala Ser Thr Arg Ala Ser Gly Ala Pro Ala Arg Phe Ser Gly
    50                  55                  60

Ser Gly Tyr Gly Thr Glu Phe Thr Leu Thr Ile Thr Ser Leu Gln Ser
65                  70                  75                  80
```

```
Glu Asp Phe Ala Val Tyr Tyr Cys Leu Gln Tyr Asn Thr Trp Pro Arg
                85                  90                  95

Thr Phe Gly Gln Gly Thr Lys Val Glu Val Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 618
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 618

Asp Val Val Met Thr Gln Ser Pro Ser Phe Leu Ser Ala Ser Val Gly
1               5                   10                  15

Asp Arg Val Thr Leu Thr Cys Arg Ala Ser Gln Asp Ile Gly Ser Ser
            20                  25                  30

Leu Ala Trp Tyr Gln Gln Arg Pro Gly Lys Ala Pro Asn Leu Leu Ile
        35                  40                  45

Tyr Ala Thr Ser Thr Leu Gln Ser Gly Val Pro Ser Arg Phe Ser Gly
    50                  55                  60

Ser Gly Phe Gly Thr Glu Phe Thr Leu Thr Ile Ser Thr Leu Gln Pro
65                  70                  75                  80

Glu Asp Phe Ala Thr Tyr Tyr Cys Gln Gln Leu Asn Asn Tyr Val His
                85                  90                  95

Ser Phe Gly Pro Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 619
<211> LENGTH: 213
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 619

Glu Thr Thr Leu Thr Gln Ser Pro Ser Thr Leu Ser Ala Ser Val Gly
1 5 10 15

Asp Arg Val Thr Ile Thr Cys Arg Ala Ser Gln Ser Ile Gly Asp Arg
20 25 30

Leu Ala Trp Tyr Gln Gln Lys Pro Gly Lys Ala Pro Lys Val Leu Ile
35 40 45

Tyr Trp Ala Ser Asn Leu Glu Gly Gly Val Pro Ser Arg Phe Ser Gly
50 55 60

Thr Gly Ser Gly Thr Glu Phe Ala Leu Thr Ile Ser Gly Leu Gln Pro
65 70 75 80

Asp Asp Leu Ala Thr Tyr Tyr Cys Gln Gln Tyr Lys Ser Gln Trp Ser
85 90 95

Phe Gly Gln Gly Thr Lys Val Glu Ile Lys Arg Thr Val Ala Ala Pro
100 105 110

Ser Val Phe Ile Phe Pro Pro Ser Asp Glu Gln Leu Lys Ser Gly Thr
115 120 125

Ala Ser Val Val Cys Leu Leu Asn Asn Phe Tyr Pro Arg Glu Ala Lys
130 135 140

Val Gln Trp Lys Val Asp Asn Ala Leu Gln Ser Gly Asn Ser Gln Glu
145 150 155 160

Ser Val Thr Glu Gln Asp Ser Lys Asp Ser Thr Tyr Ser Leu Ser Ser
165 170 175

Thr Leu Thr Leu Ser Lys Ala Asp Tyr Glu Lys His Lys Val Tyr Ala
180 185 190

Cys Glu Val Thr His Gln Gly Leu Ser Ser Pro Val Thr Lys Ser Phe
195 200 205

Asn Arg Gly Glu Cys
210

<210> SEQ ID NO 620
<211> LENGTH: 214
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 620

Asp Ile Gln Leu Thr Gln Ser Pro Ser Ser Leu Ser Ala Ser Val Gly
1 5 10 15

Asp Arg Val Thr Ile Thr Cys Arg Ala Ser Gln Phe Thr Asn His Tyr
20 25 30

Leu Asn Trp Tyr Gln His Lys Pro Gly Arg Ala Pro Lys Leu Met Ile
35 40 45

Ser Val Ala Ser Asn Leu Gln Ser Gly Val Pro Ser Arg Phe Thr Gly
50 55 60

Ser Glu Ser Gly Thr Asp Phe Thr Leu Thr Ile Ser Gly Leu Gln Pro
65 70 75 80

```
Glu Asp Phe Ala Thr Tyr Tyr Cys Gln Gln Ser Tyr Arg Thr Pro Tyr
                85                  90                  95

Thr Phe Gly Gln Gly Ser Arg Leu Glu Met Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 621
<211> LENGTH: 453
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 621

Gln Val Gln Leu Gln Gln Ser Gly Ala Glu Val Lys Lys Pro Gly Ala
1               5                   10                  15

Ser Val Lys Val Ser Cys Glu Ala Ser Gly Tyr Thr Leu Thr Ser Tyr
            20                  25                  30

Asp Ile Asn Trp Val Arg Gln Ala Thr Gly Gln Gly Pro Glu Trp Met
        35                  40                  45

Gly Trp Met Asn Ala Asn Ser Gly Asn Thr Gly Tyr Ala Gln Lys Phe
    50                  55                  60

Gln Gly Arg Val Thr Leu Thr Gly Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Gly Ser Ser Ile Leu Val Arg Gly Ala Leu Gly Arg Tyr Phe Asp
            100                 105                 110

Leu Trp Gly Arg Gly Thr Leu Val Thr Val Ser Ser Ala Ser Thr Lys
        115                 120                 125

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
```

```
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Glu Glu Met Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly
    450


<210> SEQ ID NO 622
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 622

Glu Val Gln Leu Val Gln Ser Gly Ala Glu Val Val Lys Pro Gly Ala
1               5                   10                  15

Ser Leu Lys Val Ser Cys Lys Ala Ser Gly Tyr Ile Ile Ile Asn Tyr
            20                  25                  30

Asp Phe Ile Trp Val Arg Gln Ala Thr Gly Gln Gly Pro Glu Trp Met
        35                  40                  45

Gly Trp Met Asn Pro Asn Ser Tyr Asn Thr Gly Tyr Gly Gln Lys Phe
    50                  55                  60

Gln Gly Arg Val Thr Met Thr Trp Asp Ser Ser Met Ser Thr Ala Tyr
65                  70                  75                  80

Met Glu Leu Ser Ser Leu Thr Ser Ala Asp Thr Ala Val Tyr Tyr Cys
                85                  90                  95

Ala Arg Ala Val Arg Gly Gln Leu Leu Ser Glu Tyr Trp Gly Gln Gly
            100                 105                 110
```

```
Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445
```

<210> SEQ ID NO 623
<211> LENGTH: 455
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 623

```
Gln Val Gln Leu Gln Gln Ser Gly Ala Glu Val Lys Lys Pro Gly Ala
1               5                   10                  15

Ser Val Lys Val Ser Cys Arg Ala Ser Gly Tyr Thr Phe Thr Ser Tyr
            20                  25                  30
```

-continued

```
Asp Ile Asn Trp Val Arg Gln Ala Pro Gly Gln Gly Leu Glu Trp Met
        35                  40                  45

Gly Trp Met Asn Pro Asn Ser Gly Asn Thr Asn Tyr Ala Gln Arg Phe
    50                  55                  60

Gln Gly Arg Leu Thr Met Thr Lys Asn Thr Ser Ile Asn Thr Ala Tyr
65                  70                  75                  80

Met Glu Leu Ser Ser Leu Arg Ser Glu Asp Thr Ala Val Tyr Tyr Cys
                85                  90                  95

Ala Thr Glu Arg Trp Ser Lys Asp Thr Gly His Tyr Tyr Tyr Tyr Gly
            100                 105                 110

Met Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445
```

Ser Leu Ser Leu Ser Pro Gly
450 455

<210> SEQ ID NO 624
<211> LENGTH: 456
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 624

Gln Val Gln Leu Gln Gln Ser Gly Ala Glu Val Lys Arg Pro Gly Ala
1 5 10 15

Ser Val Lys Val Ser Cys Glu Ala Ser Gly Tyr Thr Val Ser Asn Tyr
20 25 30

Asp Ile Asn Trp Val Arg Gln Ala Thr Gly Gln Gly Leu Glu Trp Met
35 40 45

Gly Trp Met Asn Pro Ser Ser Gly Arg Thr Gly Tyr Ala Pro Lys Phe
50 55 60

Arg Gly Arg Val Thr Met Thr Arg Ser Thr Ser Ile Ser Thr Ala Tyr
65 70 75 80

Met Glu Leu Ser Ser Leu Thr Ser Glu Asp Thr Ala Val Tyr Tyr Cys
85 90 95

Ala Arg Gly Gly Gly Tyr Tyr Asp Ser Ser Gly Asn Tyr His Ile Ser
100 105 110

Gly Leu Asp Val Trp Gly Gln Gly Thr Thr Val Thr Val Ser Ser Ala
115 120 125

Ser Thr Lys Gly Pro Ser Val Phe Pro Leu Ala Pro Ser Ser Lys Ser
130 135 140

Thr Ser Gly Gly Thr Ala Ala Leu Gly Cys Leu Val Lys Asp Tyr Phe
145 150 155 160

Pro Glu Pro Val Thr Val Ser Trp Asn Ser Gly Ala Leu Thr Ser Gly
165 170 175

Val His Thr Phe Pro Ala Val Leu Gln Ser Ser Gly Leu Tyr Ser Leu
180 185 190

Ser Ser Val Val Thr Val Pro Ser Ser Ser Leu Gly Thr Gln Thr Tyr
195 200 205

Ile Cys Asn Val Asn His Lys Pro Ser Asn Thr Lys Val Asp Lys Lys
210 215 220

Val Glu Pro Lys Ser Cys Asp Lys Thr His Thr Cys Pro Pro Cys Pro
225 230 235 240

Ala Pro Glu Leu Leu Gly Gly Pro Ser Val Phe Leu Phe Pro Pro Lys
245 250 255

Pro Lys Asp Thr Leu Met Ile Ser Arg Thr Pro Glu Val Thr Cys Val
260 265 270

Val Val Asp Val Ser His Glu Asp Pro Glu Val Lys Phe Asn Trp Tyr
275 280 285

Val Asp Gly Val Glu Val His Asn Ala Lys Thr Lys Pro Arg Glu Glu
290 295 300

Gln Tyr Asn Ser Thr Tyr Arg Val Val Ser Val Leu Thr Val Leu His
305 310 315 320

Gln Asp Trp Leu Asn Gly Lys Glu Tyr Lys Cys Lys Val Ser Asn Lys
325 330 335

Ala Leu Pro Ala Pro Ile Glu Lys Thr Ile Ser Lys Ala Lys Gly Gln
340 345 350

```
Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455


<210> SEQ ID NO 625
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 625

Gln Ile Thr Leu Lys Glu Ser Gly Gly Gly Leu Ile Lys Pro Gly Gly
1               5                   10                  15

Ser Leu Arg Leu Ser Cys Ala Thr Ser Gly Phe Pro Phe Ser Ala Tyr
            20                  25                  30

Ala Met Asn Trp Val Arg Gln Ala Pro Gly Arg Gly Leu Glu Trp Val
        35                  40                  45

Ser Ser Ile Thr Lys Asn Ser Asp Ser Leu Tyr Tyr Ala Asp Ser Val
    50                  55                  60

Lys Gly Arg Phe Thr Ile Ser Arg Asp Asn Ala Gly Asn Ser Leu Tyr
65                  70                  75                  80

Leu Gln Met Asn Ser Leu Arg Val Glu Asp Thr Ala Val Tyr Tyr Cys
                85                  90                  95

Ala Thr Leu Ala Ala Arg Ile Met Ala Thr Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
```

```
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 626
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 626

Glu Val Gln Leu Val Gln Ser Gly Gly Gly Leu Val Lys Pro Gly Glu
1               5                   10                  15

Ser Leu Arg Leu Ser Cys Ala Ala Ser Gly Phe Ser Phe Asp Tyr Tyr
            20                  25                  30

Ser Met Ile Trp Val Arg Gln Ala Pro Gly Lys Gly Leu Glu Trp Val
        35                  40                  45

Ser Ser Ile Asp Ser Ser Ser Arg Tyr Leu Tyr Tyr Ala Asp Ser Val
    50                  55                  60

Lys Gly Arg Phe Thr Ile Ser Arg Asp Asn Ala Gln Asn Ser Leu Tyr
65                  70                  75                  80

Leu Gln Met Ser Gly Leu Arg Val Glu Asp Thr Ala Val Tyr Tyr Cys
                85                  90                  95

Ala Arg Asp Gly Asp Asp Ile Leu Ser Val Tyr Arg Gly Ser Gly Arg
            100                 105                 110

Pro Phe Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160
```

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455

<210> SEQ ID NO 627
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 627

Gln Val Gln Leu Gln Gln Ser Gly Gly Gly Leu Val Asn Pro Gly Glu
1               5                   10                  15

Ser Leu Arg Leu Ser Cys Ala Ala Ser Gly Phe Ser Phe Asn Tyr Tyr
            20                  25                  30

Ser Met Ile Trp Val Arg Gln Ala Pro Gly Lys Gly Leu Glu Trp Val
        35                  40                  45

Ser Ser Ile Asp Ser Ser Ser Arg Tyr Arg Tyr Tyr Thr Asp Ser Val
    50                  55                  60

```
Lys Gly Arg Phe Thr Ile Ser Arg Asp Asn Ala Gln Asn Ser Leu Tyr
65                  70                  75                  80

Leu Gln Met Ser Ala Leu Arg Val Glu Asp Thr Ala Val Tyr Tyr Cys
                85                  90                  95

Ala Arg Asp Gly Asp Asp Ile Leu Ser Val Tyr Gln Gly Ser Gly Arg
            100                 105                 110

Pro Phe Asp Tyr Trp Gly Gln Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190

Ser Ser Val Val Thr Val Pro Ser Ser Ser Leu Gly Thr Gln Thr Tyr
        195                 200                 205

Ile Cys Asn Val Asn His Lys Pro Ser Asn Thr Lys Val Asp Lys Lys
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly
    450                 455
```

<210> SEQ ID NO 628
<211> LENGTH: 445

<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 628

```
Gln Val Gln Leu Gln Gln Ser Gly Gly Gly Leu Glu Gln Pro Gly Gly
1               5                   10                  15

Ser Leu Arg Ile Ser Cys Ala Ala Ser Gly Phe Thr Phe Asn Thr Asn
            20                  25                  30

Asp Met Ser Trp Val Arg Gln Ala Pro Gly Lys Gly Leu Gln Trp Val
        35                  40                  45

Ser Thr Ile Ile Gly Ile Asp Asp Thr Thr His Tyr Ala Asp Ser Val
    50                  55                  60

Arg Gly Arg Phe Thr Val Ser Arg Asp Thr Ser Lys Asn Met Val Tyr
65                  70                  75                  80

Leu Gln Met Asn Ser Leu Arg Val Glu Asp Thr Ala Leu Tyr Tyr Cys
                85                  90                  95

Val Lys Asn Ser Gly Ile Tyr Ser Phe Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Leu Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Pro Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380
```

-continued

Gln Pro Glu Asn Asn Tyr Lys Thr Thr Pro Pro Val Leu Asp Ser Asp
385 390 395 400

Gly Ser Phe Phe Leu Tyr Ser Lys Leu Thr Val Asp Lys Ser Arg Trp
405 410 415

Gln Gln Gly Asn Val Phe Ser Cys Ser Val Met His Glu Ala Leu His
420 425 430

Asn His Tyr Thr Gln Lys Ser Leu Ser Leu Ser Pro Gly
435 440 445

<210> SEQ ID NO 629
<211> LENGTH: 351
<212> TYPE: DNA
<213> ORGANISM: Artificial Sequence
<220> FEATURE:
<223> OTHER INFORMATION: synthetic

<400> SEQUENCE: 629
gaggtgcagc tggtggagtc tgggggaggc ttggtacagc ctggggggtc cctgacactc 60
tcctgtacag cctctggatt ctcctttagc agctatgtca tgagctgggt ccgccagtct 120
cctgggaagg ggctggagtg ggtctcagct attggtggta gtggtactag tacatactac 180
agagactccg tgaagggccg gttcaccatc tccagagaca attccaagaa cacactgaat 240
ctgcaaatga gcagcctgag agccgaggac acggccgtat attactgtgc gagagatggg 300
ctggggcacc gggactactg gggccaggga accctggtca ccgtctcctc a 351

<210> SEQ ID NO 630
<211> LENGTH: 117
<212> TYPE: PRT
<213> ORGANISM: Artificial Sequence
<220> FEATURE:
<223> OTHER INFORMATION: synthetic

<400> SEQUENCE: 630

Glu Val Gln Leu Val Glu Ser Gly Gly Gly Leu Val Gln Pro Gly Gly
1 5 10 15

Ser Leu Thr Leu Ser Cys Thr Ala Ser Gly Phe Ser Phe Ser Ser Tyr
20 25 30

Val Met Ser Trp Val Arg Gln Ser Pro Gly Lys Gly Leu Glu Trp Val
35 40 45

Ser Ala Ile Gly Gly Ser Gly Thr Ser Thr Tyr Tyr Arg Asp Ser Val
50 55 60

Lys Gly Arg Phe Thr Ile Ser Arg Asp Asn Ser Lys Asn Thr Leu Asn
65 70 75 80

Leu Gln Met Ser Ser Leu Arg Ala Glu Asp Thr Ala Val Tyr Tyr Cys
85 90 95

Ala Arg Asp Gly Leu Gly His Arg Asp Tyr Trp Gly Gln Gly Thr Leu
100 105 110

Val Thr Val Ser Ser
115

<210> SEQ ID NO 631
<211> LENGTH: 24
<212> TYPE: DNA
<213> ORGANISM: Artificial Sequence
<220> FEATURE:
<223> OTHER INFORMATION: synthetic

<400> SEQUENCE: 631
ggattctcct ttagcagcta tgtc 24

<210> SEQ ID NO 632
<211> LENGTH: 8
<212> TYPE: PRT
<213> ORGANISM: Artificial Sequence
<220> FEATURE:
<223> OTHER INFORMATION: synthetic

<400> SEQUENCE: 632

Gly Phe Ser Phe Ser Ser Tyr Val
1 5

<210> SEQ ID NO 633
<211> LENGTH: 24
<212> TYPE: DNA
<213> ORGANISM: Artificial Sequence
<220> FEATURE:
<223> OTHER INFORMATION: synthetic

<400> SEQUENCE: 633
attggtggta gtggtactag taca 24

<210> SEQ ID NO 634
<211> LENGTH: 8
<212> TYPE: PRT
<213> ORGANISM: Artificial Sequence
<220> FEATURE:
<223> OTHER INFORMATION: synthetic

<400> SEQUENCE: 634

Ile Gly Gly Ser Gly Thr Ser Thr
1 5

<210> SEQ ID NO 635
<211> LENGTH: 30
<212> TYPE: DNA
<213> ORGANISM: Artificial Sequence
<220> FEATURE:
<223> OTHER INFORMATION: synthetic

<400> SEQUENCE: 635
gcgagagatg ggctggggca ccgggactac 30

<210> SEQ ID NO 636
<211> LENGTH: 10
<212> TYPE: PRT
<213> ORGANISM: Artificial Sequence
<220> FEATURE:
<223> OTHER INFORMATION: synthetic

<400> SEQUENCE: 636

Ala Arg Asp Gly Leu Gly His Arg Asp Tyr
1 5 10

<210> SEQ ID NO 637
<211> LENGTH: 321
<212> TYPE: DNA
<213> ORGANISM: Artificial Sequence
<220> FEATURE:
<223> OTHER INFORMATION: synthetic

<400> SEQUENCE: 637
gacatccaga tgacccagtc tccatcttcc gtgtctgcat ctgtaggaga cagagtcacc 60
atcacttgtc gggcgagtca gggtattaac agctggttag cctggtatca gcagaaacca 120

-continued

```
gggaaagccc ctaaactcct gatctatgct gcatccagtt tacaaagtgg ggtcccatca    180

aggttcagcg gcagtggttc tgggacagat ttcactctca ccatcagcag cctccagcct    240

gaagattttg caacttacta ttgtcaacag gctaacagtt tcccattcac tttcggccct    300

gggaccaaag tggatatcaa a                                              321


<210> SEQ ID NO 638
<211> LENGTH: 107
<212> TYPE: PRT
<213> ORGANISM: Artificial Sequence
<220> FEATURE:
<223> OTHER INFORMATION: synthetic

<400> SEQUENCE: 638

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Asn Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Ser Phe Pro Phe
                85                  90                  95

Thr Phe Gly Pro Gly Thr Lys Val Asp Ile Lys
            100                 105


<210> SEQ ID NO 639
<211> LENGTH: 18
<212> TYPE: DNA
<213> ORGANISM: Artificial Sequence
<220> FEATURE:
<223> OTHER INFORMATION: synthetic

<400> SEQUENCE: 639

cagggtatta acagctgg                                                   18


<210> SEQ ID NO 640
<211> LENGTH: 6
<212> TYPE: PRT
<213> ORGANISM: Artificial Sequence
<220> FEATURE:
<223> OTHER INFORMATION: synthetic

<400> SEQUENCE: 640

Gln Gly Ile Asn Ser Trp
1               5


<210> SEQ ID NO 641
<211> LENGTH: 9
<212> TYPE: DNA
<213> ORGANISM: Artificial Sequence
<220> FEATURE:
<223> OTHER INFORMATION: synthetic

<400> SEQUENCE: 641

gctgcatcc                                                              9


<210> SEQ ID NO 642
<211> LENGTH: 3
```

<212> TYPE: PRT
<213> ORGANISM: Artificial Sequence
<220> FEATURE:
<223> OTHER INFORMATION: synthetic

<400> SEQUENCE: 642

Ala Ala Ser
1

<210> SEQ ID NO 643
<211> LENGTH: 27
<212> TYPE: DNA
<213> ORGANISM: Artificial Sequence
<220> FEATURE:
<223> OTHER INFORMATION: synthetic

<400> SEQUENCE: 643
caacaggcta acagtttccc attcact 27

<210> SEQ ID NO 644
<211> LENGTH: 9
<212> TYPE: PRT
<213> ORGANISM: Artificial Sequence
<220> FEATURE:
<223> OTHER INFORMATION: synthetic

<400> SEQUENCE: 644

Gln Gln Ala Asn Ser Phe Pro Phe Thr
1 5

<210> SEQ ID NO 645
<211> LENGTH: 990
<212> TYPE: DNA
<213> ORGANISM: Artificial Sequence
<220> FEATURE:
<223> OTHER INFORMATION: hIgG1 Heavy Chain (WT) NA

<400> SEQUENCE: 645
gcctccacca agggcccatc ggtcttcccc ctggcaccct cctccaagag cacctctggg 60
ggcacagcgg ccctgggctg cctggtcaag gactacttcc ccgaaccggt gacggtgtcg 120
tggaactcag gcgccctgac cagcggcgtg cacaccttcc cggctgtcct acagtcctca 180
ggactctact ccctcagcag cgtggtgacc gtgccctcca gcagcttggg cacccagacc 240
tacatctgca acgtgaatca caagcccagc aacaccaagg tggacaagaa agttgagccc 300
aaatcttgtg acaaaactca cacatgccca ccgtgcccag cacctgaact cctgggggga 360
ccgtcagtct tcctcttccc cccaaaaccc aaggacaccc tcatgatctc ccggacccct 420
gaggtcacat gcgtggtggt ggacgtgagc cacgaagacc ctgaggtcaa gttcaactgg 480
tacgtggacg gcgtggaggt gcataatgcc aagacaaagc cgcgggagga gcagtacaac 540
agcacgtacc gtgtggtcag cgtcctcacc gtcctgcacc aggactggct gaatggcaag 600
gagtacaagt gcaaggtctc caacaaagcc ctcccagccc ccatcgagaa aaccatctcc 660
aaagccaaag ggcagccccg agaaccacag gtgtacaccc tgcccccatc ccgggatgag 720
ctgaccaaga accaggtcag cctgacctgc ctggtcaaag gcttctatcc cagcgacatc 780
gccgtggagt gggagagcaa tgggcagccg gagaacaact acaagaccac gcctcccgtg 840
ctggactccg acggctcctt cttcctctac agcaagctca ccgtggacaa gagcaggtgg 900
cagcagggga acgtcttctc atgctccgtg atgcatgagg ctctgcacaa ccactacacg 960
cagaagtccc tctccctgtc tccgggtaaa 990

<210> SEQ ID NO 646
<211> LENGTH: 330
<212> TYPE: PRT
<213> ORGANISM: Artificial Sequence
<220> FEATURE:
<223> OTHER INFORMATION: hIgG1 Heavy Chain (WT)

<400> SEQUENCE: 646

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 647
<211> LENGTH: 990
<212> TYPE: DNA
<213> ORGANISM: Artificial Sequence
<220> FEATURE:

<223> OTHER INFORMATION: hIgG1 Heavy Chain */* Mutation NA

<400> SEQUENCE: 647

```
gcctcaacta agggcccaag cgtctttcca ttggctccat ccagtaaatc aacttcaggg     60
gggaccgcag ctctggggtg cctcgtgaag gactacttcc ctgaacctgt cacagtctcc    120
tggaactccg gggctctgac cagcggagtt cacacctttc ctgccgtgct tcagtcttcc    180
gggctgtact cattgagcag tgtcgttact gtaccatcct cctccctggg tactcaaacc    240
tacatctgta atgtgaacca caagccctcc aacaccaagg ttgacaaaaa ggtggaacca    300
aagagttgtg ataagactca tacctgcccc ccatgtcctg cccccgagct gctgggagga    360
ccttcagtgt tcttgttccc tcccaaacca aaagacactt tgatgatttc acgaacccct    420
gaagtgacct gtgtggtggt cgatgtcagc cacgaagacc ctgaagttaa gtttaactgg    480
tatgtggatg gcgtagaggt tcacaacgct aagactaaac ccagagagga gcaatataat    540
agtacctata gggtcgtgtc tgtgctgaca gtcttgcatc aggactggct taacggtaag    600
gagtacaagt gtaaggtgtc aaacaaggca ctgcctgcac ctatcgagaa gaccatctct    660
aaggccaaag gtcaaccaag ggagccccag gtatatactt tgccaccctc tcgggacgag    720
ctgacaaaaa atcaggtgag tctgacctgt ctcgtgaaag gattttaccc tagcgacatc    780
gccgtggagt gggagagtaa tggccagccc gagaataact acaagaccac cccaccagtt    840
ctggactctg acgggtcttt cttcctttat agtaagctga ccgtagataa gtctcgctgg    900
cagcaaggca atgtattctc ttgcagtgtc atgcacgagg ccctccataa ccgattcacc    960
caaaaatctc tgtctctgtc tcctggaaag                                     990
```

<210> SEQ ID NO 648
<211> LENGTH: 330
<212> TYPE: PRT
<213> ORGANISM: Artificial Sequence
<220> FEATURE:
<223> OTHER INFORMATION: hIgG1 Heavy Chain */* Mutation (H435R,Y436F)

<400> SEQUENCE: 648

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
```

```
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn Arg Phe Thr
305                 310                 315                 320

Gln Lys Ser Leu Ser Leu Ser Pro Gly Lys
                325                 330


<210> SEQ ID NO 649
<211> LENGTH: 378
<212> TYPE: DNA
<213> ORGANISM: Artificial Sequence
<220> FEATURE:
<223> OTHER INFORMATION: synthetic

<400> SEQUENCE: 649

caggtgcagc tggtggagtc tgggggaggc gtggtccagc ctgggaggtc cctgagactc      60

tcctgtgcag tgtctggact catcttcagt aactatggca tgcactgggt ccgccaggct     120

ccaggcaagg ggctggagtg ggtggcagtt atatggtatg atggaagtaa taaatactat     180

gtagactccg tgaagggccg cttcaccatc tccagagaca attccaagaa cacgctgtat     240

ctgcaaatga acagcctgag aggcgaggac acggctatat attactgtgc gagagatcgg     300

agagggctgg aactatttaa ctactactac cacggtttgg acgtctgggg ccaagggacc     360

acggtcaccg tctcctca                                                   378


<210> SEQ ID NO 650
<211> LENGTH: 126
<212> TYPE: PRT
<213> ORGANISM: Artificial Sequence
<220> FEATURE:
<223> OTHER INFORMATION: synthetic

<400> SEQUENCE: 650

Gln Val Gln Leu Val Glu Ser Gly Gly Gly Val Val Gln Pro Gly Arg
1               5                   10                  15

Ser Leu Arg Leu Ser Cys Ala Val Ser Gly Leu Ile Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
```

65 70 75 80

Leu Gln Met Asn Ser Leu Arg Gly Glu Asp Thr Ala Ile Tyr Tyr Cys
85 90 95

Ala Arg Asp Arg Arg Gly Leu Glu Leu Phe Asn Tyr Tyr Tyr His Gly
100 105 110

Leu Asp Val Trp Gly Gln Gly Thr Thr Val Thr Val Ser Ser
115 120 125

<210> SEQ ID NO 651
<211> LENGTH: 24
<212> TYPE: DNA
<213> ORGANISM: Artificial Sequence
<220> FEATURE:
<223> OTHER INFORMATION: synthetic

<400> SEQUENCE: 651
ggactcatct tcagtaacta tggc 24

<210> SEQ ID NO 652
<211> LENGTH: 8
<212> TYPE: PRT
<213> ORGANISM: Artificial Sequence
<220> FEATURE:
<223> OTHER INFORMATION: synthetic

<400> SEQUENCE: 652

Gly Leu Ile Phe Ser Asn Tyr Gly
1 5

<210> SEQ ID NO 653
<211> LENGTH: 24
<212> TYPE: DNA
<213> ORGANISM: Artificial Sequence
<220> FEATURE:
<223> OTHER INFORMATION: synthetic

<400> SEQUENCE: 653
atatggtatg atggaagtaa taaa 24

<210> SEQ ID NO 654
<211> LENGTH: 8
<212> TYPE: PRT
<213> ORGANISM: Artificial Sequence
<220> FEATURE:
<223> OTHER INFORMATION: synthetic

<400> SEQUENCE: 654

Ile Trp Tyr Asp Gly Ser Asn Lys
1 5

<210> SEQ ID NO 655
<211> LENGTH: 57
<212> TYPE: DNA
<213> ORGANISM: Artificial Sequence
<220> FEATURE:
<223> OTHER INFORMATION: synthetic

<400> SEQUENCE: 655
gcgagagatc ggagagggct ggaactattt aactactact accacggttt ggacgtc 57

<210> SEQ ID NO 656
<211> LENGTH: 19
<212> TYPE: PRT
<213> ORGANISM: Artificial Sequence
<220> FEATURE:

<223> OTHER INFORMATION: synthetic

<400> SEQUENCE: 656

Ala Arg Asp Arg Arg Gly Leu Glu Leu Phe Asn Tyr Tyr Tyr His Gly
1 5 10 15

Leu Asp Val

<210> SEQ ID NO 657
<211> LENGTH: 321
<212> TYPE: DNA
<213> ORGANISM: Artificial Sequence
<220> FEATURE:
<223> OTHER INFORMATION: synthetic

<400> SEQUENCE: 657
gacatccaga tgacccagtc tccatcctca ctgtctgcat ctgtaggaga cagagtcacc 60
atcacttgtc gggcgagtca gggcattagc aatttttag cctggtttca gcagaaacca 120
gggaaagccc ctaagtccct gatctatgct gcatccagtt tgcaaagtgg ggtcccatca 180
aagttcagcg gcagtggatc tgggacagat ttcactctca ccatcagcag cctgcagcct 240
gaagattttg caacttatta ctgccaacag tataatagtt acccattcac tttcggccct 300
gggaccaaag tggatatcaa a 321

<210> SEQ ID NO 658
<211> LENGTH: 107
<212> TYPE: PRT
<213> ORGANISM: Artificial Sequence
<220> FEATURE:
<223> OTHER INFORMATION: synthetic

<400> SEQUENCE: 658

Asp Ile Gln Met Thr Gln Ser Pro Ser Ser Leu Ser Ala Ser Val Gly
1 5 10 15

Asp Arg Val Thr Ile Thr Cys Arg Ala Ser Gln Gly Ile Ser Asn Phe
20 25 30

Leu Ala Trp Phe Gln Gln Lys Pro Gly Lys Ala Pro Lys Ser Leu Ile
35 40 45

Tyr Ala Ala Ser Ser Leu Gln Ser Gly Val Pro Ser Lys Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Tyr Pro Phe
85 90 95

Thr Phe Gly Pro Gly Thr Lys Val Asp Ile Lys
100 105

<210> SEQ ID NO 659
<211> LENGTH: 18
<212> TYPE: DNA
<213> ORGANISM: Artificial Sequence
<220> FEATURE:
<223> OTHER INFORMATION: synthetic

<400> SEQUENCE: 659
cagggcatta gcaatttt 18

<210> SEQ ID NO 660
<211> LENGTH: 6
<212> TYPE: PRT
<213> ORGANISM: Artificial Sequence -continued
<220> FEATURE:
<223> OTHER INFORMATION: synthetic

<400> SEQUENCE: 660

Gln Gly Ile Ser Asn Phe
1               5

<210> SEQ ID NO 661
<211> LENGTH: 9
<212> TYPE: DNA
<213> ORGANISM: Artificial Sequence
<220> FEATURE:
<223> OTHER INFORMATION: synthetic

<400> SEQUENCE: 661 gctgcatcc 9

<210> SEQ ID NO 662
<211> LENGTH: 3
<212> TYPE: PRT
<213> ORGANISM: Artificial Sequence
<220> FEATURE:
<223> OTHER INFORMATION: synthetic

<400> SEQUENCE: 662

Ala Ala Ser
1

<210> SEQ ID NO 663
<211> LENGTH: 27
<212> TYPE: DNA
<213> ORGANISM: Artificial Sequence
<220> FEATURE:
<223> OTHER INFORMATION: synthetic

<400> SEQUENCE: 663
caacagtata atagttaccc attcact 27

<210> SEQ ID NO 664
<211> LENGTH: 9
<212> TYPE: PRT
<213> ORGANISM: Artificial Sequence
<220> FEATURE:
<223> OTHER INFORMATION: synthetic

<400> SEQUENCE: 664

Gln Gln Tyr Asn Ser Tyr Pro Phe Thr
1               5

<210> SEQ ID NO 665
<211> LENGTH: 1371
<212> TYPE: DNA
<213> ORGANISM: Artificial Sequence
<220> FEATURE:
<223> OTHER INFORMATION: synthetic

<400> SEQUENCE: 665
caggtgcagc tggtggagtc tgggggaggc gtggtccagc ctgggaggtc cctgagactc 60
tcctgtgcag tgtctggact catcttcagt aactatggca tgcactgggt ccgccaggct 120
ccaggcaagg ggctggagtg ggtggcagtt atatggtatg atggaagtaa taaatactat 180
gtagactccg tgaagggccg cttcaccatc tccagagaca attccaagaa cacgctgtat 240
ctgcaaatga acagcctgag aggcgaggac acggctatat attactgtgc gagagatcgg 300
agagggctgg aactatttaa ctactactac cacggtttgg acgtctgggg ccaagggacc 360

```
acggtcaccg tctcctcagc ctcaacaaaa ggtccctcag tctttcctct tgctccatcc    420

tccaaaagta catcaggagg taccgcagcc cttggatgcc tcgtcaagga ttattttccc    480

gaaccagtta ccgtttcctg gaactcaggc gctctcacct ctggagtaca tacttttcct    540

gcagtcctcc aatcctctgg cctttactcc ctttctagcg tagtaaccgt accatcatca    600

tccctcggaa cccaaactta tatctgtaat gttaatcaca aacccagcaa caccaaagta    660

gacaaaaaag ttgaacctaa atcatgcgat aaaacccaca cttgcccccc ctgtccagca    720

ccagaactcc ttggcggccc ctcagttttc ctttttccac caaagcccaa agacaccctt    780

atgatctcca gaacccccga agttacatgc gtagtcgttg acgtttctca cgaagatcca    840

gaagtcaaat tcaattggta cgttgatggc gttgaagtcc ataatgcaaa aacaaaaccc    900

cgagaagaac agtacaattc aacatatcga gtagttagcg tacttacagt tctgcaccaa    960

gattggctga acggaaaaga atataaatgt aaagtctcta acaaagcact ccctgcccca   1020

attgaaaaaa caatctcaaa agccaaaggc caacctcgcg aacctcaggt ttacacactt   1080

ccccctccc gcgacgaact gactaaaaac caggtttcct tgacatgcct tgtaaaaggt    1140

ttttacccct ccgatatcgc cgtagaatgg gaatctaatg gacaaccaga aaacaattac   1200

aaaactaccc ctcctgtgct cgattccgat ggctcttttt tcctctattc taagctcacc   1260

gttgacaagt ctcgttggca gcagggaaac gtattcagtt gcagcgtcat gcacgaagcc   1320

cttcataata gattcaccca aaagtctctt tctctctctc ctggtaagta g            1371
```

<210> SEQ ID NO 666
<211> LENGTH: 456
<212> TYPE: PRT
<213> ORGANISM: Artificial Sequence
<220> FEATURE:
<223> OTHER INFORMATION: synthetic

<400> SEQUENCE: 666

```
Gln Val Gln Leu Val Glu Ser Gly Gly Gly Val Val Gln Pro Gly Arg
1               5                   10                  15

Ser Leu Arg Leu Ser Cys Ala Val Ser Gly Leu Ile Phe Ser Asn Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Lys Tyr Tyr Val Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Gly Glu Asp Thr Ala Ile Tyr Tyr Cys
                85                  90                  95

Ala Arg Asp Arg Arg Gly Leu Glu Leu Phe Asn Tyr Tyr Tyr His Gly
            100                 105                 110

Leu Asp Val Trp Gly Gln Gly Thr Thr Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
```

-continued

```
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Asp Glu Leu Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn Arg Phe Thr Gln Lys
        435                 440                 445

Ser Leu Ser Leu Ser Pro Gly Lys
    450                 455


<210> SEQ ID NO 667
<211> LENGTH: 645
<212> TYPE: DNA
<213> ORGANISM: Artificial Sequence
<220> FEATURE:
<223> OTHER INFORMATION: synthetic

<400> SEQUENCE: 667

gacatccaga tgacccagtc tccatcctca ctgtctgcat ctgtaggaga cagagtcacc      60

atcacttgtc gggcgagtca gggcattagc aatttttttag cctggtttca gcagaaacca    120

gggaaagccc ctaagtccct gatctatgct gcatccagtt tgcaaagtgg ggtcccatca    180

aagttcagcg gcagtggatc tgggacagat ttcactctca ccatcagcag cctgcagcct    240

gaagattttg caacttatta ctgccaacag tataatagtt acccattcac tttcggccct    300

gggaccaaag tggatatcaa acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480
```

```
gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645


<210> SEQ ID NO 668
<211> LENGTH: 214
<212> TYPE: PRT
<213> ORGANISM: Artificial Sequence
<220> FEATURE:
<223> OTHER INFORMATION: synthetic

<400> SEQUENCE: 668

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Phe
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Ser Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 669
<211> LENGTH: 354
<212> TYPE: DNA
<213> ORGANISM: Artificial Sequence
<220> FEATURE:
<223> OTHER INFORMATION: synthetic

<400> SEQUENCE: 669

gaggtgcagc tggtggagtc tgggggaggc ctggtacagc ctggggggtc cctgagactc     60

tcctgtgcag cctctggatt cacctttaac agctatgcca tgagctggtt ccgccagact    120

ccagggaagg ggctggagtg gctctcagct atgactggta gtggtggtaa cacatactac    180

gcagactccg tgaagggccg gttcaccatc tccagagaca attccaagaa cacgctgtat    240

ctgcaaatga acaacctgag agccgaggac acggccgtat attactgtgc ggtggataca    300

accatggccc actttgacta ctggggccag ggaaccctgg tcaccgtctc ctca          354
```

<210> SEQ ID NO 670
<211> LENGTH: 118
<212> TYPE: PRT
<213> ORGANISM: Artificial Sequence
<220> FEATURE:
<223> OTHER INFORMATION: synthetic

<400> SEQUENCE: 670

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Ser Tyr
20 25 30

Ala Met Ser Trp Phe Arg Gln Thr Pro Gly Lys Gly Leu Glu Trp Leu
35 40 45

Ser Ala Met Thr Gly Ser Gly Gly Asn Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Asn Leu Arg Ala Glu Asp Thr Ala Val Tyr Tyr Cys
85 90 95

Ala Val Asp Thr Thr Met Ala His Phe Asp Tyr Trp Gly Gln Gly Thr
100 105 110

Leu Val Thr Val Ser Ser
115

<210> SEQ ID NO 671
<211> LENGTH: 24
<212> TYPE: DNA
<213> ORGANISM: Artificial Sequence
<220> FEATURE:
<223> OTHER INFORMATION: synthetic

<400> SEQUENCE: 671
ggattcacct ttaacagcta tgcc 24

<210> SEQ ID NO 672
<211> LENGTH: 8
<212> TYPE: PRT
<213> ORGANISM: Artificial Sequence
<220> FEATURE:
<223> OTHER INFORMATION: synthetic

<400> SEQUENCE: 672

Gly Phe Thr Phe Asn Ser Tyr Ala
1 5

<210> SEQ ID NO 673
<211> LENGTH: 24
<212> TYPE: DNA
<213> ORGANISM: Artificial Sequence
<220> FEATURE:
<223> OTHER INFORMATION: synthetic

<400> SEQUENCE: 673
atgactggta gtggtggtaa caca 24

<210> SEQ ID NO 674
<211> LENGTH: 8
<212> TYPE: PRT
<213> ORGANISM: Artificial Sequence
<220> FEATURE:
<223> OTHER INFORMATION: synthetic

<400> SEQUENCE: 674

Met Thr Gly Ser Gly Gly Asn Thr
1 5

<210> SEQ ID NO 675
<211> LENGTH: 33
<212> TYPE: DNA
<213> ORGANISM: Artificial Sequence
<220> FEATURE:
<223> OTHER INFORMATION: synthetic

<400> SEQUENCE: 675
gcggtggata caaccatggc ccactttgac tac 33

<210> SEQ ID NO 676
<211> LENGTH: 11
<212> TYPE: PRT
<213> ORGANISM: Artificial Sequence
<220> FEATURE:
<223> OTHER INFORMATION: synthetic

<400> SEQUENCE: 676

Ala Val Asp Thr Thr Met Ala His Phe Asp Tyr
1 5 10

<210> SEQ ID NO 677
<211> LENGTH: 321
<212> TYPE: DNA
<213> ORGANISM: Artificial Sequence
<220> FEATURE:
<223> OTHER INFORMATION: synthetic

<400> SEQUENCE: 677
gacatccaga tgacccagtc tccatcttcc gtgtctgcat ctgtaggaga cagagtcacc 60
atcacttgtc gggcgagtca gggtattagc agctggttag cctggtatca gcagaaacca 120
gggaaagccc ctaagctcct gatctatgct gcttccactt tacaaagtgg ggtcccatca 180
aggttcagtg gcagtggatc tgggacagat ttcactctca ccatcagcag cctgcagcct 240
gaagattttg caacttacta ttgtcaacgg attaacagtt tcccattcac tttcggccct 300
gggaccaaag tggatatcaa a 321

<210> SEQ ID NO 678
<211> LENGTH: 107
<212> TYPE: PRT
<213> ORGANISM: Artificial Sequence
<220> FEATURE:
<223> OTHER INFORMATION: synthetic

<400> SEQUENCE: 678

Asp Ile Gln Met Thr Gln Ser Pro Ser Ser Val Ser Ala Ser Val Gly
1 5 10 15

Asp Arg Val Thr Ile Thr Cys Arg Ala Ser Gln Gly Ile Ser Ser Trp
20 25 30

Leu Ala Trp Tyr Gln Gln Lys Pro Gly Lys Ala Pro Lys Leu Leu Ile
35 40 45

Tyr Ala Ala Ser Thr Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Arg Ile Asn Ser Phe Pro Phe

```
                    85                  90                  95
Thr Phe Gly Pro Gly Thr Lys Val Asp Ile Lys
                100                 105

<210> SEQ ID NO 679
<211> LENGTH: 18
<212> TYPE: DNA
<213> ORGANISM: Artificial Sequence
<220> FEATURE:
<223> OTHER INFORMATION: synthetic

<400> SEQUENCE: 679

cagggtatta gcagctgg                                                  18

<210> SEQ ID NO 680
<211> LENGTH: 6
<212> TYPE: PRT
<213> ORGANISM: Artificial Sequence
<220> FEATURE:
<223> OTHER INFORMATION: synthetic

<400> SEQUENCE: 680

Gln Gly Ile Ser Ser Trp
1               5

<210> SEQ ID NO 681
<211> LENGTH: 9
<212> TYPE: DNA
<213> ORGANISM: Artificial Sequence
<220> FEATURE:
<223> OTHER INFORMATION: synthetic

<400> SEQUENCE: 681

gctgcttcc                                                             9

<210> SEQ ID NO 682
<211> LENGTH: 27
<212> TYPE: DNA
<213> ORGANISM: Artificial Sequence
<220> FEATURE:
<223> OTHER INFORMATION: synthetic

<400> SEQUENCE: 682

caacggatta acagtttccc attcact                                        27

<210> SEQ ID NO 683
<211> LENGTH: 9
<212> TYPE: PRT
<213> ORGANISM: Artificial Sequence
<220> FEATURE:
<223> OTHER INFORMATION: synthetic

<400> SEQUENCE: 683

Gln Arg Ile Asn Ser Phe Pro Phe Thr
1               5

<210> SEQ ID NO 684
<211> LENGTH: 1347
<212> TYPE: DNA
<213> ORGANISM: Artificial Sequence
<220> FEATURE:
<223> OTHER INFORMATION: synthetic

<400> SEQUENCE: 684

gaggtgcagc tggtggagtc tgggggaggc ctggtacagc ctggggggtc cctgagactc    60
```

```
tcctgtgcag cctctggatt cacctttaac agctatgcca tgagctggtt ccgccagact    120

ccagggaagg ggctggagtg gctctcagct atgactggta gtggtggtaa cacatactac    180

gcagactccg tgaagggccg gttcaccatc tccagagaca attccaagaa cacgctgtat    240

ctgcaaatga acaacctgag agccgaggac acggccgtat attactgtgc ggtggataca    300

accatggccc actttgacta ctggggccag ggaaccctgg tcaccgtctc ctcagcctca    360

acaaaaggtc cctcagtctt tcctcttgct ccatcctcca aaagtacatc aggaggtacc    420

gcagcccttg gatgcctcgt caaggattat tttcccgaac cagttaccgt ttcctggaac    480

tcaggcgctc tcacctctgg agtacatact tttcctgcag tcctccaatc ctctggcctt    540

tactcccttt ctagcgtagt aaccgtacca tcatcatccc tcggaaccca aacttatatc    600

tgtaatgtta atcacaaacc cagcaacacc aaagtagaca aaaaagttga acctaaatca    660

tgcgataaaa cccacacttg cccccccctgt ccagcaccag aactccttgg cggcccctca    720

gttttccttt ttccaccaaa gcccaaagac acccttatga tctccagaac ccccgaagtt    780

acatgcgtag tcgttgacgt ttctcacgaa gatccagaag tcaaattcaa ttggtacgtt    840

gatggcgttg aagtccataa tgcaaaaaca aaaccccgag aagaacagta caattcaaca    900

tatcgagtag ttagcgtact tacagttctg caccaagatt ggctgaacgg aaaagaatat    960

aaatgtaaag tctctaacaa agcactccct gccccaattg aaaaaacaat ctcaaaagcc   1020

aaaggccaac ctcgcgaacc tcaggtttac acacttcccc cctcccgcga cgaactgact   1080

aaaaaccagg tttccttgac atgccttgta aaaggttttt acccctccga tatcgccgta   1140

gaatgggaat ctaatggaca accagaaaac aattacaaaa ctacccctcc tgtgctcgat   1200

tccgatggct ctttttttcct ctattctaag ctcaccgttg acaagtctcg ttggcagcag   1260

ggaaacgtat tcagttgcag cgtcatgcac gaagcccttc ataatagatt cacccaaaag   1320

tctctttctc tctctcctgg taagtag                                       1347
```

<210> SEQ ID NO 685
<211> LENGTH: 448
<212> TYPE: PRT
<213> ORGANISM: Artificial Sequence
<220> FEATURE:
<223> OTHER INFORMATION: synthetic

<400> SEQUENCE: 685

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Tyr
            20                  25                  30

Ala Met Ser Trp Phe Arg Gln Thr Pro Gly Lys Gly Leu Glu Trp Leu
        35                  40                  45

Ser Ala Met Thr Gly Ser Gly Gly Asn Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Asn Leu Arg Ala Glu Asp Thr Ala Val Tyr Tyr Cys
                85                  90                  95

Ala Val Asp Thr Thr Met Ala His Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
```

-continued

```
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn Arg Phe Thr Gln Lys Ser Leu Ser Leu Ser Pro Gly Lys
        435                 440                 445
```

<210> SEQ ID NO 686
<211> LENGTH: 645
<212> TYPE: DNA
<213> ORGANISM: Artificial Sequence
<220> FEATURE:
<223> OTHER INFORMATION: synthetic

<400> SEQUENCE: 686

```
gacatccaga tgacccagtc tccatcttcc gtgtctgcat ctgtaggaga cagagtcacc      60

atcacttgtc gggcgagtca gggtattagc agctggttag cctggtatca gcagaaacca     120

gggaaagccc ctaagctcct gatctatgct gcttccactt tacaaagtgg ggtcccatca     180

aggttcagtg gcagtggatc tgggacagat ttcactctca ccatcagcag cctgcagcct     240

gaagattttg caacttacta ttgtcaacgg attaacagtt tcccattcac tttcggccct     300
```

```
gggaccaaag tggatatcaa acgaactgtg gctgcaccat ctgtcttcat cttcccgcca    360

tctgatgagc agttgaaatc tggaactgcc tctgttgtgt gcctgctgaa taacttctat    420

cccagagagg ccaaagtaca gtggaaggtg gataacgccc tccaatcggg taactcccag    480

gagagtgtca cagagcagga cagcaaggac agcacctaca gcctcagcag caccctgacg    540

ctgagcaaag cagactacga gaaacacaaa gtctacgcct gcgaagtcac ccatcagggc    600

ctgagctcgc ccgtcacaaa gagcttcaac aggggagagt gttag                    645


<210> SEQ ID NO 687
<211> LENGTH: 214
<212> TYPE: PRT
<213> ORGANISM: Artificial Sequence
<220> FEATURE:
<223> OTHER INFORMATION: synthetic

<400> SEQUENCE: 687

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Arg Ile Asn Ser Phe Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 688
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 688

His His His His His His His His His
1               5
```

-continued

<210> SEQ ID NO 689
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 689

His His His His His His
1               5

<210> SEQ ID NO 690
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 690

His His His His His
1               5